(12) United States Patent
Maxwell et al.

(10) Patent No.: US 12,043,607 B2
(45) Date of Patent: Jul. 23, 2024

(54) HDAC INHIBITORS AND THERAPEUTIC USE THEREOF

(71) Applicant: Tango Therapeutics, Inc., Boston, MA (US)

(72) Inventors: John P. Maxwell, Hingham, MA (US); Xinyuan Wu, Chestnut Hill, MA (US); David Guerin, Natick, MA (US)

(73) Assignee: Tango Therapeutics, Inc., Boston, MA (US)

( * ) Notice: Subject to any disclaimer, the term of this patent is extended or adjusted under 35 U.S.C. 154(b) by 0 days.

(21) Appl. No.: 18/074,163

(22) Filed: Dec. 2, 2022

(65) Prior Publication Data

US 2023/0174501 A1 Jun. 8, 2023

Related U.S. Application Data

(60) Provisional application No. 63/285,558, filed on Dec. 3, 2021.

(51) Int. Cl.
| | | |
|---|---|---|
| *C07C 381/10* | (2006.01) | |
| *C07D 213/71* | (2006.01) | |
| *C07D 275/02* | (2006.01) | |
| *C07D 333/24* | (2006.01) | |
| *C07D 409/12* | (2006.01) | |

(52) U.S. Cl.
CPC .......... *C07D 333/24* (2013.01); *C07C 381/10* (2013.01); *C07D 213/71* (2013.01); *C07D 275/02* (2013.01); *C07D 409/12* (2013.01)

(58) Field of Classification Search
CPC .................................................. C07C 381/10
See application file for complete search history.

(56) References Cited

U.S. PATENT DOCUMENTS

2014/0128391 A1    5/2014    van Duzer et al.

FOREIGN PATENT DOCUMENTS

| CN | 107879975 A | 4/2018 |
|---|---|---|
| WO | WO-2005030704 A1 | 4/2005 |
| WO | WO-2005030705 A1 | 4/2005 |
| WO | WO-2007087129 A2 | 8/2007 |
| WO | 2007118137 A1 | 10/2007 |
| WO | WO-2009020589 A1 | 2/2009 |
| WO | WO-2009033281 A1 | 3/2009 |
| WO | WO-2010065117 A1 | 6/2010 |
| WO | WO-2017007756 A1 | 1/2017 |
| WO | WO-2018098296 A1 | 5/2018 |
| WO | WO-2018119362 A2 | 6/2018 |
| WO | WO-2018132533 A1 | 7/2018 |
| WO | WO-2019012172 A1 | 1/2019 |
| WO | WO-2019169267 A1 | 9/2019 |
| WO | WO-2020014602 A1 | 1/2020 |
| WO | WO-2020014605 A1 | 1/2020 |
| WO | WO-2020068950 A1 | 4/2020 |
| WO | WO-2020076951 A1 | 4/2020 |

OTHER PUBLICATIONS

International Search Report and Written Opinion for International Patent Application No. PCT/US2022/051616, dated Mar. 8, 2023, 8 pages.
Fuller, Nathan O, "CoRest Complex-Selective Histone Deacetylase Inhibitors Show Prosynaptic Effects and an Improved Safety Profile to Enable Treatment of Synaptopathies", ACS Chemical Neuroscience, Nov. 29, 2018, p. 1729-1743, vol. 10.
Fuller, Nathan O, "CoRest Complex-Selective HDAC Inhibitors Promote Prosynaptic Effects Represent Promising Therapies to Treat Synaptopathies", NESACS Presentation, Dec. 10, 2020.
Methot, Joey L, "Exploration of the internal cavity of histone deacetylase (HDAC) with selective HDAC1/HDAC2 inhibitors (SHI-1:2)", Bioorganic & Medicinal Chemistry Letters, Jan. 7, 2008, p. 973-978, vol. 18.
Luo, Yuxiang, "Structure-Based Inhibitor Discovery of Class I Histone Deacetylases (HDACs)", International Journal of Molecular Sciences, Nov. 22, 2020, p. 8828, vol. 21.
Maolanon, Alex R, "Innovative Strategies for Selective Inhibition of Histone Deacetylases", Cell Chemical Biology, Jul. 21, 2016, p. 759-768, vol. 23.
Huang, Meiling, "Small molecule HDAC inhibitors: Promising agents for breast cancer treatment", Bioorganic Chemistry, Aug. 5, 2019, p. 103184, vol. 91.

*Primary Examiner* — Rebecca L Anderson
(74) *Attorney, Agent, or Firm* — GOODWIN PROCTER LLP

(57) ABSTRACT

Described herein are novel compounds, compositions and methods for treatment of diseases including cancer using such compounds, compositions, and methods. The compounds include those of Formula (I):

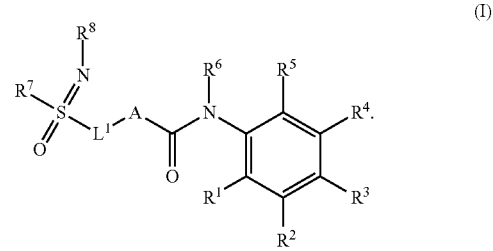

34 Claims, No Drawings

HDAC INHIBITORS AND THERAPEUTIC USE THEREOF

CROSS-REFERENCE TO RELATED APPLICATION

This application claims the benefit of and priority to U.S. Provisional Application No. 63/285,558, filed on Dec. 3, 2021, the entire disclosure of which is hereby incorporated by reference herein in its entirety for all purposes.

FIELD

Provided herein are compounds, and compositions and methods thereof. In some embodiments, provided are compounds for inhibiting histone deacetylase (HDAC). In some embodiments, provided are methods for treatment of diseases or disorders, such as cancer.

BACKGROUND

Histone deacetylases (HDAC) are a class of epigenetic proteins implicated in a variety of diseases, including cancers, and inhibition of specific HDACs in certain patients may treat or otherwise ameliorate such diseases. There are four families of HDACs encompassing 18 HDAC isoforms. Jenke, R., et al. Anticancer Therapy with HDAC Inhibitors: Mechanism-Based Combination Strategies and Future Perspectives. Cancers 13: 634 (2021). Some HDAC inhibitors have been approved by the United States Food and Drug Administration (FDA), but currently approved HDAC therapies are not known to be specific to only a few HDAC isoforms, increasing the potential for adverse effects due to broad inhibitory properties. Thus, there is a need for selective HDAC inhibitors for treating diseases or disorders, such as cancers.

SUMMARY

In one embodiment, provided is a compound of Formula (I)

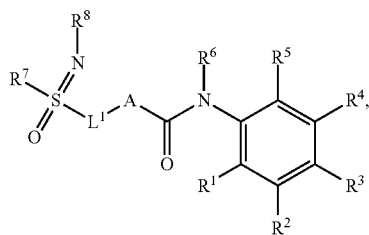

or a pharmaceutically acceptable salt thereof,
wherein
A is an optionally substituted aryl or heteroaryl;
$L^1$ is —$CR'_2$—, —$CR'_2CR'_2$—, or a bond;
each R' is independently H or $C_1$-$C_6$ alkyl; or two R' together with the carbon or carbons to which they are attached form a 3-6-membered cycloalkyl ring;
each $R^1$, $R^3$ and $R^4$ is independently H, $C_1$-$C_6$ alkyl, $C_1$-$C_6$ haloalkyl, or halogen;
$R^2$ is aryl or heteroaryl, each optionally substituted;
$R^5$ is $NH_2$ or OH;
$R^6$ is H or $C_1$-$C_6$ alkyl;
$R^7$ is $C_1$-$C_6$ alkyl, $C_1$-$C_6$ heteroalkyl, —$(CH_2)_{0-2}$-phenyl, —$(CH_2)_{0-2}$-$C_3$-$C_7$ cycloalkyl, —$(CH_2)_{0-2}$-heteroaryl or —$(CH_2)_{0-2}$-heterocyclyl, wherein each alkyl, heteroalkyl, phenyl, cycloalkyl, heteroaryl or heterocyclyl is optionally substituted;
$R^8$ is H, $C_1$-$C_6$ alkyl, $C_1$-$C_6$ heteroalkyl, phenyl, cycloalkyl, heterocyclyl, cyano, CO—R', or $CO_2$—R', wherein each alkyl, heteroalkyl, phenyl, cycloalkyl, or heterocyclyl is optionally substituted; or
$R^7$ and $R^8$ are taken together with the nitrogen and sulfur to which they are attached to form a 4-7 membered heterocycle with 0-2 additional ring heteroatoms selected from O, S, and N, and wherein the heterocycle is optionally substituted.

In some embodiments, provided is a composition comprising a compound as described herein, or a pharmaceutically acceptable salt thereof, and one or more pharmaceutically acceptable excipients.

In some embodiments, provided is a method of treating a disease or disorder that can be treated by inhibition of HDAC, the method comprising administering to a patient in need thereof a compound described herein or a composition described herein.

In some embodiments, provided is a use of a compound disclosed herein in the manufacture of a medicament for the treatment of a disease or disorder that can be treated by inhibition of a histone deacetylase (HDAC). In some embodiments, provided is a use of a compound disclosed herein in the manufacture of a medicament for the treatment of cancer.

In one embodiment, provided is a use of a compound as described herein, or a pharmaceutically acceptable salt thereof, or a composition as described herein in treating a disease or disorder that can be treated by inhibition of a histone deacetylase (HDAC).

In one embodiment, provided is a compound as described herein, or a pharmaceutically acceptable salt thereof, or a composition as described herein for use in a method of treating a disease or disorder that can be treated by inhibition of a histone deacetylase (HDAC), the method comprising administering to a patient in need thereof a compound as described herein, or a pharmaceutically acceptable salt thereof, or a composition as described herein.

Still other objects and advantages of the invention will become apparent to those of skill in the art from the disclosure herein, which is simply illustrative and not restrictive. Thus, other embodiments will be recognized by the skilled artisan without departing from the spirit and scope of the invention.

DETAILED DESCRIPTION

In some embodiments, provided herein are compounds (e.g., compounds of Formula (I), (Ia), (Ib), (Ic), (Id), (Ie), and (If), or compounds of Table 1, or pharmaceutically acceptable salts thereof) that are useful for treating diseases or disorders (e.g., cancer) associated with inhibition of HDAC.

Compounds

Provided herein are compounds of Formula (I). Unless the context requires otherwise, reference throughout this specification to "a compound of Formula (I)" or "compounds of Formula (I)" refers to all embodiments of Formula (I), including, for example, compounds of Formulas (Ia), (Ib), (Ic), (Id), (Ie), and (If), as well as the compounds of Table 1. In some embodiments, provided are compounds of Formula (I) or pharmaceutically acceptable salts thereof. In some embodiments, the compounds of Formula (I) are provided as pharmaceutically acceptable salts. In some embodiments, the compounds of Formula (I) are provided as the corresponding free base (i.e., are not salts).

In some embodiments, provided herein is a compound of Formula (I)

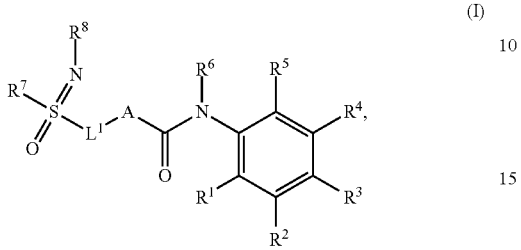

or a pharmaceutically acceptable salt thereof, wherein
  A is an optionally substituted aryl or heteroaryl;
  $L^1$ is —$CR'_2$—, —$CR'_2CR'_2$—, or a bond;
  each R' is independently H or $C_1$-$C_6$ alkyl; or two R' together with the carbon or carbons to which they are attached form a 3-6-membered cycloalkyl ring;
  each $R^1$, $R^3$ and $R^4$ is independently H, $C_1$-$C_6$ alkyl, $C_1$-$C_6$ haloalkyl, or halogen;
  $R^2$ is aryl or heteroaryl, each optionally substituted;
  $R^5$ is $NH_2$ or OH;
  $R^6$ is H or $C_1$-$C_6$ alkyl;
  $R^7$ is $C_1$-$C_6$ alkyl, $C_1$-$C_6$ heteroalkyl, —$(CH_2)_{0-2}$-phenyl, —$(CH_2)_{0-2}$—$C_3$-$C_7$ cycloalkyl, —$(CH_2)_{0-2}$-heteroaryl or —$(CH_2)_{0-2}$-heterocyclyl, wherein each alkyl, heteroalkyl, phenyl, cycloalkyl, heteroaryl or heterocyclyl is optionally substituted;
  $R^8$ is H, $C_1$-$C_6$ alkyl, $C_1$-$C_6$ heteroalkyl, phenyl, cycloalkyl, heterocyclyl, cyano, CO—R', or $CO_2$—R', wherein each alkyl, heteroalkyl, phenyl, cycloalkyl, or heterocyclyl is optionally substituted; or
  $R^7$ and $R^8$ are taken together with the nitrogen and sulfur to which they are attached to form a 4-7 membered heterocycle with 0-2 additional ring heteroatoms selected from O, S, and N, and wherein the heterocycle is optionally substituted.

In some embodiments, provided herein is a compound of Formula (I)

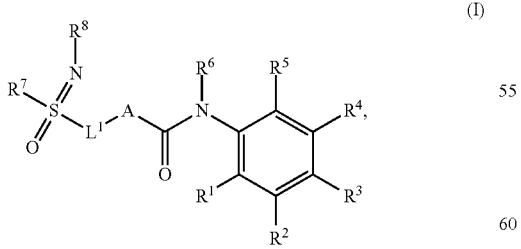

or a pharmaceutically acceptable salt thereof, wherein
  A is an aryl or heteroaryl, wherein heteroaryl has 5-10 ring atoms, 1 to 4 ring atoms selected from N, O, and S, and wherein A is substituted with 0-4 $R^9$ groups;
  $L^1$ is —$CR'_2$—, —$CR'_2CR'_2$—, or a bond;
  each R' is independently H or $C_1$-$C_6$ alkyl; or two R' together with the carbon or carbons to which they are attached form a 3-6-membered cycloalkyl ring;
  each $R^1$, $R^3$ and $R^4$ is independently H, $C_1$-$C_6$ alkyl, $C_1$-$C_6$ haloalkyl, or halogen;
  $R^2$ is aryl or heteroaryl, wherein heteroaryl has 5-10 ring atoms, 1 to 4 ring atoms selected from N, O, and S, and $R^2$ is substituted with 0-4 $R^{10}$ groups;
  $R^5$ is $NH_2$ or OH;
  $R^6$ is H or $C_1$-$C_6$ alkyl;
  $R^7$ is $C_1$-$C_6$ alkyl, $C_1$-$C_6$ heteroalkyl, —$(CH_2)_{0-2}$-phenyl, —$(CH_2)_{0-2}$—$C_3$-$C_7$ cycloalkyl, —$(CH_2)_{0-2}$-heteroaryl or —$(CH_2)_{0-2}$-heterocyclyl; wherein heteroaryl has 5-10 ring atoms with 1 to 4 ring atoms selected from N, O, and S, and wherein heterocyclyl has 4-11 ring atoms with 1 to 4 ring atoms selected from N, O, and S; wherein each alkyl, heteroalkyl, phenyl, cycloalkyl, heteroaryl or heterocyclyl is substituted with 0-4 $R^{11}$ groups;
  $R^8$ is H, $C_1$-$C_6$ alkyl, $C_1$-$C_6$ heteroalkyl, phenyl, cycloalkyl, heterocyclyl, cyano, CO—R', or $CO_2$—R', wherein heterocyclyl has 4-11 ring atoms with 1 to 4 ring atoms selected from N, O, and S; each alkyl or heteroalkyl is substituted with 0-4 groups independently selected from halogen and OH, and each phenyl, cycloalkyl, or heterocyclyl is substituted with 0-4 $R^{10}$ groups; or
  $R^7$ and $R^8$ are taken together with the nitrogen and sulfur to which they are attached to form a 4-7 membered heterocycle with 0-2 additional ring heteroatoms selected from O, S, and N, and wherein the heterocycle is substituted with 0-4 $R^{10}$ groups;
  each $R^9$ is independently $C_1$-$C_6$ alkyl, $C_1$-$C_6$ heteroalkyl, $C_3$-$C_7$ cycloalkyl, hydroxy, cyano, or halogen, wherein each alkyl or heteroalkyl is optionally substituted with 1-4 groups independently selected from halogen and OH;
  each $R^{10}$ or $R^{11}$ is independently $C_1$-$C_6$ alkyl, $C_1$-$C_6$ heteroalkyl, phenyl, $C_3$-$C_7$ cycloalkyl, heterocyclyl, $C_1$-$C_6$ alkylene-phenyl, $C_1$-$C_6$ alkylene-$C_3$-$C_7$ cycloalkyl, $C_1$-$C_6$ alkylene-heterocyclyl, hydroxy, cyano, CO—$R^C$, $NR^D{}_2$, or halogen, wherein heterocyclyl has 4-11 ring atoms with 1 to 4 ring atoms selected from N, O, and S; each alkyl or heteroalkyl is optionally substituted with 1-4 groups independently selected from halogen and OH, and wherein each phenyl, cycloalkyl, or heterocyclyl is optionally substituted with 1-4 $R^E$;
  each $R^C$ is independently H, OH, $NR^{12}{}_2$, $C_1$-$C_6$ alkyl, $C_1$-$C_6$ alkoxy, $C_1$-$C_6$ heteroalkyl, wherein each alkyl or heteroalkyl is optionally substituted with 1-4 substituents independently selected from halogen and OH;
  each $R^D$ is independently H, $C_1$-$C_6$ alkyl, CO—$C_1$-$C_6$ alkyl; $CO_2$—$C_1$-$C_6$ alkyl; $SO_w$—$C_1$-$C_6$ alkyl; $C_1$-$C_6$ heteroalkyl, wherein each alkyl or heteroalkyl is optionally substituted with 1-4 substituents independently selected from halogen and OH; or
  two $R^D$ attached to the same nitrogen are taken together with the nitrogen to which they are attached to form a 3-7 membered heterocycle with 0-2 additional ring heteroatoms selected from 0, S, and N, and wherein the heterocycle is optionally substituted with 1-4 substituents independently selected from halogen, $C_1$-$C_6$ alkyl, $C_1$-$C_6$ haloalkyl, $C_1$-$C_6$ alkoxy, and OH; and
  w is 0, 1, or 2.

In some embodiments, provided is a compound of Formula (I)

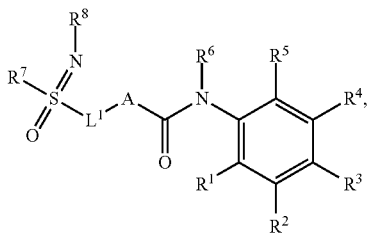

or a pharmaceutically acceptable salt thereof,
wherein
A is an aryl or heteroaryl, wherein heteroaryl has 5-10 ring atoms, 1 to 4 ring atoms selected from N, O, and S, and wherein A is substituted with 0-4 $R^9$ groups;
$L^1$ is —$CR'_2$—, —$CR'_2CR'_2$—, or a bond;
each R' is independently H or $C_1$-$C_6$ alkyl; or two R' together with the carbon or carbons to which they are attached form a 3-6-membered cycloalkyl ring;
each $R^1$, $R^3$ and $R^4$ is independently H, $C_1$-$C_6$ alkyl, $C_1$-$C_6$ haloalkyl, or halogen;
$R^2$ is aryl or heteroaryl, wherein heteroaryl has 5-10 ring atoms, 1 to 4 ring atoms selected from N, O, and S, and $R^2$ is substituted with 0-4 $R^{10}$ groups;
$R^5$ is $NH_2$ or OH;
$R^6$ is H or $C_1$-$C_6$ alkyl;
$R^7$ is $C_1$-$C_6$ alkyl, $C_1$-$C_6$ heteroalkyl, —$(CH_2)_{0-2}$-phenyl, —$(CH_2)_{0-2}$-$C_3$-$C_7$ cycloalkyl, —$(CH_2)_{0-2}$-heteroaryl or —$(CH_2)_{0-2}$-heterocyclyl; wherein heteroaryl has 5-10 ring atoms with 1 to 4 ring atoms selected from N, O, and S, and wherein heterocyclyl has 4-11 ring atoms with 1 to 4 ring atoms selected from N, O, and S; wherein each alkyl, heteroalkyl, phenyl, cycloalkyl, heteroaryl or heterocyclyl is substituted with 0-4 $R^{11}$ groups;
$R^8$ is H, $C_1$-$C_6$ alkyl, $C_1$-$C_6$ heteroalkyl, phenyl, cycloalkyl, heterocyclyl, cyano, CO—R', or $CO_2$—R', wherein heterocyclyl has 4-11 ring atoms with 1 to 4 ring atoms selected from N, O, and S; each alkyl or heteroalkyl is substituted with 0-4 groups independently selected from halogen and OH, and each phenyl, cycloalkyl, or heterocyclyl is substituted with 0-4 $R^{10}$ groups; or
$R^7$ and $R^8$ are taken together with the nitrogen and sulfur to which they are attached to form a 4-7 membered heterocycle with 0-2 additional ring heteroatoms selected from O, S, and N, and wherein the heterocycle is substituted with 0-4 $R^{10}$ groups;
each $R^9$ is independently $C_1$-$C_6$ alkyl, $C_1$-$C_6$ heteroalkyl, $C_3$-$C_7$ cycloalkyl, hydroxy, cyano, or halogen, wherein each alkyl or heteroalkyl is optionally substituted with 1-4 groups independently selected from halogen and OH;
each $R^{10}$ and $R^{11}$ is independently $C_1$-$C_6$ alkyl, $C_1$-$C_6$ alkenyl, $C_1$-$C_6$ heteroalkyl, phenyl, $C_3$-$C_7$ cycloalkyl, heterocyclyl, $C_1$-$C_6$ alkylene-phenyl, $C_1$-$C_6$ alkylene-$C_3$-$C_7$ cycloalkyl, $C_1$-$C_6$ alkylene-heterocyclyl, hydroxy, cyano, CO—$R^C$, $NR^D_2$, or halogen, wherein heterocyclyl has 4-11 ring atoms with 1 to 4 ring atoms selected from N, O, and S; each alkyl or heteroalkyl is optionally substituted with 1-4 groups independently selected from halogen and OH, and wherein each phenyl, cycloalkyl, or heterocyclyl is optionally substituted with 1-4 $R^E$;
each $R^C$ is independently H, OH, $NR^{12}_2$, $C_1$-$C_6$ alkyl, $C_1$-$C_6$ alkoxy, $C_1$-$C_6$ heteroalkyl, wherein each alkyl or heteroalkyl is optionally substituted with 1-4 substituents independently selected from halogen and OH;
each $R^D$ is independently H, $C_1$-$C_6$ alkyl, CO—$C_1$-$C_6$ alkyl; $CO_2$—$C_1$-$C_6$ alkyl; $SO_w$—$C_1$-$C_6$ alkyl; $C_1$-$C_6$ heteroalkyl, wherein each alkyl or heteroalkyl is optionally substituted with 1-4 substituents independently selected from halogen and OH; or
two $R^D$ attached to the same nitrogen are taken together with the nitrogen to which they are attached to form a 3-7 membered heterocycle with 0-2 additional ring heteroatoms selected from 0, S, and N, and wherein the heterocycle is optionally substituted with 1-4 substituents independently selected from halogen, $C_1$-$C_6$ alkyl, $C_1$-$C_6$ haloalkyl, $C_1$-$C_6$ alkoxy, and OH;
each $R^E$ is independently H, halo, OH, O—$C_1$-$C_6$ alkyl, —$C_1$-$C_6$ alkyl, —$C_1$-$C_6$ haloalkyl;
each $R^{12}$ is independently H or $C_1$-$C_6$ alkyl; and
w is 0, 1, or 2.

As generally defined herein, A is an optionally substituted aryl or heteroaryl. In some embodiments, A is an aryl or heteroaryl, wherein heteroaryl has 5-10 ring atoms, 1 to 4 ring atoms selected from N, O, and S, and wherein A is substituted with 0-4 $R^9$ groups, wherein $R^9$ is as defined herein. In some embodiments of a compound of Formula (I), A is phenyl or heteroaryl, wherein heteroaryl has 5, 6 or 9 ring atoms, 1 to 4 ring atoms selected from N, O, and S, and wherein A is substituted with 0-4 $R^9$ groups.

In some embodiments, A is phenyl, thiazole, thiophene, pyridine, pyridazine, benzofuran, benzthiophene, thienopyridine (e.g., thieno[3,2-b]pyridine, thieno[3,2-c]pyridine, thieno[2,3-b]pyridine) or furopyridine (e.g., furo[3,2-b]pyridine, furo[3,2-c]pyridine, furo[2,3-b]pyridine), each substituted with 0-9 $R^9$ groups.

In some embodiments, A is phenyl, benzofuran, or benzthiophene, each substituted with 0-9 $R^9$ groups.

In some embodiments, A is phenyl substituted with 0-9 $R^9$ groups.

In some embodiments, A is benzofuran substituted with 0-9 $R^9$ groups.

In some embodiments, A is benzthiophene substituted with 0-9 $R^9$ groups.

In some embodiments, A is thiazole substituted with 0-9 $R^9$ groups. In some embodiments, A is thiophene substituted with 0-9 $R^9$ groups. In some embodiments, A is pyridine substituted with 0-9 $R^9$ groups. In some embodiments, A is pyridazine substituted with 0-9 $R^9$ groups. In some embodiments, A is thienopyridine (e.g., thieno[3,2-b]pyridine, thieno[3,2-c]pyridine, thieno[2,3-b]pyridine) substituted with 0-9 $R^9$ groups. In some embodiments, A is furopyridine (e.g., furo[3,2-b]pyridine, furo[3,2-c]pyridine, furo[2,3-b]pyridine) substituted with 0-9 $R^9$ groups.

In some embodiments, A is selected from:

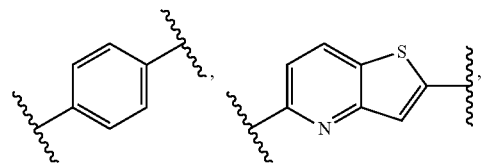

-continued

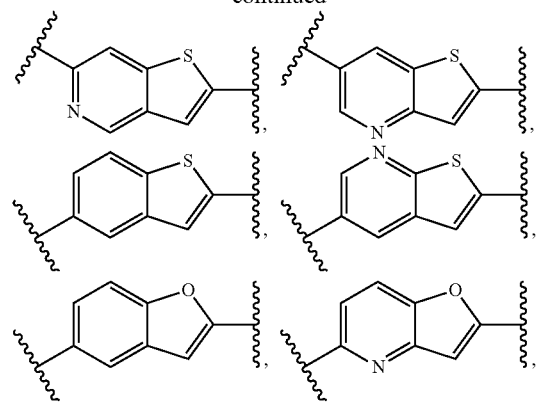

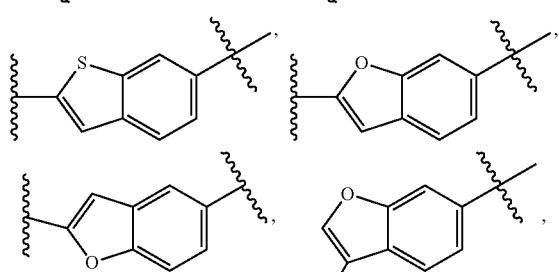

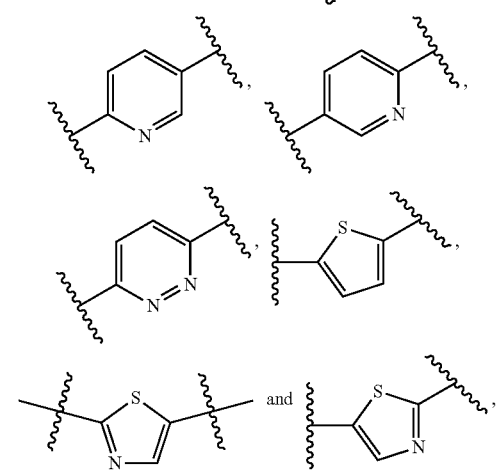

each substituted with 0-9 $R^9$ groups, wherein the left attachment point

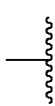

represents the attachment point to $L^1$ and the right attachment point

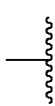

represents the attachment point to the carbonyl.

In some embodiments, A is selected from:

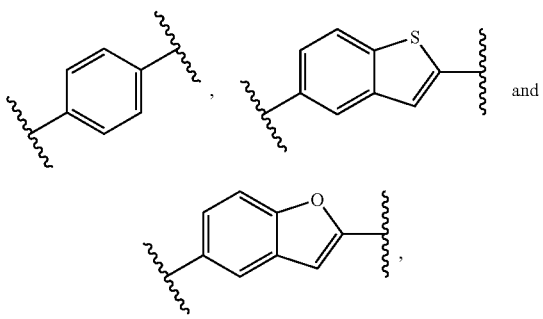
and

each substituted with 0-9 $R^9$ groups, wherein the left attachment point

represents the attachment point to $L^1$ and the right attachment point

represents the attachment point to the carbonyl.

In some embodiments of a compound of Formula (I), A is phenyl, thiazole, thiophene, pyridine, pyridazine, benzofuran, or benzthiophene;

e.g., wherein A is

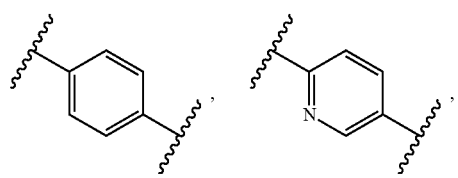

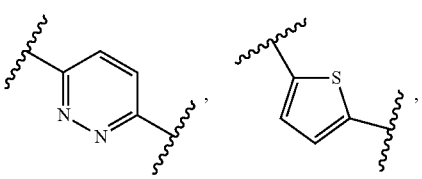

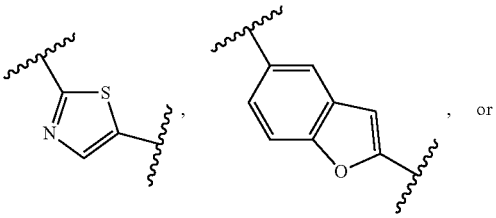
, or

-continued

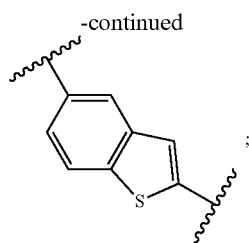

and A is substituted with 0-4 $R^9$ groups.

In some embodiments, A is

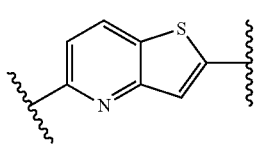 [SMILES: *c1ccc2sc(*)cc2n1]

substituted with 0-9 $R^9$ groups, wherein the left attachment point

represents the attachment point to $L^1$ and the right attachment point

represents the attachment point to the carbonyl.

In some embodiments, A is

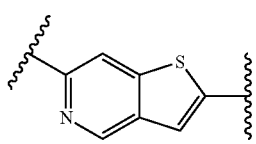 [SMILES: *c1cc2sc(*)cc2cn1]

substituted with 0-9 $R^9$ groups, wherein the left attachment point

represents the attachment point to $L^1$ and the right attachment point

represents the attachment point to the carbonyl.

In some embodiments, A is

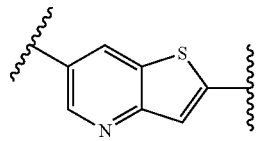 [SMILES: *c1cnc2cc(*)sc2c1]

substituted with 0-9 $R^9$ groups, wherein the left attachment point

represents the attachment point to $L^1$ and the right attachment point

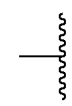

represents the attachment point to the carbonyl.

In some embodiments, A is

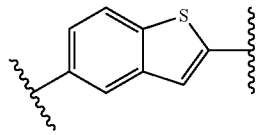 [SMILES: *c1ccc2sc(*)cc2c1]

substituted with 0-9 $R^9$ groups, wherein the left attachment point

represents the attachment point to $L^1$ and the right attachment point

represents the attachment point to the carbonyl.

In some embodiments, A is

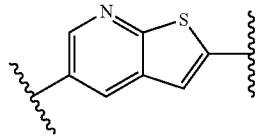 [SMILES: *c1cnc2sc(*)cc2c1]

substituted with 0-9 $R^9$ groups, wherein the left attachment point

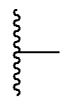

represents the attachment point to $L^1$ and the right attachment point

represents the attachment point to the carbonyl.

In some embodiments, A is

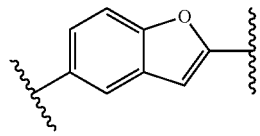 [SMILES: *c1ccc2oc(*)cc2c1]

substituted with 0-9 $R^9$ groups, wherein the left attachment point

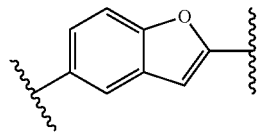

represents the attachment point to $L^1$ and the right attachment point

represents the attachment point to the carbonyl.

In some embodiments, A is

substituted with 0-9 $R^9$ groups, wherein the left attachment point

represents the attachment point to $L^1$ and the right attachment point

represents the attachment point to the carbonyl.

In some embodiments, A is

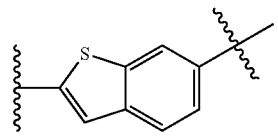

substituted with 0-9 $R^9$ groups, wherein the left attachment point

represents the attachment point to $L^1$ and the right attachment point

represents the attachment point to the carbonyl.

In some embodiments, A is

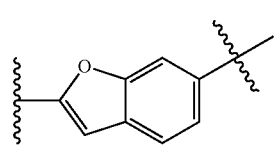 [SMILES: *c1ccc2cc(*)oc2c1]

substituted with 0-9 $R^9$ groups, wherein the left attachment point

represents the attachment point to $L^1$ and the right attachment point

represents the attachment point to the carbonyl.

In some embodiments, A is

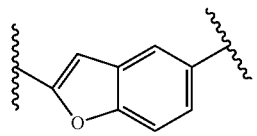 [SMILES: *c1ccc2oc(*)cc2c1]

substituted with 0-9 R⁹ groups, wherein the left attachment point

represents the attachment point to $L^1$ and the right attachment point

represents the attachment point to the carbonyl.

In some embodiments, A is

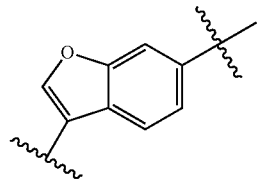 [SMILES: *c1ccc2c(*)coc2c1]

substituted with 0-9 R⁹ groups, wherein the left attachment point

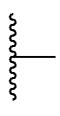

represents the attachment point to $L^1$ and the right attachment point

represents the attachment point to the carbonyl.

In some embodiments, A is

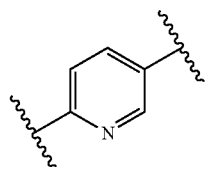 [SMILES: *c1ccc(*)nc1]

substituted with 0-9 R⁹ groups, wherein the left attachment point

represents the attachment point to $L^1$ and the right attachment point

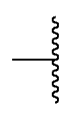

represents the attachment point to the carbonyl.

In some embodiments, A is

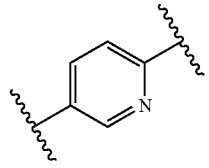 [SMILES: *c1ccc(*)nc1]

substituted with 0-9 R⁹ groups, wherein the left attachment point

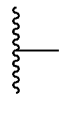

represents the attachment point to $L^1$ and the right attachment point

represents the attachment point to the carbonyl.

In some embodiments, A is

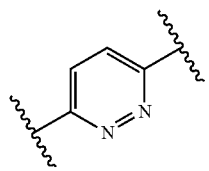

substituted with 0-9 $R^9$ groups, wherein the left attachment point

represents the attachment point to $L^1$ and the right attachment point

represents the attachment point to the carbonyl.

In some embodiments, A is

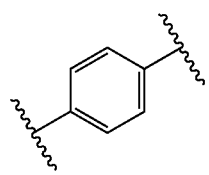 [SMILES: *c1ccc(*)cc1]

substituted with 0-9 $R^9$ groups, wherein the left attachment point

represents the attachment point to $L^1$ and the right attachment point

represents the attachment point to the carbonyl.

In some embodiments, A is

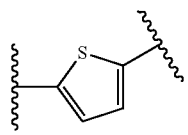 [SMILES: *c1ccc(*)s1]

substituted with 0-9 $R^9$ groups, wherein the left attachment point

represents the attachment point to $L^1$ and the right attachment point

represents the attachment point to the carbonyl.

In some embodiments, A is

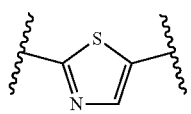 [SMILES: *c1cnc(*)s1]

substituted with 0-9 $R^9$ groups, wherein the left attachment point

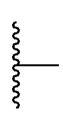

represents the attachment point to $L^1$ and the right attachment point

represents the attachment point to the carbonyl.

In some embodiments, A is

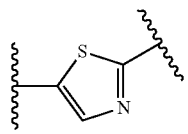 [SMILES: *c1cnc(*)s1]

substituted with 0-9 $R^9$ groups, wherein the left attachment point

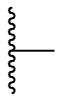

represents the attachment point to $L^1$ and the right attachment point

represents the attachment point to the carbonyl.

In some embodiments of a compound of Formula (I), A is not substituted with any $R^9$ groups.

As generally defined herein, $L^1$ is —CR'$_2$—, —CR'$_2$CR'$_2$—, or a bond, wherein R' is as defined herein.

In some embodiments of a compound of Formula (I), $L^1$ is a bond.

In some embodiments, $L^1$ is —CR'$_2$—. In some embodiments, $L^1$ is —CR'$_2$CR'$_2$—. In some embodiments, $L^1$ is selected from a bond, —CH$_2$— and

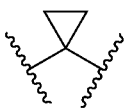

In some embodiments, $L^1$ is selected from a bond and —CH$_2$—. In some embodiments, $L^1$ is selected from a bond and

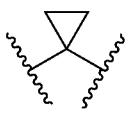

In some embodiments, $L^1$ is —CH$_2$—. In some embodiments, $L^1$ is

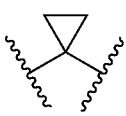

As generally defined herein, each $R^1$ is independently H, $C_1$-$C_6$ alkyl, $C_1$-$C_6$ haloalkyl, or halogen. In some embodiments of a compound of Formula (I), $R^1$ is H. In some embodiments, $R^1$ is selected from H, -Me, —CF$_3$, —Cl and —F.

As generally defined herein, each $R^3$ is independently H, $C_1$-$C_6$ alkyl, $C_1$-$C_6$ haloalkyl, or halogen. In some embodiments of a compound of Formula (I), $R^3$ is H. In some embodiments, $R^3$ is selected from H, -Me, —CF$_3$, —Cl and —F.

As generally defined herein, each $R^4$ is independently H, $C_1$-$C_6$ alkyl, $C_1$-$C_6$ haloalkyl, or halogen. In some embodiments of a compound of Formula (I), $R^4$ is H. In some embodiments, $R^4$ is selected from H, -Me, —CF$_3$, —Cl and —F.

In some embodiments of a compound of Formula (I), $R^1$ is H, or $R^3$ is H, or $R^4$ is H, or each of $R^1$, $R^3$ and $R^4$ is H.

As generally defined herein, $R^5$ is —NH$_2$ or —OH. In some embodiments of a compound of Formula (I), $R^5$ is —NH$_2$. In some embodiments, $R^5$ is —OH.

As generally defined herein, $R^6$ is H or $C_1$-$C_6$ alkyl. In some embodiments of a compound of Formula (I), $R^6$ is H. In some embodiments, $R^6$ is selected from H and -Me. In some embodiments, $R^6$ is Me.

As generally defined herein, each $R^2$ is independently aryl or heteroaryl, wherein the aryl and heteroaryl are optionally substituted. In some embodiments, $R^2$ is aryl or heteroaryl, wherein heteroaryl has 5-10 ring atoms, 1 to 4 ring atoms selected from N, O, and S, and $R^2$ is substituted with 0-4 $R^{10}$ groups (e.g., 0, 1, 2, 3 or 4 $R^{10}$ groups), wherein $R^{10}$ is as defined herein.

In some embodiments of a compound of Formula (I), $R^2$ is phenyl or monocyclic heteroaryl, wherein heteroaryl has 5 or 6 ring atoms with 1 to 2 ring atoms selected from N, O, and S, and $R^2$ is substituted with 0-4 $R^{10}$ groups (e.g., 0, 1, 2, 3 or 4 $R^{10}$ groups), wherein $R^{10}$ is as defined herein. In some embodiments, $R^2$ is phenyl substituted with 0-4 $R^{10}$ groups (e.g., 0, 1, 2, 3 or 4 $R^{10}$ groups), wherein $R^{10}$ is as defined herein. In some embodiments, $R^2$ is monocyclic heteroaryl, wherein heteroaryl has 5 or 6 ring atoms with 1 to 2 ring atoms selected from N, O, and S, and $R^2$ is substituted with 0-4 $R^{10}$ groups (e.g., 0, 1, 2, 3 or 4 $R^{10}$ groups), wherein $R^{10}$ is as defined herein. In some embodiments of a compound of Formula (I), $R^2$ is monocyclic heteroaryl, wherein heteroaryl is pyridine, pyrimidine, pyridazine, pyrazine, thiazole, or thiophene, (e.g., wherein $R^2$ is 2-thiophenyl), each $R^2$ substituted with 0-4 $R^{10}$ groups (e.g., 0, 1, 2, 3 or 4 $R^{10}$ groups), wherein $R^{10}$ is as defined herein. In some embodiments, $R^2$ is selected from phenyl, pyridine, pyrimidine, pyridazine, pyrazine, thiazole and thiophene, each substituted with 0-4 $R^{10}$ groups (e.g., 0, 1, 2, 3 or 4 $R^{10}$ groups).

In some embodiments, $R^2$ is selected from phenyl, 2-pyridine, 3-pyridine, 4-pyridine, 2-pyrimidine, 4-pyridine, 3-pyridazine, pyrazine, 2-thiazole, 5-thiazole, 2-thiophene and 3-thiophene, each substituted with 0-4 $R^{10}$ groups (e.g., 0, 1, 2, 3 or 4 $R^{10}$ groups), wherein $R^{10}$ is as defined herein.

In some embodiments, $R^2$ is selected from phenyl, 2-pyridine, 3-pyridine, 4-pyridine, 2-pyrimidine, 4-pyridine, 3-pyridazine, 5-thiazole, 2-thiophene and 3-thiophene, each substituted with 0-4 $R^{10}$ groups (e.g., 0, 1, 2, 3 or 4 $R^{10}$ groups), wherein $R^{10}$ is as defined herein.

In some embodiments, $R^2$ is selected from phenyl and thiophene, each substituted with 0-4 $R^{10}$ groups (e.g., 0, 1, 2, 3 or 4 $R^{10}$ groups), wherein $R^{10}$ is as defined herein.

In some embodiments, $R^2$ is selected from phenyl and 2-thiophene, each substituted with 0-4 $R^{10}$ groups (e.g., 0, 1, 2, 3 or 4 $R^{10}$ groups), wherein $R^{10}$ is as defined herein.

In some embodiments, $R^2$ is thiophene substituted with 0-4 $R^{10}$ groups (e.g., 0, 1, 2, 3 or 4 $R^{10}$ groups), wherein $R^{10}$ is as defined herein.

In some embodiments, $R^2$ is 2-thiophene substituted with 0-4 $R^{10}$ groups (e.g., 0, 1, 2, 3 or 4 $R^{10}$ groups), wherein $R^{10}$ is as defined herein.

In some embodiments, $R^2$ is unsubstituted. In some embodiments, $R^2$ is substituted with 1 $R^{10}$, wherein $R^{10}$ is as defined herein. In some embodiments, $R^2$ is substituted with 2 $R^{10}$, wherein $R^{10}$ is as defined herein. In some embodiments, $R^2$ is substituted with 3 $R^{10}$, wherein $R^{10}$ is as defined herein. In some embodiments, $R^2$ is substituted with 4 $R^{10}$, wherein $R^1$ is as defined herein.

In some embodiments of a compound of Formula (I), $R^2$ is selected from the group consisting of
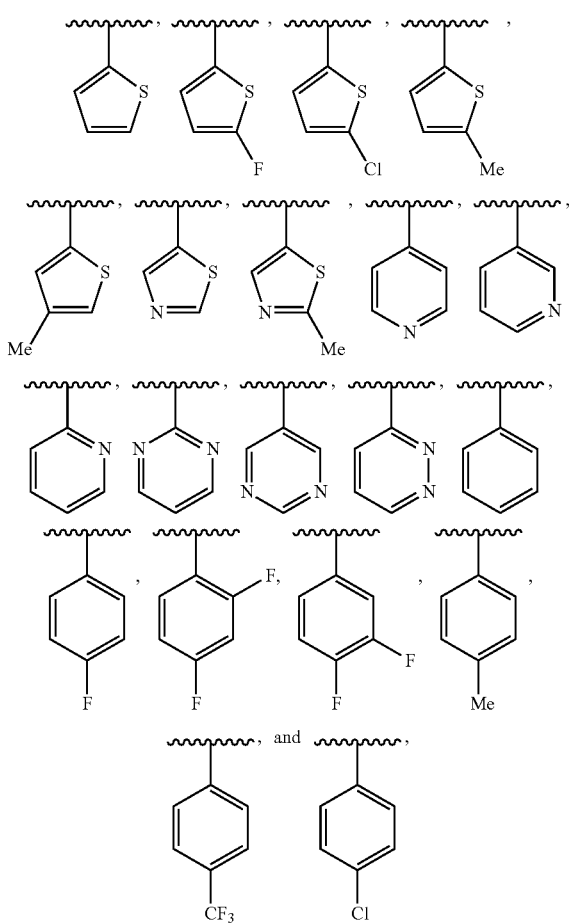
e.g., wherein $R^2$ is
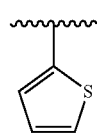
In some embodiments, $R^2$ is selected from the group consisting of:
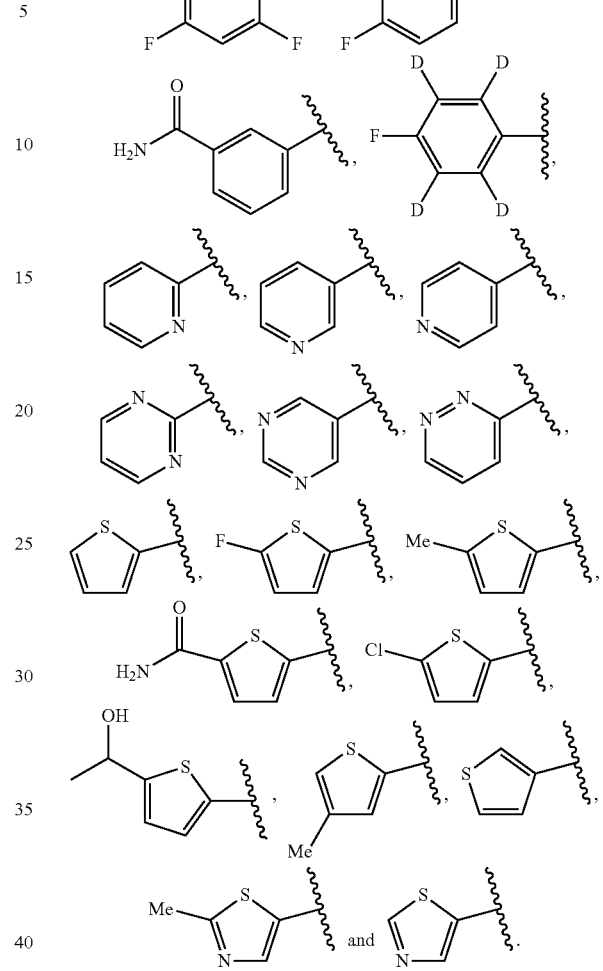
In some embodiments, $R^2$ is selected from the group consisting of:
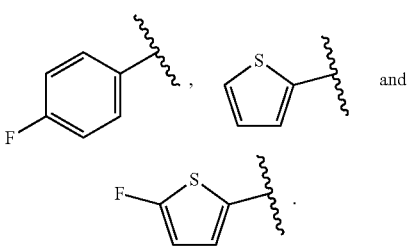
In some embodiments, $R^2$ is
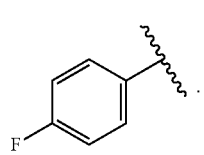

In some embodiments, R² is
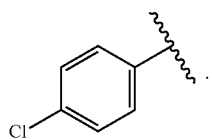 [SMILES: *c1ccc(Cl)cc1]
In some embodiments, R² is
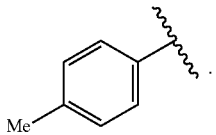 [SMILES: *c1ccc(C)cc1]
In some embodiments, R² is
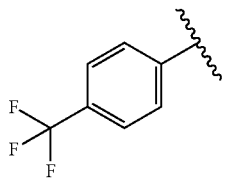
In some embodiments, R² is
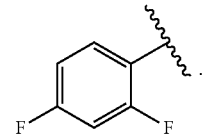
In some embodiments, R² is
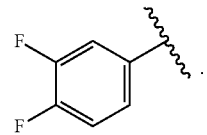
In some embodiments, R² is
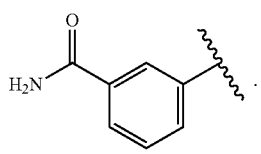
In some embodiments, R² is
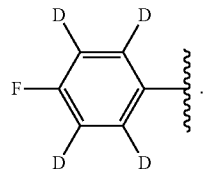
In some embodiments, R² is
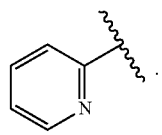
In some embodiments, R² is
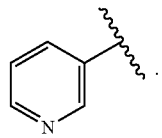
In some embodiments, R² is
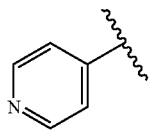
In some embodiments, R² is
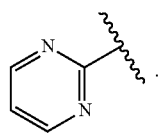
In some embodiments, R² is
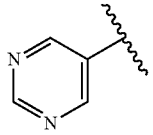
In some embodiments, R² is
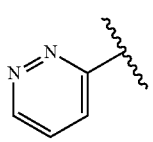

In some embodiments, $R^2$ is

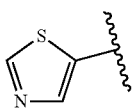

In some embodiments, $R^2$ is

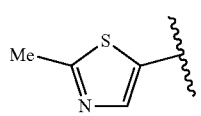

In some embodiments, $R^2$ is

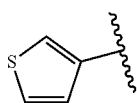

In some embodiments, $R^2$ is

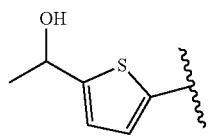

In some embodiments, $R^2$ is

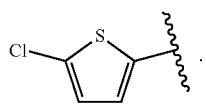

In some embodiments, $R^2$ is

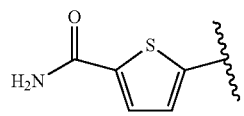

In some embodiments, $R^2$ is

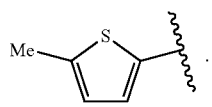

In some embodiments, $R^2$ is

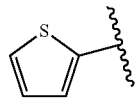

In some embodiments, $R^2$ is

F—[thiophene ring]

As generally defined herein, $R^7$ is $C_1$-$C_6$ alkyl, $C_1$-$C_6$ heteroalkyl, —(CH$_2$)$_{0-2}$-phenyl, —(CH$_2$)$_{0-2}$—$C_3$-$C_7$ cycloalkyl, —(CH$_2$)$_{0-2}$-heteroaryl or —(CH$_2$)$_{0-2}$-heterocyclyl, wherein each alkyl, heteroalkyl, phenyl, cycloalkyl, heteroaryl or heterocyclyl is optionally substituted or $R^7$ and $R^8$ are taken together with the nitrogen and sulfur to which they are attached to form a 4-7 membered heterocycle with 0-2 additional ring heteroatoms selected from O, S, and N, and wherein the heterocycle is optionally substituted.

In some embodiments, $R^7$ is $C_1$-$C_6$ alkyl, $C_1$-$C_6$ heteroalkyl, —(CH$_2$)$_{0-2}$-phenyl, —(CH$_2$)$_{0-2}$—$C_3$-$C_7$ cycloalkyl, —(CH$_2$)$_{0-2}$-heteroaryl or —(CH$_2$)$_{0-2}$-heterocyclyl, wherein each alkyl, heteroalkyl, phenyl, cycloalkyl, heteroaryl or heterocyclyl is optionally substituted.

In some embodiments, $R^7$ is $C_1$-$C_6$ alkyl, $C_1$-$C_6$ heteroalkyl, —(CH$_2$)$_{0-2}$-phenyl, —(CH$_2$)$_{0-2}$—$C_3$-$C_7$ cycloalkyl, —(CH$_2$)$_{0-2}$-heteroaryl or —(CH$_2$)$_{0-2}$-heterocyclyl; wherein heteroaryl has 5-10 ring atoms with 1 to 4 ring atoms selected from N, O, and S, and wherein heterocyclyl has 4-11 ring atoms with 1 to 4 ring atoms selected from N, O, and S; wherein each alkyl, heteroalkyl, phenyl, cycloalkyl, heteroaryl or heterocyclyl is substituted with 0-4 $R^{11}$ groups (i.e., 0, 1, 2, 3 or 4 $R^{11}$ groups) or $R^7$ and $R^8$ are taken together with the nitrogen and sulfur to which they are attached to form a 4-7 membered heterocycle with 0-2 additional ring heteroatoms selected from O, S, and N, and wherein the heterocycle is substituted with 0-4 $R^{10}$ groups, wherein $R^{10}$ and $R^{11}$ are as defined herein.

In some embodiments, $R^7$ is $C_1$-$C_6$ alkyl, $C_1$-$C_6$ heteroalkyl, —(CH$_2$)$_{0-2}$-phenyl, —(CH$_2$)$_{0-2}$—$C_3$-$C_7$ cycloalkyl, —(CH$_2$)$_{0-2}$-heteroaryl or —(CH$_2$)$_{0-2}$-heterocyclyl; wherein heteroaryl has 5-10 ring atoms with 1 to 4 ring atoms selected from N, O, and S, and wherein heterocyclyl has 4-11 ring atoms with 1 to 4 ring atoms selected from N, O, and S; wherein each alkyl, heteroalkyl, phenyl, cycloalkyl, heteroaryl or heterocyclyl is substituted with 0-4 $R^{11}$ groups (i.e., 0, 1, 2, 3 or 4 $R^{11}$ groups), wherein $R^{11}$ is as defined herein.

In some embodiments, $R^7$ is $C_1$-$C_6$ alkyl, $C_1$-$C_6$ heteroalkyl, $C_3$-$C_7$ cycloalkyl, phenyl, or a monocyclic heteroaryl, wherein the heteroaryl has 5 or 6 ring atoms with 1 to 2 ring atoms selected from N, O, and S; wherein each alkyl, heteroalkyl, phenyl, cycloalkyl and heteroaryl is substituted with 0-4 $R^{11}$ groups (i.e., 0, 1, 2, 3 or 4 $R^{11}$ groups); or $R^7$ and $R^8$ are taken together with the nitrogen and sulfur to which they are attached to form a 4-7 membered heterocycle with 0-2 additional ring heteroatoms selected from O, S, and N, wherein the heterocycle is substituted with 0-4 $R^{10}$ groups, wherein $R^{10}$ and $R^{11}$ are as defined herein.

In some embodiments, $R^7$ is $C_1$-$C_6$ alkyl, $C_1$-$C_6$ heteroalkyl, $C_3$-$C_7$ cycloalkyl, phenyl, or a monocyclic heteroaryl, wherein the heteroaryl has 5 or 6 ring atoms with 1 to 2 ring atoms selected from N, O, and S; wherein each alkyl, heteroalkyl, phenyl, cycloalkyl and heteroaryl is substituted with 0-4 $R^{11}$ groups (i.e., 0, 1, 2, 3 or 4 $R^{11}$ groups); wherein $R^{11}$ is as defined herein.

In some embodiments, $R^7$ is $C_1$-$C_6$ alkyl, $C_1$-$C_6$ haloalkyl, $C_1$-$C_6$ heteroalkyl, $C_3$-$C_7$ cycloalkyl, phenyl, or a monocyclic heteroaryl, wherein the heteroaryl has 5 or 6 ring atoms with 1 to 2 ring atoms being N; wherein each alkyl, heteroalkyl, phenyl, cycloalkyl and heteroaryl is substituted with 0-4 $R^{11}$ groups (i.e., 0, 1, 2, 3 or 4 $R^{11}$ groups); or $R^7$ and $R^8$ are taken together with the nitrogen and sulfur to which they are attached to form a 4-7 membered heterocycle with 0 additional ring heteroatoms, wherein the heterocycle is substituted with 0-4 $R^{10}$ groups, wherein $R^{10}$ and $R^{11}$ are as defined herein.

In some embodiments, $R^7$ is $C_1$-$C_6$ alkyl, $C_1$-$C_6$ haloalkyl, $C_1$-$C_6$ heteroalkyl, $C_3$-$C_7$ cycloalkyl, phenyl, or a monocyclic heteroaryl, wherein the heteroaryl has 5 or 6 ring atoms with 1 to 2 ring atoms being N; wherein each alkyl, heteroalkyl, phenyl, cycloalkyl and heteroaryl is substituted with 0-4 $R^{11}$ groups (i.e., 0, 1, 2, 3 or 4 $R^{11}$ groups), wherein $R^{11}$ is as defined herein.

In some embodiments, $R^7$ is selected from -Me, -Et, —$CF_3$, $CH_2CH_2OMe$, phenyl, imidazolyl, pyridinyl, pyrimidinyl, pyrazinyl, pyridazinyl and pyridinon-yl; each of which is substituted with 0-4 $R^{11}$ groups (i.e., 0, 1, 2, 3 or 4 $R^{11}$ groups); or $R^7$ and $R^8$ are taken together with the nitrogen and sulfur to which they are attached to form a 5 or 6 membered heterocycle with 0 additional ring heteroatoms, wherein the heterocycle is substituted with or 1 instances of methyl or phenyl, wherein $R^{10}$ and $R^{11}$ are as defined herein.

In some embodiments, $R^7$ is selected from -Me, -Et, —$CF_3$, $CH_2CH_2OMe$, phenyl, imidazolyl, pyridinyl, pyrimidinyl, pyrazinyl, pyridazinyl and pyridinon-yl; each of which is substituted with 0-4 $R^{11}$ groups (i.e., 0, 1, 2, 3 or 4 $R^{11}$ groups); wherein $R^{11}$ is as defined herein.

In some embodiments, $R^7$ is $C_1$-$C_6$ alkyl, $C_1$-$C_6$ haloalkyl, $C_1$-$C_6$ heteroalkyl, $C_3$-$C_7$ cycloalkyl, phenyl, or 6-membered heteroaryl wherein heteroaryl has 1 or 2 nitrogen ring atoms; or $R^7$ and $R^8$ are taken together with the nitrogen and sulfur to which they are attached to form a 4-7 membered heterocycle with 0-2 additional ring heteroatoms selected from O, S, and N; and $R^7$ is substituted with 0-4 $R^{11}$ groups (i.e., 0, 1, 2, 3 or 4 $R^{11}$ groups), wherein $R^{11}$ is as defined herein.

In some embodiments, $R^7$ is $C_1$-$C_6$ alkyl, $C_1$-$C_6$ haloalkyl, $C_1$-$C_6$ heteroalkyl, $C_3$-$C_7$ cycloalkyl, phenyl, or 6-membered heteroaryl wherein heteroaryl has 1 or 2 nitrogen ring atoms, and $R^7$ is substituted with 0-4 $R^{11}$ groups (i.e., 0, 1, 2, 3 or 4 $R^{11}$ groups), wherein $R^{11}$ is as defined herein.

In some embodiments of a compound of Formula (I), $R^7$ is $C_1$-$C_6$ alkyl, $C_1$-$C_6$ haloalkyl, $C_1$-$C_6$ heteroalkyl, $C_3$-$C_7$ cycloalkyl, phenyl, or 6-membered heteroaryl wherein heteroaryl has 1 or 2 nitrogen ring atoms; or $R^7$ and $R^8$ are taken together with the nitrogen and sulfur to which they are attached to form a 4-7 membered heterocycle with 0-2 additional ring heteroatoms selected from O, S, and N; and $R^7$ is substituted with 0-4 $R^{11}$ groups (i.e., 0, 1, 2, 3 or 4 $R^{11}$ groups), wherein $R^{11}$ is as defined herein.

In some embodiments of a compound of Formula (I), $R^7$ is $C_1$-$C_6$ alkyl, $C_1$-$C_6$ haloalkyl, $C_1$-$C_6$ heteroalkyl, $C_3$-$C_7$ cycloalkyl, phenyl, or 6-membered heteroaryl wherein heteroaryl has 1 or 2 nitrogen ring atoms; and $R^7$ is substituted with 0-4 $R^{11}$ groups (i.e., 0, 1, 2, 3 or 4 $R^{11}$ groups), wherein $R^{11}$ is as defined herein.

In some embodiments, $R^7$ is not substituted (i.e., is substituted with 0 $R^{11}$ groups). In some embodiments, $R^7$ is substituted with 1 $R^{11}$ group. In some embodiments, $R^7$ is substituted with 2 $R^{11}$ groups. In some embodiments, $R^7$ is substituted with 3 $R^{11}$ groups. In some embodiments, $R^7$ is substituted with 4 $R^{11}$ groups. $R^{11}$ is as defined herein.

In some embodiments, $R^7$ is selected from -Me, -Et, —$CF_3$, —$CH_2CH_2OMe$,

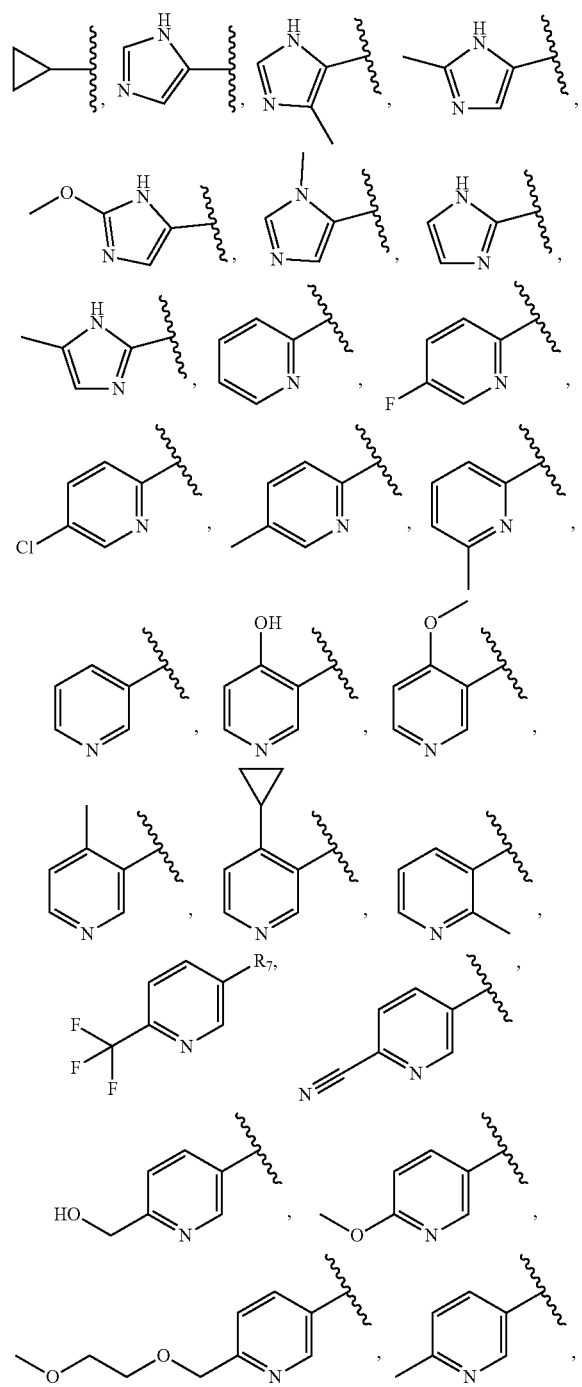

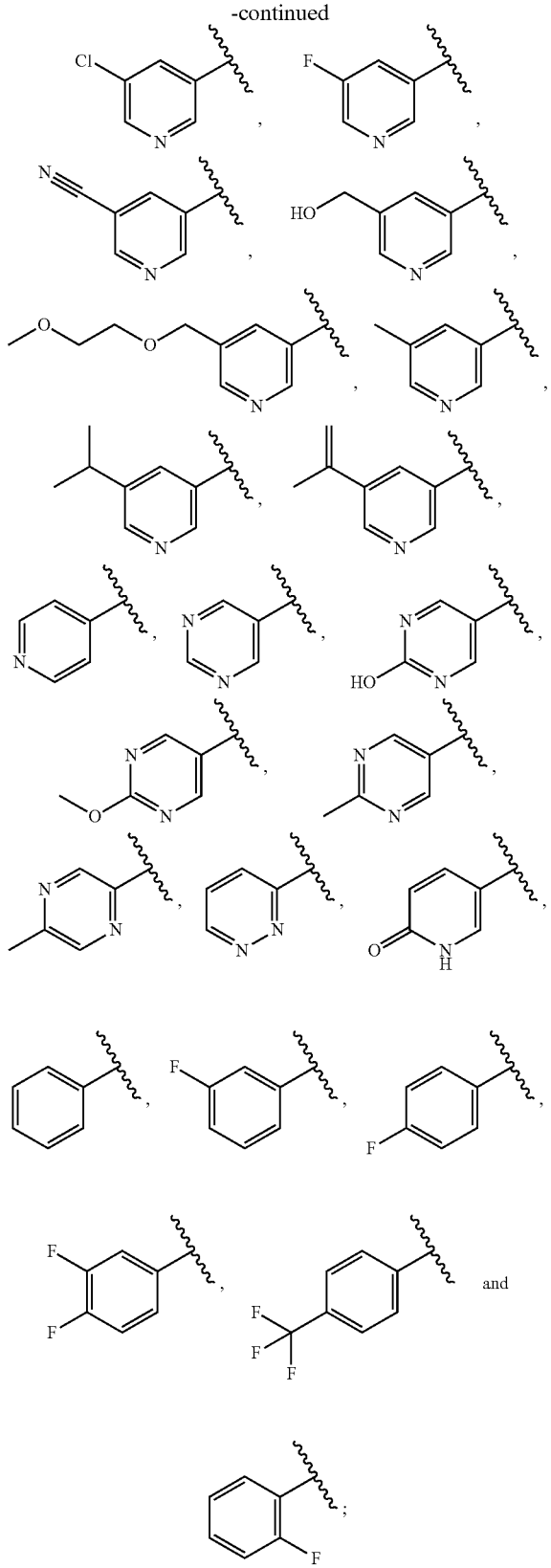
or
R[7] and R[8] are taken together with the atoms to which they are attached to form:
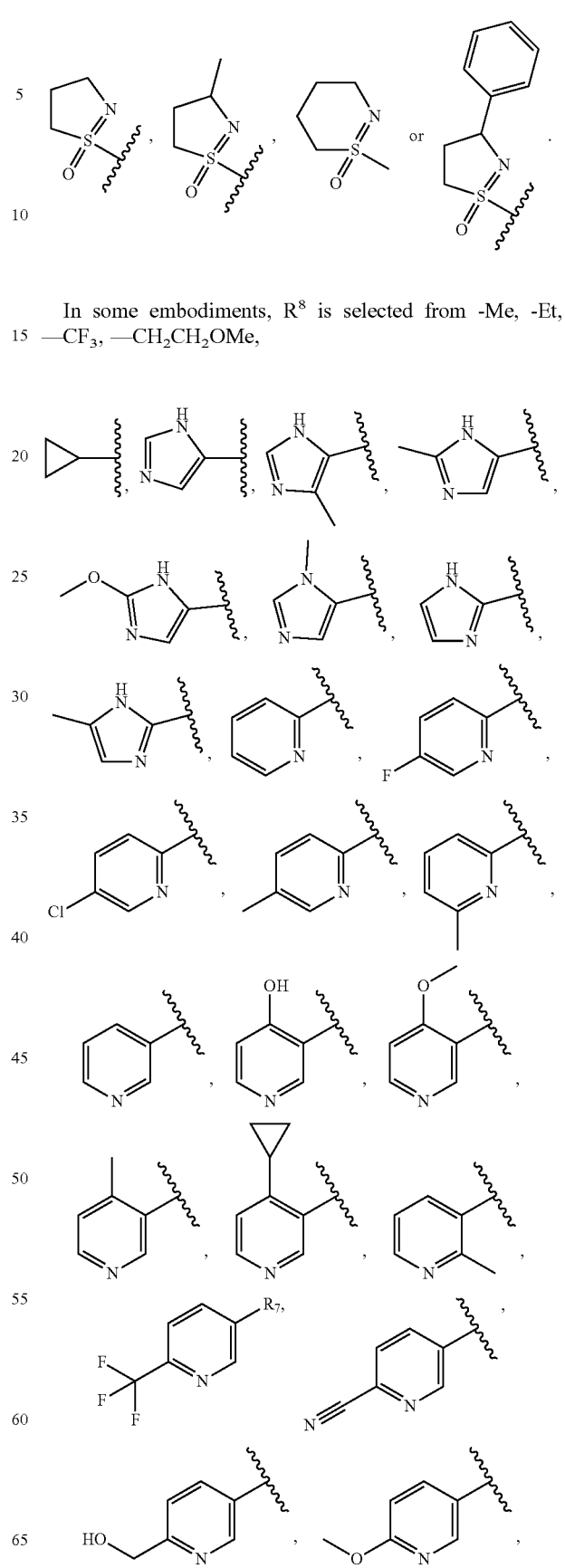
In some embodiments, R[8] is selected from -Me, -Et, —CF$_3$, —CH$_2$CH$_2$OMe,

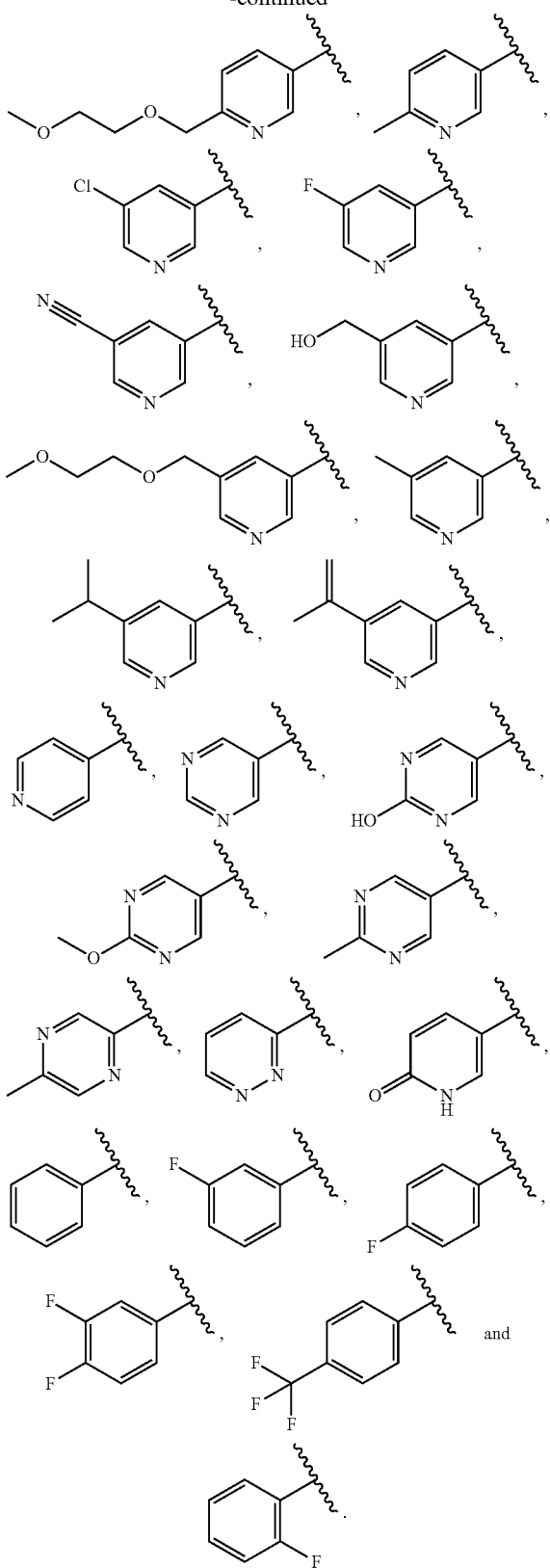

In some embodiments of a compound of Formula (I), $R^7$ is selected from the group consisting of Me, Ph, $CF_3$, $-CH_2CH_2OCH_3$, cyclopropyl,

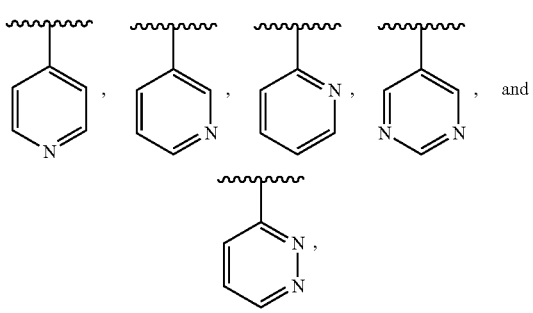

e.g., wherein $R^7$ is Me.

In some embodiments, $R^7$ is Me or cyclopropyl.

In some embodiments of a compound of Formula (I), $R^7$ is Me. In some embodiments, $R^7$ is -Et. In some embodiments, $R^7$ is $-CF_3$. In some embodiments, $R^7$ is $-CH_2CH_2OMe$. In some embodiments, $R^7$ is

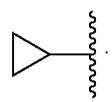

In some embodiments, $R^7$ is

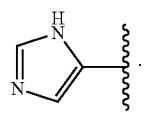

In some embodiments, $R^7$ is

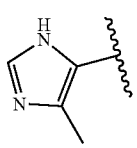

In some embodiments, $R^7$ is

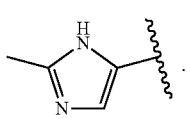

In some embodiments, $R^7$ is

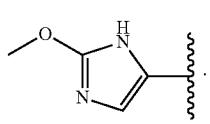

In some embodiments, R⁷ is
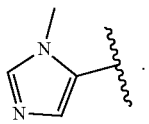 [SMILES: *c1cncn1C]
In some R⁷ is
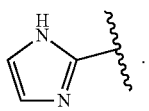 [SMILES: *c1ncc[nH]1]
In some embodiments, R⁷ is
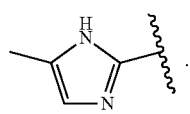 [SMILES: *c1ncc(C)[nH]1]
In some embodiments, R⁷ is
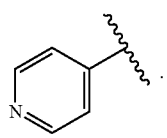
In some embodiments, R⁷ is
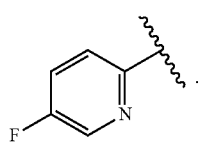
In some embodiments, R⁷ is
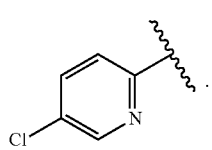 [SMILES: *c1ccc(Cl)cn1]
In some embodiments, R⁷ is
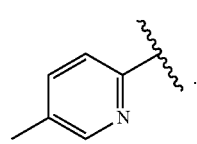 [SMILES: *c1ccc(C)cn1]
In some embodiments R⁷ is
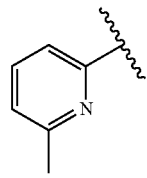
In some embodiments, R⁷ is
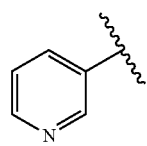
In some embodiments, R⁷ is
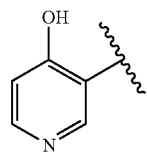
In some embodiments, R⁷ is
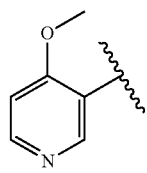
In some embodiments, R⁷ is
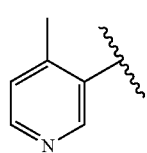
In some embodiments, R⁷ is
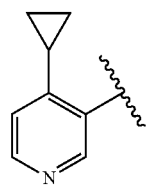

In some embodiments, R⁷ is
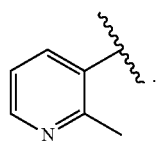 [SMILES: *c1cccnc1C]
In some embodiments, R⁷ is
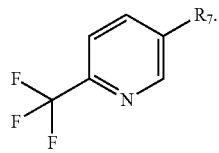
in some embodiments, R⁷ is
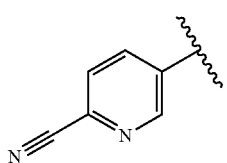
In some embodiments, R⁷ is
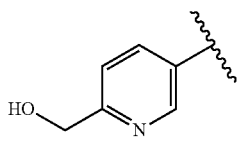
In some embodiments, R⁷ is
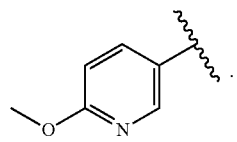 [SMILES: *c1ccc(OC)nc1]
In some embodiments, R⁷ is
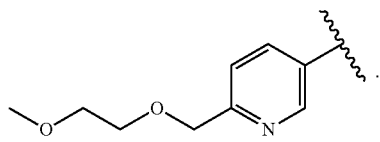 [SMILES: *c1ccc(COCCOC)nc1]
In some embodiments, R⁷ is
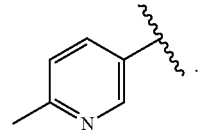 [SMILES: *c1ccc(C)nc1]
In some embodiments, R⁷ is
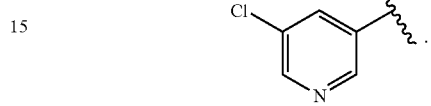
In some embodiments, R⁷ is
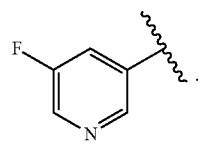
In some embodiments, R⁷ is
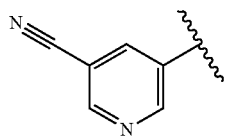
In some embodiments, R⁷ is
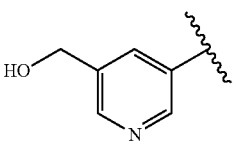
In some embodiments, R⁷ is
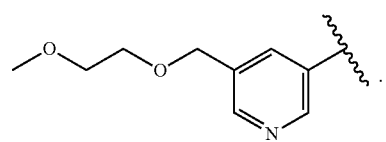
In some embodiments, R⁷ is
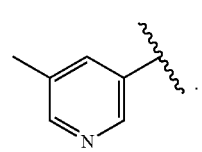

In some embodiments, R⁷ is
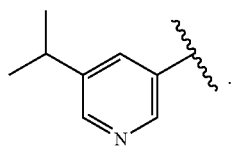 [SMILES: *c1cncc(C(C)C)c1]
In some embodiments, R⁷ is
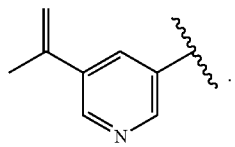 [SMILES: *c1cncc(C(=C)C)c1]
In some embodiments, R⁷ is
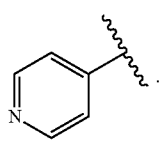
In some embodiments, R⁷ is
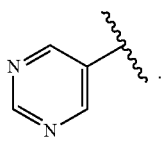
In some embodiments, R⁷ is
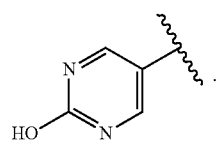
In some embodiments, R⁷ is
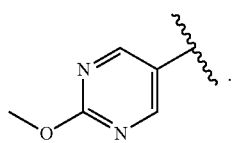 [SMILES: *c1cnc(OC)nc1]
In some embodiments, R⁷ is
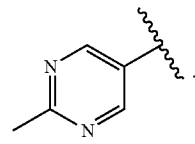 [SMILES: *c1cnc(C)nc1]
In some embodiments, R⁷ is
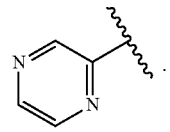
In some embodiments, R⁷ is
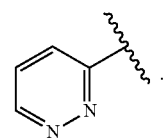
In some embodiments, R⁷ is
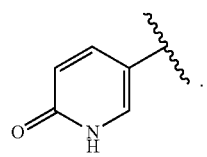 [SMILES: *c1ccc(=O)[nH]c1]
In some embodiments, R⁷ is
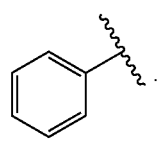 [SMILES: *c1ccccc1]
In some embodiments, R⁷ is
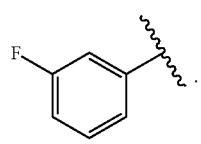
In some embodiments, R⁷ is
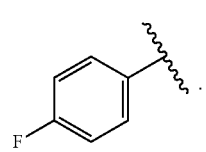

In some embodiments, $R^7$ is

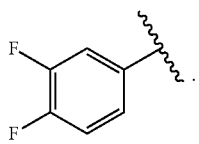

In some embodiments, $R^7$ is

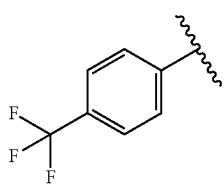

In some embodiments, $R^7$ is

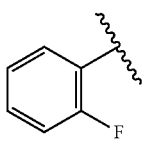

As generally defined herein, $R^8$ is H, $C_1$-$C_6$ alkyl, $C_1$-$C_6$ heteroalkyl, phenyl, cycloalkyl, heterocyclyl, cyano, CO—R', or $CO_2$—R', wherein each alkyl, heteroalkyl, phenyl, cycloalkyl, or heterocyclyl is optionally substituted; or $R^7$ and $R^8$ are taken together with the nitrogen and sulfur to which they are attached to form a 4-7 membered heterocycle with 0-2 additional ring heteroatoms selected from O, S, and N, and wherein the heterocycle is optionally substituted and wherein R' is as defined herein.

In some embodiments, $R^8$ is H, $C_1$-$C_6$ alkyl, $C_1$-$C_6$ heteroalkyl, phenyl, cycloalkyl, heterocyclyl, cyano, CO—R', or $CO_2$—R', wherein heterocyclyl has 4-11 ring atoms with 1 to 4 ring atoms selected from N, O, and S; each alkyl or heteroalkyl is substituted with 0-4 groups independently selected from halogen and OH, and each phenyl, cycloalkyl, or heterocyclyl is substituted with 0-4 $R^{10}$ groups; or $R^7$ and $R^8$ are taken together with the nitrogen and sulfur to which they are attached to form a 4-7 membered heterocycle with 0-2 additional ring heteroatoms selected from O, S, and N, and wherein the heterocycle is substituted with 0-4 $R^{10}$ groups, wherein R' and $R^{10}$ are as defined herein.

In some embodiments, $R^8$ is H, $C_1$-$C_6$ alkyl, cycloalkyl, cyano, CO—R', or $CO_2$—R', or $R^7$ and $R^8$ are taken together with the nitrogen and sulfur to which they are attached to form a 4-7 membered heterocycle with 0 additional ring heteroatoms, wherein the heterocycle is substituted with 0-4 $R^{10}$ groups, wherein R' and $R^{10}$ are as defined herein. In some embodiments, $R^8$ is H, $C_1$-$C_6$ alkyl, cycloalkyl, cyano, CO—$C_1$-$C_6$ alkyl, or $CO_2$—$C_1$-$C_6$ alkyl or $R^7$ and $R^8$ are taken together with the nitrogen and sulfur to which they are attached to form a 5-6 membered heterocycle with 0 additional ring heteroatoms, wherein the heterocycle is substituted with 0 or 1 $R^{10}$ groups, wherein $R^{10}$ is as defined herein.

In some embodiments, $R^8$ is H, Me, Et, CN, cyclopropyl, CO-t-butyl, or —$CO_2$-t-butyl or $R^7$ and $R^8$ are taken together with the nitrogen and sulfur to which they are attached to form a 5-6 membered heterocycle with 0 additional ring heteroatoms, wherein the heterocycle is substituted with 0 or 1 instances of methyl or phenyl.

In some embodiments, $R^8$ is H, Me, Et, CN, cyclopropyl, CO-t-butyl, or —$CO_2$-t-butyl or $R^7$ and $R^8$ are taken together with the nitrogen and sulfur to which they are attached to form

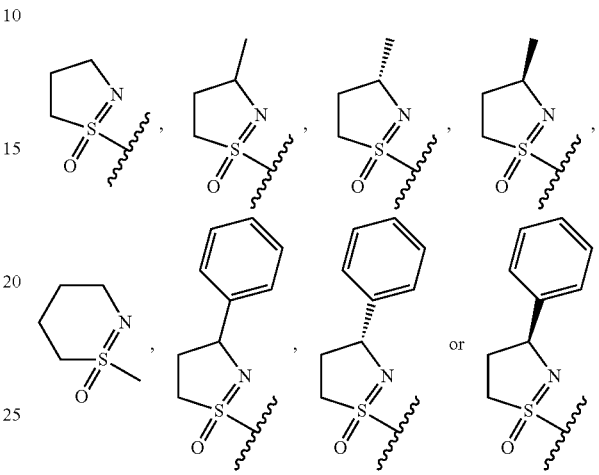

In some embodiments, $R^8$ is H, $C_1$-$C_6$ alkyl, cycloalkyl, cyano, CO—R', or $CO_2$—R', wherein R' is as defined herein. In some embodiments, $R^8$ is H, $C_1$-$C_6$ alkyl, cycloalkyl, cyano, CO—$C_1$-$C_6$ alkyl, or $CO_2$—$C_1$-$C_6$ alkyl.

In some embodiments, $R^8$ is H, Me, Et, CN, cyclopropyl, CO-t-butyl, or —$CO_2$-t-butyl.

In some embodiments, $R^8$ is H. In some embodiments, $R^8$ is Me. In some embodiments, $R^8$ is Et. In some embodiments, $R^8$ is CN. In some embodiments, $R^8$ is cyclopropyl. In some embodiments, $R^8$ is CO-t-butyl. In some embodiments, $R^8$ is-$CO_2$-t-butyl.

In some embodiments of a compound of Formula (I), $R^8$ is H, Me, Et, CN, cyclopropyl, or —$CO_2$-t-butyl, e.g., wherein $R^8$ is H.

In some embodiments of a compound of Formula (I), $R^8$ is H.

In some embodiments of a compound of Formula (I), $R^7$ and $R^8$ are joined together to form a propylene (—$CH_2$—$CH_2$—$CH_2$—). In some embodiments of a compound of Formula (I), $R^7$ and $R^8$ are joined together to form a ethylene (—$CH_2$—$CH_2$—).

In some embodiments, $R^7$ and $R^8$ are taken together with the atoms to which they are attached to form:

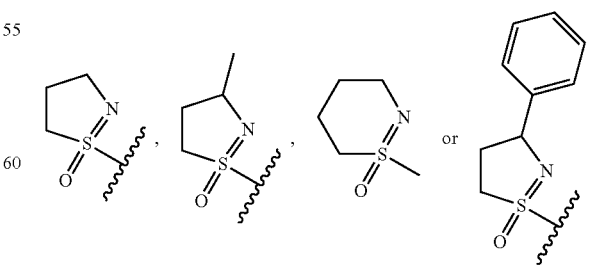

In some embodiments, $R^7$ and $R^8$ are taken together with the nitrogen and sulfur to which they are attached to form

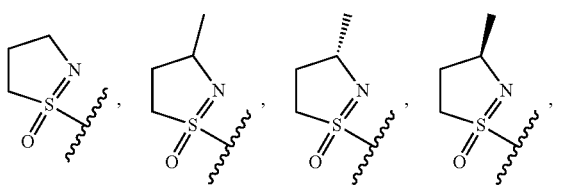

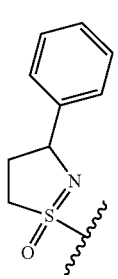 [SMILES: *S1(=O)=NC(c2ccccc2)CC1]

(e.g., including individual enantiomers thereof).

As generally defined herein, each $R^9$ is independently $C_1$-$C_6$ alkyl, $C_1$-$C_6$ heteroalkyl, $C_3$-$C_7$ cycloalkyl, hydroxy, cyano, or halogen, wherein each alkyl or heteroalkyl is optionally substituted with 1-4 groups independently selected from halogen and OH. In some embodiments, each $R^9$ is independently selected from $C_1$-$C_6$ alkyl, $C_1$-$C_6$ haloalkyl, $C_1$-$C_6$ heteroalkyl, $C_3$-$C_7$ cycloalkyl, hydroxy, cyano, or halogen. In some embodiments, each $R^9$ is independently selected from -Me, -Et, -iPr, -tBu, —$CF_3$, -OMe, cyclopropyl, hydroxy, cyano, —F or —Cl. In some embodiments, each $R^9$ is independently selected from -Me and —F.

As generally defined herein each $R^{10}$ is independently selected from $C_1$-$C_6$ alkyl, $C_1$-$C_6$ alkenyl, $C_1$-$C_6$ heteroalkyl, phenyl, $C_3$-$C_7$ cycloalkyl, heterocyclyl, $C_1$-$C_6$ alkylene-phenyl, $C_1$-$C_6$ alkylene-$C_3$-$C_7$ cycloalkyl, $C_1$-$C_6$ alkylene-heterocyclyl, hydroxy, cyano, CO—$R^C$, $NR^D_2$, or halogen, wherein heterocyclyl has 4-11 ring atoms with 1 to 4 ring atoms selected from N, O, and S; each alkyl or heteroalkyl is optionally substituted with 1-4 groups independently selected from halogen and OH, and wherein each phenyl, cycloalkyl, or heterocyclyl is optionally substituted with 1-4 $R^E$, wherein $R^C$, $R^D$, $R^E$ are as defined herein.

In some embodiments, each $R^{10}$ is independently selected from phenyl, cyano, halogen, $C_1$-$C_6$ alkyl, $C_1$-$C_6$ heteroalkyl, $C_3$-$C_7$ cycloalkyl, and CO—$R^C$, wherein $R^C$ is as defined herein and wherein the alkyl is unsubstituted or substituted with 1-4 groups independently selected from halogen and OH.

In some embodiments, each $R^{10}$ is independently selected from phenyl, halogen, $C_1$-$C_6$ alkyl, and CO—$R^C$, wherein $R^C$ is —$NH_2$ and wherein the alkyl is unsubstituted or substituted with 1-4 groups independently selected from halogen and OH.

In some embodiments, each $R^{10}$ is independently selected from halogen, $C_1$-$C_6$ alkyl, and CO—$R^C$, wherein $R^C$ is —$NH_2$ and wherein the alkyl is unsubstituted or substituted with 1-4 groups independently selected from halogen and OH. In some embodiments, each $R^{10}$ is independently selected from halogen, $C_1$-$C_6$ alkyl, and CO—$R^C$, wherein $R^C$ is —$NH_2$ and wherein the alkyl is unsubstituted or substituted with 1-4 groups independently selected from F and OH.

In some embodiments, each $R^{10}$ is independently selected from halogen and $C_1$-$C_6$ alkyl, wherein the alkyl is unsubstituted or substituted with 1-4 groups independently selected from halogen and OH. In some embodiments, each $R^{10}$ is independently selected from halogen and $C_1$-$C_6$ alkyl, wherein the alkyl is unsubstituted or substituted with 1-4 groups independently selected from F and OH. In some embodiments, each $R^{10}$ is independently halogen, $C_1$-$C_6$ alkyl, or $C_1$-$C_6$ haloalkyl. In some embodiments, each $R^{10}$ is independently halogen or $C_1$-$C_6$ alkyl. In some embodiments, $R^{10}$ is halogen. In some embodiments, $R^{10}$ is $C_1$-$C_6$ alkyl.

In some embodiments, $R^7$ and $R^8$ are taken together with the atoms to which they are attached to form:

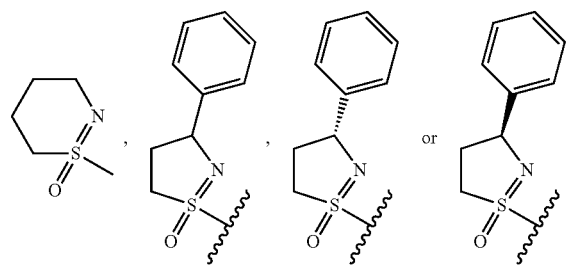

In some embodiments, $R^7$ and $R^8$ are taken together with the atoms to which they are attached to form

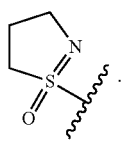

In some embodiments, $R^7$ and $R^8$ are taken together with the atoms to which they are attached to form

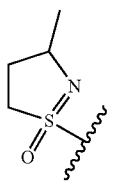

(e.g., including individual enantiomers thereof).

In some embodiments, $R^7$ and $R^8$ are taken together with the atoms to which they are attached to form

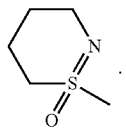

In some embodiments, $R^7$ and $R^8$ are taken together with the atoms to which they are attached to form In some embodiments, each $R^{10}$ is independently selected from phenyl, —F, —Cl, -Me, $CF_3$, —$CONH_2$ and —CH(OH)$CH_3$. In some embodiments, each $R^{10}$ is independently selected from —F, —Cl, -Me, $CF_3$, —$CONH_2$ and —CH(OH)$CH_3$.

In some embodiments, each $R^{10}$ is independently selected from —F and -Me. In some embodiments, $R^{10}$ is —F. In some embodiments, $R^{10}$ is -Me.

In some embodiments, $R^{10}$ is phenyl.

As generally defined herein each $R^{11}$ is independently selected from $C_1$-$C_6$ alkyl, $C_1$-$C_6$ alkenyl, $C_1$-$C_6$ heteroalkyl, phenyl, $C_3$-$C_7$ cycloalkyl, heterocyclyl, $C_1$-$C_6$ alkylene-phenyl, $C_1$-$C_6$ alkylene-$C_3$-$C_7$ cycloalkyl, $C_1$-$C_6$ alkylene-heterocyclyl, hydroxy, cyano, CO—$R^C$, $NR^D{}_2$, or halogen, wherein heterocyclyl has 4-11 ring atoms with 1 to 4 ring atoms selected from N, O, and S; each alkyl or heteroalkyl is optionally substituted with 1-4 groups independently selected from halogen and OH, and wherein each phenyl, cycloalkyl, or heterocyclyl is optionally substituted with 1-4 $R^E$, wherein $R^C$, $R^D$, $R^E$ are as defined herein.

In some embodiments, each $R^{11}$ is independently selected from $C_1$-$C_6$ alkyl, $C_1$-$C_6$ alkenyl, $C_1$-$C_6$ heteroalkyl, $C_3$-$C_7$ cycloalkyl, hydroxy, cyano, and halogen, wherein the alkyl and heteroalkyl are optionally substituted with 1-4 groups independently selected from halogen and OH.

In some embodiments, each $R^{11}$ is independently selected from —F, —Cl, -Me, -$^i$Pr, —C(=$CH_2$)$CH_3$, —$CF_3$, —CN, —OH, -OMe, —$CH_2OCH_2CH_2OMe$ and —$CH_2OH$.

As generally defined herein, each $R^C$ is independently H, OH, $NR^{12}{}_2$, $C_1$-$C_6$ alkyl, $C_1$-$C_6$ alkoxy, $C_1$-$C_6$ heteroalkyl, wherein each alkyl or heteroalkyl is optionally substituted with 1-4 substituents independently selected from halogen and OH, wherein $R^{12}$ is as defined herein. In some embodiments, each $R^C$ is independently H, OH, $NH_2$, NHMe, $NMe_2$, Me, Et, iPr, $^t$Bu, OMe, OEt, O$^i$Pr, O$^t$Bu or $CH_2CH_2OMe$. In some embodiments, each $R^C$ is independently $NH_2$, NHMe, $NMe_2$, OMe, OEt, O$^i$Pr or O$^t$Bu. In some embodiments, each $R^C$ is independently $NH_2$.

As generally defined herein, each $R^D$ is independently H, $C_1$-$C_6$ alkyl, CO—$C_1$-$C_6$ alkyl; $CO_2$—$C_1$-$C_6$ alkyl; $SO_w$—$C_1$-$C_6$ alkyl; $C_1$-$C_6$ heteroalkyl, wherein each alkyl or heteroalkyl is optionally substituted with 1-4 substituents independently selected from halogen and OH; or two $R^D$ attached to the same nitrogen are taken together with the nitrogen to which they are attached to form a 3-7 membered heterocycle with 0-2 additional ring heteroatoms selected from O, S, and N, and wherein the heterocycle is optionally substituted with 1-4 substituents independently selected from halogen, $C_1$-$C_6$ alkyl, $C_1$-$C_6$ haloalkyl, $C_1$-$C_6$ alkoxy, and OH, wherein w is as defined herein. In some embodiments each $R^D$ is selected from H, Me, Et, COMe, COtBu, COOMe, COOtBu, SOMe and $SO_2$Me, or two $R^D$ are taken together to form a heterocyclic ring selected from azetidine, pyrrolidine, and piperidine. In some embodiments each $R^D$ is selected from H and Me, or two $R^D$ are taken together to form a heterocyclic ring selected from azetidine, pyrrolidine, and piperidine. In some embodiments each $R^D$ is selected from H and Me. In some embodiments two $R^D$ are taken together to form a heterocyclic ring selected from azetidine, pyrrolidine, and piperidine. In some embodiments, each $R^D$ is independently H.

As generally defined herein, each R' is independently H or $C_1$-$C_6$ alkyl; or two R' together with the carbon or carbons to which they are attached form a 3-6-membered cycloalkyl ring. In some embodiments, each R' is independently H or Me; or two R' together with the carbon or carbons to which they are attached form a 3-4-membered cycloalkyl ring. In some embodiments, each R' is independently H or Me; or two R' together with the carbon or carbons to which they are attached form cyclopropyl ring. In some embodiments, both R' are H. In some embodiments, one R' is Me and the remaining R' are H. In some embodiments, two R' on the same carbon atom are Me. In some embodiments, two R' together with the carbon to which they are attached form a cyclopropyl.

In some embodiments, each R' is independently H, Me, Et, $^i$Pr or $^t$Bu. In some embodiments, R' is Me. In some embodiments, R' is $^t$Bu.

As generally defined herein, each $R^E$ is independently H, halo, OH, O—$C_1$-$C_6$ alkyl, —$C_1$-$C_6$ alkyl, —$C_1$-$C_6$ haloalkyl. In some embodiment, each $R^E$ is independently H or $C_1$-$C_6$ alkyl. In some embodiments, each $R^E$ is independently H, Cl, F, OH, OMe, $CF_3$ or Me. In some embodiments, each $R^E$ is H. In some embodiments, each $R^E$ is Me.

As generally defined herein, each $R^{12}$ is independently H or $C_1$-$C_6$ alkyl. In some embodiments, each $R^{12}$ is independently H or Me. In some embodiments, each $R^{12}$ is independently H. In some embodiments, each $R^{12}$ is independently Me.

As generally defined herein, w is 0, 1 or 2. In some embodiments, w is 0 or 1. In some embodiments, w is 1 or 2. In some embodiments, w is 0. In some embodiments, w is 1. In some embodiments, w is 2.

In some embodiments of a compound of Formula (I), the compound is of Formula (Ia)

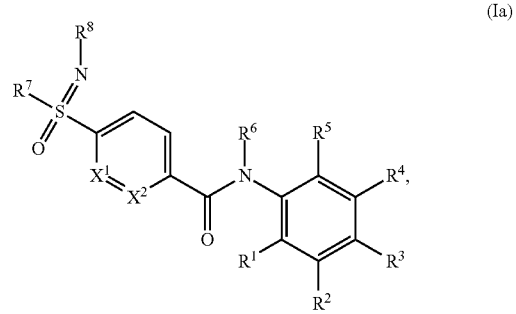

(Ia)

or a pharmaceutically acceptable salt thereof,
wherein
$X^1$ is N or CH; $X^2$ is N or CH; and $R^1$, $R^2$, $R^3$, $R^4$, $R^5$, $R^6$, $R^7$ and $R^8$ are as defined herein.

In some embodiments of a compound of Formula (I), the compound is of Formula (Ib)

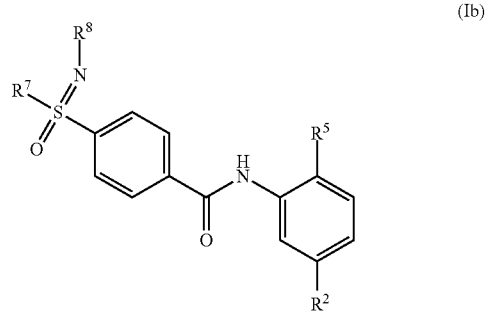

(Ib)

or a pharmaceutically acceptable salt thereof, wherein $R^2$, $R^5$, $R^7$ and $R^8$ are as defined herein.

In some embodiments of a compound of Formula (I), the compound is of Formula (Ic)

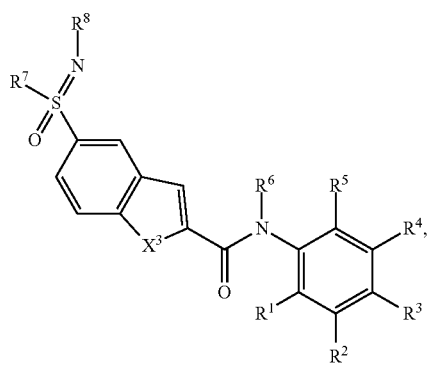

(Ic)

or a pharmaceutically acceptable salt thereof,
wherein $X^3$ is O or S; and $R^1$, $R^2$, $R^3$, $R^4$, $R^5$, $R^6$, $R^7$ and $R^8$ are as defined herein.

In some embodiments of a compound of Formula (I), the compound is of Formula (Id)

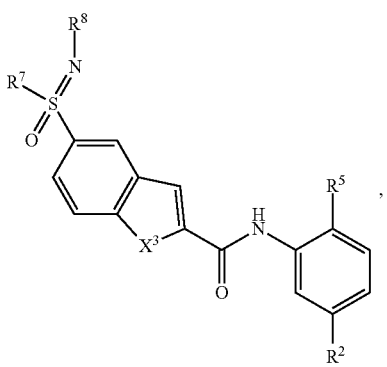

(Id)

or a pharmaceutically acceptable salt thereof,
wherein $X^3$ is O or S; and $R^2$, $R^5$, $R^7$ and $R^8$ are as defined herein.

In some embodiments of a compound of Formula (I), the compound is of Formula (Ie)

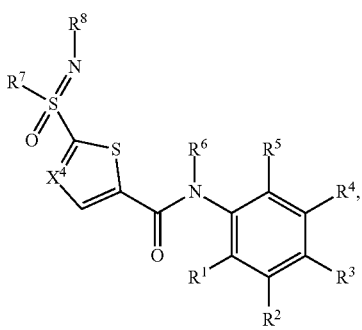

(Ie)

or a pharmaceutically acceptable salt thereof,
wherein $X^4$ is N or CH; and $R^1$, $R^2$, $R^3$, $R^4$, $R^5$, $R^6$, $R^7$ and $R^8$ are as defined herein.

In some embodiments of a compound of Formula (I), the compound is of Formula (If)

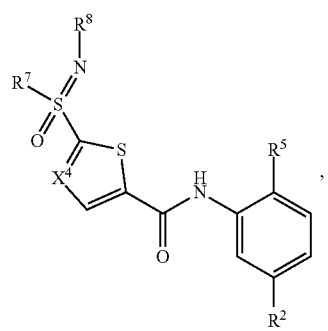

(If)

or a pharmaceutically acceptable salt thereof,
wherein $X^4$ is N or CH; and $R^2$, $R^5$, $R^7$ and $R^8$ are as defined herein.

In some embodiments, the compound is a compound of Formula (Ig)

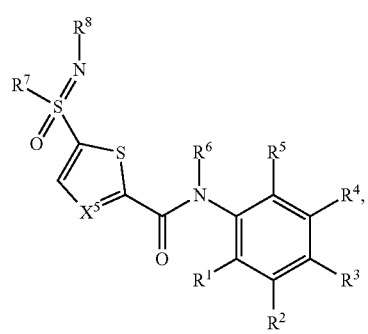

(Ig)

or a pharmaceutically acceptable salt thereof,
wherein $X^5$ is N or CH; and $R^1$, $R^2$, $R^3$, $R^4$, $R^5$, $R^6$, $R^7$ and $R^8$ are as defined herein.

In some embodiments, the compound is a compound of Formula (Ih)

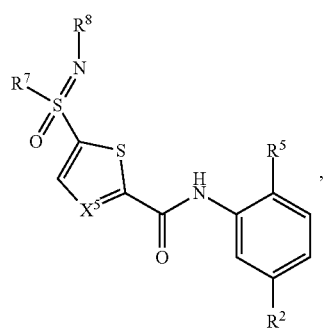

(Ih)

or a pharmaceutically acceptable salt thereof,
wherein $X^5$ is N or CH; and $R^2$, $R^5$, $R^7$ and $R^8$ are as defined herein.

In some embodiments, the compound is a compound of Formula (Ii)

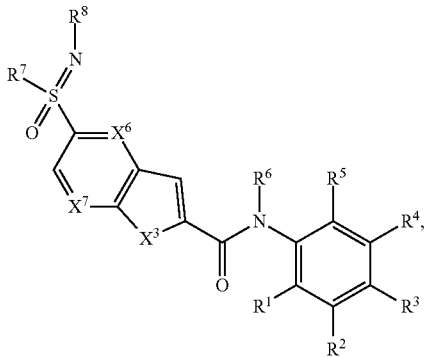

(Ii)

or a pharmaceutically acceptable salt thereof,
wherein $X^3$ is O or S;
$X^6$ is N or CH; $X^7$ is N or CH; and $R^1$, $R^2$, $R^3$, $R^4$, $R^5$, $R^6$, $R^7$ and $R^8$ are as defined herein.

In some embodiments, the compound is a compound of Formula (Ij)

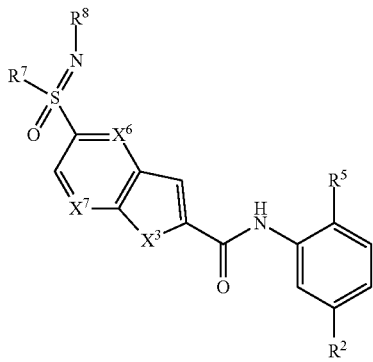

(Ij)

or a pharmaceutically acceptable salt thereof,
wherein $X^3$ is O or S;
$X^6$ is N or CH; $X^7$ is N or CH; and $R^2$, $R^5$, $R^7$ and $R^8$ are as defined herein.

In some embodiments, $X^6$ is N and $X^7$ is CH.
In some embodiments, $X^6$ is CH and $X^7$ is N.
In some embodiments, the compound is a compound of Formula (Ik)

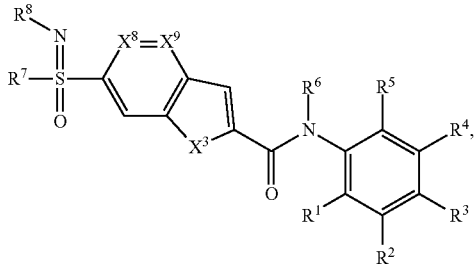

(Ik)

or a pharmaceutically acceptable salt thereof,
wherein $X^3$ is O or S;
$X^8$ is N or CH; $X^9$ is N or CH; and $R^1$, $R^2$, $R^3$, $R^4$, $R^5$, $R^6$, $R^7$ and $R^8$ are as defined herein.

In some embodiments, the compound is a compound of Formula (Im)

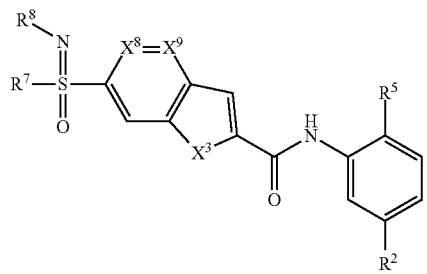

(Im)

or a pharmaceutically acceptable salt thereof,
wherein $X^3$ is O or S;
$X^8$ is N or CH; $X^9$ is N or CH; and $R^2$, $R^5$, $R^7$ and $R^8$ are as defined herein.

In some embodiments, $X^8$ is N and $X^9$ is CH.
In some embodiments, $X^8$ is CH and $X^9$ is N.
In some embodiments, the compound is a compound of Formula (In)

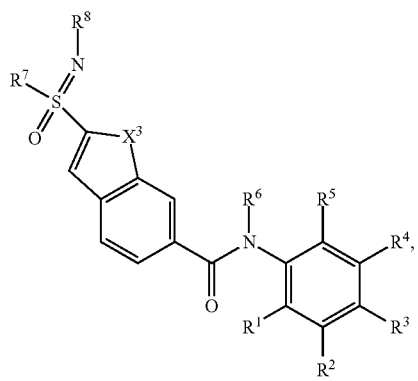

(In)

or a pharmaceutically acceptable salt thereof,
wherein $X^3$ is O or S; and $R^1$, $R^2$, $R^3$, $R^4$, $R^5$, $R^6$, $R^7$ and $R^8$ are as defined herein.

In some embodiments, the compound is a compound of Formula (Io)

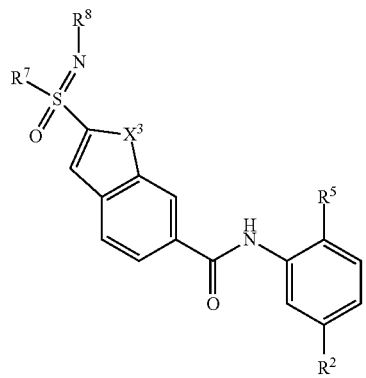

(Io)

or a pharmaceutically acceptable salt thereof,
wherein $X^3$ is O or S; and $R^2$, $R^5$, $R^7$ and $R^8$ are as defined herein.

In some embodiments, the compound is a compound of Formula (Ip)

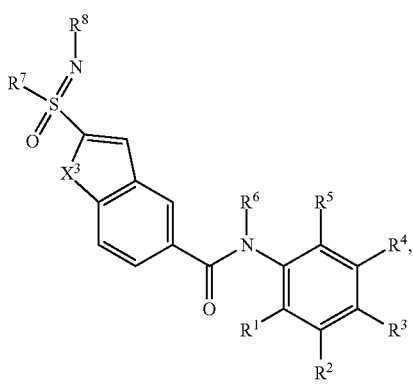

(Ip)

or a pharmaceutically acceptable salt thereof,
wherein $X^3$ is O or S; and $R^1$, $R^2$, $R^3$, $R^4$, $R^5$, $R^6$, $R^7$ and $R^8$ are as defined herein.

In some embodiments, the compound is a compound of Formula (Iq)

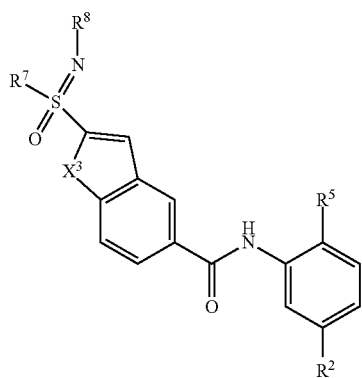

(Iq)

or a pharmaceutically acceptable salt thereof,
wherein $X^3$ is O or S; and $R^2$, $R^5$, $R^7$ and $R^8$ are as defined herein.

In some embodiments, the compound is a compound of Formula (Ir)

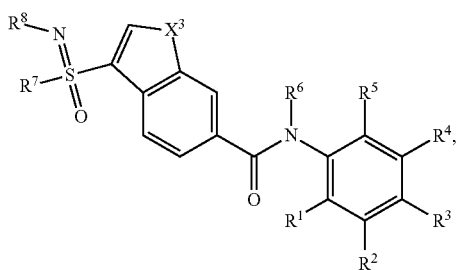

(Ir)

or a pharmaceutically acceptable salt thereof,
wherein $X^3$ is O or S; and $R^1$, $R^2$, $R^3$, $R^4$, $R^5$, $R^6$, $R^7$ and $R^8$ are as defined herein.

In some embodiments, the compound is a compound of Formula (Is)

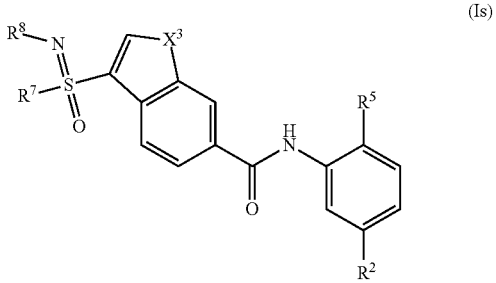

(Is)

or a pharmaceutically acceptable salt thereof,
wherein $X^3$ is O or S; and $R^2$, $R^5$, $R^7$ and $R^8$ are as defined herein.

In some embodiments, $X^3$ is S.

In some embodiments, $X^3$ is O.

In some embodiments of a compound of Formula (I), the compound is selected from the compounds disclosed in Table 1, or a pharmaceutically acceptable salt thereof, or elsewhere in the specification and figures.

In some embodiments, provided herein is a composition comprising a compound described herein and a pharmaceutically acceptable excipient.

In some embodiments, the compound is a compound identified in Table 1 below or a pharmaceutically acceptable salt thereof.

Unless otherwise indicated, the absolute stereochemistry of all chiral atoms is as depicted. Compounds marked with (or) or (rel) in Table 1 and the Examples section are single enantiomers wherein the absolute stereochemistry was arbitrarily assigned (e.g., based on chiral SFC elution as described in the Examples section). Compounds marked with (and) or (rac) are mixtures of enantiomers wherein the relative stereochemistry is as shown. Compounds that have a stereogenic center where the configuration is not indicated in the structure as depicted and that have no designation in the stereochemistry column of Table 1 are mixtures of enantiomers at that center. Compounds that have a stereogenic center where the configuration is indicated in the structure as depicted and have no designation in the stereochemistry column of Table 1 or that are marked with (abs) are single enantiomers wherein the absolute stereochemistry is as indicated.

A person of skill in the art would be able to separate racemic compounds into the respective enantiomers using methods known in the art, such as chiral chromatography, chiral recrystallization and the like. References to compounds that are racemic mixtures are meant to also include the individual enantiomers contained in the mixture.

TABLE 1

Exemplary compounds

| Cmpd No. | Stereochemistry | Structure |
|---|---|---|
| 101 | | 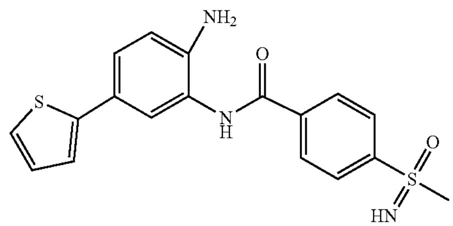 [SMILES: CS(=N)(=O)c1ccc(C(=O)Nc2cc(-c3cccs3)ccc2N)cc1] |
| 102 | | 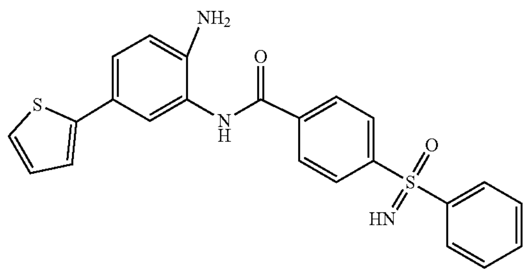 [SMILES: CNc1ccc(-c2cccs2)cc1NC(=O)c1ccc(S(=N)(=O)c2ccccc2)cc1] |
| 103 | | 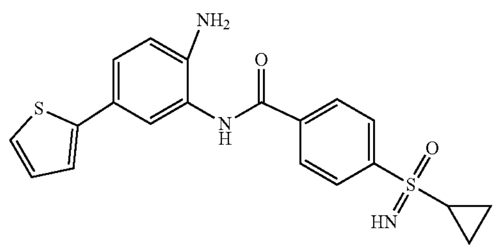 [SMILES: CNc1ccc(-c2cccs2)cc1NC(=O)c1ccc(S(=N)(=O)C2CC2)cc1] |
| 104 | | 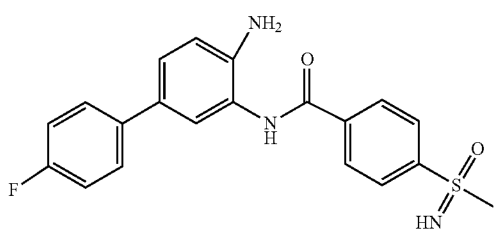 |
| 105 | (or) | 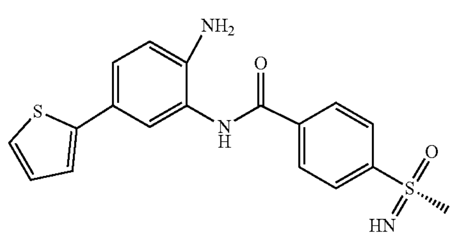 [SMILES: C[S@@](=N)(=O)c1ccc(C(=O)Nc2cc(-c3cccs3)ccc2N)cc1] |
| 106 | (or) | 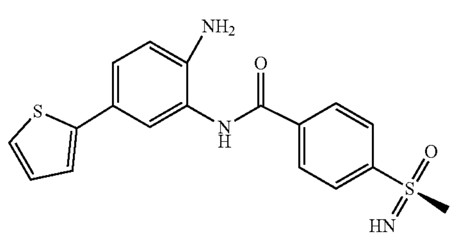 [SMILES: C[S@](=N)(=O)c1ccc(C(=O)Nc2cc(-c3cccs3)ccc2N)cc1] |

TABLE 1-continued
Exemplary compounds
| Cmpd No. | Stereochemistry | Structure |
|---|---|---|
| 107 | | 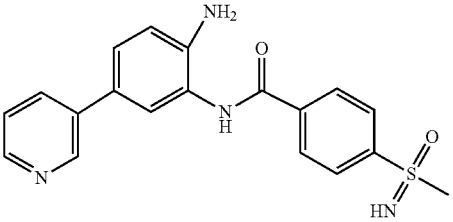 [SMILES: CS(=N)(=O)c1ccc(C(=O)Nc2cc(-c3cccnc3)ccc2N)cc1] |
| 108 | | 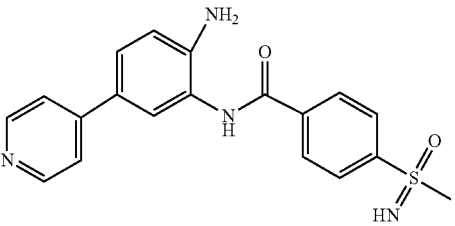 [SMILES: CS(=N)(=O)c1ccc(C(=O)Nc2cc(-c3ccncc3)ccc2N)cc1] |
| 109 | | 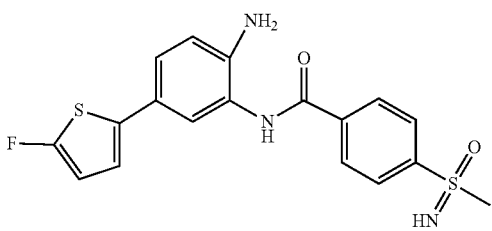 [SMILES: CS(=N)(=O)c1ccc(C(=O)Nc2cc(-c3ccc(F)s3)ccc2N)cc1] |
| 110 | | 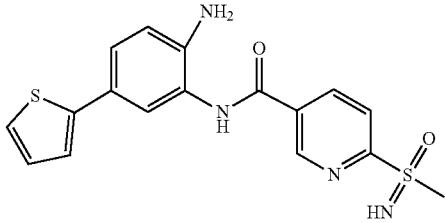 [SMILES: CS(=N)(=O)c1ccc(C(=O)Nc2cc(-c3cccs3)ccc2N)cn1] |
| 111 | | 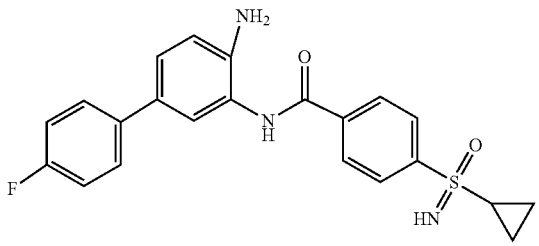 [SMILES: N=S(=O)(c1ccc(C(=O)Nc2cc(-c3ccc(F)cc3)ccc2N)cc1)C1CC1] |

TABLE 1-continued

Exemplary compounds

| Cmpd No. | Stereochemistry | Structure |
|---|---|---|
| 112 | | 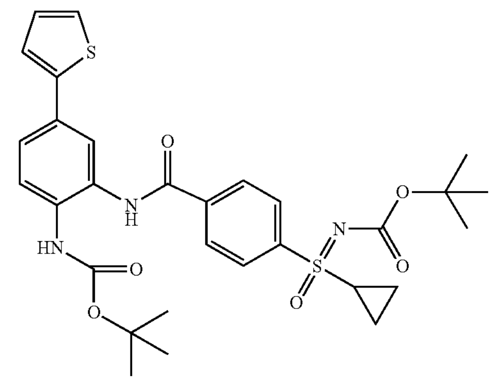 [SMILES: CC(C)(C)OC(=O)N=S(=O)(c1ccc(C(=O)Nc2cc(-c3cccs3)ccc2NC(=O)OC(C)(C)C)cc1)C1CC1] |
| 113 | | 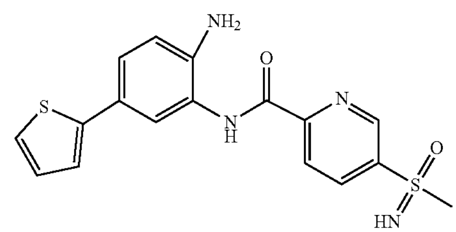 [SMILES: CS(=N)(=O)c1ccc(C(=O)Nc2cc(-c3cccs3)ccc2N)nc1] |
| 114 | (or) | 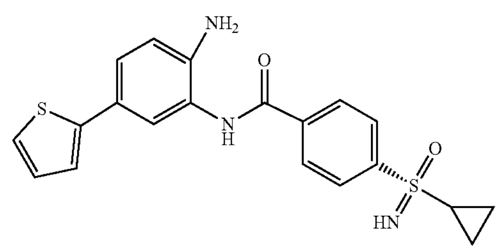 |
| 115 | (or) | 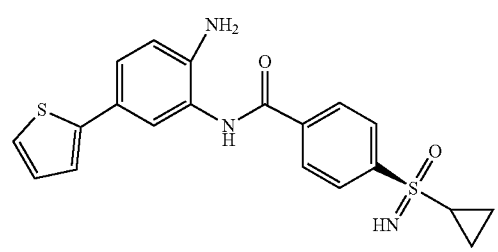 [SMILES: N=[S@@](=O)(c1ccc(C(=O)Nc2cc(-c3cccs3)ccc2N)cc1)C1CC1] |
| 116 | | 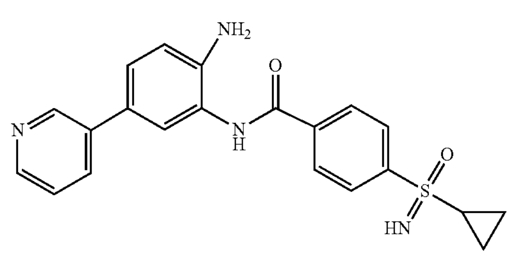 [SMILES: N=S(=O)(c1ccc(C(=O)Nc2cc(-c3cccnc3)ccc2N)cc1)C1CC1] |

TABLE 1-continued

Exemplary compounds

| Cmpd No. | Stereochemistry | Structure |
|---|---|---|
| 117 | | 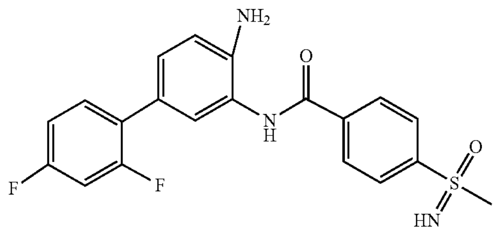 [SMILES: CS(=N)(=O)c1ccc(C(=O)Nc2cc(-c3ccc(F)cc3F)ccc2N)cc1] |
| 118 | | 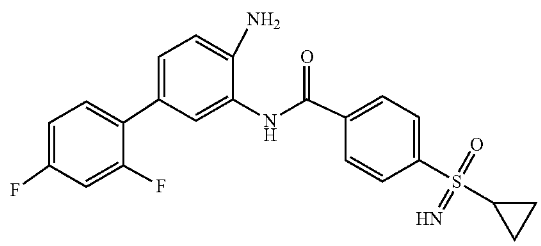 [SMILES: N=S(=O)(c1ccc(C(=O)Nc2cc(-c3ccc(F)cc3F)ccc2N)cc1)C1CC1] |
| 119 | | 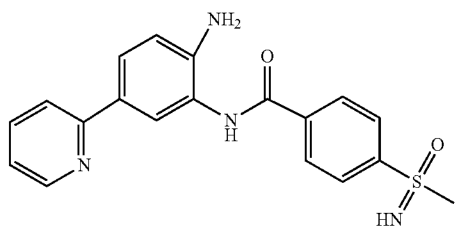 [SMILES: CS(=N)(=O)c1ccc(C(=O)Nc2cc(-c3ccccn3)ccc2N)cc1] |
| 120 | | 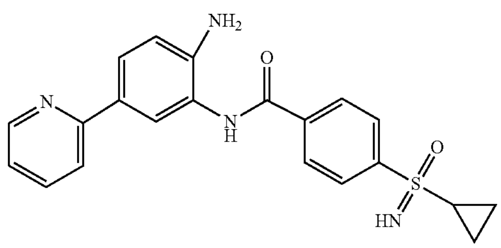 [SMILES: N=S(=O)(c1ccc(C(=O)Nc2cc(-c3ccccn3)ccc2N)cc1)C1CC1] |
| 121 | | 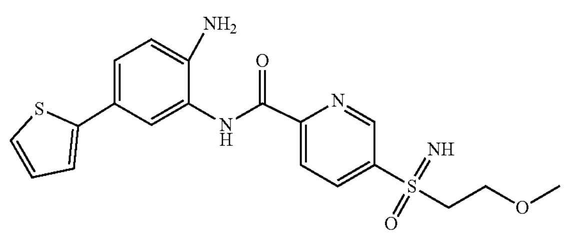 [SMILES: COCCS(=N)(=O)c1ccc(C(=O)Nc2cc(-c3cccs3)ccc2N)nc1] |
| 122 | | 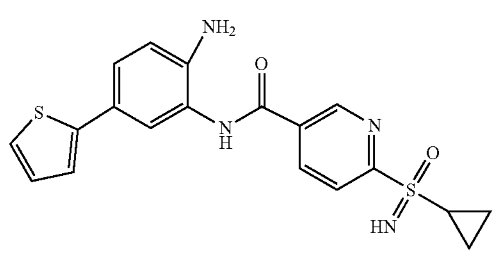 [SMILES: N=S(=O)(c1ccc(C(=O)Nc2cc(-c3cccs3)ccc2N)cn1)C1CC1] |

TABLE 1-continued
Exemplary compounds
| Cmpd No. | Stereochemistry | Structure |
|---|---|---|
| 123 | | 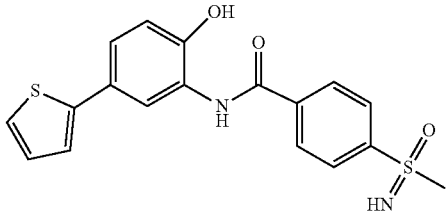 [SMILES: CS(=N)(=O)c1ccc(C(=O)Nc2cc(-c3cccs3)ccc2O)cc1] |
| 124 | | 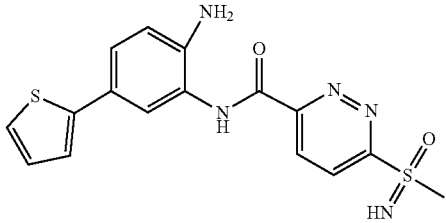 [SMILES: CS(=N)(=O)c1ccc(C(=O)Nc2cc(-c3cccs3)ccc2N)nn1] |
| 125 | | 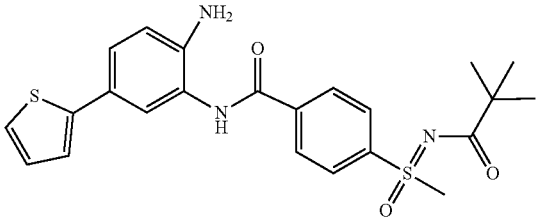 [SMILES: CC(C)(C)C(=O)N=S(C)(=O)c1ccc(C(=O)Nc2cc(-c3cccs3)ccc2N)cc1] |
| 126 | | 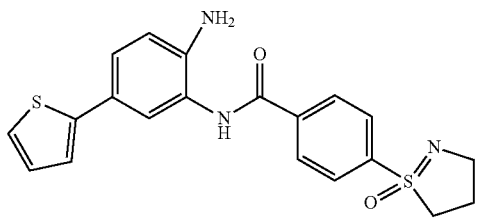 [SMILES: Nc1ccc(-c2cccs2)cc1NC(=O)c1ccc(S2(=O)=NCCC2)cc1] |
| 127 | | 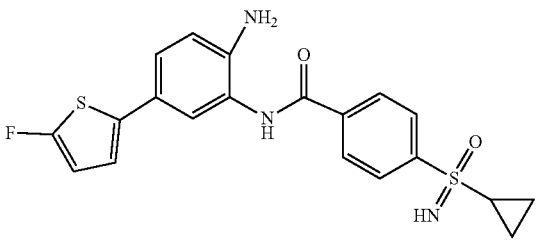 [SMILES: N=S(=O)(c1ccc(C(=O)Nc2cc(-c3ccc(F)s3)ccc2N)cc1)C1CC1] |
| 128 | | 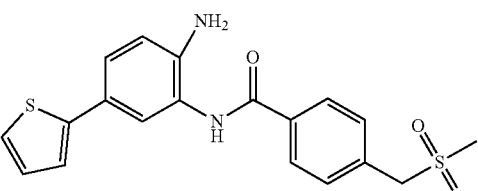 |

TABLE 1-continued

Exemplary compounds

| Cmpd No. | Stereochemistry | Structure |
|---|---|---|
| 129 | | 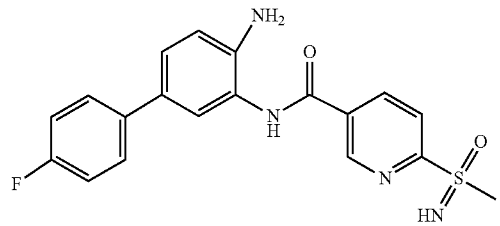 [SMILES: CS(=N)(=O)c1ccc(C(=O)Nc2cc(-c3ccc(F)cc3)ccc2N)cn1] |
| 130 | | 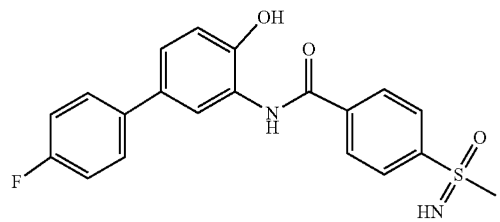 [SMILES: CS(=N)(=O)c1ccc(C(=O)Nc2cc(-c3ccc(F)cc3)ccc2O)cc1] |
| 131 | (or) | 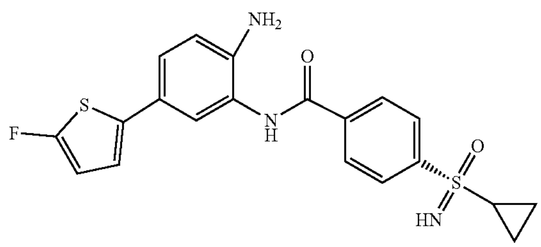 [SMILES: N=[S@](=O)(c1ccc(C(=O)Nc2cc(-c3ccc(F)s3)ccc2N)cc1)C1CC1] |
| 132 | | 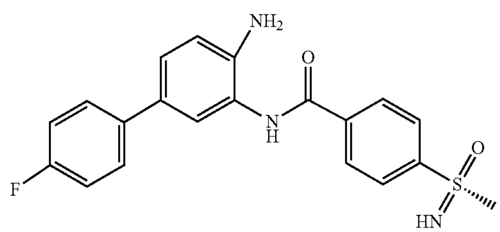 [SMILES: C[S@@](=N)(=O)c1ccc(C(=O)Nc2cc(-c3ccc(F)cc3)ccc2N)cc1] |
| 133 | (or) | 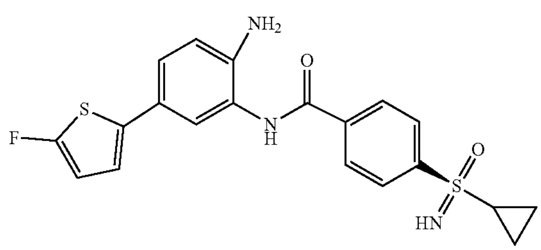 [SMILES: N=[S@@](=O)(c1ccc(C(=O)Nc2cc(-c3ccc(F)s3)ccc2N)cc1)C1CC1] |
| 134 | | 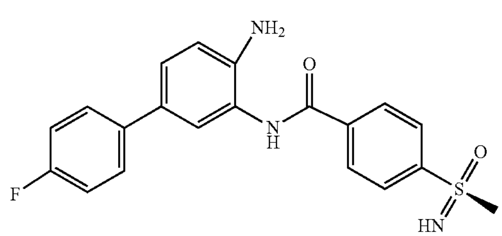 [SMILES: C[S@](=N)(=O)c1ccc(C(=O)Nc2cc(-c3ccc(F)cc3)ccc2N)cc1] |

TABLE 1-continued

Exemplary compounds

| Cmpd No. | Stereochemistry | Structure |
|---|---|---|
| 135 | | 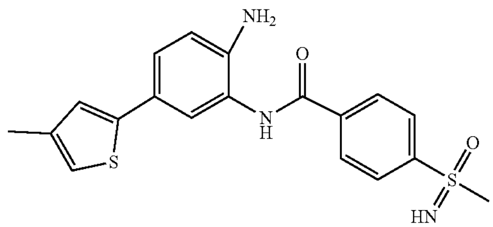 |
| 136 | | 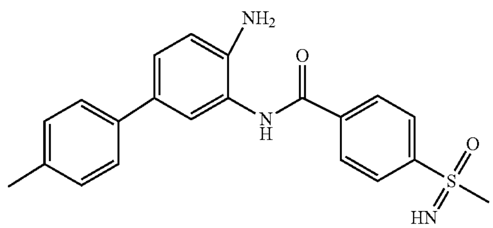 |
| 137 | | 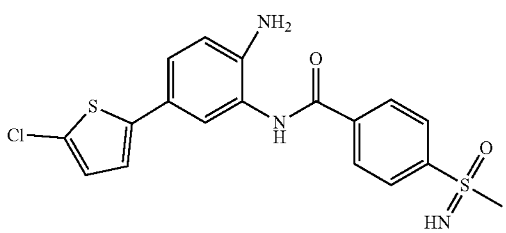 [SMILES: CS(=N)(=O)c1ccc(C(=O)Nc2cc(-c3ccc(Cl)s3)ccc2N)cc1] |
| 138 | | 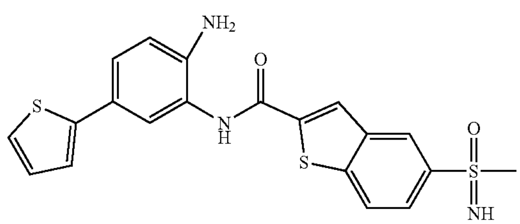 [SMILES: CS(=N)(=O)c1ccc2sc(C(=O)Nc3cc(-c4cccs4)ccc3N)cc2c1] |
| 139 | | 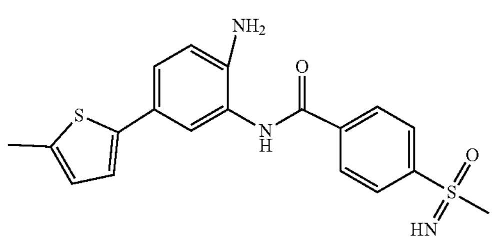 |
| 140 | | 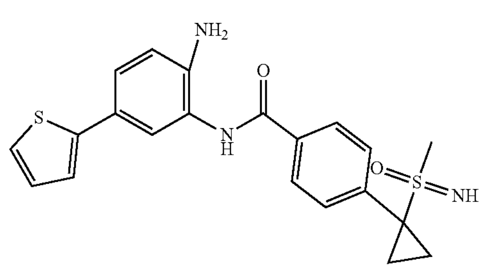 [SMILES: CS(=N)(=O)C1(c2ccc(C(=O)Nc3cc(-c4cccs4)ccc3N)cc2)CC1] |

TABLE 1-continued

Exemplary compounds

| Cmpd No. | Stereochemistry | Structure |
|---|---|---|
| 141 | | 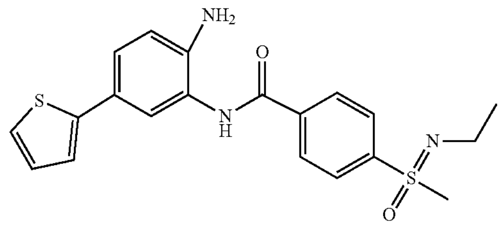 [SMILES: CCN=S(C)(=O)c1ccc(C(=O)Nc2cc(-c3cccs3)ccc2N)cc1] |
| 142 | | 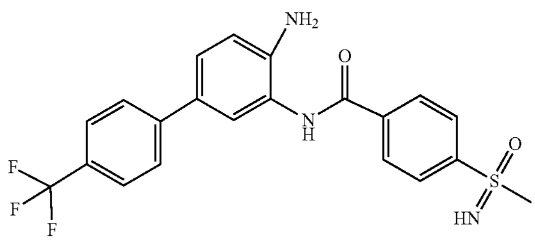 [SMILES: CS(=N)(=O)c1ccc(C(=O)Nc2cc(-c3ccc(C(F)(F)F)cc3)ccc2N)cc1] |
| 143 | | 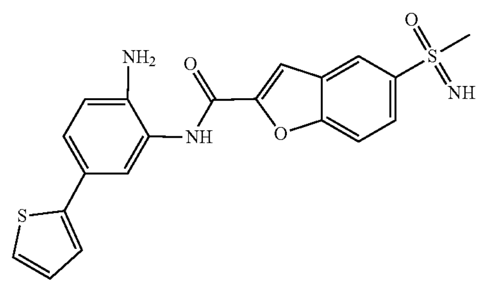 [SMILES: CS(=N)(=O)c1ccc2oc(C(=O)Nc3cc(-c4cccs4)ccc3N)cc2c1] |
| 144 | | 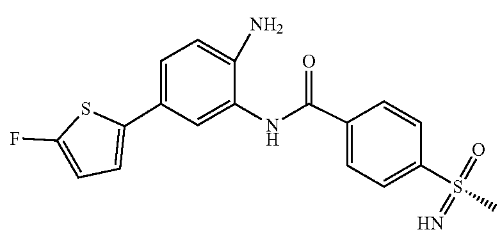 [SMILES: C[S@@](=N)(=O)c1ccc(C(=O)Nc2cc(-c3ccc(F)s3)ccc2N)cc1] |
| 145 | (or) | 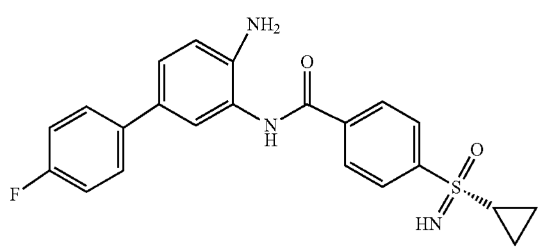 [SMILES: N=[S@](=O)(c1ccc(C(=O)Nc2cc(-c3ccc(F)cc3)ccc2N)cc1)C1CC1] |
| 146 | (or) | 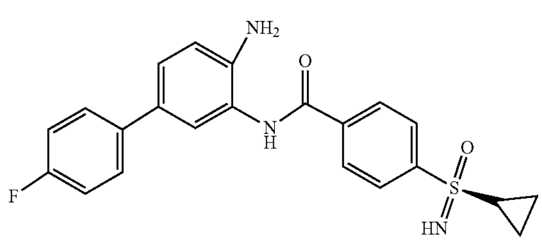 [SMILES: N=[S@@](=O)(c1ccc(C(=O)Nc2cc(-c3ccc(F)cc3)ccc2N)cc1)C1CC1] |

TABLE 1-continued

Exemplary compounds

| Cmpd No. | Stereochemistry | Structure |
|---|---|---|
| 147 | | (3,4-difluorophenyl-aminophenyl)-N-(4-(S-methylsulfonimidoyl)benzamide) |
| 148 | | (thiazol-5-yl-aminophenyl)-N-(4-(S-methylsulfonimidoyl)benzamide) |
| 149 | | (5-fluorothiophen-2-yl-aminophenyl)-N-(4-(S-methylsulfonimidoyl)benzamide) |
| 150 | | (thiophen-2-yl-aminophenyl)-N-(4-(S-pyridin-2-ylsulfonimidoyl)benzamide) |
| 151 | | (pyrimidin-5-yl-aminophenyl)-N-(4-(S-methylsulfonimidoyl)benzamide) |
| 152 | | (5-fluorothiophen-2-yl-aminophenyl)-N-(6-(S-methylsulfonimidoyl)pyridazine-3-carboxamide) |

TABLE 1-continued

Exemplary compounds

| Cmpd No. | Stereochemistry | Structure |
|---|---|---|
| 153 | | 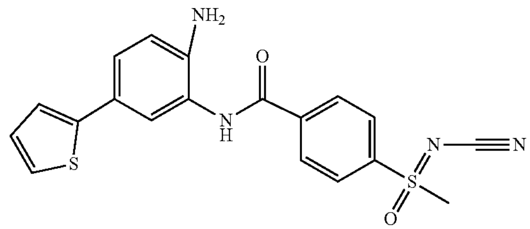 [SMILES: CS(=O)(=NC#N)c1ccc(C(=O)Nc2cc(-c3cccs3)ccc2N)cc1] |
| 154 | | 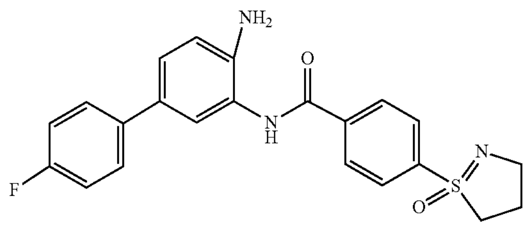 [SMILES: Nc1ccc(-c2ccc(F)cc2)cc1NC(=O)c1ccc(S2(=O)=NCCC2)cc1] |
| 155 | | 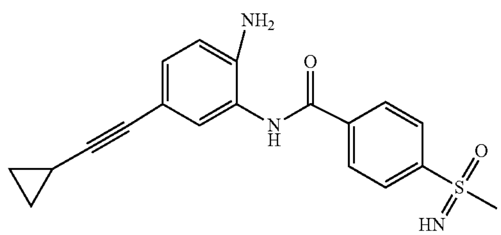 [SMILES: CS(=N)(=O)c1ccc(C(=O)Nc2cc(C#CC3CC3)ccc2N)cc1] |
| 156 | | 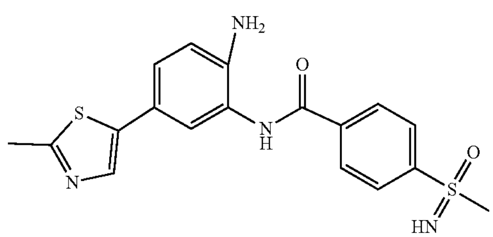 |
| 157 | | 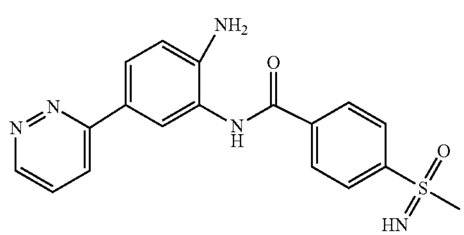 [SMILES: CS(=N)(=O)c1ccc(C(=O)Nc2cc(-c3cccnn3)ccc2N)cc1] |
| 158 | | 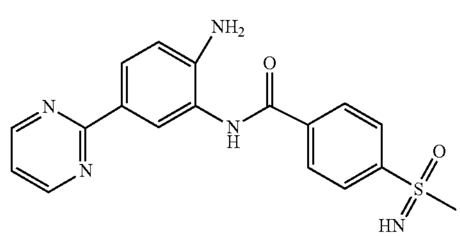 [SMILES: CS(=N)(=O)c1ccc(C(=O)Nc2cc(-c3ncccn3)ccc2N)cc1] |

TABLE 1-continued

Exemplary compounds

| Cmpd No. | Stereochemistry | Structure |
|---|---|---|
| 159 | | 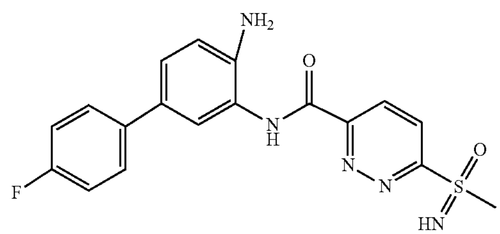 [SMILES: CS(=N)(=O)c1ccc(C(=O)Nc2cc(-c3ccc(F)cc3)ccc2N)nn1] |
| 160 | | 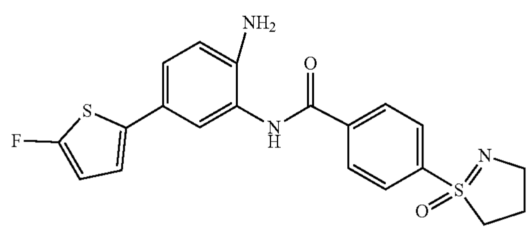 [SMILES: Nc1ccc(-c2ccc(F)s2)cc1NC(=O)c1ccc(S2(=O)=NCCC2)cc1] |
| 161 | | 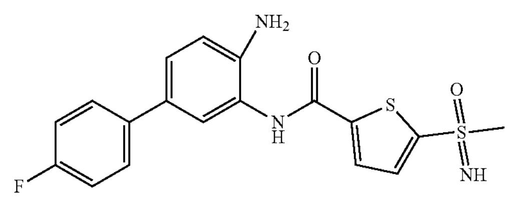 [SMILES: CS(=N)(=O)c1ccc(C(=O)Nc2cc(-c3ccc(F)cc3)ccc2N)s1] |
| 162 | | 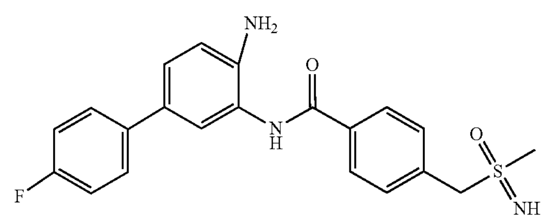 [SMILES: CS(=N)(=O)Cc1ccc(C(=O)Nc2cc(-c3ccc(F)cc3)ccc2N)cc1] |
| 163 | | 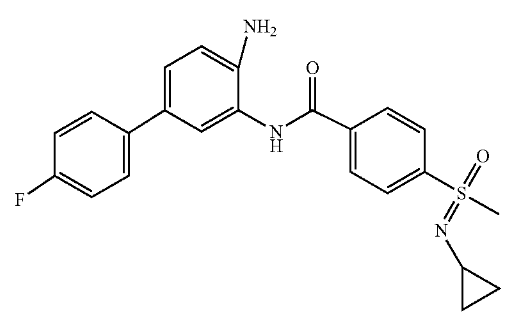 [SMILES: CS(=O)(=NC1CC1)c1ccc(C(=O)Nc2cc(-c3ccc(F)cc3)ccc2N)cc1] |
| 164 | | 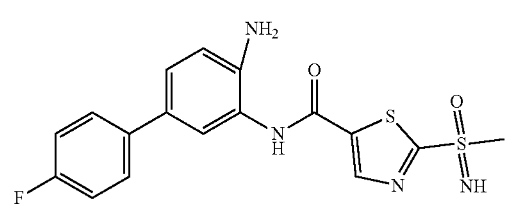 [SMILES: CS(=N)(=O)c1ncc(C(=O)Nc2cc(-c3ccc(F)cc3)ccc2N)s1] |

TABLE 1-continued

Exemplary compounds

| Cmpd No. | Stereochemistry | Structure |
|---|---|---|
| 165 | | 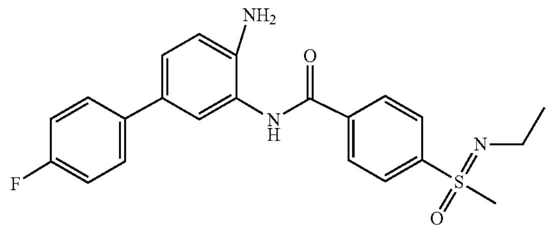 [SMILES: CCN=S(C)(=O)c1ccc(C(=O)Nc2cc(-c3ccc(F)cc3)ccc2N)cc1] |
| 166 | | 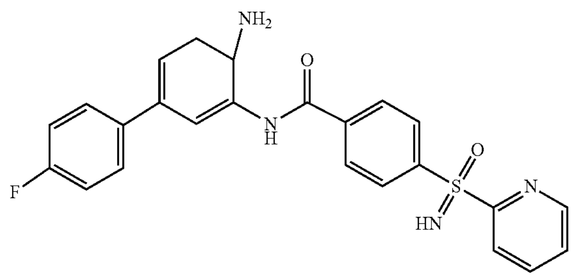 [SMILES: N=S(=O)(c1ccc(C(=O)NC2=CC(c3ccc(F)cc3)=CCC2N)cc1)c1ccccn1] |
| 167 | | 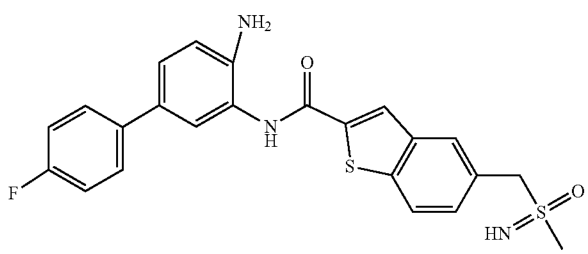 [SMILES: CS(=N)(=O)Cc1ccc2sc(C(=O)Nc3cc(-c4ccc(F)cc4)ccc3N)cc2c1] |
| 168 | | 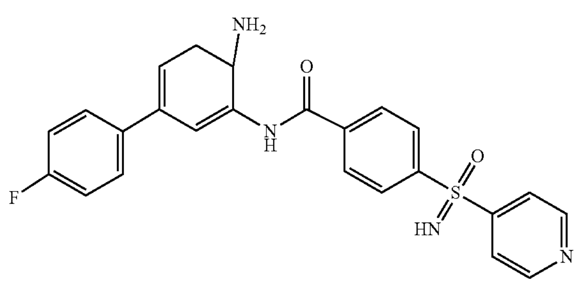 [SMILES: N=S(=O)(c1ccncc1)c1ccc(C(=O)NC2=CC(c3ccc(F)cc3)=CCC2N)cc1] |
| 169 | | 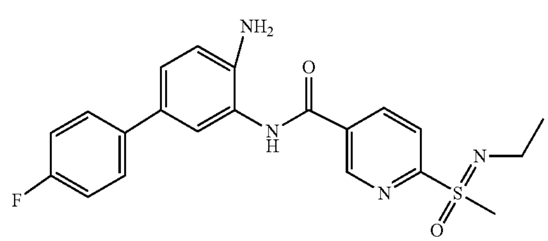 [SMILES: CCN=S(C)(=O)c1ccc(C(=O)Nc2cc(-c3ccc(F)cc3)ccc2N)cn1] |

TABLE 1-continued

Exemplary compounds

| Cmpd No. | Stereochemistry | Structure |
|---|---|---|
| 170 | | 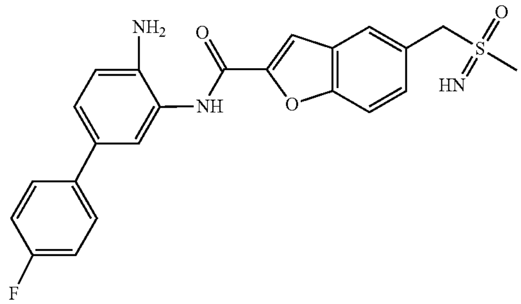 [SMILES: CS(=N)(=O)Cc1ccc2oc(C(=O)Nc3cc(-c4ccc(F)cc4)ccc3N)cc2c1] |
| 171 | | 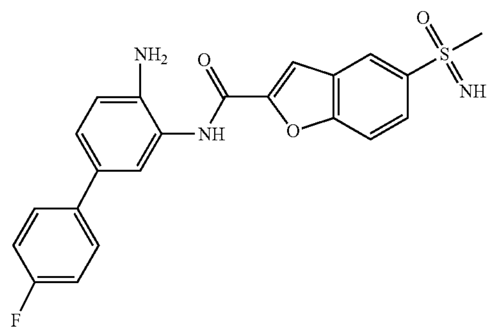 [SMILES: CS(=N)(=O)c1ccc2oc(C(=O)Nc3cc(-c4ccc(F)cc4)ccc3N)cc2c1] |
| 172 | | 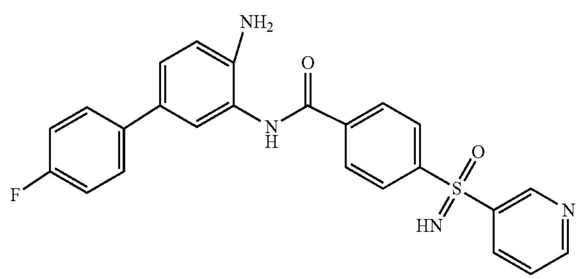 [SMILES: N=S(=O)(c1ccc(C(=O)Nc2cc(-c3ccc(F)cc3)ccc2N)cc1)c1cccnc1] |
| 173 | | 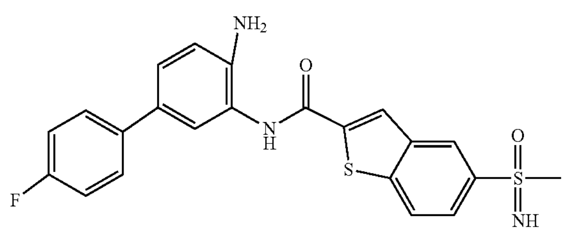 [SMILES: CS(=N)(=O)c1ccc2sc(C(=O)Nc3cc(-c4ccc(F)cc4)ccc3N)cc2c1] |
| 174 | | 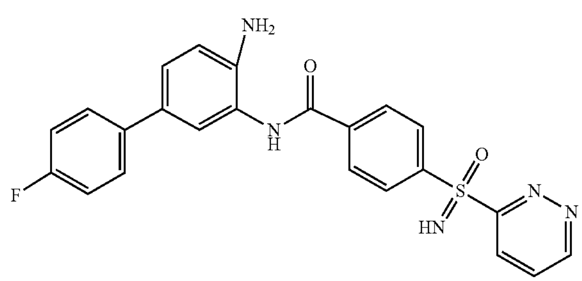 [SMILES: N=S(=O)(c1ccc(C(=O)Nc2cc(-c3ccc(F)cc3)ccc2N)cc1)c1cccnn1] |

TABLE 1-continued

Exemplary compounds

| Cmpd No. | Stereochemistry | Structure |
|---|---|---|
| 175 | | 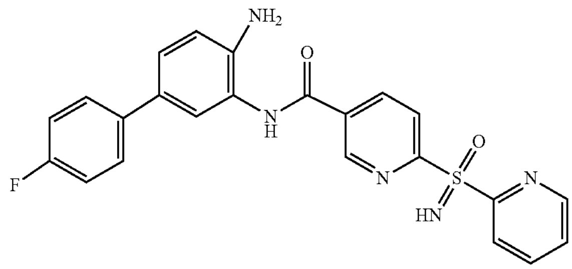 [SMILES: N=S(=O)(c1ccccn1)c1ccc(C(=O)Nc2cc(-c3ccc(F)cc3)ccc2N)cn1] |
| 176 | | 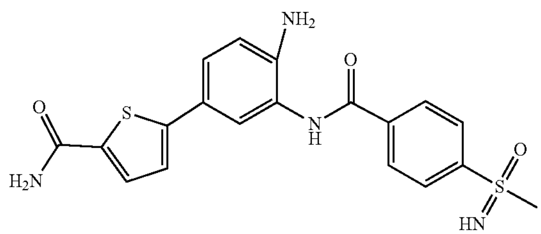 [SMILES: CS(=N)(=O)c1ccc(C(=O)Nc2cc(-c3ccc(C(N)=O)s3)ccc2N)cc1] |
| 177 | | 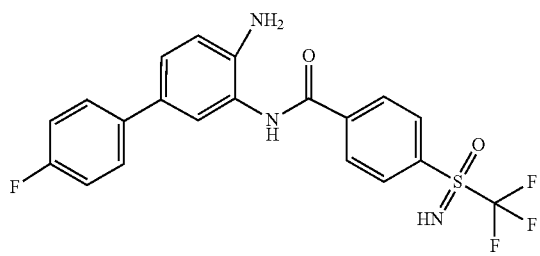 [SMILES: N=S(=O)(c1ccc(C(=O)Nc2cc(-c3ccc(F)cc3)ccc2N)cc1)C(F)(F)F] |
| 178 | | 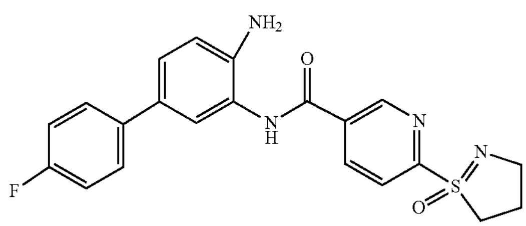 [SMILES: Nc1ccc(-c2ccc(F)cc2)cc1NC(=O)c1ccc(S2(=O)=NCCC2)nc1] |
| 179 | | 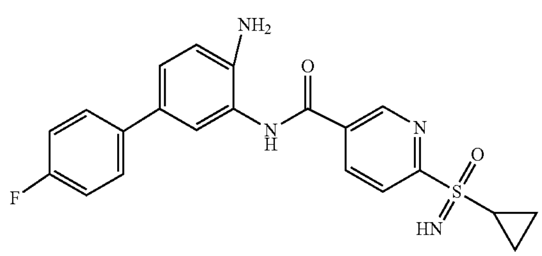 [SMILES: N=S(=O)(c1ccc(C(=O)Nc2cc(-c3ccc(F)cc3)ccc2N)cn1)C1CC1] |
| 180 | | 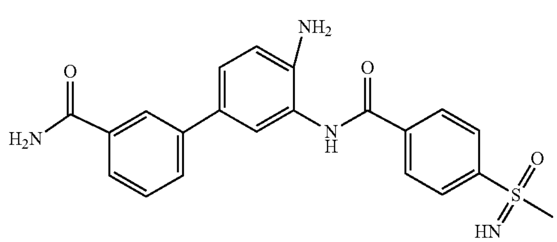 [SMILES: CS(=N)(=O)c1ccc(C(=O)Nc2cc(-c3cccc(C(N)=O)c3)ccc2N)cc1] |

TABLE 1-continued

Exemplary compounds

| Cmpd No. | Stereoche mistry | Structure |
|---|---|---|
| 181 | | 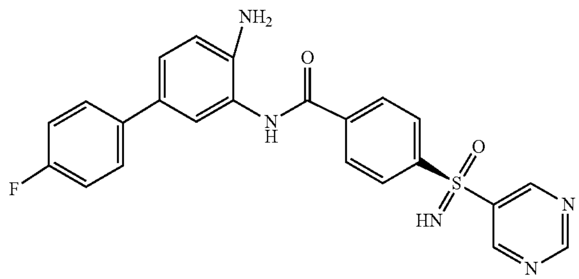 [SMILES: N=[S@@](=O)(c1ccc(C(=O)Nc2cc(-c3ccc(F)cc3)ccc2N)cc1)c1cncnc1] |
| 182 | | 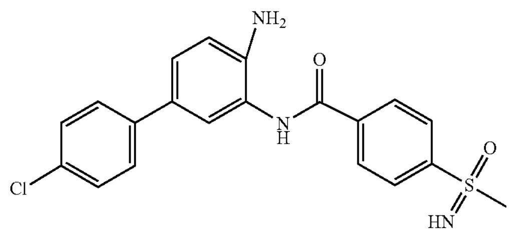 [SMILES: CS(=N)(=O)c1ccc(C(=O)Nc2cc(-c3ccc(Cl)cc3)ccc2N)cc1] |
| 183 | | 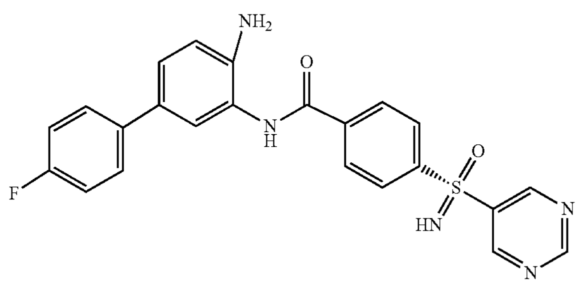 [SMILES: N=[S@](=O)(c1ccc(C(=O)Nc2cc(-c3ccc(F)cc3)ccc2N)cc1)c1cncnc1] |
| 184 | (or) | 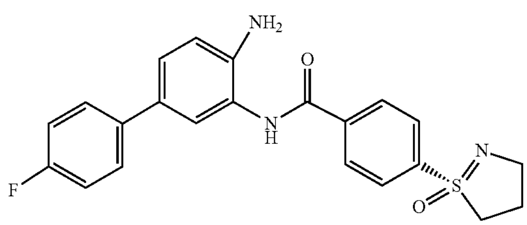 [SMILES: Nc1ccc(-c2ccc(F)cc2)cc1NC(=O)c1ccc([S@]2(=O)=NCCC2)cc1] |
| 185 | (or) | 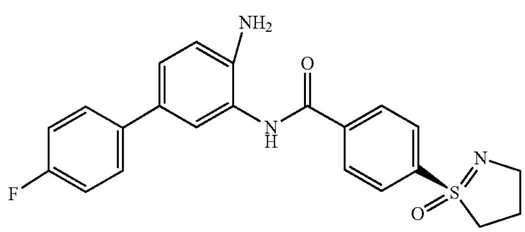 [SMILES: Nc1ccc(-c2ccc(F)cc2)cc1NC(=O)c1ccc([S@@]2(=O)=NCCC2)cc1] |
| 186 | | 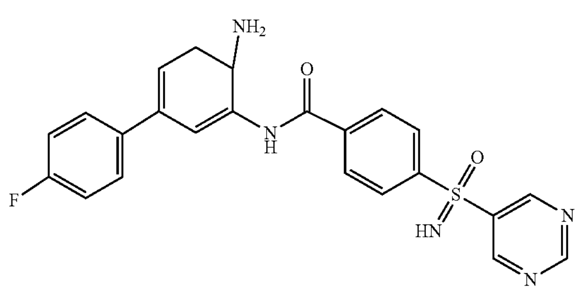 [SMILES: N=S(=O)(c1ccc(C(=O)NC2=CC(c3ccc(F)cc3)=CCC2N)cc1)c1cncnc1] |

TABLE 1-continued

Exemplary compounds

| Cmpd No. | Stereochemistry | Structure |
|---|---|---|
| 187 | | 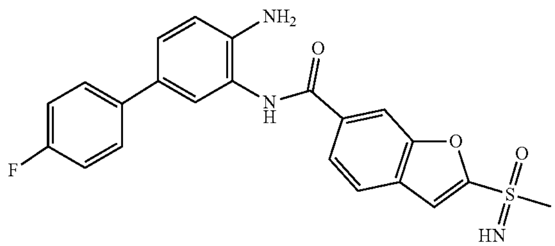 [SMILES: CS(=N)(=O)c1cc2ccc(C(=O)Nc3cc(-c4ccc(F)cc4)ccc3N)cc2o1] |
| 188 | | 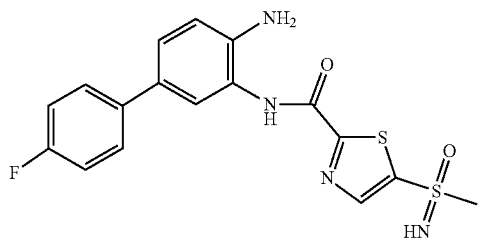 [SMILES: CS(=N)(=O)c1cnc(C(=O)Nc2cc(-c3ccc(F)cc3)ccc2N)s1] |
| 189 | | 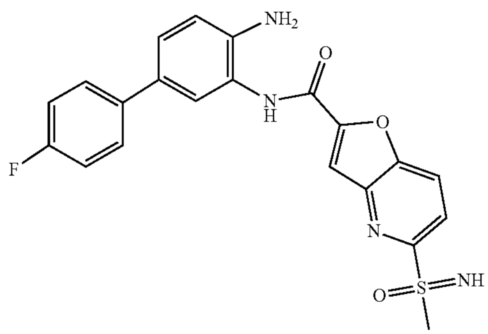 [SMILES: CS(=N)(=O)c1ccc2oc(C(=O)Nc3cc(-c4ccc(F)cc4)ccc3N)cc2n1] |
| 190 | | 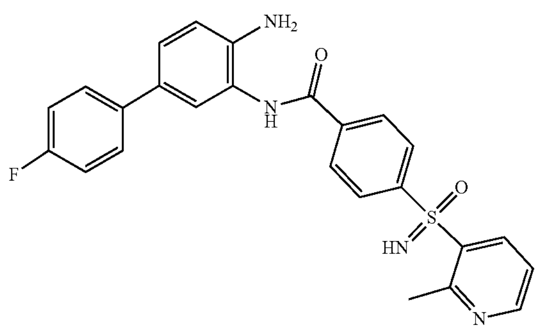 [SMILES: Cc1ncccc1S(=N)(=O)c1ccc(C(=O)Nc2cc(-c3ccc(F)cc3)ccc2N)cc1] |
| 191 | | 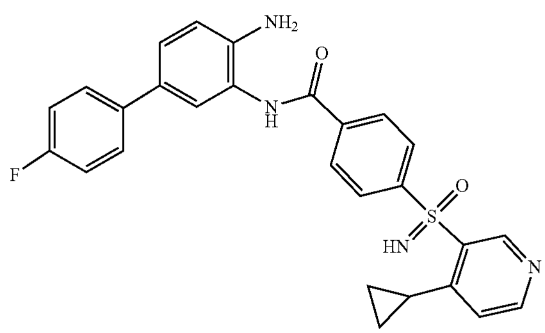 [SMILES: N=S(=O)(c1ccc(C(=O)Nc2cc(-c3ccc(F)cc3)ccc2N)cc1)c1cnccc1C1CC1] |

TABLE 1-continued

Exemplary compounds

| Cmpd No. | Stereochemistry | Structure |
|---|---|---|
| 192 | | 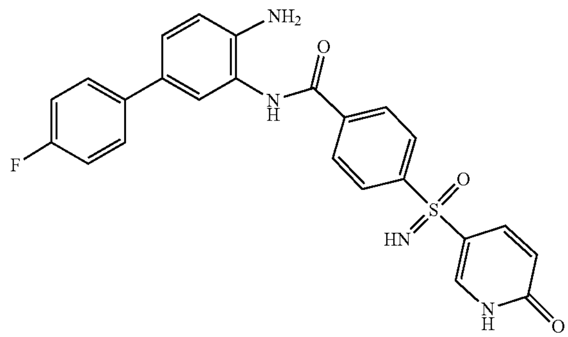 [SMILES: N=S(=O)(c1ccc(C(=O)Nc2cc(-c3ccc(F)cc3)ccc2N)cc1)c1ccc(=O)[nH]c1] |
| 193 | | 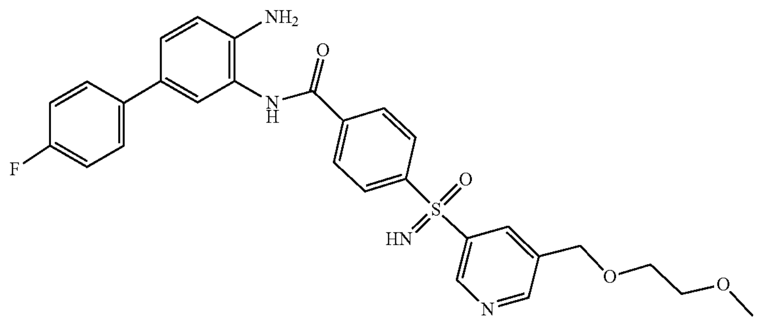 [SMILES: COCCOCc1cncc(S(=N)(=O)c2ccc(C(=O)Nc3cc(-c4ccc(F)cc4)ccc3N)cc2)c1] |
| 194 | | 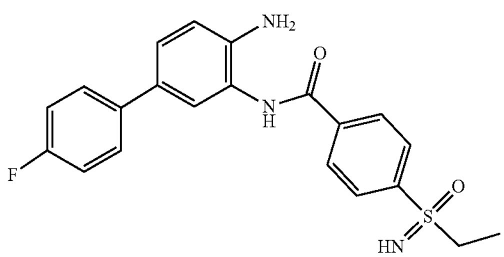 [SMILES: CCS(=N)(=O)c1ccc(C(=O)Nc2cc(-c3ccc(F)cc3)ccc2N)cc1] |
| 195 | | 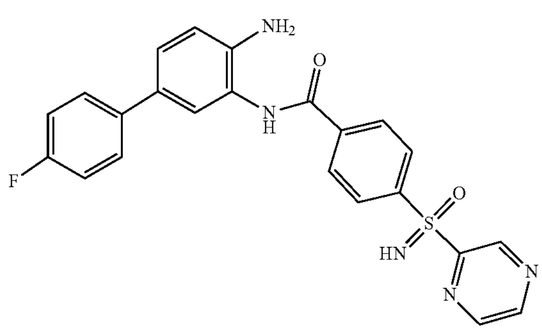 [SMILES: N=S(=O)(c1ccc(C(=O)Nc2cc(-c3ccc(F)cc3)ccc2N)cc1)c1cnccn1] |
| 196 | (and) | 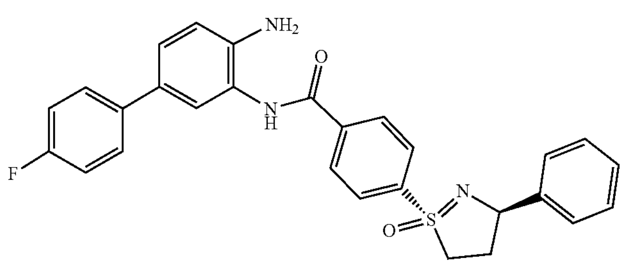 [SMILES: Nc1ccc(-c2ccc(F)cc2)cc1NC(=O)c1ccc([S@]2(=O)=N[C@@H](c3ccccc3)CC2)cc1] |

TABLE 1-continued

Exemplary compounds

| Cmpd No. | Stereochemistry | Structure |
|---|---|---|
| 197 | | 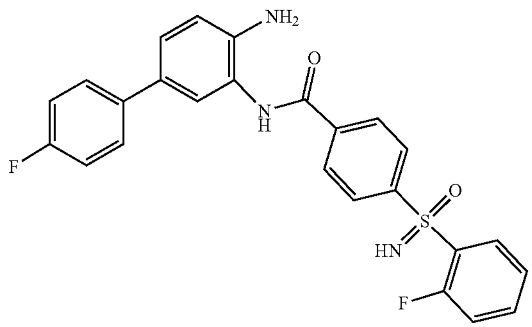 [SMILES: N=S(=O)(c1ccc(C(=O)Nc2cc(-c3ccc(F)cc3)ccc2N)cc1)c1ccccc1F] |
| 198 | | 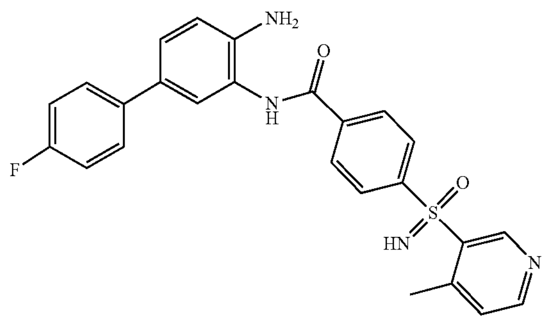 [SMILES: Cc1ccncc1S(=N)(=O)c1ccc(C(=O)Nc2cc(-c3ccc(F)cc3)ccc2N)cc1] |
| 199 | | 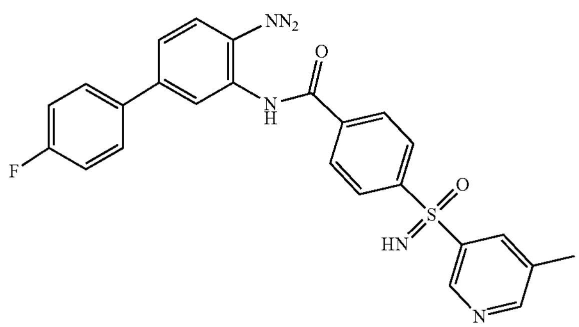 |
| 200 | | 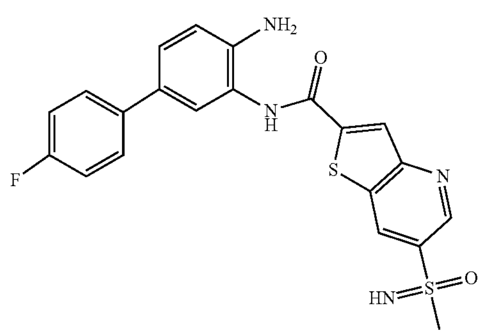 [SMILES: CS(=N)(=O)c1cnc2cc(C(=O)Nc3cc(-c4ccc(F)cc4)ccc3N)sc2c1] |
| 201 | | 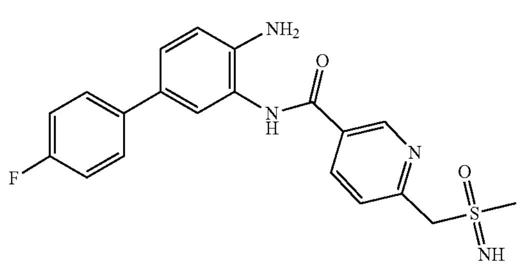 [SMILES: CS(=N)(=O)Cc1ccc(C(=O)Nc2cc(-c3ccc(F)cc3)ccc2N)cn1] |

TABLE 1-continued

Exemplary compounds

| Cmpd No. | Stereochemistry | Structure |
|---|---|---|
| 202 | | 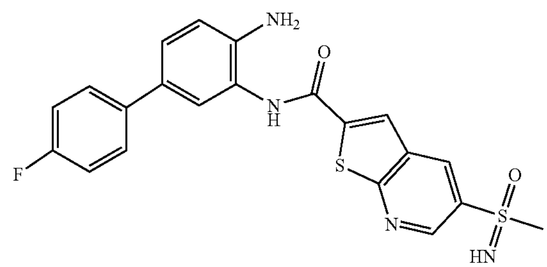 [SMILES: CS(=N)(=O)c1cnc2sc(C(=O)Nc3cc(-c4ccc(F)cc4)ccc3N)cc2c1] |
| 203 | | 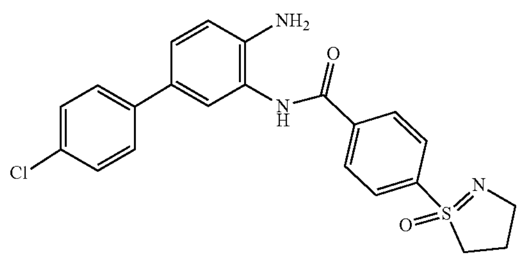 [SMILES: Nc1ccc(-c2ccc(Cl)cc2)cc1NC(=O)c1ccc(S2(=O)=NCCC2)cc1] |
| 204 | | 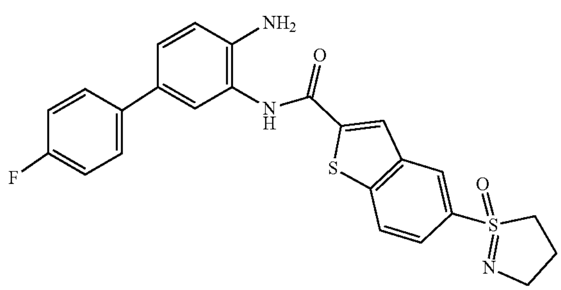 [SMILES: Nc1ccc(-c2ccc(F)cc2)cc1NC(=O)c1cc2cc(S3(=O)=NCCC3)ccc2s1] |
| 205 | | 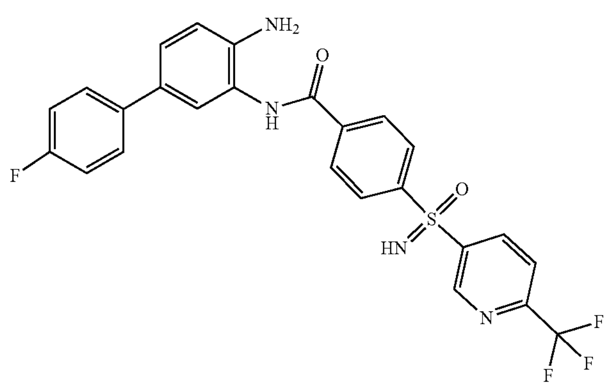 [SMILES: N=S(=O)(c1ccc(C(=O)Nc2cc(-c3ccc(F)cc3)ccc2N)cc1)c1ccc(C(F)(F)F)nc1] |
| 206 | | 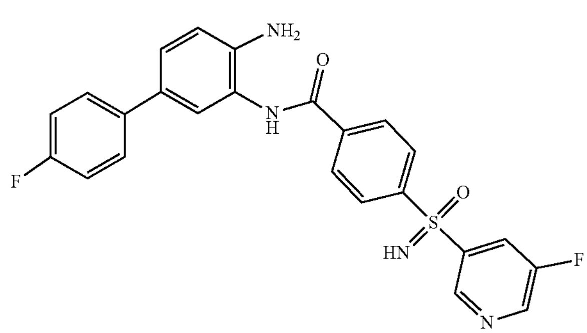 [SMILES: N=S(=O)(c1ccc(C(=O)Nc2cc(-c3ccc(F)cc3)ccc2N)cc1)c1cncc(F)c1] |

TABLE 1-continued

Exemplary compounds

| Cmpd No. | Stereochemistry | Structure |
|---|---|---|
| 207 | | 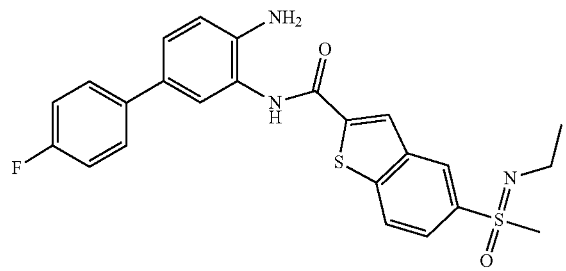 [SMILES: CCN=S(C)(=O)c1ccc2sc(C(=O)Nc3cc(-c4ccc(F)cc4)ccc3N)cc2c1] |
| 208 | | 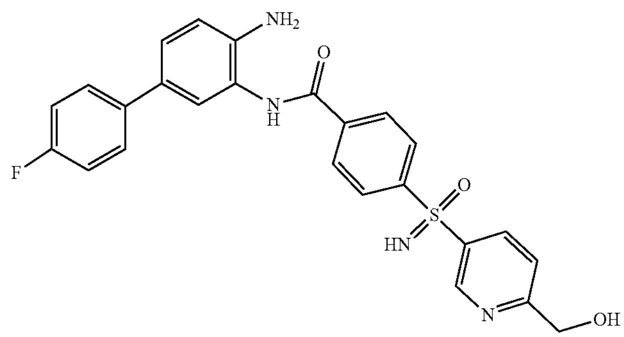 [SMILES: N=S(=O)(c1ccc(C(=O)Nc2cc(-c3ccc(F)cc3)ccc2N)cc1)c1ccc(CO)nc1] |
| 209 | | 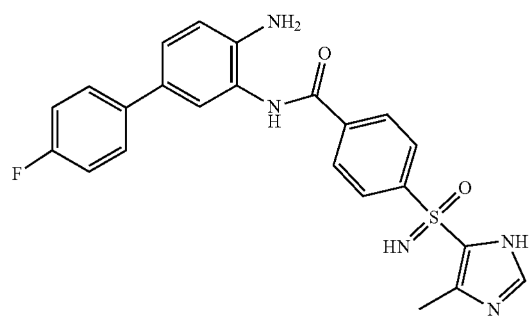 [SMILES: Cc1nc[nH]c1S(=N)(=O)c1ccc(C(=O)Nc2cc(-c3ccc(F)cc3)ccc2N)cc1] |
| 210 | | 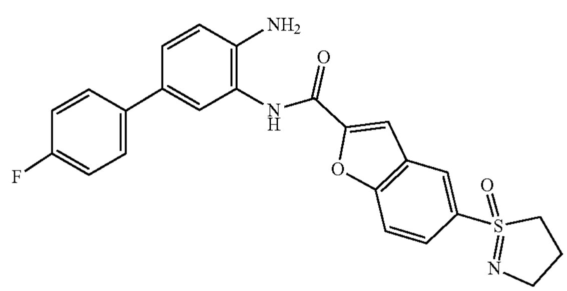 [SMILES: Nc1ccc(-c2ccc(F)cc2)cc1NC(=O)c1cc2cc(S3(=O)=NCCC3)ccc2o1] |
| 211 | | 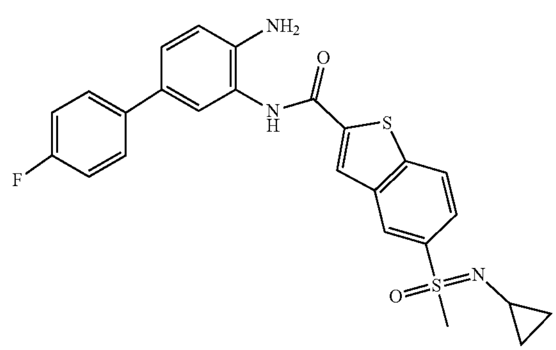 [SMILES: CS(=O)(=NC1CC1)c1ccc2sc(C(=O)Nc3cc(-c4ccc(F)cc4)ccc3N)cc2c1] |

TABLE 1-continued

Exemplary compounds

| Cmpd No. | Stereochemistry | Structure |
|---|---|---|
| 212 | (or) | 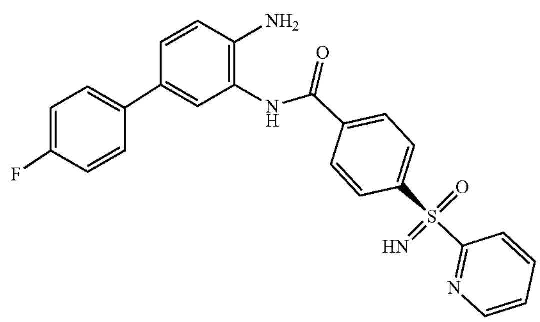 [SMILES: N=[S@@](=O)(c1ccc(C(=O)Nc2cc(-c3ccc(F)cc3)ccc2N)cc1)c1ccccn1] |
| 213 | | 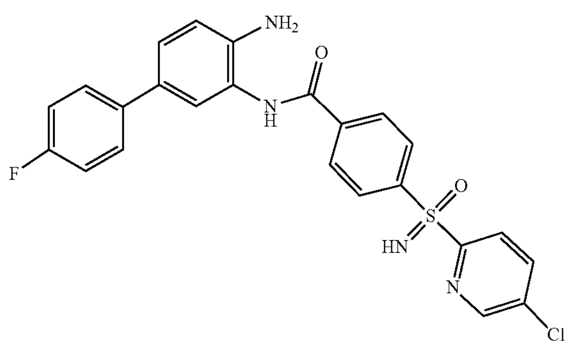 [SMILES: N=S(=O)(c1ccc(C(=O)Nc2cc(-c3ccc(F)cc3)ccc2N)cc1)c1ccc(Cl)cn1] |
| 214 | | 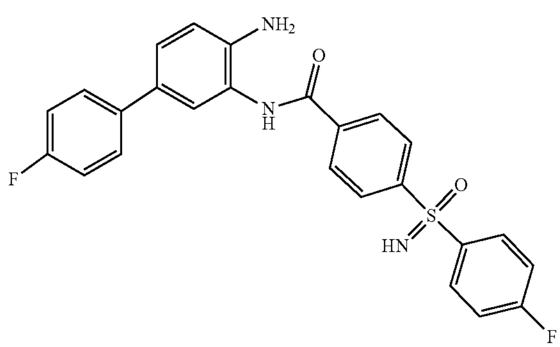 [SMILES: N=S(=O)(c1ccc(F)cc1)c1ccc(C(=O)Nc2cc(-c3ccc(F)cc3)ccc2N)cc1] |
| 215 | | 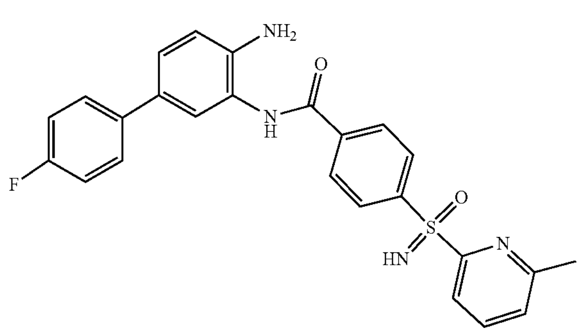 [SMILES: Cc1cccc(S(=N)(=O)c2ccc(C(=O)Nc3cc(-c4ccc(F)cc4)ccc3N)cc2)n1] |

TABLE 1-continued

Exemplary compounds

| Cmpd No. | Stereochemistry | Structure |
|---|---|---|
| 216 | | 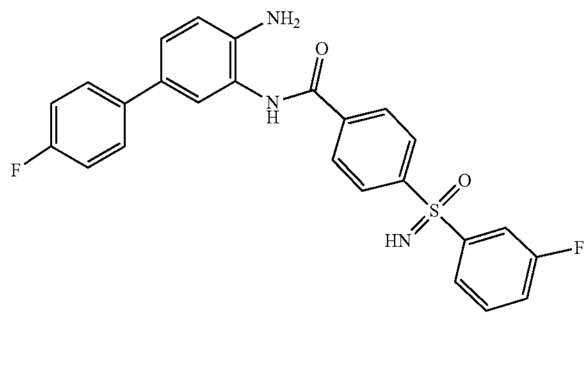 [SMILES: N=S(=O)(c1ccc(C(=O)Nc2cc(-c3ccc(F)cc3)ccc2N)cc1)c1cccc(F)c1] |
| 217 | | 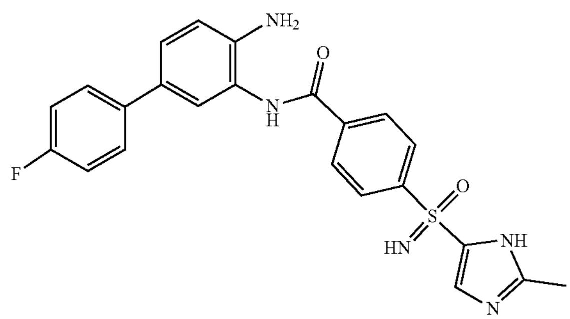 [SMILES: Cc1ncc(S(=N)(=O)c2ccc(C(=O)Nc3cc(-c4ccc(F)cc4)ccc3N)cc2)[nH]1] |
| 218 | | 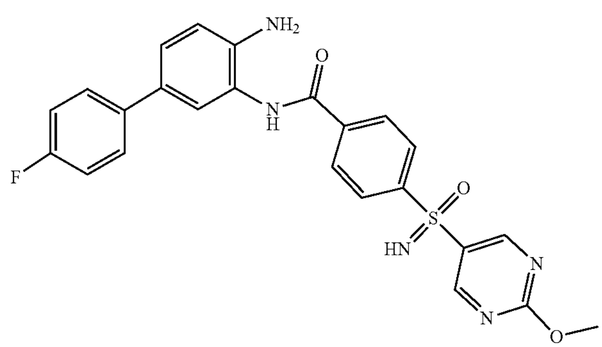 [SMILES: COc1ncc(S(=N)(=O)c2ccc(C(=O)Nc3cc(-c4ccc(F)cc4)ccc3N)cc2)cn1] |
| 219 | | 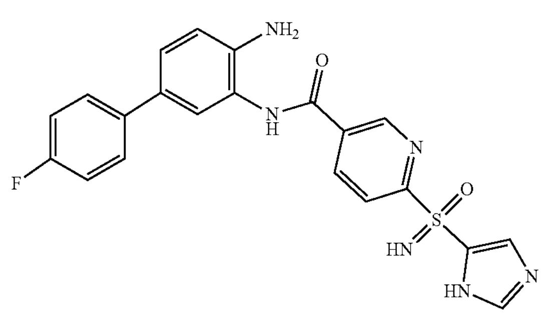 [SMILES: N=S(=O)(c1ccc(C(=O)Nc2cc(-c3ccc(F)cc3)ccc2N)cn1)c1cnc[nH]1] |

TABLE 1-continued

Exemplary compounds

| Cmpd No. | Stereochemistry | Structure |
|---|---|---|
| 220 | (or) | 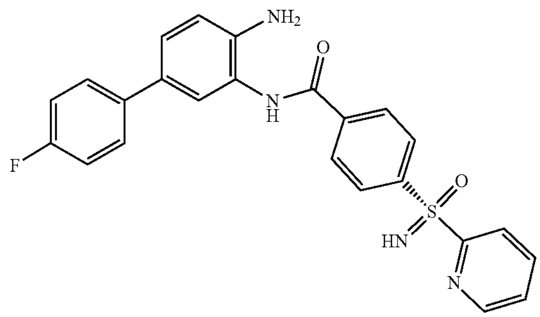 [SMILES: N=[S@](=O)(c1ccc(C(=O)Nc2cc(-c3ccc(F)cc3)ccc2N)cc1)c1ccccn1] |
| 221 | | 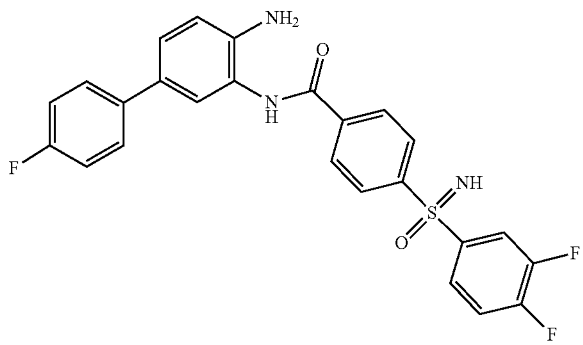 [SMILES: N=S(=O)(c1ccc(C(=O)Nc2cc(-c3ccc(F)cc3)ccc2N)cc1)c1ccc(F)c(F)c1] |
| 222 | | 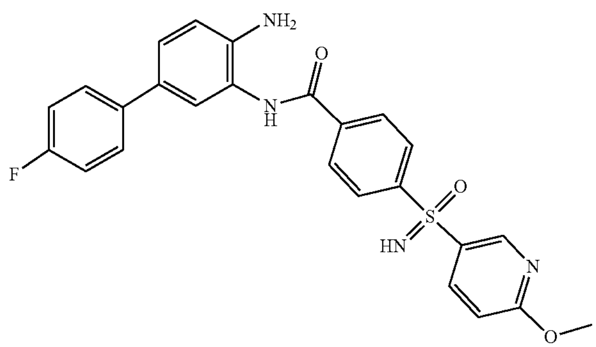 [SMILES: COc1ccc(S(=N)(=O)c2ccc(C(=O)Nc3cc(-c4ccc(F)cc4)ccc3N)cc2)cn1] |
| 223 | | 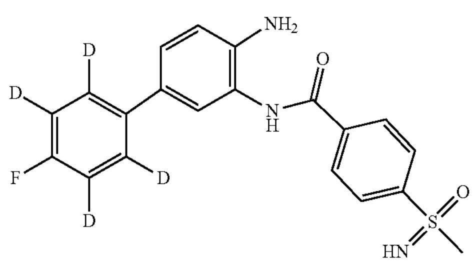 [SMILES: [2H]c1c([2H])c(-c2ccc(N)c(NC(=O)c3ccc(S(C)(=N)=O)cc3)c2)c([2H])c([2H])c1F] |
| 224 | | 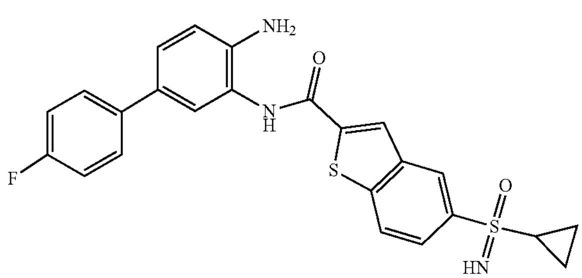 [SMILES: N=S(=O)(c1ccc2sc(C(=O)Nc3cc(-c4ccc(F)cc4)ccc3N)cc2c1)C1CC1] |

TABLE 1-continued

Exemplary compounds

| Cmpd No. | Stereochemistry | Structure |
|---|---|---|
| 225 | | 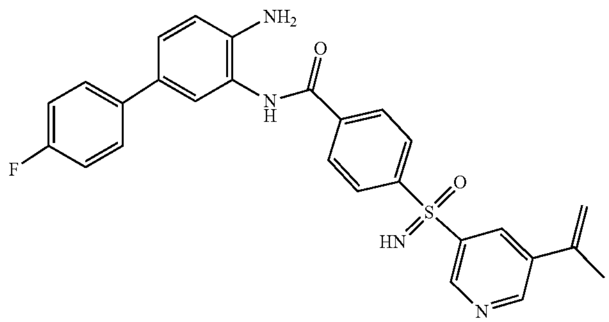 [SMILES: C=C(C)c1cncc(S(=N)(=O)c2ccc(C(=O)Nc3cc(-c4ccc(F)cc4)ccc3N)cc2)c1] |
| 226 | | 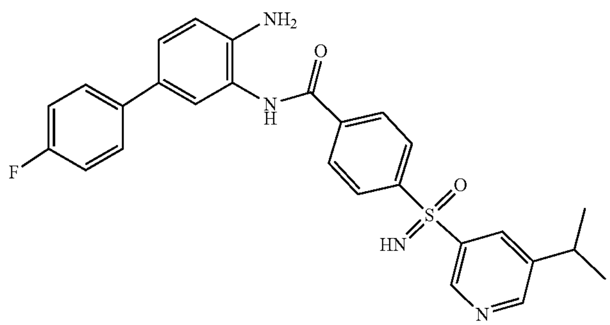 [SMILES: CC(C)c1cncc(S(=N)(=O)c2ccc(C(=O)Nc3cc(-c4ccc(F)cc4)ccc3N)cc2)c1] |
| 227 | | 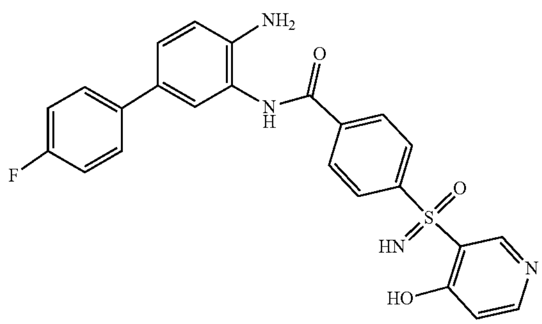 [SMILES: N=S(=O)(c1ccc(C(=O)Nc2cc(-c3ccc(F)cc3)ccc2N)cc1)c1cnccc1O] |
| 228 | | 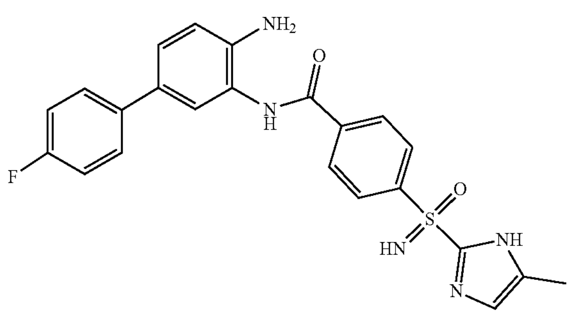 [SMILES: Cc1cnc(S(=N)(=O)c2ccc(C(=O)Nc3cc(-c4ccc(F)cc4)ccc3N)cc2)[nH]1] |
| 229 | (and) | 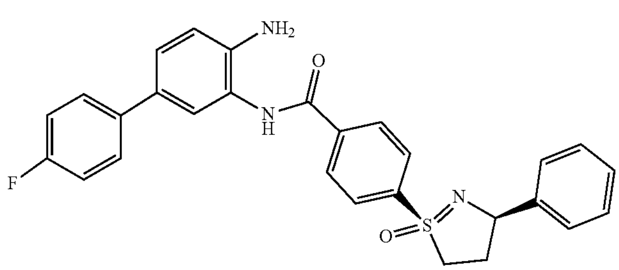 [SMILES: Nc1ccc(-c2ccc(F)cc2)cc1NC(=O)c1ccc([S@@]2(=O)=N[C@@H](c3ccccc3)CC2)cc1] |

TABLE 1-continued

Exemplary compounds

| Cmpd No. | Stereochemistry | Structure |
|---|---|---|
| 230 | | 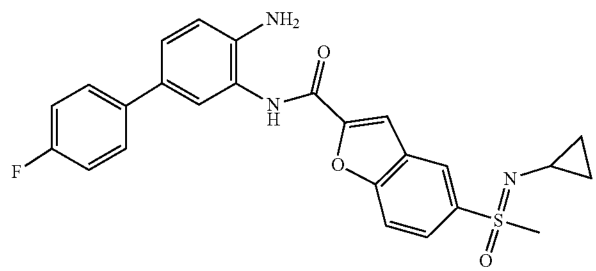 [SMILES: CS(=O)(=NC1CC1)c1ccc2oc(C(=O)Nc3cc(-c4ccc(F)cc4)ccc3N)cc2c1] |
| 231 | | 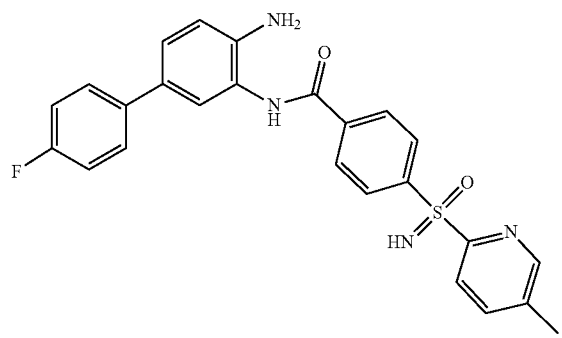 [SMILES: Cc1ccc(S(=N)(=O)c2ccc(C(=O)Nc3cc(-c4ccc(F)cc4)ccc3N)cc2)nc1] |
| 232 | | 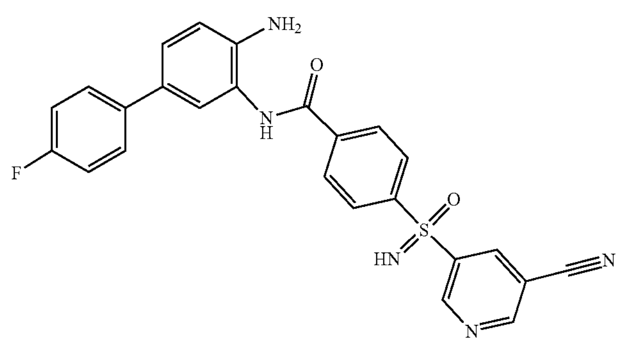 [SMILES: N#Cc1cncc(S(=N)(=O)c2ccc(C(=O)Nc3cc(-c4ccc(F)cc4)ccc3N)cc2)c1] |
| 233 | | 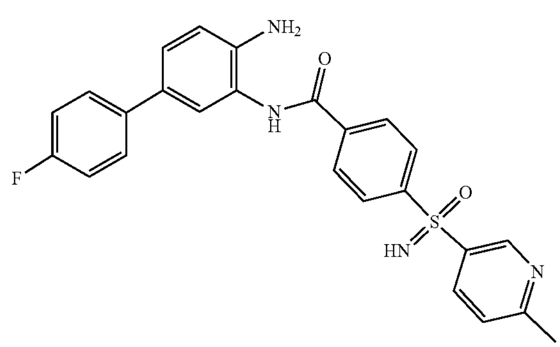 [SMILES: Cc1ccc(S(=N)(=O)c2ccc(C(=O)Nc3cc(-c4ccc(F)cc4)ccc3N)cc2)cn1] |

TABLE 1-continued
Exemplary compounds
| Cmpd No. | Stereochemistry | Structure |
|---|---|---|
| 234 | | 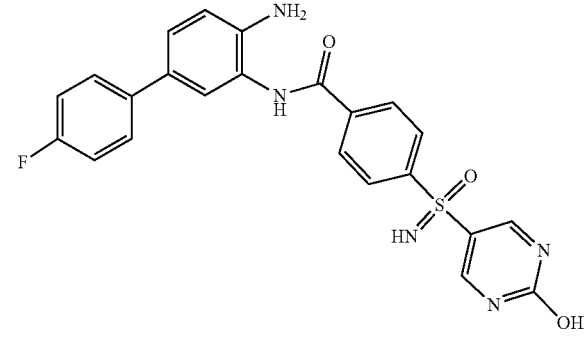 [SMILES: N=S(=O)(c1ccc(C(=O)Nc2cc(-c3ccc(F)cc3)ccc2N)cc1)c1cnc(O)nc1] |
| 235 | | 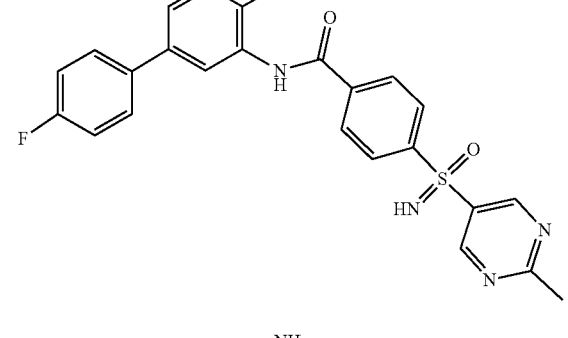 |
| 236 | | 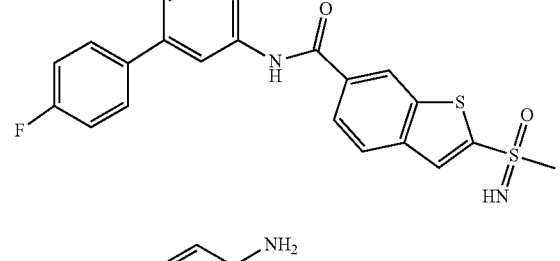 |
| 237 | | 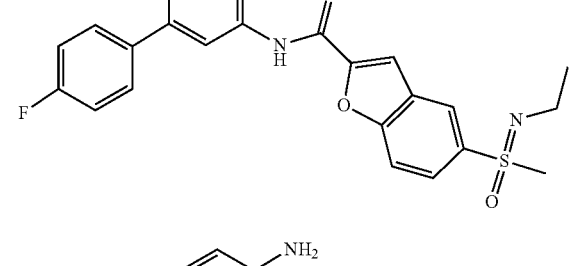 |
| 238 | | 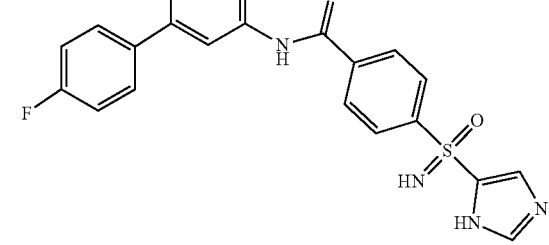 |

TABLE 1-continued

Exemplary compounds

| Cmpd No. | Stereochemistry | Structure |
|---|---|---|
| 239 | | 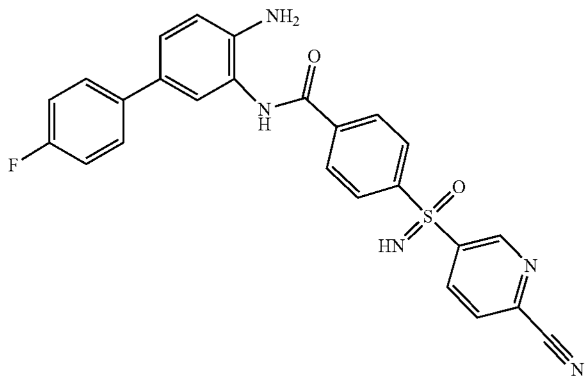 [SMILES: N#Cc1ccc(S(=N)(=O)c2ccc(C(=O)Nc3cc(-c4ccc(F)cc4)ccc3N)cc2)cn1] |
| 240 | | 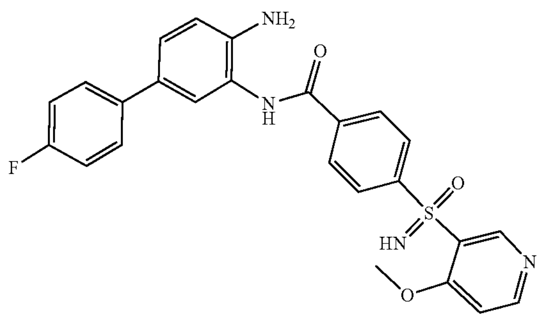 [SMILES: COc1ccncc1S(=N)(=O)c1ccc(C(=O)Nc2cc(-c3ccc(F)cc3)ccc2N)cc1] |
| 241 | | 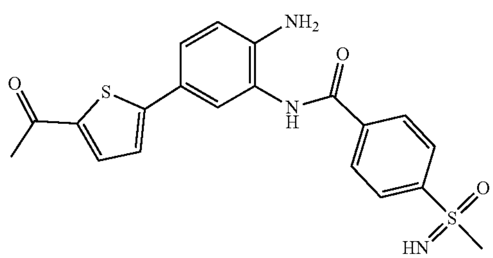 [SMILES: CC(=O)c1ccc(-c2ccc(N)c(NC(=O)c3ccc(S(C)(=N)=O)cc3)c2)s1] |
| 242 | | 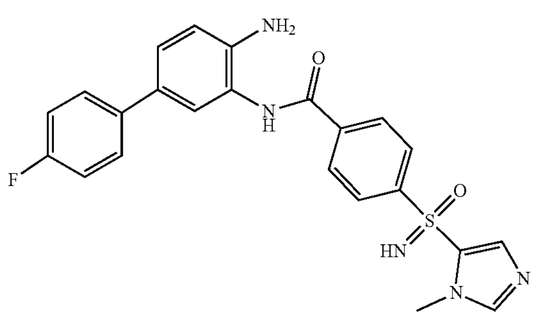 [SMILES: Cn1cncc1S(=N)(=O)c1ccc(C(=O)Nc2cc(-c3ccc(F)cc3)ccc2N)cc1] |
| 243 | | 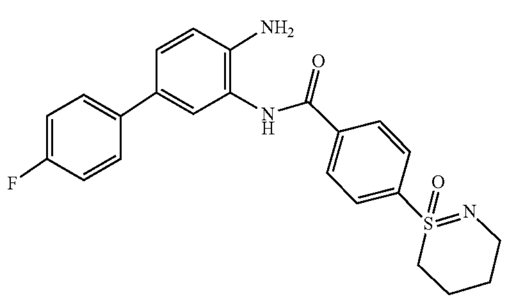 [SMILES: Nc1ccc(-c2ccc(F)cc2)cc1NC(=O)c1ccc(S2(=O)=NCCCC2)cc1] |

TABLE 1-continued

Exemplary compounds

| Cmpd No. | Stereochemistry | Structure |
|---|---|---|
| 244 | | 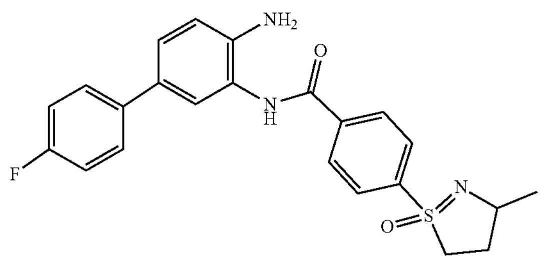 [SMILES: CC1CCS(=O)(c2ccc(C(=O)Nc3cc(-c4ccc(F)cc4)ccc3N)cc2)=N1] |
| 245 | | 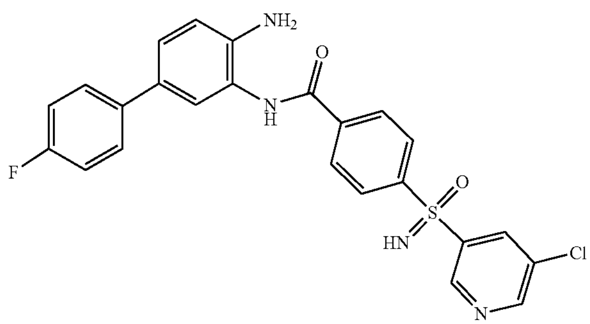 [SMILES: N=S(=O)(c1ccc(C(=O)Nc2cc(-c3ccc(F)cc3)ccc2N)cc1)c1cncc(Cl)c1] |
| 246 | | 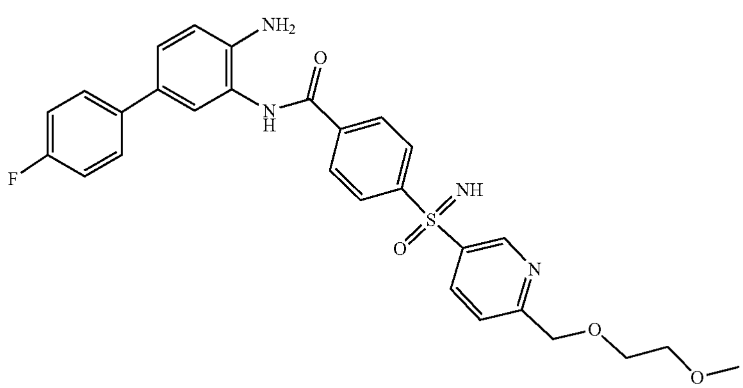 [SMILES: COCCOCc1ccc(S(=N)(=O)c2ccc(C(=O)Nc3cc(-c4ccc(F)cc4)ccc3N)cc2)cn1] |
| 247 | | 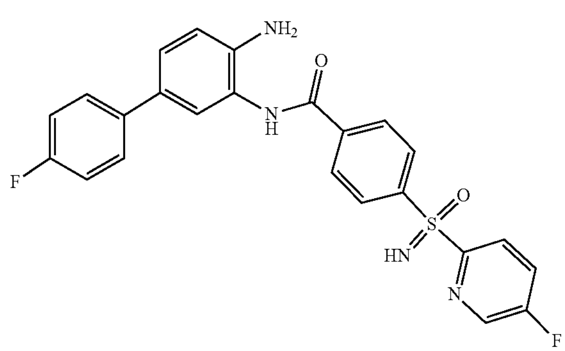 [SMILES: N=S(=O)(c1ccc(C(=O)Nc2cc(-c3ccc(F)cc3)ccc2N)cc1)c1ccc(F)cn1] |

TABLE 1-continued
Exemplary compounds
| Cmpd No. | Stereochemistry | Structure |
|---|---|---|
| 248 | | 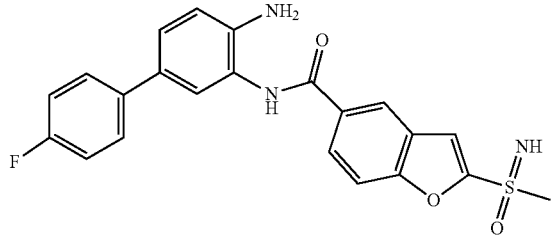 [SMILES: CS(=N)(=O)c1cc2cc(C(=O)Nc3cc(-c4ccc(F)cc4)ccc3N)ccc2o1] |
| 249 | | 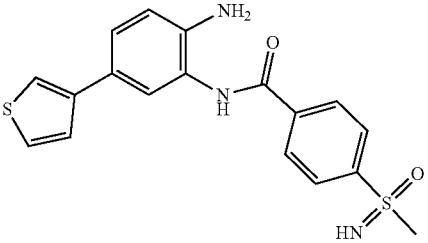 [SMILES: CS(=N)(=O)c1ccc(C(=O)Nc2cc(-c3ccsc3)ccc2N)cc1] |
| 250 | | 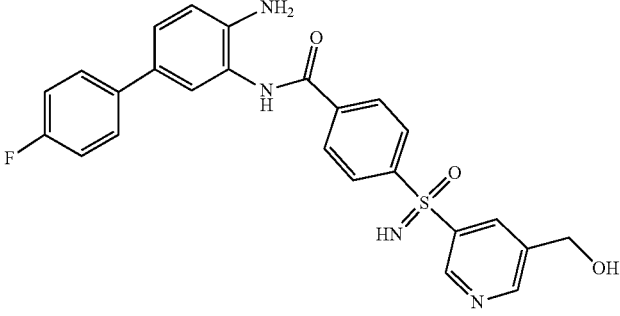 [SMILES: N=S(=O)(c1ccc(C(=O)Nc2cc(-c3ccc(F)cc3)ccc2N)cc1)c1cncc(CO)c1] |
| 251 | | 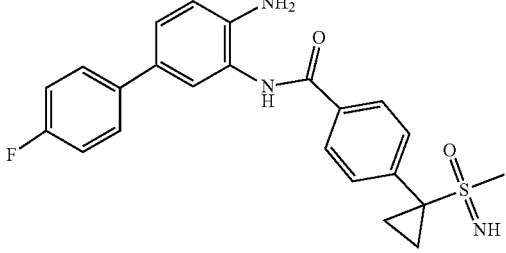 |
| 252 | | 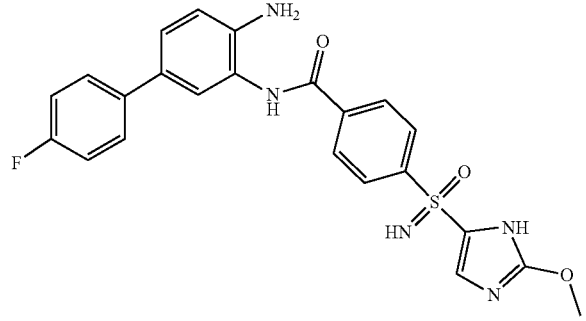 [SMILES: COc1ncc(S(=N)(=O)c2ccc(C(=O)Nc3cc(-c4ccc(F)cc4)ccc3N)cc2)[nH]1] |

TABLE 1-continued

Exemplary compounds

| Cmpd No. | Stereochemistry | Structure |
|---|---|---|
| 253 | | 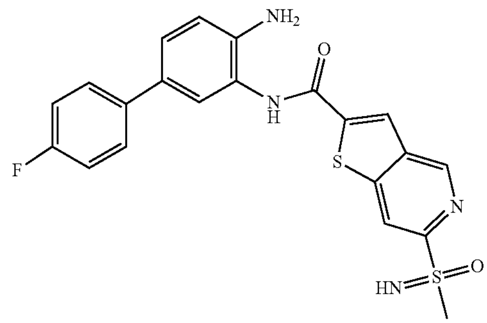 [SMILES: CS(=N)(=O)c1cc2sc(C(=O)Nc3cc(-c4ccc(F)cc4)ccc3N)cc2cn1] |
| 254 | | 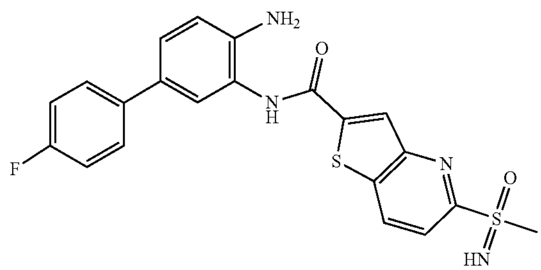 [SMILES: CS(=N)(=O)c1ccc2sc(C(=O)Nc3cc(-c4ccc(F)cc4)ccc3N)cc2n1] |
| 255 | | 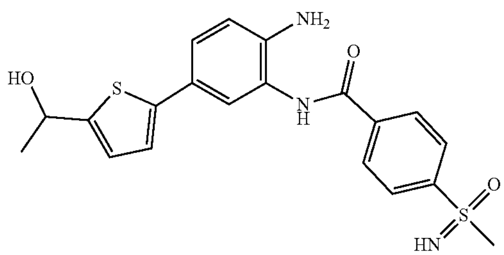 [SMILES: CC(O)c1ccc(-c2ccc(N)c(NC(=O)c3ccc(S(C)(=N)=O)cc3)c2)s1] |
| 256 | | 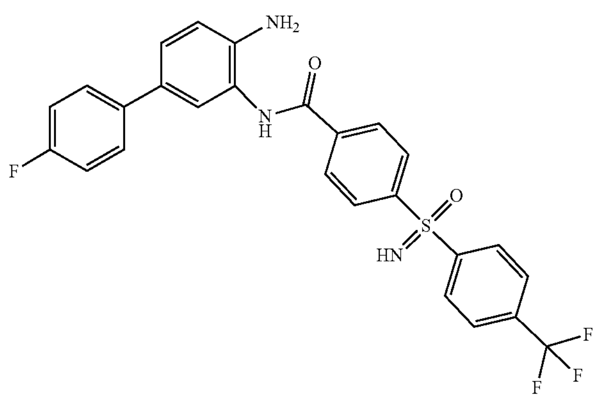 [SMILES: CNc1ccc(-c2ccc(F)cc2)cc1NC(=O)c1ccc(S(=N)(=O)c2ccc(C(F)(F)F)cc2)cc1] |
| 257 | | 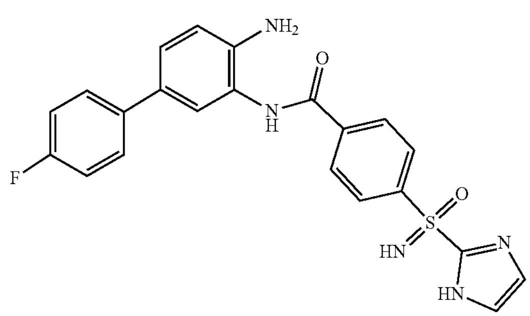 [SMILES: N=S(=O)(c1ccc(C(=O)Nc2cc(-c3ccc(F)cc3)ccc2N)cc1)c1ncc[nH]1] |

TABLE 1-continued

Exemplary compounds

| Cmpd No. | Stereochemistry | Structure |
|---|---|---|
| 258 | | 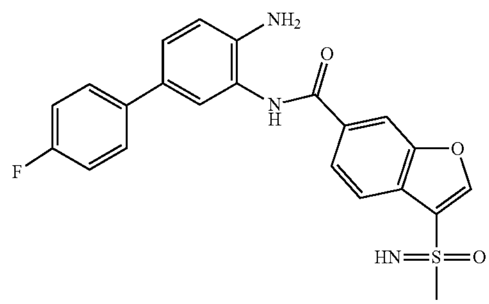 [SMILES: CS(=N)(=O)c1coc2cc(C(=O)Nc3cc(-c4ccc(F)cc4)ccc3N)ccc12] |
| 259 | | 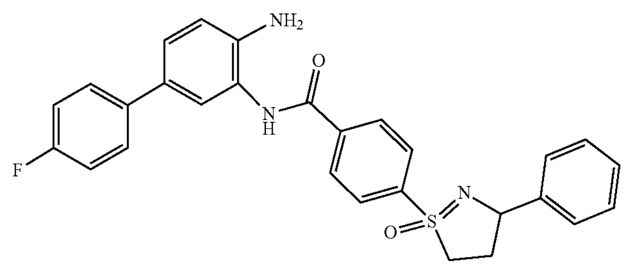 [SMILES: Nc1ccc(-c2ccc(F)cc2)cc1NC(=O)c1ccc(S2(=O)=NC(c3ccccc3)CC2)cc1] |
| 260 | | 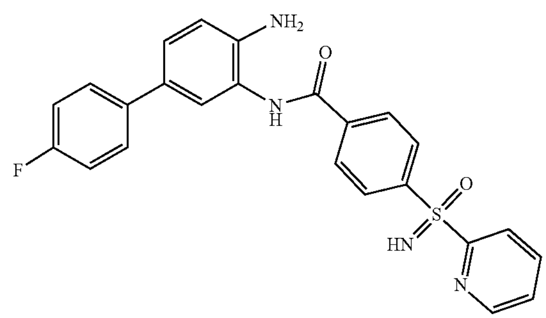 [SMILES: N=S(=O)(c1ccc(C(=O)Nc2cc(-c3ccc(F)cc3)ccc2N)cc1)c1ccccn1] |

Methods of Treatment

In some embodiments, provided herein is a method of treating a disease or disorder that can be treated by inhibition of HDAC, the method comprising administering to a patient in need thereof a compound described herein or a composition described herein.

In some embodiments, provided herein are methods of treating human or animal subjects having or having been diagnosed with a disease or disorder that can be treated by inhibition of HDAC (e.g., cancer) comprising administering to the subject in need thereof a therapeutically effective amount of a compound of the present invention (e.g., a compound of Formula (I) or a compound of Table 1) or a pharmaceutically acceptable salt thereof.

In some embodiments, the disease or disorder is cancer.

In some embodiments, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

In some embodiments, the cancer is brain tumors such as astrocytoma and glioblastoma, brain metastases, medulloblastomas, meningiomas and oligodendrogliomas; tumors of the peripheral or central nervous systems; nerve tumors; non-Hodgkin's lymphomas, such as for example low-malignancy non-Hodgkin's lymphomas, Burkitt's lymphoma; lymphoma (lymphosarcoma); Hodgkin's disease, non-Hodgkin's lymphomas; bone cancers; leukemias, such as acute lymphatic/lymphoblastic leukemia, acute myeloid leukemia, chronic lymphatic leukemia, chronic myeloid leukemia; intestinal cancers such as for example carcinomas of the rectum, colon, colorectal carcinoma, anal carcinoma, large bowel; pancreatic cancer or carcinoma of the pancreas; gallbladder cancer; bile duct cancer; liver cancers; stomach cancer or gastric carcinoma; bladder cancer or carcinoma of the bladder; renal cancers; lung cancer (bronchial carcinoma) such as for example small-cell bronchial carcinomas and non-small cell bronchial carcinomas (NSCLC); plate epithelial carcinomas, adenocarcinomas and large-cell bronchial carcinomas; breast cancers; uterine cancer or endometrial carcinoma; ovarian cancer or ovarian carcinoma; testicular cancer; penile cancer; prostate cancer; vaginal cancer; cancers of the urethra and cancer of the vulva; laryngeal cancer; head and neck tumors; throat cancer or carcinomas of the pharynx; esophageal cancer; melanomas; epidermoid carcinoma and plate epithelial carcinoma of the skin; retinoblastoma, thyroid carcinomas; thymomas, or Cancer of Unknown Primary (CUP).

In some embodiments, the cancer is a HDAC-related glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

In some embodiments, the cancer (e.g., the HDAC-related cancer) is carcinoma of unknown primary (CUP), colorectal cancer (e.g., colorectal carcinoma), cervical cancer or non-small cell lung cancer (NSCLC; e.g., lung squamous or lung adenocarcinoma). In some embodiments, the cancer is non-small cell lung cancer (NSCLC; e.g., lung squamous or lung adenocarcinoma). In some embodiments, the cancer is cervical cancer. In some embodiments, the cancer is colorectal cancer (e.g., colorectal carcinoma). In some embodiments, the cancer is carcinoma of unknown primary (CUP).

The compounds described herein (e.g., a compound of Formula (I) or a compound of Table 1, or pharmaceutically acceptable salts thereof) described herein can be used in a method of comprising the step of administering to the subject, a HDAC inhibitor (e.g., a compound of Formula (I) or a compound of Table 1, or pharmaceutically acceptable salts thereof) in an amount that is effective to inhibit HDAC. In one embodiment, the subject in need thereof suffers from a cancer selected from glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

In some embodiments, the cancer is selected from the group consisting of a melanoma, bladder cancer, colorectal cancer, head and neck cancer, esophageal cancer, liver cancer, lung cancer, pancreas cancer, and stomach cancer.

In another aspect, provided is a use of a compound of the disclosure in the manufacture of a medicament for the treatment of cancer.

Cancers: Cancer cells grow quickly and in low oxygen environments by activating different elements of the cellular stress response. Without wishing to be bound by a theory, compounds of Formula (I) or subformulas thereof may also be used for treatment of cancer, as a greater understanding of the role of HDACs in cancer has recently begun to emerge. Additionally, HDAC inhibitors can be combined with one or more cancer therapies, such as chemotherapy and radiation therapy. A "cancer" in a subject refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within an animal, or may be a non-tumorigenic cancer cell, such as a leukemia cell. In some circumstances, cancer cells will be in the form of a tumor; such cells may exist locally within an animal, or circulate in the blood stream as independent cells, for example, leukemic cells.

Exemplary cancers include but are not limited to glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

Another exemplary list of cancers includes but is not limited to brain tumors such as astrocytoma and glioblastoma, brain metastases, medulloblastomas, meningiomas and oligodendrogliomas; tumors of the peripheral or central nervous systems; nerve tumors; non-Hodgkin's lymphomas, such as for example low-malignancy non-Hodgkin's lymphomas, Burkitt's lymphoma; lymphoma (lymphosarcoma); Hodgkin's disease, non-Hodgkin's lymphomas; bone cancers; leukemias, such as acute lymphatic/lymphoblastic leukemia, acute myeloid leukemia, chronic lymphatic leukemia, chronic myeloid leukemia; intestinal cancers such as for example carcinomas of the rectum, colon, colorectal carcinoma, anal carcinoma, large bowel; pancreatic cancer or carcinoma of the pancreas; gallbladder cancer; bile duct cancer; liver cancers; stomach cancer or gastric carcinoma; bladder cancer or carcinoma of the bladder; renal cancers; lung cancer (bronchial carcinoma) such as for example small-cell bronchial carcinomas and non-small cell bronchial carcinomas (NSCLC); plate epithelial carcinomas, adenocarcinomas and large-cell bronchial carcinomas; breast cancers; uterine cancer or endometrial carcinoma; ovarian cancer or ovarian carcinoma; testicular cancer; penile cancer; prostate cancer; vaginal cancer; cancers of the urethra and cancer of the vulva; laryngeal cancer; head and neck tumors; throat cancer or carcinomas of the pharynx; esophageal cancer; melanomas; epidermoid carcinoma and plate epithelial carcinoma of the skin; retinoblastoma, thyroid carcinomas; thymomas, or Cancer of Unknown Primary.

In some cases, the cancer is a HDAC-related glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

In some cases, the cancer is a HDAC-related brain tumor such as astrocytoma and glioblastoma, brain metastases, medulloblastomas, meningiomas and oligodendrogliomas; tumors of the peripheral or central nervous systems; nerve tumors; non-Hodgkin's lymphomas, such as for example low-malignancy non-Hodgkin's lymphomas, Burkitt's lymphoma; lymphoma (lymphosarcoma); Hodgkin's disease, non-Hodgkin's lymphomas; bone cancers; leukemias, such as acute lymphatic/lymphoblastic leukemia, acute myeloid leukemia, chronic lymphatic leukemia, chronic myeloid leukemia; intestinal cancers such as for example carcinomas of the rectum, colon, colorectal carcinoma, anal carcinoma, large bowel; pancreatic cancer or carcinoma of the pancreas; gallbladder cancer; bile duct cancer; liver cancers; stomach cancer or gastric carcinoma; bladder cancer or carcinoma of the bladder; renal cancers; lung cancer (bronchial carcinoma) such as for example small-cell bronchial carcinomas and non-small cell bronchial carcinomas (NSCLC); plate epithelial carcinomas, adenocarcinomas and large-cell bronchial carcinomas; breast cancers; uterine cancer or endometrial carcinoma; ovarian cancer or ovarian carcinoma; testicular cancer; penile cancer; prostate cancer; vaginal cancer; cancers of the urethra and cancer of the vulva; laryngeal cancer; head and neck tumors; throat cancer or carcinomas of the pharynx; esophageal cancer; melanomas; epidermoid carcinoma and plate epithelial carcinoma of the skin; retinoblastoma, thyroid carcinomas; thymomas, or Cancer of Unknown Primary.

In some cases, the cancer (e.g., the HDAC-related cancer) is carcinoma of unknown primary (CUP), colorectal cancer (e.g., colorectal carcinoma), cervical cancer or non-small cell lung cancer (NSCLC; e.g., lung squamous or lung adenocarcinoma). In some embodiments, the cancer is non-small cell lung cancer (NSCLC; e.g., lung squamous or lung adenocarcinoma). In some embodiments, the cancer is cervical cancer. In some embodiments, the cancer is colorectal cancer (e.g., colorectal carcinoma). In some embodiments, the cancer is carcinoma of unknown primary (CUP).

In some cases, the subject in need thereof suffers from a cancer selected from glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

Combination Therapy

Provided herein are methods of treatment of diseases or disorders (e.g., cancers) with a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), or a compound of Table 1, or pharmaceutically acceptable salts thereof) in combination with a second therapeutic agent.

The term "Combination" refers to either a fixed combination in one dosage unit form, or a combined administration where a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is) or a compound of Table 1, or pharmaceutically acceptable salts thereof) and a combination partner (e.g., another drug as explained below, also referred to as "therapeutic agent" or "co-agent") may be administered independently at the same time or separately within time intervals, especially where these time intervals allow that the combination partners show a cooperative, e.g., synergistic effect. The single components may be packaged in a kit or separately. One or both of the components (e.g., powders or liquids) may be reconstituted or diluted to a desired dose prior to administration. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one therapeutic agent and includes both fixed and non-fixed combinations of the therapeutic agents. The term "fixed combination" means that the therapeutic agents, e.g., a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), or a compound of Table 1, or pharmaceutically acceptable salts thereof) and a combination partner, are both administered to a patient simultaneously in the form of a single entity or dosage. The term "non-fixed combination" means that the therapeutic agents, e.g., a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), or a compound of Table 1, or pharmaceutically acceptable salts thereof) and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more therapeutic agent.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., tablets, capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times.

In certain embodiments, compounds of the present invention are combined with other therapeutic agents, including, but not limited to, other anti-cancer agents, anti-allergic agents, anti-nausea agents (or anti-emetics), pain relievers, cytoprotective agents, and combinations thereof.

General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), nab-paclitaxel (Abraxane®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Further compounds of particular interest for combinations with the compounds of the present invention include: EGFR-inhibitors, such as cetuximab, panitumimab, erlotinib, gefitinib and EGFRi NOS; MAPK-pathway inhibitors, such as BRAFi, panRAFi, MEKi, ERKi; PI3K-mTOR pathway inhibitors, such as alpha-specific PI3Ki, pan-class I PI3Ki and mTOR/PI3Ki, particularly everolimus and analogues thereof.

Specific compounds and classes of compounds acting via specific mechanisms can be particularly effective in conjunction with compounds of Formula (I) (e.g., compounds of Formula (Ia), (Ib), (Ic), (Id), (Ie), (If), (Ig), (Ih), (Ii), (Ij), (Ik), (Im), (In), (Io), (Ip), (Iq), (Ir) or (Is), or a compound of Table 1, or pharmaceutically acceptable salts thereof). For example, PRMT5 is known to associate with SWI/SNF chromatin remodeling complexes along with other co-repressor molecules like HDAC2. PRMT5 activity on target H4R3 and H3R8 is enhanced when lysine residues become deacetylated by HDAC enzymes. Thus, HDAC inhibitors can be effective (e.g., synergistic) when used in conjunction with PRMT5 inhibitors (WO 011/079236).

Thus, compound of Formula (I) can be used in combination with other compounds, for example: PRMT5 inhibitor or DNA methyltransferase inhibitor. In some embodiments, the DNA methyltransferase inhibitor is 5-azacytidine.

In some embodiments, provided is a method of treating a disease or disorder (e.g., cancer) comprising administering or coadministering, in any order, to a patient in need thereof, a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), or a compound of Table 1, or pharmaceutically acceptable salts thereof) and a MAT2A inhibitor.

In some embodiments, provided is a method of treating a disease or disorder (e.g., cancer) comprising administering or coadministering, in any order, to a patient in need thereof, a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), or a compound of Table 1, or pharmaceutically acceptable salts thereof) and an inhibitor of a protein which interacts with or is required for PRMT5 function, including, but not limited to, pICIN, WDR77 or RIOK1.

In some embodiments, provided is a method of treating a disease or disorder (e.g., cancer) comprising administering or coadministering, in any order, to a patient in need thereof, a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), or a compound of Table 1, or pharmaceutically acceptable salts thereof) and an HDM2 inhibitor and/or with 5-FU.

In some embodiments, provided is a method of treating a disease or disorder (e.g., cancer) comprising administering or coadministering, in any order, to a patient in need thereof, a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), or a compound of Table 1, or pharmaceutically acceptable salts thereof) and a CDK4 inhibitor, including, but not limited to, LEE011 or a CDK 4/6 inhibitor (e.g., palbociclib (Ibrance®), ribociclib (Kisqali®), and abemaciclib (Verzenio®).

In some embodiments, provided is a method of treating a disease or disorder (e.g., cancer) comprising administering or coadministering, in any order, to a patient in need thereof, a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), a compound of Table 1, or pharmaceutically acceptable salts thereof) and targeted treatments contingent on the dependency of individual target tumors on relevant pathways as determined by suitable predictive markers, including but not limited to: inhibitors of HDM2i, PI3K/mTOR-I, MAPKi, RTKi (EGFRi, FGFRi, METi, IGFiRi, JAKi, and WNTi.

In some embodiments, provided is a method of treating a disease or disorder (e.g., cancer) comprising administering or coadministering, in any order, to a patient in need thereof, a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), a compound of Table 1, or pharmaceutically acceptable salts thereof) and immunotherapy.

In some embodiments, provided is a method of treating a disease or disorder (e.g., cancer) comprising administering or coadministering, in any order, to a patient in need thereof, a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), a compound of Table 1, or pharmaceutically acceptable salts thereof) and an immunotherapeutic agent. In some embodiments, the immunotherapeutic agent is a cancer vaccine such as a neoantigen. These vaccines can be developed using peptides or RNA, In some embodiments, the immunotherapeutic agent is an oncolytic virus. In some embodiments, the immunotherapeutic agent is a STING pathway agonist. Exemplary STING agonists include MK-1454 and ADU-S100.

In some embodiments, the immunotherapeutic agent is an anti-CTLA-4 antibody. In some embodiments, provided is a method of treating a disease or disorder (e.g., cancer) comprising administering or coadministering, in any order, to a patient in need thereof, a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), a compound of Table 1, or pharmaceutically acceptable salts thereof) and an anti-CTLA-4 antibody (e.g., ipilimumab, tremelimumab).

In some embodiments, the immunotherapeutic agent is an anti-PD-1 ligand or an anti-PD-L1 ligand. In some embodiments, provided is a method of treating a disease or disorder (e.g., cancer) comprising administering or coadministering, in any order, to a patient in need thereof, a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), a compound of Table 1, or pharmaceutically acceptable salts thereof) and an anti-PD-1 ligand (e.g., PD-LI (e.g., B7-HI or CD274); or PD-L2 (e.g., B7-DC or CD273)). In some embodiments, the immunotherapeutic agent is an anti-PD-1 antibody (e.g., anti-PD-1 or anti-PD-L1). In some embodiments, the immunotherapeutic agent is an anti-PD-1 agent (e.g., an anti-PD-1 antibody, e.g., nivolumab (i.e., MDX-1106, BMS-936558, ONO-4538); CT-011; AMP-224; pembrolizumab (MK-3475); pidilizumab; cemiplimab; dostarlimab; prolgolimab; spartalizumab; camrelizumab; sasanlimab, sintilimab; tislelizumab; toripalimab; retifanlimab; MEDI0680; budigalimab; geptanolimab). In some embodiments, the immunotherapeutic agent is an anti-PD-L1 agent (e.g., an anti-PD-L1 antibody, e.g., BMS936559 (i.e., MDX-1105); durvalumab (MEDI4736); avelumab (MSB0010718C); envafolimab; cosibelimab; sugemalimab, AUNP-12 or atezolizumab (MPDL-3280A) or an anti-PD-L1 small molecule (e.g., CA-170)).

In some embodiments, provided is a method of treating a disease or disorder (e.g., cancer) comprising administering or coadministering, in any order, to a patient in need thereof, a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), a compound of Table 1, or pharmaceutically acceptable salts thereof) and a KRAS inhibitor. In some embodiments, the KRAS inhibitor is a KRAS G12C inhibitor. In some embodiments, the KRAS inhibitor is sotorasib.

In some embodiments, provided is a method of treating a disease or disorder (e.g., cancer) comprising administering or coadministering, in any order, to a patient in need thereof, a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), a compound of Table 1, or pharmaceutically acceptable salts thereof) and a checkpoint blocking antibody (e.g., anti-TIM3, anti-LAG3, anti-TIGIT including IMP321 and MGA271).

In some embodiments, provided is a method of treating a disease or disorder (e.g., cancer) comprising administering or coadministering, in any order, to a patient in need thereof, a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), a compound of Table 1, or pharmaceutically acceptable salts thereof) and a checkpoint inhibitor.

In some embodiments, provided is a method of treating a disease or disorder (e.g., cancer) comprising administering or coadministering, in any order, to a patient in need thereof, a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), a compound of Table 1, or pharmaceutically acceptable salts thereof) and a cell-based therapy. In some embodiments, the cell-based therapy is a CAR-T therapy.

In some embodiments, provided is a method of treating a disease or disorder (e.g., cancer) comprising administering or coadministering, in any order, to a patient in need thereof, a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), a compound of Table 1, or pharmaceutically acceptable salts thereof) and a co-stimulatory antibody (e.g., anti-4-1BB, anti-OX40, anti-GITR, anti-CD27, anti-CD40).

In some embodiments, provided is a method of treating a disease or disorder (e.g., cancer) comprising administering or coadministering, in any order, to a patient in need thereof, a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), a compound of Table 1, or pharmaceutically acceptable salts thereof) and a disease-specific huMABs (e.g., an anti-HER3 huMAB).

In some embodiments, provided is a method of treating a disease or disorder (e.g., cancer) comprising administering or coadministering, in any order, to a patient in need thereof, a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), a compound of Table 1, or pharmaceutically acceptable salts thereof) and ADCs/ADCCs contingent on the expression of relevant surface targets on target tumors of interest.

Some patients may experience allergic reactions to the compounds of Formula (I) and/or other anti-cancer agent(s) during or after administration; therefore, anti-allergic agents are often administered to minimize the risk of an allergic reaction. Suitable anti-allergic agents include corticosteroids, including, but not limited to, dexamethasone (e.g., Decadron®), beclomethasone (e.g., Beclovent®), hydrocortisone (also known as cortisone, hydrocortisone sodium succinate, hydrocortisone sodium phosphate, and sold under the tradenames Ala-Cort®, hydrocortisone phosphate, Solu-Cortef®, Hydrocort Acetate® and Lanacort®), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-methylprednisolone, methylprednisolone acetate, methylprednisolone sodium succinate, sold under the tradenames Duralone®, Medralone®, Medrol®, M-Prednisol® and Solu-Medrol®); antihistamines, such as diphenhydramine (e.g., Benadryl®), hydroxyzine, and cyproheptadine; and bronchodilators, such as the beta-adrenergic receptor agonists, albuterol (e.g., Proventil®), and terbutaline (Brethine®).

Some patients may experience nausea during and after administration of the compound of Formula (I) and/or other anti-cancer agent(s); therefore, anti-emetics are used in preventing nausea (upper stomach) and vomiting. Suitable anti-emetics include aprepitant (Emend®), ondansetron (Zofran®), granisetron HCl (Kytril®), lorazepam (Ativan®. dexamethasone (Decadron®), prochlorperazine (Compazine®), casopitant (Rezonic® and Zunrisa®), and combinations thereof.

Medication to alleviate the pain experienced during the treatment period is often prescribed to make the patient more comfortable. Common over-the-counter analgesics, such Tylenol®, are often used. However, opioid analgesic drugs including, but not limited to, hydrocodone/paracetamol or hydrocodone/acetaminophen (e.g., Vicodin®), morphine (e.g., Astramorph® or Avinza®), oxycodone (e.g., OxyContin® or Percocet®), oxymorphone hydrochloride (Opana®), and fentanyl (e.g., Duragesic®) are also useful for moderate or severe pain.

In an effort to protect normal cells from treatment toxicity and to limit organ toxicities, cytoprotective agents (such as neuroprotectants, free-radical scavengers, cardioprotectors, anthracycline extravasation neutralizers, nutrients and the like) may be used as an adjunct therapy. Suitable cytoprotective agents include Amifostine (Ethyol®), glutamine, dimesna (Tavocept®), mesna (Mesnex®), dexrazoxane (Zinecard® or Totect®), xaliproden (Xaprila®), and leucovorin (also known as calcium leucovorin, citrovorum factor and folinic acid).

The structure of the active compounds identified by code numbers, generic or trade names may be taken from the actual edition of the standard compendium "The Merck Index" or from databases, e.g., Patents International (e.g., IMS World Publications).

The above-mentioned compounds, which can be used in combination with a compound of Formula (I), can be prepared and administered as described in the art, including, but not limited to, in the documents cited above.

In one embodiment, the present invention provides pharmaceutical compositions comprising at least one compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), a compound of Table 1) or a pharmaceutically acceptable salt thereof together with a pharmaceutically acceptable carrier suitable for administration to a human or animal subject, either alone or together with other anti-cancer agents. In particular, compositions will either be formulated together as a combination therapeutic or administered separately.

In combination therapy, the compound of Formula (I) and other anti-cancer agent(s) may be administered either simultaneously, concurrently or sequentially with no specific time limits, wherein such administration provides therapeutically effective levels of the two compounds in the body of the patient.

In some embodiments, the compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), a compound of Table 1, or pharmaceutically acceptable salts thereof) and the other anti-cancer agent(s) is generally administered sequentially in any order by infusion or orally. The dosing regimen may vary depending upon the stage of the disease, physical fitness of the patient, safety profiles of the individual drugs, and tolerance of the individual drugs, as well as other criteria well-known to the attending physician and medical practitioner(s) administering the combination. The compound of the present invention and other anti-cancer agent(s) may be administered within minutes of each other, hours, days, or even weeks apart depending upon the particular cycle being used for treatment. In addition, the cycle could include administration of one drug more often than the other during the treatment cycle and at different doses per administration of the drug.

In some embodiments, provided are kits that include one or more compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), a compound of Table 1, or pharmaceutically acceptable salts thereof) and a second therapeutic agent as disclosed herein are provided. Representative kits include (a) a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), a compound of Table 1, or pharmaceutically acceptable salts thereof), (b) at least one other therapeutic agent, e.g., as indicated above, whereby such kit may comprise a package insert or other labeling including directions for administration.

A compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), a compound of Table 1, or pharmaceutically acceptable salts thereof) may also be used in combination with known therapeutic processes, for example, the administration of hormones or especially radiation. A compound of Formula (I) may in particular be used as a radiosensitizer, especially for the treatment of tumors which exhibit poor sensitivity to radiotherapy.

In certain instances, compounds of the present invention are combined with other therapeutic agents, including, but not limited to, other anti-cancer agents, anti-allergic agents, anti-nausea agents (or anti-emetics), pain relievers, cytoprotective agents, and combinations thereof.

In some embodiments, provided is a method of treating a disease or disorder (e.g., cancer) comprising administering or coadministering, in any order, to a patient in need thereof, a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), a compound of Table 1, or pharmaceutically acceptable salts thereof) and a CAAP1 inhibitor.

In some embodiments, provided is a method of treating a disease or disorder (e.g., cancer) comprising administering or coadministering, in any order, to a patient in need thereof, a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), a compound of Table 1, or pharmaceutically acceptable salts thereof) and a AKAP17A inhibitor.

In some embodiments, provided is a method of treating a disease or disorder (e.g., cancer) comprising administering or coadministering, in any order, to a patient in need thereof, a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), a compound of Table 1, or pharmaceutically acceptable salts thereof) and a BCL2L1 inhibitor. In some embodiments, the BCL2L1 inhibitor is AT-101.

In some embodiments, provided is a method of treating a disease or disorder (e.g., cancer) comprising administering or coadministering, in any order, to a patient in need thereof, a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), a compound of Table 1, or pharmaceutically acceptable salts thereof) and a TSC1/2 inhibitor.

In some embodiments, provided is a method of treating a disease or disorder (e.g., cancer) comprising administering or coadministering, in any order, to a patient in need thereof, a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), a compound of Table 1, or pharmaceutically acceptable salts thereof) and a UBE2H inhibitor.

In some embodiments, provided is a method of treating a disease or disorder (e.g., cancer) comprising administering or coadministering, in any order, to a patient in need thereof, a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), a compound of Table 1, or pharmaceutically acceptable salts thereof) and a NF2 inhibitor.

In some embodiments, provided is a method of treating a disease or disorder (e.g., cancer) comprising administering or coadministering, in any order, to a patient in need thereof, a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), a compound of Table 1, or pharmaceutically acceptable salts thereof) and a ZC3HCl inhibitor.

In some embodiments, provided is a method of treating a disease or disorder (e.g., cancer) comprising administering or coadministering, in any order, to a patient in need thereof, a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), a compound of Table 1, or pharmaceutically acceptable salts thereof) and a MGEA5 inhibitor.

In some embodiments, provided is a method of treating a disease or disorder (e.g., cancer) comprising administering or coadministering, in any order, to a patient in need thereof, a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), a compound of Table 1, or pharmaceutically acceptable salts thereof) and a CNOT4 inhibitor.

In some embodiments, provided is a method of treating a disease or disorder (e.g., cancer) comprising administering or coadministering, in any order, to a patient in need thereof, a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), a compound of Table 1, or pharmaceutically acceptable salts thereof) and a API5 inhibitor.

In some embodiments, provided is a method of treating a disease or disorder (e.g., cancer) comprising administering or coadministering, in any order, to a patient in need thereof, a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), a compound of Table 1, or pharmaceutically acceptable salts thereof) and a HEXIM1 inhibitor.

In some embodiments, provided is a method of treating a disease or disorder (e.g., cancer) comprising administering or coadministering, in any order, to a patient in need thereof, a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), a compound of Table 1, or pharmaceutically acceptable salts thereof) and a PTEN inhibitor.

In some embodiments, provided is a method of treating a disease or disorder (e.g., cancer) comprising administering or coadministering, in any order, to a patient in need thereof, a compound of Formula (I) (e.g., a compound of Formula (Ia), (Ib), (Ic), (Id), (Ie), (If), (Ig), (Ih), (Ii), (Ij), (Ik), (Im), (In), (Io), (Ip), (Iq), (Ir) or (Is), a compound of Table 1, or pharmaceutically acceptable salts thereof) and a DNA damage pathway inhibitor. In some embodiments, the DNA damage pathway inhibitor is selected from the group consisting of bleomycin, an ATM inhibitor (e.g., AZD1390), a USP1 inhibitor, a WEE1 inhibitor (e.g., AZD1775), and a Chk1 inhibitor (e.g., AZD7762).

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein, the terms "compounds" and "agent" are used interchangeably to refer to the inhibitors/antagonists/agonists of the invention. In certain embodiments, the compounds are small organic or inorganic molecules, e.g., with molecular weights less than 7500 amu, preferably less than 5000 amu, and even more preferably less than 2000, 1500, 1000, 750, 600, or 500 amu. In certain embodiments, one class of small organic or inorganic molecules are non-peptidyl, e.g., containing 2, 1, or no peptide and/or saccharide linkages.

Unless otherwise indicated, all numbers expressing quantities of ingredients or reaction conditions used herein should be understood as modified in all instances by the term "about." The term "about" when used in connection with percentages may mean±1%.

The singular terms "a," "an," and "the" refer to one or to more than one, unless context clearly indicates otherwise. Similarly, the word "or" is intended to include "and" unless the context clearly indicates otherwise.

Although methods and materials similar or equivalent to those described herein can be used in the practice or testing of this disclosure, suitable methods and materials are described below.

As used herein, the term "administer" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, intrathecal, and topical (including buccal and sublingual) administration.

The terms "decrease", "reduced", "reduction", "decrease" or "inhibit" are all used herein generally to mean a decrease by a statistically significant amount. In some embodiments, the terms "reduced", "reduction", "decrease" or "inhibit" mean a decrease by at least 0.1% as compared to a reference level, for example a decrease by at least about 1%, or at least about 5%, or at least about 10%, or at least about 15%, or at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 1-100%, e.g., 10-100% as compared to a reference level.

The terms "increased", "increase", "enhance" or "activate" are all used herein to generally mean an increase by a statically significant amount. In some embodiments, the terms "increased", "increase", "enhance" or "activate" mean an increase by at least 0.1% as compared to a reference level, for example a decrease by at least about 1%, or at least about 5%, or at least about 10%, or at least about 15%, or at least about 20%, or at least about 30%, or at least about 40%, or at least about 50%, or at least about 60%, or at least about 70%, or at least about 80%, or at least about 90% or up to and including a 100% increase (e.g. absent level as compared to a reference sample), or any increase between 1-100%, e.g., 10-100% as compared to a reference level.

By "treatment", "prevention" or "amelioration" of a disease or disorder is meant delaying or preventing the onset of such a disease or disorder, reversing, alleviating, ameliorating, inhibiting, slowing down or stopping the progression, aggravation or deterioration the progression or severity of a condition associated with such a disease or disorder. In one embodiment, at least one symptom of a disease or disorder is alleviated by at least about 1%, or at least about 5%, or at least about 10%, or at least about 15%, or at least about 20%, or at least about 30%, or at least about 40%, or at least about 50%.

As used herein, an amount of a compound or combination effective to treat a disorder (e.g., a disorder as described herein), "therapeutically effective amount" or "effective amount" refers to an amount of the compound or combination which is effective, upon single or multiple dose administration(s) to a subject, in treating a subject, or in curing, alleviating, relieving or improving a subject with a disorder (e.g., a disorder as described herein) beyond that expected in the absence of such treatment. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein. The terms, "patient" and "subject" are used interchangeably herein.

The term "nucleic acid" as used herein refers to a polymeric form of nucleotides, either ribonucleotides or deoxynucleotides or a modified form of either type of nucleotide. The terms should also be understood to include, as equivalents, analogs of either RNA or DNA made from nucleotide analogs, and, as applicable to the embodiment being described, single-stranded (such as sense or antisense) and double-stranded polynucleotides.

As used herein, the term "inhibitor of HDAC" refers to compounds and compositions of Formula (I) (e.g., Formula (I), (Ia), (Ib), (Ic), and (Id), Compounds for Table 1, or pharmaceutically acceptable salts thereof) that are capable of inhibiting the deacetylase activity of HDAC enzymes. These include, as non-limiting examples, any compound inhibiting the posttranslational modification of the protein, the enzymatic activity of the protein, the interaction of same with protein complexes, interaction with substrate, etc. The term also refers to any agent that inhibits the cellular function of the HDAC protein, either by ATP-competitive inhibition of the active site, allosteric modulation of the protein structure, disruption of protein-protein interactions, or by inhibiting the transcription, translation, post-translational modification, or stability of HDAC protein.

Selected Chemical Definitions

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, propyl, butyl, pentyl and hexyl.

For compounds of the invention in which a variable appears more than once, each variable can be a different moiety selected from the Markush group defining the variable. For example, where a structure is described having two R groups that are simultaneously present on the same compound; the two R groups can represent different moieties selected from the Markush group defined for R.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

If a compound of the present invention is depicted in the form of a chemical name and as a formula, in case of any discrepancy, the formula shall prevail.

The symbol ～, whether utilized as a bond or displayed perpendicular to a bond indicates the point at which the displayed moiety is attached to the remainder of the molecule, solid support, etc.

The following terms are intended to have the meanings presented therewith below and are useful in understanding the description and intended scope of the present invention.

As used herein, "alkyl" refers to a radical of a straight-chain or branched saturated hydrocarbon group having from 1 to 24 carbon atoms ("$C_1$-$C_{24}$ alkyl"). In some embodiments, an alkyl group has 1 to 12 carbon atoms ("$C_1$-$C_{12}$ alkyl"). In some embodiments, an alkyl group has 1 to 8 carbon atoms ("$C_1$-$C_8$ alkyl"). In some embodiments, an alkyl group has 1 to 6 carbon atoms ("$C_1$-$C_6$ alkyl"). In some embodiments, an alkyl group has 1 to 5 carbon atoms ("$C_1$-$C_5$ alkyl"). In some embodiments, an alkyl group has 1 to 4 carbon atoms ("$C_1$-$C_4$ alkyl"). In some embodiments, an alkyl group has 1 to 3 carbon atoms ("$C_1$-$C_3$ alkyl"). In some embodiments, an alkyl group has 1 to 2 carbon atoms ("$C_1$-$C_2$ alkyl"). In some embodiments, an alkyl group has 1 carbon atom ("$C_1$ alkyl"). In some embodiments, an alkyl group has 2 to 6 carbon atoms ("$C_2$-$C_6$ alkyl"). Examples of $C_1$-$C_6$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Each instance of an alkyl group may be independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-6}$ alkyl.

The term "alkylene" refers to a diradical of an alkyl group. An exemplary alkylene group is —$CH_2CH_2$—.

As used herein, "alkenyl" refers to a radical of a straight-chain or branched hydrocarbon group having from 2 to 24 carbon atoms, one or more carbon-carbon double bonds, and no triple bonds ("$C_2$-$C_{24}$ alkenyl"). In some embodiments, an alkenyl group has 2 to 10 carbon atoms ("$C_2$-$C_{10}$ alkenyl"). In some embodiments, an alkenyl group has 2 to 8 carbon atoms ("$C_2$-$C_5$ alkenyl"). In some embodiments, an alkenyl group has 2 to 6 carbon atoms ("$C_2$-$C_6$ alkenyl"). In some embodiments, an alkenyl group has 2 to 5 carbon atoms ("$C_2$-$C_5$ alkenyl"). In some embodiments, an alkenyl group has 2 to 4 carbon atoms ("$C_2$-$C_4$ alkenyl"). In some embodiments, an alkenyl group has 2 to 3 carbon atoms ("$C_2$-$C_3$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_2$-$C_4$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_2$-$C_6$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Each instance of an alkenyl group may be independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-6}$ alkenyl.

As used herein, the term "alkynyl" refers to a radical of a straight-chain or branched hydrocarbon group having from 2 to 24 carbon atoms, one or more carbon-carbon triple bonds ("$C_2$-$C_{24}$ alkenyl"). In some embodiments, an alkynyl group has 2 to 10 carbon atoms ("$C_2$-$C_{10}$ alkynyl"). In some embodiments, an alkynyl group has 2 to 8 carbon atoms ("$C_2$-$C_5$ alkynyl"). In some embodiments, an alkynyl group has 2 to 6 carbon atoms ("$C_2$-$C_6$ alkynyl"). In some embodiments, an alkynyl group has 2 to 5 carbon atoms ("$C_2$-$C_5$ alkynyl"). In some embodiments, an alkynyl group has 2 to 4 carbon atoms ("$C_2$-$C_4$ alkynyl"). In some embodiments, an alkynyl group has 2 to 3 carbon atoms ("$C_2$-$C_3$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_2$-$C_4$ alkynyl groups include ethynyl ($C_2$), 1-propynyl ($C_3$), 2-propynyl ($C_3$), 1-butynyl ($C_4$), 2-butynyl ($C_4$), and the like. Each instance of an alkynyl group may be independently optionally substituted, i.e., unsubstituted (an "unsubstituted alkynyl") or substituted (a "substituted alkynyl") with one or more substituents e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-6}$ alkynyl.

As used herein, the term "heteroalkyl," refers to a non-cyclic stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any position of the heteroalkyl group. Exemplary heteroalkyl groups include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —NH$CH_2$—, —C(O)NH—, —C(O)N($CH_3$), —C(O)N($CH_2CH_3$)—, —C(O)N($CH_2CF_3$)—, —S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, —CH=CH—N($CH_3$)—$CH_3$, —O—$CH_3$, and —O—$CH_2$—$CH_3$. Up to two or three heteroatoms may be consecutive, such as, for example, —$CH_2$—NH—O$CH_3$ and —$CH_2$—O—Si($CH_3$)$_3$. Where "heteroalkyl" is recited, followed by recitations of specific heteroalkyl groups, such as —$CH_2$O, —NR$^C$R$^D$, or the like, it will be understood that the terms heteroalkyl and —$CH_2$O or —NR$^C$R$^D$ are not redundant or mutually exclusive. Rather, the specific heteroalkyl groups are recited to add clarity. Thus, the term "heteroalkyl" should not be interpreted herein as excluding specific heteroalkyl groups, such as —$CH_2$O, —NR$^C$R$^D$, or the like. One type of heteroalkyl group is an "alkoxyl" group.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, O-alkynyl, —O—($CH_2$)$_{mm}$—R$^{aaa}$, where mm is an integer (e.g., 1, 2, 3, 4, 5, 6, 7, 8, 9, 10, or 11) and R$^{aaa}$ may be halogen, haloalkyl, nitrile, —$NH_2$, —$NO_2$, —$SO_2$, Si($CH_3$)$_3$, cycloalkyl, heterocyclyl, aryl, or heteroaryl. are described above. The term "haloalkoxyl" refers to an alkoxyl group that is substituted with at least one halogen. For example, —O—$CH_2$F, —O—$CHF_2$, —O—$CF_3$, and the like. In certain embodiments, the haloalkoxyl is an alkoxyl group that is substituted with at least one fluoro group. In certain embodiments, the haloalkoxyl is an alkoxyl group that is substituted with from 1-6, 1-5, 1-4, 2-4, or 3 fluoro groups.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_6$-$C_{14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). An aryl group may be described as, e.g., a $C_6$-$C_{10}$-membered aryl, wherein the term "membered" refers to the non-hydrogen ring atoms within the moiety. Aryl groups include phenyl, naphthyl, indenyl, and tetrahydronaphthyl. Each instance of an aryl group may be independently optionally substituted, i.e., unsubstituted (an "unsubstituted aryl") or substituted (a "substituted aryl") with one or more substituents. In certain embodiments, the aryl group is unsubstituted $C_6$-$C_{14}$ aryl. In certain embodiments, the aryl group is substituted $C_6$-$C_{14}$ aryl.

As used herein, "heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). A heteroaryl group may be described as, e.g., a 6-10-membered heteroaryl, wherein the term "membered" refers to the non-hydrogen ring atoms within the moiety.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Each instance of a heteroaryl group may be independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Other exemplary heteroaryl groups include heme and heme derivatives. "heteroaryl" also includes ring systems wherein the heteroaryl ring, as defined above, is fused with one or more heterocycloalkyl groups wherein the point of attachment is on the heteroaryl ring, and in such instances, the number of carbons continue to designate the number of carbons in the heteroaryl ring system. Exemplary ring systems of this type include 7,8-dihydro-5H-pyrano[4,3-b]pyridine and 1,4,6,7-tetrahydropyrano[4,3-b]pyrrole.

As used herein, "cycloalkyl" refers to a radical of a non-aromatic cyclic hydrocarbon group having from 3 to 10 ring carbon atoms ("$C_3$-$C_{10}$ cycloalkyl") and zero heteroatoms in the non-aromatic ring system. In some embodiments, a cycloalkyl group has 3 to 8 ring carbon atoms ("$C_3$-$C_8$cycloalkyl"). In some embodiments, a cycloalkyl group has 3 to 6 ring carbon atoms ("$C_3$-$C_6$ cycloalkyl"). In some embodiments, a cycloalkyl group has 3 to 6 ring carbon atoms ("$C_3$-$C_6$ cycloalkyl"). In some embodiments, a cycloalkyl group has 5 to 10 ring carbon atoms ("$C_5$-$C_{10}$ cycloalkyl"). A cycloalkyl group may be described as, e.g., a $C_4$-$C_7$-membered cycloalkyl, wherein the term "membered" refers to the non-hydrogen ring atoms within the moiety. Exemplary $C_3$-$C_6$ cycloalkyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_8$), cyclohexyl ($C_6$), cyclohexenyl ($C_6$), cyclohexadienyl ($C_6$), and the like. Exemplary $C_3$-$C_5$ cycloalkyl groups include, without limitation, the aforementioned $C_3$-$C_6$ cycloalkyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), cubanyl ($C_8$), bicyclo[1.1.1]pentanyl ($C_8$), bicyclo[2.2.2]octanyl ($C_8$), bicyclo[2.1.1]hexanyl ($C_6$), bicyclo[3.1.1]heptanyl ($C_7$), and the like. Exemplary $C_3$-$C_{10}$ cycloalkyl groups include, without limitation, the aforementioned $C_3$-$C_5$ cycloalkyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the cycloalkyl group is either monocyclic ("monocyclic cycloalkyl") or contain a fused, bridged or spiro ring system such as a bicyclic system ("bicyclic cycloalkyl") and can be saturated or can be partially unsaturated. "Cycloalkyl" also includes ring systems wherein the cycloalkyl ring, as defined above, is fused with one or more aryl groups wherein the point of attachment is on the cycloalkyl ring, and in such instances, the number of carbons continue to designate the number of carbons in the cycloalkyl ring system. Each instance of a cycloalkyl group may be independently optionally substituted, i.e., unsubstituted (an "unsubstituted cycloalkyl") or substituted (a "substituted cycloalkyl") with one or more substituents. In certain embodiments, the cycloalkyl group is unsubstituted $C_3$-$C_{10}$ cycloalkyl. In certain embodiments, the cycloalkyl group is a substituted $C_3$-$C_{10}$ cycloalkyl.

"Heterocyclyl," "heterocycle" or "heterocycloalkyl" as used herein refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more cycloalkyl groups wherein the point of attachment is either on the cycloalkyl or heterocyclyl ring, or ring systems wherein the heterocyclyl ring, as defined above, is fused with one or more aryl or heteroaryl groups, wherein the point of attachment is on the heterocyclyl or aryl or heteroaryl ring, and in such instances, the number of ring members continue to designate the number of ring members in the heterocyclyl ring system. A heterocyclyl group may be described as, e.g., a 3-7-membered heterocyclyl, wherein the term "membered" refers to the non-hydrogen ring atoms, i.e., carbon, nitrogen, oxygen, sulfur, boron, phosphorus, and silicon, within the moiety. Each instance of heterocyclyl may be independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, aziridinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

As used herein, "cyano" refers to the radical —CN.

As used herein, "halo" or "halogen," independently or as part of another substituent, mean, unless otherwise stated, a fluorine (F), chlorine (Cl), bromine (Br), or iodine (I) atom.

As used herein, "haloalkyl" can include alkyl structures that are substituted with one or more halo groups or with combinations thereof. For example, the terms "fluoroalkyl" includes haloalkyl groups in which the halo is fluorine (e.g., —$C_1$-$C_6$ alkyl-$CF_3$, —$C_1$-$C_6$ alkyl-$CH_2F$). Non-limiting examples of haloalkyl include trifluoroethyl, trifluoropropyl, trifluoromethyl, fluoromethyl, difluoromethyl, and fluroisopropyl.

As used herein, "hydroxy" refers to the radical —OH.

As used herein, "nitro" refers to —$NO_2$.

As used herein, "oxo" refers to =O, in which both bonds from the oxygen are connected to the same atom. For example, a carbon atom substituted with oxo forms a carbonyl group —C=O.

Two or more substituents may optionally be joined to form aryl, heteroaryl, cycloalkyl, or heterocyclyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, IN 1972). The invention additionally encompasses compounds described herein as individual isomers substantially free of other isomers, and alternatively, as mixtures of various isomers.

As used herein, a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 99% by weight, more than 99.5% by weight, or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient.

Compound described herein may also comprise one or more isotopic substitutions. For example, H may be in any isotopic form, including $^1H$, $^2H$ (D or deuterium), and $^3H$ (T or tritium); C may be in any isotopic form, including $^{12}C$, $^{13}C$, and $^{14}C$; O may be in any isotopic form, including $^{16}O$ and $^{18}O$; and the like.

Many of the terms given above may be used repeatedly in the definition of a formula or group and in each case have one of the meanings given above, independently of one another.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. A moiety described as "optionally substituted" (e.g., optionally substituted with a number or range of numbers of substituents selected from a list) can be unsubstituted or substituted (e.g., can be unsubstituted or substituted with the number of substituents indicated). For example, a moiety that is optionally substituted with 1-4 R groups can be unsubstituted, substituted with one R group, substituted with two R groups, substituted with 3 R groups or substituted with 4 R groups. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable substituents for an optionally substituted alkyl, alkylene, heteroalkyl, heteroalkylene, carbocyclyl, heterocyclyl, aryl group and heteroaryl group include halogen, =O, —CN, —$OR^{cc}$, —$NR^{dd}R^{ee}$, —$S(O)_kR^{cc}$, —$NR^{cc}S$ $(O)_2 R^{cc}$, —$S(O)_2NR^{dd}R^{ee}$, —$C(=O)OR^{cc}$, —$OC(=O)$ $OR^{cc}$, —$OC(=O)R^{cc}$, —$OC(=S)OR^{cc}$, —$C(=S)OR^{cc}$, —$O(C=S) R^{cc}$, —$C(=O)NR^{dd}R^{ee}$, —$NR^{cc}C(=O)R^{cc}$, —$C(=S)NR^{dd}R^{ee}$, —$NR^{cc}C(=S)R^{cc}$, —$NR^{cc}(C=O)$ $OR^{cc}$, —$O(C=O)NR^{dd}R^{ee}$, —$NR^{cc}=S)OR^{cc}$, —$O(C=S)$ $NR^{dd}R^{ee}$, —$NR^{cc}(C=O)NR^{dd}R^{ee}$, —$NR(C=S)NR^{dd}R^{ee}$ $C(=S)R^{cc}$, —$C(=O)R^C$, —$C_1$-$C_6$ alkyl, —$C_1$-$C_6$ haloalkyl, —$C_1$-$C_6$ heteroalkyl, -carbocyclyl, —($C_1$-$C_6$-alkylene)-carbocyclyl, —($C_1$-$C_6$-heteroalkylene)-carbocyclyl, -heterocyclyl, ($C_1$-$C_6$-alkylene)-heterocyclyl, ($C_1$-$C_6$-heteroalkylene)-heterocyclyl, aryl, ($C_1$-$C_6$-alkylene)-aryl, ($C_1$-$C_6$-heteroalkylene)-aryl, heteroaryl, ($C_1$-$C_6$-alkylene)-heteroaryl, or ($C_1$-$C_6$-heteroalkylene)-heteroaryl, wherein each of said alkyl, alkylene, heteroalkyl, heteroalkylene, carbocyclyl, heterocyclyl, aryl and heteroaryl are optionally substituted with one or more of halogen, $OR^{cc}$, —$NO_2$, —CN, —$NR^{cc}C(=O)W$, —$NR^{dd}R^{ee}$, —$S(O)_kR^{cc}$, —$C(=O)OR^{cc}$, —$C(=O)NR^{dd}R^{ee}$, —$C(=O)R^{cc}$, $C_1$-$C_6$ alkyl, $C_1$-$C_6$ haloalkyl, or $C_1$-$C_6$ heteroalkyl, and wherein $R^{cc}$ is hydrogen, hydroxy, $C_1$-$C_6$ alkyl, $C_1$-$C_6$ heteroalkyl, carbocyclyl, ($C_1$-$C_6$-alkylene)-carbocyclyl, ($C_1$-$C_6$-heteroalkylene)-carbocyclyl, heterocyclyl, ($C_1$-$C_6$-alkylene)-heterocyclyl, ($C_1$-$C_6$-heteroalkylene)-heterocyclyl, aryl, ($C_1$-$C_6$-alkylene)-aryl, ($C_1$-$C_6$-heteroalkylene)-aryl, heteroaryl, ($C_1$-$C_6$-alkylene)-heteroaryl, or ($C_1$-$C_6$-heteroalkylene)-heteroaryl, each of which is optionally substituted with one or more of halogen, hydroxy, $C_1$-$C_6$ alkyl, $C_1$-$C_6$ haloalkyl, $C_1$-$C_6$ heteroalkyl, carbocyclyl, heterocyclyl, aryl, or heteroaryl; $R^{dd}$ and $R^{ee}$ are each independently selected from hydrogen, $C_1$-$C_6$ alkyl, or $C_1$-$C_6$ heteroalkyl; and k is 0, 1 or 2. The invention is not intended to be limited in any manner by the above exemplary listing of substituents.

Contemplated equivalents of the compounds described above include compounds which otherwise correspond thereto, and which have the same general properties thereof (e.g., the ability to inhibit HDAC), wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

Pharmaceutical Compositions and Routes of Administration

Pharmaceutical compositions containing compounds described herein such as a compound of Formula (I) or pharmaceutically acceptable salt thereof can be used to treat or ameliorate a disorder described herein, for example, a neurodegenerative disease, a cancer, an ophthalmological disease (e.g., a retinal disease), or a viral infection.

The amount and concentration of compounds of Formula (I) in the pharmaceutical compositions, as well as the quantity of the pharmaceutical composition administered to a subject, can be selected based on clinically relevant factors, such as medically relevant characteristics of the subject (e.g., age, weight, gender, other medical conditions, and the like), the solubility of compounds in the pharmaceutical compositions, the potency and activity of the compounds, and the manner of administration of the pharmaceutical compositions. For further information on Routes of Administration and Dosage Regimes the reader is referred to Chapter 25.3 in Volume 5 of *Comprehensive Medicinal Chemistry* (Corwin Hansch; Chairman of Editorial Board), Pergamon Press 1990.

In some embodiments, provided is a pharmaceutical formulation (composition), wherein a compound described herein is combined with one or more pharmaceutically acceptable excipients. The compounds according to the invention may be formulated for administration in any convenient way for use in human or veterinary medicine. In certain embodiments, the compound included in the pharmaceutical preparation may be active itself, or may be a prodrug, e.g., capable of being converted to an active compound in a physiological setting. Regardless of the route of administration selected, the compounds of the present invention, which may be used in a suitable hydrated form, and/or the pharmaceutical compositions of the present invention, are formulated into pharmaceutically acceptable dosage forms such as described below or by other conventional methods known to those of skill in the art.

In some embodiments, provided are pharmaceutically acceptable compositions comprising a therapeutically effective amount of one or more of the compounds described above, formulated together with one or more pharmaceutically acceptable excipients. As described in detail below and herein, the pharmaceutical compositions disclosed herein may be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; (9) nasally; or (10) intrathecally. Additionally, compounds can be implanted into a patient or injected using a drug delivery system. See, for example, Urquhart, et al., (1994) *Ann Rev Pharmacol Toxicol* 24:199-236; Lewis, ed. "Controlled Release of Pesticides and Pharmaceuticals" (Plenum Press, New York, 1981); U.S. Pat. No. 3,773,919; and U.S. Pat. No. 35 3,270,960.

The phrase "therapeutically effective amount" as used herein means that amount of a compound, material, or composition comprising a compound of the present invention, which is effective for producing some desired therapeutic effect, e.g., by inhibiting HDAC, in at least a subpopulation of cells in an animal and thereby blocking the biological consequences of that function in the treated cells, at a reasonable benefit/risk ratio applicable to any medical treatment.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" as used herein means a pharmaceutically acceptable material, composition or vehicle, such as a liquid or solid filler, diluent, carrier, solvent or encapsulating material, involved in carrying or transporting the subject antagonists from one organ, or portion of the body, to another organ, or portion of the body. Each excipient must be "acceptable" in the sense of being compatible with the other ingredients of the formulation and not injurious to the patient. Some examples of materials which can serve as pharmaceutically acceptable excipients include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) cyclodextrins such as Captisol®; and (22) other non-toxic compatible substances employed in pharmaceutical formulations.

The term "pharmaceutically acceptable salt" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds disclosed herein contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, e.g., Berge et al, *Journal of Pharmaceutical Science* 66: 1-19 (1977)). Certain specific compounds of the present invention contain both basic and acidic functionalities that allow the compounds to be converted into either base or acid addition salts. These salts may be prepared by methods known to those skilled in the art. Other pharmaceutically acceptable excipients known to those of skill in the art are suitable for the present invention.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with an excipient material to produce a single dosage form will vary depending upon the host being treated, the particular mode of administration. The amount of active ingredient that can be combined with an excipient material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound disclosed herein with the excipient and, optionally, one or more accessory ingredients. In general, the formulations are prepared by uniformly and intimately bringing into association a compound of the present invention with liquid excipients (e.g., carriers), or finely divided solid excipients (e.g., carriers), or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound disclosed herein may also be administered as a bolus, electuary or paste.

In solid dosage forms of the pharmaceutical compositions disclosed herein for oral administration (capsules, tablets, pills, dragees, powders, granules and the like), the active ingredient is mixed with one or more pharmaceutically acceptable excipients, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof, and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions disclosed herein for rectal, vaginal, or urethral administration may be presented as a suppository, which may be prepared by mixing one or more compounds of the invention with one or more suitable nonirritating excipients comprising, for example, cocoa butter, polyethylene glycol, a suppository wax or a salicylate, and which is solid at room temperature, but liquid at body temperature and, therefore, will melt in the rectum or vaginal cavity and release the active compound.

Alternatively or additionally, compositions can be formulated for delivery via a catheter, stent, wire, or other intraluminal device. Delivery via such devices may be especially useful for delivery to the heart, lung, bladder, urethra, ureter, rectum, or intestine. Furthermore, compositions can be formulated for delivery via a dialysis port.

Ophthalmic formulations, eye ointments, powders, solutions and the like, are also contemplated as being within the scope of this invention.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, the compositions are administered by intravenous infusion or injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous excipients that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable excipient.

The addition of the active compound of the invention to animal feed is preferably accomplished by preparing an appropriate feed premix containing the active compound in an effective amount and incorporating the premix into the complete ration. Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Ore., U.S.A., 1977).

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Preferably, the subject is a mammal. The mammal can be a human, non-human primate, mouse, rat, dog, cat, horse, or cow, but are not limited to these examples. Mammals other than humans can be advantageously used as subjects that represent animal models of disorders associated with neurodegenerative disease or disorder, cancer, or viral infections.

In addition, the methods described herein can be used to treat domesticated animals and/or pets. A subject can be male or female. A subject can be one who has been previously diagnosed with or identified as suffering from or having a neurodegenerative disease or disorder, a disease or disorder associated with cancer, a disease or disorder associated with viral infection, or one or more complications related to such diseases or disorders but need not have already undergone treatment.

Dosages

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

The compound and the pharmaceutically active agent can be administered to the subject in the same pharmaceutical composition or in different pharmaceutical compositions (at the same time or at different times). When administrated at different times, the compound and the pharmaceutically active agent can be administered within 5 minutes, 10 minutes, 20 minutes, 60 minutes, 2 hours, 3 hours, 4, hours, 8 hours, 12 hours, 24 hours of administration of the other agent. When the inhibitor and the pharmaceutically active agent are administered in different pharmaceutical compositions, routes of administration can be different.

The amount of compound that can be combined with an excipient material to produce a single dosage form will generally be that amount of the inhibitor that produces a therapeutic effect. Generally out of one hundred percent, this amount will range from about 0.1% to 99% of inhibitor, preferably from about 5% to about 70%, most preferably from 10% to about 30%.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferred.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the $IC_{50}$ (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

The dosage may be determined by a physician and adjusted, as necessary, to suit observed effects of the treatment.

The present invention contemplates formulation of the subject compounds in any of the aforementioned pharmaceutical compositions and preparations. Furthermore, the present invention contemplates administration via any of the foregoing routes of administration. One of skill in the art can select the appropriate formulation and route of administration based on the condition being treated and the overall health, age, and size of the patient being treated.

SELECTED EMBODIMENTS

Embodiment 1. A compound of Formula (I)

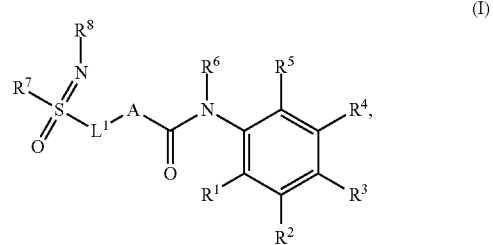

(I)

or a pharmaceutically acceptable salt thereof,
wherein
A is an optionally substituted aryl or heteroaryl;
$L^1$ is —CR'$_2$—, —CR'$_2$CR'$_2$—, or a bond;
each R' is independently H or $C_1$-$C_6$ alkyl; or two R' together with the carbon or carbons to which they are attached form a 3-6-membered cycloalkyl ring;
each $R^1$, $R^3$ and $R^4$ is independently H, $C_1$-$C_6$ alkyl, $C_1$-$C_6$ haloalkyl, or halogen;
$R^2$ is aryl or heteroaryl, each optionally substituted;
$R^5$ is $NH_2$ or OH;
$R^6$ is H or $C_1$-$C_6$ alkyl;
$R^7$ is $C_1$-$C_6$ alkyl, $C_1$-$C_6$ heteroalkyl, —(CH$_2$)$_{0-2}$-phenyl, —(CH$_2$)$_{0-2}$—$C_3$-$C_7$ cycloalkyl, —(CH$_2$)$_{0-2}$-heteroaryl or —(CH$_2$)$_{0-2}$-heterocyclyl, wherein each alkyl, heteroalkyl, phenyl, cycloalkyl, heteroaryl or heterocyclyl is optionally substituted;
$R^8$ is H, $C_1$-$C_6$ alkyl, $C_1$-$C_6$ heteroalkyl, phenyl, cycloalkyl, heterocyclyl, cyano, CO—R', or $CO_2$—R', wherein each alkyl, heteroalkyl, phenyl, cycloalkyl, or heterocyclyl is optionally substituted; or
$R^7$ and $R^8$ are taken together with the nitrogen and sulfur to which they are attached to form a 4-7 membered heterocycle with 0-2 additional ring heteroatoms selected from O, S, and N, and wherein the heterocycle is optionally substituted.

Embodiment 2. A compound of Formula (I)

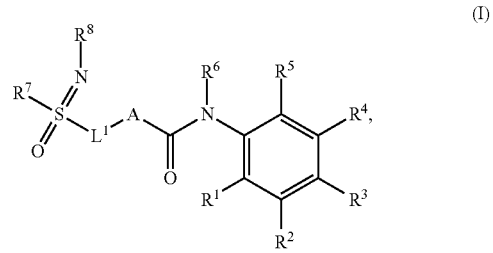

(I)

or a pharmaceutically acceptable salt thereof,
wherein
A is an aryl or heteroaryl, wherein heteroaryl has 5-10 ring atoms, 1 to 4 ring atoms selected from N, O, and S, and wherein A is substituted with 0-4 $R^9$ groups;
$L^1$ is —$CR'_2$—, —$CR'_2CR'_2$—, or a bond;
each R' is independently H or $C_1$-$C_6$ alkyl; or two R' together with the carbon or carbons to which they are attached form a 3-6-membered cycloalkyl ring;
each $R^1$, $R^3$ and $R^4$ is independently H, $C_1$-$C_6$ alkyl, $C_1$-$C_6$ haloalkyl, or halogen;
$R^2$ is aryl or heteroaryl, wherein heteroaryl has 5-10 ring atoms, 1 to 4 ring atoms selected from N, O, and S, and $R^2$ is substituted with 0-4 $R^{10}$ groups;
$R^5$ is $NH_2$ or OH;
$R^6$ is H or $C_1$-$C_6$ alkyl;
$R^7$ is $C_1$-$C_6$ alkyl, $C_1$-$C_6$ heteroalkyl, —$(CH_2)_{0-2}$-phenyl, —$(CH_2)_{0-2}$—$C_3$-$C_7$ cycloalkyl, —$(CH_2)_{0-2}$-heteroaryl or —$(CH_2)_{0-2}$-heterocyclyl; wherein heteroaryl has 5-10 ring atoms with 1 to 4 ring atoms selected from N, O, and S, and wherein heterocyclyl has 4-11 ring atoms with 1 to 4 ring atoms selected from N, O, and S; wherein each alkyl, heteroalkyl, phenyl, cycloalkyl, heteroaryl or heterocyclyl is substituted with 0-4 $R^{11}$ groups;
$R^8$ is H, $C_1$-$C_6$ alkyl, $C_1$-$C_6$ heteroalkyl, phenyl, cycloalkyl, heterocyclyl, cyano, CO—R', or $CO_2$—R', wherein heterocyclyl has 4-11 ring atoms with 1 to 4 ring atoms selected from N, O, and S; each alkyl or heteroalkyl is substituted with 0-4 groups independently selected from halogen and OH, and each phenyl, cycloalkyl, or heterocyclyl is substituted with 0-4 $R^{10}$ groups; or
$R^7$ and $R^8$ are taken together with the nitrogen and sulfur to which they are attached to form a 4-7 membered heterocycle with 0-2 additional ring heteroatoms selected from O, S, and N, and wherein the heterocycle is substituted with 0-4 $R^{10}$ groups;
each $R^9$ is independently $C_1$-$C_6$ alkyl, $C_1$-$C_6$ heteroalkyl, $C_3$-$C_7$ cycloalkyl, hydroxy, cyano, or halogen, wherein each alkyl or heteroalkyl is optionally substituted with 1-4 groups independently selected from halogen and OH;
each $R^{10}$ and $R^{11}$ is independently $C_1$-$C_6$ alkyl, $C_1$-$C_6$ alkenyl, $C_1$-$C_6$ heteroalkyl, phenyl, $C_3$-$C_7$ cycloalkyl, heterocyclyl, $C_1$-$C_6$ alkylene-phenyl, $C_1$-$C_6$ alkylene-$C_3$-$C_7$ cycloalkyl, $C_1$-$C_6$ alkylene-heterocyclyl, hydroxy, cyano, CO—$R^C$, $NR^D{}_2$, or halogen, wherein heterocyclyl has 4-11 ring atoms with 1 to 4 ring atoms selected from N, O, and S; each alkyl or heteroalkyl is optionally substituted with 1-4 groups independently selected from halogen and OH, and wherein each phenyl, cycloalkyl, or heterocyclyl is optionally substituted with 1-4 $R^E$;
each $R^C$ is independently H, OH, $NR^{12}{}_2$, $C_1$-$C_6$ alkyl, $C_1$-$C_6$ alkoxy, $C_1$-$C_6$ heteroalkyl, wherein each alkyl or heteroalkyl is optionally substituted with 1-4 substituents independently selected from halogen and OH;
each $R^D$ is independently H, $C_1$-$C_6$ alkyl, CO—$C_1$-$C_6$ alkyl; $CO_2$—$C_1$-$C_6$ alkyl; $SO_w$—$C_1$-$C_6$ alkyl; $C_1$-$C_6$ heteroalkyl, wherein each alkyl or heteroalkyl is optionally substituted with 1-4 substituents independently selected from halogen and OH; or
two $R^D$ attached to the same nitrogen are taken together with the nitrogen to which they are attached to form a 3-7 membered heterocycle with 0-2 additional ring heteroatoms selected from O, S, and N, and wherein the heterocycle is optionally substituted with 1-4 substituents independently selected from halogen, $C_1$-$C_6$ alkyl, $C_1$-$C_6$ haloalkyl, $C_1$-$C_6$ alkoxy, and OH;
each $R^E$ is independently H, halo, OH, O—$C_1$-$C_6$ alkyl, —$C_1$-$C_6$ alkyl, —$C_1$-$C_6$ haloalkyl;
each $R^{12}$ is independently H or $C_1$-$C_6$ alkyl; and
w is 0, 1, or 2.

Embodiment 3. A compound of Formula (I)

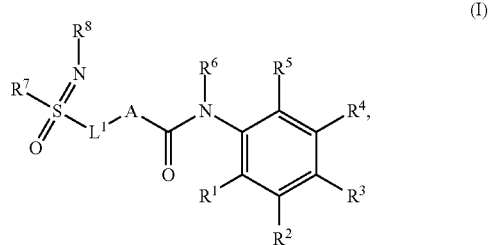

(I)

or a pharmaceutically acceptable salt thereof,
wherein
A is an aryl or heteroaryl, wherein heteroaryl has 5-10 ring atoms, 1 to 4 ring atoms selected from N, O, and S, and wherein A is substituted with 0-4 $R^9$ groups;
$L^1$ is —$CR'_2$—, —$CR'_2CR'_2$—, or a bond;
each R' is independently H or $C_1$-$C_6$ alkyl; or two R' together with the carbon or carbons to which they are attached form a 3-6-membered cycloalkyl ring;
each $R^1$, $R^3$ and $R^4$ is independently H, $C_1$-$C_6$ alkyl, $C_1$-$C_6$ haloalkyl, or halogen;
$R^2$ is aryl or heteroaryl, wherein heteroaryl has 5-10 ring atoms, 1 to 4 ring atoms selected from N, O, and S, and $R^2$ is substituted with 0-4 $R^{10}$ groups;
$R^5$ is $NH_2$ or OH;
$R^6$ is H or $C_1$-$C_6$ alkyl;
$R^7$ is $C_1$-$C_6$ alkyl, $C_1$-$C_6$ heteroalkyl, —$(CH_2)_{0-2}$-phenyl, —$(CH_2)_{0-2}$—$C_3$-$C_7$ cycloalkyl, —$(CH_2)_{0-2}$-heteroaryl or —$(CH_2)_{0-2}$-heterocyclyl; wherein heteroaryl has 5-10 ring atoms with 1 to 4 ring atoms selected from N, O, and S, and wherein heterocyclyl has 4-11 ring atoms with 1 to 4 ring atoms selected from N, O, and S; wherein each alkyl, heteroalkyl, phenyl, cycloalkyl, heteroaryl or heterocyclyl is substituted with 0-4 $R^{11}$ groups;
$R^8$ is H, $C_1$-$C_6$ alkyl, $C_1$-$C_6$ heteroalkyl, phenyl, cycloalkyl, heterocyclyl, cyano, CO—R', or $CO_2$—R', wherein heterocyclyl has 4-11 ring atoms with 1 to 4 ring atoms selected from N, O, and S; each alkyl or heteroalkyl is substituted with 0-4 groups independently selected from halogen and OH, and each phenyl, cycloalkyl, or heterocyclyl is substituted with 0-4 $R^{10}$ groups; or
$R^7$ and $R^8$ are taken together with the nitrogen and sulfur to which they are attached to form a 4-7 membered heterocycle with 0-2 additional ring heteroatoms selected from O, S, and N, and wherein the heterocycle is substituted with 0-4 $R^{10}$ groups;
each $R^9$ is independently $C_1$-$C_6$ alkyl, $C_1$-$C_6$ heteroalkyl, $C_3$-$C_7$ cycloalkyl, hydroxy, cyano, or halogen, wherein each alkyl or heteroalkyl is optionally substituted with 1-4 groups independently selected from halogen and OH;
each $R^{10}$ or $R^{11}$ is independently $C_1$-$C_6$ alkyl, $C_1$-$C_6$ heteroalkyl, phenyl, $C_3$-$C_7$ cycloalkyl, heterocyclyl, C$_1$-C$_6$ alkylene-phenyl, C$_1$-C$_6$ alkylene-C$_3$-C$_7$ cycloalkyl, C$_1$-C$_6$ alkylene-heterocyclyl, hydroxy, cyano, CO—R$^C$, NR$^D{}_2$, or halogen, wherein heterocyclyl has 4-11 ring atoms with 1 to 4 ring atoms selected from N, O, and S; each alkyl or heteroalkyl is optionally substituted with 1-4 groups independently selected from halogen and OH, and wherein each phenyl, cycloalkyl, or heterocyclyl is optionally substituted with 1-4 R$^E$;

each R$^C$ is independently H, OH, NR$^{12}{}_2$, C$_1$-C$_6$ alkyl, C$_1$-C$_6$ alkoxy, C$_1$-C$_6$ heteroalkyl, wherein each alkyl or heteroalkyl is optionally substituted with 1-4 substituents independently selected from halogen and OH;

each R$^D$ is independently H, C$_1$-C$_6$ alkyl, CO—C$_1$-C$_6$ alkyl; CO$_2$—C$_1$-C$_6$ alkyl; SO$_w$—C$_1$-C$_6$ alkyl; C$_1$-C$_6$ heteroalkyl, wherein each alkyl or heteroalkyl is optionally substituted with 1-4 substituents independently selected from halogen and OH; or two R$^D$ attached to the same nitrogen are taken together with the nitrogen to which they are attached to form a 3-7 membered heterocycle with 0-2 additional ring heteroatoms selected from O, S, and N, and wherein the heterocycle is optionally substituted with 1-4 substituents independently selected from halogen, C$_1$-C$_6$ alkyl, C$_1$-C$_6$ haloalkyl, C$_1$-C$_6$ alkoxy, and OH; and w is 0, 1, or 2.

Embodiment 4. The compound of any one of embodiments 1-3, or a pharmaceutically acceptable salt thereof, wherein A is phenyl or heteroaryl, wherein heteroaryl has 5, 6 or 9 ring atoms, 1 to 4 ring atoms selected from N, O, and S, and wherein A is substituted with 0-4 R$^9$ groups, wherein each R$^9$ is independently C$_1$-C$_6$ alkyl, C$_1$-C$_6$ heteroalkyl, C$_3$-C$_7$ cycloalkyl, hydroxy, cyano, or halogen, wherein each alkyl or heteroalkyl is optionally substituted with 1-4 groups independently selected from halogen and OH.

Embodiment 5. The compound of embodiment 4, or a pharmaceutically acceptable salt thereof, wherein A is phenyl, thiazole, thiophene, pyridine, pyridazine, benzofuran, benzthiophene, thienopyridine (e.g., thieno[3,2-b]pyridine, thieno[3,2-c]pyridine, thieno[2,3-b]pyridine) or furopyridine (e.g., furo[3,2-b]pyridine, furo[3,2-c]pyridine, furo[2,3-b]pyridine), each substituted with 0-9 R$^9$ groups.

Embodiment 6. The compound of embodiment 4, or a pharmaceutically acceptable salt thereof, wherein A is phenyl, benzofuran, or benzthiophene, each substituted with 0-9 R$^9$ groups.

Embodiment 7. The compound of embodiment 4, or a pharmaceutically acceptable salt thereof, wherein A is phenyl substituted with 0-9 R$^9$ groups.

Embodiment 8. The compound of embodiment 4, or a pharmaceutically acceptable salt thereof, wherein A is benzofuran substituted with 0-9 R$^9$ groups.

Embodiment 9. The compound of embodiment 4, or a pharmaceutically acceptable salt thereof, wherein A is benzthiophene substituted with 0-9 R$^9$ groups.

Embodiment 10. The compound of embodiment 4, or a pharmaceutically acceptable salt thereof, wherein A is selected from:

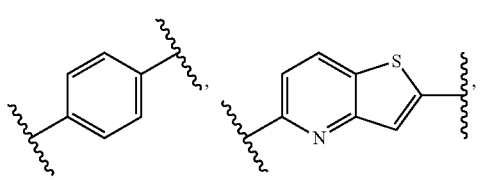

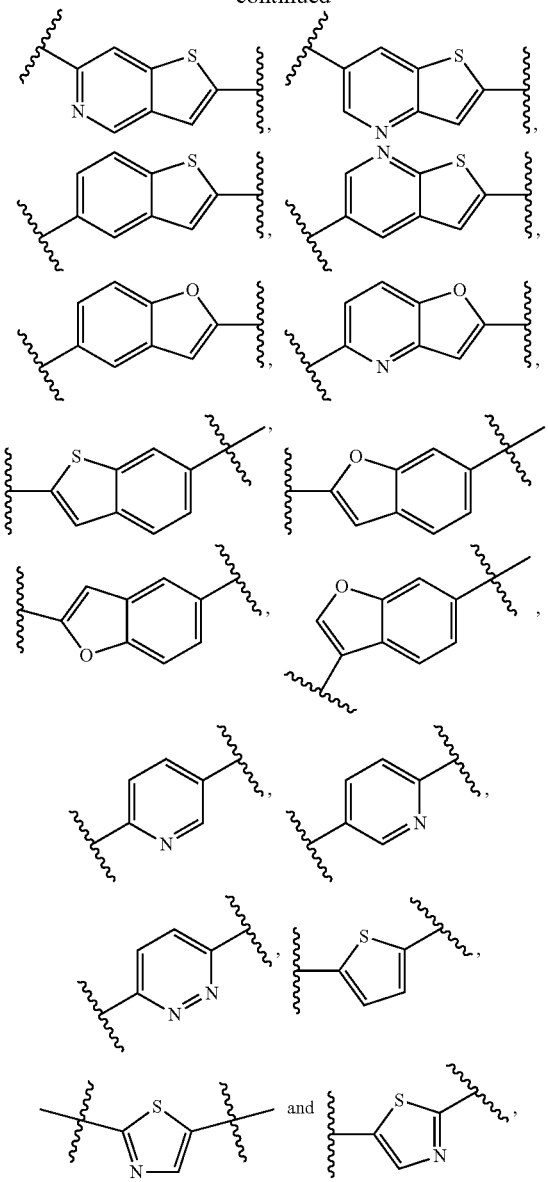

each substituted with 0-9 R$^9$ groups, wherein the left attachment point

represents the attachment point to L$^1$ and the right attachment point

represents the attachment point to the carbonyl.

Embodiment 11. The compound of embodiment 4, or a pharmaceutically acceptable salt thereof, wherein A is selected from:

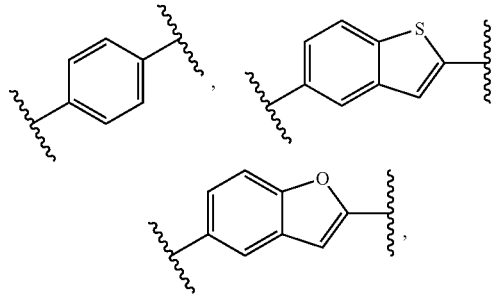

each substituted with 0-9 R⁹ groups, wherein the left attachment point

represents the attachment point to L¹ and the right attachment point

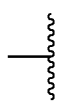

represents the attachment point to the carbonyl.

Embodiment 12. The compound of embodiment 4, or a pharmaceutically acceptable salt thereof, wherein A is phenyl, thiazole, thiophene, pyridine, pyridazine, benzofuran, or benzthiophene;

e.g., wherein A is

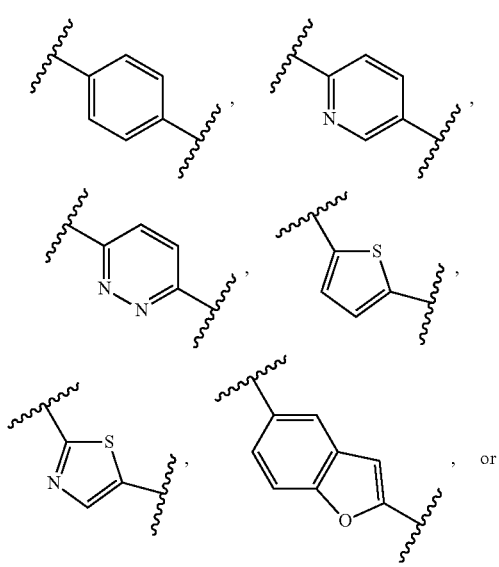

-continued

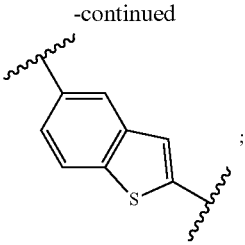

and

A is substituted with 0-4 R⁹ groups.

Embodiment 13. The compound of embodiment 4, or a pharmaceutically acceptable salt thereof, wherein A is

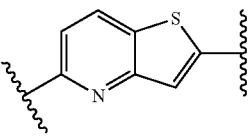

substituted with 0-9 R⁹ groups, wherein the left attachment point

represents the attachment point to L¹ and the right attachment point

represents the attachment point to the carbonyl.

Embodiment 14. The compound of embodiment 4, or a pharmaceutically acceptable salt thereof, wherein A is

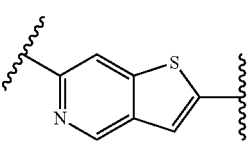 [SMILES: *c1cc2sc(*)cc2cn1]

substituted with 0-9 R⁹ groups, wherein the left attachment point

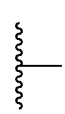

represents the attachment point to L¹ and the right attachment point

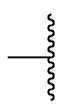

represents the attachment point to the carbonyl.

Embodiment 15. The compound of embodiment 4, or a pharmaceutically acceptable salt thereof, wherein A is

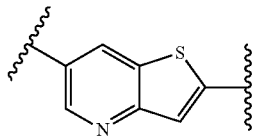 [SMILES: *c1cnc2cc(*)sc2c1]

substituted with 0-9 $R^9$ groups, wherein the left attachment point

represents the attachment point to $L^1$ and the right attachment point

represents the attachment point to the carbonyl.

Embodiment 16. The compound of embodiment 4, or a pharmaceutically acceptable salt thereof, wherein A is

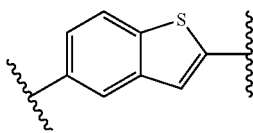 [SMILES: *c1ccc2sc(*)cc2c1]

substituted with 0-9 $R^9$ groups, wherein the left attachment point

represents the attachment point to $L^1$ and the right attachment point

represents the attachment point to the carbonyl.

Embodiment 17. The compound of embodiment 4, or a pharmaceutically acceptable salt thereof, wherein A is

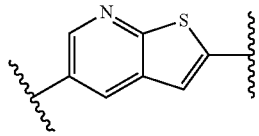 [SMILES: *c1cnc2sc(*)cc2c1]

substituted with 0-9 $R^9$ groups, wherein the left attachment point

represents the attachment point to $L^1$ and the right attachment point

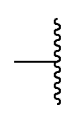

represents the attachment point to the carbonyl.

Embodiment 18. The compound of embodiment 4, or a pharmaceutically acceptable salt thereof, wherein A is

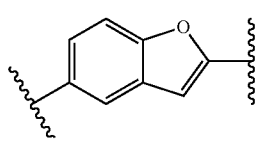 [SMILES: *c1ccc2oc(*)cc2c1]

substituted with 0-9 $R^9$ groups, wherein the left attachment point

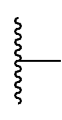

represents the attachment point to $L^1$ and the right attachment point

represents the attachment point to the carbonyl.

Embodiment 19. The compound of embodiment 4, or a pharmaceutically acceptable salt thereof, wherein A is

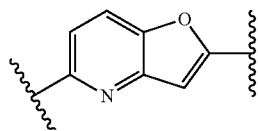 [SMILES: *c1ccc2oc(*)cc2n1]

substituted with 0-9 R⁹ groups, wherein the left attachment point

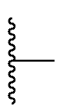

represents the attachment point to L¹ and the right attachment point

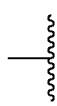

represents the attachment point to the carbonyl.

Embodiment 20. The compound of embodiment 4, or a pharmaceutically acceptable salt thereof, wherein A is

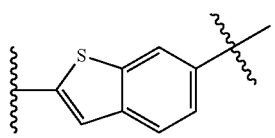 [SMILES: *c1ccc2cc(*)sc2c1]

substituted with 0-9 R⁹ groups, wherein the left attachment point

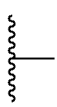

represents the attachment point to L¹ and the right attachment point

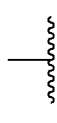

represents the attachment point to the carbonyl.

Embodiment 21. The compound of embodiment 4, or a pharmaceutically acceptable salt thereof, wherein A is

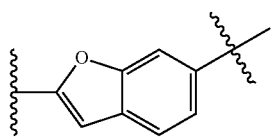 [SMILES: *c1ccc2cc(*)oc2c1]

substituted with 0-9 R⁹ groups, wherein the left attachment point

represents the attachment point to L¹ and the right attachment point

represents the attachment point to the carbonyl.

Embodiment 22. The compound of embodiment 4, or a pharmaceutically acceptable salt thereof, wherein A is

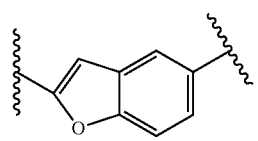 [SMILES: *c1ccc2oc(*)cc2c1]

substituted with 0-9 R⁹ groups, wherein the left attachment point

represents the attachment point to L¹ and the right attachment point

represents the attachment point to the carbonyl.

Embodiment 23. The compound of embodiment 4, or a pharmaceutically acceptable salt thereof, wherein A is

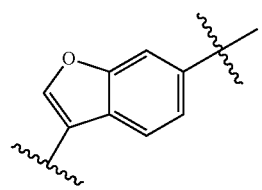 [SMILES: *c1ccc2c(*)coc2c1]

substituted with 0-9 R⁹ groups, wherein the left attachment point

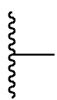

represents the attachment point to L¹ and the right attachment point

represents the attachment point to the carbonyl.

Embodiment 24. The compound of embodiment 4, or a pharmaceutically acceptable salt thereof, wherein A is

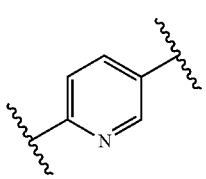 [SMILES: *c1ccc(*)nc1]

substituted with 0-9 R⁹ groups, wherein the left attachment point

represents the attachment point to L¹ and the right attachment point

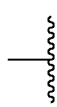

represents the attachment point to the carbonyl.

Embodiment 25. The compound of embodiment 4, or a pharmaceutically acceptable salt thereof, wherein A is

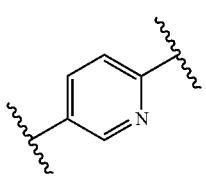 [SMILES: *c1ccc(*)nc1]

substituted with 0-9 R⁹ groups, wherein the left attachment point

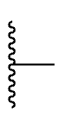

represents the attachment point to L¹ and the right attachment point

represents the attachment point to the carbonyl.

Embodiment 26. The compound of embodiment 4, or a pharmaceutically acceptable salt thereof, wherein A is

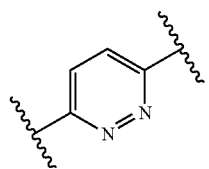 [SMILES: *c1ccc(*)nn1]

substituted with 0-9 R⁹ groups, wherein the left attachment point

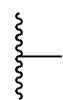

represents the attachment point to L¹ and the right attachment point

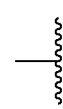

represents the attachment point to the carbonyl.

Embodiment 27. The compound of embodiment 4, or a pharmaceutically acceptable salt thereof, wherein A is

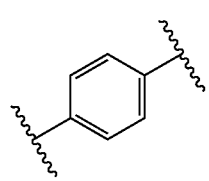 [SMILES: *c1ccc(*)cc1]

substituted with 0-9 R⁹ groups, wherein the left attachment point

represents the attachment point to L¹ and the right attachment point

represents the attachment point to the carbonyl.

Embodiment 28. The compound of embodiment 4, or a pharmaceutically acceptable salt thereof, wherein A is

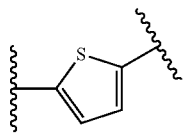 [SMILES: *c1ccc(*)s1]

substituted with 0-9 $R^9$ groups, wherein the left attachment point

represents the attachment point to $L^1$ and the right attachment point

represents the attachment point to the carbonyl.

Embodiment 29. The compound of embodiment 4, or a pharmaceutically acceptable salt thereof, wherein A is

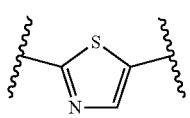 [SMILES: *c1cnc(*)s1]

substituted with 0-9 $R^9$ groups, wherein the left attachment point

represents the attachment point to $L^1$ and the right attachment point

represents the attachment point to the carbonyl.

Embodiment 30. The compound of embodiment 4, or a pharmaceutically acceptable salt thereof, wherein A is

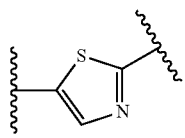 [SMILES: *c1cnc(*)s1]

substituted with 0-9 $R^9$ groups, wherein the left attachment point

represents the attachment point to $L^1$ and the right attachment point represents the attachment point to the carbonyl.

Embodiment 31. The compound of any one of embodiments 1-30, or a pharmaceutically acceptable salt thereof, wherein A is not substituted with any $R^9$ groups.

Embodiment 32. The compound of any one of embodiments 1-31, or a pharmaceutically acceptable salt thereof, wherein $L^1$ is a bond.

Embodiment 33. The compound of any one of embodiments 1-31, or a pharmaceutically acceptable salt thereof, wherein $L^1$ is —CR'$_2$—.

Embodiment 34. The compound of any one of embodiments 1-31, or a pharmaceutically acceptable salt thereof, wherein $L^1$ is —CR'$_2$CR'$_2$—.

Embodiment 35. The compound of any one of embodiments 1-34, or a pharmaceutically acceptable salt thereof, wherein each R' is independently H.

Embodiment 36. The compound of any one of embodiments 1-34, or a pharmaceutically acceptable salt thereof, wherein two R' together with the carbon to which they are attached form a cyclopropyl ring.

Embodiment 37. The compound of any one of embodiments 1-31, or a pharmaceutically acceptable salt thereof, wherein $L^1$ is selected from a bond, —CH$_2$— and

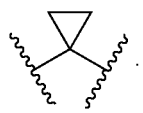 [SMILES: *C1(*)CC1].

Embodiment 38. The compound of any one of embodiments 1-31, or a pharmaceutically acceptable salt thereof, wherein $L^1$ is —CH$_2$—.

Embodiment 39. The compound of any one of embodiments 1-31, or a pharmaceutically acceptable salt thereof, wherein $L^1$ is

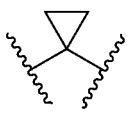

Embodiment 40. The compound of any one of embodiments 1-39, or a pharmaceutically acceptable salt thereof, wherein $R^1$ is H.

Embodiment 41. The compound of any one of embodiments 1-40, or a pharmaceutically acceptable salt thereof, wherein $R^3$ is H.

Embodiment 42. The compound of any one of embodiments 1-41, or a pharmaceutically acceptable salt thereof, wherein $R^4$ is H.

Embodiment 43. The compound of any one of embodiments 1-6, or a pharmaceutically acceptable salt thereof, wherein $R^1$ is H, or $R^3$ is H, or $R^4$ is H, or each of $R^1$, $R^3$ and $R^4$ is H.

Embodiment 44. The compound of any one of embodiments 1-43, or a pharmaceutically acceptable salt thereof, wherein $R^5$ is —$NH_2$.

Embodiment 45. The compound of any one of embodiments 1-43, or a pharmaceutically acceptable salt thereof, wherein $R^5$ is —OH.

Embodiment 46. The compound of any one of embodiments 1-45, or a pharmaceutically acceptable salt thereof, wherein $R^6$ is H.

Embodiment 47. The compound of any one of embodiments 1-46, or a pharmaceutically acceptable salt thereof, wherein $R^2$ is phenyl or monocyclic heteroaryl, wherein heteroaryl has 5 or 6 ring atoms with 1 to 2 ring atoms selected from N, O, and S, and $R^2$ is substituted with 0-4 $R^{10}$ groups, wherein each $R^{10}$ is independently $C_1$-$C_6$ alkyl, $C_1$-$C_6$ alkenyl, $C_1$-$C_6$ heteroalkyl, phenyl, $C_3$-$C_7$ cycloalkyl, heterocyclyl, $C_1$-$C_6$ alkylene-phenyl, $C_1$-$C_6$ alkylene-$C_3$-$C_7$ cycloalkyl, $C_1$-$C_6$ alkylene-heterocyclyl, hydroxy, cyano, CO—$R^C$, $NR^D{}_2$, or halogen, wherein heterocyclyl has 4-11 ring atoms with 1 to 4 ring atoms selected from N, O, and S; each alkyl or heteroalkyl is optionally substituted with 1-4 groups independently selected from halogen and OH, and wherein each phenyl, cycloalkyl, or heterocyclyl is optionally substituted with 1-4 $R^E$;

each $R^C$ is independently H, OH, $NR^{12}{}_2$, $C_1$-$C_6$ alkyl, $C_1$-$C_6$ alkoxy, $C_1$-$C_6$ heteroalkyl, wherein each alkyl or heteroalkyl is optionally substituted with 1-4 substituents independently selected from halogen and OH;

each $R^D$ is independently H, $C_1$-$C_6$ alkyl, CO—$C_1$-$C_6$ alkyl; $CO_2$—$C_1$-$C_6$ alkyl; $SO_w$—$C_1$-$C_6$ alkyl; $C_1$-$C_6$ heteroalkyl, wherein each alkyl or heteroalkyl is optionally substituted with 1-4 substituents independently selected from halogen and OH; or two $R^D$ attached to the same nitrogen are taken together with the nitrogen to which they are attached to form a 3-7 membered heterocycle with 0-2 additional ring heteroatoms selected from O, S, and N, and wherein the heterocycle is optionally substituted with 1-4 substituents independently selected from halogen, $C_1$-$C_6$ alkyl, $C_1$-$C_6$ haloalkyl, $C_1$-$C_6$ alkoxy, and OH;

each $R^E$ is independently H, halo, OH, O—$C_1$-$C_6$ alkyl, —$C_1$-$C_6$ alkyl, —$C_1$-$C_6$ haloalkyl;

each $R^{12}$ is independently H or $C_1$-$C_6$ alkyl; and w is 0, 1, or 2.

Embodiment 48. The compound of embodiment 47, or a pharmaceutically acceptable salt thereof, wherein $R^2$ is phenyl substituted with 0-4 $R^{10}$ groups.

Embodiment 49. The compound of embodiment 47, or a pharmaceutically acceptable salt thereof, wherein $R^2$ is phenyl substituted with 0-4 $R^{10}$ groups, and optionally wherein each $R^{10}$ is independently halogen, $C_1$-$C_6$ alkyl, or $C_1$-$C_6$ haloalkyl.

Embodiment 50. The compound of embodiment 47, or a pharmaceutically acceptable salt thereof, wherein $R^2$ is a monocyclic heteroaryl substituted with 0-4 $R^{10}$ groups.

Embodiment 51. The compound of embodiment 50, or a pharmaceutically acceptable salt thereof, wherein the monocyclic heteroaryl is selected from pyridine, pyrimidine, pyridazine, pyrazine, thiazole and thiophene, each substituted with 0-4 $R^{10}$ groups.

Embodiment 52. The compound of embodiment 47, or a pharmaceutically acceptable salt thereof, wherein $R^2$ is selected from phenyl, pyridine, pyrimidine, pyridazine, pyrazine, thiazole and thiophene, each substituted with 0-4 $R^{10}$ groups.

Embodiment 53. The compound of embodiment 47, or a pharmaceutically acceptable salt thereof, wherein $R^2$ is selected from phenyl, 2-pyridine, 3-pyridine, 4-pyridine, 2-pyrimidine, 4-pyridine, 3-pyridazine, pyrazine, 2-thiazole, 5-thiazole, 2-thiophene and 3-thiophene, each substituted with 0-4 $R^{10}$ groups.

Embodiment 54. The compound of embodiment 47, or a pharmaceutically acceptable salt thereof, wherein $R^2$ is selected from phenyl, 2-pyridine, 3-pyridine, 4-pyridine, 2-pyrimidine, 4-pyridine, 3-pyridazine, 5-thiazole, 2-thiophene and 3-thiophene, each substituted with 0-4 $R^{10}$ groups.

Embodiment 55. The compound of embodiment 47, or a pharmaceutically acceptable salt thereof, wherein $R^2$ is selected from phenyl and thiophene, each substituted with 0-4 $R^{10}$ groups.

Embodiment 56. The compound of embodiment 47, or a pharmaceutically acceptable salt thereof, wherein $R^2$ is selected from phenyl and 2-thiophene, each substituted with 0-4 $R^{10}$ groups.

Embodiment 57. The compound of embodiment 47, or a pharmaceutically acceptable salt thereof, wherein $R^2$ is thiophene substituted with 0-4 $R^{10}$ groups.

Embodiment 58. The compound of embodiment 47, or a pharmaceutically acceptable salt thereof, wherein $R^2$ is 2-thiophene substituted with 0-4 $R^{10}$ groups.

Embodiment 59. The compound of any one of embodiments 2-58, or a pharmaceutically acceptable salt thereof, wherein each $R^{10}$ is independently selected from halogen, $C_1$-$C_6$ alkyl, and CO—$R^C$, wherein $R^C$ is —$NH_2$ and wherein the alkyl is unsubstituted or substituted with 1-4 groups independently selected from halogen and OH.

Embodiment 60. The compound of any one of embodiments 2-58, or a pharmaceutically acceptable salt thereof, wherein each $R^{10}$ is independently selected from halogen and $C_1$-$C_6$ alkyl, wherein the alkyl is unsubstituted or substituted with 1-4 groups independently selected from halogen and OH.

Embodiment 61. The compound of any one of embodiments 2-58, or a pharmaceutically acceptable salt thereof, wherein each $R^{10}$ is independently selected from —F, —Cl, -Me, $CF_3$, —$CONH_2$ and —$CH(OH)CH_3$.

Embodiment 62. The compound of any one of embodiments 2-58, or a pharmaceutically acceptable salt thereof, wherein each $R^{10}$ is independently selected from —F, and -Me.

Embodiment 63. The compound of any one of embodiments 2-58, or a pharmaceutically acceptable salt thereof, wherein $R^2$ is monocyclic heteroaryl, wherein heteroaryl is pyridine, pyrimidine, pyridazine, pyrazine, thiazole, or thiophene, e.g., wherein $R^2$ is 2-thiophenyl, and each $R^2$ is substituted with 0-4 $R^{10}$ groups, and optionally wherein each $R^{10}$ is independently halogen, $C_1$-$C_6$ alkyl, or $C_1$-$C_6$ haloalkyl.

Embodiment 64. The compound of any one of embodiments 1-46, or a pharmaceutically acceptable salt thereof, wherein $R^2$ is selected from the group consisting of

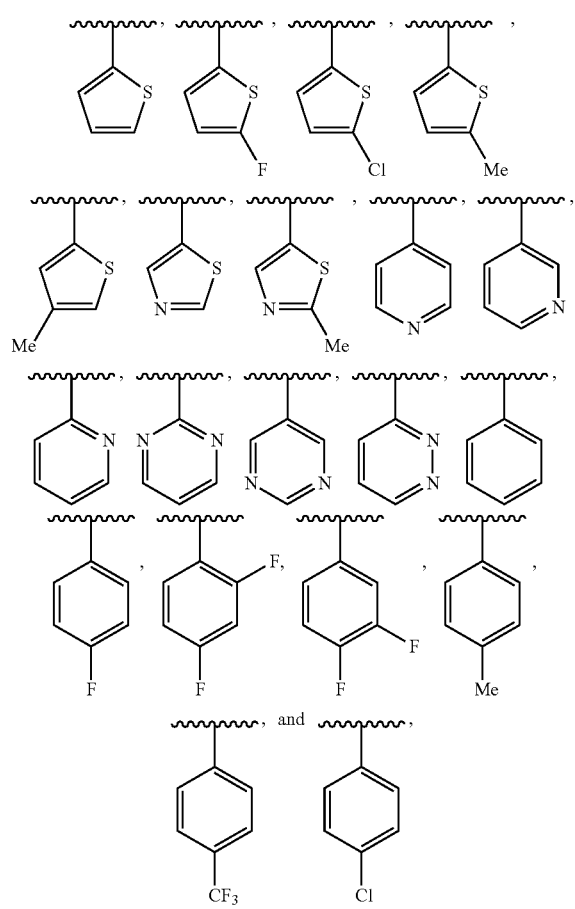

e.g., wherein $R^2$ is

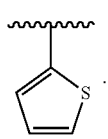

Embodiment 65. The compound of any one of embodiments 1-46, or a pharmaceutically acceptable salt thereof, wherein $R^2$ is selected from the group consisting of:

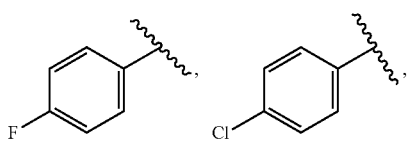

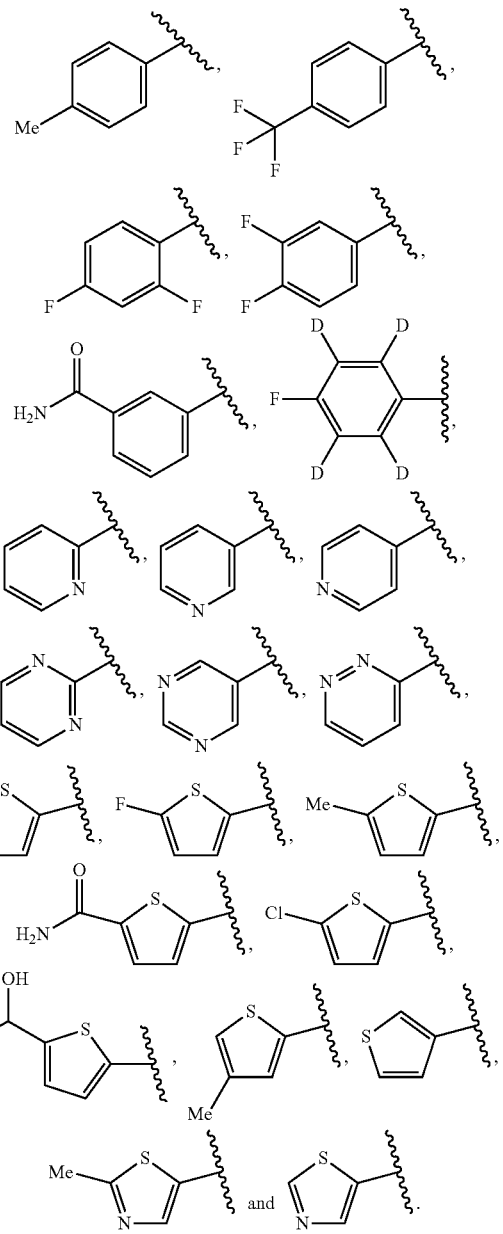

Embodiment 66. The compound of any one of embodiments 1-46, or a pharmaceutically acceptable salt thereof, wherein $R^2$ is selected from the group consisting of:

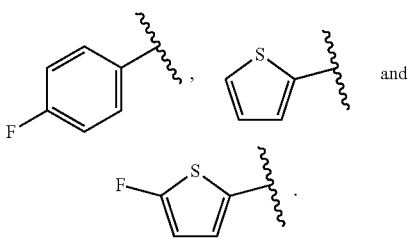

Embodiment 67. The compound of any one of embodiments 1-46, or a pharmaceutically acceptable salt thereof, wherein $R^2$ is

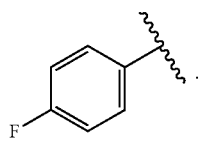

Embodiment 68. The compound of any one of embodiments 1-46, or a pharmaceutically acceptable salt thereof, wherein R² is

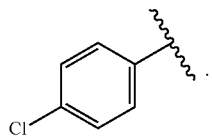 [SMILES: *c1ccc(Cl)cc1]

Embodiment 69. The compound of any one of embodiments 1-46, or a pharmaceutically acceptable salt thereof, wherein R² is

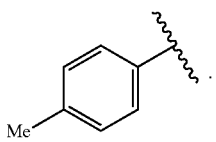 [SMILES: *c1ccc(C)cc1]

Embodiment 70. The compound of any one of embodiments 1-46, or a pharmaceutically acceptable salt thereof, wherein R² is

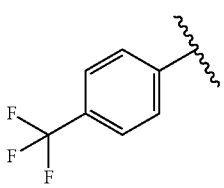

Embodiment 71. The compound of any one of embodiments 1-46, or a pharmaceutically acceptable salt thereof, wherein R² is

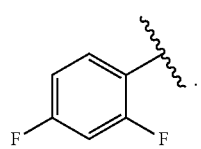

Embodiment 72. The compound of any one of embodiments 1-46, or a pharmaceutically acceptable salt thereof, wherein R² is

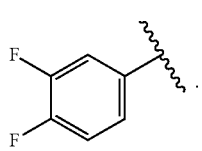

Embodiment 73. The compound of any one of embodiments 1-46, or a pharmaceutically acceptable salt thereof, wherein R² is

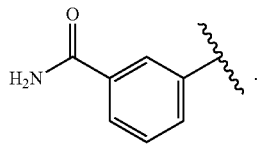

Embodiment 74. The compound of any one of embodiments 1-46, or a pharmaceutically acceptable salt thereof, wherein R² is

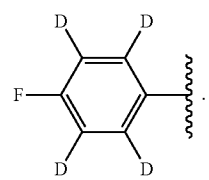

Embodiment 75. The compound of any one of embodiments 1-46, or a pharmaceutically acceptable salt thereof, wherein R² is

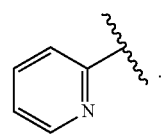

Embodiment 76. The compound of any one of embodiments 1-46, or a pharmaceutically acceptable salt thereof, wherein R² is

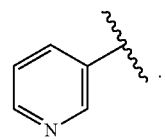

Embodiment 77. The compound of any one of embodiments 1-46, or a pharmaceutically acceptable salt thereof, wherein R² is Embodiment 78. The compound of any one of embodiments 1-46, or a pharmaceutically acceptable salt thereof, wherein R² is

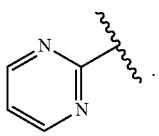

Embodiment 79. The compound of any one of embodiments 1-46, or a pharmaceutically acceptable salt thereof, wherein $R^2$ is

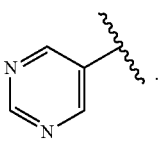

Embodiment 80. The compound of any one of embodiments 1-46, or a pharmaceutically acceptable salt thereof, wherein $R^2$ is

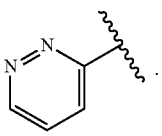

Embodiment 81. The compound of any one of embodiments 1-46, or a pharmaceutically acceptable salt thereof, wherein $R^2$ is

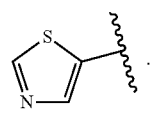 [SMILES: *c1cncs1]

Embodiment 82. The compound of any one of embodiments 1-46, or a pharmaceutically acceptable salt thereof, wherein $R^2$ is

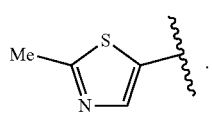 [SMILES: *c1cnc(C)s1]

Embodiment 83. The compound of any one of embodiments 1-46, or a pharmaceutically acceptable salt thereof, wherein $R^2$ is

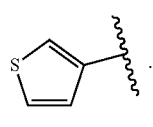

Embodiment 84. The compound of any one of embodiments 1-46, or a pharmaceutically acceptable salt thereof, wherein $R^2$ is

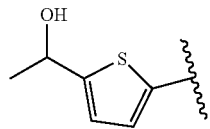

Embodiment 85. The compound of any one of embodiments 1-46, or a pharmaceutically acceptable salt thereof, wherein $R^2$ is

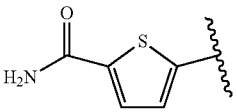

Embodiment 86. The compound of any one of embodiments 1-46, or a pharmaceutically acceptable salt thereof, wherein $R^2$ is

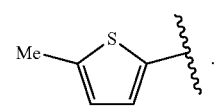

Embodiment 87. The compound of any one of embodiments 1-46, or a pharmaceutically acceptable salt thereof, wherein $R^2$ is

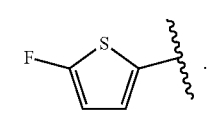 [SMILES: *c1ccc(F)s1]

Embodiment 88. The compound of any one of embodiments 1-46, or a pharmaceutically acceptable salt thereof, wherein $R^2$ is

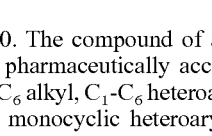

Embodiment 89. The compound of any one of embodiments 1-46, or a pharmaceutically acceptable salt thereof, wherein $R^2$ is

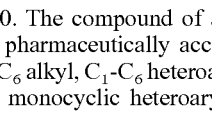

Embodiment 90. The compound of any one of embodiments 1-89, or a pharmaceutically acceptable salt thereof, wherein $R^7$ is $C_1$-$C_6$ alkyl, $C_1$-$C_6$ heteroalkyl, $C_3$-$C_7$ cycloalkyl, phenyl, or a monocyclic heteroaryl, wherein the heteroaryl has 5 or 6 ring atoms with 1 to 2 ring atoms selected from N, O, and S; wherein each alkyl, heteroalkyl, phenyl, cycloalkyl and heteroaryl is substituted with 0-4 $R^{11}$ groups; or $R^7$ and $R^8$ are taken together with the nitrogen and sulfur to which they are attached to form a 4-7 membered heterocycle with 0-2 additional ring heteroatoms selected from O, S, and N, wherein the heterocycle is substituted with 0-4 $R^{10}$ groups.

Embodiment 91. The compound of any one of embodiments 2-89, or a pharmaceutically acceptable salt thereof, wherein $R^7$ is $C_1$-$C_6$ alkyl, $C_1$-$C_6$ haloalkyl, $C_1$-$C_6$ heteroalkyl, $C_3$-$C_7$ cycloalkyl, phenyl, or a monocyclic heteroaryl, wherein the heteroaryl has 5 or 6 ring atoms with 1 to 2 ring atoms being N; wherein each alkyl, heteroalkyl, phenyl, cycloalkyl and heteroaryl is substituted with 0-4 $R^{11}$ groups; or $R^7$ and $R^8$ are taken together with the nitrogen and sulfur to which they are attached to form a 4-7 membered heterocycle with 0 additional ring heteroatoms, wherein the heterocycle is substituted with 0-4 $R^{10}$ groups.

Embodiment 92. The compound of any one of embodiments 2-89, or a pharmaceutically acceptable salt thereof, wherein $R^7$ is selected from -Me, -Et, —$CF_3$, $CH_2CH_2OMe$, phenyl, imidazolyl, pyridinyl, pyrimidinyl, pyrazinyl, pyridazinyl and pyridinon-yl; each of which is substituted with 0-4 $R^{11}$ groups; or $R^7$ and $R^8$ are taken together with the nitrogen and sulfur to which they are attached to form a 5 or 6 membered heterocycle with 0 additional ring heteroatoms, wherein the heterocycle is substituted with or 1 instances of methyl or phenyl.

Embodiment 93. The compound of any one of embodiments 2-89, or a pharmaceutically acceptable salt thereof, wherein $R^7$ is $C_1$-$C_6$ alkyl, $C_1$-$C_6$ haloalkyl, $C_1$-$C_6$ heteroalkyl, $C_3$-$C_7$ cycloalkyl, phenyl, or 6-membered heteroaryl wherein heteroaryl has 1 or 2 nitrogen ring atoms; or $R^7$ and $R^8$ are taken together with the nitrogen and sulfur to which they are attached to form a 4-7 membered heterocycle with 0-2 additional ring heteroatoms selected from O, S, and N; and $R^7$ is substituted with 0-4 $R^{11}$ groups.

Embodiment 94. The compound of any one of embodiments 2-93, or a pharmaceutically acceptable salt thereof, wherein each $R^{11}$ is independently selected from $C_1$-$C_6$ alkyl, $C_1$-$C_6$ alkenyl, $C_1$-$C_6$ heteroalkyl, $C_3$-$C_7$ cycloalkyl, hydroxy, cyano, and halogen, wherein the alkyl and heteroalkyl are optionally substituted with 1-4 groups independently selected from halogen and OH.

Embodiment 95. The compound of any one of embodiments 2-93, or a pharmaceutically acceptable salt thereof, wherein each $R^{11}$ is independently selected from —F, —Cl, -Me, -$^i$Pr, —C(=$CH_2$)$CH_3$, —$CF_3$, —CN, —OH, -OMe, —$CH_2OCH_2CH_2OMe$ and —$CH_2OH$.

Embodiment 96. The compound of any one of embodiments 1-89, or a pharmaceutically acceptable salt thereof, wherein $R^7$ is selected from -Me, -Et, —$CF_3$, —$CH_2CH_2OMe$,

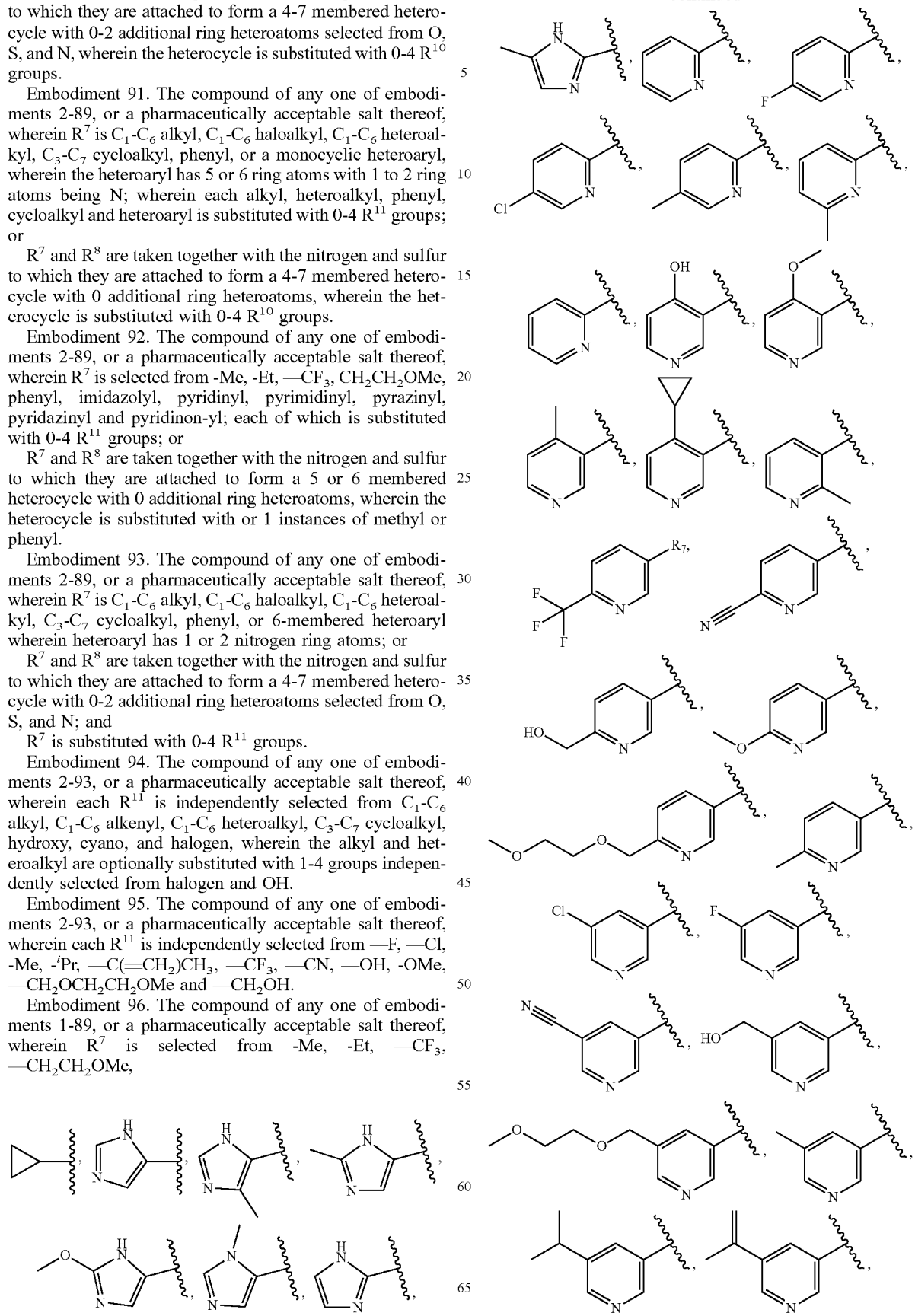

-continued

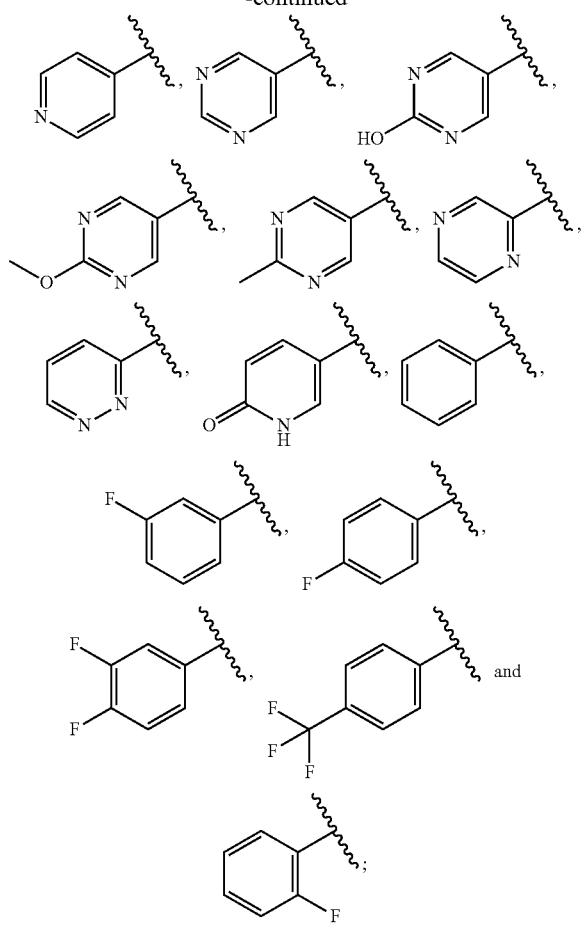

or
R⁷ and R⁸ are taken together with the atoms to which they are attached to form:

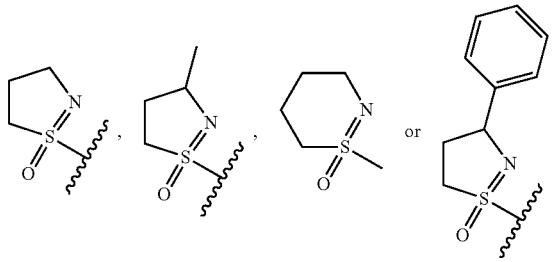

Embodiment 97. The compound of any one of embodiments 1-89, or a pharmaceutically acceptable salt thereof, wherein R⁷ is selected from the group consisting of Me, Ph, CF₃, —CH₂CH₂OCH₃, cyclopropyl,

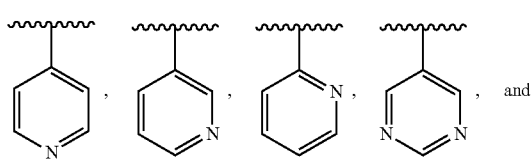, and

-continued

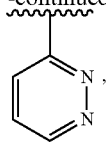, e.g., wherein R⁷ is Me.

Embodiment 98. The compound of any one of embodiments 1-89, or a pharmaceutically acceptable salt thereof, wherein R⁷ is -Me.

Embodiment 99. The compound of any one of embodiments 1-89, or a pharmaceutically acceptable salt thereof, wherein R⁷ is wherein R⁷ is -Et.

Embodiment 100. The compound of any one of embodiments 1-89, or a pharmaceutically acceptable salt thereof, wherein R⁷ is —CF₃.

Embodiment 101. The compound of any one of embodiments 1-89, or a pharmaceutically acceptable salt thereof, wherein R⁷ is —CH₂CH₂OMe.

Embodiment 102. The compound of any one of embodiments 1-89, or a pharmaceutically acceptable salt thereof, wherein R⁷ is

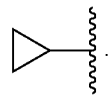

Embodiment 103. The compound of any one of embodiments 1-89, or a pharmaceutically acceptable salt thereof, wherein R⁷ is

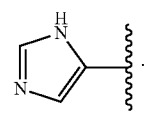

Embodiment 104. The compound of any one of embodiments 1-89, or a pharmaceutically acceptable salt thereof, wherein R⁷ is

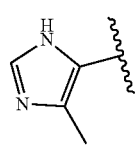

Embodiment 105. The compound of any one of embodiments 1-89, or a pharmaceutically acceptable salt thereof, wherein R⁷ is

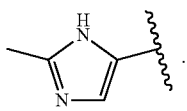

Embodiment 106. The compound of any one of embodiments 1-89, or a pharmaceutically acceptable salt thereof, wherein R⁷ is

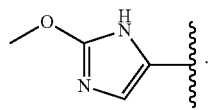

Embodiment 107. The compound of any one of embodiments 1-89, or a pharmaceutically acceptable salt thereof, wherein $R^7$ is

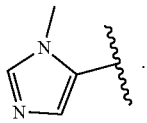

Embodiment 108. The compound of any one of embodiments 1-89, or a pharmaceutically acceptable salt thereof, wherein $R^7$ is

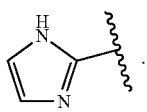

Embodiment 109. The compound of any one of embodiments 1-89, or a pharmaceutically acceptable salt thereof, wherein $R^7$ is

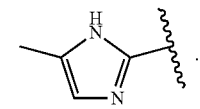

Embodiment 110. The compound of any one of embodiments 1-89, or a pharmaceutically acceptable salt thereof, wherein $R^7$ is

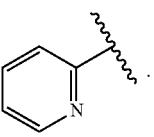

Embodiment 111. The compound of any one of embodiments 1-89, or a pharmaceutically acceptable salt thereof, wherein $R^7$ is

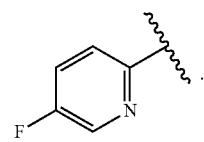

Embodiment 112. The compound of any one of embodiments 1-89, or a pharmaceutically acceptable salt thereof, wherein $R^7$ is

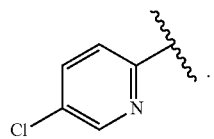

Embodiment 113. The compound of any one of embodiments 1-89, or a pharmaceutically acceptable salt thereof, wherein $R^7$ is

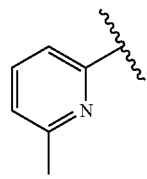

Embodiment 114. The compound of any one of embodiments 1-89, or a pharmaceutically acceptable salt thereof, wherein $R^7$ is

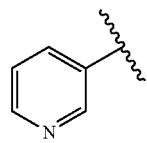

Embodiment 115. The compound of any one of embodiments 1-89, or a pharmaceutically acceptable salt thereof, wherein $R^7$ is

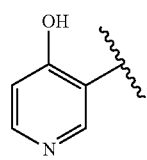

Embodiment 116. The compound of any one of embodiments 1-89, or a pharmaceutically acceptable salt thereof, wherein $R^7$ is Embodiment 117. The compound of any one of embodiments 1-89, or a pharmaceutically acceptable salt thereof, wherein $R^7$ is

169

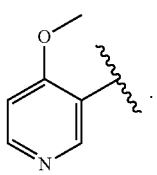 [SMILES: *c1cnccc1OC]

Embodiment 118. The compound of any one of embodiments 1-89, or a pharmaceutically acceptable salt thereof, wherein $R^7$ is

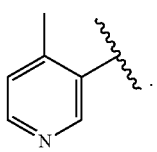 [SMILES: *c1cnccc1C]

Embodiment 119. The compound of any one of embodiments 1-89, or a pharmaceutically acceptable salt thereof, wherein $R^7$ is

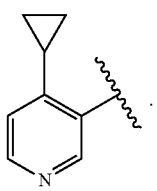 [SMILES: *c1cnccc1C1CC1]

Embodiment 120. The compound of any one of embodiments 1-89, or a pharmaceutically acceptable salt thereof, wherein $R^7$ is

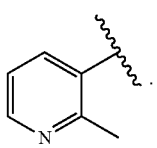 [SMILES: *c1cccnc1C]

Embodiment 121. The compound of any one of embodiments 1-89, or a pharmaceutically acceptable salt thereof, wherein $R^7$ is

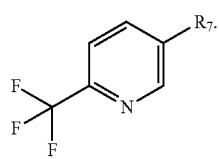

Embodiment 122. The compound of any one of embodiments 1-89, or a pharmaceutically acceptable salt thereof, wherein $R^7$ is

170

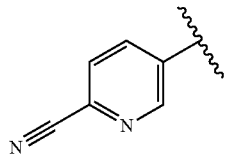

Embodiment 123. The compound of any one of embodiments 1-89, or a pharmaceutically acceptable salt thereof, wherein $R^7$ is

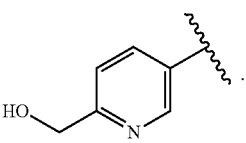

Embodiment 124. The compound of any one of embodiments 1-89, or a pharmaceutically acceptable salt thereof, wherein $R^7$ is

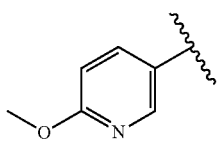

Embodiment 125. The compound of any one of embodiments 1-89, or a pharmaceutically acceptable salt thereof, wherein $R^7$ is

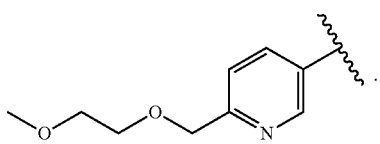

Embodiment 126. The compound of any one of embodiments 1-89, or a pharmaceutically acceptable salt thereof, wherein $R^7$ is

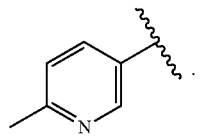 [SMILES: *c1ccc(C)nc1]

Embodiment 127. The compound of any one of embodiments 1-89, or a pharmaceutically acceptable salt thereof, wherein $R^7$ is

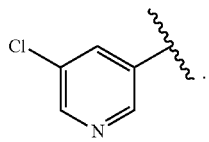 [SMILES: *c1cncc(Cl)c1]

Embodiment 128. The compound of any one of embodiments 1-89, or a pharmaceutically acceptable salt thereof, wherein R⁷ is

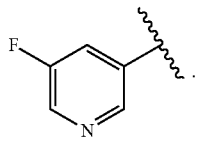

Embodiment 129. The compound of any one of embodiments 1-89, or a pharmaceutically acceptable salt thereof, wherein R⁷ is

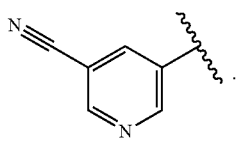 [SMILES: *c1cncc(C#N)c1]

Embodiment 130. The compound of any one of embodiments 1-89, or a pharmaceutically acceptable salt thereof, wherein R⁷ is

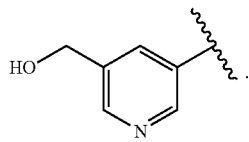

Embodiment 131. The compound of any one of embodiments 1-89, or a pharmaceutically acceptable salt thereof, wherein R⁷ is

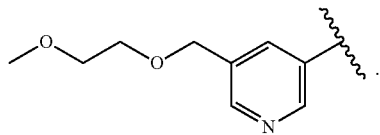 [SMILES: *c1cncc(COCCOC)c1]

Embodiment 132. The compound of any one of embodiments 1-89, or a pharmaceutically acceptable salt thereof, wherein R⁷ is

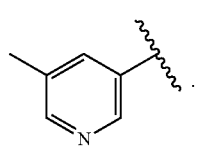 [SMILES: *c1cncc(C)c1]

Embodiment 133. The compound of any one of embodiments 1-89, or a pharmaceutically acceptable salt thereof, wherein R⁷ is

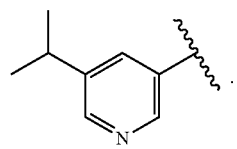 [SMILES: *c1cncc(C(C)C)c1]

Embodiment 134. The compound of any one of embodiments 1-89, or a pharmaceutically acceptable salt thereof, wherein R⁷ is

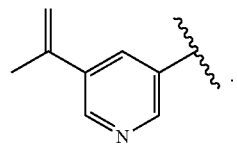 [SMILES: *c1cncc(C(=C)C)c1]

Embodiment 135. The compound of any one of embodiments 1-89, or a pharmaceutically acceptable salt thereof, wherein R⁷ is

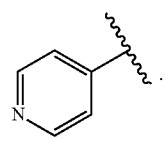

Embodiment 136. The compound of any one of embodiments 1-89, or a pharmaceutically acceptable salt thereof, wherein R⁷ is

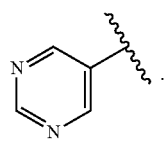 [SMILES: *c1cncnc1]

Embodiment 137. The compound of any one of embodiments 1-89, or a pharmaceutically acceptable salt thereof, wherein R⁷ is

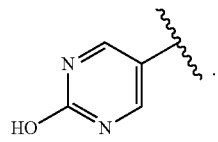 [SMILES: *c1cnc(O)nc1]

Embodiment 138. The compound of any one of embodiments 1-89, or a pharmaceutically acceptable salt thereof, wherein R⁷ is

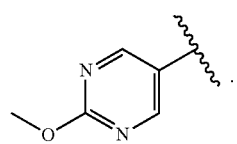 [SMILES: *c1cnc(OC)nc1]

Embodiment 139. The compound of any one of embodiments 1-89, or a pharmaceutically acceptable salt thereof, wherein $R^7$ is

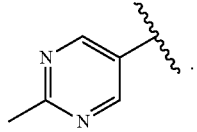 [SMILES: *c1cnc(C)nc1]

Embodiment 140. The compound of any one of embodiments 1-89, or a pharmaceutically acceptable salt thereof, wherein $R^7$ is

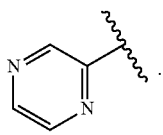

Embodiment 141. The compound of any one of embodiments 1-89, or a pharmaceutically acceptable salt thereof, wherein $R^7$ is

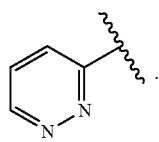 [SMILES: *c1cccnn1]

Embodiment 142. The compound of any one of embodiments 1-89, or a pharmaceutically acceptable salt thereof, wherein $R^7$ is

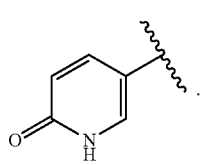 [SMILES: *c1ccc(=O)[nH]c1]

Embodiment 143. The compound of any one of embodiments 1-89, or a pharmaceutically acceptable salt thereof, wherein $R^7$ is

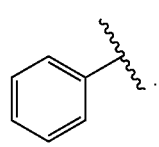

Embodiment 144. The compound of any one of embodiments 1-89, or a pharmaceutically acceptable salt thereof, wherein $R^7$ is

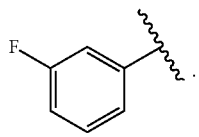 [SMILES: *c1cccc(F)c1]

Embodiment 145. The compound of any one of embodiments 1-89, or a pharmaceutically acceptable salt thereof, wherein $R^7$ is

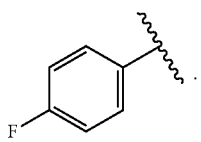

Embodiment 146. The compound of any one of embodiments 1-89, or a pharmaceutically acceptable salt thereof, wherein $R^7$ is

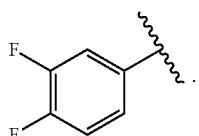

Embodiment 147. The compound of any one of embodiments 1-89, or a pharmaceutically acceptable salt thereof, wherein $R^7$ is

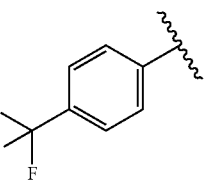

Embodiment 148. The compound of any one of embodiments 1-89, or a pharmaceutically acceptable salt thereof, wherein $R^7$ is

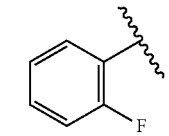

Embodiment 149. The compound of any one of embodiments 1-89, or a pharmaceutically acceptable salt thereof, wherein $R^7$ and $R^8$ are taken together with the atoms to which they are attached to form:

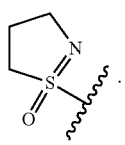

Embodiment 150. The compound of any one of embodiments 1-89, or a pharmaceutically acceptable salt thereof, wherein $R^7$ and $R^8$ are taken together with the atoms to which they are attached to form

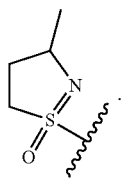

Embodiment 151. The compound of any one of embodiments 1-89, or a pharmaceutically acceptable salt thereof, wherein $R^7$ and $R^8$ are taken together with the atoms to which they are attached to form

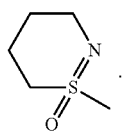

Embodiment 152. The compound of any one of embodiments 1-89, or a pharmaceutically acceptable salt thereof, wherein $R^7$ and $R^8$ are taken together with the atoms to which they are attached to form

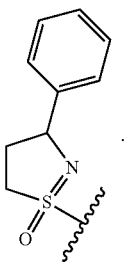 [SMILES: *S1(=O)=NC(c2ccccc2)CC1]

Embodiment 153. The compound of any one of embodiments 1-148, or a pharmaceutically acceptable salt thereof, wherein $R^8$ is H, Me, Et, CN, cyclopropyl, CO-t-butyl, or —CO$_2$-t-butyl.

Embodiment 154. The compound of any one of embodiments 1-148, or a pharmaceutically acceptable salt thereof, wherein $R^8$ is H, Me, Et, CN, cyclopropyl, or —CO$_2$-t-butyl, e.g., wherein $R^8$ is H.

Embodiment 155. The compound of any one of embodiments 1-148, or a pharmaceutically acceptable salt thereof, wherein $R^8$ is H.

Embodiment 156. The compound of any one of embodiments 1-148, or a pharmaceutically acceptable salt thereof, wherein $R^8$ is Me.

Embodiment 157. The compound of any one of embodiments 1-148, or a pharmaceutically acceptable salt thereof, wherein $R^8$ is Et.

Embodiment 158. The compound of any one of embodiments 1-148, or a pharmaceutically acceptable salt thereof, wherein $R^8$ is CN.

Embodiment 159. The compound of any one of embodiments 1-148, or a pharmaceutically acceptable salt thereof, wherein $R^8$ is cyclopropyl.

Embodiment 160. The compound of any one of embodiments 1-148, or a pharmaceutically acceptable salt thereof, wherein $R^8$ is CO-t-butyl.

Embodiment 161. The compound of any one of embodiments 1-148, or a pharmaceutically acceptable salt thereof, wherein $R^8$ is-CO$_2$-t-butyl.

Embodiment 162. The compound of any one of embodiments 1-89, or a pharmaceutically acceptable salt thereof, wherein $R^7$ and $R^8$ are joined together to form a propylene (—CH$_2$—CH$_2$—CH$_2$—).

Embodiment 163. The compound of any one of embodiments 1-3 and 40 to 162 of Formula (Ia)

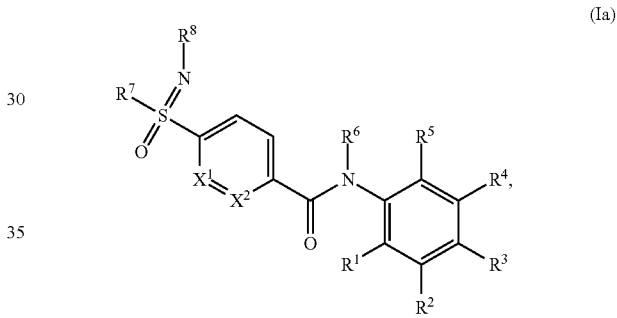

or a pharmaceutically acceptable salt thereof,
wherein:
$X^1$ is N or CH; $X^2$ is N or CH.

Embodiment 164. The compound of embodiment 163 of Formula (Ib)

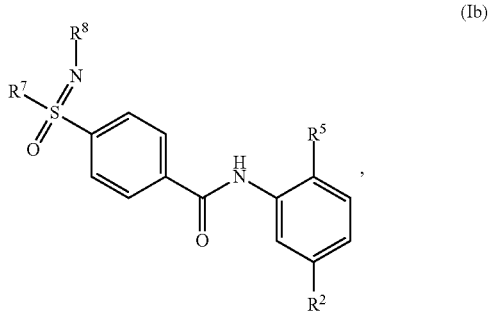

or a pharmaceutically acceptable salt thereof.

Embodiment 165. The compound of any one of embodiments 1-3 and 40 to 162 of Formula (Ic)

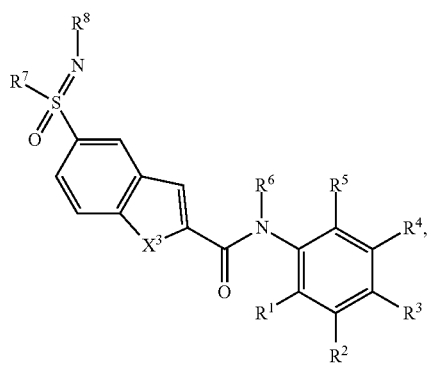

(Ic)

or a pharmaceutically acceptable salt thereof,
wherein $X^3$ is O or S.

Embodiment 166. The compound of embodiment 165 of Formula (Id)

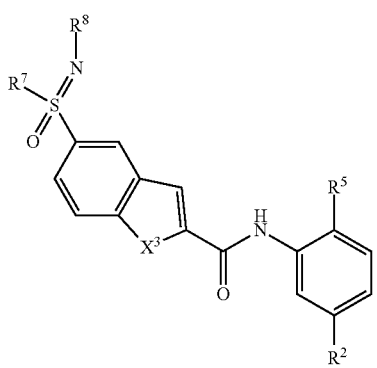

(Id)

or a pharmaceutically acceptable salt thereof,
wherein $X^3$ is O or S.

Embodiment 167. The compound of any one of embodiments 1-3 and 40 to 162 of Formula (Ie)

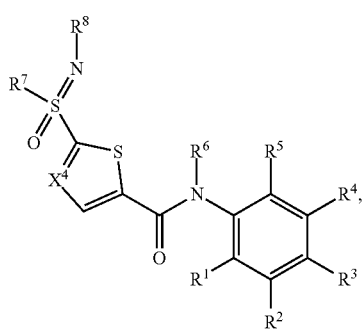

(Ie)

or a pharmaceutically acceptable salt thereof,
wherein $X^4$ is N or CH.

Embodiment 168. The compound of embodiment 167 of Formula (If)

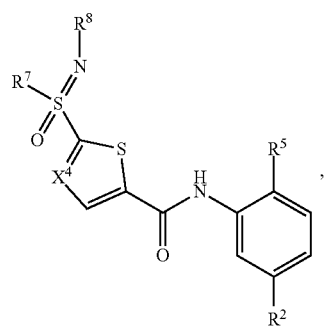

(If)

or a pharmaceutically acceptable salt thereof,
wherein $X^4$ is N or CH.

Embodiment 169. The compound of any one of embodiments 1-3 and 40 to 162 of Formula (Ig)

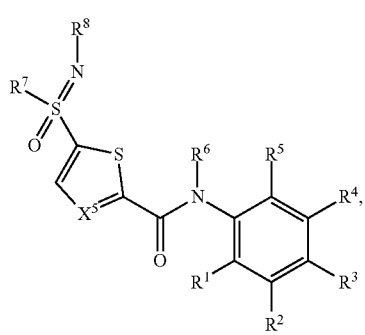

(Ig)

or a pharmaceutically acceptable salt thereof,
wherein $X^5$ is N or CH.

Embodiment 170. The compound of embodiment 169 of Formula (Ih)

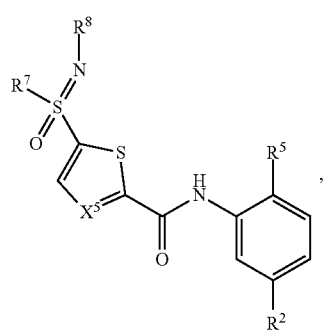

(Ih)

or a pharmaceutically acceptable salt thereof,
wherein $X^5$ is N or CH.

Embodiment 171. The compound of any one of embodiments 1-3 and 40 to 162 of Formula (Ii)

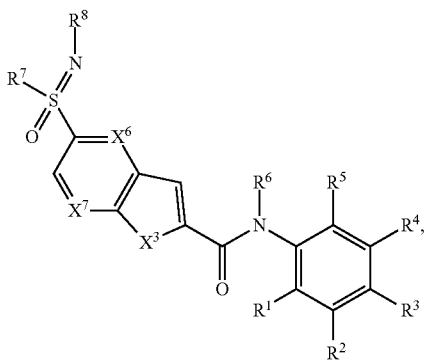

or a pharmaceutically acceptable salt thereof,
wherein $X^3$ is O or S;
$X^6$ is N or CH; and
$X^7$ is N or CH.

Embodiment 172. The compound of embodiment 171 of Formula (Ij)

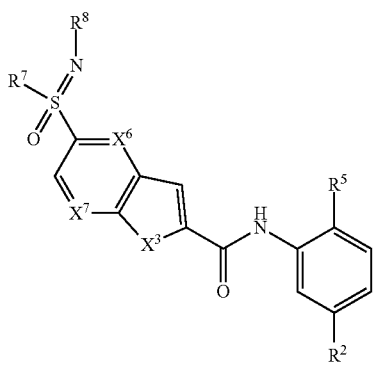

or a pharmaceutically acceptable salt thereof,
wherein $X^3$ is O or S;
$X^6$ is N or CH; and
$X^7$ is N or CH.

Embodiment 173. The compound of embodiment 170 or 171, or a pharmaceutically acceptable salt thereof, wherein $X^6$ is N and $X^7$ is CH.

Embodiment 174. The compound of embodiment 170 or 171, or a pharmaceutically acceptable salt thereof, wherein $X^6$ is CH and $X^7$ is N.

Embodiment 175. The compound of any one of embodiments 1-3 and 40 to 162 of Formula (Ik)

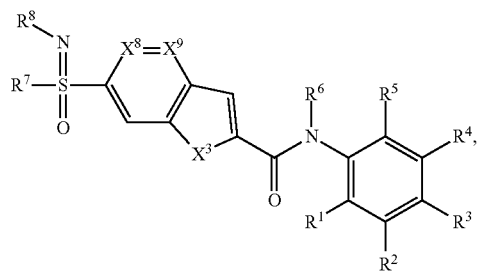

or a pharmaceutically acceptable salt thereof,
wherein $X^3$ is O or S;
$X^8$ is N or CH; and
$X^9$ is N or CH.

Embodiment 176. The compound of embodiment 175 of Formula (Im)

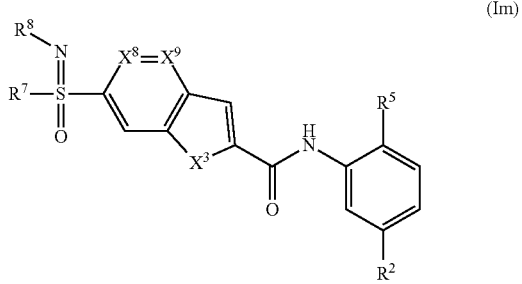

or a pharmaceutically acceptable salt thereof,
wherein $X^3$ is O or S;
$X^8$ is N or CH; and
$X^9$ is N or CH.

Embodiment 177. The compound of embodiment 175 or 176, or a pharmaceutically acceptable salt thereof, wherein $X^8$ is N and $X^9$ is CH.

Embodiment 178. The compound of embodiment 175 or 176, or a pharmaceutically acceptable salt thereof, wherein $X^8$ is CH and $X^9$ is N.

Embodiment 179. The compound of any one of embodiments 1-3 and 40 to 162 of Formula (In)

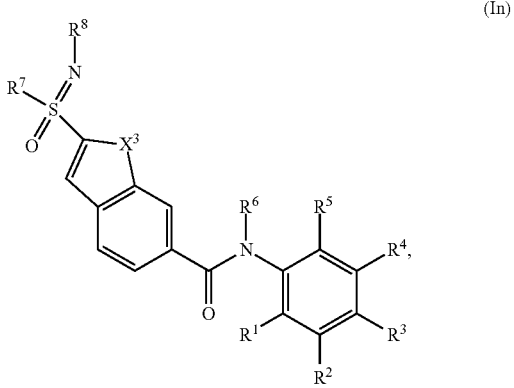

or a pharmaceutically acceptable salt thereof,
wherein $X^3$ is O or S.

Embodiment 180. The compound of embodiment 179 of Formula (Io)

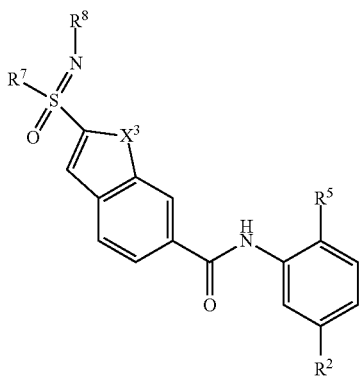

(Io)

or a pharmaceutically acceptable salt thereof,
wherein $X^3$ is O or S.

Embodiment 181. The compound of any one of embodiments 1-3 and 40 to 162 of Formula (Ip)

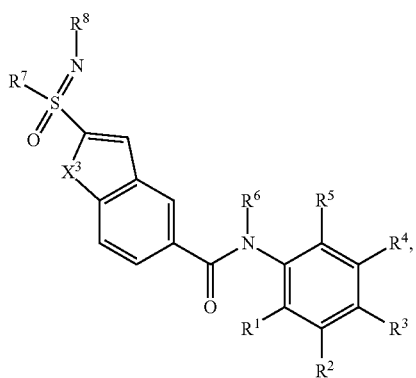

(Ip)

or a pharmaceutically acceptable salt thereof,
wherein $X^3$ is O or S.

Embodiment 182. The compound of embodiment 181 of Formula (Iq)

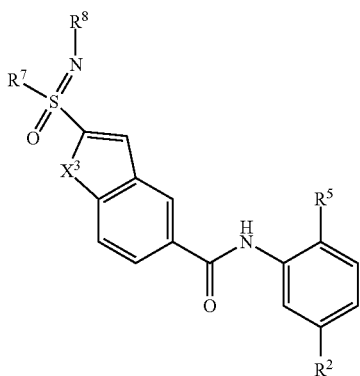

(Iq)

or a pharmaceutically acceptable salt thereof,
wherein $X^3$ is O or S.

Embodiment 183. The compound of any one of embodiments 1-3 and 40 to 162 of Formula (Ir)

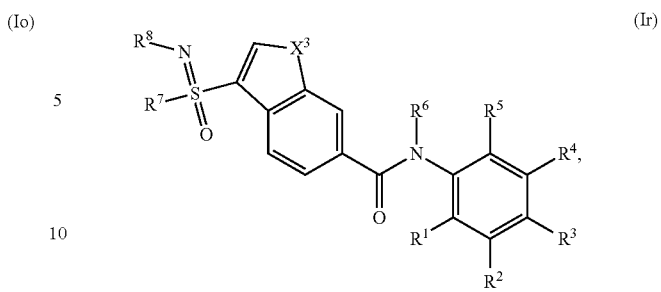

(Ir)

or a pharmaceutically acceptable salt thereof,
wherein $X^3$ is O or S.

Embodiment 184. The compound of embodiment 183 of Formula (Is)

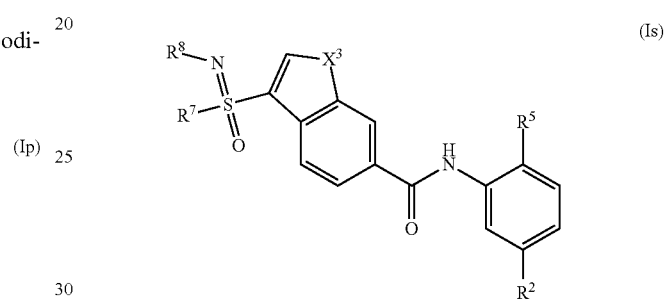

(Is)

or a pharmaceutically acceptable salt thereof,
wherein $X^3$ is O or S.

Embodiment 185. The compound of any one of embodiments 165, 166 and 171-184, or a pharmaceutically acceptable salt thereof, wherein $X^3$ is S.

Embodiment 186. The compound of any one of embodiments 165, 166 and 171-184, or a pharmaceutically acceptable salt thereof, wherein $X^3$ is O.

Embodiment 187. A compound selected from the compounds disclosed in Table 1, or a pharmaceutically acceptable salt thereof, or elsewhere in the specification and figures.

Embodiment 188. A compound of any one of embodiments 1-186 or a pharmaceutically acceptable salt thereof, wherein the compound is selected from:

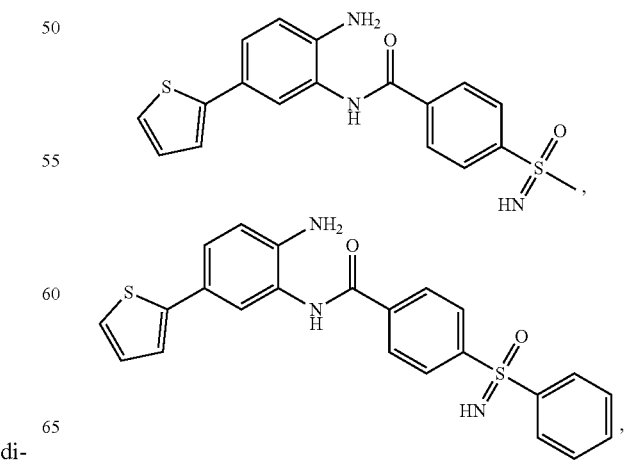

-continued
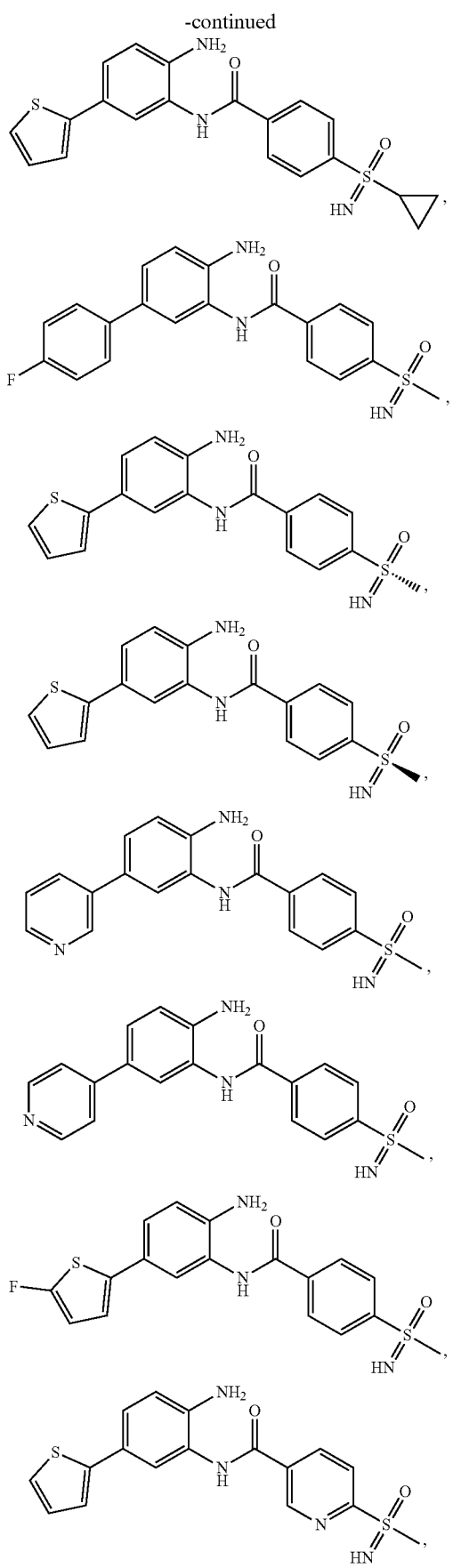
-continued
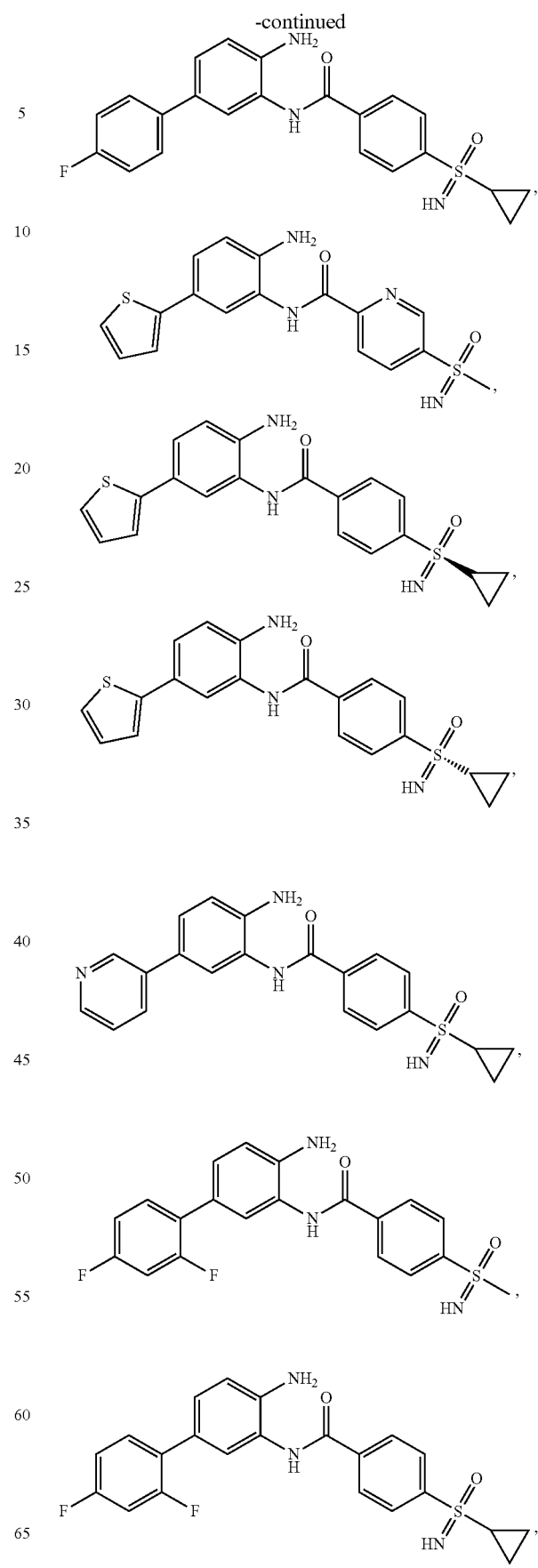

-continued
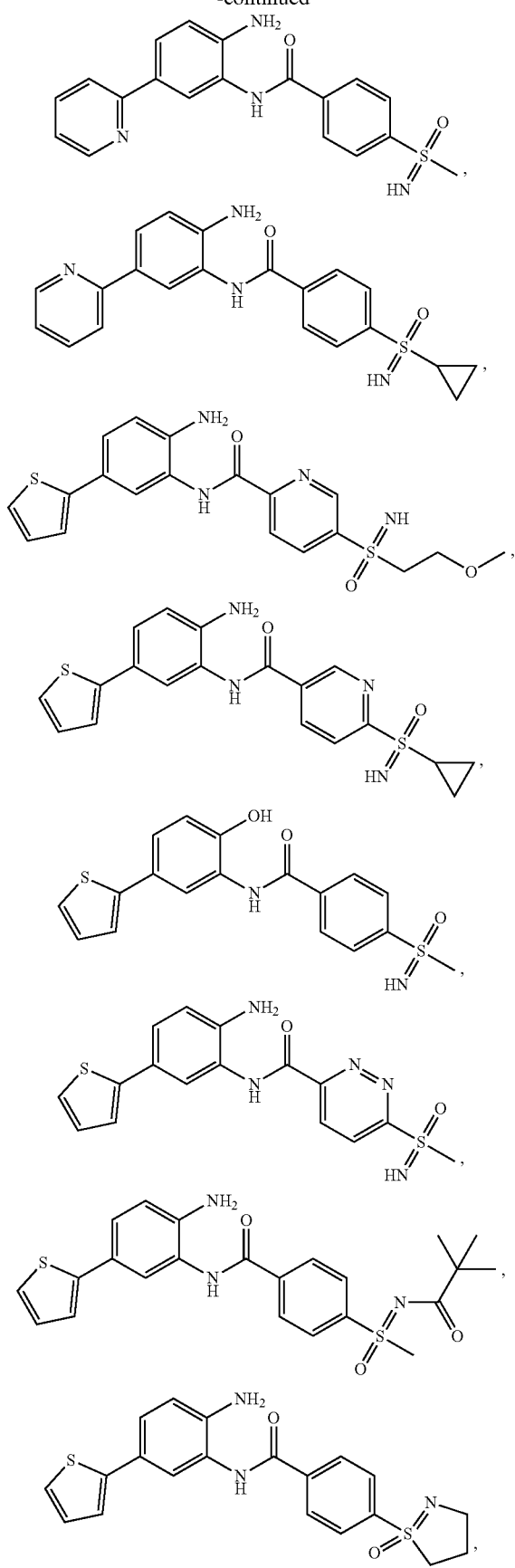
-continued
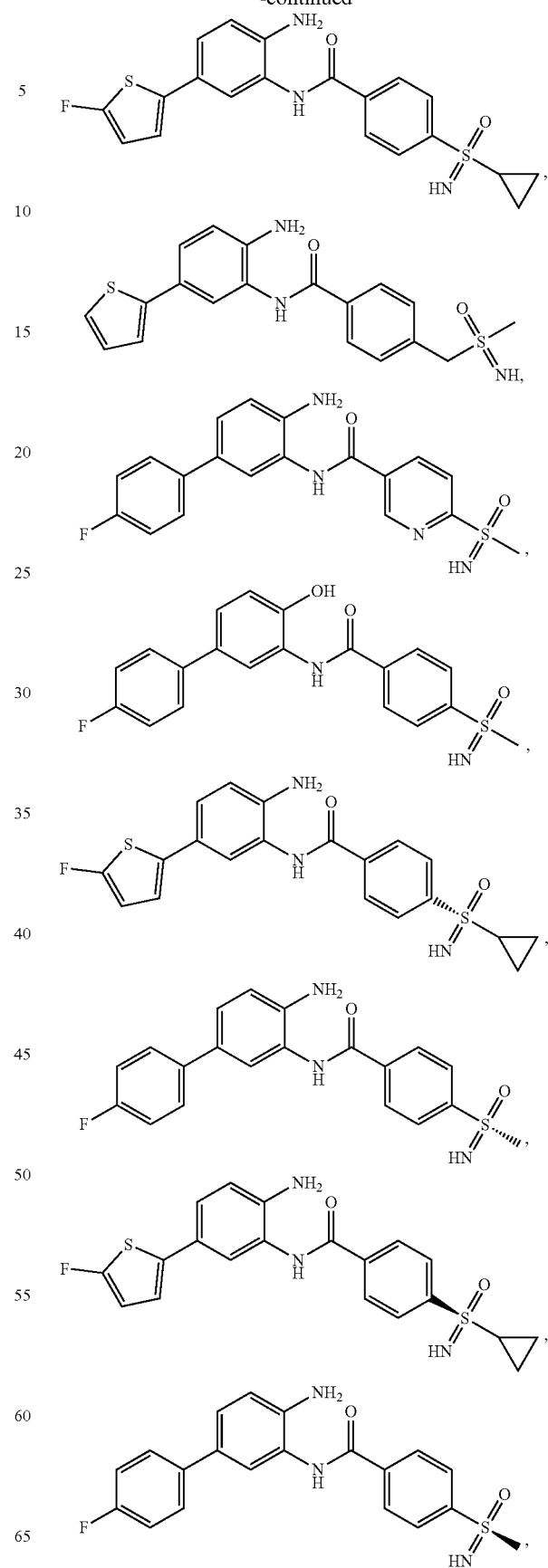

187
-continued
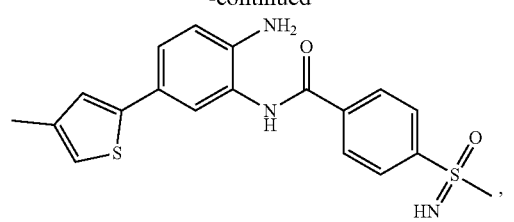
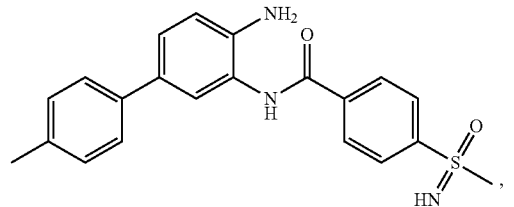
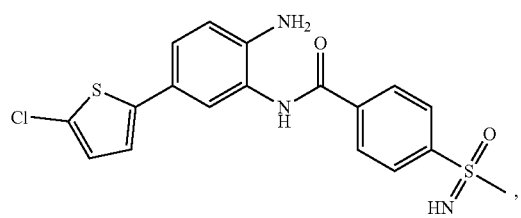
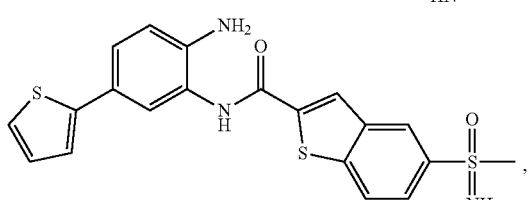
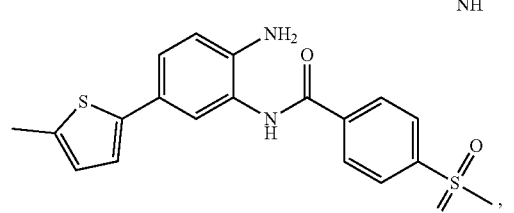
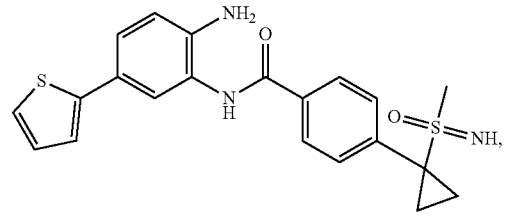
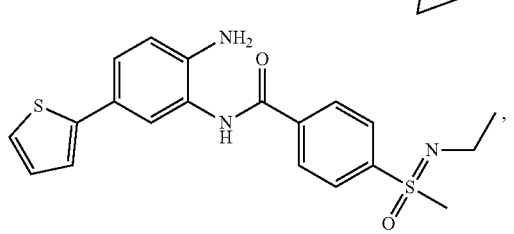
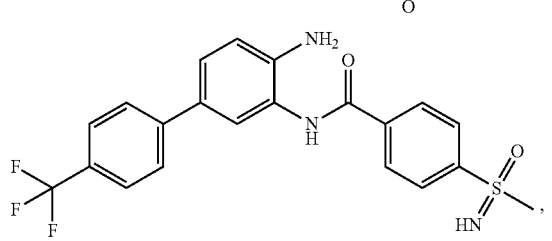
188
-continued
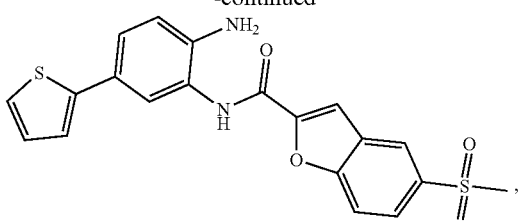
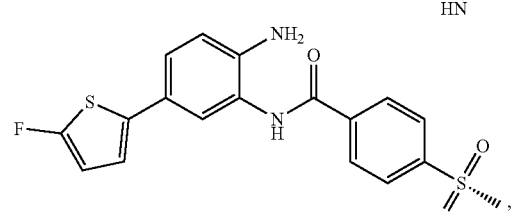
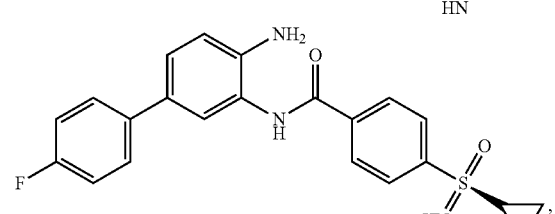
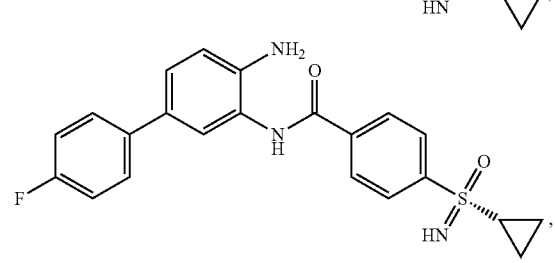
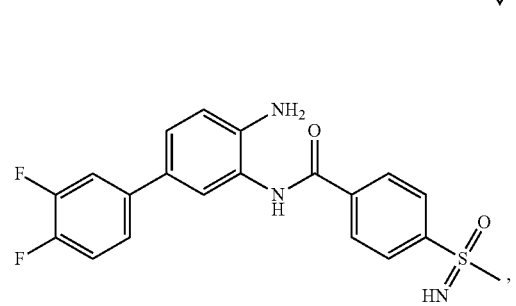
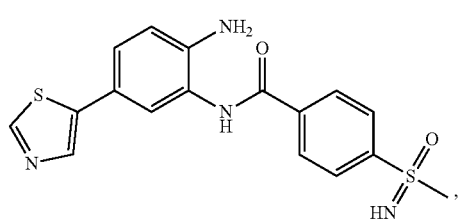
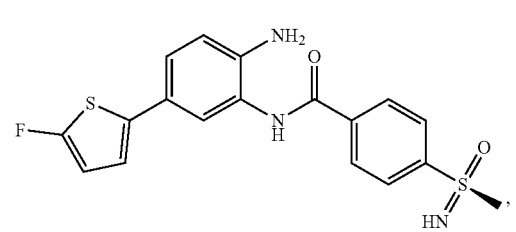

-continued
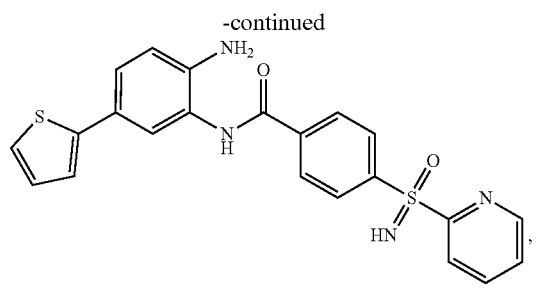
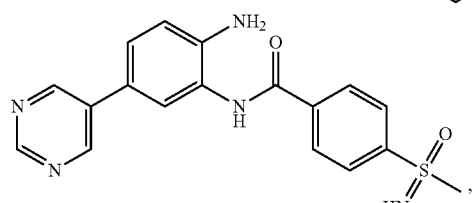
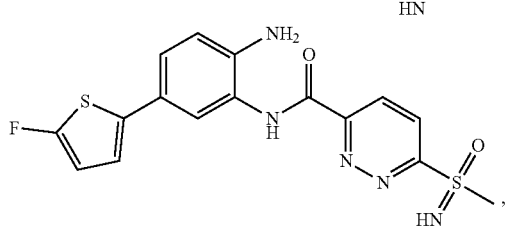
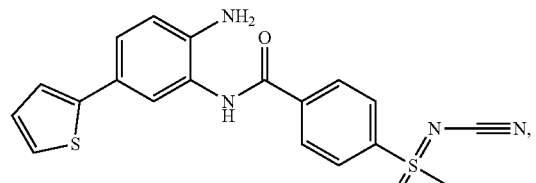
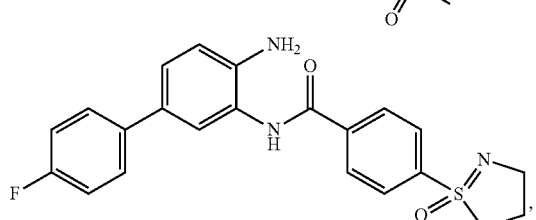
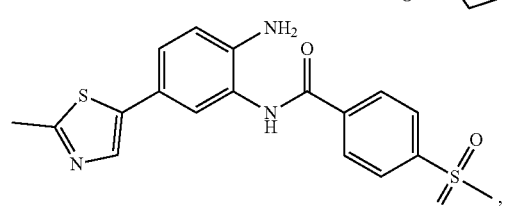
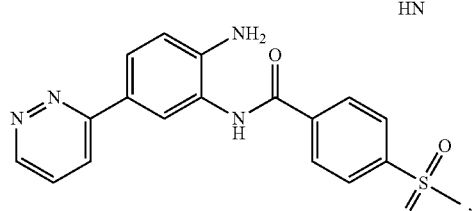
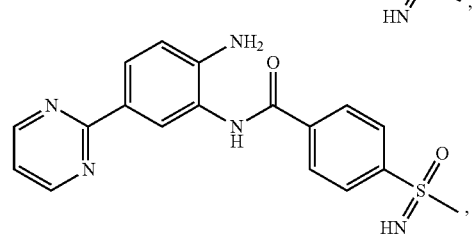
-continued
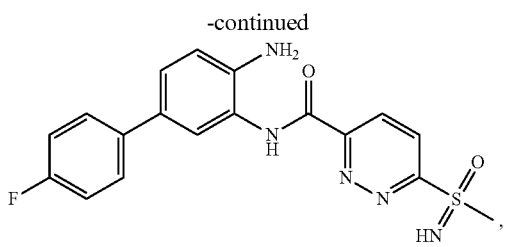
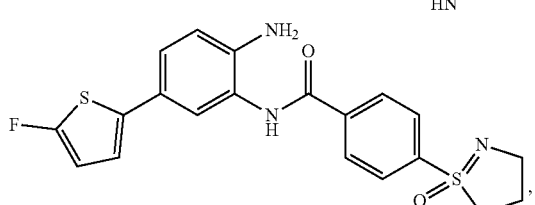
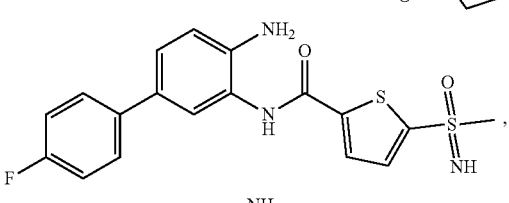
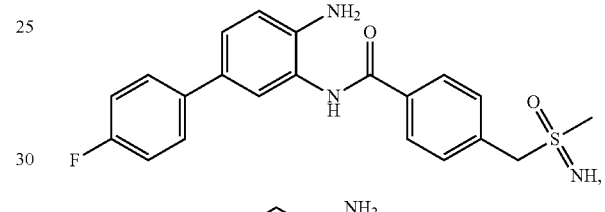
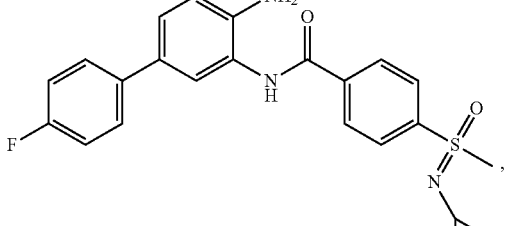
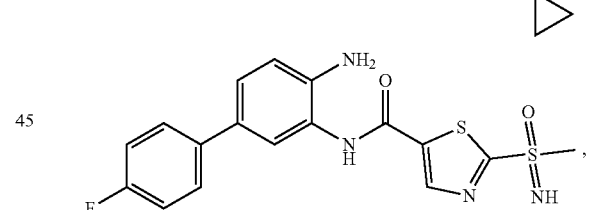
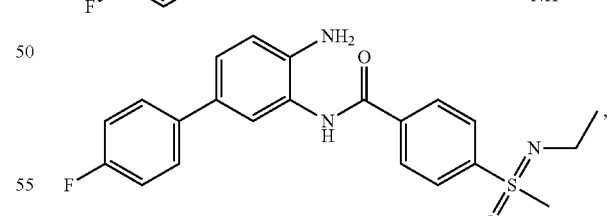
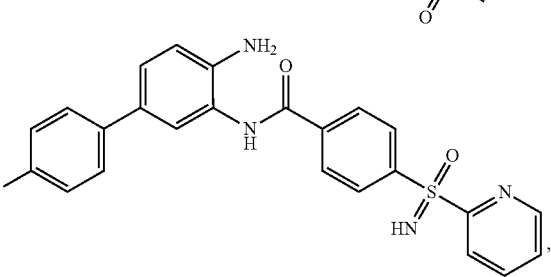

-continued
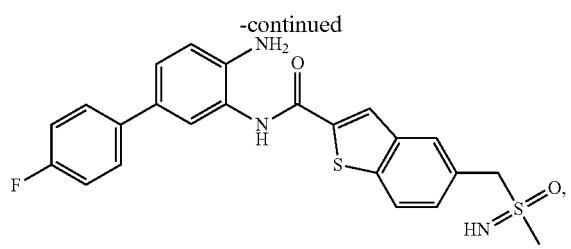
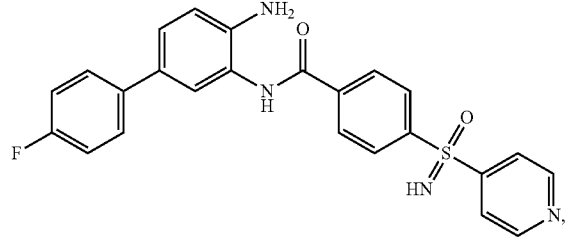
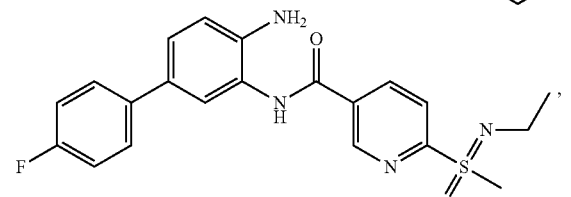
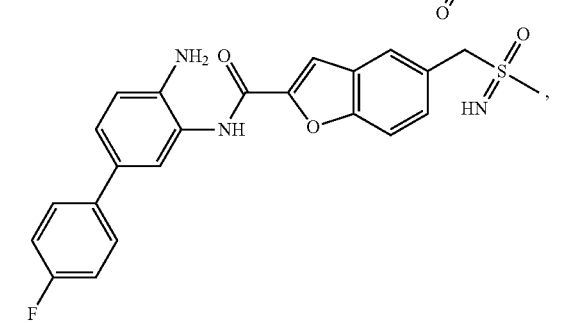
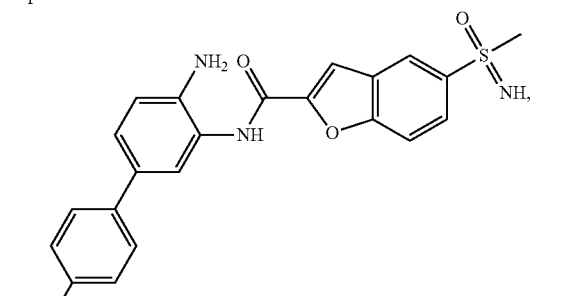
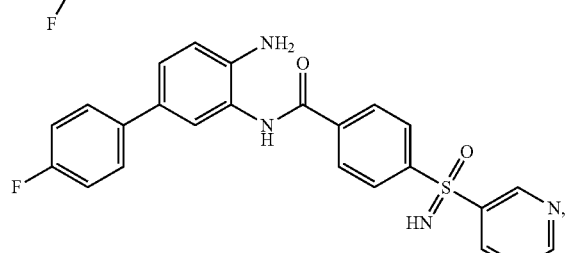
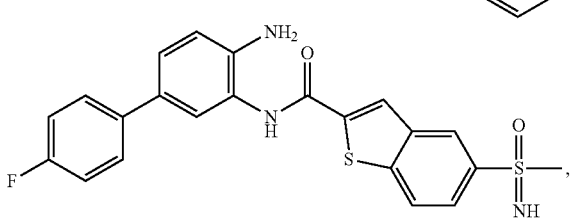
-continued
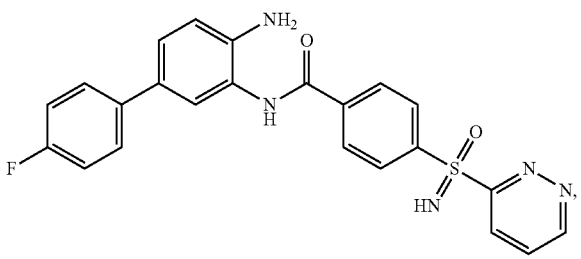
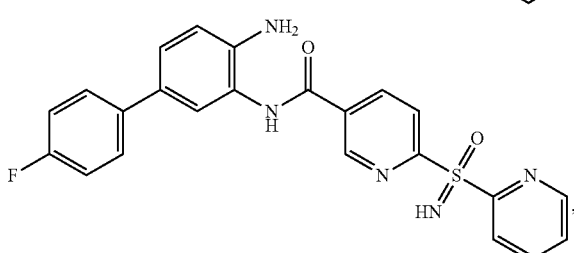
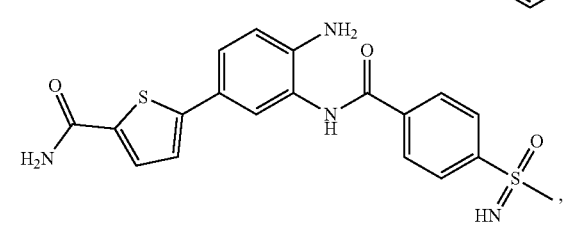
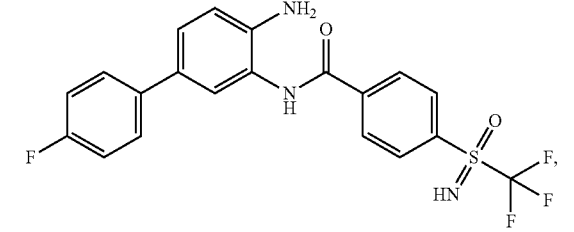
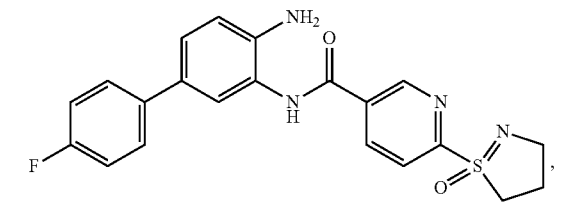
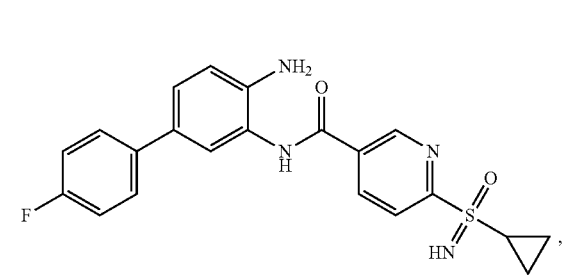
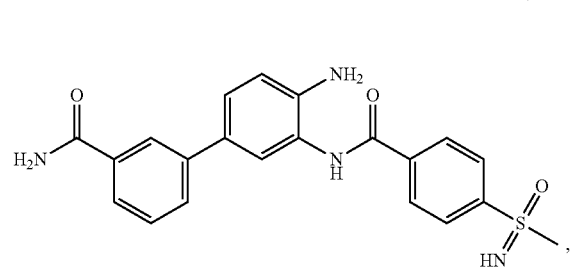

193
-continued
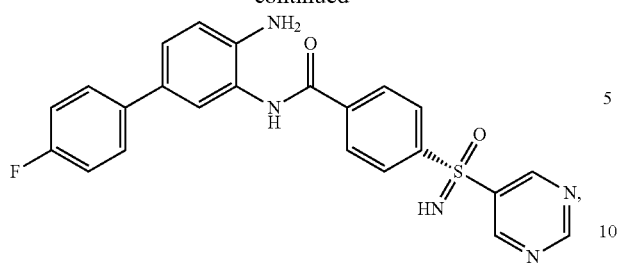
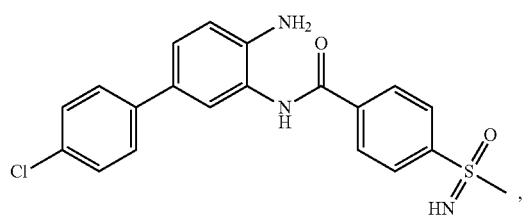
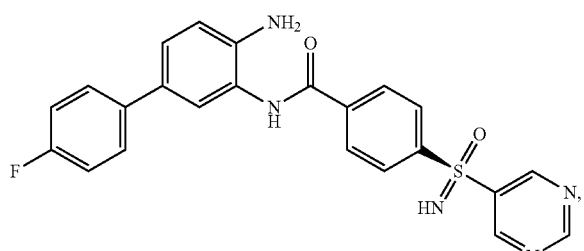
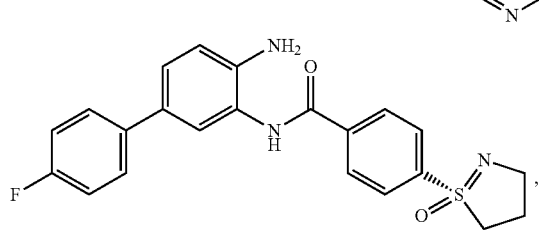
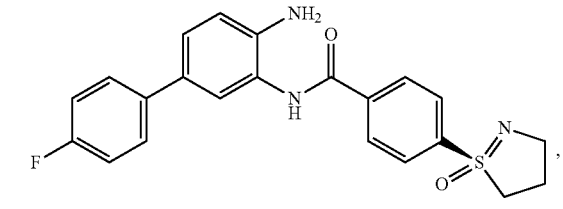
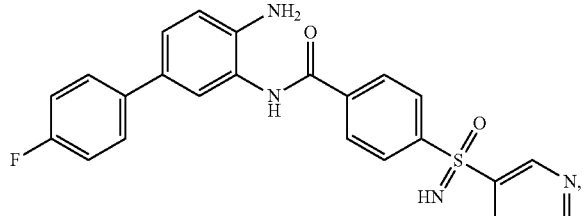
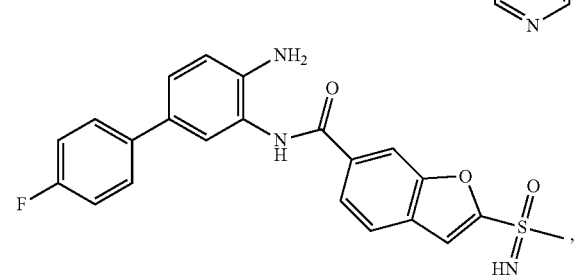
194
-continued
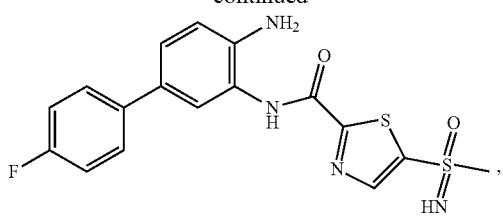
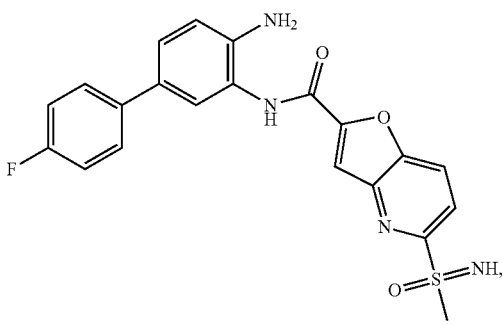
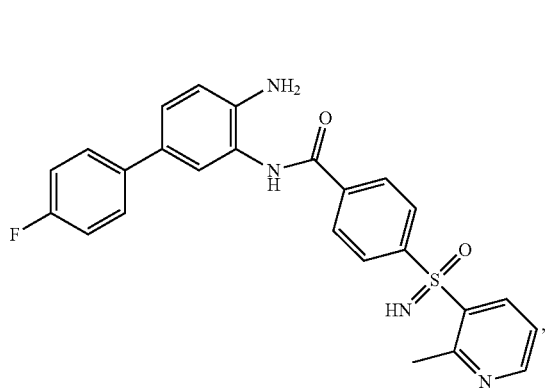
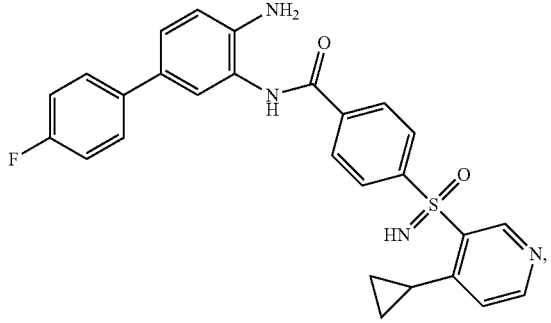
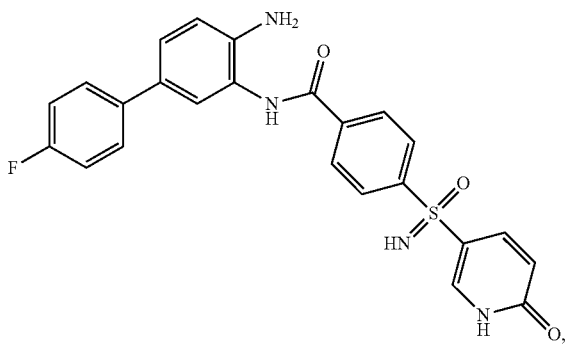

-continued
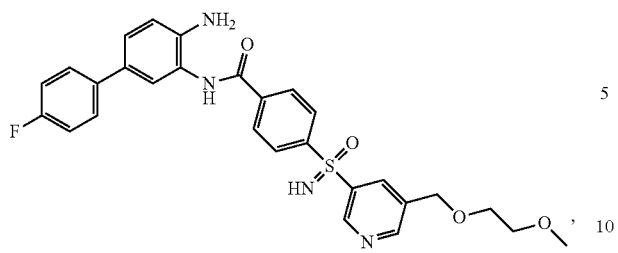
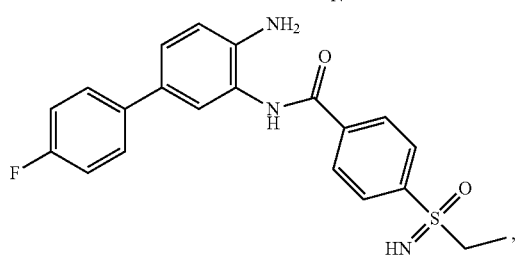
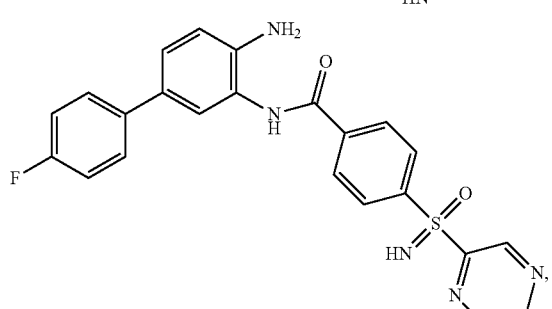
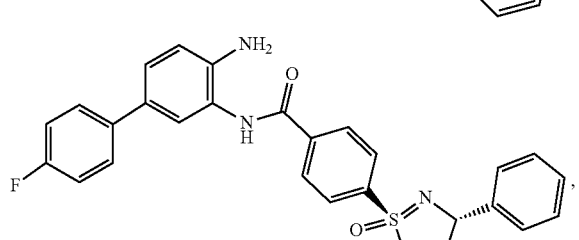
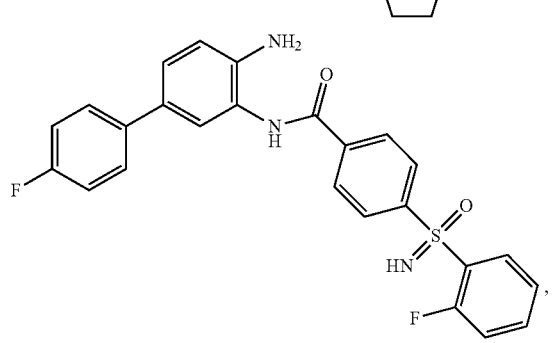
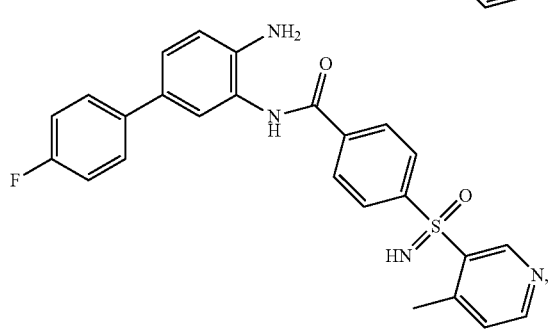
-continued
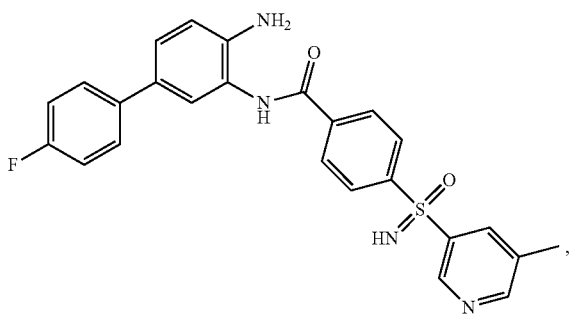
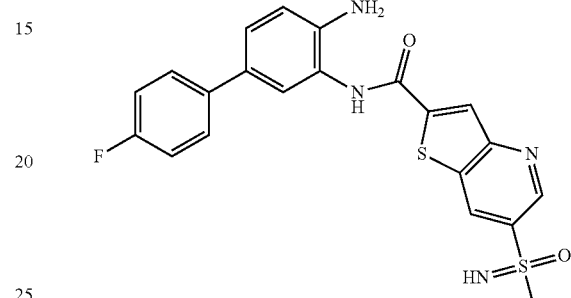
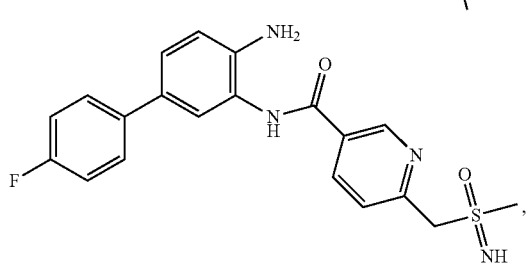
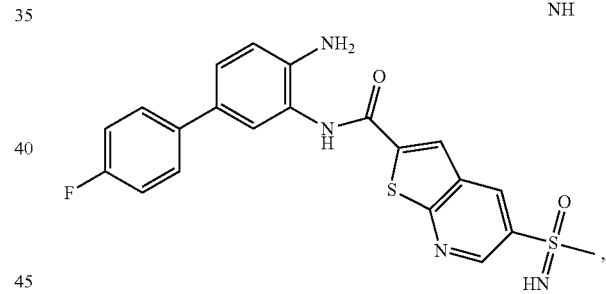
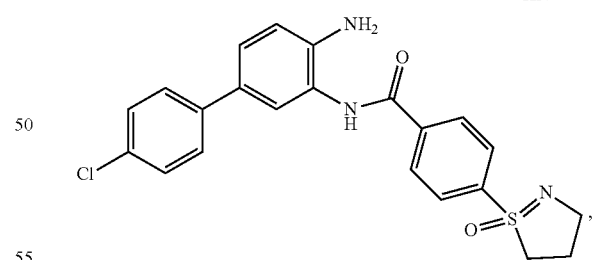
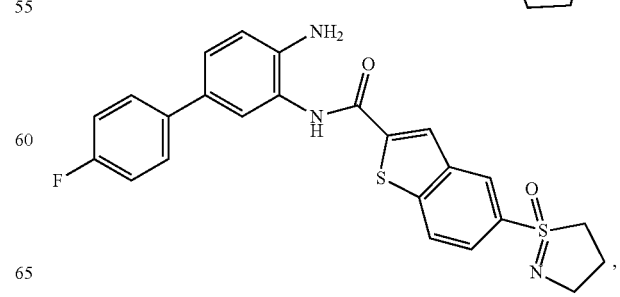

197
-continued
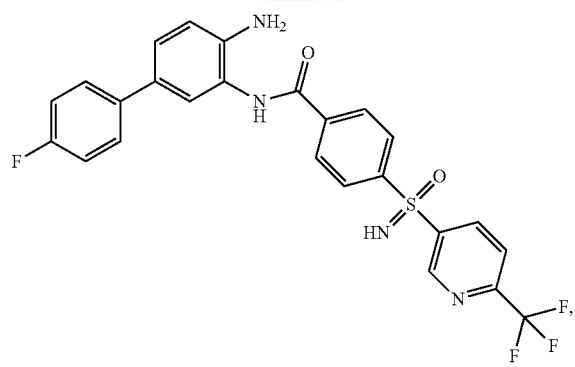
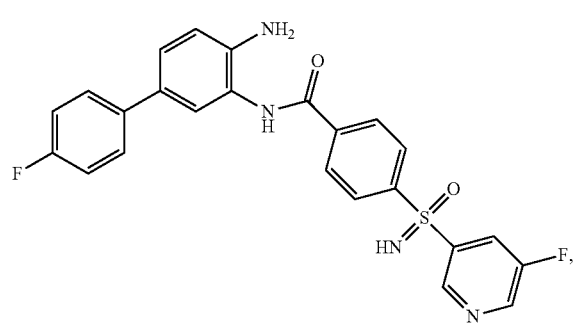
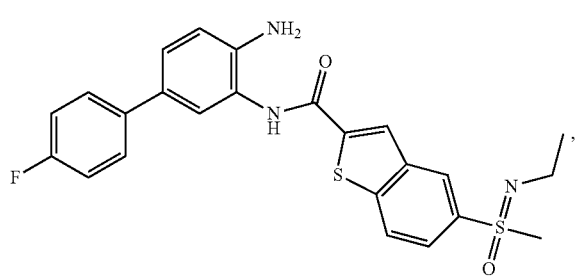
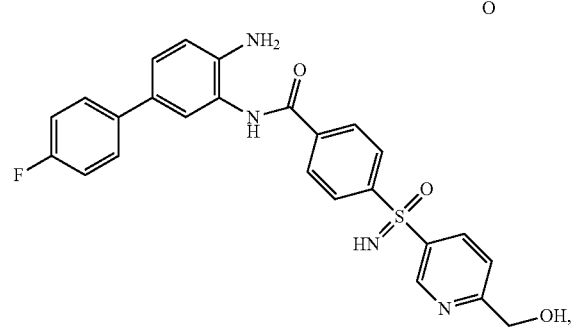
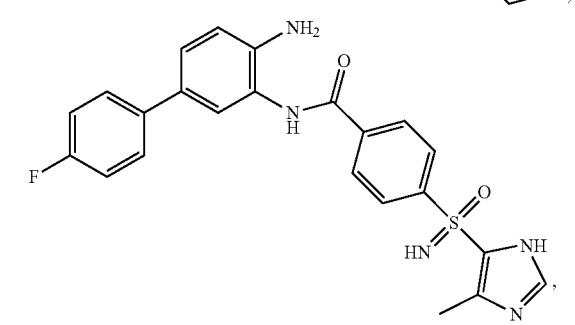
198
-continued
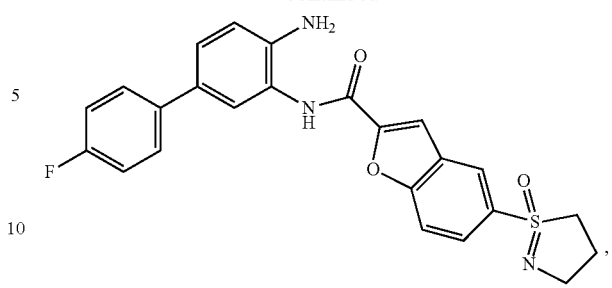
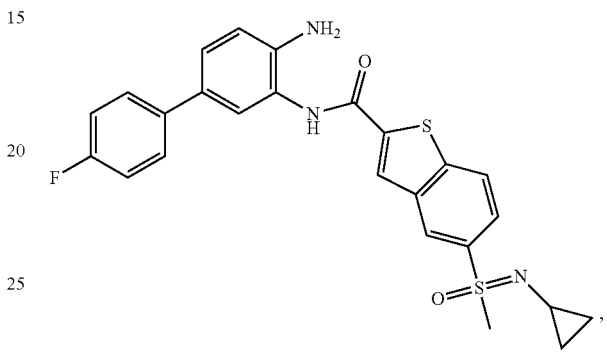
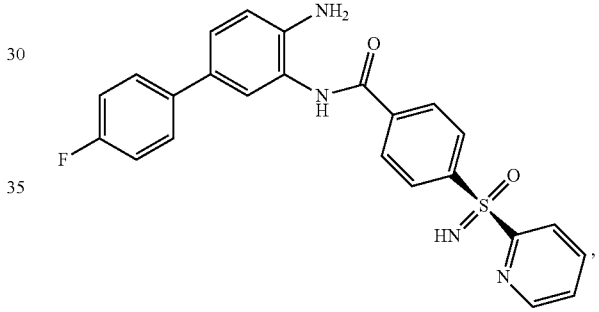
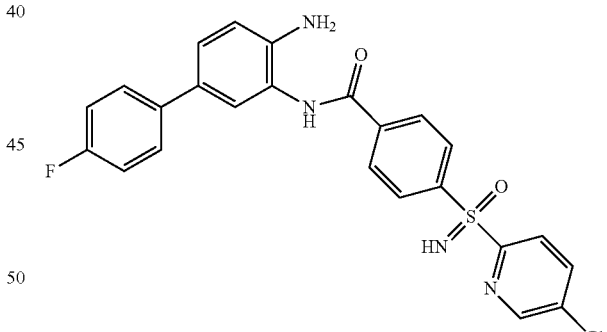
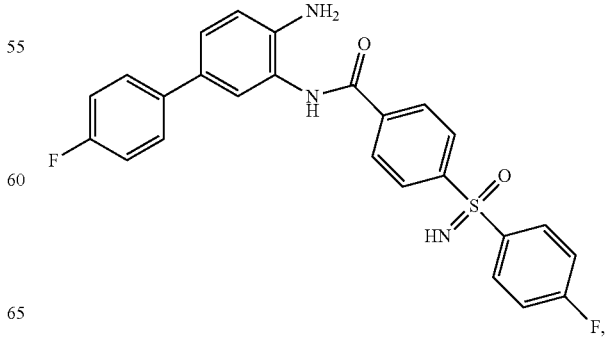

199
-continued
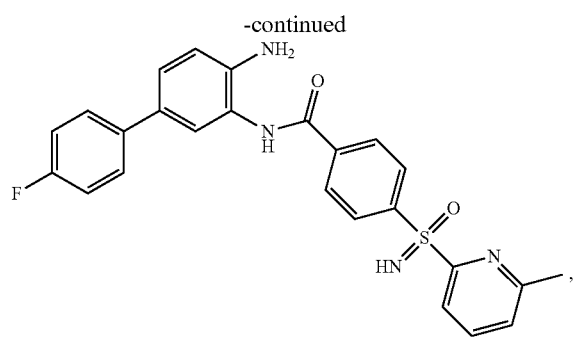
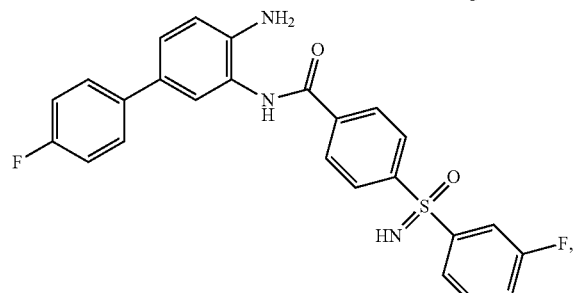
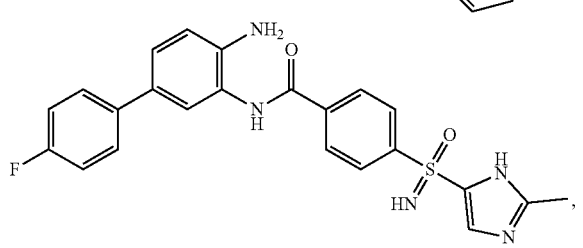
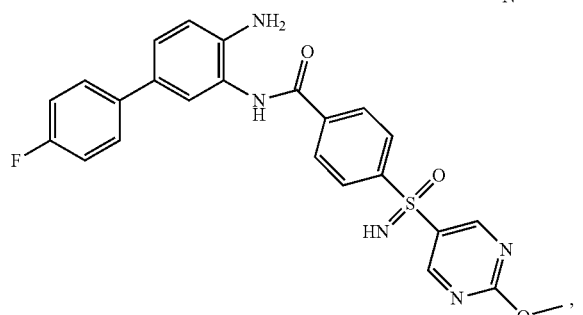
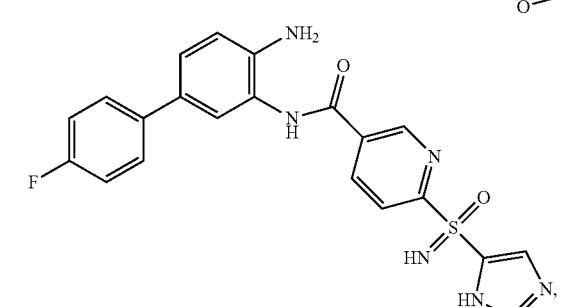
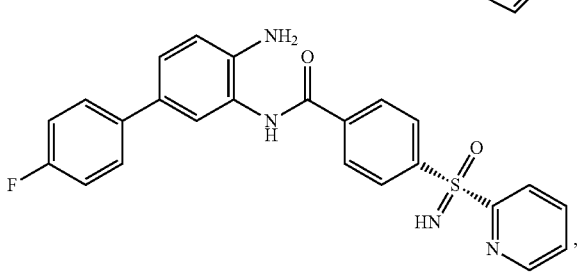
200
-continued
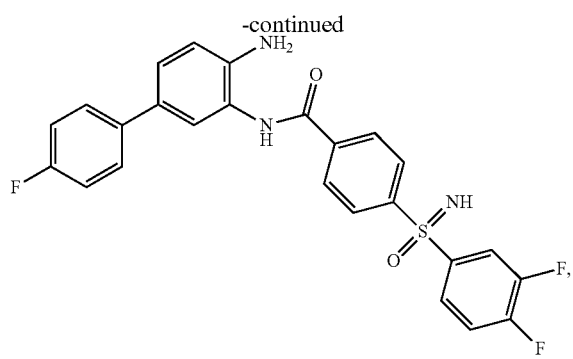
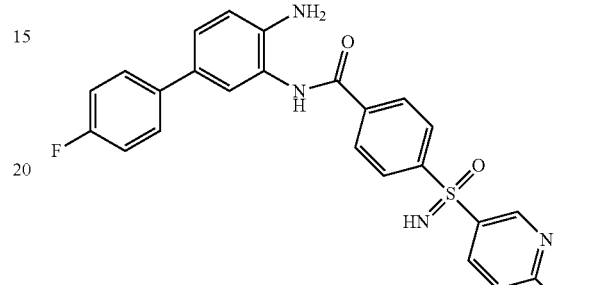
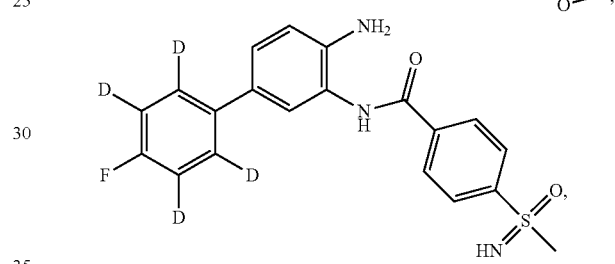
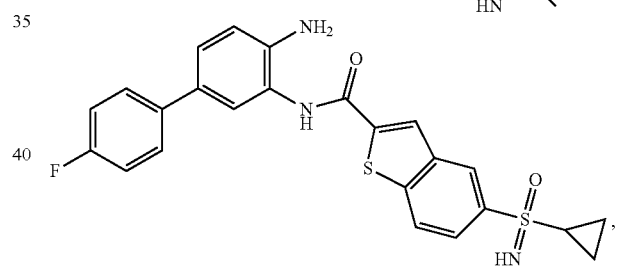
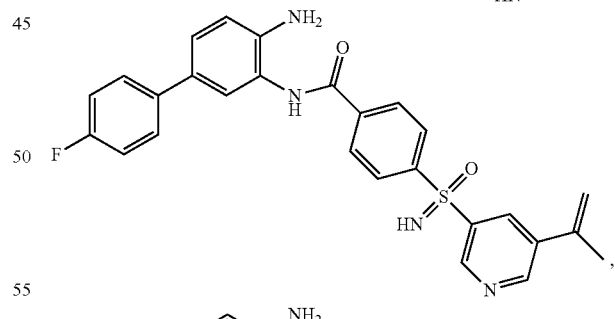
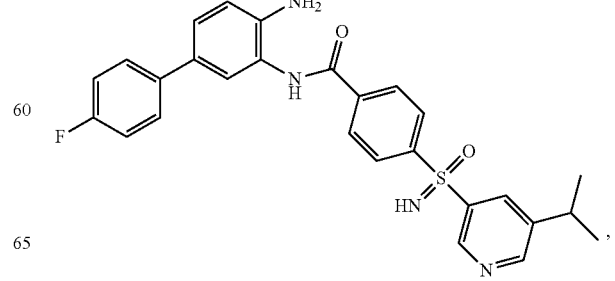

-continued
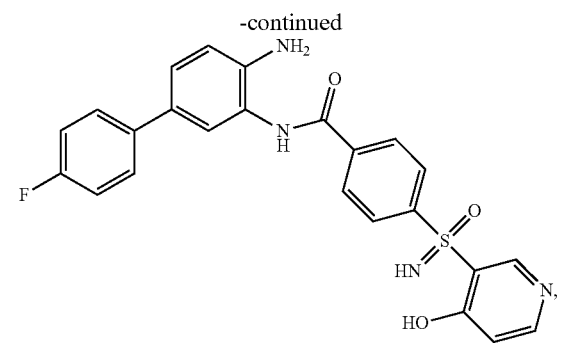
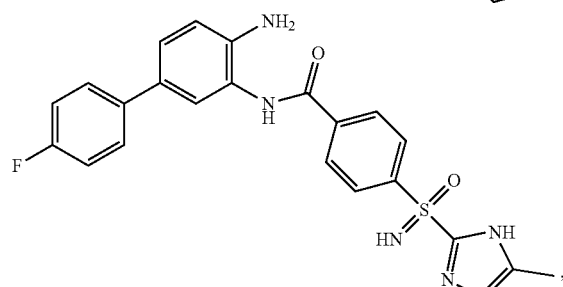
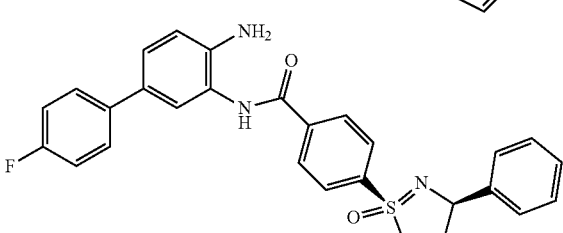
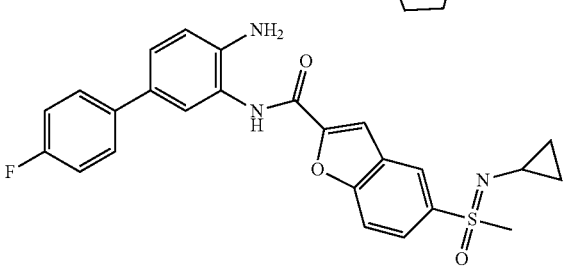
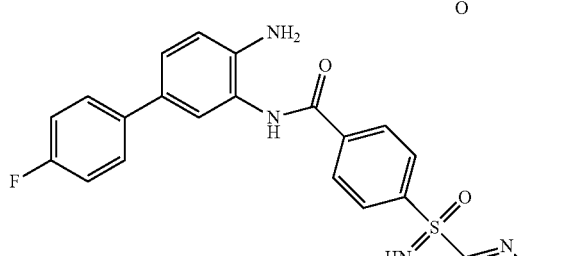
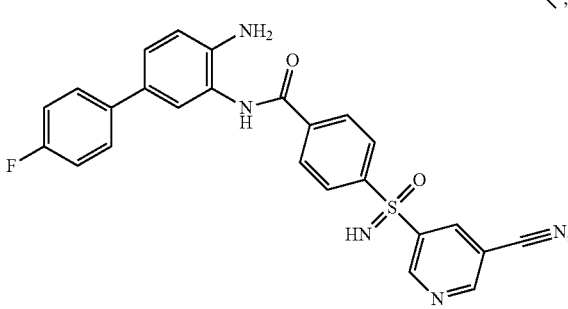
-continued
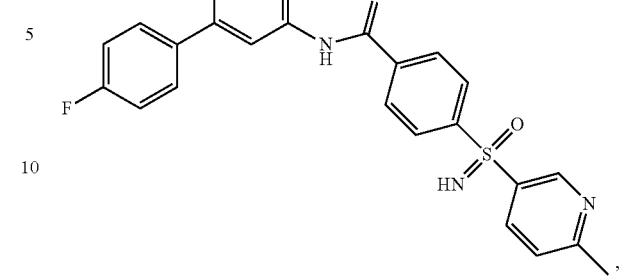
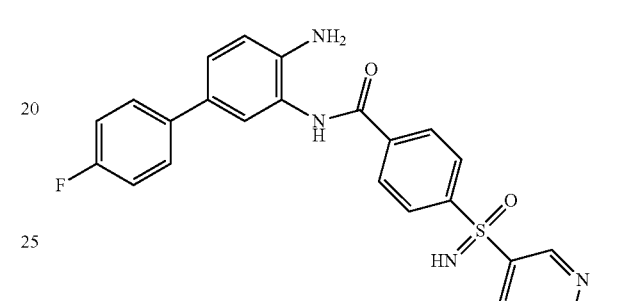
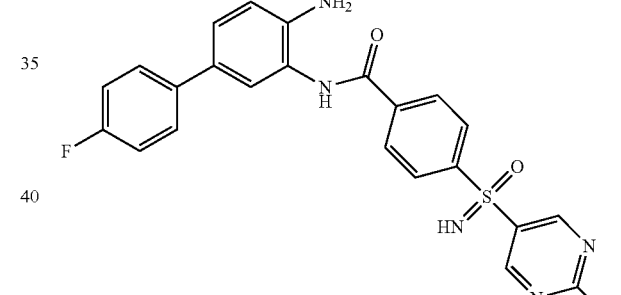
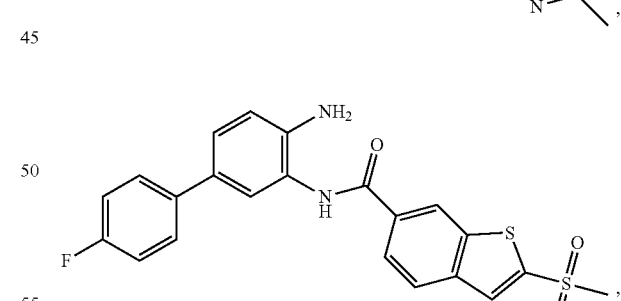
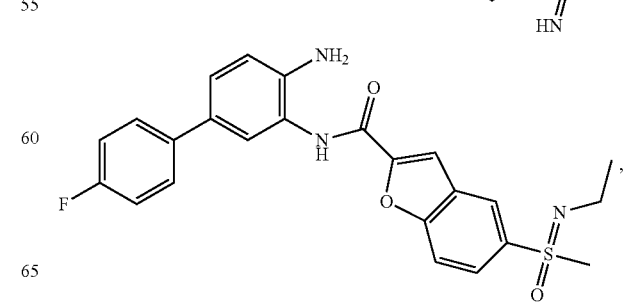

-continued
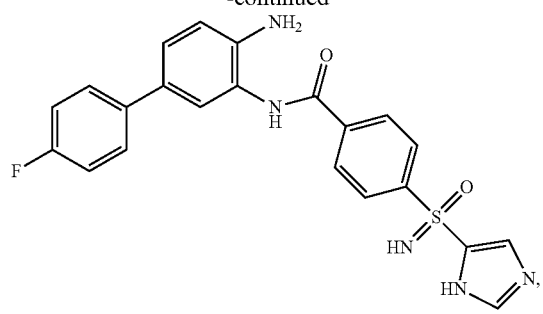
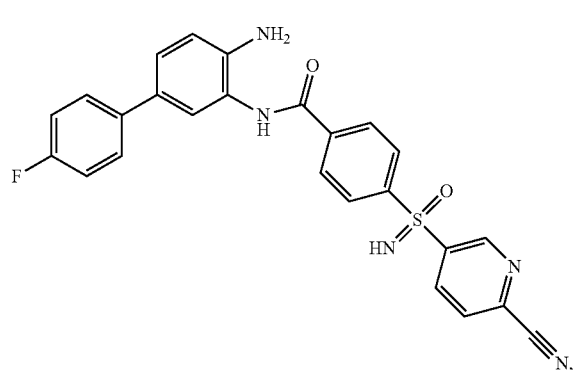
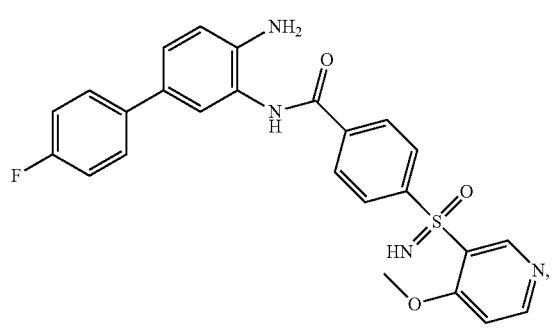
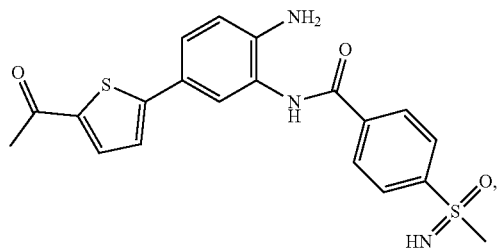
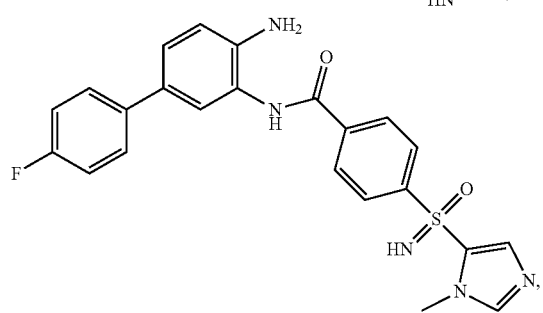
-continued
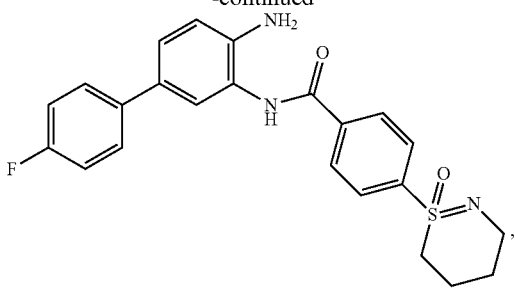
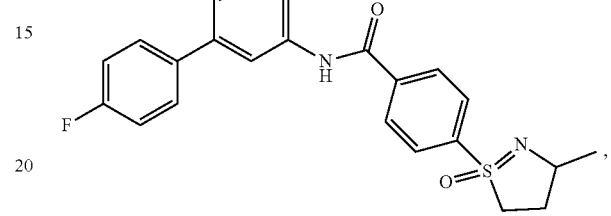
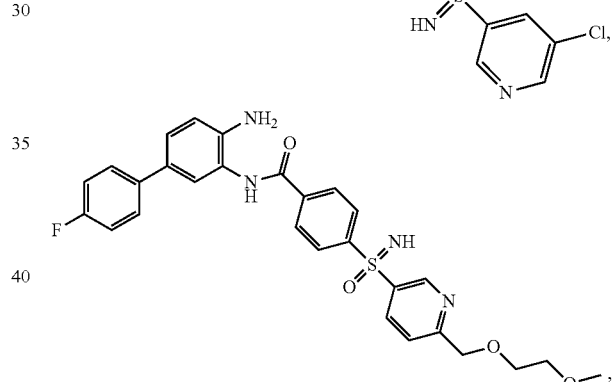
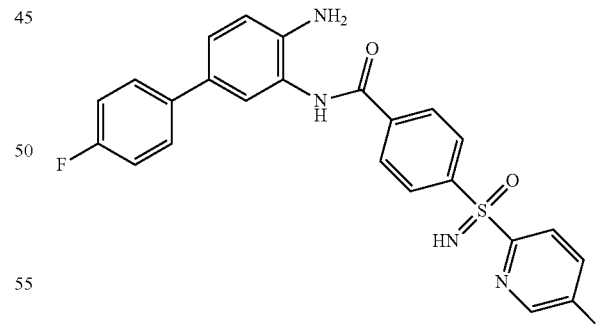
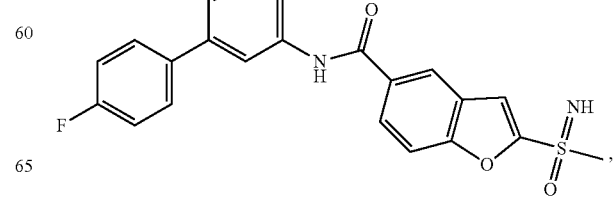

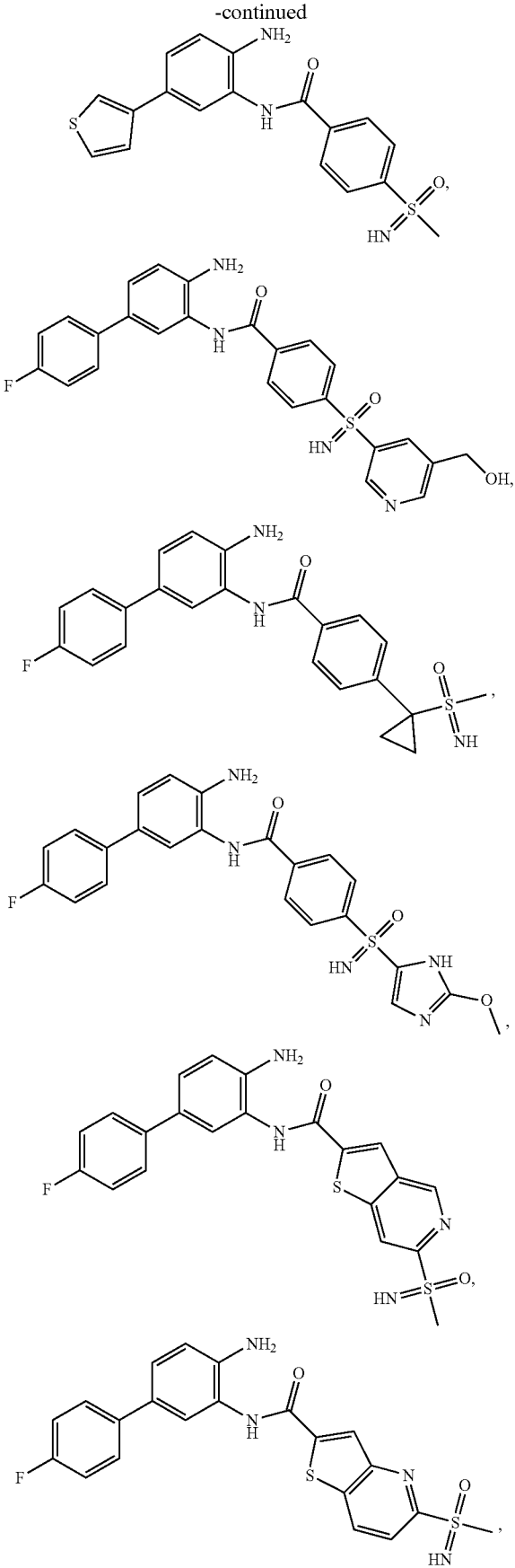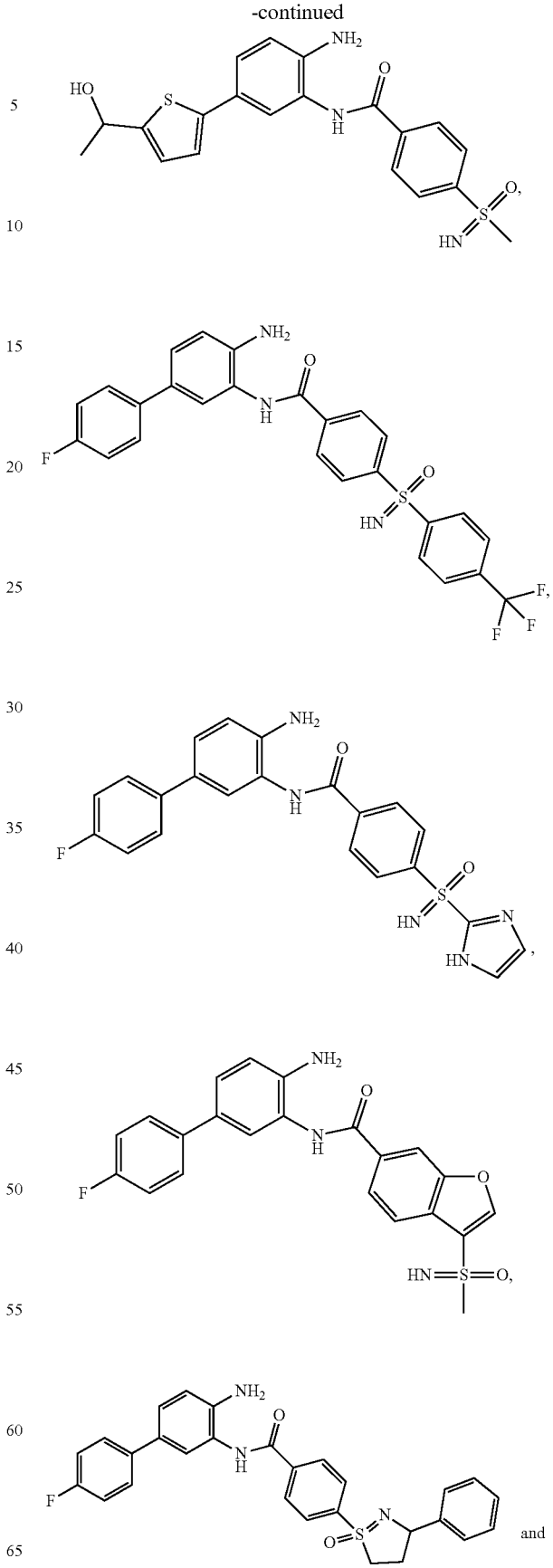

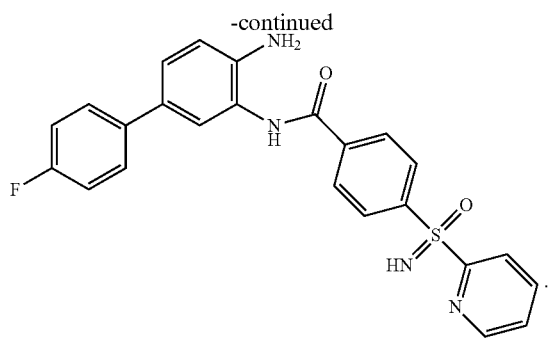

Embodiment 189. A composition comprising a compound of any one of embodiments 1-188, or a pharmaceutically acceptable salt thereof, and one or more pharmaceutically acceptable excipients.

Embodiment 190. A method of treating a disease or disorder that can be treated by inhibition of a histone deacetylase (HDAC), the method comprising administering to a patient in need thereof a compound of any one of embodiments 1-188, or a pharmaceutically acceptable salt thereof, or a composition of embodiment 189.

Embodiment 191. The method of embodiment 190, wherein the disease or disorder is cancer.

Embodiment 192. The method of embodiment 191, wherein the cancer is selected from the group consisting of glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, and cancer of the brain, stomach, kidney, breast, endometrium, urinary tract, liver, soft tissue, pleura and large intestine or sarcoma.

Embodiment 193. The method of embodiment 191, wherein the cancer is selected from the group consisting of a melanoma, bladder cancer, colorectal cancer, head and neck cancer, esophageal cancer, liver cancer, lung cancer, pancreas cancer, and stomach cancer.

Embodiment 194. The method of embodiment 191, wherein the cancer (e.g., the HDAC-related cancer) is carcinoma of unknown primary (CUP), colorectal cancer (e.g., colorectal carcinoma), cervical cancer or non-small cell lung cancer (NSCLC; e.g., lung squamous or lung adenocarcinoma).

Embodiment 195. The method of embodiment 191, wherein the cancer is non-small cell lung cancer (NSCLC; e.g., lung squamous or lung adenocarcinoma).

Embodiment 196. The method of embodiment 191, wherein the cancer is cervical cancer.

Embodiment 197. The method of embodiment 191, wherein the cancer is colorectal cancer (e.g., colorectal carcinoma).

Embodiment 198. The method of embodiment 191, wherein the cancer is carcinoma of unknown primary (CUP).

Embodiment 199. The method of any one of embodiments 189-198, further comprising use of at least one additional therapeutic agent.

Embodiment 200. The method of embodiment 199, wherein the at least one additional therapeutic agent is chemotherapy or radiation.

Embodiment 201. The method of embodiment 199, wherein the at least one additional therapeutic agent is an immunotherapeutic agent (e.g., an anti-PD-1 ligand or an anti-PD-L1 ligand).

Embodiment 202. The method of embodiment 201, wherein the immunotherapeutic agent is an anti-PD-1 antibody (e.g., nivolumab; CT-011; AMP-224; pembrolizumab; pidilizumab; cemiplimab; dostarlimab; prolgolimab; spartalizumab; camrelizumab; sasanlimab, sintilimab; tislelizumab; toripalimab; retifanlimab; MEDI0680; budigalimab; geptanolimab).

Embodiment 203. The method of embodiment 201, wherein the immunotherapeutic agent is an anti-PD-L1 antibody (e.g., BMS936559; durvalumab; avelumab; envafolimab; cosibelimab; sugemalimab, AUNP-12; or atezolizumab) or an anti-PD-L1 small molecule (e.g., CA-170)).

Embodiment 204. Use of a compound of any one of embodiments 1-188, or a pharmaceutically acceptable salt thereof, or a composition of embodiment 189 in the manufacturing of a medicament for treating a disease or disorder that can be treated by inhibition of a histone deacetylase (HDAC).

Embodiment 205. The use of embodiment 204, wherein the disease or disorder is cancer.

Embodiment 206. The use of embodiment 205, wherein the cancer is selected from the group consisting of glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, and cancer of the brain, stomach, kidney, breast, endometrium, urinary tract, liver, soft tissue, pleura and large intestine or sarcoma.

Embodiment 207. The use of embodiment 205, wherein the cancer is selected from the group consisting of a melanoma, bladder cancer, colorectal cancer, head and neck cancer, esophageal cancer, liver cancer, lung cancer, pancreas cancer, and stomach cancer.

Embodiment 208. The use of embodiment 205, wherein the cancer (e.g., the HDAC-related cancer) is carcinoma of unknown primary (CUP), colorectal cancer (e.g., colorectal carcinoma), cervical cancer or non-small cell lung cancer (NSCLC; e.g., lung squamous or lung adenocarcinoma).

Embodiment 209. The use of embodiment 205, wherein the cancer is non-small cell lung cancer (NSCLC; e.g., lung squamous or lung adenocarcinoma).

Embodiment 210. The use of embodiment 205, wherein the cancer is cervical cancer.

Embodiment 211. The use of embodiment 205, wherein the cancer is colorectal cancer (e.g., colorectal carcinoma).

Embodiment 212. The use of embodiment 205, wherein the cancer is carcinoma of unknown primary (CUP).

Embodiment 213. The use of any one of embodiments 204-212, wherein the medicament is configured for administration with at least one additional therapeutic agent.

Embodiment 214. The use of embodiment 213, wherein the at least one additional therapeutic agent is chemotherapy or radiation.

Embodiment 215. The use of embodiment 213, wherein the at least one additional therapeutic agent is an immunotherapeutic agent (e.g., an anti-PD-1 ligand or an anti-PD-L1 ligand).

Embodiment 216. The use of embodiment 215, wherein the immunotherapeutic agent is an anti-PD-1 antibody (e.g., nivolumab; CT-011; AMP-224; pembrolizumab; pidilizumab; cemiplimab; dostarlimab; prolgolimab; spartalizumab; camrelizumab; sasanlimab, sintilimab; tislelizumab; toripalimab; retifanlimab; MEDI0680; budigalimab; geptanolimab).

Embodiment 217. The use of embodiment 215, wherein the immunotherapeutic agent is an anti-PD-L1 antibody (e.g., BMS936559; durvalumab; avelumab; envafolimab; cosibelimab; sugemalimab, AUNP-12; or atezolizumab) or an anti-PD-L1 small molecule (e.g., CA-170)).

Embodiment 218. Use of the compound of any one of embodiments 1-188 in the manufacture of a medicament for the treatment of cancer.

Embodiment 219. Use of a compound of any one of embodiments 1-188, or a pharmaceutically acceptable salt thereof, or a composition of embodiment 189 in treating a disease or disorder that can be treated by inhibition of a histone deacetylase (HDAC).

Embodiment 220. The use of embodiment 219, wherein the disease or disorder is cancer.

Embodiment 221. The use of embodiment 220, wherein the cancer is selected from the group consisting of glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, and cancer of the brain, stomach, kidney, breast, endometrium, urinary tract, liver, soft tissue, pleura and large intestine or sarcoma.

Embodiment 222. The use of embodiment 220, wherein the cancer is selected from the group consisting of a melanoma, bladder cancer, colorectal cancer, head and neck cancer, esophageal cancer, liver cancer, lung cancer, pancreas cancer, and stomach cancer.

Embodiment 223. The use of embodiment 220, wherein the cancer (e.g., the HDAC-related cancer) is carcinoma of unknown primary (CUP), colorectal cancer (e.g., colorectal carcinoma), cervical cancer or non-small cell lung cancer (NSCLC; e.g., lung squamous or lung adenocarcinoma).

Embodiment 224. The use of embodiment 220, wherein the cancer is non-small cell lung cancer (NSCLC; e.g., lung squamous or lung adenocarcinoma).

Embodiment 225. The use of embodiment 220, wherein the cancer is cervical cancer.

Embodiment 226. The use of embodiment 220, wherein the cancer is colorectal cancer (e.g., colorectal carcinoma).

Embodiment 227. The use of embodiment 220, wherein the cancer is carcinoma of unknown primary (CUP).

Embodiment 228. The use of any one of embodiments 219-227, wherein the use further comprises administration of at least one additional therapeutic agent.

Embodiment 229. The use of embodiment 228, wherein the at least one additional therapeutic agent is chemotherapy or radiation.

Embodiment 230. The use of embodiment 228, wherein the at least one additional therapeutic agent is an immunotherapeutic agent (e.g., an anti-PD-1 ligand or an anti-PD-L1 ligand).

Embodiment 231. The use of embodiment 230, wherein the immunotherapeutic agent is an anti-PD-1 antibody (e.g., nivolumab; CT-011; AMP-224; pembrolizumab; pidilizumab; cemiplimab; dostarlimab; prolgolimab; spartalizumab; camrelizumab; sasanlimab, sintilimab; tislelizumab; toripalimab; retifanlimab; MEDI0680; budigalimab; geptanolimab).

Embodiment 232. The use of embodiment 230, wherein the immunotherapeutic agent is an anti-PD-L1 antibody (e.g., BMS936559; durvalumab; avelumab; envafolimab; cosibelimab; sugemalimab, AUNP-12; or atezolizumab) or an anti-PD-L1 small molecule (e.g., CA-170)).

Embodiment 233. A compound of any one of embodiments 1-188, or a pharmaceutically acceptable salt thereof, or a composition of embodiment 189 for use in a method of treating a disease or disorder that can be treated by inhibition of a histone deacetylase (HDAC), the method comprising administering to a patient in need thereof a compound of any one of embodiments 1-188, or a pharmaceutically acceptable salt thereof, or a composition of embodiment 189.

Embodiment 234. The compound or composition for use of embodiment 233, wherein the disease or disorder is cancer.

Embodiment 235. The compound or composition for use of embodiment 234, wherein the cancer is selected from the group consisting of glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, and cancer of the brain, stomach, kidney, breast, endometrium, urinary tract, liver, soft tissue, pleura and large intestine or sarcoma.

Embodiment 236. The compound or composition for use of embodiment 234, wherein the cancer is selected from the group consisting of a melanoma, bladder cancer, colorectal cancer, head and neck cancer, esophageal cancer, liver cancer, lung cancer, pancreas cancer, and stomach cancer.

Embodiment 237. The compound or composition for use of embodiment 235, wherein the cancer (e.g., the HDAC-related cancer) is carcinoma of unknown primary (CUP), colorectal cancer (e.g., colorectal carcinoma), cervical cancer or non-small cell lung cancer (NSCLC; e.g., lung squamous or lung adenocarcinoma).

Embodiment 238. The compound or composition for use of embodiment 235, wherein the cancer is non-small cell lung cancer (NSCLC; e.g., lung squamous or lung adenocarcinoma).

Embodiment 239. The compound or composition for use of embodiment 235, wherein the cancer is cervical cancer.

Embodiment 240. The compound or composition for use of embodiment 235, wherein the cancer is colorectal cancer (e.g., colorectal carcinoma).

Embodiment 241. The compound or composition for use of embodiment 235, wherein the cancer is carcinoma of unknown primary (CUP).

Embodiment 242. The compound or composition for use of any one of embodiments 233-241, further comprising use of at least one additional therapeutic agent.

Embodiment 243. The compound or composition for use of embodiment 242, wherein the at least one additional therapeutic agent is chemotherapy or radiation.

Embodiment 244. The compound or composition for use of embodiment 242, wherein the at least one additional therapeutic agent is an immunotherapeutic agent (e.g., an anti-PD-1 ligand or an anti-PD-L1 ligand).

Embodiment 245. The compound or composition for use of embodiment 244, wherein the immunotherapeutic agent is an anti-PD-1 antibody (e.g., nivolumab; CT-011; AMP-224; pembrolizumab; pidilizumab; cemiplimab; dostarlimab; prolgolimab; spartalizumab; camrelizumab; sasanlimab, sintilimab; tislelizumab; toripalimab; retifanlimab; MEDI0680; budigalimab; geptanolimab).

Embodiment 246. The compound or composition for use of embodiment 244, wherein the immunotherapeutic agent is an anti-PD-L1 antibody (e.g., BMS936559; durvalumab; avelumab; envafolimab; cosibelimab; sugemalimab, AUNP-12; or atezolizumab) or an anti-PD-L1 small molecule (e.g., CA-170)).

EXAMPLES

Examples are provided below to facilitate a more complete understanding of the invention. The following examples illustrate exemplary modes of making and practicing the invention. However, the scope of the invention is not limited to specific embodiments disclosed in these Examples, which are for purposes of illustration only, since alternative methods can be utilized to obtain similar results.

In the following examples, the chemical reagents were purchased from commercial sources (such as Alfa, Acros, Sigma Aldrich, TCI and Shanghai Chemical Reagent Company), and used without further purification.

In some examples, purification of intermediates and final compounds was performed using HPLC ($H_2O$-MeOH; Agilent 1260 Infinity systems equipped with DAD and mass-detectors. Waters Sunfire C18 OBD Prep Column, 100 Å, 5 µm, 19 mm×100 mm with SunFire C18 Prep Guard Cartridge, 100 Å, 10 µm, 19 mm×10 mm) The material was dissolved in 0.7 mL DMSO. Flow: 30 mL/min. Purity of the obtained fractions was checked via the analytical LCMS. Spectra were recorded for each fraction as it was obtained straight after chromatography in the solution form. The solvent was evaporated under the $N_2$ flow upon heating to 80° C. On the basis of post-chromatography LCMS analysis fractions were united. Solid fractions were dissolved in 0.5 mL MeOH and transferred into pre-weighted marked vials. Obtained solutions were again evaporated under the $N_2$ flow upon heating to 80° C. After drying, products were subjected to lyophilization using acetonitrile-water mixtures and finally characterized by LCMS and $^1H$ NMR.

Nuclear magnetic resonance (NMR) spectra were recorded using Brucker AVANCE DRX 500, Bruker 400 spectrometer or Varian UNITYplus 400. Chemical shifts for protons were reported as parts per million in δ scale using solvent residual peak ($CHCl_3$: 7.27 ppm) (methanol-$d_4$: 3.31 ppm) (DMSO-$d_6$: 2.50 ppm) or tetramethylsilane (0.00 ppm) as internal standards. Chemical shifts of $^{13}C$ NMR spectra were reported in ppm from the central peak of $CDCl_3$ (77.00 ppm) (methanol-$d_4$: 49.15 ppm) (DMSO-$d_6$: 39.51 ppm) on the δ scale. Data are represented as follows: chemical shift, multiplicity (s=singlet, d=doublet, t=triplet, q=quartet, qn=quintuplet, sx=sextet, sp=septuplet, m=multiplet, br=broad), coupling constant (J, Hz) and integration.

In certain examples, mass spectra were recorded on an Agilent 1100 Series LC/MSD system with DAD\ELSD and Agilent LC\MSD VL (G1956A), SL (G1956B) mass-spectrometer or an Agilent 1200 Series LC/MSD system with DAD\ELSD and Agilent LC\MSD SL (G6130A), SL (G6140A) mass-spectrometer.

All the LC/MS data were obtained using positive/negative mode switching.

Column Zorbax SB-C18 1.8 µm 4.6×15 mm Rapid Resolution cartridge (PN 821975-932)

Mobile phase A—acetonitrile, 0.1% formic acid

B—water (0.1% formic acid)

Flow rate 3 ml/min

Gradient 0 min—100% B 0.01 min—100% B 1.5 min—0% B 1.8 min—0% B 1.81 min—100% B

Injection volume 1 µl

Ionization mode atmospheric pressure chemical ionization (APCI)

Scan range m/z 80-1000.

Other exemplary analytical LC/MS instruments and conditions are described below:

Instrument: Agilent LC1100-MS6100 series G1956B; Column: Xbridge Shield RP-18, 50*2.1 mm*5 µm; Mobile Phase A: $H_2O$ with 0.05% $NH_3$—$H_2O$ (v %); Mobile Phase B: MeCN; Flow rate: 1.0 mL/min; Wavelength: UV 220 nm, 254 nm; Column temperature: 30° C.; MS ionization: ESI.

0-30CD: Gradient: B from 0%~30% over 2 minutes and holding at 30% for 0.48 minutes;

0-60CD: Gradient: B from 0%~60% over 2 minutes and holding at 60% for 0.48 minutes;

10-80CD: Gradient: B from 10%~80% over 2 minutes and holding at 80% for 0.48 minutes;

30-90CD: Gradient: B from 30%~90% over 2 minutes and holding at 90% for 0.48 minutes;

50-100CD: Gradient: B from 50%~100% over 2 minutes and holding at 100% for 0.48 minutes.

Instrument: Agilent LC1100-MS6100 series G1956B; Column: Xtimate C18, 30*2.1 mm*3 µm; Mobile Phase A: $H_2O$ with 0.0375% TFA (v %); Mobile Phase B: MeCN with 0.01875% TFA (v %): Flow rate: 0.8 mL/min; Wavelength: UV 220 nm, 254 nm; Column temperature: 50° C.; MS ionization: ESI.

0-30AB: Gradient: B from 0%~30% over 3 minutes and holding at 30% for 0.5 minutes;

0-60AB: Gradient: B from 0%~60% over 3 minutes and holding at 30% for 0.5 minutes;

10-80AB: Gradient: B from 10%~80% over 3 minutes and holding at 30% for 0.5 minutes;

30-90AB: Gradient: B from 0%~30% over 3 minutes and holding at 30% for 0.5 minutes;

50-100AB: Gradient: B from 50%~100% over 3 minutes and holding at 100% for 0.5 minutes.

Instrument: Shimadzu LC20-MS2010; Column: Agilent Pursit 5 C18 20*2.0 mm; Mobile Phase A: $H_2O$ with 0.0375% of TFA (v %); Mobile Phase B: MeCN with 0.01875% of TFA (v %); Gradient: B from 5~95% over 0.7 minutes and holding at 95% for 0.4 minutes; Flow Rate: 1.5 mL/min; Wavelength: UV 220 nm, 254 nm, 215 nm; Column temperature: 50° C.; MS ionization: ESI.

Instrument: Shimadzu LC20-MS2020; Column: Agilent Pursit 5 C18 20*2.0 mm; Mobile Phase A: $H_2O$ with 0.0375% of TFA (v %); Mobile Phase B: MeCN with 0.01875% of TFA (v %); Gradient: B from 5~95% over 0.7 minutes and holding at 95% for 0.4 minutes; Flow Rate: 1.5 mL/min; Wavelength: UV 220 nm, 254 nm; Column temperature: 50° C.; MS ionization: ESI.

Exemplary HPLC Instruments and Conditions

Instrument: Shimadzu LC20; Column: YMC-Pack ODS-A 150*4.6 mm; Mobile Phase A: $H_2O$ with 0.06875% TFA (v %); Mobile Phase B: MeCN with 0.0625% TFA (v %); Flow rate: 1.5 mL/min; Wavelength: UV 220 nm, 215 nm, 254 nm; Column temperature: 40° C.

0-30: Gradient: B from 0~30% over 10 minutes and holding at 30% for 5 minutes;
0-60: Gradient: B from 0~60% over 10 minutes and holding at 60% for 5 minutes;
0-95: Gradient: B from 0~95% over 10 minutes and holding at 95% for 5 minutes;
10-80: Gradient: B from 10~80% over 10 minutes and holding at 80% for 5 minutes;
30-90: Gradient: B from 30~90% over 10 minutes and holding at 90% for 5 minutes;
50-100: Gradient: B from 50~100% over 10 minutes and holding at 100% for 5 minutes.

Instrument: Shimadzu LC20; Column: Xbridge Shield RP-18 50*2.1 mm, 5 μm; Mobile Phase A: $H_2O$ with 0.01% $NH_3$—$H_2O$; Mobile Phase B: MeCN; Flow Rate: 1.2 mL/min; Wavelength: UV 220 nm, 215 nm, 254 nm; Column temperature: 40° C.

0-30CD: Gradient: B from 0~30% over 6 minutes and holding at 30% for 2 minutes;
0-60CD: Gradient: B from 0~60% over 6 minutes and holding at 60% for 2 minutes;
10-80CD: Gradient: B from 10~80% over 6 minutes and holding at 80% for 2 minutes;
30-90CD: Gradient: B from 30~90% over 6 minutes and holding at 90% for 2 minutes;
50-100CD: Gradient: B from 10~80% over 6 minutes and holding at 100% for 2 minutes.

Instrument: Shimadzu LC20; Column: Ultimate C18 50*3 mm, 3 μm; Mobile Phase A: $H_2O$ with 0.06875% TFA (v %); Mobile Phase B: MeCN with 0.0625% TFA (v %); Flow Rate: 1.2 mL/min; Wavelength: UV 220 nm, 215 nm, 254 nm; Column temperature: 40° C.

0-30AB: Gradient: B from 0~30% over 2.5 minutes and holding at 30% for 0.75 minutes;
0-60AB: Gradient: B from 0~60% over 2.5 minutes and holding at 60% for 0.75 minutes;
5-95AB: Gradient: B from 5~95% over 2.5 minutes and holding at 95% for 0.75 minutes.

Instrument: Shimadzu LC20; Column: Ultimate C18 50*3 mm, 3 μm; Mobile Phase A: $H_2O$ with 0.06875% TFA (v %); Mobile Phase B: MeCN with 0.0625% TFA (v %); Flow Rate: 1.2 mL/min; Wavelength: UV 220 nm, 215 nm, 254 nm; Column temperature: 40° C. 10-80AB: Gradient: B from 10~80% over 4 minutes and holding at 80% for 2 minutes.

Exemplary TLC, Concentration and Normal Phase Chromatography.

Analytical thin layer chromatography (TLC) was performed with silica gel 60 F254 aluminum plates. Visualization was done under a UV lamp (254 nm) and by iodine or immersion in ethanolic phosphomolybdic acid (PMA) or potassium permanganate ($KMnO_4$), followed by heating using a heat gun. Organic solutions were concentrated by rotary evaporation at 20-40° C. Purification of reaction products were generally done by flash column chromatography with 230-400 mesh silica gel or Agela flash silica column.

Exemplary Chiral SFC Analytical Methods

Column: Chiralpak AD-3 150×4.6 mm I.D., 3 μm; Mobile phase: A: supercritical $CO_2$; Mobile phase B: EtOH (0.05% DEA); Gradient: from 5% to 40% of B in 5 min and hold 40% for 2.5 min, then 5% of B for 2.5 min; Flow rate: 2.5 mL/min; Column temperature: 35° C.; ABPR: 1500 psi.

Column: Chiralpak AD-3 100×4.6 mm I.D., 3 μm; Mobile phase: A: supercritical $CO_2$ Mobile phase B: EtOH (0.1% ethanolamine); Gradient: from 5% to 40% of B in 4.5 min and hold 40% for 2.5 min, then 5% of B for 1 min; Flow rate: 2.8 mL/min; Column temperature: 40° C.

Exemplary Preparative HPLC Separation Methods

Basic condition ($NH_3$—$H_2O$): Instrument: Gilson GX-281 Liquid Handler, Gilson 322 Pump, Gilson 156 UV Detector; Column: Waters Xbridge 150×25 mm×5 μm; Mobile phase A: $H_2O$ with 0.05% $NH_3$—$H_2O$ (v %); Mobile phase B: MeCN; Gradient: B from 22% to 52% in 9.5 min, hold 100% B for 1 min; Flow Rate: 25 mL/min; Column Temperature: 30° C.; Wavelength: 220 nm, 254 nm.

Acid condition (HCOOH): Instrument: Gilson GX-281 Liquid Handler, Gilson 322 Pump, Gilson 156 UV Detector; Column: Agela Durashell C18 150*25 mm 5 μm; Mobile phase A: $H_2O$ (0.0225% HCOOH); Mobile phase B: MeCN; Gradient: B from 7% to 37% in 9 min, hold 100% B for 0 min; Flow Rate: 25 mL/min; Column Temperature: 30° C.; Wavelength: 220 nm, 254 nm.

Acid condition (HCl): Gilson GX-281 Liquid Handler, Gilson 322 Pump, Gilson 156 UV Detector; Column: Xtimate C18 150*25 mm*5 μm; Mobile phase A: $H_2O$ with 0.05% HCl (v %); Mobile phase B: MeCN; Gradient: B from 0% to 30% in 6.5 min, hold 100% B for 2.5 min; Flow Rate: 25 mL/min; Column Temperature: 30° C.; Wavelength: 220 nm, 254 nm).

Neutral condition ($NH_4HCO_3$): (Instrument: Gilson GX-281 Liquid Handler, Gilson 322 Pump, Gilson 156 UV Detector; Column: Waters Xbridge 150×25 mm×5 μm; Mobile phase A: $H_2O$ with 10 mmol $NH_4HCO_3$; Mobile phase B: MeCN; Gradient: B from 39% to 69% in 10 min, hold 100% B for 2.5 min; Flow Rate: 25 mL/min; Column Temperature: 30° C.; Wavelength: 220 nm, 254 nm).

Exemplary Large-Scale Separation

Basic condition: Instrument: Shimadzu LC-8A Pumps, Shimadzu SCL-10A VP System Controller, Shimadzu SPD-20AV UV/VIS Detector; Column: Phenomenex Gemini C18 250*50 mm*10 μm; Mobile phase A: water (0.04% $NH_3$—$H_2O$+10 mM $NH_4HCO_3$); Mobile phase B: MeCN; Gradient: B from 65% to 95% in 26 min, hold 100% B for 3 min; Flow Rate: 110 mL/min; Column Temperature: 30° C.; Wavelength: 220 nm, 254 nm.

Acid condition (TFA): Instrument: Shimadzu LC-20AP Pumps, Shimadzu CBM-20A System Controller Shimadzu SPD-20AV UV/VIS Detector; Column: Phenomenex luna C18 250×50 mm×10 μm; Mobile phase A: $H_2O$ with 0.1% TFA (v %); Mobile phase B: MeCN; Gradient: B from 0% to 25% in 15 min, hold 100% B for 4 min; Flow Rate: 120 mL/min; Column Temperature: 30° C.; Wavelength: 220 nm, 254 nm.

Exemplary Preparative Chiral SFC Method:

Exemplary chiral columns available for use in the separation/purification of the enantiomers/diastereomers provided herein include, but are not limited to, CHIRALPAK® AD-10, CHIRALCEL® OB, CHIRALCEL® OB-H, CHIRALCEL® OD, CHIRALCEL® OD-H, CHIRALCEL® OF, CHIRALCEL® OG, CHIRALCEL® OJ and CHIRALCEL® OK.

In certain examples, the chiral separation was performed under the following conditions: Instrument: Thar 80; Column: Daicel Chiralpak AD. 250×30 mm I.D. 10 μm; Mobile phase: supercritical $CO_2$/MeOH (0.1% $NH_3$—$H_2O$, v %)=60/40; Flow Rate: 70 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm.

Materials and Methods

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) recrystallization, column chromatography, HPLC, or supercritical fluid chromatography (SFC). The following schemes are presented with details as to the preparation of representative pyrazoles that have been listed herein. The compounds provided herein may be prepared from known or commercially available starting materials and reagents by one skilled in the art of organic synthesis.

Exemplary general method for preparative HPLC: Column: Waters RBridge prep 10 μm C18, 19*250 mm. Mobile phase: acetonitrile, water ($NH_4HCO_3$) (30 L water, 24 g $NH_4HCO_3$, 30 mL $NH_3 \cdot H_2O$). Flow rate: 25 mL/min Exemplary general method for analytical HPLC: Mobile phase: A: water (10 mM $NH_4HCO_3$), B: acetonitrile Gradient: 5%-95% B in 1.6 or 2 min Flow rate: 1.8 or 2 mL/min; Column: XBridge C18, 4.6*50 mm, 3.5 μm at 45° C.

TABLE 2

| Abbreviations | |
|---|---|
| ACN | acetonitrile |
| Boc | t-butoxycarbonyl |
| (Boc)$_2$O | di-tert-butyl dicarbonate |
| BSA | bis (trimethylsilyl)acetamide |
| Cu(OAc)$_2$ | copper(II) acetate |
| t-BuOK | potassium tert-butoxide |
| DCE | dichloroethane |
| DCM | dichloromethane |
| DIEA | N,N-diisopropylethylamine |
| DIPEA | N,N-diisopropylethylamine |
| DMAP | 4-dimethylaminopyridine |
| DME | dimethyl ether |
| DMF | N,N-dimethylformamide |
| DMSO | dimethyl sulfoxide |
| dppf | 1,1'-bis(diphenylphosphino)ferrocene |
| EDCI | 1-ethyl-3-(3-dimethylaminopropyl)carbodiimide |
| EtOAc | ethyl acetate |

TABLE 2-continued

| Abbreviations | |
|---|---|
| EtOH | ethanol |
| HATU | 1-[bis(dimethylamino)methylene]-1H-1,2,3-triazolo[4,5-b]pyridinium 3-oxide hexafluorophosphate |
| HDAC | histone deacetylases |
| HFIP | hexafluoro-2-propanol |
| HPLC | high performance liquid chromatography |
| IPA | isopropyl alcohol |
| KOAc | potassium acetate |
| LCMS | liquid chromatography-mass spectrum |
| Me | methyl |
| MeOH | methanol |
| m-CPBA | meta-chloroperoxybenzoic acid |
| MeCN | acetonitrile |
| NBS | N-bromosuccinimide |
| NH$_2$Boc | tert-butyl carbamate, |
| NMR | nuclear magnetic resonance spectroscopy |
| Pd$_2$(dba)$_3$ | tris(dibenzylideneacetone) dipalladium |
| Pd(dppf)Cl$_2$ | [1,1'-bis(diphenylphosphino)ferrocene]dichloropalladium(II) |
| Pd(dppf)Cl$_2$_ DCM | [1,1'-bis (diphenylphosphino)ferrocene]dichloropalladium (II), complex with dichloromethane |
| PhI(OAc)$_2$ | (diacetoxyiodo)benzene |
| PSI | pounds per square inch |
| Rh$_2$(OAc)$_4$ | Rhodium(II) acetate dimer |
| Py or pyr | pyridine |
| TEA | triethylamine |
| TFA | trifluoroacetic acid |
| THF | tetrahydrofuran |
| TLC | thin layer chromatography |
| TSA | toluenesulfonic acid |
| UV | ultraviolet-visible |
| XantPhos | (9,9-dimethyl-9H-xanthene-4,5-diyl)bis(diphenylphosphane) |

Example 1. Synthesis of N-[2-amino-5-(4-fluorophenyl)phenyl]-4-[rel-(1R)-1-oxo-4,5-dihydro-3H-isothiazol-1-yl]benzamide (Compound 185) and N-[2-amino-5-(4-fluorophenyl)phenyl]-4-[rel-(1S)-1-oxo-4,5-dihydro-3H-isothiazol-1-yl]benzamide (Compound 184)

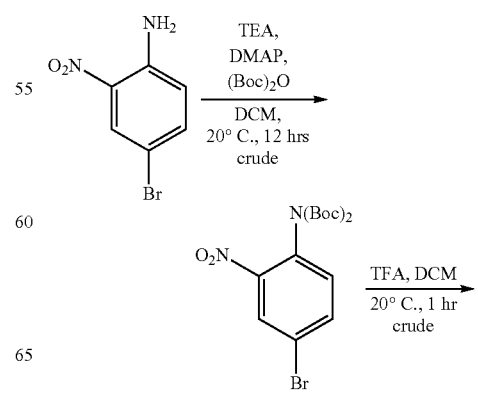

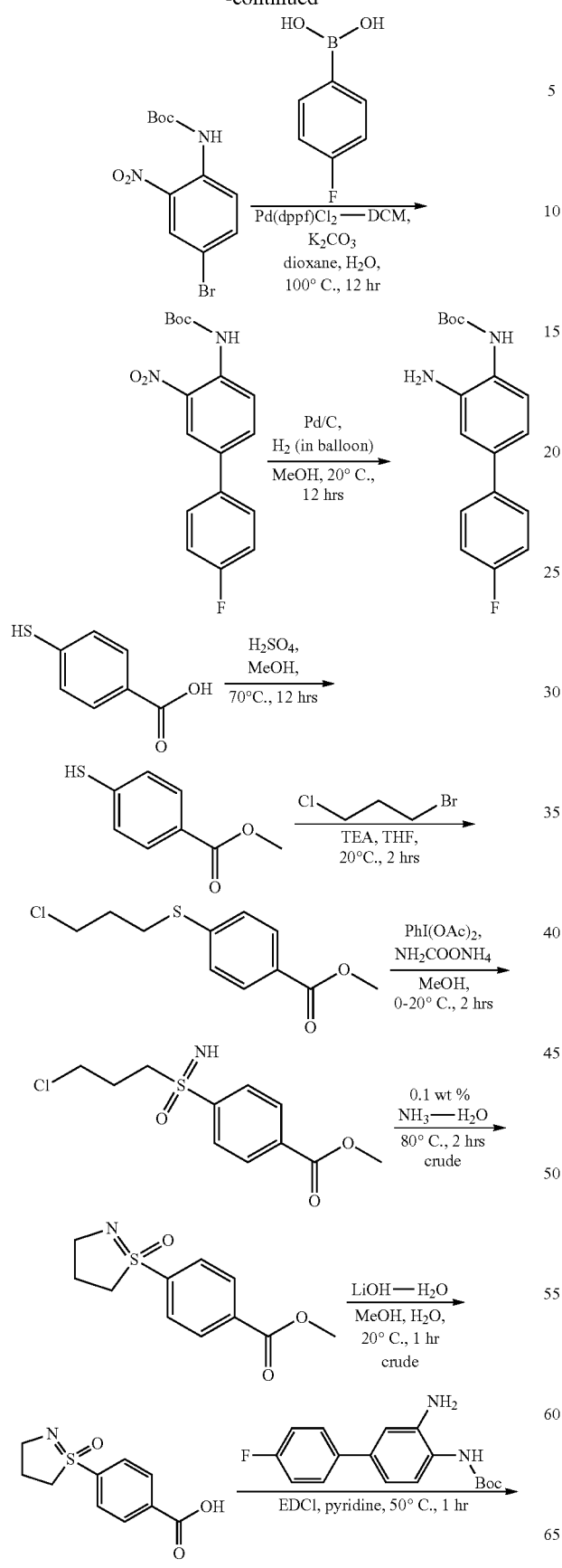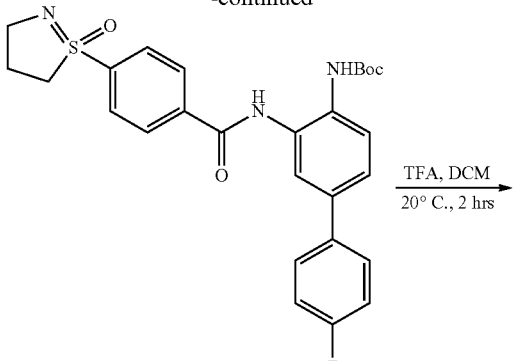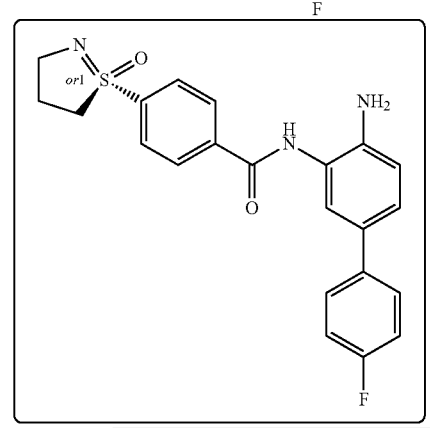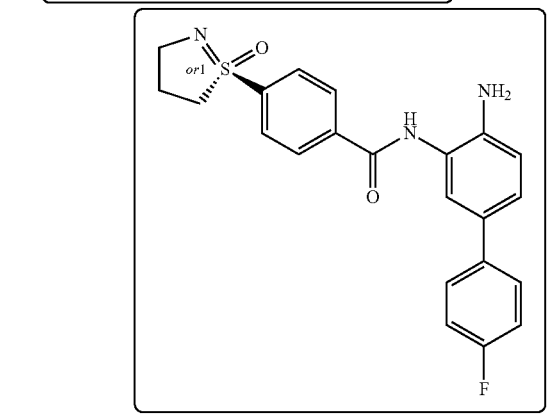
Step 1: Synthesis of tert-butyl N-(4-bromo-2-nitrophenyl)-N-tert-butoxycarbonyl-carbamate
To a solution of 4-bromo-2-nitro-aniline (30 g, 0.138 mol), tert-butoxycarbonyl tert-butyl carbonate (about 79 mL, 0.344 mol), DMAP (about 5 g, 40.9 mmol) in DCM (about 300 mL) was added TEA (about 58 mL, 0.416 mol). The mixture was stirred at about 20° C. for about 12 hours. The mixture was concentrated under reduced pressure. The residue was triturated in a solution (about 300 mL, MeOH) to afford tert-butyl N-(4-bromo-2-nitro-phenyl)-N-tert-butoxycarbonyl-carbamate (57 g). $^1$H NMR (400 MHz, DMSO-d$_6$) δ ppm 8.34 (d, J=2.3 Hz, 1H), 8.01 (dd, J=8.5, 2.3 Hz, 1H), 7.59 (d, J=8.6 Hz, 1H), 1.33 (s, 18H).

Step 2: Synthesis of tert-butyl
N-(4-bromo-2-nitro-phenyl)carbamate

To a solution of tert-butyl N-(4-bromo-2-nitro-phenyl)-N-tert-butoxycarbonyl-carbamate (about 57 g, 0.137 mol) in DCM (about 50 mL) was added TFA (about 18 mL, 0.234 mol). The mixture was stirred at about 20° C. for about 1 hour. The resulting mixture was adjusted to about pH=8 with saturated Na$_2$CO$_3$ aqueous solution and extracted with DCM (about 100 mL*3). The combined organic layer was washed with saturated NH$_4$Cl aqueous solution (about 100 mL*2), brine (about 100 mL), dried over anhydrous Na$_2$SO$_4$, filtered and concentrated under reduced pressure to afford tert-butyl N-(4-bromo-2-nitro-phenyl)carbamate (about 46 g), which was used directly on next step without further purification. $^1$H NMR (400 MHz, DMSO-d$_6$) δ ppm 9.69 (s, 1H), 8.12 (d, J=2.3 Hz, 1H), 7.86 (dd, J=8.8, 2.4 Hz, 1H), 7.58 (d, J=8.8 Hz, 1H), 1.38 (s, 9H).

Step 3: Synthesis of tert-butyl N-[4-(4-fluorophenyl)-2-nitro-phenyl]carbamate

To a solution of tert-butyl N-(4-bromo-2-nitro-phenyl)carbamate (46 g, 0.145 mol), (4-fluorophenyl)boronic acid (about 26 g, 0.186 mol), K$_2$CO$_3$ (about 58 g, 0.420 mol) in dioxane (about 300 mL) and H$_2$O (about 30 mL) was added cyclopentyl(diphenyl)phosphane;dichloromethane;dichloropalladium;iron (about 9 g, 11.0 mmol). The mixture was stirred at about 100° C. for about 12 hours under N$_2$. The resulting mixture was quenched by addition of H$_2$O (about 200 mL), and extracted with EtOAc (about 150 mL*3). The combined organic layer was washed with brine (about 200 mL*3), dried over anhydrous Na$_2$SO$_4$, filtered and concentrated under reduced pressure. The residue was triturated in a solution (about 500 mL, contained about PE 450 mL, about EtOAc 50 mL) to afford tert-butyl N-[4-(4-fluorophenyl)-2-nitro-phenyl]carbamate (about 33 g). $^1$H NMR (400 MHz, DMSO-d$_6$) δ ppm 9.66 (s, 1H), 8.17 (d, J 2.3 Hz, 1H), 7.97 (dd, J=8.6, 2.3 Hz, 1H), 7.75-7.83 (m, 2H), 7.71 (d, J=8.6 Hz, 1H), 7.28-7.37 (m, 2H), 1.45 (s, 9H); $^{19}$F NMR (376 MHz, DMSO-d$_6$) δ ppm−114.395.

Step 4: Synthesis of tert-butyl N-[2-amino-4-(4-fluorophenyl)phenyl]carbamate

To a solution of tert-butyl N-[4-(4-fluorophenyl)-2-nitro-phenyl]carbamate (about 33 g, 99.3 mmol) in MeOH (about 300 mL) was added Pd/C (about 12 g, 10% Pd/C with 50% of water, wt %). The resulting mixture was sealed and degassed under vacuum and purged with N$_2$ for three times, and then stirred at about 20° C. for about 12 hours under H$_2$ (in balloon). The resulting mixture was filtered and concentrated under reduced pressure to afford tert-butyl N-[2-amino-4-(4-fluorophenyl)phenyl]carbamate (about 28 g). $^1$H NMR (400 MHz, DMSO-d$_6$) δ ppm 8.36 (brs, 1H), 7.52-7.62 (m, 2H), 7.20-7.37 (m, 3H), 6.95 (d, J=2.1 Hz, 1H), 6.80 (dd, J=8.2, 2.1 Hz, 1H), 4.97 (s, 2H), 1.47 (s, 9H); $^{19}$F NMR (376 MHz, DMSO-d$_6$) δ ppm−116.338.

Step 5: Synthesis of methyl 4-sulfanylbenzoate

To a solution of 4-sulfanylbenzoic acid (about 50 g, 0.324 mol) in MeOH (about 300 mL) was added sulfuric acid (about 10 mL, 0.188 mol). The reaction mixture was stirred at about 70° C. for 12 hours. The mixture was concentrated under reduced pressure. The residue was triturated with MeOH (about 40 mL). The mixture was filtered. The filter cake was dried under reduced pressure to give desired product (about 23 g). The filtrate was concentrated under reduced pressure. The residue was triturated with MeOH (about 20 mL) again. The mixture was filtered. The filter cake was dried under reduced pressure to give desired product (about 20 g). The filtrate was concentrated under reduced pressure. The residue was purified by flash chromatography (ISCO®; 330 g AgelaFlash® Silica Flash Column, petroleum ether/EtOAc with EtOAc from 0~10%, flow rate=100 mL/min, 254 nm) to give desired product (about 10 g). Totally methyl 4-sulfanylbenzoate (about 53 g) was obtained. LCMS (ESI) [M+H]$^+$ m/z: calcd 169.0, found 169.1.

Step 6: Synthesis of methyl
4-(3-chloropropylsulfanyl)benzoate

To a mixture of methyl 4-sulfanylbenzoate (about 20 g, 0.119 mol) and 1-bromo-3-chloro-propane (about 24 mL, 0.243 mol) in THF (about 100 mL) was added N,N-diethylethanamine (about 33 mL, 0.237 mol). The mixture was stirred at about 20° C. for about 2 hours. The reaction mixture was concentrated under reduced pressure. The residue was purified by flash chromatography (ISCO®; 330 g AgelaFlash® Silica Flash Column, Petroleum ether/EtOAc with EtOAc from 0~20%, 100 mL/min, 254 nm) to afford methyl 4-(3-chloropropylsulfanyl)benzoate (about 26.6 g). $^1$H NMR (400 MHz, chloroform-d) δ ppm 7.94 (d, J=8.5 Hz, 2H), 7.32 (d, J=8.5 Hz, 2H), 3.90 (s, 3H), 3.68 (t, J=6.1 Hz, 2H), 3.16 (t, J=7.0 Hz, 2H), 2.13 (quin, J=6.6 Hz, 2H); LCMS (ESI) [M+H]+m/z: calcd 245.0, found 245.0.

Step 7: Synthesis of methyl
4-(3-chloropropylsulfonimidoyl)benzoate

To a solution of methyl 4-(3-chloropropylsulfanyl)benzoate (about 26.6 g, 0.109 mol) in MeOH (about 200 mL) was added ammonia; carbamic acid (about 17 g, 0.218 mol) and [acetoxy(phenyl)-iodanyl] acetate (about 87.5 g, 0.272 mol) at 0° C. slowly. The mixture was stirred at about 20° C. for about 2 hours. The reaction mixture was diluted with H$_2$O (about 100 mL) and extracted with EtOAc (about 100 mL*3). The combined organic layers were dried over anhydrous Na$_2$SO$_4$, filtered and concentrated under reduced pressure. The residue was purified by flash chromatography (Biotage®; 330 g AgelaFlash® Silica Flash Column, Petroleum ether/EtOAc with EtOAc from 0~100%, 100 mL/min, 254 nm) to afford methyl 4-(3-chloropropylsulfonimidoyl)benzoate (about 21 g). $^1$H NMR (400 MHz, chloroform-d) δ ppm 8.22 (d, J=8.5 Hz, 2H), 8.05 (d, J=8.3 Hz, 2H), 3.97 (s, 3H), 3.62 (t, J=6.1 Hz, 2H), 3.25-3.41 (m, 2H), 2.14-2.30 (m, 4H); LCMS (ESI) [M+H]$^+$ m/z: calcd 276.0, found 275.9.

Step 8: Synthesis of methyl
4-(1-oxo-4,5-dihydro-3H-isothiazol-1-yl)benzoate

A mixture of methyl 4-(3-chloropropylsulfonimidoyl) benzoate (about 19 g, 68.9 mmol) in 0.1 wt % NH$_3$—H$_2$O (about 200 mL) was stirred at about 80° C. for about 2 hours. The reaction mixture was concentrated under reduced pressure to afford methyl 4-(1-oxo-4,5-dihydro-3H-isothiazol-1-yl)benzoate (about 17 g), which was directly used without further purification.

Step 9: Synthesis of 4-(1-oxo-4,5-dihydro-3H-isothiazol-1-yl)benzoic acid

To a solution of methyl 4-(1-oxo-4,5-dihydro-3H-isothiazol-1-yl)benzoate (17 g, 71.0 mmol) in MeOH (about 100 mL) and $H_2O$ (about 30 mL) was added LiOH—$H_2O$ (about 8.94 g, 0.213 mol). The mixture was stirred at about 20° C. for about 1 hour. The reaction mixture was concentrated under reduced pressure to afford a residue (about 22 g). The residue (about 21.5 g) in $H_2O$ (about 100 mL) was adjusted about pH=4 with 2N HCl aqueous solution. The mixture was concentrated under reduced pressure to afford 4-(1-oxo-4,5-dihydro-3H-isothiazol-1-yl)benzoic acid (about 33 g).

Step 10: Synthesis of tert-butyl N-[4-(4-fluorophenyl)-2-[[4-(1-oxo-4,5-dihydro-3H-isothiazol-1-yl)benzoyl]amino]phenyl]carbamate A mixture of 4-(1-oxo-4,5-dihydro-3H-isothiazol-1-yl)benzoic acid (about 32 g, 71.0 mmol), tert-butyl N-[2-amino-4-(4-fluorophenyl)phenyl]carbamate (about 21 g, 69.5 mmol) and EDCI (about 20 g, 0.104 mol) in pyridine (about 100 mL) was stirred at about 50° C. for about 1 hour. The resulting mixture was quenched by addition of water (about 100 mL) and extracted with EtOAc (about 100 mL*3). The combined organic layer was washed with saturated $NH_4Cl$ aqueous solution (100 mL*2), dried over anhydrous $Na_2SO_4$, filtered and concentrated under reduced pressure. The residue was purified by flash chromatography (ISCO®; about 330 g AgelaFlash® Silica Flash Column, petroleum ether/EtOAc with EtOAc from 0~100%, 100 mL/min, 254 nm) to afford tert-butyl N-[4-(4-fluorophenyl)-2-[[4-(1-oxo-4,5-dihydro-3H-isothiazol-1-yl)benzoyl]amino]phenyl]carbamate (about 8 g). LCMS (ESI) [M+H]+ m/z: calcd 510.2; found 510.2; HPLC: 98.96%@220 nm, 99.57%@254 nm.

Step 11: Synthesis of N-[2-amino-5-(4-fluorophenyl)phenyl]-4-(1-oxo-4,5-dihydro-3H-isothiazol-1-yl)benzamide To a solution of tert-butyl N-[4-(4-fluorophenyl)-2-[[4-(1-oxo-4,5-dihydro-3H-isothiazol-1-yl)benzoyl]amino]phenyl]carbamate (about 8 g, 15.7 mmol) in DCM (about 100 mL) was added TFA (about 25 mL, 0.325 mol). The mixture was stirred at about 20° C. for about 2 hours. The mixture was concentrated under reduced pressure. The residue was diluted with $H_2O$ (about 50 mL), and adjusted about pH=8 with saturated $NaHCO_3$ aqueous solution. The mixture was extracted with 10:1 DCM/MeOH (about 150 mL*3). The combined organic layer was dried over anhydrous $Na_2SO_4$, filtered and concentrated under reduced pressure to give N-[2-amino-5-(4-fluorophenyl)phenyl]-4-(1-oxo-4,5-dihydro-3H-isothiazol-1-yl)benzamide (about 6 g), which was directly used without further purification. $^1$H NMR (400 MHz, DMSO-$d_6$) δ ppm 9.97 (s, 1H), 8.20 (d, J=8.5 Hz, 2H), 8.00 (d, J=8.5 Hz, 2H), 7.59 (dd, J=8.8, 5.5 Hz, 2H), 7.51 (d, J=2.0 Hz, 1H), 7.33 (dd, J=8.3, 2.3 Hz, 1H), 7.22 (t, J=8.8 Hz, 2H), 6.87 (d, J=8.3 Hz, 1H), 5.19 (s, 2H), 3.82-3.89 (m, 1H), 3.71 (dt, J=10.3, 6.5 Hz, 1H), 3.41-3.50 (m, 2H), 2.20-2.32 (m, 2H); LCMS (ESI) [M+H]+ m/z: calcd 410.1; found 410.1; HPLC: 98.22%@220 nm, 99.14%@254 nm.

Step 12: Synthesis of N-[2-amino-5-(4-fluorophenyl)phenyl]-4-[rel-(1R)-1-oxo-4,5-dihydro-3H-isothiazol-1-yl]benzamide and N-[2-amino-5-(4-fluorophenyl)phenyl]-4-[rel-(1S)-1-oxo-4,5-dihydro-3H-isothiazol-1-yl]benzamide N-[2-amino-5-(4-fluorophenyl)phenyl]-4-(1-oxo-4,5-dihydro-3H-isothiazol-1-yl)benzamide (about 6 g, 14.7 mmol) was purified by Chiral SFC separation (Instrument: Berger, multigr AM-II; Column: Daicel chiralpak AS 250×50 mm I.D. 10 μm; Mobile phase: supercritical $CO_2$/EtOH (0.1% $NH_3$—$H_2O$, v %)=40/60; Flow Rate: 200 mL/min; Column Temperature: about 35° C.; Nozzle Pressure: 100 bar; Nozzle Temperature: 60° C.; Evaporator Temperature: about 20° C.; Trimmer Temperature: 25° C.; Wavelength: 220 nm) to afford the products. Stereochemistry was arbitrarily assigned N-[2-amino-5-(4-fluorophenyl)phenyl]-4-[rel-(1R)-1-oxo-4,5-dihydro-3H-isothiazol-1-yl]benzamide (about 2.88 g, peak 1, retention time=1.565 min, single enantiomer). $^1$H NMR (400 MHz, DMSO-$d_6$) δ ppm 9.97 (brs, 1H), 8.20 (d, J=8.4 Hz, 2H), 7.99 (d, J=8.4 Hz, 2H), 7.58 (dd, J=8.8, 5.5 Hz, 2H), 7.50 (d, J=2.1 Hz, 1H), 7.32 (dd, J=8.3, 2.2 Hz, 1H), 7.22 (t, J=8.9 Hz, 2H), 6.86 (d, J=8.4 Hz, 1H), 5.17 (s, 2H), 3.80-3.88 (m, 1H), 3.70 (dt, J=10.3, 6.5 Hz, 1H), 3.41-3.48 (m, 2H), 2.20-2.35 (m, 2H); $^{19}$F NMR (376 MHz, DMSO-$d_6$) δ ppm −117.464; LCMS (ESI) [M+H]+ m/z: calcd 410.1; found 410.2; HPLC: 95.64%@220 nm, 98.19%@254 nm; 99.5% ee.

N-[2-amino-5-(4-fluorophenyl)phenyl]-4-[rel-(1S)-1-oxo-4,5-dihydro-3H-isothiazol-1-yl]benzamide (about 2.88 g, peak 2, retention time=3.296 min, single enantiomer). $^1$H NMR (400 MHz, DMSO-$d_6$) δ ppm 9.96 (s, 1H), 8.20 (d, J=8.4 Hz, 2H), 7.99 (d, J=8.4 Hz, 2H), 7.58 (dd, J=8.7, 5.4 Hz, 2H), 7.50 (d, J=2.0 Hz, 1H), 7.32 (dd, J=8.3, 2.2 Hz, 1H), 7.22 (t, J=8.8 Hz, 2H), 6.86 (d, J=8.4 Hz, 1H), 5.17 (s, 2H), 3.79-3.89 (m, 1H), 3.70 (dt, J=10.3, 6.6 Hz, 1H), 3.41-3.49 (m, 2H), 2.19-2.32 (m, 2H); $^{19}$F NMR (376 MHz, DMSO-$d_6$) δ ppm −117.456; LCMS (ESI) [M+H]+ m/z: calcd 410.1; found 410.2; HPLC: 97.48%@220 nm, 99.53%@254 nm; 99.4% ee.

Example 2. Synthesis of N-[2-amino-5-(4-chlorophenyl)phenyl]-4-(methylsulfonimidoyl)benzamide (Compound 182)

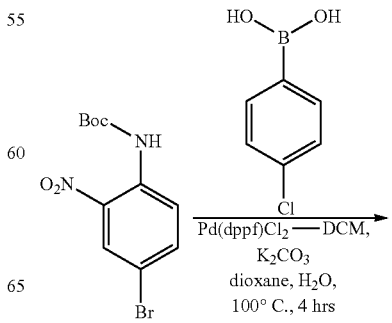

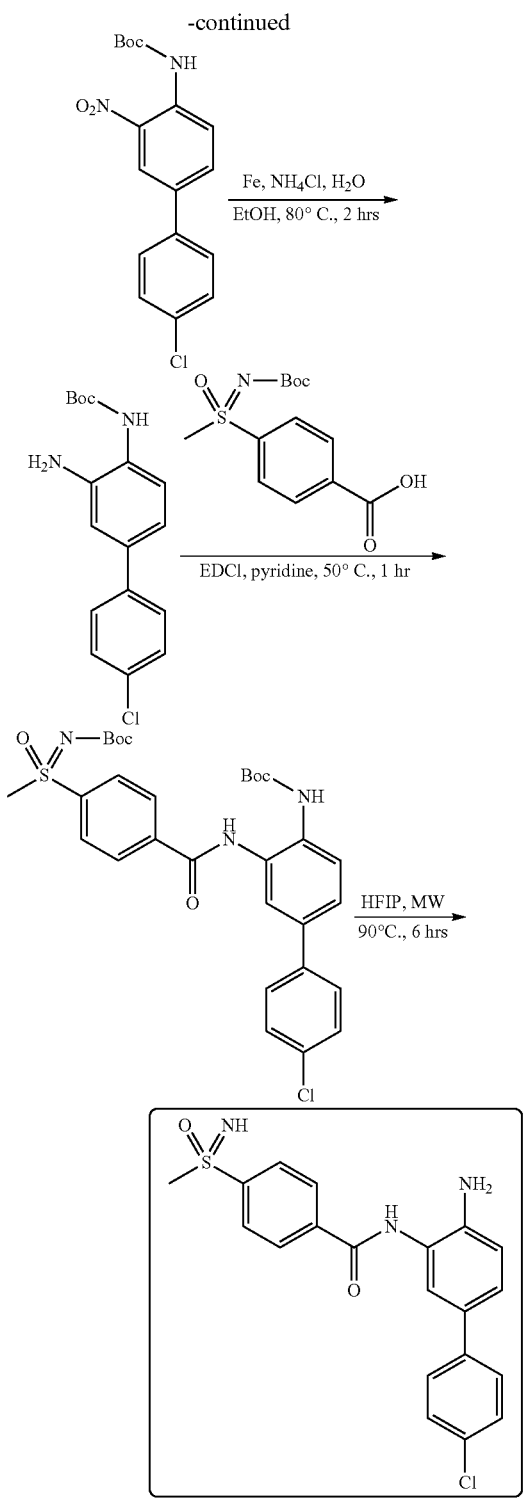

Step 1: Synthesis of tert-butyl N-[4-(4-chlorophenyl)-2-nitro-phenyl]carbamate

To a solution of tert-butyl N-(4-bromo-2-nitro-phenyl)carbamate (about 1 g, 3.15 mmol), (4-chlorophenyl)boronic acid (about 591 mg, 3.78 mmol), K$_2$CO$_3$ (about 1.09 g, 7.88 mmol) in dioxane (about 12 mL)/H$_2$O (about 1.2 mL) was added Pd(dppf)Cl$_2$-DCM (about 257 mg, 0.315 mmol) and the reaction mixture was stirred at about 100° C. for about 4 hours. The resulting mixture was quenched by addition of water (about 10 mL) and extracted with EtOAc (about 10 mL*3). The combined organic layers were washed with brine (about 10 mL*3), dried over anhydrous Na$_2$SO$_4$, filtered and concentrated under reduced pressure. The residue was purified by purified by flash chromatography (ISCO®; about 40 g AgelaFlash® Silica Flash Column, petroleum ether/EtOAc with EtOAc from 0~100%, flow rate=40 mL/min) to afford compound tert-butyl N-[4-(4-chlorophenyl)-2-nitro-phenyl] carbamate (about 0.855 g). $^1$H NMR (400 MHz, chloroform-d) δ ppm 9.69 (s, 1H), 8.65 (d, J=8.88 Hz, 1H), 8.40 (d, J=2.25 Hz, 1H), 7.81 (dd, J=8.88, 2.25 Hz, 1H), 7.37-7.57 (m, 4H), 1.57 (s, 9H).

Step 2: Synthesis of tert-butyl N-[2-amino-4-(4-chlorophenyl)phenyl]carbamate

A solution of tert-butyl N-[4-(4-chlorophenyl)-2-nitro-phenyl]carbamate (about 855 mg, 2.45 mmol), Fe (about 684 mg, 12.3 mmol), NH$_4$Cl (about 655 mg, 12.3 mmol) in EtOH (about 20 mL)/H$_2$O (about 4 mL) was stirred at about 80° C. for about 2 hours. The resulting mixture was quenched by addition of water (about 10 mL) and extracted with EtOAc (about 10 mL*3). The combined organic layers were washed with brine (about 10 mL*3), dried over anhydrous Na$_2$SO$_4$, filtered and concentrated under reduced pressure. Compound tert-butyl N-[2-amino-4-(4-chlorophenyl)phenyl]carbamate (about 366 mg) was obtained. LCMS (ESI) [M+H]$^+$ m/z: calcd 319.1, found 319.1.

Step 3: Synthesis of tert-butyl N-[[4-[[2-(tert-butoxycarbonylamino)-5-(4-chlorophenyl)phenyl]carbamoyl]phenyl]-methyl-oxo-sulfanylidene]carbamate A solution of tert-butyl N-[2-amino-4-(4-chlorophenyl)phenyl]carbamate (about 100 mg, 0.313 mmol), 4-(N-tert-butoxycarbonyl-S-methyl-sulfonimidoyl)benzoic acid (about 94 mg, 0.313 mmol), 3-(ethyliminomethyleneamino)-N,N-dimethyl-propan-1-amine;hydrochloride (about 60 mg, 0.313 mmol) in pyridine (about 5 mL) was stirred at about 50° C. for about 1 hour. The resulting mixture was quenched by addition of water (about 10 mL) and extracted with EtOAc (10 mL*3). The combined organic layers were washed with brine (about 10 mL*3), dried over anhydrous Na$_2$SO$_4$, filtered and concentrated under reduced pressure. The residue was purified by flash chromatography (ISCO®; 20 g AgelaFlash® Silica Flash Column, petroleum ether/EtOAc with EtOAc from 0-50%, flow rate=35 mL/min, 254 nm) to afford compound tert-butyl N-[[4-[[2-(tert-butoxycarbonylamino)-5-(4-chlorophenyl)phenyl]carbamoyl]phenyl]-methyl-oxo-sulfanylidene]carbamate (about 106 mg) was obtained. $^1$H NMR (400 MHz, chloroform-d) δ ppm 9.70 (br s, 1H), 8.10 (d, J=8.53 Hz, 3H), 7.98 (d, J=8.53 Hz, 2H), 7.43 (d, J=8.53 Hz, 2H), 7.26-7.34 (m, 3H), 3.16 (s, 3H), 1.47 (s, 18H); LCMS (ESI) [M+H]+m/z: calcd 600.2, found 600.2.

Step 4: Synthesis of N-[2-amino-5-(4-chlorophenyl)phenyl]-4-(methylsulfonimidoyl)benzamide A solution of tert-butyl N-[[4-[[2-(tert-butoxycarbonylamino)-5-(4-chlorophenyl)phenyl]carbamoyl]phenyl]-methyl-oxo-sulfanylidene]carbamate (about 90 mg, 0.150 mmol) in HFIP (about 5 mL) was heated at about 90° C. for about 6 hours in microwave. The reaction mixture was concentrated under reduced pressure. The residue was purified by preparative HPLC (Instrument: Gilson GX-281 Liquid Handler, Gilson 322 Pump, Gilson 156 UV Detector; Column: Durashell 150×25 mm×5 μm; Mobile phase A: $H_2O$ with 0.05% $NH_3$—$H_2O$ (v %); Mobile phase B: MeCN; Gradient: B from 39% to 69% in 10 min, hold 100% B for 2.5 min; Flow Rate: 25 mL/min; Column Temperature: 30° C.; Wavelength: 220 nm, 254 nm) to afford N-[2-amino-5-(4-chlorophenyl)phenyl]-4-(methylsulfonimidoyl)benzamide (15.8 mg). $^1$H NMR (400 MHz, chloroform-d) δ ppm 8.17 (s, 2H), 8.07-8.13 (m, 2H), 7.98 (br s, 1H), 7.65 (s, 1H), 7.48 (d, J=8.5 Hz, 2H), 7.38 (d, J=8.5 Hz, 3H), 6.96 (d, J=8.3 Hz, 1H), 3.16 (s, 3H); LCMS (ESI) [M+H]$^+$ m/z: calcd 400.1, found 400.2; HPLC: 97.13%@254 nm, 97.05%@254 nm. 96.5%.

Example 3. Synthesis of rel-(R)—N-[2-amino-5-(4-fluorophenyl)phenyl]-4-(pyrimidin-5-ylsulfonimidoyl)benzamide (Compound 181) and rel-(S)—N-[2-amino-5-(4-fluorophenyl)phenyl]-4-(pyrimidin-5-ylsulfonimidoyl)benzamide (Compound 183)

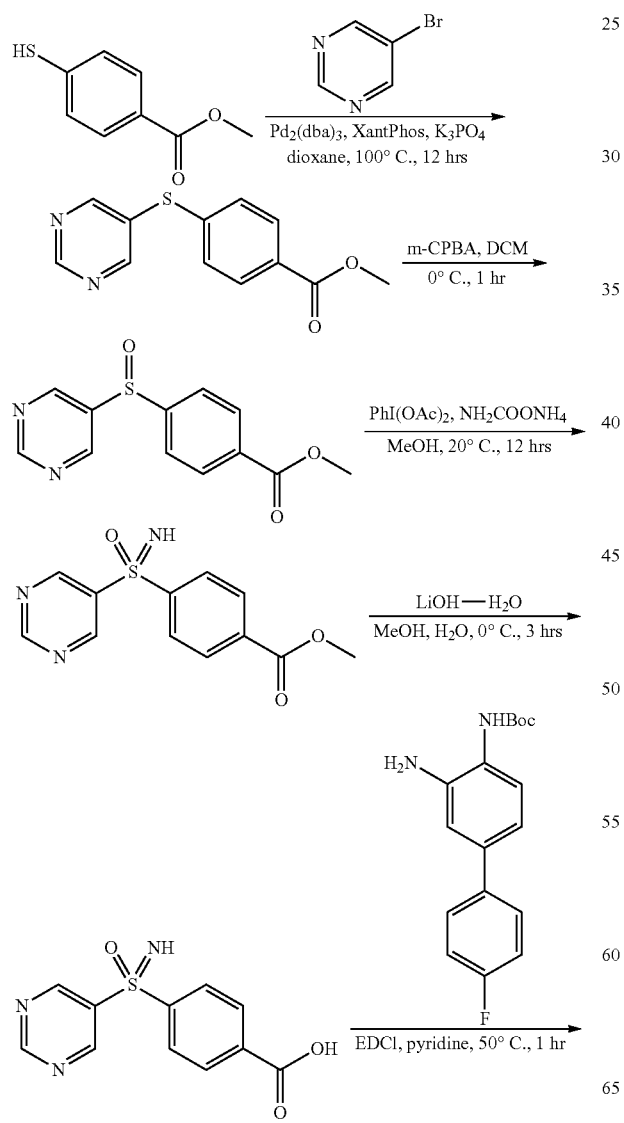

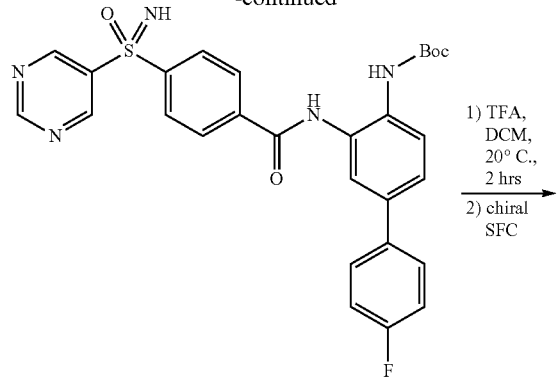

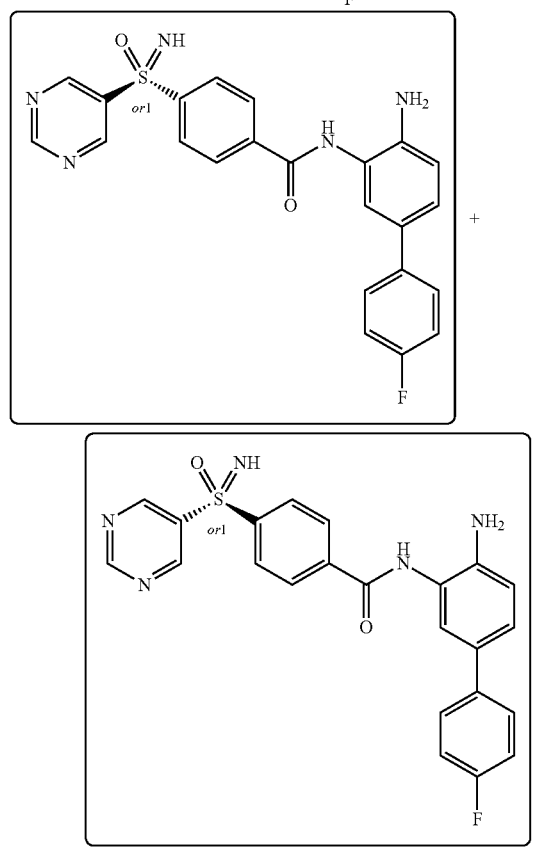

Step 1: Synthesis of methyl 4-pyrimidin-5-ylsulfanylbenzoate

A mixture of 5-bromopyrimidine (about 2.83 g, 17.8 mmol), methyl 4-sulfanylbenzoate (about 1 g, 5.94 mmol), $K_3PO_4$ (about 3.78 g, 17.8 mmol), (5-diphenylphosphanyl-9,9-dimethyl-xanthen-4-yl)-diphenyl-phosphane (about 690 mg, 1.19 mmol) and (1E,4E)-1,5-diphenylpenta-1,4-dien-3-one;palladium (about 545 mg, 0.595 mmol) in dioxane (about 20 mL) was stirred at about 100° C. for about 12 hours under $N_2$ atmosphere. The mixture was filtered. The filtrate was concentrated under reduced pressure. The residue was purified by flash chromatography (ISCO®; about 20 g AgelaFlash® Silica Flash Column, petroleum ether/EtOAc with EtOAc from 0~12%, flow rate=30 mL/min, 254 nm) to afford methyl 4-pyrimidin-5-ylsulfanylbenzoate (about 1.42 g). LCMS (ESI) [M+H]$^+$ m/z: calcd 247.0, found 247.0.

Step 2: Synthesis of methyl 4-pyrimidin-5-ylsulfinylbenzoate

To a solution of methyl 4-pyrimidin-5-ylsulfanylbenzoate (about 1.42 g, 5.77 mmol) in DCM (about 50 mL) was added 3-chlorobenzenecarboperoxoic acid (about 1.3 g, 6.40 mmol, 85 wt %). The mixture was stirred at about 0° C. for about 1 hour. The resulting mixture was quenched by addition of saturated $Na_2SO_3$ aqueous solution (about 30 mL) and adjusted to about pH=8 with saturated $NaHCO_3$ aqueous solution (about 10 mL). The mixture was extracted with DCM (about 20 mL*3). The combined organic layer was dried over anhydrous $Na_2SO_4$, filtered and concentrated under reduced pressure. The residue was purified by flash chromatography (ISCO®; about 20 g AgelaFlash® Silica Flash Column, petroleum ether/EtOAc with EtOAc from 0~35%, flow rate=40 mL/min, 254 nm) to afford methyl 4-pyrimidin-5-ylsulfinylbenzoate (about 1.15 g). LCMS (ESI) [M+H]$^+$ m/z: calcd 263.0, found 263.0.

Step 3: Synthesis of methyl 4-(pyrimidin-5-ylsulfonimidoyl)benzoate

A mixture of methyl 4-pyrimidin-5-ylsulfinylbenzoate (about 1.15 g, 4.38 mmol), [acetoxy(phenyl)-iodanyl] acetate (about 3.53 g, 11.0 mmol), ammonia; carbamic acid (about 690 mg, 8.84 mmol) and MeOH (about 50 mL) was stirred at about 20° C. for about 12 hours. The resulting mixture was concentrated under reduced pressure. The residue was purified by flash chromatography (ISCO®; about 12 g AgelaFlash® Silica Flash Column, petroleum ether/EtOAc with EtOAc from 0~40%, flow rate=30 mL/min, 254 nm) to afford methyl 4-(pyrimidin-5-ylsulfonimidoyl) benzoate (about 570 mg). $^1$H NMR (400 MHz, DMSO-$d_6$) δ ppm 9.33 (s, 1H), 9.14 (s, 2H), 8.11-8.14 (m, 2H), 8.00 (d, J=8.5 Hz, 2H), 3.87 (s, 3H); LCMS (ESI) [M+H]$^+$ m/z: calcd 278.1, found 278.1.

Step 4: Synthesis of 4-(pyrimidin-5-ylsulfonimidoyl)benzoic acid

To a solution of methyl 4-(pyrimidin-5-ylsulfonimidoyl) benzoate (about 350 mg, 1.26 mmol) in $H_2O$ (about 2 mL) and MeOH (about 6 mL) was added lithium;hydroxide; hydrate (about 530 mg, 12.6 mmol). The mixture was stirred at about 0° C. for about 3 hours. The mixture was adjusted to about pH=5 with 2N HCl aqueous solution (about 10 mL). The resulting mixture was extracted with EtOAc (about 20 mL*3). The combined organic layer was dried over anhydrous $Na_2SO_4$, filtered and concentrated under reduced pressure to give 4-(pyrimidin-5-ylsulfonimidoyl)benzoic acid (about 270 mg). LCMS (ESI) [M+H]$^+$ m/z: calcd 264.0, found 264.0.

Step 5: Synthesis of tert-butyl N-[4-(4-fluorophenyl)-2-[[4-(pyrimidin-5-ylsulfonimidoyl)benzoyl]amino]phenyl]carbamate A mixture of 4-(pyrimidin-5-ylsulfonimidoyl)benzoic acid (about 270 mg, 1.03 mmol), tert-butyl N-[2-amino-4-(4-fluorophenyl)phenyl]carbamate (about 370 mg, 1.22 mmol), 3-(ethyliminomethyleneamino)-N,N-dimethyl-propan-1-amine;hydrochloride (about 300 mg, 1.56 mmol) and pyridine (about 6 mL) was stirred at about 50° C. for about 1 hour. The resulting mixture was concentrated under reduced pressure. The residue was purified by flash chromatography (ISCO®; about 12 g AgelaFlash® Silica Flash Column, petroleum ether/EtOAc with EtOAc from 0~50%, flow rate=35 mL/min, 254 nm) to afford tert-butyl N-[4-(4-fluorophenyl)-2-[[4-(pyrimidin-5-ylsulfonimidoyl)benzoyl] amino]phenyl]carbamate (about 330 mg). $^1$H NMR (400 MHz, DMSO-$d_6$) δ ppm 9.98-10.05 (m, 1H), 9.34 (d, J=3.8 Hz, 1H), 9.16 (s, 1H), 8.76 (s, 1H), 8.00-8.29 (m, 4H), 7.76 (s, 1H), 7.63-7.72 (m, 3H), 7.51 (dd, J=8.4, 2.1 Hz, 1H), 7.28 (t, J=8.9 Hz, 2H), 3.71 (s, 1H), 1.43 (s, 9H); LCMS (ESI) [M+H]$^+$ m/z: calcd 548.2, found 548.2.

Step 6: Synthesis of N-[2-amino-5-(4-fluorophenyl)phenyl]-4-(pyrimidin-5-ylsulfonimidoyl)benzamide and N-[2-amino-5-(4-fluorophenyl)phenyl]-4-(pyrimidin-5-ylsulfonimidoyl)benzamide To a solution of tert-butyl N-[4-(4-fluorophenyl)-2-[[4-(pyrimidin-5-ylsulfonimidoyl)benzoyl]amino]phenyl]carbamate (about 300 mg, 0.548 mmol) in DCM (about 6 mL) was added TFA (about 1 mL, 13.0 mmol). The mixture was stirred at about 20° C. for about 2 hours. The resulting mixture was adjusted to about pH=8 with saturated $NaHCO_3$ aqueous solution (about 10 mL) and extracted with EtOAc (about 20 mL*2). The combined organic layer was dried over anhydrous $Na_2SO_4$, filtered and concentrated under reduced pressure. The residue was purified by preparative HPLC (Instrument: Gilson GX-281 Liquid Handler, Gilson 322 Pump, Gilson 156 UV Detector; Column: Durashell 75×40 mm×3 μm; Mobile phase A: $H_2O$ with 10 mmol $NH_4HCO_3$ (v %); Mobile phase B: MeCN; Gradient: B from 35% to 65% in 7.8 min, hold 100% B for 2 min; Flow Rate: 30 mL/min; Column Temperature: about 30° C.; Wavelength: 220 nm, 254 nm) to give a racemic N-[2-amino-5-(4-fluorophenyl)phenyl]-4-(pyrimidin-5-ylsulfonimidoyl) benzamide (Compound 186). The compound was further purified by chiral SFC (Instrument: Instrument: Thar800Q; Column: Chiralpak AD 250×30 mm I.D. 10 μm; Mobile phase: supercritical $CO_2$/EtOH (0.1% $NH_3·H_2O$, v %)=70/30; Flow Rate: 80 mL/min; Column Temperature: about 38° C.; Nozzle Pressure: 100 bar; Nozzle Temperature: about 60° C.; Evaporator Temperature: about 20° C.; Trimmer Temperature: about 25° C.; Wavelength: 220 nm). The fraction was concentrated under reduced pressure and then lyophilized for overnight to give the products. Stereochemistry was arbitrarily assigned rel-(R)—N-[2-amino-5-(4-fluorophenyl)phenyl]-4-(pyrimidin-5-ylsulfonimidoyl)benzamide (about 9.8 mg, single enantiomer, Peak 1, Retention time: 3.068 min). $^1$H NMR (400 MHz, DMSO-$d_6$) δ ppm 9.89 (s, 1H), 9.41 (s, 1H), 9.35 (s, 2H), 8.10-8.26 (m, 4H), 7.56 (dd, J=8.8, 5.5 Hz, 2H), 7.46 (d, J=1.8 Hz, 1H), 7.31 (dd, J=8.3, 2.0 Hz, 1H), 7.21 (t, J=8.9 Hz, 2H), 6.84 (d, J=8.3 Hz, 1H), 5.78 (s, 1H), 5.15 (s, 2H); $^{19}$F NMR (376 MHz, DMSO-$d_6$) δ ppm−117.469; LCMS (ESI) [M+H]$^+$ m/z: calcd 448.1, found 448.2; HPLC: 94.320%@220 nm, 99.720%@254 nm; 99.3% ee.

rel-(S)—N-[2-amino-5-(4-fluorophenyl)phenyl]-4-(pyrimidin-5-ylsulfonimidoyl)benzamide was further purified by chiral SFC (Instrument: Sepiatec Prep SFC100; Column: Chiralpak AD 250×30 mm I.D. 10 μm; Mobile phase: supercritical $CO_2$/EtOH (0.1% $NH_3$—$H_2O$, v %)=70/30; Flow Rate: 80 mL/min; Column Temperature: about 38° C.; Nozzle Pressure: 100 bar; Nozzle Temperature: about 60° C.; Evaporator Temperature: about 20° C.; Trimmer Temperature: about 25° C.; Wavelength: 220 nm). The fraction was concentrated under reduced pressure and then lyophilized for overnight to give N-[2-amino-5-(4-fluorophenyl)phenyl]-4-(pyrimidin-5-ylsulfonimidoyl)benzamide.

N-[2-amino-5-(4-fluorophenyl)phenyl]-4-(pyrimidin-5-ylsulfonimidoyl)benzamide (about 9.1 mg, single enantiomer, Peak 2, Retention time: 2.042 min). $^1$H NMR (400 MHz, DMSO-$d_6$) δ ppm 9.89 (s, 1H), 9.41 (s, 1H), 9.35 (s, 2H), 8.13-8.25 (m, 4H), 7.56 (dd, J=8.6, 5.5 Hz, 2H), 7.46 (d, J=1.9 Hz, 1H), 7.31 (dd, J=8.3, 2.1 Hz, 1H), 7.21 (t, J=8.9 Hz, 2H), 6.84 (d, J=8.4 Hz, 1H), 5.78 (s, 1H), 5.15 (s, 2H); $^{19}$F NMR (376 MHz, DMSO-$d_6$) δ ppm −117.471; LCMS (ESI) [M+H]$^+$ m/z: calcd 448.1, found 448.2; HPLC: 92.25%@220 nm, 98.72%@254 nm; 98.3% ee.

Example 4. Synthesis of N-[[2-[[2-(tert-butoxycarbonylamino)-5-(4-fluorophenyl)phenyl]carbamoyl]benzothiophen-5-yl]-methyl-oxo-sulfanylidene]carbamate (Compound 173)

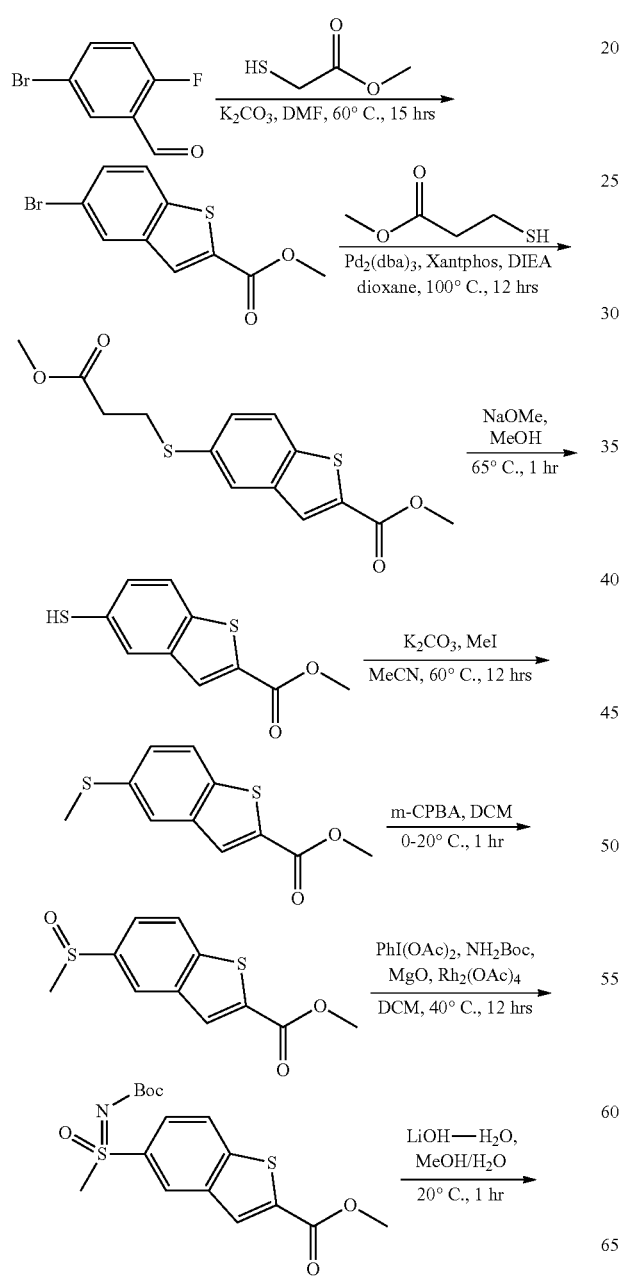

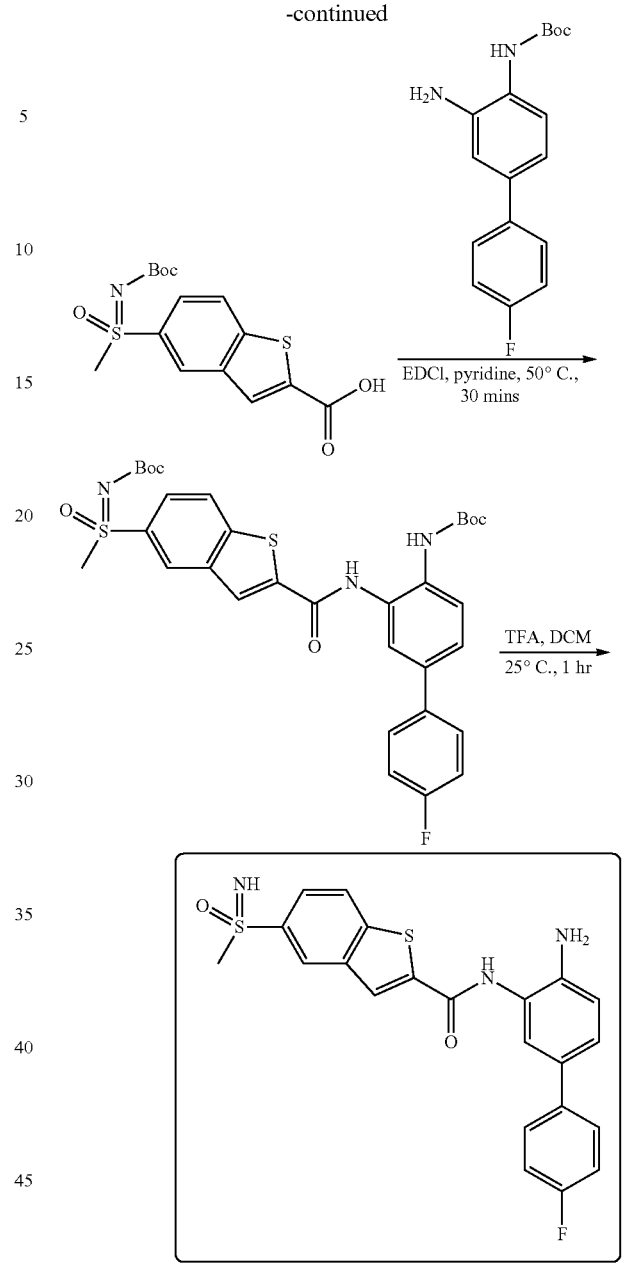

Step 1: Synthesis of methyl 5-bromobenzothiophene-2-carboxylate

A mixture of 5-bromo-2-fluoro-benzaldehyde (about 5 g, 24.6 mmol), $K_2CO_3$ (about 13.6 g, 98.4 mmol) in DMF (about 50 mL) methyl 2-sulfanylacetate (about 2.9 g, 27.3 mmol) was added. The mixture was stirred at about 60° C. for about 15 hours. The resulting mixture was quenched by addition of water (about 100 mL) and extracted with EtOAc (about 100 mL*3). The combined organic layer was washed with brine (about 100 mL), dried over anhydrous $Na_2SO_4$, filtered and concentrated under reduce pressure to give methyl 5-bromobenzothiophene-2-carboxylate (about 6 g). $^1$H NMR (400 MHz, chloroform-d) δ ppm 7.96 (d, J=1.6 Hz, 1H), 7.91 (s, 1H), 7.66 (d, J=8.8 Hz, 1H), 7.46-7.49 (m, 1H), 3.89 (s, 3H); LCMS (ESI) [M+H]$^+$ m/z: calcd 270.9, found 270.9.

Step 2: Synthesis of methyl 5-(3-methoxy-3-oxo-propyl)sulfanylbenzothiophene-2-carboxylate A mixture of methyl 5-bromobenzothiophene-2-carboxylate (about 1 g, 3.69 mmol), methyl 3-sulfanylpropanoate (about 488 mg, 4.06 mmol), (1E,4E)-1,5-diphenylpenta-1,4-dien-3-one;palladium (about 338 mg, 0.369 mmol), (5-diphenylphosphanyl-9,9-dimethyl-xanthen-4-yl)-diphenyl-phosphane (about 427 mg, 0.738 mmol), N-ethyl-N-isopropyl-propan-2-amine (about 1.4 g, 10.8 mmol) in dioxane (about 10 mL) was stirred at about 100° C. for about 12 hours. The resulting mixture was quenched by addition of water (about 100 mL) and extracted with EtOAc (about 100 mL*3). The combined organic layer was washed with brine (about 100 mL*2), dried over anhydrous $Na_2SO_4$, filtered and concentrated under reduced pressure. The residue was purified by flash chromatography (ISCO®; about 12 g AgelaFlash® Silica Flash Column, petroleum ether/EtOAc with EtOAc from 0~30%, flow rate=30 mL/min, 254 nm) to afford methyl 5-(3-methoxy-3-oxo-propyl)sulfanylbenzothiophene-2-carboxylate (about 1 g). LCMS (ESI) $[M+H]^+$ m/z: calcd 311.0, found 311.0.

Step 3: Synthesis of methyl 5-sulfanylbenzothiophene-2-carboxylate

A mixture of methyl 5-(3-methoxy-3-oxo-propyl)sulfanylbenzothiophene-2-carboxylate (about 1 g, 3.22 mmol), sodium; methanolate (about 697 mg, 12.9 mmol) in MeOH (about 10 mL) was stirred at about 65° C. for about 1 hour. The mixture was basified with $Na_2CO_3$ to about pH=6. The resulting mixture was quenched by addition of water (about 100 mL) and extracted with EtOAc (about 100 mL*3). The combined organic layer was washed with brine (about 100 mL*2), dried over anhydrous $Na_2SO_4$, filtered and concentrated under reduced pressure. The residue was purified by column chromatography (silica, petroleum ether/EtOAc=0 to 30%, 254 nm) to afford methyl 5-sulfanylbenzothiophene-2-carboxylate (about 210 mg). $^1$H NMR (400 MHz, chloroform-d) δ ppm 7.88 (s, 1H), 7.75 (d, J=1.6 Hz, 1H), 7.66 (d, J=8.4 Hz, 1H), 7.27-7.32 (m, 1H), 3.88 (s, 3H), 3.51 (s, 1H); LCMS (ESI) $[M+H]^+$ m/z: calcd 225.0, found 225.0.

Step 4: Synthesis of methyl 5-methylsulfanylbenzothiophene-2-carboxylate

A mixture of methyl 5-sulfanylbenzothiophene-2-carboxylate (about 180 mg, 0.803 mmol), iodomethane (about 0.1 mL, 1.61 mmol), $K_2CO_3$ (about 333 mg, 2.41 mmol) in MeCN (about 3 mL) was stirred at about 60° C. for about 12 hours. The resulting mixture was quenched by addition of water (about 100 mL) and extracted with EtOAc (about 100 mL*3). The combined organic layer was washed with brine (about 100 mL*2), dried over anhydrous $Na_2SO_4$, filtered and concentrated under reduced pressure. The residue was purified by column chromatography (silica, petroleum ether/EtOAc=0 to 60%, 254 nm) to afford methyl 5-methylsulfanylbenzothiophene-2-carboxylate (about 130 mg). $^1$H NMR (400 MHz, chloroform-d) δ ppm 7.91 (s, 1H), 7.61-7.72 (m, 2H), 7.31-7.37 (m, 1H), 3.84-3.91 (m, 3H), 2.48 (s, 3H); LCMS (ESI) $[M+H]^+$ m/z: calcd 239.0, found 239.0.

Step 5: Synthesis of methyl 5-methylsulfinylbenzothiophene-2-carboxylate

To a mixture of methyl 5-methylsulfanylbenzothiophene-2-carboxylate (about 125 mg, 0.524 mmol) in DCM (about 3 mL) was added 3-chlorobenzenecarboperoxoic acid (about 136 mg, 0.788 mmol, 85 wt %) at about 0° C. The mixture was stirred at about 20° C. for about 1 hour. The resulting mixture was quenched by addition of water (about 100 mL) and extracted with EtOAc (about 100 mL*3). The combined organic layer was washed with brine (about 100 mL*2), dried over anhydrous $Na_2SO_4$, filtered and concentrated under reduced pressure. The residue was purified by column chromatography (silica, petroleum ether/EtOAc=0 to 60%, 254 nm) to afford methyl 5-methylsulfinylbenzothiophene-2-carboxylate (about 130 mg). LCMS (ESI) $[M+H]^+$ m/z: calcd 255.0, found 255.0.

Step 6: Synthesis of methyl 5-(N-tert-butoxycarbonyl-S-methyl-sulfonimidoyl)benzothiophene-2-carboxylate A mixture of methyl 5-methylsulfinylbenzothiophene-2-carboxylate (about 120 mg, 0.472 mmol), diacetoxyrhodium (about 10 mg, 0.0236 mmol), [acetoxy(phenyl)-iodanyl] acetate (about 228 mg, 0.708 mmol), oxomagnesium (about 95 mg, 2.36 mmol), tert-butyl carbamate (about 111 mg, 0.944 mmol) in DCM (about 3 mL) was stirred at about 40° C. for about 12 hours. The resulting mixture was quenched by addition of water (about 100 mL) and extracted with EtOAc (about 100 mL*3). The combined organic layer was washed with brine (about 100 mL*2), dried over anhydrous $Na_2SO_4$, filtered and concentrated under reduced pressure. The residue was purified by column chromatography (silica, petroleum ether/EtOAc=0 to 80%, 254 nm) to afford methyl 5-(N-tert-butoxycarbonyl-S-methyl-sulfonimidoyl)benzothiophene-2-carboxylate (about 100 mg). $^1$H NMR (400 MHz, chloroform-d) δ ppm 8.49 (d, J=1.6 Hz, 1H), 7.85-8.12 (m, 3H), 3.88-3.94 (m, 3H), 3.19-3.27 (m, 3H), 1.55 (s, 9H); LCMS (ESI) $[M+H]^+$ m/z: calcd 370.1, found 370.0.

Step 7: Synthesis of 5-(N-tert-butoxycarbonyl-S-methyl-sulfonimidoyl)benzothiophene-2-carboxylic acid A mixture of methyl 5-(N-tert-butoxycarbonyl-S-methyl-sulfonimidoyl)benzothiophene-2-carboxylate (about 90 mg, 0.244 mmol), lithium; hydroxide; hydrate (about 51 mg, 1.22 mmol) in MeOH (about 3 mL) and $H_2O$ (about 2 mL) was stirred at about 20° C. for about 1 hour. The resulting mixture was quenched by addition of water (about 100 mL) and extracted with EtOAc (about 100 mL*3). The mixture was acidified with 2N HCl to about pH=2-3 and extracted with EtOAc (about 10 mL*3). Then the combined organic layers were washed with brine (about 10 mL), dried over anhydrous $Na_2SO_4$, filtered and concentrated under reduced pressure to afford 5-(N-tert-butoxycarbonyl-S-methyl-sulfonimidoyl)benzothiophene-2-carboxylic acid (about 86 mg). LCMS (ESI) $[M+H]^+$ m/z: calcd 356.1, found 300.0 (t-Bu cleaved mass).

Step 8: Synthesis of tert-butyl N-[[2-[[2-(tert-butoxycarbonylamino)-5-(4-fluorophenyl)phenyl]carbamoyl]benzothiophen-5-yl]-methyl-oxo-sulfanylidene]carbamate A mixture of 5-(N-tert-butoxycarbonyl-S-methyl-sulfonimidoyl)benzothiophene-2-carboxylic acid (about 70 mg, 0.197 mmol), tert-butyl N-[2-amino-4-(4-fluorophenyl)phenyl]carbamate (about 65 mg, 0.217 mmol), 3-(ethyliminomethyleneamino)-N,N-dimethyl-propan-1-amine;hydrochloride (about 45 mg, 0.236 mmol) in pyridine (about 2 mL)

was stirred at about 50° C. for about 30 minutes. The mixture was concentrated under reduced pressure. The residue was purified by column chromatography (silica, petroleum ether/EtOAc=10:0 to 0:10, 254 nm) to afford tert-butyl N-[[2-[[2-(tert-butoxycarbonylamino)-5-(4-fluorophenyl)phenyl]carbamoyl]benzothiophen-5-yl]-methyl-oxo-sulfanylidene]carbamate (about 120 mg). ¹H NMR (400 MHz, chloroform-d) δ ppm 9.93 (brs, 1H), 8.43 (s, 1H), 7.85-8.09 (m, 4H), 7.45-7.53 (m, 2H), 7.25-7.35 (m, 1H), 7.07-7.17 (m, 1H), 6.95-7.05 (m, 2H), 6.72 (s, 1H), 3.24 (s, 3H), 1.52 (s, 9H), 1.33 (s, 9H); LCMS (ESI) [M+H]⁺ m/z: calcd 640.2, found 640.2.

Step 9: Synthesis of N-[[2-[[2-(tert-butoxycarbonylamino)-5-(4-fluorophenyl)phenyl]carbamoyl]benzothiophen-5-yl]-methyl-oxo-sulfanylidene]carbamate A mixture of tert-butyl N-[[2-[[2-(tert-butoxycarbonylamino)-5-(4-fluorophenyl)phenyl]carbamoyl]benzothiophen-5-yl]-methyl-oxo-sulfanylidene]carbamate (about 100 mg, 0.156 mmol) in TFA (about 1.5 mL) and DCM (about 5 mL) was stirred at about 25° C. for 1 hour. The mixture was concentrated. The residue was purified by preparative HPLC (Instrument: Gilson GX-281 Liquid Handler, Gilson 322 Pump, Gilson 156 UV Detector; Column: Durashell 75×40 mm×3 µm; Mobile phase A: H₂O with NH₄HCO₃ (v %); Mobile phase B: MeCN; Gradient: B from 40% to 70% in 7.8 min, hold 100% B for 2 min; Flow Rate: 30 mL/min; Column Temperature: about 30° C.; Wavelength: 220 nm, 254 nm) to afford N-[2-amino-5-(4-fluorophenyl)phenyl]-5-(methylsulfonimidoyl)benzothiophene-2-carboxamide (about 30 mg). ¹H NMR (400 MHz, DMSO-d6) δ ppm 10.16 (s, 1H), 8.42-8.59 (m, 2H), 8.29 (d, J=8.28 Hz, 1H), 7.98 (d, J=8.4 Hz, 1H), 7.57-7.61 (m, 2H), 7.50 (s, 1H), 7.34 (d, J=8.4 Hz, 1H), 7.19-7.24 (m, 2H), 6.88 (d, J=8.4 Hz, 1H), 5.21 (brs, 2H), 4.37 (s, 1H), 3.14 (s, 3H); 19F NMR (376 MHz, DMSO-d6) δ ppm−117.395; LCMS (ESI) [M+H]⁺ m/z: calcd 440.1, found 440.1; HPLC: 99.11%@254 nm, 99.83%@254 nm.

Example 5. Synthesis of N-[2-amino-5-(4-fluorophenyl)phenyl]-4-(3-pyridylsulfonimidoyl)benzamide (Compound 172)

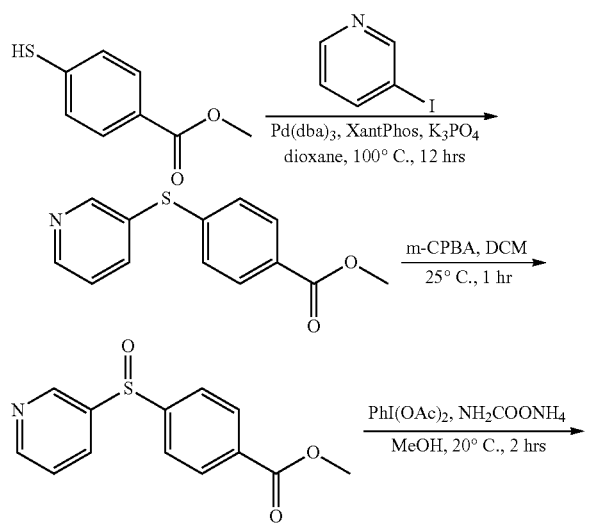

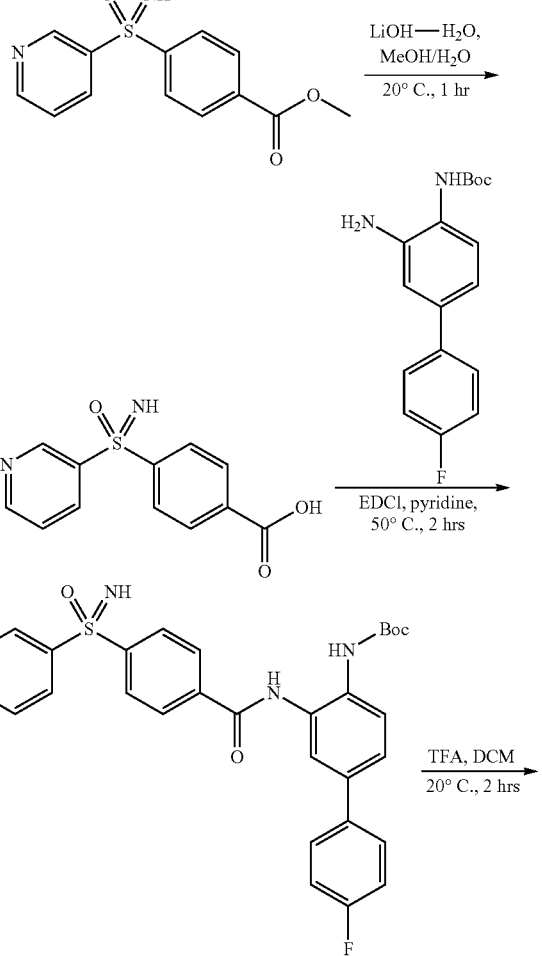

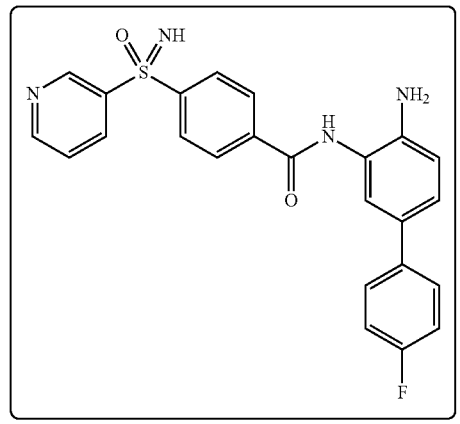

Step 1: Synthesis of methyl 4-(3-pyridylsulfanyl)benzoate

A mixture of 3-iodopyridine (about 1.1 g, 5.35 mmol), methyl 4-sulfanylbenzoate (about 300 mg, 1.78 mmol), K₃PO₄ (about 1.13 g, 5.34 mmol), (5-diphenylphosphanyl-9,9-dimethyl-xanthen-4-yl)-diphenyl-phosphane (about 210 mg, 0.363 mmol) and (1E,4E)-1,5-diphenylpenta-1,4-dien-3-one;palladium (about 170 mg, 0.186 mmol) in dioxane (about 3 mL) was stirred at about 100° C. for about 12 hours under N₂ atmosphere. The mixture was filtered. The filtrate was concentrated under reduced pressure. The residue was purified by flash chromatography (ISCO®; about 12 g AgelaFlash® Silica Flash Column, petroleum ether/EtOAc with EtOAc from 0~14%, flow rate=30 mL/min, 254 nm) to afford methyl 4-(3-pyridylsulfanyl)benzoate (about 400 mg). LCMS (ESI) [M+H]$^+$ m/z: calcd 246.1, found 246.1.

Step 2: Synthesis of methyl 4-(3-pyridylsulfinyl)benzoate

A mixture of methyl 4-(3-pyridylsulfanyl)benzoate (about 400 mg, 1.63 mmol) and 3-chlorobenzenecarboperoxoic acid (about 497 mg, 2.45 mmol, 85 wt %) in DCM (about 4 mL) was stirred at 25° C. for 1 hour. The mixture was quenched by saturated $Na_2SO_3$ solution (about 8 mL) and $NaHCO_3$ (about 10 mL). The combined organic layer was extracted with DCM (about 10 mL*3), washed with brine (about 10 mL), dried over anhydrous $Na_2SO_4$, filtered and concentrated to give methyl 4-(3-pyridylsulfinyl)benzoate (about 360 mg). LCMS (ESI) [M+H]$^+$ m/z: calcd 262.0, found 262.0.

Step 3: Synthesis of methyl 4-(3-pyridylsulfonimidoyl)benzoate

A mixture of methyl 4-(3-pyridylsulfinyl)benzoate (about 260 mg, 0.995 mmol), [acetoxy(phenyl)-iodanyl] acetate (about 805 mg, 2.50 mmol), ammonia; carbamic acid (about 163 mg, 2.09 mmol) and MeOH (about 10 mL) was stirred at about 20° C. for about 2 hours. The resulting mixture was quenched by addition of water (about 10 mL) and extracted with EtOAc (about 30 mL*3). The combined organic layer was washed with brine (about 30 mL), dried over anhydrous $Na_2SO_4$, filtered and concentrated under reduced pressure. The residue was purified by flash chromatography (ISCO®; about 20 g AgelaFlash® Silica Flash Column, petroleum ether/EtOAc with EtOAc from 0~70%, flow rate=30 mL/min, 254 nm) to afford methyl 4-(3-pyridylsulfonimidoyl)benzoate (310 mg). LCMS (ESI) [M+H]$^+$ m/z: calcd 277.1, found 277.0.

Step 4: Synthesis of 4-(3-pyridylsulfonimidoyl)benzoic acid

To a solution of methyl 4-(3-pyridylsulfonimidoyl)benzoate (about 310 mg, 1.12 mmol) in MeOH (about 1 mL) was added a solution of LiOH—$H_2O$ (about 474 mg, 11.3 mmol) in $H_2O$ (about 0.5 mL). The mixture was stirred at about 20° C. for about 1 hour. The mixture was concentrated and then the mixture was adjusted about pH=5 with 2N HCl aqueous solution. The resulting mixture was diluted with water (about 10 mL) and extracted with EtOAc (about 20 mL*3). The combined organic layer was washed with brine (about 20 mL), dried over anhydrous $Na_2SO_4$, filtered and concentrated to give 4-(3-pyridylsulfonimidoyl)benzoic acid (about 261 mg). LCMS (ESI) [M+H]$^+$ m/z: calcd 263.0, found 263.0.

Step 5: Synthesis of tert-butyl N-[4-(4-fluorophenyl)-2-[[4-(3-pyridylsulfonimidoyl)benzoyl]amino]phenyl]carbamate To the mixture of 4-(3-pyridylsulfonimidoyl)benzoic acid (about 198 mg, 0.755 mmol), tert-butyl N-[2-amino-4-(4-fluorophenyl)phenyl]carbamate (about 251 mg, 0.830 mmol) and 3-(ethyliminomethyleneamino)-N,N-dimethylpropan-1-amine;hydrochloride (about 174 mg, 0.908 mmol) in pyridine (about 4 mL) was stirred at about 50° C. for about 2 hours. The resulting mixture was quenched by addition of water (about 10 mL) and extracted with EtOAc (about 20 mL*3). The combined organic layer was washed with brine (about 20 mL), dried over anhydrous $Na_2SO_4$, filtered and concentrated under reduced pressure. The residue was purified by flash chromatography (ISCO®; about 20 g AgelaFlash® Silica Flash Column, petroleum ether/EtOAc with EtOAc from 0~65%, flow rate=30 mL/min, 254 nm) to afford tert-butyl N-[4-(4-fluorophenyl)-2-[[4-(3-pyridylsulfonimidoyl)benzoyl]amino]phenyl]carbamate (about 361 mg). LCMS (ESI) [M+H]$^+$ m/z: calcd 547.2, found 547.2.

Step 6: Synthesis of N-[2-amino-5-(4-fluorophenyl)phenyl]-4-(3-pyridylsulfonimidoyl)benzamide A mixture of tert-butyl N-[4-(4-fluorophenyl)-2-[[4-(3-pyridylsulfonimidoyl)benzoyl]amino]phenyl]carbamate (about 361 mg, 0.660 mmol) and TFA (about 10.8 mL, 0.140 mol) in DCM (about 30 mL) was stirred at about 20° C. for about 2 hours. The reaction mixture was concentrated under reduced pressure. The mixture was adjusted pH to about 8 with 25 wt % $NH_3$—$H_2O$. The mixture was purified by preparative HPLC (Instrument: Gilson GX-281 Liquid Handler, Gilson 322 Pump, Gilson 156 UV Detector; Column: 2_Phenomenex Gemini C18 75*40 mm*3 µm; Mobile phase A: water ($NH_4HCO_3$); Mobile phase B: MeCN; Gradient: B from 35% to 65% in 9.5 min, hold 100% B for 2 min; Flow Rate: 30 mL/min; Column Temperature: 30° C.; Wavelength: 220 nm, 254 nm) to afford N-[2-amino-5-(4-fluorophenyl)phenyl]-4-(3-pyridylsulfonimidoyl)benzamide (about 103.8 mg). $^1$H NMR (400 MHz, DMSO-d6) δ 9.87 (s, 1H), 9.15 (d, J=2.4 Hz, 1H), 8.79 (dd, J=4.8, 1.4 Hz, 1H), 8.31-8.44 (m, 1H), 8.15 (s, 4H), 7.53-7.65 (m, 3H), 7.47 (d, J=2.0 Hz, 1H), 7.25-7.32 (m, 1H), 7.15-7.23 (m, 2H), 6.85 (d, J=8.4 Hz, 1H), 5.51 (brs, 1H), 5.16 (s, 2H); $^{19}$F NMR (376 MHz, DMSO-d$_6$) δ ppm −117.479; LCMS (ESI) [M+H]$^+$ m/z: calcd 447.1, found 447.2; HPLC: 99.820%@220 nm, 99.800%@254 nm.

Example 6. Synthesis of N-(4-amino-4'-fluoro-[1,1'-biphenyl]-3-yl)-5-(S-methylsulfonimidoyl)benzofuran-2-carboxamide (Compound 171)

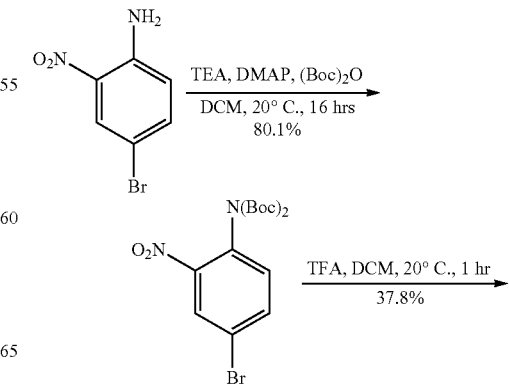

Scheme 1

237
-continued

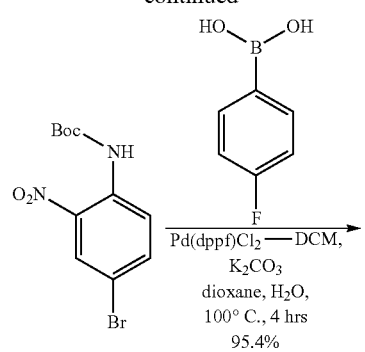

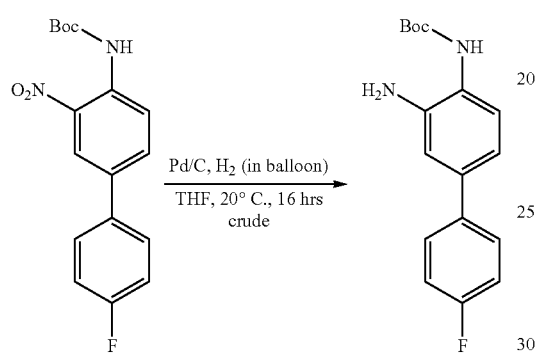

Scheme 2

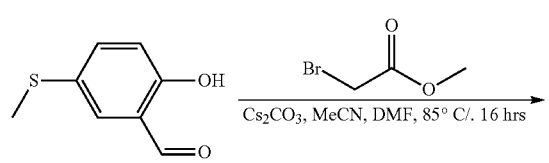

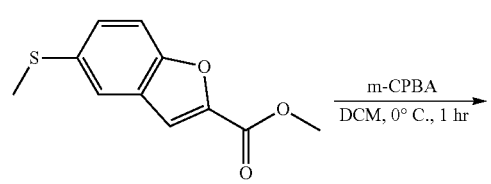

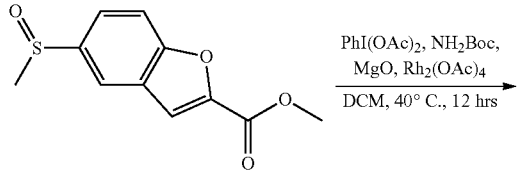

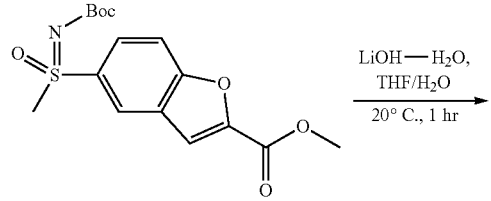

238
-continued

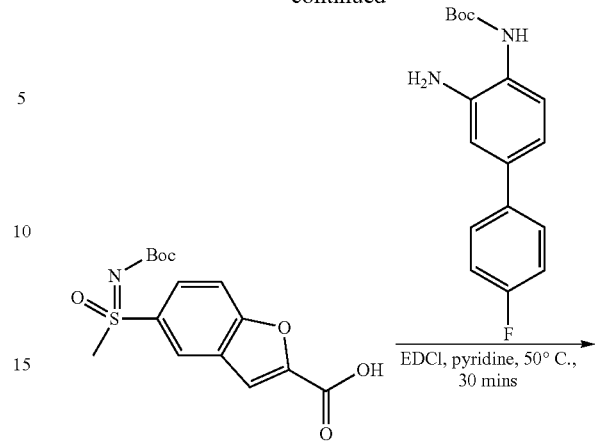

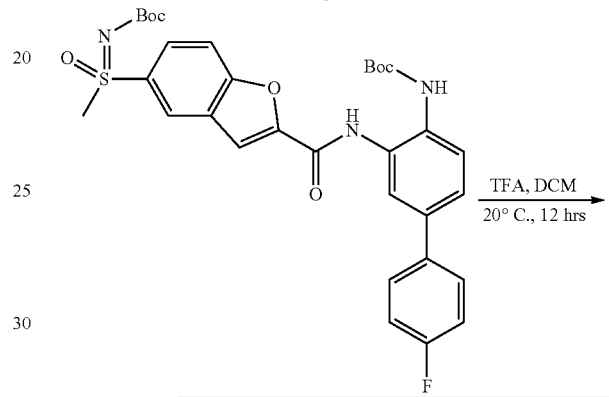

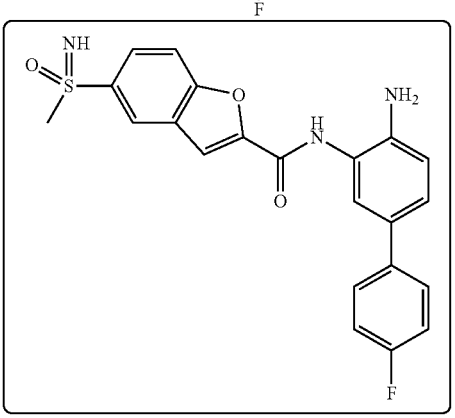

Step 1: Synthesis of tert-butyl N-(4-bromo-2-nitro-phenyl)-N-tert-butoxycarbonyl-carbamate To a solution of 4-bromo-2-nitro-aniline (about 5 g, 23.0 mmol), TEA (about 9.5 mL, 68.2 mmol), DMAP (about 1.40 g, 11.5 mmol) in DCM (about 50 mL) was added Boc$_2$O (about 13.5 mL, 58.75 mmol) at about 20° C. and the reaction mixture was stirred at about 20° C. for about 16 hours. The resulting mixture was quenched by addition of water (about 100 mL) and extracted with DCM (about 100 mL*3). The combined organic layer was washed with brine (about 50 mL), dried over anhydrous Na$_2$SO$_4$, filtered and concentrated under reduced pressure. The residue was purified by flash silica gel chromatography (ISCO®; about 220 g SepaFlash® Silica Flash Column, Petroleum ether/EtOAc with EtOAc from 0~10%, flow rate=100 mL/min, 254 nm) to afford tert-butyl N-(4-bromo-2-nitro-phenyl)-N-tert-butoxycarbonyl-carbamate (about 7.7 g). $^1$H NMR (400 MHz, chloroform-d) δ ppm 8.21 (d, J=2.26 Hz, 1H), 7.76 (dd, J=8.53, 2.26 Hz, 1H), 7.19-7.28 (m, 1H), 1.41 (s, 18H).

Step 2: Synthesis of tert-butyl (4-bromo-2-nitrophenyl)carbamate

To a solution of tert-butyl N-(4-bromo-2-nitro-phenyl)-N-tert-butoxycarbonyl-carbamate (about 7.4 g, 17.7 mmol) in DCM (about 75 mL) was added TFA (about 2.1 mL, 27.26 mmol) at about 20° C. and the mixture was stirred at about 20° C. for about 1 hour. The reaction mixture was quenched by addition water (about 100 mL) at about 20° C., extracted with DCM (about 100 mL*3). The combined organic layers were washed with brine (50 mL*3), dried over anhydrous Na$_2$SO$_4$, filtered and concentrated under reduced pressure. The residue was purified by flash chromatography (ISCO®; about 4 g SepaFlash® Silica Flash Column, Petroleum ether/EtOAc with EtOAc from 0~10%, flow rate=80 mL/min, 254 nm) to afford tert-butyl (4-bromo-2-nitrophenyl)carbamate (about 130 mg). $^1$H NMR (400 MHz, chloroform-d) δ ppm 9.61 (br s, 1H), 8.51 (d, J=9.13 Hz, 1H), 8.33 (d, J=2.38 Hz, 1H), 7.69 (dd, J=9.13, 2.13 Hz, 1H), 1.54 (s, 9H); LCMS (ESI) [M+H]$^+$ m/z: calcd 217.0, found 217.0 (Boc and t-Bu cleaved mass).

Step 3: Synthesis of tert-butyl (4'-fluoro-3-nitro-[1,1'-biphenyl]-4-yl)carbamate To a solution of tert-butyl N-(4-bromo-2-nitro-phenyl)carbamate (about 500 mg, 1.58 mmol), (4-fluorophenyl)boronic acid (about 265 mg, 1.89 mmol) and K$_2$CO$_3$ (about 545 mg, 3.94 mmol) in H$_2$O (about 1 mL) and dioxane (about 10 mL) was added Pd(dppf)Cl$_2$ (about 57 mg, 0.079 mmol) at about 20° C. and the mixture was stirred at about 100° C. for about 4 hours. The reaction mixture was quenched by addition water (about 30 mL) at about 20° C., extracted with EtOAc (about 30 mL*3). The combined organic layers were washed with brine (about 50 mL*3), dried over anhydrous Na$_2$SO$_4$, filtered and concentrated under reduced pressure. The residue was purified by flash silica gel chromatography (ISCO®; about 80 g SepaFlash® Silica Flash Column, Petroleum ether/EtOAc with EtOAc from 0~10%, flow rate=60 mL/min, 254 nm) to afford tert-butyl (4'-fluoro-3-nitro-[1,1'-biphenyl]-4-yl)carbamate (about 500 mg) was obtained. $^1$H NMR (400 MHz, chloroform-d) δ ppm 9.68 (s, 1H), 8.64 (d, J=8.88 Hz, 1H), 8.38 (d, J=2.25 Hz, 1H), 7.80 (dd, J=8.88, 2.25 Hz, 1H), 7.52-7.59 (m, 2H), 7.17 (t, J=8.63 Hz, 2H), 1.57 (s, 9H); LCMS (ESI) [M+H]$^+$ m/z: calcd 233.1, found 233.1 (Boc and t-Bu cleaved mass).

Step 4: Synthesis of tert-butyl (3-amino-4'-fluoro-[1,1'-biphenyl]-4-yl)carbamate To a solution of tert-butyl N-[4-(4-fluorophenyl)-2-nitrophenyl]carbamate (about 500 mg, 1.50 mmol) in THF (about 10 mL) was added Pd/C (about 100 mg, 0.823 mmol) (10 wt % Pd with 50 wt % water) at about 20° C. and the mixture was stirred at about 20° C. for about 16 hours under H$_2$ (in balloon). The reaction solution was filtered, and the filter cake containing Pd/C was washed with water. The reaction solution was filtered, and the filtrate was concentrated under reduced pressure to afford tert-butyl (3-amino-4'-fluoro-[1,1'-biphenyl]-4-yl)carbamate (about 497 mg). $^1$H NMR (400 MHz, chloroform-d) δ ppm 7.47-7.57 (m, 2H), 7.36 (br d, J=7.78 Hz, 1H), 7.08-7.17 (m, 2H), 6.93-7.05 (m, 2H), 6.25 (br s, 1H), 1.55 (s, 9H); LCMS (ESI) [M+H]$^+$ m/z: calcd 303.2, found 303.1.

Step 5: Synthesis of methyl 5-(methylthio)benzofuran-2-carboxylate

To a solution of 2-hydroxy-5-methylsulfanyl-benzaldehyde (about 500 mg, 2.97 mmol) and dicesium;carbonate (about 1.94 g, 5.94 mmol) in DMF (about 5 mL)/MeCN (about 5 mL) was added methyl 2-bromoacetate (about 0.33 mL, 3.57 mmol) at about 20° C. and the mixture was stirred at about 85° C. for about 16 hours. The reaction mixture was quenched by addition water (about 30 mL) at about 20° C., extracted with EtOAc (about 30 mL*3). The combined organic layers were washed with brine (about 30 mL*3), dried over anhydrous Na$_2$SO$_4$, filtered and concentrated under reduced pressure. The residue was purified by flash silica gel chromatography (ISCO®; about 20 g SepaFlash® Silica Flash Column, Petroleum ether/EtOAc with EtOAc from 0~10%, flow rate: 35 mL/min, 254 nm) to afford methyl 5-methylsulfanylbenzofuran-2-carboxylate (about 374 mg). LCMS (ESI) [M+H]$^+$ m/z: calcd 223.0, found 223.1.

Step 6: Synthesis of methyl 5-(methylsulfinyl)benzofuran-2-carboxylate

To a solution of methyl 5-methylsulfanylbenzofuran-2-carboxylate (about 300 mg, 1.35 mmol) in DCM (about 10 mL) was added m-CPBA (about 329 mg, 1.62 mmol, 85% purity) at about 0° C. and the mixture was stirred at about 0° C. for about 1 hour. The reaction mixture was added saturated sodium thiosulfate solution was used to quench. The reaction mixture was quenched by addition water (about 30 mL) at about 20° C., extracted with DCM (about 30 mL*3). The combined organic layers were washed with brine (about 20 mL*3), dried over anhydrous Na$_2$SO$_4$, filtered and concentrated under reduced pressure. The residue was purified by flash silica gel chromatography (ISCO®; about 20 g SepaFlash® Silica Flash Column, Petroleum ether/EtOAc with EtOAc from 50-100%, flow rate=35 mL/min, 254 nm) to afford methyl 5-methylsulfinylbenzofuran-2-carboxylate (about 181 mg). $^1$H NMR (400 MHz, chloroform-d) δ ppm 8.10 (d, J=1.13 Hz, 1H), 7.72-7.78 (m, 1H), 7.65-7.71 (m, 1H), 7.60 (s, 1H), 4.01 (s, 3H), 2.78 (s, 3H); LCMS (ESI) [M+H]$^+$ m/z: calcd 239.0, found 239.0.

Step 7: Synthesis of methyl 5-(N-(tert-butoxycarbonyl)-S-methylsulfonimidoyl)benzofuran-2-carboxylate To a solution of methyl 5-methylsulfinylbenzofuran-2-carboxylate (about 140 mg, 0.588 mmol), PhI(OAc)$_2$ (about 284 mg, 0.882 mmol), NH$_2$BOC (about 138 mg, 1.18 mmol), MgO (about 121 mg, 2.93 mmol) in DCM (about 10 mL) was added Rh$_2$(OA)$_4$ (about 26 mg, 0.059 mmol) at about 20° C. and the mixture was stirred at about 40° C. for about 12 hours. The reaction mixture was quenched by addition water (about 20 mL) at about 20° C., extracted with DCM (about 20 mL*3). The combined organic layers were washed with brine (about 15 mL*3), dried over anhydrous Na$_2$SO$_4$, filtered and concentrated under reduced pressure. The residue was purified by flash silica gel chromatography (ISCO®; about 12 g SepaFlash® Silica Flash Column, Petroleum ether/EtOAc with EtOAc from 30~50%, flow rate=50 mL/min, 254 nm) to afford methyl 5-(N-tert-butoxycarbonyl-S-methyl-sulfonimidoyl)benzofuran-2-carboxylate (about 182 mg). $^1$H NMR (400 MHz, chloroform-d) δ ppm 8.43 (d, J=1.63 Hz, 1H), 8.04 (dd, J=8.88, 2.00 Hz, 1H), 7.79 (d, J=8.88 Hz, 1H), 7.63 (d, J=0.88 Hz, 1H), 3.97-4.08 (m, 3H), 3.29-3.36 (m, 3H), 1.40 (s, 9H); LCMS (ESI) [M+H]$^+$ m/z: calcd 354.1, found 354.0.

Step 8: Synthesis of 5-(N-(tert-butoxycarbonyl)-S-methylsulfonimidoyl)benzofuran-2-carboxylic acid To a solution of methyl 5-(N-tert-butoxycarbonyl-S-methyl-sulfonimidoyl)benzofuran-2-carboxylate (about 200 mg, 0.566 mmol) in THF (about 5 mL)/H$_2$O (about 5 mL) was added LiOH—H$_2$O (about 238 mg, 5.67 mmol) at about 20° C. and the mixture was stirred at about 20° C. for about 1 hour. The mixture was concentrated under reduced pressure. The residue was diluted with H$_2$O (4 mL). The mixture was adjusted pH ~4 with 0.5 M HCl aqueous solution and extracted with EtOAc (about 50 mL*2). The combined organic layers was concentrated under reduced pressure. Compound 5-(N-tert-butoxycarbonyl-S-methyl-sulfonimidoyl)benzofuran-2-carboxylic acid (about 190 mg) was obtained. $^1$H NMR (400 MHz, chloroform-d) δ ppm 8.46 (d, J=1.76 Hz, 1H), 8.06 (dd, J=9.03, 2.01 Hz, 1H), 7.81 (d, J=8.78 Hz, 1H), 7.66 (s, 1H), 3.31 (s, 3H), 1.42 (s, 9H); LCMS (ESI) [M+Na]$^+$ m/z: calcd 340.1, found 340.0.

Step 9: Synthesis of tert-butyl (3-(5-(N-(tert-butoxycarbonyl)-S-methylsulfonimidoyl)benzofuran-2-carboxamido)-4'-fluoro-[1,1'-biphenyl]-4-yl)carbamate To a solution of 5-(N-tert-butoxycarbonyl-S-methyl-sulfonimidoyl)benzofuran-2-carboxylic acid (about 100 mg, 0.295 mmol) and tert-butyl N-[2-amino-4-(4-fluorophenyl)phenyl]carbamate (about 89 mg, 0.294 mmol) in pyridine (about 2 mL) was added EDCI (about 68 mg, 0.355 mmol) at about 20° C. and the mixture was stirred at about 50° C. for about 1 hour. The reaction mixture was quenched by addition water (about 20 mL) at about 20° C., extracted with EtOAc (about 20 mL*3). The combined organic layers were washed with brine (about 15 mL*3), dried over anhydrous Na$_2$SO$_4$, filtered and concentrated under reduced pressure. The residue was purified by flash silica gel chromatography (ISCO®; about 12 g SepaFlash® Silica Flash Column, Petroleum ether/EtOAc with EtOAc from 0~100%, flow rate: 30 mL/min, 254 nm) to afford tert-butyl (3-(5-(N-(tert-butoxycarbonyl)-S-methylsulfonimidoyl)benzofuran-2-carboxamido)-4'-fluoro-[1,1'-biphenyl]-4-yl)carbamate (about 180 mg). $^1$H NMR (400 MHz, chloroform-d) δ ppm 8.52 (s, 1H), 8.21 (s, 1H), 8.10-8.16 (m, 1H), 7.74-7.86 (m, 3H), 7.67 (br dd, J=8.63, 5.25 Hz, 3H), 7.50 (br d, J=9.01 Hz, 2H), 3.42 (s, 3H), 1.50 (s, 18H); LCMS (ESI) [M+Na]$^+$ m/z: calcd 646.2, found 646.2.

Step 10: Synthesis of N-(4-amino-4'-fluoro-[1,1'-biphenyl]-3-yl)-5-(S-methylsulfonimidoyl)benzofuran-2-carboxamide To a solution of tert-butyl N-[[2-[[2-(tert-butoxycarbonylamino)-5-(4-fluorophenyl)phenyl]carbamoyl]benzofuran-5-yl]-methyl-oxo-sulfanylidene]carbamate (about 180 mg, 0.289 mmol) in DCM (about 5 mL) was added TFA (about 329 mg, 2.89 mmol) at about 20° C. and the mixture was stirred at about 20° C. for 12 hours. The reaction mixture was adjusted pH ~8 with saturated Na$_2$CO$_3$ aqueous solution.

The reaction mixture was concentrated under reduced pressure. The residue was purified by preparative HPLC (Instrument: Gilson GX-281 Liquid Handler, Gilson 322 Pump, Gilson 156 UV Detector; Column: Durashell 75×40 mm×3 um; Mobile phase A: H$_2$O with 10 mm NH$_4$HCO$_3$ (v %); Mobile phase B: ACN; Gradient: B from 6% to 65% in 9.5 min, hold 100% B for 0 min; Flow Rate: 30 mL/min; Column Temperature: 30° C.; Wavelength: 220 nm, 254 nm) to afford N-(4-amino-4'-fluoro-[1,1'-biphenyl]-3-yl)-5-(S-methylsulfonimidoyl)benzofuran-2-carboxamide (about 32 mg). $^1$H NMR (400 MHz, chloroform-d) δ ppm 8.46 (d, J=1.63 Hz, 1H), 8.38 (s, 1H), 8.15 (dd, J=8.63, 1.88 Hz, 1H), 7.69-7.76 (m, 3H), 7.52 (dd, J=8.76, 5.38 Hz, 2H), 7.11 (t, J=8.69 Hz, 3H), 6.96 (d, J=8.25 Hz, 2H), 3.19 (s, 3H); $^{19}$F NMR (377 MHz, chloroform-d) δ ppm −116.38; LCMS (ESI) [M+H]$^+$ m/z: calcd 424.1, found 424.1; HPLC: 94.62%@220 nm, 94.66%@254 nm.

Example 7. Synthesis of N-[2-amino-5-(4-fluorophenyl)phenyl]-5-[(methylsulfonimidoyl)methyl]benzofuran-2-carboxamide (Compound 170)

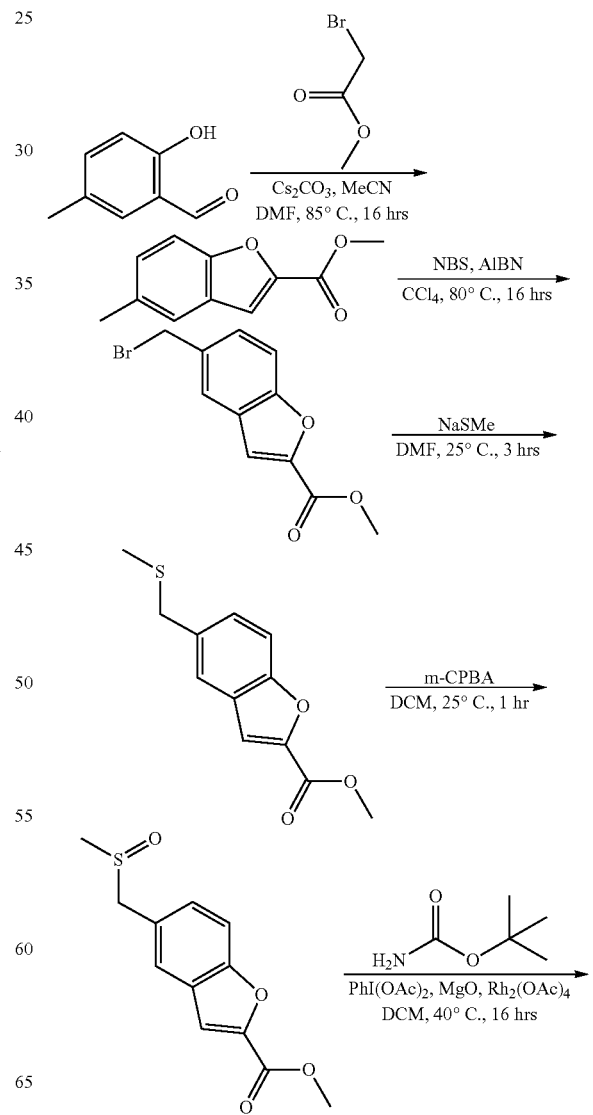

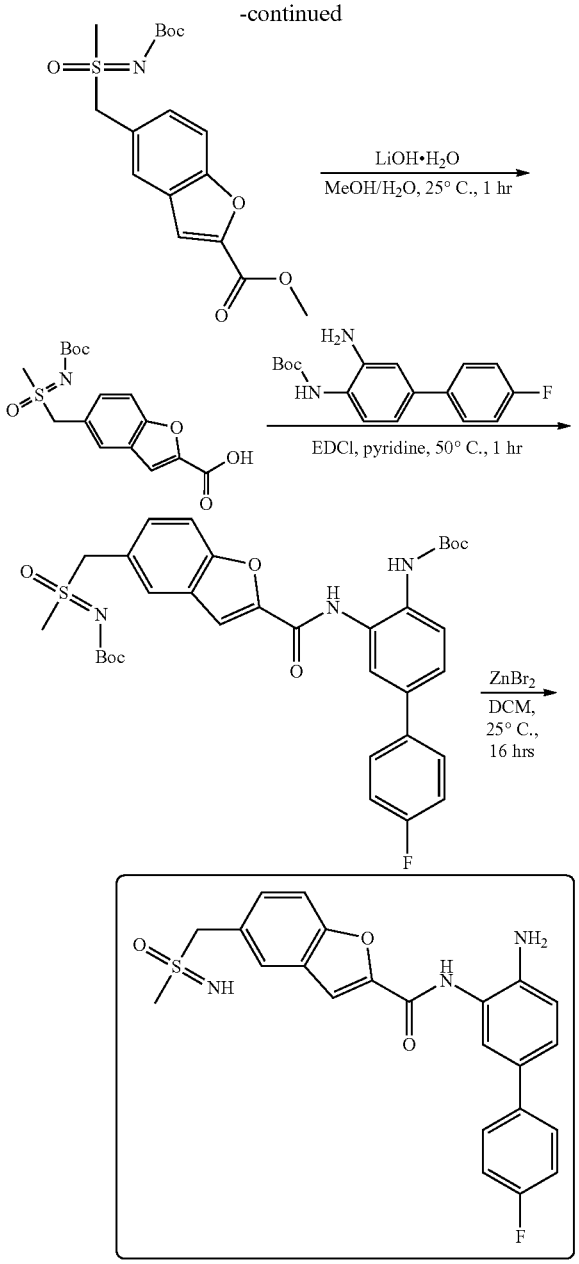

Step 1: Synthesis of methyl 5-methylbenzofuran-2-carboxylate

To a mixture of 2-hydroxy-5-methyl-benzaldehyde (about 9 g, 66.1 mmol) in CH₃CN (about 120 mL) and DMF (about 30 mL) was added Cs₂CO₃ (about 43.1 g, 132 mmol) and methyl 2-bromoacetate (about 12.1 g, 79.3 mmol) at about 20° C. under N₂. The mixture was heated to about 85° C. and stirred for about 16 hours. The mixture was filtered and concentrated in reduced pressure at about 50° C. The residue was poured into ice-water (about 30 mL) and stirred for about 10 mins. The aqueous phase was extracted with ethyl acetate (about 50 mL*2). The combined organic phase was washed with H₂O (about 50 mL*2), brine (about 50 mL), dried with anhydrous Na₂SO₄, filtered and concentrated in vacuum. The residue was purified by silica gel chromatography (column height: 250 mm, diameter: 100 mm, 100-200 mesh silica gel, Petroleum ether/Ethyl acetate=100/1, 20/1) to afford methyl 5-methylbenzofuran-2-carboxylate (about 6.2 g, 32.6 mmol). ¹H NMR (400 MHz, chloroform-d) δ ppm 7.38-7.61 (m, 3H), 7.13-7.35 (m, 1H), 3.86-4.07 (m, 3H), 2.34-2.56 (m, 3H).

Step 2: Synthesis of methyl 5-(bromomethyl)benzofuran-2-carboxylate

A mixture of methyl 5-methylbenzofuran-2-carboxylate (about 6.2 g, 32.6 mmol) in CCl₄ (about 120 mL) was added NBS (about 5.80 g, 32.6 mmol) and 2,2'-azobis(isobutyronitrile) (about 535 mg, 3.26 mmol). The reaction was heated to about 80° C. and stirred for about 16 hours. The mixture was filtered and the filtrate was evaporated. The residue was triturated with MeOH (about 20 mL) to afford methyl 5-(bromomethyl)benzofuran-2-carboxylate (about 7.0 g). ¹H NMR (400 MHz, chloroform-d) δ ppm 7.73 (d, J=1.5 Hz, 1H), 7.56-7.60 (m, 1H), 7.48-7.53 (m, 2H), 4.57-4.68 (m, 2H), 3.99-4.02 (m, 3H).

Step 3: Synthesis of methyl 5-(methylsulfanylmethyl)benzofuran-2-carboxylate To a mixture of methyl 5-(bromomethyl)benzofuran-2-carboxylate (about 7.0 g, 26.0 mmol) in DMF (about 100 mL) was cooled to 0° C., then added sodium methanethiolate (about 2.50 g, 35.6 mmol) in portions at about 0-5° C. under N₂. The mixture was stirred at about 25° C. for about 3 hours. The mixture was poured into ice-water (about 100 mL) and extracted with ethyl acetate (about 50 mL*2). The combined organic phase was washed with H₂O (about 50 mL*3), brine (about 50 mL), dried with anhydrous Na₂SO₄, filtered and concentrated in vacuum to afford methyl 5-(methylsulfanylmethyl)benzofuran-2-carboxylate (about 4.8 g). ¹H NMR (400 MHz, chloroform-d) δ ppm 7.60 (d, J=1.2 Hz, 1H), 7.52-7.57 (m, 1H), 7.48-7.52 (m, 1H), 7.43 (dd, J=8.6, 1.8 Hz, 1H), 3.91-4.04 (m, 4H), 3.68-3.85 (m, 2H), 1.93-2.06 (m, 3H).

Step 4: Synthesis of methyl 5-(methylsulfinylmethyl)benzofuran-2-carboxylate To a solution of methyl 5-(methylsulfanylmethyl)benzofuran-2-carboxylate (about 1 g, 4.23 mmol) in DCM (about 20 mL) was added 3-chlorobenzenecarboperoxoic acid (about 859 mg, 4.23 mmol, 85% purity). The mixture was stirred at about 25° C. for about 1 hour. The mixture was quenched by addition of saturated Na₂SO₃ aqueous solution (about 20 mL), saturated Na₂CO₃ aqueous solution (about 20 mL) and extracted with DCM (about 20 mL*2). The combined organic layer was dried over anhydrous Na₂SO₄, filtered and concentrated under reduced pressure to give a residue. The product was purified by silica gel chromatography (column height: 250 mm, diameter: 100 mm, 100-200 mesh silica gel, Petroleum ether/Ethyl acetate=10/1, 0/1) to afford methyl 5-(methylsulfinylmethyl)benzofuran-2-carboxylate (about 650 mg). ¹H NMR (400 MHz, chloroform-d) δ ppm 7.66 (s, 1H), 7.64-7.68 (m, 1H), 7.62 (d, J=8.5 Hz, 1H), 7.53 (s, 1H), 7.38 (dd, J=8.5, 1.5 Hz, 1H), 4.08 (d, J=2.0 Hz, 2H), 4.00 (s, 3H), 2.40-2.57 (m, 3H); LCMS (ESI) [M+H]⁺ m/z: calcd 253.1; found 253.1.

Step 5: Synthesis of methyl 5-[(N-tert-butoxycarbonyl-S-methyl-sulfonimidoyl)methyl]benzofuran-2-carboxylate To a solution of methyl 5-(methylsulfinylmethyl)benzofuran-2-carboxylate (about 650 mg, 2.58 mmol), tert-butyl carbamate (about 604 mg, 5.15 mmol) and MgO (about 532 mg, 12.9 mmol) in DCM (about 20 mL) was added rhodium (ii)acetatedimer (about 57 mg, 129 μmol), (diacetoxyiodo) benzene (about 1.24 g, 3.86 mmol) under $N_2$ protection. The reaction mixture was stirred at about 40° C. for about 16 hours. The mixture was filtered. The filtrate was concentrated under reduced pressure. The residue was purified by flash chromatography (Biotage®; about 12 g SepaFlash® Silica Flash Column, petroleum ether/EtOAc with EtOAc from 0~100%, 25 mL/min, 254 nm) to afford methyl 5-[(N-tert-butoxycarbonyl-S-methyl-sulfonimidoyl)methyl]benzofuran-2-carboxylate (about 680 mg). $^1$H NMR (400 MHz, chloroform-d) δ ppm 7.79 (s, 1H), 7.64 (d, J=8.53 Hz, 1H), 7.45-7.57 (m, 2H), 4.86 (s, 2H), 4.12 (qd, J=7.11, 1.76 Hz, 2H), 4.00 (d, J=1.76 Hz, 3H), 2.90-3.01 (m, 1H), 2.96 (s, 2H), 2.02 (br s, 1H), 1.53 (d, J=2.01 Hz, 9H), 1.26 (td, J=7.09, 1.63 Hz, 3H); LCMS (ESI) [M+H]$^+$ m/z: calcd 368.1; found 390.0.

Step 6: Synthesis of 5-[(N-tert-butoxycarbonyl-S-methyl-sulfonimidoyl)methyl]benzofuran-2-carboxylic acid To a solution of methyl 5-[(N-tert-butoxycarbonyl-S-methyl-sulfonimidoyl)methyl]benzofuran-2-carboxylate (about 200 mg, 544 μmol) in 3:1 MeOH/$H_2O$ (about 4 mL) was added LiOH·$H_2O$ (about 69.0 mg, 1.63 mmol). The mixture was stirred at about 25° C. for about 1 hour. The mixture was concentrated under reduced pressure to remove the organic solvent. The aqueous phase was adjusted to about pH=4 with 1M HCl aqueous solution. The mixture was filtered. The filter cake was dried under reduced pressure to afford 5-[(N-tert-butoxycarbonyl-S-methyl-sulfonimidoyl)methyl]benzofuran-2-carboxylic acid (about 115 mg). $^1$H NMR (400 MHz, DMSO-d6) δ ppm 7.85 (d, J=1.13 Hz, 1H), 7.77 (d, J=8.63 Hz, 1H), 7.72 (s, 1H), 7.54 (dd, J=8.69, 1.69 Hz, 1H), 4.96 (s, 2H), 3.09-3.15 (m, 3H), 1.39 (s, 8H), 1.08-1.60 (m, 1H).

Step 7: Synthesis of tert-butyl N-[[2-[[2-(tert-butoxycarbonylamino)-5-(4-fluorophenyl)phenyl]carbamoyl]benzofuran-5-yl]methyl-methyl-oxo-sulfanylidene]carbamate A mixture of 5-[(N-tert-butoxycarbonyl-S-methyl-sulfonimidoyl)methyl]benzofuran-2-carboxylic acid (about 115 mg, 325.5 μmol), tert-butyl N-[2-amino-4-(4-fluorophenyl)phenyl]carbamate (about 82 mg, 271 μmol) and EDCI (about 78 mg, 407 μmol) in pyridine (about 3 mL) was stirred at about 50° C. for about 1 hr. The mixture was concentrated under reduced pressure to give a product. The product was dissolved into DCM (about 6 mL), washed with $H_2O$ (about 10 mL). The combined organic layer was dried over anhydrous $Na_2SO_4$, filtered and concentrated under reduced pressure. The residue was purified by flash chromatography (Biotage®; about 4 g SepaFlash® Silica Flash Column, Petroleum ether/EtOAc with EtOAc from 0~100%, 15 mL/min, 254 nm) to afford tert-butyl N-[[2-[[2-(tert-butoxycarbonylamino)-5-(4-fluorophenyl)phenyl]carbamoyl]benzofuran-5-yl]methyl-methyl-oxo-sulfanylidene]carbamate (about 120 mg). $^1$H NMR (400 MHz, chloroform-d) δ ppm 9.49 (br s, 1H), 9.34-9.64 (m, 1H), 8.10 (d, J=1.75 Hz, 1H), 7.79 (d, J=1.13 Hz, 1H), 7.46-7.67 (m, 5H), 7.33-7.44 (m, 2H), 7.07-7.19 (m, 2H), 6.77 (br s, 1H), 4.88 (s, 2H), 2.98 (s, 3H), 1.61 (s, 9H), 1.54 (s, 9H); LCMS (ESI) [M+H]$^+$ m/z: calcd 638.2; found 660.1.

Step 8: Synthesis of N-[2-amino-5-(4-fluorophenyl)phenyl]-5-[(methylsulfonimidoyl)methyl]benzofuran-2-carboxamide To a solution of tert-butyl N-[[2-[[2-(tert-butoxycarbonylamino)-5-(4-fluorophenyl)phenyl]carbamoyl]benzofuran-5-yl]methyl-methyl-oxo-sulfanylidene]carbamate (about 120 mg, 188 μmol) in DCM (about 3 mL) was added $ZnBr_2$ (about 254 mg, 1.13 mmol) The mixture was stirred at about 25° C. for about 16 hours. The residue was purified by preparative HPLC (Instrument: ACSSH-CA; Column: YMC-Triart Prep C18 150*40 mm*7 um; Mobile phase A: $H_2O$ with 0.05% $NH_3$—$H_2O$ (v %); Mobile phase B: MeCN; Gradient: B from 22% to 62% in 9 min, hold 100% B for 2 min; Flow Rate: 60 mL/min; Column Temperature: 30° C.; Wavelength: 220 nm, 254 nm) to give N-[2-amino-5-(4-fluorophenyl)phenyl]-5-[(methylsulfonimidoyl)methyl]benzofuran-2-carboxamide (about 7.7 mg). $^1$H NMR (400 MHz, DMSO-d6) δ ppm 9.99 (s, 1H), 7.87 (s, 1H), 7.77 (s, 1H), 7.73 (d, J=8.53 Hz, 1H), 7.53-7.63 (m, 3H), 7.51 (d, J=1.76 Hz, 1H), 7.33 (dd, J=8.41, 2.13 Hz, 1H), 7.22 (t, J=8.78 Hz, 2H), 6.88 (d, J=8.28 Hz, 1H), 5.18 (s, 2H), 4.44-4.58 (m, 2H), 3.66 (s, 1H), 2.80 (s, 3H); LCMS (ESI) [M+H]$^+$ m/z: calcd 438.1; found 438.1; HPLC: 99.85%@220 nm, 99.26%@254 nm.

Example 8. Synthesis of N-[2-amino-5-(4-fluorophenyl)phenyl]-6-(N-ethyl-S-methyl-sulfonimidoyl)pyridine-3-carboxamide (Compound 169)

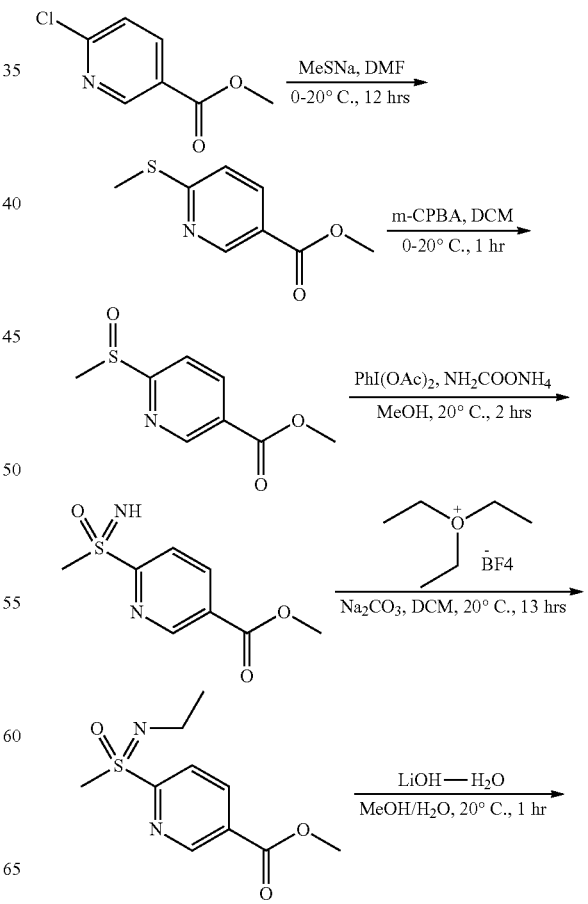

-continued

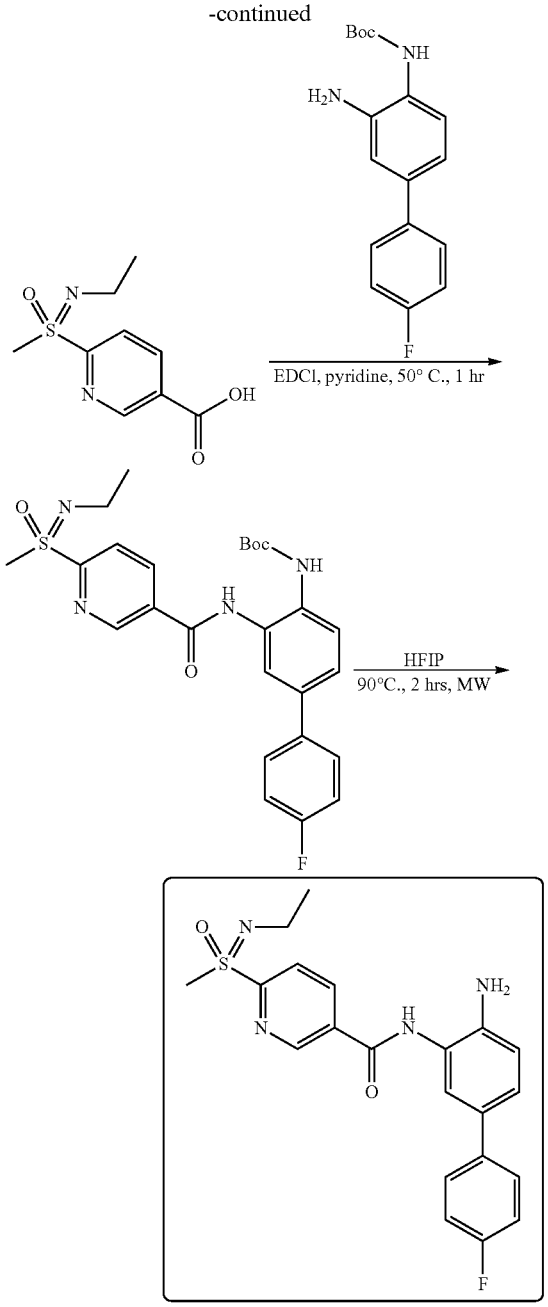

Step 1: Synthesis of methyl 6-methylsulfanylpyridine-3-carboxylate

To a solution of methyl 6-chloropyridine-3-carboxylate (about 5 g, 29.1 mmol) in DMF (about 50 mL) was added sodium;methanethiolate (about 2.26 g, 32.2 mmol) at about 0° C. After addition, the mixture was stirred at about 20° C. for about 12 hours. The reaction solution was added with water (about 50 mL) and extracted with EtOAc (about 80 mL*3). The combined organic layers were washed with brine (about 80 mL*3), dried over anhydrous $Na_2SO_4$ and filtered. The filtrate was concentrated under reduced pressure. The residue was purified by flash chromatography (ISCO®; about 25 g AgelaFlash® Silica Flash Column, petroleum ether/EtOAc with EtOAc from 0-10%, flow rate=50 mL/min, 254 nm) to afford methyl 6-methylsulfanylpyridine-3-carboxylate (about 4.1 g). $^1$H NMR (400 MHz, chloroform-d) δ ppm 8.99-9.05 (m, 1H), 8.01-8.07 (m, 1H), 7.22 (d, J=8.4 Hz, 1H), 3.92 (s, 3H), 2.60 (s, 3H).

Step 2: Synthesis of methyl 6-methylsulfinylpyridine-3-carboxylate

To a solution of methyl 6-methylsulfanylpyridine-3-carboxylate (about 4.1 g, 22.4 mmol) in DCM (about 50 mL) was added 3-chlorobenzenecarboperoxoic acid (about 5.1 g, 25.1 mmol, 85 wt %) at about 0° C. After addition, the mixture was stirred at about 20° C. for about 1 hour. The reaction mixture was quenched with saturated $NaHCO_3$ aqueous (about 50 mL) and extracted with DCM (about 60 mL*3). The combined organic layers were dried over $Na_2SO_4$ and filtered. The filtrate was concentrated under reduced pressure. The residue was purified by flash chromatography (ISCO®; about 25 g AgelaFlash® Silica Flash Column, petroleum ether/EtOAc with EtOAc from 0~80%, flow rate=40 mL/min, 254 nm) to afford methyl 6-methylsulfinylpyridine-3-carboxylate (about 3.7 g). $^1$H NMR (400 MHz, chloroform-d) δ ppm 9.19 (d, J=1.6 Hz, 1H), 8.53 (dd, J=8.0, 2.0 Hz, 1H), 8.12 (d, J=8.0 Hz, 1H), 3.98 (s, 3H), 2.88 (s, 3H).

Step 3: Synthesis of methyl 6-(methylsulfonimidoyl)pyridine-3-carboxylate

To a solution of methyl 6-methylsulfinylpyridine-3-carboxylate (about 3.2 g, 16.1 mmol) in MeOH (about 30 mL) were added [acetoxy(phenyl)-iodanyl] acetate (about 12.9 g, 40.2 mmol) and ammonia;carbamic acid (about 2.5 g, 32.0 mmol). The mixture was stirred at about 20° C. for about 2 hours. The resulting mixture was concentrated under reduced pressure. The residue was purified by flash chromatography (ISCO®; about 40 g AgelaFlash®Silica Flash Column, petroleumether/EtOAc with EtOAc from 0~80%, flow rate=45 mL/min, 254 nm) to afford methyl 6-(methylsulfonimidoyl)pyridine-3-carboxylate (about 2.49 g). $^1$H NMR (400 MHz, DMSO-$d_6$) δ ppm 9.10-9.20 (m, 1H), 8.57 (dd, J=8.0, 2.0 Hz, 1H), 8.19 (d, J=8.0 Hz, 1H), 4.67 (s, 1H), 3.93 (s, 3H), 3.21 (s, 3H); LCMS (ESI) [M+H]$^+$ m/z: calcd 215.0, found 214.9.

Step 4: Synthesis of methyl 6-(N-ethyl-S-methyl-sulfonimidoyl)pyridine-3-carboxylate To a mixture of methyl 6-(methylsulfonimidoyl)pyridine-3-carboxylate (about 2 g, 9.34 mmol) in DCM (about 20 mL) was added 1M triethyloxonium;tetrafluoroborate/DCM (about 28 mL, 28.0 mmol). The mixture was stirred at about 20° C. for about 1 hour. Then disodium;carbonate (about 5 g, 47.2 mmol) was added. The mixture was stirred at about 20° C. for about 12 hours. The reaction mixture was filtered and the filtrate was concentrated under reduced pressure. The residue was purified by flash chromatography (ISCO®; about 40 g SepaFlash® Silica Flash Column, petroleum ether/EtOAc with EtOAc from 30~50%, flow rate: 50 mL/min, 254 nm) to afford methyl 6-(N-ethyl-S-methyl-sulfonimidoyl)pyridine-3-carboxylate (about 400 mg). LCMS (ESI) [M+H]$^+$ m/z: calcd 243.1, found 242.9.

Step 5: Synthesis of 6-(N-ethyl-S-methyl-sulfonimidoyl)pyridine-3-carboxylic acid To a solution of methyl 6-(N-ethyl-S-methyl-sulfonimidoyl)pyridine-3-carboxylate (about 400 mg, 1.65 mmol) in MeOH (about 6 mL) and H₂O (about 3 mL) was added lithium;hydroxide;hydrate (about 700 mg, 16.7 mmol). The mixture was stirred at about 20° C. for about 1 hour. The reaction mixture was adjusted to about pH=4 with 1N HCl and extracted with DCM/IPA (v/v=3/1, 30 mL*3). The combined organic layers were dried over Na₂SO₄ and filtered. The filtrate was concentrated under reduced pressure to afford 6-(N-ethyl-S-methyl-sulfonimidoyl)pyridine-3-carboxylic acid (about 370 mg).

Step 6: Synthesis of tert-butyl N-[2-[[6-(N-ethyl-S-methyl-sulfonimidoyl)pyridine-3-carbonyl]amino]-4-(4-fluorophenyl)phenyl]carbamate To a solution of 6-(N-ethyl-S-methyl-sulfonimidoyl)pyridine-3-carboxylic acid (about 100 mg, 0.438 mmol) in pyridine (about 3 mL) was added tert-butyl N-[2-amino-4-(4-fluorophenyl)phenyl]carbamate (about 120 mg, 0.397 mmol) and 3-(ethyliminomethyleneamino)-N,N-dimethyl-propan-1-amine (about 100 mg, 0.644 mmol). The mixture was stirred at about 50° C. for about 1 hour. The reaction mixture was concentrated under reduced pressure. The residue was purified by flash chromatography (ISCO®; about 12 g SepaFlash® Silica Flash Column, petroleum ether/EtOAc with EtOAc from 0~70%, flow rate: 50 mL/min, 254 nm) to afford tert-butyl N-[2-[[6-(N-ethyl-S-methyl-sulfonimidoyl)pyridine-3-carbonyl]amino]-4-(4-fluorophenyl)phenyl]carbamate (about 140 mg). LCMS (ESI) [M+H]⁺ m/z: calcd 513.2, found 513.1.

Step 7: Synthesis of N-[2-amino-5-(4-fluorophenyl)phenyl]-6-(N-ethyl-S-methyl-sulfonimidoyl)pyridine-3-carboxamide A solution of tert-butyl N-[2-[[6-(N-ethyl-S-methyl-sulfonimidoyl)pyridine-3-carbonyl]amino]-4-(4-fluorophenyl)phenyl]carbamate (about 140 mg, 0.273 mmol) in HFIP (about 12 mL) was stirred at about 90° C. for about 2 hours in microwave. The reaction mixture was concentrated under reduced pressure. The residue was purified by preparative HPLC (Instrument: Gilson GX-281 Liquid Handler, Gilson 322 Pump, Gilson 156 UV Detector; Column: Phenomenex C18 80*40 mm*3 μm; Mobile phase A:water with 10 mmol NH₄HCO₃ (v %); Mobile phase B:MeCN; Gradient: B from 30% to 60% in 9.5 min, hold 100% B for 2 min; Flow Rate: 30 mL/min; Column Temperature: 30° C.; Wavelength: 220 nm, 254 nm) to afford N-[2-amino-5-(4-fluorophenyl)phenyl]-6-(N-ethyl-S-methyl-sulfonimidoyl)pyridine-3-carboxamide (about 51.4 mg). ¹H NMR (400 MHz, chloroform-d) δ ppm 9.27 (s, 1H), 8.48 (d, J=7.2 Hz, 1H), 8.18-8.31 (m, 2H), 7.66 (s, 1H), 7.44-7.55 (m, 2H), 7.34 (dd, J=8.4, 2.0 Hz, 1H), 7.10 (t, J=8.8 Hz, 2H), 6.96 (d, J=8.4 Hz, 1H), 3.30 (s, 3H), 3.06-3.15 (m, 1H), 2.83-2.92 (m, 1H), 1.15 (t, J=7.2 Hz, 3H); ¹⁹F NMR (376 MHz, chloroform-d) δ ppm −116.228; HPLC: 99.60%@220 nm, 99.87%@254 nm; LCMS (ESI) [M+H]⁺ m/z: calcd 413.1, found 413.0.

Example 9. Synthesis of N-[2-amino-5-(4-fluorophenyl)phenyl]-4-(4-pyridylsulfonimidoyl)benzamide (Compound 168)

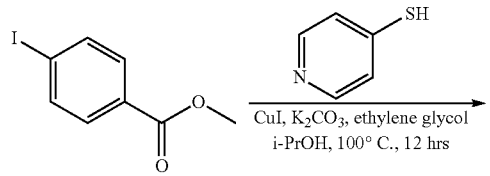

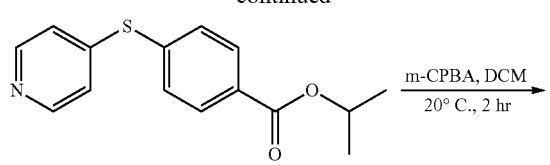

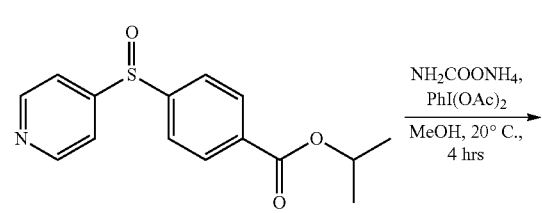

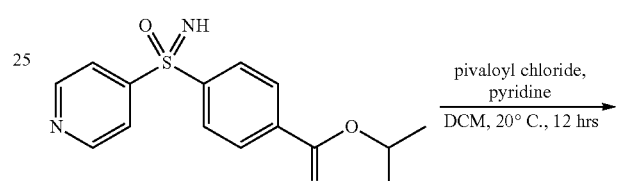

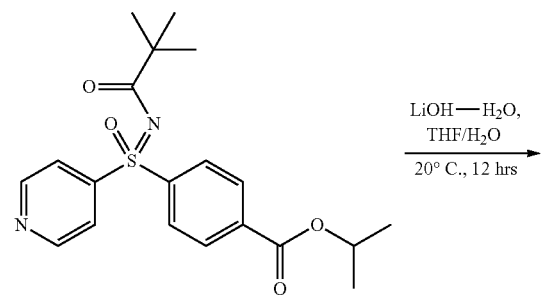

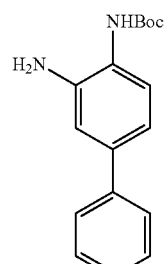

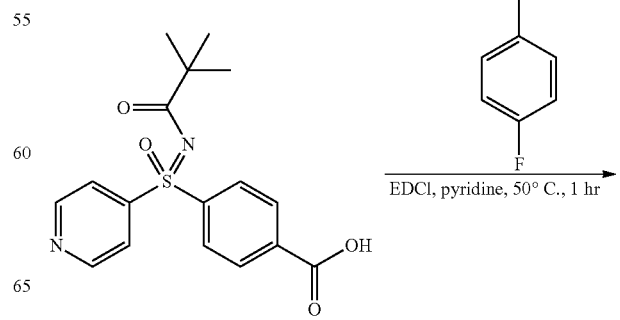

-continued

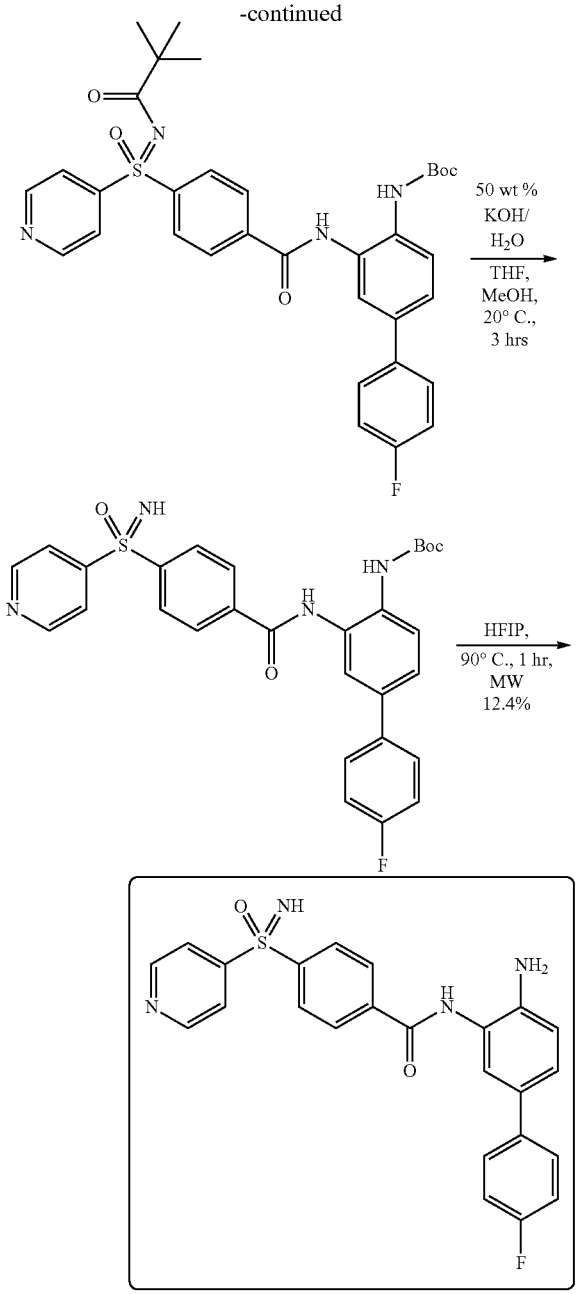

Step 1: Synthesis of isopropyl 4-(4-pyridylsulfanyl)benzoate

To a solution of methyl 4-iodobenzoate (about 2 g, 7.63 mmol) in IPA (about 30 mL) was added CuI (about 300 mg, 1.58 mmol), $K_2CO_3$ (about 2.11 g, 15.3 mmol), ethylene glycol (about 0.9 mL, 16.1 mmol) and pyridine-4-thiol (about 860 mg, 7.74 mmol). The mixture was stirred at about 100° C. for about 12 hours. The reaction mixture was filtered and the filtrate was concentrated under reduced pressure. The mixture was diluted with water (about 20 mL) and extracted with DCM/MeOH (v/v)=10/1 (about 30 mL*3). The combined organic layers were washed with brine (about 20 mL), dried over $Na_2SO_4$ and filtered. The filtrate was concentrated under reduced pressure. The residue was purified by flash chromatography (ISCO®; about 25 g SepaFlash® Silica Flash Column, petroleum ether/EtOAc with EtOAc from 0~10%, flow rate: 40 mL/min, 254 nm) to give isopropyl 4-(4-pyridylsulfanyl)benzoate (about 540 mg). LCMS (ESI) [M+H]$^+$ m/z: calcd 274.1, found 274.0.

Step 2: Synthesis of isopropyl 4-(4-pyridylsulfinyl)benzoate

To a solution of isopropyl 4-(4-pyridylsulfanyl)benzoate (about 540 mg, 1.98 mmol) in DCM (about 8 mL) was added 3-chlorobenzenecarboperoxoic acid (about 480 mg, 2.36 mmol, 85 wt %). The mixture was stirred at about 20° C. for about 2 hours. The mixture was quenched by addition of saturated $Na_2SO_3$ aqueous solution (about 10 mL) and saturated $NaHCO_3$ aqueous solution (about 10 mL). The resulting mixture was extracted with DCM (about 30 mL). The combined organic layer was dried over anhydrous $Na_2SO_4$, filtered and concentrated under reduced pressure. The residue was purified by flash chromatography (ISCO®; 25 g SepaFlash® Silica Flash Column, petroleum ether/EtOAc with EtOAc from 0~20%, flow rate: 30 mL/min, 254 nm) to give isopropyl 4-(4-pyridylsulfinyl)benzoate (about 360 mg). LCMS (ESI) [M+H]$^+$ m/z: calcd 290.1, found 290.0.

Step 3: Synthesis of isopropyl 4-(4-pyridylsulfonimidoyl)benzoate

To a solution of isopropyl 4-(4-pyridylsulfinyl)benzoate (about 350 mg, 1.21 mmol) in MeOH (about 5 mL) was added [acetoxy(phenyl)-iodanyl] acetate (about 975 mg, 3.03 mmol) and ammonia;carbamic acid (about 190 mg, 2.43 mmol). The mixture was stirred at about 20° C. for about 4 hours. The reaction mixture was concentrated under reduced pressure. The residue was purified by flash chromatography (ISCO®; about 25 g SepaFlash® Silica Flash Column, petroleum ether/EtOAc with EtOAc from 0~50%, flow rate: 30 mL/min, 254 nm) to give isopropyl 4-(4-pyridylsulfonimidoyl)benzoate (about 300 mg). LCMS (ESI) [M+H]$^+$ m/z: calcd 305.1, found 305.0.

Step 4: Synthesis of isopropyl 4-[N-(2,2-dimethylpropanoyl)-S-(4-pyridyl)sulfonimidoyl]benzoate To a solution of isopropyl 4-(4-pyridylsulfonimidoyl)benzoate (about 300 mg, 0.985 mmol) in DCM (about 5 mL) was added pyridine (about 0.12 mL, 1.48 mmol) and 2,2-dimethylpropanoyl chloride (about 0.14 mL, 1.14 mmol). The mixture was stirred at about 20° C. for about 12 hours. The mixture was quenched by addition $H_2O$ (about 10 mL). The resulting mixture was extracted with DCM (about 20 mL). The combined organic layer was dried over anhydrous $Na_2SO_4$, filtered and concentrated under reduced pressure. The residue was purified by flash chromatography (ISCO®; about 25 g SepaFlash® Silica Flash Column, petroleum ether/EtOAc with EtOAc from 0~35%, flow rate: 30 mL/min, 254 nm) to give isopropyl 4-[N-(2,2-dimethylpropanoyl)-S-(4-pyridyl)sulfonimidoyl]benzoate (about 200 mg). LCMS (ESI) [M+H]+m/z: calcd 389.1, found 389.1.

Step 5: Synthesis of 4-[N-(2,2-dimethylpropanoyl)-S-(4-pyridyl)sulfonimidoyl]benzoic acid To a solution of isopropyl 4-[N-(2,2-dimethylpropanoyl)-S-(4-pyridyl)sulfonimidoyl]benzoate (about 200 mg, 0.514 mmol) in THF (about 5 mL) and $H_2O$ (about 0.5 mL) was added lithium;hydroxide;hydrate (about 55 mg, 1.31 mmol) at about 0° C. The mixture was stirred at about 20° C. for about 12 hours. The mixture was concentrated under reduced pressure to remove the organic solvent. The aqueous phase was adjusted to about pH=4 with 1N HCl aqueous solution. The mixture was filtered. The filter cake was dried under reduced pressure to give 4-[N-(2,2-dimethylpropanoyl)-S-(4-pyridyl)sulfonimidoyl]benzoic acid (about 260 mg). LCMS (ESI) [2M+Na]$^+$ m/z: calcd 715.2, found 715.2.

Step 6: Synthesis of tert-butyl N-[2-[[4-[N-(2,2-dimethylpropanoyl)-S-(4-pyridyl)sulfonimidoyl]benzoyl]amino]-4-(4-fluorophenyl)phenyl]carbamate To a solution of 4-[N-(2,2-dimethylpropanoyl)-S-(4-pyridyl)sulfonimidoyl]benzoic acid (about 160 mg, 0.461 mmol) in pyridine (about 5 mL) was added EDCI (about 130 mg, 0.678 mmol) and tert-butyl N-[2-amino-4-(4-fluorophenyl)phenyl]carbamate (about 170 mg, 0.562 mmol). The mixture was stirred at about 50° C. for about 1 hour. The reaction mixture was concentrated under reduced pressure. The residue was purified by flash chromatography (ISCO®; about 25 g SepaFlash® Silica Flash Column, petroleum ether/EtOAc with EtOAc from 0~50%, flow rate: 30 mL/min, 254 nm) to give tert-butyl N-[2-[[4-[N-(2,2-dimethylpropanoyl)-S-(4-pyridyl)sulfonimidoyl]benzoyl]amino]-4-(4-fluorophenyl)phenyl]carbamate (about 75 mg). LCMS (ESI) [M+H]$^+$ m/z: calcd 631.2, found 631.3.

Step 7: Synthesis of tert-butyl N-[4-(4-fluorophenyl)-2-[[4-(4-pyridylsulfonimidoyl)benzoyl]amino]phenyl]carbamate To a solution of tert-butyl N-[2-[[4-[N-(2,2-dimethylpropanoyl)-S-(4-pyridyl)sulfonimidoyl]benzoyl]amino]-4-(4-fluorophenyl)phenyl]carbamate (about 120 mg, 0.190 mmol) in THF (about 5 mL) and MeOH (about 5 mL) was added 50 wt % KOH/H$_2$O (about 1.04 mL, 19.0 mmol). The mixture was stirred at about 20° C. for about 3 hours. The reaction mixture was dilute with water (about 10 mL) and extracted with EtOAc (about 20 mL*3). The combined organic layers were washed with brine (about 20 mL), dried over Na$_2$SO$_4$ and filtered. The filtrate was concentrated under reduced pressure to give tert-butyl N-[4-(4-fluorophenyl)-2-[[4-(4-pyridylsulfonimidoyl)benzoyl]amino]phenyl]carbamate (about 105 mg). LCMS (ESI) [M+H]$^+$ m/z: calcd 547.2, found 547.2.

Step 8: Synthesis of N-[2-amino-5-(4-fluorophenyl)phenyl]-4-(4-pyridylsulfonimidoyl)benzamide A solution of tert-butyl N-[4-(4-fluorophenyl)-2-[[4-(4-pyridylsulfonimidoyl)benzoyl]amino]phenyl]carbamate (about 100 mg, 0.182 mmol) in HFIP (about 12 mL) was taken up into a microwave tube. The sealed tube was heated at about 90° C. for about 1 hour in microwave. The reaction mixture was concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 μm; Mobile phase A: H$_2$O with 10 mmol NH$_4$HCO$_3$ (v %); Mobile phase B: ACN; Gradient: B from 33% to 63% in 9.5 min, hold 100% B for 2 min; Flow Rate: 30 mL/min; Column Temperature: 30° C.; Wavelength: 220 nm, 254 nm) to afford N-[2-amino-5-(4-fluorophenyl)phenyl]-4-(4-pyridylsulfonimidoyl)benzamide (about 10.1 mg). $^1$H NMR (400 MHz, methanol-d$_4$) δ ppm 8.78-8.83 (m, 2H), 8.21-8.26 (m, 2H), 8.16-8.20 (m, 2H), 8.00-8.04 (m, 2H), 7.55 (dd, J=8.8, 5.6 Hz, 2H), 7.45 (d, J=2.4 Hz, 1H), 7.34 (dd, J=8.4, 2.0 Hz, 1H), 7.10 (t, J=8.8 Hz, 2H), 6.96 (d, J=8.4 Hz, 1H); $^{19}$F NMR (376 MHz, methanol-d$_4$) δ ppm −119.360; LCMS [M+H]$^+$ m/z: calcd 447.1; found 447.1; HPLC: 98.81%@220 nm; 99.53%@254 nm.

Example 10. Synthesis of N-[2-amino-5-(4-fluorophenyl)phenyl]-5-[(methylsulfonimidoyl)methyl]benzothiophene-2-carboxamide (Compound 167)

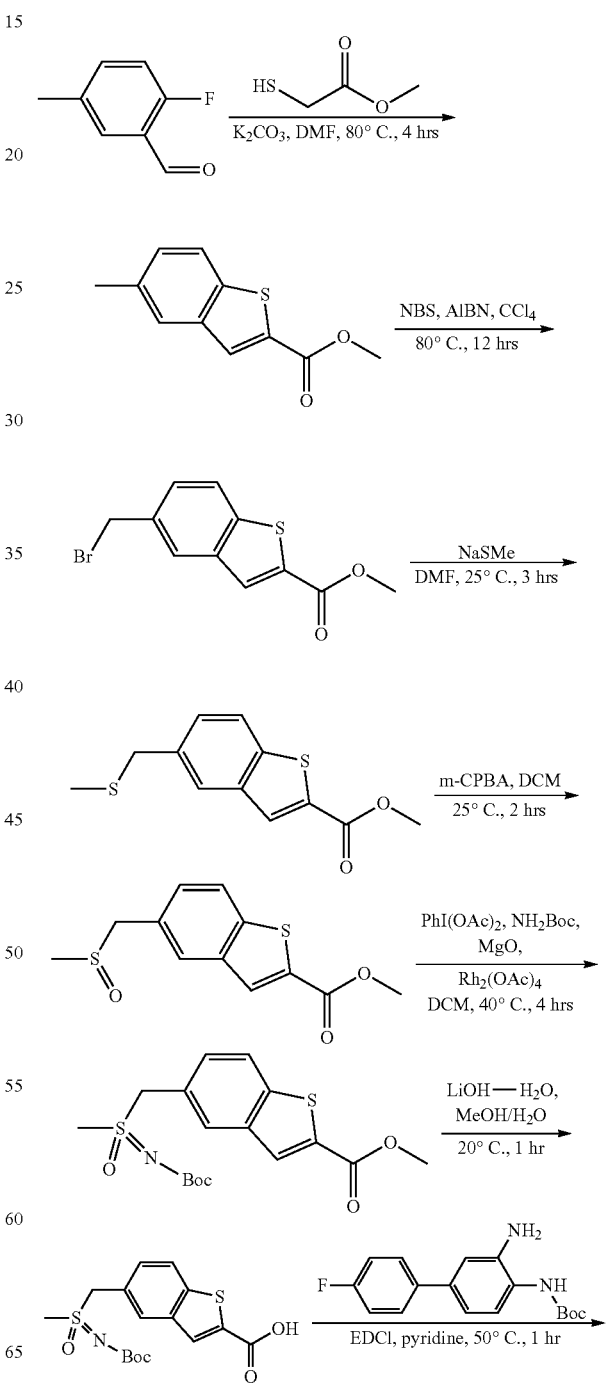

-continued

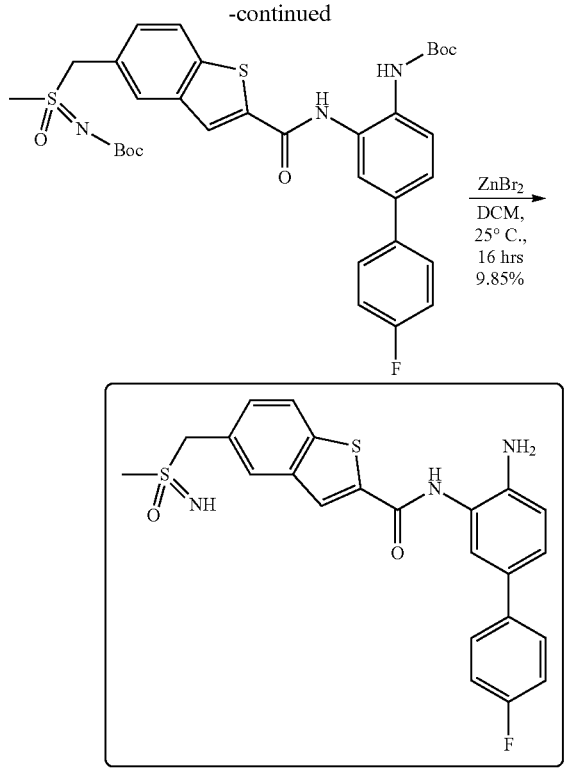

Step 1: Synthesis of methyl 5-methylbenzothiophene-2-carboxylate

To a mixture of 2-fluoro-5-methyl-benzaldehyde (about 2 g, 14.5 mmol) in DMF (about 30 mL) was added $K_2CO_3$ (about 4.00 g, 28.9 mmol) and 2-fluoro-5-methyl-benzaldehyde (about 2 g, 14.5 mmol). The resulting mixture was stirred at about 80° C. for about 4 hours under $N_2$. The resulting mixture was cooled to about 25° C. and filtered, the filtrate was poured into ice-water (about 40 mL) and extracted with EtOAc (about 20 mL*2). The combined organic layer was washed with $H_2O$ (about 20 mL*2), brine (about 20 mL), dried over anhydrous $Na_2SO_4$, filtered and concentrated under reduced pressure. The residue was triturated with PE (about 10 mL) to afford methyl 5-methylbenzothiophene-2-carboxylate (about 1.5 g). $^1H$ NMR (400 MHz, chloroform-d) δ ppm 8.00 (s, 1H), 7.75 (d, J=8.5 Hz, 1H), 7.68 (s, 1H), 7.30 (dd, J=8.4, 1.1 Hz, 1H), 3.87-4.00 (m, 3H), 2.48 (s, 3H).

Step 2: Synthesis of methyl 5-(bromomethyl)benzothiophene-2-carboxylate

A mixture of methyl 5-methylbenzothiophene-2-carboxylate (about 1.5 g, 7.27 mmol) in $CCl_4$ (about 30 mL) was added NBS (about 1.29 g, 7.27 mmol) and 2,2'-azobis(isobutyronitrile) (about 119 mg, 727 μmol) was heated to about 80° C. and stirred for about 12 hours under $N_2$. The resulting mixture was cooled to about 25° C. and filtered, the filtrate was concentrated. The mixture was filtered and the filtrate was evaporated. The residue was triturated with MeOH (about 5 mL) to afford methyl 5-(bromomethyl)benzothiophene-2-carboxylate (about 1.2 g). $^1H$ NMR (400 MHz, chloroform-d) δ ppm 8.04 (s, 1H), 7.90 (d, J=1.5 Hz, 1H), 7.86 (d, J=8.4 Hz, 1H), 7.51 (dd, J=8.4, 1.7 Hz, 1H), 4.64 (s, 2H), 3.96 (s, 3H).

Step 3: Synthesis of methyl 5-(methylsulfanylmethyl)benzothiophene-2-carboxylate A mixture of methyl 5-(bromomethyl)benzothiophene-2-carboxylate (about 600 mg, 2.10 mmol) in DMF (about 10 mL) was cooled to about 0° C., then added sodium methanethiolate (about 199 mg, 2.84 mmol) in portions at about 0-5° C. under $N_2$. The reaction mixture was stirred at about 25° C. for about 3 hour. The resulting mixture was quenched by addition of water (about 10 mL) and extracted with EtOAc (about 10 mL*3). The combined organic layer was washed with $H_2O$ (about 15 mL*2), brine (about 20 mL), dried over anhydrous $Na_2SO_4$, filtered and concentrated afford methyl 5-(methylsulfanylmethyl)benzothiophene-2-carboxylate (about 360 mg). $^1H$ NMR (400 MHz, chloroform-d) δ ppm 7.98-8.06 (m, 1H), 7.83 (d, J=8.5 Hz, 1H), 7.78 (s, 1H), 7.46 (dd, J=8.3, 1.5 Hz, 1H), 3.94-3.98 (m, 3H), 3.80 (s, 2H), 2.01 (s, 3H).

Step 4: Synthesis of methyl 5-(methylsulfinylmethyl)benzothiophene-2-carboxylate To a solution of methyl 5-(methylsulfanylmethyl)benzothiophene-2-carboxylate (about 710 mg, 2.81 mmol) in DCM (about 20 mL) was added 3-chlorobenzenecarboperoxoic acid (about 571 mg, 2.81 mmol, 85% purity). The mixture was stirred at about 25° C. for about 2 hours. The mixture was quenched by addition of saturated $Na_2SO_3$ aqueous solution (about 10 mL), saturated $Na_2CO_3$ aqueous solution (about 10 mL) and extracted with DCM (about 10 mL*2). The combined organic layer was dried over anhydrous $Na_2SO_4$, filtered and concentrated under reduced pressure. The residue was purified by flash chromatography (ISCO®; about 12 g SepaFlash® Silica Flash Column, petroleum ether/EtOAc with EtOAc from 0~100%, 20 mL/min, 254 nm) to give methyl 5-(methylsulfinylmethyl)benzothiophene-2-carboxylate (about 390 mg). $^1H$ NMR (400 MHz, chloroform-d) δ ppm 8.06 (s, 1H), 7.89 (d, J=8.4 Hz, 1H), 7.83 (s, 1H), 7.40 (dd, J=8.4, 1.6 Hz, 1H), 4.03-4.17 (m, 2H), 3.97 (s, 3H), 2.51 (s, 3H).

Step 5: Synthesis of methyl 5-[(N-tert-butoxycarbonyl-S-methyl-sulfonimidoyl)methyl]benzothiophene-2-carboxylate To a solution of methyl 5-(methylsulfinylmethyl) benzothiophene-2-carboxylate (390 mg, 1.45 mmol) tert-butyl carbamate (about 340 mg, 2.91 mmol) and MgO (about 300 mg, 7.27 mmol) in DCM (about 6 mL) was added rhodium (II)acetatedimer (about 32.1 mg, 72.7 μmol) under $N_2$ protection. The reaction mixture was stirred at about 40° C. for about 4 hours. The mixture was filtered. The filtrate was concentrated under reduced pressure. The residue was purified by flash chromatography (Biotage®; about 12 g SepaFlash® Silica Flash Column, petroleum ether/EtOAc with EtOAc from 0~50%, 20 mL/min, 254 nm) to afford methyl 5-[(N-tert-butoxycarbonyl-S-methyl-sulfonimidoyl)methyl] benzothiophene-2-carboxylate (about 400 mg). $^1H$ NMR (400 MHz, chloroform-d) δ ppm 8.05 (s, 1H), 7.89-7.99 (m, 2H), 7.50 (dd, J=8.4, 1.6 Hz, 1H), 4.77-4.99 (m, 2H), 3.97 (s, 3H), 2.97 (s, 3H), 1.43-1.60 (m, 11H); LCMS (ESI) [M+H]+ m/z: calcd 384.1; found 406.1.

Step 6: Synthesis of 5-[(N-tert-butoxycarbonyl-S-methyl-sulfonimidoyl)methyl] benzothiophene-2-carboxylic acid A solution of methyl 5-[(N-tert-butoxycarbonyl-S-methyl-sulfonimidoyl)methyl]benzothiophene-2-carboxylate (about 200 mg, 521 µmol) in MeOH/H₂O (about 6 mL, 2:1) was added LiOH·H₂O (about 54.7 mg, 1.30 mmol). The mixture was stirred at about 20° C. for about 1 hour. The mixture was concentrated under reduced pressure to remove the organic solvent. The aqueous phase was adjusted to about pH=4 with 2N HCl aqueous solution. The mixture was filtered. The filter cake was dried under reduced pressure to give 5-[(N-tert-butoxycarbonyl-S-methyl-sulfonimidoyl)methyl]benzothiophene-2-carboxylic acid (about 130 mg), which was directly used without further purification. ¹H NMR (400 MHz, DMSO-d6) δ ppm 12.46-14.23 (m, 1H), 8.08-8.16 (m, 2H), 8.04 (s, 1H), 7.54 (dd, J=8.5, 1.5 Hz, 1H), 4.54-5.18 (m, 2H), 3.14 (s, 3H), 1.39 (s, 9H); LCMS (ESI) [M+H]⁺ m/z: calcd 370.1; found 392.0.

Step 7: Synthesis of tert-butyl N-[[2-[[2-(tert-butoxycarbonylamino)-5-(4-fluorophenyl)phenyl]carbamoyl]benzothiophen-5-yl]methyl-methyl-oxo-sulfanylidene]carbamate A mixture of tert-butyl N-[2-amino-4-(4-fluorophenyl)phenyl]carbamate (about 90 mg, 298 µmol), 5-[(N-tert-butoxycarbonyl-S-methyl-sulfonimidoyl)methyl]benzothiophene-2-carboxylic acid (about 132 mg, 357 µmol) and EDCI (about 85.6 mg, 447 µmol) in pyridine (about 3 mL) was stirred at about 50° C. for about 1 hour. The mixture was concentrated under reduced pressure to give a product. The product was dissolved into DCM (about 6 mL), washed with H₂O (about 10 mL). The combined organic layer was dried over anhydrous Na₂SO₄, filtered and concentrated. The residue was purified by flash chromatography (Biotage®; about 12 g SepaFlash® Silica Flash Column, petroleum ether/EtOAc with EtOAc from 0~50%, 20 mL/min, 254 nm) to give tert-butyl N-[[2-[[2-(tert-butoxycarbonylamino)-5-(4-fluorophenyl)phenyl]carbamoyl]benzothiophen-5-yl]methyl-methyl-oxo-sulfanylidene]carbamate (about 150 mg). ¹H NMR (400 MHz, chloroform-d) δ ppm 9.73 (br s, 1H), 8.12 (d, J=1.6 Hz, 1H), 7.91-8.01 (m, 2H), 7.89 (s, 1H), 7.54 (dd, J=8.7, 5.3 Hz, 2H), 7.48 (d, J=8.5 Hz, 1H), 7.36 (dd, J=8.3, 2.0 Hz, 1H), 7.22-7.26 (m, 1H), 7.24 (d, J=8.3 Hz, 1H), 7.08 (t, J=8.7 Hz, 2H), 6.78 (s, 1H), 4.74-4.97 (m, 2H), 2.98 (s, 3H), 1.59 (s, 9H), 1.55 (s, 10H); LCMS (ESI) [M+H]⁺ m/z: calcd 654.2; found 676.3.

Step 8: Synthesis of N-[2-amino-5-(4-fluorophenyl)phenyl]-5-[(methylsulfonimidoyl)methyl]benzothiophene-2-carboxamide A mixture of tert-butyl N-[[2-[[2-(tert-butoxycarbonylamino)-5-(4-fluorophenyl)phenyl]carbamoyl]benzothiophen-5-yl]methyl-methyl-oxo-sulfanylidene]carbamate (about 50 mg, 76.5 µmol) in DCM (about 5 mL) was added ZnBr₂ (about 103 mg, 457 µmol). The reaction was stirred at about 20° C. for about 16 hours. The mixture was adjusted to about pH=8 with saturated Na₂CO₃ aqueous solution and extracted with a mixture of DCM/MeOH (10 mL*4, v/v=10:1). The combined organic layer was concentrated under reduced pressure to give a product. The residue was purified by preparative HPLC (Instrument: ACSSH-CA; Column: YMC-Triart Prep C18 150*40 mm*7 um; Mobile phase A: H₂O with 0.05% NH₃—H₂O (v %); Mobile phase B: MeCN; Gradient: B from 22% to 62% in 9 min, hold 100% B for 2 min; Flow Rate: 60 mL/min; Column Temperature: 30° C.; Wavelength: 220 nm, 254 nm) to give N-[2-amino-5-(4-fluorophenyl)phenyl]-5-[(methylsulfonimidoyl)methyl]benzothiophene-2-carboxamide (about 6.83 mg). ¹H NMR (400 MHz, DMSO-d₆) δ ppm 10.00 (s, 1H) 8.36 (s, 1H), 7.98-8.11 (m, 2H), 7.46-7.65 (m, 4H), 7.33 (dd, J=8.4, 2.1 Hz, 1H), 7.21 (t, J=8.9 Hz, 2H), 6.88 (d, J=8.4 Hz, 1H), 5.20 (s, 2H), 4.46-4.59 (m, 2H), 3.68 (s, 1H), 2.80 (s, 3H); LCMS (ESI) [M+H]⁺ m/z: calcd 454.2; found 454.1; HPLC: 97.20%@220 nm, 97.98%@254 nm.

Example 11. Synthesis of N-[2-amino-5-(4-fluorophenyl)phenyl]-4-(2-pyridylsulfonimidoyl)benzamide (Compound 166)

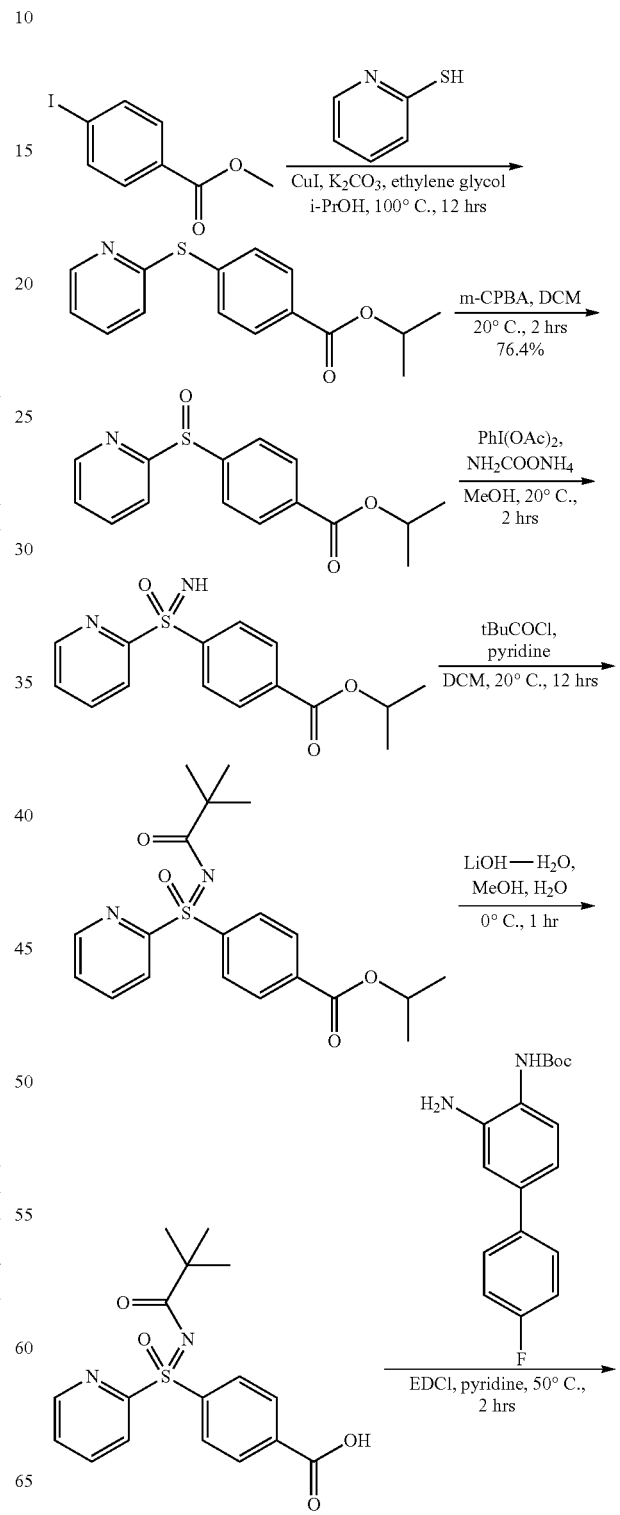

-continued

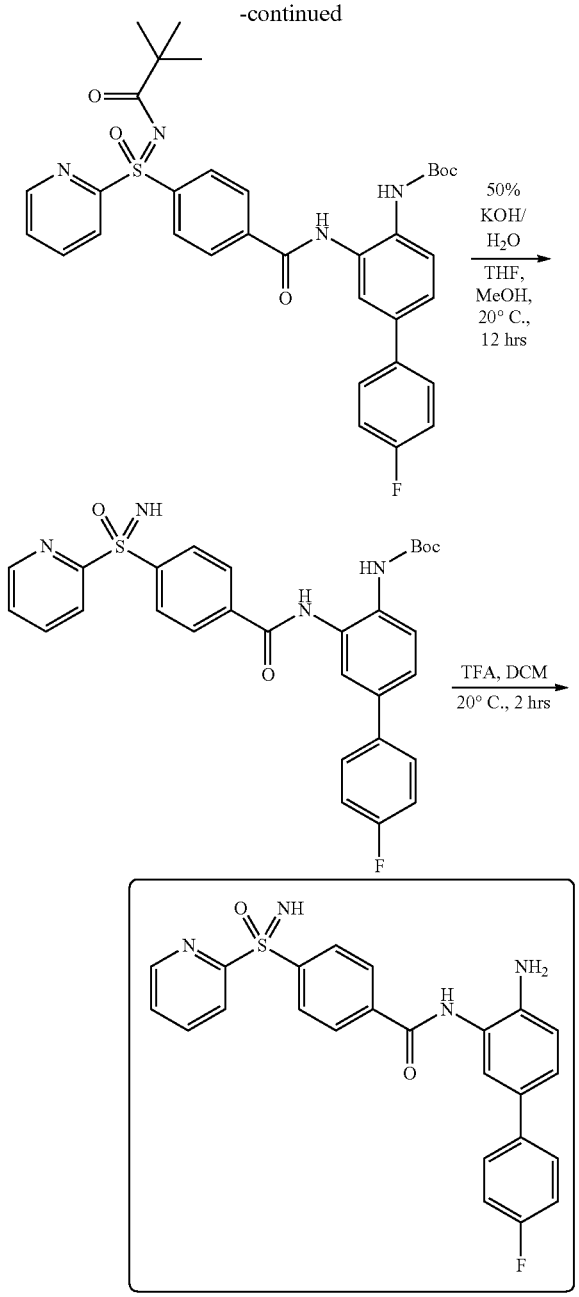

Step 1: Synthesis of isopropyl 4-(2-pyridylsulfanyl)benzoate

To a mixture of methyl 4-iodobenzoate (about 3 g, 11.5 mmol), pyridine-2-thiol (about 1.29 g, 11.6 mmol), CuI (about 450 mg, 2.36 mmol), $K_2CO_3$ (about 3.16 g, 22.9 mmol) and ethylene glycol (about 1.35 mL, 24.2 mmol) was added isopropyl alcohol (about 15 mL). The mixture was stirred at about 100° C. for about 12 hours under $N_2$ atmosphere. The mixture was filtered and the filtrate was concentrated under reduced pressure. The resulting mixture was extracted with $H_2O$ (about 50 mL) and EtOAc (about 50 mL*3). The combined organic layer was dried over anhydrous $Na_2SO_4$, filtered and concentrated under reduced pressure. The residue was purified by flash chromatography (ISCO®; about 20 g AgelaFlash® Silica Flash Column, petroleum ether/EtOAc with EtOAc from 0~18%, flow rate=30 mL/min, 254 nm) to afford isopropyl 4-(2-pyridylsulfanyl)benzoate (about 680 mg). $^1$H NMR (400 MHz, DMSO-$d_6$) δ ppm 8.41-8.65 (m, 1H), 7.93-8.24 (m, 2H), 7.51-7.92 (m, 3H), 7.00-7.50 (m, 2H) 5.30-5.15 (m, 1H), 1.13-1.57 (m, 6H); LCMS (ESI) [M+H]$^+$ m/z: calcd 274.1, found 274.0.

Step 2: Synthesis of isopropyl 4-(2-pyridylsulfinyl)benzoate

To a solution of isopropyl 4-(2-pyridylsulfanyl)benzoate (about 680 mg, 2.49 mmol) in DCM (about 8 mL) was added 3-chlorobenzenecarboperoxoic acid (about 464 mg, 2.29 mmol, 85 wt %). The mixture was stirred at about 20° C. for about 1 hour. To the mixture was added 3-chlorobenzenecarboperoxoic acid (about 464 mg, 2.29 mmol, 85 wt %). The mixture was stirred at about 20° C. for about 1 hour. The mixture was quenched by addition of saturated $Na_2SO_3$ aqueous solution (10 mL) and saturated $NaHCO_3$ aqueous solution (about 10 mL). The resulting mixture was extracted with EtOAc (about 20 mL*2). The combined organic layer was dried over anhydrous $Na_2SO_4$, filtered and concentrated under reduced pressure. The residue was purified by flash chromatography (Biotage®; 20 g AgelaFlash® Silica Flash Column, petroleum ether/EtOAc with EtOAc from 0~50%, flow rate=30 mL/min, 254 nm) to afford isopropyl 4-(2-pyridylsulfinyl)benzoate (about 550 mg). LCMS (ESI) [M+H]$^+$ m/z: calcd 290.1, found 290.1.

Step 3: Synthesis of isopropyl 4-(2-pyridylsulfonimidoyl)benzoate

To a solution of isopropyl 4-(2-pyridylsulfinyl)benzoate (about 550 mg, 1.90 mmol) in MeOH (5 mL) was added [bis(acetoxy)iodo]benzene (about 1.53 g, 4.75 mmol) and ammonia;carbamic acid (about 297 mg, 3.80 mmol). The mixture was stirred at about 20° C. for about 2 hours. The reaction mixture was concentrated under reduced pressure. The residue was purified by flash chromatography (Biotage®; about 12 g AgelaFlash® Silica Flash Column, petroleum ether/EtOAc with EtOAc from 0~50%, flow rate=30 mL/min, 254 nm) to afford isopropyl 4-(2-pyridylsulfonimidoyl)benzoate (about 200 mg). $^1$H NMR (400 MHz, DMSO-$d_6$) δ ppm 8.61 (brs, 1H), 8.24 (br dd, J=7.82, 3.94 Hz, 1H), 8.10 (br d, J=4.13 Hz, 5H), 7.53-7.66 (m, 1H), 5.08-5.22 (m, 2H), 1.24-1.36 (m, 6H); LCMS (ESI) [M+H]$^+$ m/z: calcd 305.1, found 305.0.

Step 4: Synthesis of isopropyl 4-[N-(2,2-dimethylpropanoyl)-S-(2-pyridyl)sulfonimidoyl]benzoate To a solution of isopropyl 4-(2-pyridylsulfonimidoyl) benzoate (about 200 mg, 0.657 mmol) in DCM (about 5 mL) was added pyridine (about 0.08 mL, 0.989 mmol) and 2,2-dimethylpropanoyl chloride (about 0.1 mL, 0.817 mmol). The mixture was stirred at about 20° C. for about 2 hours. The reaction mixture was concentrated under reduced pressure. The residue was purified by flash chromatography (Biotage®; about 12 g AgelaFlash® Silica Flash Column, petroleum ether/EtOAc with EtOAc from 0~30%, flow rate=30 mL/min, 254 nm) to afford isopropyl 4-[N-(2,2-dimethylpropanoyl)-S-(2-pyridyl)sulfonimidoyl]benzoate (about 190 mg). $^1$H NMR (400 MHz, DMSO-$d_6$) δ ppm 8.66 (dd, J=4.63, 0.88 Hz, 1H), 8.35 (d, J=7.88 Hz, 1H), 8.11-8.21 (m, 5H), 7.68 (ddd, J=7.60, 4.66, 0.88 Hz, 1H), 5.20-5.10 (m, 1H), 1.28-1.33 (m, 6H), 1.18 (s, 9H); LCMS (ESI) [M+H]+ m/z: calcd 389.1, found 389.1.

Step 5: Synthesis of 4-[N-(2,2-dimethylpropanoyl)-S-(2-pyridyl)sulfonimidoyl]benzoic acid To a solution of isopropyl 4-[N-(2,2-dimethylpropanoyl)-S-(2-pyridyl)sulfonimidoyl]benzoate (about 190 mg, 0.489 mmol) in MeOH (about 3 mL) and H₂O (about 1 mL) was added LiOH—H₂O (about 21 mg, 0.500 mmol). The mixture was stirred at about 0° C. for about 1 hour. The mixture was concentrated under reduced pressure. The mixture was adjusted to about pH=5 with 2N HCl aqueous solution (about 1 mL). The resulting mixture was extracted with EtOAc (about 20 mL*2). The combined organic layer was dried over anhydrous Na₂SO₄, filtered and concentrated under reduced pressure to give 4-[N-(2,2-dimethylpropanoyl)-S-(2-pyridyl)sulfonimidoyl]benzoic acid (about 130 mg). LCMS (ESI) [M+H]+ m/z: calcd 347.1, found 347.1.

Step 6: Synthesis of tert-butyl N-[2-[[4-[N-(2,2-dimethylpropanoyl)-S-(2-pyridyl)sulfonimidoyl]benzoyl]amino]-4-(4-fluorophenyl)phenyl]carbamate To a solution of 4-[N-(2,2-dimethylpropanoyl)-S-(2-pyridyl)sulfonimidoyl]benzoic acid (about 130 mg, 0.375 mmol) and tert-butyl N-[2-amino-4-(4-fluorophenyl)phenyl]carbamate (about 113 mg, 0.375 mmol) in pyridine (about 5 mL) was added 3-(ethyliminomethyleneamino)-N,N-dimethyl-propan-1-amine;hydrochloride (about 108 mg, 0.563 mmol). The mixture was stirred at about 50° C. for about 1 hour. To the mixture was added 3-(ethyliminomethyleneamino)-N,N-dimethyl-propan-1-amine;hydrochloride (about 108 mg, 0.563 mmol) and the mixture was stirred at about 50° C. for about 1 hour. The reaction mixture was concentrated under reduced pressure. The residue was purified by flash chromatography (Biotage®; about 12 g AgelaFlash® Silica Flash Column, petroleum ether/EtOAc with EtOAc from 0~40%, flow rate=30 mL/min, 254 nm) to afford tert-butyl N-[2-[[4-[N-(2,2-dimethylpropanoyl)-S-(2-pyridyl)sulfonimidoyl]benzoyl]amino]-4-(4-fluorophenyl)phenyl]carbamate (about 120 mg). ¹H NMR (400 MHz, DMSO-d₆) δ ppm 10.05 (brs, 1H), 8.77 (brs, 1H), 8.68 (s, 1H), 8.37 (d, J=8.03 Hz, 1H), 8.17 (s, 5H), 7.63-7.78 (m, 5H), 7.51 (d, J=8.28 Hz, 1H), 7.24-7.32 (m, 2H), 1.43 (d, J=2.76 Hz, 9H), 1.20 (d, J=3.01 Hz, 9H); ¹⁹F NMR (376 MHz, DMSO-d₆) δ ppm −115.627; LCMS (ESI) [M+H]+ m/z: calcd 631.2, found 631.2.

Step 7: Synthesis of tert-butyl N-[4-(4-fluorophenyl)-2-[[4-(2-pyridylsulfonimidoyl)benzoyl]amino]phenyl]carbamate To a solution of tert-butyl N-[2-[[4-[N-(2,2-dimethylpropanoyl)-S-(2-pyridyl)sulfonimidoyl]benzoyl]amino]-4-(4-fluorophenyl)phenyl]carbamate (about 120 mg, 0.190 mmol) in MeOH (about 2 mL) and THF (about 2 mL) was added 50% KOH aqueous solution (about 2.1 mL, 38.3 mmol). The mixture was stirred at about 20° C. for about 12 hours. The mixture was adjusted to about pH=5 with 2N HCl aqueous solution. The resulting mixture was extracted with EtOAc (about 20 mL*3). The combined organic layer was filtered and concentrated under reduced pressure to afford tert-butyl N-[4-(4-fluorophenyl)-2-[[4-(2-pyridylsulfonimidoyl)benzoyl]amino]phenyl]carbamate (about 90 mg). LCMS (ESI) [M+H]+ m/z: calcd 547.2, found 547.2.

Step 8: Synthesis of N-[2-amino-5-(4-fluorophenyl)phenyl]-4-(2-pyridylsulfonimidoyl)benzamide To a solution of tert-butyl N-[4-(4-fluorophenyl)-2-[[4-(2-pyridylsulfonimidoyl)benzoyl]amino]phenyl]carbamate (about 90 mg, 0.164 mmol) in DCM (about 5 mL) was added TFA (about 0.25 mL, 3.24 mmol). The mixture was stirred at about 20° C. for about 1 hour. The mixture was concentrated under reduced pressure, and adjusted to about pH=8 with 28% NH₃—H₂O solution. The mixture was purified by preparative HPLC (Instrument: Gilson GX-281 Liquid Handler, Gilson 322 Pump, Gilson 156 UV; Column: Durashell 75×40 mm×3 m; Mobile phase A: H₂O with 10 mmol NH₄HCO₃ (v %); Mobile phase B: ACN; Gradient: B from 40% to 70% in 7.8 min, hold 100% B for 2 min; Flow Rate=30 mL/min; Column Temperature: about 30° C.; Wavelength: 220 nm, 254 nm) to afford N-[2-amino-5-(4-fluorophenyl)phenyl]-4-(2-pyridylsulfonimidoyl)benzamide (about 25.1 mg). ¹H NMR (400 MHz, DMSO-d₆) δ ppm 9.88 (s, 1H), 8.63 (d, J=3.75 Hz, 1H), 8.26 (d, J=7.88 Hz, 1H), 8.02-8.17 (m, 5H), 7.53-7.65 (m, 3H), 7.47 (s, 1H), 7.31 (dd, J=8.19, 1.94 Hz, 1H), 7.21 (t, J=8.88 Hz, 2H), 6.84 (d, J=8.38 Hz, 1H), 5.28 (s, 1H), 5.15 (s, 2H); ¹⁹F NMR (376 MHz, DMSO-d₆) δ ppm−117.471; LCMS (ESI) [M+H]+ m/z: calcd 447.1, found 447.1; HPLC: 97.160%@220 nm; 97.430%@254 nm.

Example 12. Synthesis of 3-[4-amino-3-[[4-(methylsulfonimidoyl)benzoyl]amino]phenyl]benzamide (Compound 180)

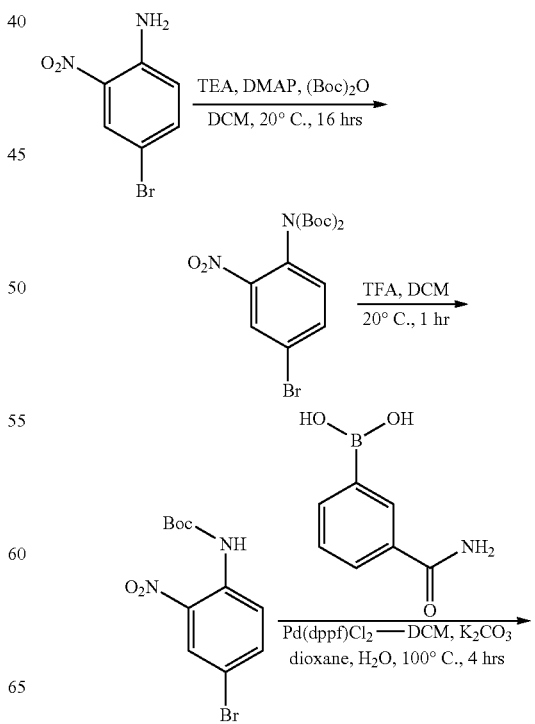

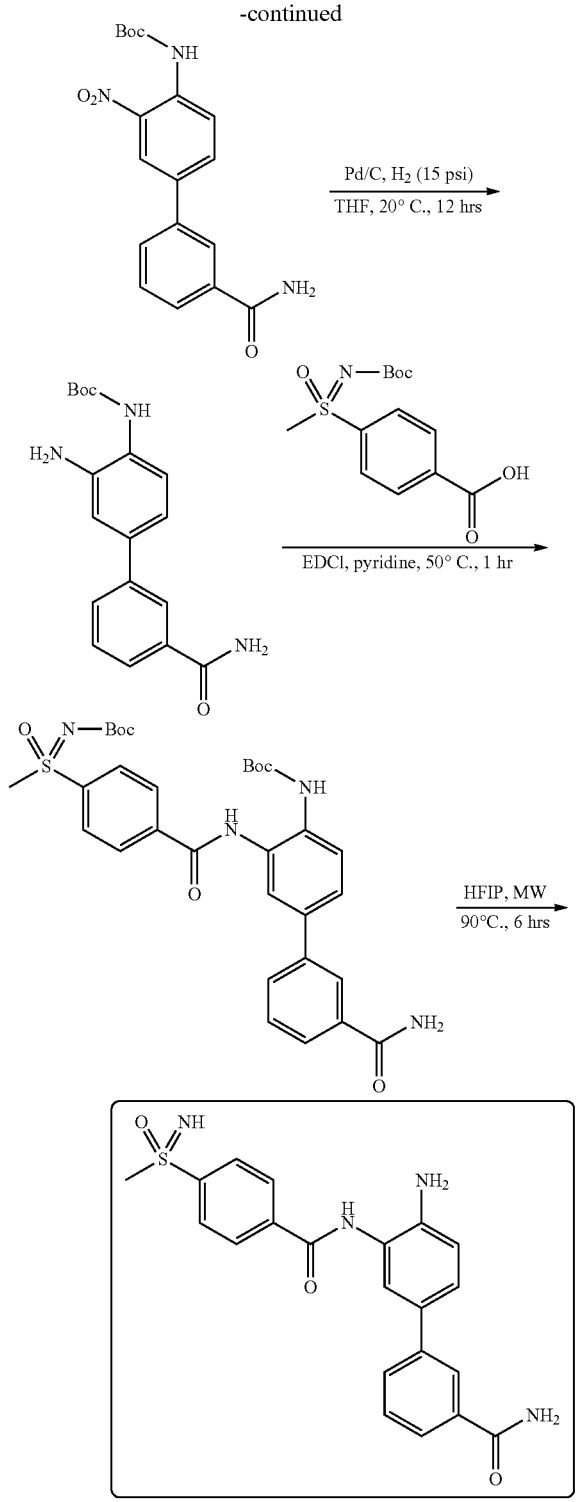

Step 1: Synthesis of tert-butyl N-(4-bromo-2-nitro-phenyl)-N-tert-butoxycarbonyl-carbamate To a solution of 4-bromo-2-nitro-aniline (about 5 g, 23.0 mmol), DMAP (about 1.4 g, 11.5 mmol), TEA (about 9.5 mL, 68.2 mmol), in DCM (about 50 mL) was added Boc₂O (about 13.5 mL, 58.8 mmol) at about 20° C. and the reaction mixture was stirred at about 20° C. for about 16 hours. The resulting mixture was quenched by addition of water (about 100 mL) and extracted with DCM (about 100 mL*3). The combined organic layers were washed with brine (about 50 mL*3), dried over anhydrous Na₂SO₄, filtered and concentrated under reduced pressure. The residue was purified by purified by flash chromatography (ISCO®; about 120 g AgelaFlash® Silica Flash Column, petroleum ether/EtOAc with EtOAc from 0~100%, flow rate=30 mL/min) to afford compound tert-butyl N-(4-bromo-2-nitro-phenyl)-N-tert-butoxycarbonyl-carbamate (about 8.81 g).

Step 2: Synthesis of tert-butyl (4-bromo-2-nitrophenyl)carbamate

A solution of tert-butyl N-(4-bromo-2-nitro-phenyl)-N-tert-butoxycarbonyl-carbamate (about 8.23 g, 19.7 mmol), TFA (about 3 mL, 39.4 mmol) in DCM (about 85 mL) was stirred at about 20° C. for about 1 hour. The resulting mixture was quenched by addition of water (about 100 mL) and extracted with DCM (about 100 mL*3). The combined organic layers were washed with brine (about 50 mL*3), dried over anhydrous Na₂SO₄, filtered and concentrated under reduced pressure. Compound tert-butyl N-(4-bromo-2-nitro-phenyl)carbamate (about 5.62 g) was obtained. $^1$H NMR (400 MHz, chloroform-d) δ ppm 9.61 (br s, 1H), 8.46-8.55 (m, 1H), 8.34 (d, J=2.51 Hz, 1H), 7.70 (dd, J=9.16, 2.38 Hz, 1H), 1.40-2.04 (m, 9H).

Step 3: Synthesis of tert-butyl N-[4-(3-carbamoylphenyl)-2-nitro-phenyl] carbamate To a solution of tert-butyl N-(4-bromo-2-nitro-phenyl) carbamate (about 500 mg, 1.58 mmol), (3-carbamoylphenyl) boronic acid (about 312 mg, 1.89 mmol), K₂CO₃ (about 545 mg, 3.94 mmol) in dioxane (about 6 mL)/H₂O (about 0.6 mL) was added Pd(dppf)Cl₂-DCM (about 128 mg, 0.158 mmol) at about 20° C. and the reaction mixture was stirred at about 100° C. for about 4 hours. The resulting mixture was quenched by addition of water (about 10 mL) and extracted with EtOAc (about 10 mL*3). The combined organic layers were washed with brine (about 10 mL*3), dried over anhydrous Na₂SO₄, filtered and concentrated under reduced pressure. The residue was purified by purified by flash chromatography (ISCO®; about 20 g AgelaFlash® Silica Flash Column, petroleum ether/EtOAc with EtOAc from 0~100%, flow rate=30 mL/min, 254 nm) to afford compound tert-butyl N-[4-(3-carbamoylphenyl)-2-nitrophenyl] carbamate (about 454 mg). $^1$H NMR (400 MHz, chloroform-d) δ ppm 9.68 (br s, 1H), 8.54-8.79 (m, 1H), 8.42 (d, J=2.26 Hz, 1H), 8.05 (br s, 1H), 7.84-7.91 (m, 1H), 7.76 (br s, 1H), 7.54 (br d, J=7.78 Hz, 1H), 1.53 (br s, 9H).

Step 4: Synthesis of tert-butyl N-[2-amino-4-(3-carbamoylphenyl)phenyl]carbamate To a solution of tert-butyl N-[4-(3-carbamoylphenyl)-2-nitro-phenyl]carbamate (about 0.455 g, 1.27 mmol) in THF (about 8 mL) was added Pd/C (about 100 mg, 10 wt % Pd/C with 50 wt % water) and the mixture was stirred at about 20° C. for about 12 hours under H₂ (about 15 psi). The resulting mixture was quenched by addition of water (10 mL) and extracted with EtOAc (about 10 mL*3). The combined organic layers were washed with brine (about 10 mL*3), dried over anhydrous Na₂SO₄, filtered and concentrated under reduced pressure. Compound tert-butyl N-[2-amino-4-(3-carbamoylphenyl)phenyl]carbamate (about 449 mg) was obtained. $^1$H NMR (400 MHz, chloroform-d) δ ppm 7.98 (br s, 1H), 7.70 (br dd, J=18.82, 6.82 Hz, 2H), 7.39-7.53 (m, 2H), 6.99-7.11 (m, 2H), 1.53 (s, 9H); LCMS (ESI) [M+H]⁺ m/z: calcd 328.2, found 328.1.

Step 5: Synthesis of tert-butyl N-[[4-[[2-(tert-butoxycarbonylamino)-5-(3-carbamoylphenyl)phenyl]carbamoyl]phenyl]-methyl-oxo-sulfanylidene]carbamate A solution of tert-butyl N-[2-amino-4-(3-carbamoylphenyl)phenyl]carbamate (about 100 mg, 0.305 mmol), 3-(ethyliminomethyleneamino)-N,N-dimethyl-propan-1-amine; hydrochloride (about 70 mg, 0.366 mmol) in pyridine (about 5 mL) was stirred at about 50° C. for about 1 hour. The resulting mixture was quenched by addition of water (about 10 mL) and extracted with EtOAc (about 10 mL*3). The combined organic layers were washed with brine (about 10 mL*3), dried over anhydrous Na₂SO₄, filtered and concentrated under reduced pressure. The residue was purified by purified by flash chromatography (ISCO®; about 12 g AgelaFlash® Silica Flash Column, petroleum ether/EtOAc with EtOAc from 0~100%, flow rate=30 mL/min) to afford compound tert-butyl N-[[4-[[2-(tert-butoxycarbonylamino)-5-(3-carbamoylphenyl)phenyl]carbamoyl]phenyl]-methyl-oxo-sulfanylidene]carbamate (about 174 mg). ¹H NMR (400 MHz, chloroform-d) δ ppm 9.25-10.50 (m, 1H), 8.13-8.31 (m, 3H), 8.10 (s, 3H), 7.80 (br d, J=7.53 Hz, 2H), 7.52 (s, 1H), 7.45 (s, 1H), 7.11-7.17 (m, 1H), 6.93-7.08 (m, 1H), 6.81-6.92 (m, 1H), 4.68-4.89 (m, 1H), 3.28 (s, 3H), 1.55 (s, 9H), 1.41 (s, 9H); LCMS (ESI) [M+H]⁺ m/z: calcd 609.2, found 609.2.

Step 6: Synthesis of 3-[4-amino-3-[[4-(methylsulfonimidoyl)benzoyl]amino]phenyl]benzamide A solution of tert-butyl N-[[4-[[2-(tert-butoxycarbonylamino)-5-(3-carbamoylphenyl)phenyl]carbamoyl]phenyl]-methyl-oxo-sulfanylidene]carbamate (about 250 mg, 0.410 mmol) in HFIP (about 10 mL) was heated at 90° C. for 6 hours in microwave. The reaction mixture was concentrated under reduced pressure. The residue was purified by preparative HPLC (Instrument: Gilson GX-281 Liquid Handler, Gilson 322 Pump, Gilson 156 UV Detector; Column: Durashell 150×25 mm×5 μm; Mobile phase A: H₂O with 0.05% NH₃—H₂O (v %); Mobile phase B: MeCN; Gradient: B from 39% to 69% in 10 min, hold 100% B for 2.5 min; Flow Rate: 25 mL/min; Column Temperature: 30° C.; Wavelength: 254 nm) to afford 3-[4-amino-3-[[4-(methylsulfonimidoyl)benzoyl]amino]phenyl]benzamide (about 71.8 mg). ¹H NMR (400 MHz, DMSO-d₆) δ ppm 9.97 (s, 1H), 8.20 (d, J=8.38 Hz, 2H), 8.08 (s, 3H), 7.73 (s, 2H), 7.61 (d, J=1.88 Hz, 1H), 7.29-7.55 (m, 3H), 6.90 (d, J=8.38 Hz, 1H), 5.22 (s, 2H), 4.41 (s, 1H), 3.13 (s, 3H); LCMS (ESI) [M+H]⁺ m/z: calcd 409.1, found 409.2; HPLC: 90.90@215 nm, 94.03%@254 nm.

Example 13. Synthesis of N-[2-amino-5-(4-fluorophenyl)phenyl]-6-(cyclopropylsulfonimidoyl)pyridine-3-carboxamide (Compound 179)

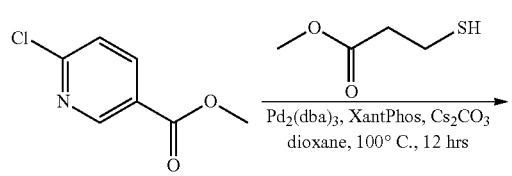

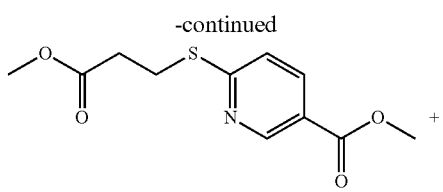

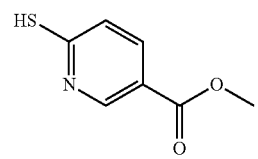

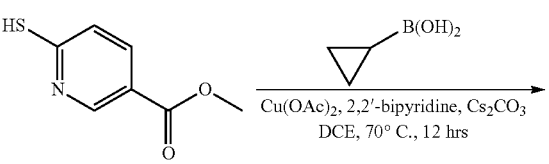

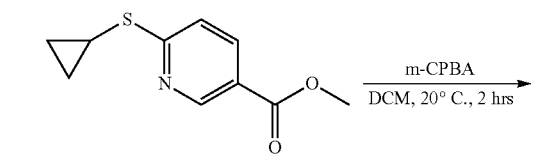

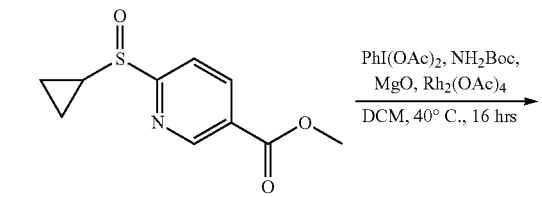

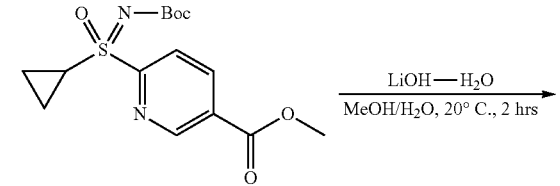

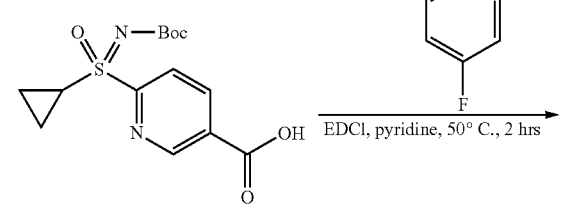

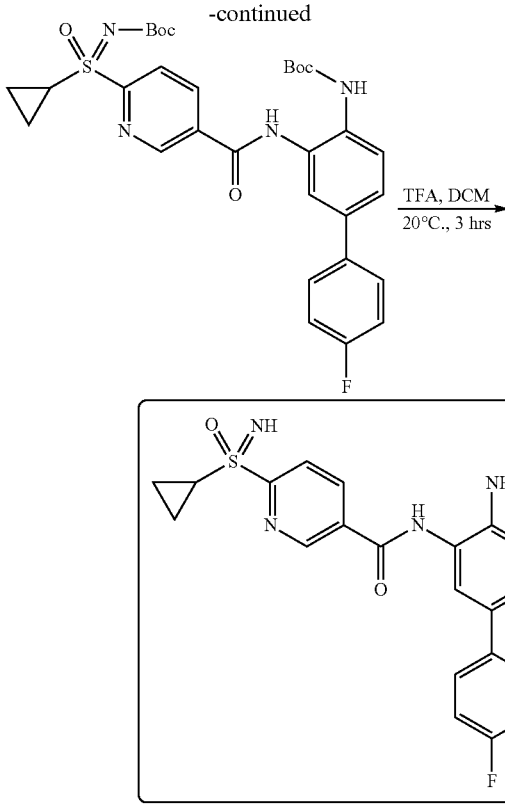

Step 1: Synthesis of methyl 6-sulfanylpyridine-3-carboxylate

To a solution of methyl 6-chloropyridine-3-carboxylate (about 4 g, 23.3 mmol) in dioxane (about 50 mL) was added methyl 3-sulfanylpropanoate (about 3.36 g, 27.98 mmol), Pd$_2$(dba)$_3$ (about 427 mg, 0.466 mmol), XantPhos (about 2.7 g, 4.66 mmol), Cs$_2$CO$_3$ (about 22.8 g, 69.9 mmol). The reaction mixture was stirred at about 100° C. for about 5 hours. The resulting mixture was quenched by addition of water (about 50 mL) and extracted with EtOAc (about 50 mL*3). The combined organic layer was washed with brine (about 50 mL), dried over anhydrous Na$_2$SO$_4$, filtered and concentrated under reduced pressure. The residue was purified by flash chromatography (ISCO®; about 80 g AgelaFlash® Silica Flash Column, petroleum ether/EtOAc with EtOAc from 0~30%, flow rate=80 mL/min, 254 nm) to afford methyl 6-(3-methoxy-3-oxo-propyl)sulfanylpyridine-3-carboxylate (about 3.3 g). LCMS (ESI) [M+H]$^+$ m/z: calcd 256.1, found 256.0. The water layer was acidified with 2N HCl aqueous solution to pH 2~3, and then collected the product by filtration to give methyl 6-sulfanylpyridine-3-carboxylate (about 0.85 g). LCMS (ESI) [M+H]$^+$ m/z: calcd 170.0, found 170.0.

Step 2: Synthesis of methyl 6-cyclopropylsulfanylpyridine-3-carboxylate

To a solution of methyl 6-sulfanylpyridine-3-carboxylate (about 0.85 g, 5.02 mmol) in 1,2-dichloroethane (about 10 mL) was added cyclopropylboronic acid (about 690 mg, 8.04 mmol), 2,2'-bipyridine (about 785 mg, 5.02 mmol), copper;diacetate;hydrate (about 912 mg, 5.02 mmol), dicesium;carbonate (about 1.64 g, 5.02 mmol). The reaction mixture was stirred at about 70° C. for about 12 hours. The resulting mixture was quenched by addition of water (about 50 mL), 25% NH$_3$—H$_2$O (about 5 mL), and extracted with DCM (about 50 mL*3). The combined organic layer was washed with brine (about 50 mL*2), dried over anhydrous Na$_2$SO$_4$, filtered and concentrated under reduced pressure. The residue was purified by flash chromatography (ISCO®; about 20 g AgelaFlash® Silica Flash Column, petroleum ether/EtOAc with EtOAc from 0~30%, flow rate=30 mL/min, 254 nm) to afford methyl 6-cyclopropylsulfanylpyridine-3-carboxylate (about 0.82 g). $^1$H NMR (400 MHz, chloroform-d) δ ppm 9.01 (d, J=2.1 Hz, 1H), 8.14 (dd, J=8.4, 2.2 Hz, 1H), 7.46 (d, J=8.4 Hz, 1H), 3.87-3.96 (m, 3H), 2.21-2.36 (m, 1H), 1.16-1.23 (m, 2H), 0.70-0.82 (m, 2H); LCMS (ESI) [M+H]$^+$ m/z: calcd 210.1, found 210.0.

Step 3: Synthesis of methyl 6-cyclopropylsulfinylpyridine-3-carboxylate

To a solution of m-CPBA (about 677 mg, 3.92 mmol, 85 wt %) in DCM (about 10 mL) was added methyl 6-cyclopropylsulfanylpyridine-3-carboxylate (about 0.8 g, 3.82 mmol). The mixture was stirred at about 20° C. for about 2 hours. The mixture was quenched by addition of saturated Na$_2$SO$_3$ aqueous solution (about 20 mL) and extracted with DCM (about 30 mL*3). The combined organic layer was dried over anhydrous Na$_2$SO$_4$, filtered and concentrated under reduced pressure to afford methyl 6-cyclopropylsulfinylpyridine-3-carboxylate (about 0.82 g). $^1$H NMR (400 MHz, chloroform-d) δ ppm 9.22 (d, J=1.5 Hz, 1H), 8.52 (dd, J=8.1, 2.0 Hz, 1H), 8.02 (d, J=8.1 Hz, 1H), 4.00 (s, 3H), 2.48 (tt, J=8.0, 4.9 Hz, 1H), 1.01-1.20 (m, 3H), 0.69-0.79 (m, 1H); LCMS (ESI) [M+H]$^+$ m/z: calcd 226.0, found 226.0.

Step 4: Synthesis of methyl 6-(N-tert-butoxycarbonyl-S-cyclopropyl-sulfonimidoyl)pyridine-3-carboxylate To a solution of NH$_2$Boc (about 1.87 g, 16.0 mmol), [bis(acetoxy)iodo]benzene (3.43 g, 10.7 mmol), MgO (about 1.47 g, 35.5 mmol) and diacetoxyrhodium (about 157 mg, 0.710 mmol) in DCM (about 10 mL) was added methyl 6-cyclopropylsulfinylpyridine-3-carboxylate (about 800 mg, 3.55 mmol). The reaction mixture was stirred at about 40° C. for about 16 hours. The resulting mixture was quenched by addition of water (about 30 mL) and extracted with EtOAc (about 30 mL*3). The combined organic layer was washed with brine (about 30 mL), dried over anhydrous Na$_2$SO$_4$, filtered and concentrated under reduced pressure. The residue was purified by flash chromatography (Biotage®; about 40 g SepaFlash® Silica Flash Column, petroleum ether/EtOAc with EtOAc from 0~50%, 30 mL/min, 254 nm) to afford methyl 6-(N-tert-butoxycarbonyl-S-cyclopropyl-sulfonimidoyl)pyridine-3-carboxylate (about 0.7 g). LCMS (ESI) [M+H]$^+$ m/z: calcd 341.1, found 341.1.

Step 5: Synthesis of 6-(N-tert-butoxycarbonyl-S-cyclopropyl-sulfonimidoyl)pyridine-3-carboxylic acid To a solution of methyl 6-(N-tert-butoxycarbonyl-S-cyclopropyl-sulfonimidoyl)pyridine-3-carboxylate (about 200 mg, 0.588 mmol) in MeOH (about 4 mL) was added a solution of LiOH—H$_2$O (about 296 mg, 7.05 mmol) in H$_2$O (about 2 mL). The mixture was stirred at about 20° C. for about 2 hours. The mixture was adjusted to about pH=4 with 3M HCl aqueous solution. The mixture was diluted with water (about 30 mL) and extracted with DCM (about 20 mL*3). The combined organic layer was concentrated under reduced pressure to afford 6-(N-tert-butoxycarbonyl-S-cyclopropyl-sulfonimidoyl)pyridine-3-carboxylic acid (about 135 mg). LCMS (ESI) [M+H]+ m/z: calcd 327.1, found 327.1.

Step 6: Synthesis of tert-butyl N-[[5-[[2-(tert-butoxycarbonylamino)-5-(4-fluorophenyl)phenyl]carbamoyl]-2-pyridyl]-cyclopropyl-oxo-sulfanylidene] carbamate To a solution of EDCI (about 153 mg, 0.797 mmol) in pyridine (about 5 mL) was added 6-(N-tert-butoxycarbonyl-S-cyclopropyl-sulfonimidoyl)pyridine-3-carboxylic acid (about 130 mg, 0.398 mmol) and tert-butyl N-[2-amino-4-(4-fluorophenyl)phenyl]carbamate (about 120 mg, 0.398 mmol). The mixture was stirred at about 50° C. for about 2 hours. The mixture was concentrated under reduced pressure. The residue was purified by flash chromatography (ISCO®; about 20 g AgelaFlash® Silica Flash Column, petroleum ether/EtOAc with EtOAc from 0~50%, flow rate=35 mL/min, 254 nm) to afford tert-butyl N-[[5-[[2-(tert-butoxycarbonylamino)-5-(4-fluorophenyl)phenyl]carbamoyl]-2-pyridyl]-cyclopropyl-oxo-sulfanylidene]carbamate (about 150 mg). LCMS (ESI) [M+H]+ m/z: calcd 611.2, found 611.2.

Step 7: Synthesis of N-[2-amino-5-(4-fluorophenyl) phenyl]-6-(cyclopropylsulfonimidoyl)pyridine-3-carboxamide To a solution of tert-butyl N-[[5-[[2-(tert-butoxycarbonylamino)-5-(4-fluorophenyl)phenyl]carbamoyl]-2-pyridyl]-cyclopropyl-oxo-sulfanylidene]carbamate (about 100 mg, 0.164 mmol) in DCM (about 1 mL) was added TFA (about 0.25 mL, 3.27 mmol). The mixture was stirred at about 20° C. for about 3 hours. The resulting mixture was concentrated under reduced pressure. The residue was purified by preparative HPLC (Instrument: AD; Column: 2_Phenomenex Gemini C18 75*40 mm*3 µm; Mobile phase A: water (NH4HCO3); Mobile phase B: ACN; Gradient: B from 32% to 62% in 9.5 min, hold 100% B for 2 min; Flow Rate: 30 mL/min; Column Temperature: 30° C.; Wavelength: 220 nm, 254 nm) to afford N-[2-amino-5-(4-fluorophenyl)phenyl]-6-(cyclopropylsulfonimidoyl)pyridine-3-carboxamide (about 42.8 mg). 1H NMR (400 MHz, chloroform-d) δ ppm 9.24 (s, 1H), 8.36-8.58 (m, 2H), 8.16 (d, J=7.8 Hz, 1H), 7.64 (s, 1H), 7.50 (s, 2H), 7.34 (d, J=8.3 Hz, 1H), 7.10 (t, J=8.7 Hz, 2H), 6.95 (d, J=7.8 Hz, 1H), 2.90 (s, 1H), 1.42 (s, 1H), 1.23 (dd, J=16.6, 5.5 Hz, 2H), 1.06-1.18 (m, 2H), 0.97-1.05 (m, 1H); 19F NMR (376 MHz, DMSO-d6) δ ppm–116.299; LCMS (ESI) [M+H]+ m/z: calcd 411.1, found 411.1; HPLC: 97.67%@220 nm, 100%@254 nm.

Example 14. Synthesis of N-[2-amino-5-(4-fluorophenyl)phenyl]-6-(1-oxo-4,5-dihydro-3H-isothiazol-1-yl)pyridine-3-carboxamide (Compound 178)

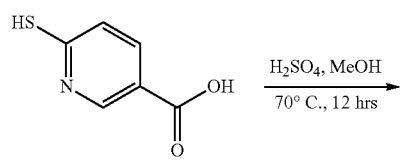

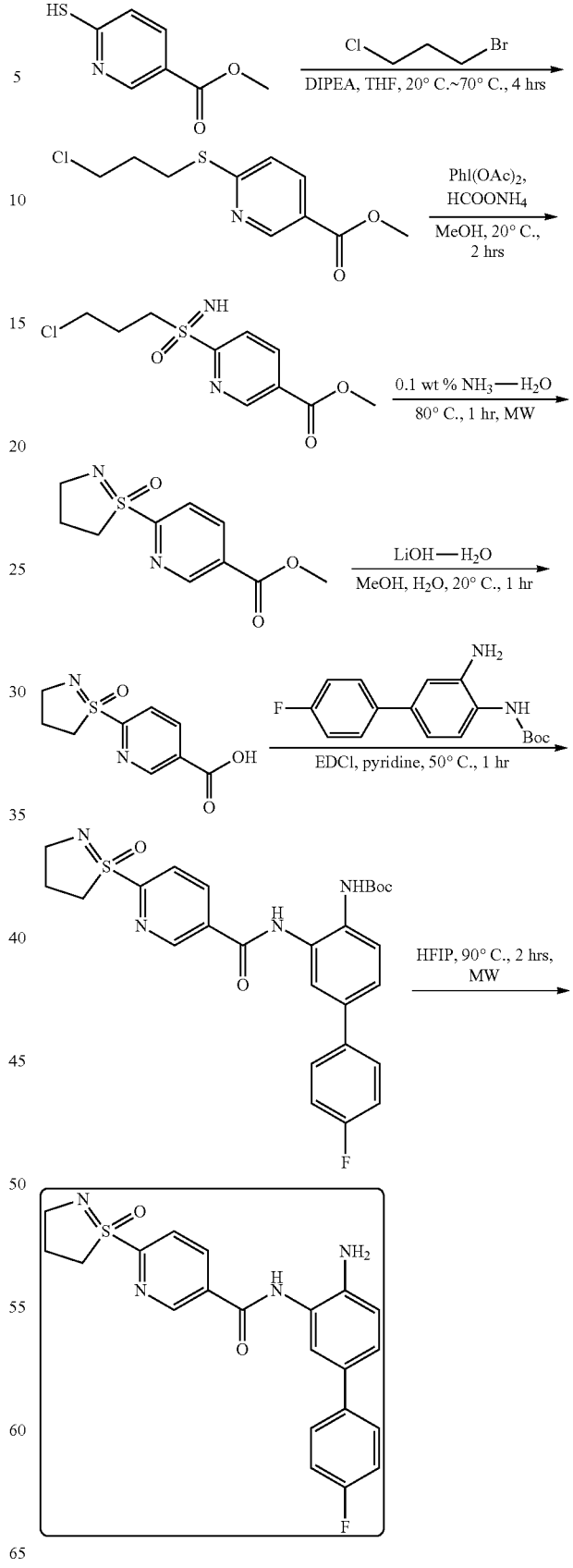

Step 1: Synthesis of methyl 6-sulfanylpyridine-3-carboxylate

To a solution of 6-sulfanylpyridine-3-carboxylic acid (about 3 g, 19.3 mmol) in MeOH (20 mL) was added $H_2SO_4$ (about 1 mL, 19.3 mmol). The mixture was stirred at about 70° C. for about 12 hours. The reaction mixture was poured into about 50 mL ice water. The resultant mixture concentrated under reduced pressure to remove MeOH. The residue was adjusted to about pH=9 with saturated $Na_2CO_3$ aqueous solution. The mixture was extracted with EtOAc (about 80 mL*3). The combined organic layers were washed with brine (about 50 mL), dried over $Na_2SO_4$ and filtered. The filtrate was concentrated under reduced pressure to afford methyl 6-methylsulfanylpyridine-3-carboxylate (about 1.7 g). The aqueous layer was adjusted with 1N HCl to about pH=3 and extracted with EtOAc (about 100 mL*3). The combined organic layers were washed with brine (about 50 mL), dried over $Na_2SO_4$ and filtered. The filtrate was concentrated under reduced pressure to afford methyl 6-sulfanylpyridine-3-carboxylate (about 1 g). LCMS (ESI) $[M+H]^+$ m/z: calcd 170.0, found 169.8.

Step 2: Synthesis of methyl 6-(3-chloropropylsulfanyl)pyridine-3-carboxylate To a solution of methyl 6-sulfanylpyridine-3-carboxylate (1 g, 5.91 mmol) in THF (about 30 mL) were added DIPEA (about 2 mL, 11.5 mmol) and 1-bromo-3-chloro-propane (about 2 mL, 20.2 mmol). The mixture was stirred at about 20° C. for about 2 hours. The mixture was then heated at about 70° C. for about 2 hours. The reaction mixture was diluted with water (30 mL) and extracted with EtOAc (about 50 mL*3). The combined organic layers were washed with brine (about 50 mL), dried over $Na_2SO_4$ and filtered. The filtrate was concentrated under reduced pressure. The residue was purified by flash chromatography (ISCO®; 20 g SepaFlash® Silica Flash Column, petroleum ether/EtOAc with EtOAc from 0~5%, flow rate: 40 mL/min, 254 nm) to afford methyl 6-(3-chloropropylsulfanyl)pyridine-3-carboxylate (about 960 mg). LCMS (ESI) $[M+H]^+$ m/z: calcd 246.0, found 245.8.

Step 3: Synthesis of methyl 6-(3-chloropropylsulfonimidoyl)pyridine-3-carboxylate To a solution of methyl 6-(3-chloropropylsulfanyl)pyridine-3-carboxylate (about 860 mg, 3.50 mmol) in MeOH (about 20 mL) was added ammonia;carbamic acid (about 600 mg, 7.69 mmol) and [acetoxy(phenyl)-iodanyl] acetate (about 3.01 g, 9.35 mmol). The mixture was stirred at about 20° C. for about 2 hours. The reaction mixture was concentrated under reduced pressure. The residue was purified by flash chromatography (ISCO®; about 40 g SepaFlash® Silica Flash Column, petroleum ether/EtOAc with EtOAc from 0~30%, flow rate: 60 mL/min, 254 nm) to afford methyl 6-(3-chloropropylsulfonimidoyl)pyridine-3-carboxylate (about 440 mg). LCMS (ESI) $[M+H]^+$ m/z: calcd 277.0, found 276.9.

Step 4: Synthesis of methyl 6-(1-oxo-4,5-dihydro-3H-isothiazol-1-yl)pyridine-3-carboxylate A solution of methyl 6-(3-chloropropylsulfonimidoyl)pyridine-3-carboxylate (about 390 mg, 1.41 mmol) in $NH_3$—$H_2O$ (about 15 mL, 0.1 wt %) was taken in a sealed tube. The tube was heated at about 80° C. for about 1 hour in microwave. The reaction mixture was concentrated under reduced pressure to afford methyl 6-(1-oxo-4,5-dihydro-3H-isothiazol-1-yl)pyridine-3-carboxylate (about 340 mg).

Step 5: Synthesis of 6-(1-oxo-4,5-dihydro-3H-isothiazol-1-yl)pyridine-3-carboxylic acid To a solution of methyl 6-(1-oxo-4,5-dihydro-3H-isothiazol-1-yl)pyridine-3-carboxylate (about 340 mg, 1.42 mmol) in MeOH (about 10 mL) and $H_2O$ (about 5 mL) was added lithium;hydroxide;hydrate (about 250 mg, 5.96 mmol). The mixture was stirred at about 20° C. for about 1 hour. The reaction mixture was concentrated under reduced pressure to remove MeOH. The residue was adjusted to about pH=4 with 1N HCl aqueous solution. The resultant mixture was extracted with DCM/IPA (about 30 mL*3). The combined organic layers were dried over $Na_2SO_4$ and filtered. The filtrate was concentrated under reduced pressure to afford 6-(1-oxo-4,5-dihydro-3H-isothiazol-1-yl)pyridine-3-carboxylic acid (about 240 mg).

Step 6: Synthesis of tert-butyl N-[4-(4-fluorophenyl)-2-[[6-(1-oxo-4,5-dihydro-3H-isothiazol-1-yl)pyridine-3-carbonyl]amino]phenyl]carbamate To a solution of 6-(1-oxo-4,5-dihydro-3H-isothiazol-1-yl)pyridine-3-carboxylic acid (about 120 mg, 0.530 mmol) in pyridine (about 5 mL) were added tert-butyl N-[2-amino-4-(4-fluorophenyl)phenyl]carbamate (about 160 mg, 0.530 mmol) and 3-(ethyliminomethyleneamino)-N,N-dimethyl-propan-1-amine;hydrochloride (about 160 mg, 0.835 mmol). The mixture was stirred at about 50° C. for about 1 hour. The reaction mixture was concentrated under reduced pressure. The residue was purified by preparative TLC (silica, petroleum ether/EtOAc=2/1; 254 nm) to afford tert-butyl N-[4-(4-fluorophenyl)-2-[[6-(1-oxo-4,5-dihydro-3H-isothiazol-1-yl)pyridine-3-carbonyl]amino]phenyl]carbamate (about 63 mg). LCMS (ESI) $[M+H]^+$ m/z: calcd 511.2, found 511.1.

Step 7: Synthesis of N-[2-amino-5-(4-fluorophenyl)phenyl]-6-(1-oxo-4,5-dihydro-3H-isothiazol-1-yl)pyridine-3-carboxamide To a solution of tert-butyl N-[4-(4-fluorophenyl)-2-[[6-(1-oxo-4,5-dihydro-3H-isothiazol-1-yl)pyridine-3-carbonyl]amino]phenyl]carbamate (about 58 mg, 0.113 mmol) in HFIP (about 12 mL) was heated at about 90° C. for about 2 hours in microwave. The reaction mixture was concentrated under reduced pressure. The residue was purified by preparative HPLC (Instrument: Gilson GX-281 Liquid Handler, Gilson 322 Pump, Gilson 156 UV Detector; Column: Phenomenex C18 80*40 mm*3 μm; Mobile phase A:water with 10 mmol $NH_4HCO_3$ (v %); Mobile phase B: MeCN; Gradient: B from 26% to 56% in 9.5 min, hold 100% B for 2 minutes; Flow Rate: 30 mL/min; Column Temperature: 30° C.; Wavelength: 220 nm, 254 nm) to afford N-[2-amino-5-(4-fluorophenyl)phenyl]-6-(1-oxo-4,5-dihydro-3H-isothiazol-1-yl)pyridine-3-carboxamide (about 20.7 mg). $^1$H NMR (400 MHz, chloroform-d) δ ppm 9.74 (s, 1H), 9.09 (d, J=1.2 Hz, 1H), 8.37 (dd, J=8.0, 2.0 Hz, 1H), 7.99 (d, J=8.0 Hz, 1H), 7.60 (d, J=1.6 Hz, 1H), 7.51 (dd, J=8.8, 5.2 Hz, 2H), 7.32 (dd, J=8.4, 2.0 Hz, 1H), 7.05-7.16 (m, 2H), 6.89 (d, J=8.4 Hz, 1H), 3.94-4.36 (m, 3H), 3.86 (dt, J=13.2, 9.6 Hz, 1H), 3.71 (dt, J=10.4, 7.2 Hz, 1H), 3.29 (ddd, J=13.2, 8.0, 4.8 Hz, 1H), 2.31-2.51 (m, 2H); $^{19}$F NMR (377 MHz, chloroform-d) δ ppm −116.593; HPLC: 98.99%@220 nm, 99.35%@254 nm; LCMS (ESI) [M+H]+ m/z: calcd 411.1, found 411.1.

Example 15. Synthesis of N-[2-amino-5-(4-fluorophenyl)phenyl]-4-(trifluoromethylsulfonimidoyl)benzamide (Compound 177)

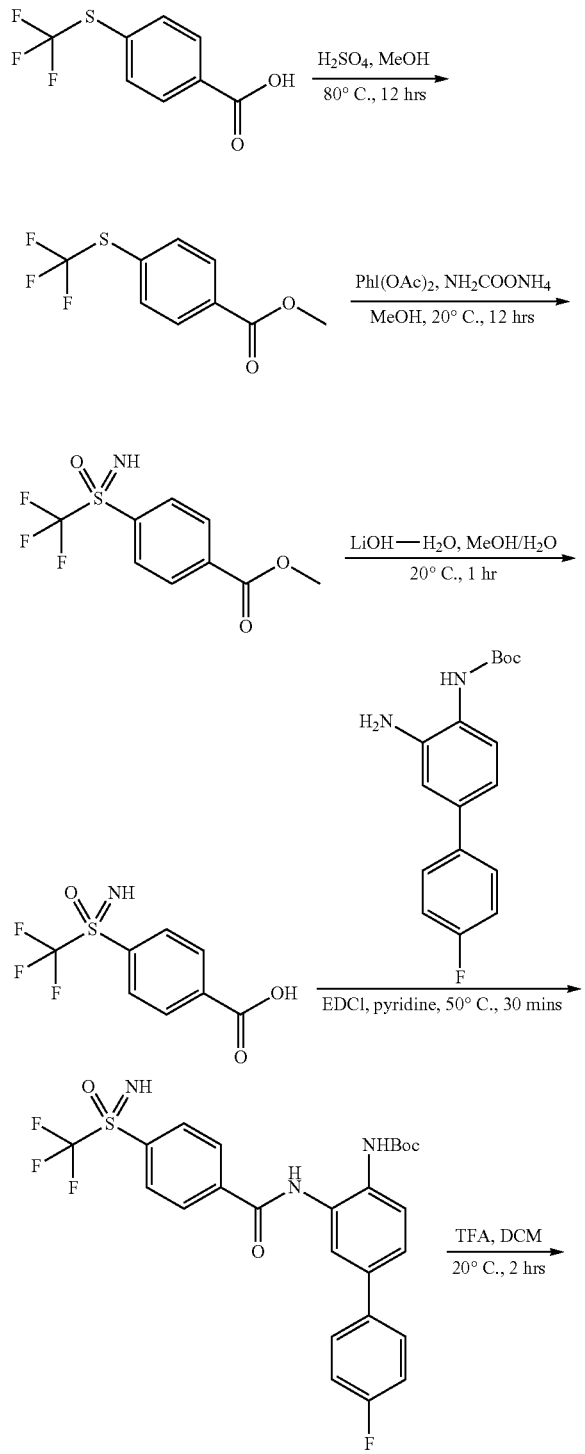

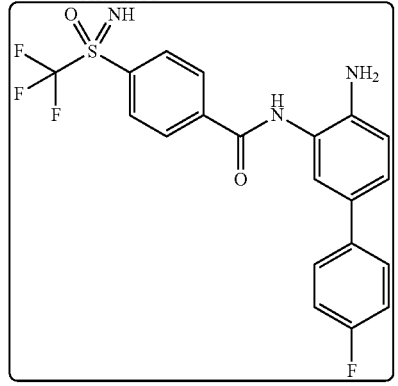

Step 1: Synthesis of methyl 4-(trifluoromethylsulfanyl)benzoate

To a solution of 4-(trifluoromethylsulfanyl)benzoic acid (about 3.9 g, 17.6 mmol) in MeOH (about 40 mL) was added $H_2SO_4$ (about 5 mL, 17.6 mmol, 98 wt %). The mixture was stirred at about 80° C. for about 12 hours. The reaction mixture was added to ice-water (about 20 mL) and extracted with EtOAc (about 30 mL*3). The combined organic layers were washed with saturated $Na_2CO_3$ aqueous solution (about 30 mL), dried over $Na_2SO_4$ and filtered. The filtrate was concentrated under reduced pressure to give methyl 4-(trifluoromethylsulfanyl)benzoate (about 3.15 g). $^1$H NMR (400 MHz, chloroform-d) δ ppm 8.08 (d, J=8.4 Hz, 2H), 7.73 (d, J=8.4 Hz, 2H), 3.95 (s, 3H); $^{19}$F NMR (377 MHz, chloroform-d) δ ppm −41.832.

Step 2: Synthesis of methyl 4-(trifluoromethylsulfonimidoyl)benzoate

To a solution of methyl 4-(trifluoromethylsulfanyl)benzoate (about 100 mg, 0.423 mmol) in $CF_3CH_2OH$ (about 2 mL) was added [acetoxy(phenyl)-iodanyl] acetate (about 285 mg, 0.884 mmol) and ammonia;carbamic acid (about 50 mg, 0.640 mmol). The mixture was stirred at about 20° C. for about 12 hours. The reaction mixture was concentrated under reduced pressure. The residue was purified by preparative TLC (silica, petroleum ether/EtOAc=5/1; 254 nm) to give methyl 4-(trifluoromethylsulfonimidoyl)benzoate (about 40 mg). $^1$H NMR (400 MHz, chloroform-d) δ ppm 8.27-8.31 (m, 2H), 8.15-8.25 (m, 2H), 4.00 (s, 3H); $^{19}$F NMR (376 MHz, chloroform-d) δ ppm −78.482; LCMS (ESI) [M+H]+ m/z: calcd 268.0, found 267.9.

Step 3: Synthesis of 4-(trifluoromethylsulfonimidoyl)benzoic acid

To a solution of methyl 4-(trifluoromethylsulfonimidoyl)benzoate (about 40 mg, 0.149 mmol) in MeOH (about 2 mL) and $H_2O$ (about 1 mL) was added lithium;hydroxide;hydrate (about 30 mg, 0.714 mmol). The mixture was stirred at about 20° C. for about 1 hour. The mixture was concentrated under reduced pressure to remove the organic solvent. The aqueous phase was adjusted to about pH=4 with 1N HCl aqueous solution. The mixture was filtered. The filter cake was dried under reduced pressure to give 4-(trifluoromethylsulfonimidoyl)benzoic acid (about 70 mg).

Step 4: Synthesis of tert-butyl N-[4-(4-fluorophenyl)-2-[[4-(trifluoromethylsulfonimidoyl)benzoyl]amino]phenyl]carbamate To a solution of 4-(trifluoromethylsulfonimidoyl)benzoic acid (about 70 mg, 0.276 mmol) in pyridine (about 2 mL) were added EDCI (about 80 mg, 0.417 mmol) and tert-butyl N-[2-amino-4-(4-fluorophenyl)phenyl]carbamate (about 100 mg, 0.330 mmol). The mixture was stirred at about 50° C. for about 30 minutes. The reaction mixture was concentrated under reduced pressure. The residue was purified by flash chromatography (ISCO®; about 4 g SepaFlash® Silica Flash Column, petroleum ether/EtOAc with EtOAc from 0~20%, flow rate: 18 mL/min, 254 nm) to give tert-butyl N-[4-(4-fluorophenyl)-2-[[4-(trifluoromethylsulfonimidoyl)benzoyl]amino]phenyl]carbamate (about 90 mg). LCMS (ESI) [M+H]$^+$ m/z: calcd 538.1, found 438.0 (Boc cleaved mass).

Step 5: Synthesis of N-[2-amino-5-(4-fluorophenyl)phenyl]-4-(trifluoromethylsulfonimidoyl)benzamide To a solution of tert-butyl N-[4-(4-fluorophenyl)-2-[[4-(trifluoromethylsulfonimidoyl)benzoyl]amino]phenyl]carbamate (about 85 mg, 0.158 mmol) in DCM (about 3 mL) was added TFA (about 0.5 mL, 6.49 mmol). The mixture was stirred at about 20° C. for about 2 hours. The reaction mixture was adjusted to about pH=8 with saturated NaHCO$_3$ aqueous and extracted with DCM (about 20 mL*3). The combined organic layers were dried over Na$_2$SO$_4$ and filtered. The filtrate was concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 µm; Mobile phase A: H$_2$O with 10 mmol NH$_4$HCO$_3$ (v %); Mobile phase B: ACN; Gradient: B from 46% to 76% in 9.5 min, hold 100% B for 1 min; Flow Rate: 30 mL/min; Column Temperature: 30° C.; Wavelength: 220 nm, 254 nm) to give N-[2-amino-5-(4-fluorophenyl)phenyl]-4-(trifluoromethylsulfonimidoyl)benzamide (about 7.3 mg). $^1$H NMR (400 MHz, chloroform-d) δ ppm 8.29 (d, J=8.0 Hz, 2H), 8.11-8.21 (m, 3H), 7.62 (s, 1H), 7.49 (dd, J=8.4, 5.6 Hz, 2H), 7.33 (dd, J=8.4, 2.0 Hz, 1H), 7.10 (t, J=8.8 Hz, 2H), 6.95 (d, J=8.4 Hz, 1H), 3.90 (brs, 2H), 3.76 (brs, 1H); $^{19}$F NMR (377 MHz, chloroform-d) δ ppm −78.421, −116.293; LCMS [M+H]$^+$ m/z: calcd 438.1; found 438.0; HPLC: 97.92%@220 nm; 98.48%@254 nm.

Example 16. Synthesis of 5-[4-amino-3-[[4-(methylsulfonimidoyl)benzoyl]amino]phenyl]thiophene-2-carboxamide (Compound 176)

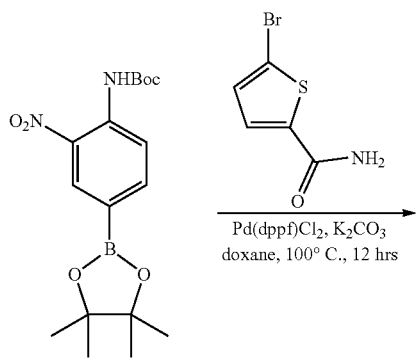

Step 1: Synthesis of tert-butyl N-[4-(5-carbamoyl-2-thienyl)-2-nitro-phenyl]carbamate To a mixture of tert-butyl N-[2-nitro-4-(4,4,5,5-tetramethyl-1,3,2-dioxaborolan-2-yl)phenyl]carbamate (about 200 mg, 0.549 mmol), 5-bromothiophene-2-carboxamide (about 86 mg, 0.419 mmol) in dioxane (about 3 mL) were added Pd(dppf)Cl$_2$ (about 31 mg, 0.0420 mmol) and K$_2$CO$_3$ (about 173 mg, 1.25 mmol). The resulting mixture was stirred at about 100° C. for about 12 hours under N$_2$. The resulting mixture was quenched by addition of water (about 10 mL) and extracted with EtOAc (about 20 mL*3). The combined organic layer was washed with brine (about 10 mL), dried over anhydrous Na$_2$SO$_4$, filtered and concentrated under reduced pressure. The residue was purified by flash chromatography (ISCO®; about 20 g AgelaFlash® Silica Flash Column, petroleum ether/EtOAc with EtOAc from 0~50%, flow rate=35 mL/min, 254 nm) to afford tert-butyl N-[4-(5-carbamoyl-2-thienyl)-2-nitro-phenyl]carbamate (about 150 mg). LCMS (ESI) [M+H]$^+$ m/z: calcd 364.1, found 363.9.

Step 2: Synthesis of tert-butyl N-[2-amino-4-(5-carbamoyl-2-thienyl) phenyl]carbamate A mixture of tert-butyl N-[4-(5-carbamoyl-2-thienyl)-2-nitro-phenyl]carbamate (about 150 mg, 0.413 mmol) in MeOH (about 1 mL) was added Pd/C (about 53 mg, 10 wt % Pd with 50 wt % water). The mixture was stirred at about 25° C. for about 2 hours under H$_2$ (in balloon). The mixture was filtered and concentrated to give tert-butyl N-[2-amino-4-(5-carbamoyl-2-thienyl)phenyl]carbamate (about 100 mg).

Step 3: Synthesis of tert-butyl N-[[4-[[2-(tert-butoxycarbonylamino)-5-(5-carbamoyl-2-thienyl)phenyl]carbamoyl]phenyl]-methyl-oxo-sulfanylidene]carbamate A mixture of tert-butyl N-[2-amino-4-(5-carbamoyl-2-thienyl)phenyl]carbamate (about 30 mg, 0.0900 mmol), 4-(N-tert-butoxycarbonyl-S-methyl-sulfonimidoyl)benzoic acid (about 30 mg, 0.0990 mmol) and EDCI (about 21 mg, 0.108 mmol) in pyridine (about 1 mL) was stirred at about 50° C. for about 12 hours. The mixture was concentrated. The residue was purified by flash chromatography (ISCO®; about 20 g AgelaFlash® Silica Flash Column, petroleum ether/EtOAc with EtOAc from 0~100%, flow rate=35 mL/min, 254 nm) to afford tert-butyl N-[[4-[[2-(tert-butoxycarbonylamino)-5-(5-carbamoyl-2-thienyl)phenyl]carbamoyl]phenyl]-methyl-oxo-sulfanylidene]carbamate (about 50 mg). LCMS (ESI) [M+H]$^+$ m/z: calcd 615.2, found 615.3.

Step 4: Synthesis of 5-[4-amino-3-[[4-(methylsulfonimidoyl)benzoyl]amino]phenyl]thiophene-2-carboxamide A mixture of tert-butyl N-[[4-[[2-(tert-butoxycarbonylamino)-5-(5-carbamoyl-2-thienyl)phenyl]carbamoyl]phenyl]-methyl-oxo-sulfanylidene]carbamate (about 50 mg, 0.0813 mmol) and TFA (about 0.06 mL, 0.818 mmol) in DCM (about 1 mL) was stirred at 25° C. for 1 hour. The mixture was concentrated under reduced pressure. The residue was adjusted the pH to 8 with 25 wt % NH$_3$—H$_2$O. The residue was purified by preparative HPLC (Instrument: Gilson GX-281 Liquid Handler, Gilson 322 Pump, Gilson 156 UV Detector; Column: Durashell 150×25 mm×5 μm; Mobile phase A: H$_2$O with (NH$_4$HCO$_3$); Mobile phase B: MeCN; Gradient: B from 15% to 45% in 9.5 min, hold 100% B for 2 min; Flow Rate: 30 mL/min; Column Temperature: 30° C.; Wavelength: 220 nm, 254 nm) to afford 5-[4-amino-3-[[4-(methylsulfonimidoyl)benzoyl]amino]phenyl]thiophene-2-carboxamide (about 7.4 mg). $^1$H NMR (400 MHz, methanol-d$_4$) δ ppm 8.22-8.30 (m, 2H), 8.15-8.21 (m, 2H), 7.65 (d, J=3.9 Hz, 1H), 7.59 (d, J=2.0 Hz, 1H), 7.46 (dd, J=8.4, 2.1 Hz, 1H), 7.26 (d, J=3.9 Hz, 1H), 6.95 (d, J=8.4 Hz, 1H), 3.24 (s, 3H); LCMS (ESI) [M+H]$^+$ m/z: calcd 415.1, found 415.1; HPLC: 96.87%@220 nm, 97.90%@254 nm.

Example 17. Synthesis of N-[2-amino-5-(4-fluorophenyl)phenyl]-6-(2-pyridylsulfonimidoyl)pyridine-3-carboxamide (Compound 175)

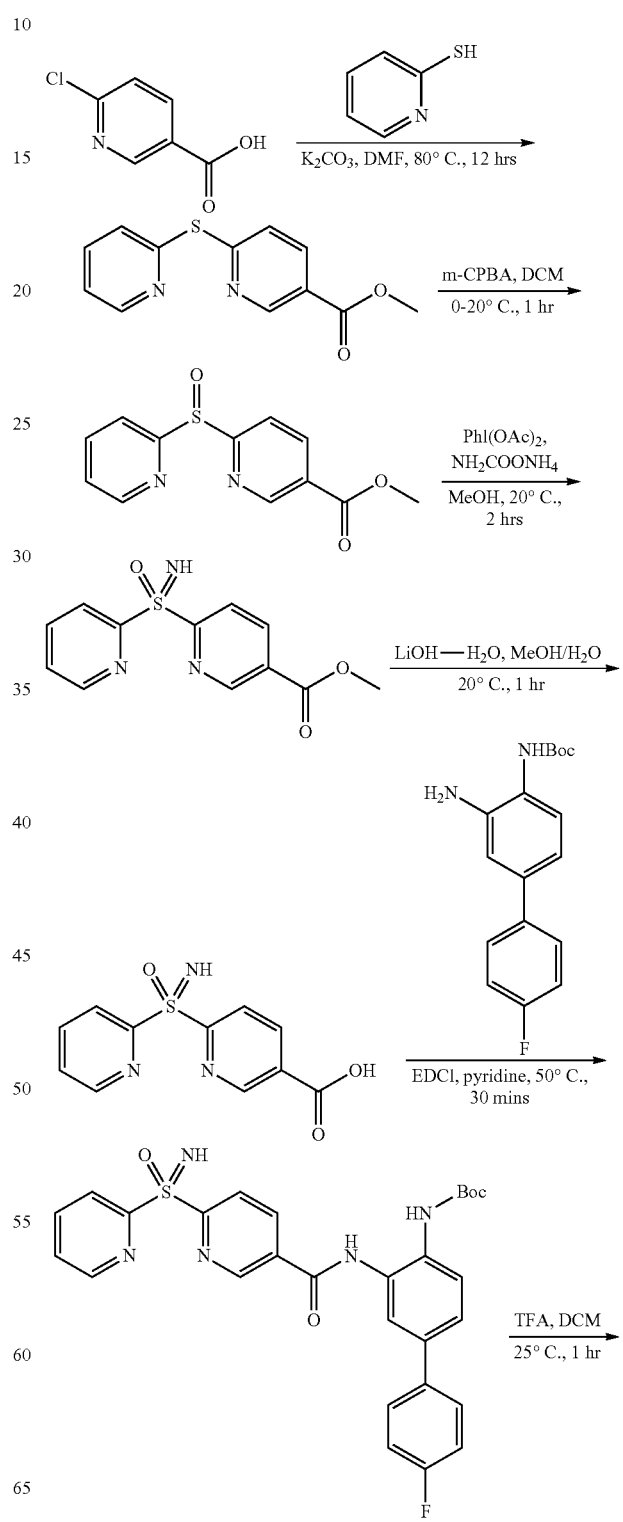

-continued

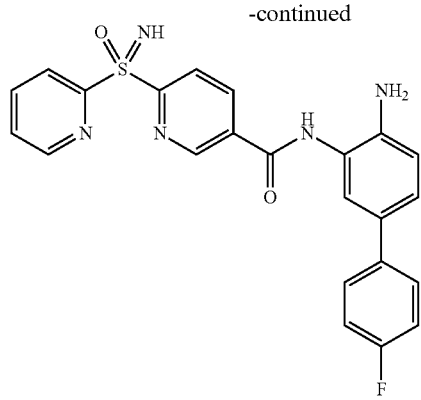

Step 1: Synthesis of methyl 6-(2-pyridylsulfanyl)pyridine-3-carboxylate

A mixture of pyridine-2-thiol (about 778 mg, 7.00 mmol), methyl 6-chloropyridine-3-carboxylate (about 1 g, 5.83 mmol), tripotassium; carbonate (about 2.4 g, 17.4 mmol) in DMF (about 10 mL) was stirred at about 80° C. for about 12 hours. The resulting mixture was quenched by addition of water (about 100 mL) and extracted with EtOAc (about 100 mL*3). The combined organic layer was washed with brine (about 100 mL*2), dried over anhydrous $Na_2SO_4$, filtered and concentrated under reduced pressure. The residue was purified by column chromatography (silica, petroleum ether/EtOAc=0 to 50%, 254 nm) to afford methyl 6-(2-pyridylsulfanyl)pyridine-3-carboxylate (about 1.01 g). $^1$H NMR (400 MHz, chloroform-d) δ ppm 9.06 (d, J=1.5 Hz, 1H), 8.63-8.65 (m, 1H), 8.14-8.17 (m, 1H), 7.56-7.80 (m, 2H), 7.40-7.42 (m, 1H), 7.26-7.34 (m, 1H), 3.91-3.99 (m, 3H); LCMS (ESI) $[M+H]^+$ m/z: calcd 247.0, found 247.0.

Step 2: Synthesis of methyl 6-(2-pyridylsulfinyl)pyridine-3-carboxylate

To a mixture of methyl 6-(2-pyridylsulfanyl)pyridine-3-carboxylate (about 970 mg, 3.94 mmol) in DCM (about 10 mL) was added 3-chlorobenzenecarboperoxoic acid (about 1.20 g, 5.91 mmol, 85 wt %) at about 0° C. The mixture was stirred at about 20° C. for about 1 hour. The resulting mixture was quenched by addition of water (about 100 mL) and extracted with EtOAc (about 100 mL*3). The combined organic layer was washed with brine (about 100 mL*2), dried over anhydrous $Na_2SO_4$, filtered and concentrated under reduced pressure. The residue was purified by column chromatography (silica, petroleum ether/EtOAc=10:0 to 1:1, 254 nm) to afford methyl 6-(2-pyridylsulfinyl)pyridine-3-carboxylate (about 690 mg). $^1$H NMR (400 MHz, chloroform-d) δ ppm 9.07-9.16 (m, 1H), 8.53-8.64 (m, 1H), 8.35-8.45 (m, 1H), 8.03-8.12 (m, 1H), 7.89-7.98 (m, 1H), 7.79-7.81 (m, 1H), 7.29 (s, 1H), 3.88 (s, 3H); LCMS (ESI) $[M+H]^+$ m/z: calcd 263.0, found 263.0.

Step 3: Synthesis of methyl 6-(2-pyridylsulfonimidoyl)pyridine-3-carboxylate A mixture of methyl 6-(2-pyridylsulfinyl)pyridine-3-carboxylate (about 650 mg, 2.48 mmol), [acetoxy(phenyl)-iodanyl] acetate (about 2 g, 6.20 mmol), ammonia; carbamic acid (about 406 mg, 5.20 mmol) in MeOH (about 6 mL) was stirred at about 20° C. for about 2 hours. The resulting mixture was quenched by addition of water (about 100 mL) and extracted with EtOAc (about 100 mL*3). The combined organic layer was washed with saturated brine (100 mL*2), dried over anhydrous $Na_2SO_4$, filtered and concentrated under reduced pressure. The residue was purified by column chromatography (silica, petroleum ether/EtOAc=0 to 60%, 254 nm) to afford methyl 6-(2-pyridylsulfonimidoyl)pyridine-3-carboxylate (about 320 mg). $^1$H NMR (400 MHz, chloroform-d) δ ppm 9.12 (s, 1H), 8.58 (d, J=4.0 Hz, 1H), 8.42-8.48 (m, 2H), 8.39 (d, J=8.0 Hz, 1H), 7.89-7.91 (m, 1H), 7.40-7.43 (m, 1H), 3.90 (s, 3H); LCMS (ESI) $[M+H]^+$ m/z: calcd 278.1, found 278.0.

Step 4: Synthesis of 6-(2-pyridylsulfonimidoyl)pyridine-3-carboxylic acid

A mixture of methyl 6-(2-pyridylsulfonimidoyl)pyridine-3-carboxylate (about 270 mg, 0.974 mmol), lithium; hydroxide; hydrate (about 204 mg, 4.87 mmol) in $H_2O$ (about 2.5 mL) and MeOH (about 2.5 mL) was stirred at about 20° C. for about 1 hour. The mixture was acidified with 2N HCl to about pH=2-3 and extracted with EtOAc (about 10 mL×3). The combined organic layers were washed with brine (about 10 mL), dried with anhydrous $Na_2SO_4$, filtered and concentrated under reduced pressure to afford 6-(2-pyridylsulfonimidoyl)pyridine-3-carboxylic acid (about 220 mg). $^1$H NMR (400 MHz, chloroform-d) δ ppm 9.20-9.32 (m, 1H), 8.43-8.72 (m, 4H), 7.99-8.02 (m, 1H), 7.47-7.59 (m, 1H); LCMS (ESI) $[M+H]^+$ m/z: calcd 264.0, found 264.0.

Step 5: Synthesis of tert-butyl N-[4-(4-fluorophenyl)-2-[[6-(2-pyridylsulfonimidoyl)pyridine-3-carbonyl]amino]phenyl]carbamate A mixture of 6-(2-pyridylsulfonimidoyl)pyridine-3-carboxylic acid (about 200 mg, 0.760 mmol), tert-butyl N-[2-amino-4-(4-fluorophenyl)phenyl]carbamate (about 253 mg, 0.837 mmol), 3-(ethyliminomethyleneamino)-N,N-dimethyl-propan-1-amine;hydrochloride (about 175 mg, 0.913 mmol) in pyridine (about 3 mL) was stirred at about 50° C. for about 30 minutes. The mixture was concentrated under reduced pressure. The residue was purified by column chromatography (silica, petroleum ether/EtOAc=0~100%, 254 nm) to afford tert-butyl N-[4-(4-fluorophenyl)-2-[[6-(2-pyridylsulfonimidoyl)pyridine-3-carbonyl]amino]phenyl]carbamate (about 310 mg). $^1$H NMR (400 MHz, chloroform-d) δ ppm 9.89 (s, 1H), 9.15 (s, 1H), 8.59 (d, J=4.6 Hz, 1H), 8.37-8.45 (m, 3H), 8.01 (s, 1H), 7.90-8.01 (m, 1H), 7.38-7.53 (m, 3H), 7.28-7.30 (m, 1H), 7.13 (d, J=8.2 Hz, 1H), 6.99-7.08 (m, 2H), 6.69 (s, 1H), 5.23 (s, 1H), 1.45 (s, 9H); LCMS (ESI) $[M+H]^+$ m/z: calcd 548.2, found 548.2.

Step 6: Synthesis of N-[2-amino-5-(4-fluorophenyl)phenyl]-6-(2-pyridylsulfonimidoyl)pyridine-3-carboxamide A mixture of tert-butyl N-[4-(4-fluorophenyl)-2-[[6-(2-pyridylsulfonimidoyl)pyridine-3-carbonyl]amino]phenyl]carbamate (about 290 mg, 0.530 mmol) in TFA (1.5 mL) and DCM (about 5 mL) was stirred at about 25° C. for about 1 hour. The mixture was concentrated under reduce pressure. The residue was diluted with MeOH (about 4 mL) and adjusted pH to about 6-7 with $Na_2CO_3$, filtered and filtrate was purified by preparative HPLC (Instrument: Gilson GX-281 Liquid Handler, Gilson 322 Pump, Gilson 156 UV Detector; Column: 2_Phenomenex Gemini C18 75*40 mm*3 µm; Mobile phase A: $H_2O$ with $NH_4HCO_3$ (v %); Mobile phase B: MeCN; Gradient: B from 34% to 64% in 9.5 min, hold 100% B for 1 min; Flow Rate: 30 mL/min; Column Temperature: 30° C.; Wavelength: 220 nm, 254 nm) to afford N-[2-amino-5-(4-fluorophenyl)phenyl]-6-(2-pyridylsulfonimidoyl)pyridine-3-carboxamide (about 115 mg). $^1H$ NMR (400 MHz, DMSO-$d_6$) δ ppm 9.97-10.08 (m, 1H), 9.08-9.18 (m, 1H), 8.56-8.69 (m, 2H), 8.30-8.47 (m, 2H), 8.14-8.18 (m, 1H), 7.47-7.69 (m, 4H), 7.18-7.38 (m, 3H), 6.86 (d, J=8.4 Hz, 1H), 5.37 (s, 1H), 5.25 (s, 2H); $^{19}F$ NMR (376 MHz, DMSO-$d_6$) δ ppm−117.471; LCMS (ESI) [M+H]$^+$ m/z: calcd 448.1, found 448.1; HPLC: 98.62%@220 nm, 99.75%@254 nm.

Example 18. Synthesis of N-[2-amino-5-(4-fluorophenyl)phenyl]-4-(pyridazin-3-ylsulfonimidoyl)benzamide (Compound 174)

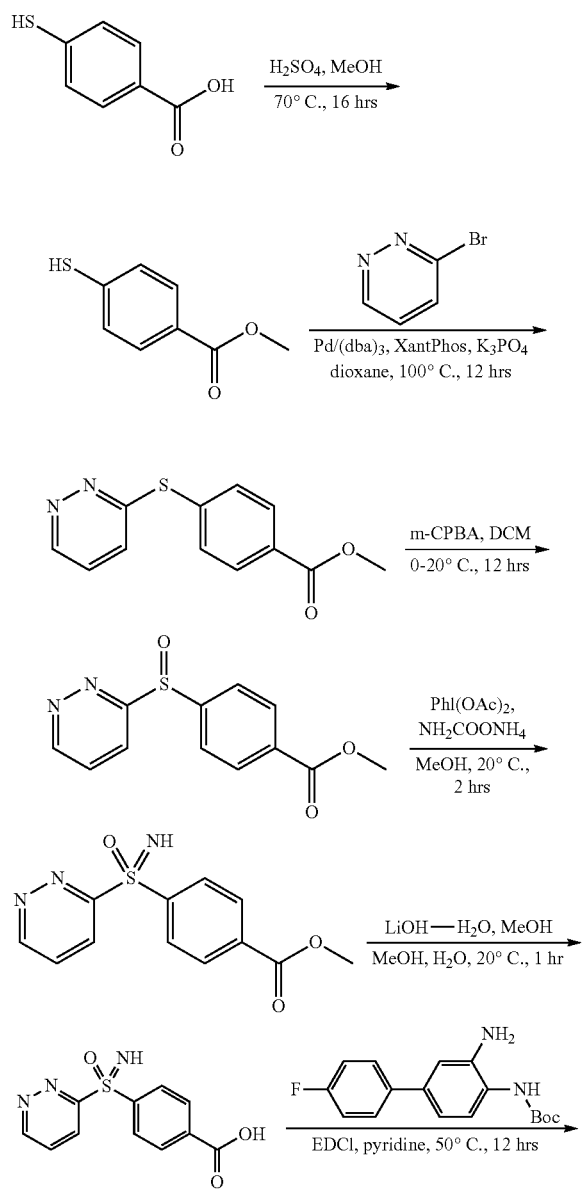

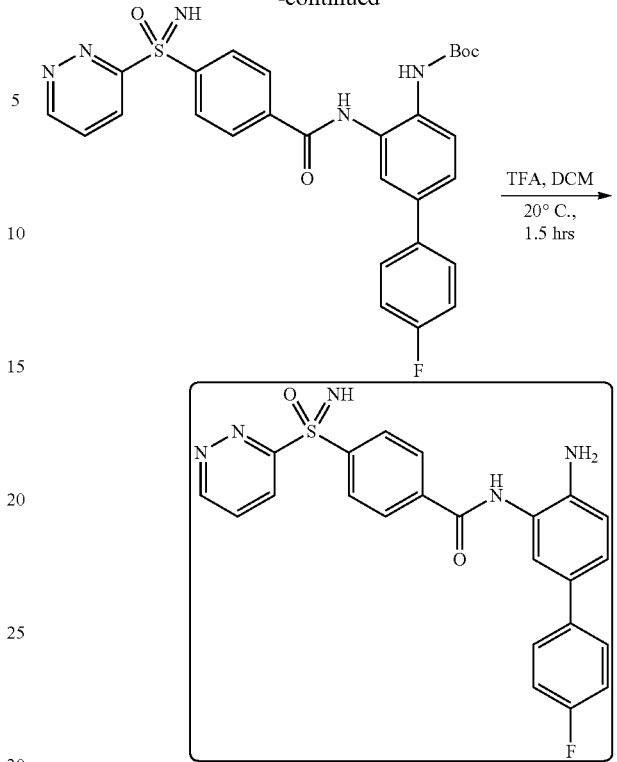

Step 1: Synthesis of methyl 4-sulfanylbenzoate

To a solution of 4-sulfanylbenzoic acid (about 3 g, 19.5 mmol) in MeOH (about 20 mL) was added $H_2SO_4$ (about 1 mL, 18.8 mmol). The reaction mixture was stirred at about 70° C. for about 16 hours. The resulting mixture was filtered and concentrated under reduced pressure. The residue was purified by flash chromatography (ISCO®; about 20 g AgelaFlash® Silica Flash Column, petroleum ether/EtOAc with EtOAc from 0~10%, flow rate=30 mL/min, 254 nm) to afford methyl 4-sulfanylbenzoate (about 2.7 g). $^1H$ NMR (400 MHz, methanol-$d_4$) δ ppm 7.81-7.88 (m, 2H), 7.32-7.38 (m, 2H), 3.87 (s, 3H); LCMS (ESI) [M+H]$^+$ m/z: calcd 169.0, found 169.1.

Step 2: Synthesis of methyl 4-pyridazin-3-ylsulfanylbenzoate

A mixture of methyl 4-sulfanylbenzoate (about 1 g, 5.94 mmol), 3-bromopyridazine (about 2.84 g, 17.8 mmol), $K_3PO_4$ (about 3.79 g, 17.8 mmol), (5-diphenylphosphanyl-9,9-dimethyl-xanthen-4-yl)-diphenyl-phosphane (about 688 mg, 1.19 mmol) and (1E,4E)-1,5-diphenylpenta-1,4-dien-3-one;palladium (about 545 mg, 0.595 mmol) in dioxane (about 15 mL) was stirred at about 100° C. for about 12 hours. The resulting mixture was filtered and concentrated under reduced pressure. The residue was purified by flash chromatography (ISCO®; about 20 g AgelaFlash® Silica Flash Column, petroleum ether/EtOAc with EtOAc from 0~45%, flow rate=30 mL/min, 254 nm) to afford methyl 4-pyridazin-3-ylsulfanylbenzoate (about 1.13 g). $^1H$ NMR (400 MHz, DMSO-$d_6$) δ ppm 9.08 (dd, J=4.9, 1.4 Hz, 1H), 7.99-8.06 (m, 2H), 7.67-7.75 (m, 2H), 7.61 (dd, J=8.8, 4.8 Hz, 1H), 7.49-7.54 (m, 1H), 3.88 (s, 3H); LCMS (ESI) [M+H]$^+$ m/z: calcd 247.0, found 247.0.

Step 3: Synthesis of methyl 4-pyridazin-3-ylsulfinylbenzoate

To a solution of methyl 4-pyridazin-3-ylsulfanylbenzoate (about 1.1 g, 4.47 mmol) in DCM (about 10 mL) was added m-CPBA (about 1 g, 4.93 mmol, 85 wt %) at about 0° C. The mixture was stirred at about 20° C. for about 13 hours. The mixture was quenched by addition of saturated $Na_2SO_3$ aqueous solution (about 30 mL), saturated $Na_2CO_3$ aqueous solution (about 30 mL) and extracted with DCM (about 30 mL*2). The combined organic layer was dried over anhydrous $Na_2SO_4$, filtered and concentrated under reduced pressure. The residue was purified by flash chromatography (ISCO®; about 40 g AgelaFlash® Silica Flash Column, petroleum ether/EtOAc with EtOAc from 0~60%, flow rate=80 mL/min, 254 nm) to afford methyl 4-pyridazin-3-ylsulfinylbenzoate (about 850 mg). $^1H$ NMR (400 MHz, DMSO-$d_6$) δ ppm 9.33 (dd, J=5.0, 1.5 Hz, 1H), 8.19 (dd, J=8.5, 1.5 Hz, 1H), 8.11 (d, J=8.5 Hz, 2H), 7.92-8.00 (m, 3H), 3.85 (s, 3H); LCMS (ESI) [M+H]$^+$ m/z: calcd 263.0, found 263.0.

Step 4: Synthesis of methyl 4-(pyridazin-3-ylsulfonimidoyl)benzoate

A mixture of methyl 4-pyridazin-3-ylsulfinylbenzoate (about 700 mg, 2.67 mmol), [acetoxy(phenyl)-iodanyl] acetate (about 2.15 g, 6.66 mmol), ammonia;carbamic acid (about 420 mg, 5.38 mmol) and MeOH (about 10 mL) was stirred at about 20° C. for about 2 hours. The resulting mixture was concentrated under reduced pressure. The residue was purified by flash chromatography (ISCO®; about 12 g AgelaFlash® Silica Flash Column, petroleum ether/EtOAc with EtOAc from 0~70%, flow rate=50 mL/min, 254 nm) to afford methyl 4-(pyridazin-3-ylsulfonimidoyl)benzoate (about 190 mg). methyl 4-pyridazin-3-ylsulfinylbenzoate (390 mg) was recovered. LCMS (ESI) [M+H]$^+$ m/z: calcd 278.1, found 278.1.

Step 5: Synthesis of 4-(pyridazin-3-ylsulfonimidoyl)benzoic acid

To a solution of methyl 4-(pyridazin-3-ylsulfonimidoyl) benzoate (about 380 mg, 1.37 mmol) in MeOH (about 3 mL) and $H_2O$ (about 1 mL) was added LiOH—$H_2O$ (about 570 mg, 13.6 mmol). The mixture was stirred at about 20° C. for about 1 hour. The resulting mixture was concentrated under reduced pressure to remove MeOH. The mixture was adjusted to about pH=5 with saturated 2N HCl aqueous solution. The fraction was concentrated under reduced pressure and then lyophilized for overnight to afford 4-(pyridazin-3-ylsulfonimidoyl)benzoic acid (about 1.3 g). LCMS (ESI) [M+H]$^+$ m/z: calcd 264.0, found 264.0.

Step 6: Synthesis of tert-butyl N-[4-(4-fluorophenyl)-2-[[4-(pyridazin-3-ylsulfonimidoyl)benzoyl]amino]phenyl]carbamate A mixture of tert-butyl N-[2-amino-4-(4-fluorophenyl) phenyl]carbamate (about 400 mg, 1.32 mmol), 4-(pyridazin-3-ylsulfonimidoyl)benzoic acid (about 1.3 g, 1.33 mmol, 27 wt %) and 3-(ethyliminomethyleneamino)-N,N-dimethylpropan-1-amine;hydrochloride (about 468 mg, 2.44 mmol) in pyridine (about 10 mL) was stirred at about 50° C. for about 12 hours. The resulting mixture was concentrated under reduced pressure. The residue was purified by flash chromatography (ISCO®; about 12 g AgelaFlash® Silica Flash Column, petroleum ether/EtOAc with EtOAc from 0~100%, flow rate=30 mL/min, 254 nm) to afford tert-butyl N-[4-(4-fluorophenyl)-2-[[4-(pyridazin-3-ylsulfonimidoyl) benzoyl]amino]phenyl]carbamate (about 70 mg). LCMS (ESI) [M+H]$^+$ m/z: calcd 548.2, found 548.2.

Step 7: Synthesis of N-[2-amino-5-(4-fluorophenyl) phenyl]-4-(pyridazin-3-ylsulfonimidoyl)benzamide A mixture of tert-butyl N-[4-(4-fluorophenyl)-2-[[4-(pyridazin-3-ylsulfonimidoyl)benzoyl]amino]phenyl]carbamate (about 60 mg, 0.110 mmol), DCM (about 2 mL) and TFA (about 0.2 mL, 2.60 mmol) was stirred at about 20° C. for about 1.5 hours. The mixture was concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 μm; Mobile phase A: water ($NH_4HCO_3$); Mobile phase B: MeCN; Gradient: B from 30% to 60% in 9.5 min, hold 100% B for 2 min; Flow Rate: 30 mL/min; Column Temperature: about 30° C.; Wavelength: 220 nm, 254 nm). The fraction was concentrated under reduced pressure and then lyophilized for overnight to afford N-[2-amino-5-(4-fluorophenyl)phenyl]-4-(pyridazin-3-ylsulfonimidoyl)benzamide (about 18.5 mg). $^1H$ NMR (400 MHz, DMSO-$d_6$) δ ppm 9.92 (s, 1H), 9.39 (dd, J=5.1, 1.5 Hz, 1H), 8.46 (dd, J=8.6, 1.5 Hz, 1H), 8.18 (s, 4H), 8.01 (dd, J=8.6, 5.1 Hz, 1H), 7.57 (dd, J=8.8, 5.4 Hz, 2H), 7.48 (d, J=2.0 Hz, 1H), 7.31 (dd, J=8.3, 2.2 Hz, 1H), 7.21 (t, J=8.9 Hz, 2H), 6.85 (d, J=8.4 Hz, 1H), 5.77 (s, 1H), 5.16 (brs, 2H); $^{19}F$ NMR (376 MHz, DMSO-$d_6$) δ ppm−117.449; LCMS (ESI) [M+H]$^+$ m/z: calcd 448.1, found 448.2; HPLC: 91.78%@220 nm, 97.61%@254 nm.

Example 19. Synthesis of N-[2-amino-5-(p-tolyl) phenyl]-4-(methylsulfonimidoyl)benzamide (Compound 158)

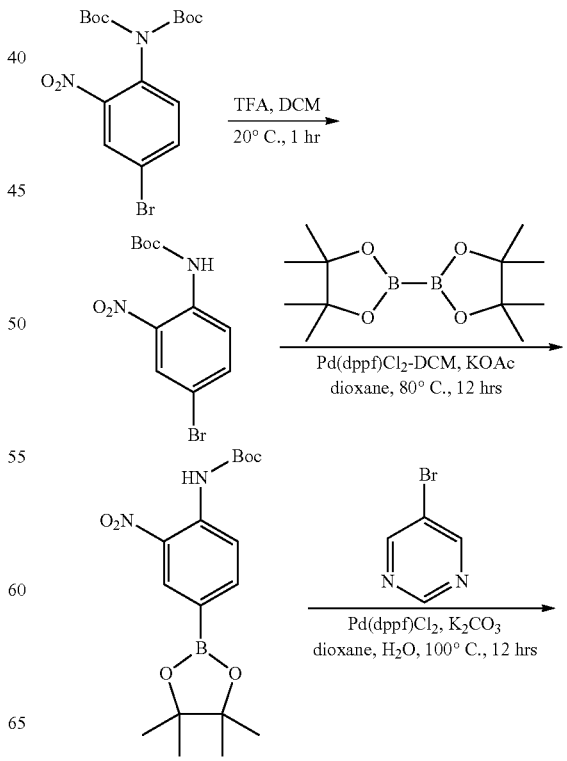

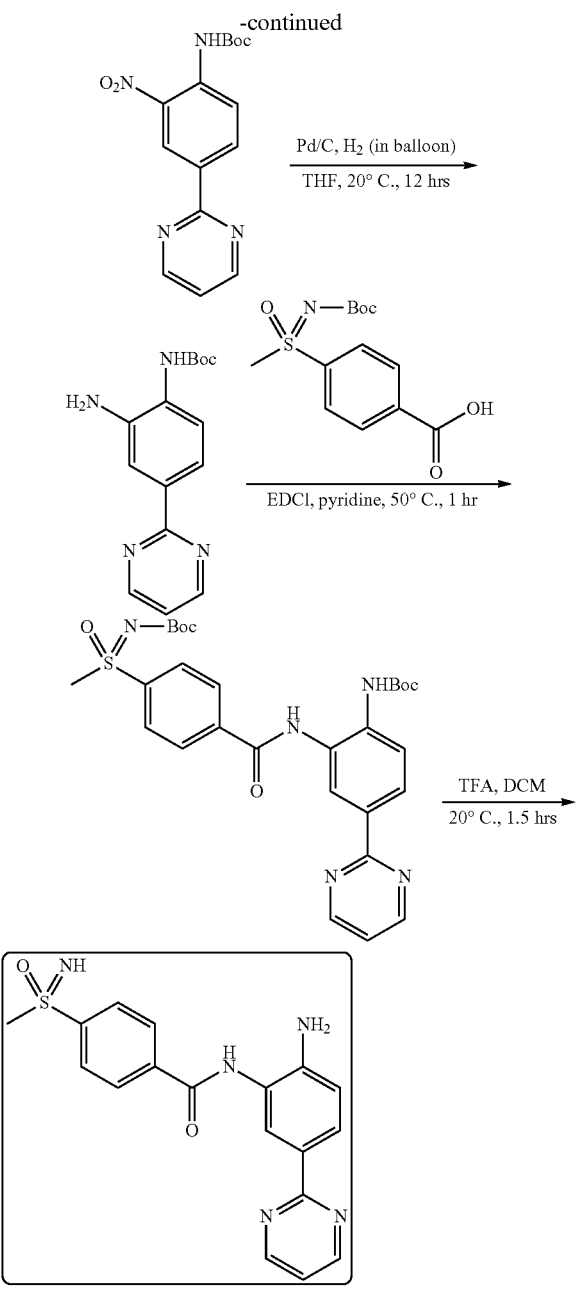

Step 1: Synthesis of tert-butyl N-(4-bromo-2-nitro-phenyl)carbamate

A mixture of tert-butyl N-(4-bromo-2-nitro-phenyl)-N-tert-butoxycarbonyl-carbamate (about 14 g, 33.5 mmol), DCM (about 140 mL) and TFA (about 3.9 mL, 50.6 mmol) was stirred at about 20° C. for 1 hour. The mixture was adjusted to about pH=8 with saturated $Na_2CO_3$ aqueous solution (about 50 mL). The resulting mixture was extracted with about DCM (about 50 mL*3). The combined organic layer was dried over anhydrous about $Na_2SO_4$, filtered and concentrated under reduced pressure to give tert-butyl N-(4-bromo-2-nitro-phenyl)carbamate (about 11 g), which was directly used to next step without further purification. $^1$H NMR (400 MHz, methanol-$d_4$) δ ppm 8.26-8.29 (m, 1H), 8.18-8.24 (m, 1H), 7.77-7.81 (m, 1H), 1.49-1.58 (m, 9H).

Step 2: Synthesis of tert-butyl N-[2-nitro-4-(4,4,5,5-tetramethyl-1,3,2-dioxaborolan-2-yl)phenyl]carbamate To a mixture of 4,4,5,5-tetramethyl-2-(4,4,5,5-tetramethyl-1,3,2-dioxaborolan-2-yl)-1,3,2-dioxaborolane (about 6 g, 23.6 mmol), tert-butyl N-(4-bromo-2-nitro-phenyl)carbamate (about 5 g, 15.8 mmol) in 1,4-dioxane (about 30 mL) were added KOAc (about 8.9 g, 31.5 mmol) and cyclopentyl (diphenyl)phosphane;dichloromethane dichloropalladium;iron (about 1.29 g, 1.58 mmol). The solution was degassed with $N_2$ for about 3 times. Then the mixture was stirred at about 80° C. for about 12 hours. The resulting mixture was quenched by addition of water (about 50 mL) and extracted with DCM (about 50 mL*3). The combined organic layer was dried over anhydrous $Na_2SO_4$, filtered and concentrated under reduced pressure. The residue was purified by flash chromatography (ISCO®; 80 g AgelaFlash® Silica Flash Column, petroleum ether/EtOAc with EtOAc from 0~10%, flow rate=35 mL/min, 254 nm) to afford tert-butyl N-[2-nitro-4-(4,4,5,5-tetramethyl-1,3,2-dioxaborolan-2-yl)phenyl]carbamate (about 5.7 g). $^1$H NMR (400 MHz, DMSO-$d_6$) δ ppm 9.76 (s, 1H), 8.14 (d, J=1.3 Hz, 1H), 7.86-7.90 (m, 1H), 7.79-7.83 (m, 1H), 1.45 (s, 9H), 1.30 (s, 12H); LCMS (ESI) [M+H]$^+$ m/z: calcd 365.2, found 265.1 (Boc cleaved mass).

Step 3: Synthesis of tert-butyl N-(2-nitro-4-pyrimidin-2-yl-phenyl)carbamate To a mixture of tert-butyl N-[2-nitro-4-(4,4,5,5-tetramethyl-1,3,2-dioxaborolan-2-yl)phenyl]carbamate (about 1.50 g, 4.12 mmol), 2-bromopyrimidine (about 500 mg, 3.14 mmol) in dioxane (about 15 mL) and $H_2O$ (about 5 mL) were added Pd(dppf)Cl$_2$ (about 230 mg, 0.315 mmol) and $K_2CO_3$ (about 1.3 g, 9.41 mmol). The resulting mixture was stirred at about 100° C. for about 12 hours under $N_2$. The resulting mixture was quenched by addition of water (about 50 mL) and extracted with EtOAc (about 50 mL*3). The combined organic layer was dried over anhydrous $Na_2SO_4$, filtered and concentrated under reduced pressure. The residue was purified by flash chromatography (ISCO®; about 12 g AgelaFlash® Silica Flash Column, petroleum ether/EtOAc with EtOAc from 0~20%, flow rate=35 mL/min, 254 nm) to afford tert-butyl N-(2-nitro-4-pyrimidin-2-yl-phenyl)carbamate (about 160 mg). $^1$H NMR (400 MHz, chloroform-d) δ ppm 9.85 (s, 1H), 9.33 (d, J=1.3 Hz, 1H), 8.82 (d, J=4.8 Hz, 2H), 8.69-8.72 (m, 2H), 7.18-7.22 (m, 1H), 1.57 (s, 9H); LCMS (ESI) [M+H]$^+$ m/z: calcd 317.1, found 317.1.

Step 4: Synthesis of tert-butyl N-(2-amino-4-pyrimidin-2-yl-phenyl)carbamate To a solution of tert-butyl N-(2-nitro-4-pyrimidin-2-yl-phenyl)carbamate (about 140 mg, 0.443 mmol) in THF (about 5 mL) was added Pd/C (about 50 mg, 10 wt % Pd with 50 wt % water). The suspension was degassed and purged with hydrogen for about 3 times. The mixture was stirred at about 20° C. for about 12 hours under hydrogen (in balloon). The resulting mixture was filtered. The filtrate was concentrated under reduced pressure to afford tert-butyl N-(2-amino-4-pyrimidin-2-yl-phenyl)carbamate (about 120 mg). LCMS (ESI) [M+H]$^+$ m/z: calcd 287.1, found 287.1.

Step 5: Synthesis of tert-butyl N-[[4-[[2-(tert-butoxycarbonylamino)-5-pyrimidin-2-yl-phenyl]carbamoyl]phenyl]-methyl-oxo-sulfanylidene]carbamate A mixture of tert-butyl N-(2-amino-4-pyrimidin-2-yl-phenyl)carbamate (about 120 mg, 0.419 mmol), 4-(N-tertbutoxycarbonyl-S-methyl-sulfonimidoyl)benzoic acid (about 100 mg, 0.334 mmol) and 3-(ethyliminomethyleneamino)-N,N-dimethyl-propan-1-amine;hydrochloride (about 96 mg, 0.501 mmol) in pyridine (about 4 mL) was stirred at about 50° C. for about 1 hour. The mixture was concentrated under reduced pressure. The residue was purified by flash chromatography (ISCO®; about 8 g SepaFlash® Silica Flash Column, petroleum ether/EtOAc with EtOAc from 0~80%, flow rate=40 mL/min, 254 nm) to afford tert-butyl N-[[4-[[2-(tert-butoxycarbonylamino)-5-pyrimidin-2-yl-phenyl]carbamoyl]phenyl]-methyl-oxo-sulfanylidene]carbamate (about 87 mg). LCMS (ESI) [M+H]$^+$ m/z: calcd 568.2, found 568.2.

Step 6: Synthesis of N-(2-amino-5-pyrimidin-2-yl-phenyl)-4-(methylsulfonimidoyl)benzamide A mixture of tert-butyl N-[[4-[[2-(tert-butoxycarbonylamino)-5-pyrimidin-2-yl-phenyl]carbamoyl]phenyl]-methyl-oxo-sulfanylidene]carbamate (about 87 mg, 0.153 mmol), DCM (about 2 mL) and TFA (about 1.5 mL, 19.5 mmol) was stirred at about 20° C. for about 1.5 hours. The mixture was concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 μm; Mobile phase A: H$_2$O with NH$_4$HCO$_3$ (v %); Mobile phase B: MeCN; Gradient: B from 4% to 34% in 9.5 min, hold 100% B for 2 min; Flow Rate: 25 mL/min; Column Temperature: 30° C.; Wavelength: 220 nm, 254 nm) to give N-(2-amino-5-pyrimidin-2-yl-phenyl)-4-(methylsulfonimidoyl)benzamide (about 16 mg). $^1$H NMR (400 MHz, DMSO-d$_6$) δ ppm 9.89 (s, 1H), 8.76 (d, J=4.8 Hz, 2H), 8.25 (d, J=1.8 Hz, 1H), 8.20 (br d, J=8.3 Hz, 2H), 8.06 (br d, J=8.3 Hz, 3H), 7.25 (t, J=4.8 Hz, 1H), 6.85 (d, J=8.5 Hz, 1H), 5.60 (s, 2H), 4.40 (s, 1H), 3.13 (s, 3H); LCMS (ESI) [M+H]$^+$ m/z: calcd 368.1, found 368.1; HPLC: 1000%@254 nm, 1000%@254 nm.

Example 20. Synthesis of N-(2-amino-5-pyridazin-3-yl-phenyl)-4-(methylsulfonimidoyl)benzamide (Compound 157)

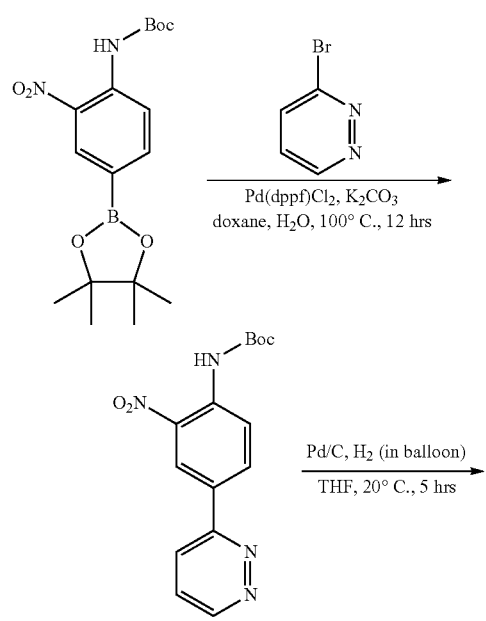

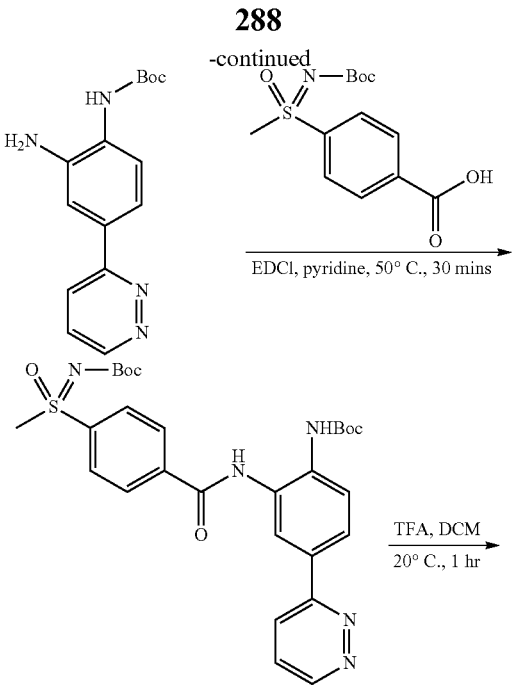

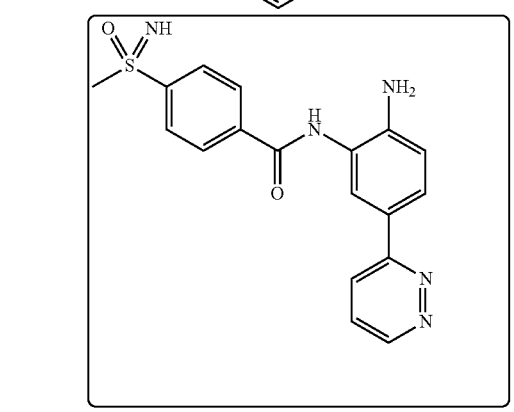

Step 1: Synthesis of tert-butyl N-(2-nitro-4-pyridazin-3-yl-phenyl)carbamate

To a mixture of tert-butyl N-[2-nitro-4-(4,4,5,5-tetramethyl-1,3,2-dioxaborolan-2-yl)phenyl]carbamate (about 1 g, 2.75 mmol), 3-bromopyridazine (about 360 mg, 2.26 mmol) in H$_2$O (3 mL) and dioxane (about 15 mL) was added Pd(dppf)Cl$_2$ (about 333 mg, 0.456 mmol) and K$_2$CO$_3$ (about 938 mg, 6.79 mmol). The resulting mixture was stirred at about 100° C. for about 12 hours under N$_2$. The resulting mixture was quenched by addition of water (about 100 mL) and extracted with EtOAc (about 100 mL*3). The combined organic layer was washed with brine (about 100 mL), dried over anhydrous Na$_2$SO$_4$, filtered and concentrated under reduced pressure. The residue was purified by flash chromatography (ISCO®; about 20 g AgelaFlash® Silica Flash Column, petroleum ether/EtOAc with EtOAc from 0~65%, flow rate=30 mL/min, 254 nm) to afford tert-butyl N-(2-nitro-4-pyridazin-3-yl-phenyl)carbamate (about 556 mg). LCMS (ESI) [M+H]$^+$ m/z: calcd 317.1, found 316.9.

Step 2: Synthesis of tert-butyl N-(2-amino-4-pyridazin-3-yl-phenyl)carbamate

A solution of tert-butyl N-(2-nitro-4-pyridazin-3-yl-phenyl)carbamate (about 450 mg, 1.42 mmol) in THF (about 10 mL) was added Pd/C (about 200 mg, 10 wt % Pd with 50 wt % water). The suspension was degassed and purged with hydrogen for about 3 times. The filtrate was concentrated under reduced pressure at about 20° C. for about 5 hours. The resulting mixture was filtered and filter cake was washed by MeOH (about 50 mL*3) and the filtrate was concentrated under reduced pressure to give tert-butyl N-(2-amino-4-pyridazin-3-yl-phenyl)carbamate (about 490 mg), which was used to next step without further purification. $^1$H NMR (400 MHz, DMSO-d$_6$) δ ppm 9.13 (dd, J=4.8, 1.3 Hz, 1H), 8.48 (s, 1H), 8.03 (d, J=1.4 Hz, 1H), 7.71 (dd, J=8.8, 4.9 Hz, 1H), 7.59 (d, J=1.9 Hz, 1H), 7.48 (d, J=8.3 Hz, 1H), 7.28 (dd, J=8.4, 1.9 Hz, 1H), 5.14 (s, 2H), 1.48 (s, 9H). LCMS (ESI) [M+H]$^+$ m/z: calcd 287.1, found 287.1.

Step 3: Synthesis of tert-butyl N-[[4-[[2-(tert-butoxycarbonylamino)-5-pyridazin-3-yl-phenyl]carbamoyl]phenyl]-methyl-oxo-sulfanylidene]carbamate A mixture of 4-(N-tert-butoxycarbonyl-S-methyl-sulfonimidoyl)benzoic acid (about 100 mg, 0.334 mmol), 3-(ethyliminomethyleneamino)-N,N-dimethyl-propan-1-amine; hydrochloride (about 96 mg, 0.501 mmol) and tert-butyl N-(2-amino-4-pyridazin-3-yl-phenyl)carbamate (about 106 mg, 0.370 mmol) in pyridine (about 4 mL) was stirred at about 50° C. for about 30 minutes. The resulting mixture was concentrated under reduced pressure. The residue was purified by flash chromatography (ISCO®; about 12 g AgelaFlash®Silica Flash Column, petroleumether/EtOAc with EtOAc from 0~80%, flow rate=30 mL/min, 254 nm) to afford tert-butyl N-[[4-[[2-(tert-butoxycarbonylamino)-5-pyridazin-3-yl-phenyl]carbamoyl]phenyl]-methyl-oxo-sulfanylidene]carbamate (about 70 mg). LCMS (ESI) [M+H]$^+$ m/z: calcd 568.2, found 568.2.

Step 4: Synthesis of N-(2-amino-5-pyridazin-3-yl-phenyl)-4-(methylsulfonimidoyl)benzamide To a solution of tert-butyl N-[[4-[[2-(tert-butoxycarbonylamino)-5-pyridazin-3-yl-phenyl]carbamoyl]phenyl]-methyl-oxo-sulfanylidene]carbamate (about 70 mg, 0.123 mmol) and TFA (about 1.5 mL) was stirred at about 20° C. for about 1 hour. The mixture was adjusted to about pH=8 with 28 wt % NH$_3$—H$_2$O. The mixture was purified by preparative HPLC (Instrument: Gilson GX-281 Liquid Handler, Gilson 322 Pump, Gilson 156 UV Detector; Column: 2_Phenomenex Gemini C18 75*40 mm*3 µm; Mobile phase A: water (10 mm NH$_4$HCO$_3$)-ACN; Mobile phase B: MeCN; Gradient: B from 7% to 37% in 7.8 min, hold 100% B for 1 min; Flow Rate: 30 mL/min; Column Temperature: 30° C.; Wavelength: 220 nm, 254 nm) to afford N-(2-amino-5-pyridazin-3-yl-phenyl)-4-(methylsulfonimidoyl)benzamide (about 15 mg). $^1$H NMR (400 MHz, DMSO-d$_6$) δ ppm 9.99 (s, 1H), 9.05 (dd, J=4.8, 1.3 Hz, 1H), 8.21 (d, J=8.4 Hz, 2H), 8.00-8.13 (m, 4H), 7.84 (dd, J=8.5, 2.2 Hz, 1H), 7.65 (dd, J=8.8, 4.8 Hz, 1H), 6.91 (d, J=8.5 Hz, 1H), 5.54 (brs, 2H), 3.14 (s, 3H); LCMS (ESI) [M+H]$^+$ m/z: calcd 368.1, found 368.2; HPLC: 100%@220 nm, 100%@254 nm.

Example 21. Synthesis of N-[2-amino-5-(2-methylthiazol-5-yl)phenyl]-4-(methylsulfonimidoyl)benzamide (Compound 156)

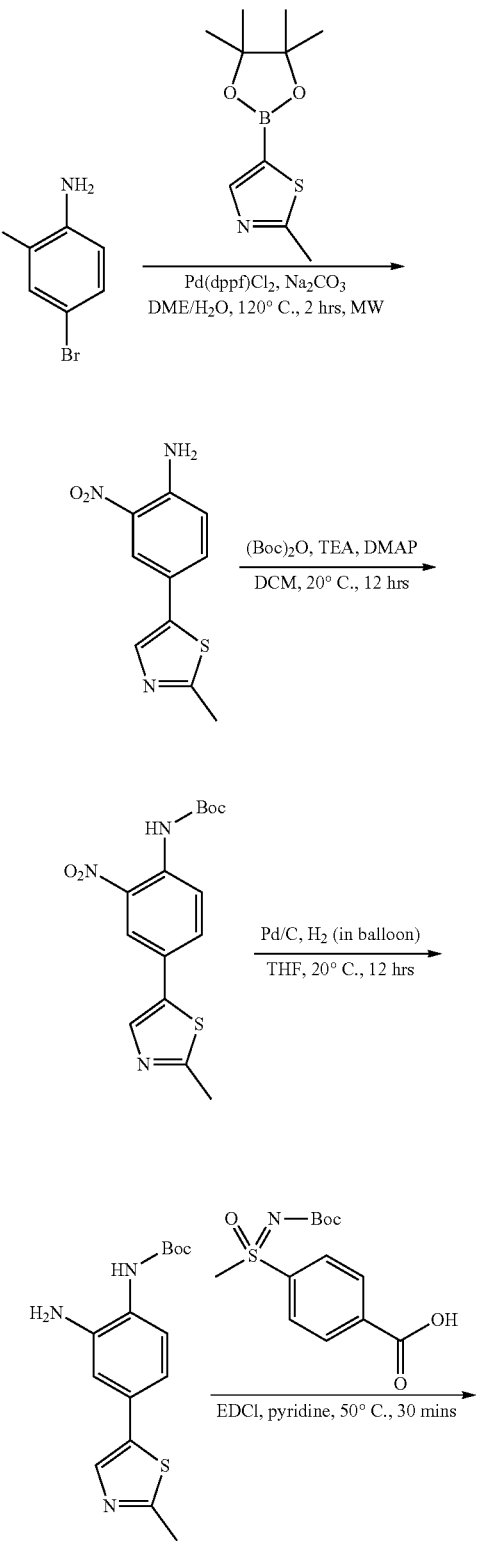

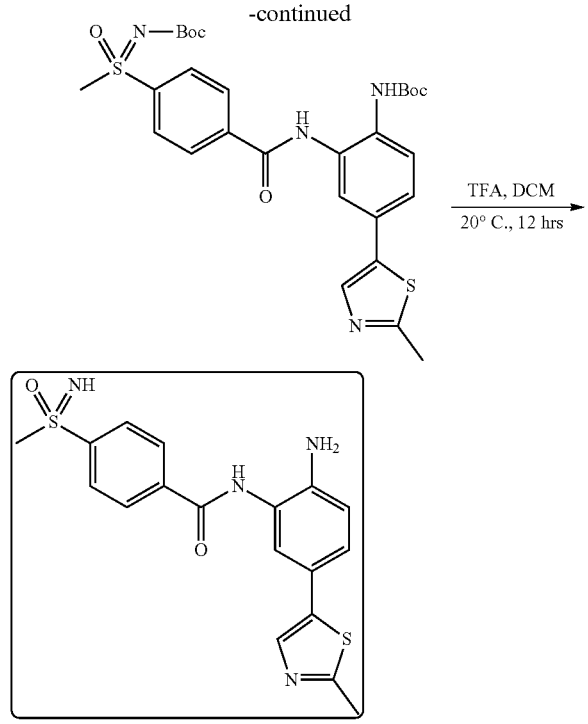

Step 1: Synthesis of 4-(2-methylthiazol-5-yl)-2-nitro-aniline

A mixture of 4-bromo-2-nitro-aniline (about 330 mg, 1.52 mmol), 2-methyl-5-(4,4,5,5-tetramethyl-1,3,2-dioxaborolan-2-yl)thiazole (about 445 mg, 1.98 mmol), cyclopentyl(diphenyl)phosphane;dichloromethane; dichloropalladium; iron (about 248 mg, 0.304 mmol), Na$_2$CO$_3$ (about 483 mg, 4.56 mmol) in H$_2$O (about 5 mL) and DME (about 15 mL) was stirred at about 120° C. for about 2 hours in microwave. The resulting mixture was quenched by addition of water (about 10 mL) and extracted with EtOAc (about 20 mL*3). The combined organic layer was washed with brine (about 30 mL*3), dried over anhydrous Na$_2$SO$_4$, filtered and concentrated under reduced pressure. The residue was purified by flash chromatography (Biotage®; about 25 g Agela-Flash® Silica Flash Column, petroleum ether/EtOAc with EtOAc from 0~50%, flow rate=40 mL/min, 254 nm) to afford 4-(2-methylthiazol-5-yl)-2-nitro-aniline (about 311 mg). $^1$H NMR (400 MHz, DMSO-d$_6$) δ ppm 8.06 (d, J=2.0 Hz, 1H), 7.93 (s, 1H), 7.64 (s, 1H), 7.09 (d, J=8.9 Hz, 1H), 3.93 (s, 2H), 2.65 (s, 3H). LCMS (ESI) [M+H]$^+$ m/z: calcd 236.0, found 236.0.

Step 2: Synthesis of tert-butyl N-[4-(2-methylthiazol-5-yl)-2-nitro-phenyl]carbamate A mixture of 4-(2-methylthiazol-5-yl)-2-nitro-aniline (about 311 mg, 1.32 mmol), tert-butoxycarbonyl tert-butyl carbonate (about 0.7 mL, 3.05 mmol), TEA (about 0.6 mL, 4.30 mmol) and DMAP (about 80 mg, 0.655 mmol) in DCM (about 5 mL) was stirred at about 20° C. for about 12 hours. The reaction mixture was diluted with H$_2$O (about 20 mL) and extracted with dichloromethane (about 20 mL*3). The combined organic layers were dried over anhydrous Na$_2$SO$_4$, filtered and concentrated under reduced pressure. The residue was diluted with DCM (about 5 mL). To the mixture was added TEA (about 0.6 mL, 4.30 mmol), DMAP (about 80 mg, 0.655 mmol) and tert-butoxycarbonyl tert-butyl carbonate (about 0.7 mL, 3.05 mmol), The mixture was stirred about 20° C. for about 12 hours. The reaction mixture was diluted with H$_2$O (about 20 mL) and extracted with dichloromethane (about 20 mL*3). The combined organic layers were dried over anhydrous Na$_2$SO$_4$, filtered and concentrated under reduced pressure. The residue was purified by flash chromatography (Biotage®; about 20 g SepaFlash® Silica Flash Column, Petroleum ether/EtOAc with EtOAc from 0~30%, flow rate=40 mL/min, 254 nm) to afford tert-butyl N-[4-(2-methylthiazol-5-yl)-2-nitro-phenyl]carbamate (about 143 mg). $^1$H NMR (400 MHz, DMSO-d$_6$) δ ppm 9.69 (s, 1H), 8.14 (s, 1H), 8.12 (d, J=2.26 Hz, 1H), 7.89 (dd, J=8.53, 2.26 Hz, 1H), 7.68 (d, J=8.53 Hz, 1H), 2.68 (s, 3H), 1.45 (s, 9H); LCMS (ESI) [M+H]$^+$ m/z: calcd 336.1, found 336.1.

Step 3: Synthesis of tert-butyl N-[2-amino-4-(2-methylthiazol-5-yl)phenyl]carbamate To a solution of tert-butyl N-[4-(2-methylthiazol-5-yl)-2-nitro-phenyl]carbamate (about 143 mg, 0.426 mmol) in THF (about 5 mL) was added Pd—C(about 15 mg, 10% of Pd with 50% of water, wt %) under N$_2$ atmosphere. The suspension was degassed and purged with hydrogen for about 3 times. The mixture was stirred under hydrogen (in balloon) at about 20° C. for about 12 hours. The mixture was filtered. The filtrate was concentrated under reduced pressure to give tert-butyl N-[2-amino-4-(2-methylthiazol-5-yl) phenyl]carbamate (about 93.4 mg), which was directly used without further purification. $^1$H NMR (400 MHz, DMSO-d$_6$) δ ppm 8.37 (brs, 1H), 7.79 (s, 1H), 7.28 (d, J=8.03 Hz, 1H), 6.89 (d, J=2.26 Hz, 1H), 6.80 (dd, J=8.16, 2.13 Hz, 1H), 5.04 (s, 2H), 2.64 (s, 3H), 1.46 (s, 9H). LCMS (ESI) [M+H]$^+$ m/z: calcd 306.1, found 306.1.

Step 4: Synthesis of tert-butyl N-[[4-[[2-(tert-butoxycarbonylamino)-5-(2-methylthiazol-5-yl)phenyl]carbamoyl]phenyl]-methyl-oxo-sulfanylidene]carbamate To a solution of tert-butyl N-[2-amino-4-(2-methylthiazol-5-yl)phenyl]carbamate (about 93.4 mg, 0.305 mmol) and 4-(N-tert-butoxycarbonyl-S-methyl-sulfonimidoyl)benzoic acid (about 92 mg, 0.307 mmol) in pyridine (about 5 mL) was added 3-(ethyliminomethyleneamino)-N,N-dimethyl-propan-1-amine;hydrochloride (about 88 mg, 0.459 mmol). The mixture was stirred at about 50° C. for about 30 mins. The reaction mixture was concentrated under reduced pressure. The residue was purified by flash chromatography (Biotage®; about 20 g SepaFlash® Silica Flash Column, Petroleum ether/EtOAc with EtOAc from 0~100%, flow rate=30 mL/min, 254 nm) to afford tert-butyl N-[[4-[[2-(tert-butoxycarbonylamino)-5-(2-methylthiazol-5-yl)phenyl]carbamoyl]phenyl]-methyl-oxo-sulfanylidene]carbamate (about 120 mg). $^1$H NMR (400 MHz, chloroform-d) δ ppm 9.70-9.87 (m, 1H), 8.21 (d, J=8.28 Hz, 2H), 8.06-8.12 (m, 3H), 7.80 (s, 1H), 7.35 (dd, J=8.28, 1.76 Hz, 1H), 7.21 (d, J=8.28 Hz, 1H), 6.82 (s, 1H), 3.50 (s, 3H), 3.28 (s, 3H), 1.54 (s, 9H), 1.41 (s, 9H). LCMS (ESI) [M+H]$^+$ m/z: calcd 587.2, found 587.2.

Step 5: Synthesis of N-[2-amino-5-(2-methylthiazol-5-yl)phenyl]-4-(methylsulfonimidoyl)benzamide To a solution of tert-butyl N-[[4-[[2-(tert-butoxycarbonylamino)-5-(2-methylthiazol-5-yl)phenyl]carbamoyl]phenyl]-methyl-oxo-sulfanylidene]carbamate (about 120 mg, 0.204 mmol) in DCM (about 5 mL) was added TFA (about 0.32 mL, 4.15 mmol). The mixture was stirred at about 20° C. for about 12 hours. The reaction mixture was concentrated under reduced pressure. The mixture was adjusted to about pH=8 with 28% NH₄OH solution. The residue was purified by preparative HPLC (Instrument: Gilson GX-281 Liquid Handler, Gilson 322 Pump, Gilson 156 UV Detector; Column: Durashell 75×40 mm×3 μm; Mobile phase A: H₂O with 10 mmol NH₄HCO₃ (v %); Mobile phase B: ACN; Gradient: B from 25% to 55% in 7.8 min, hold 100% B for 2 min; Flow Rate: 30 mL/min; Column Temperature: 30° C.; Wavelength: 220 nm, 254 nm) to afford N-[2-amino-5-(2-methylthiazol-5-yl)phenyl]-4-(methylsulfonimidoyl)benzamide (about 14.4 mg). $^1$H NMR (400 MHz, DMSO-d₆) δ ppm 9.89-10.00 (m, 1H), 8.16 (d, J=8.03 Hz, 2H), 7.97-8.10 (m, 2H), 7.70-7.82 (m, 1H), 7.40 (s, 1H), 7.20-7.32 (m, 1H), 6.81 (d, J=8.53 Hz, 1H), 5.24-5.36 (m, 2H), 4.40-4.43 (m, 1H), 3.12 (s, 3H), 2.62 (s, 3H). LCMS (ESI) [M+H]⁺ m/z: calcd 387.1, found 387.2; HPLC: 98.630%@220 nm, 95.080%@254 nm.

Example 22. Synthesis of N-[2-amino-5-(2-cyclopropylethynyl)phenyl]-4-(methylsulfonimidoyl)benzamide (Compound 155)

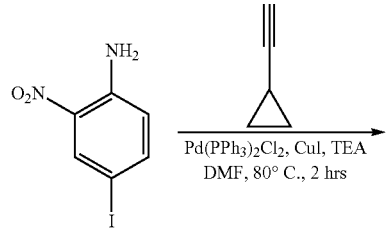

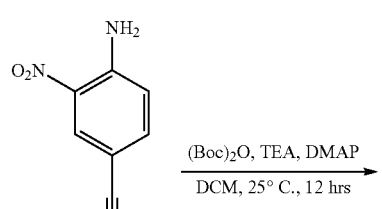

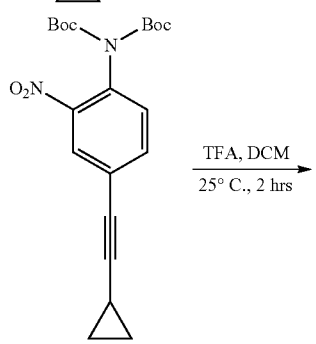

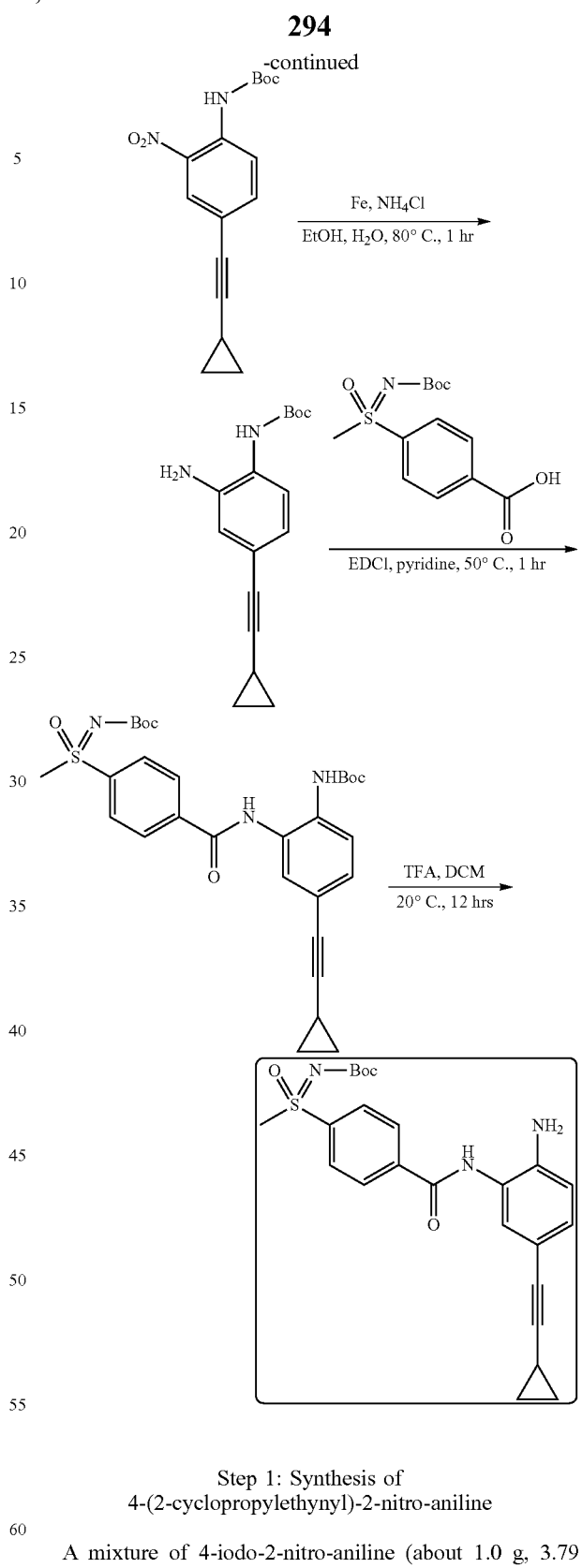

Step 1: Synthesis of 4-(2-cyclopropylethynyl)-2-nitro-aniline

A mixture of 4-iodo-2-nitro-aniline (about 1.0 g, 3.79 mmol), ethynylcyclopropane (about 0.3 mL, 3.78 mmol), iodocopper (about 721 mg, 3.79 mmol), TEA (about 3.78 mmol, 0.5 mL) and dichloropalladium;triphenylphosphane (about 266 mg, 0.378 mmol) in DMF (about 10 mL) was degassed and purged with N₂ for about 3 times, and then the mixture was stirred at about 80° C. for about 2 hours under N₂ atmosphere. The reaction mixture was diluted with NH₄Cl (about 30 mL) and extracted with EtOAc (about 40 mL*2). The combined organic layers were washed with brine (about 40 mL), dried over anhydrous Na₂SO₄, filtered and concentrated under reduced pressure. The residue was purified by flash chromatography (ISCO®; about 20 g SepaFlash® Silica Flash Column, Petroleum Ether/EtOAc with EtOAc from 0~30%, 40 mL/min, 254 nm) to afford 4-(2-cyclopropylethynyl)-2-nitro-aniline (about 880 mg). LCMS (ESI) [M+H]⁺ m/z: calcd 203.1, found 202.9.

Step 2: Synthesis of tert-butyl N-tert-butoxycarbonyl-N-[4-(2-cyclopropylethynyl)-2-nitro-phenyl]carbamate To a solution of 4-(2-cyclopropylethynyl)-2-nitro-aniline (about 880 mg, 4.35 mmol) in THF (about 10 mL) were added tert-butoxycarbonyl tert-butyl carbonate (about 2.5 mL, 10.9 mmol), N,N-diethylethanamine (about 1.8 mL, 13.1 mmol) and N,N-dimethylpyridin-4-amine (about 53 mg, 0.434 mmol). The mixture was stirred at about 25° C. for about 12 hours. The reaction mixture was diluted with water (about 20 mL) and extracted with EtOAc (about 30 mL*3). The combined organic layers were washed with brine (about 30 mL), dried over Na₂SO₄ and filtered. The filtrate was concentrated under reduced pressure. The residue was purified by flash chromatography (ISCO®; about 12 g AgelaFlash® Silica Flash Column, petroleum ether/EtOAc with EtOAc from 0~15%, flow rate=40 mL/min, 254 nm) to afford tert-butyl N-tert-butoxycarbonyl-N-[4-(2-cyclopropylethynyl)-2-nitro-phenyl]carbamate (about 1.32 g). ¹H NMR (400 MHz, CDCl₃) δ ppm 8.02 (d, J=2.0 Hz, 1H), 7.56 (dd, J=8.0, 1.9 Hz, 1H), 7.19 (d, J=8.4 Hz, 1H), 1.44-1.51 (m, 1H), 1.38 (s, 18H), 0.89-0.96 (m, 2H), 0.85 (qd, J=5.2, 2.8 Hz, 2H). LCMS (ESI) [M+H]⁺ m/z: calcd 403.2, found 202.9 (Boc cleaved mass).

Step 3: Synthesis of tert-butyl N-[4-(2-cyclopropylethynyl)-2-nitro-phenyl]carbamate To a solution of tert-butyl N-tert-butoxycarbonyl-N-[4-(2-cyclopropylethynyl)-2-nitro-phenyl]carbamate (about 1.32 g, 3.28 mmol) in DCM (about 10 mL) was added TFA (about 0.4 mL, 4.92 mmol). The mixture was stirred at about 25° C. for about 2 hours. The reaction mixture was diluted with DCM (about 30 mL) and adjusted to about pH=8 with saturated Na₂CO₃ aqueous solution. The resultant mixture was dried over Na₂SO₄ and filtered. The filtrate was concentrated under reduced pressure. The residue was purified by flash chromatography (ISCO®; about 12 g SepaFlash® Silica Flash Column, Petroleum Ether/EtOAc with EtOAc from 0~15%, 60 mL/min, 254 nm) to afford tert-butyl N-[4-(2-cyclopropylethynyl)-2-nitro-phenyl]carbamate (about 915 mg). ¹H NMR (400 MHz, CDCl₃) δ ppm 9.66 (s, 1H), 8.49 (d, J=8.8 Hz, 1H), 8.19 (d, J=1.6 Hz, 1H), 7.57 (dd, J=8.8, 2.0 Hz, 1H), 1.54 (s, 9H), 1.40-1.48 (m, 1H), 0.87-0.93 (m, 2H), 0.80-0.85 (m, 2H).

Step 4: Synthesis of tert-butyl N-[2-amino-4-(2-cyclopropylethynyl)phenyl]carbamate To a solution of tert-butyl N-[4-(2-cyclopropylethynyl)-2-nitro-phenyl]carbamate (about 915 mg, 3.03 mmol) in EtOH (about 9 mL) and H₂O (about 3 mL) was added Iron (about 845 mg, 15.1 mmol) and ammonia;hydrochloride (about 809 mg, 15.1 mmol). The mixture was stirred at about 80° C. for about 1 hour. The reaction mixture was filtered. The filtrate was diluted with water (about 20 mL) and extracted with EtOAc (about 30 mL*2). The combined organic layers were washed with brine (about 30 mL), dried over Na₂SO₄ and filtered. The filtrate was concentrated under reduced pressure. The residue was purified by flash chromatography (ISCO®; about 12 g AgelaFlash® Silica Flash Column, petroleum ether/EtOAc with EtOAc from 0~15%, flow rate=40 mL/min, 254 nm) to afford tert-butyl N-[2-amino-4-(2-cyclopropylethynyl)phenyl]carbamate (about 371 mg). LCMS (ESI) [M+H]⁺ m/z: calcd 273.2, found 216.9.

Step 5: Synthesis of tert-butyl N-[[4-[[2-(tert-butoxycarbonylamino)-5-(2-cyclopropylethynyl)phenyl]carbamoyl]phenyl]-methyl-oxo-sulfanylidene]carbamate To a solution of tert-butyl N-[2-amino-4-(2-cyclopropylethynyl)phenyl]carbamate (about 120 mg, 0.441 mmol) in pyridine (about 6 mL) was added 4-(N-tert-butoxycarbonyl-S-methyl-sulfonimidoyl)benzoic acid (about 109 mg, 0.364 mmol) and 3-(ethyliminomethyleneamino)-N,N-dimethyl-propan-1-amine (about 85 mg, 0.548 mmol). The mixture was stirred at about 50° C. for about 1 hour. The reaction mixture was diluted with NH₄Cl (about 30 mL) and extracted with EtOAc (about 40 mL*2). The combined organic layers were washed with brine (about 40 mL), dried over anhydrous Na₂SO₄, filtered and concentrated under reduced pressure. The residue was purified by flash chromatography (ISCO®; about 4 g SepaFlash® Silica Flash Column, Petroleum Ether/EtOAc with EtOAc from 0~100%, 40 mL/min, 254 nm) to afford tert-butyl N-[[4-[[2-(tert-butoxycarbonylamino)-5-(2-cyclopropylethynyl)phenyl]carbamoyl]phenyl]-methyl-oxo-sulfanylidene]carbamate (about 123 mg). LCMS (ESI) [M+Na]⁺ m/z: calcd 576.2, found 576.1.

Step 6: Synthesis of N-[2-amino-5-(2-cyclopropylethynyl)phenyl]-4-(methylsulfonimidoyl)benzamide To a solution of tert-butyl N-[[4-[[2-(tert-butoxycarbonylamino)-5-(2-cyclopropylethynyl)phenyl]carbamoyl]phenyl]-methyl-oxo-sulfanylidene]carbamate (about 126 mg, 0.228 mmol) in DCM (about 10 mL) was added TFA (about 0.2 mL, 2.27 mmol). The mixture was stirred at about 20° C. for about 12 hours. The reaction mixture was diluted with DCM (about 30 mL) and adjusted to about pH=8 with saturated Na₂CO₃ aqueous solution. The resultant mixture was dried over Na₂SO₄ and filtered. The filtrate was concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75*40 mm*3 μm; Mobile phase A: H₂O with 10 mmol NH₄HCO₃ (v %); B: ACN; Gradient: B from 31% to 61% in 9.5 min, hold 100% B for 2 min; Flow Rate: 30 mL/min; Column Temperature: 30° C.; Wavelength: 220 nm, 254 nm) to afford N-[2-amino-5-(2-cyclopropylethynyl)phenyl]-4-(methylsulfonimidoyl)benzamide (about 4 mg). ¹H NMR (400 MHz, CDCl₃) δ ppm 8.15 (d, J=8.0 Hz, 2H), 8.07 (d, J=8.0 Hz, 2H), 7.83-7.92 (m, 1H), 7.39 (s, 1H), 7.16 (dd, J=8.0, 1.6 Hz, 1H), 6.77 (d, J=8.4 Hz, 1H), 3.16 (s, 3H), 1.39-1.46 (m, 1H), 0.81-0.88 (m, 2H), 0.73-0.80 (m, 2H); LCMS (ESI) [M+H]⁺ m/z: calcd 354.1, found 353.9. HPLC: 95.35%@220 nm, 94.82%@254 nm.

Example 23. Synthesis of N-[2-amino-5-(4-fluorophenyl)phenyl]-4-(1-oxo-4,5-dihydro-3H-isothiazol-1-yl)benzamide (Compound 154)

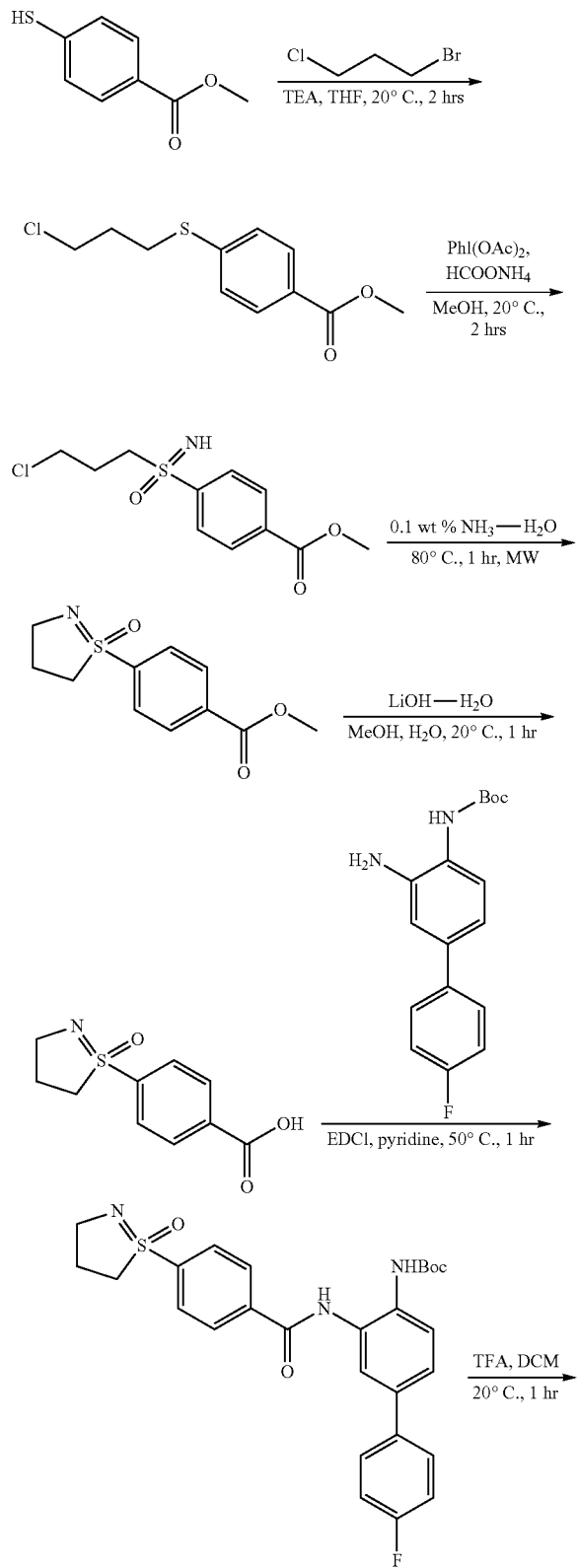

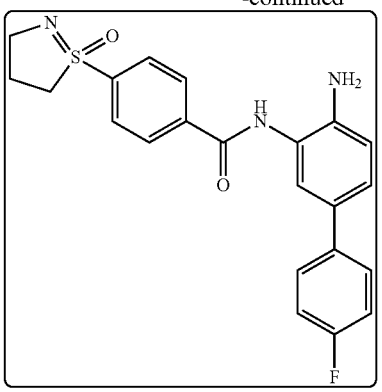

Step 1: methyl 4-(3-chloropropylsulfanyl)benzoate

A mixture of methyl 4-sulfanylbenzoate (about 1 g, 5.94 mmol), 1-bromo-3-chloro-propane (about 1.2 mL, 11.9 mmol), N,N-diethylethanamine (about 1.7 mL, 11.9 mmol) in THF (about 30 mL) was stirred at about 20° C. for about 2 hours. The reaction mixture was diluted with $H_2O$ (about 20 mL) and extracted with EtOAc (about 40 mL*2). The combined organic layers were dried over anhydrous $Na_2SO_4$, filtered and concentrated under reduced pressure. The residue was purified by flash chromatography (ISCO®; about 25 g SepaFlash® Silica Flash Column, Petroleum ether/EtOAc with EtOAc from 0~20%, flow rate=25 mL/min, 254 nm) to afford methyl 4-(3-chloropropylsulfanyl)benzoate (about 1.3 g). $^1$H NMR (400 MHz, chloroform-d) δ ppm 7.89-7.94 (m, 2H), 7.26-7.33 (m, 2H), 3.88 (s, 3H), 3.65 (t, J=6.15 Hz, 2H), 3.13 (t, J=7.03 Hz, 2H), 2.11 (quin, J=6.59 Hz, 2H); LCMS (ESI) [M+H]$^+$ m/z: calcd 245.0, found 245.0.

Step 2: Synthesis of methyl 4-(3-chloropropylsulfonimidoyl)benzoate

To a solution of methyl 4-(3-chloropropylsulfanyl)benzoate (about 1.3 g, 5.31 mmol) in MeOH (about 20 mL) was added ammonia;carbamic acid (about 0.83 g, 10.6 mmol) and [acetoxy(phenyl)-iodanyl] acetate (about 4.28 g, 13.3 mmol). The mixture was stirred at about 20° C. for about 2 hours. The reaction mixture was diluted with $H_2O$ (about 20 mL) and extracted with EtOAc (about 20 mL*3). The combined organic layers were dried over anhydrous $Na_2SO_4$, filtered and concentrated under reduced pressure. The residue was purified by flash chromatography (Biotage®; about 20 g SepaFlash® Silica Flash Column, Petroleum ether/EtOAc with EtOAc from 0~100%, flow rate=45 mL/min, 254 nm) to afford methyl 4-(3-chloropropylsulfonimidoyl)benzoate (about 0.98 g). $^1$H NMR (400 MHz, chloroform-d) δ ppm 8.22 (d, J=8.50 Hz, 2H), 8.05 (d, J=8.50 Hz, 2H), 3.97 (s, 3H), 3.62 (t, J=6.19 Hz, 2H), 3.27-3.41 (m, 2H), 2.30-2.41 (m, 2H). LCMS (ESI) [M+H]$^+$ m/z: calcd 276.0, found 276.0.

Step 3: Synthesis of methyl 4-(1-oxo-4,5-dihydro-3H-isothiazol-1-yl)benzoate A methyl 4-(3-chloropropylsulfonimidoyl)benzoate (about 980 mg, 3.55 mmol) in 0.1 wt % $NH_3$—$H_2O$ (about 10 mL) were taken up into a microwave tube. The sealed tube was heated at about 80° C. for about 1 hour in microwave. The reaction mixture was concentrated under reduced pressure. The residue was purified by flash chromatography (Biotage®; about 20 g SepaFlash® Silica Flash Column, Petroleum ether/EtOAc with EtOAc from 0~100%, flow rate=30 mL/min, 254 nm) to afford methyl 4-(1-oxo-4,5-dihydro-3H-isothiazol-1-yl)benzoate (about 243 mg). LCMS (ESI) [M+H]$^+$ m/z: calcd 240.1, found 240.1.

Step 4: Synthesis of 4-(1-oxo-4,5-dihydro-3H-isothiazol-1-yl)benzoic acid

To a solution of methyl 4-(1-oxo-4,5-dihydro-3H-isothiazol-1-yl)benzoate (about 245 mg, 1.02 mmol) in MeOH (about 4 mL) and H$_2$O (about 2 mL) was added LiOH—H$_2$O (about 430 mg, 10.3 mmol). The mixture was stirred at about 20° C. for about 1 hour. The mixture was filtered. The filtrate was concentrated under reduced pressure to give 4-(1-oxo-4,5-dihydro-3H-isothiazol-1-yl)benzoic acid (about 1.3 g), which was directly used without further purification. $^1$H NMR (400 MHz, methanol-d$_4$) δ ppm 8.32-8.38 (m, 2H), 8.27-8.31 (m, 2H), 3.95-4.47 (m, 4H), 2.68-2.95 (m, 2H); LCMS (ESI) [M+H]$^+$ m/z: calcd 226.0, found 226.1.

Step 5: Synthesis of tert-butyl N-[4-(4-fluorophenyl)-2-[[4-(1-oxo-4,5-dihydro-3H-isothiazol-1-yl)benzoyl]amino]phenyl]carbamate To a solution of 4-(1-oxo-4,5-dihydro-3H-isothiazol-1-yl)benzoic acid (about 600 mg, 0.453 mmol) and tert-butyl N-[2-amino-4-(4-fluorophenyl)phenyl]carbamate (about 137 mg, 0.453 mmol) in pyridine (about 6 mL) was added 3-(ethyliminomethyleneamino)-N,N-dimethyl-propan-1-amine;hydrochloride (about 130 mg, 0.678 mmol). The mixture was stirred at about 50° C. for about 1 hour. The reaction mixture was concentrated under reduced pressure. The residue was purified by flash chromatography (Biotage®; about 20 g SepaFlash® Silica Flash Column, Petroleum ether/EtOAc with EtOAc from 0~100%, flow rate=30 mL/min, 254 nm) to afford tert-butyl N-[4-(4-fluorophenyl)-2-[[4-(1-oxo-4,5-dihydro-3H-isothiazol-1-yl)benzoyl]amino]phenyl]carbamate (about 70 mg). $^1$H NMR (400 MHz, DMSO-d$_6$) δ ppm 10.09-10.14 (m, 1H), 8.77-8.85 (m, 1H), 8.18 (d, J=8.38 Hz, 2H), 8.02 (d, J=8.38 Hz, 2H), 7.80 (d, J=1.88 Hz, 1H), 7.65-7.74 (m, 3H), 7.53 (dd, J=8.50, 2.13 Hz, 1H), 7.30 (t, J=8.88 Hz, 2H), 3.82-3.88 (m, 1H), 3.66-3.74 (m, 1H), 3.44-3.48 (m, 2H), 2.22-2.31 (m, 2H), 1.46 (s, 9H); LCMS (ESI) [M+H]$^+$ m/z: calcd 510.2, found 510.2.

Step 6: Synthesis of N-[2-amino-5-(4-fluorophenyl)phenyl]-4-(1-oxo-4,5-dihydro-3H-isothiazol-1-yl)benzamide To a solution of tert-butyl N-[4-(4-fluorophenyl)-2-[[4-(1-oxo-4,5-dihydro-3H-isothiazol-1-yl)benzoyl]amino]phenyl]carbamate (about 70 mg, 0.137 mmol) in DCM (about 5 mL) was added TFA (about 0.2 mL, 2.60 mmol). The mixture was stirred at about 20° C. for about 1 hour. The reaction mixture was concentrated under reduced pressure. The mixture adjusted to about pH=8 with 28 wt % NH$_3$—H$_2$O. The mixture was purified by preparative HPLC (Instrument: Gilson GX-281 Liquid Handler, Gilson 322 Pump, Gilson 156 UV Detector; Column: Du-rashell 75*40 mm*3 µm; Mobile phase A: H$_2$O with 0.05% NH$_4$HCO$_3$ (v %); Mobile phase B: MeCN; Gradient: B from 35% to 65% in 7.8 min, hold 100% B for 2 min; Flow Rate: 30 mL/min; Column Temperature: 30° C.; Wavelength: 220 nm, 254 nm) to afford N-[2-amino-5-(4-fluorophenyl)phenyl]-4-(1-oxo-4,5-dihydro-3H-isothiazol-1-yl)benzamide (about 24.4 mg). $^1$H NMR (400 MHz, DMSO-d$_6$) δ ppm 9.91-10.01 (m, 1H), 8.19 (s, 2H), 8.00 (s, 2H), 7.58 (dd, J=8.69, 5.44 Hz, 2H), 7.50 (d, J=1.88 Hz, 1H), 7.32 (dd, J=8.38, 2.13 Hz, 1H), 7.22 (t, J=8.88 Hz, 2H), 6.86 (d, J=8.38 Hz, 1H), 5.18 (brs, 2H), 3.81-3.88 (m, 1H), 3.70 (dt, J=10.22, 6.58 Hz, 1H), 3.44-3.48 (m, 2H), 2.22-2.31 (m, 2H); $^{19}$F NMR (376 MHz, DMSO-d$_6$) δ ppm−117.456; LCMS (ESI) [M+H]$^+$ m/z: calcd 410.1, found 410.2; HPLC: 98.720%@220 nm; 98.39%@254 nm.

Example 24. Synthesis of N-[2-amino-5-(2-thienyl)phenyl]-4-(N-cyano-S-methyl-sulfonimidoyl)benzamide (Compound 153)

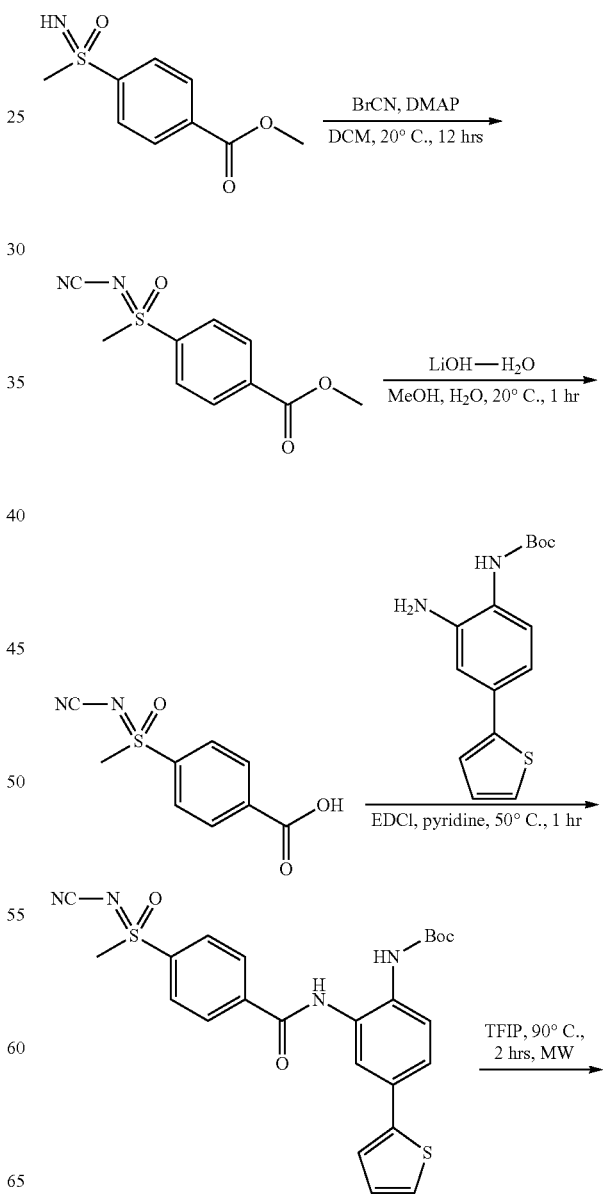

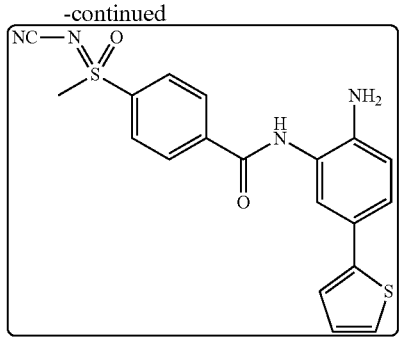

Step 1: Synthesis of methyl 4-(N-cyano-S-methyl-sulfonimidoyl)benzoate

To a solution of methyl 4-(methylsulfonimidoyl)benzoate (about 260 mg, 1.22 mmol) in DCM (about 6 mL) was added DMAP (about 150 mg, 1.23 mmol) and BrCN (about 140 mg, 1.32 mmol). The mixture was stirred at about 20° C. for about 12 hours. The reaction mixture was quenched with H$_2$O. The mixture was extracted with DCM (about 15 mL*3). The combined organic layers were washed with brine (about 40 mL), dried over Na$_2$SO$_4$ and then concentrated. The residue was purified by flash chromatography (ISCO®; about 25 g SepaFlash® Silica Flash Column, petroleum ether/EtOAc with EtOAc from 0~50%, flow rate: 20 mL/min, 254 nm) to give methyl 4-(N-cyano-S-methyl-sulfonimidoyl)benzoate (about 230 mg). LCMS (ESI) [M+H]$^+$ m/z: calcd 239.0, found 238.8.

Step 2: Synthesis of 4-(N-cyano-S-methyl-sulfonimidoyl)benzoic acid

To a solution of methyl 4-(N-cyano-S-methyl-sulfonimidoyl)benzoate (about 230 mg, 0.965 mmol) in MeOH (about 2 mL) and H$_2$O (about 1 mL) was added lithium;hydroxide;hydrate (about 150 mg, 3.57 mmol). The mixture was stirred at about 20° C. for about 1 hour. The reaction mixture was concentrated under reduced pressure to remove the organic solvent. The aqueous phase was adjusted to about pH=4 with 2N HCl aqueous solution. The mixture was filtered. The filter cake was dried under reduced pressure to give 4-(N-cyano-S-methyl-sulfonimidoyl)benzoic acid (about 160 mg). $^1$H NMR (400 MHz, DMSO-d$_6$) δ ppm 8.23-8.29 (m, 2H), 8.15-8.20 (m, 2H), 3.79 (s, 3H); LCMS (ESI) [M+H]$^+$ m/z: calcd 225.0, found 224.8.

Step 3: Synthesis of tert-butyl N-[2-[[4-(N-cyano-S-methyl-sulfonimidoyl)benzoyl]amino]-4-(2-thienyl)phenyl]carbamate To a solution of 4-(N-cyano-S-methyl-sulfonimidoyl)benzoic acid (about 160 mg, 0.713 mmol) in pyridine (about 3 mL) was added EDCI (about 200 mg, 1.04 mmol) and tert-butyl N-[2-amino-4-(2-thienyl)phenyl]carbamate (about 250 mg, 0.860 mmol). The mixture was stirred at about 50° C. for about 1 hour. The reaction mixture was concentrated under reduced pressure. The reaction mixture was dilute with water (about 5 mL) and extracted with DCM (about 10 mL*3). The combined organic layers were washed with brine (about 15 mL), dried over Na$_2$SO$_4$ and filtered. The filtrate was concentrated under reduced pressure. The residue was purified by flash chromatography (ISCO®; about 25 g SepaFlash® Silica Flash Column, petroleum ether/EtOAc with EtOAc from 0~50%, flow rate: 18 mL/min, 254 nm) to give tert-butyl N-[2-[[4-(N-cyano-S-methyl-sulfonimidoyl)benzoyl]amino]-4-(2-thienyl)phenyl]carbamate (about 110 mg). $^1$H NMR (400 MHz, DMSO-d$_6$) δ ppm 10.17 (s, 1H), 8.82 (s, 1H), 8.29-8.34 (m, 2H), 8.21-8.26 (m, 2H), 7.79 (s, 1H), 7.72 (d, J=8.8 Hz, 1H), 7.51-7.57 (m, 2H), 7.46 (d, J=2.4 Hz, 1H), 7.13 (t, J=4.4 Hz, 1H), 3.82 (s, 3H), 1.45 (s, 9H); LCMS (ESI) [M+H]$^+$ m/z: calcd 497.1, found 396.8 (Boc cleaved mass).

Step 4: Synthesis of N-[2-amino-5-(2-thienyl)phenyl]-4-(N-cyano-S-methyl-sulfonimidoyl)benzamide To a solution of tert-butyl N-[2-[[4-(N-cyano-S-methyl-sulfonimidoyl)benzoyl]amino]-4-(2-thienyl)phenyl]carbamate (about 100 mg, 0.201 mmol) in HFIP (about 12 mL) was taken up into a microwave tube. The sealed tube was heated at about 90° C. for about 2 hours in microwave. The mixture was concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 µm; Mobile phase A: H$_2$O with 10 mm NH$_4$HCO$_3$ (v %); Mobile phase B: ACN; Gradient: B from 32% to 62% in 9.5 min, hold 100% B for 2 min; Flow Rate: 30 mL/min; Column Temperature: 30° C.; Wavelength: 220 nm, 254 nm) to give N-[2-amino-5-(2-thienyl)phenyl]-4-(N-cyano-S-methyl-sulfonimidoyl)benzamide (about 36.4 mg). $^1$H NMR (400 MHz, methanol-d$_4$) δ ppm 8.33-8.37 (m, 2H), 8.22-8.28 (m, 2H), 7.54 (d, J=2.0 Hz, 1H), 7.41 (dd, J=8.4, 2.0 Hz, 1H), 7.25 (dd, J=7.6, 4.4 Hz, 2H), 7.05 (dd, J=5.2, 3.6 Hz, 1H), 6.94 (d, J=8.4 Hz, 1H), 3.65 (s, 3H); LCMS [M+H]$^+$ m/z: calcd 397.1; found 396.9; HPLC: 99.290%@220 nm; 99.270%@254 nm.

Example 25. Synthesis of N-[2-amino-5-(5-fluoro-2-thienyl)phenyl]-6-(methylsulfonimidoyl)pyridazine-3-carboxamide (Compound 152)

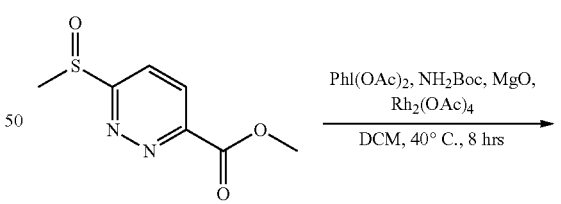

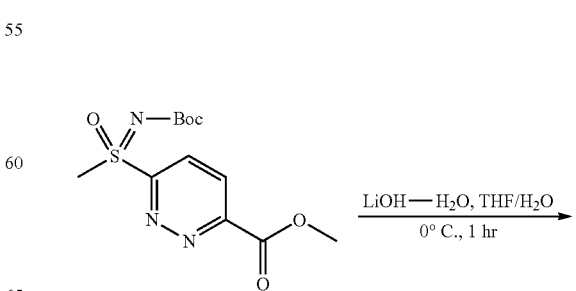

-continued

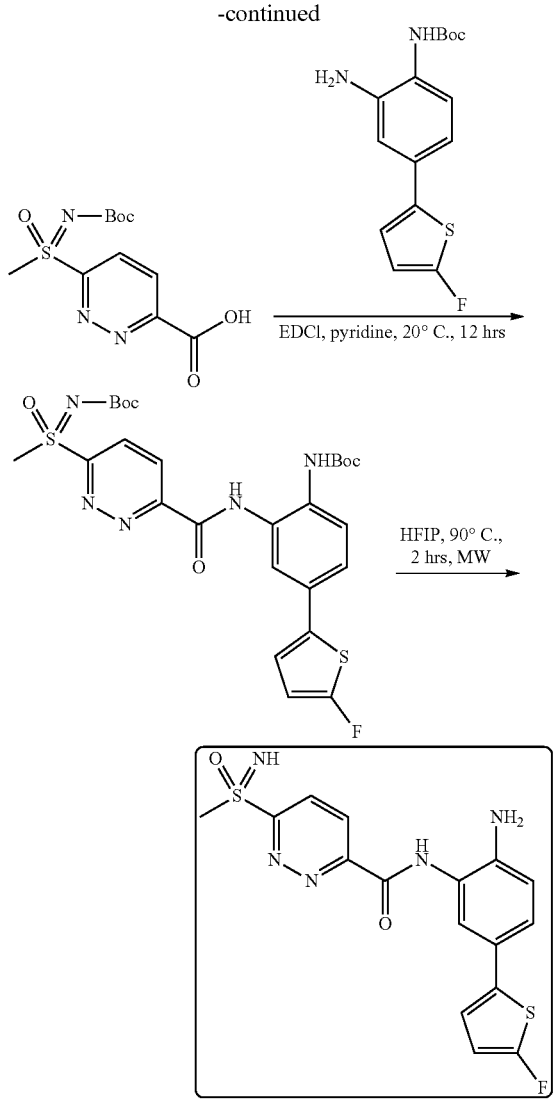

Step 1: Synthesis of methyl 6-(N-tert-butoxycarbonyl-S-methyl-sulfonimidoyl)pyridazine-3-carboxylate To a solution of methyl 6-methylsulfinylpyridazine-3-carboxylate (about 1.3 g, 6.49 mmol), tert-butyl carbamate (about 910 mg, 7.77 mmol), [acetoxy(phenyl)-iodanyl] acetate (about 3.16 g, 9.82 mmol) and oxomagnesium (about 1.3 g, 32.3 mmol) in DCM (about 30 mL) was added diacetoxyrhodium (about 70 mg, 0.317 mmol). The reaction mixture was stirred at about 40° C. for about 8 hours. The reaction mixture was concentrated under reduced pressure. The residue was purified by flash chromatography (ISCO®; about 40 g AgelaFlash® Silica Flash Column, petroleum ether/EtOAc with EtOAc from 0~70%, flow rate=50 mL/min, 254 nm) to afford methyl 6-(N-tert-butoxycarbonyl-S-methyl-sulfonimidoyl)pyridazine-3-carboxylate (about 1.1 g). $^1$H NMR (400 MHz, chloroform-d) δ ppm 8.58 (d, J=8.8 Hz, 1H), 8.47 (d, J=8.8 Hz, 1H), 4.13 (s, 3H), 3.59 (s, 3H), 1.38 (s, 9H); LCMS (ESI) [M+H]$^+$ m/z: calcd 316.1, found 215.8 (Boc cleaved mass).

Step 2: Synthesis of 6-(N-tert-butoxycarbonyl-S-methyl-sulfonimidoyl)pyridazine-3-carboxylic acid To a solution of methyl 6-(N-tert-butoxycarbonyl-S-methyl-sulfonimidoyl)pyridazine-3-carboxylate (about 500 mg, 1.59 mmol) in THF (about 5 mL) and H$_2$O (about 0.5 mL) was added lithium;hydroxide;hydrate (about 150 mg, 3.57 mmol). The mixture was stirred at about 0° C. for about 1 hour. The reaction mixture was diluted with DCM (about 50 mL), adjusted to about pH=4 with 2 N HCl aqueous solution and dried over Na$_2$SO$_4$. The suspension was filtered and the filtrate was concentrated under reduced pressure to give 6-(N-tert-butoxycarbonyl-S-methyl-sulfonimidoyl) pyridazine-3-carboxylic acid (about 470 mg). $^1$H NMR (400 MHz, DMSO-d$_6$) δ ppm 8.49-8.56 (m, 2H), 3.60 (s, 3H), 1.22 (s, 9H).

Step 3: Synthesis of tert-butyl N-[[6-[[2-(tert-butoxycarbonylamino)-5-(5-fluoro-2-thienyl)phenyl]carbamoyl]pyridazin-3-yl]-methyl-oxo-sulfanylidene]carbamate To a solution of 6-(N-tert-butoxycarbonyl-S-methyl-sulfonimidoyl)pyridazine-3-carboxylic acid (about 200 mg, 0.664 mmol) in pyridine (about 5 mL) were added tert-butyl N-[2-amino-4-(5-fluoro-2-thienyl)phenyl]carbamate (about 90 mg, 0.291 mmol) and 3-(ethyliminomethyleneamino)-N,N-dimethyl-propan-1-amine;hydrochloride (about 110 mg, 0.574 mmol). The mixture was stirred at about 20° C. for about 12 hours. The reaction mixture was quenched with 2N HCl aqueous solution to adjust to about pH=4 and extracted with DCM (about 20 mL*3). The combined organic layers were dried over Na$_2$SO$_4$ and filtered. The filtrate was concentrated under reduced pressure. The residue was purified by preparative TLC (silica, petroleum ether/EtOAc=1/1, 254 nm) to give tert-butyl N-[[6-[[2-(tert-butoxycarbonylamino)-5-(5-fluoro-2-thienyl)phenyl]carbamoyl]pyridazin-3-yl]-methyl-oxo-sulfanylidene]carbamate (about 130 mg). LCMS (ESI) [M+Na]$^+$ m/z: calcd 614.2, found 614.1.

Step 4: Synthesis of N-[2-amino-5-(5-fluoro-2-thienyl)phenyl]-6-(methylsulfonimidoyl)pyridazine-3-carboxamide Tert-butyl N-[[6-[[2-(tert-butoxycarbonylamino)-5-(5-fluoro-2-thienyl)phenyl]carbamoyl]pyridazin-3-yl]-methyl-oxo-sulfanylidene]carbamate (about 120 mg, 0.208 mmol) in HFIP (about 12 mL) was stirred at about 90° C. for about 2 hours in microwave. The reaction mixture was concentrated under reduced pressure. The residue was purified by preparative TLC (silica, EtOAc/MeOH=10/1; 254 nm) to give a product. The product was further purified by preparative HPLC (Instrument: Gilson GX-281 Liquid Handler, Gilson 322 Pump, Gilson 156 UV Detector; Column: Phenomenex C18 80*40 mm*3 μm; Mobile phase A: water with 10 mmol NH$_4$HCO$_3$ (v %); Mobile phase B: MeCN; Gradient: B from 30% to 60% in 9.5 min, hold 100% B for 2 min; Flow Rate: 30 mL/min; Column Temperature: 30° C.; Wavelength: 220 nm, 254 nm) to afford N-[2-amino-5-(5-fluoro-2-thienyl)phenyl]-6-(methylsulfonimidoyl)pyridazine-3-carboxamide (about 25.3 mg). $^1$H NMR (400 MHz, methanol-d$_4$) δ ppm 8.60-8.65 (m, 1H), 8.50-8.56 (m, 1H), 7.65 (d, J=2.0 Hz, 1H), 7.27 (dd, J=8.4, 2.0 Hz, 1H), 6.93 (d, J=8.4 Hz, 1H), 6.85 (t, J=4.0 Hz, 1H), 6.49 (dd, J=4.0, 2.4 Hz, 1H), 3.47 (s, 3H); $^{19}$F NMR (377 MHz, methanol-d₄) δ ppm −135.50; LCMS (ESI) [M+H]⁺ m/z: calcd 392.1; found 391.9; HPLC: 97.80%@220 nm; 95.71%@254 nm.

Example 26. Synthesis of N-(2-amino-5-pyrimidin-5-yl-phenyl)-4-(methylsulfonimidoyl)benzamide (Compound 151)

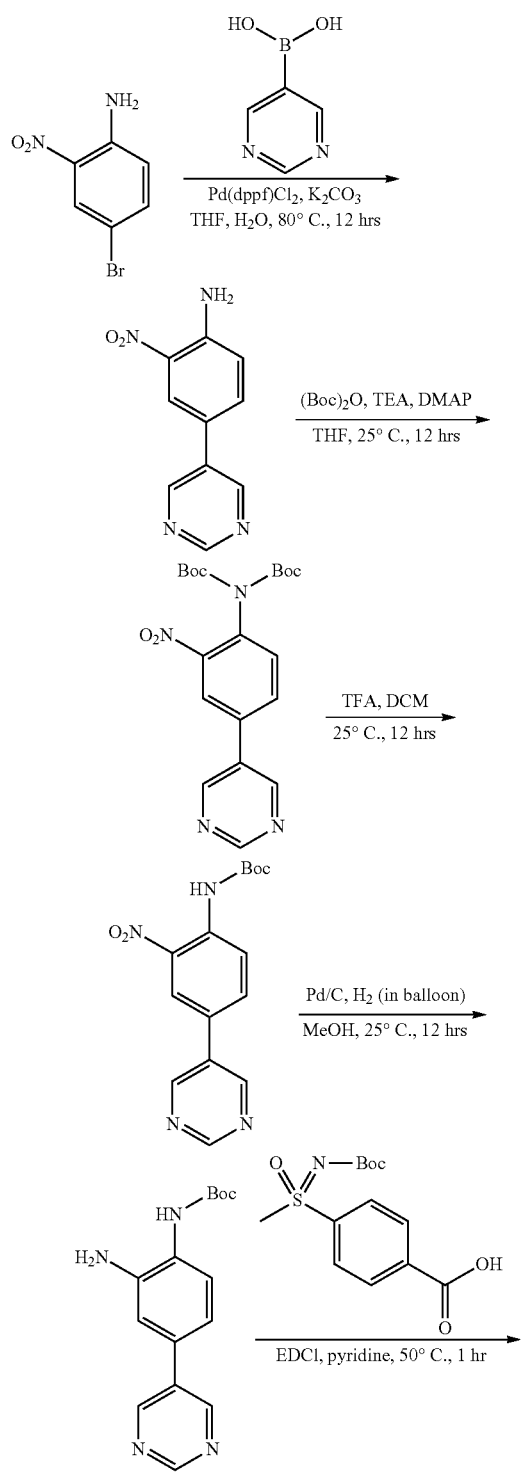

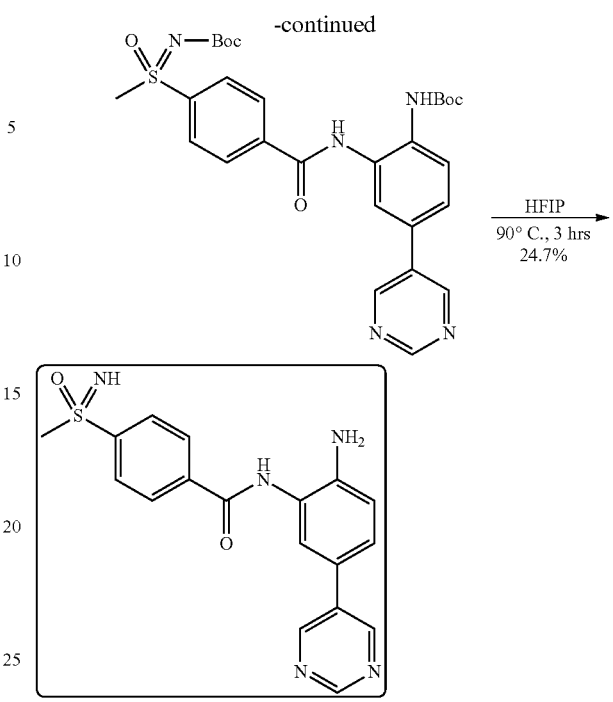

Step 1: Synthesis of 2-nitro-4-pyrimidin-5-yl-aniline

A mixture of 4-bromo-2-nitro-aniline (about 1 g, 4.61 mmol), pyrimidin-5-ylboronic acid (about 685 mg, 5.53 mmol), cyclopentyl(diphenyl)phosphane;dichloropalladium;iron (about 337 mg, 0.461 mmol) and tripotassium;carbonate (about 1.9 g, 13.8 mmol) in tetrahydrofuran (about 10 mL) and H₂O (about 1 mL) was degassed and purged with N₂ for 3 times, and then the mixture was stirred at about 80° C. for about 12 hours under N₂ atmosphere. The reaction mixture was filtered. The filtrate was diluted with H₂O (about 30 mL) and extracted with EtOAc (about 40 mL*2). The combined organic layers were washed with brine (about 40 mL), dried over anhydrous Na₂SO₄, filtered and concentrated under reduced pressure. The residue was purified by flash chromatography (ISCO®; about 20 g SepaFlash® Silica Flash Column, Petroleum Ether/EtOAc with EtOAc from 0~100%, 40 mL/min, 254 nm) to afford 2-nitro-4-pyrimidin-5-yl-aniline (about 337 mg). ¹H NMR (400 MHz, DMSO) δ ppm 9.08-9.15 (m, 3H), 8.38 (d, J=2.4 Hz, 1H), 7.89 (dd, J=9.0, 2.4 Hz, 1H), 7.63-7.70 (m, 2H), 7.16 (d, J=8.8 Hz, 1H); LCMS (ESI) [M+H]⁺ m/z: calcd 217.1, found 216.9.

Step 2: Synthesis of tert-butyl N-tert-butoxycarbonyl-N-(2-nitro-4-pyrimidin-5-yl-phenyl)carbamate To a solution of 2-nitro-4-pyrimidin-5-yl-aniline (about 337 mg, 1.56 mmol) in THF (about 10 mL) were added tert-butoxycarbonyl tert-butyl carbonate (about 0.9 mL, 3.89 mmol), N,N-diethylethanamine (about 473 mg, 4.67 mmol, 0.651 mL), and N,N-dimethylpyridin-4-amine (about 19 mg, 0.156 mmol). The mixture was stirred at about 25° C. for about 12 hours. The reaction mixture was diluted with water (about 20 mL), and extracted with EtOAc (about 30 mL*3). The combined organic layers were washed with brine (about 30 mL), dried over Na₂SO₄ and filtered. The filtrate was concentrated under reduced pressure. The residue was purified by flash chromatography (ISCO®; about 12 g AgelaFlash® Silica Flash Column, petroleum ether/EtOAc with EtOAc from 0~15%, flow rate=40 mL/min, 254 nm) to afford tert-butyl N-tert-butoxycarbonyl-N-(2-nitro-4-pyrimidin-5-yl-phenyl)carbamate (about 397 mg). $^1$H NMR (400 MHz, CDCl$_3$) δ ppm 9.31 (s, 1H), 9.03 (s, 2H), 8.31 (s, 1H), 7.87 (d, J=6.8 Hz, 1H), 7.53 (d, J=7.6 Hz, 1H), 1.45 (s, 18H); LCMS (ESI) [M+H]$^+$ m/z: calcd 417.2, found 316.9 (Boc cleaved mass).

Step 3: Synthesis of tert-butyl N-(2-nitro-4-pyrimidin-5-yl-phenyl)carbamate

To a solution of tert-butyl N-tert-butoxycarbonyl-N-(2-nitro-4-pyrimidin-5-yl-phenyl)carbamate (about 397 mg, 0.953 mmol) in DCM (about 12 mL) was added TFA (about 0.1 mL, 1.43 mmol). The mixture was stirred at about 25° C. for about 12 hours. The reaction mixture was diluted with DCM (30 mL) and adjusted to about pH=8 with saturated Na$_2$CO$_3$ aqueous solution. The resultant mixture was dried over Na$_2$SO$_4$ and filtered. The filtrate was concentrated under reduced pressure. The residue was purified by flash chromatography (ISCO®; about 12 g SepaFlash® Silica Flash Column, Petroleum Ether/EtOAc with EtOAc from 0~15%, 60 mL/min, 254 nm) to afford tert-butyl N-(2-nitro-4-pyrimidin-5-yl-phenyl)carbamate (about 216 mg). $^1$H NMR (400 MHz, CDCl$_3$) δ ppm 9.76 (s, 1H), 9.23-9.30 (m, 1H), 8.93-9.03 (m, 2H), 8.79 (d, J=8.8 Hz, 1H), 8.46 (d, J=2.0 Hz, 1H), 7.85 (dd, J=8.8, 2.3 Hz, 1H), 1.57 (s, 9H). LCMS (ESI) [M+H]$^+$ m/z: calcd 317.1, found 316.9.

Step 4: Synthesis of tert-butyl N-(2-amino-4-pyrimidin-5-yl-phenyl)carbamate

To a solution of tert-butyl N-(2-nitro-4-pyrimidin-5-yl-phenyl)carbamate (about 150 mg, 0.474 mmol) in MeOH (about 10 mL) was added Pd/C (about 45 mg, 10 wt % Pd with 50 wt % water). The mixture was purged with H$_2$ for about 3 times and stirred at about 25° C. for about 12 hours under H$_2$ (in balloon). The reaction mixture was filtered and the filtrate was concentrated under reduced pressure to afford tert-butyl N-(2-amino-4-pyrimidin-5-yl-phenyl)carbamate (about 130 mg). $^1$H NMR (400 MHz, CDCl$_3$) δ ppm 9.18 (s, 1H), 8.90 (s, 2H), 7.49 (d, J=8.4 Hz, 1H), 6.96-7.04 (m, 2H), 1.54 (s, 9H). LCMS (ESI) [M+H]$^+$ m/z: calcd 287.1, found 230.9 (t-Bu cleaved mass).

Step 5: Synthesis of tert-butyl N-[[4-[[2-(tert-butoxycarbonylamino)-5-pyrimidin-5-yl-phenyl]carbamoyl]phenyl]-methyl-oxo-sulfanylidene]carbamate To a solution of tert-butyl N-(2-amino-4-pyrimidin-5-yl-phenyl)carbamate (about 120 mg, 0.419 mmol) in pyridine (about 2 mL) was added 4-(N-tert-butoxycarbonyl-S-methyl-sulfonimidoyl)benzoic acid (about 150 mg, 0.501 mmol) and 3-(ethyliminomethyleneamino)-N,N-dimethyl-propan-1-amine;hydrochloride (about 120 mg, 0.626 mmol). The mixture was stirred at about 50° C. for 1 hour. The reaction mixture was diluted with NH$_4$Cl (30 mL) and extracted with EtOAc (about 40 mL*2). The combined organic layers were washed with brine (about 40 mL), dried over anhydrous Na$_2$SO$_4$, filtered and concentrated under reduced pressure. The residue was purified by flash chromatography (ISCO®; about 4 g SepaFlash® Silica Flash Column, Petroleum Ether/EtOAc with EtOAc from 0~100%, 40 mL/min, 254 nm) to afford tert-butyl N-[[4-[[2-(tert-butoxycarbonylamino)-5-pyrimidin-5-yl-phenyl]carbamoyl]phenyl]-methyl-oxo-sulfanylidene]carbamate (about 260 mg). $^1$H NMR (400 MHz, CDCl$_3$) δ ppm 9.91 (brs, 1H), 9.18-9.24 (m, 1H), 8.98 (s, 2H), 8.19-8.25 (m, 3H), 8.10 (d, J=8.4 Hz, 2H), 7.33-7.46 (m, 2H), 6.91 (s, 1H), 3.28 (s, 3H), 1.56 (s, 9H), 1.41 (s, 9H); LCMS (ESI) [M+H]$^+$ m/z: calcd 568.2, found 468.1 (Boc cleaved mass).

Step 6: Synthesis of N-(2-amino-5-pyrimidin-5-yl-phenyl)-4-(methylsulfonimidoyl)benzamide To a solution of tert-butyl N-[[4-[[2-(tert-butoxycarbonylamino)-5-pyrimidin-5-yl-phenyl]carbamoyl]phenyl]-methyl-oxo-sulfanylidene]carbamate (about 150 mg, 0.264 mmol) in HFIP (about 15 mL) was stirred at about 90° C. for about 3 hours in microwave. The reaction mixture was concentrated under reduced pressure. The residue was purified by preparative HPLC (Instrument: AD; Column: 2_Phenomenex Gemini C18 75*40 mm*3 μm; Mobile phase A: H$_2$O with 10 mmol NH$_4$HCO$_3$ (v %); B: ACN; Gradient: B from 7% to 37% in 9.5 min, hold 100% B for 2 min; Flow Rate: 30 mL/min; Column Temperature: 30° C.; Wavelength: 220 nm, 254 nm) to afford N-(2-amino-5-pyrimidin-5-yl-phenyl)-4-(methylsulfonimidoyl)benzamide (about 24 mg). $^1$H NMR (400 MHz, DMSO) δ ppm 9.98 (s, 1H), 9.05 (s, 1H), 9.03 (s, 2H), 8.19 (d, J=8.4 Hz, 2H), 8.06 (d, J=8.4 Hz, 2H), 7.65 (d, J=1.6 Hz, 1H), 7.50 (dd, J=8.4, 2.0 Hz, 1H), 6.92 (d, J=8.4 Hz, 1H), 5.40 (s, 2H), 4.42 (s, 1H), 3.12 (s, 3H); LCMS (ESI) [M+Na]$^+$ m/z: calcd 390.1, found 390.0. HPLC: 97.38%@220 nm, 97.55%@254 nm.

Example 27. Synthesis of N-[2-amino-5-(2-thienyl)phenyl]-4-(2-pyridylsulfonimidoyl)benzamide (Compound 150)

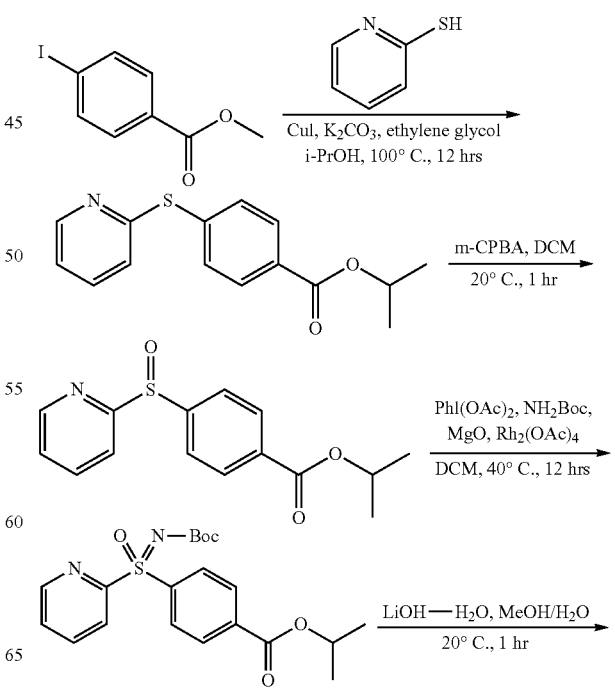

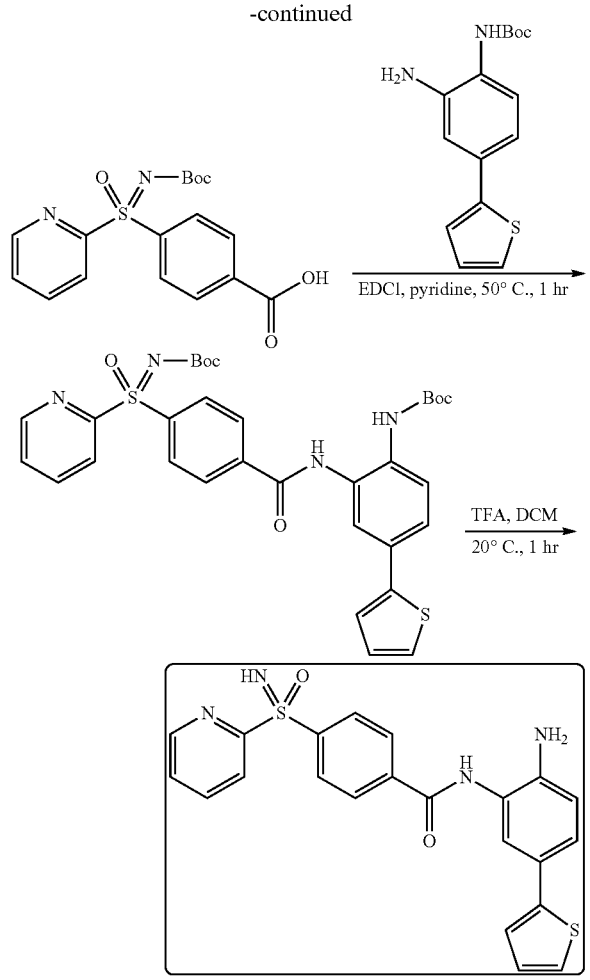

Step 1: Synthesis of isopropyl 4-(2-pyridylsulfanyl)benzoate

To a solution of methyl 4-iodobenzoate (about 1 g, 3.82 mmol), pyridine-2-thiol (about 430 mg, 3.87 mmol), CuI (about 150 mg, 0.788 mmol), K$_2$CO$_3$ (about 1.05 g, 7.63 mmol) and ethylene glycol (about 0.45 mL, 8.07 mmol) was added isopropyl alcohol (about 15 mL). The mixture was stirred at about 100° C. for about 12 hours under N$_2$ atmosphere. The mixture was filtered and the filtrate was concentrated under reduced pressure. The resulting mixture was extracted with H$_2$O (about 50 mL) and EtOAc (about 50 mL*2). The combined organic layer was dried over anhydrous Na$_2$SO$_4$, filtered and concentrated under reduced pressure. The residue was purified by flash chromatography (ISCO®; about 20 g AgelaFlash® Silica Flash Column, petroleum ether/EtOAc with EtOAc from 0~11%, flow rate=30 mL/min, 254 nm) to afford isopropyl 4-(2-pyridylsulfanyl)benzoate (about 220 mg). $^1$H NMR (400 MHz, DMSO-d$_6$) δ ppm 8.43-8.48 (m, 1H), 7.97 (d, J=8.5 Hz, 2H), 7.72 (td, J=7.8, 2.0 Hz, 1H), 7.62-7.65 (m, 2H), 7.24 (ddd, J=7.4, 4.9, 0.8 Hz, 1H), 7.20 (d, J=8.0 Hz, 1H), 5.15 (quin, J=6.3 Hz, 1H), 1.33 (d, J=6.3 Hz, 6H); LCMS (ESI) [M+H]$^+$ m/z: calcd 274.1, found 274.0.

Step 2: Synthesis of isopropyl 4-(2-pyridylsulfinyl)benzoate

To a solution of isopropyl 4-(2-pyridylsulfanyl)benzoate (about 220 mg, 0.805 mmol) in DCM (about 8 mL) was added 3-chlorobenzenecarboperoxoic acid (about 150 mg, 0.869 mmol, 85 wt %). The mixture was stirred at about 20° C. for about 1 hour. The mixture was quenched by addition of saturated Na$_2$SO$_3$ aqueous solution (about 10 mL) and saturated NaHCO$_3$ aqueous solution (about 10 mL). The resulting mixture was extracted with DCM (about 20 mL). The combined organic layer was dried over anhydrous Na$_2$SO$_4$, filtered and concentrated under reduced pressure to give isopropyl 4-(2-pyridylsulfinyl)benzoate (about 220 mg). $^1$H NMR (400 MHz, DMSO-d$_6$) δ ppm 8.62 (d, J=3.9 Hz, 1H), 8.06 (d, J=8.5 Hz, 2H), 7.96 (d, J=7.9 Hz, 1H), 7.89 (d, J=8.4 Hz, 2H), 7.51 (ddd, J=7.4, 4.8, 1.0 Hz, 1H), 5.12 (dt, J=12.5, 6.3 Hz, 1H), 1.30 (d, J=6.3 Hz, 6H); LCMS (ESI) [M+H]$^+$ m/z: calcd 290.1, found 290.0.

Step 3: Synthesis of isopropyl 4-[N-tert-butoxycarbonyl-S-(2-pyridyl)sulfonimidoyl]benzoate To a solution of isopropyl 4-(2-pyridylsulfinyl)benzoate (about 220 mg, 0.760 mmol), NH$_2$Boc (about 180 mg, 1.54 mmol), [bis(acetoxy)iodo]benzene (about 370 mg, 1.15 mmol) and MgO (about 160 mg, 3.87 mmol) in DCM (about 10 mL) was added dirhodium tetraacetate (about 20 mg, 0.0450 mmol). The reaction mixture was stirred at about 40° C. for about 12 hours. The mixture was filtered. The filtrate was concentrated under reduced pressure. The residue was purified by flash chromatography (ISCO®; about 12 g AgelaFlash® Silica Flash Column, petroleum ether/EtOAc with EtOAc from 0~30%, flow rate=30 mL/min, 254 nm) to give a product. The residue was further purified by preparative TLC (silica, petroleum ether/EtOAc=3:1) to afford isopropyl 4-[N-tert-butoxycarbonyl-S-(2-pyridyl)sulfonimidoyl]benzoate (about 100 mg). LCMS (ESI) [M+H]$^+$ m/z: calcd 405.1, found 405.1.

Step 4: Synthesis of 4-[N-tert-butoxycarbonyl-S-(2-pyridyl)sulfonimidoyl]benzoic acid To a solution of isopropyl 4-[N-tert-butoxycarbonyl-S-(2-pyridyl)sulfonimidoyl]benzoate (about 100 mg, 0.247 mmol) in MeOH (about 8 mL) was added a solution of lithium;hydroxide;hydrate (about 110 mg, 2.62 mmol) in H$_2$O (about 4 mL). The mixture was stirred at about 20° C. for about 1 hour. The mixture was adjusted to about pH=5 with 2N HCl aqueous solution. The resulting mixture was extracted with EtOAc (about 20 mL*2). The combined organic layer was dried over anhydrous Na$_2$SO$_4$, filtered and concentrated under reduced pressure to give 4-[N-tert-butoxycarbonyl-S-(2-pyridyl)sulfonimidoyl]benzoic acid (about 90 mg). LCMS (ESI) [M+H]$^+$ m/z: calcd 363.1, found 363.1.

Step 5: Synthesis of tert-butyl N-[[4-[[2-(tert-butoxycarbonylamino)-5-(2-thienyl)phenyl]carbamoyl]phenyl]-oxo-(2-pyridyl)-sulfanylidene]carbamate A mixture of 4-[N-tert-butoxycarbonyl-S-(2-pyridyl)sulfonimidoyl]benzoic acid (about 90 mg, 0.248 mmol), tert-butyl N-[2-amino-4-(2-thienyl)phenyl]carbamate (about 80 mg, 0.276 mmol), 3-(ethyliminomethyleneamino)-N,N-dimethyl-propan-1-amine;hydrochloride (about 80 mg, 0.417 mmol) and pyridine (about 5 mL) was stirred at about 50° C. for about 1 hour. The mixture was concentrated under reduced pressure. The residue was purified by flash chromatography (ISCO®; about 4 g AgelaFlash® Silica Flash Column, petroleum ether/EtOAc with EtOAc from 0~30%, flow rate=35 mL/min, 254 nm) to afford tert-butyl N-[[4-

311

[[2-(tert-butoxycarbonylamino)-5-(2-thienyl)phenyl]carbamoyl]phenyl]-oxo-(2-pyridyl)-sulfanylidene]carbamate (about 65 mg). LCMS (ESI) [M+H]+ m/z: calcd 635.2, found 635.3.

Step 6: Synthesis of N-[2-amino-5-(2-thienyl)phenyl]-4-(2-pyridylsulfonimidoyl)benzamide To a solution of tert-butyl N-[[4-[[2-(tert-butoxycarbonylamino)-5-(2-thienyl)phenyl]carbamoyl]phenyl]-oxo-(2-pyridyl)-sulfanylidene]carbamate (about 65 mg, 0.102 mmol) in DCM (about 2 mL) was added TFA (about 0.2 mL, 2.60 mmol). The mixture was stirred at about 20° C. for about 1 hour. The resulting mixture was adjusted to about pH=8 with saturated NaHCO₃ aqueous solution (about 10 mL) and extracted with DCM (about 20 mL*2). The combined organic layer was dried over anhydrous Na₂SO₄, filtered and concentrated under reduced pressure. The residue was purified by preparative HPLC (Instrument: Gilson GX-281 Liquid Handler, Gilson 322 Pump, Gilson 156 UV Detector; Column: Durashell 75×40 mm×3 μm; Mobile phase A: H₂O with 10 mmol NH₄HCO₃ (v %); Mobile phase B: MeCN; Gradient: B from 43% to 53% in 7.8 min, hold 100% B for 2 min; Flow Rate: 30 mL/min; Column Temperature: 30° C.; Wavelength: 220 nm, 254 nm) to afford N-[2-amino-5-(2-thienyl)phenyl]-4-(2-pyridylsulfonimidoyl)benzamide (about 5 mg). ¹H NMR (400 MHz, DMSO-d₆) δ ppm 9.88 (s, 1H), 8.63 (d, J=3.9 Hz, 1H), 8.27 (d, J=7.9 Hz, 1H), 8.06-8.17 (m, 5H), 7.60 (ddd, J=7.6, 4.7, 1.0 Hz, 1H), 7.45 (d, J=2.0 Hz, 1H), 7.35 (dd, J=5.0, 1.0 Hz, 1H), 7.30 (dd, J=8.3, 2.1 Hz, 1H), 7.23 (d, J=2.5 Hz, 1H), 7.04 (dd, J=5.1, 3.6 Hz, 1H), 6.79 (d, J=8.4 Hz, 1H), 5.29 (s, 1H), 5.22 (s, 2H); LCMS (ESI) [M+H]+ m/z: calcd 435.1, found 435.2; HPLC: 96.16%@220 nm; 99.71%@254 nm.

Example 28. Synthesis of N-[2-amino-5-(4-fluorophenyl)phenyl]-4-(N-ethyl-S-methyl-sulfonimidoyl)benzamide (Compound 165)

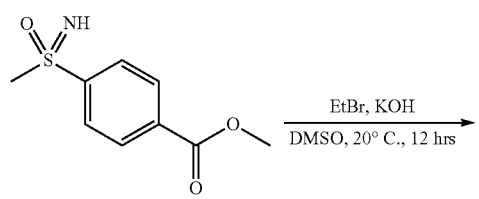

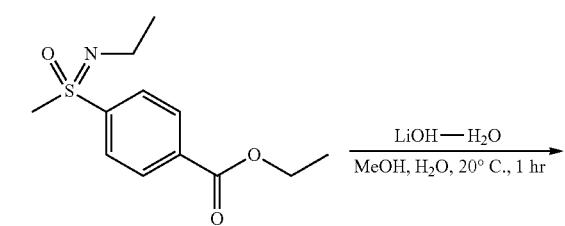

312

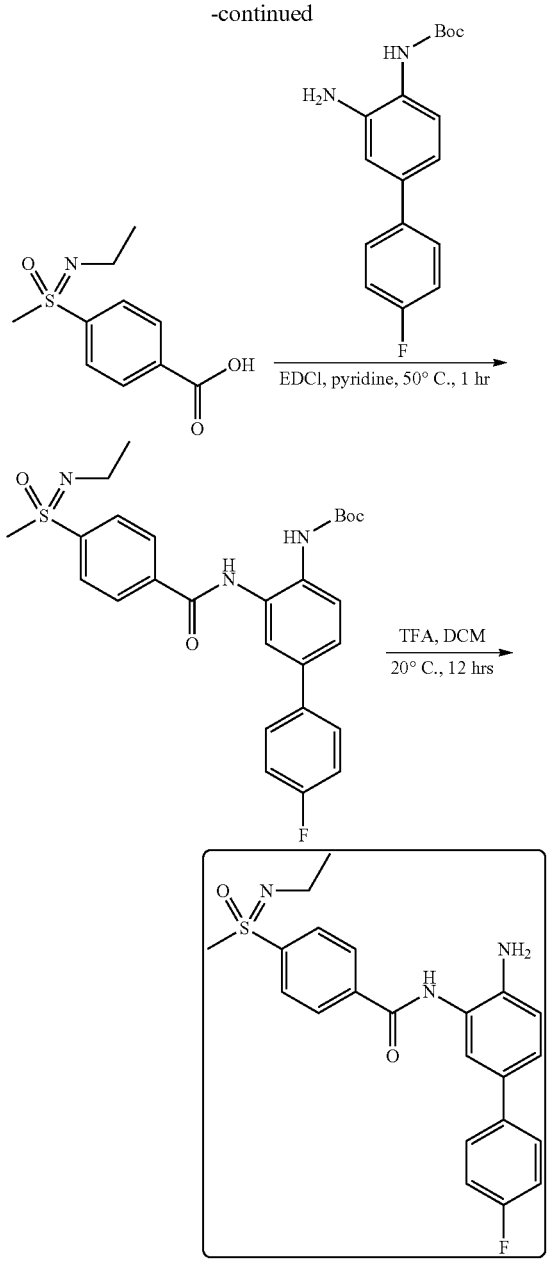

Step 1: Synthesis of ethyl 4-(N-ethyl-S-methyl-sulfonimidoyl)benzoate

To a solution of methyl 4-(methylsulfonimidoyl)benzoate (about 850 mg, 3.99 mmol) in DMSO (about 10 mL) was added potassium;hydroxide (about 895 mg, 5.95 mmol) and bromoethane (about 2.17 g, 19.9 mmol). The mixture was stirred at about 20° C. for about 12 hours. The mixture was filtered and the filtrate was concentrated under reduced pressure. The resulting mixture was extracted with H₂O (about 50 mL) and EtOAc (about 50 mL*2). The combined organic layer was dried over anhydrous Na₂SO₄, filtered and concentrated under reduced pressure. The residue was purified by flash chromatography (ISCO®; about 20 g Agela-Flash® Silica Flash Column, petroleum ether/EtOAc with EtOAc from 0~50%, flow rate=30 mL/min, 254 nm) to afford ethyl 4-(N-ethyl-S-methyl-sulfonimidoyl)benzoate (about 910 mg). $^1$H NMR (400 MHz, DMSO-$d_6$) δ ppm 8.12-8.19 (m, 2H), 7.98 (d, J=8.4 Hz, 2H), 4.36 (q, J=7.0 Hz, 2H), 3.17 (s, 3H), 2.67-2.86 (m, 2H), 1.34 (t, J=7.1 Hz, 3H), 1.03 (t, J=7.2 Hz, 3H); LCMS (ESI) [M+H]$^+$ m/z: calcd 256.1, found 256.0.

Step 2: Synthesis of 4-(N-ethyl-S-methyl-sulfonimidoyl)benzoic acid

A mixture of ethyl 4-(N-ethyl-S-methyl-sulfonimidoyl) benzoate (about 915 mg, 3.58 mmol) and lithium;hydroxide; hydrate (about 752 mg, 17.9 mmol) in MeOH (about 8 mL) and H$_2$O (about 8 mL) was stirred at about 20° C. for about 1 hour. The mixture was concentrated under reduced pressure to remove solvent. 1N HCl aqueous solution was added to adjust to about pH=5. The mixture was concentrated under reduced pressure to afford a product (about 1.4 g). The residue (about 700 mg) was purified by preparative HPLC (Instrument: AD; Column: 2_Phenomenex Gemini C18 75*40 mm*3 µm; Mobile phase A: water (HCl)-ACN; B: ACN; Gradient: B from 0% to 30% in 8.5 min, hold 100% B for 2 min; Flow Rate: 40 mL/min; Column Temperature: 30° C.; Wavelength: 220 nm, 254 nm) to afford 4-(N-ethyl-S-methyl-sulfonimidoyl)benzoic acid (about 140 mg). $^1$H NMR (400 MHz, DMSO-$d_6$) δ ppm 8.06 (d, J=8.1 Hz, 2H), 7.77 (d, J=8.3 Hz, 2H), 3.09 (s, 3H), 2.67-2.83 (m, 2H), 1.02 (t, J=7.1 Hz, 3H); LCMS (ESI) [M+H]$^+$ m/z: calcd 228.1, found 227.9.

Step 3: Synthesis of tert-butyl N-[2-[[4-(N-ethyl-S-methyl-sulfonimidoyl)benzoyl]amino]-4-(4-fluorophenyl)phenyl]carbamate A mixture of 4-(N-ethyl-S-methyl-sulfonimidoyl)benzoic acid (about 140 mg, 0.616 mmol), tert-butyl N-[2-amino-4-(4-fluorophenyl)phenyl]carbamate (about 185 mg, 0.612 mmol) and 3-(ethyliminomethyleneamino)-N,N-dimethyl-propan-1-amine (about 143 mg, 0.921 mmol) in pyridine (about 5 mL) was degassed and purged with N$_2$ for about 3 times, and then the mixture was stirred at about 50° C. for about 1 hour under N$_2$ atmosphere. The resulting mixture was quenched by addition of saturated NH$_4$Cl (about 50 mL), and extracted with EtOAc (about 50 mL*2). The combined organic layer was dried over anhydrous Na$_2$SO$_4$, filtered and concentrated under reduced pressure to afford tert-butyl N-[2-[[4-(N-ethyl-S-methyl-sulfonimidoyl)benzoyl]amino]-4-(4-fluorophenyl)phenyl]carbamate (about 270 mg). LCMS (ESI) [M+H]$^+$ m/z: calcd 512.2, found 512.1.

Step 4: Synthesis of N-[2-amino-5-(4-fluorophenyl)phenyl]-4-(N-ethyl-S-methyl-sulfonimidoyl)benzamide To a solution of tert-butyl N-[2-[[4-(N-ethyl-S-methyl-sulfonimidoyl)benzoyl]amino]-4-(4-fluorophenyl)phenyl] carbamate (about 270 mg, 0.528 mmol) in DCM (about 6 mL) was added TFA (about 0.4 mL, 5.28 mmol). The mixture was stirred at about 20° C. for about 12 hours. The reaction mixture was diluted with DCM (about 30 mL) and adjusted to about pH=8 with saturated Na$_2$CO$_3$ aqueous solution. The resultant mixture was dried over Na$_2$SO$_4$ and filtered. The filtrate was concentrated under reduced pressure. The residue was purified by preparative HPLC (Instrument: 2_Phenomenex Gemini C18 75*40 mm*3 µm; Column: Waters Xbridge 150*25 mm*5 µm; Mobile phase A: H$_2$O with 0.05% NH$_3$—H$_2$O (v %); B: ACN; Gradient: B from 40% to 70% in 7.8 min, hold 100% B for 0 min; Flow Rate: 30 mL/min; Column Temperature: 30° C.; Wavelength: 220 nm, 254 nm) to afford N-[2-amino-5-(4-fluorophenyl)phenyl]-4-(N-ethyl-S-methyl-sulfonimidoyl)benzamide (about 31.2 mg). $^1$H NMR (400 MHz, DMSO-$d_6$) δ ppm 9.94 (s, 1H), 8.21 (d, J=8.4 Hz, 2H), 7.98 (d, J=8.4 Hz, 2H), 7.58 (dd, J=8.4, 5.6 Hz, 2H), 7.48-7.52 (m, 1H), 7.32 (dd, J=8.4, 2.0 Hz, 1H), 7.22 (t, J=8.8 Hz, 2H), 6.87 (d, J=8.4 Hz, 1H), 3.18 (s, 3H), 2.83-2.92 (m, 1H), 2.70-2.78 (m, 1H), 1.06 (t, J=7.2 Hz, 3H); $^{19}$F NMR (376 MHz, DMSO-$d_6$) δ ppm−117.435; LCMS (ESI) [M+H]$^+$ m/z: calcd 412.1, found 412.2; HPLC: 92.280%@220 nm, 92.990%@254 nm.

Example 29. Synthesis of N-[2-amino-5-(4-fluorophenyl)phenyl]-2-(methylsulfonimidoyl)thiazole-5-carboxamide (Compound 164)

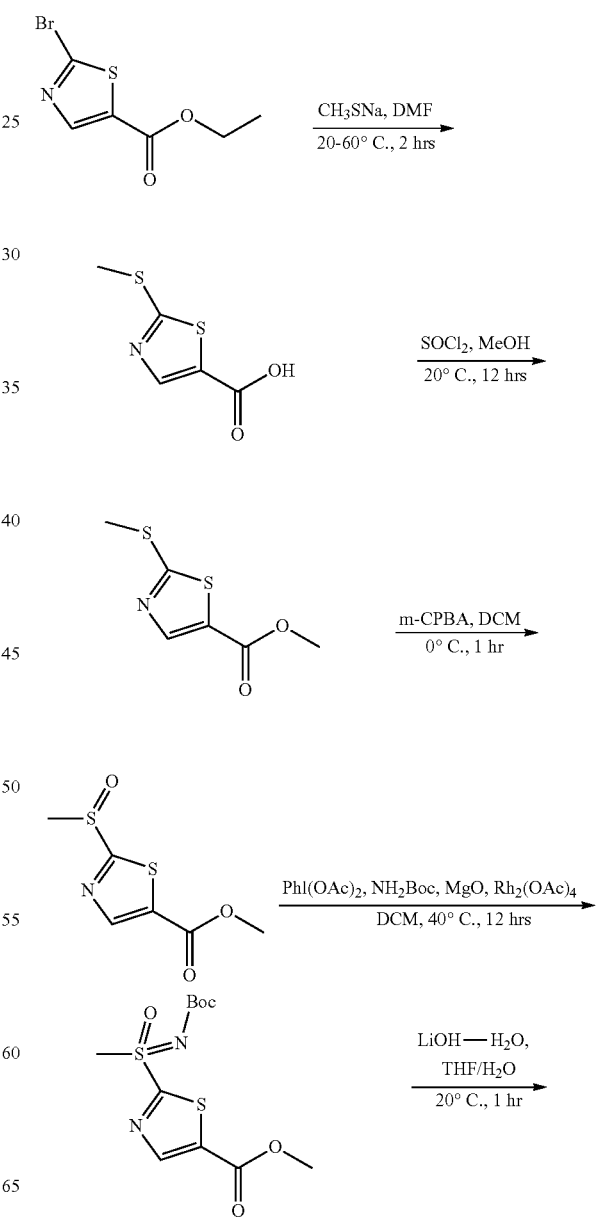

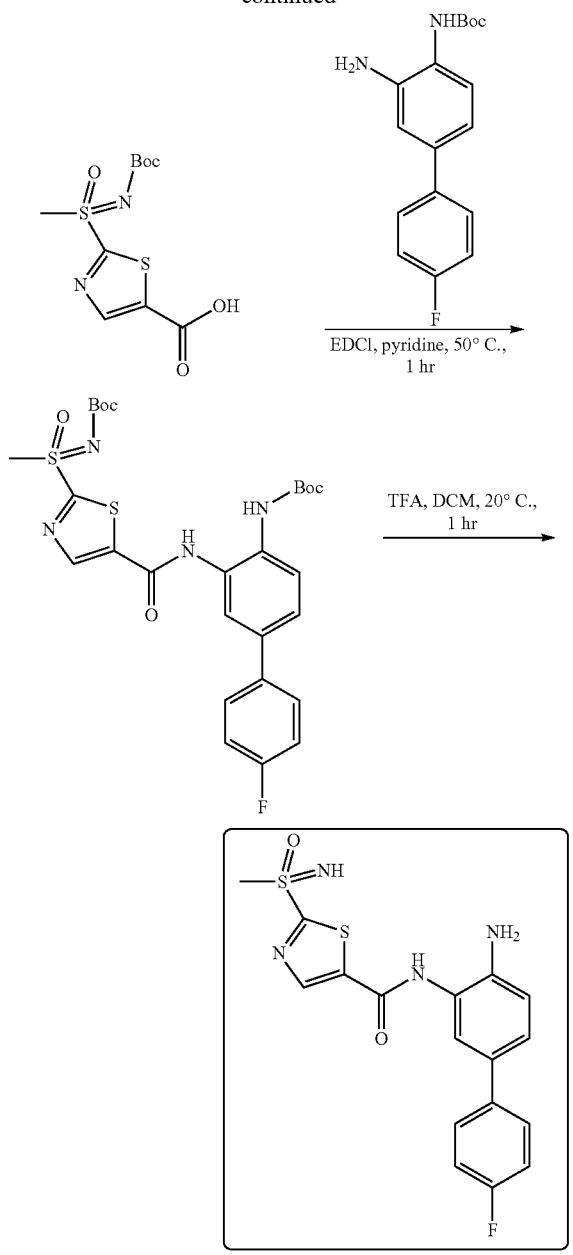

Step 1: Synthesis of 2-methylsulfanylthiazole-5-carboxylic acid

To a mixture of ethyl 2-bromothiazole-5-carboxylate (about 5 g, 21.2 mmol) in DMF (about 30 mL) was added CH$_3$SNa (about 3 g, 42.8 mmol) at 20° C. The mixture was stirred at about 60° C. for about 2 hours. 2N HCl aqueous solution was added to adjust pH to about 5. Then about 30 mL of water was added and the mixture was extracted with EtOAc (about 30 mL*5). The combined organic layer was washed with brine (about 30 mL*3) and concentrated under reduced pressure to give 2-methylsulfanylthiazole-5-carboxylic acid (about 1.03 g). LCMS (ESI) [M+H]$^+$ m/z: calcd 176.0, found 176.0; $^1$H NMR (400 MHz, methanol-d$_4$) δ ppm 8.24 (s, 1H), 2.75 (s, 3H).

Step 2: Synthesis of methyl 2-methylsulfanylthiazole-5-carboxylate

To a mixture of 2-methylsulfanylthiazole-5-carboxylic acid (about 950 mg, 5.42 mmol) in MeOH (about 10 mL) was dropwise added SOCl$_2$ (about 4 mL, 55.1 mmol) at about 20° C. The mixture was stirred at about 20° C. for about 12 hours. The mixture was concentrated under reduced pressure to remove solvent. Then saturated NaHCO$_3$ aqueous solution was added to adjust pH to about 8. The mixture was extracted with EtOAc (about 10 mL*3). The combined organic layer was washed with brine (about 10 mL*3), dried over anhydrous Na$_2$SO$_4$, filtered and concentrated under reduced pressure to give methyl 2-methylsulfanylthiazole-5-carboxylate (about 610 mg). $^1$H NMR (400 MHz, chloroform-d) δ ppm 8.05 (s, 1H), 3.94 (s, 3H), 2.74 (s, 3H); LCMS (ESI) [M+H]$^+$ m/z: calcd 190.0, found 190.0.

Step 3: Synthesis of methyl 2-methylsulfinylthiazole-5-carboxylate

To a mixture of methyl 2-methylsulfanylthiazole-5-carboxylate (about 550 mg, 2.91 mmol) in DCM (about 1 mL) was added m-CPBA (about 550 mg, 2.55 mmol, 80 wt %) at about 0° C. The mixture was stirred at about 0° C. for about 1 hour. About 3 mL of water was added to the mixture and saturated NaHCO$_3$ aqueous solution was added to adjust to about pH=8. Then the mixture was extracted with DCM (about 10 mL*3). The combined organic layer was washed with brine (about 10 mL*3), dried over anhydrous Na$_2$SO$_4$, filtered and concentrated under reduced pressure. The residue was purified by flash chromatography (Biotage®; about 12 g AgelaFlash® Silica Flash Column, petroleumether/EtOAc with EtOAc from 0~35%, flow rate=40 mL/min, 254 nm) to afford methyl 2-methylsulfinylthiazole-5-carboxylate (about 360 mg). LCMS (ESI) [M+H]$^+$ m/z: calcd 206.0, found 206.0.

Step 4: Synthesis of methyl 2-(N-tert-butoxycarbonyl-S-methyl-sulfonimidoyl)thiazole-5-carboxylate A mixture of methyl 2-methylsulfinylthiazole-5-carboxylate (about 100 mg, 0.487 mmol), PhI(OAc)$_2$ (about 236 mg, 0.733 mmol), NH$_2$Boc (about 115 mg, 0.982 mmol), Rh$_2$(OAc)$_4$ (about 11 mg, 0.025 mmol) and MgO (about 100 mg, 2.48 mmol) in DCM (about 5 mL) was stirred at about 40° C. for about 12 hours. About 5 mL of water was added and the mixture was extracted with DCM (about 5 mL*2). The combined organic layer was washed with brine (about 5 mL*3), dried over anhydrous Na$_2$SO$_4$, filtered and concentrated under reduced pressure. The residue was purified by flash chromatography (Biotage®; about 4 g AgelaFlash® Silica Flash Column, petroleumether/EtOAc with EtOAc from 0~42%, flow rate=30 mL/min, 254 nm) to afford methyl 2-(N-tert-butoxycarbonyl-S-methyl-sulfonimidoyl)thiazole-5-carboxylate (about 150 mg). $^1$H NMR (400 MHz, DMSO-d$_6$) δ ppm 8.98 (s, 1H), 3.89 (s, 3H), 3.61 (s, 3H), 1.28 (s, 9H); LCMS (ESI) [M+H]$^+$ m/z: calcd 321.1, found 221.0 (Boc cleaved mass).

Step 5: Synthesis of 2-(methylsulfonimidoyl)thiazole-5-carboxylic acid

A mixture of methyl 2-(N-tert-butoxycarbonyl-S-methyl-sulfonimidoyl)thiazole-5-carboxylate (about 120 mg, 0.375 mmol) and LiOH—H$_2$O (about 80 mg, 1.91 mmol) in THF (about 2 mL) and H$_2$O (about 2 mL) was stirred at about 20° C. for about 1 hour. The mixture was concentrated under reduced pressure to remove solvent. 1N HCl aqueous solution was added to adjust to about pH to 5. The mixture was extracted with EtOAc (about 5 mL*3), combined organic layer was dried over anhydrous Na$_2$SO$_4$, filtered and concentrated under reduced pressure to give 2-(methylsulfonimidoyl)thiazole-5-carboxylic acid (about 50 mg). LCMS (ESI) [M+H]$^+$ m/z: calcd 207.0, found 207.0 (Boc cleaved mass).

Step 6: Synthesis of tert-butyl N-[[5-[[2-(tert-butoxycarbonylamino)-5-(4-fluorophenyl)phenyl]carbamoyl]thiazol-2-yl]-methyl-oxo-sulfanylidene]carbamate A mixture of 2-(N-tert-butoxycarbonyl-S-methyl-sulfonimidoyl)thiazole-5-carboxylic acid (about 40 mg, 0.131 mmol), tert-butyl N-[2-amino-4-(4-fluorophenyl)phenyl]carbamate (about 45 mg, 0.149 mmol) and EDCI (about 45 mg, 0.235 mmol) in pyridine (about 1 mL) was stirred at about 50° C. for about 1 hour. The mixture was concentrated under reduced pressure. The residue was purified by flash chromatography (Biotage®; about 4 g AgelaFlash®Silica Flash Column, eluent: petroleumether/EtOAc with EtOAc from 0~51%, flow rate=40 mL/min, 254 nm) to afford tert-butyl N-[[5-[[2-(tert-butoxycarbonylamino)-5-(4-fluorophenyl)phenyl]carbamoyl]thiazol-2-yl]-methyl-oxo-sulfanylidene]carbamate (about 40 mg). $^1$H NMR (400 MHz, chloroform-d) δ ppm 9.48 (s, 1H), 8.57 (s, 1H), 7.81 (s, 1H), 7.66 (d, J=8.4 Hz, 1H), 7.55 (dd, J=8.5, 5.4 Hz, 2H), 7.42-7.46 (m, 1H), 7.12 (t, J=8.6 Hz, 2H), 3.40 (s, 3H), 1.53-1.79 (m, 18H); LCMS (ESI) [M+H]$^+$ m/z: calcd 591.2, found 491.1 (Boc cleaved mass).

Step 7: Synthesis of N-[2-amino-5-(4-fluorophenyl)phenyl]-2-(methylsulfonimidoyl)thiazole-5-carboxamide To a mixture of tert-butyl N-[[5-[[2-(tert-butoxycarbonylamino)-5-(4-fluorophenyl)phenyl]carbamoyl]thiazol-2-yl]-methyl-oxo-sulfanylidene]carbamate (about 30 mg, 0.0510 mmol) in DCM (about 1 mL) was added TFA (about 111 mg, 0.973 mmol) at about 20° C. The mixture was stirred at about 20° C. for about 1 hour. The mixture was concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 μm; Mobile phase A: H$_2$O with 0.05% NH$_3$—H$_2$O (v %); Mobile phase B: MeCN; Gradient: B from 31% to 61% in 9.5 mins, hold 100% B for 2 mins; Flow Rate: 30 mL/min; Column Temperature: 30° C.; Wavelength: 220 nm, 254 nm) to afford N-[2-amino-5-(4-fluorophenyl)phenyl]-2-(methylsulfonimidoyl)thiazole-5-carboxamide (about 6.4 mg). $^1$H NMR (400 MHz, chloroform-d) δ ppm 9.08 (s, 1H), 8.54 (s, 1H), 7.60 (d, J=2.0 Hz, 1H), 7.50 (dd, J=8.7, 5.4 Hz, 2H), 7.33 (dd, J=8.2, 1.9 Hz, 1H), 7.10 (t, J=8.7 Hz, 2H), 6.93 (s, 1H), 4.03 (s, 2H), 3.42 (s, 1H), 3.40 (s, 3H); $^{19}$F NMR (376 MHz, chloroform-d) δ ppm −116.560; HPLC: 97.00%@220 nm, 100%@254 nm; LCMS (ESI) [M+H]$^+$ m/z: calcd 391.1, found 391.0.

Example 30. Synthesis of N-[2-amino-5-(4-fluorophenyl)phenyl]-4-(N-cyclopropyl-S-methyl-sulfonimidoyl)benzamide (Compound 163)

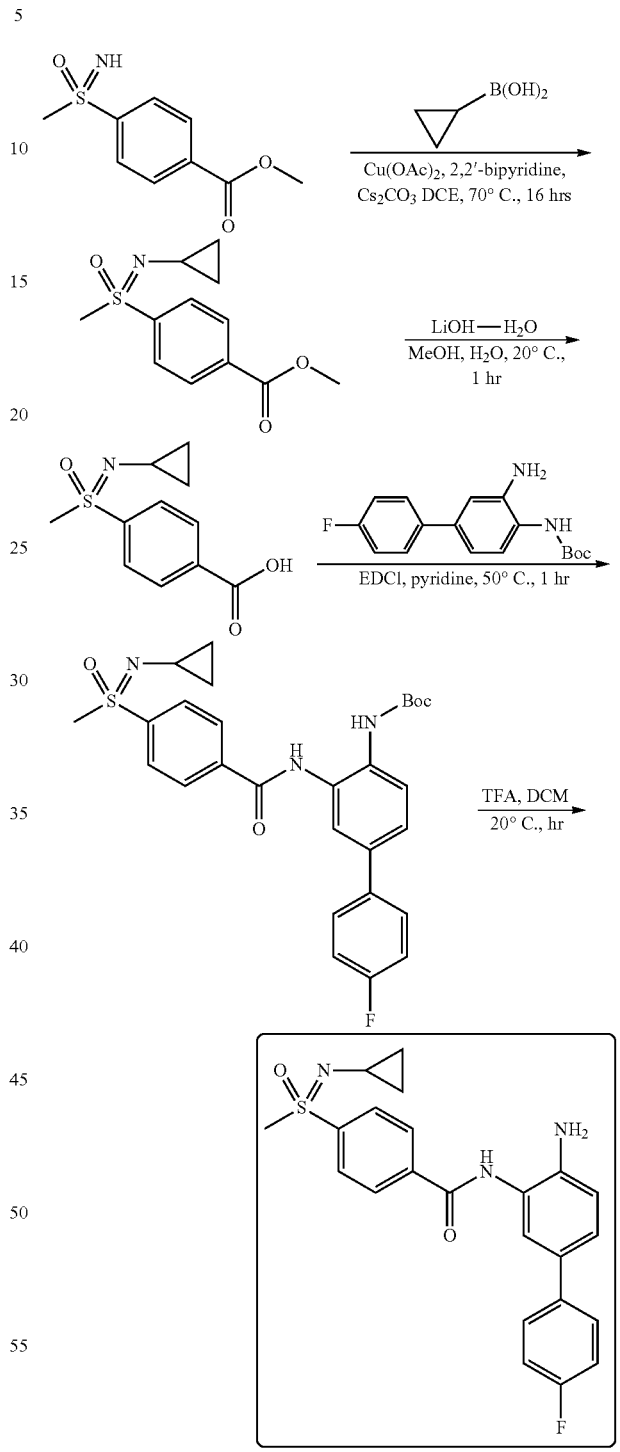

Step 1: Synthesis of methyl 4-(N-cyclopropyl-S-methyl-sulfonimidoyl)benzoate

To a solution of methyl 4-(methylsulfonimidoyl)benzoate (300 mg, 1.41 mmol) and cyclopropylboronic acid (about 181 mg, 2.11 mmol) in DCE (about 5 mL) was added Cu(OAc)$_2$ (about 256 mg, 1.41 mmol), 2,2'-bipyridine (about 220 mg, 1.41 mmol) and Cs$_2$CO$_3$ (about 458 mg, 1.41 mmol). The mixture was stirred at about 70° C. for about 16 hours. The reaction mixture was concentrated under reduced pressure. The residue was purified by flash chromatography (Biotage®; about 12 g AgelaFlash® Silica Flash Column, petroleum ether/EtOAc with EtOAc from 0~50%, flow rate=30 mL/min, 254 nm) to afford methyl 4-(N-cyclopropyl-S-methyl-sulfonimidoyl)benzoate (about 366 mg). $^1$H NMR (400 MHz, DMSO-d$_6$) δ ppm 8.11-8.22 (m, 2H), 7.99-8.06 (m, 2H), 3.90 (s, 3H), 3.18 (s, 3H), 2.21-2.31 (m, 1H), 0.11-0.44 (m, 4H); LCMS (ESI) [M+H]$^+$ m/z: calcd 254.1, found 254.0.

Step 2: Synthesis of 4-(N-cyclopropyl-S-methyl-sulfonimidoyl)benzoic acid

To a solution of methyl 4-(N-cyclopropyl-S-methyl-sulfonimidoyl)benzoate (about 366 mg, 1.44 mmol) in H$_2$O (about 1 mL) and MeOH (about 3 mL) was added LiOH—H$_2$O (about 61 mg, 1.45 mmol). The mixture was stirred at about 20° C. for about 1 hour. The reaction mixture was concentrated under reduced pressure. The mixture adjusted to about pH=5 with 2N HCl aqueous solution. The mixture was filtered and concentrated under reduced pressure to give 4-(N-cyclopropyl-S-methyl-sulfonimidoyl)benzoic acid (about 102 mg), which was directly used without further purification. $^1$H NMR (400 MHz, DMSO-d$_6$) δ ppm 13.47 (s, 1H), 8.14 (d, J=8.25 Hz, 2H), 7.94-8.03 (m, 2H), 3.17 (s, 3H), 2.21-2.30 (m, 1H), 0.32-0.44 (m, 2H), 0.14-0.32 (m, 2H); LCMS (ESI) [M+H]$^+$ m/z: calcd 240.1, found 240.1.

Step 3: Synthesis of tert-butyl N-[2-[[4-(N-cyclopropyl-S-methyl-sulfonimidoyl)benzoyl]amino]-4-(4-fluorophenyl)phenyl]carbamate To a solution of 4-(N-cyclopropyl-S-methyl-sulfonimidoyl)benzoic acid (about 102 mg, 0.43 mmol) and tert-butyl N-[2-amino-4-(4-fluorophenyl)phenyl]carbamate (about 129 mg, 0.43 mmol) in pyridine (about 5 mL) was added 3-(ethyliminomethyleneamino)-N,N-dimethyl-propan-1-amine;hydrochloride (about 123 mg, 0.64 mmol). The mixture was stirred at about 50° C. for about 1 hour. The reaction mixture was concentrated under reduced pressure. The residue was purified by flash chromatography (Biotage®; about 20 g AgelaFlash® Silica Flash Column, petroleum ether/EtOAc with EtOAc from 0~90%, flow rate=30 mL/min, 254 nm) to afford tert-butyl N-[2-[[4-(N-cyclopropyl-S-methyl-sulfonimidoyl)benzoyl]amino]-4-(4-fluorophenyl)phenyl]carbamate (about 182 mg). $^1$H NMR (400 MHz, DMSO-d$_6$) δ ppm 10.09 (s, 1H), 8.82 (s, 1H), 8.19 (m, J=8.28 Hz, 2H), 8.05 (d, J=8.28 Hz, 2H), 7.81 (d, J=1.51 Hz, 1H), 7.65-7.74 (m, 3H), 7.53 (dd, J=8.53, 2.26 Hz, 1H), 7.27-7.33 (m, 2H), 3.20 (s, 3H), 2.24-2.32 (m, 1H), 1.46 (s, 9H), 0.16-0.44 (m, 4H); LCMS (ESI) [M+H]$^+$ m/z: calcd 524.2, found 524.2.

Step 4: Synthesis of N-[2-amino-5-(4-fluorophenyl)phenyl]-4-(N-cyclopropyl-S-methyl-sulfonimidoyl)benzamide To a solution of tert-butyl N-[2-[[4-(N-cyclopropyl-S-methyl-sulfonimidoyl)benzoyl]amino]-4-(4-fluorophenyl)phenyl]carbamate (about 182 mg, 0.35 mmol) in DCM (about 5 mL) was added TFA (about 0.5 mL, 6.49 mmol). The mixture was stirred at about 20° C. for about 1 hour. The reaction mixture was concentrated under reduced pressure. The mixture was adjusted the pH=8 with 28% NH$_4$OH solution. The mixture was purified by preparative HPLC (Instrument: Gilson GX-215, Gilson 322 Pump, Gilson 156 UV Detector; Column: Durashell 75×40 mm×3 µm; Mobile phase A: H$_2$O with 0.05% NH$_4$HCO$_3$ (v %); Mobile phase B: ACN; Gradient: B from 40% to 70% in 7.8 min, hold 100% B for 2 min; Flow Rate=30 mL/min; Column Temperature: 30° C.; Wavelength: 220 nm, 254 nm) to afford N-[2-amino-5-(4-fluorophenyl)phenyl]-4-(N-cyclopropyl-S-methyl-sulfonimidoyl)benzamide (about 68.4 mg). $^1$H NMR (400 MHz, DMSO-d$_6$) δ ppm 9.94 (s, 1H), 8.21 (m, J=8.28 Hz, 2H), 8.02 (d, J=8.28 Hz, 2H), 7.58 (dd, J=8.53, 5.52 Hz, 2H), 7.48-7.54 (m, 1H), 7.32 (dd, J=8.41, 2.13 Hz, 1H), 7.22 (t, J=8.91 Hz, 2H), 6.87 (d, J=8.28 Hz, 1H), 5.18 (brs, 2H), 3.33 (s, 3H), 2.25-2.32 (m, 1H), 0.18-0.44 (m, 4H); $^{19}$F NMR (376 MHz, DMSO-d$_6$) δ ppm −117.463; LCMS (ESI) [M+H]$^+$ m/z: calcd 424.1, found 424.2; HPLC: 94.12%@220 nm, 100%@254 nm.

Example 31. Synthesis of N-[2-amino-5-(4-fluorophenyl)phenyl]-4-[(methylsulfonimidoyl)methyl]benzamide (Compound 162)

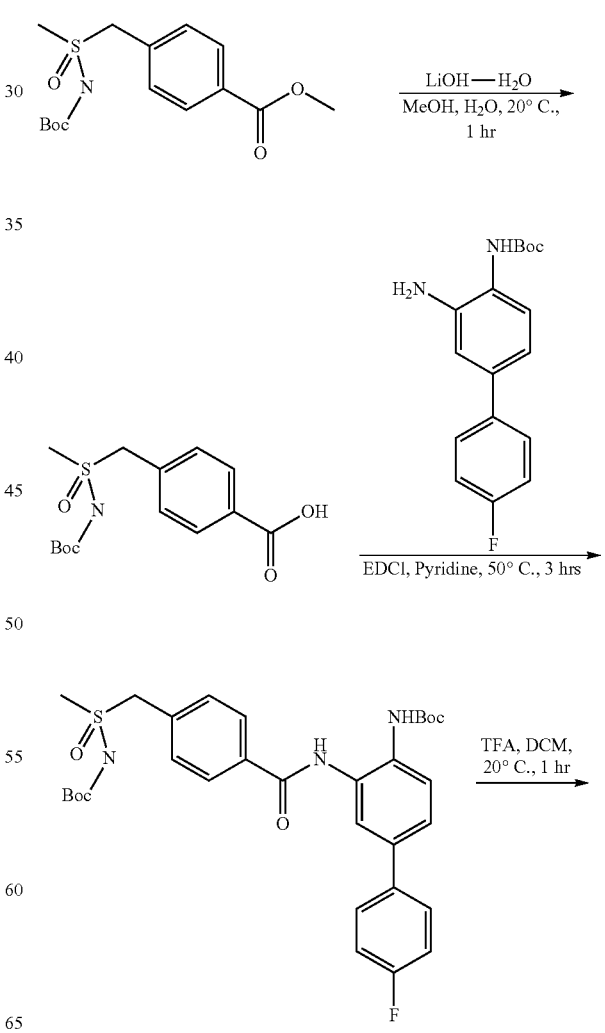

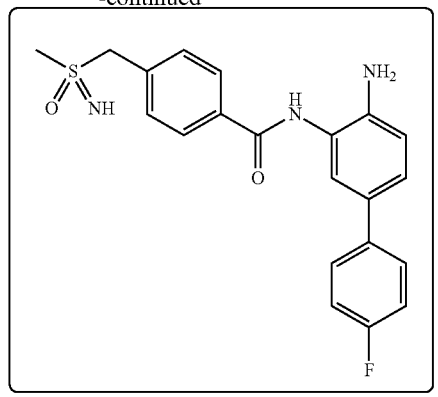

Step 1: Synthesis of 4-[(N-tert-butoxycarbonyl-S-methyl-sulfonimidoyl)methyl]benzoic acid A mixture of methyl 4-[(N-tert-butoxycarbonyl-S-methyl-sulfonimidoyl)methyl]benzoate (about 85 mg, 0.260 mmol) and LiOH—H₂O (about 55 mg, 1.31 mmol) in MeOH (about 1 mL) and H₂O (about 1 mL) was stirred at about 20° C. for about 1 hour. The mixture was concentrated under reduced pressure to remove organic solvent. 2N HCl aqueous solution was added to adjust to about pH=5. Then the mixture was extracted with EtOAc (about 10 mL*3). The combined organic layer was dried over anhydrous Na₂SO₄, filtered and concentrated under reduced pressure to give 4-[(N-tert-butoxycarbonyl-S-methyl-sulfonimidoyl)methyl] benzoic acid (about 100 mg). LCMS (ESI) [M+H]⁺ m/z: calcd 314.1, found 314.1.

Step 2: Synthesis of tert-butyl N-[[4-[[2-(tert-butoxycarbonylamino)-5-(4-fluorophenyl)phenyl]carbamoyl]phenyl]methyl-methyl-oxo-sulfanylidene] carbamate A mixture of 4-[(N-tert-butoxycarbonyl-S-methyl-sulfonimidoyl)methyl]benzoic acid (about 100 mg, 0.319 mmol), tert-butyl N-[2-amino-4-(4-fluorophenyl)phenyl]carbamate (about 110 mg, 0.364 mmol), and EDCI (about 70 mg, 0.365 mmol) in pyridine (about 2 mL) was stirred at about 50° C. for about 3 hours. The mixture was concentrated under reduced pressure to remove solvent. The residue was purified by flash chromatography (Biotage®; about 4 g AgelaFlash®Silica Flash Column, petroleumether/EtOAc with EtOAc from 0~44%, flow rate=25 mL/min, 254 nm) to afford tert-butyl N-[[4-[[2-(tert-butoxycarbonylamino)-5-(4-fluorophenyl)phenyl]carbamoyl]phenyl]methyl-methyl-oxo-sulfanylidene]carbamate (about 190 mg). LCMS (ESI) [M+H]⁺ m/z: calcd 598.2, found 498.2 (Boc cleaved mass).

Step 3: Synthesis of N-[2-amino-5-(4-fluorophenyl) phenyl]-4-[(methylsulfonimidoyl)methyl]benzamide To a mixture of tert-butyl N-[[4-[[2-(tert-butoxycarbonylamino)-5-(4-fluorophenyl)phenyl]carbamoyl]phenyl] methyl-methyl-oxo-sulfanylidene]carbamate (about 190 mg, 0.318 mmol) in DCM (about 1 mL) was added TFA (about 0.5 mL, 6.49 mmol) at 20° C. The mixture was stirred at about 20° C. for about 1 hour. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 μm; Mobile phase A: H₂O with 0.05% NH₃—H₂O (v %); Mobile phase B: MeCN; Gradient: B from 37% to 67% in 7.8 mins, hold 100% B for 1 min; Flow Rate: 30 mL/min; Column Temperature: 30° C.; Wavelength: 220 nm, 254 nm) to afford N-[2-amino-5-(4-fluorophenyl)phenyl]-4-[(methylsulfonimidoyl)methyl]benzamide (about 42.9 mg). ¹H NMR (400 MHz, methanol-d₄) δ ppm 8.05 (d, J=8.3 Hz, 2H), 7.63 (d, J=8.3 Hz, 2H), 7.56 (dd, J=8.8, 5.3 Hz, 2H), 7.47 (d, J=2.0 Hz, 1H), 7.35 (dd, J=8.4, 2.1 Hz, 1H), 7.11 (t, J=8.8 Hz, 2H), 6.98 (d, J=8.3 Hz, 1H), 4.59 (s, 2H), 2.96 (s, 3H); LCMS (ESI) [M+H]⁺ m/z: calcd 398.1, found 398.1; HPLC: 99.74%@220 nm, 99.68%@254 nm.

Example 32. Synthesis of N-[2-amino-5-(4-fluorophenyl)phenyl]-5-(methylsulfonimidoyl)thiophene-2-carboxamide (Compound 161)

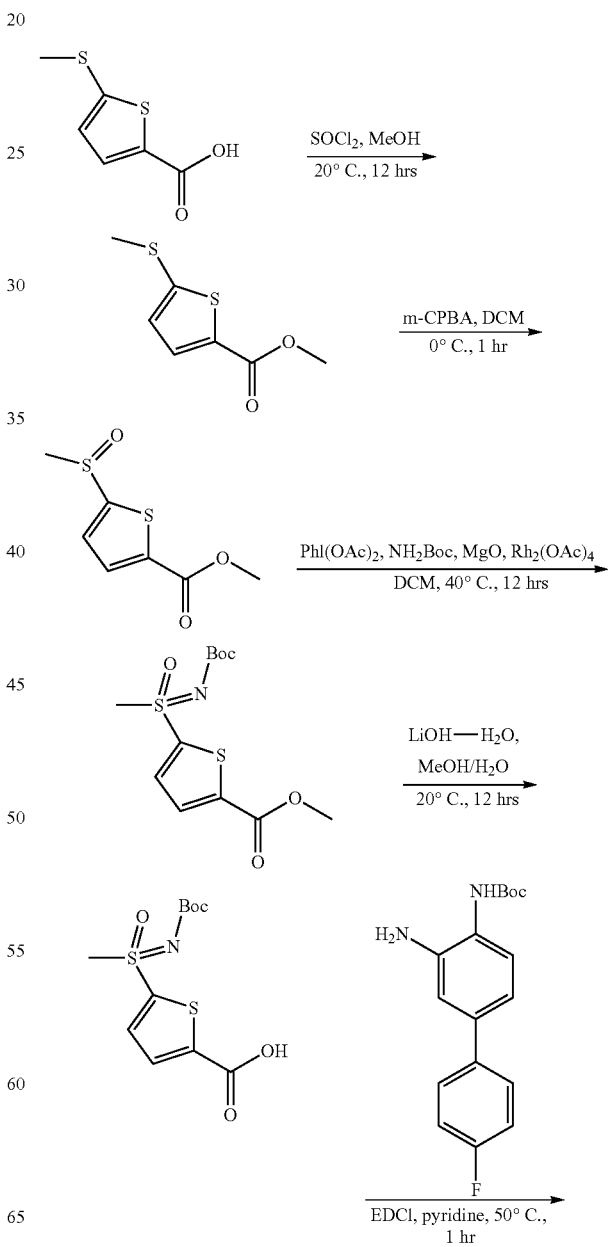

-continued

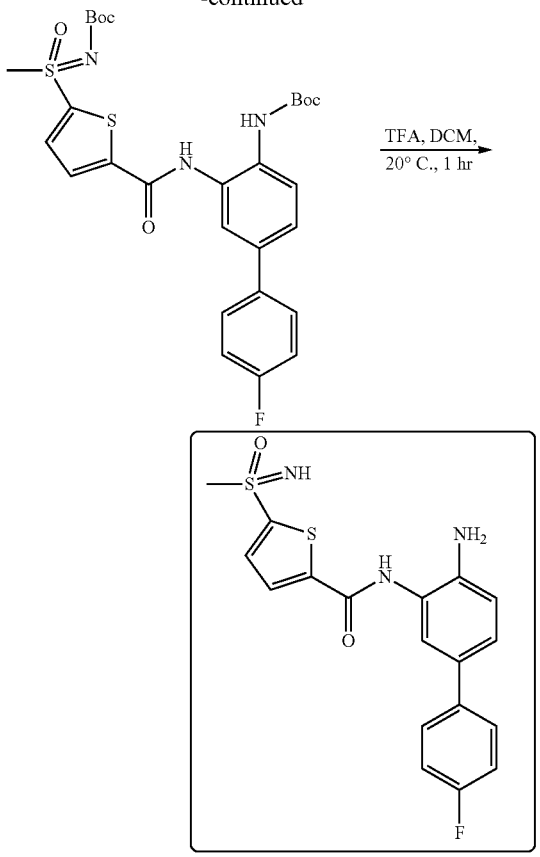

Step 1: Synthesis of methyl 5-methylsulfanylthiophene-2-carboxylate

To a solution of 5-methylsulfanylthiophene-2-carboxylic acid (about 2.9 g, 16.6 mmol) in MeOH (about 50 mL) was added SOCl$_2$ (about 12 mL, 0.165 mol). The mixture was stirred at about 20° C. for about 12 hours. The mixture was concentrated under reduced pressure. The residue was purified by flash chromatography (Biotage®; about 25 g AgelaFlash® Silica Flash Column, petroleum ether/EtOAc with EtOAc from 0~5%, 40 mL/min, 254 nm) to afford methyl 5-methylsulfanylthiophene-2-carboxylate (about 3.1 g). $^1$H NMR (400 MHz, methanol-d$_4$) δ ppm 7.65 (d, J=4.0 Hz, 1H), 7.01 (d, J=3.9 Hz, 1H), 3.85 (s, 3H), 2.59 (s, 3H); LCMS (ESI) [M+H]$^+$ m/z: calcd 189.0; found 189.0.

Step 2: Synthesis of methyl 5-methylsulfinylthiophene-2-carboxylate

To a solution of methyl 5-methylsulfanylthiophene-2-carboxylate (about 2.8 g, 14.9 mmol) in DCM (about 30 mL) was added m-CPBA (about 3.3 g, 16.25 mmol, 85 wt %) at about 0° C. The mixture was stirred at 0° C. for 1 hour. The resulting mixture was quenched by addition of saturated Na$_2$SO$_3$ aqueous solution (about 20 mL), saturated NaHCO$_3$ aqueous solution (about 20 mL) and extracted with DCM (about 30 mL*3). The combined organic layer was dried over anhydrous Na$_2$SO$_4$, filtered and concentrated under reduced pressure. The residue was purified by flash chromatography (Biotage®; about 40 g AgelaFlash® Silica Flash Column, petroleum ether/EtOAc with EtOAc from 0~65%, 60 mL/min, 254 nm) to afford methyl 5-methylsulfinylthiophene-2-carboxylate (about 2.9 g). $^1$H NMR (400 MHz, methanol-d$_4$) δ ppm 7.83 (d, J=4.0 Hz, 1H), 7.57 (d, J=4.0 Hz, 1H), 3.92 (s, 3H), 3.01 (s, 3H); LCMS (ESI) [M+H]$^+$ m/z: calcd 205.0; found 205.0.

Step 3: Synthesis of methyl 5-(N-tert-butoxycarbonyl-S-methyl-sulfonimidoyl)thiophene-2-carboxylate A mixture of methyl 5-methylsulfinylthiophene-2-carboxylate (about 200 mg, 0.979 mmol), NH$_2$Boc (about 229 mg, 1.95 mmol), [bis(acetoxy)iodo]benzene (about 472 mg, 1.47 mmol), MgO (about 197 mg, 4.89 mmol) and dirhodium tetraacetate (about 19 mg, 0.0430 mmol) in DCM (about 10 mL) was stirred at about 40° C. for about 12 hours. The mixture was filtered. The filtrate was concentrated under reduced pressure. The residue was purified by flash chromatography (ISCO®; about 12 g AgelaFlash® Silica Flash Column, petroleum ether/EtOAc with EtOAc from 0~40%, 30 mL/min, 254 nm) to afford methyl 5-(N-tert-butoxycarbonyl-S-methyl-sulfonimidoyl)thiophene-2-carboxylate (about 300 mg). LCMS (ESI) [M+H]$^+$ m/z: calcd 320.1; found 264.0.

Step 4: Synthesis of 5-(N-tert-butoxycarbonyl-S-methyl-sulfonimidoyl)thiophene-2-carboxylic acid To a solution of methyl 5-(N-tert-butoxycarbonyl-S-methyl-sulfonimidoyl)thiophene-2-carboxylate (about 300 mg, 0.939 mmol) in MeOH (about 10 mL) was added a solution of LiOH—H$_2$O (about 394 mg, 9.39 mmol) in H$_2$O (about 2 mL). The mixture was stirred at about 20° C. for about 12 hours. The mixture was concentrated under reduced pressure to remove the organic solvent. The aqueous solution was adjusted to about pH=4 with 2N HCl aqueous solution. The mixture was filtered. The filter cake was concentrated under reduced pressure to give 5-(N-tert-butoxycarbonyl-S-methyl-sulfonimidoyl)thiophene-2-carboxylic acid (about 300 mg), which was directly used without further purification. LCMS (ESI) [M+H]$^+$ m/z: calcd 306.0; found 250.0 (t-Bu cleaved mass).

Step 5: Synthesis of tert-butyl N-[[5-[[2-(tert-butoxycarbonylamino)-5-(4-fluorophenyl)phenyl]carbamoyl]-2-thienyl]-methyl-oxo-sulfanylidene]carbamate A mixture of 5-(N-tert-butoxycarbonyl-S-methyl-sulfonimidoyl)thiophene-2-carboxylic acid (about 60 mg, 0.196 mmol), tert-butyl N-[2-amino-4-(4-fluorophenyl)phenyl]carbamate (about 65 mg, 0.215 mmol) and EDCI (about 57 mg, 0.297 mmol) in pyridine (about 2 mL) was stirred at about 50° C. for about 1 hour. The mixture was concentrated under reduced pressure. The residue was purified by flash chromatography (Biotage®; about 20 g AgelaFlash® Silica Flash Column, petroleum ether/EtOAc with EtOAc from 0~50%, 30 mL/min, 254 nm) to afford tert-butyl N-[[5-[[2-(tert-butoxycarbonylamino)-5-(4-fluorophenyl)phenyl]carbamoyl]-2-thienyl]-methyl-oxo-sulfanylidene]carbamate (about 100 mg). LCMS (ESI) [M+H]$^+$ m/z: calcd 490.1; found 590.2 (Boc cleaved mass).

Step 6: Synthesis of N-[2-amino-5-(4-fluorophenyl)phenyl]-5-(methylsulfonimidoyl)thiophene-2-carboxamide To a solution of tert-butyl N-[[5-[[2-(tert-butoxycarbonylamino)-5-(4-fluorophenyl)phenyl]carbamoyl]-2-thienyl]-methyl-oxo-sulfanylidene]carbamate (about 100 mg, 0.170 mmol) in DCM (about 5 mL) was added TFA (about 0.26 mL, 3.37 mmol). The mixture was stirred at about 20° C. for about 1 hour. The mixture was adjusted to about pH=8 with 28% NH$_3$—H$_2$O, and concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 μm; Mobile phase A: H$_2$O with 10 mmol NH$_4$HCO$_3$ (v %); Mobile phase B: MeCN; Gradient: B from 32% to 62% in 7.8 min, hold 100% B for 2 min; Flow Rate: 30 mL/min; Column Temperature: 30° C.; Wavelength: 220 nm, 254 nm) to give N-[2-amino-5-(4-fluorophenyl)phenyl]-5-(methylsulfonimidoyl)thiophene-2-carboxamide (about 45 mg). $^1$H NMR (400 MHz, DMSO-d$_6$) δ ppm 10.01 (s, 1H), 7.99 (d, J=3.8 Hz, 1H), 7.69 (d, J=4.0 Hz, 1H), 7.58 (dd, J=8.8, 5.5 Hz, 2H), 7.43 (d, J=2.0 Hz, 1H), 7.33 (dd, J=8.3, 2.1 Hz, 1H), 7.21 (t, J=8.9 Hz, 2H), 6.86 (d, J=8.4 Hz, 1H), 5.18 (s, 2H), 4.89 (s, 1H), 3.23 (s, 3H); $^{19}$F NMR (376 MHz, DMSO-d$_6$) δ ppm −117.381; LCMS (ESI) [M+H]$^+$ m/z: calcd 390.1; found 390.0; HPLC: 99.54%@220 nm, 99.78%@254 nm.

Example 33. Synthesis of N-[2-amino-5-(5-fluoro-2-thienyl)phenyl]-4-(1-oxo-4,5-dihydro-3H-isothiazol-1-yl)benzamide (Compound 160)

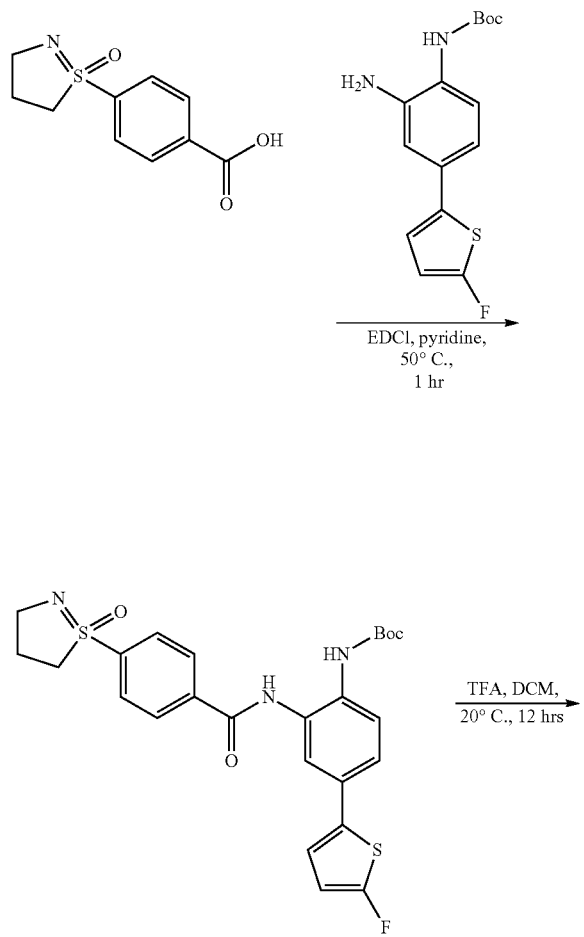

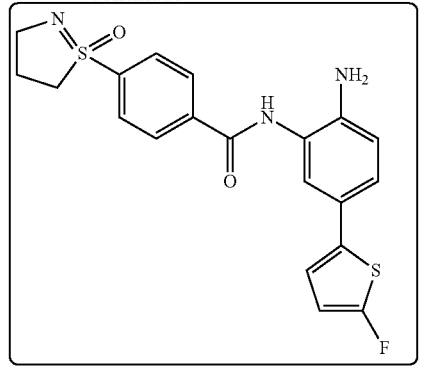

Step 1: Synthesis of tert-butyl N-[4-(5-fluoro-2-thienyl)-2-[[4-(1-oxo-4,5-dihydro-3H-isothiazol-1-yl)benzoyl]amino]phenyl]carbamate To a solution of 4-(1-oxo-4,5-dihydro-3H-isothiazol-1-yl)benzoic acid (about 500 mg, 0.377 mmol) in pyridine (about 3 mL) were added EDCI (about 100 mg, 0.521 mmol) and tert-butyl N-[2-amino-4-(5-fluoro-2-thienyl)phenyl]carbamate (about 100 mg, 0.324 mmol). The mixture was stirred at about 50° C. for about 1 hour. The reaction mixture was concentrated under reduced pressure. The mixture was dilute with water (about 5 mL) and extracted with DCM (about 10 mL*3). The combined organic layers were dried over Na$_2$SO$_4$ and filtered. The filtrate was concentrated under reduced pressure. The residue was purified by preparative TLC (silica, petroleum ether/EtOAc=1/2; 254 nm) to give tert-butyl N-[4-(5-fluoro-2-thienyl)-2-[[4-(1-oxo-4,5-dihydro-3H-isothiazol-1-yl)benzoyl]amino]phenyl]carbamate (about 30 mg). LCMS (ESI) [M+Na]$^+$ m/z: calcd 538.1, found 538.1.

Step 2: Synthesis of N-[2-amino-5-(5-fluoro-2-thienyl)phenyl]-4-(1-oxo-4,5-dihydro-3H-isothiazol-1-yl)benzamide To a solution of tert-butyl N-[4-(5-fluoro-2-thienyl)-2-[[4-(1-oxo-4,5-dihydro-3H-isothiazol-1-yl)benzoyl]amino]phenyl]carbamate (about 25 mg, 0.048 mmol) in DCM (about 3 mL) was added TFA (about 0.07 mL, 0.973 mmol). The mixture was stirred at about 20° C. for about 12 hours. The reaction mixture was adjusted to about pH=8 with saturated NaHCO$_3$ aqueous solution and extracted with DCM (about 15 mL*3). The combined organic layers were dried over Na$_2$SO$_4$ and filtered. The filtrate was concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 μm; Mobile phase A: H$_2$O with 10 mmol NH$_4$HCO$_3$ (v %); Mobile phase B: ACN; Gradient: B from 31% to 61% in 9.5 min, hold 100% B for 2 min; Flow Rate: 30 mL/min; Column Temperature: 30° C. Wavelength: 220 nm, 254 nm) to afford N-[2-amino-5-(5-fluoro-2-thienyl)phenyl]-4-(1-oxo-4,5-dihydro-3H-isothiazol-1-yl)benzamide (about 13.3 mg). $^1$H NMR (400 MHz, DMSO-d$_6$) δ ppm 9.95 (s, 1H), 8.19 (d, J=8.4 Hz, 2H), 7.98 (d, J=8.4 Hz, 2H), 7.38 (d, J=2.0 Hz, 1H), 7.23 (dd, J=8.4, 2.0 Hz, 1H), 6.92 (t, J=3.6 Hz, 1H), 6.80 (d, J=8.4 Hz, 1H), 6.67 (dd, J=4.0, 2.4 Hz, 1H), 5.26 (s, 2H), 3.84 (dd, J=10.8, 5.6 Hz, 1H), 3.70 (dt, J=10.4, 6.4 Hz, 1H), 3.42-3.46 (m, 2H), 2.21-2.32 (m, 2H); $^{19}$F NMR (377 MHz, DMSO-d$_6$) δ ppm −133.744; LCMS [M+H]$^+$ m/z: calcd 416.1; found 416.0; HPLC: 98.95%@220 nm; 96.92%@254 nm.

Example 34. Synthesis of N-[2-amino-5-(4-fluorophenyl)phenyl]-6-(methylsulfonimidoyl)pyridazine-3-carboxamide (Compound 159)

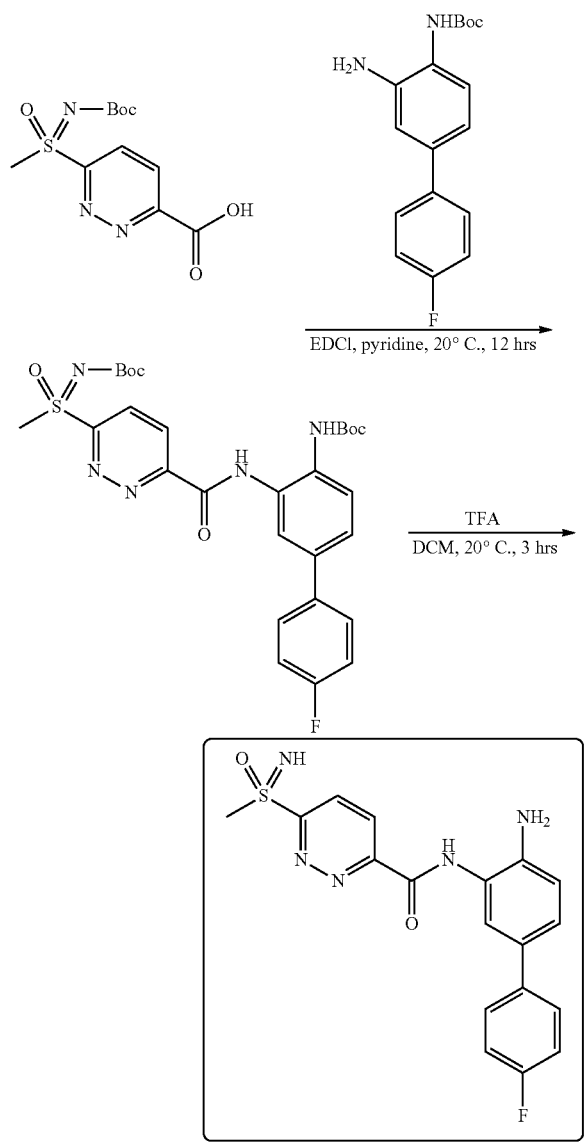

Step 1: Synthesis of tert-butyl N-[[6-[[2-(tert-butoxycarbonylamino)-5-(4-fluorophenyl)phenyl]carbamoyl]pyridazin-3-yl]-methyl-oxo-sulfanylidene]carbamate To a solution of 6-(N-tert-butoxycarbonyl-S-methylsulfonimidoyl)pyridazine-3-carboxylic acid (about 150 mg, 0.498 mmol) in pyridine (about 5 mL) was added tert-butyl N-[2-amino-4-(4-fluorophenyl)phenyl]carbamate (about 100 mg, 0.331 mmol) and 3-(ethyliminomethyleneamino)-N,N-dimethyl-propan-1-amine;hydrochloride (about 100 mg, 0.522 mmol). The mixture was stirred at about 50° C. for about 1 hour. The mixture was concentrated under reduced pressure. The residue was purified by preparative TLC (silica, petroleum ether/EtOAc=1/1; 254 nm) to give tert-butyl N-[[6-[[2-(tert-butoxycarbonylamino)-5-(4-fluorophenyl)phenyl]carbamoyl]pyridazin-3-yl]-methyl-oxo-sulfanylidene]carbamate (about 150 mg). LCMS (ESI) [M+Na]$^+$ m/z: calcd 608.2, found 608.1.

Step 2: Synthesis of N-[2-amino-5-(4-fluorophenyl)phenyl]-6-(methylsulfonimidoyl)pyridazine-3-carboxamide To a solution of tert-butyl N-[[6-[[2-(tert-butoxycarbonylamino)-5-(4-fluorophenyl)phenyl]carbamoyl]pyridazin-3-yl]-methyl-oxo-sulfanylidene]carbamate (about 130 mg, 0.222 mmol) in DCM (about 10 mL) was added TFA (about 0.35 mL, 4.54 mmol). The mixture was stirred at about 20° C. for about 3 hours. The reaction mixture was adjusted to about pH=8 with saturated Na$_2$CO$_3$ aqueous solution. The resultant mixture was extracted with DCM (about 10 mL*3). The combined organic layers were dried over Na$_2$SO$_4$ and filtered. The filtrate was concentrated under reduced pressure. The residue was purified by preparative HPLC (Instrument: Gilson GX-281 Liquid Handler, Gilson 322 Pump, Gilson 156 UV Detector; Column: Phenomenex C18 80*40 mm*3 μm; Mobile phase A: water with 10 mmol NH$_4$HCO$_3$ (v %); Mobile phase B: MeCN; Gradient: B from 28% to 58% in 9.5 min, hold 100% B for 2 min; Flow Rate: 30 mL/min; Column Temperature: about 30° C.; Wavelength: 220 nm, 254 nm) to afford N-[2-amino-5-(4-fluorophenyl)phenyl]-6-(methylsulfonimidoyl)pyridazine-3-carboxamide (about 11.4 mg). $^1$H NMR (400 MHz, methanol-d$_4$) δ ppm 8.62-8.68 (m, 1H), 8.52-8.58 (m, 1H), 7.72 (d, J=2.0 Hz, 1H), 7.60 (dd, J=8.8, 5.6 Hz, 2H), 7.38 (dd, J=8.4, 2.0 Hz, 1H), 7.14 (t, J=8.8 Hz, 2H), 7.02 (d, J=8.4 Hz, 1H), 3.49 (s, 3H); $^{19}$F NMR (377 MHz, methanol-d$_4$) δ ppm −119.293; HPLC: 99.02%@220 nm; 98.37%@254 nm; LCMS: LCMS (ESI) [M+H]$^+$ m/z: calcd 386.1, found 386.0.

Example 35. Synthesis of N-[2-amino-5-(2-thienyl)phenyl]-4-(N-ethyl-S-methyl-sulfonimidoyl)benzamide (Compound 141)

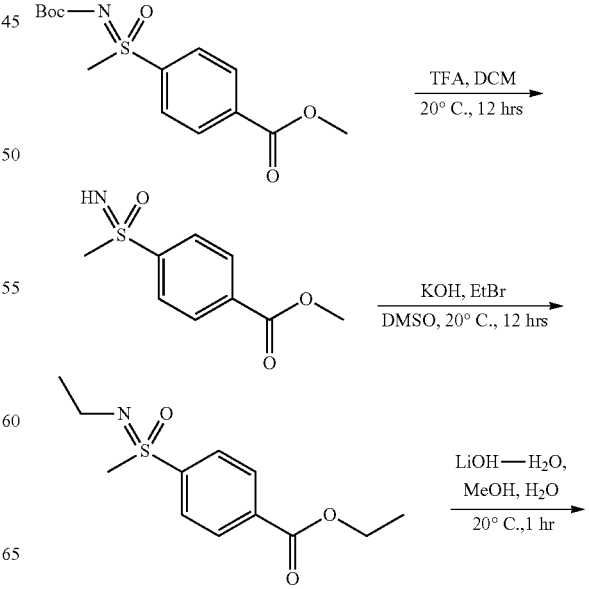

-continued

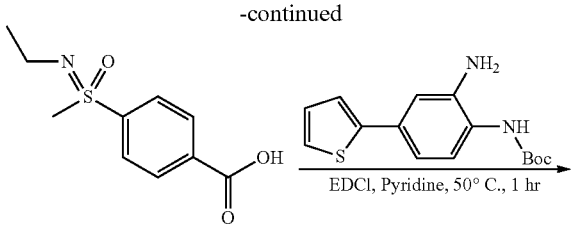
EDCl, Pyridine, 50° C., 1 hr

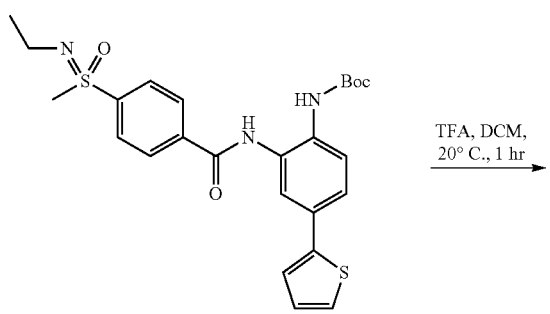
TFA, DCM, 20° C., 1 hr

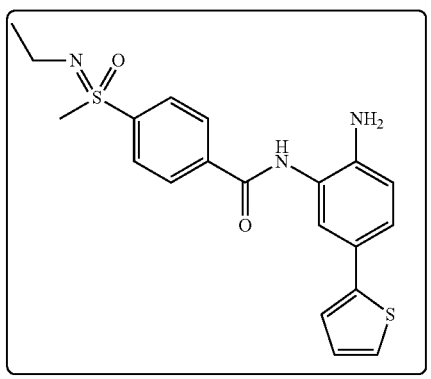 [SMILES: CCN=S(C)(=O)c1ccc(C(=O)Nc2cc(-c3cccs3)ccc2N)cc1]

Step 1: Synthesis of methyl 4-(methylsulfonimidoyl)benzoate

To a mixture of methyl 4-(N-tert-butoxycarbonyl-S-methyl-sulfonimidoyl)benzoate (about 1 g, 3.19 mmol) in DCM (about 10 mL) was added TFA (about 5 mL, 64.9 mmol) at about 20° C. The mixture was stirred at about 20° C. for about 12 hours. Saturated NaHCO$_3$ aqueous solution was added to adjust about pH=8. The mixture was extracted with DCM (about 30 mL*3). The combined organic layer was dried over anhydrous Na$_2$SO$_4$ and concentrated under reduced pressure to give methyl 4-(methylsulfonimidoyl)benzoate (about 600 mg). LCMS (ESI) [M+H]+m/z: calcd 214.0, found 214.0.

Step 2: Synthesis of ethyl 4-(N-ethyl-S-methyl-sulfonimidoyl)benzoate

A mixture of methyl 4-(methylsulfonimidoyl)benzoate (about 200 mg, 0.938 mmol) and KOH (about 210 mg, 3.74 mmol) in DMSO (about 10 mL) was stirred at about 20° C. for about 5 minutes. Then BrC$_2$H$_5$ (about 0.35 mL, 4.68 mmol) was added. The mixture was stirred at about 20° C. for about 12 hours. About 10 mL of water was added and the mixture was extracted with EtOAc (about 10 mL*3). The combined organic layer was dried over anhydrous Na$_2$SO$_4$ and concentrated under reduced pressure to give ethyl 4-(N-ethyl-S-methyl-sulfonimidoyl)benzoate (about 400 mg). LCMS (ESI) [M+H]$^+$ m/z: calcd 256.1, found 255.9.

Step 3: Synthesis of 4-(N-ethyl-S-methyl-sulfonimidoyl)benzoic acid

A mixture of ethyl 4-(N-ethyl-S-methyl-sulfonimidoyl)benzoate (about 400 mg, 1.66 mmol) and LiOH—H$_2$O (about 350 mg, 8.34 mmol) in MeOH (about 3 mL) and H$_2$O (about 3 mL) was stirred at about 20° C. for about 1 hour. The mixture was concentrated under reduced pressure to remove solvent. 1N HCl aqueous solution was added to adjust about pH=5. The mixture was concentrated under reduced pressure to give 4-(N-ethyl-S-methyl-sulfonimidoyl)benzoic acid (about 1.8 g). LCMS (ESI) [M+H]$^+$ m/z: calcd 228.1, found 228.0.

Step 4: Synthesis of tert-butyl N-[2-[[4-(N-ethyl-S-methyl-sulfonimidoyl)benzoyl]amino]-4-(2-thienyl)phenyl]carbamate A mixture of 4-(N-ethyl-S-methyl-sulfonimidoyl)benzoic acid (about 500 mg, 2.20 mmol), tert-butyl N-[2-amino-4-(2-thienyl)phenyl]carbamate (about 110 mg, 0.379 mmol) and EDCI (about 100 mg, 0.522 mmol) in pyridine (5 mL) was stirred at about 50° C. for about 1 hour. The mixture was concentrated under reduced pressure to give tert-butyl N-[2-[[4-(N-ethyl-S-methyl-sulfonimidoyl)benzoyl]amino]-4-(2-thienyl)phenyl]carbamate (about 900 mg). LCMS (ESI) [M+H]$^+$ m/z: calcd 500.2, found 500.1.

Step 5: Synthesis of N-[2-amino-5-(2-thienyl)phenyl]-4-(N-ethyl-S-methyl-sulfonimidoyl)benzamide To a mixture of tert-butyl N-[2-[[4-(N-ethyl-S-methyl-sulfonimidoyl)benzoyl]amino]-4-(2-thienyl)phenyl]carbamate (about 900 mg, 1.80 mmol) in DCM (about 5 mL) was added TFA (about 3 mL, 38.9 mmol) at about 20° C. The mixture was stirred at about 20° C. for about 1 hour. Saturated NaHCO$_3$ aqueous solution was added to adjust about pH=8. Then the mixture was extracted with DCM (about 10 mL*3). The combined organic layer was washed with brine (about 10 mL*2), dried over anhydrous Na$_2$SO$_4$ and concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 μm; Mobile phase A: H$_2$O with 0.05% NH$_3$—H$_2$O (v %); Mobile phase B: MeCN; Gradient: B from 33% to 63% in 9.5 mins, hold 100% B for 2 mins; Flow Rate: 30 mL/min; Column Temperature: 30° C.; Wavelength: 220 nm, 254 nm) to afford N-[2-amino-5-(2-thienyl)phenyl]-4-(N-ethyl-S-methyl-sulfonimidoyl)benzamide (about 17.7 mg). $^1$H NMR (400 MHz, methanol-d$_4$) δ ppm 8.23 (d, J=8.4 Hz, 2H), 8.05 (d, J=8.4 Hz, 2H), 7.52 (d, J=2.0 Hz, 1H), 7.38 (dd, J=8.4, 2.1 Hz, 1H), 7.20-7.26 (m, 2H), 7.03 (dd, J=5.0, 3.6 Hz, 1H), 6.93 (d, J=8.4 Hz, 1H), 3.21 (s, 3H), 2.90-3.05 (m, 1H), 2.79-2.88 (m, 1H), 1.17 (t, J=7.2 Hz, 3H); HPLC: 95.56%@220 nm, 95.63%@254 nm; LCMS (ESI) [M+H]$^+$ m/z: calcd 400.1, found 400.1.

Example 36. Synthesis of N-[2-amino-5-(2-thienyl)phenyl]-4-[1-(methylsulfonimidoyl)cyclopropyl]benzamide (Compound 140)

Step 1: Synthesis of methyl 4-(methylsulfinylmethyl)benzoate

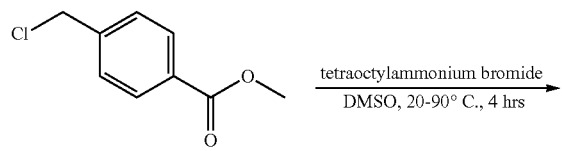

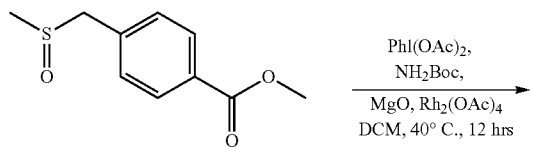

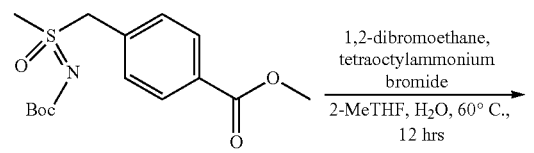

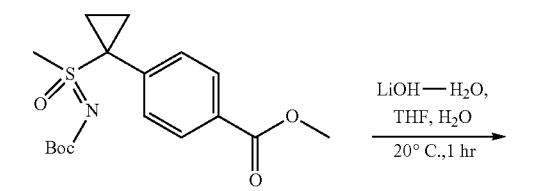

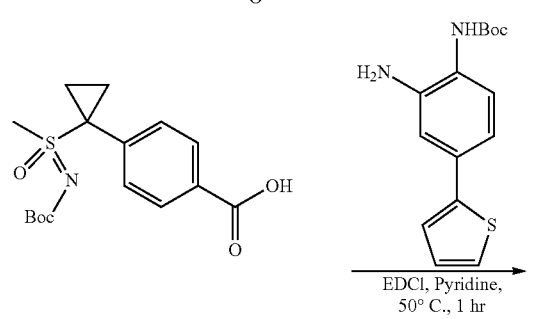

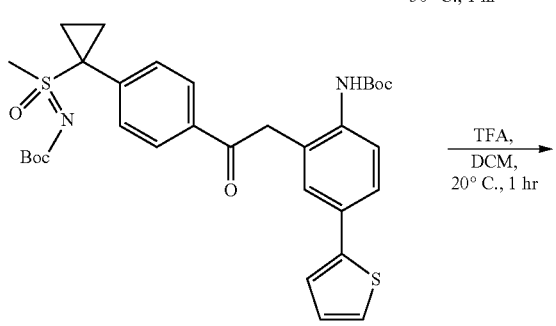

-continued

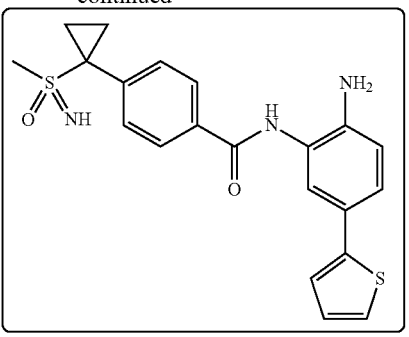

To a mixture of methyl 4-(chloromethyl)benzoate (about 5 g, 27.1 mmol) in DMSO (about 50 mL) was added tetraoctylammonium;bromide (about 15 g, 27.4 mmol) at 20° C. The mixture was stirred at about 90° C. for about 4 hours under N₂ atmosphere. The mixture was cooled to room temperature. About 50 mL of water was added and the mixture was extracted with DCM (about 50 mL*3). The combined organic layer was washed by brine (about 50 mL*3), dried over anhydrous Na₂SO₄ and filtered under reduced pressure. The residue was purified by flash chromatography (Biotage®; about 40 g AgelaFlash® Silica Flash Column, dichloromethane/methanol with methanol from 0~4%, flow rate=100 mL/min, 254 nm) to afford methyl 4-(methylsulfinylmethyl)benzoate (about 4.13 g). LCMS (ESI) [M+H]⁺ m/z: calcd 213.1, found 213.0; ¹H NMR (400 MHz, methanol-d₄) δ ppm 8.02-8.07 (m, 2H), 7.48 (d, J=8.3 Hz, 2H), 4.26 (d, J=13.1 Hz, 1H), 4.08 (d, J=13.1 Hz, 1H), 3.91 (s, 3H), 2.60 (s, 3H).

Step 2: Synthesis of methyl 4-[(N-tert-butoxycarbonyl-S-methyl-sulfonimidoyl)methyl]benzoate A mixture of methyl 4-(methylsulfinylmethyl)benzoate (2 g, 9.42 mmol), NH₂Boc (2.2 g, 18.8 mmol), MgO (1.9 g, 47.1 mmol), PhI(OAc)₂ (4.6 g, 14.3 mmol) and Rh₂(OAc)₄ (210 mg, 0.475 mmol) in DCM (100 mL) was stirred at 40° C. for 12 hours. The mixture was filtered. The filtrate was concentrated under reduced pressure. The residue was purified by flash chromatography (Biotage®; about 20 g AgelaFlash® Silica Flash Column, dichloromethane/methanol with methanol from 0~41%, flow rate=30 mL/min, 254 nm) to afford methyl 4-[(N-tert-butoxycarbonyl-S-methyl-sulfonimidoyl)methyl]benzoate (about 920 mg). ¹H NMR (400 MHz, methanol-d₄) δ ppm 8.05-8.08 (m, 2H), 7.60 (d, J=8.5 Hz, 2H), 4.92 (s, 2H), 3.92 (s, 3H), 3.12 (s, 3H), 1.48 (s, 9H); LCMS (ESI) [M+H]⁺ m/z: calcd 328.1, found 328.1.

Step 3: Synthesis of methyl 4-[1-(N-tert-butoxycarbonyl-S-methyl-sulfonimidoyl)cyclopropyl]benzoate A mixture of methyl 4-[(N-tert-butoxycarbonyl-S-methyl-sulfonimidoyl)methyl]benzoate (about 300 mg, 0.916 mmol), tetraoctylammonium;bromide (about 55 mg, 0.100 mmol), NaOH (about 400 mg, 10.0 mmol) and 1,2-dibromoethane (about 1 mL, 11.6 mmol) in 2-methyloxolane (about 5 mL) and H₂O (0.4 mL) was stirred at about 60° C. for about 12 hours. About 20 mL of water was added and the mixture was extracted with EtOAc (about 20 mL*3). The combined organic layer was washed with brine (about 20 mL*2), dried over anhydrous Na₂SO₄ and concentrated under reduced pressure. The residue was purified by flash chromatography (Biotage®; about 12 g AgelaFlash® Silica Flash Column, petroleum ether/EtOAc with EtOAc from 0~36%, flow rate=25 mL/min, 254 nm) to afford methyl 4-[1-(N-tert-butoxycarbonyl-S-methyl-sulfonimidoyl)cyclopropyl]benzoate (about 75 mg). $^1$H NMR (400 MHz, methanol-$d_4$) δ ppm 8.02-8.06 (m, 2H), 7.75-7.79 (m, 2H), 3.92 (s, 3H), 3.13 (s, 3H), 2.11-2.17 (m, 1H), 1.80-1.86 (m, 1H), 1.49-1.55 (m, 2H), 1.47 (s, 9H). LCMS (ESI) [M+H]$^+$ m/z: calcd 354.1, found 354.1.

Step 4: Synthesis of 4-[1-(N-tert-butoxycarbonyl-S-methyl-sulfonimidoyl)cyclopropyl]benzoic acid A mixture of methyl 4-[1-(N-tert-butoxycarbonyl-S-methyl-sulfonimidoyl)cyclopropyl]benzoate (about 45 mg, 0.127 mmol) and LiOH—H$_2$O (about 30 mg, 0.715 mmol) in H$_2$O (about 2 mL) and THF (about 2 mL) was stirred at about 20° C. for about 1 hour. The mixture was concentrated under reduced pressure to remove the organic solvent. 2N HCl aqueous solution was added to adjust to about pH=5. The mixture was extracted with EtOAc (about 10 mL*3), combined organic layer was concentrated under reduced pressure to give 4-[1-(N-tert-butoxycarbonyl-S-methyl-sulfonimidoyl)cyclopropyl]benzoic acid (about 50 mg). $^1$H NMR (400 MHz, methanol-$d_4$) δ ppm 8.05 (d, J=8.5 Hz, 2H), 7.76 (d, J=8.4 Hz, 2H), 3.13 (s, 3H), 2.11-2.18 (m, 1H), 1.80-1.87 (m, 1H), 1.49-1.55 (m, 2H), 1.47 (s, 9H); LCMS (ESI) [M+H]$^+$ m/z: calcd 340.1, found 340.1.

Step 5: Synthesis of tert-butyl N-[[1-[4-[[2-(tert-butoxycarbonylamino)-5-(2-thienyl)phenyl]carbamoyl]phenyl]cyclopropyl]-methyl-oxo-sulfanylidene]carbamate A mixture of 4-[1-(N-tert-butoxycarbonyl-S-methyl-sulfonimidoyl)cyclopropyl]benzoic acid (about 40 mg, 0.118 mmol), tert-butyl N-[2-amino-4-(2-thienyl)phenyl]carbamate (about 40 mg, 0.138 mmol) and EDCI (about 30 mg, 0.156 mmol) in pyridine (about 5 mL) was stirred at about 50° C. for about 1 hour. The mixture was concentrated under reduced pressure. The residue was purified by flash chromatography (Biotage®; about 4 g AgelaFlash® Silica Flash Column, petroleumether/EtOAc with EtOAc from 0~51%, flow rate=25 mL/min, 254 nm) to afford tert-butyl N-[[1-[4-[[2-(tert-butoxycarbonylamino)-5-(2-thienyl)phenyl]carbamoyl]phenyl]cyclopropyl]-methyl-oxo-sulfanylidene]carbamate (about 40 mg). LCMS (ESI) [M+H]$^+$ m/z: calcd 612.2, found 612.2.

Step 6: Synthesis of N-[2-amino-5-(2-thienyl)phenyl]-4-[1-(methylsulfonimidoyl)cyclopropyl]benzamide To a mixture of tert-butyl N-[[1-[4-[[2-(tert-butoxycarbonylamino)-5-(2-thienyl)phenyl]carbamoyl]phenyl]cyclopropyl]-methyl-oxo-sulfanylidene]carbamate (about 40 mg, 0.654 mmol) in DCM (about 3 mL) was added TFA (about 0.1 mL, 1.30 mmol) at about 20° C. The mixture was stirred at about 20° C. for about 1 hour. The mixture was concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 μm; Mobile phase A: H$_2$O with 0.05% NH$_3$—H$_2$O (v %); Mobile phase B: MeCN; Gradient: B from 36% to 66% in 7.8 mins, hold 100% B for 2 mins; Flow Rate: 30 mL/min; Column Temperature: 30° C.; Wavelength: 220 nm, 254 nm) to afford N-[2-amino-5-(2-thienyl)phenyl]-4-[1-(methylsulfonimidoyl)cyclopropyl]benzamide (about 13.7 mg). $^1$H NMR (400 MHz, methanol-$d_4$) δ ppm 8.02 (d, J=8.1 Hz, 2H), 7.79 (d, J=8.1 Hz, 2H), 7.50 (d, J=1.8 Hz, 1H), 7.37 (dd, J=8.3, 2.0 Hz, 1H), 7.19-7.27 (m, 2H), 7.03 (dd, J=4.9, 3.7 Hz, 1H), 6.92 (d, J=8.4 Hz, 1H), 2.88 (s, 3H), 1.82-1.88 (m, 1H), 1.77 (s, 1H), 1.33-1.41 (m, 2H); HPLC: 98.64%@220 nm, 99.45%@254 nm; LCMS (ESI) [M+H]$^+$ m/z: calcd 412.1, found 412.1.

Example 37. Synthesis of N-[2-amino-5-(5-methyl-2-thienyl)phenyl]-4-(methylsulfonimidoyl)benzamide (Compound 139)

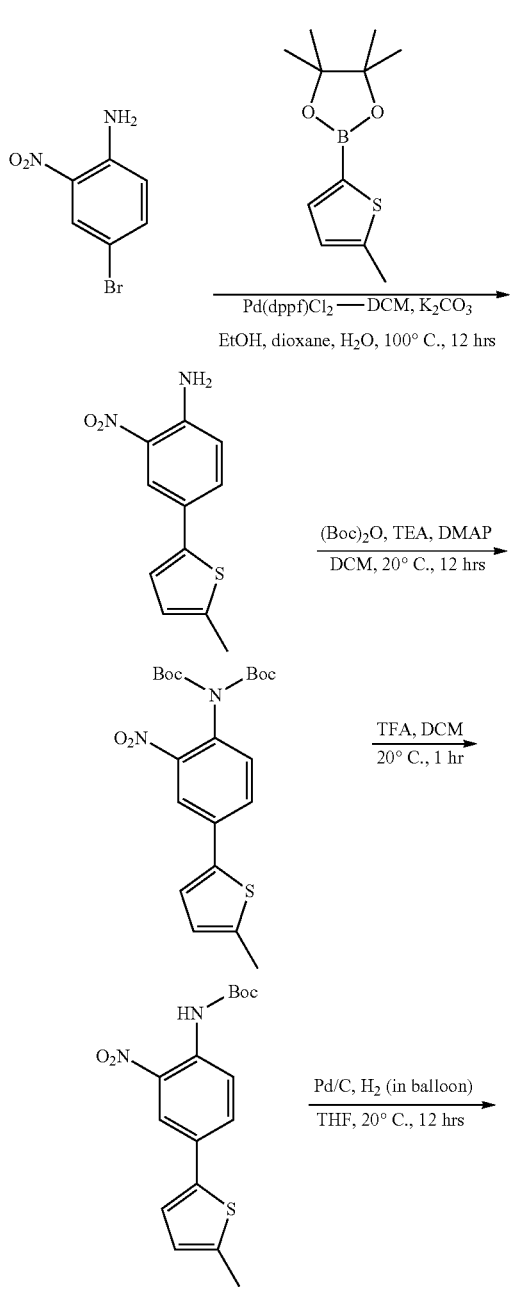

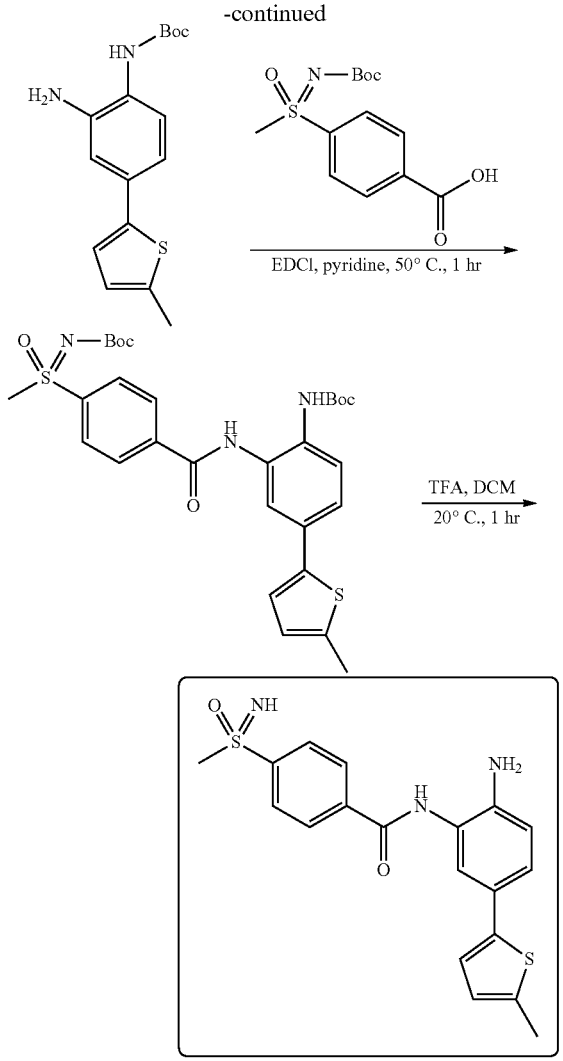

Step 1: Synthesis of 4-(5-methyl-2-thienyl)-2-nitro-aniline

To a mixture of 4,4,5,5-tetramethyl-2-(5-methyl-2-thienyl)-1,3,2-dioxaborolane (750 mg, 3.35 mmol) and 4-bromo-2-nitro-aniline (about 550 mg, 2.53 mmol) in EtOH (about 2 mL), H$_2$O (2 mL) and dioxane (about 6 mL) were added Pd(dppf)Cl$_2$-DCM (about 210 mg, 0.258 mmol) and K$_2$CO$_3$ (about 1.05 g, 7.60 mmol). The mixture was stirred at about 100° C. for about 12 hours. The resulting mixture was quenched by addition of water (about 50 mL) and extracted with EtOAc (about 100 mL*3). The combined organic layer was washed with brine (about 100 mL), dried over anhydrous Na$_2$SO$_4$, filtered and concentrated under reduced pressure. The residue was purified by flash chromatography (ISCO®; about 20 g SepaFlash® Silica Flash Column, petroleum ether/EtOAc with EtOAc from 0~30%, 30 mL/min, 254 nm) to afford 4-(5-methyl-2-thienyl)-2-nitro-aniline (about 590 mg). $^1$H NMR (400 MHz, DMSO-d$_6$) δ ppm 8.03 (d, J=2.3 Hz, 1H), 7.67 (dd, J=8.8, 2.3 Hz, 1H), 7.56 (s, 2H), 7.18 (d, J=3.5 Hz, 1H), 7.06 (d, J=9.0 Hz, 1H), 6.77 (dd, J=3.5, 1.0 Hz, 1H), 2.43 (s, 3H); LCMS (ESI) [M+H]$^+$ m/z: calcd 235.0; found 235.0.

Step 2: Synthesis of tert-butyl N-tert-butoxycarbonyl-N-[4-(5-methyl-2-thienyl)-2-nitro-phenyl]carbamate A mixture of 4-(5-methyl-2-thienyl)-2-nitro-aniline (about 590 mg, 2.52 mmol), TEA (about 1.05 mL, 7.56 mmol), DMAP (about 61 mg, 0.499 mmol) and (Boc)$_2$O (1.65 g, 7.56 mmol) in DCM (10 mL) was stirred at about 20° C. for about 12 hours. The mixture was concentrated under reduced pressure. The residue was triturated in MeOH (about 40 mL). The mixture was filtered. The filter cake was dried under reduced pressure afford tert-butyl N-tert-butoxycarbonyl-N-[4-(5-methyl-2-thienyl)-2-nitro-phenyl]carbamate (about 720 mg). $^1$H NMR (400 MHz, DMSO-d$_6$) δ ppm 8.25 (d, J=2.0 Hz, 1H), 7.95 (dd, J=8.4, 2.1 Hz, 1H), 7.59 (s, 2H), 6.88-6.97 (m, 1H), 2.51-2.51 (m, 3H), 1.35 (s, 18H).

Step 3: Synthesis of tert-butyl N-[4-(5-methyl-2-thienyl)-2-nitro-phenyl]carbamate A mixture of tert-butyl N-tert-butoxycarbonyl-N-[4-(5-methyl-2-thienyl)-2-nitro-phenyl]carbamate (about 670 mg, 1.54 mmol), DCM (about 10 mL) and TFA (about 0.18 mL, 2.31 mmol) was stirred at about 20° C. for about 1 hour. The resulting mixture was quenched by addition of saturated NaHCO$_3$ aqueous solution (about 20 mL) and extracted with DCM (about 50 mL*3). The combined organic layer was dried over anhydrous Na$_2$SO$_4$, filtered and concentrated under reduced pressure to afford tert-butyl N-[4-(5-methyl-2-thienyl)-2-nitro-phenyl]carbamate (about 520 mg).

Step 4: Synthesis of tert-butyl N-[2-amino-4-(5-methyl-2-thienyl)phenyl]carbamate To a solution of tert-butyl N-[4-(5-methyl-2-thienyl)-2-nitro-phenyl]carbamate (about 520 mg, 1.56 mmol) in THF (about 10 mL) was added Pd/C (about 200 mg, 10 wt % Pd with 50 wt % water). The suspension was degassed and purged with hydrogen for about 3 times. The mixture was stirred under hydrogen (in balloon) at about 20° C. for about 12 hours. The resulting mixture was filtered and filter cake was washed by MeOH (about 50 mL*3). The filtrate was concentrated under reduced pressure to give tert-butyl N-[2-amino-4-(5-methyl-2-thienyl)phenyl]carbamate (about 450 mg), which was used to next step without further purification. $^1$H NMR (400 MHz, DMSO-d$_6$) δ ppm 8.28-8.37 (m, 1H), 7.18-7.25 (m, 1H), 7.04-7.10 (m, 1H), 6.87-6.92 (m, 1H), 6.73-6.80 (m, 2H), 4.97 (s, 2H), 2.43 (s, 3H), 1.44-1.48 (m, 9H); LCMS (ESI) [M+H]$^+$ m/z: calcd 305.1, found 305.1.

Step 5: Synthesis of tert-butyl N-[[4-[[2-(tert-butoxycarbonylamino)-5-(5-methyl-2-thienyl)phenyl]carbamoyl]phenyl]-methyl-oxo-sulfanylidene]carbamate To a mixture of 4-(N-tert-butoxycarbonyl-S-methyl-sulfonimidoyl)benzoic acid (about 100 mg, 0.334 mmol) and tert-butyl N-[2-amino-4-(5-methyl-2-thienyl)phenyl]carbamate (about 123 mg, 0.404 mmol), 3-(ethyliminomethyleneamino)-N,N-dimethyl-propan-1-amine;hydrochloride (about 97 mg, 0.506 mmol) in pyridine (about 4 mL) was stirred at 50° C. for about 1 hour. The resulting mixture was concentrated under reduced pressure. The residue was purified by purified by flash chromatography (ISCO®; about 12 g AgelaFlash® Silica Flash Column, petroleum ether/EtOAc with EtOAc from 0~50%, flow rate=30 mL/min, 254 nm) to afford tert-butyl N-[[4-[[2-(tert-butoxycarbonylamino)-5-(5-methyl-2-thienyl)phenyl]carbamoyl]phenyl]-methyl-oxo-sulfanylidene]carbamate (about 120 mg).

Step 6: Synthesis of N-[2-amino-5-(5-methyl-2-thienyl)phenyl]-4-(methylsulfonimidoyl)benzamide To a solution of tert-butyl N-[[4-[[2-(tert-butoxycarbonylamino)-5-(5-methyl-2-thienyl)phenyl]carbamoyl]phenyl]-methyl-oxo-sulfanylidene]carbamate (about 120 mg, 0.205 mmol), DCM (2 mL) and TFA (about 2 mL, 25.9 mmol) was stirred at about 20° C. for about 1 hour. The mixture was concentrated under reduced pressure, and adjusted to about pH=8 with 28% $NH_3$—$H_2O$. The mixture was purified by preparative HPLC (Instrument: Gilson GX-281 Liquid Handler, Gilson 322 Pump, Gilson 156 UV Detector; Column: 2_Phenomenex Gemini C18 75*40 mm*3 m; Mobile phase A: water (10 mmol $NH_4HCO_3$)-ACN; Mobile phase B: MeCN; Gradient: B from 33% to 63% in 7.8 min, hold 100% B for 2 min; Flow Rate: 30 mL/min; Column Temperature: 30° C.; Wavelength: 220 nm, 254 nm) to give N-[2-amino-5-(5-methyl-2-thienyl)phenyl]-4-(methylsulfonimidoyl)benzamide (about 32.1 mg). $^1$H NMR (400 MHz, DMSO-$d_6$) δ ppm 9.91 (s, 1H), 8.18 (d, J=8.25 Hz, 2H), 8.05 (d, J=8.25 Hz, 2H), 7.40 (d, J=1.75 Hz, 1H), 7.23 (dd, J=8.38, 2.13 Hz, 1H), 7.02 (d, J=3.50 Hz, 1H), 6.80 (d, J=8.38 Hz, 1H), 6.69-6.76 (m, 1H), 5.17 (brs, 2H), 4.40 (brs, 1H), 3.12 (s, 3H), 2.42 (s, 3H); LCMS (ESI) [M+H]$^+$ m/z: calcd 386.1, found 386.1; HPLC: 99.730%@220 nm, 99.850%@254 nm.

Example 38. Synthesis of N-[2-amino-5-(5-chloro-2-thienyl)phenyl]-4-(methylsulfonimidoyl)benzamide (Compound 137)

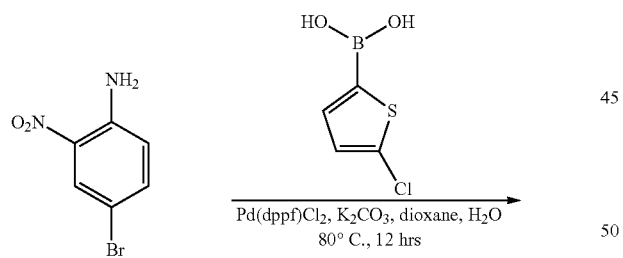

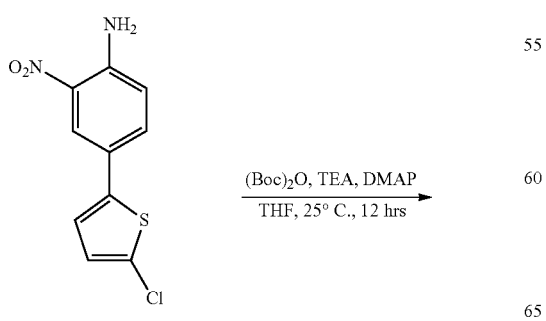

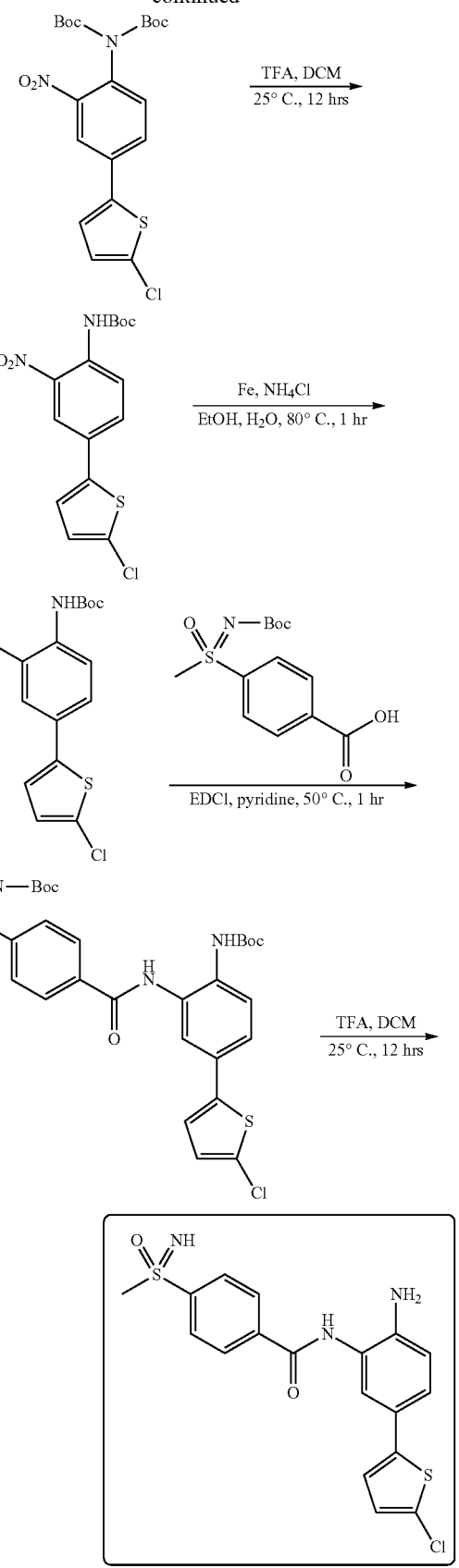

Step 1: Synthesis of 4-(5-chloro-2-thienyl)-2-nitro-aniline

A mixture of (5-chloro-2-thienyl)boronic acid (about 898 mg, 5.53 mmol), 4-bromo-2-nitro-aniline (about 1 g, 4.61 mmol), tripotassium;carbonate (about 1.91 g, 13.8 mmol) and cyclopentyl(diphenyl)phosphane;dichloropalladium; iron (about 337 mg, 0.461 mmol) in $H_2O$ (about 3 mL) and dioxane (about 15 mL) was degassed and purged with $N_2$ for about 3 times, and then the mixture was stirred at about 80° C. for about 12 hours under $N_2$ atmosphere. The reaction mixture was filtered and concentrated under reduced pressure. The residue was purified by flash chromatography (ISCO®; about 20 g SepaFlash® Silica Flash Column, Petroleum Ether/EtOAc with EtOAc from 0~50%, 40 mL/min, 254 nm) to afford 4-(5-chloro-2-thienyl)-2-nitro-aniline (about 700 mg). $^1$H NMR (400 MHz, DMSO) δ ppm 8.07 (d, J=2.4 Hz, 1H), 7.61-7.73 (m, 3H), 7.30 (d, J=4.0 Hz, 1H), 7.06-7.13 (m, 2H).

Step 2: Synthesis of tert-butyl N-tert-butoxycarbonyl-N-[4-(5-chloro-2-thienyl)-2-nitro-phenyl]carbamate To a solution of 4-(5-chloro-2-thienyl)-2-nitro-aniline (about 700 mg, 2.75 mmol) in THF (about 10 mL) were added 4-(5-chloro-2-thienyl)-2-nitro-aniline (about 700 mg, 2.75 mmol), N,N-diethylethanamine (about 1.2 mL, 8.24 mmol), and N,N-dimethylpyridin-4-amine (about 34 mg, 0.278 mmol). The mixture was stirred at about 25° C. for about 12 hours. The reaction mixture was diluted with water (about 20 mL) and extracted with EtOAc (about 30 mL*2). The combined organic layers were washed with brine (about 30 mL), dried over $Na_2SO_4$ and filtered. The filtrate was concentrated under reduced pressure. The residue was purified by flash chromatography (ISCO®; about 20 g Agela-Flash® Silica Flash Column, petroleum ether/EtOAc with EtOAc from 0~15%, flow rate=40 mL/min, 254 nm) to afford tert-butyl N-tert-butoxycarbonyl-N-[4-(5-chloro-2-thienyl)-2-nitro-phenyl]carbamate (about 920 mg). $^1$H NMR (400 MHz, CDCl$_3$) δ ppm 8.18 (d, J=2.4 Hz, 1H), 7.72 (dd, J=8.4, 2.0 Hz, 1H), 7.33 (d, J=8.4 Hz, 1H), 7.21 (d, J=3.6 Hz, 1H), 6.96 (d, J=4.0 Hz, 1H), 1.43 (s, 18H).

Step 3: Synthesis of tert-butyl N-[4-(5-chloro-2-thienyl)-2-nitro-phenyl]carbamate To a solution of tert-butyl N-tert-butoxycarbonyl-N-[4-(5-chloro-2-thienyl)-2-nitro-phenyl]carbamate (about 920 mg, 2.02 mmol) in DCM (about 10 mL) was added 2,2,2-trifluoroacetic acid (about 0.2 mL, 3.03 mmol). The mixture was stirred at about 20° C. for about 12 hours. The reaction mixture was diluted with DCM (about 30 mL), and adjusted to about pH=8 with saturated $Na_2CO_3$ aqueous solution. The resultant mixture was dried over $Na_2SO_4$ and filtered. The filtrate was concentrated under reduced pressure. The residue was purified by flash chromatography (ISCO®; about 12 g SepaFlash® Silica Flash Column, Petroleum Ether/EtOAc with EtOAc from 0~15%, 60 mL/min, 254 nm) to afford tert-butyl N-[4-(5-chloro-2-thienyl)-2-nitro-phenyl]carbamate (about 561 mg). $^1$H NMR (400 MHz, DMSO) δ ppm 9.69 (s, 1H), 8.11 (d, J=2.0 Hz, 1H), 7.88 (dd, J=8.4, 2.0 Hz, 1H), 7.67 (d, J=8.4 Hz, 1H), 7.52 (d, J=4.0 Hz, 1H), 7.20 (d, J=4.0 Hz, 1H), 1.45 (s, 9H).

Step 4: Synthesis of tert-butyl N-[2-amino-4-(5-chloro-2-thienyl)phenyl]carbamate To a solution of tert-butyl N-[4-(5-chloro-2-thienyl)-2-nitro-phenyl]carbamate (about 523 mg, 1.47 mmol) in EtOH (about 6 mL) was added Iron (about 412 mg, 7.38 mmol) and ammonia;hydrochloride (about 394 mg, 7.37 mmol). The mixture was stirred at about 80° C. for about 1 hour. The reaction mixture was filtered. The filtrate was diluted with $H_2O$ (about 30 mL) and extracted with EtOAc (about 40 mL*2). The combined organic layers were washed with brine (about 40 mL), dried over anhydrous $Na_2SO_4$, filtered and concentrated under reduced pressure. The residue was purified by flash chromatography (ISCO®; about 12 g SepaFlash® Silica Flash Column, Petroleum Ether/EtOAc with EtOAc from 0~15%, 60 mL/min, 254 nm) to afford tert-butyl N-[2-amino-4-(5-chloro-2-thienyl)phenyl]carbamate (about 270 mg). $^1$H NMR (400 MHz, CDCl$_3$) δ ppm 7.30 (d, J=8.4 Hz, 1H), 6.93-7.01 (m, 3H), 6.85 (d, J=3.6 Hz, 1H), 6.34 (s, 2H), 1.53 (s, 9H). LCMS (ESI) [M+H]$^+$ m/z: calcd 325.1, found 268.8 (t-Bu cleaved mass).

Step 5: Synthesis of tert-butyl N-[[4-[[2-(tert-butoxycarbonylamino)-5-(5-chloro-2-thienyl)phenyl]carbamoyl]phenyl]-methyl-oxo-sulfanylidene]carbamate To a solution of tert-butyl N-[2-amino-4-(5-chloro-2-thienyl)phenyl]carbamate (about 221 mg, 0.680 mmol) and 4-(N-tert-butoxycarbonyl-S-methyl-sulfonimidoyl)benzoic acid (about 170 mg, 0.568 mmol) in pyridine (about 6 mL) was added 3-(ethyliminomethyleneamino)-N,N-dimethylpropan-1-amine (about 130 mg, 0.837 mmol). The mixture was stirred at about 50° C. for about 1 hour. The reaction mixture was diluted with $NH_4Cl$ (about 30 mL) and extracted with EtOAc (about 40 mL*2). The combined organic layers were washed with brine (about 40 mL), dried over anhydrous $Na_2SO_4$, filtered and concentrated under reduced pressure. The residue was purified by flash chromatography (ISCO®; about 12 g SepaFlash® Silica Flash Column, Petroleum Ether/EtOAc with EtOAc from 0~60%, 40 mL/min, 254 nm) to afford tert-butyl N-[[4-[[2-(tert-butoxycarbonylamino)-5-(5-chloro-2-thienyl)phenyl]carbamoyl]phenyl]-methyl-oxo-sulfanylidene]carbamate (about 270 mg). $^1$H NMR (400 MHz, CDCl$_3$) δ ppm 8.20 (d, J=8.4 Hz, 2H), 8.08 (d, J=8.4 Hz, 3H), 7.31 (dd, J=8.4, 2.0 Hz, 1H), 7.20 (d, J=8.4 Hz, 1H), 7.08 (d, J=4.0 Hz, 1H), 6.89 (d, J=4.0 Hz, 1H), 6.82 (s, 1H), 3.27 (s, 3H), 1.54 (s, 9H), 1.41 (s, 9H); LCMS (ESI) [M+H]$^+$ m/z: calcd 606.1, found 506.0 (Boc cleaved mass).

Step 6: Synthesis of N-[2-amino-5-(5-chloro-2-thienyl)phenyl]-4-(methylsulfonimidoyl)benzamide To a solution of tert-butyl N-[[4-[[2-(tert-butoxycarbonylamino)-5-(5-chloro-2-thienyl)phenyl]carbamoyl]phenyl]-methyl-oxo-sulfanylidene]carbamate (about 240 mg, 0.396 mmol) in DCM (about 10 mL) was added TFA (about 0.3 mL, 3.96 mmol). The mixture was stirred at about 25° C. for about 12 hours. The reaction mixture was diluted with DCM (about 30 mL) and adjusted to about pH=8 with saturated $Na_2CO_3$ aqueous solution. The resultant mixture was dried over $Na_2SO_4$ and filtered. The filtrate was concentrated under reduced pressure. The residue was purified by flash chromatography (ISCO®; about 12 g SepaFlash® Silica Flash Column, Petroleum Ether/EtOAc with EtOAc from 0~100%, 40 mL/min, 254 nm) to give the desired product, but impure. The residue was further purified by preparative HPLC (Instrument: Gilson GX-281 Liquid Handler, Gilson 322 Pump, Gilson 156 UV Detector; Column: Waters Xbridge 150*25 mm*5 µm; Mobile phase A: $H_2O$ with 0.05% $NH_3$—$H_2O$ (v %); B: ACN; Gradient: B from 32% to 62% in 9.5 min, hold 100% B for 2 min; Flow Rate: 30 mL/min; Column Temperature: 30° C.; Wavelength: 220 nm, 254 nm) to afford N-[2-amino-5-(5-chloro-2-thienyl)phenyl]-4-(methylsulfonimidoyl)benzamide (about 27.2 mg). $^1$H NMR (400 MHz, DMSO) δ ppm 9.91 (s, 1H), 8.15-8.20 (m, 2H), 8.05 (d, J=8.4 Hz, 2H), 7.42 (d, J=2.0 Hz, 1H), 7.26 (dd, J=8.4, 2.4 Hz, 1H), 7.12 (d, J=4.0 Hz, 1H), 7.06 (d, J=3.6 Hz, 1H), 6.81 (d, J=8.4 Hz, 1H), 5.32 (s, 2H), 4.40 (s, 1H), 3.12 (s, 3H); LCMS (ESI) [M+H]$^+$ m/z: calcd 406.0, found 405.9. HPLC: 97.48%@220 nm, 99.47%@254 nm.

Example 39. Synthesis of N-[2-amino-5-(p-tolyl)phenyl]-4-(methylsulfonimidoyl)benzamide (Compound 136)

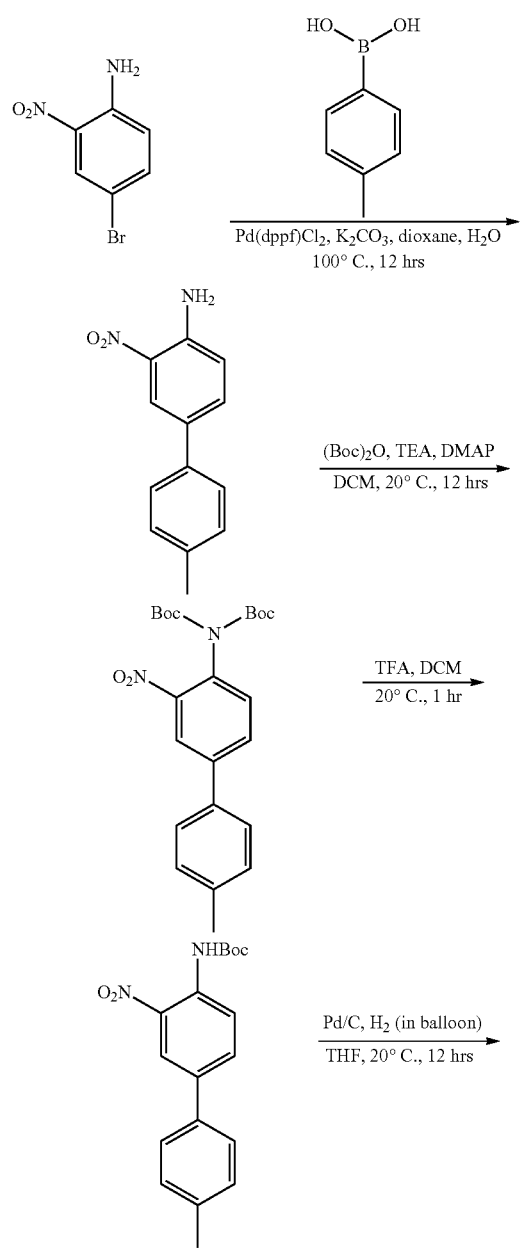

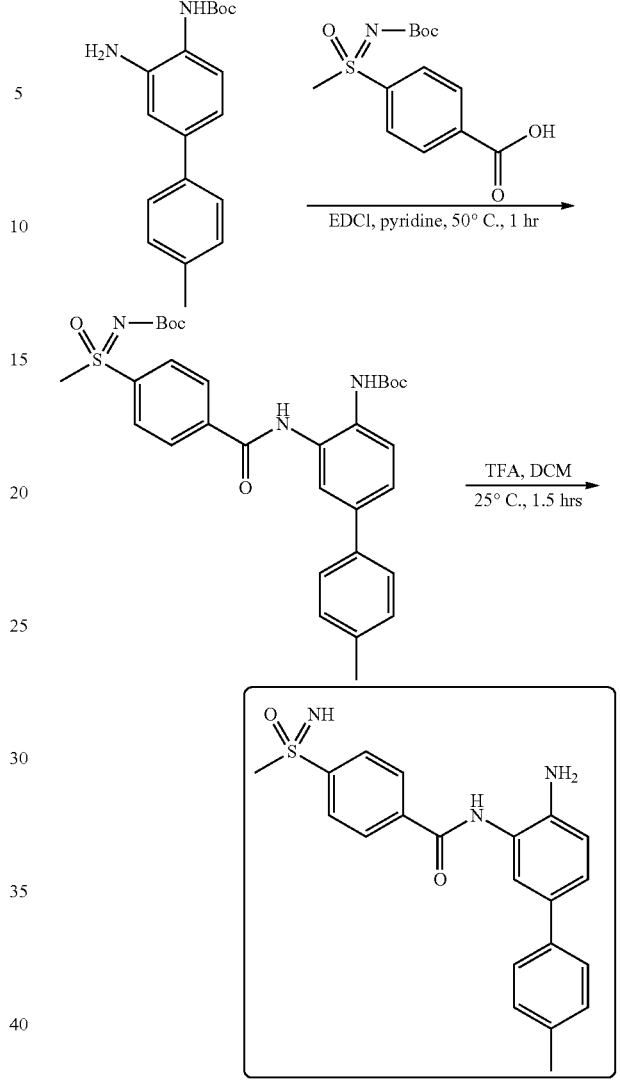

Step 1: Synthesis of 2-nitro-4-(p-tolyl)aniline

To a mixture of 4-bromo-2-nitro-aniline (about 2 g, 9.22 mmol), p-tolylboronic acid (1.88 g, 13.8 mmol) in dioxane (about 15 mL) and H$_2$O (about 5 mL) were added Pd(dppf)Cl$_2$ (about 670 mg, 0.917 mmol) and K$_2$CO$_3$ (about 3.82 g, 27.6 mmol). The resulting mixture was stirred at about 100° C. for about 12 hours under N$_2$. The resulting mixture was quenched by addition of water (about 100 mL) and extracted with EtOAc (about 100 mL*3). The combined organic layer was washed with saturated NH$_4$Cl aqueous solution (about 100 mL*2), brine (about 100 mL), dried over anhydrous Na$_2$SO$_4$, filtered and concentrated under reduced pressure. The residue was purified by flash chromatography (ISCO®; about 40 g SepaFlash® Silica Flash Column, petroleum ether/EtOAc with EtOAc from 0~20%, 40 mL/min, 254 nm) to afford 2-nitro-4-(p-tolyl)aniline (about 2.08 g). $^1$H NMR (400 MHz, DMSO-d$_6$) δ ppm 8.17 (d, J=2.3 Hz, 1H), 7.76 (dd, J=8.9, 2.1 Hz, 1H), 7.45-7.56 (m, 4H), 7.24 (d, J=7.8 Hz, 2H), 7.11 (d, J=9.0 Hz, 1H), 2.32 (s, 3H); LCMS (ESI) [M+H]$^+$ m/z: calcd 229.1; found 229.1.

Step 2: Synthesis of tert-butyl N-tert-butoxycarbonyl-N-[2-nitro-4-(p-tolyl)phenyl]carbamate A mixture of 2-nitro-4-(p-tolyl)aniline (about 2.08 g, 9.11 mmol), TEA (about 3.8 mL, 27.3 mmol), DMAP (about 220 mg, 1.80 mmol) and (Boc)$_2$O (5.97 g, 27.3 mmol) in DCM (about 25 mL) was stirred at about 20° C. for about 12 hours. The residue was triturated in a solution MeOH (about 10 mL). The mixture was filtered. The filter cake was concentrated under reduced pressure to afford tert-butyl N-tert-butoxycarbonyl-N-[2-nitro-4-(p-tolyl)phenyl]carbamate (about 3.08 g). $^1$H NMR (400 MHz, DMSO-d$_6$) δ ppm 8.33 (d, J=1.9 Hz, 1H), 8.07 (dd, J=8.3, 1.9 Hz, 1H), 7.72 (d, J=8.0 Hz, 2H), 7.63 (d, J=8.3 Hz, 1H), 7.34 (d, J=8.0 Hz, 2H), 2.37 (s, 3H), 1.35 (s, 18H).

Step 3: Synthesis of tert-butyl N-[2-nitro-4-(p-tolyl)phenyl]carbamate

A mixture of tert-butyl N-tert-butoxycarbonyl-N-[2-nitro-4-(p-tolyl)phenyl]carbamate (about 3.08 g, 7.19 mmol), DCM (about 31 mL) and TFA (about 0.8 mL, 10.8 mmol) was stirred at about 20° C. for about 1 hour. The resulting mixture was quenched by addition of water (about 50 mL) and extracted with DCM (about 50 mL*3). The combined organic layer was washed with saturated NaHCO$_3$ aqueous solution (about 50 mL*2), brine (about 50 mL), dried over anhydrous Na$_2$SO$_4$, filtered and concentrated under reduced pressure to afford tert-butyl N-[2-nitro-4-(p-tolyl)phenyl] carbamate (about 2.5 g). $^1$H NMR (400 MHz, DMSO-d$_6$) δ ppm 9.59-9.67 (m, 1H), 8.15 (d, J=2.0 Hz, 1H), 7.93-8.01 (m, 1H), 7.68-7.75 (m, 1H), 7.58-7.66 (m, 2H), 7.26-7.33 (m, 2H), 2.32-2.37 (m, 3H), 1.42-1.49 (m, 9H).

Step 4: Synthesis of tert-butyl N-[2-amino-4-(p-tolyl)phenyl]carbamate

A mixture of tert-butyl N-[2-nitro-4-(p-tolyl)phenyl]carbamate (about 2.5 g, 7.61 mmol), THF (about 25 mL) and Pd/C (about 400 mg, 10 wt % Pd with 50 wt % water) was stirred at 20° C. for 12 hours under H$_2$ (in balloon). The resulting mixture was filtered and concentrated under reduced pressure to afford tert-butyl N-[2-amino-4-(p-tolyl) phenyl]carbamate (about 2.15 g). $^1$H NMR (400 MHz, DMSO-d$_6$) δ ppm 8.32 (brs, 1H), 7.43 (d, J=8.0 Hz, 2H), 7.19-7.31 (m, 3H), 6.96 (d, J=2.0 Hz, 1H), 6.80 (dd, J=8.2, 1.9 Hz, 1H), 4.92 (s, 2H), 2.32 (s, 3H), 1.47 (s, 9H).

Step 5: Synthesis of tert-butyl N-[[4-[[2-(tert-butoxycarbonylamino)-5-(p-tolyl)phenyl]carbamoyl]phenyl]-methyl-oxo-sulfanylidene]carbamate A mixture of tert-butyl N-[2-amino-4-(p-tolyl)phenyl]carbamate (about 130 mg, 0.436 mmol), 4-(N-tert-butoxycarbonyl-S-methyl-sulfonimidoyl)benzoic acid (about 100 mg, 0.334 mmol) and 3-(ethyliminomethyleneamino)-N,N-dimethyl-propan-1-amine;hydrochloride (about 96 mg, 0.501 mmol) in pyridine (about 4 mL) was stirred at 50° C. for 1 hour. The mixture was concentrated under reduced pressure. The residue was purified by flash chromatography (ISCO®; 8 g SepaFlash® Silica Flash Column, petroleum ether/EtOAc with EtOAc from 0~50%, 40 mL/min, 254 nm) to afford tert-butyl N-[[4-[[2-(tert-butoxycarbonylamino)-5-(p-tolyl)phenyl]carbamoyl]phenyl]-methyl-oxo-sulfanylidene] carbamate (about 78 mg). LCMS (ESI) [M+H]$^+$ m/z: calcd 580.2; found 580.2.

Step 6: Synthesis of N-[2-amino-5-(p-tolyl)phenyl]-4-(methylsulfonimidoyl)benzamide A mixture of tert-butyl N-[[4-[[2-(tert-butoxycarbonylamino)-5-(p-tolyl)phenyl]carbamoyl]phenyl]-methyl-oxo-sulfanylidene]carbamate (87 mg, 0.150 mmol), DCM (2 mL) and TFA (1.5 mL, 19.5 mmol) was stirred at 20° C. for 1.5 hours. The mixture was concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 μm; Mobile phase A: H$_2$O with 0.05% NH$_3$—H$_2$O (v %); Mobile phase B: MeCN; Gradient: B from 35% to 65% in 7.8 min, hold 100% B for 2 min; Flow Rate: 25 mL/min; Column Temperature: 30° C.; Wavelength: 220 nm, 254 nm) to give N-[2-amino-5-(p-tolyl)phenyl]-4-(methylsulfonimidoyl)benzamide (30 mg). $^1$H NMR (400 MHz, DMSO-d$_6$) δ ppm 9.92 (s, 1H), 8.16-8.24 (m, 2H), 8.06 (d, J=8.3 Hz, 2H), 7.40-7.54 (m, 3H), 7.32 (dd, J=8.4, 2.1 Hz, 1H), 7.21 (d, J=8.0 Hz, 2H), 6.86 (d, J=8.3 Hz, 1H), 5.12 (s, 2H), 4.40 (s, 1H), 3.13 (s, 3H), 2.31 (s, 3H); LCMS (ESI) [M+H]$^+$ m/z: calcd 380.1; found 380.1; HPLC: 99.080%@220 nm, 99.620%@254 nm.

Example 40. Synthesis of (S)—N-[2-amino-5-(5-fluoro-2-thienyl)phenyl]-4-(methylsulfonimidoyl) benzamide (Compound 149)

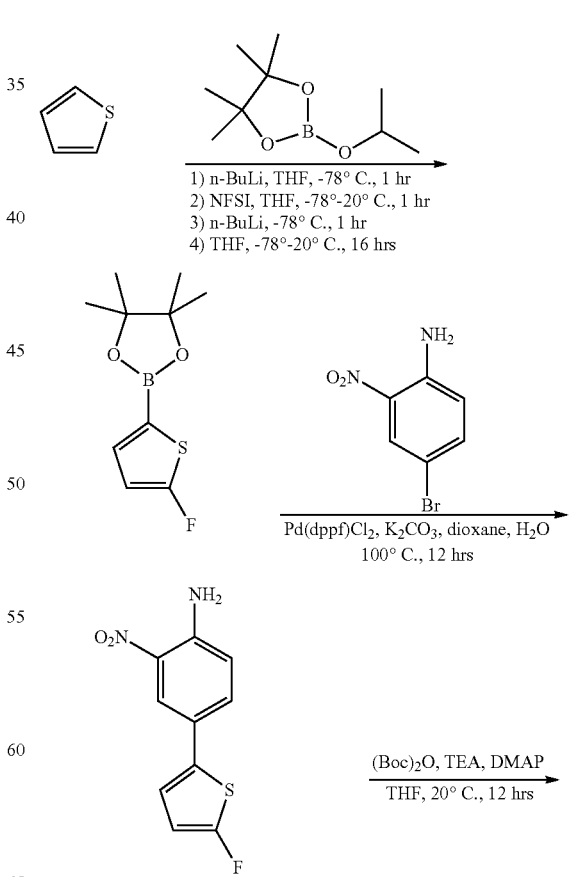

-continued

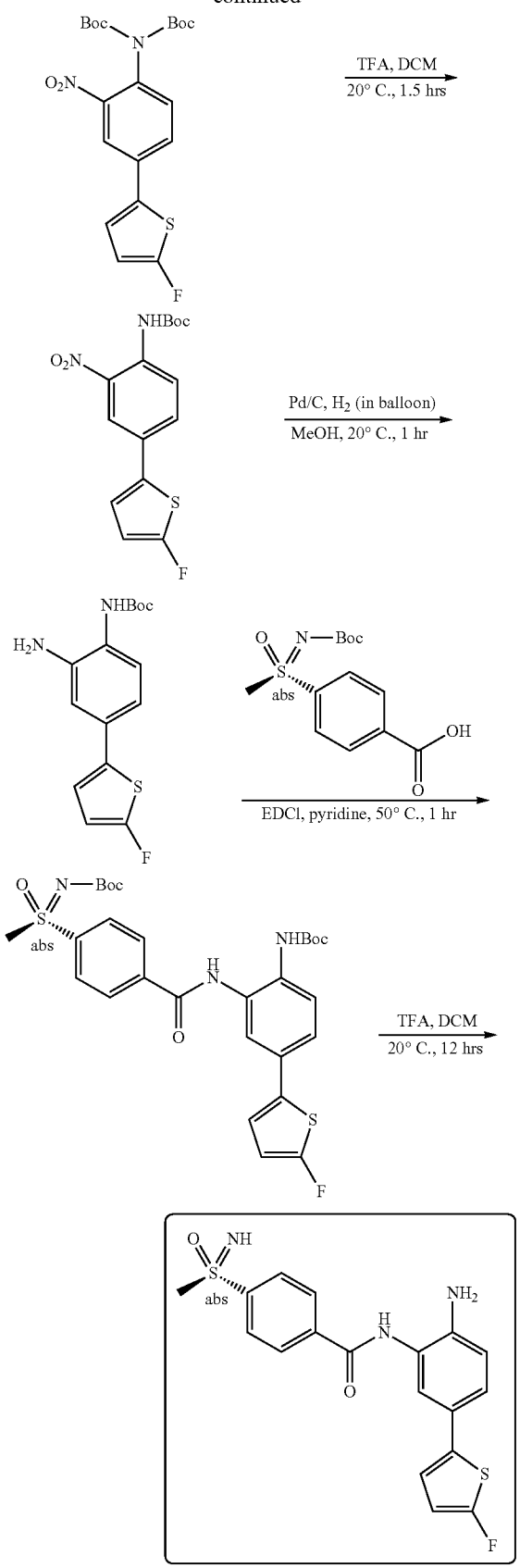

Step 1: Synthesis of 2-(5-fluoro-2-thienyl)-4,4,5,5-tetramethyl-1,3,2-dioxaborolane To a solution of thiophene (about 6 g, 71.3 mmol) in THF (about 150 mL) under nitrogen atmosphere was added 2.5 M n-BuLi/hexane (about 30 mL, 75.0 mmol) dropwise at about −78° C. and the reaction mixture was stirred at about −78° C. for 1 hour under nitrogen atmosphere. Then N-(benzenesulfonyl)-N-fluoro-benzenesulfonamide (about 23.7 g, 75.2 mmol) in THF (about 90 mL) was added into above mixture dropwise at about −78° C. and warmed to about 20° C. for about 1 hour. Then the reaction mixture was cooled to about −78° C., and another portion of about 2.5 M n-BuLi/hexane (about 30 mL, 75.0 mmol) was added dropwise at −78° C. and stirred at about −78° C. for about 1 hour. Finally, 2-isopropoxy-4,4,5,5-tetramethyl-1,3,2-dioxaborolane (about 15.5 mL, 76.0 mmol) in THF (about 60 mL) was added into above mixture dropwise at about −78° C., and the reaction mixture was allowed to warm to about 20° C. and stirred at about 20° C. for about 16 hours. The reaction mixture was cooled to about 0° C. and quenched with saturated NH$_4$Cl aqueous solution (about 100 mL). The resultant mixture was extracted with petroleum ether (about 200 mL*3). The combined organic layers were washed with brine (about 200 ml), dried over Na$_2$SO$_4$ and filtered. The filtrate was concentrated under reduced pressure to give 2-(5-fluoro-2-thienyl)-4,4,5,5-tetramethyl-1,3,2-dioxaborolane (about 12 g). $^1$H NMR (400 MHz, chloroform-d) δ ppm 7.17-7.24 (m, 1H), 6.48 (dd, J=4.0, 0.8 Hz, 1H), 1.25 (s, 12H); $^{19}$F NMR (377 MHz, chloroform-d) δ ppm −125.61.

Step 2: Synthesis of 4-(5-fluoro-2-thienyl)-2-nitro-aniline

To a solution of 4-bromo-2-nitro-aniline (about 2.8 g, 12.9 mmol) in dioxane (about 50 mL) and H$_2$O (about 10 mL) were added 2-(5-fluoro-2-thienyl)-4,4,5,5-tetramethyl-1,3,2-dioxaborolane (about 7 g, 30.7 mmol), Pd(dppf)Cl$_2$ (about 1.2 g, 1.64 mmol) and K$_2$CO$_3$ (about 5.32 g, 38.5 mmol). The mixture was stirred at about 100° C. for about 12 hours under nitrogen. The reaction mixture was concentrated under reduced pressure. The residue was purified by flash chromatography (ISCO®; about 40 g AgelaFlash® Silica Flash Column, petroleum ether/EtOAc with EtOAc from 0~15%, flow rate=45 mL/min, 254 nm) to afford 4-(5-fluoro-2-thienyl)-2-nitro-aniline (about 1.8 g). $^1$H NMR (400 MHz, chloroform-d) δ ppm 8.22 (d, J=2.0 Hz, 1H), 7.49 (dd, J=8.8, 2.0 Hz, 1H), 6.79-6.86 (m, 2H), 6.45 (dd, J=4.0, 2.0 Hz, 1H), 6.17 (s, 2H).

Step 3: Synthesis of tert-butyl N-tert-butoxycarbonyl-N-[4-(5-fluoro-2-thienyl)-2-nitro-phenyl]carbamate To a solution of 4-(5-fluoro-2-thienyl)-2-nitro-aniline (about 3.3 g, 13.9 mmol) in THF (about 40 mL) were added tert-butoxycarbonyl tert-butyl carbonate (about 7 mL, 30.5 mmol), TEA (about 7 mL, 50.2 mmol) and N,N-dimethylpyridin-4-amine (about 180 mg, 1.47 mmol). The mixture was stirred at about 20° C. for about 12 hours. The reaction mixture was diluted with water (about 50 mL) and extracted with EtOAc (about 80 mL*3). The combined organic layers were washed with brine (about 50 mL), dried over Na$_2$SO$_4$ and filtered. The filtrate was concentrated under reduced pressure. The residue was purified by flash chromatography (ISCO®; about 40 g AgelaFlash® Silica Flash Column, petroleum ether/EtOAc with EtOAc from 0~10%, flow rate=60 mL/min, 254 nm) to afford tert-butyl N-tert-butoxy-carbonyl-N-[4-(5-fluoro-2-thienyl)-2-nitro-phenyl]carbamate (about 4.9 g). LCMS (ESI) [M+Na]+ m/z: calcd 461.1; found 461.0.

Step 4: Synthesis of tert-butyl N-[4-(5-fluoro-2-thienyl)-2-nitro-phenyl]carbamate To a solution of tert-butyl N-tert-butoxycarbonyl-N-[4-(5-fluoro-2-thienyl)-2-nitro-phenyl]carbamate (about 4.9 g, 11.2 mmol) in DCM (about 50 mL) was added TFA (about 1.2 mL, 15.6 mmol). The mixture was stirred at about 20° C. for about 1.5 hours. The reaction mixture was quenched with saturated $Na_2CO_3$ aqueous to about pH=8 and extracted with DCM (about 30 mL*3). The resultant mixture was dried over $Na_2SO_4$ and filtered. The filtrate was concentrated under reduced pressure. The residue was purified by flash chromatography (ISCO®; about 40 g AgelaFlash® Silica Flash Column, petroleum ether/EtOAc with EtOAc from 0~9%, flow rate=40 mL/min, 254 nm) to afford tert-butyl N-[4-(5-fluoro-2-thienyl)-2-nitro-phenyl]carbamate (about 3.3 g). $^1$H NMR (400 MHz, chloroform-d) δ ppm 9.65 (s, 1H), 8.59 (d, J=8.8 Hz, 1H), 8.27 (d, J=2.0 Hz, 1H), 7.69 (dd, J=8.8, 2.4 Hz, 1H), 6.95 (t, J=4.0 Hz, 1H), 6.49 (dd, J=4.0, 1.6 Hz, 1H), 1.56 (s, 9H).

Step 5: Synthesis of tert-butyl N-[2-amino-4-(5-fluoro-2-thienyl)phenyl]carbamate To a solution of tert-butyl N-[4-(5-fluoro-2-thienyl)-2-nitro-phenyl]carbamate (about 4.4 g, 13.0 mmol) in MeOH (about 100 mL) was added Pd/C (about 2 g, 10 wt % Pd with 50 wt % water). The mixture was purged with $H_2$ for 3 times and stirred at about 20° C. for 1 hour under $H_2$ (in balloon). The reaction mixture was filtered and the filtrate was concentrated under reduced pressure to afford tert-butyl N-[2-amino-4-(5-fluoro-2-thienyl)phenyl]carbamate (about 3.7 g). $^1$H NMR (400 MHz, chloroform-d) δ ppm 7.28-7.32 (m, 1H), 6.92-6.97 (m, 2H), 6.81 (t, J=4.0 Hz, 1H), 6.42 (dd, J=4.0, 2.0 Hz, 1H), 6.33 (s, 1H), 1.52 (s, 9H); $^{19}$F NMR (377 MHz, chloroform-d) δ ppm −130.476.

Step 6: Synthesis of (S)-tert-butyl N-[[4-[[2-(tert-butoxycarbonylamino)-5-(5-fluoro-2-thienyl)phenyl]carbamoyl]phenyl]-methyl-oxo-sulfanylidene]carbamate To a solution of (S)-4-(N-tert-butoxycarbonyl-S-methylsulfonimidoyl)benzoic acid (about 2.3 g, 7.68 mmol) in pyridine (about 57.5 mL) was added EDCI (about 2.21 g, 11.5 mmol) and tert-butyl N-[2-amino-4-(5-fluoro-2-thienyl)phenyl]carbamate (about 3.08 g, 9.99 mmol). The mixture was stirred at about 50° C. for 1 hour. The reaction mixture was concentrated under reduced pressure. The residue was dilute with water (about 20 mL) and extracted with EtOAc (about 30 mL*3). The combined organic layers were washed with brine (about 50 mL), dried over $Na_2SO_4$ and filtered. The filtrate was concentrated under reduced pressure. The residue was purified by flash chromatography (ISCO®; about 25 g SepaFlash® Silica Flash Column, petroleum ether/EtOAc with EtOAc from 0~50%, flow rate: 50 mL/min, 254 nm) to give (S)-tert-butyl N-[[4-[[2-(tert-butoxycarbonylamino)-5-(5-fluoro-2-thienyl)phenyl]carbamoyl]phenyl]-methyl-oxo-sulfanylidene]carbamate (about 3.9 g). LCMS (ESI) [M+H]+ m/z: calcd 590.2, found 490.1 (Boc cleaved mass).

Step 7: Synthesis of (S)—N-[2-amino-5-(5-fluoro-2-thienyl)phenyl]-4-(methylsulfonimidoyl)benzamide To a solution of (S)-tert-butyl N-[[4-[[2-(tert-butoxycarbonylamino)-5-(5-fluoro-2-thienyl)phenyl]carbamoyl]phenyl]-methyl-oxo-sulfanylidene]carbamate (about 3.9 g, 6.61 mmol) in DCM (about 40 mL) was added TFA (about 5 mL, 64.9 mmol). The mixture was stirred at about 20° C. for about 12 hours. The reaction mixture was adjusted to about pH=8 with saturated $Na_2CO_3$ aqueous solution and extracted with DCM (about 50 mL*3). The combined organic layers were dried over $Na_2SO_4$ and filtered. The filtrate was concentrated under reduced pressure. The residue was purified by flash chromatography (ISCO®; about 25 g SepaFlash® Silica Flash Column, DCM/MeOH with EtOAc from 0~10%, flow rate: 50 mL/min, 254 nm). The residue was further purified by preparative HPLC (Instrument: Shimadzu LC-20AP; Column: Phenomenex C18 250×50 mm×7 μm; Mobile phase A: water with 0.04% $NH_3·H_2O$+10 mmol $NH_4HCO_3$ (v %); Mobile phase B: MeCN; Gradient: B from 5% to 95% in 25 min, hold 100% B for 3 min; Flow Rate: 120 mL/min; Column Temperature: 30° C.; Wavelength: 220 nm, 254 nm) to afford (S)—N-[2-amino-5-(5-fluoro-2-thienyl)phenyl]-4-(methylsulfonimidoyl)benzamide (about 1065.6 mg). $^1$H NMR (400 MHz, methanol-$d_4$) δ ppm 8.29-8.33 (m, 2H), 8.23-8.27 (m, 2H), 7.51 (d, J=1.9 Hz, 1H), 7.38 (dd, J=8.3, 1.9 Hz, 1H), 7.01 (d, J=8.4 Hz, 1H), 6.94 (t, J=3.6 Hz, 1H), 6.58 (dd, J=3.8, 2.1 Hz, 1H), 3.31 (s, 3H); $^{19}$F NMR (376 MHz, methanol-$d_4$) δ ppm −135.507; LCMS [M+H]+ m/z: calcd 390.1; found 389.9; HPLC: 93.260%@220 nm; 94.27%@254 nm; 98.9% ee.

Example 41. Synthesis of N-(2-amino-5-thiazol-5-yl-phenyl)-4-(methylsulfonimidoyl)benzamide (Compound 148)

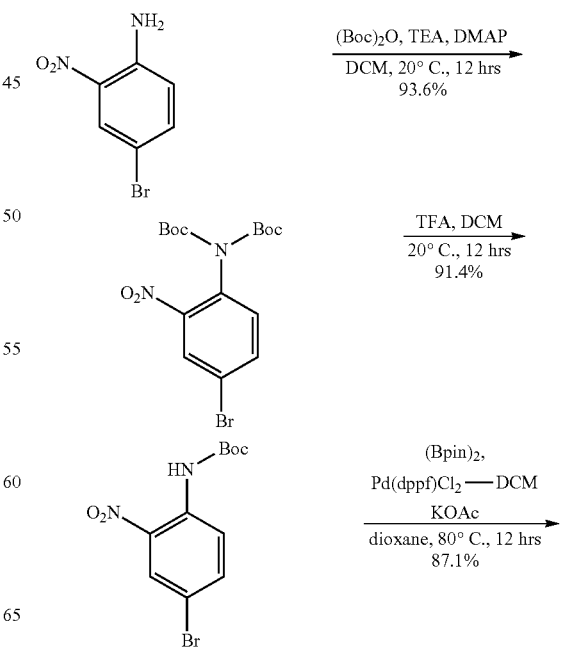

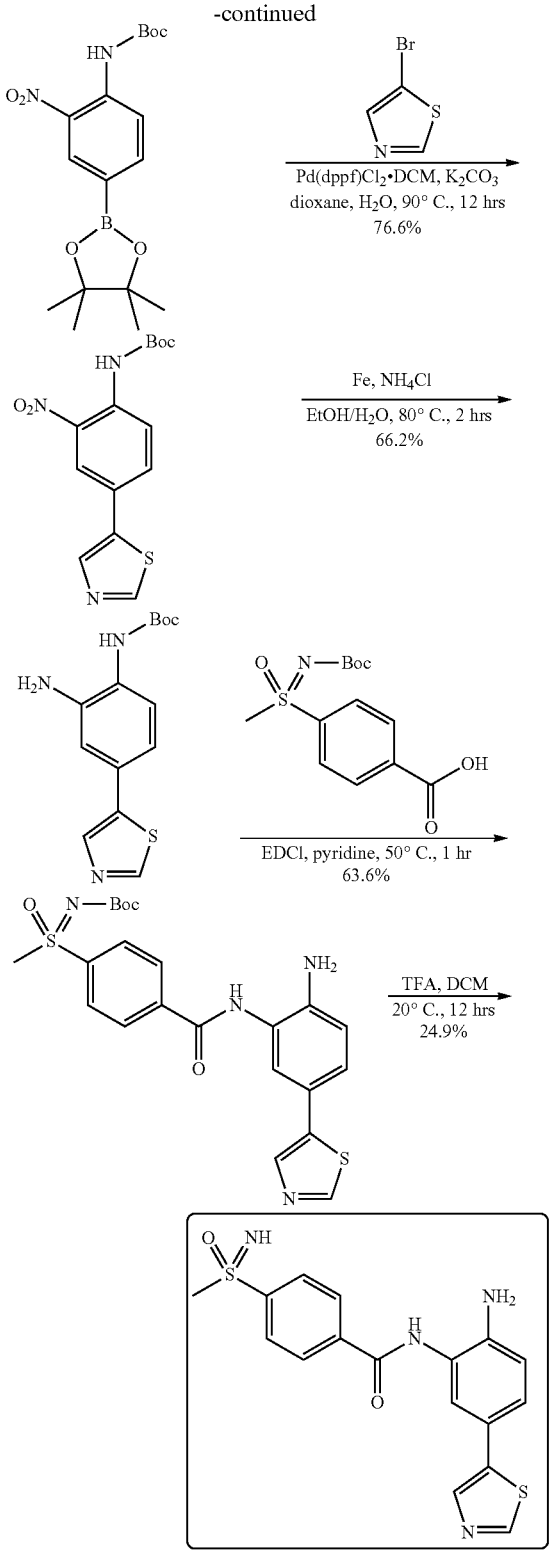

Step 1: Synthesis of tert-butyl N-(4-bromo-2-nitro-phenyl)-N-tert-butoxycarbonyl-carbamate A mixture of 4-bromo-2-nitro-aniline (about 2 g, 9.22 mmol), tert-butoxycarbonyl tert-butyl carbonate (about 5.03 g, 23.0 mmol), N,N-diethylethanamine (about 2.8 g, 27.7 mmol), N,N-dimethylpyridin-4-amine (about 113 mg, 0.922 mmol) in DCM (about 40 mL) was stirred at about 20° C. for about 12 hours. The reaction mixture was diluted with water (about 50 mL) and extracted with EtOAc (about 80 mL*3). The combined organic layers were washed with brine (about 60 mL), dried over $Na_2SO_4$ and filtered. The filtrate was concentrated under reduced pressure. The residue was purified by flash chromatography (ISCO®; about 20 g SepaFlash®Silica Flash Column, Petroleum ether/EtOAc with EtOAc from 0~10%, 18 mL/min, 254 nm) to afford tert-butyl N-(4-bromo-2-nitro-phenyl)-N-tert-butoxycarbonyl-carbamate (about 3.6 g). $^1$H NMR (400 MHz, $CDCl_3$) δ ppm 8.21 (d, J=2.0 Hz, 1H), 7.76 (dd, J=2.4, 8.4 Hz, 1H), 7.22 (d, J=8.4 Hz, 1H), 1.41 (s, 18H); LCMS (ESI) $[M+Na]^+$ m/z: calcd 439.1, found 440.8.

Step 2: Synthesis of tert-butyl N-(4-bromo-2-nitro-phenyl)carbamate

To a solution of tert-butyl N-(4-bromo-2-nitro-phenyl)-N-tert-butoxycarbonyl-carbamate (about 3.6 g, 8.63 mmol) in DCM (about 30 mL) was added 2,2,2-trifluoroacetic acid (about 984 mg, 8.63 mmol). The mixture was stirred at about 20° C. for about 12 hours. The reaction mixture was quenched by saturated aqueous $NaHCO_3$ solution (about 50 mL) and extracted with DCM (about 50 mL*2). The combined organic layers were washed with brine (about 50 mL), dried over anhydrous $Na_2SO_4$, filtered and concentrated under reduced pressure. The residue was purified by flash chromatography (ISCO®; about 20 g SepaFlash®Silica Flash Column, Petroleum ether/EtOAc with EtOAc from 0~10%, 18 mL/min, 254 nm) to afford tert-butyl N-(4-bromo-2-nitro-phenyl)carbamate (about 2.5 g). $^1$H NMR (400 MHz, $CDCl_3$) δ ppm 9.61 (brs, 1H), 8.55-8.47 (m, 1H), 8.36-8.30 (m, 1H), 7.69 (dd, J=2.4, 9.2 Hz, 1H), 1.56-1.53 (m, 9H).

Step 3: Synthesis of tert-butyl N-[2-nitro-4-(4,4,5,5-tetramethyl-1,3,2-dioxaborolan-2-yl)phenyl]carbamate A mixture of tert-butyl N-(4-bromo-2-nitro-phenyl)carbamate (about 2.5 g, 7.88 mmol), 4,4,5,5-tetramethyl-2-(4,4,5,5-tetramethyl-1,3,2-dioxaborolan-2-yl)-1,3,2-dioxaborolane (about 3 g, 11.8 mmol), potassium;acetate (about 1.93 g, 19.7 mmol) and cyclopentyl(diphenyl)phosphane;dichloromethane;dichloropalladium;iron (about 644 mg, 0.788 mmol) in dioxane (about 30 mL) was degassed and purged with $N_2$ for about 3 times, and then the mixture was stirred at about 80° C. for about 12 hours under $N_2$ atmosphere. The reaction mixture filtered and concentrated under reduced pressure. The residue was purified by flash chromatography (ISCO®; about 40 g SepaFlash® Silica Flash Column, Petroleum ether/EtOAc with EtOAc from 0~5%, 80 mL/min, 254 nm) to afford tert-butyl N-[2-nitro-4-(4,4,5,5-tetramethyl-1,3,2-dioxaborolan-2-yl)phenyl]carbamate (about 2.5 g). LCMS (ESI) $[M+H]^+$ m/z: calcd 365.2, found 264.9 (Boc cleaved mass).

Step 4: Synthesis of tert-butyl N-(2-nitro-4-thiazol-5-yl-phenyl)carbamate

A mixture of tert-butyl N-[2-nitro-4-(4,4,5,5-tetramethyl-1,3,2-dioxaborolan-2-yl)phenyl]carbamate (about 1.33 g, 3.66 mmol), 5-bromothiazole (about 500 mg, 3.05 mmol), cyclopentyl(diphenyl)phosphane;dichloropalladium;iron (about 335 mg, 0.457 mmol), tripotassium;carbonate (about 843 mg, 6.10 mmol) in dioxane (about 10 mL) and H$_2$O (about 2 mL) was degassed and purged with N$_2$ for about 3 times, and then the mixture was stirred at 90° C. for 12 hours under N$_2$ atmosphere. The reaction mixture was diluted with H$_2$O (about 50 mL) and extracted with EtOAc (about 80 mL*2), the combined organic layers were washed with brine (about 80 mL), dried over anhydrous Na$_2$SO$_4$, filtered and concentrated under reduced pressure. The residue was purified by flash chromatography (ISCO®; about 20 g SepaFlash®Silica Flash Column, Petroleum ether/EtOAc with EtOAc from 0~100%, 18 mL/min, 254 nm) to afford tert-butyl N-(2-nitro-4-thiazol-5-yl-phenyl)carbamate (about 750 mg). $^1$H NMR (400 MHz, CDCl$_3$) δ ppm 9.71 (s, 1H), 8.83 (s, 1H), 8.68 (d, J=8.8 Hz, 1H), 8.39 (d, J=2.0 Hz, 1H), 8.12 (s, 1H), 7.80 (dd, J=2.0, 9.0 Hz, 1H), 1.57 (s, 9H); LCMS (ESI) [M+H]$^+$ m/z: calcd 322.1, found 321.9.

Step 5: Synthesis of tert-butyl N-(2-amino-4-thiazol-5-yl-phenyl)carbamate

To a solution of tert-butyl N-(2-nitro-4-thiazol-5-yl-phenyl)carbamate (about 200 mg, 0.622 mmol) in EtOH (about 10 mL) and H$_2$O (about 5 mL) was added Fe (about 174 mg, 3.11 mmol) and ammonia;hydrochloride (about 167 mg, 3.11 mmol). The mixture was stirred at 80° C. for 2 hours. The reaction mixture was filtered and then diluted with H$_2$O (about 10 mL) and extracted with EtOAc (about 20 mL*2). The combined organic layers were washed with brine (about 20 mL), dried over anhydrous Na$_2$SO$_4$, filtered and concentrated under reduced pressure. The residue was purified by flash chromatography (ISCO®; about 4 g SepaFlash® Silica Flash Column, petroleum ether/EtOAc with EtOAc from 0~100%, 100 mL/min, 254 nm) to afford tert-butyl N-(2-amino-4-thiazol-5-yl-phenyl)carbamate (about 120 mg). $^1$H NMR (400 MHz, CDCl$_3$) δ ppm 8.72 (s, 1H), 8.00 (s, 1H), 7.37 (d, J=8.0 Hz, 1H), 7.05-7.00 (m, 2H), 6.44-6.23 (m, 1H), 1.53 (s, 9H). LCMS (ESI) [M+H]$^+$ m/z: calcd 292.1, found 291.9.

Step 6: Synthesis of tert-butyl N-[[4-[[2-(tert-butoxycarbonylamino)-5-thiazol-5-yl-phenyl]carbamoyl]phenyl]-methyl-oxo-sulfanylidene]carbamate To a solution of tert-butyl N-(2-amino-4-thiazol-5-yl-phenyl)carbamate (about 120 mg, 0.412 mmol) and 4-(N-tert-butoxycarbonyl-S-methyl-sulfonimidoyl)benzoic acid (about 136 mg, 0.453 mmol) in pyridine (about 2 mL) was added 3-(ethyliminomethyleneamino)-N,N-dimethyl-propan-1-amine (about 96 mg, 0.618 mmol). The mixture was stirred at about 50° C. for about 1 hour. The reaction mixture was diluted with saturated NH$_4$Cl aqueous solution (about 10 mL) and extracted with EtOAc (about 20 mL*2). The combined organic layers were washed with brine (about 10 mL), dried over anhydrous Na$_2$SO$_4$, filtered and concentrated under reduced pressure. The residue was purified by flash chromatography (ISCO®; about 4 g SepaFlash® Silica Flash Column, Petroleum ether/EtOAc with EtOAc from 0~100%, 40 mL/min, 254 nm) to afford tert-butyl N-[[4-[[2-(tert-butoxycarbonylamino)-5-thiazol-5-yl-phenyl]carbamoyl]phenyl]-methyl-oxo-sulfanylidene]carbamate (about 150 mg). LCMS (ESI) [M+Na]$^+$ m/z: calcd 595.2, found 595.1.

Step 7: Synthesis of N-(2-amino-5-thiazol-5-yl-phenyl)-4-(methylsulfonimidoyl)benzamide To a solution of tert-butyl N-[[4-[[2-(tert-butoxycarbonylamino)-5-thiazol-5-yl-phenyl]carbamoyl]phenyl]-methyl-oxo-sulfanylidene]carbamate (about 150 mg, 0.262 mmol) in DCM (about 10 mL) was added 2,2,2-trifluoroacetic acid (about 0.2 mL, 2.62 mmol). The mixture was stirred at about 20° C. for about 12 hours. The reaction mixture was diluted with DCM (about 15 mL) and added saturated Na$_2$CO$_3$ aqueous solution to adjust to about pH=8, then concentrated. The residue was purified by preparative HPLC (Instrument: Gilson GX-281 Liquid Handler, Gilson 322 Pump, Gilson 156 UV Detector; Column: Welch Xtimate C18 150*25 mm*5 μm; Mobile phase A: water (FA); Mobile phase B: MeCN; Gradient: B from 10% to 40% in 9.5 min, hold 100% B for 2 min; Flow Rate: 25 mL/min; Column Temperature: 30° C.; Wavelength: 220 nm, 254 nm) to afford N-(2-amino-5-thiazol-5-yl-phenyl)-4-(methylsulfonimidoyl)benzamide (about 24.3 mg). $^1$H NMR (400 MHz, DMSO-d$_6$) δ ppm 9.94 (s, 1H), 8.92 (s, 1H), 8.18 (d, J=8.4 Hz, 2H), 8.09-8.01 (m, 3H), 7.49 (d, J=2.0 Hz, 1H), 7.35 (dd, J=2.0, 8.4 Hz, 1H), 6.84 (d, J=8.4 Hz, 1H), 5.35 (brs, 2H), 4.42 (s, 1H), 3.12 (s, 3H). LCMS (ESI) [M+Na]$^+$ m/z: calcd 395.1, found 394.9. HPLC: 98.91%@220 nm, 98.94%@254 nm.

Example 42. Synthesis of N-[2-amino-5-(3,4-difluorophenyl)phenyl]-4-(methylsulfonimidoyl)benzamide (Compound 147)

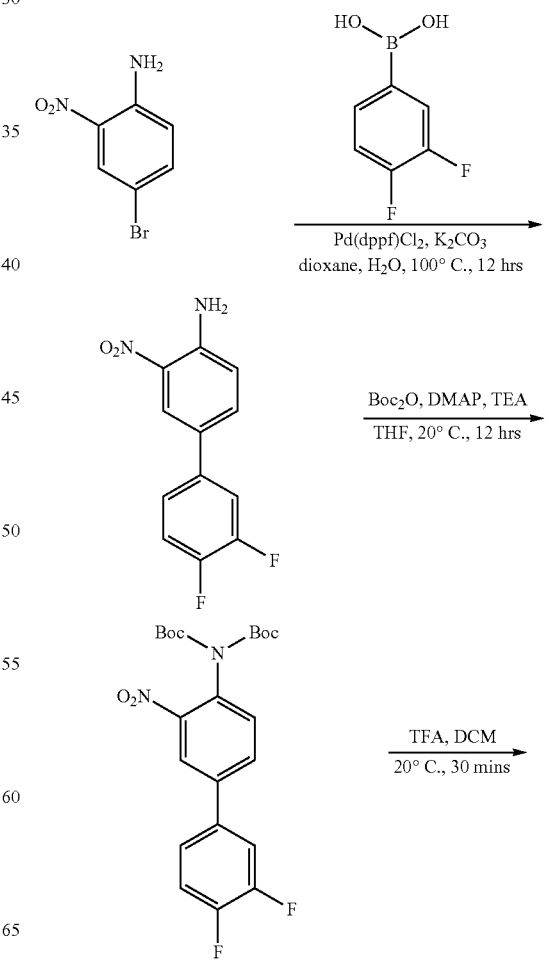

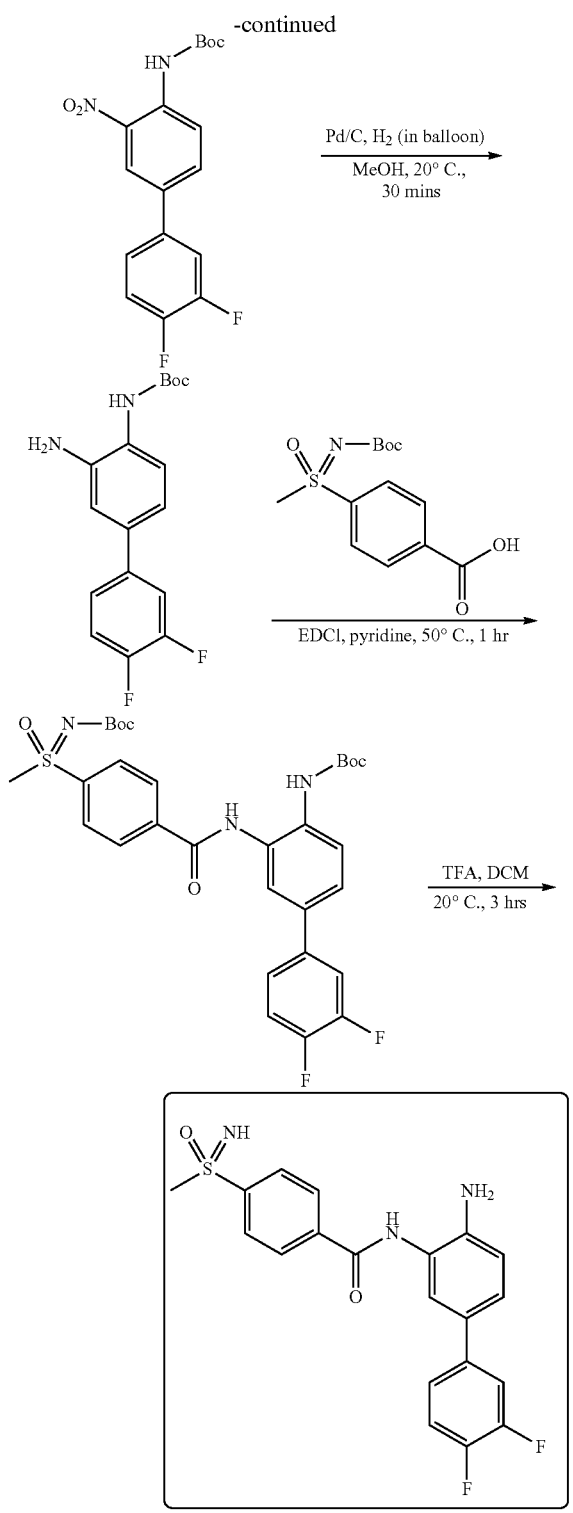

acid (about 1.09 g, 6.91 mmol). The mixture was stirred at about 100° C. for about 12 hours. The reaction mixture was filtered and the filtrate was concentrated under reduced pressure. The residue was purified by flash chromatography (ISCO®; about 25 g SepaFlash® Silica Flash Column, petroleum ether/EtOAc with EtOAc from 0~35%, flow rate: 40 mL/min, 254 nm) to give 4-(3,4-difluorophenyl)-2-nitro-aniline (about 1.03 g). $^1$H NMR (400 MHz, chloroform-d) δ ppm 8.32 (d, J=2.0 Hz, 1H), 7.58 (dd, J=8.8, 2.4 Hz, 1H), 7.36 (ddd, J=11.2, 7.6, 2.0 Hz, 1H), 7.20-7.31 (m, 2H), 6.93 (d, J=8.4 Hz, 1H), 6.19 (brs, 2H).

Step 2: Synthesis of tert-butyl N-tert-butoxycarbonyl-N-[4-(3,4-difluorophenyl)-2-nitro-phenyl]carbamate To a solution of 4-(3,4-difluorophenyl)-2-nitro-aniline (about 1 g, 4.00 mmol) in THF (about 20 mL) was added DMAP (about 50 mg, 0.409 mmol), TEA (about 1.4 mL, 10.0 mmol) and tert-butoxycarbonyl tert-butyl carbonate (about 2 mL, 8.71 mmol). The mixture was stirred at about 20° C. for about 12 hours. The reaction mixture was dilute with water (about 20 mL) and extracted with EtOAc (about 40 mL*3). The combined organic layers were washed with brine (about 40 mL), dried over Na$_2$SO$_4$ and filtered. The filtrate was concentrated under reduced pressure. The residue was disturbed with MeOH (about 30 mL) and filtered. The filter cake was dried under reduced pressure to give tert-butyl N-tert-butoxycarbonyl-N-[4-(3,4-difluorophenyl)-2-nitro-phenyl]carbamate (about 1.3 g). $^1$H NMR (400 MHz, chloroform-d) δ ppm 8.23 (d, J=2.0 Hz, 1H), 7.79 (dd, J=8.4, 2.4 Hz, 1H), 7.43-7.48 (m, 1H), 7.40-7.43 (m, 1H), 7.34-7.39 (m, 1H), 7.31 (dd, J=9.6, 8.0 Hz, 1H), 1.44 (s, 18H); $^{19}$F NMR (377 MHz, chloroform-d) δ ppm –136.038, –136.093, –137.281, –137.336.

Step 3: Synthesis of tert-butyl N-[4-(3,4-difluorophenyl)-2-nitro-phenyl]carbamate To a solution of tert-butyl N-tert-butoxycarbonyl-N-[4-(3,4-difluorophenyl)-2-nitro-phenyl]carbamate (about 1 g, 2.22 mmol) in DCM (about 10 mL) was added TFA (about 0.18 mL, 2.34 mmol). The mixture was stirred at about 20° C. for about 30 minutes. The reaction mixture was adjusted to about pH=8 with saturated NaHCO$_3$ aqueous solution and extracted with DCM (about 30 mL*3). The combined organic layers were dried over Na$_2$SO$_4$ and filtered. The filtrate was concentrated under reduced pressure. The residue was purified by flash chromatography (ISCO®; about 25 g SepaFlash® Silica Flash Column, petroleum ether/EtOAc with EtOAc from 0~25%, flow rate: 50 mL/min, 254 nm) to give tert-butyl N-[4-(3,4-difluorophenyl)-2-nitro-phenyl]carbamate (about 700 mg). $^1$H NMR (400 MHz, chloroform-d) δ ppm 9.69 (s, 1H), 8.67 (d, J=8.8 Hz, 1H), 8.36 (d, J=2.4 Hz, 1H), 7.78 (dd, J=8.8, 2.4 Hz, 1H), 7.40 (ddd, J=11.2, 7.6, 2.0 Hz, 1H), 7.32-7.34 (m, 1H), 7.23-7.29 (m, 1H), 1.57 (s, 9H); $^{19}$F NMR (376 MHz, chloroform-d) δ ppm –136.465, –136.520, –138.528, –138.583.

Step 4: Synthesis of tert-butyl N-[2-amino-4-(3,4-difluorophenyl)phenyl]carbamate To a solution of tert-butyl N-[4-(3,4-difluorophenyl)-2-nitro-phenyl]carbamate (about 450 mg, 1.28 mmol) in MeOH (about 10 mL) was added Pd/C (about 200 mg, 10 wt % Pd with 50 wt % water). The mixture was stirred at about 20° C. for about 30 minutes. The reaction mixture was Step 1: Synthesis of 4-(3,4-difluorophenyl)-2-nitro-aniline To a solution of 4-bromo-2-nitro-aniline (about 1 g, 4.61 mmol) in dioxane (about 10 mL) and H$_2$O (2 mL) were added cyclopentyl(diphenyl)phosphane;dichloropalladium; iron (about 500 mg, 0.683 mmol), tripotassium;carbonate (about 1.91 g, 13.8 mmol) and (3,4-difluorophenyl)boronic filtered and the filtrate was concentrated under reduced pressure to give tert-butyl N-[2-amino-4-(3,4-difluorophenyl)phenyl]carbamate (about 400 mg). LCMS (ESI) [M+H]$^+$ m/z: calcd 321.1, found 220.9 (Boc cleaved mass).

Step 5: Synthesis of tert-butyl N-[[4-[[2-(tert-butoxycarbonylamino)-5-(3,4-difluorophenyl)phenyl]carbamoyl]phenyl]-methyl-oxo-sulfanylidene]carbamate To a solution of 4-(N-tert-butoxycarbonyl-S-methylsulfonimidoyl)benzoic acid (about 100 mg, 0.334 mmol) in pyridine (about 3 mL) were added EDCI (about 100 mg, 0.521 mmol) and tert-butyl N-[2-amino-4-(3,4-difluorophenyl)phenyl]carbamate (about 130 mg, 0.405 mmol). The mixture was stirred at about 50° C. for about 1 hour. The reaction mixture was concentrated under reduced pressure. The reaction mixture was dilute with water (about 10 mL) and extracted with DCM (about 15 mL*3). The combined organic layers were washed with brine (about 30 mL), dried over Na$_2$SO$_4$ and filtered. The filtrate was concentrated under reduced pressure. The residue was purified by flash chromatography (ISCO®; about 25 g SepaFlash® Silica Flash Column, petroleum ether/EtOAc with EtOAc from 0~35%, flow rate: 50 mL/min, 254 nm) to give tert-butyl N-[[4-[[2-(tert-butoxycarbonylamino)-5-(3,4-difluorophenyl)phenyl]carbamoyl]phenyl]-methyl-oxo-sulfanylidene]carbamate (about 130 mg). LCMS (ESI) [M+H]$^+$ m/z: calcd 602.2, found 502.1 (Boc cleaved mass).

Step 6: Synthesis of N-[2-amino-5-(3,4-difluorophenyl)phenyl]-4-(methylsulfonimidoyl)benzamide To a solution of tert-butyl N-[[4-[[2-(tert-butoxycarbonylamino)-5-(3,4-difluorophenyl)phenyl]carbamoyl]phenyl]-methyl-oxo-sulfanylidene]carbamate (about 130 mg, 0.216 mmol) in DCM (about 3 mL) was added TFA (about 0.3 mL, 3.89 mmol). The mixture was stirred at about 20° C. for about 3 hours. The reaction mixture was adjusted to about pH=8 with saturated NaHCO$_3$ aqueous solution and extracted with DCM (about 10 mL*3). The combined organic layers were dried over Na$_2$SO$_4$ and filtered. The filtrate was concentrated under reduced pressure. The residue was combined with another batch and purified by preparative HPLC (Instrument: Gilson GX-281 Liquid Handler, Gilson 322 Pump, Gilson 156 UV Detector; Column: 2_Phenomenex Gemini C18 75×40 mm×3 µm; Mobile phase A: H$_2$O with 10 mmol NH$_4$HCO$_3$ (v %); Mobile phase B: ACN; Gradient: B from 34% to 64% in 9.5 min, hold 100% B for 2 min; Flow Rate: 30 mL/min; Column Temperature: 30° C.; Wavelength: 220 nm, 254 nm) to give N-[2-amino-5-(3,4-difluorophenyl)phenyl]-4-(methylsulfonimidoyl)benzamide (about 62.4 mg). $^1$H NMR (400 MHz, methanol-d$_4$) δ ppm 8.20-8.24 (m, 2H), 8.13-8.17 (m, 2H), 7.43-7.50 (m, 2H), 7.36 (dd, J=8.4, 2.4 Hz, 2H), 7.26 (dt, J=10.4, 8.4 Hz, 1H), 6.98 (d, J=8.4 Hz, 1H), 3.21 (s, 3H); $^{19}$F NMR (377 MHz, methanol-d$_4$) δ ppm −140.598, −140.651, −144.598, −144.650; LCMS (ESI) [M+H]$^+$ m/z: calcd 402.1, found 402.0; HPLC: 99.330%@220 nm, 99.540%@254 nm.

Example 43. Synthesis of rac-N-[2-amino-5-(4-fluorophenyl)phenyl]-4-(cyclopropylsulfonimidoyl)benzamide (Compound 111) rel-(S)—N-[2-amino-5-(4-fluorophenyl)phenyl]-4-(cyclopropylsulfonimidoyl)benzamide (Compound 146) and rel-(R)—N-[2-amino-5-(4-fluorophenyl)phenyl]-4-(cyclopropylsulfonimidoyl)benzamide (Compound 145)

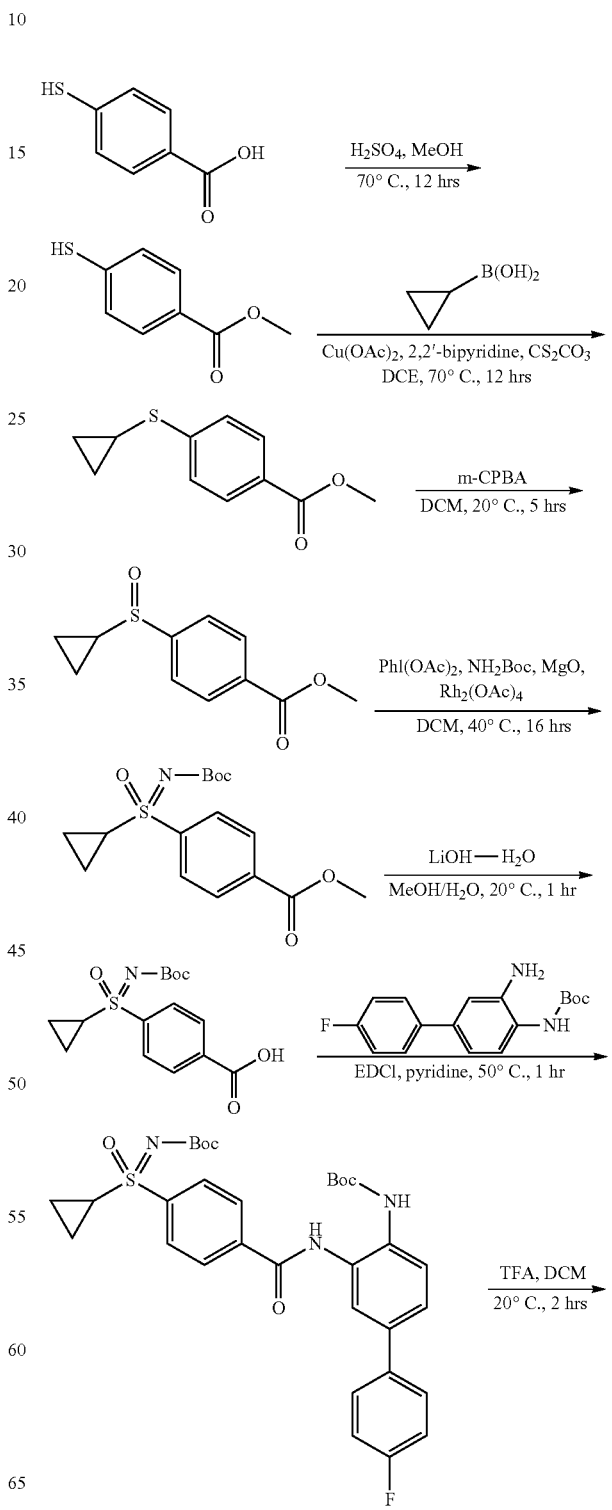

-continued

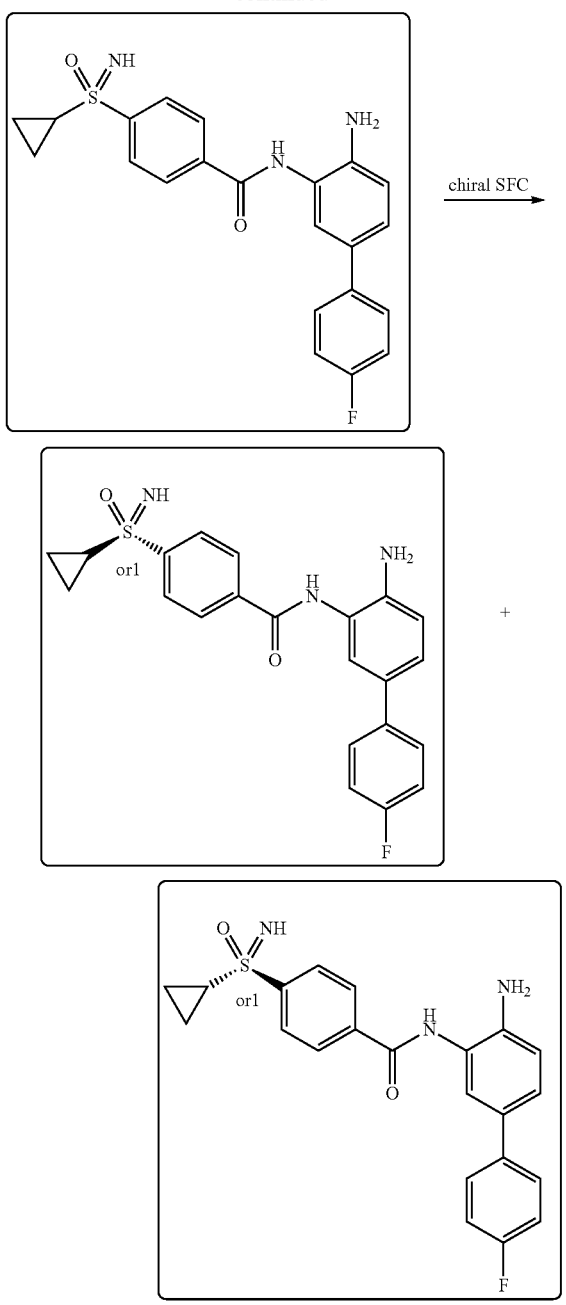

Step 1: Synthesis of methyl 4-sulfanylbenzoate

To a solution of 4-sulfanylbenzoic acid (about 10 g, 64.9 mmol) in MeOH (about 100 mL) was added sulfuric acid (about 2 mL, 37.5 mmol). The reaction mixture was then warmed to reflux for about 16 hours. The mixture was concentrated under reduced pressure to remove solvent. The residue was purified by flash chromatography (ISCO®; about 80 g AgelaFlash® Silica Flash Column, petroleum ether/EtOAc with EtOAc from 0~26%, flow rate=100 mL/min, 254 nm) to afford methyl 4-sulfanylbenzoate (about 10.1 g). LCMS (ESI) [M+H]$^+$ m/z: calcd 169.0, found 169.0.

Step 2: Synthesis of methyl 4-cyclopropylsulfanylbenzoate

A mixture of methyl 4-sulfanylbenzoate (about 10.1 g, 60.0 mmol), cyclopropylboronic acid (about 7.8 g, 90.8 mmol), dicesium;carbonate (about 20 g, 61.4 mmol), copper;diacetate (about 11 g, 60.6 mmol) and 2-(2-pyridyl)pyridine (about 9.5 g, 60.8 mmol) in 1,2-dichloroethane (about 50 mL) was stirred at about 70° C. for about 12 hours. The aqueous NH$_4$OH 25% (about 20 mL) was added to mixture. The resulting mixture was filtered, the filtrate was extracted with DCM (about 50 mL*3). The combined organic layer was dried over anhydrous Na$_2$SO$_4$, filtered and concentrated under reduced pressure. The residue was purified by flash chromatography (Biotage®; 80 g AgelaFlash® Silica Flash Column, petroleum ether/EtOAc with EtOAc from 0~20%, flow rate=100 mL/min, 254 nm) to afford methyl 4-cyclopropylsulfanylbenzoate (about 10.2 g). $^1$H NMR (400 MHz, DMSO-d$_6$) δ ppm 7.85-7.91 (m, 2H), 7.45-7.50 (m, 2H), 3.83 (s, 3H), 1.17 (s, 1H), 1.13-1.16 (m, 2H), 0.57-0.64 (m, 2H); LCMS (ESI) [M+H]$^+$ m/z: calcd 209.1, found 209.0.

Step 3: Synthesis of methyl 4-cyclopropylsulfinylbenzoate

To a solution of methyl 4-cyclopropylsulfanylbenzoate (about 10 g, 48.0 mmol) in DCM (about 100 mL) was added m-CPBA (about 8.5 g, 49.3 mmol, 85 wt %). The mixture was stirred at about 20° C. for about 2 hours. The mixture was stirred at about 20° C. for about 2 hours. m-CPBA (about 1 g, 5.80 mmol, 85 wt %) was added. The mixture was stirred at about 20° C. for about 1 hour. The mixture was quenched by addition of saturated Na$_2$SO$_3$ aqueous solution (about 100 mL*3), saturated Na$_2$CO$_3$ aqueous solution (about 150 mL) and extracted with DCM (about 150 mL*3). The combined organic layer was dried over anhydrous Na$_2$SO$_4$, filtered and concentrated under reduced pressure to afford methyl 4-cyclopropylsulfinylbenzoate (about 8.2 g).

Step 4: Synthesis of methyl 4-(N-tert-butoxycarbonyl-S-cyclopropyl-sulfonimidoyl)benzoate A mixture of NH$_2$Boc (about 9.5 g, 81.1 mmol), [bis(acetoxy)iodo]benzene (about 18 g, 55.9 mmol), MgO (about 8.5 g, 0.206 mol), dirhodium tetraacetate (about 810 mg, 1.83 mmol) and methyl 4-cyclopropylsulfinylbenzoate (about 8.2 g, 36.6 mmol) in DCM (about 100 mL) was stirred at about 40° C. for about 16 hours. The mixture was filtered and concentrated under reduced pressure. The residue was purified by flash chromatography (Biotage®; about 80 g SepaFlash® Silica Flash Column, petroleum ether/EtOAc with EtOAc from 0~40%, 80 mL/min, 254 nm) to afford methyl 4-(N-tert-butoxycarbonyl-S-cyclopropyl-sulfonimidoyl)benzoate (about 3 g). LCMS (ESI) [M+H]$^+$ m/z: calcd 340.1; found 340.1.

Step 5: Synthesis of 4-(N-tert-butoxycarbonyl-S-cyclopropyl-sulfonimidoyl)benzoic acid To a solution of methyl 4-(N-tert-butoxycarbonyl-S-cyclopropyl-sulfonimidoyl)benzoate (about 3 g, 8.84 mmol) in MeOH (about 25 mL) was added a solution of LiOH—H$_2$O (about 3.7 g, 88.2 mmol) in H$_2$O (about 10 mL). The mixture was stirred at about 20° C. for about 1 hour. The mixture was concentrated under reduced pressure to remove the organic solvent. The aqueous phase was adjusted to about pH=4 with 2N HCl aqueous solution. The mixture was extracted with EtOAc (about 40 mL*3). The combined organic layer was dried over anhydrous Na$_2$SO$_4$, filtered and concentrated under reduced pressure to give 4-(N-tert-butoxycarbonyl-S-cyclopropyl-sulfonimidoyl)benzoic acid (about 1.8 g), which was directly used without further purification. LCMS (ESI) [M+H]$^+$ m/z: calcd 326.1; found 326.1.

Step 6: Synthesis of tert-butyl N-[[4-[[2-(tert-butoxycarbonylamino)-5-(4-fluorophenyl)phenyl]carbamoyl]phenyl]-cyclopropyl-oxo-sulfanylidene]carbamate A mixture of 4-(N-tert-butoxycarbonyl-S-cyclopropyl-sulfonimidoyl)benzoic acid (about 1.8 g, 5.53 mmol), tert-butyl N-[2-amino-4-(4-fluorophenyl)phenyl]carbamate (about 1.7 g, 5.62 mmol) and EDCI (about 1.6 g, 8.35 mmol) in pyridine (about 20 mL) was stirred at about 50° C. for about 1 hour. The mixture was concentrated under reduced pressure. The residue was purified by flash chromatography (Biotage®; about 40 g AgelaFlash® Silica Flash Column, petroleum ether/EtOAc with EtOAc from 0~50%, 60 mL/min, 254 nm) to afford tert-butyl N-[[4-[[2-(tert-butoxycarbonylamino)-5-(4-fluorophenyl)phenyl]carbamoyl]phenyl]-cyclopropyl-oxo-sulfanylidene]carbamate (about 2.9 g). LCMS (ESI) [M+H]$^+$ m/z: calcd 610.2; found 610.2.

Step 7: Synthesis of rac-N-[2-amino-5-(4-fluorophenyl)phenyl]-4-(cyclopropylsulfonimidoyl)benzamide To a solution of tert-butyl N-[[4-[[2-(tert-butoxycarbonylamino)-5-(4-fluorophenyl)phenyl]carbamoyl]phenyl]-cyclopropyl-oxo-sulfanylidene]carbamate (about 2.9 g, 4.76 mmol) in DCM (about 15 mL) was added TFA (about 7.5 mL, 97.4 mmol). The mixture was stirred at 20° C. for 2 hours. The resulting mixture was concentrated under reduced pressure. The resulting mixture was diluted with water (about 50 mL) and adjusted to about pH=8 with saturated Na$_2$CO$_3$ aqueous solution. The mixture was extracted with DCM/MeOH (10:1, 50 mL*3). The combined organic layer was dried over anhydrous Na$_2$SO$_4$, filtered and concentrated under reduced pressure to afford N-[2-amino-5-(4-fluorophenyl)phenyl]-4-(cyclopropylsulfonimidoyl)benzamide (about 1.9 g). $^1$H NMR (400 MHz, DMSO-d$_6$) δ ppm 9.91 (s, 1H), 8.17 (d, J=8.3 Hz, 2H), 8.02 (d, J=8.3 Hz, 2H), 7.58 (dd, J=8.5, 5.5 Hz, 2H), 7.51 (d, J=2.0 Hz, 1H), 7.32 (dd, J=8.3, 2.0 Hz, 1H), 7.22 (t, J=8.8 Hz, 2H), 6.86 (d, J=8.3 Hz, 1H), 5.18 (brs, 2H), 2.69-2.78 (m, 1H), 1.09-1.16 (m, 1H), 0.87-1.04 (m, 3H); $^{19}$F NMR (376 MHz, DMSO-d$_6$) δ ppm−117.460; HPLC: 92.78%@220 nm; 97.64%@254 nm.

Step 8: Synthesis of rel-(S)—N-[2-amino-5-(4-fluorophenyl)phenyl]-4-(cyclopropylsulfonimidoyl)benzamide and rel-(R)—N-[2-amino-5-(4-fluorophenyl)phenyl]-4-(cyclopropylsulfonimidoyl)benzamide N-[2-amino-5-(4-fluorophenyl)phenyl]-4-(cyclopropylsulfonimidoyl)benzamide (about 1.9 g, 4.64 mmol) was separated by chiral SFC (Instrument: Berger MG III; Column: Daicel chiralpak IC 250×50 mm I.D. 10 μm; Mobile phase: supercritical CO$_2$/EtOH (0.1% NH$_3$—H$_2$O, v %)=55/45; Flow Rate: 200 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm) to afford the products. Stereochemistry was arbitrarily assigned rel-(S)—N-[2-amino-5-(4-fluorophenyl)phenyl]-4-(cyclopropylsulfonimidoyl)benzamide (about 773.1 mg, peak 1, retention time=3.251 min, single enantiomer). $^1$H NMR (400 MHz, DMSO-d$_6$) δ ppm 9.91 (s, 1H), 8.17 (d, J=8.3 Hz, 2H), 8.01 (d, J=8.4 Hz, 2H), 7.58 (dd, J=8.7, 5.6 Hz, 2H), 7.50 (d, J=1.9 Hz, 1H), 7.32 (dd, J=8.4, 2.1 Hz, 1H), 7.22 (t, J=8.9 Hz, 2H), 6.86 (d, J=8.4 Hz, 1H), 5.17 (s, 2H), 4.40 (s, 1H), 2.69-2.77 (m, 1H), 1.10-1.19 (m, 1H), 0.89-1.04 (m, 3H); $^{19}$F NMR (376 MHz, DMSO-d$_6$) δ ppm −117.464; LCMS (ESI) [M+H]$^+$ m/z: calcd 410.1, found 410.1; HPLC: 97.58%@220 nm, 98.28%@254 nm; 98.9% ee.

rel-(R)—N-[2-amino-5-(4-fluorophenyl)phenyl]-4-(cyclopropylsulfonimidoyl)benzamide (about 775.1 mg, peak 2, retention time=5.706 min, single enantiomer). $^1$H NMR (400 MHz, DMSO-d$_6$) δ ppm 9.91 (s, 1H), 8.17 (d, J=8.4 Hz, 2H), 8.02 (d, J=8.4 Hz, 2H), 7.58 (dd, J=8.6, 5.5 Hz, 2H), 7.50 (d, J=1.8 Hz, 1H), 7.32 (dd, J=8.3, 2.1 Hz, 1H), 7.22 (t, J=8.9 Hz, 2H), 6.86 (d, J=8.4 Hz, 1H), 5.17 (s, 2H), 4.40 (s, 1H), 2.69-2.79 (m, 1H), 1.10-1.19 (m, 1H), 0.88-1.04 (m, 3H); $^{19}$F NMR (376 MHz, DMSO-d$_6$) δ ppm −117.464; LCMS (ESI) [M+H]$^+$ m/z: calcd 410.1, found 410.1; HPLC: 95.87%@220 nm, 97.18%@254 nm; 99.1% ee.

Example 44. Synthesis of (R)—N-[2-amino-5-(5-fluoro-2-thienyl)phenyl]-4-(methylsulfonimidoyl)benzamide (Compound 144)

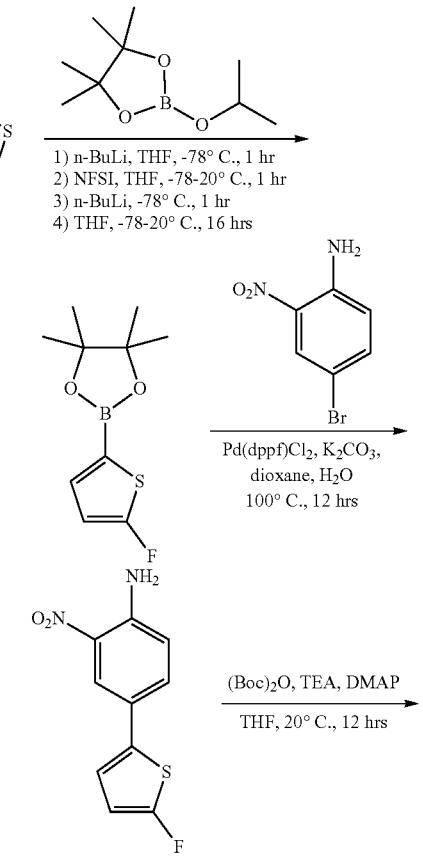

-continued

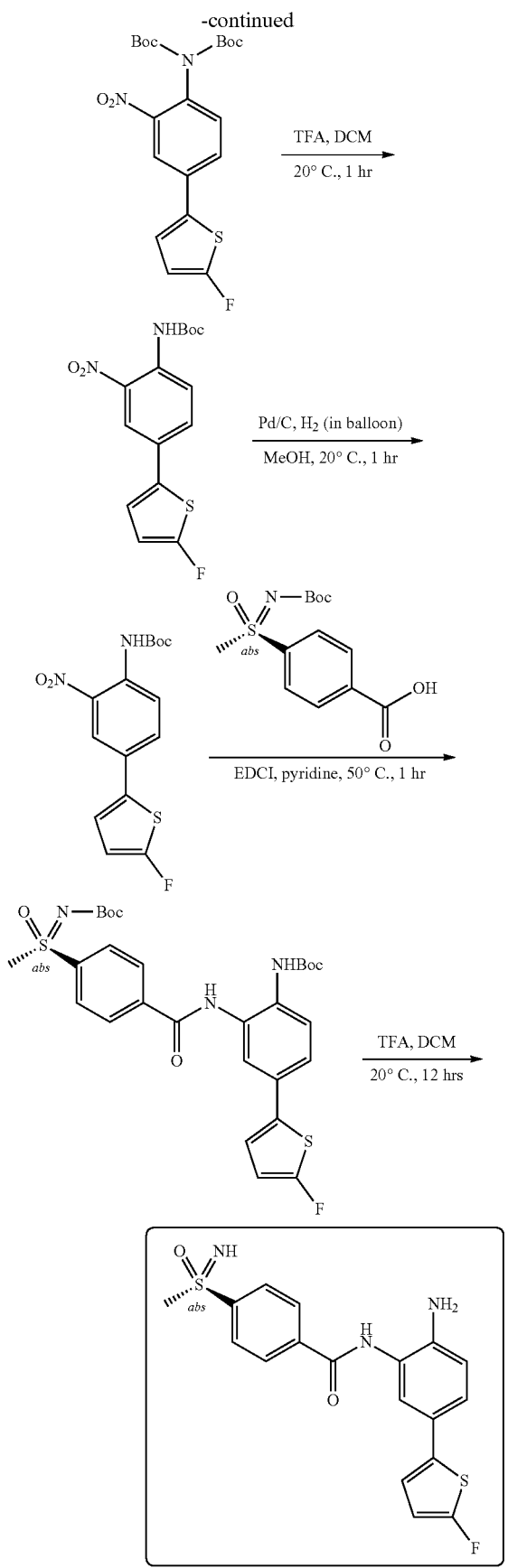

Step 1: Synthesis of 2-(5-fluoro-2-thienyl)-4,4,5,5-tetramethyl-1,3,2-dioxaborolane To a solution of thiophene (about 6 g, 71.3 mmol) in THF (about 150 mL) under nitrogen atmosphere was added 2.5M n-BuLi/hexane (about 30 mL, 75.0 mmol) dropwise at about −78° C. and the reaction mixture was stirred at about −78° C. for about 1 hour under nitrogen atmosphere. Then N-(benzenesulfonyl)-N-fluoro-benzenesulfonamide (about 23.7 g, 75.2 mmol) in THF (about 90 mL) was added into above mixture dropwise at about −78° C. and warmed to about 20° C. for about 1 hour. Then the reaction mixture was cooled to about −78° C., and another portion of 2.5M n-BuLi/hexane (about 30 mL, 75.0 mmol) was added dropwise at about −78° C. and stirred at about −78° C. for 1 hour. Finally, 2-isopropoxy-4,4,5,5-tetramethyl-1,3,2-dioxaborolane (about 15.5 mL, 76.0 mmol) in THF (about 60 mL) was added into above mixture dropwise at about −78° C., and the reaction mixture was allowed to warm to about 20° C. and stirred at about 20° C. for about 16 hours. The reaction mixture was cooled to about 0° C. and quenched with saturated $NH_4Cl$ (about 150 mL). The resultant mixture was extracted with petroleum ether (about 300 mL*3). The combined organic layers were washed with brine (about 200 mL), dried over $Na_2SO_4$ and filtered. The filtrate was concentrated under reduced pressure to give 2-(5-fluoro-2-thienyl)-4,4,5,5-tetramethyl-1,3,2-dioxaborolane (about 12.7 g). $^1H$ NMR (400 MHz, chloroform-d) δ ppm 7.19 (t, J=3.6 Hz, 1H), 6.47 (dd, J=4.0, 0.8 Hz, 1H), 1.25 (s, 12H); $^{19}F$ NMR (377 MHz, chloroform-d) δ ppm −125.63.

Step 2: Synthesis of 4-(5-fluoro-2-thienyl)-2-nitro-aniline

To a solution of 4-bromo-2-nitro-aniline (about 5 g, 23.0 mmol) in dioxane (about 100 mL) and $H_2O$ (about 20 mL) were added 2-(5-fluoro-2-thienyl)-4,4,5,5-tetramethyl-1,3,2-dioxaborolane (about 12.5 g, 54.8 mmol), Pd(dppf)Cl$_2$ (about 2 g, 2.73 mmol) and $K_2CO_3$ (about 9.5 g, 68.7 mmol). The mixture was stirred at about 100° C. for about 12 hours under nitrogen. The reaction mixture was concentrated under reduced pressure. The residue was purified by flash chromatography (ISCO®; about 40 g AgelaFlash® Silica Flash Column, petroleum ether/EtOAc with EtOAc from 0~15%, flow rate=45 mL/min, 254 nm) to afford 4-(5-fluoro-2-thienyl)-2-nitro-aniline (about 5 g). $^1H$ NMR (400 MHz, chloroform-d) δ ppm 8.22 (d, J=2.0 Hz, 1H), 7.47-7.69 (m, 3H), 6.80-6.90 (m, 2H), 6.40-6.54 (m, 1H); $^{19}F$ NMR (376 MHz, chloroform-d) δ ppm−130.10.

Step 3: Synthesis of tert-butyl N-tert-butoxycarbonyl-N-[4-(5-fluoro-2-thienyl)-2-nitro-phenyl]carbamate To a solution of 4-(5-fluoro-2-thienyl)-2-nitro-aniline (about 5 g, 21.0 mmol) in THF (about 50 mL) were added tert-butoxycarbonyl tert-butyl carbonate (about 11 mL, 47.9 mmol), TEA (about 11 mL, 78.9 mmol) and N,N-dimethylpyridin-4-amine (about 288 mg, 2.36 mmol). The mixture was stirred at about 20° C. for about 12 hours. The reaction mixture was diluted with water (about 50 mL) and extracted with EtOAc (about 80 mL*3). The combined organic layers were washed with brine (about 50 mL), dried over $Na_2SO_4$ and filtered. The filtrate was concentrated under reduced pressure. The residue was triturated with MeOH (about 30 mL) and filtered. The cake was dried over reduced pressure to afford tert-butyl N-tert-butoxycarbonyl-N-[4-(5-fluoro-2- thienyl)-2-nitro-phenyl]carbamate (about 3.8 g). $^1$H NMR (400 MHz, chloroform-d) δ ppm 8.16 (d, J=2.0 Hz, 1H), 7.69 (dd, J=8.0, 2.0 Hz, 1H), 7.32 (d, J=8.4 Hz, 1H), 7.07 (t, J=4.0 Hz, 1H), 6.54 (dd, J=4.0, 1.6 Hz, 1H), 1.38-1.49 (m, 18H); $^{19}$F NMR (377 MHz, chloroform-d) δ ppm −126.707; LCMS (ESI) [M+Na]$^+$ m/z: calcd 461.1; found 461.0.

Step 4: Synthesis of tert-butyl N-[4-(5-fluoro-2-thienyl)-2-nitro-phenyl]carbamate To a solution of tert-butyl N-tert-butoxycarbonyl-N-[4-(5-fluoro-2-thienyl)-2-nitro-phenyl]carbamate (about 3.8 g, 8.67 mmol) in DCM (about 40 mL) was added TFA (about 1 mL, 13.0 mmol). The mixture was stirred at about 20° C. for about 1 hour. The reaction mixture was quenched with saturated Na$_2$CO$_3$ aqueous to about pH=8 and extracted with DCM (about 30 mL*3). The resultant mixture was dried over Na$_2$SO$_4$ and filtered. The filtrate was concentrated under reduced pressure. The residue was purified by flash chromatography (ISCO®; about 40 g AgelaFlash® Silica Flash Column, petroleum ether/EtOAc with EtOAc from 0~9%, flow rate=40 mL/min, 254 nm) to afford tert-butyl N-[4-(5-fluoro-2-thienyl)-2-nitro-phenyl]carbamate (about 2.88 g). $^1$H NMR (400 MHz, chloroform-d) δ ppm 9.66 (s, 1H), 8.59 (d, J=9.2 Hz, 1H), 8.28 (d, J=2.4 Hz, 1H), 7.70 (dd, J=8.8, 2.4 Hz, 1H), 6.95 (t, J=4.0 Hz, 1H), 6.50 (dd, J=4.0, 2.0 Hz, 1H), 1.56 (s, 9H); $^{19}$F NMR (377 MHz, chloroform-d) δ ppm −128.42.

Step 5: Synthesis of tert-butyl N-[2-amino-4-(5-fluoro-2-thienyl)phenyl]carbamate To a solution of tert-butyl N-[4-(5-fluoro-2-thienyl)-2-nitro-phenyl]carbamate (about 2.88 g, 8.51 mmol) in MeOH (about 100 mL) was added Pd/C (about 1.5 g, 10 wt % Pd with 50 wt % water). The mixture was purged with H$_2$ for about 3 times and stirred at about 20° C. for about 1 hour under H$_2$ (in balloon). The reaction mixture was filtered and the filtrate was concentrated under reduced pressure to afford tert-butyl N-[2-amino-4-(5-fluoro-2-thienyl)phenyl] carbamate (about 2.55 g). $^1$H NMR (400 MHz, chloroform-d) δ ppm 7.29 (s, 1H), 6.92-6.98 (m, 2H), 6.81 (t, J=4.0 Hz, 1H), 6.42 (dd, J=4.0, 2.0 Hz, 1H), 6.31 (s, 1H), 1.52 (s, 9H).

Step 6: Synthesis of (R)-tert-butyl N-[[4-[[2-(tert-butoxycarbonylamino)-5-(5-fluoro-2-thienyl)phenyl]carbamoyl]phenyl]-methyl-oxo-sulfanylidene]carbamate To a solution of (R)-4-(N-tert-butoxycarbonyl-S-methyl-sulfonimidoyl)benzoic acid (about 2 g, 6.68 mmol) in pyridine (about 50 mL) were added tert-butyl N-[2-amino-4-(5-fluoro-2-thienyl)phenyl]carbamate (about 2.7 g, 8.76 mmol) and 3-(ethyliminomethyleneamino)-N,N-dimethyl-propan-1-amine;hydrochloride (about 2 g, 10.4 mmol). The mixture was stirred at 50° C. for 1 hour. The reaction mixture was concentrated under reduced pressure. The residue was diluted with H$_2$O (about 30 mL) and extracted with DCM (about 50 mL*3). The combined organic layers were washed with brine (about 30 mL*2), dried over Na$_2$SO$_4$ and filtered. The filtrate was concentrated under reduced pressure. The residue was purified by flash chromatography (ISCO®; about 40 g AgelaFlash® Silica Flash Column, petroleum ether/EtOAc with EtOAc from 0~60%, flow rate=40 mL/min, 254 nm) to afford (R)-tert-butyl N-[[4-[[2-(tert-butoxycarbonylamino)-5-(5-fluoro-2-thienyl)phenyl]carbamoyl]phenyl]-methyl-oxo-sulfanylidene]carbamate (about 3.3 g). $^1$H NMR (400 MHz, chloroform-d) δ ppm 9.76 (brs, 1H), 8.20 (d, J=8.4 Hz, 2H), 8.04-8.12 (m, 3H), 7.29 (dd, J=8.4, 2.0 Hz, 1H), 7.12-7.22 (m, 1H), 6.92 (t, J=3.6 Hz, 1H), 6.74-6.82 (m, 1H), 6.46 (dd, J=4.0, 1.6 Hz, 1H), 3.27 (s, 3H), 1.54 (s, 9H), 1.41 (s, 9H); $^{19}$F NMR (377 MHz, chloroform-d) δ ppm −129.526; LCMS (ESI) [M+H]$^+$ m/z: calcd 590.2, found 490.0 (Boc cleaved mass).

Step 7: Synthesis of (R)—N-[2-amino-5-(5-fluoro-2-thienyl)phenyl]-4-(methylsulfonimidoyl)benzamide To a solution of (R)-tert-butyl N-[[4-[[2-(tert-butoxycarbonylamino)-5-(5-fluoro-2-thienyl)phenyl]carbamoyl]phenyl]-methyl-oxo-sulfanylidene]carbamate (about 3.3 g, 5.60 mmol) in DCM (about 40 mL) was added TFA (about 3.8 mL, 49.3 mmol). The mixture was stirred at about 20° C. for about 12 hours. The reaction mixture was quenched with saturated Na$_2$CO$_3$ aqueous solution to about pH=9. The suspension was concentrated under reduced pressure to remove the organic solvent. The resultant suspension was filtered. The filter cake was dried under reduced pressure to give a residue. The residue was triturated with DCM (about 30 mL) and filtered. The filter cake was triturated with EtOAc (about 30 mL) and filtered. The filter cake was then triturated with EtOAc/MeOH (V/V=10/1, about 30 mL) and filtered. The filter cake was dried under reduced pressure to give a residue. The residue was then triturated with DCM/MeOH (V/V=10/1, about 30 mL) and filtered. The filter cake was dried under reduced pressure to give a residue. The residue was purified by preparative HPLC (Instrument: Shimadzu LC-20AP; Column: Phenomenex C18 250*50 mm*7 μm; Mobile phase A: water with 0.04% NH$_3$—H$_2$O+ 10 mmol NH$_4$HCO$_3$ (v %); Mobile phase B: MeCN; Gradient: B from 5% to 95% in 25 min, hold 100% B for 3 min; Flow Rate: 120 mL/min; Column Temperature: 30° C.; Wavelength: 220 nm, 254 nm) to afford (R)—N-[2-amino-5-(5-fluoro-2-thienyl)phenyl]-4-(methylsulfonimidoyl)benzamide (about 1.05 g). $^1$H NMR (400 MHz, methanol-d$_4$) δ ppm 8.19-8.23 (m, 2H), 8.13-8.17 (m, 2H), 7.41 (d, J=2.0 Hz, 1H), 7.27 (dd, J=8.3, 2.3 Hz, 1H), 6.91 (d, J=8.5 Hz, 1H), 6.84 (t, J=3.8 Hz, 1H), 6.48 (dd, J=4.0, 2.3 Hz, 1H), 3.21 (s, 3H); $^{19}$F NMR (377 MHz, methanol-d$_4$) δ ppm −135.54; LCMS (ESI) [M+H]$^+$ m/z: calcd 390.1, found 389.9; HPLC: 96.79%@220 nm; 96.20%@254 nm; SFC: 96.4% ee.

Example 45. Synthesis of N-[2-amino-5-[4-(trifluoromethyl)phenyl]phenyl]-4-(methylsulfonimidoyl) benzamide (Compound 142)

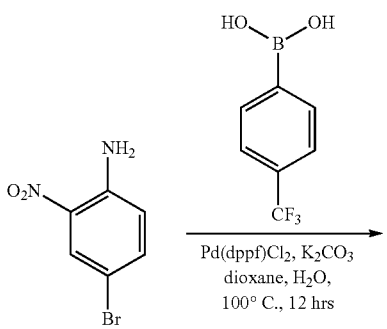

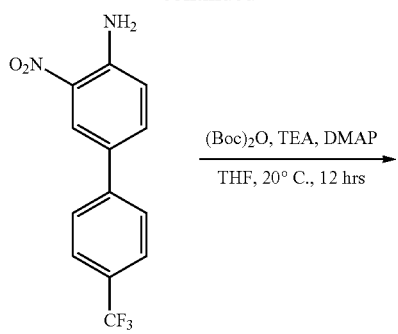

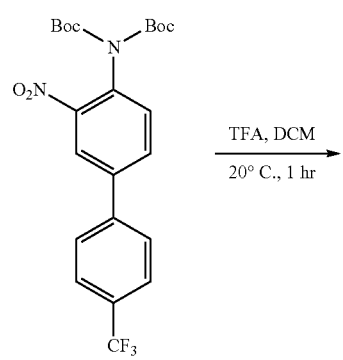

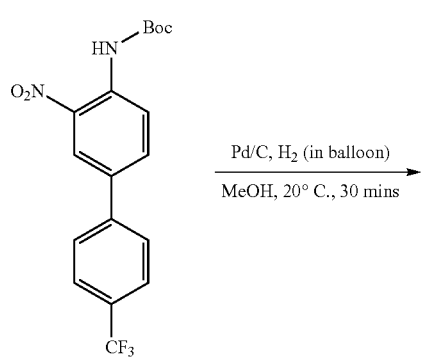

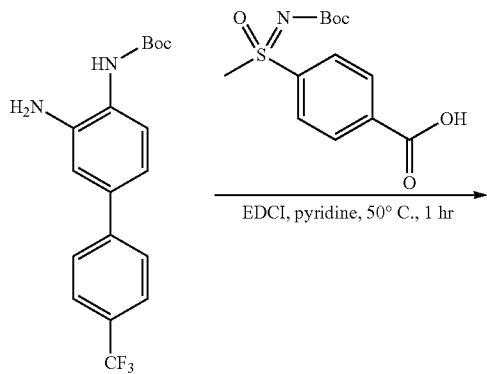

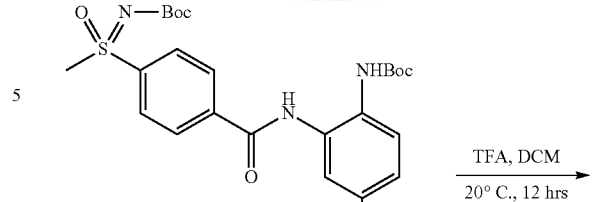

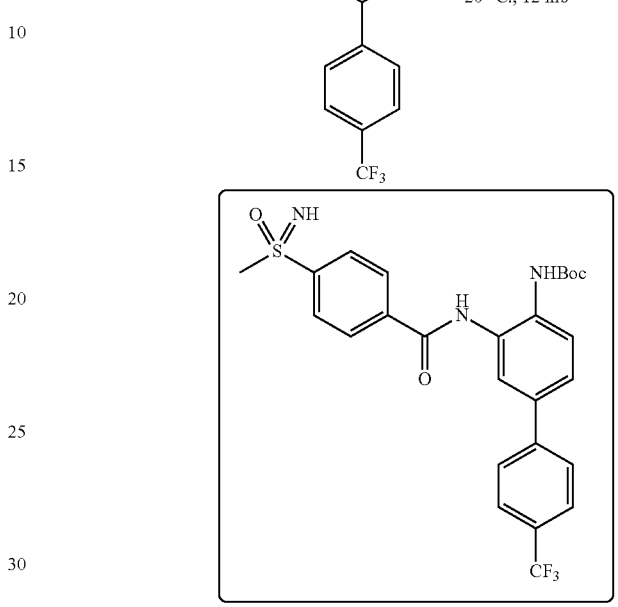

Step 1: Synthesis of 2-nitro-4-[4-(trifluoromethyl)phenyl]aniline

A solution of 4-bromo-2-nitro-aniline (2 g, 9.22 mmol), [4-(trifluoromethyl)phenyl]boronic acid (about 2.7 g, 14.2 mmol), cyclopentyl(diphenyl)phosphane;dichloromethane;dichloropalladium;iron (about 750 mg, 0.918 mmol), tripotassium;carbonate (about 3.8 g, 27.5 mmol), $H_2O$ (about 10 mL) and dioxane (about 20 mL) was stirred at about 100° C. for about 12 hours. The resulting mixture was quenched by addition of water (about 100 mL) and extracted with EtOAc (about 150 mL*3). The combined organic layer was washed with brine (about 100 mL*2), dried over anhydrous $Na_2SO_4$, filtered and concentrated under reduced pressure. The residue was purified by flash chromatography (ISCO®; about 20 g AgelaFlash® Silica Flash Column, petroleum ether/EtOAc with EtOAc from 0~20%, flow rate=30 mL/min, 254 nm) to afford 2-nitro-4-[4-(trifluoromethyl)phenyl]aniline (about 2.5 g). $^1$H NMR (400 MHz, DMSO-$d_6$) δ ppm 8.31 (d, J=2.1 Hz, 1H), 7.88 (s, 1H), 7.83-7.87 (m, 2H), 7.77 (d, J=8.4 Hz, 2H), 7.64 (s, 2H), 7.15 (d, J=8.9 Hz, 1H); LCMS (ESI) [M+H]$^+$ m/z: calcd 283.1, found 283.0.

Step 2: Synthesis of tert-butyl N-tert-butoxycarbonyl-N-[2-nitro-4-[4-(trifluoromethyl)phenyl]phenyl]carbamate A mixture of 2-nitro-4-[4-(trifluoromethyl)phenyl]aniline (about 2.5 g, 8.86 mmol), tert-butoxycarbonyl tert-butyl carbonate (about 3.1 mL, 13.5 mmol), TEA (about 3.7 mL, 26.6 mmol), DMAP (about 540 mg, 4.42 mmol) and DCM (about 20 mL) was stirred at about 20° C. for about 12 hours. The resulting mixture was concentrated under reduced pressure. The residue was triturated with MeOH (about 50 mL). The mixture was filtered. The filter cake was concentrated under reduced pressure to give tert-butyl N-tert-butoxycarbonyl-N-[2-nitro-4-[4-(trifluoromethyl)phenyl]phenyl]carbamate (about 3.2 g). $^1$H NMR (400 MHz, DMSO-$d_6$) δ ppm 8.46 (d, J=2.0 Hz, 1H), 8.18 (dd, J=8.3, 2.3 Hz, 1H), 8.06 (d, J=8.0 Hz, 2H), 7.88 (d, J=8.3 Hz, 2H), 7.73 (d, J=8.3 Hz, 1H), 1.36 (s, 18H).

Step 3: Synthesis of tert-butyl N-[2-nitro-4-[4-(trifluoromethyl)phenyl]phenyl]carbamate To a solution of tert-butyl N-tert-butoxycarbonyl-N-[2-nitro-4-[4-(trifluoromethyl)phenyl]phenyl]carbamate (3.2 g, 6.63 mmol) in DCM (15 mL) was added TFA (1.3 mL, 16.9 mmol). The mixture was stirred at 20° C. for 1 hour. The resulting mixture was quenched by addition of NaHCO$_3$ (100 mL) and extracted with DCM (100 mL*2). The combined organic layer was dried over anhydrous Na$_2$SO$_4$, filtered and concentrated under reduced pressure to give tert-butyl N-[2-nitro-4-[4-(trifluoromethyl)phenyl]phenyl]carbamate (2.5 g). $^1$H NMR (400 MHz, DMSO-$d_6$) δ ppm 9.73 (s, 1H), 8.28 (d, J=2.3 Hz, 1H), 8.07 (dd, J=8.5, 2.3 Hz, 1H), 7.97 (d, J=8.0 Hz, 2H), 7.84 (d, J=8.3 Hz, 2H), 7.78 (d, J=8.5 Hz, 1H), 1.46 (s, 9H); $^{19}$F NMR (376 MHz, DMSO-$d_6$) δ ppm−60.974; LCMS (ESI) [M+H]$^+$ m/z: calcd 383.1, found 282.9 (Boc cleaved mass).

Step 4: Synthesis of tert-butyl N-[2-amino-4-[4-(trifluoromethyl)phenyl]phenyl]carbamate To a solution of tert-butyl N-[2-nitro-4-[4-(trifluoromethyl)phenyl]phenyl]carbamate (about 2.5 g, 6.54 mmol) in MeOH (about 20 mL) was added Pd—C(about 250 mg, 10% of Pd with 50% of water, wt %) under N$_2$ atmosphere. The suspension was degassed and purged with hydrogen for about 5 times. The mixture was stirred under hydrogen (in balloon) at about 20° C. for about 12 hours. The mixture was filtered. The filter cake was washed with MeOH (about 20 mL) and THF (about 30 mL). The filtrate was filtered and concentrated under reduced pressure to give tert-butyl N-[2-amino-4-[4-(trifluoromethyl)phenyl]phenyl]carbamate (about 2.2 g). $^1$H NMR (400 MHz, DMSO-$d_6$) δ ppm 8.42 (brs, 1H), 7.76 (s, 4H), 7.38 (d, J=7.9 Hz, 1H), 7.05 (d, J=1.9 Hz, 1H), 6.90 (dd, J=8.2, 1.8 Hz, 1H), 5.05 (s, 2H), 1.47 (s, 9H); $^{19}$F NMR (376 MHz, DMSO-$d_6$) δ ppm −60.757; LCMS (ESI) [M+H]$^+$ m/z: calcd 353.1, found 353.1.

Step 5: Synthesis of tert-butyl N-[[4-[[2-(tert-butoxycarbonylamino)-5-[4-(trifluoromethyl)phenyl]phenyl]carbamoyl]phenyl]-methyl-oxo-sulfanylidene]carbamate A mixture of 4-(N-tert-butoxycarbonyl-S-methyl-sulfonimidoyl)benzoic acid (about 200 mg, 0.668 mmol), tert-butyl N-[2-amino-4-[4-(trifluoromethyl)phenyl]phenyl]carbamate (about 240 mg, 0.681 mmol), 3-(ethyliminomethyleneamino)-N,N-dimethyl-propan-1-amine;hydrochloride (about 200 mg, 1.04 mmol) and pyridine (about 12 mL) was stirred at about 50° C. for about 1 hour. The resulting mixture was concentrated under reduced pressure. The residue was purified by flash chromatography (ISCO®; about 12 g AgelaFlash® Silica Flash Column, petroleum ether/EtOAc with EtOAc from 0~50%, flow rate=30 mL/min, 254 nm) to afford tert-butyl N-[[4-[[2-(tert-butoxycarbonylamino)-5-[4-(trifluoromethyl)phenyl]phenyl]carbamoyl]phenyl]-methyl-oxo-sulfanylidene]carbamate (about 360 mg). $^1$H NMR (400 MHz, DMSO-$d_6$) δ ppm 10.16 (s, 1H), 8.91 (s, 1H), 8.24 (d, J=8.4 Hz, 2H), 8.11 (d, J=8.6 Hz, 2H), 7.91 (br d, J=3.8 Hz, 2H), 7.88 (s, 1H), 7.83 (d, J=8.6 Hz, 3H), 7.65 (dd, J=8.6, 2.2 Hz, 1H), 3.46 (s, 3H), 1.47 (s, 9H), 1.28 (s, 9H); $^{19}$F NMR (376 MHz, DMSO-$d_6$) δ ppm −60.824; LCMS (ESI) [M+H]$^+$ m/z: calcd 634.2, found 534.2 (Boc cleaved mass).

Step 6: Synthesis of N-[2-amino-5-[4-(trifluoromethyl)phenyl]phenyl]-4-(methylsulfonimidoyl)benzamide To a solution of tert-butyl N-[[4-[[2-(tert-butoxycarbonylamino)-5-[4-(trifluoromethyl)phenyl]phenyl]carbamoyl]phenyl]-methyl-oxo-sulfanylidene]carbamate (about 360 mg, 0.568 mmol) in DCM (about 10 mL) was added TFA (about 1.1 mL, 14.3 mmol). The mixture was stirred at about 20° C. for about 12 hours. The resulting mixture was quenched by addition of NaHCO$_3$ (about 20 mL) and extracted with DCM (about 20 mL*3). The combined organic layer was dried over anhydrous Na$_2$SO$_4$, filtered and concentrated under reduced pressure. The residue was purified by preparative HPLC (Instrument: Gilson GX-281 Liquid Handler, Gilson 322 Pump, Gilson 156 UV Detector; Column: Durashell 75×40 mm×3 µm; Mobile phase A: H$_2$O with 10 mmol NH$_4$HCO$_3$ (v %); Mobile phase B: MeCN; Gradient: B from 34% to 64% in 9.5 min, hold 100% B for 2 min; Flow Rate: 30 mL/min; Column Temperature: 30° C.; Wavelength: 220 nm, 254 nm) to afford N-[2-amino-5-[4-(trifluoromethyl)phenyl]phenyl]-4-(methylsulfonimidoyl)benzamide (about 100 mg). $^1$H NMR (400 MHz, DMSO-$d_6$) δ ppm 9.93 (s, 1H), 8.19 (d, J=8.3 Hz, 2H), 8.06 (d, J=8.3 Hz, 2H), 7.77-7.81 (m, 2H), 7.71-7.75 (m, 2H), 7.63 (s, 1H), 7.45 (dd, J=8.3, 2.3 Hz, 1H), 5.34 (s, 2H), 4.39 (s, 1H), 3.13 (s, 3H); $^{19}$F NMR (376 MHz, DMSO-$d_6$) δ ppm −60.622; LCMS (ESI) [M+H]$^+$ m/z: calcd 434.1, found 434.2; HPLC: 98.86%@220 nm; 99.20%@254 nm.

Example 46. Synthesis of N-[2-amino-5-(2-thienyl)phenyl]-6-(methylsulfonimidoyl)pyridazine-3-carboxamide (Compound 124)

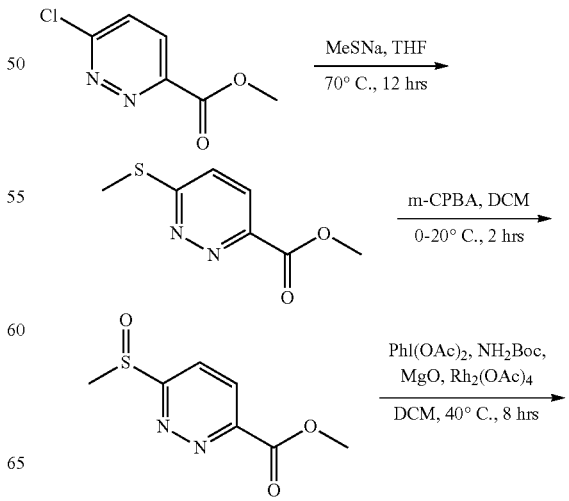

-continued

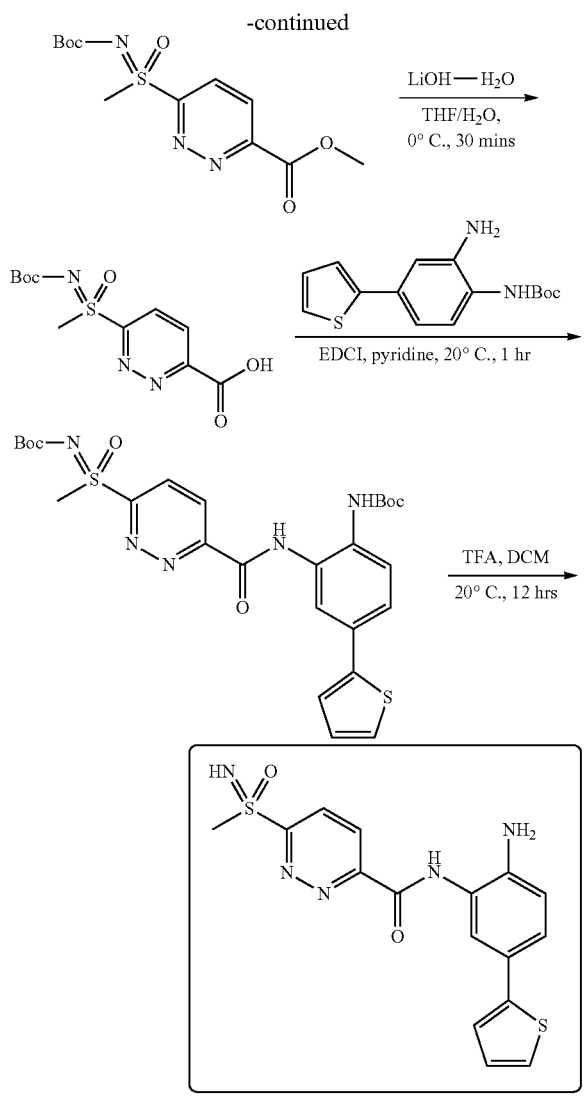

Step 1: Synthesis of methyl 6-methylsulfanylpyridazine-3-carboxylate

To a solution of methyl 6-chloropyridazine-3-carboxylate (about 1 g, 5.79 mmol) in THF (about 15 mL) was added sodium;methanethiolate (about 440 mg, 6.28 mmol). The mixture was stirred at about 70° C. for about 12 hours. The reaction mixture was concentrated under reduced pressure. The residue was purified by flash chromatography (ISCO®; about 25 g AgelaFlash® Silica Flash Column, petroleum ether/EtOAc with EtOAc from 0~50%, flow rate=50 mL/min, 254 nm) to afford methyl 6-methylsulfanylpyridazine-3-carboxylate (about 800 mg). $^1$H NMR (400 MHz, chloroform-d) δ ppm 7.92 (d, J=8.8 Hz, 1H), 7.45 (d, J=8.8 Hz, 1H), 4.05 (s, 3H), 2.78 (s, 3H); LCMS (ESI) [M+H]$^+$ m/z: calcd 185.0, found 184.8.

Step 2: Synthesis of methyl 6-methylsulfinylpyridazine-3-carboxylate

To a solution of methyl 6-methylsulfanylpyridazine-3-carboxylate (about 1.8 g, 9.77 mmol) in DCM (about 40 mL) was added 3-chlorobenzenecarboperoxoic acid (about 2.18 g, 10.8 mmol, 85 wt %) at about 0° C. After addition, the reaction mixture was stirred at about 20° C. for about 2 hours. The reaction mixture was quenched with saturated NaHCO$_3$ aqueous (about 30 mL) and extracted with DCM (about 50 mL*3). The combined organic layers were dried over Na$_2$SO$_4$ and filtered. The filtrate was concentrated under reduced pressure. The residue was purified by flash chromatography (ISCO®; about 40 g AgelaFlash® Silica Flash Column, petroleum ether/EtOAc with EtOAc from 0~100%, flow rate=50 mL/min, 254 nm) to afford methyl 6-methylsulfinylpyridazine-3-carboxylate (about 1.6 g). $^1$H NMR (400 MHz, chloroform-d) δ ppm 8.46 (d, J=8.8 Hz, 1H), 8.36 (d, J=8.8 Hz, 1H), 4.12 (s, 3H), 3.06 (s, 3H); LCMS (ESI) [M+H]$^+$ m/z: calcd 201.0; found 200.8.

Step 3: Synthesis of methyl 6-(N-tert-butoxycarbonyl-S-methyl-sulfonimidoyl)pyridazine-3-carboxylate To a solution of methyl 6-methylsulfinylpyridazine-3-carboxylate (about 300 mg, 1.50 mmol), tert-butyl carbamate (about 210 mg, 1.79 mmol), [acetoxy(phenyl)-iodanyl]acetate (about 730 mg, 2.27 mmol) and oxomagnesium (about 300 mg, 7.44 mmol) in DCM (about 15 mL) was added diacetoxyrhodium (about 16 mg, 0.0720 mmol). The reaction mixture was stirred at about 40° C. for about 8 hours. The reaction mixture was concentrated under reduced pressure. The residue was purified by flash chromatography (ISCO®; about 25 g AgelaFlash® Silica Flash Column, petroleum ether/EtOAc with EtOAc from 0~60%, flow rate=50 mL/min, 254 nm) to afford methyl 6-(N-tert-butoxycarbonyl-S-methyl-sulfonimidoyl)pyridazine-3-carboxylate (about 250 mg). $^1$H NMR (400 MHz, chloroform-d) δ ppm 8.58 (d, J=8.8 Hz, 1H), 8.47 (d, J=8.4 Hz, 1H), 4.13 (s, 3H), 3.60 (s, 3H), 1.38 (s, 9H); LCMS (ESI) [M+H]$^+$ m/z: calcd 316.1, found 215.8 (Boc cleaved mass).

Step 4: Synthesis of 6-(N-tert-butoxycarbonyl-S-methyl-sulfonimidoyl)pyridazine-3-carboxylic acid To a solution of methyl 6-(N-tert-butoxycarbonyl-S-methyl-sulfonimidoyl)pyridazine-3-carboxylate (about 170 mg, 0.539 mmol) in THF (about 10 mL) and H$_2$O (about 1 mL) was added lithium hydroxide;hydrate (about 50 mg, 1.19 mmol). The mixture was stirred at about 0° C. for about 30 minutes. The reaction mixture was diluted with DCM (30 mL), adjusted to about pH=4 with 2N HCl aqueous solution and dried over Na$_2$SO$_4$. The suspension was filtered and the filtrate was concentrated under reduced pressure to give 6-(N-tert-butoxycarbonyl-S-methyl-sulfonimidoyl)pyridazine-3-carboxylic acid (about 160 mg).

Step 5: Synthesis of tert-butyl N-[[6-[[2-(tert-butoxycarbonylamino)-5-(2-thienyl)phenyl]carbamoyl]pyridazin-3-yl]-methyl-oxo-sulfanylidene]carbamate To a solution of 6-(N-tert-butoxycarbonyl-S-methyl-sulfonimidoyl)pyridazine-3-carboxylic acid (about 90 mg, 0.299 mmol) in pyridine (about 2 mL) were added tert-butyl N-[2-amino-4-(2-thienyl)phenyl]carbamate (about 70 mg, 0.241 mmol) and 3-(ethyliminomethyleneamino)-N,N-dimethyl-propan-1-amine;hydrochloride (about 70 mg, 0.365 mmol). The mixture was stirred at about 20° C. for about 1 hour. The reaction mixture was quenched with 2N HCl aqueous solution to about pH=4 and extracted with DCM (about 20 mL*3). The combined organic layers were dried over Na$_2$SO$_4$ and filtered. The filtrate was concentrated under reduced pressure. The residue was purified by preparative TLC (silica, PE/EtOAc=2/1; 254 nm) to give tert-butyl N-[[6-[[2-(tert-butoxycarbonylamino)-5-(2-thienyl)phenyl]carbamoyl]pyridazin-3-yl]-methyl-oxo-sulfanylidene]carbamate (about 90 mg). LCMS (ESI) [M+H]$^+$ m/z: calcd 574.2, found 373.9 (Boc cleaved mass).

Step 6: Synthesis of N-[2-amino-5-(2-thienyl)phenyl]-6-(methylsulfonimidoyl)pyridazine-3-carboxamide To a solution of tert-butyl N-[[6-[[2-(tert-butoxycarbonylamino)-5-(2-thienyl)phenyl]carbamoyl]pyridazin-3-yl]-methyl-oxo-sulfanylidene]carbamate (about 75 mg, 0.131 mmol) in DCM (about 5 mL) was added TFA (about 0.1 mL, 1.30 mmol). The mixture was stirred at about 20° C. for about 12 hours. The reaction mixture was diluted with DCM (about 30 mL) and adjusted to about pH=8 with saturated Na$_2$CO$_3$ aqueous solution. The resultant mixture was dried over Na$_2$SO$_4$ and filtered. The filtrate was concentrated under reduced pressure. The residue was purified by preparative TLC (silica, DCM/MeOH=10/1, 254 nm) to give a residue. The residue was further purified by preparative HPLC (Instrument: Gilson GX-281 Liquid Handler, Gilson 322 Pump, Gilson 156 UV Detector; Column: Phenomenex C18 80*40 mm*3 μm; Mobile phase A: water with 10 mmol NH$_4$HCO$_3$ (v %); Mobile phase B: MeCN; Gradient: B from 25% to 55% in 9.5 min, hold 100% B for 1 min; Flow Rate: 30 mL/min; Column Temperature: 30° C.; Wavelength: 220 nm, 254 nm) to afford N-[2-amino-5-(2-thienyl)phenyl]-6-(methylsulfonimidoyl)pyridazine-3-carboxamide (about 6.8 mg). $^1$H NMR (400 MHz, methanol-d$_4$) δ ppm 8.61-8.68 (m, 1H), 8.50-8.56 (m, 1H), 7.76 (d, J=2.0 Hz, 1H), 7.39 (dd, J=8.4, 2.0 Hz, 1H), 7.24 (t, J=4.4 Hz, 2H), 7.04 (dd, J=5.2, 3.6 Hz, 1H), 6.94 (d, J=8.4 Hz, 1H), 3.47 (s, 3H); LCMS (ESI) [M+H]$^+$ m/z: calcd 374.1, found 373.9. HPLC: 97.70%@220 nm, 96.54%@254 nm.

Example 47. Synthesis of N-[2-hydroxy-5-(2-thienyl)phenyl]-4-(methylsulfonimidoyl)benzamide (Compound 123)

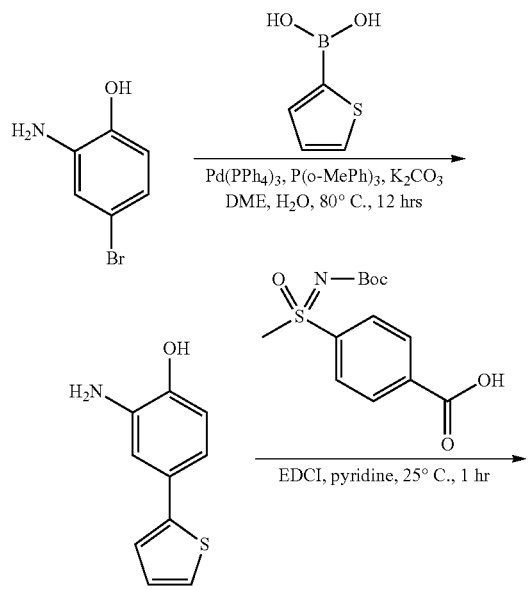

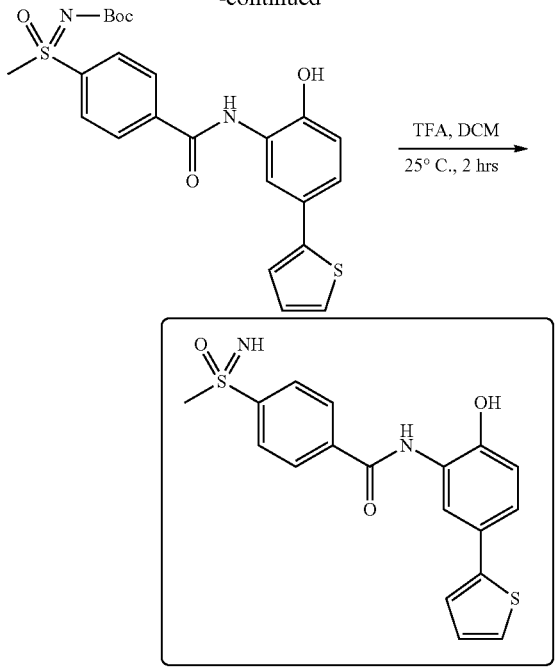

Step 1: Synthesis of 2-amino-4-(2-thienyl)phenol

A mixture of 2-amino-4-bromo-phenol (about 1 g, 5.32 mmol), 2-thienylboronic acid (about 1 g, 7.82 mmol), palladium;triphenylphosphane (about 615 mg, 0.532 mmol), tris-o-tolylphosphane (about 324 mg, 1.06 mmol) and K$_2$CO$_3$ (about 2 g, 14.47 mmol) in H$_2$O (about 7 mL) and DME (21 mL) was degassed and purged with N$_2$ for about 3 times. Then the mixture was stirred at about 80° C. for about 12 hours under N$_2$ atmosphere. The reaction mixture was diluted with H$_2$O (about 50 mL) and extracted with DCM (about 80 mL*2). The combined organic layers were washed with brine (about 50 mL), dried over anhydrous Na$_2$SO$_4$, filtered and concentrated under reduced pressure. The residue was purified by flash chromatography (ISCO®; about 20 g SepaFlash® Silica Flash Column, Petroleum ether/EtOAc with EtOAc from 0-60%, 40 mL/min, 254 nm) to afford 2-amino-4-(2-thienyl)phenol (about 618 mg). $^1$H NMR (400 MHz, CDCl$_3$) δ ppm 7.47 (s, 1H), 7.31-7.36 (m, 1H), 6.92-6.96 (m, 2H), 6.85-6.88 (m, 1H), 6.72-6.76 (m, 3H), 6.60 (d, J=8.4 Hz, 1H); LCMS (ESI) [M+H]$^+$ m/z: calcd 192.0, found 191.8.

Step 2: Synthesis of tert-butyl N-[[4-[[2-hydroxy-5-(2-thienyl)phenyl]carbamoyl]phenyl]-methyl-oxo-sulfanylidene]carbamate To a solution of 4-(N-tert-butoxycarbonyl-S-methyl-sulfonimidoyl)benzoic acid (100 mg, 0.334 mmol) in pyridine (about 3 mL) were added 2-amino-4-(2-thienyl)phenol (about 96 mg, 0.502 mmol) and 3-(ethyliminomethyleneamino)-N,N-dimethyl-propan-1-amine (about 78 mg, 0.502 mmol). The mixture was stirred at about 25° C. for about 1 hour. The reaction mixture was diluted with NH$_4$Cl (about 30 mL) and extracted with EtOAc (about 40 mL*2). The combined organic layers were washed with brine (about 40 mL), dried anhydrous Na$_2$SO$_4$, filtered and concentrated under reduced pressure. The residue was purified by flash chromatography (ISCO®; about 12 g SepaFlash® Silica Flash Column, Petroleum Ether/EtOAc with EtOAc from 0~60%, 40 mL/min, 254 nm) to afford tert-butyl N-[[4-[[2-hydroxy-5-(2-thienyl)phenyl]carbamoyl]phenyl]-methyl-oxo-sulfanylidene]carbamate (about 70 mg). $^1$H NMR (400 MHz, CDCl$_3$) δ ppm 8.80 (br s, 1H), 8.08-8.18 (m, 2H), 8.04 (br d, J=7.2 Hz, 2H), 7.68-7.78 (m, 1H), 7.42 (d, J=8.4 Hz, 1H), 7.22-7.26 (m, 2H), 7.00-7.10 (m, 2H), 3.26 (s, 3H), 1.41 (s, 9H); LCMS (ESI) [M+H]$^+$ m/z: calcd 473.1, found 372.9 (Boc cleaved mass).

Step 3: Synthesis of N-[2-hydroxy-5-(2-thienyl) phenyl]-4-(methylsulfonimidoyl)benzamide To a solution of tert-butyl N-[[4-[[2-hydroxy-5-(2-thienyl)phenyl]carbamoyl]phenyl]-methyl-oxo-sulfanylidene] carbamate (about 70 mg, 0.148 mmol) in DCM (about 7 mL) was added 2,2,2-trifluoroacetic acid (about 0.11 mL, 1.48 mmol). The mixture was stirred at about 25° C. for about 2 hours. The reaction mixture was diluted with H$_2$O (about 30 mL) and extracted with EtOAc (about 40 mL*2). The combined organic layers were washed with brine (about 40 mL), dried over anhydrous Na$_2$SO$_4$, filtered and concentrated under reduced pressure. The residue was purified by preparative HPLC (Instrument: Gilson GX-281 Liquid Handler, Gilson 322 Pump, Gilson 156 UV Detector; Column: Phenomenex C18 80*40 mm*3 μm; Mobile phase A: H$_2$O with 10 mmol NH$_4$HCO$_3$ (v %); Mobile phase B: ACN; Gradient: B from 29% to 59% in 7.8 min, hold 100% B for 2 min; Flow Rate: 30 mL/min; Column Temperature: 30° C.; Wavelength: 220 nm, 254 nm) to afford N-[2-hydroxy-5-(2-thienyl)phenyl]-4-(methylsulfonimidoyl)benzamide (about 19 mg). $^1$H NMR (400 MHz, DMSO) δ ppm 9.20 (br s, 1H), 8.96 (br s, 1H), 7.33 (d, J=8.4 Hz, 2H), 7.21-7.25 (m, 2H), 7.13 (d, J=2.4 Hz, 1H), 6.61 (d, J=5.2 Hz, 1H), 6.55 (dd, J=8.4, 2.4 Hz, 1H), 6.49 (d, J=3.6 Hz, 1H), 6.26 (dd, J=5.2, 3.6 Hz, 1H), 6.14 (d, J=8.4 Hz, 1H), 3.57 (s, 1H), 2.29 (s, 3H); LCMS (ESI) [M+H]$^+$ m/z: calcd 373.1, found 372.9; HPLC: 95.60%@220 nm, 97.19%@254 nm.

Example 48. Synthesis of tert-butyl N-[2-[[4-(methylsulfonimidoyl)benzoyl]amino]-4-(2-thienyl)phenyl]carbamate (Compound 101)

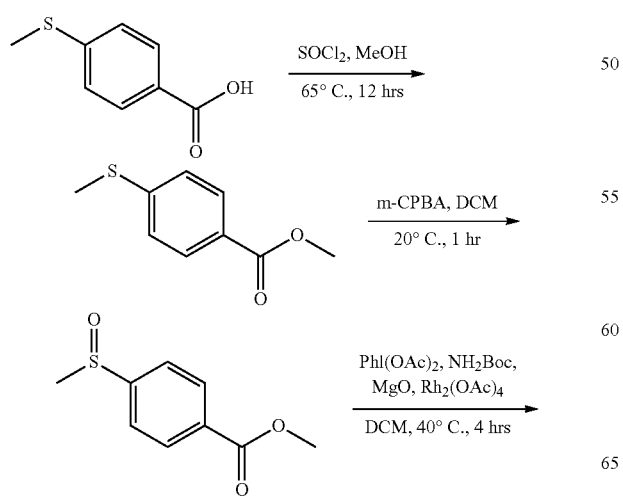

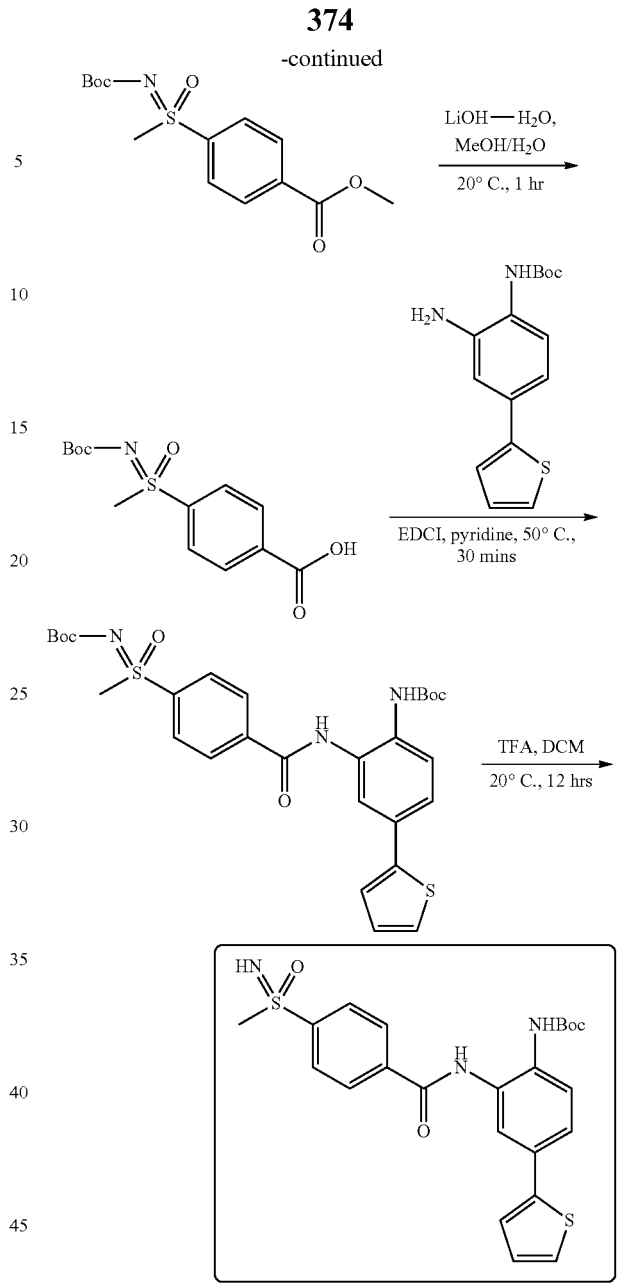

Step 1: Synthesis of methyl 4-methylsulfanylbenzoate

To a solution of 4-methylsulfanylbenzoic acid (about 1 g, 5.94 mmol) in MeOH (about 20 mL) was added SOCl$_2$ (about 5 mL, 68.9 mmol). The mixture was stirred at about 65° C. for about 12 hours. The mixture was concentrated under reduced pressure to give a product, which was diluted with EtOAc (about 30 mL). The mixture was washed with saturated Na$_2$CO$_3$ aqueous solution (about 50 mL), dried over anhydrous Na$_2$SO$_4$, filtered and concentrated under reduced pressure to give methyl 4-methylsulfanylbenzoate (about 1.1 g), which was directly used without further purification. $^1$H NMR (400 MHz, methanol-d$_4$) δ ppm 7.91 (d, J=8.5 Hz, 2H), 7.31 (d, J=8.5 Hz, 2H), 3.88 (s, 3H), 2.52 (s, 3H); LCMS (ESI) [M+H]$^+$ m/z: calcd 183.0; found 183.0.

Step 2: Synthesis of methyl 4-methylsulfinylbenzoate

To a solution of methyl 4-methylsulfanylbenzoate (about 1.1 g, 6.04 mmol) in DCM (about 20 mL) was added m-CPBA (about 1.3 g, 6.40 mmol, 85% purity). The mixture was stirred at about 20° C. for about 1 hour. The mixture was quenched by addition of saturated $Na_2S_2O_3$ aqueous solution (about 30 mL), saturated $Na_2CO_3$ aqueous solution (about 30 mL) and extracted with DCM (about 50 mL*2). The combined organic layer was dried over anhydrous $Na_2SO_4$, filtered and concentrated under reduced pressure to give methyl 4-methylsulfinylbenzoate (about 1.2 g), which was directly used without further purification. $^1$H NMR (400 MHz, methanol-$d_4$) δ ppm 8.20-8.23 (m, 2H), 7.79-7.84 (m, 2H), 3.95 (s, 3H), 2.84 (s, 3H); LCMS (ESI) [M+H]$^+$ m/z: calcd 199.0; found 199.0.

Step 3: Synthesis of methyl 4-(N-tert-butoxycarbonyl-S-methyl-sulfonimidoyl)benzoate To a solution of methyl 4-methylsulfinylbenzoate (about 300 mg, 1.51 mmol), $NH_2$Boc (about 355 mg, 3.03 mmol), [bis(acetoxy)iodo]benzene (about 731 mg, 2.27 mmol) and MgO (about 305 mg, 7.57 mmol) in DCM (about 5 mL) was added dirhodium tetraacetate (about 30 mg, 0.0679 mmol). The reaction mixture was stirred at about 40° C. for about 4 hours. The mixture was filtered. The filtrate was concentrated under reduced pressure. The residue was purified by flash chromatography (Biotage®; about 12 g SepaFlash® Silica Flash Column, petroleum ether/EtOAc with EtOAc from 0~36%, 80 mL/min, 254 nm) to afford methyl 4-(N-tert-butoxycarbonyl-S-methyl-sulfonimidoyl)benzoate (about 260 mg). $^1$H NMR (400 MHz, methanol-$d_4$) δ ppm 8.24-8.32 (m, 2H), 8.07-8.14 (m, 2H), 3.97 (s, 3H), 3.36 (s, 3H), 1.28 (s, 9H); LCMS (ESI) [M+H]$^+$ m/z: calcd 314.1; found 314.1.

Step 4: Synthesis of 4-(N-tert-butoxycarbonyl-S-methyl-sulfonimidoyl)benzoic acid To a solution of methyl 4-(N-tert-butoxycarbonyl-S-methyl-sulfonimidoyl)benzoate (about 260 mg, 0.830 mmol) in MeOH (about 6 mL) was added a solution of LiOH—$H_2O$ (about 348 mg, 8.29 mmol) in $H_2O$ (about 3 mL). The mixture was stirred at about 20° C. for about 1 hour. The mixture was concentrated under reduced pressure to remove the organic solvent. The aqueous phase was adjusted to about pH=4 with 2N HCl aqueous solution. The mixture was filtered. The filter cake was dried under reduced pressure to give 4-(N-tert-butoxycarbonyl-S-methyl-sulfonimidoyl)benzoic acid (about 200 mg), which was directly used without further purification. LCMS (ESI) [M+H]$^+$ m/z: calcd 300.1; found 244.0 (t-Bu cleaved mass).

Step 5: Synthesis of tert-butyl N-[[4-[[2-(tert-butoxycarbonylamino)-5-(2-thienyl)phenyl]carbamoyl]phenyl]-methyl-oxo-{6}-sulfanylidene]carbamate A mixture of 4-(N-tert-butoxycarbonyl-S-methyl-sulfonimidoyl)benzoic acid (about 100 mg, 0.334 mmol), tert-butyl N-[2-amino-4-(2-thienyl)phenyl]carbamate (about 80 mg, 0.276 mmol) and EDCI (about 79 mg, 0.412 mmol) in pyridine (about 3 mL) was stirred at about 50° C. for about 30 minutes. The mixture was concentrated under reduced pressure to give a product, which was purified by flash chromatography (ISCO®; about 4 g AgelaFlash® Silica Flash Column, petroleum ether/EtOAc with EtOAc from 0~60%, 30 mL/min, 254 nm) to afford tert-butyl N-[[4-[[2-(tert-butoxycarbonylamino)-5-(2-thienyl)phenyl]carbamoyl]phenyl]-methyl-oxo-{6}-sulfanylidene]carbamate (about 120 mg). LCMS (ESI) [M+H]$^+$ m/z: calcd 572.1; found 472.1 (Boc cleaved mass).

Step 6: Synthesis of tert-butyl N-[2-[[4-(methyl-sulfonimidoyl)benzoyl]amino]-4-(2-thienyl)phenyl]carbamate To a solution of tert-butyl N-[[4-[[2-(tert-butoxycarbonylamino)-5-(2-thienyl)phenyl]carbamoyl]phenyl]-methyl-oxo-{6}-sulfanylidene]carbamate (about 120 mg, 0.210 mmol) in DCM (about 5 mL) was added TFA (about 0.16 mL, 2.08 mmol). The mixture was stirred at about 20° C. for about 12 hours. The mixture was adjusted to about pH=8 with saturated $NaHCO_3$ aqueous solution, and extracted with a mixture of DCM/MeOH (about 15 mL*3, v/v=10:1). The combined organic layer was concentrated under reduced pressure to give a product, which was purified by preparative HPLC (Instrument: Gilson GX-281 Liquid Handler, Gilson 322 Pump, Gilson 156 UV Detector; Column: Phenomenex Gemini-NX 80×40 mm×3 μm; Mobile phase A: $H_2O$ with 10 mmol $NH_4HCO_3$ (v %); Mobile phase B: MeCN; Gradient: B from 23% to 53% in 7.8 min, hold 100% B for 2 min; Flow Rate: 25 mL/min; Column Temperature: 30° C.; Wavelength: 220 nm, 254 nm) to give tert-butyl N-[2-[[4-(methylsulfonimidoyl)benzoyl]amino]-4-(2-thienyl)phenyl]carbamate (about 65 mg). $^1$H NMR (400 MHz, DMSO-$d_6$) δ ppm 9.92 (s, 1H), 8.19 (d, J=8.3 Hz, 2H), 8.06 (d, J=8.3 Hz, 2H), 7.49 (d, J=1.8 Hz, 1H), 7.36 (dd, J=5.0, 1.0 Hz, 1H), 7.32 (dd, J=8.3, 2.3 Hz, 1H), 7.22-7.27 (m, 1H), 7.05 (dd, J=5.1, 3.6 Hz, 1H), 6.82 (d, J=8.3 Hz, 1H), 5.22 (s, 2H), 4.39 (s, 1H), 3.13 (s, 3H); LCMS (ESI) [M+H]$^+$ m/z: calcd 372.1; found 372.0; HPLC: 95.10%@220 nm, 95.63%@254 nm; racemic mixture.

Example 49. Synthesis of N-[2-amino-5-(4-methyl-2-thienyl)phenyl]-4-(methylsulfonimidoyl)benzamide (Compound 135)

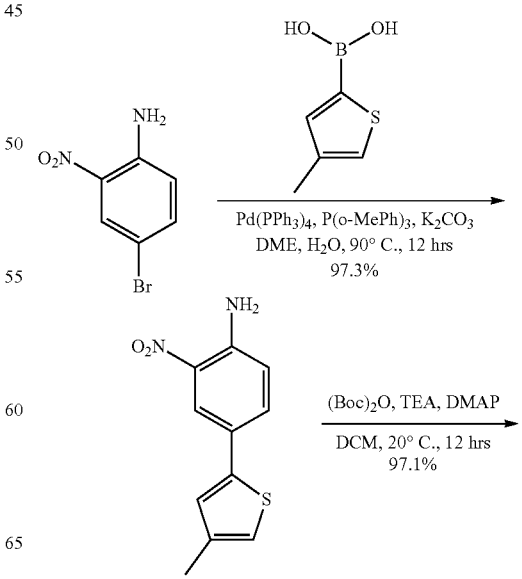

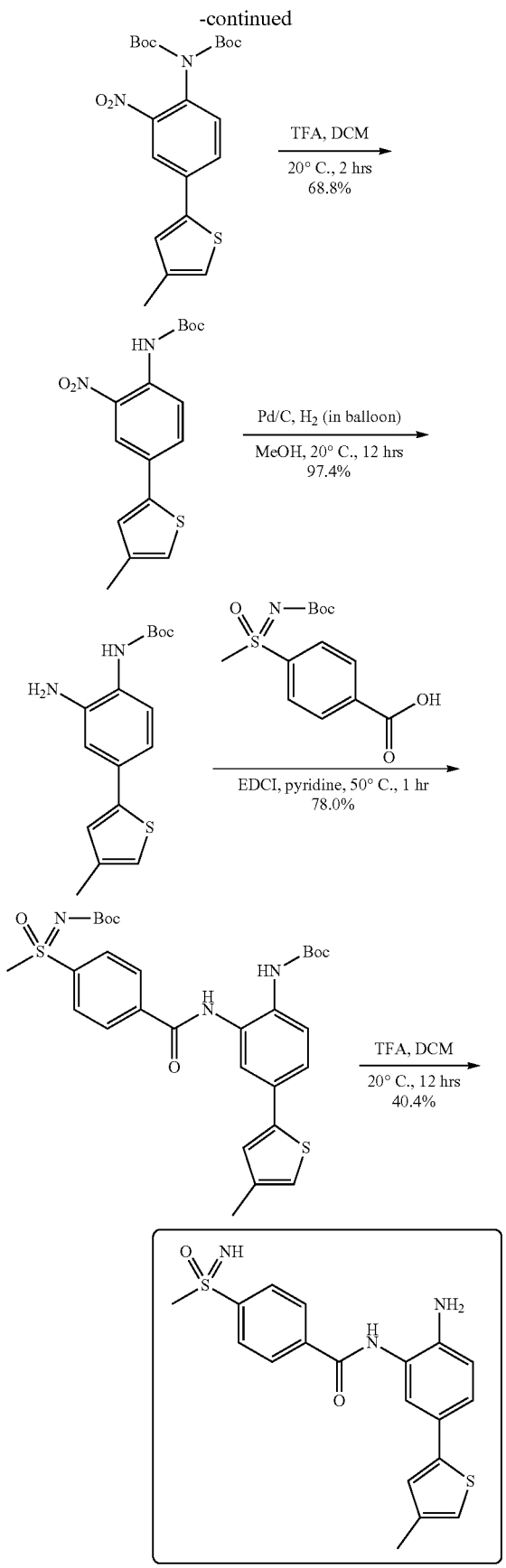

Step 1: Synthesis of 4-(4-methyl-2-thienyl)-2-nitro-aniline

A mixture of 4-bromo-2-nitro-aniline (about 1 g, 4.61 mmol), (4-methyl-2-thienyl)boronic acid (about 981 mg, 6.91 mmol), palladium;triphenylphosphane (about 532 mg, 0.461 mmol), tripotassium;carbonate (about 1.91 g, 13.8 mmol) and tris-o-tolylphosphane (about 281 mg, 0.922 mmol) in H$_2$O (about 10 mL) and DME (about 30 mL) was degassed and purged with N$_2$ for about 3 times, and then the mixture was stirred at about 90° C. for about 12 hours under N$_2$ atmosphere. The reaction mixture was diluted with H$_2$O (about 50 mL) and extracted with DCM (about 80 mL*2). The combined organic layers were washed with brine (about 50 mL), dried over anhydrous Na$_2$SO$_4$, filtered and concentrated under reduced pressure. The residue was purified by flash chromatography (ISCO®; about 20 g SepaFlash®Silica Flash Column, Petroleum ether/EtOAc with EtOAc from 0~20%, 40 mL/min, 254 nm) to afford 4-(4-methyl-2-thienyl)-2-nitro-aniline (about 1.05 g). $^1$H NMR (400 MHz, CDCl$_3$) δ ppm 8.34 (d, J=2.4 Hz, 1H), 7.60 (dd, J=2.0, 8.8 Hz, 1H), 7.07 (d, J=1.2 Hz, 1H), 6.88-6.81 (m, 2H), 6.61-5.61 (m, 2H), 2.29 (s, 3H). LCMS (ESI) [M+H]$^+$ m/z: calcd 235.0, found 234.9.

Step 2: Synthesis of tert-butyl N-tert-butoxycarbonyl-N-[4-(4-methyl-2-thienyl)-2-nitro-phenyl]carbamate A mixture of 4-(4-methyl-2-thienyl)-2-nitro-aniline (about 1.05 g, 4.48 mmol), tert-butoxycarbonyl tert-butyl carbonate (about 2.45 g, 11.2 mmol), N,N-diethylethanamine (about 1.36 g, 13.5 mmol), N,N-dimethylpyridin-4-amine (about 55 mg, 0.448 mmol) in DCM (about 15 mL) was stirred at about 20° C. for about 12 hours. The reaction mixture was diluted with water (about 20 mL) and extracted with EtOAc (about 30 mL*3). The combined organic layers were washed with brine (about 30 mL), dried over Na$_2$SO$_4$ and filtered. The filtrate was concentrated under reduced pressure. The residue was purified by flash chromatography (ISCO®; about 4 g SepaFlash® Silica Flash Column, Petroleum ether/EtOAc with EtOAc from 0~10%, 18 mL/min, 254 nm) to afford tert-butyl N-tert-butoxycarbonyl-N-[4-(4-methyl-2-thienyl)-2-nitro-phenyl] carbamate (about 1.89 g). $^1$H NMR (400 MHz, CDCl$_3$) δ ppm 8.25 (d, J=2.0 Hz, 1H), 7.79 (dd, J=2.4, 8.4 Hz, 1H), 7.30 (d, J=8.4 Hz, 1H), 7.26 (d, J=1.2 Hz, 1H), 7.00-6.96 (m, 1H), 2.32 (s, 3H), 1.42 (s, 18H). LCMS (ESI) [M+Na]$^+$ m/z: calcd 457.2, found 457.0.

Step 3: Synthesis of afford tert-butyl N-[4-(4-methyl-2-thienyl)-2-nitro-phenyl]carbamate To a solution of tert-butyl N-tert-butoxycarbonyl-N-[4-(4-methyl-2-thienyl)-2-nitro-phenyl]carbamate (about 1.89 g, 4.35 mmol) in DCM (about 30 mL) was added 2,2,2-trifluoroacetic acid (about 0.35 mL, 4.35 mmol). The mixture was stirred at about 20° C. for about 2 hours. The reaction mixture was quenched by saturated aqueous NaHCO$_3$ solution (about 50 mL) and extracted with DCM (about 50 mL*2), the combined organic layers were washed with brine (about 50 mL), dried over anhydrous Na$_2$SO$_4$, filtered and concentrated under reduced to afford tert-butyl N-[4-(4-methyl-2-thienyl)-2-nitro-phenyl]carbamate (about 1 g). $^1$H NMR (400 MHz, CDCl$_3$) δ ppm 9.66 (s, 1H), 8.57

(d, J=9.2 Hz, 1H), 8.37 (d, J=2.0 Hz, 1H), 7.79 (dd, J=2.4, 8.8 Hz, 1H), 7.16 (d, J=1.2 Hz, 1H), 6.91 (s, 1H), 2.30 (s, 3H), 1.56 (s, 9H).

Step 4: Synthesis of afford tert-butyl N-[2-amino-4-(4-methyl-2-thienyl)phenyl]carbamate To a solution of tert-butyl N-[4-(4-methyl-2-thienyl)-2-nitro-phenyl]carbamate (about 400 mg, 1.20 mmol) in MeOH (about 20 mL) was added Pd/C (about 76 mg, 10 wt % Pd with 50 wt % water). The mixture was stirred at about 20° C. for about 12 hours under H₂ (in balloon). The reaction mixture was filtered and concentrated under reduced pressure to afford tert-butyl N-[2-amino-4-(4-methyl-2-thienyl)phenyl]carbamate (about 340 mg). ¹H NMR (400 MHz, MeOD) δ ppm 7.16 (d, J=8.0 Hz, 1H), 7.09 (dd, J=1.6, 12.4 Hz, 2H), 6.94 (dd, J=2.0, 8.4 Hz, 1H), 6.89-6.84 (m, 1H), 2.25 (d, J=0.8 Hz, 3H), 1.52 (s, 9H).

Step 5: Synthesis of tert-butyl N-[[4-[[2-(tert-butoxycarbonylamino)-5-(4-methyl-2-thienyl)phenyl]carbamoyl]phenyl]-methyl-oxo-sulfanylidene]carbamate To a solution of tert-butyl N-[2-amino-4-(4-methyl-2-thienyl)phenyl]carbamate (about 100 mg, 0.329 mmol) in pyridine (about 2 mL) was added 3-(ethyliminomethyleneamino)-N,N-dimethyl-propan-1-amine (about 77 mg, 0.493 mmol). The mixture was stirred at about 50° C. for about 1 hour. The reaction mixture was diluted with saturated NH₄Cl aqueous solution (about 10 mL) and extracted with EtOAc (about 20 mL*2). The combined organic layers were washed with brine (about 10 mL), dried over anhydrous Na₂SO₄, filtered and concentrated under reduced pressure. The residue was purified by flash chromatography (ISCO®; about 4 g SepaFlash® Silica Flash Column, Petroleum ether/EtOAc with EtOAc from 0~100%, 40 mL/min, 254 nm) to afford tert-butyl N-[[4-[[2-(tert-butoxycarbonylamino)-5-(4-methyl-2-thienyl)phenyl]carbamoyl]phenyl]-methyl-oxo-sulfanylidene]carbamate (about 150 mg). ¹H NMR (400 MHz, CDCl₃) δ ppm 9.88-9.63 (m, 1H), 8.20 (d, J=7.2 Hz, 2H), 8.14 (s, 1H), 8.10-8.05 (m, 2H), 7.39 (d, J=8.4 Hz, 1H), 7.20-7.13 (m, 2H), 6.86 (s, 1H), 6.78 (s, 1H), 3.27 (d, J=1.6 Hz, 3H), 2.28 (s, 3H), 1.54 (d, J=1.6 Hz, 9H), 1.41 (d, J=1.6 Hz, 9H). LCMS (ESI) [M+Na]⁺ m/z: calcd 608.2, found 608.1.

Step 6: Synthesis of N-[2-amino-5-(4-methyl-2-thienyl)phenyl]-4-(methylsulfonimidoyl)benzamide To a solution of tert-butyl N-[[4-[[2-(tert-butoxycarbonylamino)-5-(4-methyl-2-thienyl)phenyl]carbamoyl]phenyl]-methyl-oxo-sulfanylidene]carbamate (about 150 mg, 0.256 mmol) in DCM (about 10 mL) was added 2,2,2-trifluoroacetic acid (about 0.2 mL, 2.56 mmol). The mixture was stirred at about 20° C. for about 12 hours. The reaction mixture was diluted with DCM (about 15 mL) and added saturated aqueous Na₂CO₃ solution to adjust to about pH=8. Then the mixture was concentrated. The residue was purified by preparative HPLC (Instrument: Gilson GX-281 Liquid Handler, Gilson 322 Pump, Gilson 156 UV Detector; Column: Phenomenex C18 80*40 mm*3 μm; Mobile phase A: H₂O with 0.05% NH₃—H₂O (v %); B: ACN; Gradient: B from 28% to 58% in 9.5 min, hold 100% B for 2 min; Flow Rate: 30 mL/min; Column Temperature: 30° C.; Wavelength: 220 nm, 254 nm) to afford N-[2-amino-5-(4-methyl-2-thienyl)phenyl]-4-(methylsulfonimidoyl)benzamide (about 39.9 mg). ¹H NMR (400 MHz, DMSO-d₆) δ ppm 9.91 (s, 1H), 8.18 (d, J=7.6 Hz, 2H), 8.05 (d, J=7.2 Hz, 2H), 7.45 (s, 1H), 7.27 (d, J=8.4 Hz, 1H), 7.07 (s, 1H), 6.92 (d, J=0.8 Hz, 1H), 6.80 (d, J=8.4 Hz, 1H), 5.21 (s, 2H), 4.41 (s, 1H), 3.12 (s, 3H), 2.20 (s, 3H). LCMS (ESI) [M+H]⁺ m/z: calcd 386.1, found 386.0. HPLC: 100%@220 nm, 99.58%@254 nm.

Example 50. Synthesis of (S)—N-[2-amino-5-(4-fluorophenyl)phenyl]-4-(methylsulfonimidoyl)benzamide (Compound 134)

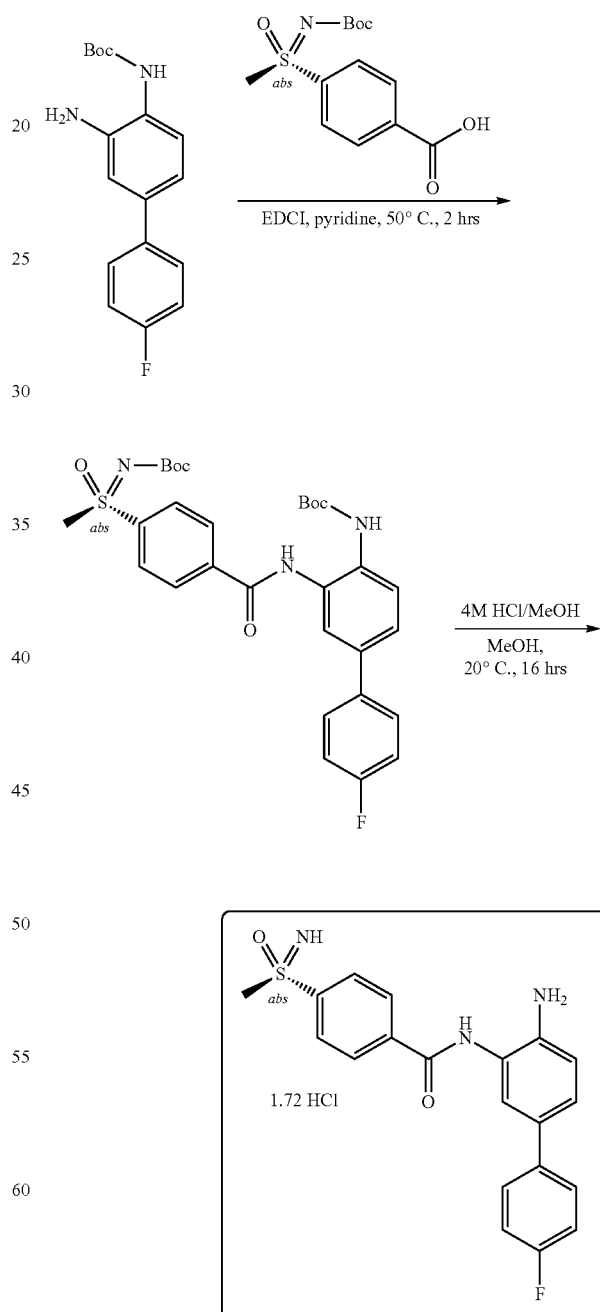

Step 1: Synthesis of (S)-tert-butyl N-[[4-[[2-(tert-butoxycarbonylamino)-5-(4-fluorophenyl)phenyl]carbamoyl]phenyl]-methyl-oxo-sulfanylidene]carbamate To a solution of EDCI (about 9.3 g, 48.5 mmol) in pyridine (about 100 mL) was added a solution of (S)-4-(N-tert-butoxycarbonyl-S-methyl-sulfonimidoyl)benzoic acid (about 9 g, 30.1 mmol) and tert-butyl N-[2-amino-4-(4-fluorophenyl)phenyl]carbamate (about 10 g, 33.1 mmol). The mixture was stirred at about 50° C. for about 2 hours. The mixture was concentrated under reduced pressure. The residue was triturated in a solution (about 50 mL, contained PE 45 mL, EtOAc 5 mL) for some times till almost no solid separated out. Then the mother liquid was purified by flash chromatography (ISCO®; about 80 g AgelaFlash® Silica Flash Column, petroleum ether/EtOAc with EtOAc from 0~58%, flow rate=80 mL/min, 254 nm) to afford (S)-tert-butyl N-[[4-[[2-(tert-butoxycarbonylamino)-5-(4-fluorophenyl)phenyl]carbamoyl]phenyl]-methyl-oxo-sulfanylidene]carbamate (about 15.5 g). $^1$H NMR (400 MHz, DMSO-d$_6$) δ ppm 10.14 (s, 1H), 8.82 (brs, 1H), 8.22 (d, J=8.3 Hz, 2H), 8.04-8.16 (m, 2H), 7.81 (s, 1H), 7.63-7.76 (m, 3H), 7.53 (dd, J=8.5, 1.9 Hz, 1H), 7.29 (t, J=8.8 Hz, 2H), 3.45 (s, 3H), 1.45 (s, 9H), 1.26 (s, 9H); $^{19}$F NMR (377 MHz, DMSO-d$_6$) δ ppm −115.580; LCMS (ESI) [M+H]$^+$ m/z: calcd 584.2, found 428.0 (Boc and t-Bu cleaved mass); HPLC: 99.500%@220 nm, 99.510%@254 nm.

Step 2: Synthesis of (S)—N-[2-amino-5-(4-fluorophenyl)phenyl]-4-(methylsulfonimidoyl)benzamide To a solution of (S)-tert-butyl N-[[4-[[2-(tert-butoxycarbonylamino)-5-(4-fluorophenyl)phenyl]carbamoyl]phenyl]-methyl-oxo-sulfanylidene]carbamate (about 14.5 g, 24.8 mmol) in MeOH (about 50 mL) was added 4M HCl/MeOH (about 50 mL, 0.200 mol). The mixture was stirred at about 20° C. for about 16 hours. The mixture was concentrated under reduced pressure. The residue was triturated with solution (about 100 mL, contained MeOH about 60 mL, EtOAc about 20 mL, DCM about 20 mL) for some times till almost no solid separated out to afford (S)—N-[2-amino-5-(4-fluorophenyl)phenyl]-4-(methylsulfonimidoyl)benzamide (about 6.1 g, 1.72 HCl). $^1$H NMR (400 MHz, DMSO-d$_6$) δ ppm 10.91 (s, 1H), 8.45 (d, J=8.5 Hz, 2H), 8.29 (d, J=8.5 Hz, 2H), 7.84 (d, J=1.8 Hz, 1H), 7.71 (dd, J=8.8, 5.3 Hz, 2H), 7.61 (dd, J=8.5, 2.0 Hz, 1H), 7.46 (d, J=8.3 Hz, 1H), 7.32 (t, J=8.9 Hz, 2H), 4.08 (s, 2H), 3.91 (s, 3H); $^{19}$F NMR (376 MHz, DMSO-d$_6$) δ ppm −115.160; LCMS (ESI) [M+H]$^+$ m/z: calcd 384.1, found 384.1; HPLC: 92.36%@220 nm, 90.88%@254 nm; 99.8% ee. The mother liquid was concentrated under reduced pressure to afford N-[2-amino-5-(4-fluorophenyl)phenyl]-4-(methylsulfonimidoyl)benzamide (about 3.4 g).

Example 51. Synthesis of rac-N-[2-amino-5-(5-fluoro-2-thienyl)phenyl]-4-(cyclopropylsulfonimidoyl)benzamide (Compound 127), rel-(S)—N-[2-amino-5-(5-fluoro-2-thienyl)phenyl]-4-(cyclopropylsulfonimidoyl)benzamide (Compound 133) and rel-(R)—N-[2-amino-5-(5-fluoro-2-thienyl)phenyl]-4-(cyclopropylsulfonimidoyl)benzamide (Compound 131)

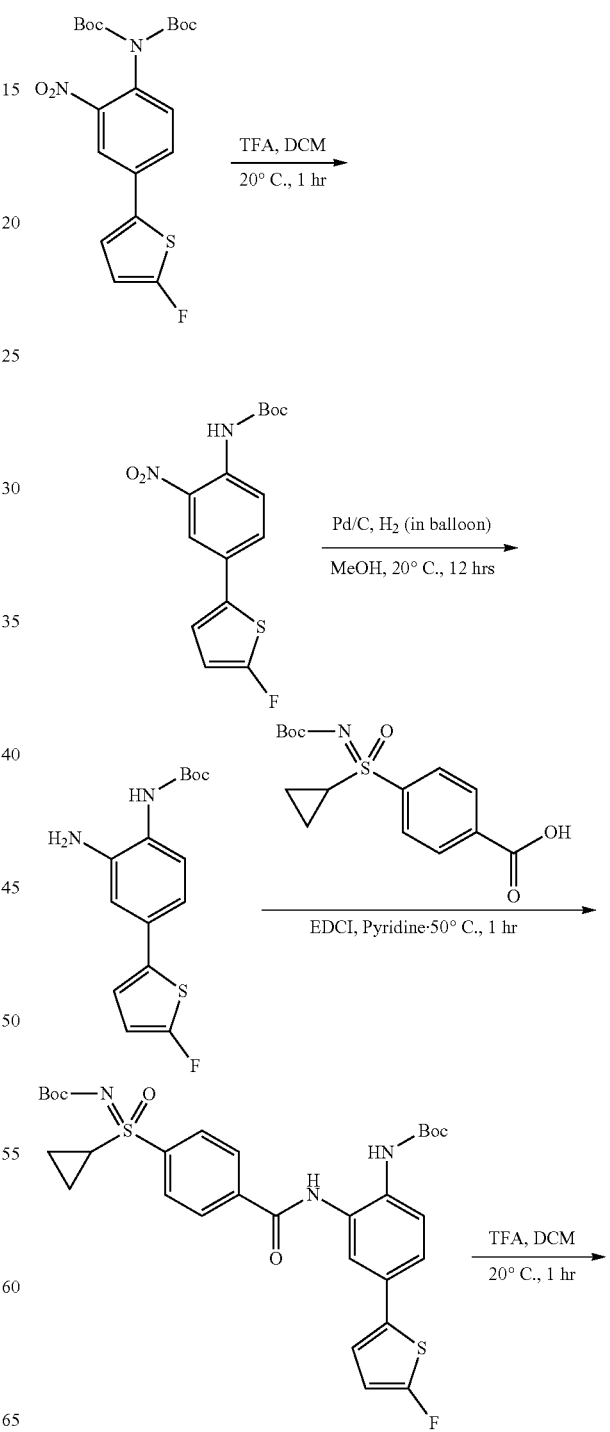

-continued

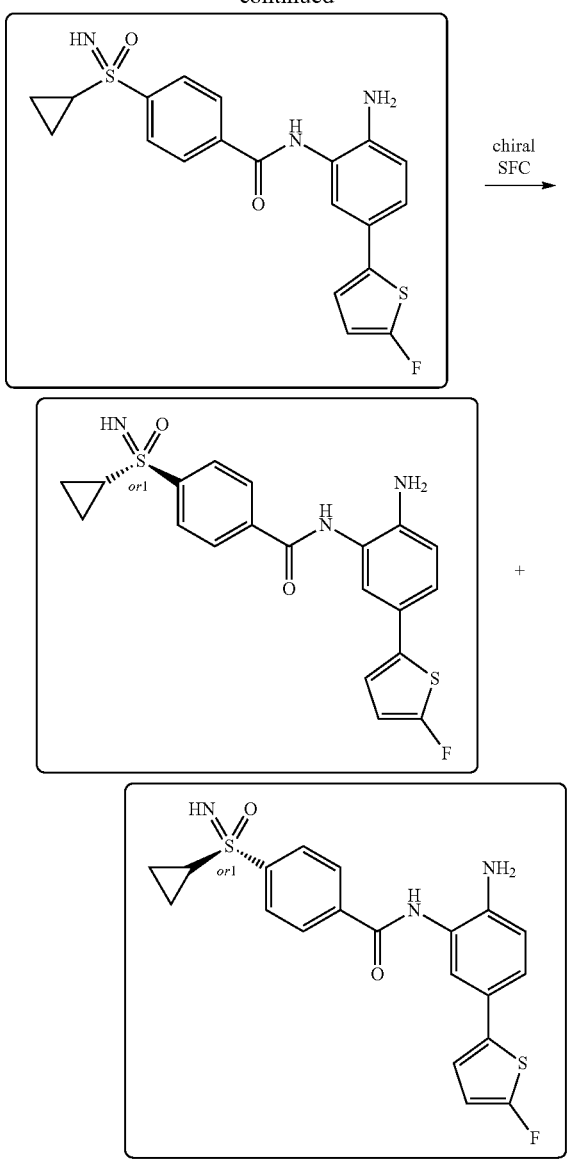

Step 1: Synthesis of tert-butyl N-[4-(5-fluoro-2-thienyl)-2-nitro-phenyl]carbamate To a mixture of tert-butyl N-tert-butoxycarbonyl-N-[4-(5-fluoro-2-thienyl)-2-nitro-phenyl]carbamate (about 320 mg, 0.730 mmol) in DCM (about 3 mL) was added TFA (about 0.9 mL, 1.17 mmol) at about 20° C. The mixture was stirred at about 20° C. for about 1 hour. The mixture was quenched by addition of saturated NaHCO₃ aqueous solution (about 20 mL), and extracted with DCM (about 15 mL*3). The combined organic layers were dried over anhydrous $Na_2SO_4$, filtered, and concentrated under reduced pressure to give tert-butyl N-[4-(5-fluoro-2-thienyl)-2-nitro-phenyl]carbamate (about 200 mg). $^1$H NMR (400 MHz, chloroform-d) δ ppm 9.97 (s, 1H), 8.91 (d, J=8.9 Hz, 1H), 8.60 (s, 1H), 8.02 (d, J=8.9 Hz, 1H), 7.27 (s, 1H), 6.82 (s, 1H), 1.88 (s, 9H); $^{19}$F NMR (376 MHz, chloroform-d) δ ppm −128.442.

Step 2: Synthesis of tert-butyl N-[2-amino-4-(5-fluoro-2-thienyl)phenyl]carbamate To a solution of tert-butyl N-[4-(5-fluoro-2-thienyl)-2-nitro-phenyl]carbamate (200 mg, 0.591 mmol) in MeOH (about 10 mL) was added Pd—C(about 50 mg, 10% of Pd with 50% of water, wt %) under N₂ atmosphere. The suspension was degassed and purged with hydrogen for about 3 times. The mixture was stirred under hydrogen (in balloon) at about 20° C. for about 12 hours. The resulting mixture was filtered. The filtrate was concentrated under reduced pressure to give tert-butyl N-[2-amino-4-(5-fluoro-2-thienyl)phenyl]carbamate (about 180 mg).

Step 3: Synthesis of tert-butyl N-[[4-[[2-(tert-butoxycarbonylamino)-5-(5-fluoro-2-thienyl)phenyl]carbamoyl]phenyl]-cyclopropyl-oxo-sulfanylidene]carbamate A mixture of 4-(N-tert-butoxycarbonyl-S-cyclopropyl-sulfonimidoyl)benzoic acid (about 190 mg, 0.584 mmol), tert-butyl N-[2-amino-4-(5-fluoro-2-thienyl)phenyl]carbamate (180 mg, 0.584 mmol) and EDCI (about 135 mg, 0.870 mmol) in pyridine (about 5 mL) was stirred at 50° C. for 1 hour. The mixture was concentrated under reduced pressure to give tert-butyl N-[[4-[[2-(tert-butoxycarbonylamino)-5-(5-fluoro-2-thienyl)phenyl]carbamoyl]phenyl]-cyclopropyl-oxo-sulfanylidene]carbamate (about 230 mg).

Step 4: Synthesis of N-[2-amino-5-(5-fluoro-2-thienyl)phenyl]-4-(cyclopropylsulfonimidoyl)benzamide To a mixture of tert-butyl N-[[4-[[2-(tert-butoxycarbonylamino)-5-(5-fluoro-2-thienyl)phenyl]carbamoyl]phenyl]-cyclopropyl-oxo-sulfanylidene]carbamate (about 230 mg, 0.374 mmol) in DCM (about 10 mL) was added TFA (about 0.580 mL, 7.53 mmol) at 20° C. The mixture was stirred at about 20° C. for about 1 hour. The residue was purified by preparative HPLC (Instrument: Gilson GX-281 Liquid Handler, Gilson 322 Pump, Gilson 156 UV Detector; Column: Phenomenex C18 80×40 mm×3 μm; Mobile phase A: H₂O with 0.05% NH₃—H₂O (v %); Mobile phase B: MeCN; Gradient: B from 40% to 70% in 7.8 mins, hold 100% B for 2 mins; Flow Rate: 30 mL/min; Column Temperature: 30° C.; Wavelength: 220 nm, 254 nm) to afford N-[2-amino-5-(5-fluoro-2-thienyl)phenyl]-4-(cyclopropylsulfonimidoyl)benzamide (about 97.8 mg). $^1$H NMR (400 MHz, DMSO-d₆) δ ppm 9.91 (s, 1H), 8.17 (d, J=8.4 Hz, 2H), 8.02 (d, J=8.4 Hz, 2H), 7.39 (d, J=1.9 Hz, 1H), 7.23 (dd, J=8.4, 2.1 Hz, 1H), 6.92 (t, J=3.8 Hz, 1H), 6.81 (d, J=8.3 Hz, 1H), 6.67 (dd, J=3.9, 2.2 Hz, 1H), 5.12 (s, 2H), 2.69-2.78 (m, 1H), 1.10-1.18 (m, 1H), 0.98-1.05 (m, 1H), 0.87-0.97 (m, 2H); $^{19}$F NMR (376 MHz, DMSO-d₆) δ ppm −133.740; LCMS (ESI) [M+H]⁺ m/z: calcd 416.1, found 415.9; HPLC: 97.68%@220 nm, 99.16%@254 nm.

Step 5: Synthesis of N-[2-amino-5-(5-fluoro-2-thienyl)phenyl]-4-(cyclopropylsulfonimidoyl)benzamide and N-[2-amino-5-(5-fluoro-2-thienyl)phenyl]-4-(cyclopropylsulfonimidoyl)benzamide N-[2-amino-5-(5-fluoro-2-thienyl)phenyl]-4-(cyclopropylsulfonimidoyl)benzamide (about 85 mg, 0.205 mmol) was purified by chiral SFC (Instrument: Berger, multigr AM-II; Column: Daicel chiralcel OJ (250 mm*30 mm*10 μm); Mobile phase: supercritical CO₂/MeOH (0.1% NH₃⁻ rel-(S)—N-[2-amino-5-(5-fluoro-2-thienyl)phenyl]-4-(cyclopropylsulfonimidoyl)benzamide (about 32.5 mg, single enantiomer, Peak 1, Retention time: 4.492 min). $^1$H NMR (400 MHz, DMSO-$d_6$) δ ppm 9.89 (s, 1H), 8.16 (d, J=8.5 Hz, 2H), 8.01 (d, J=8.3 Hz, 2H), 7.39 (d, J=1.8 Hz, 1H), 7.23 (dd, J=8.4, 2.1 Hz, 1H), 6.91 (t, J=3.8 Hz, 1H), 6.80 (d, J=8.5 Hz, 1H), 6.67 (dd, J=4.0, 2.3 Hz, 1H), 5.25 (s, 2H), 4.39 (s, 1H), 2.68-2.76 (m, 1H), 1.14 (t, J=10.5, 3.8 Hz, 1H), 0.97-1.03 (m, 1H), 0.87-0.95 (m, 2H); $^{19}$F NMR (376 MHz, DMSO-$d_6$) δ ppm −133.766; LCMS (ESI) [M+H]$^+$ m/z: calcd 416.1, found 415.9; HPLC: 98.80%@220 nm, 98.07%@254 nm; 95.0% ee.

rel-(R)—N-[2-amino-5-(5-fluoro-2-thienyl)phenyl]-4-(cyclopropylsulfonimidoyl)benzamide (about 33.1 mg, single enantiomer, Peak 2, Retention time: 6.836 min); $^1$H NMR (400 MHz, DMSO-$d_6$) δ ppm 9.89 (s, 1H), 8.16 (d, J=8.3 Hz, 2H), 8.01 (d, J=8.3 Hz, 2H), 7.38 (s, 1H), 7.23 (dd, J=8.3, 2.0 Hz, 1H), 6.91 (t, J=3.8 Hz, 1H), 6.80 (d, J=8.3 Hz, 1H), 6.67 (dd, J=3.8, 2.3 Hz, 1H), 5.26 (s, 2H), 4.40 (s, 1H), 2.67-2.76 (m, 1H), 1.11-1.16 (m, 1H), 0.99 (d, J=6.0 Hz, 1H), 0.88-0.95 (m, 2H); $^{19}$F NMR (376 MHz, DMSO-$d_6$) δ ppm −133.772; LCMS (ESI) [M+H]$^+$ m/z: calcd 416.1, found 416.0; HPLC: 99.66%@220 nm, 99.45%@254 nm; 98.4% ee.

Example 52. Synthesis of (R)—N-[2-amino-5-(4-fluorophenyl)phenyl]-4-(methylsulfonimidoyl)benzamide (Compound 132)

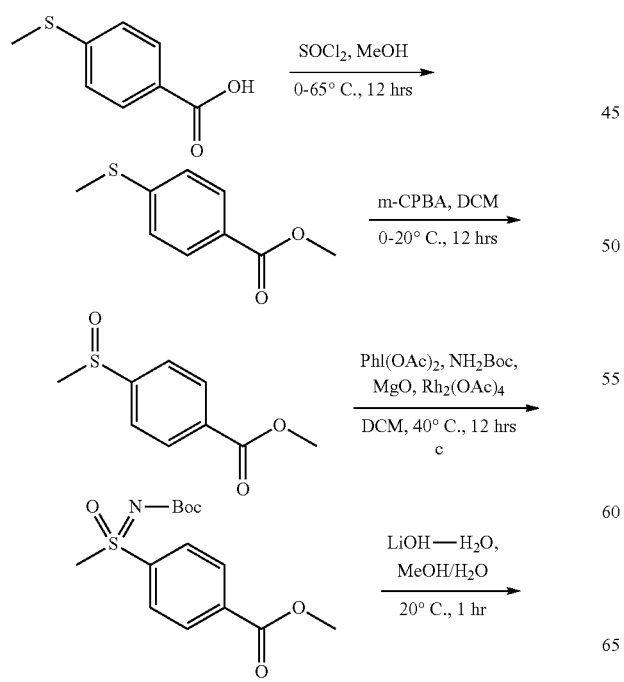

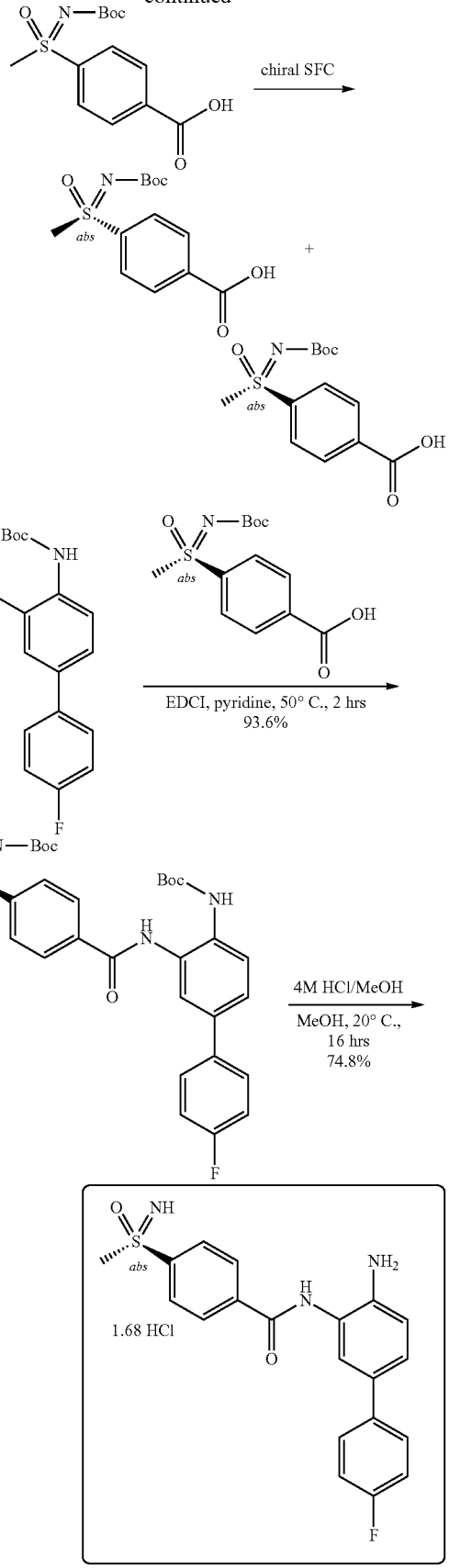

Step 1: Synthesis of methyl 4-methylsulfanylbenzoate

To a solution of 4-methylsulfanylbenzoic acid (about 50 g, 0.297 mol) in MeOH (about 200 mL) was added $SOCl_2$ (6 about 5 mL, 0.896 mol) at about 0° C. The mixture was stirred at about 65° C. for about 12 hours. The mixture was concentrated under reduced pressure. The residue was diluted with EtOAc (about 500 mL). The mixture was washed with saturated $NaHCO_3$ aqueous solution (about 500 mL*2), dried over anhydrous $Na_2SO_4$, filtered and concentrated under reduced pressure to give methyl 4-methylsulfanylbenzoate (about 54 g), which was directly used without further purification. $^1H$ NMR (400 MHz, methanol-$d_4$) δ ppm 7.87-7.93 (m, 2H), 7.27-7.32 (m, 2H), 3.86-3.89 (m, 3H), 2.49-2.53 (m, 3H).

Step 2: Synthesis of methyl 4-methylsulfinylbenzoate

To a solution of methyl 4-methylsulfanylbenzoate (about 54 g, 0.296 mol) in DCM (about 400 mL) was added m-CPBA (about 66 g, 0.325 mol, 85% purity) at about 0° C. The mixture was stirred at about 20° C. for about 12 hours. The mixture was quenched by addition of saturated $Na_2SO_3$ aqueous solution (about 150 mL), saturated $Na_2CO_3$ aqueous solution (about 150 mL) and extracted with DCM (about 150 mL*2). The combined organic layer was dried over anhydrous $Na_2SO_4$, filtered and concentrated under reduced pressure to give methyl 4-methylsulfinylbenzoate (about 58 g), which was directly used without further purification. $^1H$ NMR (400 MHz, methanol-$d_4$) δ ppm 8.17-8.23 (m, 2H), 7.78-7.83 (m, 2H), 3.94 (s, 3H), 2.84 (s, 3H); LCMS (ESI) $[M+H]^+$ m/z: calcd 199.0; found 199.0.

Step 3: Synthesis of methyl 4-(N-tert-butoxycarbonyl-S-methyl-sulfonimidoyl)benzoate To a solution of methyl 4-methylsulfinylbenzoate (about 24 g, 0.121 mol), $NH_2Boc$ (about 28.4 g, 0.242 mol), $PhI(OAc)_2$ (about 58.5 g, 0.182 mmol) and MgO (about 25 g, 0.605 mol) in DCM (about 500 mL) was added $Rh_2(OAc)_4$ (about 2.41 g, 5.45 mmol). The reaction mixture was stirred at about 40° C. for about 12 hours. The mixture was combined with another batch. The mixture was filtered and concentrated under reduced pressure. The residue was triturated with EtOAc (about 100 mL). The mixture was filtered. The filter cake was concentrated under reduced pressure to afford methyl 4-(N-tert-butoxycarbonyl-S-methyl-sulfonimidoyl)benzoate (about 69 g). The filtrate was concentrated under reduced pressure to give methyl 4-(N-tert-butoxycarbonyl-S-methyl-sulfonimidoyl)benzoate (about 60 g). $^1H$ NMR (400 MHz, DMSO-$d_6$) δ ppm 8.19-8.23 (m, 2H), 8.06-8.10 (m, 2H), 3.91 (s, 3H), 3.43-3.46 (m, 3H), 1.20-1.24 (m, 9H); LCMS (ESI) $[M+H]^+$ m/z: calcd 314.1, found 258.0 (t-Bu cleaved mass).

Step 4: Synthesis of 4-(N-tert-butoxycarbonyl-S-methyl-sulfonimidoyl)benzoic acid To a solution of methyl 4-(N-tert-butoxycarbonyl-S-methyl-sulfonimidoyl)benzoate (about 34 g, 0.109 mol) in MeOH (260 mL) was added a solution of LiOH—$H_2O$ (about 45.9 g, 1.09 mol) in $H_2O$ (about 90 mL). The mixture was stirred at about 20° C. for about 1 hour. The mixture was combined with another batch. The mixture was concentrated under reduced pressure to remove the organic solvent. The resulting mixture was quenched by addition of water (about 100 mL) and extracted with EtOAc (about 100 mL). The water layer was adjusted to about pH=4 with 2N HCl aqueous solution. The mixture was filtered. The filter cake was dried under reduced pressure to give 4-(N-tert-butoxycarbonyl-S-methyl-sulfonimidoyl)benzoic acid (about 39 g), which was directly used without further purification. $^1H$ NMR (400 MHz, DMSO-$d_6$) δ ppm 8.18 (d, J=8.3 Hz, 2H), 8.05 (d, J=8.3 Hz, 2H), 3.43 (s, 3H), 1.22 (s, 9H); LCMS (ESI) $[M+H]^+$ m/z: calcd 300.1; found 244.0 (t-Bu cleaved mass).

Step 5: Synthesis of (R)-4-(N-tert-butoxycarbonyl-S-methyl-sulfonimidoyl)benzoic acid and (S)-4-(N-tert-butoxycarbonyl-S-methyl-sulfonimidoyl)benzoic acid 4-(N-tert-butoxycarbonyl-S-methyl-sulfonimidoyl)benzoic acid (about 39 g, 0.130 mol) was purified by chiral SFC (Instrument: Thar SFC Prep 200; Column: Daicel chiralpak IG (250 mm*50 mm, 10 um); Mobile phase: supercritical $CO_2$/Neu-EtOH=75/25; Flow Rate: 200 mL/min; Column Temperature: about 38° C.; Nozzle Pressure: 100 bar; Nozzle Temperature: about 60° C.; Evaporator Temperature: 20° C.; Trimmer Temperature: about 25° C.; Wavelength: 220 nm. The fraction was concentrated under reduced pressure and then lyophilized for overnight to give the products.

(S)-4-(N-tert-butoxycarbonyl-S-methyl-sulfonimidoyl) benzoic acid (about 16 g, single known enantiomer, Peak 1, Retention time: 2.740 min). $^1H$ NMR (400 MHz, DMSO-$d_6$) δ ppm 8.18 (d, J=8.5 Hz, 2H), 8.04 (d, J=8.5 Hz, 2H), 3.40-3.42 (m, 3H), 1.22 (s, 9H); LCMS (ESI) $[M+H]^+$ m/z: calcd 300.1, found 300.0; 99.7% ee.

(R)-4-(N-tert-butoxycarbonyl-S-methyl-sulfonimidoyl) benzoic acid (about 14.3 g, single known enantiomer, Peak 2, Retention time: 3.212 min). $^1H$ NMR (400 MHz, DMSO-$d_6$) δ ppm 8.18 (d, J=8.5 Hz, 2H), 8.05 (d, J=8.5 Hz, 2H), 3.43 (s, 3H), 1.20-1.25 (m, 9H); LCMS (ESI) $[M+H]^+$ m/z: calcd 300.1, found 300.0; 95.0% ee.

Step 6: Synthesis of (R)-tert-butyl N-[[4-[[2-(tert-butoxycarbonylamino)-5-(4-fluorophenyl)phenyl]carbamoyl]phenyl]-methyl-oxo-sulfanylidene]carbamate To a solution of EDCI (about 8.2 g, 42.8 mmol) in pyridine (about 100 mL) was added a solution of (R)-4-(N-tert-butoxycarbonyl-S-methyl-sulfonimidoyl)benzoic acid (about 8 g, 26.7 mmol) and tert-butyl N-[2-amino-4-(4-fluorophenyl)phenyl]carbamate (about 9 g, 29.8 mmol). The mixture was stirred at about 50° C. for about 2 hours. The mixture was concentrated under reduced pressure. The residue was triturated in a solution (about 100 mL, contained petroleum ether about 50 mL, EtOAc about 50 mL). The mixture was filtered. The filtered cake was concentrated under reduced pressure to afford (R)-tert-butyl N-[[4-[[2-(tert-butoxycarbonylamino)-5-(4-fluorophenyl)phenyl]carbamoyl]phenyl]-methyl-oxo-sulfanylidene]carbamate (about 14.6 g). $^1H$ NMR (400 MHz, DMSO-$d_6$) δ ppm 10.25 (s, 1H), 8.86 (s, 1H), 8.26 (m, J=8.4 Hz, 2H), 8.10 (d, J 8.5 Hz, 2H), 7.82 (d, J=1.5 Hz, 1H), 7.66-7.74 (m, 3H), 7.53 (dd, J=8.5, 2.1 Hz, 1H), 7.29 (t, J=8.9 Hz, 2H), 2.72 (s, 3H), 1.45 (s, 9H), 1.27 (s, 9H); $^{19}F$ NMR (377 MHz, DMSO-$d_6$) δ ppm −115.603; LCMS (ESI) $[M+H]^+$ m/z: calcd 584.2, found 484.1 (Boc cleaved mass); HPLC: 98.350%@220 nm, 99.180%@254 nm.

Step 7: Synthesis of (R)—N-[2-amino-5-(4-fluoro-phenyl)phenyl]-4-(methylsulfonimidoyl)benzamide To a solution of (R)-tert-butyl N-[[4-[[2-(tert-butoxycarbonylamino)-5-(4-fluorophenyl)phenyl]carbamoyl]phenyl]-methyl-oxo-sulfanylidene]carbamate (about 14.6 g, 25.0 mmol) in MeOH (about 70 mL) was added 4M HCl/MeOH (about 70 mL, 0.280 mol). The mixture was stirred at about 20° C. for about 16 hours. The mixture was concentrated under reduced pressure. The residue was triturated in a solution (about 100 mL, contained MeOH about 60 mL, EtOAc about 20 mL, DCM 20 mL). The mixture was filtered. The filtered cake was concentrated under reduced pressure to afford (R)—N-[2-amino-5-(4-fluorophenyl)phenyl]-4-(methylsulfonimidoyl)benzamide (about 7.17 g, 1.68 HCl). $^1$H NMR (400 MHz, DMSO-$d_6$) δ ppm 10.89 (s, 1H), 8.45 (d, J=8.5 Hz, 2H), 8.28 (d, J=8.6 Hz, 2H), 7.83 (d, J=1.5 Hz, 1H), 7.70 (dd, J=8.7, 5.4 Hz, 2H), 7.60 (dd, J=8.4, 1.9 Hz, 1H), 7.45 (d, J=8.3 Hz, 1H), 7.31 (t, J=8.9 Hz, 2H), 3.89 (s, 3H); $^{19}$F NMR (377 MHz, DMSO-$d_6$) δ ppm −115.228; LCMS (ESI) [M+H]$^+$ m/z: calcd 384.1, found 384.1; HPLC: 89.40%@220 nm; 89.68%@254 nm; 97.3% ee.

Example 53. Synthesis of N-[5-(4-fluorophenyl)-2-hydroxy-phenyl]-4-(methylsulfonimidoyl)benzamide (Compound 130)

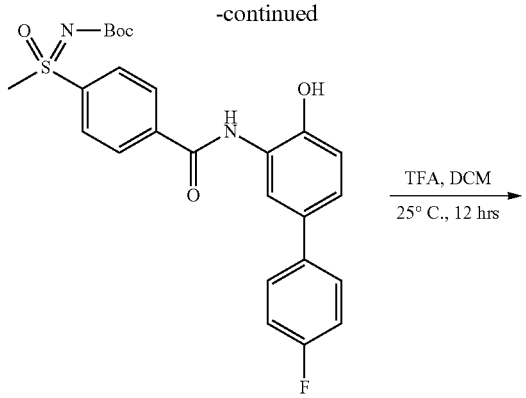

Step 1: Synthesis of 2-amino-4-(4-fluorophenyl)phenol

A mixture of 2-amino-4-bromo-phenol (about 1 g, 5.32 mmol), (4-fluorophenyl)boronic acid (about 1.1 g, 7.86 mmol), palladium;triphenylphosphane (about 1.23 g, 1.06 mmol) and tripotassium;carbonate (about 2.21 g, 16.0 mmol) in H$_2$O (about 3 mL) and toluene (about 9 mL) was degassed and purged with N$_2$ for about 3 times. Then the mixture was stirred at about 100° C. for about 12 hours under N$_2$ atmosphere. The reaction mixture was diluted with H$_2$O (about 30 mL) and extracted with EtOAc (about 40 mL*2). The combined organic layers were washed with brine (about 40 mL), dried over anhydrous Na$_2$SO$_4$, filtered and concentrated under reduced pressure. The residue was purified by flash chromatography (ISCO®; about 20 g SepaFlash® Silica Flash Column, Petroleum Ether/EtOAc with EtOAc from 0~60%, 80 mL/min, 254 nm) to afford 2-amino-4-(4-fluorophenyl)phenol (about 300 mg). $^1$H NMR (400 MHz, DMSO-$d_6$) δ ppm 7.48-7.52 (m, 2H), 7.16-7.22 (m, 2H), 6.86 (d, J=2.0 Hz, 1H), 6.69 (s, 1H), 6.67 (d, J=2.0 Hz, 1H), 6.50-6.59 (m, 1H), 4.59 (brs, 2H); LCMS (ESI) [M+H]$^+$ m/z: calcd 204.1, found 203.8.

Step 2: Synthesis of tert-butyl N-[[4-[[5-(4-fluorophenyl)-2-hydroxy-phenyl]carbamoyl]phenyl]-methyl-oxo-sulfanylidene]carbamate To a solution of 2-amino-4-(4-fluorophenyl)phenol (about 163 mg, 0.802 mmol) in pyridine (about 3 mL) were added 4-(N-tert-butoxycarbonyl-S-methyl-sulfonimidoyl)benzoic acid (about 160 mg, 0.534 mmol) and 3-(ethyliminomethyleneamino)-N,N-dimethyl-propan-1-amine (about 124 mg, 0.799 mmol). The mixture was stirred at about 50° C. for about 1 hour. The reaction mixture was diluted with H$_2$O (about 30 mL) and extracted with EtOAc (about 40 mL*2). The combined organic layers were washed with brine (about 40 mL), dried over anhydrous Na$_2$SO$_4$, filtered and concentrated under reduced pressure. The residue was purified by flash chromatography (ISCO®; about 12 g SepaFlash® Silica Flash Column, Petroleum Ether/EtOAc with EtOAc from 0~100%, 40 mL/min, 254 nm) to afford tert-butyl N-[[4-[[5-(4-fluorophenyl)-2-hydroxy-phenyl]carbamoyl]phenyl]-methyl-oxo-sulfanylidene]carbamate (about 170 mg). LCMS (ESI) [M+H]$^+$ m/z: calcd 485.1, found 385.0 (Boc cleaved mass).

Step 3: Synthesis of N-[5-(4-fluorophenyl)-2-hydroxy-phenyl]-4-(methylsulfonimidoyl)benzamide To a solution of tert-butyl N-[[4-[[5-(4-fluorophenyl)-2-hydroxy-phenyl]carbamoyl]phenyl]-methyl-oxo-sulfanylidene]carbamate (about 110 mg, 0.227 mmol) in DCM (about 10 mL) was added TFA (about 0.18 mL, 2.27 mmol). The mixture was stirred at about 25° C. for about 12 hours. The reaction mixture was diluted with DCM (about 30 mL) and adjusted to about pH=8 with saturated Na$_2$CO$_3$ aqueous solution. The resultant mixture was dried over Na$_2$SO$_4$ and filtered. The filtrate was concentrated under reduced pressure. The residue was purified by flash chromatography (ISCO®; about 4 g SepaFlash® Silica Flash Column, Petroleum Ether/EtOAc with EtOAc from 0~60%, 40 mL/min, 254 nm). The residue was further purified by preparative HPLC (Instrument: Gilson GX-281 Liquid Handler, Gilson 322 Pump, Gilson 156 UV Detector; Column: Waters Xbridge 150*25 mm*5 μm; Mobile phase A: H$_2$O with 0.05% FA (v %); B: ACN; Gradient: B from 30% to 60% in 9.5 min, hold 100% B for 2 min; Flow Rate: 25 mL/min; Column Temperature: 30° C.; Wavelength: 220 nm, 254 nm) to afford N-[5-(4-fluorophenyl)-2-hydroxy-phenyl]-4-(methylsulfonimidoyl)benzamide (about 11.7 mg). $^1$H NMR (400 MHz, DMSO) δ ppm 9.98 (s, 1H), 9.80 (s, 1H), 8.17 (d, J=8.4 Hz, 2H), 8.05-8.09 (m, 2H), 7.95 (d, J=2.0 Hz, 1H), 7.62 (dd, J=8.8, 5.6 Hz, 2H), 7.36 (dd, J=8.4, 2.4 Hz, 1H), 7.26 (t, J=8.8 Hz, 2H), 7.01 (d, J=8.8 Hz, 1H), 3.13 (s, 3H); $^{19}$F NMR (377 MHz, DMSO-d$_6$) δ ppm −116.643; LCMS (ESI) [M+H]$^+$ m/z: calcd 385.1, found 385.0. HPLC: 97.89%@220 nm, 98.17%@254 nm.

Example 54. Synthesis of N-[2-amino-5-(4-fluorophenyl)phenyl]-6-(methylsulfonimidoyl)pyridine-3-carboxamide (Compound 129)

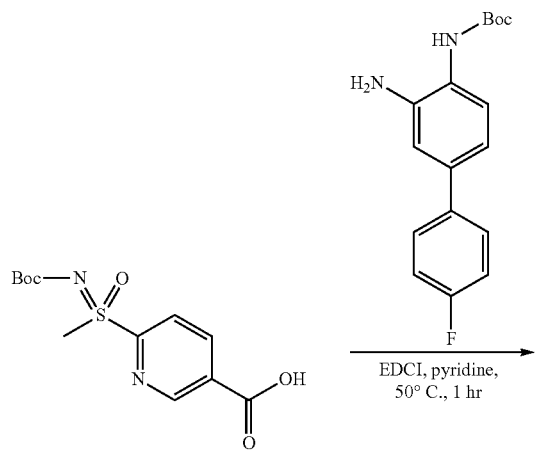
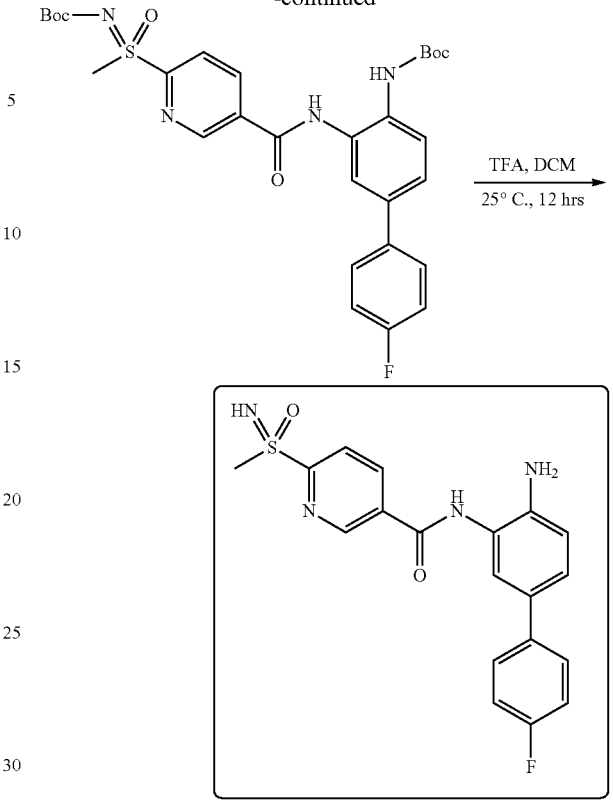

Step 1: Synthesis of tert-butyl N-[[5-[[2-(tert-butoxycarbonylamino)-5-(4-fluorophenyl)phenyl]carbamoyl]-2-pyridyl]-methyl-oxo-sulfanylidene]carbamate To a solution of 6-(N-tert-butoxycarbonyl-S-methylsulfonimidoyl)pyridine-3-carboxylic acid (about 100 mg, 0.332 mmol) in pyridine (about 3 mL) was added EDCI (about 95 mg, 0.495 mmol) and 6-(N-tert-butoxycarbonyl-S-methyl-sulfonimidoyl)pyridine-3-carboxylic acid (about 100 mg, 0.332 mmol). The mixture was stirred at about 50° C. for about 1 hour. The reaction mixture was concentrated under reduced pressure. The residue was purified by preparative TLC (silica, petroleum ether/EtOAc=3/1; 254 nm) to give tert-butyl N-[[5-[[2-(tert-butoxycarbonylamino)-5-(4-fluorophenyl)phenyl]carbamoyl]-2-pyridyl]-methyl-oxo-sulfanylidene]carbamate (about 150 mg). LCMS (ESI) [M+H]$^+$ m/z: calcd 585.2, found 485.1. (Boc cleaved mass).

Step 2: Synthesis of N-[2-amino-5-(4-fluorophenyl)phenyl]-6-(methylsulfonimidoyl)pyridine-3-carboxamide To a solution of tert-butyl N-[[5-[[2-(tert-butoxycarbonylamino)-5-(4-fluorophenyl)phenyl]carbamoyl]-2-pyridyl]-methyl-oxo-sulfanylidene]carbamate (about 50 mg, 0.0850 mmol) in DCM (about 2 mL) was added TFA (about 0.06 mL, 0.843 mmol). The mixture was stirred at about 20° C. for about 12 hours. The reaction mixture was adjusted to about pH=8 with saturated NaHCO$_3$ aqueous solution and extracted with DCM (about 15 mL*3). The combined organic layers were dried over Na$_2$SO$_4$ and filtered. The filtrate was concentrated under reduced pressure.

The residue was purified by preparative HPLC (Instrument: Gilson GX-281 Liquid Handler, Gilson 322 Pump, Gilson 156 UV Detector; Column: Phenomenex C18 80×40 mm×3 um; Mobile phase A: water with 10 mmol NH$_4$HCO$_3$ (v %); Mobile phase B: ACN; Gradient: B from 28% to 58% in 9.5 min, hold 100% B for 2 min; Flow Rate: 30 mL/min; Column Temperature: 30° C.; Wavelength: 220 nm, 254 nm) to give N-[2-amino-5-(4-fluorophenyl)phenyl]-6-(methyl-sulfonimidoyl)pyridine-3-carboxamide (about 12.9 mg). $^1$H NMR (400 MHz, chloroform-d) δ ppm 9.24 (s, 1H), 8.49 (d, J=8.0 Hz, 1H), 8.34 (s, 1H), 8.24 (d, J=8.4 Hz, 1H), 7.66 (s, 1H), 7.50 (s, 2H), 7.34 (d, J=8.0 Hz, 1H), 7.10 (t, J=8.8 Hz, 2H), 6.97 (d, J=8.4 Hz, 1H), 3.32 (s, 3H); $^{19}$F NMR (377 MHz, chloroform-d) δ ppm −116.158; LCMS [M+H]$^+$ m/z: calcd 385.1; found 384.9; HPLC: 99.63%@220 nm; 99.64%@254 nm.

Example 55. Synthesis of N-[2-amino-5-(2-thienyl)phenyl]-4-[(methylsulfonimidoyl)methyl]benzamide (Compound 128)

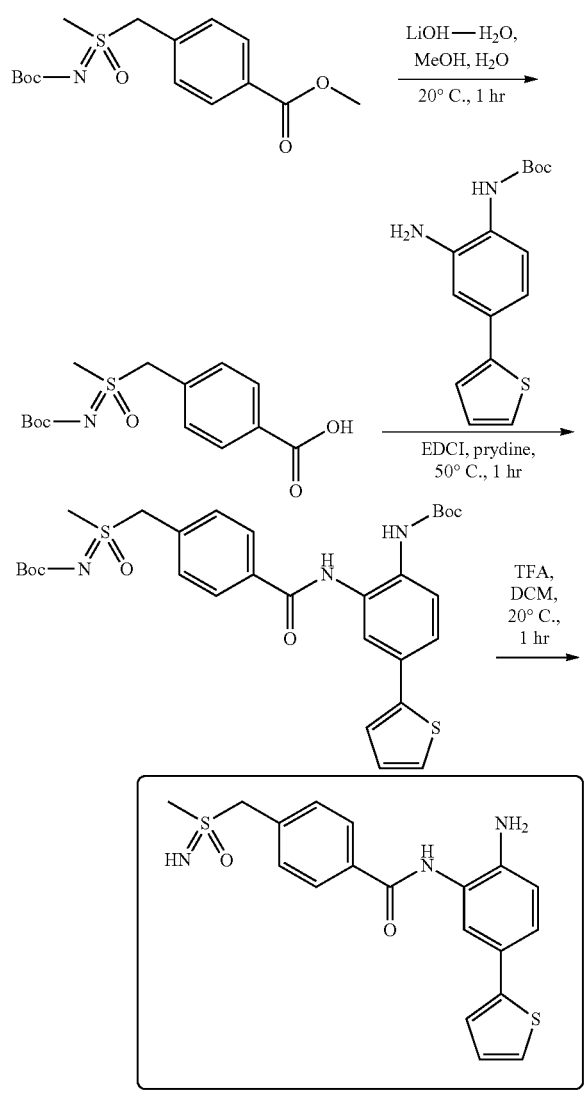

Step 1: Synthesis of 4-[(N-tert-butoxycarbonyl-S-methyl-sulfonimidoyl)methyl]benzoic acid A mixture of methyl 4-[(N-tert-butoxycarbonyl-S-methyl-sulfonimidoyl)methyl]benzoate (about 200 mg, 0.611 mmol) and LiOH—H$_2$O (about 175 mg, 3.07 mmol) in MeOH (about 2 mL) and H$_2$O (about 2 mL) was stirred at about 20° C. for about 1 hour. The mixture was concentrated under reduced pressure to remove solvent. Then 1N HCl aqueous solution was added to adjust pH to about 6. The mixture was extracted with EtOAc (about 10 mL*3), combined organic layer was dried over anhydrous Na$_2$SO$_4$ and concentrated under reduced pressure to give 4-[(N-tert-butoxycarbonyl-S-methyl-sulfonimidoyl)methyl]benzoic acid (about 250 mg). $^1$H NMR (400 MHz, methanol-d$_4$) δ ppm 8.05-8.08 (m, 2H), 7.59 (d, J=8.3 Hz, 2H), 4.93 (s, 2H), 3.11 (s, 3H), 1.48 (s, 9H); LCMS (ESI) [M+H]$^+$ m/z: calcd 314.1, found 258.0 (t-Bu cleaved mass).

Step 2: Synthesis of tert-butyl N-[[4-[[2-(tert-butoxycarbonylamino)-5-(2-thienyl)phenyl]carbamoyl]phenyl]methyl-methyl-oxo-sulfanylidene]carbamate A mixture of 4-[(N-tert-butoxycarbonyl-S-methyl-sulfonimidoyl)methyl]benzoic acid (about 200 mg, 0.638 mmol), tert-butyl N-[2-amino-4-(2-thienyl)phenyl]carbamate (about 250 mg, 0.861 mmol) and EDCI (about 170 mg, 0.887 mmol) in pyridine (about 5 mL) was stirred at about 50° C. for about 1 hour. The mixture was concentrated under reduced pressure. The residue was purified by flash chromatography (Biotage®; about 12 g AgelaFlash®Silica Flash Column, petroleumether/EtOAc with EtOAc from 0~53%, flow rate=25 mL/min, 254 nm) to afford tert-butyl N-[[4-[[2-(tert-butoxycarbonylamino)-5-(2-thienyl)phenyl]carbamoyl]phenyl]methyl-methyl-oxo-sulfanylidene]carbamate (about 300 mg). LCMS (ESI) [M+H]$^+$ m/z: calcd 586.2, found 586.2.

Step 3: Synthesis of N-[2-amino-5-(2-thienyl)phenyl]-4-[(methylsulfonimidoyl)methyl]benzamide To a mixture of tert-butyl N-[[4-[[2-(tert-butoxycarbonylamino)-5-(2-thienyl)phenyl]carbamoyl]phenyl]methyl-methyl-oxo-sulfanylidene]carbamate (about 300 mg, 0.512 mmol) in DCM (about 5 mL) was added TFA (about 0.8 mL, 10.4 mmol) at about 20° C. The mixture was stirred at about 20° C. for about 1 hour. The mixture was concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 μm; Mobile phase A: H$_2$O with 0.05% NH$_3$—H$_2$O (v %); Mobile phase B: MeCN; Gradient: B from 30% to 60% in 9.5 mins, hold 100% B for 2 mins; Flow Rate: 30 mL/min; Column Temperature: 30° C.; Wavelength: 220 nm, 254 nm) to afford N-[2-amino-5-(2-thienyl)phenyl]-4-[(methylsulfonimidoyl)methyl]benzamide (about 60.4 mg). $^1$H NMR (400 MHz, methanol-d$_4$) δ ppm 8.05 (d, J=8.0 Hz, 2H), 7.63 (d, J=8.3 Hz, 2H), 7.51 (d, J=2.0 Hz, 1H), 7.37 (dd, J=8.4, 2.1 Hz, 1H), 7.18-7.28 (m, 2H), 7.03 (dd, J=5.0, 3.8 Hz, 1H), 6.92 (d, J=8.3 Hz, 1H), 4.59 (s, 2H), 2.96 (s, 3H); LCMS (ESI) [M+H]$^+$ m/z: calcd 386.1, found 386.2; HPLC: 99.38%@220 nm, 99.17%@254 nm.

Example 56. Synthesis of N-[2-amino-5-(2-thienyl)phenyl]-4-(1-oxo-4,5-dihydro-3H-isothiazol-1-yl)benzamide (Compound 126)

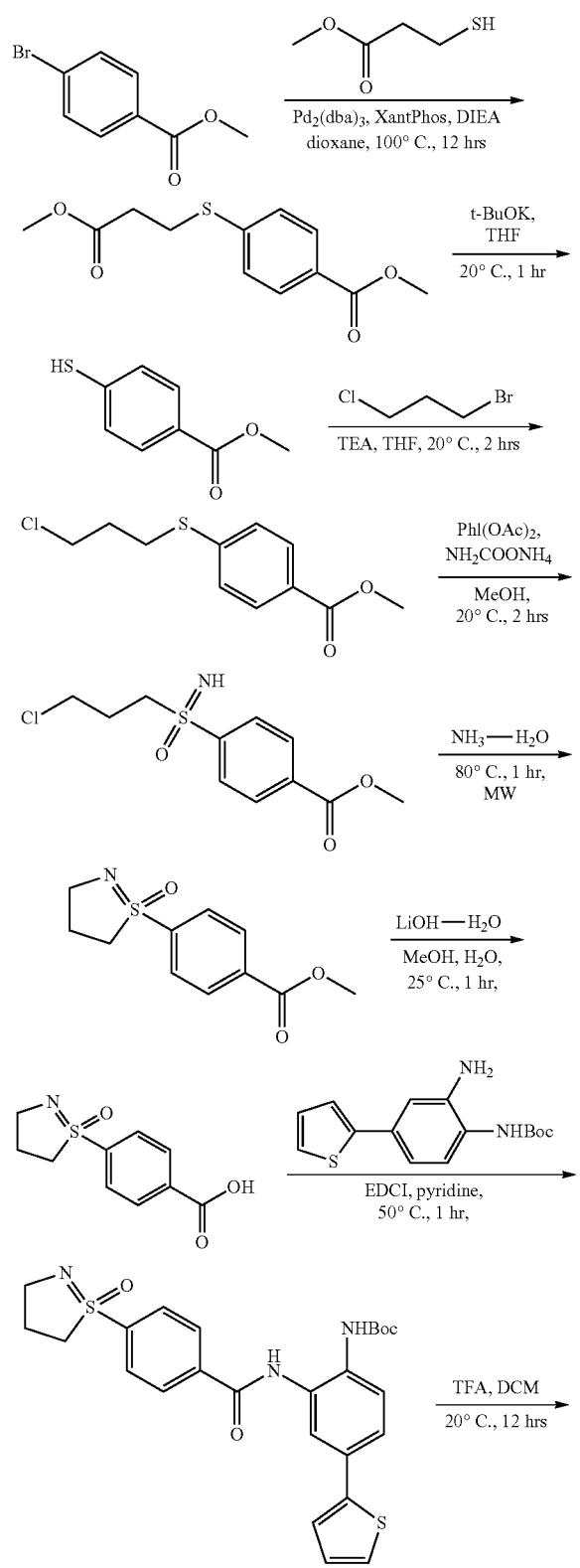

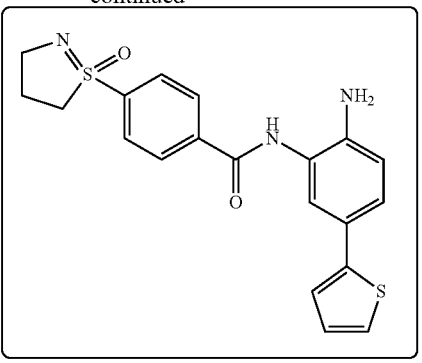

Step 1: Synthesis of methyl 4-(3-methoxy-3-oxo-propyl)sulfanylbenzoate

A mixture of methyl 4-bromobenzoate (about 1 g, 4.65 mmol), methyl 3-sulfanylpropanoate (about 615 mg, 5.12 mmol), (1E,4E)-1,5-diphenylpenta-1,4-dien-3-one;palladium (about 426 mg, 0.465 mmol), (5-diphenylphosphanyl-9,9-dimethyl-xanthen-4-yl)-diphenyl-phosphane (about 538 mg, 0.930 mmol) and N-ethyl-N-isopropyl-propan-2-amine (about 1.6 mL, 9.30 mmol) in dioxane (about 20 mL) was stirred at about 100° C. for about 12 hours. The resulting mixture was quenched by addition of water (about 30 mL) and extracted with EtOAc (about 30 mL*3). The combined organic layer was washed with saturated $NH_4Cl$ aqueous solution (about 50 mL*2), brine (about 50 mL), dried over anhydrous $Na_2SO_4$, filtered and concentrated under reduced pressure. The residue was purified by flash chromatography (ISCO®; about 12 g SepaFlash® Silica Flash Column, Petroleum ether/EtOAc with EtOAc from 0~20%, 40 mL/min, 254 nm) to afford methyl 4-(3-methoxy-3-oxo-propyl)sulfanylbenzoate (about 1.18 g). $^1$H NMR (400 MHz, $CDCl_3$) δ ppm 7.98-7.93 (m, 2H), 7.36-7.31 (m, 2H), 3.91 (s, 3H), 3.71 (s, 3H), 3.26 (t, J=7.2 Hz, 2H), 2.70 (t, J=7.2 Hz, 2H).

Step 2: Synthesis of methyl 4-sulfanylbenzoate

To a solution of methyl 4-(3-methoxy-3-oxo-propyl)sulfanylbenzoate (about 600 mg, 2.36 mmol) in THF (about 10 mL) was added 1M potassium; 2-methylpropan-2-olate/THF (about 7.1 mL, 36.0 mmol). Then the mixture was stirred at about 20° C. for about 1 hour. The reaction mixture was added 1N HCl to adjust to about pH~5, then extracted with EtOAc (about 40 mL*2). The combined organic layers were washed with brine (about 20 mL), dried over anhydrous $Na_2SO_4$, filtered and concentrated under reduced pressure to afford methyl 4-sulfanylbenzoate (about 340 mg). $^1$H NMR (400 MHz, $CDCl_3$) δ ppm 7.89 (d, J=8.4 Hz, 2H), 7.29 (d, J=8.4 Hz, 2H), 3.90 (s, 3H).

Step 3: Synthesis of methyl 4-(3-chloropropylsulfanyl)benzoate

To a solution of methyl 4-sulfanylbenzoate (about 340 mg, 2.02 mmol) and 1-bromo-3-chloro-propane (about 637 mg, 4.05 mmol) in THF (about 10 mL) was added N,N-diethylethanamine (about 0.6 mL, 4.05 mmol). The mixture was stirred at about 20° C. for about 2 hours. The reaction mixture was diluted with $H_2O$ (about 20 mL) and extracted with EtOAc (about 40 mL*2). The combined organic layers were washed with brine (about 20 mL), dried over anhydrous Na₂SO₄, filtered and concentrated under reduced pressure. The residue was purified by flash chromatography (ISCO®; about 4 g SepaFlash® Silica Flash Column, Petroleum ether/EtOAc with EtOAc from 0~20%, 18 mL/min, 254 nm) to afford methyl 4-(3-chloropropylsulfanyl)benzoate (about 220 mg). $^1$H NMR (400 MHz, CDCl₃) δ ppm 7.98-7.93 (m, 2H), 7.35-7.31 (m, 2H), 3.91 (s, 3H), 3.69 (t, J=6.0 Hz, 2H), 3.17 (t, J=7.2 Hz, 2H), 2.14 (quin, J=6.4 Hz, 2H).

Step 4: Synthesis of methyl 4-(3-chloropropylsulfonimidoyl)benzoate

To a solution of methyl 4-(3-chloropropylsulfanyl)benzoate (about 220 mg, 0.899 mmol) in MeOH (about 5 mL) was added ammonia;carbamic acid (about 150 mg, 1.92 mmol) and [acetoxy(phenyl)-iodanyl] acetate (about 730 mg, 2.27 mmol). The mixture was stirred at about 20° C. for about 2 hours. The reaction mixture was diluted with H₂O (about 10 mL) and extracted with EtOAc (about 20 mL*2). The combined organic layers were washed with brine (about 10 mL), dried over anhydrous Na₂SO₄, filtered and concentrated under reduced pressure. The residue was purified by flash chromatography (ISCO®; about 4 g SepaFlash® Silica Flash Column, Petroleum ether/EtOAc with EtOAc from 0~100%, 18 mL/min, 254 nm) to afford methyl 4-(3-chloropropylsulfonimidoyl)benzoate (about 210 mg). $^1$H NMR (400 MHz, CDCl₃) δ ppm 8.22 (d, J=8.4 Hz, 2H), 8.06 (d, J=8.4 Hz, 2H), 3.98 (s, 3H), 3.63 (t, J=6.4 Hz, 2H), 3.41-3.29 (m, 2H), 2.29-2.16 (m, 2H).

Step 5: Synthesis of methyl 4-(1-oxo-4,5-dihydro-3H-isothiazol-1-yl)benzoate methyl 4-(3-chloropropylsulfonimidoyl)benzoate (about 210 mg, 0.762 mmol) in NH₃—H₂O (about 2 mL, 0.1% purity) were taken up into a microwave tube. The sealed tube was heated at about 80° C. for about 1 hour under microwave. The reaction mixture was concentrated under reduced pressure. The residue was purified by flash chromatography (ISCO®; about 4 g SepaFlash® Silica Flash Column, Petroleum ether/EtOAc with EtOAc from 0~100%, 18 mL/min, 254 nm) to afford methyl 4-(1-oxo-4,5-dihydro-3H-isothiazol-1-yl)benzoate (about 100 mg). $^1$H NMR (400 MHz, CDCl₃) δ ppm 8.22 (d, J=8.4 Hz, 2H), 8.06 (d, J=8.4 Hz, 2H), 4.19-4.08 (m, 1H), 3.98 (s, 3H), 3.95-3.88 (m, 1H), 3.53-3.43 (m, 1H), 3.29 (td, J=8.8, 13.2 Hz, 1H), 2.59-2.46 (m, 1H), 2.40-2.27 (m, 1H).

Step 6: Synthesis of 4-(1-oxo-4,5-dihydro-3H-isothiazol-1-yl)benzoic acid

To a solution of methyl 4-(1-oxo-4,5-dihydro-3H-isothiazol-1-yl)benzoate (about 100 mg, 0.418 mmol) in MeOH (about 2 mL) and H₂O (about 1 mL) was added lithium;hydroxide;hydrate (about 176 mg, 4.18 mmol). The mixture was stirred at about 25° C. for about 1 hour. The mixture was adjusted to about pH=5 with 1N HCl aqueous solution. The mixture was concentrated under reduced pressure to afford 4-(1-oxo-4,5-dihydro-3H-isothiazol-1-yl)benzoic acid (about 100 mg). $^1$H NMR (400 MHz, MeOD) δ ppm 8.40 (d, J=8.4 Hz, 2H), 8.33-8.27 (m, 2H), 4.38-4.11 (m, 2H), 3.38-3.35 (m, 2H), 2.90-2.72 (m, 2H).

Step 7: Synthesis of tert-butyl 5-[[2-hydroxy-5-(2-thienyl)phenyl]carbamoyl]isoindoline-2-carboxylate To a solution of 4-(1-oxo-4,5-dihydro-3H-isothiazol-1-yl)benzoic acid (about 100 mg, 0.444 mmol) and tert-butyl N-[2-amino-4-(2-thienyl)phenyl]carbamate (about 194 mg, 0.666 mmol) in pyridine (about 1 mL) was added 3-(ethyl-iminomethyleneamino)-N,N-dimethyl-propan-1-amine (about 76 mg, 0.488 mmol). The mixture was stirred at about 50° C. for about 1 hour. The reaction mixture was diluted with saturated NH₄Cl aqueous solution (10 mL) and extracted with EtOAc (about 20 mL*2). The combined organic layers were washed with brine (about 10 mL), dried over anhydrous Na₂SO₄, filtered and concentrated under reduced pressure. The residue was purified by flash chromatography (ISCO®; about 4 g SepaFlash® Silica Flash Column, Petroleum ether/EtOAc with EtOAc from 0~100%, 40 mL/min, 254 nm) to afford tert-butyl 5-[[2-hydroxy-5-(2-thienyl)phenyl]carbamoyl]isoindoline-2-carboxylate (about 190 mg). LCMS (ESI) [M+H]⁺ m/z: calcd 498.1, found 498.1.

Step 8: Synthesis of N-[2-amino-5-(2-thienyl)phenyl]-4-(1-oxo-4,5-dihydro-3H-isothiazol-1-yl)benzamide To a solution of tert-butyl N-[2-[[4-(1-oxo-4,5-dihydro-3H-isothiazol-1-yl)benzoyl]amino]-4-(2-thienyl)phenyl]carbamate (about 70 mg, 0.141 mmol) in DCM (about 5 mL) was added 2,2,2-trifluoroacetic acid (about 0.1 mL, 1.41 mmol). The mixture was stirred at about 20° C. for about 12 hours. The reaction mixture was diluted with DCM (about 15 mL) and added saturated aqueous Na₂CO₃ solution to adjust pH-8, then concentrated. The residue was purified by preparative HPLC (Instrument: Gilson GX-281 Liquid Handler, Gilson 322 Pump, Gilson 156 UV Detector; Column: Phenomenex C18 80*40 mm*3 μm; Mobile phase A: water with 0.05% NH₃—H₂O (v %); Mobile phase B: MeCN; Gradient: B from 28% to 58% in 9.5 min, hold 100% B for 1 min; Flow Rate: 30 mL/min; Column Temperature: 30° C.; Wavelength: 220 nm, 254 nm) to afford N-[2-amino-5-(2-thienyl)phenyl]-4-(1-oxo-4,5-dihydro-3H-isothiazol-1-yl)benzamide (about 25 mg). $^1$H NMR (400 MHz, DMSO-d₆) δ ppm 10.05-9.84 (m, 1H), 8.18 (d, J=8.4 Hz, 2H), 7.98 (d, J=8.4 Hz, 2H), 7.47 (d, J=1.6 Hz, 1H), 7.37-7.27 (m, 2H), 7.24 (d, J=3.2 Hz, 1H), 7.05 (dd, J=3.6, 5.0 Hz, 1H), 6.82 (d, J=8.4 Hz, 1H), 5.20 (s, 2H), 3.88-3.80 (m, 1H), 3.73-3.66 (m, 1H), 3.56-3.52 (m, 2H), 2.27 (qd, J=6.8, 13.6 Hz, 2H); LCMS (ESI) [M+H]⁺ m/z: calcd 398.1, found 397.9; HPLC: 98.46%@220 nm, 98.97%@254 nm; racemic mixture.

Example 57. Synthesis of N-[2-amino-5-(2-thienyl)phenyl]-6-(cyclopropylsulfonimidoyl)pyridine-3-carboxamide (Compound 122)

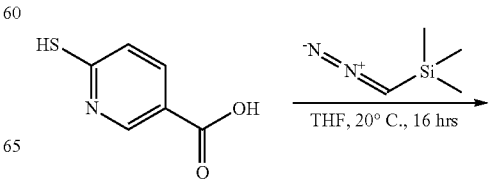

Step 1: Synthesis of methyl 6-sulfanylpyridine-3-carboxylate

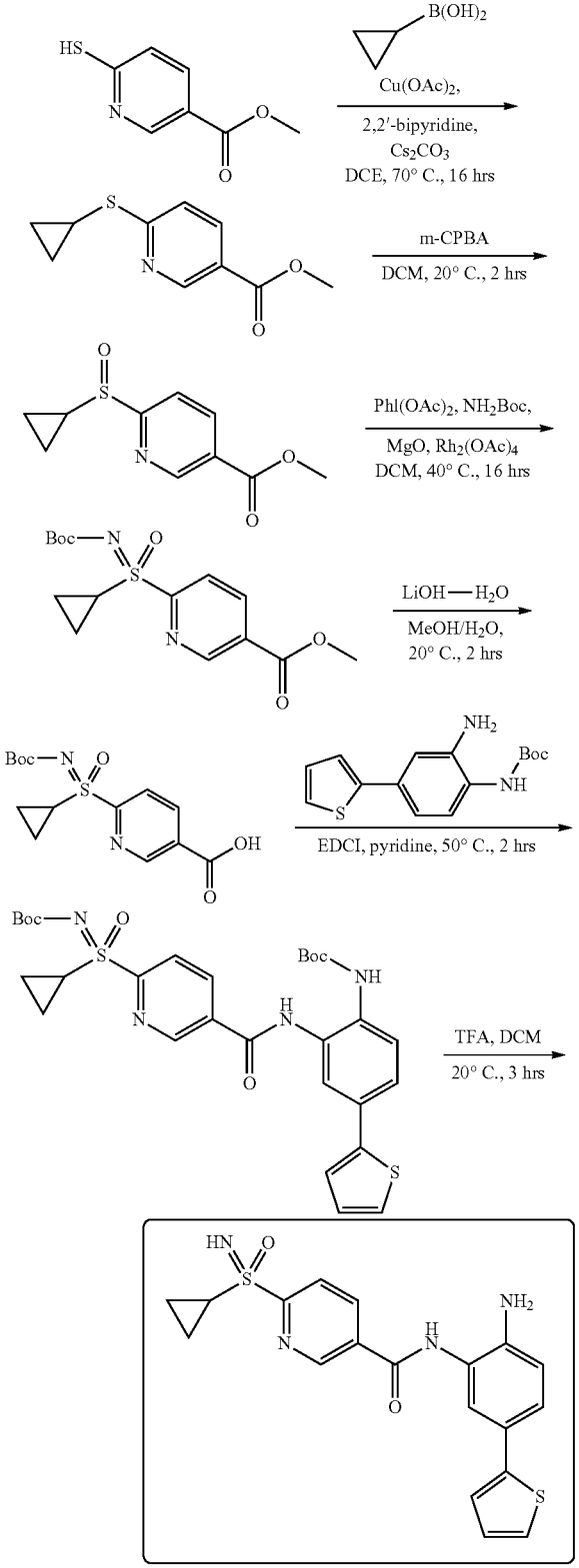

To a solution of 2M diazomethyl(trimethyl)silane/hexane (about 1.8 mL, 3.22 mmol) was added a solution of 6-sulfanylpyridine-3-carboxylic acid (about 500 mg, 3.22 mmol) in THF (about 20 mL). The mixture was stirred at about 20° C. for about 16 hours. The resulting mixture was concentrated under reduced pressure. The residue was purified by flash chromatography (ISCO®; about 80 g AgelaFlash® Silica Flash Column, DCM/MeOH with MeOH from 0~16%, flow rate=80 mL/min, 254 nm) to afford methyl 6-sulfanylpyridine-3-carboxylate (about 700 mg). LCMS (ESI) [M+H]+ m/z: calcd 170.0, found 170.1.

Step 2: Synthesis of methyl 6-cyclopropylsulfanylpyridine-3-carboxylate

A mixture of methyl 6-sulfanylpyridine-3-carboxylate (about 430 mg, 2.54 mmol), cyclopropylboronic acid (about 350 mg, 4.07 mmol), dicesium;carbonate (about 860 mg, 2.64 mmol), copper;diacetate (about 475 mg, 2.62 mmol) and 2,2'-bipyridine (about 410 mg, 2.63 mmol) in 1,2-dichloroethane (about 8 mL) was stirred at about 70° C. for about 16 hours. The resulting mixture was quenched by addition of water (about 30 mL), 28% NH$_3$·H$_2$O (about 5 mL), and extracted with DCM (about 30 mL*3). The combined organic layer was washed with brine (about 30 mL*2), dried over anhydrous Na$_2$SO$_4$, filtered and concentrated under reduced pressure. The residue was purified by flash chromatography (ISCO®; about 40 g AgelaFlash® Silica Flash Column, petroleum ether/EtOAc with EtOAc from 0~50%, flow rate=30 mL/min, 254 nm) to afford methyl 6-cyclopropylsulfanylpyridine-3-carboxylate (about 145 mg). $^1$H NMR (400 MHz, methanol-d$_4$) δ ppm 8.87 (d, J=1.6 Hz, 1H), 8.21 (dd, J=8.5, 2.3 Hz, 1H), 7.64 (d, J=8.5 Hz, 1H), 3.92 (s, 3H), 2.34 (ddd, J=7.5, 4.3, 3.1 Hz, 1H), 1.16-1.38 (m, 2H), 0.62-0.81 (m, 2H); LCMS (ESI) [M+H]+ m/z: calcd 210.1, found 210.0.

Step 3: Synthesis of methyl 6-cyclopropylsulfinylpyridine-3-carboxylate

To a solution of m-CPBA (about 110 mg, 0.637 mmol, 85 wt %) in DCM (about 5 mL) was added methyl 6-cyclopropylsulfanylpyridine-3-carboxylate (about 130 mg, 0.621 mmol). The mixture was stirred at about 20° C. for about 2 hours. The mixture was quenched by addition of saturated Na$_2$SO$_3$ aqueous solution (about 20 mL), saturated Na$_2$CO$_3$ aqueous solution (about 20 mL) and extracted with DCM (about 30 mL×3). The combined organic layer was dried over anhydrous Na$_2$SO$_4$, filtered and concentrated under reduced pressure to afford methyl 6-cyclopropylsulfinylpyridine-3-carboxylate (about 190 mg).

Step 4: Synthesis of methyl 6-(N-tert-butoxycarbonyl-S-cyclopropyl-sulfonimidoyl)pyridine-3-carboxylate To a solution of NH$_2$Boc (about 440 mg, 3.76 mmol), [bis(acetoxy)iodo]benzene (about 820 mg, 2.55 mmol), MgO (about 380 mg, 9.20 mmol) and diacetoxyrhodium (about 40 mg, 0.181 mmol) in DCM (about 10 mL) was added methyl 6-cyclopropylsulfinylpyridine-3-carboxylate (about 190 mg). The reaction mixture was stirred at about 40° C. for about 16 hours. The mixture was filtered and concentrated under reduced pressure. The residue was purified by flash chromatography (Biotage®; about 40 g Sepa-Flash® Silica Flash Column, petroleum ether/EtOAc with EtOAc from 0~50%, 30 mL/min, 254 nm) to afford methyl 6-(N-tert-butoxycarbonyl-S-cyclopropyl-sulfonimidoyl)pyridine-3-carboxylate (about 150 mg). $^1$H NMR (400 MHz, DMSO-d$_6$) δ ppm 9.24 (dd, J=2.0, 0.8 Hz, 1H), 8.62 (dd, J=8.2, 2.1 Hz, 1H), 8.19 (dd, J=8.3, 0.8 Hz, 1H), 3.93 (s, 3H), 3.03 (tt, J=7.8, 4.8 Hz, 1H), 1.29-1.40 (m, 2H), 1.15-1.17 (m, 9H), 0.93-1.02 (m, 2H); LCMS (ESI) [M+H]$^+$ m/z: calcd 341.1; found 341.1.

Step 5: Synthesis of 6-(N-tert-butoxycarbonyl-S-cyclopropyl-sulfonimidoyl)pyridine-3-carboxylic acid To a solution of methyl 6-(N-tert-butoxycarbonyl-S-cyclopropyl-sulfonimidoyl)pyridine-3-carboxylate (about 150 mg, 0.441 mmol) in MeOH (about 4 mL) was added a solution of LiOH—H$_2$O (about 220 mg, 5.24 mmol) in H$_2$O (about 2 mL). The mixture was stirred at about 20° C. for about 2 hours. The mixture was adjusted to about pH=4 with 2N HCl aqueous solution. The mixture was quenched by addition of water (about 30 mL) and extracted with DCM (about 20 mL×3). The combined organic layer was concentrated under reduced pressure to afford 6-(N-tert-butoxycarbonyl-S-cyclopropyl-sulfonimidoyl)pyridine-3-carboxylic acid (about 100 mg). LCMS (ESI) [M+H]$^+$ m/z: calcd 327.1; found 327.0.

Step 6: Synthesis of tert-butyl N-[[5-[[2-(tert-butoxycarbonylamino)-5-(2-thienyl)phenyl]carbamoyl]-2-pyridyl]-cyclopropyl-oxo-sulfanylidene]carbamate To a solution of EDCI (about 120 mg, 0.626 mmol) was added a solution of 6-(N-tert-butoxycarbonyl-S-cyclopropyl-sulfonimidoyl)pyridine-3-carboxylic acid (about 100 mg, 0.306 mmol) and tert-butyl N-[2-amino-4-(2-thienyl)phenyl]carbamate (about 90 mg, 0.310 mmol) in pyridine (about 5 mL). The mixture was stirred at 50° C. for 2 hours. The resulting mixture was concentrated under reduced pressure. The residue was purified by flash chromatography (ISCO®; about 20 g AgelaFlash® Silica Flash Column, petroleum ether/EtOAc with EtOAc from 0~37%, flow rate=30 mL/min, 254 nm) to afford tert-butyl N-[[5-[[2-(tert-butoxycarbonylamino)-5-(2-thienyl)phenyl]carbamoyl]-2-pyridyl]-cyclopropyl-oxo-sulfanylidene]carbamate (about 75 mg). LCMS (ESI) [M+H]$^+$ m/z: calcd 599.2, found 599.2.

Step 7: Synthesis of N-[2-amino-5-(2-thienyl)phenyl]-6-(cyclopropylsulfonimidoyl)pyridine-3-carboxamide To a solution of tert-butyl N-[[5-[[2-(tert-butoxycarbonylamino)-5-(2-thienyl)phenyl]carbamoyl]-2-pyridyl]-cyclopropyl-oxo-sulfanylidene]carbamate (about 75 mg, 0.125 mmol) in DCM (about 4 mL) was added TFA (about 0.2 mL, 2.60 mmol). The mixture was stirred at about 20° C. for about 3 hours. The resulting mixture was concentrated under reduced pressure. The residue was purified by preparative HPLC (Instrument: Gilson GX-281 Liquid Handler, Gilson 322 Pump, Gilson 156 UV Detector; Column: Phenomenex C18 80×40 mm×3 um; Mobile phase A: water (10 mmol NH$_4$HCO$_3$); Mobile phase B: ACN; Gradient: B from 27% to 57% in 9.5 min, hold 100% B for 2 min; Flow Rate: 30 mL/min; Column Temperature: about 30° C.; Wavelength: 220 nm, 254 nm) to afford N-[2-amino-5-(2-thienyl)phenyl]-6-(cyclopropylsulfonimidoyl)pyridine-3-carboxamide (about 19 mg). $^1$H NMR (400 MHz, DMSO-d$_6$) δ ppm 10.03 (s, 1H), 9.25 (d, J=1.8 Hz, 1H), 8.57 (dd, J=8.0, 2.0 Hz, 1H), 8.15 (d, J=8.0 Hz, 1H), 7.49 (d, J=2.0 Hz, 1H), 7.29-7.38 (m, 2H), 7.25 (d, J=2.8 Hz, 1H), 7.05 (dd, J=5.0, 3.5 Hz, 1H), 6.81 (d, J=8.3 Hz, 1H), 5.32 (s, 2H), 4.55 (s, 1H), 2.87-2.97 (m, 1H), 1.10-1.18 (m, 1H), 0.94-1.02 (m, 3H); LCMS (ESI) [M+H]$^+$ m/z: calcd 399.1; found 399.1; HPLC: 97.710%@220 nm; 97.090%@254 nm.

Example 58. Synthesis of N-[2-amino-5-(2-thienyl)phenyl]-5-(2-methoxyethylsulfonimidoyl)pyridine-2-carboxamide (Compound 121)

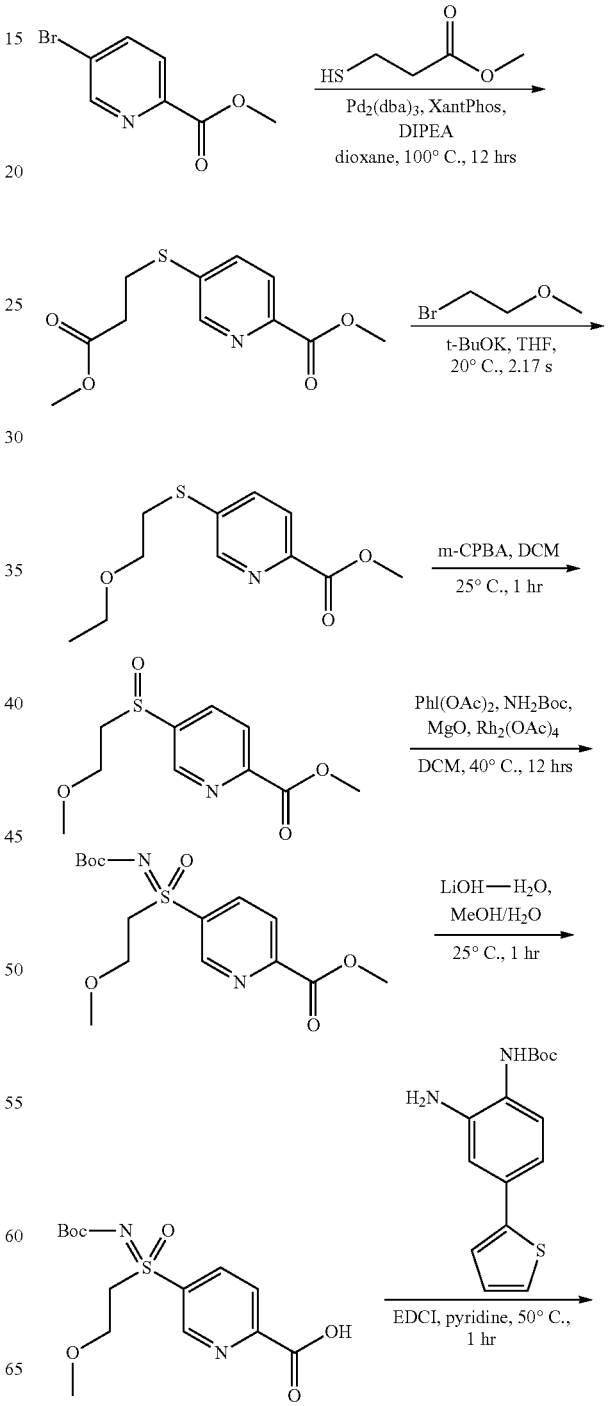

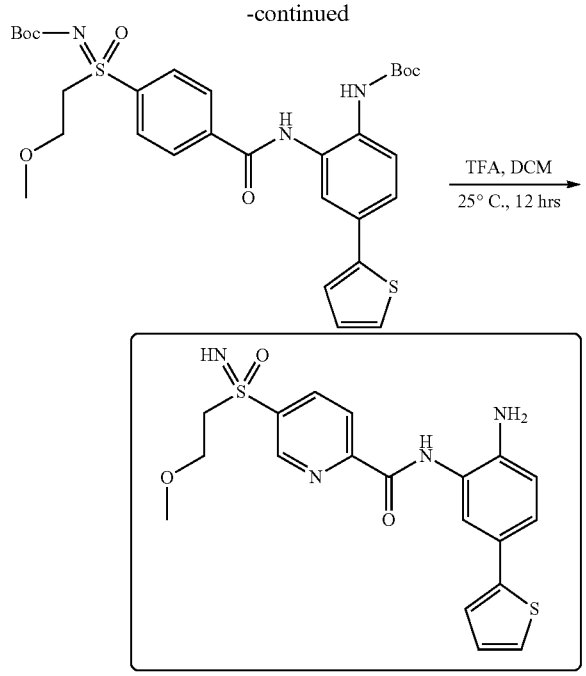

Step 1: Synthesis of methyl 5-(3-methoxy-3-oxo-propyl)sulfanylpyridine-2-carboxylate A mixture of methyl 5-bromopyridine-2-carboxylate (about 3 g, 13.9 mmol), methyl 3-sulfanylpropanoate (about 1.6 mL, 14.5 mmol), $Pd_2(dba)_3$ (about 318 mg, 0.347 mmol), XantPhos (about 402 mg, 0.695 mmol) and DIPEA (about 4.8 mL, 27.6 mmol) in dioxane (about 20 mL) was stirred at about 100° C. for about 12 hours. The resulting mixture was quenched by addition of water (about 30 mL) and extracted with EtOAc (about 30 mL*3). The combined organic layer was washed with saturated $NH_4Cl$ aqueous solution (about 50 mL*2), brine (about 50 mL), dried over anhydrous $Na_2SO_4$, filtered and concentrated under reduced pressure. The residue was purified by flash chromatography (ISCO®; about 24 g AgelaFlash® Silica Flash Column, petroleum ether/EtOAc with EtOAc from 0~50%, 35 mL/min, 254 nm) to afford methyl 5-(3-methoxy-3-oxo-propyl)sulfanylpyridine-2-carboxylate (about 3.1 g). LCMS (ESI) $[M+H]^+$ m/z: calcd 256.1; found 256.0.

Step 2: Synthesis of methyl 5-(2-methoxyethylsulfanyl)pyridine-2-carboxylate

To a solution of methyl 5-(3-methoxy-3-oxo-propyl)sulfanylpyridine-2-carboxylate (about 3.1 g, 12.1 mmol) in THF (about 15 mL) was added 1M t-BuOK/THF (36.0 mmol, 36 mL). Then the mixture was stirred at about 20° C. for about 10 minutes. 1-bromo-2-methoxy-ethane (about 1.3 mL, 13.8 mmol) was added, and the mixture was stirred at about 20° C. for about 1 hour. 1-bromo-2-methoxy-ethane (about 1.3 mL, 13.8 mmol) was added, and the mixture was stirred at about 20° C. for about 1 hour. The resulting mixture was quenched by addition of water (about 30 mL) and extracted with EtOAc (about 30 mL*3). The combined organic layer was dried over anhydrous $Na_2SO_4$, filtered and concentrated under reduced pressure. The residue was purified by flash chromatography (ISCO®; about 24 g Agela-Flash® Silica Flash Column, petroleum ether/EtOAc with EtOAc from 0~50%, 40 mL/min, 254 nm) to afford methyl 5-(2-methoxyethylsulfanyl)pyridine-2-carboxylate (about 2 g). $^1$H NMR (400 MHz, methanol-$d_4$) δ ppm 8.56 (d, J=2.3 Hz, 1H), 8.03 (d, J=8.3 Hz, 1H), 7.92 (dd, J=8.4, 2.4 Hz, 1H), 3.95 (s, 3H), 3.66 (t, J=6.1 Hz, 2H), 3.35 (s, 3H), 3.27-3.31 (m, 2H); LCMS (ESI) $[M+H]^+$ m/z: calcd 228.1; found 228.0.

Step 3: Synthesis of methyl 5-(2-methoxyethylsulfanyl)pyridine-2-carboxylate

To a solution of methyl 5-(2-methoxyethylsulfanyl)pyridine-2-carboxylate (about 500 mg, 2.20 mmol) in DCM (about 10 mL) was added 3-chlorobenzenecarboperoxoic acid (about 491 mg, 2.42 mmol, 85 wt %). The mixture was stirred at about 25° C. for about 1 hour. The reaction mixture was quenched by addition of $Na_2S_2O_4$, diluted with $H_2O$ (about 30 mL) and extracted with DCM (about 30 mL*2). The combined organic layers were washed with brine (about 50 mL), dried over anhydrous $Na_2SO_4$, filtered and concentrated under reduced pressure. The residue was purified by flash chromatography (ISCO®; about 4 g SepaFlash® Silica Flash Column, Petroleum Ether/EtOAc with EtOAc from 0~30%, 40 mL/min, 254 nm) to afford methyl 5-(2-methoxyethylsulfinyl)pyridine-2-carboxylate (about 360 mg). $^1$H NMR (400 MHz, $CDCl_3$) δ ppm 8.89 (d, J=1.6 Hz, 1H), 8.30-8.33 (m, 1H), 8.22-8.25 (m, 1H), 4.06 (s, 3H), 3.90 (ddd, J=10.8, 7.6, 4.8 Hz, 1H), 3.70-3.76 (m, 1H), 3.38 (s, 3H), 3.09-3.13 (m, 2H). LCMS (ESI) $[M+H]^+$ m/z: calcd 244.1, found 243.9.

Step 4: Synthesis of methyl 5-[N-tert-butoxycarbonyl-S-(2-methoxyethyl)sulfonimidoyl]pyridine-2-carboxylate A mixture of methyl 5-(2-methoxyethylsulfinyl)pyridine-2-carboxylate (360 mg, 1.48 mmol), tert-butyl carbamate (about 196 mg, 1.67 mmol), oxomagnesium (about 295 mg, 7.32 mmol), diacetoxyrhodium (about 30 mg, 0.0680 mmol) and [acetoxy(phenyl)-iodanyl] acetate (about 715 mg, 2.22 mmol) in DCM (about 10 mL) was degassed and purged with $N_2$ for 3 times, and then the mixture was stirred at about 40° C. for about 12 hours under $N_2$ atmosphere. The reaction mixture was concentrated under reduced pressure. The residue was purified by flash chromatography (ISCO®; about 12 g AgelaFlash® Silica Flash Column, petroleum ether/EtOAc with EtOAc from 0~100%, flow rate=40 mL/min, 254 nm) to afford methyl 5-[N-tert-butoxycarbonyl-S-(2-methoxyethyl)sulfonimidoyl]pyridine-2-carboxylate (about 320 mg). $^1$H NMR (400 MHz, $CDCl_3$) δ ppm 9.18 (d, J=1.6 Hz, 1H), 8.38 (d, J=2.4 Hz, 1H), 8.27-8.33 (m, 1H), 4.07 (s, 3H), 3.67-3.88 (m, 4H), 3.11 (s, 3H), 1.39 (s, 9H). LCMS (ESI) $[M+H]^+$ m/z: calcd 359.1, found 302.9 (Boc cleaved mass).

Step 5: Synthesis of 5-[N-tert-butoxycarbonyl-S-(2-methoxyethyl)sulfonimidoyl]pyridine-2-carboxylic acid To a solution of methyl 5-[N-tert-butoxycarbonyl-S-(2-methoxyethyl)sulfonimidoyl]pyridine-2-carboxylate (about 320 mg, 0.893 mmol) in MeOH (about 6 mL) and $H_2O$ (about 3 mL) was added lithium;hydroxide;hydrate (about 375 mg, 8.93 mmol). The mixture was stirred at about 25° C. for about 1 hour. The mixture was concentrated under reduced pressure to remove the organic solvent. The aqueous phase was adjusted to about pH=4 with 2N HCl aqueous solution. The mixture was filtered. The filter cake was concentrated under reduced pressure to afford 5-[N-tert-butoxycarbonyl-S-(2-methoxyethyl)sulfonimidoyl]pyridine-2-carboxylic acid (about 170 mg). ¹H NMR (400 MHz, CDCl₃) δ ppm 9.12 (d, J=1.6 Hz, 1H), 8.43-8.52 (m, 1H), 8.38-8.41 (m, 1H), 3.69-3.82 (m, 4H), 3.11 (s, 3H), 1.40 (s, 9H). LCMS (ESI) [M+H]⁺ m/z: calcd 345.1, found 244.9 (Boc cleaved mass).

Step 6: Synthesis of tert-butyl N-[[6-[[2-(tert-butoxycarbonylamino)-5-(2-thienyl)phenyl]carbamoyl]-3-pyridyl]-(2-methoxyethyl)-oxo-sulfanylidene]carbamate A mixture of 5-[N-tert-butoxycarbonyl-S-(2-methoxyethyl)sulfonimidoyl]pyridine-2-carboxylic acid (85 mg, 0.247 mmol), tert-butyl N-[2-amino-4-(2-thienyl)phenyl]carbamate (about 74 mg, 0.255 mmol) and 3-(ethyliminomethyleneamino)-N,N-dimethyl-propan-1-amine (about 60 mg, 0.387 mmol) in pyridine (about 2 mL) was degassed and purged with N₂ for about 3 times, and then the mixture was stirred at about 50° C. for about 1 hour under N₂ atmosphere. The reaction mixture was diluted with H₂O (about 30 mL) and extracted with EtOAc (about 40 mL*2). The combined organic layers were washed with brine (about 40 mL), dried over anhydrous Na₂SO₄, filtered and concentrated under reduced pressure to afford tert-butyl N-[[6-[[2-(tert-butoxycarbonylamino)-5-(2-thienyl)phenyl]carbamoyl]-3-pyridyl]-(2-methoxyethyl)-oxo-sulfanylidene]carbamate (about 48 mg). LCMS (ESI) [M+H]⁺ m/z: calcd 616.2, found 417.0 (Boc cleaved mass).

Step 7: Synthesis of N-[2-amino-5-(2-thienyl)phenyl]-5-(2-methoxyethylsulfonimidoyl)pyridine-2-carboxamide To a solution of tert-butyl N-[[6-[[2-(tert-butoxycarbonylamino)-5-(2-thienyl)phenyl]carbamoyl]-3-pyridyl]-(2-methoxyethyl)-oxo-sulfanylidene]carbamate (about 54 mg, 0.0880 mmol) in DCM (about 8 mL) was added 2,2,2-trifluoroacetic acid (about 0.1 mL, 0.877 mmol). The mixture was stirred at about 25° C. for about 12 hours. The reaction mixture was diluted with DCM (about 30 mL) and adjusted to about pH=8 with saturated Na₂CO₃ aqueous solution. The resultant mixture was dried over Na₂SO₄ and filtered. The filtrate was concentrated under reduced pressure. The residue was combined with another batch, and purified by flash chromatography (ISCO®; about 12 g SepaFlash® Silica Flash Column, Petroleum Ether/EtOAc with EtOAc from 0~60%, 40 mL/min, 254 nm) to give a product. The residue was further purified by preparative HPLC (Instrument: Gilson GX-281 Liquid Handler, Gilson 322 Pump, Gilson 156 UV Detector; Column: Phenomenex C18 80*40 mm*3 μm; Mobile phase A: H₂O with 0.05% NH₃—H₂O (v %); B:ACN; Gradient: B from 28% to 58% in 7.8 min, hold 100% B for 2 min; Flow Rate: 25 mL/min; Column Temperature: 30° C.; Wavelength: 220 nm, 254 nm) to afford N-[2-amino-5-(2-thienyl)phenyl]-5-(2-methoxyethylsulfonimidoyl)pyridine-2-carboxamide (about 37.5 mg). ¹H NMR (400 MHz, CDCl₃) δ ppm 9.88 (s, 1H), 9.18 (s, 1H), 8.42-8.53 (m, 2H), 7.77 (d, J=2.0 Hz, 1H), 7.39 (dd, J=8.4, 2.0 Hz, 1H), 7.22 (br d, J=4.4 Hz, 2H), 7.04-7.07 (m, 1H), 6.90 (d, J=8.0 Hz, 1H), 3.86 (t, J=5.6 Hz, 2H), 3.51 (q, J=5.6 Hz, 2H), 3.23 (s, 3H); LCMS (ESI) [M+H]⁺ m/z: calcd 417.1, found 416.9; HPLC: 93.35%@220 nm, 95.670%@254 nm.

Example 59. Synthesis of N-[2-amino-5-(2-pyridyl)phenyl]-4-(cyclopropylsulfonimidoyl)benzamide (Compound 120)

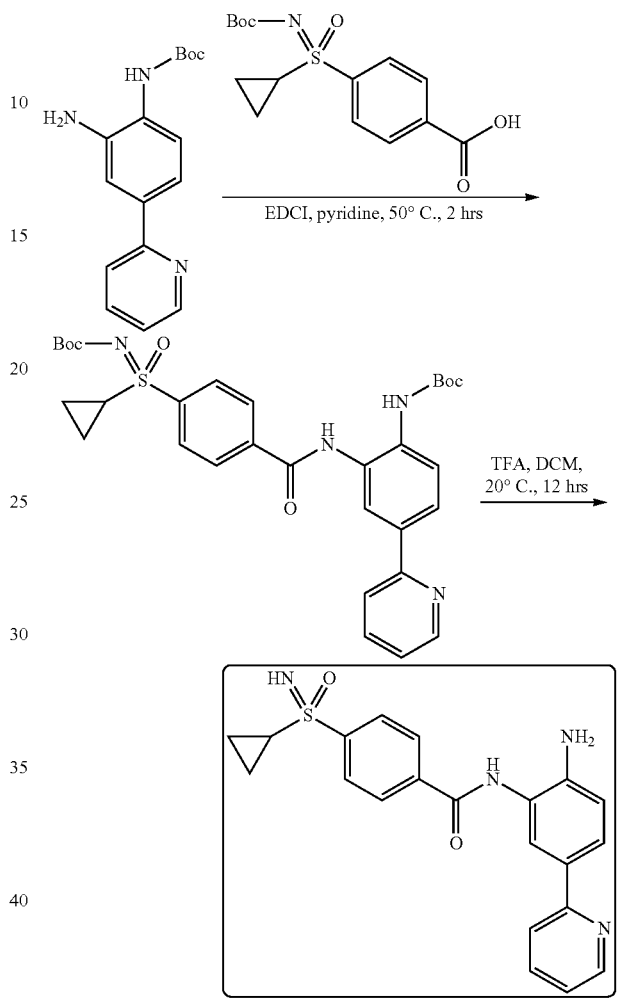

Step 1: Synthesis of tert-butyl N-[[4-[[2-(tert-butoxycarbonylamino)-5-(2-pyridyl)phenyl]carbamoyl]phenyl]-cyclopropyl-oxo-sulfanylidene]carbamate A mixture of tert-butyl N-[2-amino-4-(2-pyridyl)phenyl]carbamate (about 100 mg, 0.350 mmol), 4-(N-tert-butoxycarbonyl-S-cyclopropyl-sulfonimidoyl)benzoic acid (about 137 mg, 0.421 mmol), 3-(ethyliminomethyleneamino)-N,N-dimethyl-propan-1-amine;hydrochloride (about 101 mg, 0.527 mmol) and pyridine (about 8 mL) was stirred at about 50° C. for about 2 hours. The resulting mixture was concentrated under reduced pressure. The residue was purified by flash chromatography (ISCO®; about 4 g AgelaFlash® Silica Flash Column, petroleum ether/EtOAc with EtOAc from 0~60%, flow rate=30 mL/min, 254 nm) to afford tert-butyl N-[[4-[[2-(tert-butoxycarbonylamino)-5-(2-pyridyl)phenyl]carbamoyl]phenyl]-cyclopropyl-oxo-sulfanylidene]carbamate (about 200 mg). ¹H NMR (400 MHz, DMSO-d₆) δ ppm 10.15 (s, 1H), 8.86 (s, 1H), 8.65 (d, J=4.0 Hz, 1H), 8.20-8.28 (m, 3H), 8.05 (d, J=8.3 Hz, 2H), 7.78-7.98 (m, 4H), 7.31-7.36 (m, 1H), 3.10 (s, 1H), 1.46 (s, 9H), 1.36 (d, J=4.0 Hz, 2H), 1.25 (s, 9H), 1.02 (d, J=7.3 Hz, 2H); LCMS (ESI) [M+H]⁺ m/z: calcd 593.2, found 593.3.

Step 2: Synthesis of N-[2-amino-5-(2-pyridyl)phenyl]-4-(cyclopropylsulfonimidoyl)benzamide To a solution of tert-butyl N-[[4-[[2-(tert-butoxycarbonylamino)-5-(2-pyridyl)phenyl]carbamoyl]phenyl]-cyclopropyl-oxo-sulfanylidene]carbamate (about 200 mg, 0.337 mmol) in DCM (about 10 mL) was added TFA (about 0.6 mL, 7.79 mmol). The mixture was stirred at about 20° C. for about 12 hours. The resulting mixture was concentrated under reduced pressure and adjusted to about pH=8 with 28% NH₃—H₂O aqueous solution (about 1 mL). The residue was purified by preparative HPLC (Instrument: Gilson GX-281 Liquid Handler, Gilson 322 Pump, Gilson 156 UV Detector; Column: Durashell 80×40 mm×3 µm; Mobile phase A: H₂O with 10 mmol NH₄HCO₃ (v %); Mobile phase B: MeCN; Gradient: B from 14% to 44% in 9.5 min, hold 100% B for 2 min; Flow Rate: 25 mL/min; Column Temperature: 30° C.; Wavelength: 220 nm, 254 nm) to afford N-[2-amino-5-(2-pyridyl)phenyl]-4-(cyclopropylsulfonimidoyl)benzamide (about 47.7 mg). ¹H NMR (400 MHz, DMSO-d₆) δ ppm 9.93 (s, 1H), 8.55 (d, J=4.6 Hz, 1H), 8.19 (d, J=8.3 Hz, 2H), 7.98-8.05 (m, 3H), 7.73-7.79 (m, 3H), 7.19 (td, J=5.2, 2.7 Hz, 1H), 6.86 (d, J=8.5 Hz, 1H), 5.36 (s, 2H), 4.41 (s, 1H), 2.64-2.79 (m, 1H), 1.11-1.19 (m, 1H), 0.88-1.04 (m, 3H); LCMS (ESI) [M+H]⁺ m/z: calcd 393.1, found 393.2; HPLC: 98.49%@220 nm, 100%@254 nm.

Example 60. Synthesis of N-[2-amino-5-(2-pyridyl)phenyl]-4-(methylsulfonimidoyl)benzamide (Compound 119)

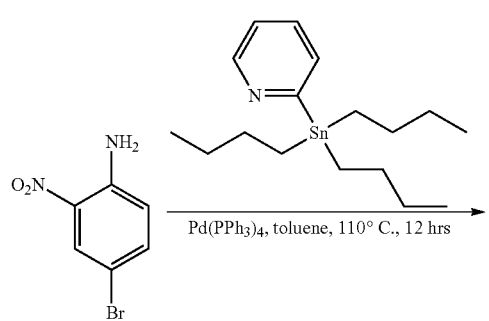

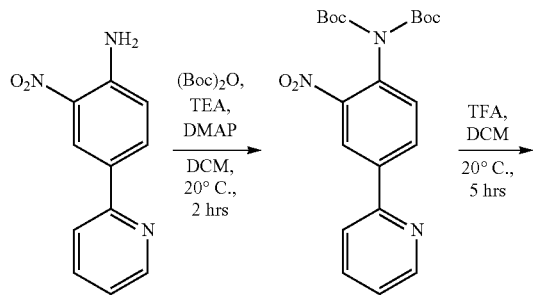

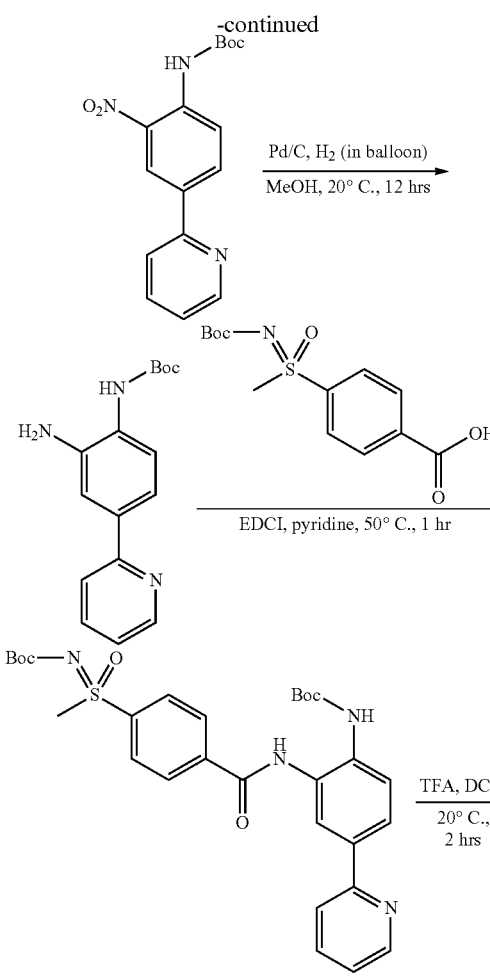

Step 1: Synthesis of 2-nitro-4-(2-pyridyl)aniline

A mixture of 4-bromo-2-nitro-aniline (about 3 g, 13.8 mmol), tributyl(2-pyridyl)stannane (about 5.4 mL, 16.7 mmol), palladium;triphenylphosphane (about 800 mg, 0.692 mmol) and toluene (about 30 mL) was stirred at about 110° C. for about 12 hours. The mixture was added anhydrous potassium fluoride, and stirred at about 20° C. for about 1 hour. The resulting mixture was quenched by addition of water (about 50 mL) and extracted with EtOAc (about 100 mL*3). The combined organic layer was dried over anhydrous Na₂SO₄, filtered and concentrated under reduced pressure. The residue was purified by flash chromatography (ISCO®; about 40 g AgelaFlash® Silica Flash Column, petroleum ether/EtOAc with EtOAc from 0~39%, flow rate=50 mL/min, 254 nm) to afford 2-nitro-4-(2-pyridyl) aniline (about 1.6 g). LCMS (ESI) [M+H]⁺ m/z: calcd 216.1, found 216.1.

Step 2: Synthesis of tert-butyl N-tert-butoxycarbonyl-N-[2-nitro-4-(2-pyridyl)phenyl]carbamate To a solution of 2-nitro-4-(2-pyridyl)aniline (about 1.6 g, 7.43 mmol), TEA (about 3.1 mL, 22.2 mmol) and DMAP (about 454 mg, 3.72 mmol) in DCM (about 15 mL) was added tert-butoxycarbonyl tert-butyl carbonate (about 4.3 mL, 18.7 mmol). The mixture was stirred at about 20° C. for about 2 hours. The resulting mixture was concentrated under reduced pressure. The residue was triturated with MeOH (about 10 mL). The mixture was filtered. The filter cake was concentrated under reduced pressure to give tert-butyl N-tert-butoxycarbonyl-N-[2-nitro-4-(2-pyridyl)phenyl]carbamate (about 2 g). LCMS (ESI) [M+H]⁺ m/z: calcd 416.2, found 416.1.

Step 3: Synthesis of tert-butyl N-[2-nitro-4-(2-pyridyl)phenyl]carbamate

To a solution of tert-butyl N-tert-butoxycarbonyl-N-[2-nitro-4-(2-pyridyl)phenyl]carbamate (about 1.92 g, 4.62 mmol) in DCM (about 12 mL) was added TFA (about 0.9 mL, 11.7 mmol). The mixture was stirred at about 20° C. for about 3 hours. To the mixture was added TFA (about 0.36 mL, 4.67 mmol). The mixture was stirred at about 20° C. for about 2 hours. The resulting mixture was quenched by addition of NaHCO₃ (about 20 mL) to adjust the pH=8, and extracted with DCM (about 20 mL*3). The combined organic layer was dried over anhydrous Na₂SO₄, filtered and concentrated under reduced pressure to give tert-butyl N-[2-nitro-4-(2-pyridyl)phenyl]carbamate (about 1.42 g). ¹H NMR (400 MHz, DMSO-d₆) δ ppm 9.74 (s, 1H), 8.68-8.71 (m, 1H), 8.67 (d, J=2.0 Hz, 1H), 8.39 (dd, J=8.5, 2.3 Hz, 1H), 8.07 (d, J=8.0 Hz, 1H), 7.92 (td, J=7.7, 1.9 Hz, 1H), 7.82 (d, J=8.8 Hz, 1H), 7.41 (ddd, J=7.4, 4.8, 0.9 Hz, 1H), 1.47 (s, 9H). LCMS (ESI) [M+H]⁺ m/z: calcd 316.1, found 316.0.

Step 4: Synthesis of tert-butyl N-[2-amino-4-(2-pyridyl)phenyl]carbamate

To a solution of tert-butyl N-[2-nitro-4-(2-pyridyl)phenyl]carbamate (about 1.42 g, 4.50 mmol) in MeOH (about 12 mL) was added Pd—C(about 142 mg, 10% of Pd with 50% of water, wt %) under N₂ atmosphere. The suspension was degassed and purged with hydrogen for 3 times. The mixture was stirred under hydrogen (in balloon) at about 20° C. for about 12 hours. The mixture was filtered. The filtrate was concentrated under reduced pressure to give tert-butyl N-[2-amino-4-(2-pyridyl)phenyl]carbamate (about 1.3 g). ¹H NMR (400 MHz, DMSO-d₆) δ ppm 8.59 (d, J=4.5 Hz, 1H), 8.39 (s, 1H), 7.73-7.87 (m, 2H), 7.50 (d, J=1.9 Hz, 1H), 7.39 (d, J=8.3 Hz, 1H), 7.20-7.32 (m, 2H), 5.01 (s, 2H), 1.48 (s, 9H). LCMS (ESI) [M+H]⁺ m/z: calcd 286.1, found 286.1.

Step 5: Synthesis of tert-butyl N-[[4-[[2-(tert-butoxycarbonylamino)-5-(2-pyridyl)phenyl]carbamoyl] phenyl]-methyl-oxo-sulfanylidene]carbamate A mixture of tert-butyl N-[2-amino-4-(2-pyridyl)phenyl]carbamate (about 100 mg, 0.350 mmol), 4-(N-tert-butoxycarbonyl-S-methyl-sulfonimidoyl)benzoic acid (about 105 mg, 0.351 mmol), 3-(ethyliminomethyleneamino)-N,N-dimethyl-propan-1-amine;hydrochloride (about 101 mg, 0.527 mmol) and pyridine (about 4 mL) was stirred at about 50° C. for about 1 hour. The resulting mixture was concentrated under reduced pressure. The residue was purified by purified by flash chromatography (ISCO®; about 4 g AgelaFlash® Silica Flash Column, petroleum ether/EtOAc with EtOAc from 0~69%, flow rate=30 mL/min, 254 nm) to afford tert-butyl N-[[4-[[2-(tert-butoxycarbonylamino)-5-(2-pyridyl)phenyl]carbamoyl]phenyl]-methyl-oxo-sulfanylidene]carbamate (about 140 mg). ¹H NMR (400 MHz, DMSO-d₆) δ ppm 10.17 (s, 1H), 8.86 (s, 1H), 8.65 (d, J=4.0 Hz, 1H), 8.22-8.28 (m, 3H), 8.10 (d, J=8.6 Hz, 2H), 7.92-7.98 (m, 2H), 7.85-7.90 (m, 1H), 7.79 (d, J=8.6 Hz, 1H), 7.34 (ddd, J=6.7, 5.4, 1.0 Hz, 1H), 3.46 (s, 3H), 1.46 (s, 9H), 1.27 (s, 9H); LCMS (ESI) [M+H]⁺ m/z: calcd 567.2, found 567.3.

Step 6: Synthesis of N-[2-amino-5-(2-pyridyl)phenyl]-4-(methylsulfonimidoyl)benzamide To a solution of tert-butyl N-[[4-[[2-(tert-butoxycarbonylamino)-5-(2-pyridyl)phenyl]carbamoyl]phenyl]-methyl-oxo-sulfanylidene]carbamate (about 140 mg, 0.247 mmol) in DCM (about 10 mL) was added TFA (about 0.4 mL, 5.19 mmol). The mixture was stirred at about 20° C. for about 1 hour. To the solution was added TFA (about 0.4 mL, 5.19 mmol). The mixture was stirred at about 20° C. for about 1 hour. The resulting mixture was concentrated under reduced pressure and adjusted to about pH=8 with 28% NH₃—H₂O aqueous solution. The residue was purified by preparative HPLC (Instrument: Gilson GX-281 Liquid Handler, Gilson 322 Pump, Gilson 156 UV Detector; Column: Durashell 80×40 mm×3 μm; Mobile phase A: H₂O with 10 mmol NH₄HCO₃ (v %); Mobile phase B: MeCN; Gradient: B from 12% to 42% in 9.5 min, hold 100% B for 2 min; Flow Rate: 25 mL/min; Column Temperature: about 30° C.; Wavelength: 220 nm, 254 nm) to afford N-[2-amino-5-(2-pyridyl)phenyl]-4-(methylsulfonimidoyl)benzamide (about 44.8 mg). ¹H NMR (400 MHz, DMSO-d₆) δ ppm 9.94 (s, 1H), 8.55 (d, J=4.8 Hz, 1H), 8.20 (d, J=8.3 Hz, 2H), 8.06 (d, J=8.3 Hz, 2H), 7.99 (s, 1H), 7.75-7.80 (m, 3H), 7.20 (td, J=5.1, 2.8 Hz, 1H), 6.86 (d, J=8.5 Hz, 1H), 5.34 (s, 2H), 3.13 (s, 3H); LCMS (ESI) [M+H]⁺ m/z: calcd 367.1, found 367.2; HPLC: 96.62%@220 nm; 98.44%@254 nm.

Example 61. Synthesis of N-[2-amino-5-(2,4-difluorophenyl)phenyl]-4-(cyclopropylsulfonimidoyl)benzamide (Compound 118)

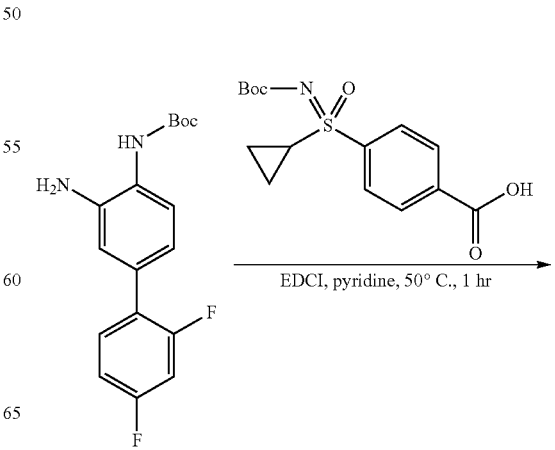

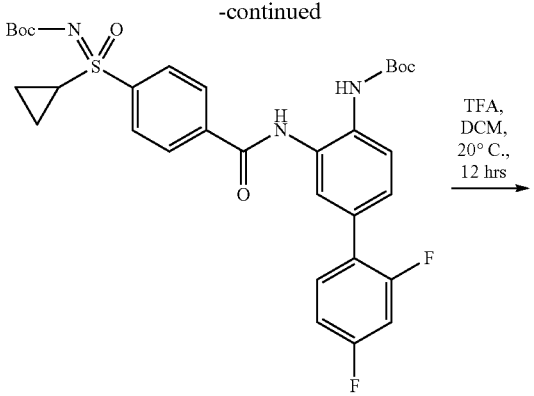

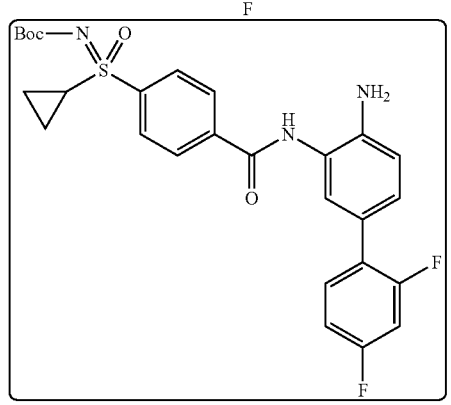

Step 1: Synthesis of tert-butyl N-[[4-[[2-(tert-butoxycarbonylamino)-5-(2,4-difluorophenyl)phenyl]carbamoyl]phenyl]-cyclopropyl-oxo-sulfanylidene]carbamate A mixture of 4-(N-tert-butoxycarbonyl-S-cyclopropylsulfonimidoyl)benzoic acid (about 150 mg, 0.461 mmol), tert-butyl N-[2-amino-4-(2,4-difluorophenyl)phenyl]carbamate (about 150 mg, 0.468 mmol) and EDCI (about 100 mg, 0.522 mmol) in pyridine (about 10 mL) was stirred at about 50° C. for about 1 hour. The mixture was concentrated under reduced pressure. The residue was purified by flash chromatography (Biotage®; about 12 g AgelaFlash® Silica Flash Column, petroleum ether/EtOAc with EtOAc from 0~45%, flow rate=15 mL/min, 254 nm) to afford tert-butyl N-[[4-[[2-(tert-butoxycarbonylamino)-5-(2,4-difluorophenyl)phenyl]carbamoyl]phenyl]-cyclopropyl-oxo-sulfanylidene]carbamate (about 180 mg). LCMS (ESI) [M+H]$^+$ m/z: calcd 628.2, found 628.3.

Step 2: Synthesis of N-[2-amino-5-(2,4-difluorophenyl)phenyl]-4-(cyclopropylsulfonimidoyl)benzamide To a mixture of tert-butyl N-[[4-[[2-(tert-butoxycarbonylamino)-5-(2,4-difluorophenyl)phenyl]carbamoyl]phenyl]-cyclopropyl-oxo-sulfanylidene]carbamate (about 180 mg, 0.287 mmol) in DCM (about 5 mL) was added TFA (about 0.45 mL, 5.84 mmol) at about 20° C. The mixture was stirred at about 20° C. for about 1 hour. The mixture was concentrated under reduced pressure. The residue was purified by preparative HPLC (Instrument: Gilson GX-281 Liquid Handler, Gilson 322 Pump, Gilson 156 UV Detector; Column: Phenomenex C18 80×40 mm×3 μm; Mobile phase A: H$_2$O with 0.05% NH$_3$—H$_2$O (v %); Mobile phase B: MeCN; Gradient: B from 30% to 60% in 7.8 mins, hold 100% B for 1 min; Flow Rate: 25 mL/min; Column Temperature: about 30° C.; Wavelength: 220 nm, 254 nm) to afford N-[2-amino-5-(2,4-difluorophenyl)phenyl]-4-(cyclopropylsulfonimidoyl)benzamide (about 30.4 mg). $^1$H NMR (400 MHz, DMSO-d$_6$) δ ppm 9.91 (s, 1H), 8.17 (d, J=8.3 Hz, 2H), 8.01 (d, J=8.5 Hz, 2H), 7.45-7.54 (m, 1H), 7.39 (s, 1H), 7.29 (ddd, J=11.4, 9.2, 2.8 Hz, 1H), 7.19 (d, J=8.5 Hz, 1H), 7.13 (d, J=8.3, 2.4 Hz, 1H), 6.87 (d, J=8.3 Hz, 1H), 5.14 (s, 2H), 2.69-2.77 (m, 1H), 1.10-1.17 (m, 1H), 0.98-1.04 (m, 1H), 0.90-0.97 (m, 2H); $^{19}$F NMR (376 MHz, DMSO-d$_6$) δ ppm −113.023, −113.907; LCMS (ESI) [M+H]$^+$ m/z: calcd 428.1, found 428.1; HPLC: 95.09%@220 nm, 98.28%@254 nm.

Example 62. Synthesis of N-[2-amino-5-(2,4-difluorophenyl)phenyl]-4-(methylsulfonimidoyl)benzamide (Compound 117)

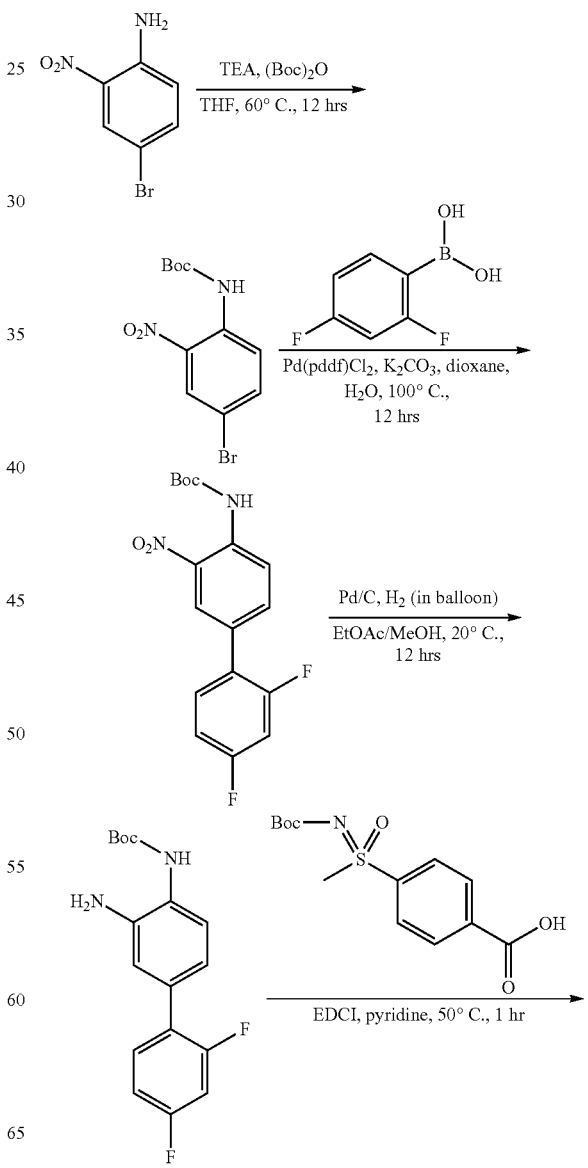

-continued

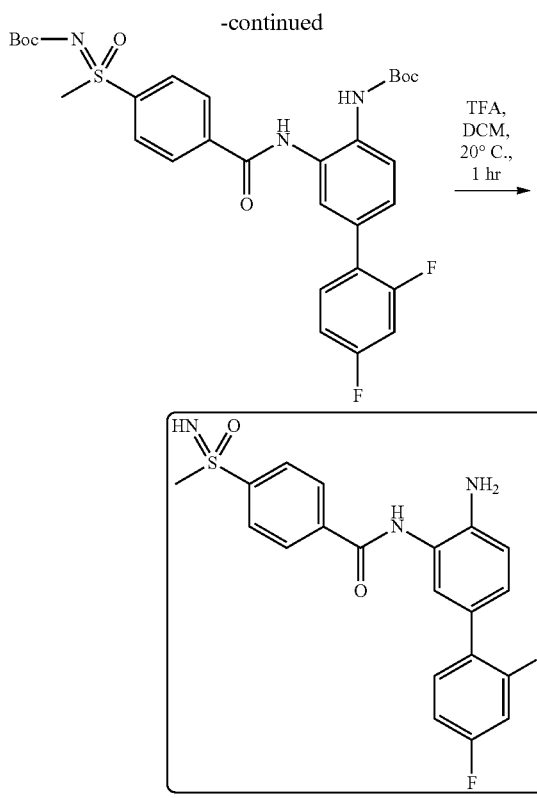

Step 1: Synthesis of tert-butyl N-(4-bromo-2-nitro-phenyl)carbamate

A mixture of 4-bromo-2-nitro-aniline (about 4.1 g, 18.9 mmol), (Boc)$_2$O (about 10 g, 45.8 mmol) and TEA (about 10 mL, 71.8 mmol) in THF (about 50 mL) was stirred at about 60° C. for about 12 hours. The resulting mixture was concentrated under reduced pressure. The residue was purified by flash chromatography (Biotage®; about 20 g AgelaFlash® Silica Flash Column, petroleum ether/EtOAc with EtOAc from 0~0%, flow rate=50 mL/min, 254 nm) to afford tert-butyl N-(4-bromo-2-nitro-phenyl)carbamate (about 1.97 g). $^1$H NMR (400 MHz, DMSO-d$_6$) δ ppm 9.68 (s, 1H), 8.12 (d, J=2.5 Hz, 1H), 7.86 (dd, J=8.8, 2.3 Hz, 1H), 7.58 (d, J=8.8 Hz, 1H), 1.43 (s, 9H); LCMS (ESI) [M+H]$^+$ m/z: calcd 317.0, found 217.0 (Boc cleaved mass).

Step 2: Synthesis of tert-butyl N-[4-(2,4-difluoro-phenyl)-2-nitro-phenyl]carbamate A mixture of tert-butyl N-(4-bromo-2-nitro-phenyl)carbamate (about 1.97 g, 6.21 mmol), (2,4-difluorophenyl) boronic acid (about 1.3 g, 8.23 mmol), K$_2$CO$_3$ (about 2.6 g, 18.8 mmol) and Pd(dppf)Cl$_2$ (about 455 mg, 0.622 mmol) in H$_2$O (about 40 mL) and dioxane (about 40 mL) was stirred at about 100° C. for about 12 hours under N$_2$ atmosphere. The mixture was extracted with EtOAc (about 50 mL*3). The combined organic layers were washed with brine (about 50 mL*3), dried over anhydrous Na$_2$SO$_4$, filtered and concentrated under reduced pressure. The residue was purified by flash chromatography (Biotage®; about 40 g Agela-Flash® Silica Flash Column, petroleum ether/EtOAc with EtOAc from 0~21%, flow rate=100 mL/min, 254 nm) to afford tert-butyl N-[4-(2,4-difluorophenyl)-2-nitro-phenyl] carbamate (about 580 mg). $^1$H NMR (400 MHz, DMSO-d$_6$) δ ppm 9.74 (s, 1H), 8.08 (s, 1H), 7.82-7.88 (m, 1H), 7.76 (d, J=8.5 Hz, 1H), 7.65-7.68 (m, 1H), 7.42 (ddd, J=11.3, 9.2, 2.6 Hz, 1H), 7.24 (d, J=8.6, 2.4 Hz, 1H), 1.47 (s, 9H). $^{19}$F NMR (376 MHz, DMSO-d$_6$) δ ppm −109.916, −113.775.

Step 3: Synthesis of tert-butyl N-[2-amino-4-(2,4-difluorophenyl)phenyl]carbamate To a mixture of tert-butyl N-[4-(2,4-difluorophenyl)-2-nitro-phenyl]carbamate (about 580 mg, 1.66 mmol) in EtOAc (about 10 mL) and MeOH (about 10 mL) was added Pd—C(about 60 mg, 10% of Pd with 50% of water, wt %) under N$_2$ atmosphere. The suspension was degassed and purged with hydrogen for about 3 times. The mixture was stirred under hydrogen (in balloon) at about 20° C. for about 12 hours. The resulting mixture was filtered. The filtrate was concentrated under reduced pressure to give tert-butyl N-[2-amino-4-(2,4-difluorophenyl)phenyl]carbamate (about 520 mg). $^1$H NMR (400 MHz, DMSO-d$_6$) δ ppm 8.37 (s, 1H), 7.47 (d, J=8.9, 6.8 Hz, 1H), 7.25-7.34 (m, 2H), 7.11-7.16 (m, 1H), 6.85 (s, 1H), 6.67 (dd, J=8.0, 1.5 Hz, 1H), 4.99 (s, 2H), 1.47 (s, 9H); LCMS (ESI) [M+H]$^+$ m/z: calcd 321.1, found 321.1. $^{19}$F NMR (376 MHz, DMSO-d$_6$) δ ppm −112.090, −113.416.

Step 4: Synthesis of tert-butyl N-[[4-[[2-(tert-butoxycarbonylamino)-5-(2,4-difluorophenyl)phenyl]carbamoyl]phenyl]-methyl-oxo-sulfanylidene]carbamate A mixture of tert-butyl N-[2-amino-4-(2,4-difluorophenyl)phenyl]carbamate (about 200 mg, 0.624 mmol), 4-(N-tert-butoxycarbonyl-S-methyl-sulfonimidoyl)benzoic acid (about 100 mg, 0.334 mmol) and EDCI (about 132 mg, 0.689 mmol) in pyridine (about 10 mL) was stirred at about 50° C. for about 1 hour. The resulting mixture was concentrated under reduced pressure. The residue was purified by flash chromatography (Biotage®; about 12 g AgelaFlash® Silica Flash Column, petroleum ether/EtOAc with EtOAc from 0~47%, flow rate=15 mL/min, 254 nm) to afford tert-butyl N-[[4-[[2-(tert-butoxycarbonylamino)-5-(2,4-difluorophenyl)phenyl]carbamoyl]phenyl]-methyl-oxo-sulfanylidene]carbamate (about 110 mg). LCMS (ESI) [M+H]$^+$ m/z: calcd 602.2, found 502.1 (Boc cleaved mass).

Step 5: Synthesis of N-[2-amino-5-(2,4-difluorophenyl)phenyl]-4-(methylsulfonimidoyl)benzamide To a mixture of tert-butyl N-[4-(2,4-difluorophenyl)-2-[[4-(methylsulfonimidoyl)benzoyl]amino]phenyl]carbamate (about 110 mg, 0.219 mmol) in DCM (about 5 mL) was added TFA (about 0.34 mL, 4.41 mmol) at about 20° C. The mixture was stirred at about 20° C. for about 1 hour. The mixture was concentrated under reduced pressure. The residue was purified by preparative HPLC (Instrument: Gilson GX-281 Liquid Handler, Gilson 322 Pump, Gilson 156 UV Detector; Column: Phenomenex C18 80×40 mm×3 μm; Mobile phase A: H$_2$O with 0.05% NH$_3$—H$_2$O (v %); Mobile phase B: MeCN; Gradient: B from 35% to 65% in 9.5 mins, hold 100% B for 0 min; Flow Rate: 30 mL/min; Column Temperature: 30° C.; Wavelength: 220 nm, 254 nm) to afford N-[2-amino-5-(2,4-difluorophenyl)phenyl]-4-(methylsulfonimidoyl)benzamide (about 29 mg). LCMS (ESI) [M+H]$^+$ m/z: calcd 402.1, found 402.1; $^1$H NMR (400 MHz, DMSO-d$_6$) δ ppm 9.92 (s, 1H), 8.18 (d, J=8.3 Hz, 2H), 8.05 (d, J=8.3 Hz, 2H), 7.45-7.53 (m, 1H), 7.39 (s, 1H), 7.28

(ddd, J=11.4, 9.2, 2.5 Hz, 1H), 7.17-7.23 (m, 1H), 7.09-7.16 (m, 1H), 6.87 (d, J=8.3 Hz, 1H), 3.13 (s, 3H); $^{19}$F NMR (376 MHz, DMSO-$d_6$) δ ppm −113.032, −113.916; HPLC: 97.72%@220 nm, 98.75%@254 nm.

Example 63. Synthesis of N-[2-amino-5-(3-pyridyl)phenyl]-4-(cyclopropylsulfonimidoyl)benzamide (Compound 116)

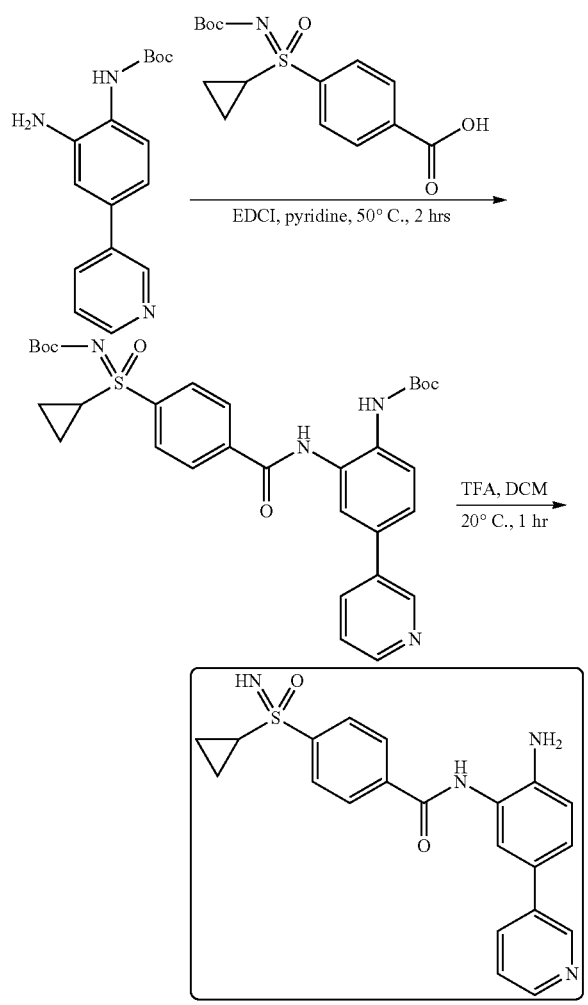

Step 1: Synthesis of tert-butyl N-[[4-[[2-(tert-butoxycarbonylamino)-5-(3-pyridyl)phenyl]carbamoyl]phenyl]-cyclopropyl-oxo-sulfanylidene]carbamate A mixture of tert-butyl N-[2-amino-4-(3-pyridyl)phenyl]carbamate (about 100 mg, 0.350 mmol), 4-(N-tert-butoxycarbonyl-S-cyclopropyl-sulfonimidoyl)benzoic acid (about 137 mg, 0.421 mmol), 3-(ethyliminomethyleneamino)-N,N-dimethyl-propan-1-amine;hydrochloride (about 101 mg, 0.527 mmol) and pyridine (about 8 mL) was stirred at about 50° C. for about 2 hours. The resulting mixture was concentrated under reduced pressure. The residue was purified by flash chromatography (ISCO®; about 4 g AgelaFlash® Silica Flash Column, petroleum ether/EtOAc with EtOAc from 0~69%, flow rate=35 mL/min, 254 nm) to afford tert-butyl N-[[4-[[2-(tert-butoxycarbonylamino)-5-(3-pyridyl)phenyl]carbamoyl]phenyl]-cyclopropyl-oxo-sulfanylidene]carbamate (about 180 mg). LCMS (ESI) [M+H]$^+$ m/z: calcd 593.2, found 593.3.

Step 2: Synthesis of N-[2-amino-5-(3-pyridyl)phenyl]-4-(cyclopropylsulfonimidoyl)benzamide A mixture of tert-butyl N-[[4-[[2-(tert-butoxycarbonylamino)-5-(3-pyridyl)phenyl]carbamoyl]phenyl]-cyclopropyl-oxo-sulfanylidene]carbamate (about 180 mg, 0.304 mmol), TFA (about 0.47 mL, 6.10 mmol) and DCM (about 8 mL) was stirred at 20° C. for 1 hour. The resulting mixture was concentrated under reduced pressure. The residue was purified by preparative HPLC (Instrument: Gilson GX-281 Liquid Handler, Gilson 322 Pump, Gilson 156 UV Detector; Column: Durashell 80×40 mm×3 µm; Mobile phase A: $H_2O$ with 10 mmol $NH_4HCO_3$ (v %); Mobile phase B: MeCN; Gradient: B from 22% to 52% in 9.5 min, hold 100% B for 2 min; Flow Rate: 30 mL/min; Column Temperature: about 30° C.; Wavelength: 220 nm, 254 nm). The product was not clear on HPLC. The residue was further purified by preparative HPLC (Instrument: Gilson GX-281 Liquid Handler, Gilson 322 Pump, Gilson 156 UV Detector; Column: Durashell 80×40 mm×3 µm; Mobile phase A: $H_2O$ with 10 mmol $NH_4HCO_3$ (v %); Mobile phase B: MeCN; Gradient: B from 20% to 50% in 9.5 min, hold 100% B for 0 min; Flow Rate: 30 mL/min; Column Temperature: 30° C.; Wavelength: 220 nm, 254 nm) to afford N-[2-amino-5-(3-pyridyl)phenyl]-4-(cyclopropylsulfonimidoyl)benzamide (about 100 mg). $^1$H NMR (400 MHz, DMSO-$d_6$) δ ppm 9.92 (s, 1H), 8.80 (s, 1H), 8.45 (d, J=3.5 Hz, 1H), 8.18 (d, J=8.3 Hz, 2H), 8.02 (d, J=8.5 Hz, 2H), 7.95 (d, J=8.3 Hz, 1H), 7.59 (d, J=1.8 Hz, 1H), 7.37-7.45 (m, 2H), 6.90 (d, J=8.5 Hz, 1H), 5.28 (brs, 2H), 4.40 (brs, 1H), 2.69-2.76 (m, 1H), 1.11-1.19 (m, 1H), 0.88-1.04 (m, 3H). LCMS (ESI) [M+H]$^+$ m/z: calcd 393.1, found 393.2. HPLC: 97.280%@220 nm, 96.850%@254 nm.

Example 64. Synthesis of N-[[4-[[2-(tert-butoxycarbonylamino)-5-(2-thienyl)phenyl]carbamoyl]phenyl]-cyclopropyl-oxo-sulfanylidene]carbamate (Compound 112), rel-(R)—N-[2-amino-5-(2-thienyl)phenyl]-4-(cyclopropylsulfonimidoyl)benzamide (Compound 114) and rel-(S)—N-[2-amino-5-(2-thienyl)phenyl]-4-(cyclopropylsulfonimidoyl)benzamide (Compound 115)

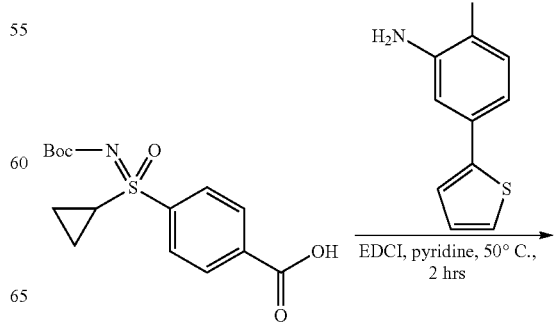

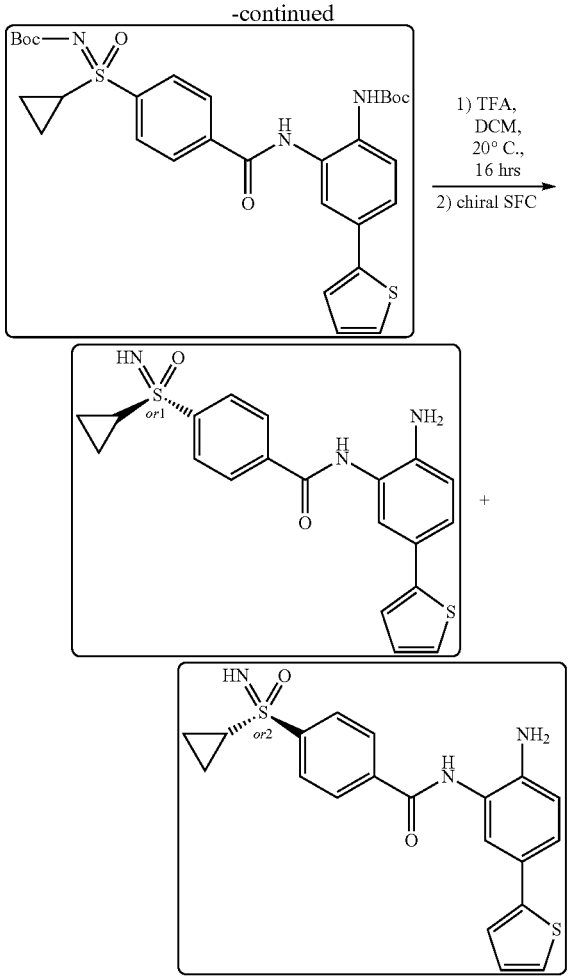

Step 1: Synthesis of tert-butyl N-[[4-[[2-(tert-butoxycarbonylamino)-5-(2-thienyl)phenyl]carbamoyl]phenyl]-cyclopropyl-oxo-sulfanylidene]carbamate To a solution of 4-(N-tert-butoxycarbonyl-S-cyclopropyl-sulfonimidoyl)benzoic acid (about 350 mg, 1.08 mmol) and tert-butyl N-[2-amino-4-(2-thienyl)phenyl]carbamate (about 470 mg, 1.62 mmol) in pyridine (about 10 mL) was added EDCI (about 410 mg, 2.14 mmol). The mixture was stirred at about 50° C. for about 2 hours. The resulting mixture was concentrated under reduced pressure. The residue was purified by flash chromatography (ISCO®; about 20 g Agela-Flash® Silica Flash Column, petroleum ether/EtOAc with EtOAc from 0~78%, flow rate=30 mL/min, 254 nm) to afford tert-butyl N-[[4-[[2-(tert-butoxycarbonylamino)-5-(2-thienyl)phenyl]carbamoyl]phenyl]-cyclopropyl-oxo-sulfanylidene]carbamate (about 500 mg). $^1$H NMR (400 MHz, DMSO-$d_6$) δ ppm 10.11 (s, 1H), 8.79 (s, 1H), 8.21 (d, J=8.4 Hz, 2H), 8.04 (d, J 8.5 Hz, 2H), 7.78 (d, J=1.8 Hz, 1H), 7.68 (d, J=8.6 Hz, 1H), 7.50-7.56 (m, 2H), 7.45 (d, J 2.8 Hz, 1H), 7.13 (dd, J=5.0, 3.6 Hz, 1H), 3.03-3.14 (m, 1H), 1.44 (s, 9H), 1.31-1.40 (m, 1H), 1.17-1.30 (m, 10H), 0.94-1.08 (m, 2H); LCMS (ESI) [M+H]$^+$ m/z: calcd 598.2; found 598.2; HPLC: 100%@220 nm; 100%@254 nm.

Step 2: Synthesis of N-[2-amino-5-(2-thienyl)phenyl]-4-(cyclopropylsulfonimidoyl)benzamide and N-[2-amino-5-(2-thienyl)phenyl]-4-(cyclopropylsulfonimidoyl)benzamide To a solution of tert-butyl N-[[4-[[2-(tert-butoxycarbonylamino)-5-(2-thienyl)phenyl]carbamoyl]phenyl]-cyclopropyl-oxo-sulfanylidene]carbamate (about 485 mg, 0.811 mmol) in DCM (about 5 mL) was added TFA (about 1 mL, 13.0 mmol). The mixture was stirred at about 20° C. for about 16 hours. The resulting mixture was concentrated under reduced pressure. The residue was purified by flash chromatography (Biotage®, Column: SepaFlash®Sphercial C18, 20 g, 40-60 μm, 120 Å; MeCN/water (0.05% NH$_3$—H$_2$O) with MeCN from 0~40%, 30 mL/min, 254 nm) to afford N-[2-amino-5-(2-thienyl)phenyl]-4-(cyclopropylsulfonimidoyl)benzamide (about 220 mg). The residue was purified by SFC (Instrument: Thar800Q; Column: Daicel chiralcel OJ (250 mm*30 mm, 10 um); Mobile phase: supercritical CO$_2$/EtOH (0.1% NH$_3$·H$_2$O, 60%)=40/60; Flow Rate: 80 mL/min; Column Temperature: about 38° C.; Nozzle Pressure: 100 bar; Nozzle Temperature: about 60° C.; Evaporator Temperature: about 20° C.; Trimmer Temperature: about 25° C.; Wavelength: 220 nm) to afford the products. Stereochemistry was arbitrarily assigned Rel-(R)—N-[2-amino-5-(2-thienyl)phenyl]-4-(cyclopropylsulfonimidoyl)benzamide (about 66 mg, single enantiomer, Peak 1, Retention time: 3.763 min). $^1$H NMR (400 MHz, DMSO-$d_6$) δ ppm 9.92 (s, 1H), 8.18 (d, J=8.3 Hz, 2H), 8.02 (d, J=8.3 Hz, 2H), 7.48 (d, J=1.8 Hz, 1H), 7.29-7.40 (m, 2H), 7.25 (d, J=2.8 Hz, 1H), 7.06 (dd, J=5.0, 3.5 Hz, 1H), 6.82 (d, J=8.5 Hz, 1H), 5.23 (s, 2H), 4.41 (s, 1H), 2.68-2.79 (m, 1H), 1.14 (dt, J=10.4, 4.0 Hz, 1H), 0.86-1.05 (m, 3H); LCMS (ESI) [M+H]$^+$ m/z: calcd 398.1, found 398.1; HPLC: 99.820%@220 nm, 99.830%@254 nm; 100% ee.

Rel-(S)—N-[2-amino-5-(2-thienyl)phenyl]-4-(cyclopropylsulfonimidoyl)benzamide (about 76 mg, single enantiomer, Peak 2, Retention time: 3.763 min). $^1$H NMR (400 MHz, DMSO-$d_6$) δ ppm 9.91 (s, 1H), 8.17 (d, J=8.3 Hz, 2H), 8.01 (d, J=8.3 Hz, 2H), 7.48 (d, J=1.8 Hz, 1H), 7.29-7.38 (m, 2H), 7.25 (d, J=2.8 Hz, 1H), 7.05 (dd, J=5.0, 3.5 Hz, 1H), 6.81 (d, J=8.5 Hz, 1H), 5.22 (s, 2H), 4.40 (s, 1H), 2.66-2.76 (m, 1H), 1.14 (ddd, J=10.3, 7.2, 3.1 Hz, 1H), 0.88-1.03 (m, 3H); LCMS (ESI) [M+H]$^+$ m/z: calcd 398.1, found 398.0; HPLC: 99.170%@220 nm, 1000%@254 nm; 96.9% ee.

Example 65. Synthesis of N-[2-amino-5-(2-thienyl)phenyl]-5-(methylsulfonimidoyl)pyridine-2-carboxamide (Compound 113)

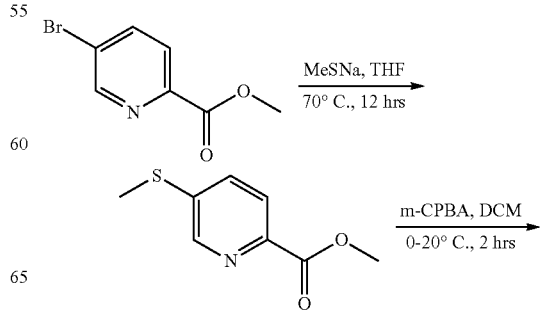

419

-continued

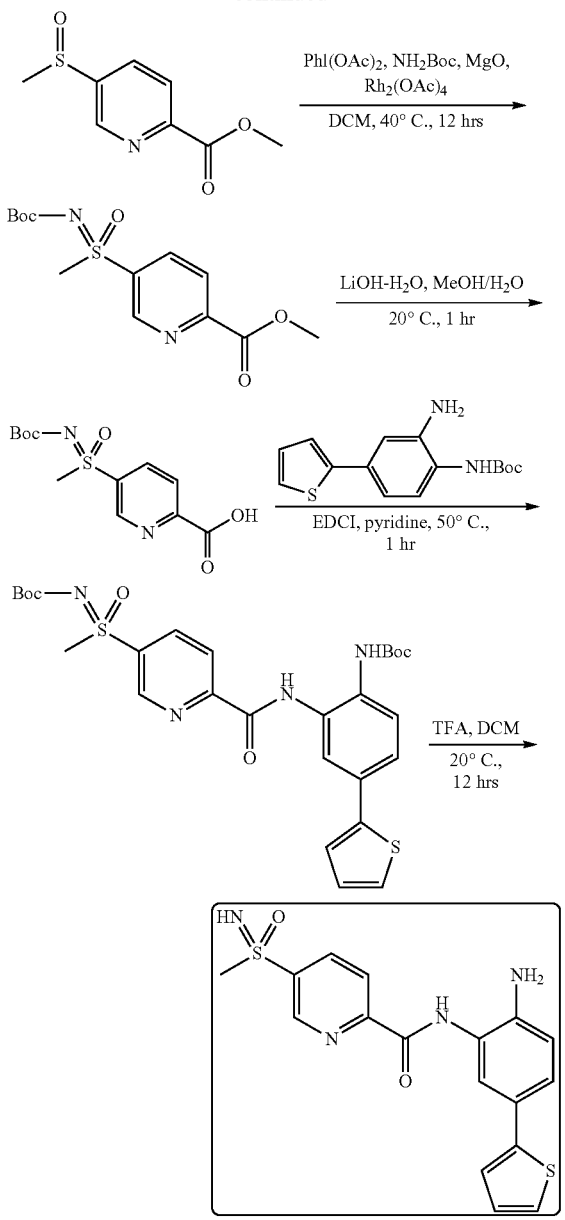

Step 1: Synthesis of methyl 5-methylsulfanylpyridine-2-carboxylate

To a solution of methyl 5-bromopyridine-2-carboxylate (about 2 g, 9.26 mmol) in THF (30 mL) was added sodium; methanethiolate (about 810 mg, 11.6 mmol). The mixture was stirred at about 70° C. for about 12 hours. The reaction mixture was concentrated under reduced pressure. The residue was purified by flash chromatography (ISCO®; about 20 g AgelaFlash® Silica Flash Column, petroleum ether/EtOAc with EtOAc from 0~50%, flow rate=50 mL/min, 254 nm) to afford methyl 5-methylsulfanylpyridine-2-carboxylate (about 1.25 g). $^1$H NMR (400 MHz, chloroform-d) δ ppm 8.55 (d, J=2.4 Hz, 1H), 8.03 (d, J=8.4 Hz, 1H), 7.61 (dd, J=8.4, 2.4 Hz, 1H), 4.00 (s, 3H), 2.56 (s, 3H); LCMS (ESI) [M+H]$^+$ m/z: calcd 184.0, found 183.8.

420

Step 2: Synthesis of methyl 5-methylsulfinylpyridine-2-carboxylate

To a solution of methyl 5-methylsulfanylpyridine-2-carboxylate (about 1.25 g, 6.82 mmol) in DCM (about 20 mL) was added 3-chlorobenzenecarboperoxoic acid (about 1.53 g, 7.54 mmol, 85 wt %) at about 0° C. After addition, the reaction mixture was stirred at 20° C. for 2 hours. The reaction mixture was quenched with saturated NaHCO$_3$ aqueous (about 20 mL) and extracted with DCM (about 30 mL*3). The combined organic layers were dried over Na$_2$SO$_4$ and filtered. The filtrate was concentrated under reduced pressure. The residue was purified by flash chromatography (ISCO®; about 40 g AgelaFlash® Silica Flash Column, EtOAc/MeOH with MeOH from 0~20%, flow rate=40 mL/min, 254 nm) to afford methyl 5-methylsulfinylpyridine-2-carboxylate (about 1.2 g). $^1$H NMR (400 MHz, chloroform-d) δ ppm 8.83-8.93 (m, 1H), 8.28-8.37 (m, 1H), 8.24 (dd, J=8.0, 2.4 Hz, 1H), 4.05 (s, 3H), 2.85 (s, 3H); LCMS (ESI) [M+H]$^+$ m/z: calcd 200.0, found 199.8.

Step 3: Synthesis of methyl 5-(N-tert-butoxycarbonyl-S-methyl-sulfonimidoyl)pyridine-2-carboxylate To a solution of methyl 5-methylsulfinylpyridine-2-carboxylate (about 1.2 g, 6.02 mmol), tert-butyl carbamate (about 800 mg, 6.83 mmol), [acetoxy(phenyl)-iodanyl] acetate (about 2.91 g, 9.03 mmol) and oxomagnesium (about 1.20 g, 29.8 mmol) in DCM (about 50 mL) was added diacetoxyrhodium (about 60 mg, 0.272 mmol). The reaction mixture was stirred at about 40° C. for about 12 hours. The reaction mixture was concentrated under reduced pressure. The residue was purified by flash chromatography (ISCO®; about 40 g AgelaFlash® Silica Flash Column, petroleum ether/EtOAc with EtOAc from 0~100%, flow rate=40 mL/min, 254 nm) to afford methyl 5-(N-tert-butoxycarbonyl-S-methyl-sulfonimidoyl)pyridine-2-carboxylate (about 1.26 g). LCMS (ESI) [M+H]$^+$ m/z: calcd 259.1, found 258.9 (t-Bu cleaved mass).

Step 4: Synthesis of 5-(N-tert-butoxycarbonyl-S-methyl-sulfonimidoyl)pyridine-2-carboxylic acid To a solution of methyl 5-(N-tert-butoxycarbonyl-S-methyl-sulfonimidoyl)pyridine-2-carboxylate (about 1.26 g, 4.01 mmol) in MeOH (about 20 mL) and H$_2$O (about 10 mL) was added lithium;hydroxide;hydrate (1.68 g, 40.1 mmol). The mixture was stirred at about 20° C. for about 1 hour. The mixture was concentrated under reduced pressure to remove the organic solvent. The aqueous phase was adjusted to about pH=4 with 2N HCl aqueous solution. The mixture was filtered. The filter cake was dried under reduced pressure to give 5-(N-tert-butoxycarbonyl-S-methyl-sulfonimidoyl) pyridine-2-carboxylic acid (about 0.9 g), which was directly used without further purification. $^1$H NMR (400 MHz, DMSO-d$_6$) δ ppm 9.14 (d, J=2.0 Hz, 1H), 8.49 (dd, J=8.4, 2.4 Hz, 1H), 8.28 (d, J=8.4 Hz, 1H), 3.54 (s, 3H), 1.23 (s, 9H).

Step 5: Synthesis of tert-butyl N-[[6-[[2-(tert-butoxycarbonylamino)-5-(2-thienyl)phenyl]carbamoyl]-3-pyridyl]-methyl-oxo-sulfanylidene]carbamate To a solution of 5-(N-tert-butoxycarbonyl-S-methyl-sulfonimidoyl)pyridine-2-carboxylic acid (about 60 mg, 0.20 mmol) in pyridine (about 2 mL) were added tert-butyl N-[2-amino-4-(2-thienyl)phenyl]carbamate (about 60 mg, 0.207 mmol) and 3-(ethyliminomethyleneamino)-N,N-dimethyl-propan-1-amine;hydrochloride (about 60 mg, 0.313 mmol). The mixture was stirred at about 50° C. for about 1 hour. The reaction mixture was concentrated under reduced pressure. The residue was purified by preparative TLC (silica, petroleum ether/EtOAc=1/1) to afford tert-butyl N-[[6-[[2-(tert-butoxycarbonylamino)-5-(2-thienyl)phenyl]carbamoyl]-3-pyridyl]-methyl-oxo-sulfanylidene]carbamate (about 40 mg). LCMS (ESI) [M+H]$^+$ m/z: calcd 573.2; found 373.0 (Boc cleaved mass).

Step 6: Synthesis of N-[2-amino-5-(2-thienyl)phenyl]-5-(methylsulfonimidoyl)pyridine-2-carboxamide To a solution of tert-butyl N-[[6-[[2-(tert-butoxycarbonylamino)-5-(2-thienyl)phenyl]carbamoyl]-3-pyridyl]-methyl-oxo-sulfanylidene]carbamate (about 40 mg, 0.070 mmol) in DCM (about 2 mL) was added TFA (about 0.05 mL, 0.65 mmol). The mixture was stirred at about 20° C. for about 12 hours. The reaction mixture was diluted with DCM (about 30 mL) and adjusted to about pH=8 with saturated Na$_2$CO$_3$ aqueous solution. The resultant mixture was dried over Na$_2$SO$_4$ and filtered. The filtrate was concentrated under reduced pressure. The residue was purified by preparative TLC (silica, DCM/MeOH=10/1, 254 nm) to afford a residue. The residue was purified by preparative HPLC (Instrument: Gilson GX-281 Liquid Handler, Gilson 322 Pump, Gilson 156 UV Detector; Column: Durashell 80×40 mm×3 μm; Mobile phase A: H$_2$O with 10 mmol NH$_4$HCO$_3$; Mobile phase B: MeCN; Gradient: B from 23% to 53% in 9.5 min, hold 100% B for 1 min; Flow Rate: 30 mL/min; Column Temperature: 30° C.; Wavelength: 220 nm, 254 nm) to afford N-[2-amino-5-(2-thienyl)phenyl]-5-(methylsulfonimidoyl)pyridine-2-carboxamide (about 14.0 mg). $^1$H NMR (400 MHz, chloroform-d) δ ppm 9.86 (s, 1H), 9.23 (dd, J=2.0, 0.8 Hz, 1H), 8.45-8.56 (m, 2H), 7.78 (d, J=2.0 Hz, 1H), 7.38 (dd, J=8.4, 2.0 Hz, 1H), 7.18-7.25 (m, 2H), 7.05 (dd, J=5.2, 4.0 Hz, 1H), 6.88 (d, J=8.4 Hz, 1H), 4.02 (br s, 2H), 3.21 (d, J=1.2 Hz, 3H), 2.97 (s, 1H) LCMS (ESI) [M+H]$^+$ m/z: calcd 373.1, found 372.9; HPLC: 100%@220 nm; 99.81%@254 nm.

Example 66. Synthesis of N-[2-amino-5-(4-fluorophenyl)phenyl]-4-(cyclopropylsulfonimidoyl)benzamide (Compound 111)

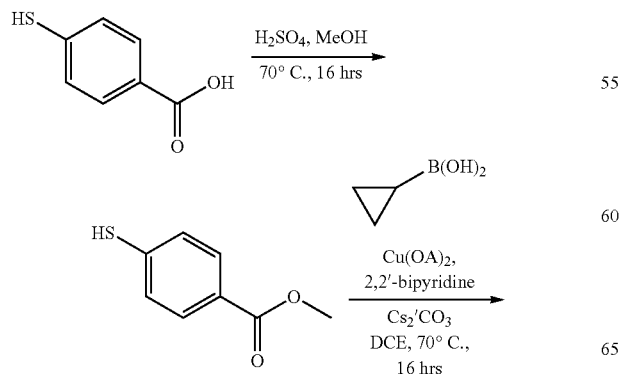

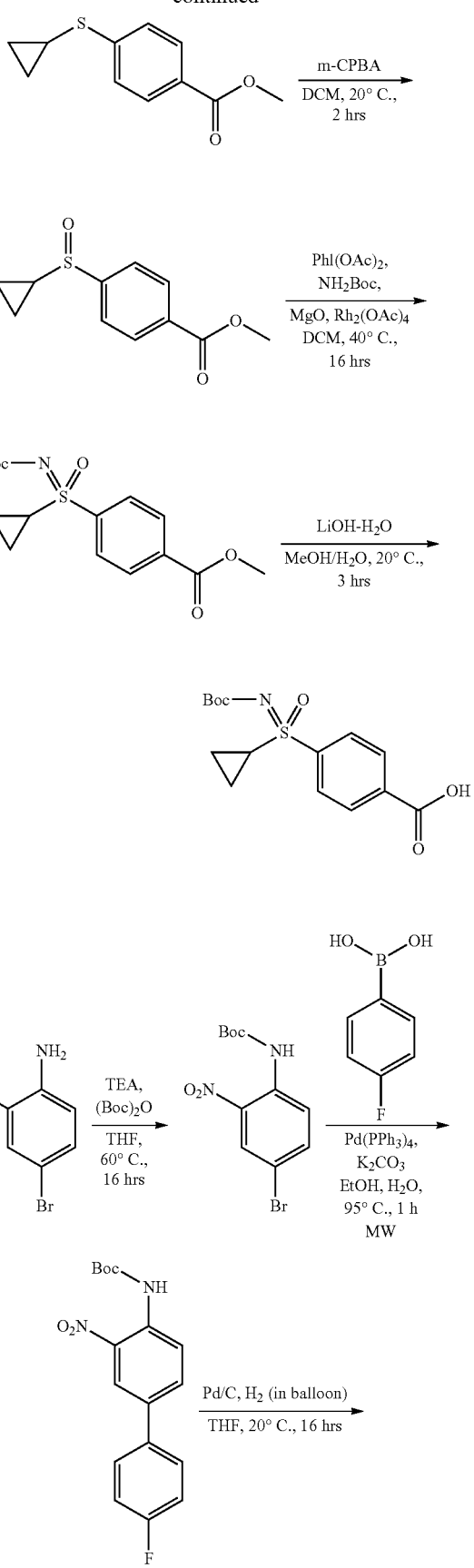

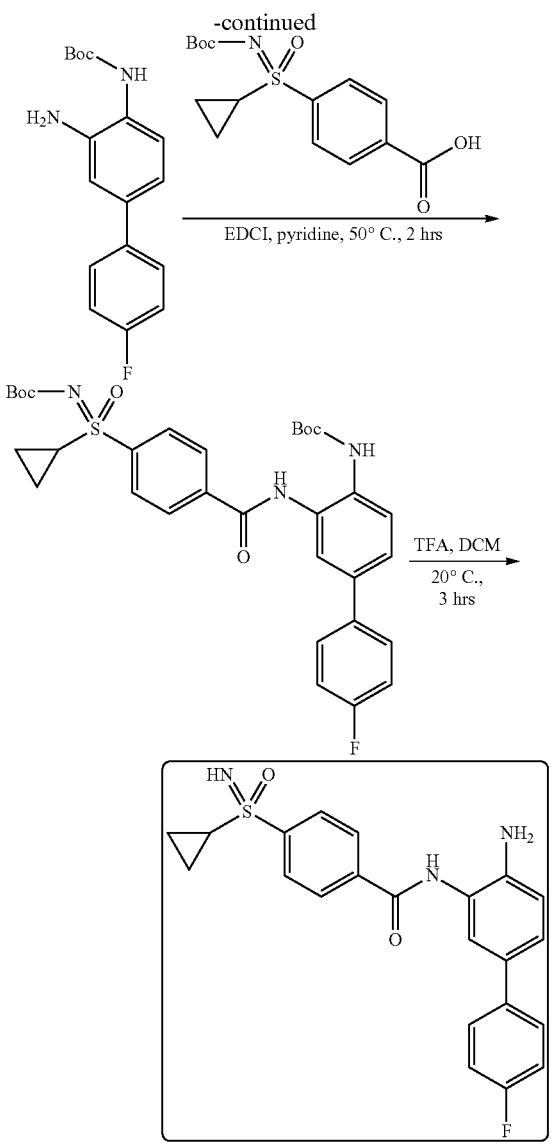

Step 1: Synthesis of methyl 4-sulfanylbenzoate

To a solution of 4-sulfanylbenzoic acid (about 2.9 g, 18.8 mmol) in MeOH (about 20 mL) was added sulfuric acid (about 1 mL, 0.0190 mmol). The reaction mixture was stirred at about 70° C. for about 16 hours. The mixture was concentrated under reduced pressure. The residue was purified by flash chromatography (Biotage®; about 20 g AgelaFlash® Silica Flash Column, petroleum ether/EtOAc with EtOAc from 0~16%, flow rate=30 mL/min, 254 nm) to afford methyl 4-sulfanylbenzoate (about 2.98 g). LCMS (ESI) [M+H]$^+$ m/z: calcd 169.1, found 169.0.

Step 2: Synthesis of methyl 4-cyclopropylsulfanylbenzoate

A mixture of methyl 4-sulfanylbenzoate (about 2.9 g, 17.2 mmol), cyclopropylboronic acid (about 2.3 g, 26.8 mmol), dicesium;carbonate (about 5.7 g, 17.5 mmol), copper;diacetate (about 3.2 g, 17.6 mmol) and 2,2'-bipyridine (about 2.7 g, 17.3 mmol) in 1,2-dichloroethane (about 30 mL) was stirred at about 70° C. for about 16 hours. Aqueous $NH_3$—$H_2O$ 25% (about 5 mL) was added to mixture. The resulting mixture was extracted with DCM (30 mL×3). The combined organic layer was dried over anhydrous $Na_2SO_4$, filtered and concentrated under reduced pressure. The residue was purified by flash chromatography (Biotage®; 40 g AgelaFlash® Silica Flash Column, petroleum ether/EtOAc with EtOAc from 0~16%, flow rate=50 mL/min, 254 nm) to afford methyl 4-cyclopropylsulfanylbenzoate (about 3.2 g). $^1$H NMR (400 MHz, methanol-d$_4$) δ ppm 7.84-7.96 (m, 2H), 7.39-7.46 (m, 2H), 3.88 (s, 3H), 2.19-2.31 (m, 1H), 1.11-1.19 (m, 2H), 0.57-0.68 (m, 2H); LCMS (ESI) [M+H]$^+$ m/z: calcd 209.1, found 209.0.

Step 3: Synthesis of methyl 4-cyclopropylsulfinylbenzoate

To a solution of m-CPBA (about 2.7 g, 15.7 mmol) in DCM (about 15 mL) was added methyl 4-cyclopropylsulfanylbenzoate (about 3.2 g, 15.4 mmol). The mixture was stirred at about 20° C. for about 2 hours. The mixture was quenched by addition of saturated $Na_2SO_3$ aqueous solution (about 30 mL), saturated $Na_2CO_3$ aqueous solution (about 30 mL) and extracted with DCM (about 50 mL×3). The combined organic layer was dried over anhydrous $Na_2SO_4$, filtered and concentrated under reduced pressure to afford methyl 4-cyclopropylsulfinylbenzoate (about 3 g). LCMS (ESI) [M+H]$^+$ m/z: calcd 225.1, found 225.0.

Step 4: Synthesis of methyl 4-(N-tert-butoxycarbonyl-S-cyclopropyl-sulfonimidoyl)benzoate To a solution of NH$_2$Boc (about 3.5 g, 29.9 mmol), [bis(acetoxy)iodo]benzene (about 6.5 g, 20.2 mmol), MgO (about 3 g, 72.6 mmol) and dirhodium tetraacetate (about 300 mg, 0.679 mmol) in DCM (about 20 mL) was added methyl 4-cyclopropylsulfinylbenzoate (about 3 g, 13.4 mmol). The reaction mixture was stirred at about 40° C. for about 16 hours. The mixture was filtered and concentrated under reduced pressure. The residue was purified by flash chromatography (Biotage®; about 40 g SepaFlash® Silica Flash Column, petroleum ether/EtOAc with EtOAc from 0~50%, flow rate=50 mL/min, 254 nm) to afford methyl 4-(N-tert-butoxycarbonyl-S-cyclopropyl-sulfonimidoyl) benzoate (about 2.9 g). $^1$H NMR (400 MHz, methanol-d$_4$) δ ppm 8.25-8.30 (m, 2H), 8.04 (d, J=8.3 Hz, 2H), 3.97 (s, 3H), 2.90 (ddd, J=8.0, 4.6, 3.3 Hz, 1H), 1.51 (ddt, J=10.3, 7.2, 5.1, 5.1 Hz, 1H), 1.26-1.33 (m, 1H), 1.24 (s, 9H), 1.17 (ddt, J=10.5, 7.2, 5.2, 5.2 Hz, 1H), 0.98-1.11 (m, 1H); LCMS (ESI) [M+H]$^+$ m/z: calcd 340.1; found 340.1.

Step 5: Synthesis of 4-(N-tert-butoxycarbonyl-S-cyclopropyl-sulfonimidoyl)benzoic acid To a solution of methyl 4-(N-tert-butoxycarbonyl-S-cyclopropyl-sulfonimidoyl)benzoate (about 2.9 g, 8.54 mmol) in MeOH (about 20 mL) was added a solution of LiOH—$H_2O$ (about 4.3 g, 103 mmol) in $H_2O$ (about 10 mL). The mixture was stirred at about 20° C. for about 3 hours. The mixture was concentrated under reduced pressure to remove the organic solvent. The aqueous phase was adjusted to about pH=4 with 2N HCl aqueous solution. The mixture was filtered. The filter cake was dried under reduced pressure to give 4-(N-tert-butoxycarbonyl-S-cyclopropyl-sulfonimidoyl)benzoic acid (about 2.5 g). LCMS (ESI) [M+H]$^+$ m/z: calcd 326.1; found 326.0.

Step 6: Synthesis of tert-butyl N-(4-bromo-2-nitro-phenyl)carbamate

To a solution of TEA (about 20 mL, 143 mmol) and tert-butoxycarbonyl tert-butyl carbonate (about 20 mL, 87.2 mmol) was added a solution of 4-bromo-2-nitro-aniline (about 10 g, 46.1 mmol) in THF (about 50 mL). The mixture was stirred at about 60° C. for about 16 hours. The resulting mixture was quenched by addition of water (about 100 mL) and extracted with EtOAc (about 100 mL×3). The combined organic layer was washed with saturated $NH_4Cl$ aqueous solution (about 100 mL×2), brine (about 100 mL), dried over anhydrous $Na_2SO_4$, filtered and concentrated under reduced pressure. The residue was purified by flash chromatography (ISCO®; about 80 g AgelaFlash® Silica Flash Column, petroleum ether/EtOAc with EtOAc from 0~5%, flow rate=50 mL/min, 254 nm) to afford tert-butyl N-(4-bromo-2-nitro-phenyl)carbamate (about 3.7 g). $^1$H NMR (400 MHz, methanol-$d_4$) δ ppm 8.27 (d, J=2.3 Hz, 1H), 8.23 (d, J=9.1 Hz, 1H), 7.78 (dd, J=9.1, 2.4 Hz, 1H), 1.53 (s, 9H).

Step 7: Synthesis of tert-butyl N-[4-(4-fluorophenyl)-2-nitro-phenyl]carbamate Tert-butyl N-(4-bromo-2-nitro-phenyl)carbamate (about 2 g, 6.31 mmol), (4-fluorophenyl)boronic acid (about 900 mg, 6.43 mmol), palladium;triphenylphosphane (about 700 mg, 0.606 mmol) and $K_2CO_3$ (about 2.4 g, 17.4 mmol) were taken up into a microwave tube in EtOH (about 40 mL) and $H_2O$ (about 4 mL). The sealed tube was heated at about 95° C. for about 1 hour in microwave. The resulting mixture was filtered and concentrated under reduced pressure. The residue was purified by flash chromatography (ISCO®; about 20 g AgelaFlash® Silica Flash Column, petroleum ether/EtOAc with EtOAc from 0~8%, flow rate=30 mL/min, 254 nm) to afford tert-butyl N-[4-(4-fluorophenyl)-2-nitro-phenyl]carbamate (about 1.45 g). $^1$H NMR (400 MHz, methanol-$d_4$) δ ppm 8.34-8.39 (m, 2H), 7.93 (dd, J=8.8, 2.3 Hz, 1H), 7.69 (dd, J=8.8, 5.3 Hz, 2H), 7.21 (t, J=8.8 Hz, 2H), 1.55 (s, 9H); $^{19}$F NMR (376 MHz, DMSO-$d_4$) δ ppm −116.652.

Step 8: Synthesis of tert-butyl N-[2-amino-4-(4-fluorophenyl)phenyl]carbamate To a solution of Pd/C (about 500 mg, 10 wt % Pd with 50% water) in THF (about 20 mL) was added tert-butyl N-[4-(4-fluorophenyl)-2-nitro-phenyl]carbamate (about 1.4 g, 4.21 mmol). The resulting mixture was sealed and degassed under vacuum and purged with $H_2$ for three times, and then stirred at about 20° C. for about 16 hours under $H_2$ (in balloon). The resulting mixture was filtered. The filtrate was concentrated under reduced pressure to afford tert-butyl N-[2-amino-4-(4-fluorophenyl)phenyl]carbamate (about 1.2 g). $^1$H NMR (400 MHz, DMSO-$d_6$) δ ppm 8.35 (br s, 1H), 7.52-7.61 (m, 2H), 7.30 (br d, J=8.0 Hz, 1H), 7.24 (t, J=8.9 Hz, 2H), 6.95 (d, J=2.0 Hz, 1H), 6.80 (dd, J=8.2, 2.1 Hz, 1H), 4.97 (s, 2H), 1.42-1.52 (m, 9H); $^{19}$F NMR (376 MHz, DMSO-$d_6$) δ ppm −166.354; LCMS (ESI) [M+H]$^+$ m/z: calcd 303.1, found 303.1.

Step 9: Synthesis of tert-butyl N-[[4-[[2-(tert-butoxycarbonylamino)-5-(4-fluorophenyl)phenyl]carbamoyl]phenyl]-cyclopropyl-oxo-sulfanylidene]carbamate To a solution of 4-(N-tert-butoxycarbonyl-S-cyclopropyl-sulfonimidoyl)benzoic acid (about 200 mg, 0.615 mmol) and tert-butyl N-[2-amino-4-(4-fluorophenyl)phenyl]carbamate (about 280 mg, 0.926 mmol) in pyridine (about 10 mL) was added EDCI (about 230 mg, 1.20 mmol). The mixture was stirred at about 50° C. for about 2 hours. The resulting mixture was concentrated under reduced pressure. The residue was purified by flash chromatography (ISCO®; about 20 g AgelaFlash® Silica Flash Column, petroleum ether/EtOAc with EtOAc from 0~8%, flow rate=30 mL/min, 254 nm) to afford tert-butyl N-[[4-[[2-(tert-butoxycarbonylamino)-5-(4-fluorophenyl)phenyl]carbamoyl]phenyl]-cyclopropyl-oxo-sulfanylidene]carbamate (about 370 mg). LCMS (ESI) [M+H]$^+$ m/z: calcd 610.2; found 510.2 (Boc cleaved mass).

Step 10: Synthesis of N-[2-amino-5-(4-fluorophenyl)phenyl]-4-(cyclopropylsulfonimidoyl)benzamide To a solution of tert-butyl N-[[4-[[2-(tert-butoxycarbonylamino)-5-(4-fluorophenyl)phenyl]carbamoyl]phenyl]-cyclopropyl-oxo-sulfanylidene]carbamate (about 370 mg, 0.607 mmol) in DCM (about 6 mL) was added TFA (about 1 mL, 13.0 mmol). The mixture was stirred at about 20° C. for about 3 hours. The resulting mixture was concentrated under reduced pressure. The residue was purified by preparative HPLC (Instrument: Gilson GX-215, Gilson 322 Pump, Gilson 156 UV Detector; Column: 3_Phenomenex Luna C18 75×30 mm×3 um; Mobile phase A: water (FA); Mobile phase B: ACN; Gradient: B from 22% to 52% in 9.5 min, hold 100% B for 2 min; Flow Rate: 25 mL/min; Column Temperature: 30° C.; Wavelength: 220 nm, 254 nm) to afford a residue (about 150 mg). The residue was further purified by preparative HPLC (Instrument: Gilson GX-281 Liquid Handler, Gilson 322 Pump, Gilson 156 UV Detector; Column: Phenomenex Gemini-NX 80×40 mm×3 um; Mobile phase A: water (10 mmol $NH_4HCO_3$); Mobile phase B: ACN; Gradient: B from 35% to 65% in 9.5 min, hold 100% B for 2 min; Flow Rate: 30 mL/min; Column Temperature: about 30° C.; Wavelength: 220 nm, 254 nm) to afford N-[2-amino-5-(4-fluorophenyl)phenyl]-4-(cyclopropylsulfonimidoyl)benzamide (about 45 mg). The fraction was concentrated under reduced pressure and lyophilized for overnight. $^1$H NMR (400 MHz, DMSO-$d_6$) δ ppm 10.14 (s, 1H), 8.16-8.28 (m, 2H), 8.09 (d, J=8.4 Hz, 2H), 7.54-7.66 (m, 3H), 7.41 (dd, J=8.3, 1.9 Hz, 1H), 7.24 (t, J=8.9 Hz, 2H), 7.02 (d, J=8.4 Hz, 1H), 5.17 (s, 2H), 4.40 (s, 1H), 2.65-2.78 (m, 1H), 1.07-1.17 (m, 1H), 0.85-1.02 (m, 3H); $^{19}$F NMR (376 MHz, DMSO-$d_6$) δ ppm −117.47; LCMS (ESI) [M+H]$^+$ m/z: calcd 410.1; found 410.1; HPLC: 93.98%@220 nm, 99.52%@254 nm.

Example 67. Synthesis of N-[2-amino-5-(2-thienyl)phenyl]-6-(methylsulfonimidoyl)pyridine-3-carboxamide (Compound 110)

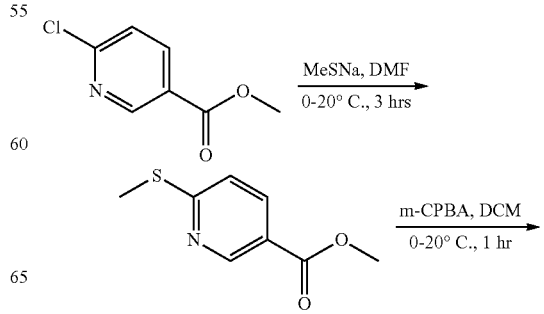

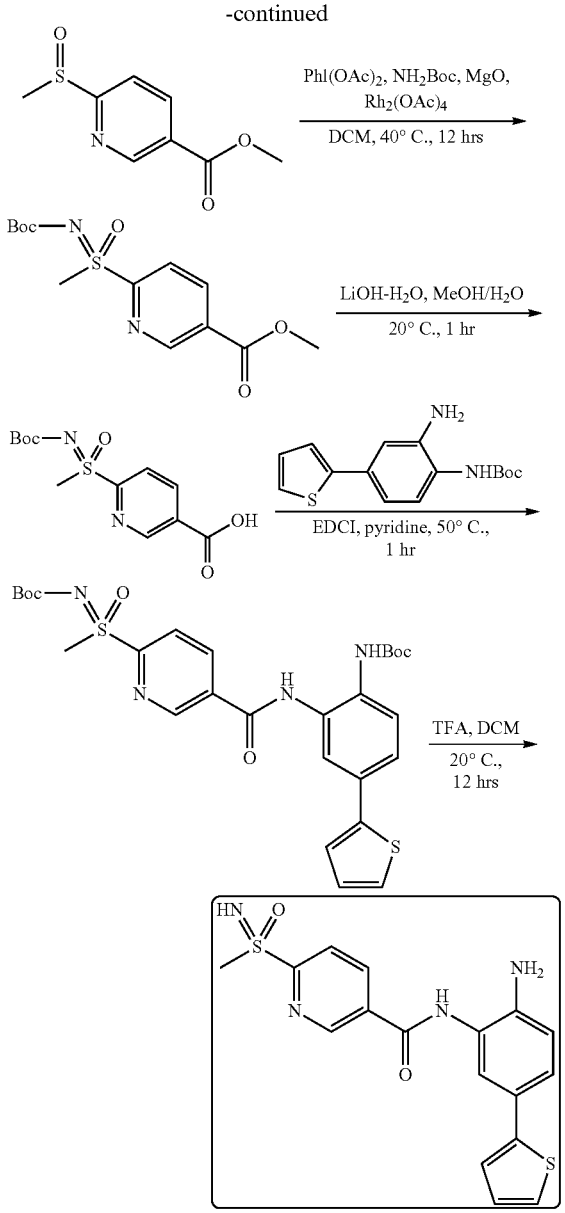

Step 1: Synthesis of methyl 6-methylsulfanylpyridine-3-carboxylate

To a solution of methyl 6-chloropyridine-3-carboxylate (about 3 g, 17.5 mmol) in DMF (about 45 mL) was added sodium;methanethiolate (about 7 g, 20.1 mmol, 20 wt % in H₂O) at about 0° C. After addition, the mixture was stirred at about 20° C. for about 3 hours. The reaction solution was added with water (about 30 mL) and extracted with EtOAc (about 50 mL*3). The combined organic layers were washed with brine (about 50 mL*3), dried over anhydrous Na₂SO₄ and filtered. The filtrate was concentrated under reduced pressure. The residue was purified by flash chromatography (ISCO®; about 25 g AgelaFlash® Silica Flash Column, petroleum ether/EtOAc with EtOAc from 0~10%, flow rate=50 mL/min, 254 nm) to afford methyl 6-methylsulfanylpyridine-3-carboxylate (about 2 g). ¹H NMR (400 MHz, chloroform-d) δ ppm 9.03 (d, J=1.6 Hz, 1H), 8.05 (dd, J=8.4, 2.4 Hz, 1H), 7.23 (dd, J=8.4, 0.8 Hz, 1H), 3.93 (s, 3H), 2.61 (s, 3H).

Step 2: Synthesis of methyl 6-methylsulfinylpyridine-3-carboxylate

To a solution of methyl 6-methylsulfanylpyridine-3-carboxylate (about 1.5 g, 8.19 mmol) in DCM (about 18 mL) was added 3-chlorobenzenecarboperoxoic acid (about 1.83 g, 9.01 mmol, 85 wt %) at about 0° C. After addition, the mixture was stirred at about 20° C. for about 1 hour. The reaction mixture was quenched with saturated NaHCO₃ aqueous (about 20 mL) and extracted with DCM (about 30 mL*3). The combined organic layers were dried over Na₂SO₄ and filtered. The filtrate was concentrated under reduced pressure. The residue was purified by flash chromatography (ISCO®; about 40 g AgelaFlash® Silica Flash Column, petroleum ether/EtOAc with EtOAc from 0~80%, flow rate=50 mL/min, 254 nm) to afford methyl 6-methylsulfinylpyridine-3-carboxylate (about 1.05 g). ¹H NMR (400 MHz, chloroform-d) δ ppm 9.17-9.24 (m, 1H), 8.54 (dd, J=8.0, 2.0 Hz, 1H), 8.14 (d, J=8.0 Hz, 1H), 3.99 (s, 3H), 2.89 (s, 3H).

Step 3: Synthesis of methyl 6-(N-tert-butoxycarbonyl-S-methyl-sulfonimidoyl)pyridine-3-carboxylate To a solution of methyl 6-methylsulfinylpyridine-3-carboxylate (about 1.05 g, 5.27 mmol), tert-butyl carbamate (about 700 mg, 5.98 mmol), [acetoxy(phenyl)-iodanyl] acetate (about 2.55 g, 7.91 mmol) and oxomagnesium (about 1.1 g, 27.3 mmol) in DCM (10 mL) was added diacetoxyrhodium (about 50 mg, 0.226 mmol). The reaction mixture was stirred at about 40° C. for about 12 hours. The reaction mixture was concentrated under reduced pressure. The residue was purified by flash chromatography (ISCO®; about 25 g AgelaFlash® Silica Flash Column, petroleum ether/EtOAc with EtOAc from 0~50%, flow rate=60 mL/min, 254 nm) to afford methyl 6-(N-tert-butoxycarbonyl-S-methyl-sulfonimidoyl)pyridine-3-carboxylate (about 700 mg). LCMS (ESI) [M+H]⁺ m/z: calcd 315.1, found 214.8 (Boc cleaved mass).

Step 4: Synthesis of 6-(N-tert-butoxycarbonyl-S-methyl-sulfonimidoyl)pyridine-3-carboxylic acid To a solution of methyl 6-(N-tert-butoxycarbonyl-S-methyl-sulfonimidoyl)pyridine-3-carboxylate (about 1.1 g, 3.50 mmol) in MeOH (about 20 mL) and H₂O (about 10 mL) was added lithium;hydroxide hydrate (about 1.47 g, 35.0 mmol). The mixture was stirred at about 20° C. for about 1 hour. The mixture was concentrated under reduced pressure to remove the organic solvent. The aqueous phase was adjusted to about pH=4 with 2N HCl aqueous solution. The mixture was filtered. The filter cake was dried under reduced pressure to give 6-(N-tert-butoxycarbonyl-S-methyl-sulfonimidoyl)pyridine-3-carboxylic acid (about 840 mg), which was directly used without further purification. ¹H NMR (400 MHz, DMSO-d₆) δ ppm 9.20 (d, J=1.6 Hz, 1H), 8.61 (dd, J=8.4, 2.0 Hz, 1H), 8.21-8.28 (m, 1H), 3.41 (s, 3H), 1.20 (s, 9H).

Step 5: Synthesis of tert-butyl N-[[5-[[2-(tert-butoxycarbonylamino)-5-(2-thienyl)phenyl]carbamoyl]-2-pyridyl]-methyl-oxo-sulfanylidene]carbamate To a solution of 6-(N-tert-butoxycarbonyl-S-methyl-sulfonimidoyl)pyridine-3-carboxylic acid (about 60 mg, 0.200 mmol) in pyridine (about 2 mL) were added tert-butyl N-[2-amino-4-(2-thienyl)phenyl]carbamate (about 60 mg, 0.207 mmol) and 3-(ethyliminomethyleneamino)-N,N-dimethyl-propan-1-amine;hydrochloride (about 60 mg, 0.313 mmol). The mixture was stirred at about 50° C. for about 1 hour. The reaction mixture was concentrated under reduced pressure. The residue was purified by preparative TLC (silica, petroleum ether/EtOAc=1:1, 254 nm) to afford tert-butyl N-[[5-[[2-(tert-butoxycarbonylamino)-5-(2-thienyl)phenyl]carbamoyl]-2-pyridyl]-methyl-oxo-sulfanylidene]carbamate (about 85 mg). LCMS (ESI) [M+H]+ m/z: calcd 573.2; found 473.0 (Boc cleaved mass).

Step 6: Synthesis of N-[2-amino-5-(2-thienyl)phenyl]-6-(methylsulfonimidoyl)pyridine-3-carboxamide To a solution of tert-butyl N-[[5-[[2-(tert-butoxycarbonylamino)-5-(2-thienyl)phenyl]carbamoyl]-2-pyridyl]-methyl-oxo-sulfanylidene]carbamate (about 85 mg, 0.148 mmol) in DCM (about 3 mL) was added TFA (about 0.1 mL, 1.30 mmol). The mixture was stirred at about 20° C. for about 12 hours. The reaction mixture was diluted with DCM (about 30 mL) and adjusted to about pH=8 with saturated $Na_2CO_3$ aqueous solution. The resultant mixture was dried over $Na_2SO_4$ and filtered. The filtrate was concentrated under reduced pressure. The residue was purified by preparative TLC (silica, DCM/MeOH=1:1, 254 nm) to afford a residue. The residue was further purified by preparative HPLC (Instrument: Gilson GX-281 Liquid Handler, Gilson 322 Pump, Gilson 156 UV Detector; Column: Durashell 80×40 mm×3 μm; Mobile phase A: $H_2O$ with 10 mmol $NH_4HCO_3$; Mobile phase B: MeCN; Gradient: B from 23% to 53% in 9.5 min, hold 100% B for 1 min; Flow Rate: 30 mL/min; Column Temperature: about 30° C.; Wavelength: 220 nm, 254 nm) to afford N-[2-amino-5-(2-thienyl)phenyl]-6-(methylsulfonimidoyl)pyridine-3-carboxamide (about 23.0 mg). $^1$H NMR (400 MHz, chloroform-d) δ ppm 9.22 (brs, 1H), 8.40-8.51 (m, 2H), 8.20 (d, J=8.0 Hz, 1H), 7.64 (s, 1H), 7.39 (dd, J=8.4, 2.0 Hz, 1H), 7.21 (t, J=5.2 Hz, 2H), 7.05 (dd, J=5.2, 4.0 Hz, 1H), 6.88 (d, J=8.4 Hz, 1H), 3.50 (s, 1H), 3.31 (s, 3H); LCMS (ESI) [M+H]+ m/z: calcd 373.1, found 372.9. HPLC: 99.15%@220 nm; 99.86%@254 nm.

Example 68. Synthesis of N-[2-amino-5-(5-fluoro-2-thienyl)phenyl]-4-(methylsulfonimidoyl)benzamide (Compound 109)

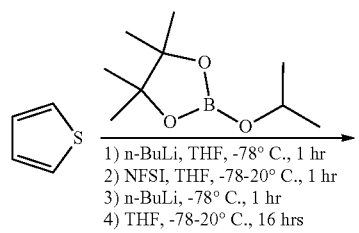

1) n-BuLi, THF, -78° C., 1 hr
2) NFSI, THF, -78-20° C., 1 hr
3) n-BuLi, -78° C., 1 hr
4) THF, -78-20° C., 16 hrs

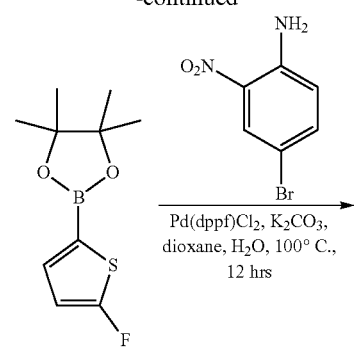

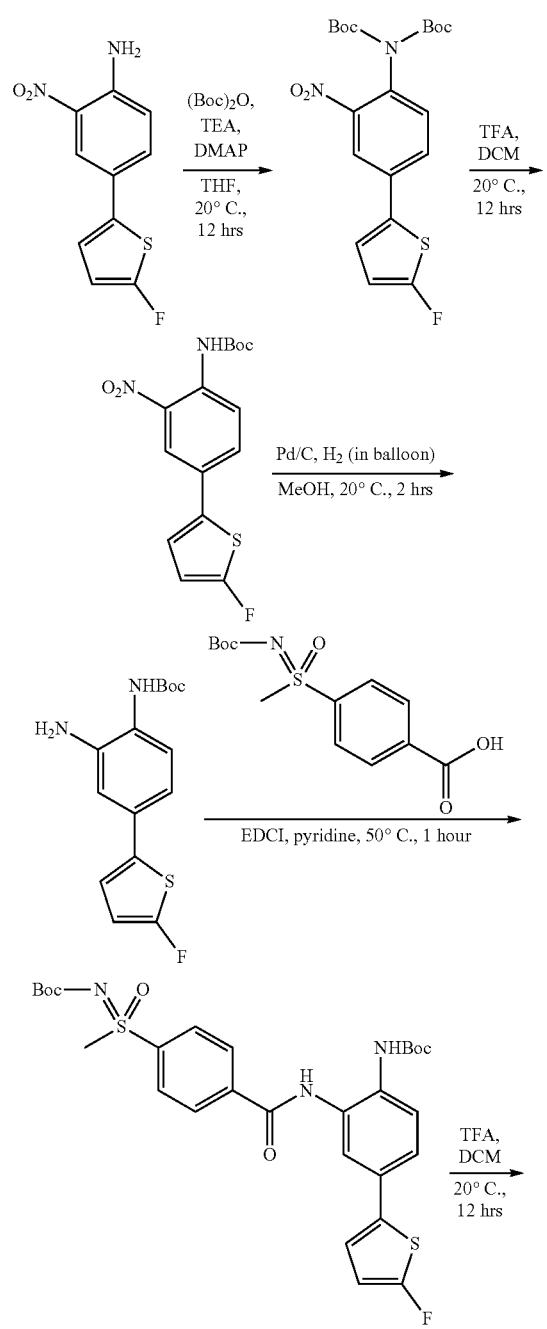

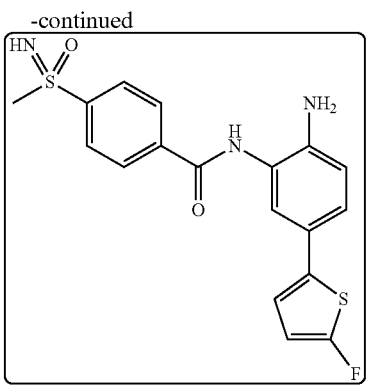

Step 1: Synthesis of 2-(5-fluoro-2-thienyl)-4,4,5,5-tetramethyl-1,3,2-dioxaborolane To a solution of thiophene (about 2.0 g, 23.8 mmol) in THF (about 50 mL) under nitrogen atmosphere was added 2.5M n-BuLi/hexane (about 10 mL, 25.0 mmol) dropwise at about −78° C. and the reaction mixture was stirred at about −78° C. for about 1 hour under nitrogen atmosphere. Then N-(benzenesulfonyl)-N-fluoro-benzenesulfonamide (about 7.9 g, 25.1 mmol) in THF (about 30 mL) was added into above mixture dropwise at about −78° C. and warmed to 20° C. for 1 hour. Then the reaction mixture was cooled to about −78° C., and another portion of 2.5M n-BuLi/hexane (about 10 mL, 25.0 mmol) was added dropwise at about −78° C. and stirred at about −78° C. for about 1 hour. Finally, 2-isopropoxy-4,4,5,5-tetramethyl-1,3,2-dioxaborolane (about 5.2 mL, 25.3 mmol) in THF (about 20 mL) was added into above mixture dropwise at about −78° C., and the reaction mixture was allowed to warm to about 20° C. and stirred for about 16 hours. The reaction mixture was cooled to about 0° C. and quenched with saturated NH$_4$Cl aqueous solution (about 50 mL). The resultant mixture was extracted with petroleum ether (about 100 mL*3). The combined organic layers were washed with brine (about 100 ml), dried over Na$_2$SO$_4$ and filtered. The filtrate was concentrated under reduced pressure to give 2-(5-fluoro-2-thienyl)-4,4,5,5-tetramethyl-1,3,2-dioxaborolane (about 5 g). $^1$H NMR (400 MHz, chloroform-d) δ ppm 7.17-7.22 (m, 1H), 6.47 (dd, J=4.0, 0.8 Hz, 1H), 1.25 (s, 12H); $^{19}$F NMR (377 MHz, chloroform-d) δ ppm −125.64.

Step 2: Synthesis of 4-(5-fluoro-2-thienyl)-2-nitro-aniline

To a solution of 4-bromo-2-nitro-aniline (about 500 mg, 2.30 mmol) in dioxane (about 10 mL) and H$_2$O (about 2 mL) were added 2-(5-fluoro-2-thienyl)-4,4,5,5-tetramethyl-1,3,2-dioxaborolane (about 1.3 g, 5.70 mmol), Pd(dppf)Cl$_2$ (about 250 mg, 0.342 mmol) and K$_2$CO$_3$ (about 950 mg, 6.87 mmol). The mixture was stirred at about 100° C. for about 12 hours under nitrogen. The reaction mixture was concentrated under reduced pressure. The residue was purified flash chromatography (ISCO®; about 25 g AgelaFlash® Silica Flash Column, petroleum ether/EtOAc with EtOAc from 0~15%, flow rate=45 mL/min, 254 nm) to afford 4-(5-fluoro-2-thienyl)-2-nitro-aniline (about 370 mg). LCMS (ESI) [M+H]$^+$ m/z: calcd 239.0; found 238.7.

Step 3: Synthesis of tert-butyl N-tert-butoxycarbonyl-N-[4-(5-fluoro-2-thienyl)-2-nitro-phenyl]carbamate To a solution of 4-(5-fluoro-2-thienyl)-2-nitro-aniline (about 370 mg, 1.55 mmol) in THF (about 5 mL) were added tert-butoxycarbonyl tert-butyl carbonate (about 0.8 mL, 3.49 mmol), TEA (about 0.7 mL, 5.02 mmol) and N,N-dimethylpyridin-4-amine (about 20 mg, 0.164 mmol). The mixture was stirred at about 20° C. for about 12 hours. The reaction mixture was diluted with water (about 20 mL) and extracted with EtOAc (about 30 mL*3). The combined organic layers were washed with brine (about 30 mL), dried over Na$_2$SO$_4$ and filtered. The filtrate was concentrated under reduced pressure. The residue was purified by flash chromatography (ISCO®; about 25 g AgelaFlash® Silica Flash Column, petroleum ether/EtOAc with EtOAc from 0~15%, flow rate=40 mL/min, 254 nm) to afford tert-butyl N-tert-butoxycarbonyl-N-[4-(5-fluoro-2-thienyl)-2-nitro-phenyl]carbamate (about 620 mg). $^1$H NMR (400 MHz, chloroform-d) δ ppm 8.16 (d, J=2.4 Hz, 1H), 7.69 (dd, J=8.4, 2.0 Hz, 1H), 7.32 (d, J=8.4 Hz, 1H), 7.07 (t, J=3.6 Hz, 1H), 6.54 (dd, J=4.0, 1.6 Hz, 1H), 1.43 (s, 18H). LCMS (ESI) [M+H]$^+$ m/z: calcd 439.1; found 238.8 (Boc cleaved mass).

Step 4: Synthesis of tert-butyl N-[4-(5-fluoro-2-thienyl)-2-nitro-phenyl]carbamate To a solution of tert-butyl N-tert-butoxycarbonyl-N-[4-(5-fluoro-2-thienyl)-2-nitro-phenyl]carbamate (about 200 mg, 0.456 mmol) in DCM (about 2 mL) was added TFA (about 0.05 mL, 0.649 mmol). The mixture was stirred at about 20° C. for about 2 hours. The reaction mixture was quenched with saturated Na$_2$CO$_3$ aqueous solution to adjust to about pH=8, and diluted with DCM (about 20 mL*1). The combined organic layer was dried over Na$_2$SO$_4$ and filtered. The filtrate was concentrated under reduced pressure to afford tert-butyl N-[4-(5-fluoro-2-thienyl)-2-nitro-phenyl]carbamate (about 150 mg). $^1$H NMR (400 MHz, chloroform-d) δ ppm 9.64 (s, 1H), 8.59 (d, J=8.8 Hz, 1H), 8.28 (d, J=2.4 Hz, 1H), 7.69 (dd, J=8.8, 2.4 Hz, 1H), 6.95 (t, J=4.0 Hz, 1H), 6.49 (dd, J=4.0, 2.0 Hz, 1H), 1.56 (s, 9H).

Step 5: Synthesis of tert-butyl N-[2-amino-4-(5-fluoro-2-thienyl)phenyl]carbamate To a solution of tert-butyl N-[4-(5-fluoro-2-thienyl)-2-nitro-phenyl]carbamate (about 150 mg, 0.443 mmol) in MeOH (about 30 mL) was added Pd/C (about 100 mg, 10 wt % Pd with 50 wt % water). The mixture was purged with H$_2$ for 3 times and stirred at about 20° C. for about 2 hours under H$_2$ (in balloon). The reaction mixture was filtered and the filtrate was concentrated under reduced pressure to afford tert-butyl N-[2-amino-4-(5-fluoro-2-thienyl)phenyl]carbamate (about 130 mg).

Step 6: Synthesis of tert-butyl N-[[4-[[2-(tert-butoxycarbonylamino)-5-(5-fluoro-2-thienyl)phenyl]carbamoyl]phenyl]-methyl-oxo-sulfanylidene]carbamate To a solution of 4-(N-tert-butoxycarbonyl-S-methyl-sulfonimidoyl)benzoic acid (about 50 mg, 0.167 mmol) in pyridine (about 2 mL) were added tert-butyl N-[2-amino-4-(5-fluoro-2-thienyl)phenyl]carbamate (about 70 mg, 0.227 mmol) and 3-(ethyliminomethyleneamino)-N,N-dimethylpropan-1-amine;hydrochloride (about 50 mg, 0.261 mmol). The mixture was stirred at about 50° C. for about 1 hour. The reaction mixture was concentrated under reduced pressure. The residue was purified by preparative TLC (silica, petroleum ether/EtOAc=2:1, 254 nm) to afford tert-butyl N-[[4-[[2-(tert-butoxycarbonylamino)-5-(5-fluoro-2-thienyl)phenyl]carbamoyl]phenyl]-methyl-oxo-sulfanylidene]

carbamate (about 86 mg). LCMS (ESI) [M+H]⁺ m/z: calcd 590.2, found 490.0 (Boc cleaved mass).

Step 7: Synthesis of N-[2-amino-5-(5-fluoro-2-thienyl)phenyl]-4-(methylsulfonimidoyl)benzamide To a solution of tert-butyl N-[[4-[[2-(tert-butoxycarbonylamino)-5-(5-fluoro-2-thienyl)phenyl]carbamoyl]phenyl]-methyl-oxo-sulfanylidene]carbamate (about 86 mg, 0.146 mmol) in DCM (about 2 mL) was added TFA (about 0.1 mL, 1.30 mmol). The mixture was stirred at about 20° C. for about 12 hours. The reaction mixture was quenched with saturated NaHCO₃ aqueous (about 20 mL) and extracted with DCM/IPA (v/v=3/1, 30 mL*3). The combined organic layers were dried over Na₂SO₄ and filtered. The filtrate was concentrated under reduced pressure. The residue was purified by preparative HPLC (Instrument: Gilson GX-281 Liquid Handler, Gilson 322 Pump, Gilson 156 UV Detector; Column: Phenomenex Gemini-NX 80*40 mm*3 μm; Mobile phase A: water with 10 mmol NH₄HCO₃ (v %); Mobile phase B: MeCN; Gradient: B from 19% to 49% in 9.5 min, hold 100% B for 2 min; Flow Rate: 30 mL/min; Column Temperature: 30° C.; Wavelength: 220 nm, 254 nm) to give N-[2-amino-5-(5-fluoro-2-thienyl)phenyl]-4-(methylsulfonimidoyl)benzamide (about 18.7 mg). ¹H NMR (400 MHz, methanol-d₄) δ ppm 8.18-8.26 (m, 2H), 8.10-8.18 (m, 2H), 7.41 (d, J=2.0 Hz, 1H), 7.28 (dd, J=8.4, 2.4 Hz, 1H), 6.91 (d, J=8.4 Hz, 1H), 6.84 (t, J=4.0 Hz, 1H), 6.48 (dd, J=4.0, 2.4 Hz, 1H), 3.21 (s, 3H); ¹⁹F NMR (377 MHz, methanol-d₄) δ ppm −135.59; LCMS (ESI) [M+H]⁺ m/z: calcd 390.1, found 390.0. HPLC: 98.840%@220 nm; 98.480%@254 nm.

Example 69. Synthesis of N-[2-amino-5-(4-pyridyl)phenyl]-4-(methylsulfonimidoyl)benzamide (Compound 108)

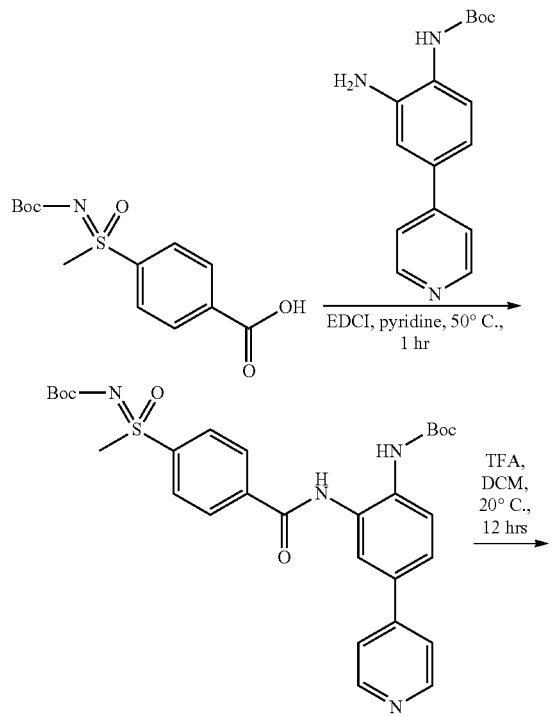

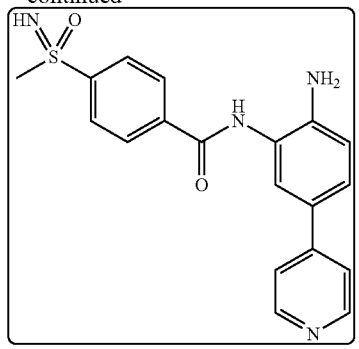

Step 1: Synthesis of tert-butyl N-[[4-[[2-(tert-butoxycarbonylamino)-5-(4-pyridyl)phenyl]carbamoyl]phenyl]-methyl-oxo-sulfanylidene]carbamate To a solution of 4-(N-tert-butoxycarbonyl-S-methylsulfonimidoyl)benzoic acid (50 mg, 0.167 mmol) in pyridine (about 2 mL) was added EDCI (about 60 mg, 0.313 mmol) and tert-butyl N-[2-amino-4-(4-pyridyl)phenyl]carbamate (about 55 mg, 0.193 mmol). The mixture was stirred at about 50° C. for about 1 hour. The reaction mixture was concentrated under reduced pressure. The residue was purified by preparative TLC (silica, petroleum ether/EtOAc=0/1, 254 nm) to afford tert-butyl N-[[4-[[2-(tert-butoxycarbonylamino)-5-(4-pyridyl)phenyl]carbamoyl]phenyl]-methyl-oxo-sulfanylidene]carbamate (about 60 mg). LCMS (ESI) [M+H]⁺ m/z: calcd 567.2, found 567.2.

Step 2: Synthesis of N-[2-amino-5-(4-pyridyl)phenyl]-4-(methylsulfonimidoyl)benzamide To a solution of tert-butyl N-[[4-[[2-(tert-butoxycarbonylamino)-5-(4-pyridyl)phenyl]carbamoyl]phenyl]-methyl-oxo-sulfanylidene]carbamate (about 60 mg, 0.105 mmol) in DCM (about 2 mL) was added TFA (about 0.1 mL, 0.105 mmol). The mixture was stirred at about 20° C. for about 12 hours. The reaction mixture was adjusted to about pH=8 with saturated Na₂CO₃ aqueous solution and extracted with DCM/IPA=3/1 (about 30 mL*3). The combined organic layers were dried over Na₂SO₄ and filtered. The mixture was concentrated under reduced pressure. The residue was purified by preparative HPLC (Instrument: Gilson GX-281 Liquid Handler, Gilson 322 Pump, Gilson 156 UV Detector; Column: Phenomenex Gemini-NX 80×40 mm×3 μm; Mobile phase A: H₂O with 10 mmol NH₄HCO₃ (v %); Mobile phase B: MeCN; Gradient: B from 10% to 40% in 9.5 min, hold 100% B for 2 min; Flow Rate: 25 mL/min; Column Temperature: 30° C.; Wavelength: 220 nm, 254 nm) to give N-[2-amino-5-(4-pyridyl)phenyl]-4-(methylsulfonimidoyl)benzamide (about 21.7 mg). ¹H NMR (400 MHz, methanol-d₄) δ ppm 8.50 (d, J=5.5 Hz, 2H), 8.22-8.33 (m, 2H), 8.12-8.20 (m, 2H), 7.66-7.74 (m, 3H), 7.59 (dd, J=8.5, 2.0 Hz, 1H), 7.03 (d, J=8.5 Hz, 1H), 3.23 (s, 3H); LCMS [M+H]⁺ m/z: calcd 367.1; found 366.9; HPLC: 93.63%@220 nm, 96.15%@254 nm.

Example 70. Synthesis of N-[2-amino-5-(3-pyridyl)phenyl]-4-(methylsulfonimidoyl)benzamide (Compound 107)

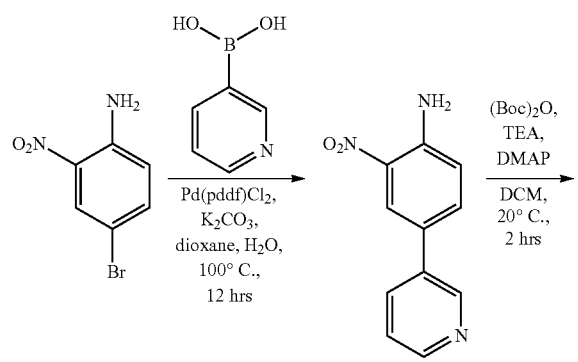

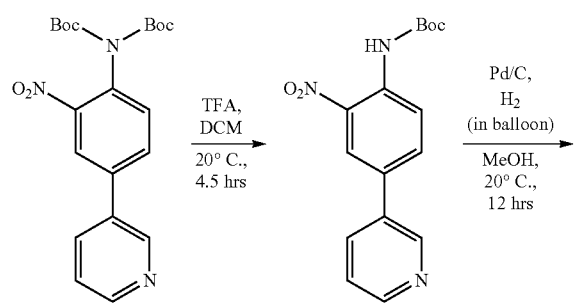

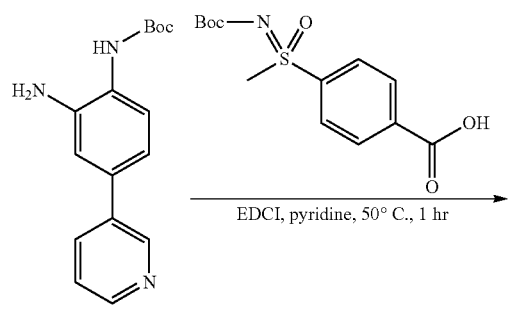

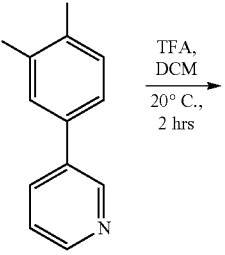

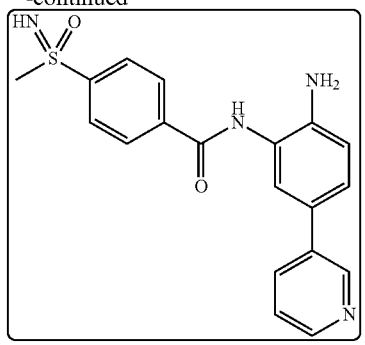

Step 1: Synthesis of 2-nitro-4-(3-pyridyl)aniline

A mixture of 4-bromo-2-nitro-aniline (about 2 g, 9.22 mmol), 3-pyridylboronic acid (about 1.36 g, 11.1 mmol), cyclopentyl(diphenyl)phosphane;dichloropalladium iron (about 680 mg, 0.929 mmol), K$_2$CO$_3$ (about 3.84 g, 27.8 mmol), dioxane (about 20 mL) and H$_2$O (about 10 mL) was stirred at about 100° C. for about 12 hours. The resulting mixture was quenched by addition of water (about 100 mL) and extracted with EtOAc (about 100 mL*4). The combined organic layer was dried over anhydrous Na$_2$SO$_4$, filtered and concentrated under reduced pressure. The residue was purified by flash chromatography (ISCO®; about 40 g Agela-Flash® Silica Flash Column, petroleum ether/EtOAc with EtOAc from 0~85%, flow rate=30 mL/min, 254 nm) to afford 2-nitro-4-(3-pyridyl) aniline (about 850 mg). $^1$H NMR (400 MHz, DMSO-d$_6$) δ ppm 8.86 (d, J=2.0 Hz, 1H), 8.52 (dd, J=4.8, 1.5 Hz, 1H), 8.27 (d, J=2.0 Hz, 1H), 8.05 (dt, J=8.0, 1.9 Hz, 1H), 7.84 (dd, J=8.8, 2.3 Hz, 1H), 7.60 (s, 2H), 7.45 (dd, J=8.0, 4.8 Hz, 1H), 7.15 (d, J=8.8 Hz, 1H); LCMS (ESI) [M+H]$^+$ m/z: calcd 216.1, found 216.1.

Step 2: Synthesis of tert-butyl N-tert-butoxycarbonyl-N-[2-nitro-4-(3-pyridyl)phenyl]carbamate To a mixture of 2-nitro-4-(3-pyridyl) aniline (about 0.85 g, 3.95 mmol), TEA (about 1.7 mL, 12.2 mmol) and DMAP (about 241 mg, 1.97 mmol) in DCM about (10 mL) was added tert-butoxycarbonyl tert-butyl carbonate (about 2.3 mL, 10.0 mmol). The mixture was stirred at about 20° C. for about 2 hours. The resulting mixture was concentrated under reduced pressure. The residue was triturated with MeOH (about 10 mL). The mixture was filtered. The filter cake was concentrated under reduced pressure to give tert-butyl N-tert-butoxycarbonyl-N-[2-nitro-4-(3-pyridyl)phenyl]carbamate (about 1 g), which was directly used to next step without further purification. $^1$H NMR (400 MHz, DMSO-d$_6$) δ ppm 9.04 (d, J=2.0 Hz, 1H), 8.66 (dd, J=4.8, 1.5 Hz, 1H), 8.46 (d, J=2.1 Hz, 1H), 8.26 (dt, J=8.4, 1.8 Hz, 1H), 8.18 (dd, J=8.3, 2.2 Hz, 1H), 7.73 (d, J=8.3 Hz, 1H), 7.55 (dd, J=7.9, 4.8 Hz, 1H), 1.36 (s, 18H); LCMS (ESI) [M+H]$^+$ m/z: calcd 416.2, found 416.1.

Step 3: Synthesis of Synthesis of tert-butyl N-[2-nitro-4-(3-pyridyl)phenyl]carbamate To a solution of tert-butyl N-tert-butoxycarbonyl-N-[2-nitro-4-(3-pyridyl)phenyl]carbamate (about 900 mg, 2.17 mmol) in DCM (about 10 mL) was added TFA (about 0.25 mL, 3.24 mmol). The mixture was stirred at about 20° C. for about 3 hours. To the solution was added TFA (about 0.25 mL, 3.24 mmol). The mixture was stirred at about 20° C. for about 1 hour. To the mixture was added TFA (about 0.05 mL, 0.648 mmol). The mixture was stirred at about 20° C. for about 30 minutes. The resulting mixture was quenched by addition of water (about 100 mL), adjusted to about pH to 8 with saturated NaHCO$_3$ aqueous solution and extracted with DCM (about 100 mL*3). The combined organic layer was dried over anhydrous Na$_2$SO$_4$, filtered and concentrated under reduced pressure to give tert-butyl N-[2-nitro-4-(3-pyridyl)phenyl]carbamate (about 730 mg). $^1$H NMR (400 MHz, DMSO-d$_6$) δ ppm 9.71 (s, 1H), 8.96 (d, J=1.8 Hz, 1H), 8.61 (dd, J=4.8, 1.5 Hz, 1H), 8.27 (d, J=2.0 Hz, 1H), 8.16-8.19 (m, 1H), 8.07 (d, J=2.3 Hz, 1H), 7.76 (s, 1H), 7.51 (dd, J=8.0, 4.8 Hz, 1H), 1.46 (s, 9H); LCMS (ESI) [M+H]$^+$ m/z: calcd 316.1, found 316.1.

Step 4: Synthesis of tert-butyl N-[2-amino-4-(3-pyridyl)phenyl]carbamate

To a solution of tert-butyl N-[2-nitro-4-(3-pyridyl)phenyl] carbamate (about 680 mg, 2.16 mmol) in MeOH (about 10 mL) was added Pd—C (about 70 mg, 10% of Pd with 50% of water, wt %) under N$_2$ atmosphere. The suspension was degassed and purged with hydrogen for 3 times. The mixture was stirred under hydrogen (in balloon) at about 20° C. for about 12 hours. The mixture was filtered. The filtrate was concentrated under reduced pressure to give tert-butyl N-[2-amino-4-(3-pyridyl)phenyl]carbamate (about 570 mg, 2.00 mmol), which was directly used to next step without further purification. $^1$H NMR (400 MHz, DMSO-d$_6$) δ ppm 8.76 (d, J=2.0 Hz, 1H), 8.51 (dd, J=4.8, 1.5 Hz, 1H), 8.40 (s, 1H), 7.93 (dt, J=8.2, 1.9 Hz, 1H), 7.44 (dd, J=7.4, 4.8 Hz, 1H), 7.36 (br d, J=8.1 Hz, 1H), 7.02 (d, J=2.1 Hz, 1H), 6.88 (dd, J=8.1, 2.1 Hz, 1H), 5.03 (s, 2H), 1.47 (s, 9H). LCMS (ESI) [M+H]$^+$ m/z: calcd 286.1, found 286.1.

Step 5: Synthesis of tert-butyl N-[[4-[[2-(tert-butoxycarbonylamino)-5-(3-pyridyl)phenyl]carbamoyl]phenyl]-methyl-oxo-sulfanylidene]carbamate A mixture of tert-butyl N-[2-amino-4-(3-pyridyl)phenyl] carbamate (about 100 mg, 0.350 mmol), 4-(N-tert-butoxycarbonyl-S-methyl-sulfonimidoyl)benzoic acid (about 110 mg, 0.367 mmol), 3-(ethyliminomethyleneamino)-N,N-dimethyl-propan-1-amine hydrochloride (about 100 mg, 0.522 mmol) and pyridine (about 4 mL) was stirred at 50° C. for 1 hour. The resulting mixture was concentrated under reduced pressure. The residue was purified by purified by flash chromatography (ISCO®; about 4 g AgelaFlash® Silica Flash Column, petroleum ether/EtOAc with EtOAc from 0~100%, flow rate=20 mL/min, 254 nm) to afford tert-butyl N-[[4-[[2-(tert-butoxycarbonylamino)-5-(3-pyridyl)phenyl]carbamoyl]phenyl]-methyl-oxo-sulfanylidene]carbamate (about 220 mg). LCMS (ESI) [M+H]$^+$ m/z: calcd 567.2, found 567.2.

Step 6: Synthesis of N-[2-amino-5-(3-pyridyl)phenyl]-4-(methylsulfonimidoyl)benzamide A mixture of tert-butyl N-[[4-[[2-(tert-butoxycarbonylamino)-5-(3-pyridyl)phenyl]carbamoyl]phenyl]-methyl-oxo-sulfanylidene]carbamate (about 220 mg, 0.388 mmol), TFA (about 0.6 mL, 7.79 mmol) and DCM (about 10 mL) was stirred at about 20° C. for about 1 hour. To the solution was added TFA (about 0.6 mL, 7.79 mmol). The mixture was stirred at 20° C. for about 1 hour. The resulting mixture was concentrated under reduced pressure. The residue was purified by preparative HPLC (Instrument: Gilson GX-281 Liquid Handler, Gilson 322 Pump, Gilson 156 UV Detector; Column: Phenomenex Gemini-NX 80×40 mm×3 µm; Mobile phase A: H$_2$O with 10 mmol NH$_4$HCO$_3$ (v %); Mobile phase B: MeCN; Gradient: B from 14% to 44% in 9.5 min, hold 100% B for 1 min; Flow Rate: 25 mL/min; Column Temperature: 30° C.; Wavelength: 220 nm, 254 nm) to afford N-[2-amino-5-(3-pyridyl)phenyl]-4-(methylsulfonimidoyl)benzamide (about 100 mg). $^1$H NMR (400 MHz, methanol-d$_4$) δ ppm 8.77 (s, 1H), 8.43 (d, J=4.3 Hz, 1H), 8.14-8.25 (m, 4H), 8.04-8.09 (m, 1H), 7.57 (d, J=2.0 Hz, 1H), 7.40-7.52 (m, 2H), 7.03 (d, J=8.4 Hz, 1H), 3.21 (s, 3H); LCMS (ESI) [M+H]$^+$ m/z: calcd 367.1, found 367.1; HPLC: 99.64%@220 nm, 99.92%@254 nm.

Example 71. Synthesis of N-[2-amino-5-(2-thienyl) phenyl]-4-(methylsulfonimidoyl)benzamide (Compound 101), rel-(S)—N-[2-amino-5-(2-thienyl)phenyl]-4-(methylsulfonimidoyl)benzamide (Compound 106) and rel-(R)—N-[2-amino-5-(2-thienyl)phenyl]-4-(methylsulfonimidoyl)benzamide (Compound 105)

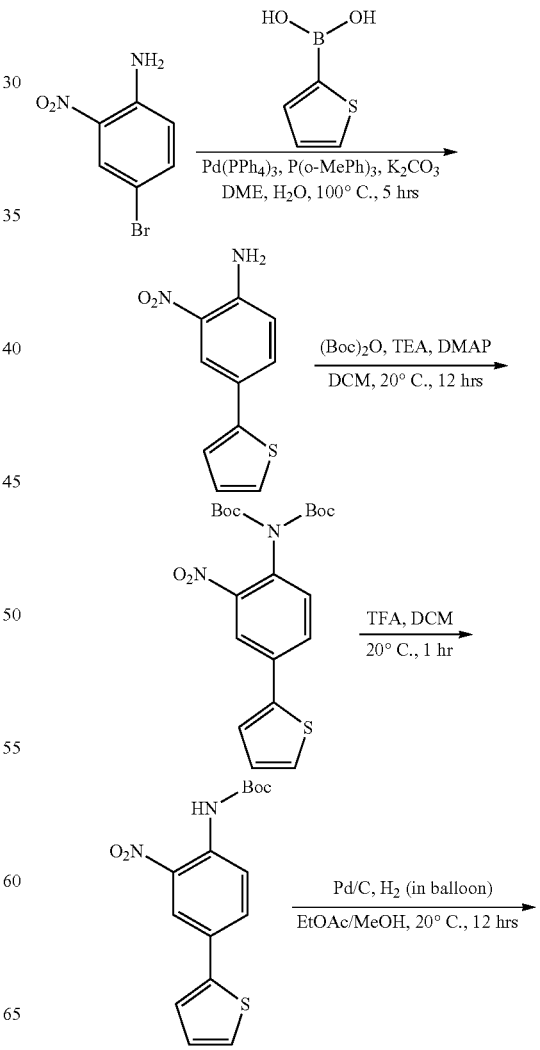

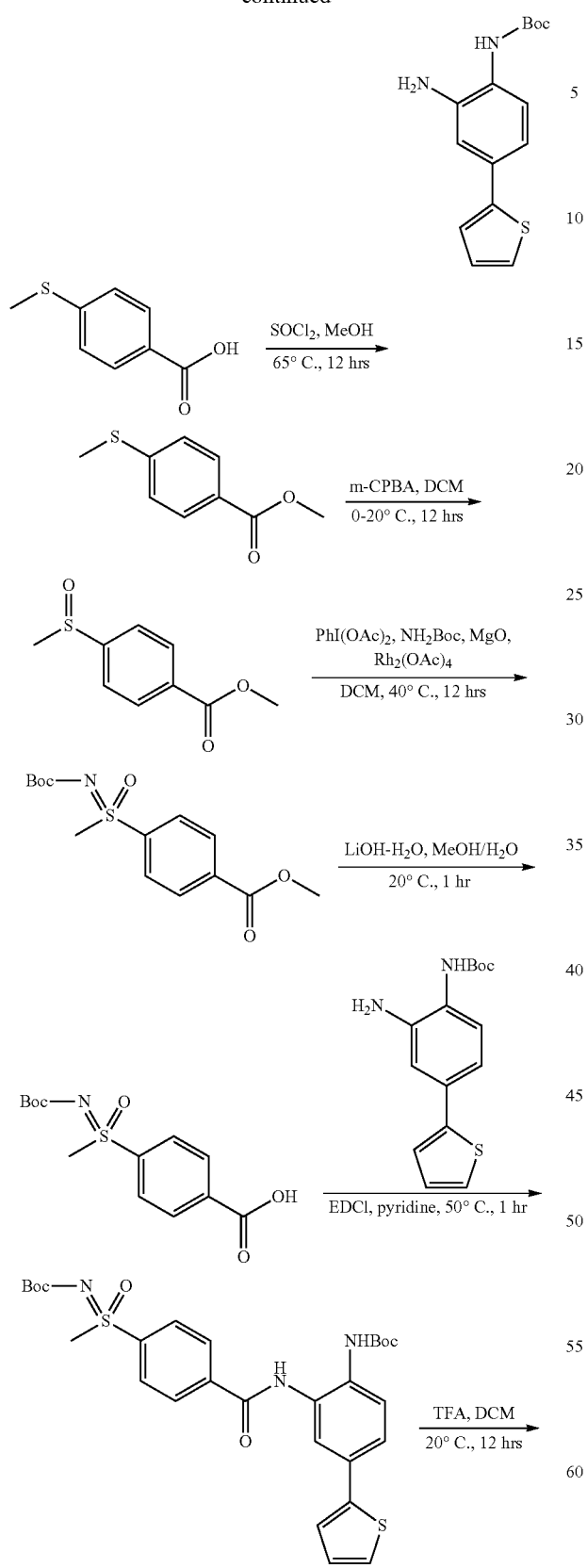

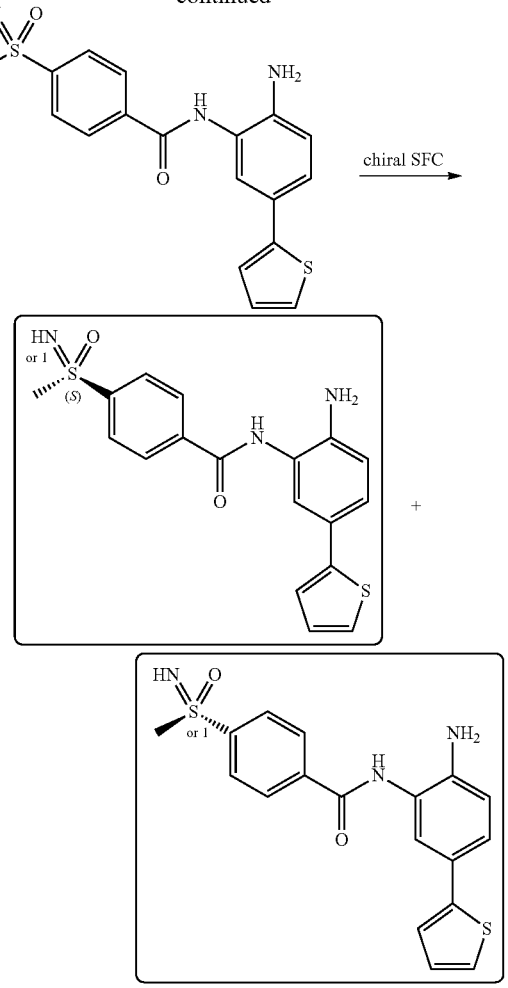

Step 1: Synthesis of 2-nitro-4-(2-thienyl)aniline

A mixture of 4-bromo-2-nitro-aniline (about 20 g, 92.2 mmol), 2-thienylboronic acid (about 13 g, 0.102 mol), Pd(PPh$_3$)$_4$ (about 5.32 g, 4.60 mmol), tris-(o-tolyl)phosphine (about 7.01 g, 23.0 mmol), K$_2$CO$_3$ (about 25 g, 0.181 mol), DME (about 300 mL) and H$_2$O (about 100 mL) was stirred at about 100° C. for about 5 hours under N$_2$. The mixture was filtered through the celite. The filtrate was extracted with EtOAc (about 100 mL*3). The combined organic layer was dried over anhydrous Na$_2$SO$_4$, filtered and concentrated under reduced pressure to afford 2-nitro-4-(2-thienyl)aniline (about 21 g).

Step 2: Synthesis of tert-butyl N-tert-butoxycarbonyl-N-[2-nitro-4-(2-thienyl)phenyl]carbamate To a solution of 2-nitro-4-(2-thienyl)aniline (about 21 g, 95.4 mmol) and DMAP (about 5.8 g, 47.5 mmol) in DCM (about 300 mL) was added TEA (about 40 mL, 0.287 mol) and (Boc)$_2$O (about 50 mL, 0.217 mol). The mixture was stirred at about 20° C. for about 12 hours. The mixture was concentrated under reduced pressure. The residue was purified by flash chromatography (ISCO®; about 330 g Agela-Flash® Silica Flash Column, petroleum ether/EtOAc with EtOAc from 0~30%, 100 mL/min, 254 nm) to afford tert-butyl N-tert-butoxycarbonyl-N-[2-nitro-4-(2-thienyl)phenyl]carbamate (about 6 g). LCMS (ESI) [M+H]⁺ m/z: calcd 421.1; found 221.0 (Boc cleaved mass).

Step 3: Synthesis of tert-butyl N-[2-nitro-4-(2-thienyl)phenyl]carbamate

To a solution of tert-butyl N-tert-butoxycarbonyl-N-[2-nitro-4-(2-thienyl)phenyl]carbamate (about 6 g, 14.3 mmol) in DCM (about 60 mL) was added TFA (about 1.6 mL, 20.8 mmol) dropwise. Then the mixture was stirred at about 20° C. for about 1 hour. The mixture was quenched by addition of saturated NaHCO₃ aqueous solution (about 50 mL). The organic layer was separation. The aqueous phase was extracted with DCM (about 50 mL*2). The combined organic layer was dried over anhydrous Na₂SO₄, filtered and concentrated under reduced pressure to give tert-butyl N-[2-nitro-4-(2-thienyl)phenyl]carbamate (about 4.3 g), which was directly used without further purification. ¹H NMR (400 MHz, DMSO-d₆) δ ppm 9.64 (s, 1H), 8.14 (d, J=2.3 Hz, 1H), 7.94 (dd, J=8.7, 2.1 Hz, 1H), 7.69 (d, J=8.5 Hz, 1H), 7.59-7.64 (m, 2H), 7.16 (dd, J=5.0, 3.5 Hz, 1H), 1.45 (s, 9H); LCMS (ESI) [M+H]⁺ m/z: calcd 321.1; found 221.0 (Boc cleaved mass).

Step 4: Synthesis of tert-butyl N-[2-amino-4-(2-thienyl)phenyl]carbamate

To a solution of tert-butyl N-[2-nitro-4-(2-thienyl)phenyl]carbamate (about 4.3 g, 13.4 mmol) in EtOAc (about 50 mL) and MeOH (about 150 mL) was added Pd—C(about 500 mg, 10% of Pd with 50% of water, wt %) under N₂ atmosphere. The suspension was degassed and purged with hydrogen for about 3 times. The mixture was stirred under hydrogen (in balloon) at about 20° C. for about 12 hours. The mixture was filtered. The filtrate was concentrated under reduced pressure to give tert-butyl N-[2-amino-4-(2-thienyl)phenyl]carbamate (about 4 g), which was directly used without further purification. LCMS (ESI) [M+H]⁺ m/z: calcd 291.1; found 291.1.

Step 5: Synthesis of methyl 4-methylsulfanylbenzoate

To a solution of 4-methylsulfanylbenzoic acid (about 25 g, 0.149 mol) in MeOH (about 100 mL) was added SOCl₂ (about 32 mL, 0.441 mol). The mixture was stirred at about 65° C. for about 12 hours. The mixture was concentrated under reduced pressure. The residue was diluted with EtOAc (about 250 mL). The mixture was washed with saturated NaHCO₃ aqueous solution (about 250 mL*2), dried over anhydrous Na₂SO₄, filtered and concentrated under reduced pressure to give methyl 4-methylsulfanylbenzoate (about 26 g), which was directly used without further purification. ¹H NMR (400 MHz, chloroform-d) δ ppm 7.89-8.00 (m, 2H), 7.23-7.28 (m, 2H), 3.91 (s, 3H), 2.53 (s, 3H); LCMS (ESI) [M+H]⁺ m/z: calcd 183.0; found 183.1.

Step 6: Synthesis of methyl 4-methylsulfinylbenzoate

To a solution of methyl 4-methylsulfanylbenzoate (about 26 g, 0.143 mol) in DCM (about 200 mL) was added m-CPBA (about 32 g, 0.158 mol, 85 wt %) at about 0° C. The mixture was stirred at about 20° C. for about 12 hours. The mixture was quenched by addition of saturated Na₂SO₃ aqueous solution (about 150 mL), saturated Na₂CO₃ aqueous solution (about 150 mL) and extracted with DCM (about 150 mL*2). The combined organic layer was dried over anhydrous Na₂SO₄, filtered and concentrated under reduced pressure to give methyl 4-methylsulfinylbenzoate (about 28 g), which was directly used without further purification. LCMS (ESI) [M+H]⁺ m/z: calcd 199.0; found 199.0.

Step 7: Synthesis of methyl 4-(N-tert-butoxycarbonyl-S-methyl-sulfonimidoyl)benzoate To a solution of methyl 4-methylsulfinylbenzoate (about 23 g, 0.116 mol), NH₂Boc (about 27.2 g, 0.232 mol), [bis(acetoxy)iodo]benzene (about 56 g, 0.174 mol) and MgO (about 23.4 g, 0.581 mol) in DCM (about 300 mL) was added dirhodium tetraacetate (about 2.3 g, 5.20 mmol). The reaction mixture was stirred at about 40° C. for about 12 hours. The mixture was filtered. The filtrate was concentrated under reduced pressure. The residue was triturated with EtOAc (about 50 mL). The mixture was filtered. The filter cake was concentrated under reduced pressure to give (about 20 g) product. The filtrate was concentrated under reduced pressure. The residue was purified by flash chromatography (Biotage®; about 330 g AgelaFlash® Silica Flash Column, petroleum ether/EtOAc with EtOAc from 0~50%, 100 mL/min, 254 nm) to give (about 12 g) product. Totally methyl 4-(N-tert-butoxycarbonyl-S-methyl-sulfonimidoyl)benzoate (about 32 g) was obtained. ¹H NMR (400 MHz, chloroform-d) δ ppm 8.26 (d, J=8.5 Hz, 2H), 8.06 (d, J=8.5 Hz, 2H), 3.98 (s, 3H), 3.27 (s, 3H), 1.39 (s, 9H); LCMS (ESI) [M+H]⁺ m/z: calcd 314.1; found 314.0.

Step 8: Synthesis of 4-(N-tert-butoxycarbonyl-S-methyl-sulfonimidoyl)benzoic acid To a solution of methyl 4-(N-tert-butoxycarbonyl-S-methyl-sulfonimidoyl)benzoate (about 20 g, 63.8 mmol) in MeOH (about 150 mL) was added a solution of LiOH—H₂O (about 27 g, 0.643 mol) in H₂O (about 50 mL). The mixture was stirred at about 20° C. for about 1 hour. The mixture was concentrated under reduced pressure to remove the organic solvent. The aqueous phase was adjusted to about pH=4 with 2N HCl aqueous solution. The mixture was filtered. The filter cake was dried under reduced pressure to give 4-(N-tert-butoxycarbonyl-S-methyl-sulfonimidoyl)benzoic acid (about 22 g), which was directly used without further purification. ¹H NMR (400 MHz, DMSO-d₆) δ ppm 8.17 (d, J=8.5 Hz, 2H), 8.04 (d, J=8.5 Hz, 2H), 3.43 (s, 3H), 1.22 (s, 9H); LCMS (ESI) [M+H]⁺ m/z: calcd 300.1; found 244.0 (t-Bu cleaved mass).

Step 9: Synthesis of tert-butyl (2-(4-(N-(tert-butoxycarbonyl)-S-methylsulfonimidoyl)benzamido)-4-(thiophen-2-yl)phenyl)carbamate A mixture of 4-(N-tert-butoxycarbonyl-S-methyl-sulfonimidoyl)benzoic acid (about 7.2 g, 24.1 mmol), tert-butyl N-[2-amino-4-(2-thienyl)phenyl]carbamate (about 7 g, 24.1 mmol) and EDCI (about 6.9 g, 36.0 mmol) in pyridine (about 50 mL) was stirred at about 50° C. for about 1 hour. The mixture was concentrated under reduced pressure. The residue was triturated with EtOAc (about 150 mL). The mixture was filtered. The filter cake was concentrated under reduced pressure to afford tert-butyl (2-(4-(N-(tert-butoxycarbonyl)-S-methylsulfonimidoyl)benzamido)-4-(thiophen-2-yl)phenyl)carbamate (about 9 g). LCMS (ESI) [M+H]⁺ m/z: calcd 572.2; found 472.2 (Boc cleaved mass).

Step 10: Synthesis of N-[2-amino-5-(2-thienyl)phenyl]-4-(methylsulfonimidoyl)benzamide To a solution of tert-butyl (2-(4-(N-(tert-butoxycarbonyl)-S-methylsulfonimidoyl)benzamido)-4-(thiophen-2-yl)phenyl)carbamate (about 9 g, 15.7 mmol) in DCM (about 100 mL) was added TFA (about 15 mL, 0.195 mol). The mixture was stirred at about 20° C. for about 12 hours. The mixture was adjusted to about pH=8 with saturated $Na_2CO_3$ aqueous solution. The mixture was filtered. The filter cake was concentrated under reduced pressure to give N-[2-amino-5-(2-thienyl)phenyl]-4-(methylsulfonimidoyl)benzamide (about 5.5 g). $^1$H NMR (400 MHz, DMSO-$d_6$) δ ppm 10.01 (s, 1H), 8.22 (d, J=8.4 Hz, 2H), 8.10 (d, J=8.4 Hz, 2H), 7.49 (d, J=2.0 Hz, 1H), 7.32-7.41 (m, 2H), 7.23-7.30 (m, 1H), 7.06 (dd, J=5.0, 3.6 Hz, 1H), 6.85 (d, J=8.4 Hz, 1H), 3.28 (s, 3H); LCMS (ESI) [M+H]$^+$ m/z: calcd 372.1; found 372.0; HPLC: 90.35%@220 nm, 90.09%@254 nm.

Step 11: Synthesis of N-[2-amino-5-(2-thienyl)phenyl]-4-(methylsulfonimidoyl) and N-[2-amino-5-(2-thienyl)phenyl]-4-(methylsulfonimidoyl)benzamide N-[2-amino-5-(2-thienyl)phenyl]-4-(methylsulfonimidoyl)benzamide (about 5.5 g, 14.8 mmol) was separated by chiral SFC (Instrument: Berger, Multigr AM-II; Column: Daicel chiralpak IC 250×50 mm I.D. 10 μm; Mobile phase: supercritical $CO_2$/EtOH (0.1% $NH_3$—$H_2O$, v %)=45/55; Flow Rate: 200 mL/min; Column Temperature: about 38° C.; Nozzle Pressure: 100 bar; Nozzle Temperature: about 60° C.; Evaporator Temperature: about 20° C.; Trimmer Temperature: 25° C.; Wavelength: 220 nm) to afford the products. Stereochemistry was arbitrarily assigned.

Rel-(S)—N-[2-amino-5-(2-thienyl)phenyl]-4-(methylsulfonimidoyl)benzamide: HNMR showed the product was impure. The residue was further purified by flash chromatography (ISCO®; about 40 g AgelaFlash® Silica Flash Column, DCM/MeOH with MeOH from 0~5%, 40 mL/min, 254 nm) to afford N-[2-amino-5-(2-thienyl)phenyl]-4-(methylsulfonimidoyl)benzamide (about 1.8 g peak 1, retention time=2.144 min, single enantiomer). $^1$H NMR (400 MHz, DMSO-$d_6$) δ ppm 9.92 (s, 1H), 8.18 (d, J=8.0 Hz, 2H), 8.06 (d, J=8.3 Hz, 2H), 7.49 (s, 1H), 7.36 (d, J=5.0 Hz, 1H), 7.32 (d, J=8.3 Hz, 1H), 7.25 (d, J=3.3 Hz, 1H), 7.03-7.08 (m, 1H), 6.78-6.86 (m, 1H), 6.82 (d, J=8.5 Hz, 1H), 5.22 (s, 2H), 4.39 (s, 1H), 3.13 (s, 3H); LCMS (ESI) [M+H]$^+$ m/z: calcd 372.1, found 372.0; HPLC: 97.04%@220 nm, 97.58%@254 nm; 99.8% ee. UROT=5.3 (MeOH).

Rel-(R)—N-[2-amino-5-(2-thienyl)phenyl]-4-(methylsulfonimidoyl)benzamide: HPLC showed the product was impure. The residue was further purified by flash chromatography (ISCO®; about 40 g AgelaFlash® Silica Flash Column, DCM/MeOH with MeOH from 0~5%, 40 mL/min, 254 nm) to afford N-[2-amino-5-(2-thienyl)phenyl]-4-(methylsulfonimidoyl)benzamide (about 1.69 g, peak 2, retention time=2.572 min, single enantiomer). $^1$H NMR (400 MHz, DMSO-$d_6$) δ ppm 9.92 (s, 1H), 8.18 (d, J=8.3 Hz, 2H), 8.06 (d, J=8.3 Hz, 2H), 7.48 (d, J=1.8 Hz, 1H), 7.36 (dd, J=5.0, 1.0 Hz, 1H), 7.32 (dd, J=8.3, 2.0 Hz, 1H), 7.25 (dd, J=3.5, 1.0 Hz, 1H), 7.05 (dd, J=5.1, 3.6 Hz, 1H), 6.82 (d, J=8.3 Hz, 1H), 5.22 (s, 2H), 4.40 (s, 1H), 3.13 (s, 3H); LCMS (ESI) [M+H]$^+$ m/z: calcd 372.1, found 372.0; HPLC: 96.280%@220 nm, 96.950%@254 nm; 98.6% ee. UROT=−6.0 (MeOH).

Example 72. Synthesis of N-[2-amino-5-(4-fluorophenyl)phenyl]-4-(methylsulfonimidoyl)benzamide (Compound 104)

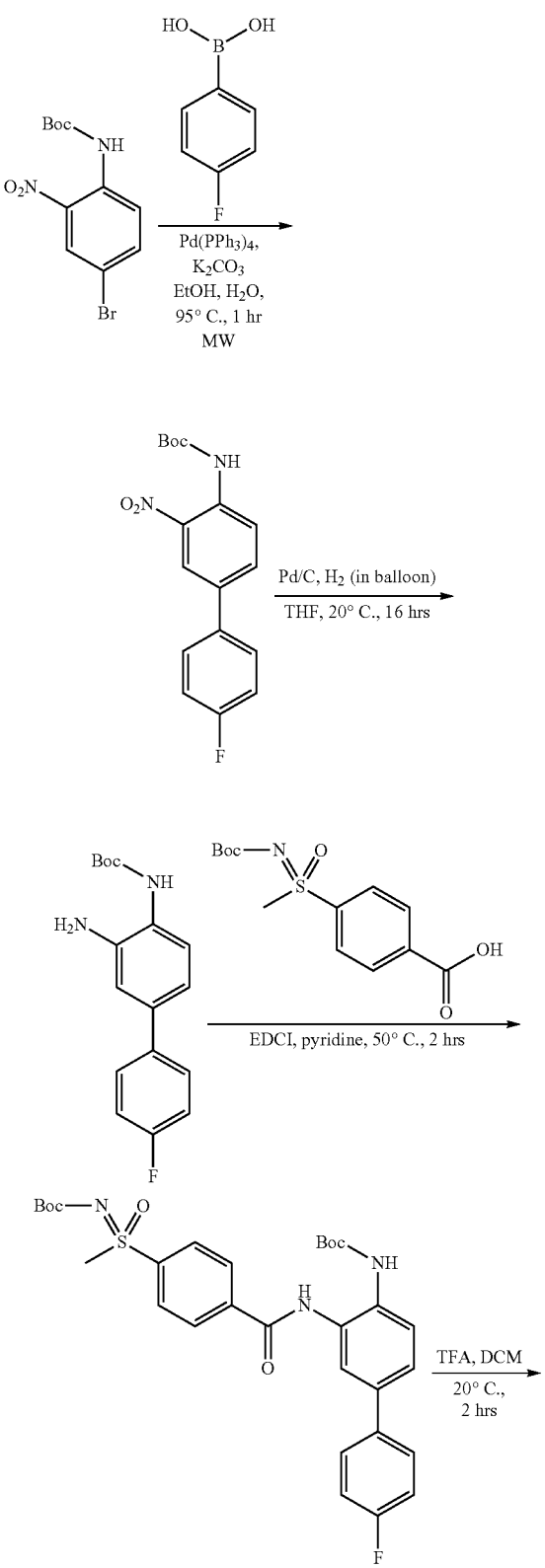

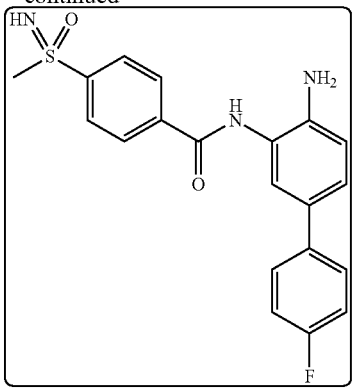

Step 1: Synthesis of tert-butyl N-[4-(4-fluorophenyl)-2-nitro-phenyl]carbamate Tert-butyl N-(4-bromo-2-nitro-phenyl)carbamate (about 300 mg, 0.946 mmol), (4-fluorophenyl)boronic acid (about 150 mg, 1.07 mmol), $K_2CO_3$ (about 350 mg, 2.53 mmol) and palladium;triphenylphosphane (about 100 mg, 0.087 mmol) were taken up into a microwave tube in EtOH (about 10 mL) and $H_2O$ (about 1 mL). The sealed tube was heated at about 95° C. for about 1 hour in microwave. The resulting mixture was filtered and concentrated under reduced pressure. The residue was purified by flash chromatography (ISCO®; about 12 g AgelaFlash® Silica Flash Column, petroleum ether/EtOAc with EtOAc from 0~5%, flow rate=30 mL/min, 254 nm) to afford tert-butyl N-[4-(4-fluorophenyl)-2-nitro-phenyl]carbamate (170 mg). $^1$H NMR (400 MHz, methanol-$d_4$) δ ppm 8.29-8.46 (m, 2H), 7.93 (dd, J=8.8, 2.3 Hz, 1H), 7.65-7.73 (m, 2H), 7.21 (t, J=8.8 Hz, 2H), 1.55 (s, 9H); $^{19}$F NMR (377 MHz, methanol-$d_4$) δ ppm −166.66.

Step 2: Synthesis of tert-butyl N-[2-amino-4-(4-fluorophenyl)phenyl]carbamate To a solution of Pd/C (about 62 mg, 10 wt % Pd with 50 wt % water) in THF (about 5 mL) was added tert-butyl N-[4-(4-fluorophenyl)-2-nitro-phenyl]carbamate (about 170 mg, 0.512 mmol). The resulting mixture was sealed and degassed under vacuum and purged with $N_2$ for three times, and then stirred at about 20° C. for about 2 hours under $H_2$ (in balloon). The resulting mixture was sealed and degassed under vacuum and purged with $N_2$ for three times, and then stirred at about 20° C. for about 2 hours under $H_2$ (in balloon). The resulting mixture was sealed and degassed under vacuum and purged with $N_2$ for three times, and then stirred at about 20° C. for about 12 hours under $H_2$ (in balloon). The resulting mixture was filtered and concentrated under reduced pressure to afford tert-butyl N-[2-amino-4-(4-fluorophenyl)phenyl]carbamate (about 150 mg), which was directly used without further purification. $^1$H NMR (400 MHz, DMSO-$d_6$) δ ppm 8.43 (d, J=1.9 Hz, 1H), 8.36 (s, 1H), 7.94-8.03 (m, 1H), 7.53-7.59 (m, 2H), 7.25 (s, 1H), 6.95 (d, J=2.1 Hz, 1H), 6.80 (dd, J=8.2, 2.1 Hz, 1H), 4.97 (s, 2H), 1.47 (s, 9H); $^{19}$F NMR (376 MHz, DMSO-$d_6$) δ ppm −116.353; LCMS (ESI) [M+H]$^+$ m/z: calcd 303.1; found 303.1.

Step 3: Synthesis of tert-butyl N-[[4-[[2-(tert-butoxycarbonylamino)-5-(4-fluorophenyl)phenyl]carbamoyl]phenyl]-methyl-oxo-sulfanylidene]carbamate To a solution of 3-(ethyliminomethyleneamino)-N,N-dimethyl-propan-1-amine;hydrochloride (about 120 mg, 0.626 mmol) in pyridine (about 6 mL) was added 4-(N-tert-butoxycarbonyl-S-methyl-sulfonimidoyl)benzoic acid (about 100 mg, 0.334 mmol) and tert-butyl N-[2-amino-4-(4-fluorophenyl)phenyl]carbamate (about 100 mg, 0.496 mmol). The mixture was stirred at about 50° C. for about 2 hours. The mixture was concentrated under reduced pressure. The residue was purified by flash chromatography (ISCO®; about 12 g AgelaFlash® Silica Flash Column, MeOH/EtOAc with EtOAc from 0~20%, flow rate=30 mL/min, 254 nm) to afford tert-butyl N-[[4-[[2-(tert-butoxycarbonylamino)-5-(4-fluorophenyl)phenyl]carbamoyl]phenyl]-methyl-oxo-sulfanylidene]carbamate (about 100 mg). LCMS (ESI) [M+H]$^+$ m/z: calcd 584.2; found 484.2 (Boc cleaved mass).

Step 4: Synthesis of N-[2-amino-5-(4-fluorophenyl)phenyl]-4-(methylsulfonimidoyl)benzamide To a solution of tert-butyl N-[[4-[[2-(tert-butoxycarbonylamino)-5-(4-fluorophenyl)phenyl]carbamoyl]phenyl]-methyl-oxo-sulfanylidene]carbamate (about 100 mg, 0.171 mmol) in DCM (about 2 mL) was added TFA (about 0.1 mL, 1.30 mmol). The mixture was stirred at about 20° C. for about 2 hours. The resulting mixture was filtered and concentrated under reduced pressure. The residue was purified by preparative HPLC (Instrument: Gilson GX-281 Liquid Handler, Gilson 322 Pump, Gilson 156 UV Detector; Column: Phenomenex Gemini-NX 80×40 mm×3 μm; Mobile phase A: water (10 mmol $NH_4HCO_3$); Mobile phase B: MeCN; Gradient: B from 32% to 62% in 7.8 min, hold 100% B for 1 min; Flow Rate: 25 mL/min; Column Temperature: about 30° C.; Wavelength: 220 nm, 254 nm) to afford N-[2-amino-5-(4-fluorophenyl)phenyl]-4-(methylsulfonimidoyl)benzamide (about 29.8 mg). $^1$H NMR (400 MHz, DMSO-$d_6$) δ ppm 9.93 (s, 1H), 8.19 (d, J=8.3 Hz, 2H), 8.07 (d, J=8.3 Hz, 2H), 7.59 (dd, J=8.7, 5.4 Hz, 2H), 7.51 (d, J=1.8 Hz, 1H), 7.33 (dd, J=8.4, 2.1 Hz, 1H), 7.22 (t, J=8.9 Hz, 2H), 6.87 (d, J=8.3 Hz, 1H), 5.17 (s, 2H), 4.40 (s, 1H), 3.13 (s, 3H); $^{19}$F NMR (377 MHz, methanol-$d_4$) δ ppm −117.463; LCMS (ESI) [M+H]$^+$ m/z: calcd 384.1; found 383.9; HPLC: 100%@220 nm, 99.91%@254 nm.

Example 73. Synthesis of N-[2-amino-5-(2-thienyl)phenyl]-4-[N-(2,2-dimethylpropanoyl)-S-methylsulfonimidoyl]benzamide (Compound 125)

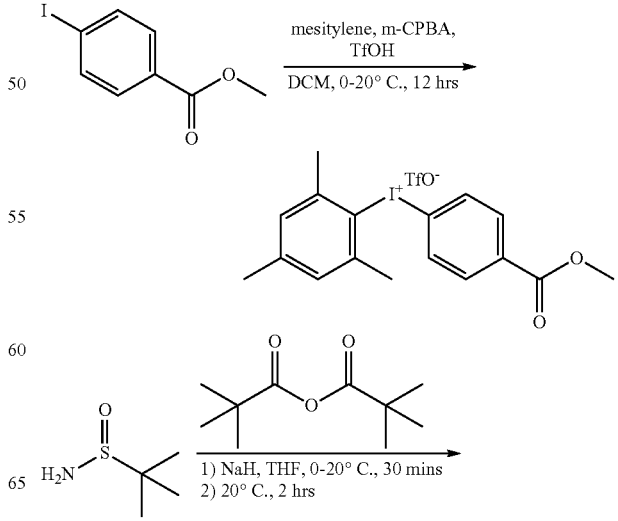

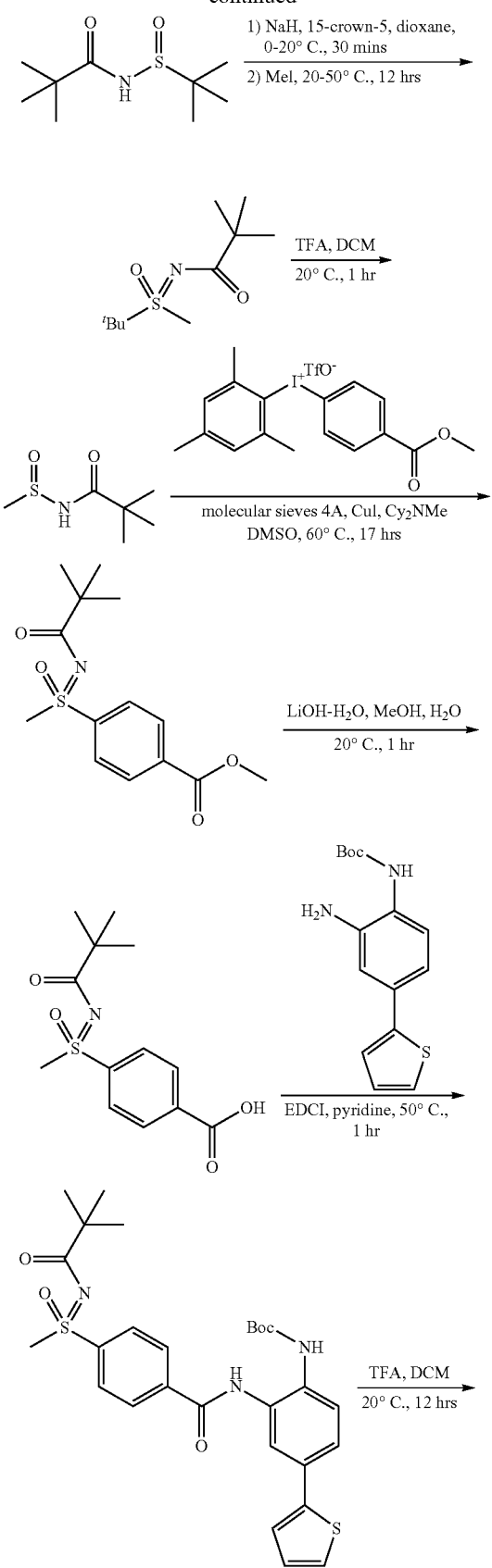

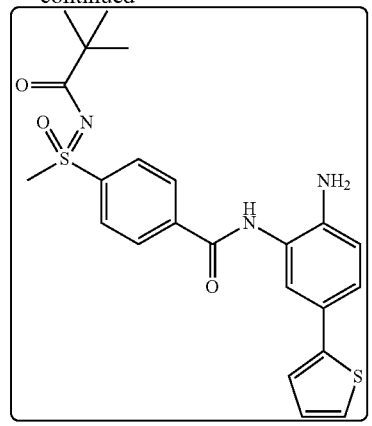

Step 1: Synthesis of (4-methoxycarbonylphenyl)-(2,4,6-trimethylphenyl)iodonium

To a solution of methyl 4-iodobenzoate (about 1 g, 3.82 mmol) in DCM (about 30 mL) at about 0° C. was added 3-chlorobenzenecarboperoxoic acid (about 720 mg, 4.17 mmol), mesitylene (about 0.6 mL, 4.32 mmol) and trifluoromethanesulfonic acid (about 0.8 mL, 9.10 mmol). The mixture was stirred at about 20° C. for about 12 hours. The mixture was concentrated and methyl tert butyl ether (about 5 mL) was added. The heterogeneous mixture was cooled to about −30° C. and stirred for about 2 hours. The resulting residue was filtered and washed on the filter with methyl tert butyl ether to give (4-methoxycarbonylphenyl)-(2,4,6-trimethylphenyl)iodonium (about 370 mg). $^1$H NMR (400 MHz, chloroform-d) δ ppm 8.02 (d, J=8.8 Hz, 2H), 7.77 (d, J=8.4 Hz, 2H), 7.12 (s, 2H), 3.84-4.01 (m, 3H), 2.62 (s, 6H), 2.37 (s, 3H); LCMS (ESI) [M+H]$^+$ m/z: calcd 382.0, found 380.9.

Step 2: Synthesis of N—[(S)-tert-butylsulfinyl]-2,2-dimethyl-propanamide

To a solution of 2-methylpropane-2-sulfinamide (about 2 g, 16.5 mmol) in THF (about 20 mL) was added NaH (about 1 g, 25.0 mmol, 60 wt %). The mixture was stirred at about 0° C. for 30 minutes. Then the mixture was warmed up to about 20° C., 2,2-dimethylpropanoyl 2,2-dimethylpropanoate (about 3.4 g, 18.2 mmol) was added to the mixture at about 20° C. and the mixture was stirred at about 20° C. for about 2 hours. The reaction mixture was adjusted to about pH=8 with saturated Na$_2$CO$_3$ aqueous solution and extracted with DCM (about 30 mL*3). The combined organic layers were dried over Na$_2$SO$_4$ and filtered. The filtrate was concentrated under reduced pressure. The residue was purified by flash chromatography (ISCO®; about 25 g SepaFlash® Silica Flash Column, petroleum ether/EtOAc with EtOAc from 0~20%, 40 mL/min, 254 nm) to give N—[(S)-tert-butylsulfinyl]-2,2-dimethyl-propanamide (about 2.12 g). LCMS (ESI) [M+H]$^+$ m/z: calcd 206.1, found 205.9.

Step 3: Synthesis of N-(tert-butyl-methyl-oxo-sulfanylidene)-2,2-dimethyl-propanamide To a solution of N—[(S)-tert-butylsulfinyl]-2,2-dimethyl-propanamide (about 2 g, 9.74 mmol) in dioxane (about 30 mL) was added 15-crown-5 (about 0.5 mL, 2.52 mmol) and NaH (about 600 mg, 15.0 mmol, 60 wt % in mineral oil).

449

The mixture was stirred at about 0° C. for about 30 minutes. Then the mixture was warmed up to about 20° C., iodomethane (about 1.8 mL, 28.9 mmol) was added to the mixture at about 20° C. and stirred at about 50° C. for about 12 hours. The reaction mixture was adjusted to about pH=8 with saturated Na$_2$CO$_3$ aqueous solution and extracted with DCM (about 30 mL*3). The combined organic layers were dried over Na$_2$SO$_4$ and filtered. The filtrate was concentrated under reduced pressure. The residue was purified by flash chromatography (ISCO®; about 25 g SepaFlash® Silica Flash Column, petroleum ether/EtOAc with EtOAc from 0~25%, 40 mL/min, 254 nm) to give N-(tert-butyl-methyl-oxo-sulfanylidene)-2,2-dimethyl-propanamide (about 1.78 g). LCMS (ESI) [M+H]$^+$ m/z: calcd 220.1, found 219.9.

Step 4: Synthesis of 2,2-dimethyl-N-(methylsulfinyl)propanamide

To a solution of N-(tert-butyl-methyl-oxo-sulfanylidene)-2,2-dimethyl-propanamide (about 1.7 g, 7.75 mmol) in DCM (about 30 mL) was added TFA (about 4 mL, 51.9 mmol). The mixture was stirred at about 20° C. for about 1 hour. The reaction mixture was adjusted to about pH=8 with saturated Na$_2$CO$_3$ aqueous solution and extracted with DCM (about 30 mL*3). The combined organic layers were dried over Na$_2$SO$_4$ and filtered. The filtrate was concentrated under reduced pressure. The residue was purified by flash chromatography (ISCO®; about 25 g SepaFlash® Silica Flash Column, petroleum ether/EtOAc with EtOAc from 0~100%, 40 mL/min, 254 nm) to give 2,2-dimethyl-N-(methylsulfinyl)propanamide (about 670 mg). LCMS (ESI) [M+H]$^+$ m/z: calcd 164.1, found 163.8.

Step 5: Synthesis of methyl 4-[N-(2,2-dimethylpropanoyl)-S-methyl-sulfonimidoyl]benzoate To a solution of 2,2-dimethyl-N—[(S)-methylsulfinyl]propanamide (55 mg, 0.336 mmol) in DMSO (about 2 mL) was added molecular sieves 4A (about 2 g, 0.336 mmol), (4-methoxycarbonylphenyl)-(2,4,6-trimethylphenyl)iodonium;trifluoromethanesulfonic acid (about 360 mg, 0.677 mmol), CuI (about 7 mg, 0.0360 mmol) and N-cyclohexyl-N-methyl-cyclohexanamine (about 0.15 mL, 0.700 mmol). The mixture was stirred at about 60° C. for about 17 hours. The reaction mixture was filtered through silica gel pad eluting with EtOAc (about 30 mL). The filtrate was washed with brine (about 30 mL*3), dried over Na$_2$SO$_4$ and then concentrated under reduced pressure. The residue was purified by preparative TLC (silica, petroleum ether/EtOAc=4/1; 254 nm) to give methyl 4-[N-(2,2-dimethylpropanoyl)-S-methyl-sulfonimidoyl]benzoate (about 55 mg). LCMS (ESI) [M+H]$^+$ m/z: calcd 298.1, found 297.9; racemic mixture.

Step 6: Synthesis of 4-[N-(2,2-dimethylpropanoyl)-S-methyl-sulfonimidoyl]benzoic acid To a solution of methyl 4-[N-(2,2-dimethylpropanoyl)-S-methyl-sulfonimidoyl]benzoate (about 45 mg, 0.151 mmol) in MeOH (about 2 mL) and H$_2$O (about 1 mL) was added lithium;hydroxide;hydrate (about 19 mg, 0.452 mmol). The mixture was stirred at about 20° C. for about 1 hour. The mixture was concentrated under reduced pressure to remove the organic solvent. The aqueous phase was adjusted to about pH=4 with 2N HCl aqueous solution. The mixture was filtered. The filter cake was dried under reduced pressure to give 4-[N-(2,2-dimethylpropanoyl)-S-methyl-sulfonimi-

450 doyl]benzoic acid (about 25 mg), which was directly used without further purification. LCMS (ESI) [M+H]$^+$ m/z: calcd 284.1, found 283.9.

Step 7: Synthesis of tert-butyl N-[2-[[4-[N-(2,2-dimethylpropanoyl)-S-methyl-sulfonimidoyl]benzoyl]amino]-4-(2-thienyl)phenyl]carbamate To a solution of 4-[N-(2,2-dimethylpropanoyl)-S-methyl-sulfonimidoyl]benzoic acid (about 40 mg, 0.141 mmol) in pyridine (about 2 mL) was added EDCI (about 40 mg, 0.208 mmol) and tert-butyl N-[2-amino-4-(2-thienyl)phenyl]carbamate (about 49 mg, 0.168 mmol). The mixture was stirred at about 50° C. for about 1 hour. The reaction mixture was concentrated under reduced pressure. The residue was purified by preparative TLC (silica, petroleum ether/EtOAc=3/1; 254 nm) to give tert-butyl N-[2-[[4-[N-(2,2-dimethylpropanoyl)-S-methyl-sulfonimidoyl]benzoyl]amino]-4-(2-thienyl)phenyl]carbamate (about 40 mg). LCMS (ESI) [M+H]$^+$ m/z: calcd 556.2, found 456.0 (Boc cleaved mass).

Step 8: Synthesis of N-[2-amino-5-(2-thienyl)phenyl]-4-[N-(2,2-dimethylpropanoyl)-S-methyl-sulfonimidoyl]benzamide To a solution of tert-butyl N-[2-[[4-[N-(2,2-dimethylpropanoyl)-S-methyl-sulfonimidoyl]benzoyl]amino]-4-(2-thienyl)phenyl]carbamate (about 20 mg, 0.036 mmol) in DCM (about 3 mL) was added TFA (about 0.1 mL, 1.30 mmol). The mixture was stirred at about 20° C. for about 12 hours. The reaction mixture was adjusted to about pH=8 with saturated Na$_2$CO$_3$ aqueous solution and extracted with DCM (about 15 mL*3). The combined organic layers were dried over Na$_2$SO$_4$ and filtered. The filtrate was concentrated under reduced pressure. The residue was purified by preparative HPLC (Instrument: Gilson GX-281 Liquid Handler, Gilson 322 Pump, Gilson 156 UV Detector; Column: Phenomenex C18 80×40 mm×3 µm; Mobile phase A: water with 10 mmol NH$_4$HCO$_3$ (v %); Mobile phase B: ACN; Gradient: B from 40% to 70% in 9.5 min, hold 100% B for 1 min; Flow Rate: 30 mL/min; Column Temperature: about 30° C.; Wavelength: 220 nm, 254 nm) to give N-[2-amino-5-(2-thienyl)phenyl]-4-[N-(2,2-dimethylpropanoyl)-S-methyl-sulfonimidoyl]benzamide (about 5.3 mg). $^1$H NMR (400 MHz, chloroform-d) δ ppm 8.63 (brs, 1H), 8.10 (d, J=7.2 Hz, 2H), 7.95 (d, J=7.6 Hz, 2H), 7.60 (s, 1H), 7.35 (d, J=8.0 Hz, 1H), 7.14-7.31 (m, 2H), 6.98-7.12 (m, 1H), 6.87 (d, J=7.6 Hz, 1H), 3.23-3.33 (m, 3H), 1.20 (s, 9H); LCMS [M+Na]*m/z: calcd 456.1; found 478.0; HPLC: 98.48%@220 nm, 1000%@254 nm.

Example 74. Synthesis of N-[2-amino-5-(2-thienyl)phenyl]-4-(cyclopropylsulfonimidoyl)benzamide (Compound 103)

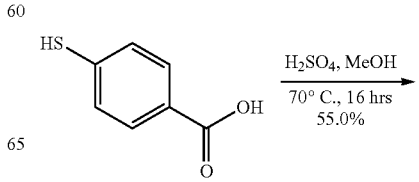

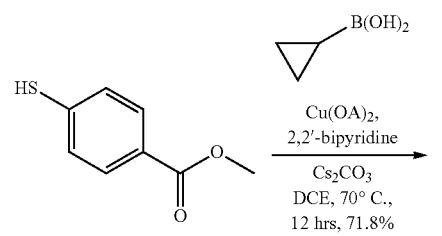
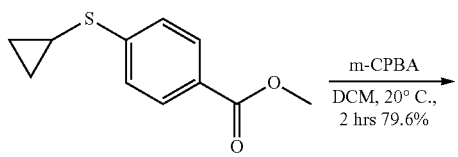
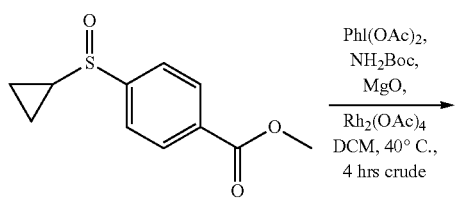
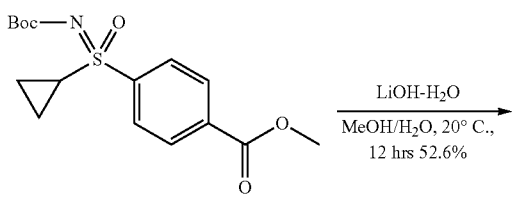
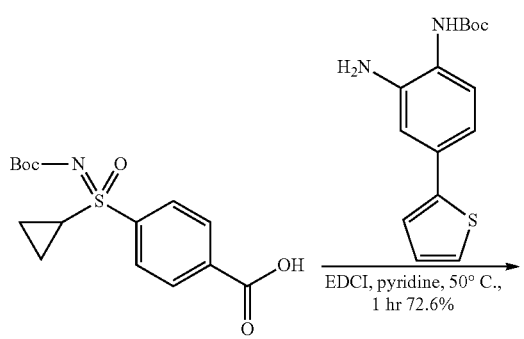
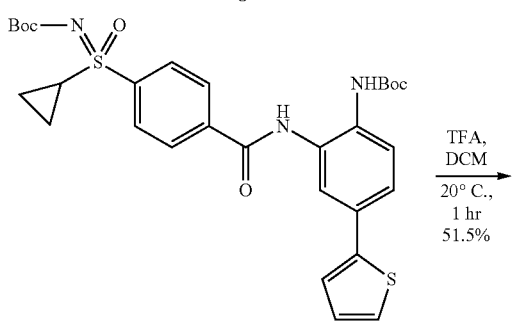

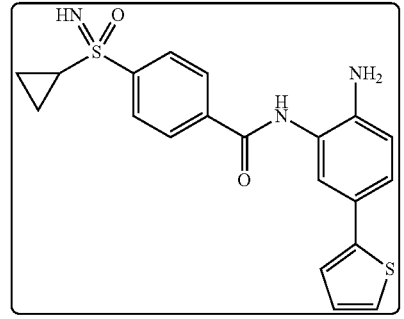 [SMILES: N=S(=O)(c1ccc(C(=O)Nc2cc(-c3cccs3)ccc2N)cc1)C1CC1]

Step 1: Synthesis of methyl 4-sulfanylbenzoate

To a solution of 4-sulfanylbenzoic acid (about 1 g, 6.49 mmol) in MeOH (about 20 mL) was added sulfuric acid (about 0.3 mL, 5.63 mmol). The reaction mixture was heated to reflux for about 16 hours. The mixture was concentrated under reduced pressure. The residue was purified by flash chromatography (Biotage®; about 20 g AgelaFlash® Silica Flash Column, petroleum ether/EtOAc with EtOAc from 0~16%, flow rate=40 mL/min) to afford methyl 4-sulfanyl-benzoate (about 600 mg). LCMS (ESI) [M+H]$^+$ m/z: calcd 169.0, found 169.1.

Step 2: Synthesis of methyl 4-cyclopropylsulfanylbenzoate

A mixture of methyl 4-sulfanylbenzoate (about 450 mg, 2.68 mmol), cyclopropylboronic acid (about 344 mg, 4.00 mmol), dicesium;carbonate (about 872 mg, 2.68 mmol), copper;diacetate (about 487 mg, 2.68 mmol) and 2,2'-bipyridine (about 418 mg, 2.68 mmol) in 1,2-dichloroethane (about 15 mL) was stirred at about 70° C. for about 12 hours. The mixture was quenched by addition of 25% NH$_3$—H$_2$O (about 5 mL) was added to mixture. The resulting mixture was extracted with DCM (about 30 mL*3). The combined organic layer was dried over anhydrous Na$_2$SO$_4$, filtered and concentrated under reduced pressure. The residue was purified by flash chromatography (Biotage®; about 4 g Agela-Flash® Silica Flash Column, petroleum ether/EtOAc with EtOAc from 0~18%, flow rate=15 mL/min) to afford methyl 4-cyclopropylsulfanylbenzoate (about 400 mg). LCMS (ESI) [M+H]$^+$ m/z: calcd 209.1, found 209.1.

Step 3: Synthesis of methyl 4-cyclopropylsulfinylbenzoate

To a solution of methyl 4-cyclopropylsulfanylbenzoate (about 350 mg, 1.68 mmol) in DCM (about 15 mL) was added m-CPBA (about 342 mg, 1.68 mmol, 85 wt %) at 20° C. The mixture was stirred at about 20° C. for about 1 hour. m-CPBA (about 70 mg, 0.344 mmol, 85 wt %) was added and mixture was stirred at about 20° C. for about 1 hour. The mixture was quenched by addition of saturated Na$_2$S$_2$O$_4$ aqueous solution (about 10 mL), and then saturated NaHCO$_3$ aqueous solution was added to adjust the pH to about 8. The mixture was extracted with DCM (about 20 mL*3). The combined organic layer was dried over anhydrous Na$_2$SO$_4$, filtered and concentrated under reduced pressure to give methyl 4-cyclopropylsulfinylbenzoate (about 300 mg). $^1$H NMR (400 MHz, methanol-d$_4$) δ ppm 8.21 (d, J=8.5 Hz, 2H), 7.83 (d, J=8.5 Hz, 2H), 3.95 (s, 3H), 2.48 (tt, J=7.8, 4.9 Hz, 1H), 1.10-1.19 (m, 2H), 0.96-1.07 (m, 2H); LCMS (ESI) [M+H]+ m/z: calcd 225.1, found 225.1.

Step 4: Synthesis of methyl 4-(N-tert-butoxycarbonyl-S-cyclopropyl-sulfonimidoyl)benzoate A mixture of methyl 4-cyclopropylsulfinylbenzoate (about 300 mg, 1.34 mmol), NH₂Boc (about 315 mg, 2.69 mmol), acetate iodosobenzene diacetate (about 647 mg, 2.01 mmol), MgO (about 270 mg, 6.70 mmol) and diacetoxyrhodium (about 11 mg, 0.024 mmol) in DCM (about 15 mL) was stirred at about 40° C. for about 4 hours. The mixture was filtered. The filtrate was concentrated under reduced pressure. The residue was purified by flash chromatography (Biotage®; about 12 g SepaFlash® Silica Flash Column, petroleum ether/EtOAc with EtOAc from 0~45%, 50 mL/min, 254 nm) to afford methyl 4-(N-tert-butoxycarbonyl-S-cyclopropyl-sulfonimidoyl)benzoate (about 350 mg). LCMS (ESI) [M+H]+ m/z: calcd 340.1, found 340.1.

Step 5: Synthesis of 4-(N-tert-butoxycarbonyl-S-cyclopropyl-sulfonimidoyl)benzoic acid To a solution of methyl 4-(N-tert-butoxycarbonyl-S-cyclopropyl-sulfonimidoyl)benzoate (about 300 mg, 0.883 mmol) in MeOH (about 3 mL) was added lithium;hydroxide;hydrate (about 185 mg, 4.41 mmol) in H₂O (about 3 mL) at about 20° C. The mixture was stirred at about 20° C. for about 12 hours. The reaction mixture was concentrated under reduced pressure to remove MeOH. 1N HCl solution was added to adjust pH to about 3~4, the mixture was extracted with EtOAc (about 10 mL*3). The combined organic layers were dried over anhydrous Na₂SO₄, filtered and concentrated to give 4-(N-tert-butoxycarbonyl-S-cyclopropyl-sulfonimidoyl)benzoic acid (about 180 mg). ¹H NMR (400 MHz, DMSO-d₆) δ ppm 8.18 (d, J=8.5 Hz, 2H), 7.99 (d, J=8.5 Hz, 2H), 1.30-1.36 (m, 1H), 1.15-1.25 (m, 11H), 0.95-1.03 (m, 2H); LCMS (ESI) [M+H]+ m/z: calcd 326.1, found 326.1.

Step 6: Synthesis of tert-butyl N-[[4-[[2-(tert-butoxycarbonylamino)-5-(2-thienyl)phenyl]carbamoyl]phenyl]-cyclopropyl-oxo-$l^{6}-sulfanylidene]carbamate A mixture of 4-(N-tert-butoxycarbonyl-S-cyclopropyl-sulfonimidoyl)benzoic acid (about 150 mg, 0.461 mmol), tert-butyl N-[2-amino-4-(2-thienyl)phenyl]carbamate (about 150 mg, 0.516 mmol) and EDCI (about 133 mg, 0.693 mmol) in pyridine (about 10 mL) was stirred at about 50° C. for about 1 hour. The reaction mixture was concentrated under reduced pressure. The residue was purified by flash chromatography (Biotage®; about 12 g AgelaFlash® Silica Flash Column, petroleum ether/EtOAc with EtOAc from 0~47%, flow rate=40 mL/min) to afford tert-butyl (2-(4-(N-(tert-butoxycarbonyl)cyclopropanesulfonimidoyl)benzamido)-4-(thiophen-2-yl)phenyl)carbamate (about 200 mg). ¹H NMR (400 MHz, DMSO-d₆) δ ppm 10.11 (s, 1H), 8.79 (s, 1H), 8.22 (d, J=8.5 Hz, 2H), 8.05 (d, J=8.5 Hz, 2H), 7.79 (d, J=1.8 Hz, 1H), 7.69 (d, J=8.8 Hz, 1H), 7.49-7.59 (m, 2H), 7.46 (d, J=2.8 Hz, 1H), 7.13 (dd, J=4.9, 3.6 Hz, 1H), 1.45 (s, 9H), 1.32-1.38 (m, 1H), 1.25 (s, 9H), 1.19 (d, J=2.3 Hz, 1H), 1.17 (s, 1H), 0.97-1.07 (m, 2H); LCMS (ESI) [M+H]+ m/z: calcd 598.2, found 598.3.

Step 7: Synthesis of N-[2-amino-5-(2-thienyl)phenyl]-4-(cyclopropylsulfonimidoyl)benzamide To a solution of tert-butyl (2-(4-(N-(tert-butoxycarbonyl)cyclopropanesulfonimidoyl)benzamido)-4-(thiophen-2-yl) phenyl)carbamate (about 180 mg, 0.301 mmol) in DCM (about 10 mL) was added TFA (about 0.47 mL, 6.10 mmol) at about 20° C. The mixture was stirred at about 20° C. for about 1 hour. The mixture was concentrated under reduced pressure. The residue was purified by preparative HPLC (Instrument: Gilson GX-281 Liquid Handler, Gilson 322 Pump, Gilson 156 UV Detector; Column: Phenomenex Gemini-NX 80×40 mm×3 μm; Mobile phase A: water with 10 mmol NH₄HCO₃ (v %); Mobile phase B: MeCN; Gradient: B from 27% to 57% in 7.8 min, hold 100% B for 1 min; Flow Rate: 25 mL/min; Column Temperature: about 30° C.; Wavelength: 220 nm, 254 nm) to afford N-[2-amino-5-(2-thienyl)phenyl]-4-(cyclopropylsulfonimidoyl)benzamide (about 61.7 mg). ¹H NMR (400 MHz, DMSO-d₆) δ ppm 9.90 (s, 1H), 8.17 (d, J=8.3 Hz, 2H), 8.01 (d, J=8.3 Hz, 2H), 7.48 (d, J=1.8 Hz, 1H), 7.22-7.38 (m, 3H), 7.05 (dd, J=5.0, 3.8 Hz, 1H), 6.82 (d, J=8.3 Hz, 1H), 5.22 (s, 2H), 4.39 (s, 1H), 2.66-2.76 (m, 1H), 1.14 (ddd, J=10.2, 7.2, 3.1 Hz, 1H), 0.87-1.04 (m, 3H); LCMS (ESI) [M+H]+ m/z: calcd 398.1, found 398.1; HPLC: 94.84@220 nm, 99.52@254 nm.

Example 75. Synthesis of N-[2-amino-5-(2-thienyl)phenyl]-4-(phenylsulfonimidoyl)benzamide (Compound 102)

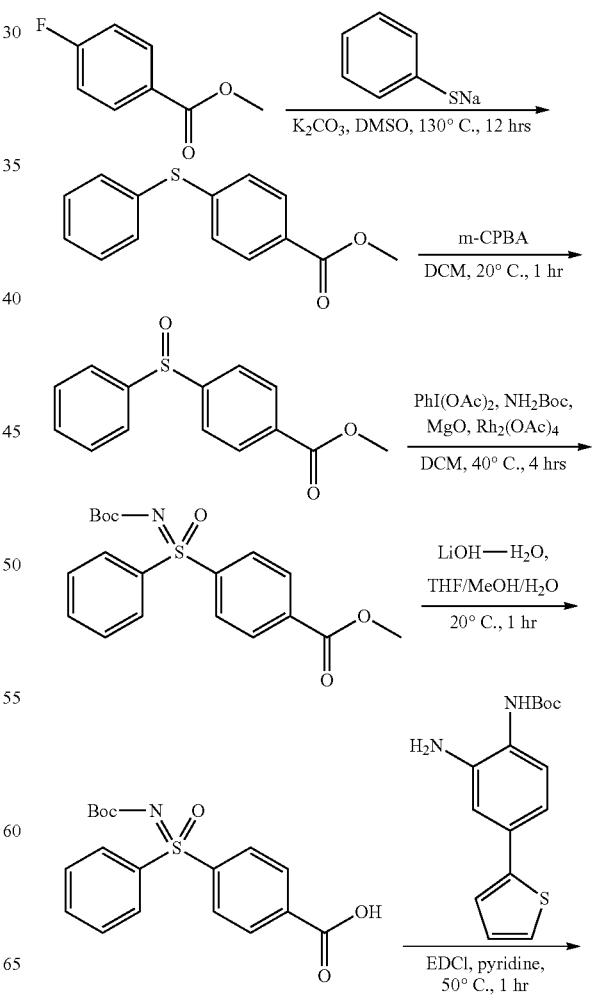

-continued

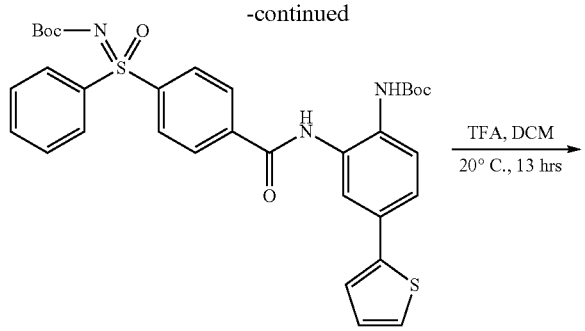

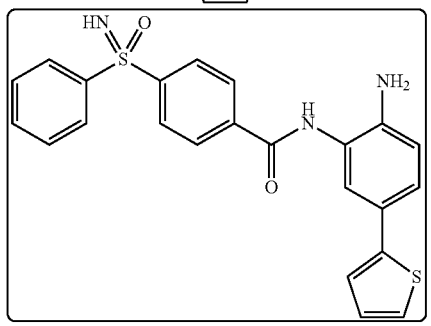

Step 1: Synthesis of methyl 4-phenylsulfanylbenzoate

A mixture of methyl 4-fluorobenzoate (about 2 g, 13.0 mmol), phenylsulfanylsodium (about 1.9 g, 14.4 mmol) and $K_2CO_3$ (about 5.4 g, 39.1 mmol) in DMSO (about 10 mL) was stirred at about 130° C. for about 12 hours. The resulting mixture was quenched by addition of water (about 30 mL) and extracted with EtOAc (about 30 mL*3). The combined organic layer was washed with brine (about 100 mL*3), dried over anhydrous $Na_2SO_4$, filtered and concentrated under reduced pressure to give a product, which was purified by flash chromatography (ISCO®; about 24 g AgelaFlash® Silica Flash Column, petroleum ether/EtOAc with EtOAc from 0~2%, 35 mL/min, 254 nm) to afford methyl 4-phenylsulfanylbenzoate (about 210 mg). LCMS (ESI) $[M+H]^+$ m/z: calcd 245.1; found 244.9.

Step 2: Synthesis of methyl 4-(benzenesulfinyl)benzoate

To a solution of methyl 4-phenylsulfanylbenzoate (about 210 mg, 0.860 mmol) in DCM (about 10 mL) was added m-CPBA (about 185 mg, 0.911 mmol, 85 wt %). The mixture was stirred at about 20° C. for about 1 hour. The mixture was quenched by addition of saturated $Na_2S_2O_3$ aqueous solution (about 15 mL), saturated $Na_2CO_3$ aqueous solution (about 15 mL) and extracted with DCM (about 20 mL*2). The combined organic layer was dried over anhydrous $Na_2SO_4$, filtered and concentrated under reduced pressure to give methyl 4-(benzenesulfinyl)benzoate (about 240 mg), which was directly used without further purification. LCMS (ESI) $[M+H]^+$ m/z: calcd 261.1; found 260.9.

Step 3: Synthesis of methyl 4-(N-tert-butoxycarbonyl-S-phenyl-sulfonimidoyl)benzoate To a solution of methyl 4-(benzenesulfinyl)benzoate (about 240 mg, 0.922 mmol), $NH_2Boc$ (about 216 mg, 1.84 mmol), [bis(acetoxy)iodo]benzene (about 445 mg, 1.38 mmol) and MgO (about 191 mg, 4.62 mmol) in DCM (about 5 mL) was added dirhodium tetraacetate (about 18 mg, 0.0407 mmol). The reaction mixture was stirred at about 40° C. for about 4 hours. The mixture was filtered. The filtrate was concentrated under reduced pressure. The residue was purified by flash chromatography (ISCO®; about 12 g AgelaFlash® Silica Flash Column, petroleum ether/EtOAc with EtOAc from 0~35%, 35 mL/min, 254 nm) to afford methyl 4-(N-tert-butoxycarbonyl-S-phenyl-sulfonimidoyl)benzoate (about 180 mg). LCMS (ESI) $[M+H]^+$ m/z: calcd 376.1; found 376.1.

Step 4: Synthesis of 4-(N-tert-butoxycarbonyl-S-phenyl-sulfonimidoyl)benzoic acid To a solution of methyl 4-(N-tert-butoxycarbonyl-S-phenyl-sulfonimidoyl)benzoate (about 180 mg, 0.479 mmol) in THF (about 3 mL) and MeOH (about 3 mL) was added a solution of $LiOH—H_2O$ (about 201 mg, 4.79 mmol) in $H_2O$ (about 2 mL). The mixture was stirred at about 20° C. for about 1 hour. The mixture was concentrated under reduced pressure to remove the organic solvent. The aqueous solution was adjusted to about pH=5 with 2N HCl aqueous solution. The mixture was filtered. The filter cake was dried under reduced pressure to give 4-(N-tert-butoxycarbonyl-S-phenyl-sulfonimidoyl)benzoic acid (about 120 mg), which was directly used without further purification. LCMS (ESI) $[M+H]^+$ m/z: calcd 362.1; found 362.0.

Step 5: Synthesis of tert-butyl (2-(4-(N-(tert-butoxycarbonyl)phenylsulfonimidoyl)benzamido)-4-(thiophen-2-yl)phenyl)carbamate A mixture of 4-(N-tert-butoxycarbonyl-S-phenyl-sulfonimidoyl)benzoic acid (about 50 mg, 0.138 mmol), tert-butyl N-[2-amino-4-(2-thienyl)phenyl]carbamate (about 40 mg, 0.138 mmol) and EDCI (about 40 mg, 0.209 mmol) in pyridine (about 3 mL) was stirred at 50° C. for 1 hour. The mixture was concentrated under reduced pressure. The residue was purified by flash chromatography (ISCO®; about 4 g AgelaFlash® Silica Flash Column, petroleum ether/EtOAc with EtOAc from 0~30%, 20 mL/min, 254 nm) to afford tert-butyl (2-(4-(N-(tert-butoxycarbonyl)phenylsulfonimidoyl)benzamido)-4-(thiophen-2-yl)phenyl)carbamate (about 80 mg). LCMS (ESI) $[M+H]^+$ m/z: calcd 634.2; found 634.4.

Step 6: Synthesis of N-[2-amino-5-(2-thienyl)phenyl]-4-(phenylsulfonimidoyl)benzamide To a solution of tert-butyl (2-(4-(N-(tert-butoxycarbonyl)phenylsulfonimidoyl)benzamido)-4-(thiophen-2-yl)phenyl)carbamate (about 80 mg, 0.126 mmol) in DCM (about 1 mL) was added TFA (about 0.1 mL, 1.30 mmol). The mixture was stirred at 20° C. for 1 hour. TFA (about 0.1 mL, 1.30 mmol) was added, the mixture was stirred at about 20° C. for about 12 hours. The mixture was adjusted to about pH=8 with saturated $NaHCO_3$ aqueous solution and extracted with a mixture of DCM/MeOH (about 15 mL*3, v/v=10:1). The combined organic layer was dried over anhydrous $Na_2SO_4$, filtered and concentrated under reduced pressure. The residue was purified by preparative HPLC (Instrument: Gilson GX-281 Liquid Handler, Gilson 322 Pump, Gilson 156 UV Detector; Column: Phenomenex Gemini-NX C18 75×30 mm×3 μm; Mobile phase A: $H_2O$ with 10 mmol $NH_4HCO_3$ (v %); Mobile phase B: MeCN; Gradient: B from 27% to 57% in 7.8 min, hold 100% B for 2 min; Flow Rate: 25 mL/min; Column Temperature: 30° C.; Wavelength: 220 nm, 254 nm) to give N-[2-amino-5-(2-thienyl)phenyl]-4-(phenylsulfonimidoyl)benzamide (about 30 mg). ¹H NMR (400 MHz, DMSO-d$_6$) δ ppm 9.84 (s, 1H), 8.04-8.14 (m, 4H), 7.96-8.03 (m, 2H), 7.54-7.65 (m, 3H), 7.44 (d, J=1.8 Hz, 1H), 7.34 (dd, J=5.0, 1.0 Hz, 1H), 7.30 (dd, J=8.3, 2.3 Hz, 1H), 7.23 (d, J=2.8 Hz, 1H), 7.04 (dd, J=5.0, 3.5 Hz, 1H), 6.79 (d, J=8.5 Hz, 1H), 5.18 (d, J=10.8 Hz, 3H); LCMS (ESI) [M+H]⁺ m/z: calcd 434.1; found 434.0; HPLC: 98.87%@220 nm, 99.16%@254 nm.

Example 76. Synthesis of N-[2-amino-5-(2-thienyl)phenyl]-5-(methylsulfonimidoyl)benzofuran-2-carboxamide (Compound 143)

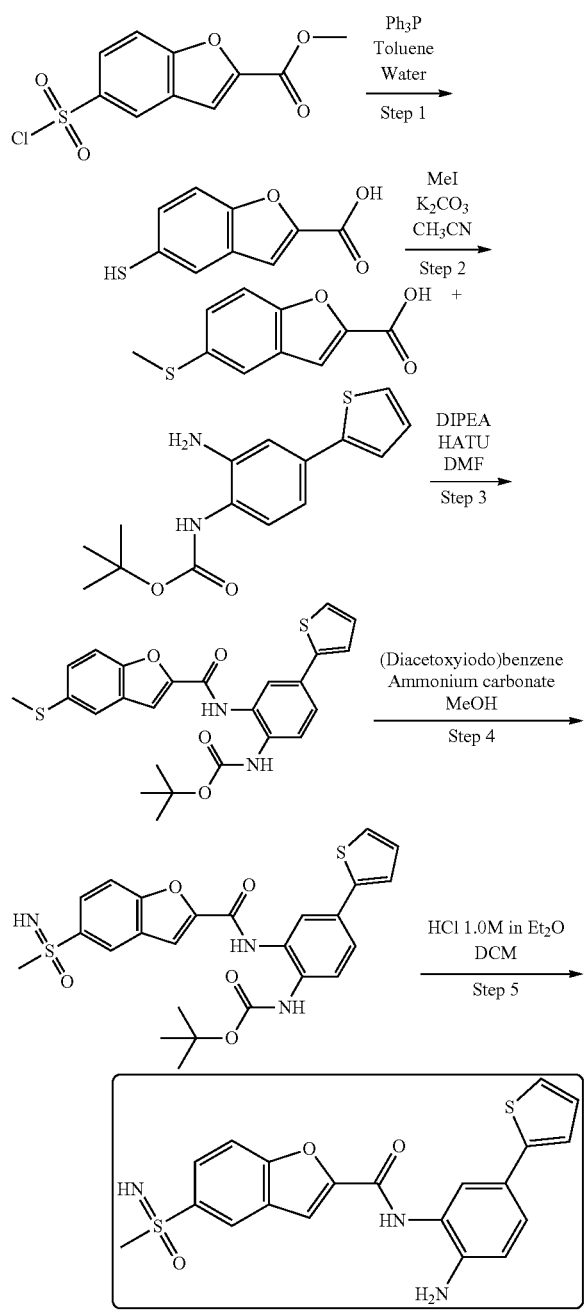

Step 1: The synthesis of 5-sulfanylbenzofuran-2-carboxylic acid

To a stirred solution of methyl 5-chlorosulfonylbenzofuran-2-carboxylate (about 1.71 g, 6.23 mmol) in toluene (about 17 mL) under argon atmosphere was added dropwise a solution of Triphenylphosphine (about 5.31 g, 20.23 mmol) in toluene (about 17 mL) at about 5° C. The resulting mixture was stirred for 2 hr. Water (about 1.9 mL) was added dropwise at about 5° C. and the resulting mixture was allowed to warm to about 20° C. and stirred for about 20 min. Then the product was extracted with 5% aqueous K$_2$CO$_3$ solution, washed with toluene and acidified with 5 M HCl to pH=1. The precipitate formed was filtered off, washed with water and dried to obtain 5-sulfanylbenzofuran-2-carboxylic acid (about 0.82 g). LCMS(ESI): [M+H]⁺ m/z: calcd 195.21; found 195.0.

Step 2: The synthesis of 5-methylsulfanylbenzofuran-2-carboxylic acid

To a stirred suspension of 5-sulfanylbenzofuran-2-carboxylic acid (about 0.82 g, 4.22 mmol) in CH$_3$CN (about 9.99 mL) was added Potassium carbonate, anhydrous, 99% (about 1.75 g, 12.67 mmol, 764.47 μL) followed by iodomethane, 99%, stab. with copper (about 3.00 g, 21.11 mmol, 1.31 mL) and the resulting mixture was stirred at about 40° C. for about 16 hr. The additional amount of potassium carbonate, anhydrous, 99% (about 583.55 mg, 4.22 mmol, 254.82 μL) and iodomethane, 99%, stab. with copper (about 1.80 g, 12.67 mmol, 788.56 μL) was added and the resulting mixture was stirred at about 50° C. for about 40 hr. After cooling the reaction mixture was poured into ice water and extracted with CHCl$_3$. The aqueous layer was separated and acidified with 5 M HCl to about pH=1. The precipitate formed was filtered off, washed with water and dried to obtain 5-methylsulfanylbenzofuran-2-carboxylic acid (about 0.47 g). ¹H NMR (400 MHz, DMSO-d$_6$) δ 2.51 (s, 3H), 7.42 (d, 1H), 7.57 (s, 1H), 7.66 (m, 2H), 13.3 (br s, 1H).

Step 3: The synthesis of tert-butyl N-[2-[(5-methylsulfanylbenzofuran-2-carbonyl)amino]-4-(2-thienyl)phenyl]carbamate To a stirred solution of 5-methylsulfanylbenzofuran-2-carboxylic acid (about 50 mg, 240.12 μmol) in DMF (about 1 mL) was added HATU (about 136.95 mg, 360.17 μmol) followed by DIPEA (about 93.10 mg, 720.35 μmol, 125.47 μL) and the resulting mixture was stirred at about 20° C. for about 15 min. Then tert-butyl N-[2-amino-4-(2-thienyl)phenyl]carbamate (about 69.72 mg, 240.12 μmol) was added and the reaction mixture was stirred at about 50° C. for about 16 hr. The reaction mixture was concentrated, diluted with water, extracted with EtOAc, washed with brine, dried over Na$_2$SO$_4$ and concentrated to obtain tert-butyl N-[2-[(5-methylsulfanylbenzofuran-2-carbonyl)amino]-4-(2-thienyl)phenyl]carbamate (about 95 mg). LCMS(ESI): [M+H-Boc]⁺ m/z: calcd 381.12; found 381.0.

Step 4: The synthesis of tert-butyl N-[2-[[5-(methylsulfonimidoyl)benzofuran-2-carbonyl]amino]-4-(2-thienyl)phenyl]carbamate To a stirred solution of tert-butyl N-[2-[(5-methylsulfanylbenzofuran-2-carbonyl)amino]-4-(2-thienyl)phenyl]carbamate (about 95 mg, 197.67 μmol) in Methanol (about 5 mL) was added ammonium carbonate (about 51.93 mg, 296.51 μmol) followed by (Diacetoxyiodo)benzene (about 146.44 mg, 454.64 μmol) and the resulting mixture was stirred at about 25° C. for about 3 hr. The reaction mixture was evaporated to dryness to obtain tert-butyl N-[2-[[5-(methylsulfonimidoyl)benzofuran-2-carbonyl]amino]-4-(2-thienyl)phenyl]carbamate (about 132 mg). LCMS(ESI): [M+H]$^+$ m/z: calcd 512.12; found 512.0.

Step 5: The synthesis of N-[2-amino-5-(2-thienyl)phenyl]-5-(methylsulfonimidoyl)benzofuran-2-carboxamide To a stirred suspension of tert-butyl N-[2-[[5-(methylsulfonimidoyl)benzofuran-2-carbonyl]amino]-4-(2-thienyl)phenyl]carbamate (about 132 mg, 258.01 μmol) in CH$_2$Cl$_2$ (about 1 mL) was added Hydrogen chloride solution 1 M in diethyl ether (about 1.60 g, 43.88 mmol, 2 mL) and the resulting mixture was stirred at about 30° C. for about 16 hr. The reaction mixture was evaporated to dryness. The product was purified by HPLC to obtain N-[2-amino-5-(2-thienyl)phenyl]-5-(methylsulfonimidoyl)benzofuran-2-carboxamide (about 12.6 mg). $^1$H NMR (600 MHz, DMSO-d$_6$) δ 3.12 (s, 3H), 4.29 (s, 1H), 5.24 (s, 2H), 6.81 (d, 1H), 7.04 (dd, 1H), 7.24 (d, 1H), 7.31 (dd, 1H), 7.35 (d, 1H), 7.46 (s, 1H), 7.87-7.93 (m, 2H), 8.03 (dd, 1H), 8.43 (s, 1H), 10.08 (s, 1H). LCMS(ESI): [M+H]$^+$ m/z: calcd 412.07; found 412.2.

Example 77. Synthesis of N-[2-amino-5-(2-thienyl)phenyl]-5-(methylsulfonimidoyl)benzothiophene-2-carboxamide (Compound 138)

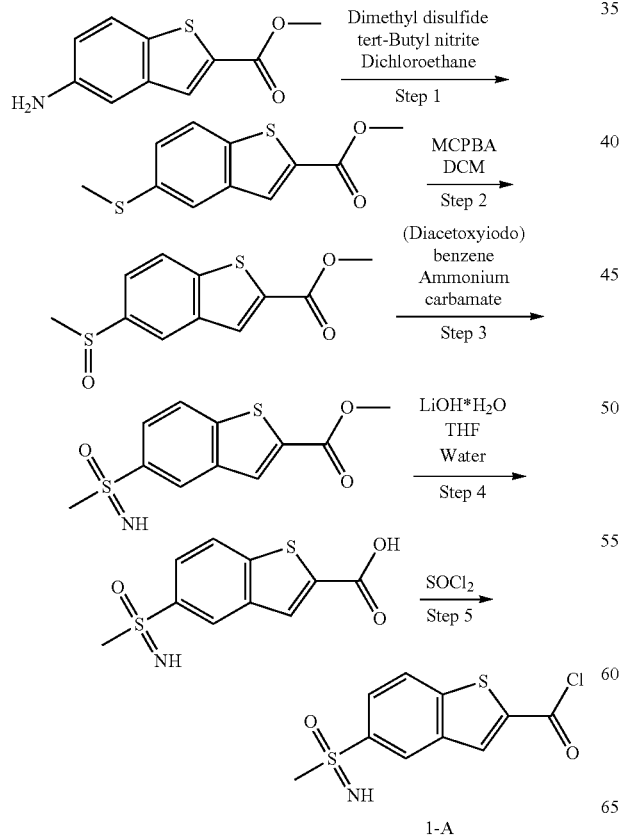

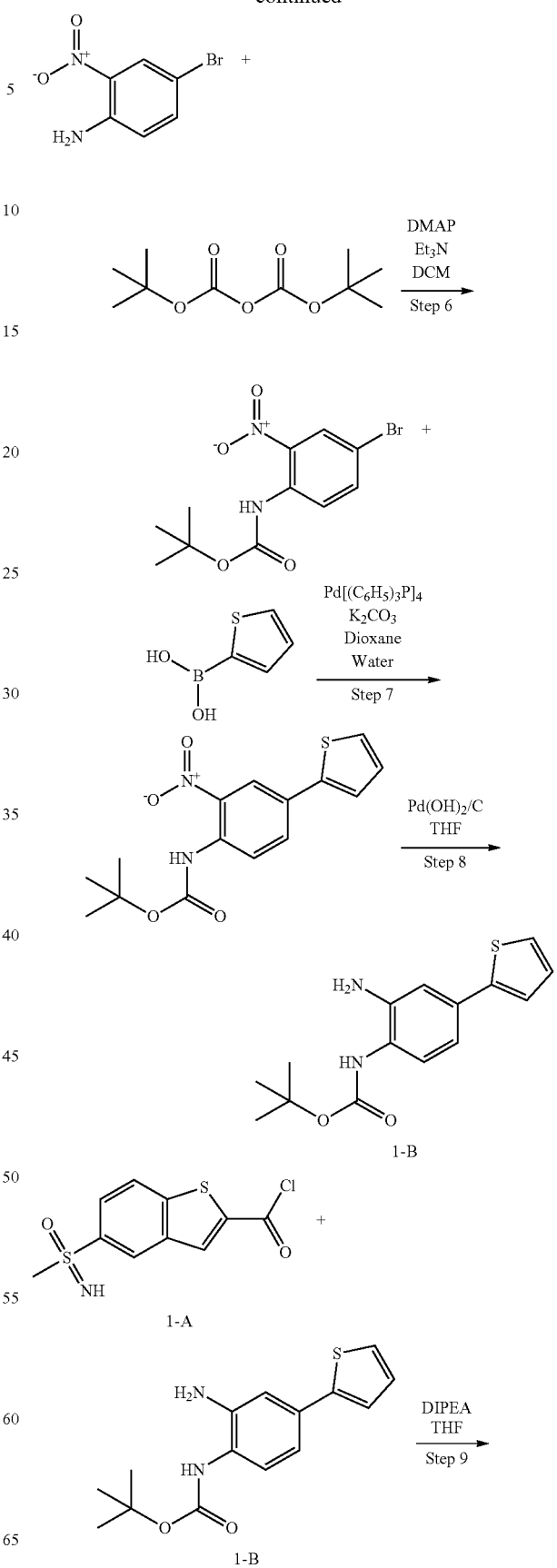

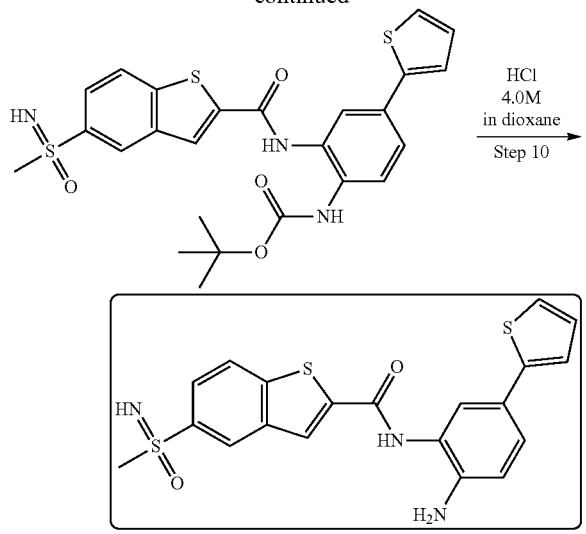

Step 1: The synthesis of methyl 5-methylsulfanylbenzothiophene-2-carboxylate To a stirred solution of methyl 5-aminobenzothiophene-2-carboxylate (about 3.71 g, 17.90 mmol) and Dimethyl disulfide (about 2.19 g, 23.27 mmol, 1.50 mL) in Dichloroethane (about 120 mL), tert-Butyl nitrite (about 2.22 g, 21.48 mmol, 2.55 mL) was added. The resulting mixture was stirred at about 55° C. for about 1.5 hr. The reaction mixture was concentrated under reduced pressure. The product was purified by flash column chromatography (ISCO® Interchim; about methylsulfanylbenzothiophene-2-carboxylate (about 400 mg). $^1$H NMR (400 MHz, CDCl$_3$) δ 2.55 (s, 3H), 3.94 (s, 3H), 7.26 (s, 1H), 7.38 (d, 1H), 7.74 (m, 2H), 7.98 (s, 1H).

Step 2: The synthesis of methyl 5-methylsulfinylbenzothiophene-2-carboxylate To a stirred solution of methyl 5-methylsulfanylbenzothiophene-2-carboxylate (about 260 mg, 1.09 mmol) in DCM (about 15 mL), mCPBA (about 197.67 mg, 1.15 mmol) was added portion-wise at about 0° C. The resulting reaction mixture was stirred at about 20° C. for about 16 hr and then evaporated to dryness. The obtained residue was dissolved in EtOAc (about 40 mL). The organic phase was washed with a 2 M solution of NaOH (about 30 mL) and brine (about 15 mL), dried over Na$_2$SO$_4$ and concentrated under reduced pressure to afford methyl 5-methylsulfinylbenzothiophene-2-carboxylate (about 280 mg). $^1$H NMR (400 MHz, CDCl$_3$) δ 2.78 (s, 3H), 3.89 (s, 3H), 7.79 (d, 1H), 8.27 (d, 1H), 8.33 (s, 1H), 8.36 (s, 1H).

Step 3: The synthesis of methyl 5-(methylsulfonimidoyl)benzothiophene-2-carboxylate To a stirred solution of methyl 5-methylsulfinylbenzothiophene-2-carboxylate (about 280 mg, 1.10 mmol) and Ammonium carbamate (about 343.81 mg, 4.40 mmol) in MeOH (8 mL), (Diacetoxyiodo)benzene (about 1.06 g, 3.30 mmol) was added portion-wise. The resulting mixture was stirred at about 20° C. for about 5 hr and evaporated to dryness. The obtained residue was dissolved in EtOAc (about 50 mL). The organic phase was washed with brine (about 25 mL), dried over Na$_2$SO$_4$ and concentrated under reduced pressure to afford methyl 5-(methylsulfonimidoyl)benzothiophene-2-carboxylate (about 620 mg). LCMS (ESI): [M+H]$^+$ m/z: calcd 370.02; found 370.0.

Step 4: The synthesis of 5-(methylsulfonimidoyl)benzothiophene-2-carboxylic acid A 50-mL round-bottomed flask, equipped with a magnetic stirrer, was charged with methyl 5-(methylsulfonimidoyl)benzothiophene-2-carboxylate (about 620 mg, 2.30 mmol), lithium hydroxide monohydrate, 98% (about 482.99 mg, 11.51 mmol, 319.86 µL), THF (about 16 mL) and water (about 4 mL). The resulting reaction mixture was stirred at about 40° C. for about 16 hr and then concentrated under reduced pressure. Water (about 5 mL) was added to the residue and the mixture was acidified with a 1 M HCl to about pH=3. The precipitate formed was filtered, washed with water and dried under reduced pressure to obtain 5-(methylsulfonimidoyl)benzothiophene-2-carboxylic acid (about 186 mg). LCMS(ESI): [M+H]$^+$ m/z: calcd 256.02; found 256.0.

Step 5: The synthesis of 5-(methylsulfonimidoyl)benzothiophene-2-carbonyl chloride Thionyl chloride (about 6.50 g, 54.64 mmol, 3.96 mL) was added to 5-(methylsulfonimidoyl)benzothiophene-2-carboxylic acid (about 186 mg, 728.52 µmol). The resulting reaction mixture was stirred at about 80° C. for about 3 hr and then concentrated under reduced pressure to afford 5-(methylsulfonimidoyl)benzothiophene-2-carbonyl chloride (about 210 mg).

Step 6: The synthesis of tert-butyl N-(4-bromo-2-nitro-phenyl)carbamate

To a stirred solution of 4-bromo-2-nitro-aniline (about 100 g, 460.79 mmol) in DCM (about 1200 mL) was added 4-dimethylaminopyridine (about 2.81 g, 23.04 mmol) and triethylamine (about 97.92 g, 967.65 mmol, 134.87 mL) followed by di-tert-butyl dicarbonate (about 110.62 g, 506.87 mmol, 116.32 mL). The resulting mixture was stirred at about 18° C. for about 16 hr. Then the reaction mixture was quenched with about 5% aqueous NaHSO$_4$ solution. The organic phase was separated, washed with about 5% aqueous NaHCO$_3$ solution, dried over Na$_2$SO$_4$ and concentrated under reduced pressure. The product was purified by flash column chromatography (SiO$_2$, 0-100% MTBE in Chloroform) to obtain tert-butyl N-(4-bromo-2-nitro-phenyl)carbamate (about 82 g). $^1$H NMR (400 MHz, DMSO-d$_6$) δ 1.43 (s, 9H), 7.59 (d, 1H), 7.83 (d, 1H), 8.12 (s, 1H), 9.62 (s, 1H).

Step 7: The synthesis of tert-butyl N-[2-nitro-4-(2-thienyl)phenyl]carbamate To a stirred solution of tert-butyl N-(4-bromo-2-nitro-phenyl)carbamate (about 30.1 g, 94.91 mmol) and 2-thienylboronic acid (about 15.79 g, 123.39 mmol) in water (about 400 mL) and dioxane (about 100 mL) was added Potassium carbonate, anhydrous, 99% (about 39.35 g, 284.74 mmol, 17.18 mL) followed by Tetrakis(triphenylphosphine)palladium(O), 99.8% (metals basis), Pd 9% min (about 10.97 g, 9.49 mmol) under argon atmosphere. The resulting mixture was heated at about 100° C. for about 16 hr. The reaction mixture was filtered through celite. The filtrate was treated with scavenger and concentrated under reduced pressure. The product was purified by flash column chromatography (ISCO® Interchim; 880 g SiO$_2$, 0-100% EtOAc in Hexane, flow rate=125 mL/min) to afford tert-butyl N-[2-nitro-4-(2-thienyl)phenyl]carbamate (about 18.6 g). $^1$H NMR (500 MHz, CDCl$_3$) δ 1.54 (s, 9H), 7.08 (m, 1H), 7.31 (m, 2H), 7.81 (d, 1H), 8.38 (s, 1H), 8.57 (d, 1H), 9.64 (s, 1H).

Step 8: The synthesis of tert-butyl N-[2-amino-4-(2-thienyl)phenyl]carbamate A solution of tert-butyl N-[2-nitro-4-(2-thienyl)phenyl]carbamate (about 18.6 g, 58.06 mmol) in THF (about 500 mL) was hydrogenated over Palladium hydroxide on carbon, 20 wt. % 50% water (about 4.08 g, 29.03 mmol) under about 1 bar pressure of H$_2$ at about 20° C. for about 48 hr. The reaction mixture was filtered. The filtrate was concentrated under reduced pressure. The obtained residue was dissolved in ethyl acetate (about 1000 mL), washed with brine (about 600 mL). The organic phase was dried over Na$_2$SO$_4$, treated with the scavenger and concentrated under reduced pressure to obtain tert-butyl N-[2-amino-4-(2-thienyl)phenyl]carbamate (about 14.2 g). $^1$H NMR (400 MHz, DMSO-d$_6$) δ 1.45 (s, 9H), 5.0 (br s, 2H), 6.83 (m, 1H), 6.96 (d, 1H), 7.07 (t, 1H), 7.28 (m, 2H), 7.43 (d, 1H), 8.34 (br s, 1H).

Step 9: The synthesis of tert-butyl N-[2-[[5-(methylsulfonimidoyl)benzothiophene-2-carbonyl]amino]-4-(2-thienyl)phenyl]carbamate To a stirred solution of tert-butyl N-[2-amino-4-(2-thienyl)phenyl]carbamate (about 222.75 mg, 767.10 μmol) and N,N-Diisopropylethylamine (about 297.43 mg, 2.30 mmol, 400.84 L) in THF (about 5 mL) was added a solution of 5-(methylsulfonimidoyl)benzothiophene-2-carbonyl chloride (about 210 mg, 767.10 μmol) in THF (about 2 mL) at about 0° C. Then the resulting reaction mixture was stirred at about 20° C. for about 16 hr. The reaction mixture was concentrated under reduced pressure to obtain tert-butyl N-[2-[[5-(methylsulfonimidoyl)benzothiophene-2-carbonyl]amino]-4-(2-thienyl)phenyl]carbamate (about 300 mg). LCMS(ESI): [M+H]$^+$ m/z: calcd 528.10; found 528.0.

Step 10: The synthesis of N-[2-amino-5-(2-thienyl)phenyl]-5-(methylsulfonimidoyl)benzothiophene-2-carboxamide Hydrogen chloride solution 4.0M in dioxane (about 1.55 g, 42.64 mmol, 1.94 mL) was added to tert-butyl N-[2-[[5-(methylsulfonimidoyl)benzothiophene-2-carbonyl]amino]-4-(2-thienyl)phenyl]carbamate (about 300 mg, 568.53 μmol) and the resulting solution was stirred at about 20° C. for about 16 hr. The reaction mixture was concentrated under reduced pressure. The product was purified by prep-HPLC (27-42% 0.5-6.5 min water-acetonitrile; flow 30 ml/min (loading pump 4 ml/min acetonitrile); column SunFireC18 100×19 mm Sum) to afford N-[2-amino-5-(2-thienyl)phenyl]-5-(methylsulfonimidoyl)benzothiophene-2-carboxamide (about 71 mg).

Example 78. Synthesis of N-[2-amino-5-(4-fluorophenyl)phenyl]-4-[(6-oxo-1H-pyridin-3-yl)sulfonimidoyl]benzamide (Compound 192)

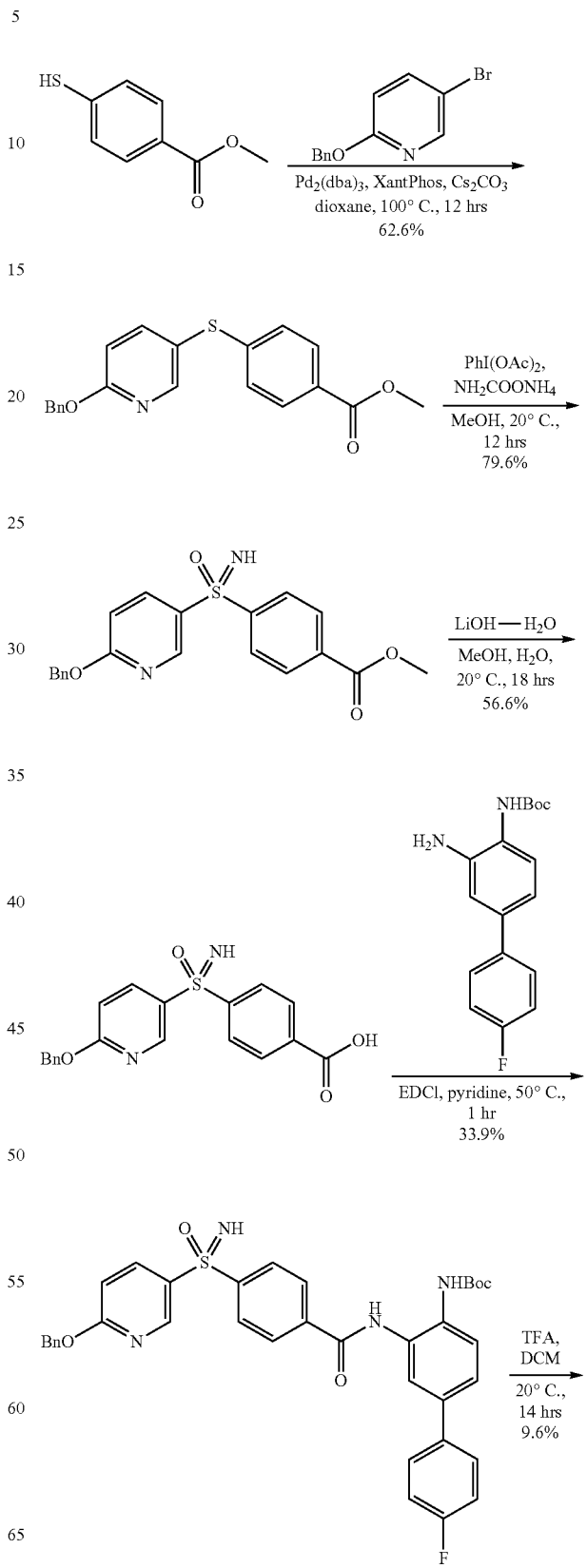

-continued

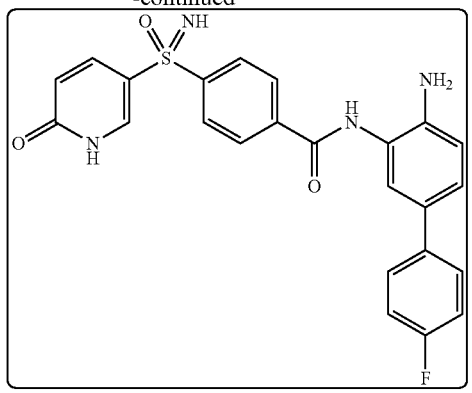

Step 1: Synthesis of methyl 4-[(6-benzyloxy-3-pyridyl)sulfanyl]benzoate

A mixture of 2-benzyloxy-5-bromo-pyridine (780 mg, 2.95 mmol), methyl 4-sulfanylbenzoate (500 mg, 2.97 mmol), $Cs_2CO_3$ (3 g, 9.21 mmol), $Pd_2(dba)_3$ (85 mg, 0.0930 mmol) and XantPhos (105 mg, 0.181 mmol) in dioxane (10 mL) was stirred at 100° C. for 12 hours. The mixture was filtered and diluted with $H_2O$ (30 mL). The filtrate was extracted with EtOAc (20 mL*3). The combined organic layer was washed with brine (20 mL*3) and concentrated under reduced pressure. The residue was purified by flash chromatography (Biotage®; 12 g AgelaFlash®Silica Flash Column, petroleumether/EtOAc with EtOAc from 0~20%, flow rate=30 mL/min, 254 nm) to afford methyl 4-[(6-benzyloxy-3-pyridyl)sulfanyl]benzoate (650 mg, 62.6% yield) as white solid. $^1$H NMR (400 MHz, DMSO-d6) δ ppm 7.91 (dd, J=8.7, 2.4 Hz, 1H), 7.85 (d, J=8.5 Hz, 2H), 7.45-7.50 (m, 3H), 7.33-7.41 (m, 3H), 7.19 (d, J=8.5 Hz, 2H), 7.03 (d, J=8.5 Hz, 1H), 5.40 (s, 2H), 3.82 (s, 3H); LCMS (ESI) [M+H]$^+$ m/z: calcd 352.1, found 352.1.

Step 2: Synthesis of methyl 4-[(6-benzyloxy-3-pyridyl)sulfonimidoyl]benzoate A mixture of methyl 4-[(6-benzyloxy-3-pyridyl)sulfanyl] benzoate (600 mg, 1.71 mmol), $NH_2COONH_4$ (270 mg, 3.46 mmol) and $PhI(OAc)_2$ (1.4 g, 4.35 mmol) in MeOH (10 mL) was stirred at 20° C. for 12 hours. The mixture was extracted with DCM (20 mL*3). The combined organic layer was washed with brine (20 mL*3), dries over anhydrous $Na_2SO_4$, filtered and concentrated under reduced pressure. The residue was purified by flash chromatography (ISCO®; 12 g AgelaFlash®Silica Flash Column, petroleumether/EtOAc with EtOAc from 0~40%, flow rate=30 mL/min, 254 nm) to afford methyl 4-[(6-benzyloxy-3-pyridyl)sulfonimidoyl]benzoate (520 mg, 79.6% yield) as yellow solid. $^1$H NMR (400 MHz, DMSO-d6) δ ppm 8.76 (d, J=2.3 Hz, 1H), 8.17 (dd, J=8.9, 2.6 Hz, 1H), 8.07-8.13 (m, 5H), 7.41-7.45 (m, 2H), 7.32-7.39 (m, 3H), 7.02 (d, J=8.8 Hz, 1H), 5.40 (s, 2H), 3.87 (s, 3H); LCMS (ESI) [M+H]$^+$ m/z: calcd 383.1, found 383.1.

Step 3: Synthesis of 4-[(6-benzyloxy-3-pyridyl)sulfonimidoyl]benzoic acid

A mixture of methyl 4-[(6-benzyloxy-3-pyridyl)sulfonimidoyl]benzoate (550 mg, 1.44 mmol) and LiOH—$H_2O$ (650 mg, 15.5 mmol) in MeOH (5 mL) and $H_2O$ (5 mL) was stirred at 20° C. for 18 hours. 2N HCl aqueous solution was added to adjust pH=5, then the mixture was filtered and filter cake was concentrated under reduced pressure to give 4-[(6-benzyloxy-3-pyridyl)sulfonimidoyl]benzoic acid (300 mg, 56.6% yield) as white solid. $^1$H NMR (400 MHz, DMSO-d6) δ ppm 13.52 (s, 1H), 8.76 (d, J=2.5 Hz, 1H), 8.17 (dd, J=8.9, 2.6 Hz, 1H), 8.01-8.14 (m, 4H), 7.29-7.46 (m, 5H), 6.98-7.05 (m, 1H), 5.40 (s, 2H); LCMS (ESI) [M+H]$^+$ m/z calcd 369.1, found 369.1.

Step 4: Synthesis of tert-butyl N-[2-[[4-[(6-benzyloxy-3-pyridyl)sulfonimidoyl]benzoyl]amino]-4-(4-fluorophenyl)phenyl]carbamate A mixture of 4-[(6-benzyloxy-3-pyridyl)sulfonimidoyl] benzoic acid (250 mg, 0.679 mmol), tert-butyl N-[2-amino-4-(4-fluorophenyl)phenyl]carbamate (160 mg, 0.529 mmol) and EDCI (200 mg, 1.04 mmol) in pyridine (2 mL) was stirred at 50° C. for 1 hour. The mixture was concentrated under reduced pressure. The residue was purified by flash chromatography (Biotage®; 20 g Agela Flash® Silica Flash Column, petroleumether/EtOAc with EtOAc from 0~50%, flow rate=25 mL/min, 254 nm) to afford tert-butyl N-[2-[[4-[(6-benzyloxy-3-pyridyl)sulfonimidoyl]benzoyl]amino]-4-(4-fluorophenyl)phenyl]carbamate (150 mg, 33.9% yield) as brown oil. $^1$H NMR (400 MHz, DMSO-d6) δ ppm 10.00 (s, 1H), 8.70-8.82 (m, 2H), 8.13 (q, J=8.4 Hz, 4H), 7.78 (s, 1H), 7.62-7.73 (m, 3H), 7.51 (dd, J=8.5, 2.0 Hz, 1H), 7.43 (d, J=7.0 Hz, 2H), 7.26-7.40 (m, 5H), 7.03 (d, J=8.8 Hz, 1H), 5.41 (s, 2H), 1.43 (s, 9H); 19F NMR (376 MHz, DMSO-d6) δ ppm−115.639; LCMS (ESI) [M+H]$^+$ m/z: calcd 653.2, found 653.2.

Step 5: Synthesis of N-[2-amino-5-(4-fluorophenyl)phenyl]-4-[(6-oxo-1H-pyridin-3-yl)sulfonimidoyl]benzamide (Compound 192)

To a mixture of tert-butyl N-[2-[[4-[(6-benzyloxy-3-pyridyl)sulfonimidoyl]benzoyl]amino]-4-(4-fluorophenyl) phenyl]carbamate (140 mg, 0.214 mmol) in DCM (1 mL) was added TFA (0.2 mL, 2.60 mmol). The mixture was stirred at 20° C. for 14 hours. Saturated $NaHCO_3$ aqueous solution was added to adjust pH=8, then the mixture was extracted with DCM (5 mL*3). The combined organic layer was concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 µm; Mobile phase A: $H_2O$ with 0.05% $NH_3$—$H_2O$ (v %); Mobile phase B: MeCN; Gradient: B from 25% to 55% in 8 mins, hold 100% B for 2 mins; Flow Rate: 30 mL/min; Column Temperature: 30° C.; Wavelength: 220 nm, 254 nm) to afford N-[2-amino-5-(4-fluorophenyl)phenyl]-4-[(6-oxo-1H-pyridin-3-yl)sulfonimidoyl]benzamide (9.5 mg, 9.6% yield) as off-white solid. $^1$H NMR (400 MHz, DMSO-d6) δ ppm 12.28 (s, 1H), 9.87 (s, 1H), 8.11-8.16 (m, 2H), 8.07 (d, J=8.3 Hz, 3H), 7.73 (dd, J=9.8, 2.8 Hz, 1H), 7.57 (dd, J=8.8, 5.5 Hz, 2H), 7.48 (d, J=2.0 Hz, 1H), 7.31 (dd, J=8.4, 2.3 Hz, 1H), 7.21 (t, J=8.9 Hz, 2H), 6.85 (d, J=8.4 Hz, 1H), 6.39 (d, J=9 0.8 Hz, 1H), 5.16 (s, 3H); 19F NMR (400 MHz, DMSO-d6) δ ppm −117.48; LCMS (ESI) [M+H]$^+$ m/z: calcd 463.1, found 463.2; HPLC: 95.43%@220 nm, 100%@254 nm.

Example 79. Synthesis of N-[2-amino-5-(4-fluorophenyl)phenyl]-6-(2-pyridylsulfonimidoyl)pyridine-3-carboxamide (Compound 238)
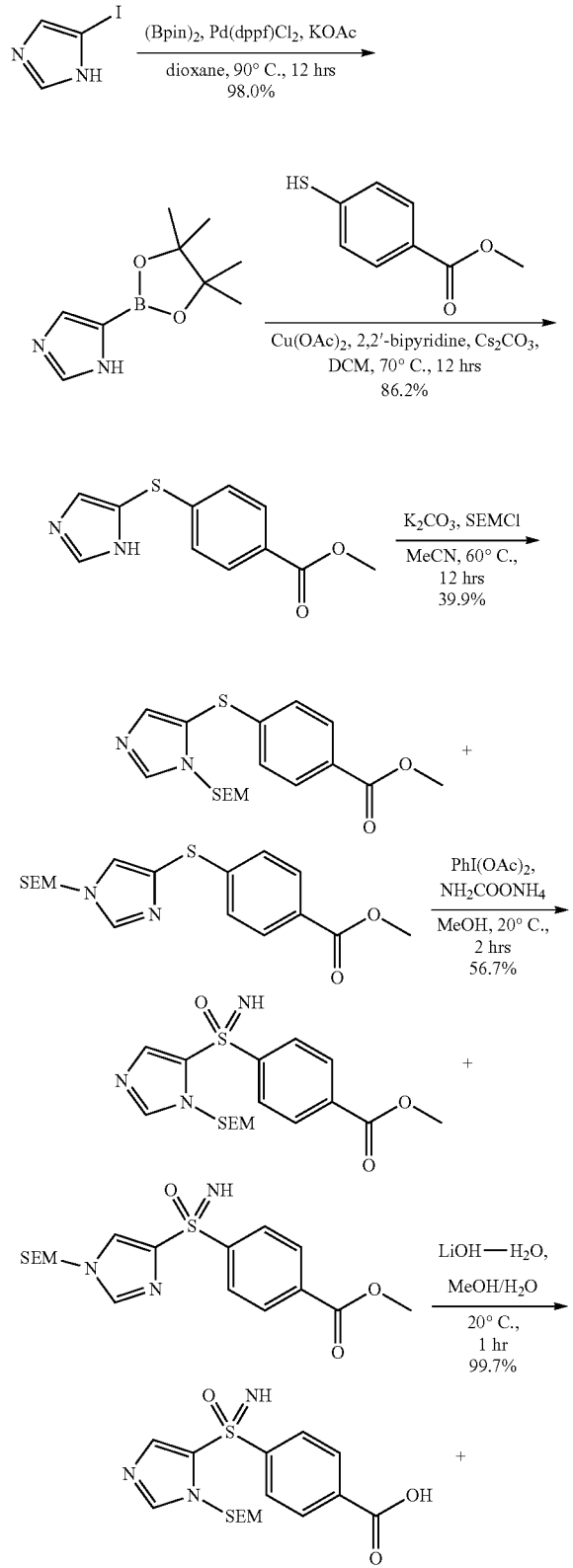
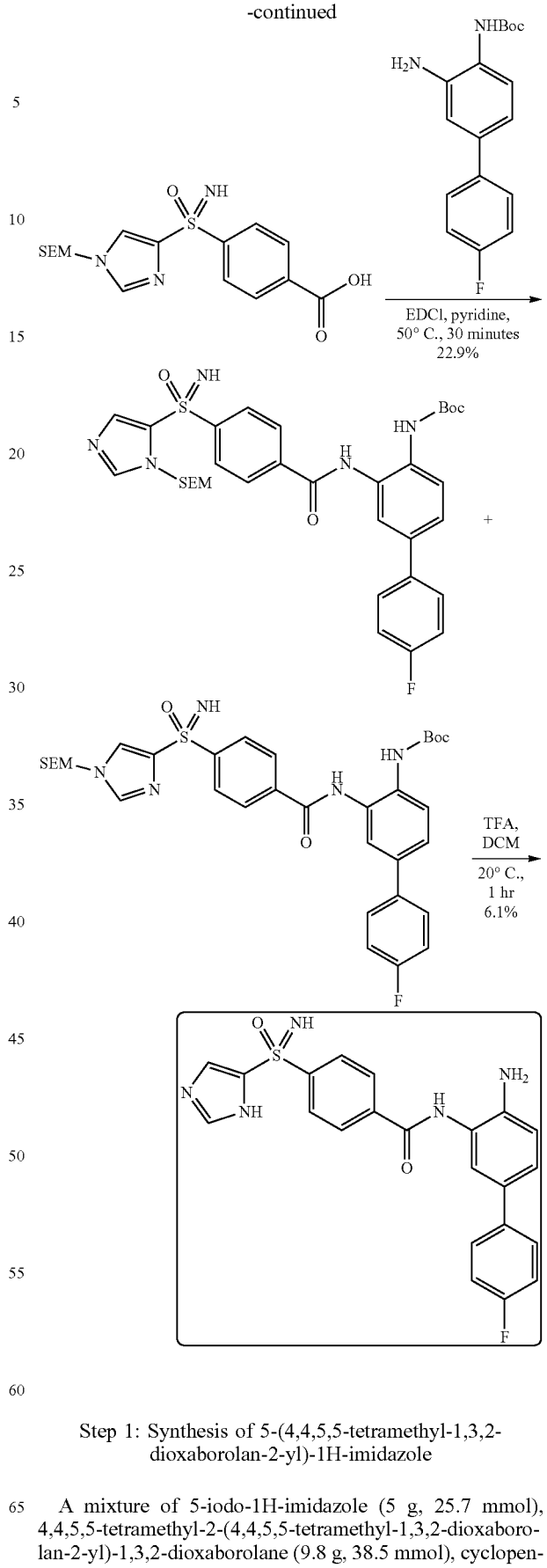
Step 1: Synthesis of 5-(4,4,5,5-tetramethyl-1,3,2-dioxaborolan-2-yl)-1H-imidazole
A mixture of 5-iodo-1H-imidazole (5 g, 25.7 mmol), 4,4,5,5-tetramethyl-2-(4,4,5,5-tetramethyl-1,3,2-dioxaborolan-2-yl)-1,3,2-dioxaborolane (9.8 g, 38.5 mmol), cyclopentyl(diphenyl)phosphane;dichloropalladium;iron (2 g, 2.73 mmol), potassium;acetate (5 g, 50.9 mmol) in dioxane (50 mL) was stirred at 90° C. for 12 hours. The mixture was diluted with ethyl acetate (30 mL) and $H_2O$ (30 mL). The aqueous layer was separated and extracted with ethyl acetate (30 mL×3). The combined organic layers were washed with brine (25 mL), dried over anhydrous $Na_2SO_4$, filtered and concentrated under reduced pressure to give 5-(4,4,5,5-tetramethyl-1,3,2-dioxaborolan-2-yl)-1H-imidazole (4.9 g, 98.0% yield) as yellow solid. $^1H$ NMR (400 MHz, DMSO-d6) δ ppm 7.64 (s, 1H), 7.31 (s, 1H), 1.17 (s, 12H); LCMS (ESI) $[M+H]^+$ m/z: calcd 195.1, found 195.0.

Step 2: Synthesis of methyl 4-(1H-imidazol-5-ylsulfanyl)benzoate

To a solution of methyl 4-sulfanylbenzoate (500 mg, 2.97 mmol), 5-(4,4,5,5-tetramethyl-1,3,2-dioxaborolan-2-yl)-1H-imidazole (3.5 g, 18.0 mmol) in DCM (30 mL) was added $Cu(OAc)_2$ (540 mg, 2.97 mmol), 2,2'-bipyridine (464 mg, 2.97 mmol) and $Cs_2CO_3$ (969 mg, 2.97 mmol). The mixture was stirred at 70° C. for 12 hours. The mixture was diluted with DCM (30 mL) and $H_2O$ (30 mL). The aqueous layer was separated and extracted with DCM (30 mL*3). The combined organic layers were washed with brine (25 mL), dried over anhydrous $Na_2SO_4$, filtered and concentrated under reduced pressure. The residue was purified by silica gel chromatography (DCM/MeOH=10:0 to 0:10, 254 nm) to afford methyl 4-(1H-imidazol-5-ylsulfanyl)benzoate (600 mg, 86.2% yield) as yellow solid. LCMS (ESI) $[M+H]^+$ m/z: calcd 235.0, found 235.1.

Step 3: Synthesis of methyl 4-[1-(2-trimethylsilylethoxymethyl)imidazol-4-yl]sulfanylbenzoate and methyl 4-[3-(2-trimethylsilylethoxymethyl)imidazol-4-yl]sulfanylbenzoate A mixture of methyl 4-(1H-imidazol-5-ylsulfanyl)benzoate (500 mg, 2.13 mmol), 2-(chloromethoxy)ethyl-trimethyl-silane (463 mg, 2.78 mmol), tripotassium;carbonate (885 mg, 6.40 mmol) in MeCN (5 mL) was stirred at 60° C. for 12 hours. The reaction mixture was added $H_2O$ (10 mL) and extracted with EtOAc (10 mL*3). The combined organic layers were washed with brine (20 mL), dried with anhydrous $Na_2SO_4$, filtered and concentrated under reduced pressure to give a mixture of methyl 4-[1-(2-trimethylsilylethoxymethyl)imidazol-4-yl]sulfanylbenzoate and methyl 4-[3-(2-trimethylsilylethoxymethyl)imidazol-4-yl]sulfanylbenzoate (310 mg, 39.9% yield) as yellow solid. LCMS (ESI) $[M+H]^+$ m/z: calcd 365.1, found 365.2.

Step 4: Synthesis of methyl 4-[[1-(2-trimethylsilylethoxymethyl)imidazol-4-yl]sulfonimidoyl]benzoate and methyl 4-[[3-(2-trimethylsilylethoxymethyl)imidazol-4-yl]sulfonimidoyl]benzoate A mixture of methyl 4-[1-(2-trimethylsilylethoxymethyl)imidazol-4-yl]sulfanylbenzoate and methyl 4-[3-(2-trimethylsilylethoxymethyl)imidazol-4-yl]sulfanylbenzoate (260 mg, 0.713 mmol), [acetoxy(phenyl)-iodanyl] acetate (574 mg, 1.78 mmol), ammonia; carbamic acid (117 mg, 1.50 mmol) in MeOH (4 mL) was stirred at 20° C. for 2 hours. The reaction mixture was added $H_2O$ (10 mL) and extracted with EtOAc (10 mL*3). The combined organic layers were washed with brine (20 mL), dried with anhydrous $Na_2SO_4$, filtered and concentrated under reduced pressure. The residue was purified by silica gel chromatography (PE/EtOAc=10:0 to 0:10, 254 nm) to afford a mixture of methyl 4-[[1-(2-trimethylsilylethoxymethyl)imidazol-4-yl]sulfonimidoyl]benzoate and methyl 4-[[3-(2-trimethylsilylethoxymethyl)imidazol-4-yl]sulfonimidoyl]benzoate (160 mg, 56.7% yield) as yellow oil. LCMS (ESI) $[M+H]^+$ m/z: calcd 396.1, found 396.2.

Step 5: Synthesis of 4-[[1-(2-trimethylsilylethoxymethyl)imidazol-4-yl]sulfonimidoyl]benzoic acid and 4-[[3-(2-trimethylsilylethoxymethyl)imidazol-4-yl]sulfonimidoyl]benzoic acid A mixture of methyl 4-[[1-(2-trimethylsilylethoxymethyl)imidazol-4-yl]sulfonimidoyl]benzoate and methyl 4-[[3-(2-trimethylsilylethoxymethyl)imidazol-4-yl]sulfonimidoyl]benzoate (130 mg, 0.328 mmol), lithium; hydroxide; hydrate (69 mg, 1.64 mmol) in MeOH (1 mL) and $H_2O$ (1 mL) was stirred at 20° C. for 1 hour. The mixture was acidified with 2N HCl to pH=6~7 and extracted with EtOAc (10 mL*3). The combined organic layers were washed with brine (10 mL), dried over anhydrous $Na_2SO_4$, filtered and concentrated under reduced pressure to give a mixture of 4-[[1-(2-trimethylsilylethoxymethyl)imidazol-4-yl]sulfonimidoyl]benzoic acid and 4-[[3-(2-trimethylsilylethoxymethyl)imidazol-4-yl]sulfonimidoyl]benzoic acid (125 mg, 99.7% yield) as yellow solid. LCMS (ESI) $[M+H]^+$ m/z: calcd 382.1, found 382.2.

Step 6: Synthesis of tert-butyl N-[4-(4-fluorophenyl)-2-[[4-[[3-(2-trimethylsilylethoxymethyl)imidazol-4-yl]sulfonimidoyl]benzoyl]amino]phenyl]carbamate and tert-butyl N-[4-(4-fluorophenyl)-2-[[4-[[1-(2-trimethylsilylethoxymethyl)imidazol-4-yl]sulfonimidoyl]benzoyl]amino]phenyl]carbamate A mixture of 4-[[3-(2-trimethylsilylethoxymethyl)imidazol-4-yl]sulfonimidoyl]benzoic acid and 4-[[1-(2-trimethylsilylethoxymethyl)imidazol-4-yl]sulfonimidoyl]benzoic acid (100 mg, 0.262 mmol), tert-butyl N-[2-amino-4-(4-fluorophenyl)phenyl]carbamate (87 mg, 0.288 mmol), 3-(ethyliminomethyleneamino)-N,N-dimethyl-propan-1-amine;hydrochloride (60 mg, 0.314 mmol) in pyridine (3 mL) was stirred at 50° C. for 30 minutes. The mixture was concentrated under reduced pressure. The residue was purified by column chromatography (silica, petroleum ether/EtOAc=10:0 to 0:10, 254 nm) to afford a mixture of tert-butyl N-[4-(4-fluorophenyl)-2-[[4-[[3-(2-trimethylsilylethoxymethyl)imidazol-4-yl]sulfonimidoyl]benzoyl]amino]phenyl]carbamate and tert-butyl N-[4-(4-fluorophenyl)-2-[[4-[[1-(2-trimethylsilylethoxymethyl)imidazol-4-yl]sulfonimidoyl]benzoyl]amino]phenyl]carbamate (40 mg, 22.9% yield) as yellow solid. LCMS (ESI) $[M+H]^+$ m/z: calcd 666.3, found 666.4.

Step 7: Synthesis of N-[2-amino-5-(4-fluorophenyl)phenyl]-4-(1H-imidazol-5-ylsulfonimidoyl)benzamide A mixture of tert-butyl N-[4-(4-fluorophenyl)-2-[[4-[[1-(2-trimethylsilylethoxymethyl)imidazol-4-yl]sulfonimidoyl]benzoyl]amino]phenyl]carbamate and tert-butyl N-[4-(4-fluorophenyl)-2-[[4-[[3-(2-trimethylsilylethoxymethyl)imidazol-4-yl]sulfonimidoyl]benzoyl]amino]phenyl]carbamate (40 mg, 0.0601 mmol), 2,2,2-trifluoroacetic acid (274 mg, 2.40 mmol) in DCM (2 mL) was stirred at 25° C. for 1 hour. The mixture was concentrated under reduced pressure. The residue was diluted with MeOH (4 mL) and adjusted pH to 6-7 with Na$_2$CO$_3$, filtered. The filtrate was purified by preparative HPLC (Instrument: AD; Column: 2_Phenomenex Gemini C18 75*40 mm*3 μm; Mobile phase A: H$_2$O with NH$_4$HCO$_3$; Mobile phase B: MeCN; Gradient: B from 20% to 50% in 9.5 min, hold 100% B for 3 min; Flow Rate: 30 mL/min; Column Temperature: 30° C.; Wavelength: 220 nm, 254 nm) to afford N-[2-amino-5-(4-fluorophenyl)phenyl]-4-(1H-imidazol-5-ylsulfonimidoyl)benzamide (1.6 mg, 6.1% yield) as white solid. $^1$H NMR (400 MHz, DMSO-d6) δ ppm 9.84 (s, 1H), 8.01-8.14 (m, 4H), 7.75-7.85 (m, 2H), 7.45-7.61 (m, 3H), 7.16-7.36 (m, 3H), 6.85 (d, J=8.38 Hz, 1H), 5.14 (s, 2H), 4.80 (s, 1H); 19F NMR (376 MHz, DMSO-d6) δ ppm –117.472; LCMS (ESI) [M+H]$^+$ m/z: calcd 436.1, found 436.2; HPLC: 94.210%@220 nm, 94.70%@254 nm.

Example 80. Synthesis of N-[2-amino-5-(4-fluorophenyl)phenyl]-4-[(5-methyl-1H-imidazol-2-yl)sulfonimidoyl]benzamide (Compound 228)

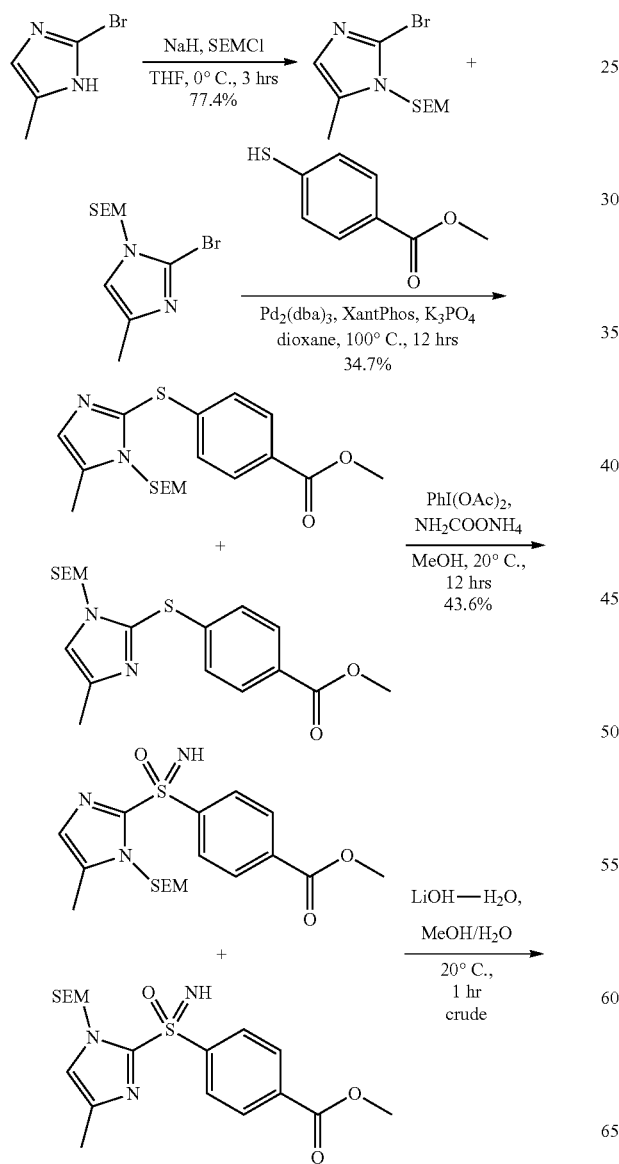

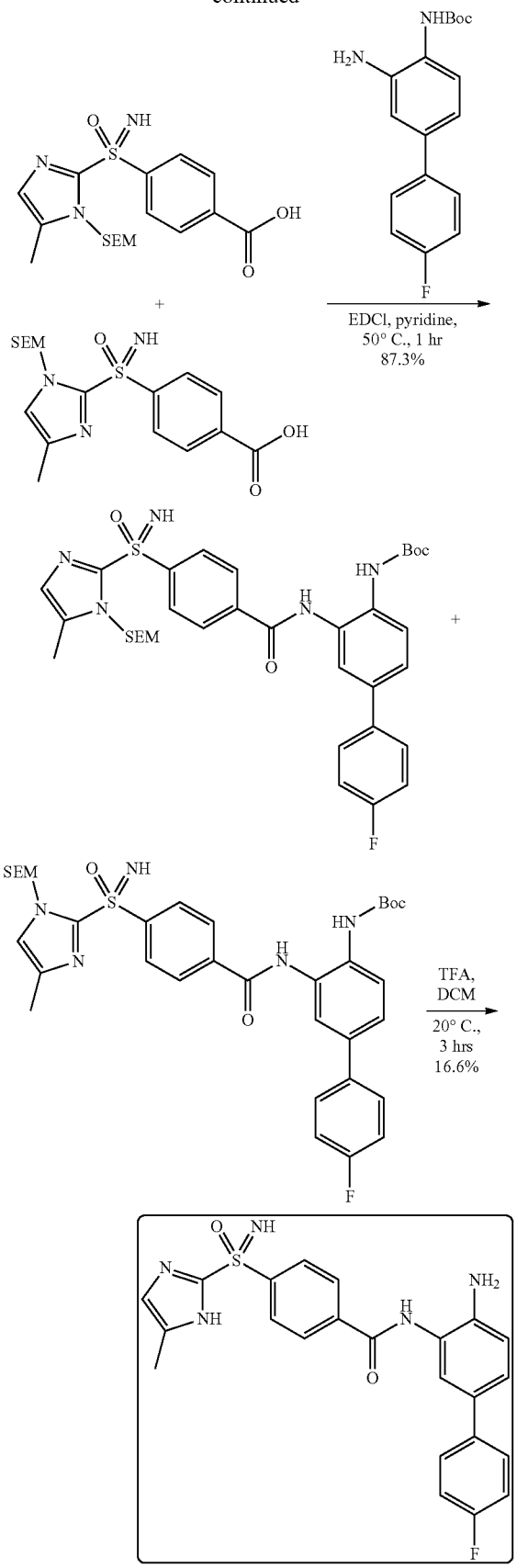

Step 1: Synthesis of 2-[(2-bromo-5-methyl-imidazol-1-yl)methoxy]ethyl-trimethyl-silane and 2-[(2-bromo-4-methyl-imidazol-1-yl)methoxy]ethyl-trimethyl-silane To a solution mixture of 2-bromo-5-methyl-1H-imidazole (5 g, 31.1 mmol) and NaH (1.04 g, 43.5 mmol) in THF (50 mL) was added dropwise 2-(chloromethoxy)ethyl-trimethyl-silane (7.15 mL, 40.4 mmol) at 0° C. The reaction mixture was stirred at 0° C. for 3 hours. The reaction mixture was quenched with $H_2O$ (50 mL) and extracted with EtOAc (50 mL*3). The combined organic layers were dried with anhydrous $Na_2SO_4$ and concentrated in vacuum. The residue was purified by flash chromatography (ISCO®; 80 g AgelaFlash® Silica Flash Column, petroleum ether/EtOAc with EtOAc from 0~30%, flow rate=60 mL/min, 254 nm) to afford a mixture of 2-[(2-bromo-5-methyl-imidazol-1-yl)methoxy]ethyl-trimethyl-silane and 2-[(2-bromo-4-methyl-imidazol-1-yl)methoxy]ethyl-trimethyl-silane (7 g, 77.4% yield) as colorless oil. LCMS (ESI) $[M+H]^+$ m/z: calcd 291.0, found 291.1.

Step 2: Synthesis of methyl 4-[5-methyl-1-(2-trimethylsilylethoxymethyl)imidazol-2-yl]sulfanylbenzoate and methyl 4-[4-methyl-1-(2-trimethylsilylethoxymethyl)imidazol-2-yl]sulfanylbenzoate A mixture of methyl 4-sulfanylbenzoate (500 mg, 2.97 mmol), 2-[(2-bromo-5-methyl-imidazol-1-yl)methoxy]ethyl-trimethyl-silane and 2-[(2-bromo-4-methyl-imidazol-1-yl)methoxy]ethyl-trimethyl-silane (1.73 g, 5.94 mmol), $Pd_2(dba)_3$ (272 mg, 0.297 mmol), XantPhos (344 mg, 0.595 mmol) and $K_3PO_4$ (1.89 g, 8.92 mmol) in dioxane (20 mL) was stirred at 100° C. for 12 hours under $N_2$ atmosphere. The resulting mixture was filtered. The filtrate was concentrated under reduced pressure. The residue was purified by flash chromatography (ISCO®; 20 g AgelaFlash® Silica Flash Column, petroleum ether/EtOAc with EtOAc from 0~40%, flow rate=40 mL/min, 254 nm) to afford a mixture of methyl 4-[5-methyl-1-(2-trimethylsilylethoxymethyl)imidazol-2-yl]sulfanylbenzoate and methyl 4-[4-methyl-1-(2-trimethylsilylethoxymethyl)imidazol-2-yl]sulfanylbenzoate (390 mg, 34.7% yield) as brown oil.

Step 3: Synthesis of methyl 4-[[5-methyl-1-(2-trimethylsilylethoxymethyl)imidazol-2-yl]sulfonimidoyl]benzoate and methyl 4-[[4-methyl-1-(2-trimethylsilylethoxymethyl)imidazol-2-yl]sulfonimidoyl]benzoate A mixture of methyl 4-[5-methyl-1-(2-trimethylsilylethoxymethyl)imidazol-2-yl]sulfanylbenzoate and methyl 4-[4-methyl-1-(2-trimethylsilylethoxymethyl)imidazol-2-yl]sulfanylbenzoate (350 mg, 0.925 mmol), [bis(acetoxy)iodo]benzene (744 mg, 2.31 mmol) and ammonia;carbamic acid (144 mg, 1.84 mmol) in MeOH (15 mL) was stirred at 20° C. for 12 hours. The resulting mixture was concentrated under reduced pressure. The residue was purified by flash chromatography (ISCO®; 12 g AgelaFlash® Silica Flash Column, petroleum ether/EtOAc with EtOAc from 0~100%, 35 mL/min, 254 nm) to afford a mixture of methyl 4-[[5-methyl-1-(2-trimethylsilylethoxymethyl)imidazol-2-yl]sulfonimidoyl]benzoate and methyl 4-[[4-methyl-1-(2-trimethylsilylethoxymethyl)imidazol-2-yl]sulfonimidoyl]benzoate (165 mg, 43.6% yield) as colorless oil. LCMS (ESI) $[M+H]^+$ m/z: calcd 410.1, found 410.2.

Step 4: Synthesis of 4-[[5-methyl-1-(2-trimethylsilylethoxymethyl)imidazol-2-yl]sulfonimidoyl]benzoic acid and 4-[[4-methyl-1-(2-trimethylsilylethoxymethyl)imidazol-2-yl]sulfonimidoyl]benzoic acid To a mixture of methyl 4-[[5-methyl-1-(2-trimethylsilylethoxymethyl)imidazol-2-yl]sulfonimidoyl]benzoate and methyl 4-[[4-methyl-1-(2-trimethylsilylethoxymethyl)imidazol-2-yl]sulfonimidoyl]benzoate (165 mg, 0.403 mmol) in MeOH (5 mL) was added a solution of LiOH—$H_2O$ (85 mg, 2.03 mmol) in $H_2O$ (2 mL). The mixture was stirred at 20° C. for 1 hour. The resulting mixture was concentrated under reduced pressure. The residue was diluted with $H_2O$ (10 mL). The mixture was adjusted pH=5 with 2N HCl aqueous solution, and extracted with EtOAc (10 mL*3). The combined organic layer was dried over anhydrous $Na_2SO_4$, filtered and concentrated under reduced pressure to give a mixture of 4-[[5-methyl-1-(2-trimethylsilylethoxymethyl)imidazol-2-yl]sulfonimidoyl]benzoic acid and 4-[[4-methyl-1-(2-trimethylsilylethoxymethyl)imidazol-2-yl]sulfonimidoyl]benzoic acid (160 mg, crude) as white solid, which was directly used without further purification. LCMS (ESI) $[M+H]^+$ m/z: calcd 396.1; found 396.2.

Step 5: Synthesis of tert-butyl N-[4-(4-fluorophenyl)-2-[[4-[[5-methyl-1-(2-trimethylsilylethoxymethyl)imidazol-2-yl]sulfonimidoyl]benzoyl]amino]phenyl]carbamate and tert-butyl N-[4-(4-fluorophenyl)-2-[[4-[[4-methyl-1-(2-trimethylsilylethoxymethyl)imidazol-2-yl]sulfonimidoyl]benzoyl]amino]phenyl]carbamate A mixture of 4-[[5-methyl-1-(2-trimethylsilylethoxymethyl)imidazol-2-yl]sulfonimidoyl]benzoic acid and 4-[[4-methyl-1-(2-trimethylsilylethoxymethyl)imidazol-2-yl]sulfonimidoyl]benzoic acid (160 mg, 0.405 mmol), tert-butyl N-[2-amino-4-(4-fluorophenyl)phenyl]carbamate (122 mg, 0.404 mmol) and EDCI (116 mg, 0.605 mmol) in pyridine (3 mL) was stirred at 50° C. for 1 hour. The resulting mixture was concentrated under reduced pressure. The residue was purified by flash chromatography (Biotage®; 12 g AgelaFlash® Silica Flash Column, petroleum ether/EtOAc with EtOAc from 0~85%, 40 mL/min, 254 nm) to afford a mixture of tert-butyl N-[4-(4-fluorophenyl)-2-[[4-[[5-methyl-1-(2-trimethylsilylethoxymethyl)imidazol-2-yl]sulfonimidoyl]benzoyl]amino]phenyl]carbamate and tert-butyl N-[4-(4-fluorophenyl)-2-[[4-[[4-methyl-1-(2-trimethylsilylethoxymethyl)imidazol-2-yl]sulfonimidoyl]benzoyl]amino]phenyl]carbamate (240 mg, 87.27% yield) as colorless oil. LCMS (ESI) $[M+H]^+$ m/z: calcd 780.3; found 680.3 (Boc cleaved mass).

Step 6: Synthesis of N-[2-amino-5-(4-fluorophenyl)phenyl]-4-[(5-methyl-1H-imidazol-2-yl)sulfonimidoyl]benzamide (Compound 228)

To a mixture of tert-butyl N-[4-(4-fluorophenyl)-2-[[4-[[5-methyl-1-(2-trimethylsilylethoxymethyl)imidazol-2-yl]sulfonimidoyl]benzoyl]amino]phenyl]carbamate and tert-butyl N-[4-(4-fluorophenyl)-2-[[4-[[4-methyl-1-(2-trimethylsilylethoxymethyl)imidazol-2-yl]sulfonimidoyl]benzoyl]amino]phenyl]carbamate (210 mg, 0.309 mmol) in DCM (5 mL) was added TFA (0.72 mL, 9.35 mmol). The mixture was stirred at 20° C. for 3 hours. The resulting mixture was concentrated under reduced pressure, and adjust pH=8 with 25% $NH_3$—$H_2O$. The mixture was purified by preparative HPLC (Instrument: Gilson GX-281 Liquid Handler, Gilson 322 Pump, Gilson 156 UV Detector; Column: 2_Phenomenex Gemini C18 75×40 mm×3 μm; Mobile phase A: H$_2$O with NH$_4$HCO$_3$ (v %); Mobile phase B: MeCN; Gradient: B from 25% to 95% in 9.5 min, hold 100% B for 3 min; Flow Rate: 30 mL/min; Column Temperature: 30° C.; Wavelength: 220 nm, 254 nm) to give N-[2-amino-5-(4-fluorophenyl)phenyl]-4-[(5-methyl-1H-imidazol-2-yl)sulfonimidoyl]benzamide (23 mg, 16.6% yield) as yellow dry powder. $^1$H NMR (400 MHz, DMSO-d6) δ ppm 12.98 (brs, 1H), 9.85 (s, 1H), 8.03-8.19 (m, 4H), 7.57 (dd, J=8.5, 5.5 Hz, 2H), 7.49 (d, J=1.8 Hz, 1H), 7.31 (dd, J=8.4, 2.1 Hz, 1H), 7.21 (t, J=8.9 Hz, 2H), 6.91 (s, 1H), 6.85 (d, J=8.4 Hz, 1H), 5.39 (s, 1H), 5.15 (s, 2H), 2.51-2.55 (m, 1H), 2.14 (s, 3H); 19F NMR (376 MHz, DMSO-d6) δ ppm−117.464; LCMS (ESI) [M+H]$^+$ m/z: calcd 450.1; found 450.2; HPLC: 96.91%@220 nm, 99.32%@254 nm.

Example 81. Synthesis of N-[2-amino-5-(4-fluorophenyl)phenyl]-4-(1H-imidazol-2-ylsulfonimidoyl)benzamide (Compound 257)

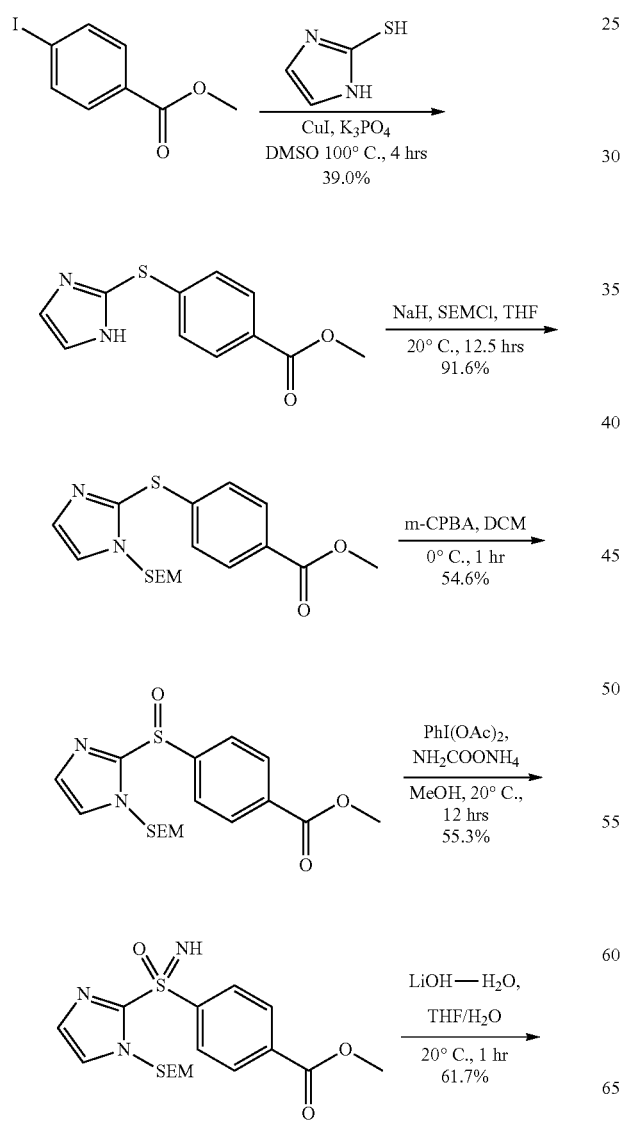

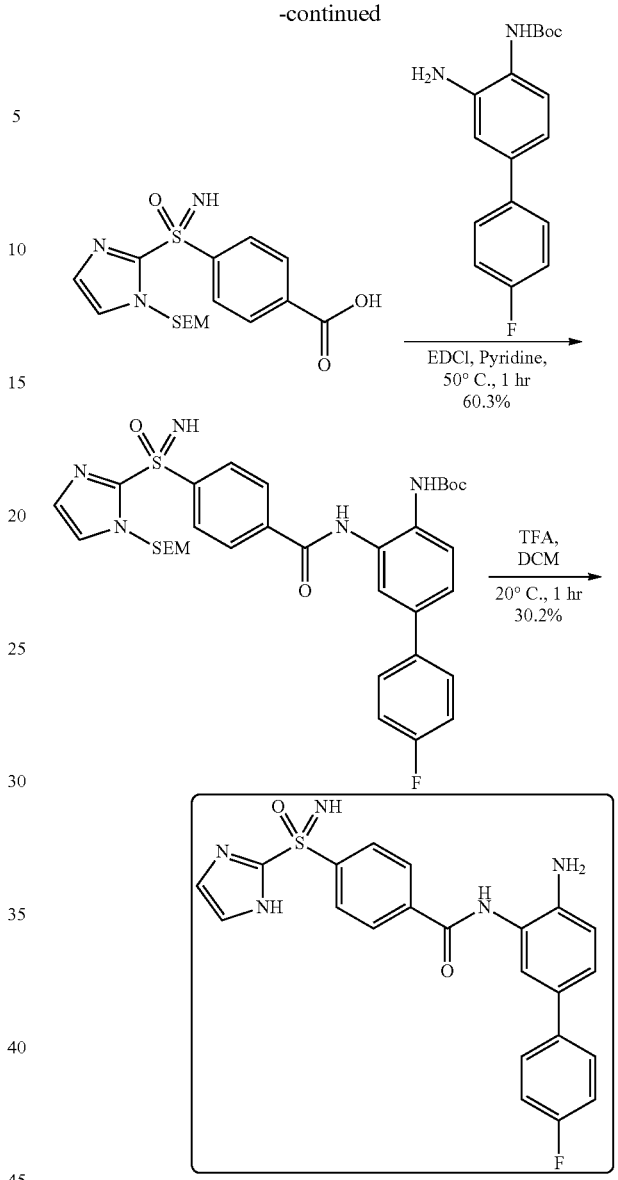

Step 1: Synthesis of methyl 4-(1H-imidazol-2-ylsulfanyl)benzoate

A mixture of 1H-imidazole-2-thiol (3 g, 30.0 mmol), methyl 4-iodobenzoate (11.78 g, 44.9 mmol), CuI (286 mg, 1.50 mmol) and K$_3$PO$_4$ (9.54 g, 44.9 mmol) in DMSO (50 mL) was stirred at 100° C. for 4 hours. The mixture was filtered. The filtrate was extracted with EtOAc (50 mL*3). The combined organic layer was washed with brine (50 mL*3), dried over anhydrous Na$_2$SO$_4$, filtered and concentrated under reduced pressure. The residue was purified by flash chromatography (Biotage®; 12 g AgelaFlash®Silica Flash Column, petroleumether/EtOAc with EtOAc from 0~52%, flow rate=40 mL/min, 254 nm) to afford methyl 4-(1H-imidazol-2-ylsulfanyl)benzoate (2.74 g, 39.0% yield) as white solid. $^1$H NMR (400 MHz, chloroform-d) δ ppm 8.01 (s, 1H), 7.27-7.31 (m, 2H), 6.96 (d, J=8.5 Hz, 2H), 5.23 (s, 2H), 3.85 (s, 3H); LCMS (ESI) [M+H]$^+$ m/z: calcd 235.0, found 235.0.

Step 2: Synthesis of methyl 4-[1-(2-trimethylsilylethoxymethyl)imidazol-2-yl]sulfanylbenzoate To a mixture of methyl 4-(1H-imidazol-2-ylsulfanyl)benzoate (2 g, 8.54 mmol) in THF (20 mL) was added NaH (515 mg, 12.9 mmol, 60 wt % in mineral oil) at 20° C. The mixture was stirred at 20° C. for 30 minutes. SEMCl (1.8 mL, 10.2 mmol) was added to the mixture. Then the mixture was stirred at 20° C. for 12 hours. 5 mL of water was added. The mixture was extracted with EtOAc (15 mL*3). The combined organic layer was washed with brine (15 mL*3), dried over anhydrous $Na_2SO_4$, filtered and concentrated under reduced pressure. The residue was purified by flash chromatography (Biotage®; 12 g AgelaFlash®Silica Flash Column, petroleum ether/EtOAc with EtOAc from 0~12%, flow rate=50 mL/min, 254 nm) to afford methyl 4-[1-(2-trimethylsilylethoxymethyl)imidazol-2-yl]sulfanylbenzoate (2.85 g, 91.6% yield) as yellow oil. $^1$H NMR (400 MHz, chloroform-d) δ ppm 8.01 (s, 1H), 7.99 (s, 1H), 7.38-7.42 (m, 2H), 7.26 (d, J=8.5 Hz, 2H), 5.46 (s, 2H), 3.94-4.02 (m, 3H), 3.43-3.49 (m, 2H), 0.84-0.91 (m, 2H), 0.02 (s, 9H); LCMS (ESI) [M+H]$^+$ m/z: calcd 365.1, found 365.1.

Step 3: Synthesis of methyl 4-[1-(2-trimethylsilylethoxymethyl)imidazol-2-yl]sulfinylbenzoate To a mixture of methyl 4-[1-(2-trimethylsilylethoxymethyl)imidazol-2-yl]sulfanylbenzoate (1 g, 2.74 mmol) in DCM (10 mL) was added m-CPBA (500 mg, 2.90 mmol, 85 wt %) at 0° C. The mixture was stirred at 0° C. for 1 hour. 1 mL of water was added and saturated $NaHCO_3$ aqueous solution was added to adjust pH to 8. Then the mixture was extracted with DCM (10 mL*3). The combined organic layer was washed with brine (10 mL*3), dried over anhydrous $Na_2SO_4$, filtered and concentrated under reduced pressure. The residue was purified by flash chromatography (Biotage®; 12 g AgelaFlash®Silica Flash Column, petroleumether/EtOAc with EtOAc from 0~46%, flow rate=30 mL/min, 254 nm) to afford methyl 4-[1-(2-trimethylsilylethoxymethyl)imidazol-2-yl]sulfinylbenzoate (570 mg, 54.6% yield) as yellow oil. $^1$H NMR (400 MHz, DMSO-d6) δ ppm 8.08-8.15 (m, 2H), 7.71-7.79 (m, 2H), 7.60 (d, J=1.0 Hz, 1H), 7.16 (d, J=1.0 Hz, 1H), 5.47-5.63 (m, 2H), 3.87 (s, 3H), 3.17-3.32 (m, 2H), 0.50-0.72 (m, 2H), −0.16--0.08 (m, 9H); LCMS (ESI) [M+H]$^+$ m/z: calcd 381.1, found 381.1.

Step 4: Synthesis of methyl 4-[[1-(2-trimethylsilylethoxymethyl)imidazol-2-yl]sulfonimidoyl]benzoate A mixture of methyl 4-[1-(2-trimethylsilylethoxymethyl)imidazol-2-yl]sulfinylbenzoate (470 mg, 1.24 mmol), PhI(OAc)$_2$ (800 mg, 2.48 mmol) and ammoniumcarbamate (240 mg, 3.07 mmol) in MeOH (5 mL) was stirred at 20° C. for 12 hours. The mixture was filtered. The residue was purified by flash chromatography (Biotage®; 12 g AgelaFlash®Silica Flash Column, petroleumether/EtOAc with EtOAc from 0~38%, flow rate=30 mL/min, 254 nm) to afford methyl 4-[[1-(2-trimethylsilylethoxymethyl)imidazol-2-yl]sulfonimidoyl]benzoate (270 mg, 55.3% yield) as colorless oil. $^1$H NMR (400 MHz, DMSO-d6) δ ppm 8.10 (s, 4H), 7.57 (d, J=1.0 Hz, 1H), 7.13 (d, J=0.8 Hz, 1H), 5.75 (s, 1H), 5.66 (d, J=4.0 Hz, 2H), 3.87 (s, 3H), 3.13-3.25 (m, 2H), 0.48-0.60 (m, 2H), −0.15--0.12 (m, 9H); LCMS (ESI) [M+H]$^+$ m/z: calcd 396.1, found 396.1.

Step 5: Synthesis of 4-[[1-(2-trimethylsilylethoxymethyl)imidazol-2-yl]sulfonimidoyl]benzoic acid A mixture of methyl 4-[[1-(2-trimethylsilylethoxymethyl)imidazol-2-yl]sulfonimidoyl]benzoate (210 mg, 0.531 mmol) and LiOH—H$_2$O (100 mg, 2.38 mmol) in THF (2 mL) and H$_2$O (2 mL) was stirred at 20° C. for 1 hour. 1N HCl aqueous solution was added to adjust pH to 5. Then the mixture was extracted with EtOAc (10 mL*3). The combined organic layer was dried over anhydrous Na$_2$SO$_4$, filtered and concentrated under reduced pressure to give 4-[[1-(2-trimethylsilylethoxymethyl)imidazol-2-yl]sulfonimidoyl]benzoic acid (125 mg, 61.7% yield) as white solid. $^1$H NMR (400 MHz, methanol-d4) δ ppm 8.18 (s, 4H), 7.49 (s, 1H), 7.20 (s, 1H), 5.79 (d, J=10.4 Hz, 1H), 5.63 (d, J=10.3 Hz, 1H), 3.23-3.30 (m, 1H), 3.18 (ddd, J=10.8, 9.3, 5.8 Hz, 1H), 0.57-0.66 (m, 1H), 0.47-0.55 (m, 1H), −0.13--0.10 (m, 9H); LCMS (ESI) [M+H]$^+$ m/z: calcd 382.1, found 382.2.

Step 6: Synthesis of tert-butyl N-[4-(4-fluorophenyl)-2-[[4-[[1-(2-trimethylsilylethoxymethyl)imidazol-2-yl]sulfonimidoyl]benzoyl]amino]phenyl]carbamate A mixture of 4-[[1-(2-trimethylsilylethoxymethyl)imidazol-2-yl]sulfonimidoyl]benzoic acid (95 mg, 0.249 mmol), tert-butyl N-[2-amino-4-(4-fluorophenyl)phenyl]carbamate (95 mg, 0.314 mmol) and EDCI (55 mg, 0.287 mmol) in pyridine (5 mL) was stirred at 50° C. for 1 hour. The mixture was concentrated under reduced pressure. The residue was purified by flash chromatography (Biotage®; 4 g AgelaFlash®Silica Flash Column, petroleumether/EtOAc with EtOAc from 0~33%, flow rate=15 mL/min, 254 nm) to afford tert-butyl N-[4-(4-fluorophenyl)-2-[[4-[[1-(2-trimethylsilylethoxymethyl)imidazol-2-yl]sulfonimidoyl]benzoyl]amino]phenyl]carbamate (100 mg, 60.3% yield) as colorless oil. LCMS (ESI) [M+H]$^+$ m/z: calcd 666.3, found 666.3.

Step 7: Synthesis of N-[2-amino-5-(4-fluorophenyl)phenyl]-4-(1H-imidazol-2-ylsulfonimidoyl)benzamide (Compound 257)

To a mixture of tert-butyl N-[4-(4-fluorophenyl)-2-[[4-[[1-(2-trimethylsilylethoxymethyl)imidazol-2-yl]sulfonimidoyl]benzoyl]amino]phenyl]carbamate (90 mg, 0.135 mmol) in DCM (2 mL) was added TFA (0.2 mL, 2.60 mmol) at 20° C. The mixture was stirred at 20° C. for 1 hour. The resulting mixture was concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 μm; Mobile phase A: H$_2$O with 0.05% NH$_3$—H$_2$O (v %); Mobile phase B: MeCN; Gradient: B from 30% to 60% in 9.5 mins, hold 100% B for 2 mins; Flow Rate: 30 mL/min; Column Temperature: 30° C.; Wavelength: 220 nm, 254 nm) to afford N-[2-amino-5-(4-fluorophenyl)phenyl]-4-(1H-imidazol-2-ylsulfonimidoyl)benzamide (17.8 mg, 30.2% yield) as white solid. $^1$H NMR (400 MHz, DMSO-d6) δ ppm 13.42 (s, 1H), 9.85 (s, 1H), 8.12-8.17 (m, 2H), 8.04-8.11 (m, 2H), 7.57 (dd, J=8.5, 5.5 Hz, 2H), 7.49 (d, J=2.0 Hz, 1H), 7.08-7.35 (m, 5H), 6.85-6.85 (m, 1H), 6.85 (d, J=8.3 Hz, 1H), 5.51 (s, 1H), 5.17 (s, 2H), 2.52 (s, 1H); 19F NMR (376 MHz, DMSO-d6) δ ppm −117.481; LCMS (ESI) [M+H]$^+$ m/z: calcd 436.1, found 436.0; HPLC: 96.98%@220 nm, 99.69%@254 nm.

479

Example 82. Synthesis of N-[2-amino-5-(4-fluorophenyl)phenyl]-5-(1-oxo-4,5-dihydro-3H-isothiazol-1-yl)benzofuran-2-carboxamide (Compound 210)

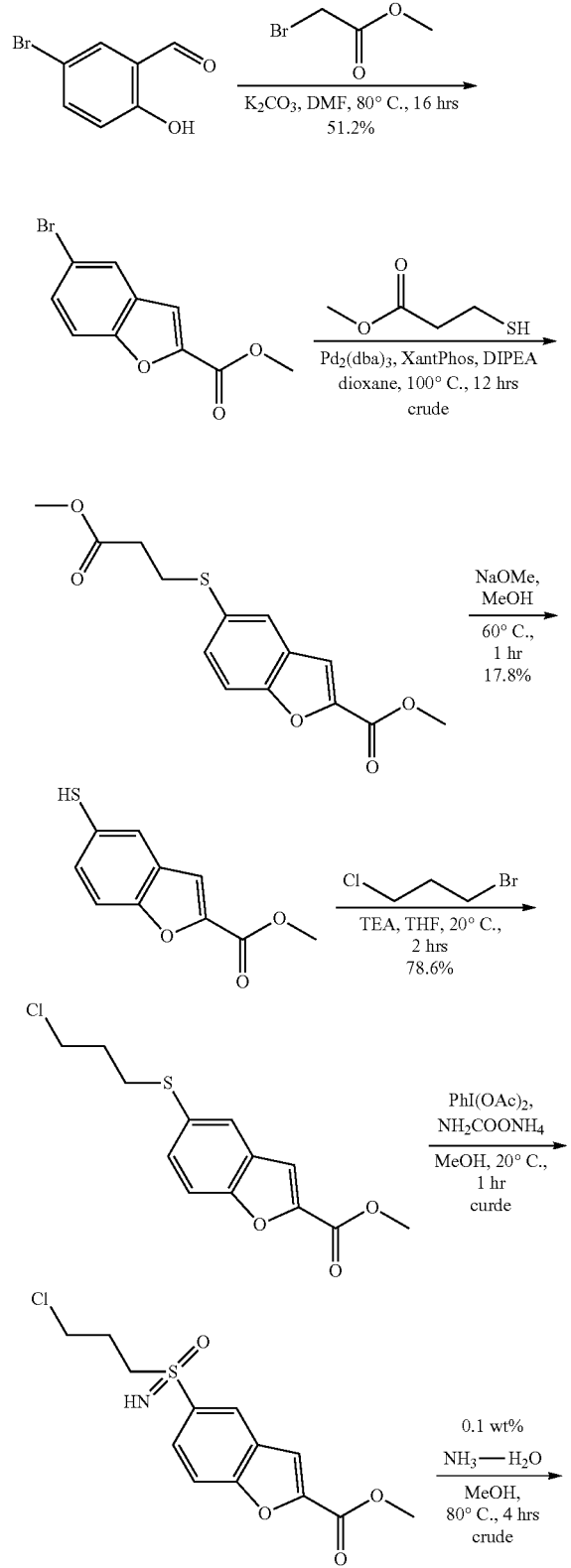

480

-continued

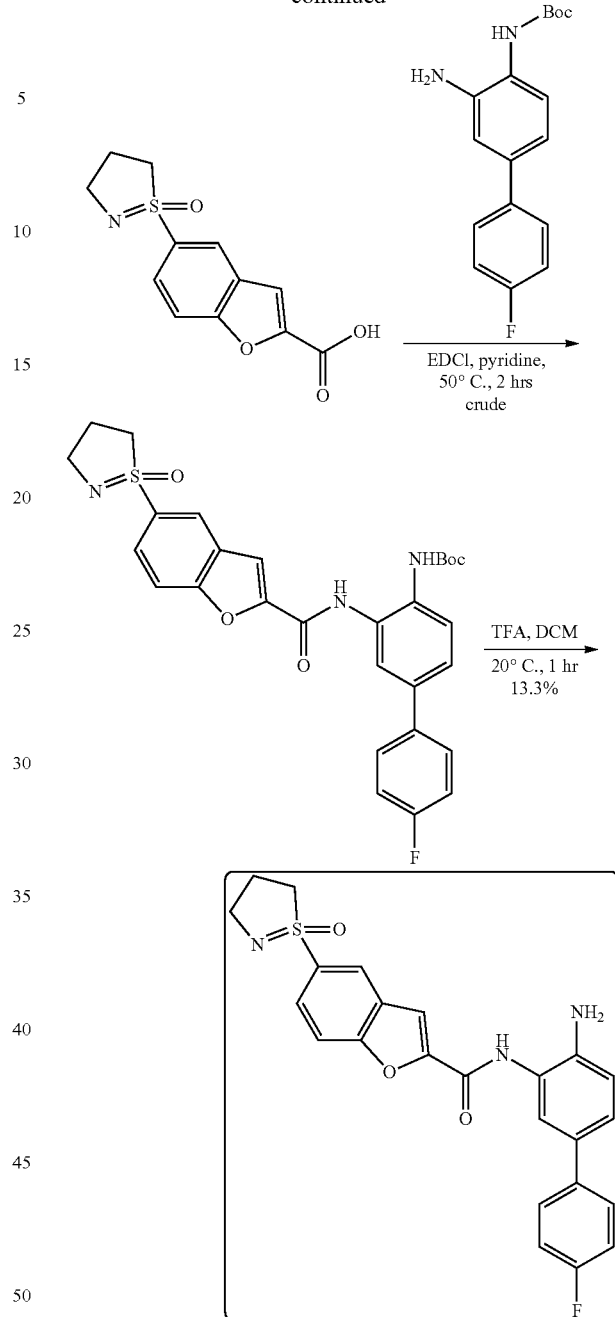

Step 1: Synthesis of methyl 5-bromobenzofuran-2-carboxylate

To a solution of 5-bromo-2-hydroxy-benzaldehyde (10 g, 49.8 mmol) and $K_2CO_3$ (20.7 g, 0.150 mol) in DMF (200 mL) was added 5-bromo-2-hydroxy-benzaldehyde (10 g, 49.8 mmol). The mixture was stirred at 80° C. for 16 hours. The resulting mixture was filtered, quenched by addition of water (100 mL) and extracted with DCM (100 mL×3). The combined organic layer was washed with saturated $NH_4Cl$ aqueous solution (50 mL), brine (100 mL×2), dried over anhydrous $Na_2SO_4$, filtered and concentrated under reduced pressure. The residue was purified by flash chromatography (ISCO®; 80 g AgelaFlash® Silica Flash Column, petroleum ether/EtOAc with EtOAc from 0~10%, flow rate=80 mL/min, 254 nm) to afford methyl 5-bromobenzofuran-2-carboxylate (6.5 g, 51.2% yield) as white solid. LCMS (ESI) [M+H]$^+$ m/z: calcd 257.0, found 257.0.

Step 2: Synthesis of methyl 5-(3-methoxy-3-oxo-propyl)sulfanylbenzofuran-2-carboxylate A mixture of methyl 5-bromobenzofuran-2-carboxylate (6.5 g, 25.5 mmol), methyl 3-sulfanylpropanoate (3.4 mL, 30.7 mmol), (5-diphenylphosphanyl-9,9-dimethyl-xanthen-4-yl)-diphenyl-phosphane (1.5 g, 2.59 mmol), (1E,4E)-1,5-diphenylpenta-1,4-dien-3-one;palladium (1.2 g, 1.31 mmol), DIPEA (13.5 mL, 77.5 mmol) in dioxane (100 mL) was degassed under vacuum and purged with N$_2$ for three times, then stirred at 100° C. for 16 hours. The resulting mixture was filtered and concentrated under reduced pressure. The residue was purified by flash chromatography (ISCO®; 80 g AgelaFlash® Silica Flash Column, petroleum ether/EtOAc with EtOAc from 0~25%, flow rate=80 mL/min, 254 nm) to afford methyl 5-(3-methoxy-3-oxo-propyl)sulfanylbenzofuran-2-carboxylate (7.6 g, crude) as white solid. LCMS (ESI) [M+H]$^+$ m/z: calcd 295.1, found 295.1.

Step 3: Synthesis of methyl 5-sulfanylbenzofuran-2-carboxylate

To a solution of methyl 5-(3-methoxy-3-oxo-propyl)sulfanylbenzofuran-2-carboxylate (6.5 g, 22.1 mmol) in MeOH (200 mL) was added NaOMe (4.8 g, 88.9 mmol). The mixture was stirred at 60° C. for 1 hour. The resulting mixture was concentrated under reduced pressure, diluted with EtOAc (20 mL), adjusted pH=8 with 2N HCl aqueous solution, quenched by addition of water (50 mL) and extracted with EtOAc (50 mL×3), DCM (50 mL×3). The combined organic layer was washed with brine (100 mL), dried over anhydrous Na$_2$SO$_4$, filtered and concentrated under reduced pressure. The residue was purified by flash chromatography (ISCO®; 40 g AgelaFlash® Silica Flash Column, petroleum ether/EtOAc with EtOAc from 0~34%, flow rate=60 mL/min, 254 nm) to afford methyl 5-sulfanyl-benzofuran-2-carboxylate (820 mg, 17.8% yield) as light-yellow solid. LCMS (ESI) [M+H]$^+$ m/z: calcd 209.0, found 209.1.

Step 4: Synthesis of methyl 6-(3-chloropropylsulfanyl)benzofuran-2-carboxylate To a solution of methyl 6-sulfanylbenzofuran-2-carboxylate (400 mg, 1.92 mmol) and 1-bromo-3-chloro-propane (0.4 mL, 4.04 mmol) in THF (30 mL) was added N,N-diethylethanamine (0.6 mL, 4.30 mmol). The mixture was stirred at 20° C. for 2 hours. The reaction mixture was concentrated under reduced pressure. The residue was purified by flash chromatography (ISCO®; 40 g AgelaFlash® Silica Flash Column, Petroleum ether/EtOAc with EtOAc from 0~19%, flow rate=50 mL/min, 254 nm) to afford methyl 6-(3-chloropropylsulfanyl)benzofuran-2-carboxylate (430 mg, 78.6% yield) as white solid. $^1$H NMR (400 MHz, DMSO-d6) δ ppm 7.82 (d, J=1.8 Hz, 1H), 7.69-7.73 (m, 2H), 7.53 (dd, J=8.8, 2.0 Hz, 1H), 3.89 (s, 3H), 3.73 (t, J=6.4 Hz, 2H), 3.09 (t, J=7.2 Hz, 2H), 1.97 (quin, J=6.7 Hz, 2H); LCMS (ESI) [M+H]$^+$ m/z: calcd 285.0, found 285.1.

Step 5: Synthesis of methyl 5-(3-chloropropylsulfonimidoyl)benzofuran-2-carboxylate A mixture of methyl 5-(3-chloropropylsulfanyl)benzofuran-2-carboxylate (420 mg, 1.47 mmol), [acetoxy(phenyl)-iodanyl] acetate (1.2 g, 3.73 mmol) and ammonia; carbamic acid (230 mg, 2.95 mmol) in MeOH (100 mL) was stirred at 20° C. for 1 hour. The resulting mixture was concentrated under reduced pressure. The residue was purified by flash chromatography (ISCO®; 40 g AgelaFlash® Silica Flash Column, petroleum ether/EtOAc with EtOAc from 0~87%, flow rate=60 mL/min, 254 nm) to afford methyl 5-(3-chloropropylsulfonimidoyl)benzofuran-2-carboxylate (370 mg, crude) as white gum. $^1$H NMR (400 MHz, DMSO-d6) δ ppm 8.41 (d, J=1.5 Hz, 1H), 8.01 (d, J=1.8 Hz, 1H), 7.94-7.99 (m, 2H), 3.92 (s, 3H), 3.67 (t, J=6.5 Hz, 2H), 3.36-3.47 (m, 1H), 3.28-3.33 (m, 2H), 1.94-2.02 (m, 2H); LCMS (ESI) [M+H]$^+$ m/z: calcd 316.0, found 316.1.

Step 6: Synthesis of 5-(1-oxo-4,5-dihydro-3H-isothiazol-1-yl)benzofuran-2-carboxylic acid A mixture of methyl 5-(3-chloropropylsulfonimidoyl)benzofuran-2-carboxylate (365 mg, 1.16 mmol) in 0.1 wt % NH$_3$—H$_2$O (100 mL, 1.16 mmol) and MeOH (30 mL) was stirred at 80° C. for 4 hours. The resulting mixture was concentrated under reduced pressure to afford 5-(1-oxo-4,5-dihydro-3H-isothiazol-1-yl)benzofuran-2-carboxylic acid (380 mg, crude) as white solid. $^1$H NMR (500 MHz, DMSO-d6) δ ppm 8.21 (s, 1H), 7.80 (d, J=0.9 Hz, 2H), 7.28 (s, 1H), 3.78-3.84 (m, 1H), 3.70 (dt, J=10.2, 6.4 Hz, 1H), 3.30-3.44 (m, 2H), 2.16-2.33 (m, 2H); LCMS (ESI) [M+H]$^+$ m/z: calcd 266.0, found 266.1.

Step 7: Synthesis of tert-butyl N-[4-(4-fluorophenyl)-2-[[5-(1-oxo-4,5-dihydro-3H-isothiazol-1-yl)benzofuran-2-carbonyl]amino]phenyl]carbamate To a solution of 5-(1-oxo-4,5-dihydro-3H-isothiazol-1-yl)benzofuran-2-carboxylic acid (100 mg, 0.377 mmol) and tert-butyl N-[2-amino-4-(4-fluorophenyl)phenyl]carbamate (120 mg, 0.397 mmol) in pyridine (30 mL) was added EDCI (110 mg, 0.574 mmol). The mixture was stirred at 50° C. for 2 hours. The resulting mixture was concentrated under reduced pressure. The residue was purified by flash chromatography (ISCO®; 20 g AgelaFlash® Silica Flash Column, petroleum ether/EtOAc with EtOAc from 0~50%, flow rate=40 mL/min, 254 nm) to afford tert-butyl N-[4-(4-fluorophenyl)-2-[[5-(1-oxo-4,5-dihydro-3H-isothiazol-1-yl)benzofuran-2-carbonyl]amino]phenyl]carbamate (120 mg, crude) as white solid. LCMS (ESI) [M+H]$^+$ m/z: calcd 550.2, found 550.3.

Step 8: Synthesis of N-[2-amino-5-(4-fluorophenyl)phenyl]-5-(1-oxo-4,5-dihydro-3H-isothiazol-1-yl)benzofuran-2-carboxamide (Compound 210)

To a solution of tert-butyl N-[4-(4-fluorophenyl)-2-[[5-(1-oxo-4,5-dihydro-3H-isothiazol-1-yl)benzofuran-2-carbonyl]amino]phenyl]carbamate (120 mg, 0.218 mmol) in DCM (5 mL) was added TFA (0.4 mL, 5.19 mmol). The mixture was stirred at 20° C. for 4 hours. The resulting mixture was adjusted pH=8 with saturated NaHCO$_3$ aqueous solution, extracted with DCM (30 mL×3). The combined organic layer was washed with brine (30 mL×2), dried over anhydrous Na$_2$SO$_4$, filtered and concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 μm; Mobile phase A: water (NH$_4$HCO$_3$); Mobile phase B: ACN; Gradient: B from 32% to 62% in 9.5 min, hold 100% B for 1 min; Flow Rate: 30 mL/min; Column Temperature: 30° C.; Wavelength: 220 nm, 254 nm). The fraction was concentrated under reduced pressure and lyophilized for overnight to afford N-[2-amino-5-(4-fluorophenyl)phenyl]-5-(1-oxo-4,5-dihydro-3H-isothiazol-1-yl)benzofuran-2-carboxamide (13 mg, 13.3% yield) as white solid. $^1$H NMR (400 MHz, DMSO-d6) δ ppm 10.11 (s, 1H), 8.40 (s, 1H), 7.94 (s, 2H), 7.90 (s, 1H), 7.56-7.61 (m, 2H), 7.50 (d, J=2.0 Hz, 1H), 7.34 (dd, J=8.4, 2.1 Hz, 1H), 7.22 (t, J=8.8 Hz, 2H), 6.87 (d, J=8.5 Hz, 1H), 5.21 (s, 2H), 3.81-3.88 (m, 1H), 3.73 (dt, J=10.3, 6.5 Hz, 1H), 3.40-3.50 (m, 2H), 2.21-2.35 (m, 2H); 19F NMR (376 MHz, DMSO-d6) δ ppm −117.417; LCMS (ESI) [M+H]$^+$ m/z: calcd 450.1, found 450.2; HPLC: 98.86%@220 nm; 99.30%@254 nm.

Example 83. Synthesis of N-[2-amino-5-(4-fluorophenyl)phenyl]-4-[(2-fluorophenyl)sulfonimidoyl]benzamide (Compound 197)

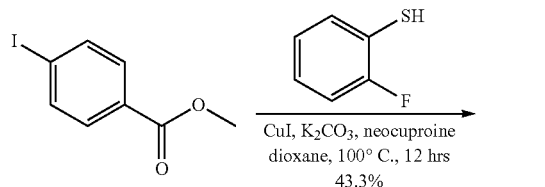

Step 1: Synthesis of methyl 4-(2-fluorophenyl)sulfanylbenzoate

A mixture of methyl 4-iodobenzoate (300 mg, 1.14 mmol), 2-fluorobenzenethiol (0.15 mL, 1.41 mmol), CuI (24 mg, 0.126 mmol), K$_2$CO$_3$ (480 mg, 3.47 mmol), neocuproine (24 mg, 0.115 mmol) in dioxane (6 mL) was stirred at 100° C. for 12 hours under N$_2$. The mixture was filtered. The filtrate was concentrated under reduced pressure. The residue was purified by flash chromatography (ISCO®; 12 g AgelaFlash® Silica Flash Column, petroleum ether/EtOAc with EtOAc from 0~8%, flow rate=35 mL/min, 254 nm) to afford methyl 4-(2-fluorophenyl)sulfanylbenzoate (130 mg, 43.3% yield) as colorless oil. LCMS (ESI) [M+H]$^+$ m/z: calcd 263.0, found 263.0.

Step 2: Synthesis of methyl 4-[(2-fluorophenyl)sulfonimidoyl]benzoate

A mixture of methyl 4-(2-fluorophenyl)sulfanylbenzoate (100 mg, 0.381 mmol), [acetoxy(phenyl)-iodanyl] acetate (310 mg, 0.962 mmol), ammonia;carbamic acid (60 mg, 0.769 mmol) in MeOH (6 mL) was stirred at 20° C. for 2 hours. To the reaction mixture was added [acetoxy(phenyl)-iodanyl] acetate (310 mg, 0.962 mmol) and ammonia;carbamic acid (60 mg, 0.769 mmol). The mixture was stirred at 20° C. for 12 hours. The resulting mixture was concentrated under reduced pressure. The residue was purified by flash chromatography (ISCO®; 12 g AgelaFlash® Silica Flash Column, petroleum ether/EtOAc with EtOAc from 0~35%, flow rate=40 mL/min, 254 nm) to afford methyl 4-[(2-fluorophenyl)sulfonimidoyl]benzoate (110 mg, 98.4% yield) as white solid. $^1$H NMR (400 MHz, DMSO-d6) δ ppm 8.02-8.18 (m, 5H), 7.63-7.73 (m, 1H), 7.40-7.48 (m, 1H), 7.26-7.34 (m, 1H), 3.87 (s, 3H); 19F NMR (377 MHz, DMSO-d6) δ ppm −108.608; LCMS (ESI) [M+H]+ m/z: calcd 294.1, found 294.0.

Step 3: Synthesis of 4-[(2-fluorophenyl)sulfonimidoyl]benzoic acid

To a solution of methyl 4-[(2-fluorophenyl)sulfonimidoyl]benzoate (90 mg, 0.307 mmol) in H₂O (1 mL) and MeOH (3 mL) was added lithium;hydroxide;hydrate (130 mg, 3.10 mmol) at 0° C. The mixture was stirred at 20° C. for 2 hours. The mixture was adjusted the pH to 8 with 2N HCl aqueous solution. The resulting mixture was quenched by addition of water (20 mL) and extracted with EtOAc (30 mL*2). The combined organic layer was dried over anhydrous Na₂SO₄, filtered and concentrated under reduced pressure to give 4-[(2-fluorophenyl)sulfonimidoyl]benzoic acid (120 mg, crude) as white solid. LCMS (ESI) [M+H]+ m/z: calcd 280.0, found 280.0.

Step 4: Synthesis of tert-butyl N-[4-(4-fluorophenyl)-2-[[4-[(2-fluorophenyl)sulfonimidoyl]benzoyl]amino]phenyl]carbamate A mixture of 4-[(2-fluorophenyl)sulfonimidoyl]benzoic acid (90 mg, 0.322 mmol), tert-butyl N-[2-amino-4-(4-fluorophenyl)phenyl]carbamate (100 mg, 0.331 mmol), 3-(ethyliminomethyleneamino)-N,N-dimethyl-propan-1-amine;hydrochloride (60 mg, 0.313 mmol) in pyridine (4 mL) was stirred at 50° C. for 1 hour. The resulting mixture was concentrated under reduced pressure. The residue was purified by flash chromatography (ISCO®; 12 g Agela-Flash® Silica Flash Column, petroleum ether/EtOAc with EtOAc from 0~38%, flow rate=40 mL/min, 254 nm) to afford tert-butyl N-[4-(4-fluorophenyl)-2-[[4-[(2-fluorophenyl)sulfonimidoyl]benzoyl]amino]phenyl]carbamate (160 mg, 88.1% yield) as white solid. LCMS (ESI) [M+H]+ m/z: calcd 564.2, found 564.1.

Step 5: Synthesis of N-[2-amino-5-(4-fluorophenyl)phenyl]-4-[(2-fluorophenyl)sulfonimidoyl]benzamide To a solution of tert-butyl N-[4-(4-fluorophenyl)-2-[[4-[(2-fluorophenyl)sulfonimidoyl]benzoyl]amino]phenyl]carbamate (110 mg, 0.195 mmol) in DCM (3 mL) was added TFA (0.4 mL, 5.19 mmol). The mixture was stirred at 20° C. for 1 hour. The resulting mixture was concentrated under reduced pressure and adjusted the pH to 8 with saturated NaHCO₃ aqueous solution. The resulting mixture was extracted with water (20 mL) and EtOAc (30 mL*2). The combined organic layer was dried over anhydrous Na₂SO₄, filtered and concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 μm; Mobile phase A: H₂O with 0.05% NH₃—H₂O and 10 mmol NH₄HCO₃ (v %); Mobile phase B: MeCN; Gradient: B from 40% to 70% in 7.8 min, hold 100% B for 2 min; Flow Rate: 30 mL/min; Column Temperature: 30° C.; Wavelength: 220 nm, 254 nm) to afford N-[2-amino-5-(4-fluorophenyl)phenyl]-4-[(2-fluorophenyl)sulfonimidoyl]benzamide (80 mg, 88.4% yield) as white solid. ¹H NMR (400 MHz, DMSO-d6) δ ppm 9.88 (s, 1H), 8.05-8.19 (m, 5H), 7.65-7.74 (m, 1H), 7.57 (dd, J=8.8, 5.5 Hz, 2H), 7.43-7.50 (m, 2H), 7.28-7.35 (m, 2H), 7.21 (t, J=8.9 Hz, 2H), 6.84 (d, J=8.5 Hz, 1H), 5.61 (s, 1H), 5.16 (s, 2H); 19F NMR (376 MHz, DMSO-d6) δ ppm −108.55, −117.49; LCMS (ESI) [M+H]+ m/z: calcd 464.1, found 464.1; HPLC: 98.24%@220 nm, 1000%@254 nm.

Example 84. Synthesis of N-[2-amino-5-(4-fluorophenyl)phenyl]-4-[(2-methyl-1H-imidazol-5-yl)sulfonimidoyl]benzamide (Compound 217)

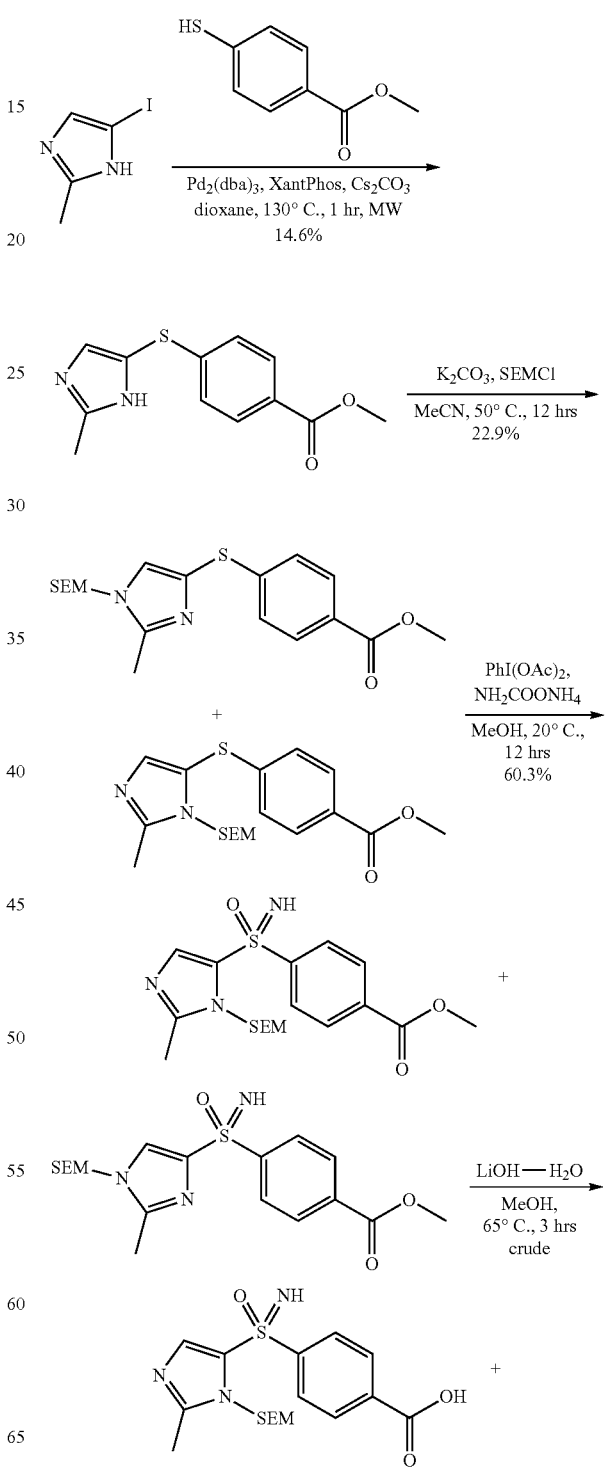

-continued

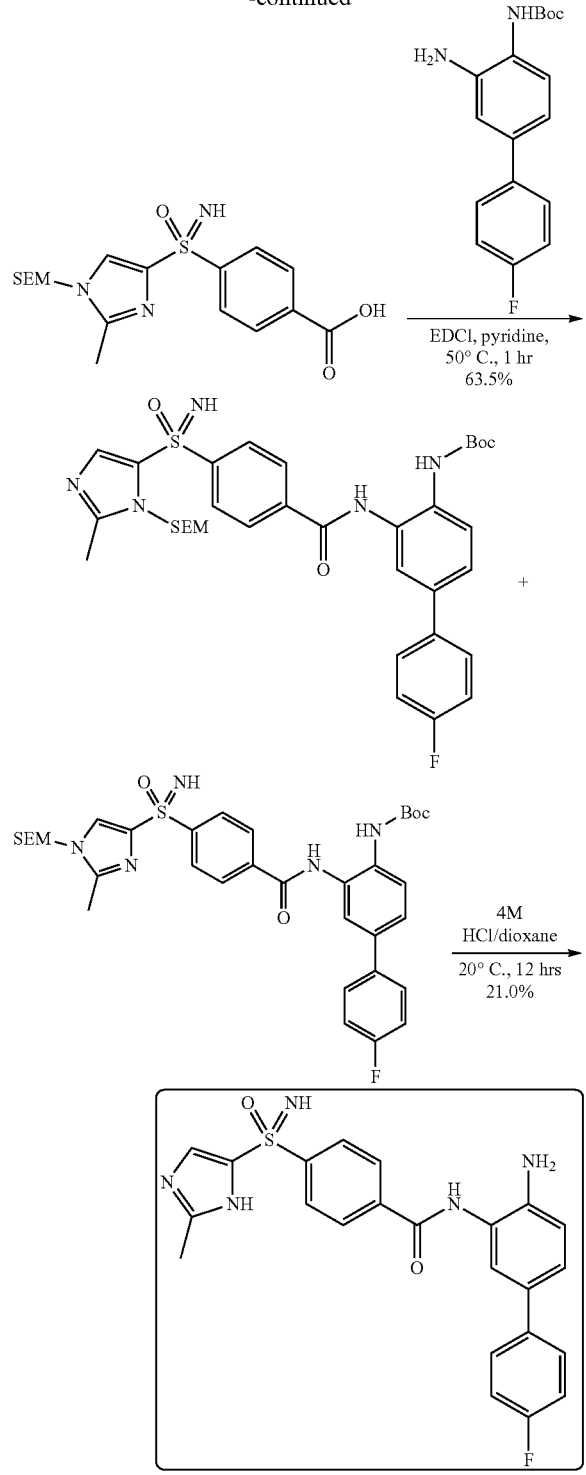

Step 1: Synthesis of methyl 4-[(2-methyl-1H-imidazol-5-yl)sulfanyl]benzoate

A mixture of methyl 4-sulfanylbenzoate (1 g, 5.94 mmol), 5-iodo-2-methyl-1H-imidazole (1.5 g, 7.21 mmol), (1E,4E)-1,5-diphenylpenta-1,4-dien-3-one;palladium (1.1 g, 1.20 mmol), (5-diphenylphosphanyl-9,9-dimethyl-xanthen-4-yl)-diphenyl-phosphane (690 mg, 1.19 mmol) and $Cs_2CO_3$ (4.85 g, 14.9 mmol) in dioxane (30 mL) was degassed and purged with $N_2$ for 3 times, and then the mixture was stirred at 130° C. for 1 hour in microwave. The reaction mixture was filtered and the filtrate was concentrated under reduced pressure. The residue was purified by flash chromatography (ISCO®; 40 g SepaFlash® Silica Flash Column, DCM/MeOH with MeOH from 0~5%, flow rate: 60 mL/min, 254 nm) to give methyl 4-[(2-methyl-1H-imidazol-5-yl)sulfanyl]benzoate (430 mg, 14.6% yield) as brown oil. LCMS (ESI) [M+H]$^+$ m/z: calcd 249.1, found 249.1.

Step 2: Synthesis of mixture of methyl 4-[2-methyl-3-(2-trimethylsilylethoxymethyl)imidazol-4-yl]sulfanylbenzoate and methyl 4-[2-methyl-1-(2-trimethylsilylethoxymethyl)imidazol-4-yl]sulfanylbenzoate To a solution of methyl 4-[(2-methyl-1H-imidazol-5-yl)sulfanyl]benzoate (430 mg, 1.73 mmol) in acetonitrile (8 mL) were added 2-(chloromethoxy)ethyl-trimethyl-silane (0.46 mL, 2.60 mmol) and $K_2CO_3$ (600 mg, 4.34 mmol). The mixture was stirred at 50° C. for 12 hours. The reaction mixture was diluted with water (20 mL) and extracted with EtOAc (50 mL*3). The combined organic layers were washed with brine (20 mL), dried over $Na_2SO_4$ and filtered. The filtrate was concentrated under reduced pressure. The residue was purified by flash chromatography (ISCO®; 12 g SepaFlash® Silica Flash Column, petroleum ether/EtOAc with EtOAc from 0~50%, flow rate: 40 mL/min, 254 nm) to give a mixture of methyl 4-[2-methyl-3-(2-trimethylsilylethoxymethyl)imidazol-4-yl]sulfanylbenzoate and methyl 4-[2-methyl-1-(2-trimethylsilylethoxymethyl)imidazol-4-yl]sulfanylbenzoate (150 mg, 22.9% yield) as yellow oil. LCMS (ESI) [M+H]$^+$ m/z: calcd 379.1, found 379.2.

Step 3: Synthesis of methyl 4-[[2-methyl-3-(2-trimethylsilylethoxymethyl)imidazol-4-yl]sulfonimidoyl]benzoate and methyl 4-[[2-methyl-1-(2-trimethylsilylethoxymethyl)imidazol-4-yl]sulfonimidoyl]benzoate To a solution of mixture of methyl 4-[2-methyl-3-(2-trimethylsilylethoxymethyl)imidazol-4-yl]sulfanylbenzoate and methyl 4-[2-methyl-1-(2-trimethylsilylethoxymethyl)imidazol-4-yl]sulfanylbenzoate (230 mg, 0.608 mmol) in MeOH (5 mL) was added [acetoxy(phenyl)-iodanyl] acetate (490 mg, 1.52 mmol) and ammonia;carbamic acid (95 mg, 1.22 mmol). The mixture was stirred at 20° C. for 12 hours. The reaction mixture was concentrated under reduced pressure. The residue was purified by flash chromatography (ISCO®; 4 g SepaFlash® Silica Flash Column, petroleum ether/EtOAc with EtOAc from 0~100%, flow rate: 18 mL/min, 254 nm) to give a mixture of methyl 4-[[2-methyl-3-(2-trimethylsilylethoxymethyl)imidazol-4-yl]sulfonimidoyl]benzoate and methyl 4-[[2-methyl-1-(2-trimethylsilylethoxymethyl)imidazol-4-yl]sulfonimidoyl]benzoate (150 mg, 60.3% yield) as light-yellow oil. LCMS (ESI) [M+H]$^+$ m/z: calcd 410.1, found 410.2.

Step 4: Synthesis of mixture of 4-[[2-methyl-3-(2-trimethylsilylethoxymethyl)imidazol-4-yl]sulfonimidoyl]benzoic acid and 4-[[2-methyl-1-(2-trimethylsilylethoxymethyl)imidazol-4-yl]sulfonimidoyl]benzoic acid To a solution of mixture of methyl 4-[[2-methyl-3-(2-trimethylsilylethoxymethyl)imidazol-4-yl]sulfonimidoyl]

benzoate and methyl 4-[[2-methyl-1-(2-trimethylsilylethoxymethyl)imidazol-4-yl]sulfonimidoyl]benzoate (130 mg, 0.317 mmol) in MeOH (5 mL) was added lithium; hydroxide;hydrate (130 mg, 3.10 mmol). The mixture was stirred at 65° C. for 3 hours. The mixture was adjusted pH=4 with 2N HCl aqueous solution. The mixture was extracted with DCM (30 mL*3). The combined organic layers were washed with brine (30 mL), dried over $Na_2SO_4$ and filtered. The filtrate was concentrated under reduced pressure to give a mixture of 4-[[2-methyl-3-(2-trimethylsilylethoxymethyl) imidazol-4-yl]sulfonimidoyl]benzoic acid and 4-[[2-methyl-1-(2-trimethylsilylethoxymethyl)imidazol-4-yl]sulfonimidoyl]benzoic acid (120 mg, crude) as light-yellow solid. LCMS (ESI) [M+H]$^+$ m/z: calcd 396.1, found 396.1.

Step 5: Synthesis of tert-butyl N-[4-(4-fluorophenyl)-2-[[4-[[2-methyl-3-(2-trimethylsilylethoxymethyl)imidazol-4-yl]sulfonimidoyl]benzoyl]amino] phenyl]carbamate and tert-butyl N-[4-(4-fluorophenyl)-2-[[4-[[2-methyl-1-(2-trimethylsilylethoxymethyl)imidazol-4-yl] sulfonimidoyl]benzoyl]amino]phenyl]carbamate To a solution of mixture of 4-[[2-methyl-3-(2-trimethylsilylethoxymethyl)imidazol-4-yl]sulfonimidoyl]benzoic acid and 4-[[2-methyl-1-(2-trimethylsilylethoxymethyl)imidazol-4-yl]sulfonimidoyl]benzoic acid (110 mg, 0.278 mmol) in pyridine (3 mL) were added EDCI (80 mg, 0.417 mmol) and tert-butyl N-[2-amino-4-(4-fluorophenyl)phenyl]carbamate (100 mg, 0.331 mmol). The mixture was stirred at 50° C. for 1 hour. The reaction mixture was concentrated under reduced pressure. The residue was purified by flash chromatography (ISCO®; 12 g SepaFlash® Silica Flash Column, petroleum ether/EtOAc with EtOAc from 0~100%, flow rate: 40 mL/min, 254 nm) to give a mixture of tert-butyl N-[4-(4-fluorophenyl)-2-[[4-[[2-methyl-3-(2-trimethylsilylethoxymethyl)imidazol-4-yl] sulfonimidoyl]benzoyl]amino]phenyl]carbamate and tert-butyl N-[4-(4-fluorophenyl)-2-[[4-[[2-methyl-1-(2-trimethylsilylethoxymethyl)imidazol-4-yl]sulfonimidoyl] benzoyl]amino]phenyl]carbamate (120 mg, 63.5% yield) as light-yellow solid. LCMS (ESI) [M+H]$^+$ m/z: calcd 680.3, found 679.9.

Step 6: Synthesis of N-[2-amino-5-(4-fluorophenyl) phenyl]-4-[(2-methyl-1H-imidazol-5-yl)sulfonimidoyl]benzamide (Compound 217)

A solution of tert-butyl N-[4-(4-fluorophenyl)-2-[[4-[[2-methyl-3-(2-trimethylsilylethoxymethyl)imidazol-4-yl] sulfonimidoyl]benzoyl]amino]phenyl]carbamate and tert-butyl N-[4-(4-fluorophenyl)-2-[[4-[[2-methyl-1-(2-trimethylsilylethoxymethyl)imidazol-4-yl]sulfonimidoyl] benzoyl]amino]phenyl]carbamate (100 mg, 0.147 mmol) in 4M HCl/dioxane (5 mL, 20.0 mmol) was stirred at 20° C. for 12 hours. The reaction mixture was concentrated under reduced pressure. The reaction mixture was adjusted to pH=8 with saturated $NaHCO_3$ aqueous solution and extracted with DCM (10 mL*3). The combined organic layers were dried over $Na_2SO_4$ and filtered. The filtrate was concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 μm; Mobile phase A: $H_2O$ with $NH_3$—$H_2O$ (v %) and $NH_4HCO_3$ (v %); Mobile phase B: ACN; Gradient: B from 25% to 55% in 9.5 min, hold 100% B for 2 min; Flow Rate: 30 mL/min; Column Temperature: 30° C.; Wavelength: 220 nm, 254 nm) to give N-[2-amino-5-(4-fluorophenyl)phenyl]-4-[(2-methyl-1H-imidazol-5-yl)sulfonimidoyl]benzamide (13.9 mg, 21.0% yield) as light-yellow solid. $^1$H NMR (400 MHz, DMSO-d6) δ ppm 9.84 (s, 1H), 8.08-8.12 (m, 2H), 8.01-8.06 (m, 2H), 7.70 (s, 1H), 7.57 (dd, J=8.8, 5.6 Hz, 2H), 7.49 (d, J=2.0 Hz, 1H), 7.31 (dd, J=8.4, 2.4 Hz, 1H), 7.21 (t, J=8.8 Hz, 2H), 6.85 (d, J=8.4 Hz, 1H), 5.15 (s, 2H), 4.67 (s, 1H), 2.23 (s, 3H); 19F NMR (376 MHz, DMSO-d6) δ ppm −117.48; LCMS [M+H]$^m$ m/z: calcd 450.1; found 450.1; HPLC: 95.68%@220 nm; 98.820%@254 nm.

Example 85. Synthesis of N-[2-amino-5-(4-fluorophenyl)phenyl]-4-[(4-methyl-1H-imidazol-5-yl) sulfonimidoyl]benzamide (Compound 209)

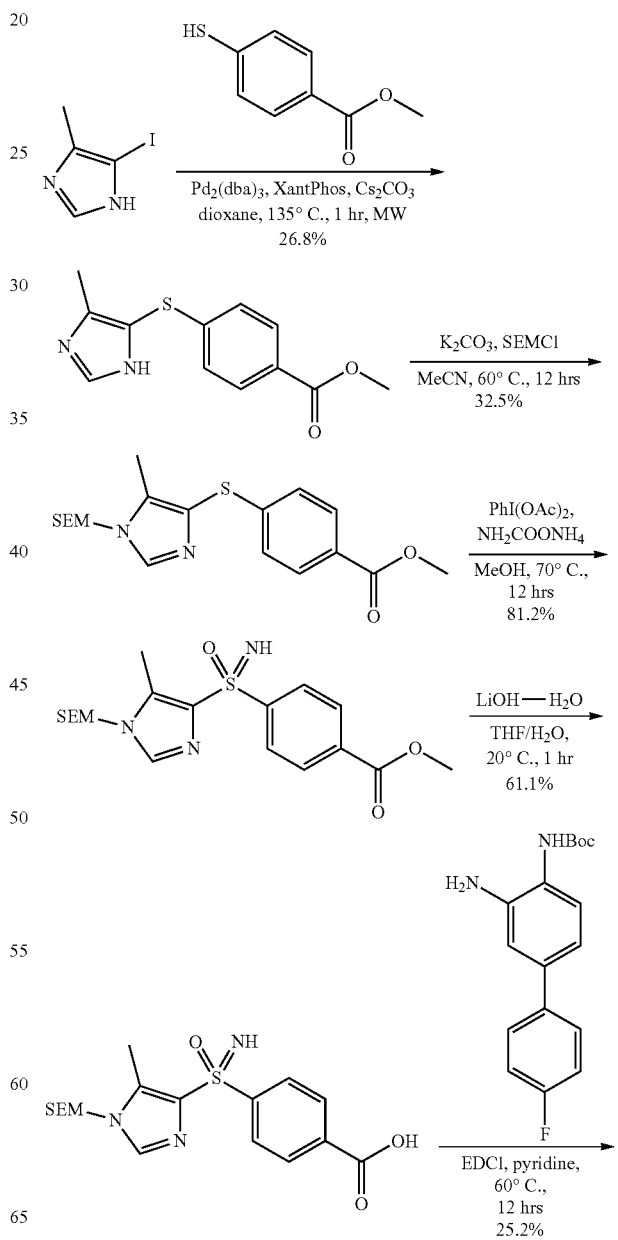

-continued

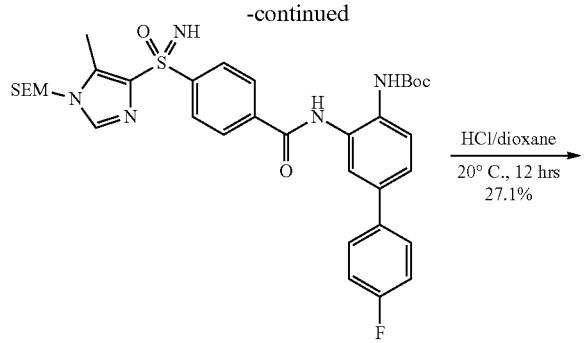

HCl/dioxane
20° C., 12 hrs
27.1%

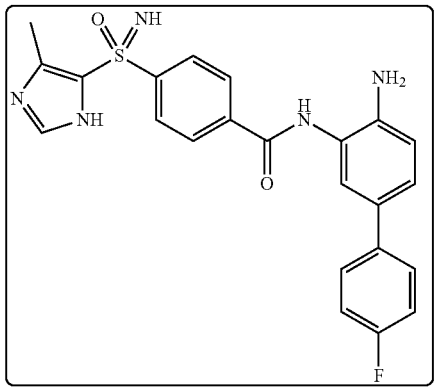

Step 1: Synthesis of methyl 4-[(4-methyl-1H-imidazol-5-yl)sulfanyl]benzoate

A mixture of 5-iodo-4-methyl-1H-imidazole (500 mg, 2.40 mmol), methyl 4-sulfanylbenzoate (400 mg, 2.38 mmol), (5-diphenylphosphanyl-9,9-dimethyl-xanthen-4-yl)-diphenyl-phosphane (270 mg, 0.467 mmol), (1E,4E)-1,5-diphenylpenta-1,4-dien-3-one;palladium (432 mg, 0.472 mmol), $Cs_2CO_3$ (2.35 g, 7.23 mmol) in dioxane (10 mL) was degassed and purged with $N_2$ gas at ambient temperature for 3 minutes. Then mixture was stirred at 135° C. for 1 hour in microwave. The resulting mixture was quenched by addition of water (50 mL) and extracted with EtOAc (200 mL*3). The combined organic layer was washed with brine (50 mL), dried over anhydrous $Na_2SO_4$, filtered and concentrated under reduced pressure. The residue was purified by flash chromatography (ISCO®; 80 g AgelaFlash® Silica Flash Column, petroleum ether/EtOAc with EtOAc from 0~77%, flow rate=60 mL/min, 254 nm) to afford methyl 4-[(4-methyl-1H-imidazol-5-yl)sulfanyl]benzoate (800 mg, 26.8% yield, 5 batches) as yellow solid. LCMS (ESI) $[M+H]^+$ m/z: calcd 249.1, found 249.0.

Step 2: Synthesis of methyl 4-[5-methyl-1-(2-trimethylsilylethoxymethyl)imidazol-4-yl]sulfanylbenzoate A mixture of methyl 4-[(4-methyl-1H-imidazol-5-yl)sulfanyl]benzoate (800 mg, 3.22 mmol), $K_2CO_3$ (1.11 g, 8.03 mmol), 2-(chloromethoxy)ethyl-trimethyl-silane (0.8 mL, 4.35 mmol) in MeCN (7 mL) was stirred at 60° C. for 12 hours. The resulting mixture was concentrated under reduced pressure. The resulting mixture was diluted with water (20 mL) and extracted with EtOAc (100 mL*3). The combined organic layer was washed with brine (50 mL), dried over anhydrous $Na_2SO_4$, filtered and concentrated under reduced pressure. The residue was purified by flash chromatography (ISCO®; 20 g AgelaFlash® Silica Flash Column, petroleum ether/EtOAc with EtOAc from 0~40%, flow rate=40 mL/min, 254 nm) to afford a mixture of methyl 4-[5-methyl-1-(2-trimethylsilylethoxymethyl)imidazol-4-yl]sulfanylbenzoate and methyl 4-[5-methyl-3-(2-trimethylsilylethoxymethyl)imidazol-4-yl]sulfanylbenzoate (330 mg, 32.5% yield) as light yellow solid. LCMS (ESI) $[M+H]^+$ m/z: calcd 379.1, found 379.1.

Step 3: Synthesis of methyl 4-[[5-methyl-1-(2-trimethylsilylethoxymethyl)imidazol-4-yl]sulfonimidoyl]benzoate A mixture of methyl 4-[5-methyl-1-(2-trimethylsilylethoxymethyl)imidazol-4-yl]sulfanylbenzoate (330 mg, 0.872 mmol), ammonia;carbamic acid (400 mg, 5.12 mmol), [acetoxy(phenyl)-iodanyl] acetate (880 mg, 2.73 mmol) in MeOH (7 mL) was stirred at 70° C. for 12 hours under $N_2$. The resulting mixture was concentrated under reduced pressure. The residue was purified by flash chromatography (ISCO®; 4 g AgelaFlash® Silica Flash Column, DCM/MeOH with MeOH from 0~7%, flow rate=30 mL/min, 254 nm) to afford methyl 4-[[5-methyl-1-(2-trimethylsilylethoxymethyl)imidazol-4-yl]sulfonimidoyl]benzoate (290 mg, 81.2% yield) as light yellow solid. LCMS (ESI) $[M+H]^+$ m/z: calcd 410.2, found 410.1.

Step 4: Synthesis of 4-[[5-methyl-1-(2-trimethylsilylethoxymethyl)imidazol-4-yl]sulfonimidoyl]benzoic acid A mixture of methyl 4-[[5-methyl-1-(2-trimethylsilylethoxymethyl)imidazol-4-yl]sulfonimidoyl]benzoate (390 mg, 0.952 mmol), lithium;hydroxide;hydrate (390 mg, 9.29 mmol) in THF (5 mL) and $H_2O$ (1 mL) was stirred at 20° C. for 1 hour. The mixture was adjusted pH to 5-6 with 1N HCl aqueous solution. The resulting mixture was diluted by addition of water (20 mL) and extracted with EtOAc (50 mL*3). The combined organic layer was washed with brine (20 mL), dried over anhydrous $Na_2SO_4$, filtered and concentrated under reduced pressure to afford 4-[[5-methyl-1-(2-trimethylsilylethoxymethyl)imidazol-4-yl]sulfonimidoyl]benzoic acid (230 mg, 61.1% yield) as light yellow solid. LCMS (ESI) $[M+H]^+$ m/z: calcd 396.1, found 396.2.

Step 5: Synthesis of tert-butyl N-[4-(4-fluorophenyl)-2-[[4-[[5-methyl-1-(2-trimethylsilylethoxymethyl)imidazol-4-yl]sulfonimidoyl]benzoyl]amino]phenyl]carbamate A mixture of tert-butyl N-[2-amino-4-(4-fluorophenyl)phenyl]carbamate (230 mg, 0.761 mmol), 4-[[5-methyl-1-(2-trimethylsilylethoxymethyl)imidazol-4-yl]sulfonimidoyl]benzoic acid (330 mg, 0.834 mmol), EDCI (170 mg, 0.887 mmol) in pyridine (5 mL) was stirred at 60° C. for 12 hours. The resulting mixture was concentrated under reduced pressure. The residue was purified by flash chromatography (ISCO®; 20 g AgelaFlash® Silica Flash Column, petroleum ether/EtOAc with EtOAc from 0~95%, flow rate=40 mL/min, 254 nm) to afford tert-butyl N-[4-(4-fluorophenyl)-2-[[4-[[5-methyl-1-(2-trimethylsilylethoxymethyl)imidazol-4-yl]sulfonimidoyl]benzoyl]amino]phenyl]

carbamate (130 mg, 25.2% yield) as light yellow solid. LCMS (ESI) [M+H]⁺ m/z: calcd 680.3, found 680.3.

Step 6: Synthesis of N-[2-amino-5-(4-fluorophenyl)phenyl]-4-[(4-methyl-1H-imidazol-5-yl)sulfonimidoyl]benzamide A mixture of tert-butyl N-[4-(4-fluorophenyl)-2-[[4-[[5-methyl-1-(2-trimethylsilylethoxymethyl)imidazol-4-yl]sulfonimidoyl]benzoyl]amino]phenyl]carbamate (125 mg, 0.184 mmol) in 4M HCl/dioxane (5 mL, 20.0 mmol) was stirred at 20° C. for 12 hours. The mixture was adjusted pH to 7-8 with saturated sodium bicarbonate solution. The resulting mixture was diluted by addition of water (20 mL) and extracted with EtOAc (50 mL*3). The combined organic layer was washed with brine (50 mL), dried over anhydrous Na₂SO₄, filtered and concentrated under reduced pressure. The residue was purified by preparative HPLC (Instrument: Gilson GX-215, Gilson 322 Pump, Gilson 156 UV Detector; Column: Xtimate C18 150*40 mm*5 μm; Mobile phase A: H₂O with NH₃—H₂O and NH₄HCO₃ (v %); Mobile phase B: MeCN; Gradient: B from 23% to 53% in 20 min, hold 100% B for 5 min; Flow Rate: 30 mL/min; Column Temperature: 30° C.; Wavelength: 220 nm, 254 nm). The fraction was concentrated under reduced pressure and then lyophilized for overnight to afford N-[2-amino-5-(4-fluorophenyl)phenyl]-4-[(4-methyl-1H-imidazol-5-yl)sulfonimidoyl]benzamide (22.4 mg, 27.1% yield) as white solid. ¹H NMR (400 MHz, DMSO-d6) δ ppm 12.57 (s, 1H), 9.86 (s, 1H), 8.07-8.15 (m, 2H), 7.97-8.06 (m, 2H), 7.62 (s, 1H), 7.57 (dd, J=8.6, 5.5 Hz, 2H), 7.48 (d, J=1.8 Hz, 1H), 7.29-7.33 (m, 1H), 7.21 (t, J=8.8 Hz, 2H), 6.85 (d, J=8.3 Hz, 1H), 4.78-5.41 (m, 2H), 2.47 (s, 3H); 19F NMR (376 MHz, DMSO-d6) δ ppm −117.45; LCMS (ESI) [M+H]⁺ m/z: calcd 450.1, found 450.1; HPLC: 96.85%@220 nm, 98.300%@254 nm.

Example 86. Synthesis of N-[2-amino-5-(4-fluorophenyl)phenyl]-4-[(6-methyl-2-pyridyl)sulfonimidoyl]benzamide (Compound 215)

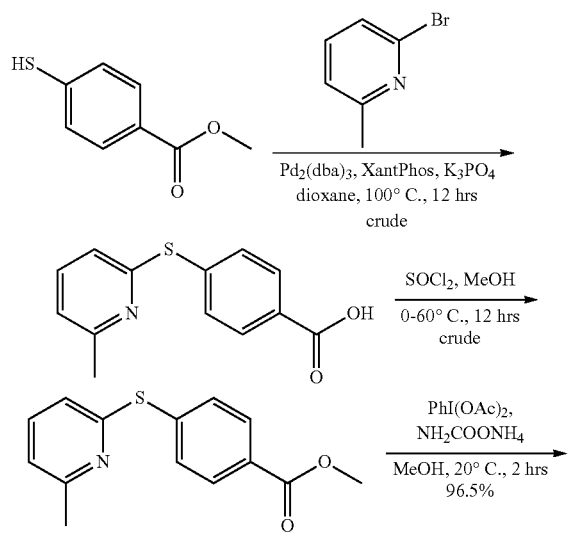

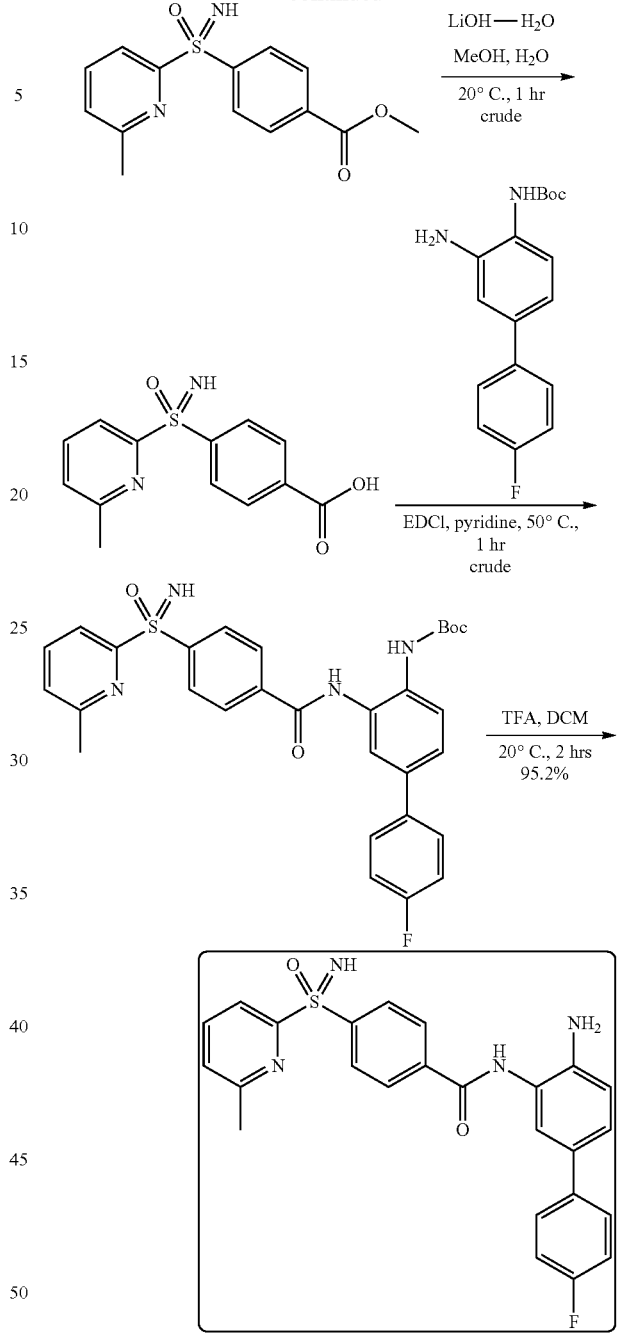

Step 1: Synthesis of 4-[(6-methyl-2-pyridyl)sulfanyl]benzoic acid

A mixture of 2-bromo-6-methyl-pyridine (1.2 mL, 10.5 mmol), methyl 4-sulfanylbenzoate (600 mg, 3.57 mmol), K₃PO₄ (2.28 g, 10.7 mmol), (5-diphenylphosphanyl-9,9-dimethyl-xanthen-4-yl)-diphenyl-phosphane (420 mg, 0.726 mmol) and (1E,4E)-1,5-diphenylpenta-1,4-dien-3-one;palladium (360 mg, 0.393 mmol) in dioxane (10 mL) was stirred at 100° C. for 12 hours under N₂. The resulting mixture was concentrated under reduced pressure. The residue was purified by flash chromatography (ISCO®; 20 g AgelaFlash® Silica Flash Column, petroleum ether/EtOAc with EtOAc from 0~70%, flow rate=50 mL/min, 254 nm) to afford 4-[(6-methyl-2-pyridyl)sulfanyl]benzoic acid (350 mg, crude) as yellow solid. LCMS (ESI) [M+H]$^+$ m/z: calcd 246.1, found 246.1.

Step 2: Synthesis of afford methyl 4-[(6-methyl-2-pyridyl)sulfanyl]benzoate

To a solution of 4-[(6-methyl-2-pyridyl)sulfanyl]benzoic acid (300 mg, 1.22 mmol) in MeOH (10 mL) was added SOCl$_2$ (1.2 mL, 16.5 mmol) at 0° C. The mixture was stirred at 60° C. for 12 hours. The resulting mixture was concentrated under reduced pressure. The resulting mixture was quenched by addition of water (20 mL) and extracted with DCM (20 mL*3). The combined organic layer was and concentrated under reduced pressure. The residue was purified by flash chromatography (ISCO®; 12 g AgelaFlash® Silica Flash Column, petroleum ether/EtOAc with EtOAc from 0~10%, flow rate=35 mL/min, 254 nm) to afford methyl 4-[(6-methyl-2-pyridyl)sulfanyl]benzoate (290 mg, crude) as yellow oil. LCMS (ESI) [M+H]$^+$ m/z: calcd 260.1, found 260.1.

Step 3: Synthesis of methyl 4-[(6-methyl-2-pyridyl) sulfonimidoyl]benzoate

A mixture of methyl 4-[(6-methyl-2-pyridyl)sulfanyl] benzoate (250 mg, 0.964 mmol), [acetoxy(phenyl)-iodanyl] acetate (775 mg, 2.41 mmol), ammonia;carbamic acid (150 mg, 1.92 mmol) and MeOH (5 mL) was stirred at 20° C. for 2 hours. The resulting mixture was filtered and concentrated under reduced pressure. The residue was purified by flash chromatography (ISCO®; 16 g AgelaFlash® Silica Flash Column, petroleum ether/EtOAc with EtOAc from 0~70%, flow rate=40 mL/min, 254 nm) to afford methyl 4-[(6-methyl-2-pyridyl)sulfonimidoyl]benzoate (270 mg, 96.5% yield) as light-yellow solid. $^1$H NMR (400 MHz, DMSO-d6) δ ppm 8.11 (s, 4H), 8.02-8.06 (m, 1H), 7.92-8.00 (m, 1H), 7.45 (d, J=7.6 Hz, 1H), 5.24 (s, 1H), 3.87 (s, 3H), 2.44 (s, 3H); LCMS (ESI) [M+H]$^+$ m/z: calcd 291.1, found 291.1.

Step 4: Synthesis of 4-[(6-methyl-2-pyridyl)sulfonimidoyl]benzoic acid

To a solution of methyl 4-[(6-methyl-2-pyridyl)sulfonimidoyl]benzoate (250 mg, 0.861 mmol) in MeOH (3 mL) and H$_2$O (1 mL) was added LiOH—H$_2$O (360 mg, 8.58 mmol). The mixture was stirred at 20° C. for 1 hour. The resulting mixture was concentrated under reduced pressure to remove MeOH. The mixture was adjusted pH=5 with saturated 2N HCl aqueous solution. The fraction was concentrated under reduced pressure and then lyophilized for overnight to afford 4-[(6-methyl-2-pyridyl)sulfonimidoyl]benzoic acid (770 mg, crude) as white solid. $^1$H NMR (400 MHz, DMSO-d6) δ ppm 8.01-8.09 (m, 5H), 7.93-7.99 (m, 1H), 7.45 (d, J=7.6 Hz, 1H), 5.18 (s, 1H), 2.43 (s, 3H); LCMS (ESI) [M+H]$^+$ m/z: calcd 277.1, found 277.1.

Step 5: Synthesis of tert-butyl N-[4-(4-fluorophenyl)-2-[[4-[(6-methyl-2-pyridyl)sulfonimidoyl]benzoyl]amino]phenyl]carbamate A mixture of tert-butyl N-[2-amino-4-(4-fluorophenyl) phenyl]carbamate (108 mg, 0.357 mmol), 4-[(6-methyl-2-pyridyl)sulfonimidoyl]benzoic acid (100 mg, 0.362 mmol) and 3-(ethyliminomethyleneamino)-N,N-dimethyl-propan-1-amine;hydrochloride (104 mg, 0.543 mmol) in pyridine (5 mL) was stirred at 50° C. for 1 hour. The resulting mixture was concentrated under reduced pressure. The residue was purified by flash chromatography (ISCO®; 12 g Agela-Flash® Silica Flash Column, petroleum ether/EtOAc with EtOAc from 0~80%, flow rate=30 mL/min, 254 nm) to afford tert-butyl N-[4-(4-fluorophenyl)-2-[[4-[(6-methyl-2-pyridyl)sulfonimidoyl]benzoyl]amino]phenyl]carbamate (50 mg, crude) as yellow oil. LCMS (ESI) [M+H]$^+$ m/z: calcd 561.2, found 561.3.

Step 6: Synthesis of N-[2-amino-5-(4-fluorophenyl) phenyl]-4-[(6-methyl-2-pyridyl)sulfonimidoyl]benzamide (Compound 215)

A mixture of tert-butyl N-[4-(4-fluorophenyl)-2-[[4-[(6-methyl-2-pyridyl)sulfonimidoyl]benzoyl]amino]phenyl] carbamate (50 mg, 0.0891 mmol), DCM (2 mL) and TFA (0.2 mL, 2.60 mmol) was stirred at 20° C. for 1 hour. The resulting mixture was concentrated under reduced pressure. The residue was purified by preparative HPLC (Instrument: Gilson GX-281 Liquid Handler, Gilson 322 Pump, Gilson 156 UV Detector; 30° C.; Column: 2_Phenomenex Gemini C18 75*40 mm*3 µm; Mobile phase A: water (NH$_4$HCO$_3$); Mobile phase B: ACN; Gradient: B from 40% to 70% in 7.8 min, hold 100% B for 1 min; Flow Rate: 30 mL/min; Column Temperature: 30° C.; Wavelength: 220 nm, 254 nm) to afford N-[2-amino-5-(4-fluorophenyl)phenyl]-4-[(6-methyl-2-pyridyl)sulfonimidoyl]benzamide (17.4 mg, 42.4% yield) as yellow solid. $^1$H NMR (400 MHz, DMSO-d6) δ ppm 9.88 (s, 1H), 8.04-8.18 (m, 5H), 7.93-8.00 (m, 1H), 7.56 (dd, J=8.8, 5.5 Hz, 2H), 7.42-7.50 (m, 2H), 7.31 (dd, J=8.3, 2.0 Hz, 1H), 7.21 (t, J=8.9 Hz, 2H), 6.85 (d, J=8.3 Hz, 1H), 5.16 (d, J=10.5 Hz, 3H), 2.46 (s, 3H); 19F NMR (376 MHz, DMSO-d6) δ ppm−117.463; LCMS (ESI) [M+H]$^+$ m/z: calcd 461.1, found 461.0; HPLC: 99.590%@220 nm, 1000%@254 nm.

Example 87. Synthesis of rac-N-[2-amino-5-(4-fluorophenyl)phenyl]-4-(2-pyridylsulfonimidoyl) benzamide (Compound 260), rel-(S)—N-[2-amino-5-(4-fluorophenyl)phenyl]-4-(2-pyridylsulfonimidoyl)benzamide (Compound 220) and rel-(R)—N-[2-amino-5-(4-fluorophenyl)phenyl]-4-(2-pyridylsulfonimidoyl)benzamide (Compound 212)

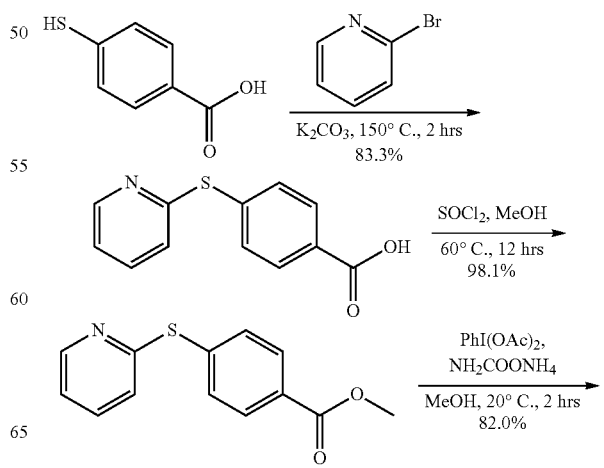

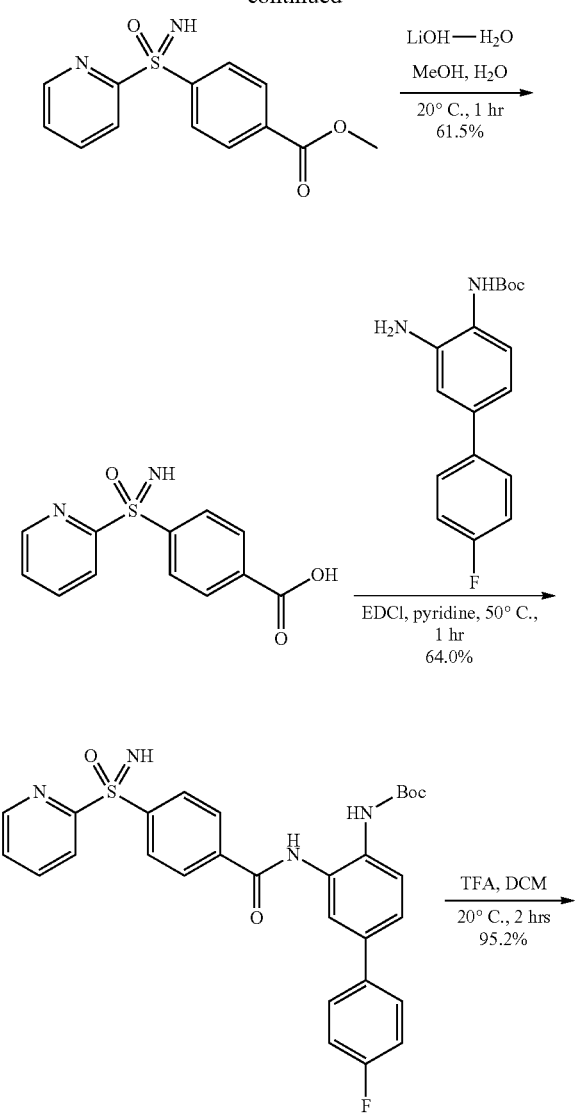

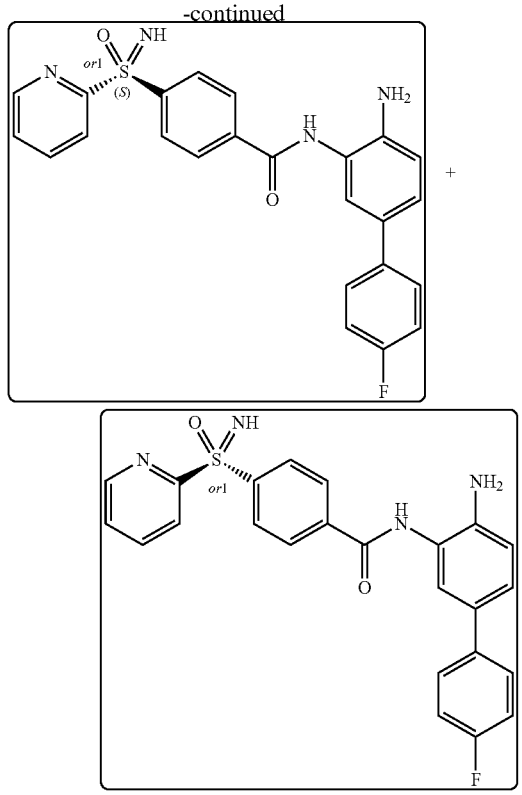

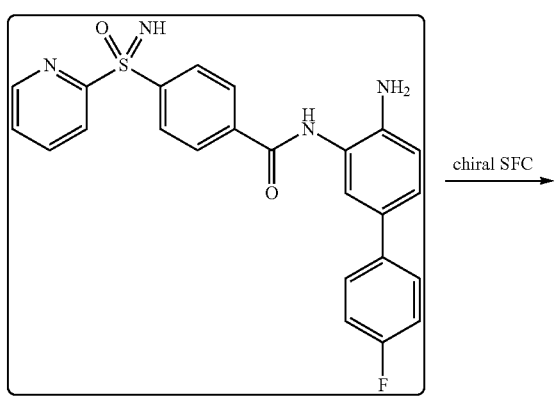

Step 1: Synthesis of 4-(2-pyridylsulfanyl)benzoic acid

To a solution of 4-sulfanylbenzoic acid (20 g, 0.130 mol) and 2-bromopyridine (75.7 mL, 0.778 mol) was added K$_2$CO$_3$ (35.9 g, 0.259 mol). The mixture was stirred at 150° C. for 2 hours. The resulting mixture was quenched by addition of water (500 mL) and extracted with methyl tert-butyl ether (100 mL*3). The combined water layer was acidified to pH to 5 with 2N HCl (aq). Then the mixture was extracted with 10% MeOH/CH$_2$Cl$_2$ (200 mL*4). The combined organic layers was filtered and concentrated under reduced pressure to give 4-(2-pyridylsulfanyl)benzoic acid (25 g, 83.3% yield) as white solid. $^1$H NMR (400 MHz, DMSO-d6) δ ppm 8.45 (d, J=3.76 Hz, 1H), 7.97 (d, J=8.28 Hz, 2H), 7.71 (td, J=7.78, 1.76 Hz, 1H), 7.61 (d, J=8.03 Hz, 2H), 7.16-7.25 (m, 2H); LCMS (ESI) [M+H]$^+$ m/z: calcd 232.0, found 232.1.

Step 2: Synthesis of methyl 4-(2-pyridylsulfanyl)benzoate

To a solution of 4-(2-pyridylsulfanyl)benzoic acid (25 g, 0.108 mol) in MeOH (100 mL) was added SOCl$_2$ (55 mL, 0.757 mol) at 0° C. The mixture was stirred at 60° C. for 12 hours. The mixture was concentrated under reduced pressure, and adjusted the pH to 5 with saturated NaHCO$_3$ solution. The resulting mixture was diluted with water (100 mL) and extracted with EtOAc (100 mL*3). The combined organic layer was washed with brine (100 mL), dried over anhydrous Na$_2$SO$_4$, filtered and concentrated under reduced pressure to afford methyl 4-(2-pyridylsulfanyl)benzoate (26 g, 98.1% yield) as brown solid. $^1$H NMR (400 MHz, DMSO-d6) δ ppm 8.45 (dt, J=3.89, 0.94 Hz, 1H), 7.92-8.02

(m, 2H), 7.72 (td, J=7.72, 1.88 Hz, 1H), 7.58-7.65 (m, 2H), 7.20-7.26 (m, 2H), 3.86 (s, 3H). LCMS (ESI) [M+H]+ m/z: calcd 246.1, found 246.1.

Step 3: Synthesis of methyl 4-(2-pyridylsulfonimidoyl)benzoate

To a solution of methyl 4-(2-pyridylsulfanyl)benzoate (26 g, 0.106 mol) in MeOH (100 mL) was added [acetoxy (phenyl)-iodanyl] acetate (85.4 g, 0.265 mol), ammonia; carbamic acid (16.5 g, 0.211 mol). The mixture was stirred at 20° C. for 2 hours. The mixture was concentrated under reduced pressure. The residue was purified by flash chromatography (Biotage®; 120 g AgelaFlash® Silica Flash Column, petroleum ether/EtOAc with EtOAc from 0~80%, flow rate=100 mL/min, 254 nm) to afford methyl 4-(2-pyridylsulfonimidoyl)benzoate (24 g, 82.0% yield) as white solid. $^1$H NMR (400 MHz, DMSO-d6) δ ppm 8.59-8.66 (m, 1H), 8.25 (d, J=8.03 Hz, 1H), 8.07-8.14 (m, 5H), 7.60 (d, J=7.65, 4.64, 1.00 Hz, 1H), 5.33 (s, 1H), 3.87 (s, 3H). LCMS (ESI) [M+H]+ m/z: calcd 277.1, found 277.1.

Step 4: Synthesis of 4-(2-pyridylsulfonimidoyl)benzoic acid

To a solution of methyl 4-(2-pyridylsulfonimidoyl)benzoate (24 g, 86.9 mmol) in MeOH (100 mL) and H$_2$O (30 mL) was added LiOH—H$_2$O (10.9 g, 0.261 mmol). The mixture was stirred at 20° C. for 1 hour. The mixture was concentrated under reduced pressure. The resulting mixture was adjusted pH to 3 with 2N HCl aqueous solution, and extracted with EtOAc (20 mL*3). The combined organic layer was dried over anhydrous Na$_2$SO$_4$, filtered and concentrated under reduced pressure to give 4-(2-pyridylsulfonimidoyl)benzoic acid (14 g, 61.5% yield) as yellow solid, which was directly used next step. $^1$H NMR (400 MHz, DMSO-d6) δ ppm 8.64 (br d, J=3.88 Hz, 1H), 8.25 (s, 1H), 8.10 (s, 5H), 7.54-7.68 (m, 1H). LCMS (ESI) [M+H]+ m/z: calcd 263.0, found 263.1.

Step 5: Synthesis of tert-butyl N-[4-(4-fluorophenyl)-2-[[4-(2-pyridylsulfonimidoyl)benzoyl]amino]phenyl]carbamate To a solution of 4-(2-pyridylsulfonimidoyl)benzoic acid (13.5 g, 51.5 mmol) and tert-butyl N-[2-amino-4-(4-fluorophenyl)phenyl]carbamate (23.4 g, 77.3 mmol) in pyridine (80 mL) was added EDCI (14.8 g, 77.2 mmol). The mixture was stirred at 50° C. for 1 hour. The mixture was concentrated under reduced pressure. The residue was purified by flash chromatography (Biotage®; 220 g AgelaFlash® Silica Flash Column, petroleum ether/EtOAc with EtOAc from 0~100%, flow rate=100 mL/min, 254 nm) to afford tert-butyl N-[4-(4-fluorophenyl)-2-[[4-(2-pyridylsulfonimidoyl)benzoyl]amino]phenyl]carbamate (18 g, 64.0% yield) as white solid. $^1$H NMR (400 MHz, DMSO-d6) δ ppm 10.04 (s, 1H), 8.71-8.77 (m, 1H), 8.63 (d, J=4.02 Hz, 1H), 8.26 (d, J=7.78 Hz, 1H), 8.12 (s, 5H), 7.77 (s, 1H), 7.64-7.71 (m, 3H), 7.57-7.62 (m, 1H), 7.51 (d, J=8.53 Hz, 1H), 7.27 (s, 2H), 5.25 (s, 2H), 1.43 (s, 9H). 19F NMR (376 MHz, DMSO-d6) δ ppm −115.57; LCMS (ESI) [M+H]+ m/z: calcd 547.2, found 547.3.

Step 6: Synthesis of rac-N-[2-amino-5-(4-fluorophenyl)phenyl]-4-(2-pyridylsulfonimidoyl)benzamide (Compound 260)

To a solution of tert-butyl N-[4-(4-fluorophenyl)-2-[[4-(2-pyridylsulfonimidoyl)benzoyl]amino]phenyl]carbamate (18 g, 32.9 mmol) in DCM (50 mL) was added TFA (54 mL, 0.702 mol). The resulting mixture was stirred at 20° C. for 2 hours. The resulting mixture was concentrated under reduced pressure, and adjusted pH to 8 with saturated NaHCO$_3$ aqueous solution. The residue was triturated with DCM (100 mL). The mixture was filtered. The filter cake was concentrated under reduced pressure to afford rac-N-[2-amino-5-(4-fluorophenyl)phenyl]-4-(2-pyridylsulfonimidoyl)benzamide (14 g, 95.2% yield) as off-white solid. $^1$H NMR (400 MHz, DMSO-d6) δ ppm 9.90 (brs, 1H), 8.63 (d, J=4.02 Hz, 1H), 8.26 (d, J=7.78 Hz, 1H), 8.05-8.16 (m, 5H), 7.54-7.65 (m, 3H), 7.44-7.53 (m, 1H), 7.30 (d, J=8.28 Hz, 1H), 7.15-7.26 (m, 2H), 6.85 (d, J=8.28 Hz, 1H), 5.28 (s, 1H), 5.16 (s, 2H); LCMS (ESI) [M+H]+ m/z: calcd 447.1, found 447.1.

Step 7: Synthesis of rel-(S)—N-[2-amino-5-(4-fluorophenyl)phenyl]-4-(2-pyridylsulfonimidoyl)benzamide (Compound 220) and rel-(R)—N-[2-amino-5-(4-fluorophenyl)phenyl]-4-(2-pyridylsulfonimidoyl)benzamide (Compound 212)

The mixture was purified by chiral SFC (Instrument: Instrument: Thar 800Q; Column: Chiralpak AD 250×50 mm I.D. 10 μm; Mobile phase: supercritical CO$_2$/NeuMeOH=60/60; Flow Rate: 200 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm). The fraction was concentrated under reduced pressure and then lyophilized for overnight to give Compound 220 and Compound 212. Stereochemistry was arbitrarily assigned.

Compound 220: N-[2-amino-5-(4-fluorophenyl)phenyl]-4-(2-pyridylsulfonimidoyl)benzamide (4.2 g, 28.6% yield, peak 1, retention time=3.283 min, single unknown enantiomer) was obtained as yellow solid. $^1$H NMR (400 MHz, DMSO-d6) δ ppm 9.88 (s, 1H), 8.63 (d, J=4.52 Hz, 1H), 8.27 (d, J=7.78 Hz, 1H), 8.08-8.16 (m, 5H), 7.54-7.62 (m, 3H), 7.48 (s, 1H), 7.31 (dd, J=8.28, 2.01 Hz, 1H), 7.21 (t, J=8.91 Hz, 2H), 6.84 (d, J=8.28 Hz, 1H), 5.29 (s, 1H), 5.16 (s, 2H); 19F NMR (376 MHz, DMSO-d6) δ ppm−117.481; LCMS (ESI) [M+H]+ m/z: calcd 447.1, found 447.2; HPLC: 98.44%@220 nm; 99.30%@254 nm; 100% ee.

Compound 212: N-[2-amino-5-(4-fluorophenyl)phenyl]-4-(2-pyridylsulfonimidoyl)benzamide (3.9 g, 26.5% yield, peak 2, retention time=5.324 min, single unknown enantiomer) as white solid. $^1$H NMR (400 MHz, DMSO-d6) δ ppm 9.88 (brs, 1H), 8.64 (d, J=4.27 Hz, 1H), 8.27 (d, J=7.53 Hz, 1H), 8.08-8.16 (m, 5H), 7.54-7.62 (m, 3H), 7.46-7.50 (m, 1H), 7.28-7.33 (m, 1H), 7.21 (s, 2H), 6.85 (d, J=8.28 Hz, 1H), 5.29 (brs, 1H), 5.19 (brs, 2H); 19F NMR (376 MHz, DMSO-d6) δ ppm−117.472; LCMS (ESI) [M+H]+ m/z: calcd 447.1, found 447.2; HPLC: 96.250%@220 nm, 97.220%@254 nm; 99.8% ee.

Example 88. Synthesis of N-[2-amino-5-(4-fluorophenyl)phenyl]-4-[(6-methyl-3-pyridyl)sulfonimidoyl]benzamide (Compound 233)

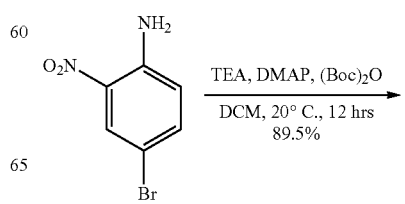

-continued

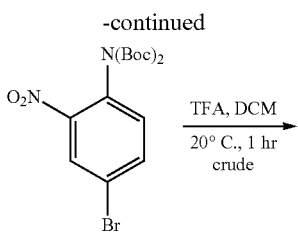

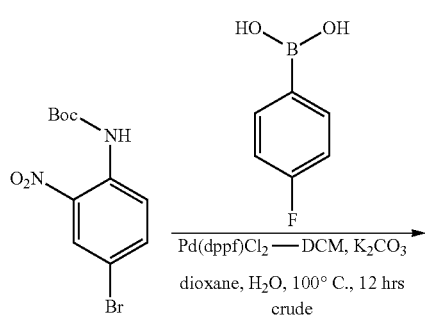

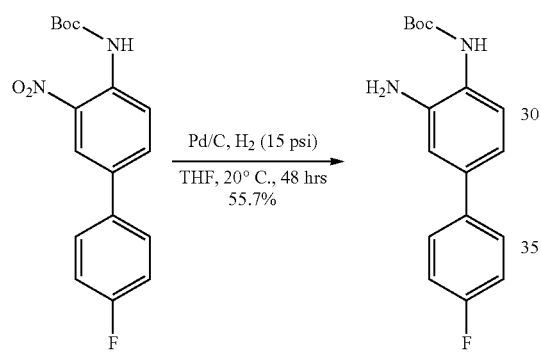

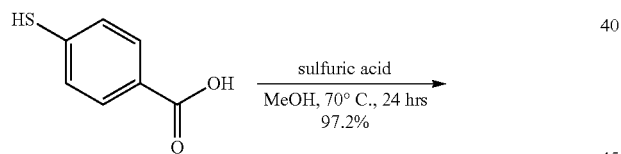

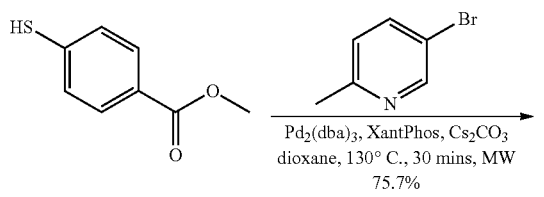

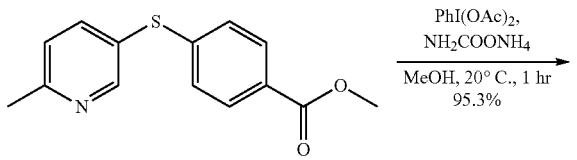

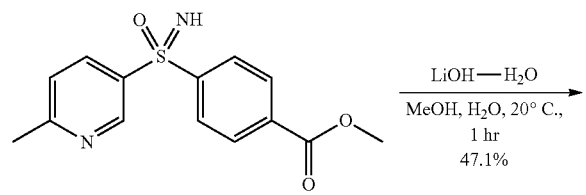

-continued

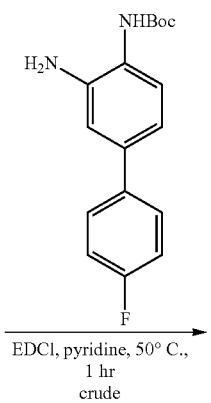

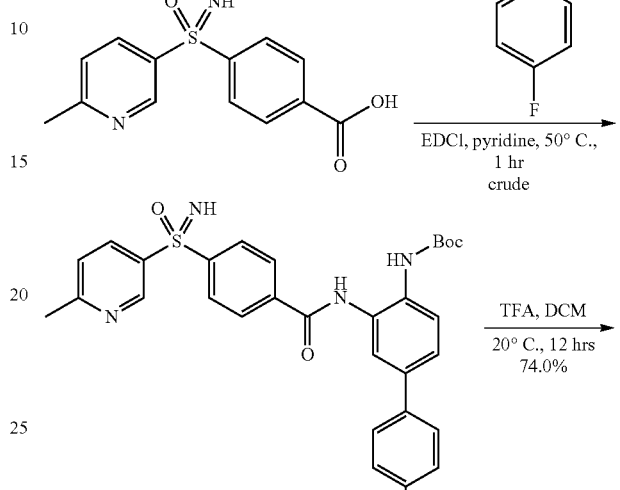

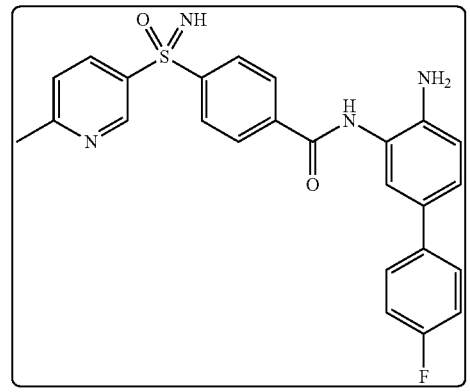

Step 1: Synthesis of tert-butyl N-(4-bromo-2-nitro-phenyl)-N-tert-butoxycarbonyl-carbamate To a solution of 4-bromo-2-nitro-aniline (250 g, 1.15 mol), DMAP (15 g, 0.123 mol), TEA (480 mL, 3.44 mol) in DCM (1000 mL) was added tertbutoxycarbonyl tert-butyl carbonate (555 mL, 2.42 mol). The mixture was stirred at 20° C. for 12 hours. The resulting mixture was concentrated under reduced pressure. The mixture was combined with another batch. The residue was triturated in a solution (2000 mL*3, MeOH) and filtered. The filter cake was concentrated under reduced pressure to afford the tert-butyl N-(4-bromo-2-nitro-phenyl)-N-tert-butoxycarbonyl-carbamate (760 g, 79.1% yield) as white solid. Then the residue (30 mg) was purified by preparative HPLC (Instrument: Gilson GX-281 Liquid Handler, Gilson 322 Pump, Gilson 156 UV Detector; Column: 2_Phenomenex Gemini C18 75×40 mm×3 μm; Mobile phase A: $H_2O$ with 10 mmol $NH_4HCO_3$ (v %); Mobile phase B: MeCN; Gradient: B from 60% to 90% in 9.5 min, hold 100% B for 2 min; Flow Rate: 30 mL/min; Column Temperature: 30° C.; Wavelength: 220 nm, 254 nm)

to afford tert-butyl N-(4-bromo-2-nitro-phenyl)-N-tert-butoxycarbonyl-carbamate (6 mg) as white solid for delivery. $^1$H NMR (400 MHz, DMSO-d6) δ ppm 8.33 (d, J=2.3 Hz, 1H), 8.01 (dd, J=8.4, 2.4 Hz, 1H), 7.59 (d, J=8.5 Hz, 1H), 1.33 (s, 18H); LCMS (ESI) [M+H]$^+$ m/z: calcd 417.1, found 217.1 (Boc cleaved mass); HPLC: 99.56%@220 nm, 98.86%@254 nm.

Step 2: Synthesis of tert-butyl N-(4-bromo-2-nitro-phenyl)carbamate

To a solution of tert-butyl N-(4-bromo-2-nitro-phenyl)-N-tert-butoxycarbonyl-carbamate (160 g, 0.383 mol) in DCM (1600 mL) was added TFA (50 mL, 0.649 mol). The mixture was stirred at 20° C. for 1 hour. The mixture was combined with another batch. The resulting mixture was adjusted to pH=8 with saturated Na$_2$CO$_3$ aqueous solution and extracted with DCM (500 mL*3). The combined organic layer was dried over anhydrous Na$_2$SO$_4$, filtered and concentrated under reduced pressure to afford tert-butyl N-(4-bromo-2-nitro-phenyl)carbamate (270 g, crude) as yellow solid. $^1$H NMR (400 MHz, DMSO-d6) δ ppm 9.67 (s, 1H), 8.12 (d, J=2.5 Hz, 1H), 7.86 (dd, J=8.8, 2.5 Hz, 1H), 7.59 (d, J=8.8 Hz, 1H), 1.44 (s, 9H).

Step 3: Synthesis of tert-butyl N-[4-(4-fluorophenyl)-2-nitro-phenyl]carbamate

To a solution of tert-butyl N-(4-bromo-2-nitro-phenyl)carbamate (170 g, 0.536 mol), (4-fluorophenyl)boronic acid (96 g, 0.686 mol), K$_2$CO$_3$ (225 g, 1.63 mol) in dioxane (1500 mL) and H$_2$O (400 mL) was added cyclopentyl(diphenyl)phosphane;dichloromethane;dichloropalladium;iron (8.76 g, 10.7 mmol). The mixture was stirred at 100° C. for 12 hours under N$_2$. The mixture was poured into ice water. The mixture was adjusted pH=8 with NH$_4$Cl solid and stirred for 1 hour. Then the mixture was filtered, and the filter cake was concentrated under reduced pressure to afford tert-butyl N-[4-(4-fluorophenyl)-2-nitro-phenyl]carbamate (288 g, crude) as green solid. $^1$H NMR (400 MHz, DMSO-d6) δ ppm 9.65 (brs, 1H), 8.17 (d, J=2.0 Hz, 1H), 7.97 (dd, J=8.5, 2.0 Hz, 1H), 7.78 (dd, J=8.5, 5.3 Hz, 2H), 7.72 (d, J=8.5 Hz, 1H), 7.32 (t, J=8.8 Hz, 2H), 1.46 (s, 9H); 19F NMR (376 MHz, DMSO-d6) δ ppm–114.402.

Step 4: Synthesis of tert-butyl N-[2-amino-4-(4-fluorophenyl)phenyl]carbamate

To a solution of tert-butyl N-[4-(4-fluorophenyl)-2-nitro-phenyl]carbamate (150 g, 0.451 mol) in THF (1200 mL) was added Pd/C (33 g, 10 wt % Pd with 50 wt % water). The suspension was degassed and purged with hydrogen for 3 times. The mixture was stirred under hydrogen (15 Psi) at 20° C. for 48 hours. The mixture was filtered and the filtrate was concentrated under reduced pressure. The residue was triturated in a solution (1000 mL*3, MeOH) and filtered. The filter cake was concentrated under reduced pressure to afford tert-butyl N-[2-amino-4-(4-fluorophenyl)phenyl]carbamate (80 g, 58.6% yield) as white solid. $^1$H NMR (400 MHz, DMSO-d6) δ ppm 8.35 (brs, 1H), 7.56 (dd, J=8.8, 5.5 Hz, 2H), 7.20-7.33 (m, 3H), 6.95 (d, J=2.0 Hz, 1H), 6.80 (dd, J=8.3, 2.0 Hz, 1H), 4.96 (s, 2H), 1.47 (s, 9H); 19F NMR (376 MHz, DMSO-d6) δ ppm –116.354.

Step 5: Synthesis of methyl 4-sulfanylbenzoate

To a solution of 4-sulfanylbenzoic acid (50 g, 0.324 mol) in MeOH (300 mL) was added sulfuric acid (2 mL, 37.5 mmol). The reaction mixture was stirred at 70° C. for 16 hours. To the mixture was added sulfuric acid (2 mL, 37.5 mmol) and the mixture was stirred at 70° C. for 8 hours. The mixture was concentrated under reduced pressure. The residue was triturated with MeOH (50 mL). The mixture was filtered. The filter cake was dried under reduced pressure to give desired product (23 g) as white solid. The filtrate was concentrated under reduced pressure. The residue was triturated with MeOH (30 mL) again. The mixture was filtered. The filter cake was dried under reduced pressure to give desired product (15 g) as white solid. The filtrate was concentrated under reduced pressure. The residue was purified by flash chromatography (ISCO®; 330 g AgelaFlash® Silica Flash Column, petroleum ether/EtOAc with EtOAc from 0~10%, flow rate=50 mL/min, 254 nm) to give desired product (15 g) as white solid. Totally methyl 4-sulfanylbenzoate (53 g, 97.2% yield) was obtained as white solid. $^1$H NMR (400 MHz, DMSO-d6) δ ppm 7.77-7.83 (m, 2H), 7.42 (d, J=8.5 Hz, 2H), 5.99 (brs, 1H), 3.82 (s, 3H); LCMS (ESI) [M+H]$^+$ m/z: calcd 169.0, found 169.1.

Step 6: Synthesis of methyl 4-[(6-methyl-3-pyridyl)sulfanyl]benzoate

A mixture of methyl 4-sulfanylbenzoate (300 mg, 1.78 mmol), 5-bromo-2-methyl-pyridine (310 mg, 1.80 mmol), (1E,4E)-1,5-diphenylpenta-1,4-dien-3-one;palladium (160 mg, 0.174 mmol), (5-diphenylphosphanyl-9,9-dimethyl-xanthen-4-yl)-diphenyl-phosphane (520 mg, 0.899 mmol), dicesium;carbonate (1.74 g, 5.35 mmol) in dioxane (12 mL) was stirred at 130° C. for 30 minutes under the N$_2$. The mixture was filtered and the filtrate was concentrated under reduced pressure. The residue was purified by flash chromatography (ISCO®; 12 g AgelaFlash® Silica Flash Column, petroleum ether/EtOAc with EtOAc from 0~12%, flow rate=40 mL/min, 254 nm) to afford methyl 4-[(6-methyl-3-pyridyl)sulfanyl]benzoate (350 mg, 75.7% yield) as yellow oil. LCMS (ESI) [M+H]$^+$ m/z: calcd 260.1, found 260.1.

Step 7: Synthesis of methyl 4-[(6-methyl-3-pyridyl)sulfonimidoyl]benzoate

To a solution of methyl 4-[(6-methyl-3-pyridyl)sulfanyl]benzoate (300 mg, 1.16 mmol) in MeOH (5 mL) was added [acetoxy(phenyl)-iodanyl] acetate (930 mg, 2.89 mmol) and ammonia;carbamic acid (180 mg, 2.31 mmol). The mixture was stirred at 20° C. for 1 hour. The resulting mixture was concentrated under reduced pressure. The residue was purified by flash chromatography (ISCO®; 12 g AgelaFlash® Silica Flash Column, petroleum ether/EtOAc with EtOAc from 0~60%, flow rate=40 mL/min, 254 nm) to afford methyl 4-[(6-methyl-3-pyridyl)sulfonimidoyl]benzoate (320 mg, 95.3% yield) as white solid. LCMS (ESI) [M+H]$^+$ m/z: calcd 291.1, found 291.1.

Step 4: Synthesis of 4-[(6-methyl-3-pyridyl)sulfonimidoyl]benzoic acid

To a solution of methyl 4-[(6-methyl-3-pyridyl)sulfonimidoyl]benzoate (290 mg, 0.999 mmol) in MeOH (6 mL) and H$_2$O (2 mL) was added lithium;hydroxide;hydrate (420 mg, 10.0 mmol). The mixture was stirred at 20° C. for 1 hour. The resulting mixture was adjusted the pH to 5 with 2N HCl and extracted with EtOAc (30 mL*2) and water. The combined organic layer was dried over anhydrous Na$_2$SO$_4$, filtered and concentrated under reduced pressure to give 4-[(6-methyl-3-pyridyl)sulfonimidoyl]benzoic acid (130 mg, 47.1% yield) as white solid. LCMS (ESI) [M+H]⁺ m/z: calcd 277.1, found 277.1.

Step 5: Synthesis of tert-butyl N-[4-(4-fluorophenyl)-2-[[4-[(6-methyl-3-pyridyl)sulfonimidoyl]benzoyl]amino]phenyl]carbamate A mixture of 4-[(6-methyl-3-pyridyl)sulfonimidoyl]benzoic acid (100 mg, 0.362 mmol), tert-butyl N-[2-amino-4-(4-fluorophenyl)phenyl]carbamate (170 mg, 0.562 mmol), 3-(ethyliminomethyleneamino)-N,N-dimethyl-propan-1-amine;hydrochloride (110 mg, 0.574 mmol) and pyridine (6 mL) was stirred at 50° C. for 1 hour. The resulting mixture was concentrated under reduced pressure. The residue was purified by flash chromatography (ISCO®; 4 g AgelaFlash® Silica Flash Column, petroleum ether/EtOAc with EtOAc from 0~64%, flow rate=40 mL/min, 254 nm) to afford tert-butyl N-[4-(4-fluorophenyl)-2-[[4-[(6-methyl-3-pyridyl)sulfonimidoyl]benzoyl]amino]phenyl]carbamate (240 mg, crude) as white solid. LCMS (ESI) [M+H]⁺ m/z: calcd 561.2, found 561.3.

Step 6: Synthesis of N-[2-amino-5-(4-fluorophenyl)phenyl]-4-[(6-methyl-3-pyridyl)sulfonimidoyl]benzamide To a solution of tert-butyl N-[4-(4-fluorophenyl)-2-[[4-[(6-methyl-3-pyridyl)sulfonimidoyl]benzoyl]amino]phenyl]carbamate (200 mg, 0.357 mmol) in DCM (3 mL) was added TFA (0.7 mL, 9.09 mmol). The mixture was stirred at 20° C. for 1 hour. The mixture was adjusted the pH to 8 with saturated NaHCO₃ aqueous solution. The resulting mixture was extracted with water (20 mL) and DCM (20 mL*2). The combined organic layer was dried over anhydrous Na₂SO₄, filtered and concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 µm; Mobile phase A: H₂O with 10 mmol NH₄HCO₃ (v %); Mobile phase B: MeCN; Gradient: B from 34% to 64% in 9.5 min, hold 100% B for 1 min; Flow Rate: 30 mL/min; Column Temperature: 30° C.; Wavelength: 220 nm, 254 nm) to afford N-[2-amino-5-(4-fluorophenyl)phenyl]-4-[(6-methyl-3-pyridyl)sulfonimidoyl]benzamide (122 mg, 74.0% yield) as a yellow solid. ¹H NMR (400 MHz, DMSO-d6) δ ppm 9.84 (s, 1H), 8.99 (d, J=2.0 Hz, 1H), 8.21 (dd, J=8.1, 2.4 Hz, 1H), 8.12 (s, 4H), 7.56 (dd, J=8.5, 5.6 Hz, 2H), 7.43-7.48 (m, 2H), 7.30 (d, J=8.5 Hz, 1H), 7.20 (t, J=8.8 Hz, 2H), 6.84 (d, J=8.4 Hz, 1H), 5.39 (s, 1H), 5.13 (s, 2H), 2.53 (s, 2H); 19F NMR (376 MHz, DMSO-d6) δ ppm−117.486; LCMS (ESI) [M+H]⁺ m/z: calcd 461.1, found 461.3; HPLC: 98.60%@220 nm; 99.42%@254 nm.

Example 89. Synthesis of N-[2-amino-5-(4-fluorophenyl)phenyl]-4-[(4-methyl-3-pyridyl)sulfonimidoyl]benzamide (Compound 198)

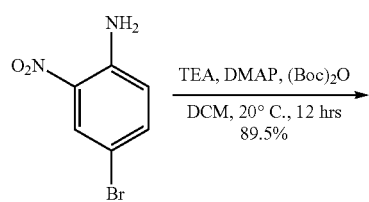

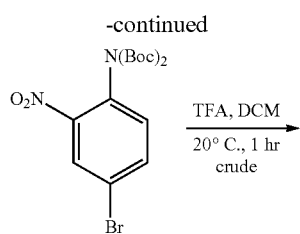

-continued

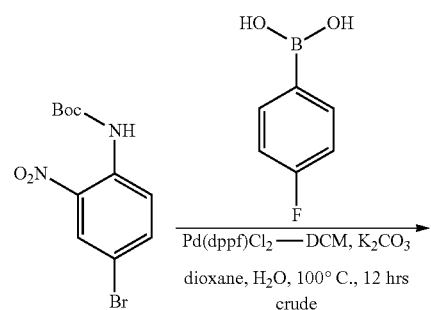

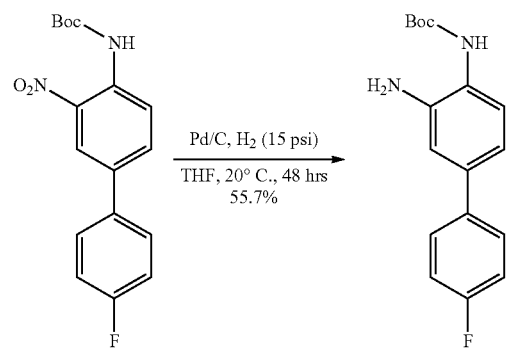

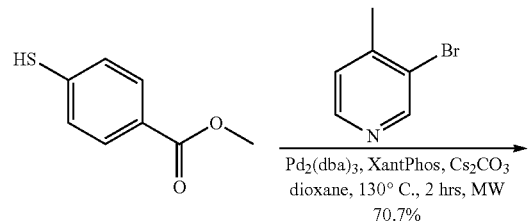

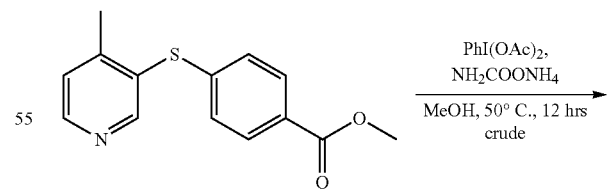

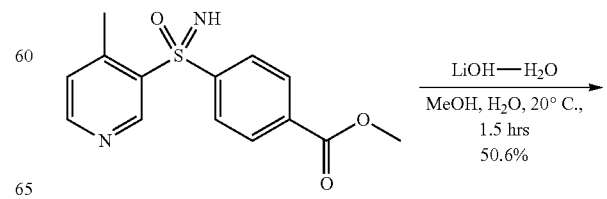

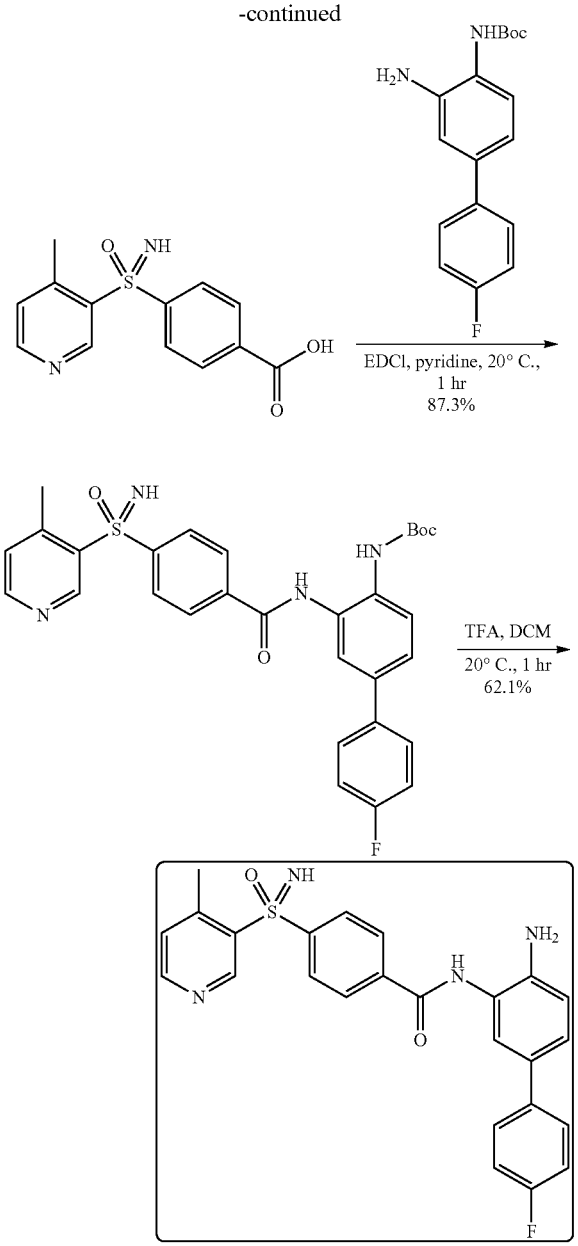

Step 1: Synthesis of tert-butyl N-(4-bromo-2-nitro-phenyl)-N-tert-butoxycarbonyl-carbamate To a solution of 4-bromo-2-nitro-aniline (250 g, 1.15 mol), DMAP (15 g, 0.123 mol), TEA (485 mL, 3.48 mol) in DCM (1.3 L) was slowly added tertbutoxycarbonyl tert-butyl carbonate (560 mL, 2.44 mol). The mixture was stirred at 20° C. for 12 hours. The mixture was combined with another batch. The mixture was concentrated under reduced pressure. The residue was triturated in a solution (MeOH, 1500 mL*4). The mixture was filtered. The filter cake was concentrated under reduced pressure to afford tert-butyl N-(4-bromo-2-nitro-phenyl)-N-tert-butoxycarbonyl-carbamate (860 g, 89.5% yield) as white solid. $^1$H NMR (400 MHz, DMSO-d6) δ ppm 8.35 (s, 1H), 8.01 (dd, J=8.4, 1.6 Hz, 1H), 7.59 (d, J=8.5 Hz, 1H), 1.30 (s, 18H).

Step 2: Synthesis of tert-butyl N-(4-bromo-2-nitro-phenyl)carbamate

To a mixture of tert-butyl N-(4-bromo-2-nitro-phenyl)-N-tert-butoxycarbonyl-carbamate (210 g, 0.503 mol) in DCM (1.8 L) was added TFA (67 mL, 0.870 mol). The mixture was stirred at 20° C. for 1 hour. The mixture was combined with another batch. The resulting mixture was quenched by addition of saturated $Na_2CO_3$ aqueous solution (500 mL) and extracted with DCM (1000 mL*3). The resulting mixture was concentrated under reduced pressure to afford tert-butyl N-(4-bromo-2-nitro-phenyl)carbamate (668 g, 77.7% yield) as yellow solid. $^1$H NMR (400 MHz, DMSO-d6) δ ppm 9.61-9.76 (m, 1H), 8.03-8.17 (m, 1H), 7.85 (dd, J=8.8, 2.3 Hz, 1H), 7.59 (d, J=8.8 Hz, 1H), 1.43 (s, 9H).

Step 3: Synthesis of tert-butyl N-[4-(4-fluorophenyl)-2-nitro-phenyl]carbamate To a solution of tert-butyl N-(4-bromo-2-nitro-phenyl)carbamate (260 g, 0.820 mol), (4-fluorophenyl)boronic acid (147 g, 1.05 mol), $K_2CO_3$ (340 g, 2.46 mol) in dioxane (1.9 L) and $H_2O$ (400 mL) was added cyclopentyl(diphenyl)phosphane;dichloromethane;dichloropalladium;iron (14.3 g, 17.5 mmol). The mixture was stirred at 100° C. for 12 hours under $N_2$. The mixture was poured into ice water. The mixture was combined with another batch. The mixture was adjusted pH=8 with $NH_4Cl$ solid and stirred for 2 hours. Then the mixture was filtered, and the filter cake was concentrated under reduced pressure to afford tert-butyl N-[4-(4-fluorophenyl)-2-nitro-phenyl]carbamate (1.2 kg, crude) as green solid. $^1$H NMR (400 MHz, DMSO-d6) δ ppm 8.15 (br s, 1H), 7.95 (d, J=7.0 Hz, 1H), 7.69-7.86 (m, 3H), 7.31 (s, 3H), 1.35-1.56 (m, 9H). The residue (200 mg) was further purified by flash chromatography (ISCO®; 12 g AgelaFlash® Silica Flash Column, petroleum ether/EtOAc with EtOAc from 0~7%, flow rate=35 mL/min, 254 nm) to afford tert-butyl N-[4-(4-fluorophenyl)-2-nitro-phenyl]carbamate (123 mg) as yellow solid for delivery. $^1$H NMR (400 MHz, DMSO-d6) δ ppm 9.65 (s, 1H), 8.17 (d, J=2.0 Hz, 1H), 7.97 (dd, J=8.5, 2.3 Hz, 1H), 7.67-7.85 (m, 3H), 7.24-7.39 (m, 2H), 1.46 (s, 9H); 19F NMR (376 MHz, DMSO-d6) δ ppm −114.395; LCMS (ESI) [M+H]$^+$ m/z: calcd 233.1, found 333.1 (Boc cleaved mass); HPLC: 96.66%@220 nm, 98.640%@254 nm.

Step 4: Synthesis of tert-butyl N-[2-amino-4-(4-fluorophenyl)phenyl]carbamate To a mixture of tert-butyl N-[4-(4-fluorophenyl)-2-nitro-phenyl]carbamate (150 g, 0.451 mol) in THF (1.2 L) was added Pd/C (33 g, 10 wt % Pd with 50 wt % water) under $N_2$ atmosphere. The suspension was degassed and purged with hydrogen for 3 times. The mixture was stirred under $H_2$ (in balloon) at 20° C. for 48 hours. The resulting mixture was filtered. The filtrate was concentrated under reduced pressure. The residue was triturated with MeOH (1 L*5). The mixture was filtered. The filter cake was dried under reduced pressure to give tert-butyl N-[2-amino-4-(4-fluorophenyl)phenyl]carbamate (76 g, 55.7% yield) as light yellow solid. $^1$H NMR (400 MHz, DMSO-d6) δ ppm 8.35 (brs, 1H), 7.56 (dd, J=8.8, 5.5 Hz, 2H), 7.16-7.36 (m, 3H), 6.95 (d, J=2.3 Hz, 1H), 6.80 (dd, J=8.2, 2.1 Hz, 1H), 4.96 (s, 2H), 1.47 (s, 9H); LCMS (ESI) [M+MeCN+H]$^+$ m/z: calcd 344.1, found 344.2; HPLC: 96.88%@220 nm, 97.90%@254 nm.

Step 5: Synthesis of methyl 4-[(4-methyl-3-pyridyl)sulfanyl]benzoate

A mixture of methyl 4-sulfanylbenzoate (310 mg, 1.84 mmol), 3-bromo-4-methyl-pyridine (0.2 mL, 1.80 mmol), (1E,4E)-1,5-diphenylpenta-1,4-dien-3-one;palladium (830 mg, 0.906 mmol), (5-diphenylphosphanyl-9,9-dimethyl-xanthen-4-yl)-diphenyl-phosphane (530 mg, 0.916 mmol) and dicesium;carbonate (1.76 g, 5.42 mmol) in dioxane (10 mL) was purged with $N_2$ gas at ambient temperature for 3 minutes. Then mixture was stirred at 130° C. for 2 hours in microwave. The resulting mixture was quenched by addition of water (20 mL) and extracted with EtOAc (50 mL*3). The combined organic layer was washed with brine (30 mL*2), dried over anhydrous $Na_2SO_4$, filtered and concentrated under reduced pressure. The residue was purified by flash chromatography (ISCO®; 20 g AgelaFlash® Silica Flash Column, petroleum ether/EtOAc with EtOAc from 0~30%, flow rate=35 mL/min, 254 nm) to afford methyl 4-[(4-methyl-3-pyridyl)sulfanyl]benzoate (330 mg, 70.7% yield) as light yellow solid. LCMS (ESI) [M+H]+ m/z: calcd 260.1, found 259.9.

Step 6: Synthesis of methyl 4-[(4-methyl-3-pyridyl)sulfonimidoyl]benzoate

A mixture of methyl 4-[(4-methyl-3-pyridyl)sulfanyl]benzoate (280 mg, 1.08 mmol), ammonia;carbamic acid (506 mg, 6.48 mmol), [acetoxy(phenyl)-iodanyl] acetate (1.04 g, 3.24 mmol) in MeOH (5 mL) was stirred at 50° C. for 12 hours. The resulting mixture was filtered and concentrated under reduced pressure. The residue was purified by flash chromatography (ISCO®; 12 g AgelaFlash® Silica Flash Column, DCM/MeOH with MeOH from 0~30%, flow rate=30 mL/min, 254 nm) to afford methyl 4-[(4-methyl-3-pyridyl)sulfonimidoyl]benzoate (420 mg, crude) as yellow solid. $^1$H NMR (400 MHz, DMSO-d6) δ ppm 9.25 (s, 1H), 8.67 (d, J=5.0 Hz, 1H), 8.01-8.22 (m, 4H), 7.38 (d, J=4.5 Hz, 1H), 5.61 (s, 1H), 3.89 (d, J=2.0 Hz, 3H), 2.38 (s, 3H); LCMS (ESI) [M+H]+ m/z: calcd 291.1, found 290.9.

Step 7: Synthesis of 4-[(4-methyl-3-pyridyl)sulfonimidoyl]benzoic acid

A mixture of methyl 4-[(4-methyl-3-pyridyl)sulfonimidoyl]benzoate (370 mg, 1.27 mmol), LiOH—$H_2O$ (165 mg, 3.93 mmol) in MeOH (6 mL) and $H_2O$ (2 mL) was stirred at 20° C. for 1.5 hours. The mixture was concentrated under reduced pressure, and adjusted the pH to 5 with 2N HCl aqueous solution. To the mixture was added water (10 mL) and extracted with DCM (50 mL*3). The combined organic layer was dried over anhydrous $Na_2SO_4$, filtered and concentrated under reduced pressure. The residue was purified by flash chromatography (ISCO®; 4 g AgelaFlash® Silica Flash Column, DCM/MeOH with MeOH from 0~10%, flow rate=25 mL/min, 254 nm) to afford 4-[(4-methyl-3-pyridyl)sulfonimidoyl]benzoic acid (178 mg, 50.6% yield) as yellow solid. LCMS (ESI) [M+H]+ m/z: calcd 277.1, found 276.9.

Step 8: Synthesis of tert-butyl N-[4-(4-fluorophenyl)-2-[[4-[(4-methyl-3-pyridyl)sulfonimidoyl]benzoyl]amino]phenyl]carbamate A mixture of 4-[(4-methyl-3-pyridyl)sulfonimidoyl]benzoic acid (160 mg, 0.580 mmol), tert-butyl N-[2-amino-4-(4-fluorophenyl)phenyl]carbamate (190 mg, 0.628 mmol), EDCI (170 mg, 0.887 mmol) in pyridine (3 mL) was stirred at 20° C. for 1 hour. The mixture was combined with another batch. The mixture was concentrated under reduced pressure. The residue was purified by flash chromatography (ISCO®; 12 g AgelaFlash® Silica Flash Column, petroleum ether/EtOAc with EtOAc from 0~70%, flow rate=35 mL/min, 254 nm) to afford tert-butyl N-[4-(4-fluorophenyl)-2-[[4-[(4-methyl-3-pyridyl)sulfonimidoyl]benzoyl]amino]phenyl]carbamate (310 mg, 87.3% yield) as light yellow solid. LCMS (ESI) [M+H]+ m/z: calcd 561.2, found 561.1.

Step 9: Synthesis of N-[2-amino-5-(4-fluorophenyl)phenyl]-4-[(4-methyl-3-pyridyl)sulfonimidoyl]benzamide A mixture of tert-butyl N-[4-(4-fluorophenyl)-2-[[4-[(4-methyl-3-pyridyl)sulfonimidoyl]benzoyl]amino]phenyl]carbamate (100 mg, 0.178 mmol), TFA (0.4 mL, 5.19 mmol) in DCM (4 mL) was stirred at 20° C. for 1 hour. The resulting mixture was concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75*40 mm*3 μm; Mobile phase A: $H_2O$ with $NH_4HCO_3$ (v %); Mobile phase B: MeCN; Gradient: B from 34% to 64% in 9.5 min, hold 100% B for 1 min; Flow Rate: 30 mL/min; Column Temperature: 30° C.; Wavelength: 220 nm, 254 nm). The fraction was concentrated under reduced pressure and then lyophilized for overnight to afford N-[2-amino-5-(4-fluorophenyl)phenyl]-4-[(4-methyl-3-pyridyl)sulfonimidoyl]benzamide (51 mg, 62.1% yield) as light yellow solid. $^1$H NMR (400 MHz, DMSO-d6) δ ppm 9.93 (s, 1H), 9.26 (s, 1H), 8.66 (d, J=5.0 Hz, 1H), 8.16 (d, J=8.5 Hz, 2H), 8.05 (d, J=8.3 Hz, 2H), 7.57 (dd, J=8.5, 5.5 Hz, 2H), 7.48 (d, J=2.0 Hz, 1H), 7.38 (d, J=5.0 Hz, 1H), 7.31 (dd, J=8.3, 2.0 Hz, 1H), 7.28 (s, 1H), 7.21 (t, J=8.8 Hz, 2H), 6.86 (d, J=8.3 Hz, 1H), 2.41 (s, 3H); 19F NMR (376 MHz, DMSO-d6) δ ppm−117.417; LCMS (ESI) [M+H]+ m/z: calcd 461.1, found 461.2; HPLC: 96.79%@220 nm, 97.29%@254 nm.

Example 90. Synthesis of N-[2-amino-5-(4-fluorophenyl)phenyl]-4-(1-oxo-1thia-2-azacyclohexen-1-yl)benzamide (Compound 231)

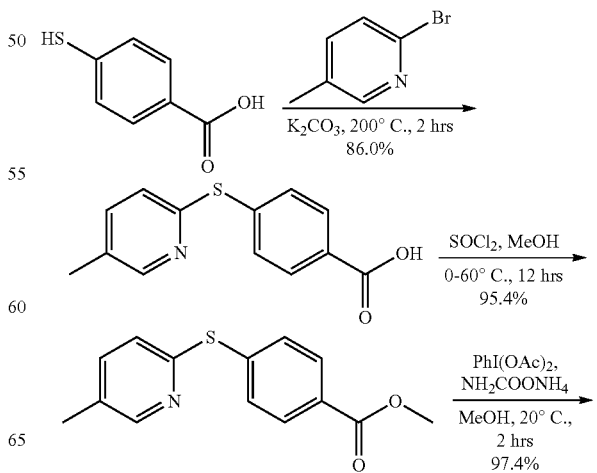

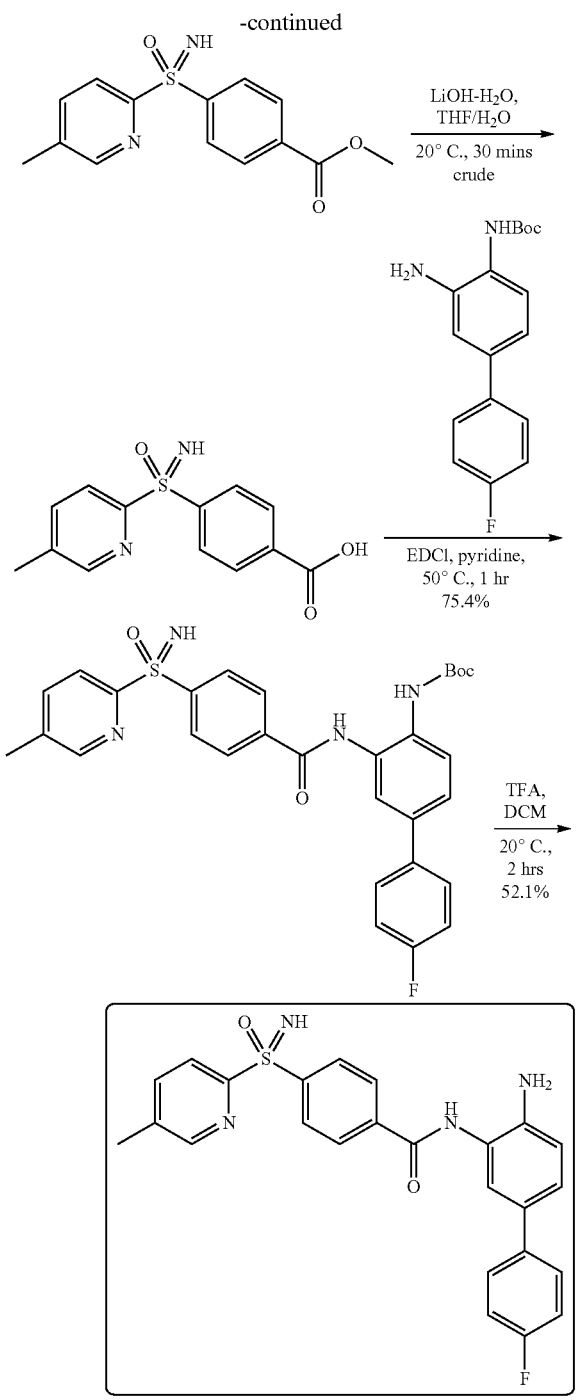

Step 1: Synthesis of 4-[(5-methyl-2-pyridyl)sulfanyl]benzoic acid

To a mixture of 4-sulfanylbenzoic acid (200 mg, 1.30 mmol) and 2-bromo-5-methyl-pyridine (1.34 g, 7.77 mmol) was added K₂CO₃ (360 mg, 2.60 mmol). The mixture was stirred at 200° C. for 2 hours. To the mixture was added H₂O (70 mL) and methyl tert-butyl ether (20 mL). The mixture was extracted with methyl tert-butyl ether (20 mL). The water phase was adjusted pH=3 with 10% HCl aqueous solution, and extracted with 10:1 CH₂Cl₂/MeOH (20 mL*4). The combined organic layers were concentrated under reduced pressure to give 4-[(5-methyl-2-pyridyl)sulfanyl]benzoic acid (273 mg, 86.0% yield) as light orange solid. LCMS (ESI) [M+H]⁺ m/z: calcd 246.1, found 246.1.

Step 2: Synthesis of methyl 4-[(5-methyl-2-pyridyl)sulfanyl]benzoate

To a solution of 4-[(5-methyl-2-pyridyl)sulfanyl]benzoic acid (240 mg, 0.978 mmol) in MeOH (10 mL) was added SOCl₂ (0.98 mL, 13.5 mmol) at 0° C. The mixture was stirred at 60° C. for 12 hours. The resulting mixture was concentrated under reduced pressure. The resulting mixture was quenched by addition of water (20 mL) and extracted with DCM (20 mL*3). The combined organic layer was and concentrated under reduced pressure. The residue was purified by flash chromatography (ISCO®; 20 g AgelaFlash®Silica Flash Column, petroleumether/EtOAc with EtOAc from 0~9%, flow rate=60 mL/min, 254 nm) to afford methyl 4-[(5-methyl-2-pyridyl)sulfanyl]benzoate (242 mg, 95.4% yield) as white solid. LCMS (ESI) [M+H]⁺ m/z: calcd 260.1, found 260.1.

Step 3: Synthesis of methyl 4-[(5-methyl-2-pyridyl)sulfonimidoyl]benzoate

To a solution of methyl 4-[(5-methyl-2-pyridyl)sulfanyl]benzoate (200 mg, 0.771 mmol) in MeOH (10 mL) was added [acetoxy(phenyl)-iodanyl] acetate (620 mg, 1.92 mmol) and ammonia;carbamic acid (120 mg, 1.54 mmol). The mixture was stirred at 20° C. for 2 hours. The residue was purified by flash chromatography (ISCO®; 12 g Agela Flash®Silica Flash Column, petroleum ether/EtOAc with EtOAc from 0~50%, flow rate=60 mL/min, 254 nm) to afford methyl 4-[(5-methyl-2-pyridyl)sulfonimidoyl]benzoate (218 mg, 97.4% yield) as white solid. LCMS (ESI) [M+H]⁺ m/z: calcd 291.1, found 291.1.

Step 4: Synthesis of 4-[(5-methyl-2-pyridyl)sulfonimidoyl]benzoic acid

To a solution of methyl 4-[(5-methyl-2-pyridyl)sulfonimidoyl]benzoate (188 mg, 0.648 mmol) in THF (6 mL) and H₂O (2 mL) was added lithium;hydroxide;hydrate (137 mg, 3.26 mmol). The mixture was stirred at 20° C. for 30 minutes. The resulting mixture was adjusted pH=4 with 2N HCl aqueous solution, and extracted with EtOAc (20 mL*3). The combined organic layer was filtered and concentrated under reduced pressure to give 4-[(5-methyl-2-pyridyl)sulfonimidoyl]benzoic acid (205 mg, crude) as white solid.

Step 5: Synthesis of tert-butyl N-[4-(4-fluorophenyl)-2-[[4-[(5-methyl-2-pyridyl)sulfonimidoyl]benzoyl]amino]phenyl]carbamate To a solution of 4-[(5-methyl-2-pyridyl)sulfonimidoyl] benzoic acid (185 mg, 0.670 mmol) and tert-butyl N-[2-amino-4-(4-fluorophenyl)phenyl]carbamate (305 mg, 1.01 mmol) in pyridine (20 mL) was added EDCI (194 mg, 1.01 mmol). The mixture was stirred at 50° C. for 1 hour. The resulting mixture was concentrated under reduced pressure. The residue was purified by flash chromatography (ISCO®; 12 g Agela Flash®Silica Flash Column, petroleum ether/ EtOAc with EtOAc from 0-80%, flow rate=60 mL/min, 254 nm) to afford tert-butyl N-[4-(4-fluorophenyl)-2-[[4-[(5-methyl-2-pyridyl)sulfonimidoyl]benzoyl]amino]phenyl]

carbamate (283 mg, 75.4% yield) as light-yellow solid. LCMS (ESI) [M+H]⁺ m/z: calcd 561.2, found 561.3.

Step 6: Synthesis of N-[2-amino-5-(4-fluorophenyl)phenyl]-4-[(5-methyl-2-pyridyl)sulfonimidoyl]benzamide To a solution of tert-butyl N-[4-(4-fluorophenyl)-2-[[4-[(5-methyl-2-pyridyl)sulfonimidoyl]benzoyl]amino]phenyl]carbamate (250 mg, 0.446 mmol) in DCM (10 mL) was added TFA (0.69 mL, 8.92 mmol). The mixture was stirred at 20° C. for 2 hours. The mixture was concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75*40 mm*3 μm; Mobile phase A: water (NH₄HCO₃)-ACN; Mobile phase B: MeCN; Gradient: B from 35% to 65% in 9.5 min, hold 100% B for 2 min; Flow Rate: 30 mL/min; Column Temperature: 30° C.; Wavelength: 220 nm, 254 nm) to afford N-[2-amino-5-(4-fluorophenyl)phenyl]-4-[(5-methyl-2-pyridyl)sulfonimidoyl]benzamide (107 mg, 52.1% yield) as yellow solid. ¹H NMR (400 MHz, DMSO-d6) δ ppm 9.87 (s, 1H), 8.47 (s, 1H), 8.03-8.25 (m, 5H), 7.89 (dd, J=8.2, 1.4 Hz, 1H), 7.43-7.65 (m, 3H), 7.10-7.36 (m, 3H), 6.85 (d, J=8.3 Hz, 1H), 5.17 (d, J=13.6 Hz, 3H), 2.34 (s, 3H); LCMS (ESI) [M+H]⁺ m/z: calcd 461.1, found 461.2; 19F NMR (376 MHz, DMSO-d6) δ ppm -117.460; HPLC: 97.090%@220 nm, 1000%@254 nm.

Example 91. Synthesis of N-[2-amino-5-(4-fluorophenyl)phenyl]-5-(methylsulfonimidoyl)thieno[3,2-b]pyridine-2-carboxamide (Compound 254)

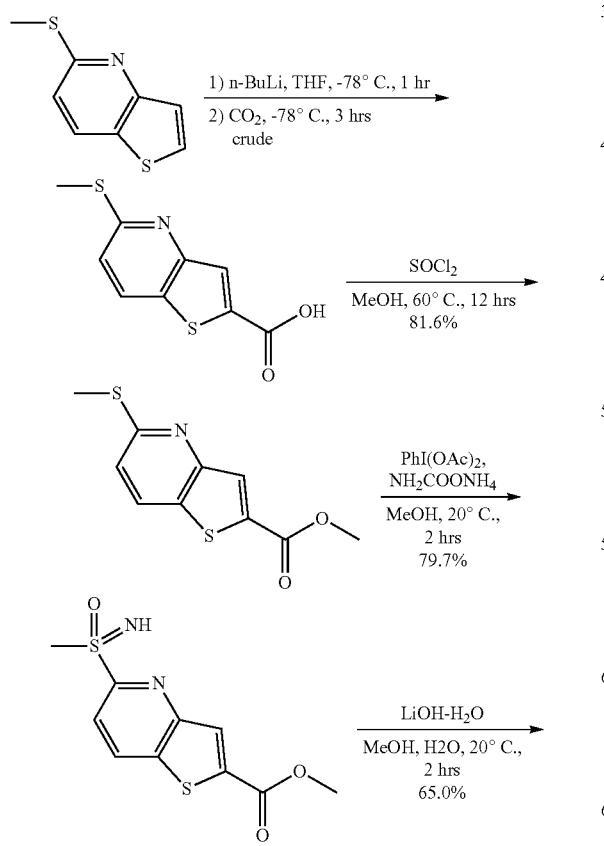

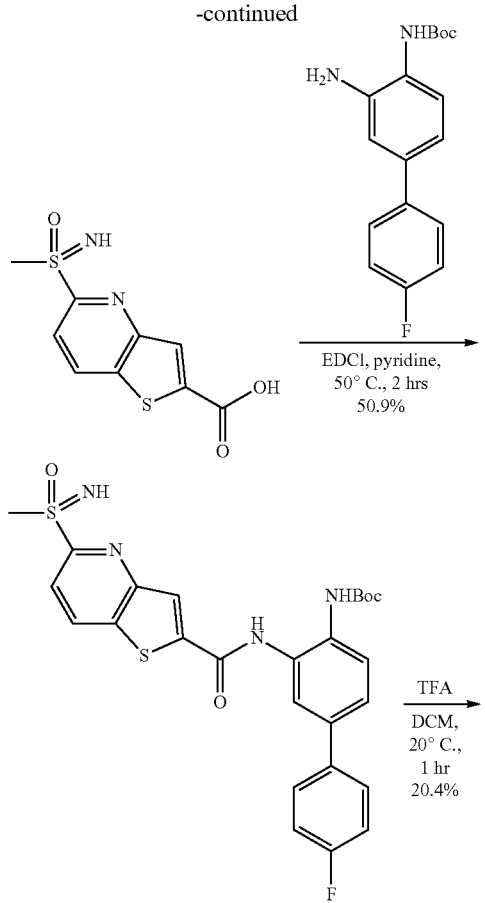

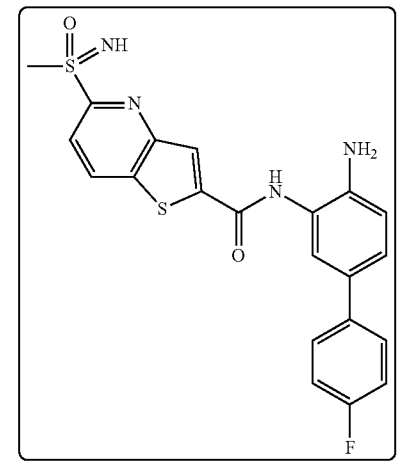 [SMILES: CS(=N)(=O)c1ccc2sc(C(=O)Nc3cc(-c4ccc(F)cc4)ccc3N)cc2n1]

Step 1: Synthesis of 5-methylsulfanylthieno[3,2-b]pyridine-2-carboxylic acid

To a solution of 5-methylsulfanylthieno[3,2-b]pyridine (2 g, 11.0 mmol) in THF (35 mL) was added 2.5M n-BuLi/hexane (6 mL, 15.0 mmol). The mixture was stirred at -78° C. for 1 hour under N₂. Then CO₂ was passed into the solution. The mixture was stirred at -78° C. for 3 hours. The resulting mixture was quenched by addition of water (5 mL) and concentrated the mixture under reduced pressure to afford 5-methylsulfanylthieno[3,2-b]pyridine-2-carboxylic acid (3.2 g, crude) as yellow solid. LCMS (ESI) [M+H]⁺ m/z: calcd 226.0, found 226.0.

Step 2: Synthesis of methyl 5-methylsulfanylthieno[3,2-b]pyridine-2-carboxylate To a solution of 5-methylsulfanylthieno[3,2-b]pyridine-2-carboxylic acid (600 mg, 2.66 mmol) in MeOH (5 mL) was added SOCl₂ (1 mL, 13.8 mmol). The mixture was stirred at 60° C. for 12 hours. The mixture was concentrated under reduced pressure. The mixture was diluted by addition of water (20 mL) and extracted with EtOAc (100 mL*3). The combined organic layer was washed with brine (50 mL), dried over anhydrous Na₂SO₄, filtered and concentrated under reduced pressure to afford methyl 5-methylsulfanylthieno[3,2-b]pyridine-2-carboxylate (520 mg, 81.6% yield) as dark yellow solid. LCMS (ESI) [M+H]⁺ m/z: calcd 240.0, found 239.9.

Step 3: Synthesis of methyl 5-(methylsulfonimidoyl)thieno[3,2-b]pyridine-2-carboxylate A mixture of methyl 5-methylsulfanylthieno[3,2-b]pyridine-2-carboxylate (500 mg, 2.09 mmol), [acetoxy(phenyl)iodanyl] acetate (2 g, 6.21 mmol), ammonia;carbamic acid (820 mg, 10.5 mmol) in MeOH (7 mL) was stirred at 20° C. for 2 hours. The mixture was concentrated under reduced pressure. The residue was purified by flash chromatography (ISCO®; 4 g AgelaFlash® Silica Flash Column, petroleum ether/EtOAc with EtOAc from 0~78%, flow rate=25 mL/min, 254 nm) to afford methyl 5-(methylsulfonimidoyl)thieno[3,2-b]pyridine-2-carboxylate (450 mg, 79.7% yield) as light yellow solid. LCMS (ESI) [M+H]⁺ m/z: calcd 271.0, found 270.9.

Step 4: Synthesis of 5-(methylsulfonimidoyl)thieno[3,2-b]pyridine-2-carboxylic acid A mixture of methyl 5-(methylsulfonimidoyl)thieno[3,2-b]pyridine-2-carboxylate (430 mg, 1.59 mmol), lithium;hydroxide;hydrate (330 mg, 7.86 mmol) in H₂O (2 mL) and MeOH (2 mL) was stirred at 20° C. for 2 hours. The mixture was concentrated under reduced pressure. The mixture was adjusted pH to 4-5 with 1N HCl aqueous solution. The mixture was diluted by addition of water (10 mL) and extracted with EtOAc (50 mL*3). The combined organic layer was washed with brine (100 mL*2), dried over anhydrous Na₂SO₄, filtered and concentrated under reduced pressure to afford 5-(methylsulfonimidoyl)thieno[3,2-b]pyridine-2-carboxylic acid (265 mg, 65.0% yield) as white solid. LCMS (ESI) [M+H]⁺ m/z: calcd 257.0, found 256.8.

Step 5: Synthesis of tert-butyl N-[4-(4-fluorophenyl)-2-[[5-(methylsulfonimidoyl)thieno[3,2-b]pyridine-2-carbonyl]amino]phenyl]carbamate A mixture of 5-(methylsulfonimidoyl)thieno[3,2-b]pyridine-2-carboxylic acid (200 mg, 0.780 mmol), tert-butyl N-[2-amino-4-(4-fluorophenyl)phenyl]carbamate (215 mg, 0.711 mmol), EDCI (230 mg, 1.20 mmol) in pyridine (3 mL) was stirred at 50° C. for 2 hours. The mixture was concentrated under reduced pressure. The residue was purified by flash chromatography (ISCO®; 4 g AgelaFlash® Silica Flash Column, petroleum ether/EtOAc with EtOAc from 0~60%, flow rate=25 mL/min, 254 nm) to afford tert-butyl N-[4-(4-fluorophenyl)-2-[[5-(methylsulfonimidoyl)thieno[3,2-b]pyridine-2-carbonyl]amino]phenyl]carbamate (195 mg, 50.9% yield) as light yellow solid. LCMS (ESI) [M+H]⁺ m/z: calcd 541.1, found 541.3.

Step 6: Synthesis of N-[2-amino-5-(4-fluorophenyl)phenyl]-5-(methylsulfonimidoyl)thieno[3,2-b]pyridine-2-carboxamide (Compound 254)

A mixture of tert-butyl N-[4-(4-fluorophenyl)-2-[[5-(methylsulfonimidoyl)thieno[3,2-b]pyridine-2-carbonyl]amino]phenyl]carbamate (180 mg, 0.333 mmol), TFA (1 mL, 13.0 mmol) in DCM (3 mL) was stirred at 20° C. for 1 hour. The mixture was adjusted pH to 7~8 with saturated NaHCO₃ aqueous solution. The mixture was diluted by addition of water (10 mL) and extracted with EtOAc (50 mL*3). The combined organic layer was washed with brine (50 mL*2), dried over anhydrous Na₂SO₄, filtered and concentrated under reduced pressure. The residue was purified by preparative HPLC (Instrument: Gilson 281, Gilson 333 and 334 Pumps, Gilson 159 UV Detector; Column: Xtimate C18 150*40 mm*5 µm; Mobile phase A: H₂O with NH₃—H₂O and NH₄HCO₃ (v %); Mobile phase B: MeCN; Gradient: B from 35% to 50% in 24 min, hold 100% B for 4 min; Flow Rate: 30 mL/min; Column Temperature: 30° C.; Wavelength: 220 nm, 254 nm). The fraction was concentrated under reduced pressure and then lyophilized for overnight to afford N-[2-amino-5-(4-fluorophenyl)phenyl]-5-(methylsulfonimidoyl)thieno[3,2-b]pyridine-2-carboxamide (29.9 mg, 20.4% yield) as light yellow solid. ¹H NMR (400 MHz, DMSO-d6) δ ppm 10.25 (brs, 1H), 8.86 (d, J=8.5 Hz, 1H), 8.60 (s, 1H), 8.14 (d, J=8.6 Hz, 1H), 7.61 (dd, J=8.6, 5.4 Hz, 2H), 7.53 (d, J=2.0 Hz, 1H), 7.36 (dd, J=8.3, 2.0 Hz, 1H), 7.22 (t, J=8.8 Hz, 2H), 6.89 (d, J=8.5 Hz, 1H), 5.31 (s, 2H), 4.62 (s, 1H), 3.27 (s, 3H); 19F NMR (376 MHz, DMSO-d6) δ ppm −117.39; LCMS (ESI) [M+H]⁺ m/z: calcd 441.1, found 441.0; HPLC: 96.99%@220 nm, 96.87%@254 nm.

Example 92. Synthesis of N-[2-amino-5-(4-fluorophenyl)phenyl]-4-[(5-methyl-3-pyridyl)sulfonimidoyl]benzamide (Compound 199)

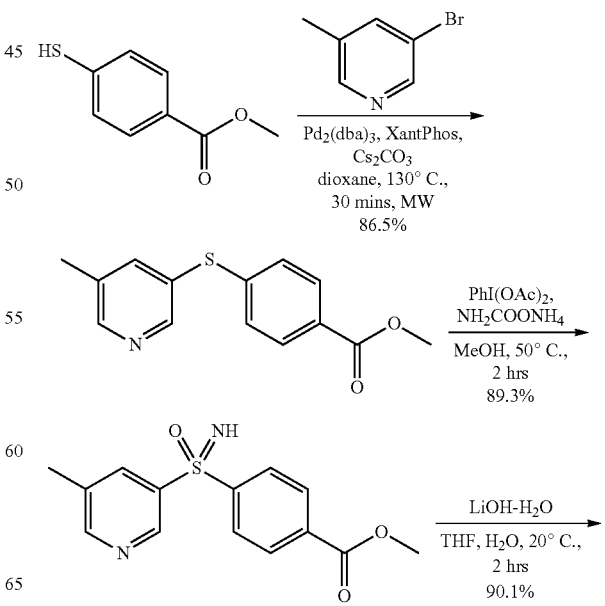

Step 1: Synthesis of methyl 4-[(5-methyl-3-pyridyl)sulfanyl]benzoate

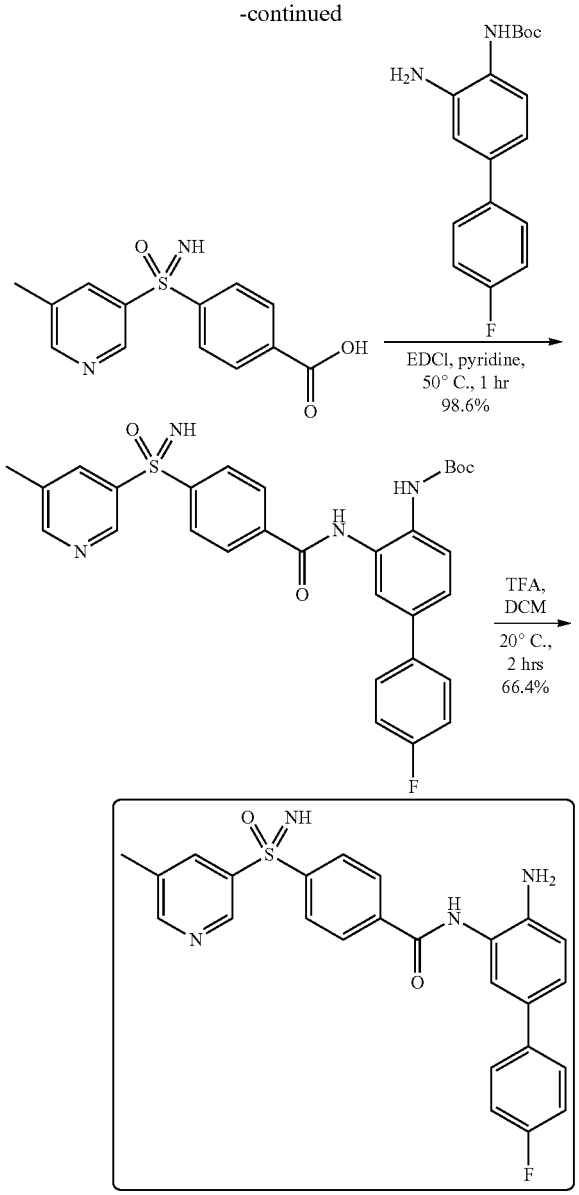

A mixture of methyl 4-sulfanylbenzoate (300 mg, 1.78 mmol), 3-bromo-5-methyl-pyridine (360 mg, 2.09 mmol), (1E,4E)-1,5-diphenylpenta-1,4-dien-3-one;palladium (326 mg, 0.356 mmol), (5-diphenylphosphanyl-9,9-dimethyl-xanthen-4-yl)-diphenyl-phosphane (309 mg, 0.534 mmol) and Cs₂CO₃ (1.74 g, 5.35 mmol) in dioxane (8 mL) was degassed and purged with N₂ for 3 times, and then the mixture was stirred at 130° C. for 30 minutes in microwave. The resulting mixture was quenched by addition of water (100 mL) and extracted with EtOAc (100 mL*3). The combined organic layer was washed with saturated NH₄Cl aqueous solution (100 mL*2), brine (100 mL), dried over anhydrous Na₂SO₄, filtered and concentrated under reduced pressure. The residue was purified by flash chromatography (ISCO®; 20 g AgelaFlash® Silica Flash Column, petroleum ether/EtOAc with EtOAc from 0~35%, flow rate=30 mL/min, 254 nm) to afford methyl 4-[(5-methyl-3-pyridyl)sulfanyl]benzoate (400 mg, 86.5% yield) as yellow solid. LCMS (ESI) [M+H]⁺ m/z: calcd 260.1, found 260.1.

Step 2: Synthesis of methyl 4-[(5-methyl-3-pyridyl)sulfonimidoyl]benzoate

To a mixture of methyl 4-[(5-methyl-3-pyridyl)sulfanyl]benzoate (350 mg, 1.35 mmol) in MeOH (10 mL) were added [acetoxy(phenyl)-iodanyl] acetate (1.3 g, 4.05 mmol) and ammonia;carbamic acid (210 mg, 2.69 mmol). The resulting mixture was sealed and degassed under vacuum and purged with N₂ for three times, and then stirred at 50° C. for 2 hours under N₂ atmosphere. The mixture was combined with another batch. The resulting mixture was filtered and concentrated under reduced pressure. The residue was purified by flash chromatography (ISCO®; 20 g AgelaFlash® Silica Flash Column, EtOAc/MeOH with MeOH from 0~5%, flow rate=30 mL/min, 254 nm) to afford methyl 4-[(5-methyl-3-pyridyl)sulfonimidoyl]benzoate (400 mg, 89.3% yield) as yellow solid. LCMS (ESI) [M+H]⁺ m/z: calcd 291.1, found 291.1.

Step 3: Synthesis of 4-[(5-methyl-3-pyridyl)sulfonimidoyl]benzoic acid

A mixture of methyl 4-[(5-methyl-3-pyridyl)sulfonimidoyl]benzoate (350 mg, 1.21 mmol), LiOH—H₂O (245 mg, 5.84 mmol) in THF (4 mL) and H₂O (2 mL) was stirred at 20° C. for 2 hours. The mixture was adjusted to pH=5 with 2N HCl aqueous solution. The resulting mixture was quenched by addition of water (10 mL) and extracted with DCM (50 mL*3). The combined organic layer was dried over anhydrous Na₂SO₄, filtered and concentrated under reduced pressure to afford 4-[(5-methyl-3-pyridyl)sulfonimidoyl]benzoic acid (300 mg, 90.1% yield) as white solid. ¹H NMR (400 MHz, DMSO-d6) δ ppm 13.43 (brs, 1H), 8.91 (d, J=2.0 Hz, 1H), 8.62 (d, J=1.3 Hz, 1H), 8.15 (s, 1H), 8.06-8.13 (m, 4H), 5.45 (s, 1H), 2.36 (s, 3H); LCMS (ESI) [M+H]⁺ m/z: calcd 277.1, found 277.1.

Step 4: Synthesis of tert-butyl N-[4-(4-fluorophenyl)-2-[[4-[(5-methyl-3-pyridyl)sulfonimidoyl]benzoyl]amino]phenyl]carbamate A mixture of 4-[(5-methyl-3-pyridyl)sulfonimidoyl]benzoic acid (100 mg, 0.362 mmol), tert-butyl N-[2-amino-4-(4-fluorophenyl)phenyl]carbamate (109 mg, 0.361 mmol), EDCI (104 mg, 0.543 mmol) in pyridine (3 mL) was stirred at 50° C. for 1 hour. The resulting mixture was concentrated under reduced pressure. The residue was purified by flash chromatography (ISCO®; 12 g AgelaFlash® Silica Flash Column, EtOAc/MeOH with MeOH from 0~10%, flow rate=30 mL/min, 254 nm) to afford tert-butyl N-[4-(4-fluorophenyl)-2-[[4-[(5-methyl-3-pyridyl)sulfonimidoyl]benzoyl]amino]phenyl]carbamate (200 mg, 98.6% yield) as yellow solid. LCMS (ESI) [M+H]⁺ m/z: calcd 561.2, found 561.3.

Step 5: Synthesis of N-[2-amino-5-(4-fluorophenyl)phenyl]-4-[(5-methyl-3-pyridyl)sulfonimidoyl]benzamide (Compound 199)

A mixture of tert-butyl N-[4-(4-fluorophenyl)-2-[[4-[(5-methyl-3-pyridyl)sulfonimidoyl]benzoyl]amino]phenyl]carbamate (200 mg, 0.357 mmol), TFA (0.6 mL, 7.79 mmol) in DCM (3 mL) was stirred at 20° C. for 2 hours. The mixture was adjusted to pH=9 with NH₃—H₂O (12 N). The mixture was concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75*40 mm*3 μm; Mobile phase A: H₂O with 0.05% NH₃—H₂O (v %); Mobile phase B: MeCN; Gradient: B from 33% to 63% in 9.5 min, hold 100% B for 1 min; Flow Rate: 30 mL/min; Column Temperature: 30° C.; Wavelength: 220 nm, 254 nm) to afford N-[2-amino-5-(4-fluorophenyl)phenyl]-4-[(5-methyl-3-pyridyl)sulfonimidoyl]benzamide (109 mg, 66.4% yield) as light-yellow solid. ¹H NMR (400 MHz, DMSO-d6) δ ppm 9.86 (s, 1H), 8.94 (d, J=2.0 Hz, 1H), 8.62 (d, J=1.3 Hz, 1H), 8.19 (s, 1H), 8.11-8.17 (m, 4H), 7.56 (dd, J=8.8, 5.5 Hz, 2H), 7.47 (d, J=1.8 Hz, 1H), 7.30 (dd, J=8.3, 2.0 Hz, 1H), 7.21 (t, J=8.9 Hz, 2H), 6.84 (d, J=8.5 Hz, 1H), 5.45 (s, 1H), 5.08-5.21 (m, 2H), 2.37 (s, 3H); 19F NMR (376 MHz, DMSO-d6) δ ppm −117.46; LCMS (ESI) [M+H]⁺ m/z: calcd 461.1, found 461.2; HPLC: 93.35%@220 nm, 100%@254 nm.

Example 93. Synthesis of N-[2-amino-5-(4-fluorophenyl)phenyl]-4-[(3-methylimidazol-4-yl)sulfonimidoyl]benzamide (Compound 242)

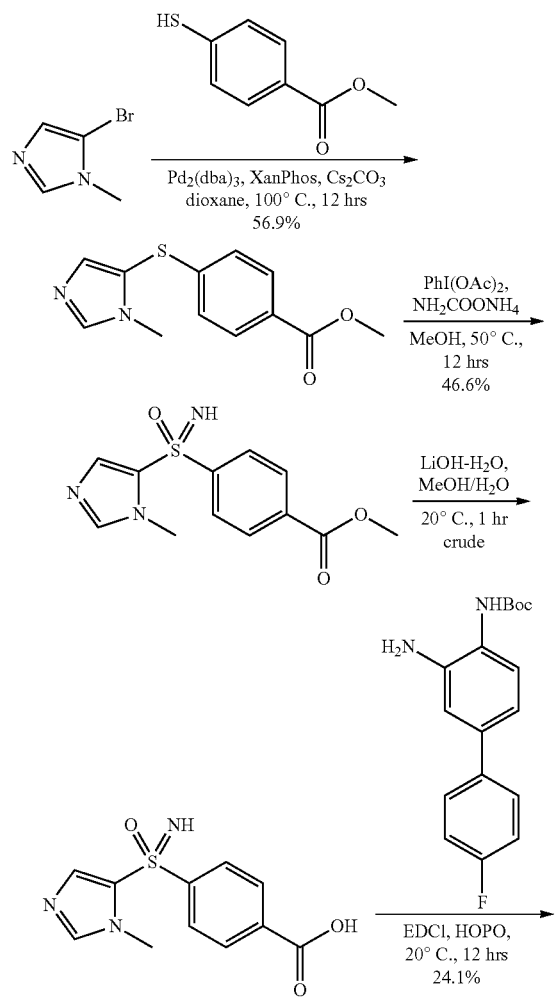

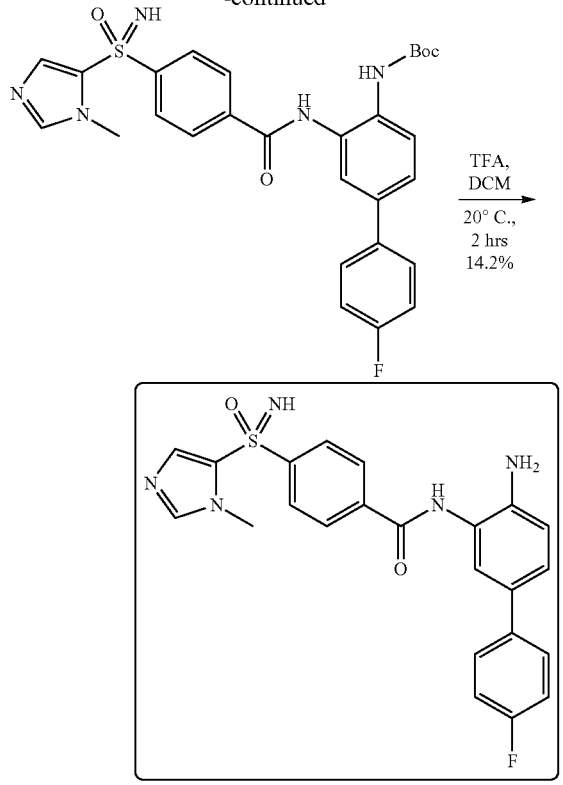

Step 1: Synthesis of methyl 4-(3-methylimidazol-4-yl)sulfanylbenzoate

To a solution of methyl 4-sulfanylbenzoate (1 g, 5.94 mmol) and 5-bromo-1-methyl-imidazole (1.16 g, 7.20 mmol) in dioxane (5 mL) was added Pd₂(dba)₃ (560 mg, 0.61 mmol), Xantphos (350 mg, 0.600 mmol) and Cs₂CO₃ (6 g, 18.42 mmol). The mixture was stirred at 100° C. for 12 hours. The resulting mixture was filtered and concentrated under reduced pressure. The residue was purified by flash chromatography (Biotage®; 4 g AgelaFlash® Silica Flash Column, Dichloromethane/Methanol with Methanol from 0~80%, flow rate=25 mL/min, 254 nm) to afford methyl 4-(3-methylimidazol-4-yl)sulfanylbenzoate (840 mg, 56.9% yield) as red solid. ¹H NMR (400 MHz, DMSO-d6) δ ppm 8.01-8.08 (m, 1H), 7.86 (d, J=8.53 Hz, 2H), 7.40 (s, 1H), 7.09 (d, J=8.53 Hz, 2H), 3.82 (s, 3H), 3.51 (s, 3H). LCMS (ESI) [M+H]⁺ m/z: calcd 249.1, found 249.1.

Step 2: Synthesis of methyl 4-[(3-methylimidazol-4-yl)sulfonimidoyl]benzoate To a solution of methyl 4-(3-methylimidazol-4-yl)sulfanylbenzoate (840 mg, 3.38 mmol) in MeOH (5 mL) was added [acetoxy(phenyl)-iodanyl] acetate (2.69 g, 8.35 mmol) and ammonia;carbamic acid (504 mg, 6.46 mmol), the mixture was stirred at 50° C. for 12 hours. The resulting mixture was filtered and concentrated under reduced pressure. The residue was purified by flash chromatography (Biotage®; 12 g AgelaFlash® Silica Flash Column, petroleum ether/EtOAc with EtOAc from 0~100%, flow rate=30 mL/min, 254 nm) to afford methyl 4-[(3-methylimidazol-4-yl)sulfonimidoyl]benzoate (440 mg, 46.6% yield) as white solid. LCMS (ESI) [M+H]⁺ m/z: calcd 280.1, found 280.1.

Step 3: Synthesis of 4-[(3-methylimidazol-4-yl) sulfonimidoyl]benzoic acid

To a solution of methyl 4-[(3-methylimidazol-4-yl)sulfonimidoyl]benzoate (440 mg, 1.58 mmol) in MeOH (5 mL) and H$_2$O (1 mL) was added LiOH—H$_2$O (200 mg, 4.77 mmol). The mixture was stirred at 20° C. for 1 hour. The mixture was concentrated under reduced pressure, and adjusted the pH to 5 with 2N HCl aqueous solution. The resulting mixture was quenched by addition of water (50 mL) and extracted with EtOAc (50 mL*3). The combined water layer was concentrated under reduced pressure to afford 4-[(3-methylimidazol-4-yl)sulfonimidoyl]benzoic acid (500 mg, crude) as yellow solid. $^1$H NMR (400 MHz, DMSO-d6) δ ppm 7.92 (d, J=8.25 Hz, 2H), 7.80 (d, J=8.38 Hz, 2H), 7.68 (s, 1H), 7.39 (s, 1H), 3.61 (s, 3H). LCMS (ESI) [M+H]$^+$ m/z: calcd 266.1, found 266.1.

Step 4: Synthesis of tert-butyl N-[4-(4-fluorophenyl)-2-[[4-[(3-methylimidazol-4-yl)sulfonimidoyl] benzoyl]amino]phenyl]carbamate To a solution of 4-[(3-methylimidazol-4-yl)sulfonimidoyl]benzoic acid (200 mg, 0.750 mmol) and tert-butyl N-[2-amino-4-(4-fluorophenyl)phenyl]carbamate (200 mg, 0.660 mmol) in THF (5 mL) was added EDCI (160 mg, 0.830 mmol) and 1-oxidopyridin-1-ium-2-ol (120 mg, 1.08 mmol). The mixture was stirred at 20° C. for 12 hours. The resulting mixture was quenched by addition of water (20 mL) and extracted with DCM (20 mL*3). The combined organic layer was dried over anhydrous Na$_2$SO$_4$, filtered and concentrated under reduced pressure to afford tert-butyl N-[4-(4-fluorophenyl)-2-[[4-[(3-methylimidazol-4-yl)sulfonimidoyl]benzoyl]amino]phenyl]carbamate (100 mg, 24.1% yield) as red solid. LCMS (ESI) [M+H]$^+$ m/z: calcd 550.2, found 550.3.

Step 5: Synthesis of N-[2-amino-5-(4-fluorophenyl) phenyl]-4-[(3-methylimidazol-4-yl)sulfonimidoyl] benzamide (Compound 242)

To a solution of tert-butyl N-[4-(4-fluorophenyl)-2-[[4-[(3-methylimidazol-4-yl)sulfonimidoyl]benzoyl]amino] phenyl]carbamate (100 mg, 0.180 mmol) in DCM (5 mL) was added TFA (0.3 mL, 3.89 mmol). The mixture was stirred at 20° C. for 2 hours. The resulting mixture was concentrated under reduced pressure, and adjusted pH=8 with saturated NaHCO$_3$ aqueous solution. The mixture was diluted with water (20 mL) and extracted with DCM (20 mL*3). The combined organic layer was dried over anhydrous Na$_2$SO$_4$, filtered and concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 μm; Mobile phase A: water (NH$_3$—H$_2$O+NH$_4$HCO$_3$ v/v)-ACN; Mobile phase B: ACN; Gradient: B from 30% to 60% in 9.5 min, hold 100% B for 1 min; Flow Rate: 30 mL/min; Column Temperature: 30° C.; Wavelength: 220 nm, 254 nm) to afford N-[2-amino-5-(4-fluorophenyl)phenyl]-4-[(3-methylimidazol-4-yl)sulfonimidoyl]benzamide (11.6 mg, 14.2% yield) as white solid. $^1$H NMR (400 MHz, DMSO-d6) δ ppm 9.88 (s, 1H), 8.16 (d, J=7.53 Hz, 2H), 8.06-8.13 (m, 2H), 7.87 (s, 1H), 7.62 (s, 1H), 7.53-7.60 (m, 2H), 7.48 (s, 1H), 7.28-7.34 (m, 1H), 7.21 (t, J=8.78 Hz, 2H), 6.85 (d, J=8.03 Hz, 1H), 5.62 (s, 1H), 5.15 (s, 2H), 3.66 (s, 3H); 19F NMR (376 MHz, DMSO-d6) δ ppm−117.47; LCMS (ESI) [M+H]$^+$ m/z: calcd 450.1, found 450.2; HPLC: 97.10%@220 nm; 98.05%@254 nm.

Example 94. Synthesis of N-[2-amino-5-(4-fluorophenyl)phenyl]-4-[(4-hydroxy-3-pyridyl)sulfonimidoyl]benzamide (Compound 227)

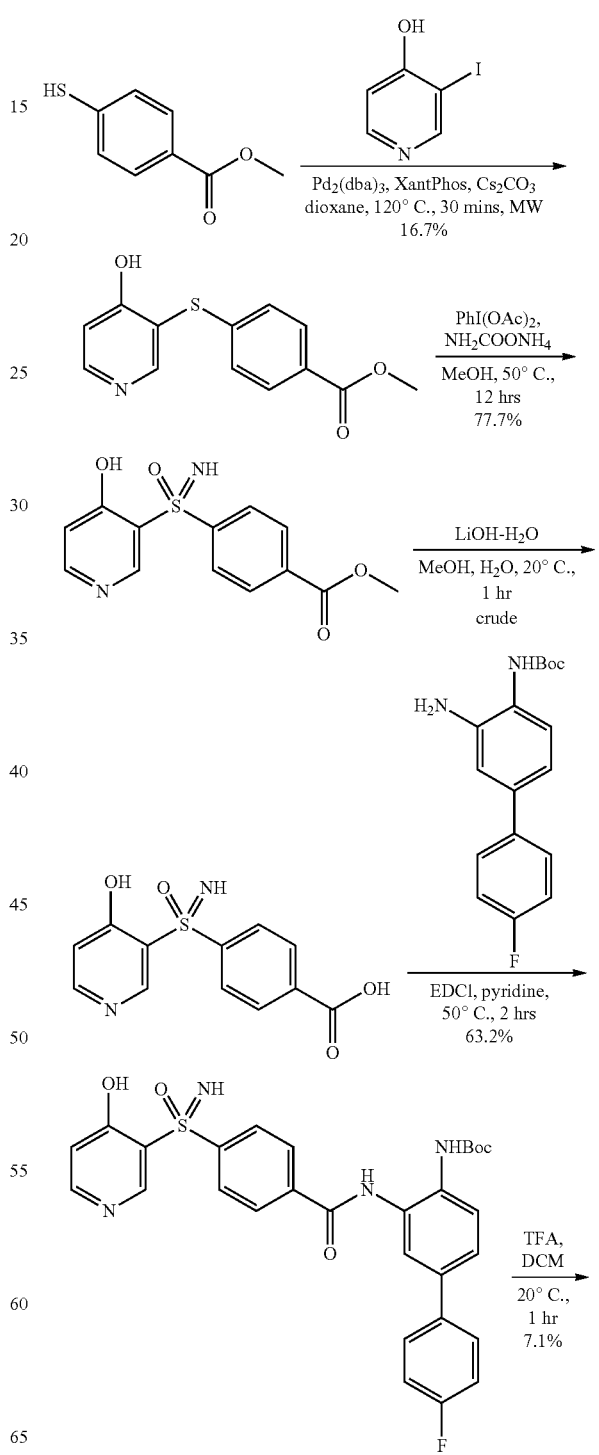

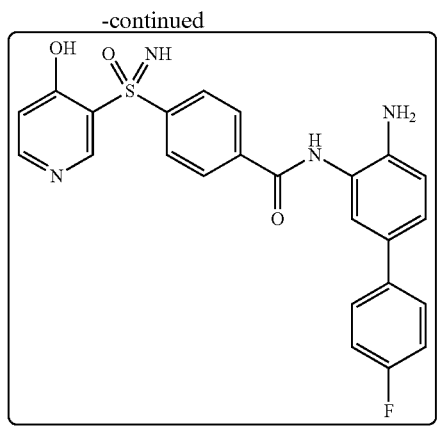

Step 1: Synthesis of methyl 4-[(4-hydroxy-3-pyridyl)sulfanyl]benzoate

A mixture of methyl 4-sulfanylbenzoate (500 mg, 2.97 mmol), 3-iodopyridin-4-ol (800 mg, 3.62 mmol), Pd$_2$(dba)$_3$ (270 mg, 0.290 mmol), Xantphos (340 mg, 0.590 mmol) and Cs$_2$CO$_3$ (1.94 g, 5.95 mmol) in dioxane (5 mL) was stirred at 130° C. for 30 minutes in microwave. The resulting mixture was filtered and concentrated under reduced pressure. The residue was purified by flash chromatography (Biotage®; 20 g AgelaFlash® Silica Flash Column, petroleum ether/EtOAc with EtOAc from 0~100%, flow rate=30 mL/min, 254 nm) to afford methyl 4-[(4-hydroxy-3-pyridyl)sulfanyl]benzoate (130 mg, 16.7% yield) as yellow solid. $^1$H NMR (400 MHz, DMSO-d6) δ ppm 11.73-11.93 (m, 1H), 8.13 (s, 1H), 7.81 (d, J=8.28 Hz, 2H), 7.72-7.79 (m, 1H), 7.16 (d, J=8.28 Hz, 2H), 6.25 (d, J=7.53 Hz, 1H), 3.82 (s, 3H); LCMS (ESI) [M+H]$^+$ m/z: calcd 262.0, found 262.1.

Step 2: Synthesis of methyl 4-[(4-hydroxy-3-pyridyl)sulfonimidoyl]benzoate

To a solution of methyl 4-[(4-hydroxy-3-pyridyl)sulfanyl]benzoate (230 mg, 0.880 mmol) in MeOH (5 mL) was added [acetoxy(phenyl)-iodanyl] acetate (690 mg, 2.14 mmol), ammonia;carbamic acid (140 mg, 1.79 mmol). The mixture was stirred at 50° C. for 12 hours. The resulting mixture was filtered and concentrated under reduced pressure. The residue was purified by flash chromatography (Biotage®; 12 g AgelaFlash® Silica Flash Column, Dichloromethane/Methanol with Methanol from 0~10%, flow rate=30 mL/min, 254 nm) to afford methyl 4-[(4-hydroxy-3-pyridyl)sulfonimidoyl]benzoate (200 mg, 77.7% yield) as yellow solid. $^1$H NMR (400 MHz, DMSO-d6) δ ppm 8.46-8.56 (m, 1H), 8.07 (d, J=7.78 Hz, 5H), 7.63-7.77 (m, 1H), 6.18 (s, 1H), 4.79 (brs, 1H), 3.88 (s, 3H).

Step 3: Synthesis of 4-[(4-hydroxy-3-pyridyl)sulfonimidoyl]benzoic acid

To a solution of methyl 4-[(4-hydroxy-3-pyridyl)sulfonimidoyl]benzoate (180 mg, 0.620 mmol) in MeOH (9 mL) and H$_2$O (3 mL), was added LiOH—H$_2$O (81 mg, 1.93 mmol). The mixture was stirred at 20° C. for 1 hour. The mixture was concentrated under reduced pressure, and adjusted the pH to 5 with 2N HCl aqueous solution. The resulting mixture was diluted with water (20 mL) and extracted with EtOAc (20 mL*3). The water layer was concentrated under reduced pressure to afford 4-[(4-hydroxy-3-pyridyl)sulfonimidoyl]benzoic acid (200 mg, crude) as yellow solid. LCMS (ESI) [M+H]$^+$ m/z: calcd 279.1, found 279.0.

Step 4: Synthesis of tert-butyl N-[4-(4-fluorophenyl)-2-[[4-[(4-hydroxy-3-pyridyl)sulfonimidoyl]benzoyl]amino]phenyl]carbamate To a solution of 4-[(4-hydroxy-3-pyridyl)sulfonimidoyl]benzoic acid (180 mg, 0.650 mmol) and tert-butyl N-[2-amino-4-(4-fluorophenyl)phenyl]carbamate (200 mg, 0.660 mmol) in pyridine (3 mL) was added EDCI (180 mg, 0.940 mmol). The mixture was stirred at 50° C. for 2 hours. The reaction mixture was concentrated under reduced pressure. The residue was purified by flash chromatography (Biotage®; 12 g AgelaFlash® Silica Flash Column, petroleum Dichloromethane/Methanol with Methanol from 0~8%, flow rate=30 mL/min, 254 nm) to afford tert-butyl N-[4-(4-fluorophenyl)-2-[[4-[(4-hydroxy-3-pyridyl)sulfonimidoyl]benzoyl]amino]phenyl]carbamate (230 mg, 63.2% yield) as yellow solid. LCMS (ESI) [M+H]$^+$ m/z: calcd 563.2, found 563.4.

Step 5: Synthesis of N-[2-amino-5-(4-fluorophenyl)phenyl]-4-[(4-hydroxy-3-pyridyl)sulfonimidoyl]benzamide (Compound 227)

To a solution of tert-butyl N-[4-(4-fluorophenyl)-2-[[4-[(4-hydroxy-3-pyridyl)sulfonimidoyl]benzoyl]amino]phenyl]carbamate (200 mg, 0.360 mmol) in DCM (5 mL) was added TFA (0.6 mL, 7.79 mmol). The mixture was stirred at 20° C. for 1 hour. The resulting mixture was concentrated under reduced pressure, and adjusted pH=8 with saturated NaHCO$_3$ aqueous solution. The mixture was diluted with water (20 mL) and extracted with DCM (20 mL*3). The combined organic layer was dried over anhydrous Na$_2$SO$_4$, filtered and concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 µm; Mobile phase A: water (NH$_3$H$_2$O+NH$_4$HCO$_3$ v/v)-ACN; Mobile phase B: ACN; Gradient: B from 20% to 50% in 9.5 min, hold 100% B for 1 min; Flow Rate: 30 mL/min; Column Temperature: 30° C.; Wavelength: 220 nm, 254 nm) to afford N-[2-amino-5-(4-fluorophenyl)phenyl]-4-[(4-hydroxy-3-pyridyl)sulfonimidoyl]benzamide (11.7 mg, 7.1% yield) as yellow solid. $^1$H NMR (400 MHz, DMSO-d6) δ ppm 9.85 (s, 1H), 8.50 (s, 1H), 8.08 (s, 4H), 7.73 (d, J=7.03 Hz, 1H), 7.55-7.60 (m, 2H), 7.49 (s, 1H), 7.31 (d, J=8.03 Hz, 1H), 7.21 (t, J=8.78 Hz, 2H), 6.85 (d, J=8.28 Hz, 1H), 6.17 (d, J=7.28 Hz, 1H), 5.15 (brs, 2H), 4.74 (s, 1H); 19F NMR (376 MHz, DMSO-d6) δ ppm−117.499; LCMS (ESI) [M+H]$^+$ m/z: calcd 463.1, found 463.3; HPLC: 99.61%@220 nm; 100.00%@254 nm.

525

Example 95. Synthesis of N-[2-amino-5-(4-fluorophenyl)phenyl]-2-piperazin-1-yl-tetralin-6-carboxamide (Compound 193)

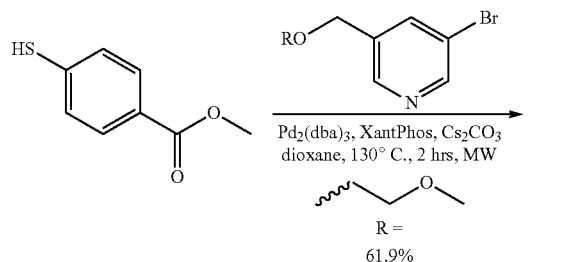

R = 
61.9%

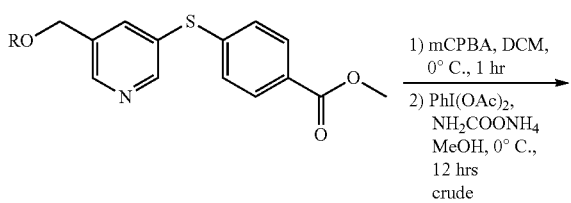

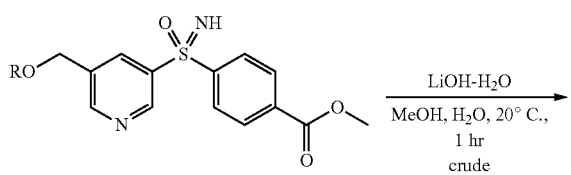

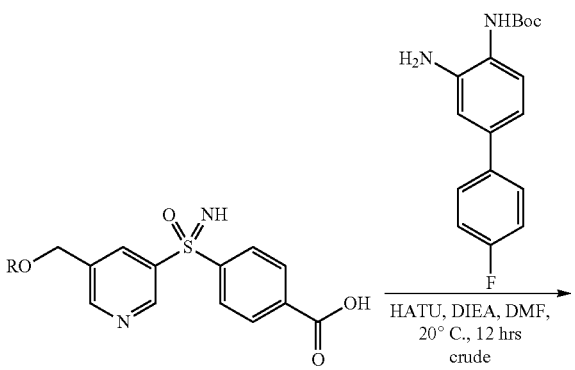

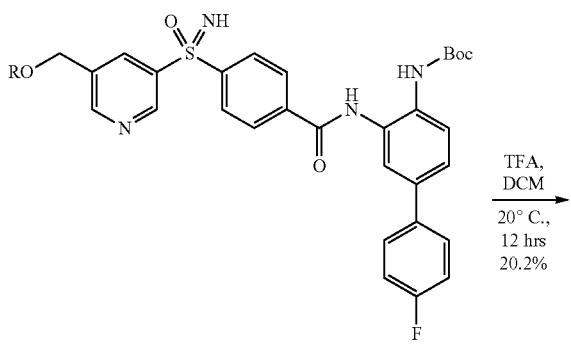

526

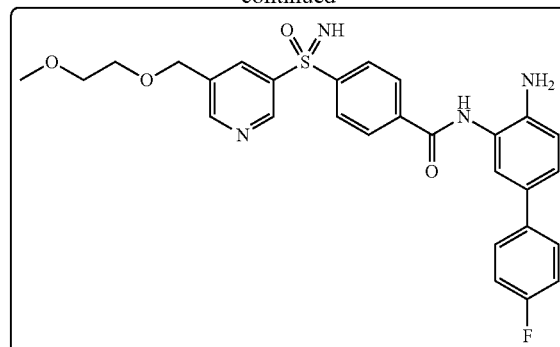

Step 1: Synthesis of tert-butyl 4-(6-methoxycarbonyltetralin-2-yl)piperazine-1-carboxylate To a solution of methyl 4-sulfanylbenzoate (1.0 g, 5.94 mmol), 3-bromo-5-(2-methoxyethoxymethyl)pyridine (1.73 g, 7.03 mmol), $Cs_2CO_3$ (5.80 g, 17.8 mmol) in dioxane (15 mL). Then $Pd_2(dba)_3$ (544.38 mg, 0.595 mmol) and XantPhos (1.03 g, 1.77 mmol) was added at 20° C. and the mixture was stirred at 130° C. for 2 hours under Microwave irradiation. The reaction mixture was quenched by addition water (100 mL) at 20° C., extracted with EtOAc (100 mL*3). The combined organic layers were washed with brine (50 mL*3), dried over anhydrous $Na_2SO_4$, filtered and concentrated under reduced pressure. The residue was purified by flash silica gel chromatography the residue was purified by flash chromatography (ISCO®; 20 g SepaFlash® Silica Flash Column, petroleum ether/EtOAc with EtOAc from 0~70%, flow rate=35 mL/min, 245 nm) to afford methyl 4-((5-((2-methoxyethoxy)methyl)pyridin-3-yl)thio)benzoate (430 mg, 61.9% yield) as brown oil. $^1$H NMR (400 MHz, chloroform-d) δ ppm 8.57 (dd, J=11.01, 1.50 Hz, 2H) 7.94 (d, J=8.38 Hz, 2H) 7.79 (s, 1H) 7.28 (s, 1H) 7.26 (s, 1H) 4.59 (s, 2H) 3.91 (s, 3H) 3.65-3.72 (m, 2H) 3.55-3.62 (m, 2H) 3.39 (s, 3H); LCMS (ESI) [M+H]$^+$ m/z: calcd 334.1, found 334.1.

Step 2: Synthesis of tert-butyl 4-(6-methoxycarbonyltetralin-2-yl)piperazine-1-carboxylate To a solution of methyl 4-[[5-(2-methoxyethoxymethyl)-3-pyridyl]sulfanyl]benzoate (200 mg, 0.599 mmol) in DCM (6 mL) was added m-CPBA (130 mg, 0.602 mmol, 80% purity) at 0° C. and the mixture was stirred at 0° C. for 1 hr. The reaction mixture was added Saturated sodium thiosulfate solution was used to quench. The reaction mixture was quenched by addition water (30 mL) at 20° C., extracted with DCM (30 mL*3). The combined organic layers were washed with brine (20 mL*3), dried over anhydrous $Na_2SO_4$, filtered and concentrated under reduced pressure. The residue was purified by flash silica gel chromatography (ISCO®; 20 g SepaFlash® Silica Flash Column, Petroleum ether/EtOAc with EtOAc from 0~100%, Flow Rate: 35 mL/min, 254 nm) to afford methyl 4-[[5-(2-methoxyethoxymethyl)-3-pyridyl]sulfinyl]benzoate (130 mg, 62.0% yield) as yellow oil. $^1$H NMR (400 MHz, chloroform-d) δ ppm 8.57-8.77 (m, 2H) 8.09-8.10 (m, 1H) 8.07-8.09 (m, 1H) 7.93 (s, 1H) 7.68-7.70 (m, 1H) 7.66-7.68 (m, 1H) 4.55 (s, 2H) 3.86 (s, 3H) 3.57-3.61 (m, 2H) 3.48-3.52 (m, 2H) 3.32 (s, 3H) 1.55 (br s, 3H); LCMS (ESI) [M+H]$^+$ m/z: calcd 350.4, found 350.6.

Step 3: Synthesis of tert-butyl 4-(6-methoxycarbonyltetralin-2-yl)piperazine-1-carboxylate To a solution of methyl 4-[[5-(2-methoxyethoxymethyl)-3-pyridyl]sulfinyl]benzoate (130 mg, 0.372 mmol) and NH$_2$COONH$_4$ (58 mg, 0.743 mmol) in MeOH (3 mL) as added PhI(OAc)$_2$ (300 mg, 0.931 mmol) at 20° C. and the mixture was stirred at 20° C. for 12 hours. The reaction mixture was added Saturated sodium thiosulfate solution was used to quench. The reaction mixture was quenched by addition water (30 mL) at 20° C., extracted with EtOAc (30 mL*3). The combined organic layers were washed with brine (20 mL*3), dried over anhydrous Na$_2$SO$_4$, filtered and concentrated under reduced pressure to give a residue. The residue was purified by flash silica gel chromatography (ISCO®; 20 g SepaFlash® Silica Flash Column, Petroleum ether/EtOAc with EtOAc from 50~100%, Flow Rate: 35 mL/min, 254 nm) to afford methyl 4-[[5-(2-methoxyethoxymethyl)-3-pyridyl]sulfonimidoyl]benzoate (80 mg, crude) as yellow oil.

$^1$H NMR (400 MHz, CHLOROFORM-d) δ ppm 9.14 (d, J=2.01 Hz, 1H) 8.72-8.77 (m, 1H) 8.31 (s, 1H) 8.15 (d, J=5.52 Hz, 4H) 4.64 (s, 2H) 3.95 (s, 3H) 3.67-3.72 (m, 2H) 3.58-3.61 (m, 2H) 3.40 (s, 3H); LCMS (ESI) [M+H]$^+$ m/z: calcd 365.2, found 365.6.

Step 4: Synthesis of 4-[[5-(2-methoxyethoxymethyl)-3-pyridyl]sulfonimidoyl]benzoic acid To a solution of methyl 4-[[5-(2-methoxyethoxymethyl)-3-pyridyl]sulfonimidoyl]benzoate (80 mg, 0.219 mmol) in H$_2$O (1 mL) and H$_2$O (1 mL) was added LiOH—H$_2$O (46.0 mg, 1.10 mmol) at 20° C. and the mixture was stirred at 20° C. for 1 hour. The mixture was concentrated under reduced pressure. Water (5 mL) was added to the concentrated system, the pH value of the mixture was adjusted to 4 with 0.5 N HCl solution. The mixture was concentrated under reduced pressure to obtain 4-[[5-(2-methoxyethoxymethyl)-3-pyridyl]sulfonimidoyl]benzoic acid (70 mg, crude) as yellow oil. LCMS (ESI) [M+H]$^+$ m/z: calcd 351.1, found 351.6.

Step 5: Synthesis of tert-butyl (4'-fluoro-3-(4-(5-((2-methoxyethoxy)methyl)pyridine-3-sulfonimidoyl)benzamido)-[1,1'-biphenyl]-4-yl)carbamate To a solution of 4-[[5-(2-methoxyethoxymethyl)-3-pyridyl]sulfonimidoyl]benzoic acid (350 mg, 1.00 mol) and tert-butyl N-[2-amino-4-(4-fluorophenyl)phenyl]carbamate (290 mg, 0.960 mmol) in DMF (5 mL) was added HATU (583 mg, 1.53 mmol) and DIEA (630 mg, 4.87 mmol) at 20° C. and the mixture was stirred at 20° C. for 12 hours. The reaction mixture was quenched by addition water (30 mL) at 20° C., extracted with EtOAc (30 mL*3). The combined organic layers were washed with brine (20 mL*3), dried over anhydrous Na$_2$SO$_4$, filtered and concentrated under reduced pressure. The residue was purified by flash silica gel chromatography (ISCO®; 20 g SepaFlash® Silica Flash Column, Petroleum ether/EtOAc with EtOAc from 50~100%, Flow Rate: 35 mL/min, 254 nm) to afford tert-butyl (4'-fluoro-3-(4-(5-((2-methoxyethoxy)methyl)pyridine-3-sulfonimidoyl)benzamido)-[1,1'-biphenyl]-4-yl)carbamate (500 mg, crude) as yellow oil. $^1$H NMR (400 MHz, chloroform-d) δ ppm 9.69 (br s, 1H) 9.15 (br s, 1H) 8.75 (br s, 1H) 8.33 (br s, 1H) 8.14-8.19 (m, 2H) 8.03 (br s, 1H) 7.79 (br d, J=8.28 Hz, 1H) 7.54-7.57 (m, 2H) 7.35 (br d, J=8.28 Hz, 1H) 7.31-7.40 (m, 1H) 7.11 (br t, J=8.66 Hz, 2H) 6.77 (br s, 1H) 4.66 (s, 2H) 3.67-3.71 (m, 2H) 3.58-3.62 (m, 2H) 3.40 (d, J=3.51 Hz, 3H) 1.54 (s, 5H); LCMS (ESI) [M+H]$^+$ m/z: calcd 635.1, found 635.2.

Step 6: Synthesis of N-[2-amino-5-(4-fluorophenyl)phenyl]-4-[[5-(2-methoxyethoxymethyl)-3-pyridyl]sulfonimidoyl]benzamide (Compound 193)

To a solution of tert-butyl N-[4-(4-fluorophenyl)-2-[[4-[[5-(2-methoxyethoxymethyl)-3-pyridyl]sulfonimidoyl]benzoyl]amino]phenyl]carbamate (200 mg, 0.315 mmol) in HFIP (2 mL) was added TFA (174 mg, 1.53 mmol). The mixture was stirred at 20° C. for 12 hours. The mixture concentrated under reduced pressure. The residue was purified by preparative TLC (silica, DCM/MeOH=10:1) to afford N-[2-amino-5-(4-fluorophenyl)phenyl]-4-[[5-(2-methoxyethoxymethyl)-3-pyridyl]sulfonimidoyl]benzamide (34 mg, 20.2% yield) as a yellow solid.

Compound 193: $^1$H NMR (400 MHz, chloroform-d) δ ppm 9.15 (d, J=2.01 Hz, 1H) 8.74 (d, J=1.76 Hz, 1H) 8.32 (s, 1H) 8.18 (d, J=8.28 Hz, 2H) 8.08 (br s, 1H) 8.04 (br d, J=8.28 Hz, 2H) 7.59 (s, 1H) 7.47 (br dd, J=8.41, 5.40 Hz, 2H) 7.30 (dd, J=8.16, 2.13 Hz, 1H) 7.08 (t, J=8.78 Hz, 2H) 6.92 (d, J=8.28 Hz, 1H) 4.65 (s, 2H) 3.69-3.72 (m, 2H) 3.59-3.62 (m, 2H) 3.40 (s, 3H) LCMS (ESI) [M+H]$^+$ m/z: calcd 535.1, found 535.2; HPLC: 92.70%@220 nm, 93.01%@254 nm.

Example 96. Synthesis of N-[2-amino-5-(3-thienyl)phenyl]-4-(methylsulfonimidoyl)benzamide (Compound 249)

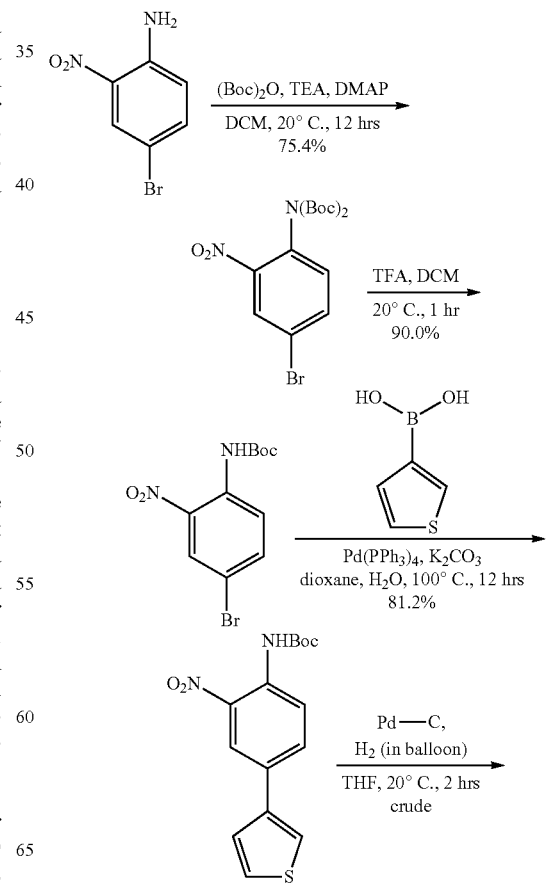

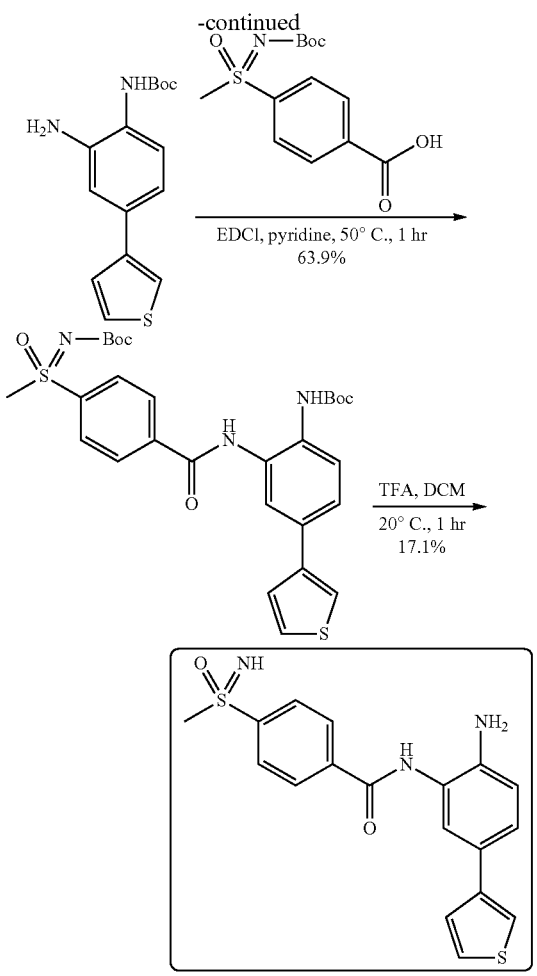

Step 1: Synthesis of tert-butyl N-(4-bromo-2-nitro-phenyl)-N-tert-butoxycarbonyl-carbamate To a solution of 4-bromo-2-nitro-aniline (20 g, 92.2 mmol) in DCM (200 mL) were added TEA (38.5 mL, 0.277 mol), N,N-dimethylpyridin-4-amine (1.13 g, 9.22 mmol) and tert-butoxycarbonyl tert-butyl carbonate (42.2 g, 0.194 mol) dropwise. The mixture was stirred at 20° C. for 12 hours. The reaction mixture was diluted with water (50 mL) and extracted with DCM (100 mL*3). The combined organic layers were dried over $Na_2SO_4$ and filtered. The filtrate was concentrated under reduced pressure. The crude product was triturated with MeOH (100 mL) for 30 minutes. The mixture was filtered. The filter cake was dried under reduced pressure to afford tert-butyl N-(4-bromo-2-nitro-phenyl)-N-tert-butoxycarbonyl-carbamate (29 g, 75.4% yield) as yellow solid. $^1$H NMR (400 MHz, chloroform-d) δ ppm 8.21 (d, J=2.3 Hz, 1H), 7.76 (dd, J=8.5, 2.3 Hz, 1H), 7.21 (d, J=8.3 Hz, 1H), 1.41 (s, 18H).

Step 2: Synthesis of tert-butyl N-(4-bromo-2-nitro-phenyl)carbamate

To a solution of tert-butyl N-(4-bromo-2-nitro-phenyl)-N-tert-butoxycarbonyl-carbamate (21 g, 50.3 mmol) in DCM (210 mL) was added TFA (11.9 g, 0.104 mol) dropwise. The mixture was stirred at 20° C. for 1 hour. The reaction mixture was adjusted to pH=8 with saturated $NaHCO_3$ aqueous solution and extracted with DCM (30 mL*3). The combined organic layers were dried over $Na_2SO_4$ and filtered. The filtrate was concentrated under reduced pressure to afford tert-butyl N-(4-bromo-2-nitro-phenyl)carbamate (14.4 g, 90.0% yield) as yellow solid. $^1$H NMR (400 MHz, chloroform-d) δ ppm 9.60 (brs, 1H), 8.52 (d, J=9.3 Hz, 1H), 8.33 (d, J=2.3 Hz, 1H), 7.69 (dd, J=9.2, 2.4 Hz, 1H), 1.55 (s, 9H).

Step 3: Synthesis of tert-butyl N-[2-nitro-4-(3-thienyl)phenyl]carbamate

To a solution of tert-butyl N-(4-bromo-2-nitro-phenyl)carbamate (200 mg, 0.631 mmol), 3-thienylboronic acid (80 mg, 0.625 mmol) in $H_2O$ (0.8 mL) and dioxane (4 mL) was added dipotassium;carbonate (220 mg, 1.59 mmol) and palladium;triphenylphosphane (110 mg, 0.0952 mmol). The mixture was stirred at 100° C. for 12 hours. The reaction mixture was concentrated under reduced pressure. The residue was purified by preparative TLC (silica, petroleum ether/EtOAc=10/1; 254 nm) to give tert-butyl N-[2-nitro-4-(3-thienyl)phenyl]carbamate (164 mg, 81.2% yield) as yellow solid.

Step 4: Synthesis of tert-butyl N-[2-amino-4-(3-thienyl)phenyl]carbamate

To a solution of tert-butyl N-[2-nitro-4-(3-thienyl)phenyl]carbamate (164 mg, 0.512 mmol) in THF (30 mL) was added Pd—C (100 mg, 10 wt % Pd with 50 wt % water). The mixture was stirred at 20° C. for 2 hours under $H_2$ (in balloon). The reaction mixture was filtered and the filtrate was concentrated under reduced pressure to afford tert-butyl N-[2-amino-4-(3-thienyl)phenyl]carbamate (147 mg, crude) as yellow solid. LCMS (ESI) [M+H]$^+$ m/z: calcd 291.1, found 234.8 (t-Bu cleaved mass).

Step 5: Synthesis of tert-butyl N-[[4-[[2-(tert-butoxycarbonylamino)-5-(3-thienyl)phenyl]carbamoyl]phenyl]-methyl-oxo-λ6-sulfanylidene]carbamate To a solution of tert-butyl N-[2-amino-4-(3-thienyl)phenyl]carbamate (147 mg, 0.506 mmol) in pyridine (6 mL) were added EDCI (145 mg, 0.756 mmol) and 4-(N-tert-butoxycarbonyl-S-methyl-sulfonimidoyl)benzoic acid (167 mg, 0.558 mmol). The mixture was stirred at 50° C. for 1 hour. The reaction mixture was concentrated under reduced pressure. The residue was purified by preparative TLC (silica, petroleum ether/EtOAc=1/1; 254 nm) to give tert-butyl N-[[4-[[2-(tert-butoxycarbonylamino)-5-(3-thienyl)phenyl]carbamoyl]phenyl]-methyl-oxo-λ6-sulfanylidene]carbamate (185 mg, 63.9% yield) as yellow solid. LCMS (ESI) [M+H]$^+$ m/z: calcd 572.2, found 572.2.

Step 6: Synthesis of N-[2-amino-5-(3-thienyl)phenyl]-4-(methylsulfonimidoyl)benzamide (Compound 249)

To a solution of tert-butyl N-[[4-[[2-(tert-butoxycarbonylamino)-5-(3-thienyl)phenyl]carbamoyl]phenyl]-oxo-λ6-sulfanylidene]carbamate (185 mg, 0.332 mmol) in DCM (10 mL) was added TFA (1.52 g, 13.3 mmol). The mixture was stirred at 20° C. for 1 hour. The reaction mixture was adjusted to pH=8 with saturated $NaHCO_3$ aqueous solution and extracted with DCM (10 mL*3). The combined organic layers were dried over $Na_2SO_4$ and filtered. The filtrate was concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75*40 mm*3 μm; Mobile phase A: water with $NH_3$—$H_2O$+$NH_4HCO_3$ (v %); Mobile phase B: MeCN; Gradient: B from 17% to 47% in 7.8 min, hold 100% B for 2 min; Flow Rate: 30 mL/min; Column Temperature: 30° C.; Wavelength: 220 nm, 254 nm) to afford N-[2-amino-5-(3-thienyl)phenyl]-4-(methylsulfonimidoyl)benzamide (20.6 mg, 17.1% yield) as white solid. $^1$H NMR (400 MHz, DMSO-d6) δ 9.92 (s, 1H), 8.18 (d, J=8.4 Hz, 2H), 8.06 (d, J=8.4 Hz, 2H), 7.62-7.50 (m, 3H), 7.46-7.34 (m, 2H), 6.82 (d, J=8.4 Hz, 1H), 5.09 (s, 2H), 4.39 (s, 1H), 3.12 (s, 3H); HPLC: 98.860%@220 nm; 99.900%@254 nm; LCMS (ESI) [M+H]$^+$ m/z: calcd 372.1, found 371.9.

Example 97. Synthesis of N-[2-amino-5-(4-fluorophenyl)phenyl]-4-[(3,4-difluorophenyl)sulfonimidoyl]benzamide (Compound 221)

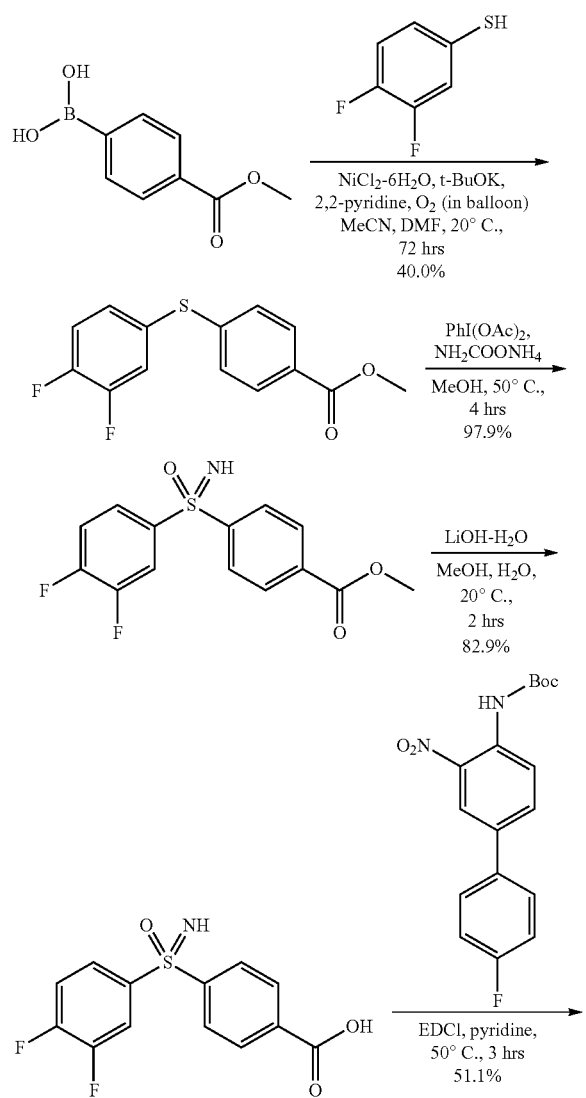

Step 1: Synthesis of methyl 4-(3,4-difluorophenyl)sulfanylbenzoate

To a solution of 3,4-difluorobenzenethiol (1.5 g, 10.3 mmol) in MeCN (10 mL) and DMF (2 mL) was added dichloronickel;hexahydrate (245 mg, 1.03 mmol), 2-(2-pyridyl)pyridine (320 mg, 2.05 mmol) was stirred at 20° C. for 5 minutes. To the mixture was added (4-methoxycarbonylphenyl)boronic acid (2.22 g, 12.3 mmol) and potassium; 2-methylpropan-2-olate (1.73 g, 15.4 mmol). The mixture was stirred at 20° C. for 48 hours under air. But no desired product was observed. It was then stirred at 20° C. for 24 hours under O2 (in balloon). The resulting mixture was concentrated under reduced pressure. The residue was purified by flash chromatography (ISCO®; 20 g AgelaFlash® Silica Flash Column, petroleum ether/EtOAc with EtOAc from 0~20%, flow rate=30 mL/min, 254 nm) to afford methyl 4-(3,4-difluorophenyl)sulfanylbenzoate (1.15 g, 40.0% yield) as white solid. LCMS (ESI) [M+H]$^+$ m/z: calcd 281.0, found 281.0.

Step 2: Synthesis of methyl 4-[(3,4-difluorophenyl)sulfonimidoyl]benzoate

A mixture of methyl 4-(3,4-difluorophenyl)sulfanylbenzoate (1.15 g, 4.10 mmol), [acetoxy(phenyl)-iodanyl] acetate (4.03 g, 12.5 mmol), ammonia;carbamic acid (1.84 g, 23.6 mmol) in MeOH (10 mL) was stirred at 50° C. for 4 hours. The resulting mixture was concentrated under reduced pressure. The residue was purified by flash chromatography (ISCO®; 4 g AgelaFlash® Silica Flash Column, petroleum ether/EtOAc with EtOAc from 0~32%, flow rate=25 mL/min, 254 nm) to afford methyl 4-[(3,4-difluo-

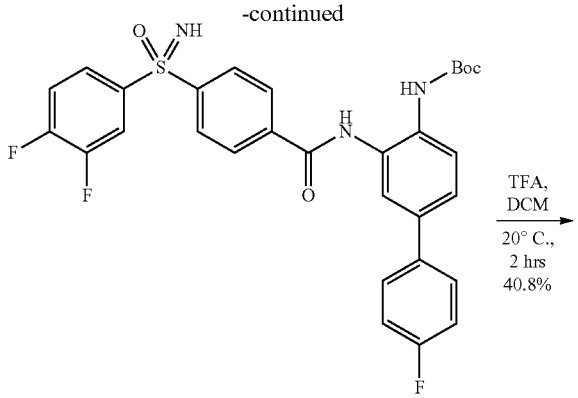

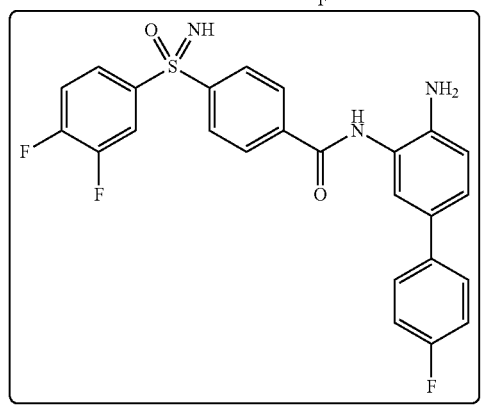

rophenyl)sulfonimidoyl]benzoate (1.25 g, 97.9% yield) as light yellow oil. LCMS (ESI) [M+H]+ m/z: calcd 312.0, found 312.0.

Step 3: Synthesis of 4-[(3,4-difluorophenyl)sulfonimidoyl]benzoic acid

A mixture of methyl 4-[(3,4-difluorophenyl)sulfonimidoyl]benzoate (1.25 g, 4.02 mmol), LiOH—H$_2$O (880 mg, 21.0 mmol) in MeOH (7 mL) and H$_2$O (7 mL) was stirred at 20° C. for 2 hours. The resulting mixture was concentrated under reduced pressure. The mixture was adjusted pH to 4-5 with 1 N HCl aqueous solution. The mixture was filtered. The filter cake was dried under reduced pressure to afford 4-[(3,4-difluorophenyl)sulfonimidoyl]benzoic acid (990 mg, 82.9% yield) as white solid. LCMS (ESI) [M+H]+ m/z: calcd 298.0, found 298.0.

Step 4: Synthesis of tert-butyl N-[2-[[4-[(3,4-difluorophenyl)sulfonimidoyl]benzoyl]amino]-4-(4-fluorophenyl)phenyl]carbamate A mixture of 4-[(3,4-difluorophenyl)sulfonimidoyl]benzoic acid (400 mg, 1.35 mmol), tert-butyl N-[4-(4-fluorophenyl)-2-nitro-phenyl]carbamate (520 mg, 1.56 mmol), EDCI (400 mg, 2.09 mmol) in pyridine (7 mL) was stirred at 50° C. for 3 hours. The resulting mixture was diluted by addition of water (10 mL) and extracted with EtOAc (100 mL*3). The combined organic layer was washed with saturated brine (60 mL*2), dried over anhydrous Na$_2$SO$_4$, filtered and concentrated under reduced pressure. The residue was purified by flash chromatography (ISCO®; 12 g AgelaFlash® Silica Flash Column, petroleum ether/EtOAc with EtOAc from 0~25%, flow rate=35 mL/min, 254 nm) to afford tert-butyl N-[2-[[4-[(3,4-difluorophenyl)sulfonimidoyl]benzoyl]amino]-4-(4-fluorophenyl)phenyl]carbamate (400 mg, 51.1% yield) as light yellow solid. LCMS (ESI) [M+H]+ m/z: calcd 582.2, found 582.1.

Step 5: Synthesis of N-[2-amino-5-(4-fluorophenyl)phenyl]-4-[(3,4-difluorophenyl)sulfonimidoyl]benzamide (Compound 221)

A mixture of tert-butyl N-[2-[[4-[(3,4-difluorophenyl)sulfonimidoyl]benzoyl]amino]-4-(4-fluorophenyl)phenyl]carbamate (400 mg, 0.668 mmol), TFA (2 mL, 26.0 mmol) in DCM (10 mL) was stirred at 20° C. for 2 hours. The mixture was adjusted pH to 7-8 with NaHCO$_3$ aqueous solution. The resulting mixture was quenched by addition of water (20 mL) and extracted with EtOAc (80 mL*3). The combined organic layer was washed with brine (50 mL), dried over anhydrous Na$_2$SO$_4$, filtered and concentrated under reduced pressure. The residue was purified by preparative HPLC (Instrument: Gilson 281, Gilson 333 and 334 Pumps, Gilson 159 UV Detector; Column: Xtimate C18 150*40 mm*5 µm; Mobile phase A: H$_2$O with NH$_3$—H$_2$O and NH$_4$HCO$_3$ (v %); Mobile phase B: MeCN; Gradient: B from 40% to 70% in 20 min, hold 100% B for 5 min; Flow Rate: 30 mL/min; Column Temperature: 30° C.; Wavelength: 220 nm, 254 nm). The fraction was concentrated under reduced pressure and then lyophilized for overnight to afford N-[2-amino-5-(4-fluorophenyl)phenyl]-4-[(3,4-difluorophenyl)sulfonimidoyl]benzamide (135.1 mg, 40.8% yield) as yellow solid. $^1$H NMR (400 MHz, DMSO-d6) δ ppm 9.89 (s, 1H), 8.05-8.31 (m, 5H), 7.83-7.92 (m, 1H), 7.61-7.72 (m, 1H), 7.56 (dd, J=8.6, 5.5 Hz, 2H), 7.48 (d, J=1.8 Hz, 1H), 7.31 (dd, J=8.3, 2.0 Hz, 1H), 7.20 (t, J=8.9 Hz, 2H), 6.85 (d, J=8.5 Hz, 1H), 5.42 (s, 1H), 5.16 (brs, 2H); 19F NMR (376 MHz, DMSO-d6) δ ppm –117.43, –131.56, –135.10; LCMS (ESI) [M+H]+ m/z: calcd 482.1, found 482.0; HPLC: 96.550%@220 nm, 96.840%@254 nm.

Example 98. Synthesis of N-[2-amino-5-(4-fluorophenyl)phenyl]-4-[(3-fluorophenyl)sulfonimidoyl]benzamide (Compound 216)

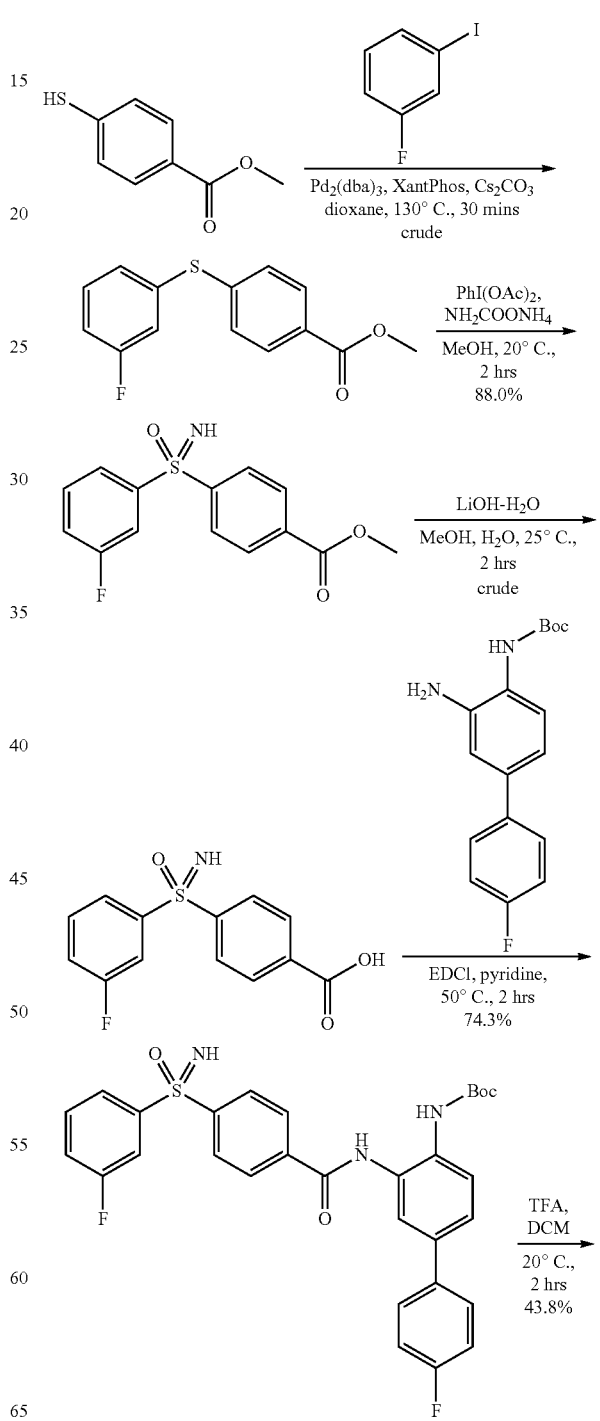

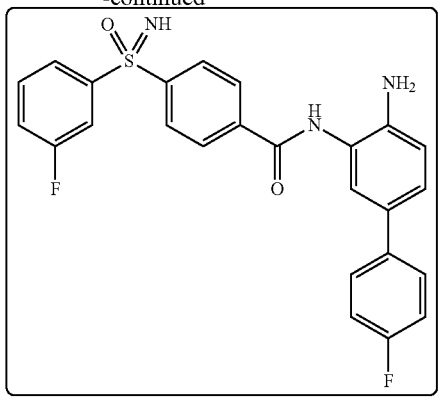

Step 1: Synthesis of methyl 4-(3-fluorophenyl)sulfanylbenzoate

A mixture of methyl 4-sulfanylbenzoate (350 mg, 2.08 mmol), 1-fluoro-3-iodo-benzene (462 mg, 2.08 mmol), Pd$_2$(dba)$_3$ (190.5 mg, 0.208 mmol), (5-diphenylphosphanyl-9,9-dimethyl-xanthen-4-yl)-diphenyl-phosphane (240.8 mg, 0.416 mmol) and Cs$_2$CO$_3$ (2 g, 6.24 mmol) in dioxane (10 mL) was stirred at 130° C. for 30 minutes in microwave. The resulting mixture was quenched by addition of water (10 mL) and extracted with EtOAc (10 mL*3). The combined organic layer was dried over anhydrous Na$_2$SO$_4$, filtered and concentrated under reduced pressure. The residue was purified by flash chromatography (ISCO®; 20 g AgelaFlash® Silica Flash Column, petroleum ether/EtOAc with EtOAc from 0~10%, flow rate=30 mL/min, 254 nm) to afford methyl 4-(3-fluorophenyl)sulfanylbenzoate (518.8 mg, crude) as white solid. $^1$H NMR (400 MHz, DMSO-d6) δ ppm 7.92 (d, J=7.5 Hz, 2H), 7.52 (q, J=7.4 Hz, 1H), 7.38 (d, J=7.8 Hz, 2H), 7.24-7.35 (m, 3H), 3.85 (s, 3H); LCMS (ESI) [M+H]$^+$ m/z: calcd 263.0, found 263.1.

Step 2: Synthesis of methyl 4-[(3-fluorophenyl)sulfonimidoyl]benzoate

A mixture of methyl 4-(3-fluorophenyl)sulfanylbenzoate (498.8 mg, 1.90 mmol), ammonia;carbamic acid (296.9 mg, 3.80 mmol) and [acetoxy(phenyl)-iodanyl] acetate (1.5 g, 4.75 mmol) in MeOH (5 mL) was stirred at 25° C. for 2 hours. The mixture was concentrated under reduced pressure. The residue was purified by flash chromatography (ISCO®; 40 g AgelaFlash® Silica Flash Column, petroleum ether/EtOAc with EtOAc from 0~62%, flow rate=40 mL/min, 254 nm) to afford methyl 4-[(3-fluorophenyl)sulfonimidoyl]benzoate (490.7 mg, 88.0% yield) as white solid. $^1$H NMR (400 MHz, DMSO-d6) δ ppm 8.12 (d, J=2.3 Hz, 4H), 7.76-7.89 (m, 2H), 7.60-7.69 (m, 1H), 7.47-7.54 (m, 1H), 5.42 (s, 1H), 3.88 (s, 3H); LCMS (ESI) [M+H]$^+$ m/z: calcd 294.1, found 294.2.

Step 3: Synthesis of 4-[(3-fluorophenyl)sulfonimidoyl]benzoic acid

A mixture of methyl 4-[(3-fluorophenyl)sulfonimidoyl]benzoate (470.7 mg, 1.60 mmol) and lithium;hydroxide;hydrate (673.4 mg, 16.1 mmol) in H$_2$O (1 mL) and MeOH (0.5 mL) was stirred at 25° C. for 2 hours. The resulting mixture was quenched by addition of water (5 mL) and extracted with dichloromethane:methanol=10:1 (5 mL*3). The combined organic layer was concentrated under reduced pressure to afforded 4-[(3-fluorophenyl)sulfonimidoyl]benzoic acid (416 mg, crude) as white solid. LCMS (ESI) [M+H]$^+$ m/z: calcd 280.0, found 280.7.

Step 4: Synthesis of tert-butyl N-[4-(4-fluorophenyl)-2-[[4-[(3-fluorophenyl)sulfonimidoyl]benzoyl]amino]phenyl]carbamate A mixture of 4-[(3-fluorophenyl)sulfonimidoyl]benzoic acid (100 mg, 0.358 mmol), tert-butyl N-[2-amino-4-(4-fluorophenyl)phenyl]carbamate (97.4 mg, 0.322 mmol) and EDCI (68.6 mg, 0.358 mmol) in pyridine (1 mL) was stirred at 50° C. for 2 hours. The mixture was concentrated under reduced pressure. The residue was purified by flash chromatography (ISCO®; 40 g AgelaFlash® Silica Flash Column, petroleum ether/EtOAc with EtOAc from 0~45%, flow rate=30 mL/min, 254 nm) to afford tert-butyl N-[4-(4-fluorophenyl)-2-[[4-[(3-fluorophenyl)sulfonimidoyl]benzoyl]amino]phenyl]carbamate (150 mg, 74.3% yield) as white solid. LCMS (ESI) [M+H]$^+$ m/z: calcd 564.2, found 564.1.

Step 4: Synthesis of N-[2-amino-5-(4-fluorophenyl)phenyl]-4-[(3-fluorophenyl)sulfonimidoyl]benzamide A mixture of tert-butyl N-[4-(4-fluorophenyl)-2-[[4-[(3-fluorophenyl)sulfonimidoyl]benzoyl]amino]phenyl]carbamate (100 mg, 0.177 mmol) and TFA (0.41 mL, 5.32 mmol) in DCM (2 mL) was stirred at 25° C. for 2 hours. The mixture was concentrated and adjusted pH=8 with 25 wt % NH$_3$—H$_2$O. The residue was purified by preparative HPLC (Instrument: Gilson GX-281 Liquid Handler, Gilson 322 Pump, Gilson 156 UV Detector; Column: 2_Phenomenex Gemini C18 75*40 mm*3 μm; Mobile phase A: H$_2$O with 0.05% NH$_3$—H$_2$O (v %); Mobile phase B: MeCN; Gradient: B from 40% to 70% in 9.5 min, hold 100% B for 1 min; Flow Rate: 30 mL/min; Column Temperature: 30° C.; Wavelength: 220 nm, 254 nm) to afford N-[2-amino-5-(4-fluorophenyl)phenyl]-4-[(3-fluorophenyl)sulfonimidoyl]benzamide (36 mg, 43.8% yield) as white solid. $^1$H NMR (400 MHz, DMSO-d6) δ ppm 9.86 (s, 1H), 8.13 (s, 4H), 7.82 (d, J=1.3 Hz, 2H), 7.61-7.70 (m, 1H), 7.57 (dd, J=8.5, 5.5 Hz, 2H), 7.48 (d, J=2.0 Hz, 2H), 7.31 (dd, J=8.4, 2.1 Hz, 1H), 7.21 (t, J=8.8 Hz, 2H), 6.85 (d, J=8.5 Hz, 1H), 5.36 (s, 1H), 5.15 (s, 2H); 19F NMR (376 MHz, DMSO-d6) δ ppm −110.52, −117.49; LCMS (ESI) [M+H]$^+$ m/z calcd 464.1, found 464.1; HPLC: 97.49%@220 nm, 99.530%@254 nm.

Example 99. Synthesis of N-[2-amino-5-(4-fluorophenyl)phenyl]-4-[(6-cyano-3-pyridyl)sulfonimidoyl]benzamide (Compound 239)

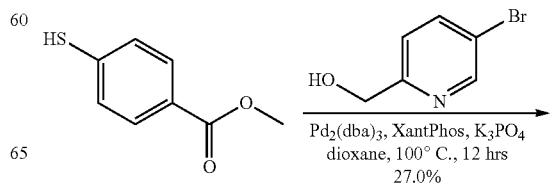

-continued

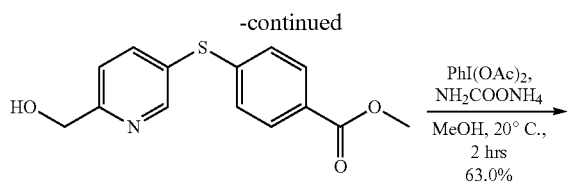
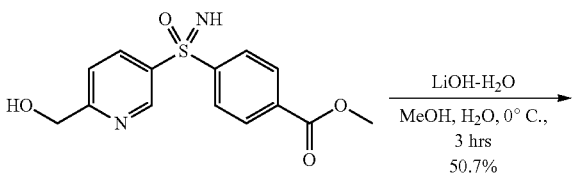
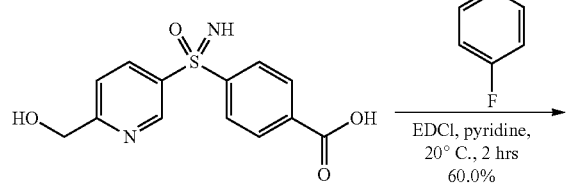
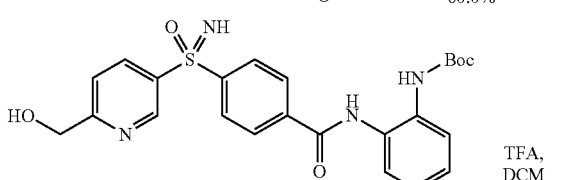
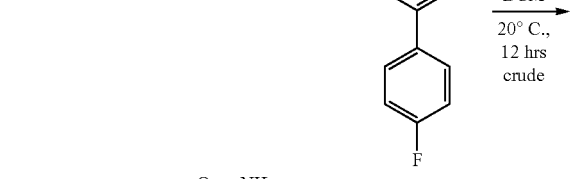
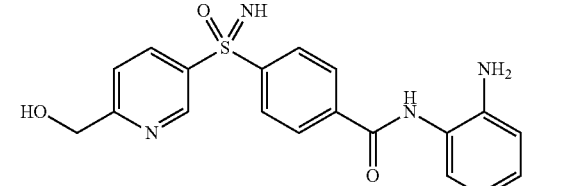
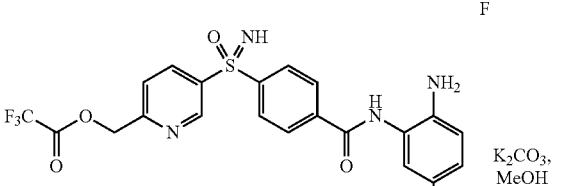

-continued

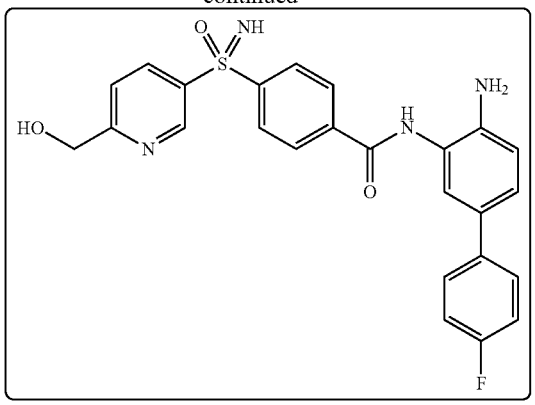

Step 1: Synthesis of methyl 4-[[6-(hydroxymethyl)-3-pyridyl]sulfanyl]benzoate To a solution of (5-bromo-2-pyridyl)methanol (670 mg, 3.56 mmol) and methyl 4-sulfanylbenzoate (500 mg, 2.97 mmol) in dioxane (15 mL) was added $Pd_2(dba)_3$ (136 mg, 0.149 mmol), XantPhos (172 mg, 0.297 mmol) and $K_3PO_4$ (1.90 g, 8.95 mmol). The mixture was stirred under $N_2$ at 100° C. for 12 hours. The resulting mixture was concentrated under reduced pressure. The residue was purified by flash chromatography (ISCO®; 20 g Agela Flash® Silica Flash Column, petroleum ether/EtOAc with EtOAc from 0~75%, flow rate=40 mL/min, 254 nm) to afford methyl 4-[[6-(hydroxymethyl)-3-pyridyl]sulfanyl]benzoate (221 mg, 27% yield) as brown solid. LCMS (ESI) $[M+H]^+$ m/z: calcd 276.1, found 276.1.

Step 2: Synthesis of methyl 4-[[6-(hydroxymethyl)-3-pyridyl]sulfonimidoyl]benzoate To a solution of methyl 4-[[6-(hydroxymethyl)-3-pyridyl]sulfanyl]benzoate (221 mg, 0.803 mmol) in MeOH (10 mL) was added $PhI(OAc)_2$ (650 mg, 2.02 mmol), $NH_2COONH_4$ (130 mg, 1.67 mmol). The mixture was stirred at 20° C. for 2 hours. The resulting mixture was concentrated under reduced pressure. The residue was purified by flash chromatography (ISCO®; 12 g Agela Flash® Silica Flash Column, MeOH/EtOAc with MeOH from 0~10%, flow rate=40 mL/min, 254 nm) to afford methyl 4-[[6-(hydroxymethyl)-3-pyridyl]sulfonimidoyl]benzoate (155 mg, 63% yield) as white solid. LCMS (ESI) $[M+H]^+$ m/z: calcd 307.1, found 307.1.

Step 3: Synthesis of 4-[[6-(hydroxymethyl)-3-pyridyl]sulfonimidoyl]benzoic acid To a solution of methyl 4-[[6-(hydroxymethyl)-3-pyridyl]sulfonimidoyl]benzoate (155 mg, 0.506 mmol) in $H_2O$ (1 mL) and MeOH (3 mL) was added lithium;hydroxide;hydrate (64 mg, 1.53 mmol) at 0° C. The mixture was stirred at 0° C. for 3 hours. The resulting mixture was concentrated under reduced pressure. The resulting mixture was adjusted pH=4 with 2N HCl aqueous solution, and extracted with EtOAc (10 mL*3) and water (30 mL). The combined organic layer was dried over anhydrous $Na_2SO_4$, filtered and concentrated under reduced pressure to give 4-[[6-(hydroxymethyl)-3-pyridyl]sulfonimidoyl]benzoic acid (75 mg, 50.7% yield) as white solid. LCMS (ESI) $[M+H]^+$ m/z: calcd 293.1, found 293.1.

Step 4: Synthesis of tert-butyl N-[4-(4-fluorophenyl)-2-[[4-[[6-(hydroxymethyl)-3-pyridyl]sulfonimidoyl]benzoyl]amino]phenyl]carbamate To a solution of 4-[[6-(hydroxymethyl)-3-pyridyl]sulfonimidoyl]benzoic acid (75 mg, 0.257 mmol) and tert-butyl N-[2-amino-4-(4-fluorophenyl)phenyl]carbamate (120 mg, 0.397 mmol) in pyridine (3 mL) was added EDCI (75 mg, 0.391 mmol). The mixture was stirred at 20° C. for 2 hours. The resulting mixture was concentrated under reduced pressure. The residue was purified by flash chromatography (ISCO®; 12 g Agela Flash® Silica Flash Column, EtOAc/methanol with methanol from 0~5%, flow rate=30 mL/min, 254 nm) to afford tert-butyl N-[4-(4-fluorophenyl)-2-[[4-[[6-(hydroxymethyl)-3-pyridyl]sulfonimidoyl]benzoyl]amino]phenyl]carbamate (88.7 mg, 60.0% yield) as light-yellow solid. LCMS (ESI) [M+H]$^+$ m/z: calcd 577.2, found 577.3.

Step 5: Synthesis of N-[2-amino-5-(4-fluorophenyl)phenyl]-4-[[6-(hydroxymethyl)-3-pyridyl]sulfonimidoyl]benzamide and [5-[[4-[[2-amino-5-(4-fluorophenyl)phenyl]carbamoyl]phenyl]sulfonimidoyl]-2-pyridyl]methyl 2,2,2-trifluoroacetate To a solution of tert-butyl N-[4-(4-fluorophenyl)-2-[[4-[[6-(hydroxymethyl)-3-pyridyl]sulfonimidoyl]benzoyl]amino]phenyl]carbamate (83.7 mg, 0.154 mmol) in DCM (3 mL) was added TFA (0.25 mL, 3.24 mmol). The mixture was stirred at 20° C. for 12 hours. The mixture was adjusted pH=8 with saturated NaHCO$_3$ aqueous solution, extracted with 10% methanol/methylene chloride. The combined organic layer was dried over anhydrous Na$_2$SO$_4$, filtered, and concentrated under reduced pressure to get a mixture of N-[2-amino-5-(4-fluorophenyl)phenyl]-4-[[6-(hydroxymethyl)-3-pyridyl]sulfonimidoyl]benzamide and [5-[[4-[[2-amino-5-(4-fluorophenyl)phenyl]carbamoyl]phenyl]sulfonimidoyl]-2-pyridyl]methyl 2,2,2-trifluoroacetate (300 mg, crude) as yellow solid. LCMS (ESI) [M+H]$^+$ m/z: calcd 477.1, 573.1, found 477.2, 573.2.

Step 6: Synthesis of N-[2-amino-5-(4-fluorophenyl)phenyl]-4-[[6-(hydroxymethyl)-3-pyridyl]sulfonimidoyl]benzamide A mixture of N-[2-amino-5-(4-fluorophenyl)phenyl]-4-[[6-(hydroxymethyl)-3-pyridyl]sulfonimidoyl]benzamide and [5-[[4-[[2-amino-5-(4-fluorophenyl)phenyl]carbamoyl]phenyl]sulfonimidoyl]-2-pyridyl]methyl 2,2,2-trifluoroacetate (270 mg, 0.472 mmol) in MeOH (5 mL) was added K$_2$CO$_3$ (325 mg, 2.35 mmol). The mixture was stirred at 20° C. for 2 hours. The mixture was diluted with H$_2$O (10 mL), and extracted with DCM/MeOH (10:1, 15 mL*3). The combined organic layer was dried over anhydrous Na$_2$SO$_4$, filtered and concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75*40 mm*3 µm; Mobile phase A: water (NH$_4$HCO$_3$)-ACN; Mobile phase B: MeCN; Gradient: B from 27% to 57% in 9.5 min, hold 100% B for 1 min; Flow Rate: 30 mL/min; Column Temperature: 30° C.; Wavelength: 220 nm, 254 nm) to afford N-[2-amino-5-(4-fluorophenyl)phenyl]-4-[[6-(hydroxymethyl)-3-pyridyl]sulfonimidoyl]benzamide (22.1 mg, 9.8% yield) as yellow solid. $^1$H NMR (400 MHz, DMSO-d6) δ ppm 9.85 (brs, 1H), 9.03 (s, 1H), 8.30-8.39 (m, 1H), 8.13 (s, 4H), 7.65 (d, J=8.0 Hz, 1H), 7.52-7.60 (m, 2H), 7.42-7.52 (m, 1H), 7.30 (d, J=8.3 Hz, 1H), 7.20 (t, J=8.7 Hz, 2H), 6.84 (d, J=8.3 Hz, 1H), 5.36-5.72 (m, 2H), 5.14 (brs, 1H), 4.61 (s, 2H). 19F NMR (376 MHz, DMSO-d6) δ ppm–117.478; LCMS (ESI) [M+H]$^+$ m/z: calcd 477.1, found 477.2; HPLC: 98.97%@220 nm; 99.90%@254 nm.

Example 100. Synthesis of N-[2-amino-5-(4-fluorophenyl)phenyl]-4-[(2-methylpyrimidin-5-yl)sulfonimidoyl]benzamide (Compound 235)

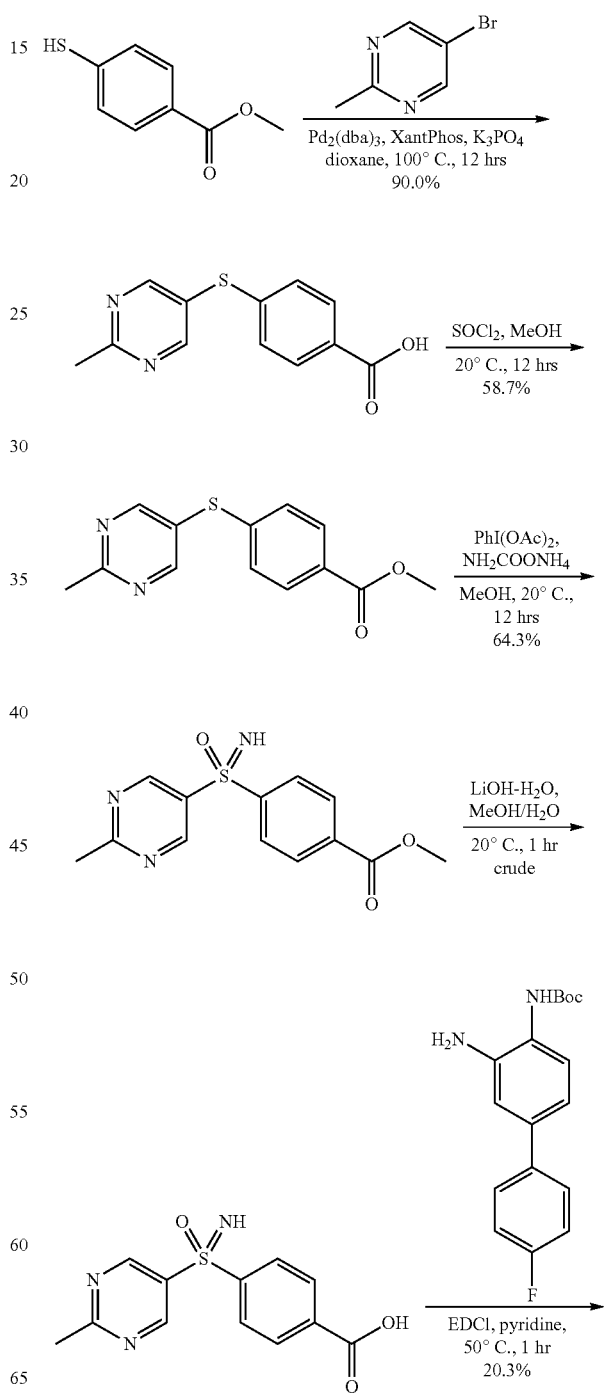

-continued

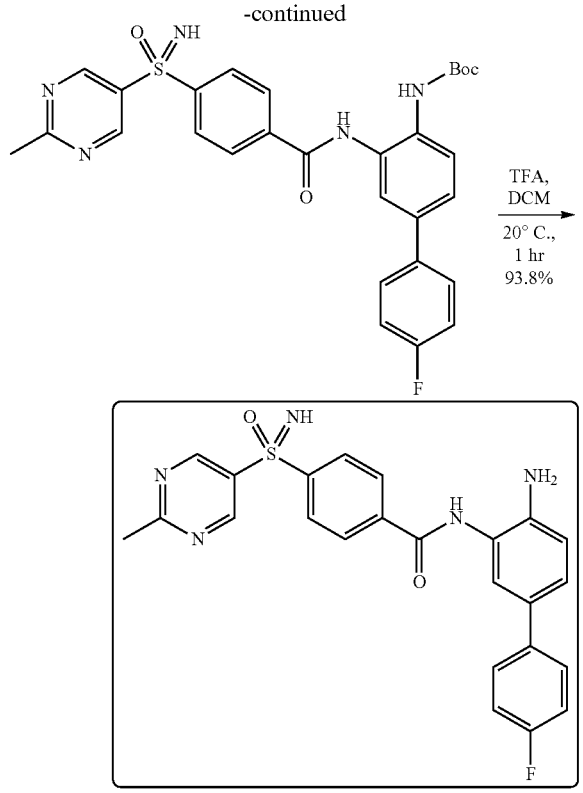

TFA, DCM
20° C., 1 hr
93.8%

Step 1: Synthesis of 4-(2-methylpyrimidin-5-yl)sulfanylbenzoic acid

A mixture of methyl 4-sulfanylbenzoate (5.3 g, 31.5 mmol), 5-bromo-2-methyl-pyrimidine (4.8 g, 27.7 mmol), $Pd_2(dba)_3$ (1.3 g, 1.42 mmol), Xantphos (32.2 g, 55.6 mmol) and $K_3PO_4$ (17.7 g, 83.2 mmol) in dioxane (200 mL) was stirred at 100° C. for 12 hours. The mixture was filtered and the filtrate was extracted with EtOAc (100 mL*3). The 1N HCl aqueous solution was added to combined aqueous layer was added to adjust to pH to 5. Then the mixture was extracted with EtOAc (100 mL*3). The combined organic layer was washed with brine (100 mL*3), dried over anhydrous $Na_2SO_4$, filtered and concentrated under reduced pressure to give 4-(2-methylpyrimidin-5-yl)sulfanylbenzoic acid (6.15 g, 90.0% yield) as off-white solid. $^1H$ NMR (400 MHz, methanol-d4) δ ppm 8.70 (s, 2H), 7.94 (d, J=8.6 Hz, 2H), 7.83 (d, J=8.4 Hz, 2H), 2.69 (s, 3H); LCMS (ESI) $[M+H]^+$ m/z: calcd 247.0, found 247.1.

Step 2: Synthesis of methyl 4-(2-methylpyrimidin-5-yl)sulfanylbenzoate

To a mixture of 4-(2-methylpyrimidin-5-yl)sulfanylbenzoic acid (5 g, 20.3 mmol) in MeOH (50 mL) was added thionyl chloride (15 mL, 0.207 mol) dropwise at 20° C. Then the mixture was stirred at 20° C. for 12 hours. Saturated $Na_2CO_3$ aqueous solution was added to adjust pH to 8. Then the mixture was extracted with DCM (100 mL*3). The combined organic layer was washed with brine (100 mL*3), filtered and concentrated under reduced pressure. The residue was purified by flash chromatography (Biotage®; 12 g AgelaFlash®Silica Flash Column, petroleumether/EtOAc with EtOAc from 0~19%, flow rate=15 mL/min, 254 nm) to afford methyl 4-(2-methylpyrimidin-5-yl)sulfanylbenzoate (3.1 g, 58.7% yield) as white solid. $^1H$ NMR (400 MHz, chloroform-d) δ ppm 8.64-8.73 (m, 2H), 7.47-7.55 (m, 2H), 7.20-7.26 (m, 2H), 3.90 (s, 3H), 2.77 (s, 3H); LCMS (ESI) $[M+H]^+$ m/z: calcd 261.1, found 261.1.

Step 3: Synthesis of methyl 4-[(2-methylpyrimidin-5-yl)sulfonimidoyl]benzoate A mixture of methyl 4-(2-methylpyrimidin-5-yl)sulfanylbenzoate (500 mg, 1.92 mmol), PhI(OAc)₂ (1.55 g, 4.81 mmol) and $NH_2COONH_4$ (300 mg, 3.84 mmol) in MeOH (5 mL) was stirred at 20° C. for 12 hours. The mixture was concentrated under reduced pressure. The residue was purified by flash chromatography (ISCO®; 12 g AgelaFlash®Silica Flash Column, petroleumether/EtOAc with EtOAc from 0~91%, flow rate=30 mL/min, 254 nm) to afford methyl 4-[(2-methylpyrimidin-5-yl)sulfonimidoyl]benzoate (360 mg, 64.3% yield) as white solid. $^1H$ NMR (400 MHz, methanol-d4) δ ppm 9.20 (s, 2H), 8.16-8.24 (m, 4H), 3.93 (s, 3H), 2.74 (m, 3H); LCMS (ESI) $[M+H]^+$ m/z: calcd 292.1, found 292.1.

Step 4: Synthesis of 4-[(2-methylpyrimidin-5-yl)sulfonimidoyl]benzoic acid

A mixture of methyl 4-[(2-methylpyrimidin-5-yl)sulfonimidoyl]benzoate (330 mg, 1.13 mmol) and $LiOH·H_2O$ (250 mg, 5.96 mmol) in $H_2O$ (2 mL) and MeOH (2 mL) was stirred at 20° C. for 1 hour. The resulting mixture was concentrated under reduced pressure. The mixture was diluted with $H_2O$ (10 mL), and adjusted pH=4 with 2N HCl aqueous solution. The mixture was extracted with EtOAc (10 mL*3). The combined organic layer was dried over anhydrous $Na_2SO_4$, filtered and concentrated under reduced pressure to give 4-[(2-methylpyrimidin-5-yl)sulfonimidoyl]benzoic acid (800 mg, crude) as off-white solid. LCMS (ESI) $[M+H]^+$ m/z: calcd 278.1, found 278.1.

Step 5: Synthesis of tert-butyl N-[4-(4-fluorophenyl)-2-[[4-[(2-methylpyrimidin-5-yl)sulfonimidoyl]benzoyl]amino]phenyl]carbamate A mixture of 4-[(2-methylpyrimidin-5-yl)sulfonimidoyl]benzoic acid (780 mg, 2.81 mmol), tert-butyl N-[2-amino-4-(4-fluorophenyl)phenyl]carbamate (850 mg, 2.81 mmol) and EDCI (810 mg, 4.23 mmol) in pyridine (3 mL) was stirred at 50° C. for 1 hour. The mixture was concentrated under recued pressure. The residue was purified by flash chromatography (Biotage®; 12 g AgelaFlash®Silica Flash Column, petroleumether/EtOAc with EtOAc from 0~66%, flow rate=30 mL/min, 254 nm) to afford tert-butyl N-[4-(4-fluorophenyl)-2-[[4-[(2-methylpyrimidin-5-yl)sulfonimidoyl]benzoyl]amino]phenyl]carbamate (320 mg, 20.3% yield) as yellow solid. LCMS (ESI) $[M+H]^+$ m/z: calcd 562.2, found 562.3.

Step 6: Synthesis of N-[2-amino-5-(4-fluorophenyl)phenyl]-4-[(2-methylpyrimidin-5-yl)sulfonimidoyl]benzamide (Compound 235)

To a mixture of tert-butyl N-[4-(4-fluorophenyl)-2-[[4-[(2-methylpyrimidin-5-yl)sulfonimidoyl]benzoyl]amino]phenyl]carbamate (270 mg, 0.481 mmol) in DCM (5 mL) was added TFA (0.8 mL, 10.4 mmol) at 20° C. The mixture was stirred at 20° C. for 1 hour. The mixture was concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 μm; Mobile phase A: H$_2$O with 0.05% NH$_3$—H$_2$O (v %); Mobile phase B: MeCN; Gradient: B from 33% to 63% in 9.5 mins, hold 100% B for 1 min; Flow Rate: 30 mL/min; Column Temperature: 30° C.; Wavelength: 220 nm, 254 nm) to afford N-[2-amino-5-(4-fluorophenyl)phenyl]-4-[(2-methylpyrimidin-5-yl)sulfonimidoyl]benzamide (208 mg, 93.8% yield) as light green solid. $^1$H NMR (400 MHz, methanol-d4) δ ppm 9.22 (s, 2H), 8.23-8.29 (m, 2H), 8.16-8.22 (m, 2H), 7.54-7.61 (m, 2H), 7.49 (d, J=2.0 Hz, 1H), 7.40 (dd, J=8.4, 2.1 Hz, 1H), 7.12 (t, J=8.8 Hz, 2H), 7.07 (d, J=8.3 Hz, 1H), 2.75 (s, 3H); 19F NMR (376 MHz, methanol-d4) δ ppm −118.789; LCMS (ESI) [M+H]$^+$ m/z: calcd 462.1, found 462.2; HPLC: 93.91%@220 nm, 98.05%@254 nm.

Example 101. Synthesis of N-(4-amino-4'-fluoro-[1,1'-biphenyl]-3-yl)-4-(5-chloropyridine-3-sulfonimidoyl)benzamide (Compound 245)

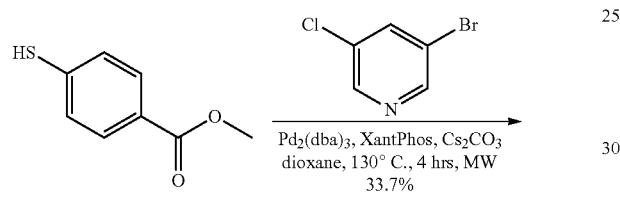

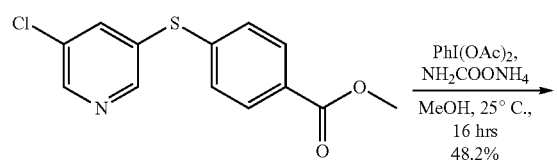

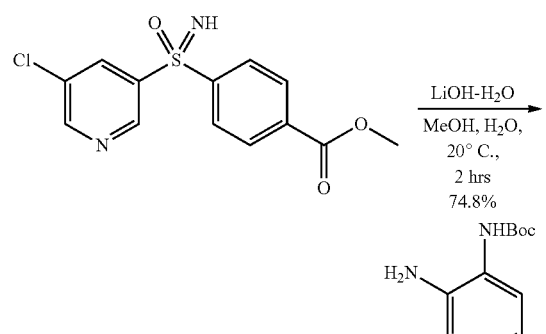

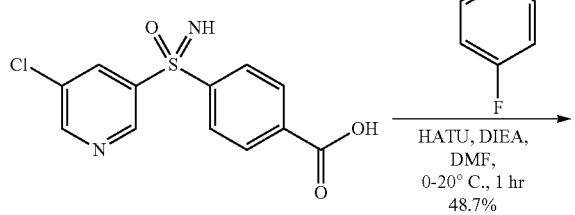

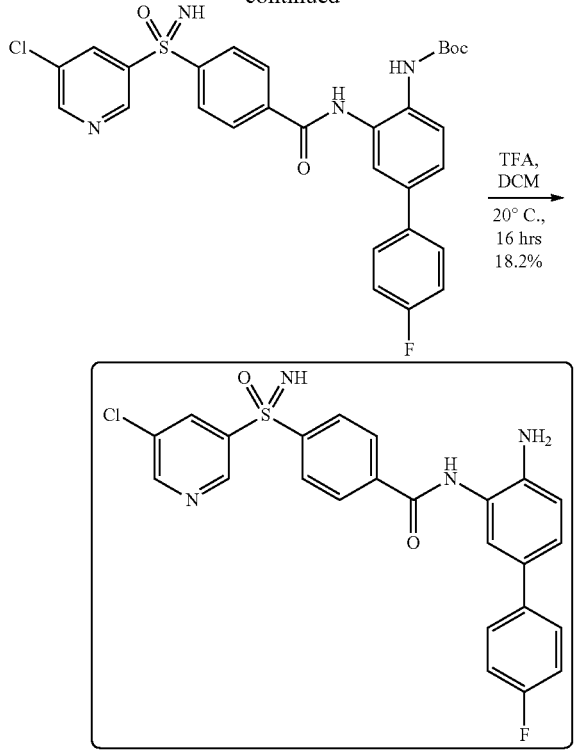

Step 1: Synthesis of methyl 4-[(5-chloro-3-pyridyl) sulfanyl] benzoate

A mixture of methyl 4-sulfanylbenzoate (500 mg, 2.97 mmol), 3-bromo-5-chloro-pyridine (858 mg, 4.46 mmol), Pd$_2$(dba)$_3$ (544.0 mg, 0.595 mmol), XantPhos (688 mg, 1.19 mmol) and Cs$_2$CO$_3$ (2.91 g, 8.92 mmol) in dioxane (10 mL) was purged with N$_2$ gas at ambient temperature for 3 minutes. Then mixture was stirred at 130° C. for 4 hours in Microwave. The resulting mixture was quenched by addition of water (50 mL) and extracted with EtOAc (50 mL*3). The combined organic layer was washed with brine (50 mL), dried over anhydrous Na$_2$SO$_4$, filtered and concentrated under reduced pressure. The residue was purified by flash chromatography (ISCO®; 20 g SepaFlash® Silica Flash Column, petroleum ether/EtOAc with EtOAc from 0~50%, flow rate=30 mL/min, 254 nm) to afford methyl 4-[(5-chloro-3-pyridyl) sulfanyl] benzoate (280 mg, 33.7% yield) as yellow solid. LCMS (ESI) [M+H]$^+$ m/z: calcd 280.0, found 280.1.

Step 2: Synthesis of methyl 4-[(5-chloro-3-pyridyl) sulfonimidoyl]benzoate

To a solution of methyl 4-[(5-chloro-3-pyridyl) sulfanyl] benzoate (280 mg, 1.00 mmol) in MeOH (10 mL) was added NH$_2$COONH$_4$ (156 mg, 2.00 mmol) and PhI(OAc)$_2$ (967 mg, 3.00 mmol) at 0° C. slowly. The mixture was stirred at 25° C. for 16 hours. The reaction mixture was diluted with H$_2$O (100 mL) and extracted with EtOAc (50 mL*3). The combined organic layers were dried over anhydrous Na$_2$SO$_4$, filtered and concentrated under reduced pressure. The residue was purified by flash chromatography (ISCO®; 20 g SepaFlash® Silica Flash Column, petroleum ether/ EtOAc with EtOAc from 0~33%, flow rate=30 mL/min, 254 nm) to give methyl 4-[(5-chloro-3-pyridyl)sulfonimidoyl] benzoate (150 mg, 48.2% yield) as a light yellow solid. LCMS (ESI) [M+H]⁺ m/z: calcd 311.0, found 311.1.

Step 3: Synthesis of 4-[(5-chloro-3-pyridyl)sulfonimidoyl]benzoic acid

To a solution of methyl 4-[(5-chloro-3-pyridyl) sulfonimidoyl] benzoate (70 mg, 0.225 mmol) in MeOH (3 mL) and H₂O (1 mL) was added LiOH—H₂O (18.9 mg, 0.450 mmol). The mixture was stirred at 20° C. for 1 hour. The reaction mixture was concentrated in vacuum to remove MeOH, the aqueous layer was acidified with 2M HCl PH ~4, extracted with EtOAc (3*50 mL). The combined organic layers were washed with brine (30 mL), dried over anhydrous Na₂SO₄, filtered and concentrated in vacuum to give 4-[(5-chloro-3-pyridyl)sulfonimidoyl]benzoic acid (50 mg, 74.8% yield) as light yellow solid. LCMS (ESI) [M+H]⁺ m/z: calcd 297.0, found 297.1.

Step 4: Synthesis of tert-butyl N-[2-[[4-[(5-chloro-3-pyridyl)sulfonimidoyl]benzoyl]amino]-4-(4-fluorophenyl)phen yl]carbamate To a solution of 4-[(5-chloro-3-pyridyl)sulfonimidoyl] benzoic acid (160 mg, 0.539 mmol), DIEA (209 mg, 1.62 mmol) in DMF (10 mL) was added HATU (307 mg, 0.808 mmol). The mixture was stirred at 0° C. for 30 min. Then tert-butyl N-[2-amino-4-(4-fluorophenyl) phenyl]carbamate (179 mg, 0.593 mmol) was added. The mixture was stirred at 20° C. for 1 hour. The reaction was combined poured into water (100 mL), the aqueous layer was filtered and the filter cake was washed with water (10 mL*2). The filter cake was purified by flash chromatography (ISCO®; 20 g SepaFlash® Silica Flash Column, petroleum ether/EtOAc with EtOAc from 0~50%, flow rate=30 mL/min, 254 nm) to give tert-butyl N-[2-[[4-[(5-chloro-3-pyridyl)sulfonimidoyl]benzoyl]amino]-4-(4-fluorophenyl)phen yl]carbamate (200 mg, 48.7% yield) as a light-yellow solid. LCMS (ESI) [M+H]⁺ m/z: calcd 581.2, found 581.3.

Step 5: Synthesis of N-[2-amino-5-(4-fluorophenyl) phenyl]-4-[(5-chloro-3-pyridyl) sulfonimidoyl]benzamide (Compound 245)

To a solution of tert-butyl N-[2-[[4-[(5-chloro-3-pyridyl) sulfonimidoyl] benzoyl]amino]-4-(4-fluorophenyl) phenyl] carbamate (150 mg, 0.258 mmol) in DCM (10 mL) was added TFA (2 mL). The mixture was stirred at 20° C. for 16 hours. The reaction was concentrated under reduced pressure. The mixture adjusted the pH ~8 with saturated aqueous NaHCO₃, extracted with EtOAc (3*50 mL). The combined organic layers were washed with brine (30 mL), dried over anhydrous Na₂SO₄, filtered and concentrated in vacuum. The residue was purified by flash chromatography (ISCO®; 20 g SepaFlash® Silica Flash Column, petroleum ether/ EtOAc with EtOAc from 0~100%, flow rate=15 mL/min, 254 nm) to give impure product (140 mg). The impure product was triturated with H₂O: EtOAc (2/1, 5 mL) to give N-[2-amino-5-(4-fluorophenyl) phenyl]-4-[(5-chloro-3-pyridyl) sulfonimidoyl] benzamide (30 mg, 18.2% yield) as a light yellow solid.

Compound 245: ¹H NMR (400 MHz, DMSO-d6) δ ppm 9.88 (1H, s) 9.08 (1H, s) 8.88 (1H, d, J=1.8 Hz) 8.48 (1H, s) 8.11-8.26 (5H, m) 7.56 (2H, br dd, J=8.2, 5.6 Hz) 7.47 (1H, s) 7.31 (1H, br d, J=8.5 Hz) 7.21 (2H, br t, J=8.7 Hz) 6.84 (1H, d, J=8.3 Hz) 5.69 (1H, s) 5.11-5.23 (2H, m); 19F NMR (377 MHz, DMSO-d6) δ ppm -117.46; LCMS (ESI) [M+H]⁺ m/z: calcd 481.1, found 481; HPLC: 98.39%0@220 nm, 99.19%@254 nm.

Example 102. Synthesis of N-[2-amino-5-(4-fluorophenyl)phenyl]-2-(methylsulfonimidoyl)benzothiophene-6-carboxamide (Compound 236)

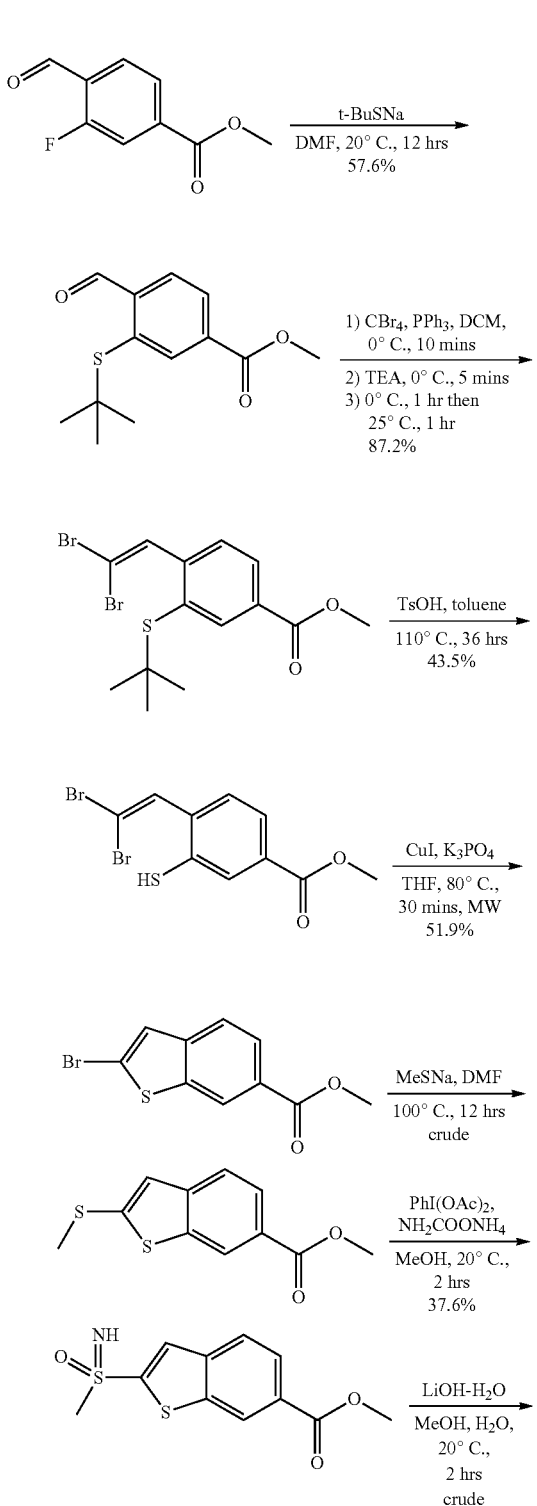

-continued

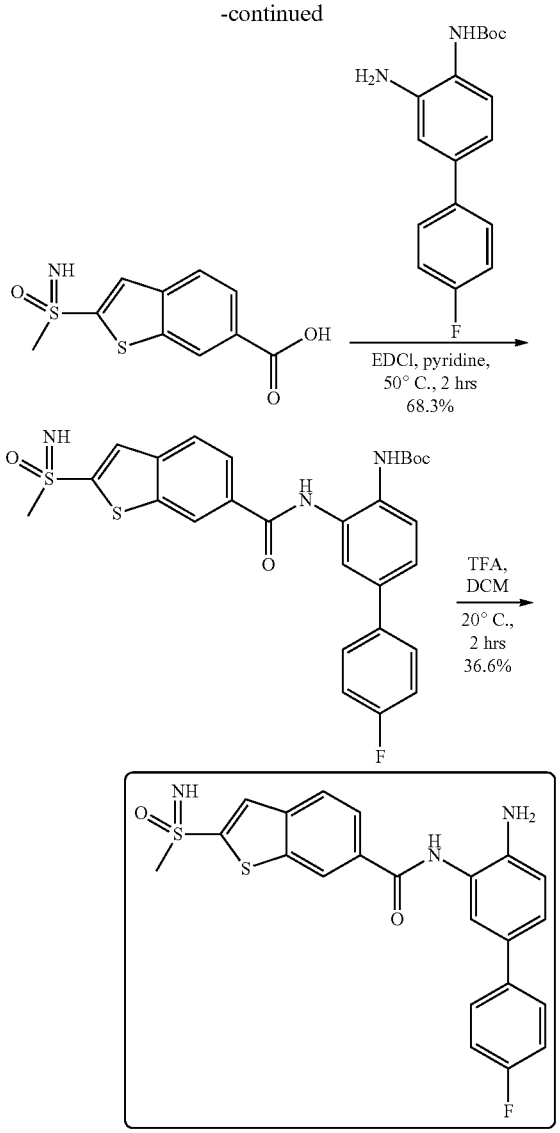

Step 1: Synthesis of methyl 3-tert-butylsulfanyl-4-formyl-benzoate

A mixture of methyl 3-fluoro-4-formyl-benzoate (10 g, 54.9 mmol), sodium;2-methylpropane-2-thiolate (7.39 g, 65.9 mmol) in DMF (100 mL) was stirred at 20° C. for 12 hours. The resulting mixture was quenched by addition of NaClO (20 mL) aqueous solution, then added saturated $Na_2SO_3$ (50 mL) aqueous solution. The mixture was diluted with water (100 mL) and extracted with EtOAc (200 mL*3). The combined organic layer was washed with brine (200 mL), dried over anhydrous $Na_2SO_4$, filtered and concentrated under reduced pressure. The residue was purified by flash chromatography (ISCO®; 80 g AgelaFlash® Silica Flash Column, petroleum ether/EtOAc with EtOAc from 0~10%, flow rate=30 mL/min, 254 nm) to afford methyl 3-tert-butylsulfanyl-4-formyl-benzoate (8 g, 57.6% yield) as light-yellow solid. $^1$H NMR (400 MHz, DMSO-d6) δ ppm 10.67 (s, 1H), 8.11-8.22 (m, 2H), 7.93-8.01 (m, 1H), 3.91 (s, 3H), 1.26 (s, 9H).

Step 2: Synthesis of methyl 3-tert-butylsulfanyl-4-(2,2-dibromovinyl)benzoate A solution of $CBr_4$ (30.2 g, 91.1 mmol) in DCM (200 mL) was added dropwise to a solution of $PPh_3$ (47.8 g, 0.182 mol) in DCM (300 mL) at 0° C. After 10 minutes, TEA (25.4 mL, 0.182 mol) was added dropwise. The mixture was stirred for 5 minutes. methyl 3-tert-butylsulfanyl-4-formyl-benzoate (7.66 g, 30.4 mmol) in DCM (20 mL) was added dropwise. The internal temperature was maintained below 10° C. over the addition of all reagents. The mixture stirred for 1 hour at 0° C. Then the mixture warmed to 25° C. and stirred for 1 hour at 25° C. The reaction was quenched by addition of saturated aqueous $NH_4Cl$ solution (300 mL) and extracted with DCM (300 mL*3). The combined organic layer was washed with saturated $NH_4Cl$ aqueous solution (200 mL), brine (200 mL), dried over anhydrous $Na_2SO_4$, filtered and concentrated under reduced pressure. The residue was purified by flash chromatography (ISCO®; 330 g AgelaFlash® Silica Flash Column, petroleum ether/EtOAc with EtOAc from 0~8%, flow rate=80 mL/min, 254 nm) to afford methyl 3-tert-butylsulfanyl-4-(2,2-dibromovinyl)benzoate (10.8 g, 87.2% yield) as light-yellow solid. $^1$H NMR (400 MHz, DMSO-d6) δ ppm 8.07 (d, J=1.8 Hz, 1H), 8.04 (dd, J=8.0, 1.8 Hz, 1H), 7.95 (s, 1H), 7.80 (d, J=8.0 Hz, 1H), 3.88 (s, 3H), 1.26 (s, 9H).

Step 3: Synthesis of methyl 4-(2,2-dibromovinyl)-3-sulfanyl-benzoate

To a mixture of methyl 3-tert-butylsulfanyl-4-(2,2-dibromovinyl)benzoate (4 g, 9.80 mmol) in toluene (30 mL) was added TsOH (2.55 g, 49.0 mmol). The resulting mixture was stirred at 110° C. for 36 hours. The resulting mixture was quenched by addition of water (100 mL) and extracted with EtOAc (100 mL*3). The combined organic layer was washed with brine (100 mL), dried over anhydrous $Na_2SO_4$, filtered and concentrated under reduced pressure. The residue was purified by flash chromatography (ISCO®; 80 g AgelaFlash® Silica Flash Column, petroleum ether/EtOAc with EtOAc from 0~25%, flow rate=40 mL/min, 254 nm) to afford methyl 4-(2,2-dibromovinyl)-3-sulfanyl-benzoate (1.5 g, 43.5% yield) as yellow solid. $^1$H NMR (400 MHz, DMSO-d6) δ ppm 8.05-8.13 (m, 1H), 7.67-7.81 (m, 1H), 7.63 (s, 1H), 7.53 (d, J=8.0 Hz, 1H), 3.85 (s, 3H), 3.42 (brs, 1H).

Step 4: Synthesis of methyl 2-bromobenzothiophene-6-carboxylate

A mixture of methyl 4-(2,2-dibromovinyl)-3-sulfanyl-benzoate (500 mg, 1.42 mmol), CuI (30 mg, 0.158 mmol), and $K_3PO_4$ (600 mg, 2.83 mmol) in THF (12 mL) was stirred at 80° C. for 30 minutes under nitrogen atmosphere in microwave. The resulting mixture was quenched by addition of water (100 mL) and extracted with EtOAc (100 mL*3). The combined organic layer was washed with brine (100 mL), dried over anhydrous $Na_2SO_4$, filtered and concentrated under reduced pressure. The residue was purified by flash chromatography (ISCO®; 20 g AgelaFlash® Silica Flash Column, petroleum ether/EtOAc with EtOAc from 0~10%, flow rate=30 mL/min, 254 nm) to afford methyl 2-bromobenzothiophene-6-carboxylate (200 mg, 51.9% yield) as yellow solid. LCMS (ESI) [M+H]$^+$ m/z: calcd 272.9, found 272.9.

Step 5: Synthesis of methyl 2-methylsulfanylbenzothiophene-6-carboxylate

A mixture of methyl 2-bromobenzothiophene-6-carboxylate (200 mg, 0.738 mmol), MeSNa (65 mg, 0.927 mmol) in DMF (5 mL) was stirred at 100° C. for 12 hours. The resulting mixture was quenched by addition of NaClO (5 mL) dropwise, and then added Na$_2$SO$_3$ (20 mL), extracted with EtOAc (50 mL*3). The combined organic layer was washed with brine (100 mL*3), dried over anhydrous Na$_2$SO$_4$, filtered and concentrated under reduced pressure. The residue was purified by flash chromatography (ISCO®; 12 g AgelaFlash® Silica Flash Column, petroleum ether/EtOAc with EtOAc from 0~10%, flow rate=30 mL/min, 254 nm) to afford methyl 2-methylsulfanylbenzothiophene-6-carboxylate (300 mg, crude) as white solid. LCMS (ESI) [M+H]$^+$ m/z: calcd 239.0, found 239.0.

Step 6: Synthesis of methyl 2-(methylsulfonimidoyl)benzothiophene-6-carboxylate A mixture of methyl 2-methylsulfanylbenzothiophene-6-carboxylate (200 mg, 0.839 mmol), ammonia;carbamic acid (200 mg, 2.56 mmol), [acetoxy(phenyl)-iodanyl] acetate (810 mg, 2.51 mmol) in MeOH (8 mL) was stirred at 20° C. for 2 hours. The resulting mixture was concentrated under reduced pressure. The residue was purified by flash chromatography (ISCO®; 12 g AgelaFlash® Silica Flash Column, petroleum ether/EtOAc with EtOAc from 0~80%, flow rate=35 mL/min, 254 nm) to afford methyl 2-(methylsulfonimidoyl)benzothiophene-6-carboxylate (85 mg, 37.6% yield) as white solid. LCMS (ESI) [M+H]$^+$ m/z: calcd 270.0, found 269.9.

Step 7: Synthesis of 2-(methylsulfonimidoyl)benzothiophene-6-carboxylic acid A mixture of methyl 2-(methylsulfonimidoyl)benzothiophene-6-carboxylate (80 mg, 0.297 mmol), LiOH—H$_2$O (120 mg, 2.86 mmol) in H$_2$O (1 mL) and MeOH (1 mL) was stirred at 20° C. for 2 hours. The resulting mixture was concentrated under reduced pressure to afford 2-(methylsulfonimidoyl)benzothiophene-6-carboxylic acid (195 mg, crude) as white solid. LCMS (ESI) [M+H]$^+$ m/z: calcd 256.0, found 256.0.

Step 8: Synthesis of tert-butyl N-[4-(4-fluorophenyl)-2-[[2-(methylsulfonimidoyl)benzothiophene-6-carbonyl]amino]phenyl]carbamate A mixture of 2-(methylsulfonimidoyl)benzothiophene-6-carboxylic acid (180 mg, 0.705 mmol), tert-butyl N-[2-amino-4-(4-fluorophenyl)phenyl]carbamate (55 mg, 0.182 mmol), EDCI (55 mg, 0.287 mmol) in pyridine (2 mL) was stirred at 50° C. for 2 hours. The resulting mixture was concentrated under reduced pressure. The residue was purified by flash chromatography (ISCO®; 4 g AgelaFlash® Silica Flash Column, petroleum ether/EtOAc with EtOAc from 0~90%, flow rate=25 mL/min, 254 nm) to afford tert-butyl N-[4-(4-fluorophenyl)-2-[[2-(methylsulfonimidoyl)benzothiophene-6-carbonyl]amino]phenyl]carbamate (65 mg, 68.3% yield) as light yellow solid. LCMS (ESI) [M+H]$^+$ m/z: calcd 540.1, found 540.1.

Step 9: Synthesis of N-[2-amino-5-(4-fluorophenyl)phenyl]-2-(methylsulfonimidoyl)benzothiophene-6-carboxamide (Compound 236)

A mixture of tert-butyl N-[4-(4-fluorophenyl)-2-[[2-(methylsulfonimidoyl)benzothiophene-6-carbonyl]amino]phenyl]carbamate (55 mg, 0.102 mmol), TFA (0.3 mL, 3.89 mmol) in DCM (2 mL) was stirred at 20° C. for 2 hours. The mixture was adjusted pH to 7-8 with saturated NaHCO$_3$ aqueous solution. The resulting mixture was diluted by addition of water (10 mL) and extracted with EtOAc (50 mL*3). The combined organic layer was washed with saturated brine (40 mL*2), dried over anhydrous Na$_2$SO$_4$, filtered and concentrated under reduced pressure. The residue was purified by preparative HPLC (Instrument: Gilson 281, Gilson 333 and 334 Pumps, Gilson 159 UV Detector; Column: Xtimate C18 150*40 mm*5 μm; Mobile phase A: H$_2$O with NH$_3$—H$_2$O and NH$_4$HCO$_3$ (v %); Mobile phase B: MeCN; Gradient: B from 50% to 56% in 13 min, hold 100% B for 4 min; Flow Rate: 30 mL/min; Column Temperature: 30° C.; Wavelength: 220 nm, 254 nm). The fraction was concentrated under reduced pressure and then lyophilized for overnight to afford N-[2-amino-5-(4-fluorophenyl)phenyl]-2-(methylsulfonimidoyl)benzothiophene-6-carboxamide (16.4 mg, 36.6% yield) as light yellow solid. $^1$H NMR (400 MHz, DMSO-d6) δ ppm 9.92 (brs, 1H), 8.75 (s, 1H), 8.13-8.17 (m, 1H), 8.04-8.12 (m, 2H), 7.55-7.63 (m, 2H), 7.53 (d, J=1.8 Hz, 1H), 7.32 (dd, J=8.4, 2.2 Hz, 1H), 7.22 (t, J=8.9 Hz, 2H), 6.87 (d, J=8.3 Hz, 1H), 5.17 (s, 2H), 5.00 (brs, 1H), 3.29 (s, 3H); 19F NMR (376 MHz, DMSO-d6) δ ppm −117.45; LCMS (ESI) [M+H]$^+$ m/z: calcd 440.1, found 440.0; HPLC: 99.880%@220 nm, 1000%@254 nm.

Example 103. Synthesis of N-[2-amino-5-(4-fluorophenyl)phenyl]-4-[(6-methyl-2-pyridyl)sulfonimidoyl]benzamide (Compound 194)

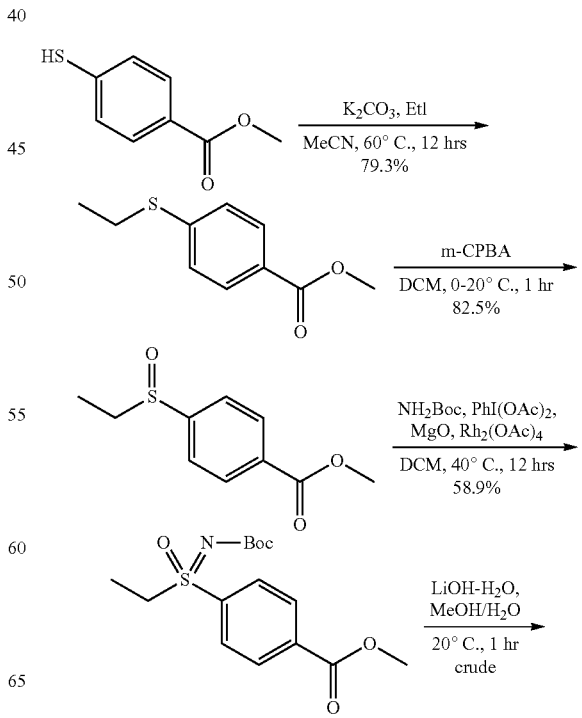

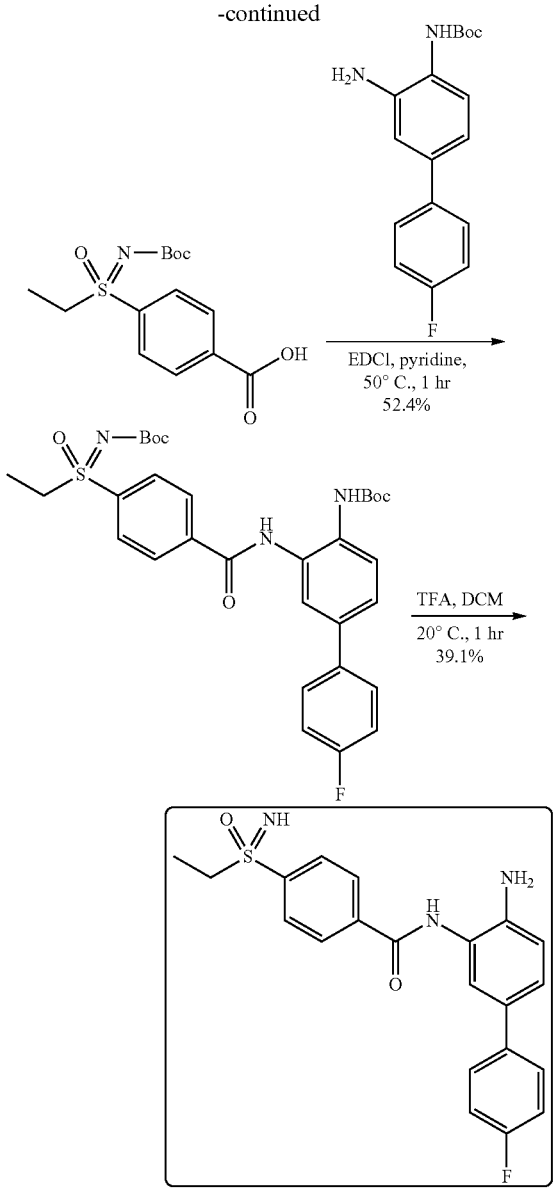

Step 1: Synthesis of methyl 4-ethylsulfanylbenzoate

A mixture of methyl 4-sulfanylbenzoate (300 mg, 1.78 mmol), tripotassium;carbonate (750 mg, 5.43 mmol), iodoethane (0.3 mL, 3.73 mmol) in MeCN (5 mL) was stirred at 60° C. for 12 hours. The resulting mixture was concentrated under reduced pressure. The residue was purified by flash chromatography (ISCO®; 16 g AgelaFlash® Silica Flash Column, petroleum ether/EtOAc with EtOAc from 0~35%, flow rate=30 mL/min, 254 nm) to afford methyl 4-ethylsulfanylbenzoate (370 mg, 79.3% yield) as light-yellow solid. $^1$H NMR (400 MHz, DMSO-d6) δ ppm 7.86 (d, J=8.5 Hz, 2H), 7.39 (d, J=8.5 Hz, 2H), 3.83 (s, 3H), 3.07 (d, J=7.3 Hz, 2H), 1.28 (t, J=7.3 Hz, 3H); LCMS (ESI) [M+H]$^+$ m/z: calcd 197.1, found 197.1.

Step 2: Synthesis of methyl 4-ethylsulfinylbenzoate

To a solution of methyl 4-ethylsulfanylbenzoate (320 mg, 1.63 mmol) in DCM (10 mL) was added m-CPBA (360 mg, 1.77 mmol, 85 wt %) at 0° C. The mixture was stirred at 20° C. for 1 hour. The mixture was quenched by addition of saturated Na$_2$SO$_3$ aqueous solution (30 mL), saturated Na$_2$CO$_3$ aqueous solution (30 mL) and extracted with DCM (30 mL*2). The combined organic layer was dried over anhydrous Na$_2$SO$_4$, filtered and concentrated under reduced pressure. The residue was purified by flash chromatography (ISCO®; 16 g AgelaFlash® Silica Flash Column, petroleum ether/EtOAc with EtOAc from 0~75%, flow rate=40 mL/min, 254 nm) to afford methyl 4-ethylsulfinylbenzoate (330 mg, 82.5% yield) as light-yellow solid. LCMS (ESI) [M+H]$^+$ m/z: calcd 213.1, found 213.1.

Step 3: Synthesis of methyl 4-(N-tert-butoxycarbonyl-S-ethyl-sulfonimidoyl)benzoate To a solution of methyl 4-ethylsulfinylbenzoate (330 mg, 1.55 mmol), NH$_2$Boc (365 mg, 3.12 mmol), [bis(acetoxy)iodo]benzene (750 mg, 2.33 mmol) and MgO (320 mg, 7.75 mmol) in DCM (5 mL) was added dirhodium tetraacetate (30 mg, 0.678 mmol). The reaction mixture was stirred at 40° C. for 12 hours. The resulting mixture was filtered and concentrated under reduced pressure. The residue was purified by flash chromatography (ISCO®; 12 g AgelaFlash® Silica Flash Column, petroleum ether/EtOAc with EtOAc from 0~50%, flow rate=30 mL/min, 254 nm) to afford methyl 4-(N-tert-butoxycarbonyl-S-ethyl-sulfonimidoyl)benzoate (300 mg, 58.9% yield) as white solid. LCMS (ESI) [M+H]$^+$ m/z: calcd 328.1, found 328.1.

Step 4: Synthesis of 4-(N-tert-butoxycarbonyl-S-ethyl-sulfonimidoyl)benzoic acid To a solution of methyl 4-(N-tert-butoxycarbonyl-S-ethyl-sulfonimidoyl)benzoate (50 mg, 0.153 mmol) in H$_2$O (1 mL) and MeOH (3 mL) was added LiOH—H$_2$O (64 mg, 1.53 mmol). The mixture was stirred at 20° C. for 1 hour. The resulting mixture was concentrated under reduced pressure. The mixture was adjusted pH=5 with saturated 2N HCl aqueous solution. The resulting mixture was concentrated under reduced pressure to afford 4-(N-tert-butoxycarbonyl-S-ethyl-sulfonimidoyl)benzoic acid (50 mg, crude) as white solid.

Step 5: Synthesis of tert-butyl N-[[4-[[2-(tert-butoxycarbonylamino)-5-(4-fluorophenyl)phenyl]carbamoyl]phenyl]-ethyl-oxo-sulfanylidene]carbamate A mixture of tert-butyl N-[2-amino-4-(4-fluorophenyl)phenyl]carbamate (45 mg, 0.149 mmol), 4-(N-tert-butoxycarbonyl-S-ethyl-sulfonimidoyl)benzoic acid (50 mg, 0.160 mmol) and 3-(ethyliminomethyleneamino)-N,N-dimethylpropan-1-amine;hydrochloride (46 mg, 0.240 mmol) in pyridine (2 mL) was stirred at 50° C. for 1 hour. The resulting mixture was concentrated under reduced pressure. The residue was purified by flash chromatography (ISCO®; 12 g AgelaFlash® Silica Flash Column, petroleum ether/EtOAc with EtOAc from 0~50%, flow rate=30 mL/min, 254 nm) to afford tert-butyl N-[[4-[[2-(tert-butoxycarbonylamino)-5-(4-fluorophenyl)phenyl]carbamoyl]phenyl]-ethyl-oxo-sulfanylidene]carbamate (50 mg, crude) as yellow oil. LCMS (ESI) [M+H]$^+$ m/z: calcd 598.2, found 598.3.

Step 6: Synthesis of N-[2-amino-5-(4-fluorophenyl)phenyl]-4-(ethylsulfonimidoyl)benzamide (Compound 194)

A mixture of tert-butyl N-[[4-[[2-(tert-butoxycarbonylamino)-5-(4-fluorophenyl)phenyl]carbamoyl]phenyl]- ethyl-oxo-sulfanylidene]carbamate (50 mg, 0.0850 mmol) and TFA (0.2 mL, 2.60 mmol) in DCM (2 mL) was stirred at 20° C. for 1 hour. The resulting mixture was adjusted to pH=8 with 25 wt % NH₃—H₂O. Then the mixture was concentrated under reduced pressure. The residue was purified by preparative HPLC (Instrument: Gilson GX-281 Liquid Handler, Gilson 322 Pump, Gilson 156 UV Detector; 30° C.; Column: 2_Phenomenex Gemini C18 75*40 mm*3 μm; Mobile phase A: water (NH₄HCO₃); Mobile phase B: ACN; Gradient: B from 30% to 60% in 9.5 min, hold 100% B for 1 min; Flow Rate=30 mL/min; Column Temperature: 30° C.; Wavelength: 220 nm, 254 nm) to afford N-[2-amino-5-(4-fluorophenyl)phenyl]-4-(ethylsulfonimidoyl)benzamide (13 mg, 39.1% yield) as light-yellow solid. ¹H NMR (400 MHz, DMSO-d6) δ ppm 9.93 (s, 1H), 8.19 (d, J=8.4 Hz, 2H), 8.00 (d, J=8.4 Hz, 2H), 7.58 (dd, J=8.6, 5.5 Hz, 2H), 7.50 (d, J=1.9 Hz, 1H), 7.32 (dd, J=8.3, 2.2 Hz, 1H), 7.18-7.26 (m, 2H), 6.86 (d, J=8.4 Hz, 1H), 5.16 (s, 2H), 4.37 (s, 1H), 3.19 (q, J=7.4 Hz, 2H), 1.08 (t, J=7.3 Hz, 3H); ¹⁹F NMR (376 MHz, DMSO-d6) δ ppm−117.456; LCMS (ESI) [M+H]⁺ m/z: calcd 398.0, found 398.1; HPLC: 99.86%@220 nm, 100%@254 nm.

Example 104. Synthesis of N-[2-amino-5-(4-fluorophenyl)phenyl]-4-[(2-methyl-3-pyridyl)sulfonimidoyl]benzamide (Compound 190)

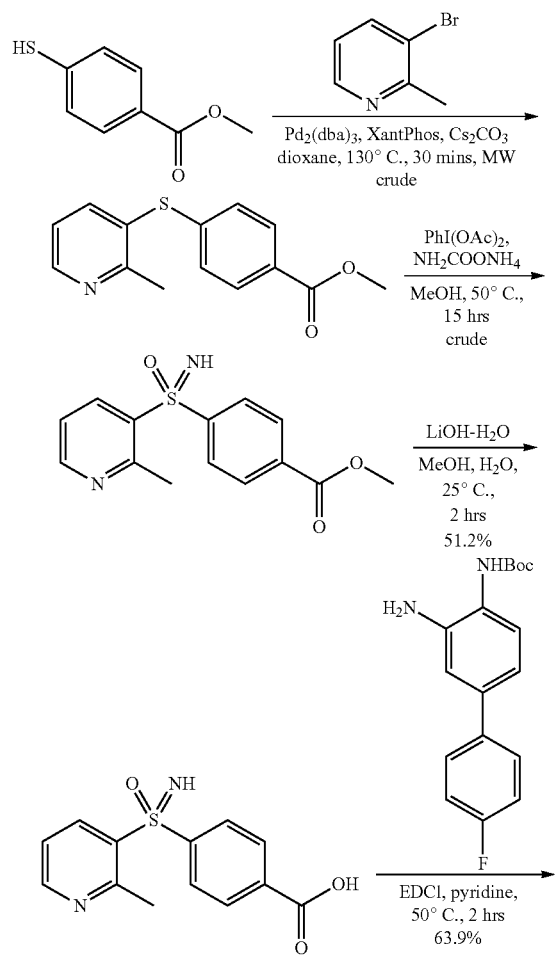

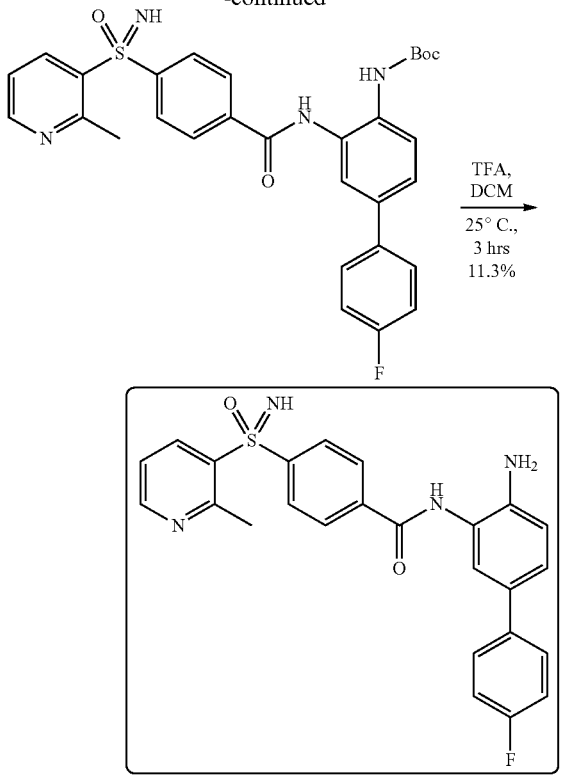

Step 1: Synthesis of methyl 4-[(2-methyl-3-pyridyl)sulfanyl]benzoate

A mixture of methyl 4-sulfanylbenzoate (100 mg, 0.594 mmol), 3-bromo-2-methyl-pyridine (62 mg, 0.360 mmol), (1E,4E)-1,5-diphenylpenta-1,4-dien-3-one;palladium (166 mg, 0.181 mmol), (5-diphenylphosphanyl-9,9-dimethyl-xanthen-4-yl)-diphenyl-phosphane (106 mg, 0.183 mmol), Cs₂CO₃ (353 mg, 1.08 mmol) in dioxane (4 mL) was stirred at 130° C. for 30 minutes under N₂ in microwave. The resulting mixture was quenched by addition of water (20 mL) and extracted with EtOAc (20 mL*3). The combined organic layer was washed with saturated brine (20 mL), dried over anhydrous Na₂SO₄, filtered and concentrated under reduced pressure. The residue was purified by flash chromatography (ISCO®; 40 g AgelaFlash® Silica Flash Column, petroleum ether/EtOAc with EtOAc from 0~40%, flow rate=40 mL/min, 254 nm) to afford methyl 4-[(2-methyl-3-pyridyl)sulfanyl]benzoate (100 mg, crude) as light-yellow oil. LCMS (ESI) [M+H]⁺ m/z: calcd 260.1, found 260.2.

Step 2: Synthesis of methyl 4-[(2-methyl-3-pyridyl)sulfonimidoyl]benzoate

A mixture of methyl 4-[(2-methyl-3-pyridyl)sulfanyl] benzoate (80 mg, 0.309 mmol), ammonia;carbamic acid (153 mg, 1.96 mmol) and [acetoxy(phenyl)-iodanyl] acetate (299 mg, 0.928 mmol) was stirred at 50° C. for 12 hours. Then ammonia;carbamic acid (153 mg, 1.96 mmol) and [acetoxy(phenyl)-iodanyl] acetate (299 mg, 0.928 mmol) was added to the mixture. The mixture was stirred at 50° C. for 3 hours. The mixture was concentrated and the residue was purified by flash chromatography (ISCO®; 20 g AgelaFlash® Silica Flash Column, petroleum ether/EtOAc with EtOAc from 0~15%, flow rate=40 mL/min, 254 nm) to afford methyl 4-[(2-methyl-3-pyridyl)sulfonimidoyl]benzoate (152 mg, crude) as yellow solid. LCMS (ESI) [M+H]+ m/z: calcd 291.1, found 291.1.

Step 3: Synthesis of 4-[(2-methyl-3-pyridyl)sulfonimidoyl]benzoic acid

A mixture of methyl 4-[(2-methyl-3-pyridyl)sulfonimidoyl]benzoate (152 mg, 0.524 mmol) and LiOH—H$_2$O (219.7 mg, 5.24 mmol) in MeOH (1 mL) and H$_2$O (3 mL) was stirred at 25° C. for 2 hours. The mixture was concentrated and adjusted pH=5 with 2N HCl aqueous solution. The resulting mixture was extracted with dichloromethane: isopropyl alcohol=3:1 (10 mL*3). The water phase was concentrated to afford a white solid. The residue was purified by preparative HPLC (Instrument: Gilson GX-281 Liquid Handler, Gilson 322 Pump, Gilson 156 UV Detector; Column: 2_Phenomenex Gemini C18 75*40 mm*3 µm; Mobile phase A: H$_2$O with 0.05% HCl (v %); Mobile phase B: MeCN; Gradient: B from 5% to 35% in 8.5 min, hold 100% B for 2 min; Flow Rate: 30 mL/min; Column Temperature: 30° C.; Wavelength: 220 nm, 254 nm) to afford 4-[(2-methyl-3-pyridyl)sulfonimidoyl]benzoic acid (74 mg, 51.2% yield) as white solid. LCMS (ESI) [M+H]+ m/z: calcd 277.1, found 277.1.

Step 4: Synthesis of tert-butyl N-[4-(4-fluorophenyl)-2-[[4-[(2-methyl-3-pyridyl)sulfonimidoyl]benzoyl]amino]phenyl]carbamate A mixture of 4-[(2-methyl-3-pyridyl)sulfonimidoyl]benzoic acid (54 mg, 0.195 mmol), tert-butyl N-[2-amino-4-(4-fluorophenyl)phenyl]carbamate (59.1 mg, 0.195 mmol) and EDCI (37.5 mg, 0.195 mmol) in pyridine (2 mL) was stirred at 50° C. for 2 hours. The mixture was concentrated and the residue was purified by flash chromatography (ISCO®; 40 g AgelaFlash® Silica Flash Column, petroleum ether/EtOAc with EtOAc from 0~100%, flow rate=60 mL/min, 254 nm) to afford tert-butyl N-[4-(4-fluorophenyl)-2-[[4-[(2-methyl-3-pyridyl)sulfonimidoyl]benzoyl]amino]phenyl]carbamate (70 mg, 63.9% yield) as yellow oil. LCMS (ESI) [M+H]+ m/z: calcd 561.2, found 561.3.

Step 5: Synthesis of N-[2-amino-5-(4-fluorophenyl)phenyl]-4-[(2-methyl-3-pyridyl)sulfonimidoyl]benzamide (Compound 190)

A mixture of tert-butyl N-[4-(4-fluorophenyl)-2-[[4-[(2-methyl-3-pyridyl)sulfonimidoyl]benzoyl]amino]phenyl]carbamate (70 mg, 0.125 mmol) and TFA (0.2 mL, 2.60 mmol) in DCM (2 mL) was stirred at 25° C. for 1 hour. Then TFA (0.2 mL, 2.60 mmol) was added to the mixture. The mixture was stirred at 25° C. for 2 hours. The mixture was concentrated and adjusted pH=8 with NH$_3$—H$_2$O solution. The residue was purified by preparative HPLC (Instrument: Gilson GX-281 Liquid Handler, Gilson 322 Pump, Gilson 156 UV Detector; Column: 2_Phenomenex Gemini C18 75*40 mm*3 µm; Mobile phase A: H$_2$O with 0.05% NH$_3$—H$_2$O (v %); Mobile phase B: MeCN; Gradient: B from 33% to 63% in 10.5 min, hold 100% B for 1 min; Flow Rate: 30 mL/min; Column Temperature: 30° C.; Wavelength: 220 nm, 254 nm) to afford N-[2-amino-5-(4-fluorophenyl)phenyl]-4-[(2-methyl-3-pyridyl)sulfonimidoyl]benzamide (6.5 mg, 11.3% yield) as light-yellow solid. $^1$H NMR (400 MHz, DMSO-d6) δ ppm 9.90 (s, 1H), 8.67 (dd, J=4.8, 1.5 Hz, 1H), 8.56 (dd, J=8.0, 1.5 Hz, 1H), 8.12-8.20 (m, 2H), 8.01 (d, J=8.5 Hz, 2H), 7.52-7.63 (m, 3H), 7.48 (d, J=1.8 Hz, 1H), 7.31 (dd, J=8.3, 2.3 Hz, 1H), 7.21 (t, J=8.9 Hz, 2H), 6.85 (d, J=8.5 Hz, 1H), 5.48 (s, 1H), 5.15 (s, 2H), 2.58 (s, 3H); 19F NMR (376 MHz, DMSO-d6) δ ppm −117.478; LCMS (ESI) [M+H]+ m/z: calcd 461.1, found 461.2; HPLC: 1000%@220 nm; 1000%@254 nm.

Example 105. Synthesis of N-[2-amino-5-(4-fluorophenyl)phenyl]-4-[(4-cyclopropyl-3-pyridyl)sulfonimidoyl]benzamide (Compound 191)

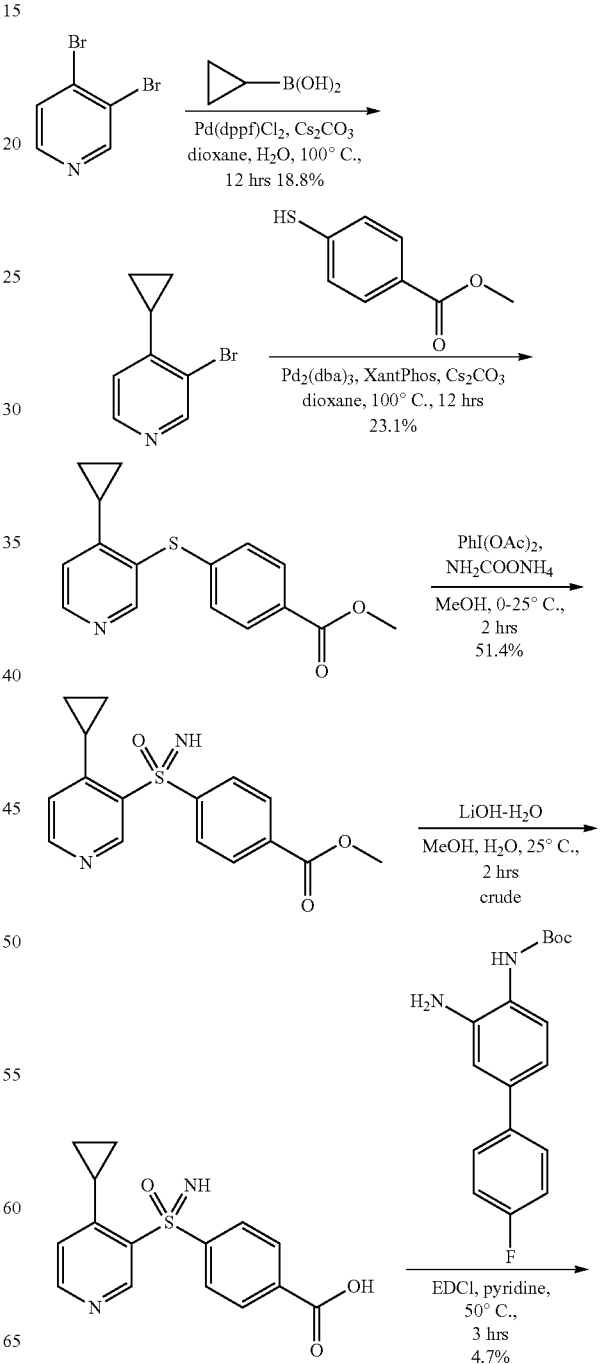

-continued

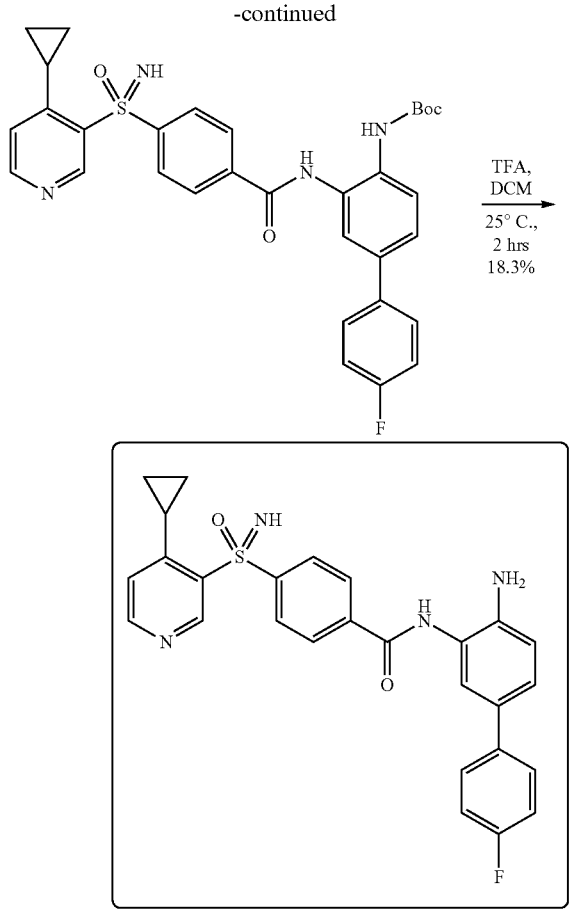

Step 1: Synthesis of 3-bromo-4-cyclopropyl-pyridine

A mixture of 3,4-dibromopyridine (3 g, 12.7 mmol), cyclopropylboronic acid (1.09 g, 12.7 mmol), $Cs_2CO_3$ (12.4 g, 38.0 mmol) and cyclopentyl(diphenyl)phosphane;dichloropalladium;iron (927 mg, 1.27 mmol) in dioxane (24 mL) and $H_2O$ (8 mL) was stirred at 100° C. for 12 hours. The resulting mixture was quenched by addition of water (50 mL) and extracted with EtOAc (50 mL*3). The combined organic layer was washed with brine (50 mL), dried over anhydrous $Na_2SO_4$, filtered and concentrated under reduced pressure. The residue was purified by flash chromatography (ISCO®; 80 g AgelaFlash® Silica Flash Column, petroleum ether/EtOAc with EtOAc from 0~50%, flow rate=80 mL/min, 254 nm) to afford 3-bromo-4-cyclopropyl-pyridine (472 mg, 18.8% yield) as light-yellow oil. $^1H$ NMR (400 MHz, chloroform-d) δ ppm 8.66 (s, 1H), 8.37 (d, J=5.0 Hz, 1H), 6.76 (d, J=5.3 Hz, 1H), 2.16-2.36 (m, 1H), 1.12-1.26 (m, 2H), 0.74-0.92 (m, 2H); LCMS (ESI) $[M+H]^+$ m/z: calcd 198.0, found 198.0.

Step 2: Synthesis of methyl 4-[(4-cyclopropyl-3-pyridyl)sulfanyl]benzoate

A mixture of 3-bromo-4-cyclopropyl-pyridine (708 mg, 3.57 mmol), methyl 4-mercaptobenzoate (722 mg, 4.29 mmol), XantPhos (207 mg, 0.357 mmol), $Pd_2(dba)_3$ (207 mg, 0.357 mmol) and $Cs_2CO_3$ (3.49 g, 10.7 mmol) in dioxane (5 mL) was stirred at 100° C. for 12 hours. The resulting mixture was quenched by addition of water (20 mL) and extracted with EtOAc (20 mL*3). The combined organic layer was washed with brine (20 mL), dried over anhydrous $Na_2SO_4$, filtered and concentrated under reduced pressure. The residue was purified by flash chromatography (ISCO®; 20 g AgelaFlash® Silica Flash Column, petroleum ether/EtOAc with EtOAc from 0~20%, flow rate=40 mL/min, 254 nm) to afford methyl 4-[(4-cyclopropyl-3-pyridyl)sulfanyl]benzoate (236 mg, 23.1% yield) as light-yellow oil. LCMS (ESI) $[M+H]^+$ m/z: calcd 286.1, found 286.1.

Step 3: Synthesis of methyl 4-[(4-cyclopropyl-3-pyridyl)sulfonimidoyl]benzoate To a solution of methyl 4-[(4-cyclopropyl-3-pyridyl)sulfanyl]benzoate (200 mg, 0.701 mmol) in MeOH (2 mL) was added ammonia;carbamic acid (110 mg, 1.40 mmol) and [acetoxy(phenyl)-iodanyl] acetate (564 mg, 1.75 mmol) at 0° C. slowly. The mixture was stirred at 25° C. for 2 hours. The mixture was concentrated and the residue was purified by flash chromatography (ISCO®; 20 g AgelaFlash® Silica Flash Column, petroleum ether/EtOAc with EtOAc from 0~100%, flow rate=40 mL/min, 254 nm) to afford methyl 4-[(4-cyclopropyl-3-pyridyl)sulfonimidoyl]benzoate (114 mg, 51.4% yield) as yellow oil. LCMS (ESI) $[M+H]^+$ m/z: calcd 317.1, found 317.1.

Step 4: Synthesis of 4-[(4-cyclopropyl-3-pyridyl)sulfonimidoyl]benzoic acid

A mixture of methyl 4-[(4-cyclopropyl-3-pyridyl)sulfonimidoyl]benzoate (114 mg, 0.360 mmol) and lithium;hydroxide;hydrate (0.1 mL, 3.60 mmol) in MeOH (0.5 mL) and $H_2O$ (1.5 mL) was stirred at 25° C. for 2 hours. The mixture was concentrated and adjusted pH=5 with 2N HCl aqueous solution. The mixture was concentrated to afford 4-[(4-cyclopropyl-3-pyridyl)sulfonimidoyl]benzoic acid (323 mg, crude) as yellow solid. LCMS (ESI) $[M+H]^+$ m/z: calcd 303.1, found 303.1.

Step 5: Synthesis of tert-butyl N-[2-[[4-[(4-cyclopropyl-3-pyridyl)sulfonimidoyl]benzoyl]amino]-4-(4-fluorophenyl)phenyl]carbamate A mixture of 4-[(4-cyclopropyl-3-pyridyl)sulfonimidoyl]benzoic acid (273 mg, 0.903 mmol), tert-butyl N-[2-amino-4-(4-fluorophenyl)phenyl]carbamate (164 mg, 0.542 mmol) and 3-(ethyliminomethyleneamino)-N,N-dimethyl-propan-1-amine;hydrochloride (208 mg, 1.08 mmol) in pyridine (0.5 mL) was stirred at 50° C. for 3 hours. The mixture was concentrated and the residue was purified by flash chromatography (ISCO®; 40 g AgelaFlash® Silica Flash Column, dichloromethane/methanol ether with methanol ether from 0~67%, flow rate=60 mL/min, 254 nm) to afford tert-butyl N-[2-[[4-[(4-cyclopropyl-3-pyridyl)sulfonimidoyl]benzoyl]amino]-4-(4-fluorophenyl)phenyl]carbamate (25 mg, 4.7% yield) as yellow solid. LCMS (ESI) $[M+H]^+$ m/z: calcd 587.2, found 587.3.

Step 5: Synthesis of N-[2-amino-5-(4-fluorophenyl)phenyl]-4-[(4-cyclopropyl-3-pyridyl)sulfonimidoyl]benzamide (Compound 191)

A mixture of tert-butyl N-[2-[[4-[(4-cyclopropyl-3-pyridyl)sulfonimidoyl]benzoyl]amino]-4-(4-fluorophenyl)phenyl]carbamate (25 mg, 0.0430 mmol) and TFA (0.07 mL, 0.852 mmol) in DCM (2 mL) was stirred at 25° C. for 2 hours. The mixture was concentrated and adjusted pH=8 with 28 wt % NH$_3$—H$_2$O solution. The residue was purified by preparative HPLC (Instrument: Gilson GX-281 Liquid Handler, Gilson 322 Pump, Gilson 156 UV Detector; Column: 2_Phenomenex Gemini C18 75*40 mm*3 μm; Mobile phase A: H$_2$O with 0.05% NH$_3$—H$_2$O (v %); Mobile phase B: MeCN; Gradient: B from 35% to 65% in 9.5 min, hold 100% B for 1 min; Flow Rate: 30 mL/min; Column Temperature: 30° C.; Wavelength: 220 nm, 254 nm) to afford N-[2-amino-5-(4-fluorophenyl)phenyl]-4-[(4-cyclopropyl-3-pyridyl)sulfonimidoyl]benzamide (3.8 mg, 18.3% yield) as yellow solid. $^1$H NMR (400 MHz, methanol-d4) δ ppm 9.33 (s, 1H), 8.58 (d, J=5.1 Hz, 1H), 8.14-8.21 (m, 2H), 8.09-8.14 (m, 2H), 7.50-7.61 (m, 2H), 7.46 (d, J=2.1 Hz, 1H), 7.35 (dd, J=8.3, 2.2 Hz, 1H), 7.06-7.15 (m, 2H), 6.93-7.02 (m, 2H), 2.85-2.97 (m, 1H), 0.96-1.08 (m, 2H), 0.76 (dd, J=5.1, 1.9 Hz, 2H); 19F NMR (376 MHz, DMSO-d6) δ ppm−119.385; LCMS (ESI) [M+H]$^+$ m/z: calcd 487.2, found 487.3; HPLC: 94.27%@220 nm; 100%@254 nm.

Example 106. Synthesis of N-[2-amino-5-(4-fluorophenyl)phenyl]-5-(N-cyclopropyl-S-methyl-sulfonimidoyl)benzofuran-2-carboxamide (Compound 230)

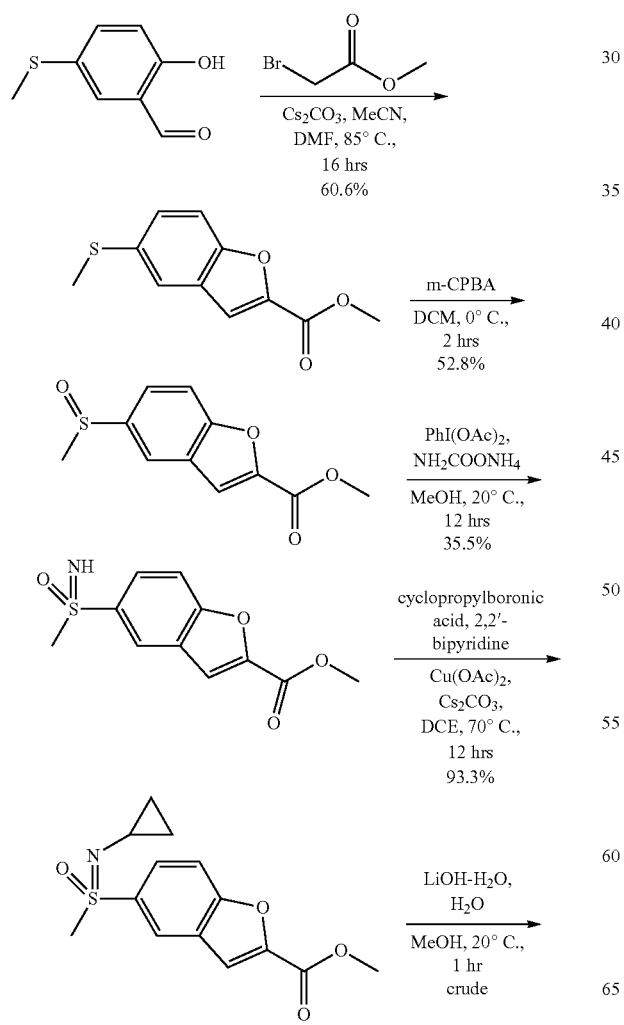

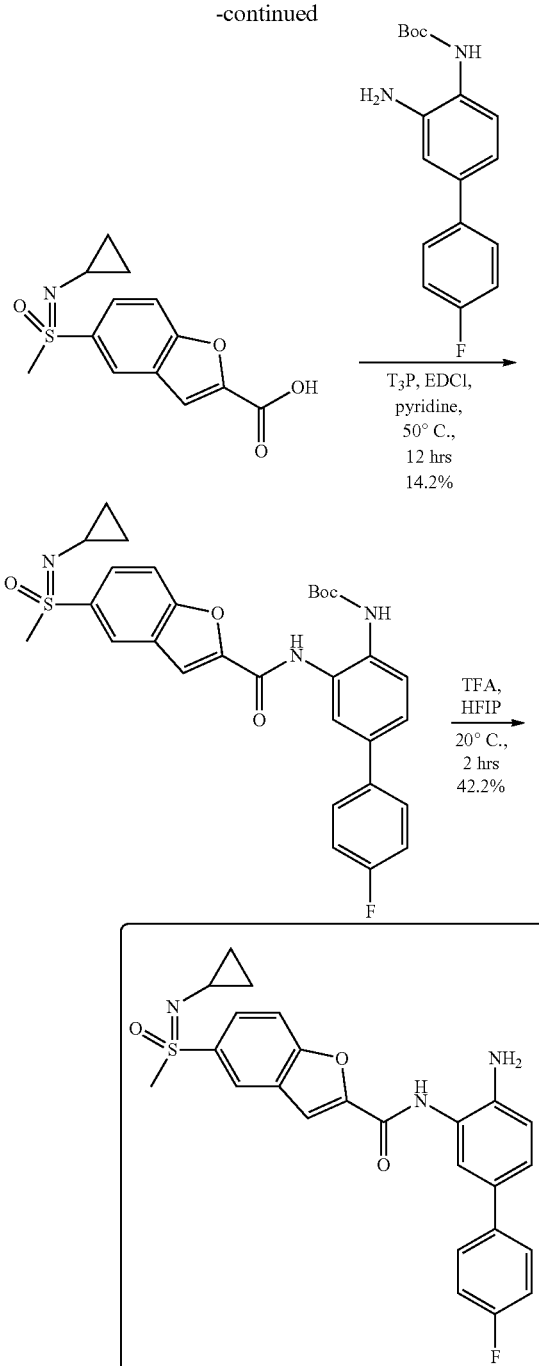

Step 1: methyl 5-methylsulfanylbenzofuran-2-carboxylate

To a solution of 2-hydroxy-5-methylsulfanyl-benzaldehyde (4.50 g, 26.8 mmol) and Cs$_2$CO$_3$ (17.5 g, 53.7 mmol) in MeCN (20 mL) and DMF (20 mL) was added methyl 2-bromoacetate (3 mL, 32.5 mmol) at 20° C. and the mixture was stirred at 85° C. for 16 hours. The reaction mixture was quenched by addition water (50 mL) at 20° C., extracted with EtOAc (50 mL*3). The combined organic layers were washed with brine (30 mL*3), dried over anhydrous Na$_2$SO$_4$, filtered and concentrated under reduced pressure.

The residue was purified by flash silica gel chromatography the residue was purified by flash chromatography (ISCO®; 20 g SepaFlash® Silica Flash Column, petroleum ether/EtOAc with EtOAc from 0~5%, flow rate=30 mL/min, 254 nm) to afford methyl 5-methylsulfanylbenzofuran-2-carboxylate (3.60 g, 60.6% yield) as white solid. $^1$H NMR (400 MHz, chloroform-d) δ ppm 7.59 (d, J=1.76 Hz, 1H), 7.52 (d, J=8.78 Hz, 1H), 7.47 (s, 1H), 7.39-7.44 (m, 1H), 3.96-4.01 (m, 3H), 2.54 (s, 3H); LCMS (ESI) [M+H]$^+$ m/z: calcd 223.0, found 223.1.

Step 2: Synthesis of methyl 5-methylsulfinylbenzofuran-2-carboxylate

To a solution of methyl 5-methylsulfanylbenzofuran-2-carboxylate (1.20 g, 5.40 mmol) in DCM (20 mL) was added m-CPBA (1.32 g, 6.50 mmol, 85% purity) at 20° C. and the mixture was stirred at 0° C. for 2 hours. The reaction mixture was quenched by addition water (50 mL) at 20° C., extracted with EtOAc (50 mL*3). The combined organic layers were washed with brine (50 mL*3), dried over anhydrous $Na_2SO_4$, filtered and concentrated under reduced pressure. The residue was purified by flash silica gel chromatography the residue was purified by flash chromatography (ISCO®; 20 g SepaFlash® Silica Flash Column, petroleum ether/EtOAc with EtOAc from 0~100%, flow rate=30 mL/min, 254 nm) to afford methyl 5-methylsulfinylbenzofuran-2-carboxylate (679 mg, 52.8% yield) was obtained as white solid. $^1$H NMR (400 MHz, chloroform-d) δ ppm 8.12 (d, J=1.51 Hz, 1H), 7.74-7.80 (m, 1H), 7.66-7.72 (m, 1H), 7.62 (s, 1H), 4.03 (s, 3H), 2.80 (s, 3H); LCMS (ESI) [M+H]$^+$ m/z: calcd 239.0, found 239.0.

Step 3: Synthesis of methyl 5-(methylsulfonimidoyl)benzofuran-2-carboxylate

To a solution of methyl 5-methylsulfinylbenzofuran-2-carboxylate (530 mg, 2.22 mmol) and $NH_2COONH_4$ (347 mg, 4.44 mmol) in MeOH (10 mL) was added PhI(OAC)$_2$ (1.79 g, 5.56 mmol) at 20° C. and the mixture was stirred at 20° C. for 12 hours. The reaction mixture was quenched by addition water (30 mL) at 20° C., extracted with EtOAc (30 mL*3). The combined organic layers were washed with brine (15 mL*3), dried over anhydrous $Na_2SO_4$, filtered and concentrated under reduced pressure. The residue was purified by flash silica gel chromatography the residue was purified by flash chromatography (ISCO®; 12 g SepaFlash® Silica Flash Column, petroleum ether/EtOAc with EtOAc from 0~100%, flow rate=30 mL/min, 254 nm) to afford methyl 5-(methylsulfonimidoyl)benzofuran-2-carboxylate (200 mg, 35.5% yield) as yellow solid. $^1$H NMR (400 MHz, chloroform-d) δ ppm 8.45 (d, J=1.51 Hz, 1H), 8.13 (dd, J=8.78, 2.01 Hz, 1H), 7.76 (d, J=8.78 Hz, 1H), 7.64 (d, J=0.75 Hz, 1H), 4.03 (s, 3H), 3.18 (s, 3H); LCMS (ESI) [M+H]$^+$ m/z: calcd 254.0, found 254.1.

Step 4: Synthesis of methyl 5-(N-cyclopropyl-S-methyl-sulfonimidoyl)benzofuran-2-carboxylate To a solution of methyl 5-(methylsulfonimidoyl)benzofuran-2-carboxylate (200 mg, 0.790 mmol), cyclopropylboronic acid (102 mg, 1.19 mmol), $Cs_2CO_3$ (515 mg, 1.58 mmol), 2,2'-bipyridine (123 mg, 0.787 mmol) and Cu(OAc)$_2$ (143 mg, 0.787 mmol) in DCE (4 mL) was stirred at 70° C. for 12 hours. The reaction mixture was quenched by addition $NH_3$—$H_2O$ (20 mL) at 20° C., extracted with DCM (20 mL*3). The combined organic layers were washed with brine (30 mL*3), dried over anhydrous $Na_2SO_4$, filtered and concentrated under reduced pressure. The residue was purified by flash silica gel chromatography the residue was purified by flash chromatography (ISCO®; 12 g SepaFlash® Silica Flash Column, petroleum ether/EtOAc with EtOAc from 0~100%, flow rate=30 mL/min, 254 nm) to afford methyl 5-(N-cyclopropyl-S-methyl-sulfonimidoyl)benzofuran-2-carboxylate (216 mg, 93.3% yield) as yellow oil. $^1$H NMR (400 MHz, chloroform-d) δ ppm 8.39 (d, J=1.51 Hz, 1H), 8.02 (dd, J=8.78, 1.76 Hz, 1H), 7.77 (d, J=8.78 Hz, 1H), 7.64 (d, J=1.00 Hz, 1H), 4.02 (s, 3H), 3.14 (s, 3H), 2.33-2.46 (m, 1H), 0.46-0.67 (m, 2H), 0.38-0.46 (m, 2H); LCMS (ESI) [M+H]$^+$ m/z: calcd 294.0, found 294.0.

Step 5: Synthesis of 5-(N-cyclopropyl-S-methyl-sulfonimidoyl)benzofuran-2-carboxylic acid To a solution of methyl 5-(N-cyclopropyl-S-methyl-sulfonimidoyl)benzofuran-2-carboxylate (160 mg, 0.545 mmol) in $H_2O$ (2.5 mL) and THF (2.5 mL) was added LiOH—$H_2O$ (114 mg, 2.73 mmol) at 20° C. and the mixture was stirred at 20° C. for 1 hour. The reaction solution was concentrated under reduced pressure. 5-(N-cyclopropyl-S-methyl-sulfonimidoyl)benzofuran-2-carboxylic acid (150 mg, crude) was obtained as yellow oil. LCMS (ESI) [M+H]$^+$ m/z: calcd 280.1, found 280.1.

Step 6: Synthesis of tert-butyl N-[2-[[5-(N-cyclopropyl-S-methyl-sulfonimidoyl)benzofuran-2-carbonyl]amino]-4-(4-fluorophenyl)phenyl]carbamate To a solution of 5-(N-cyclopropyl-S-methyl-sulfonimidoyl)benzofuran-2-carboxylic acid (140 mg, 0.501 mmol) and tert-butyl N-[2-amino-4-(4-fluorophenyl)phenyl]carbamate (152 mg, 0.501 mmol) in pyridine (2 mL) was added T3P (957 mg, 1.50 mmol, 50% purity) and the reaction mixture was stirred at 50° C. for 12 hours. The reaction mixture was quenched by addition water (30 mL) at 20° C., extracted with Ethyl acetate (30 mL*3), dried over anhydrous $Na_2SO_4$, filtered and concentrated under reduced pressure. The residue was purified by flash silica gel chromatography the residue was purified by flash chromatography (ISCO®; 12 g SepaFlash® Silica Flash Column, petroleum ether/EtOAc with EtOAc from 50~100%, flow rate=30 mL/min, 254 nm) to afford tert-butyl N-[2-[[5-(N-cyclopropyl-S-methyl-sulfonimidoyl)benzofuran-2-carbonyl]amino]-4-(4-fluorophenyl)phenyl]carbamate (40 mg, 14.2% yield) as yellow oil. LCMS (ESI) [M+H]$^+$ m/z: calcd 564.2, found 564.3.

Step 7: Synthesis of N-[2-amino-5-(4-fluorophenyl)phenyl]-5-(N-cyclopropyl-S-methyl-sulfonimidoyl)benzofuran-2-carboxamide (Compound 230)

To a solution of tert-butyl N-[2-[[5-(N-cyclopropyl-S-methyl-sulfonimidoyl)benzofuran-2-carbonyl]amino]-4-(4-fluorophenyl)phenyl]carbamate (30 mg, 0.053 mmol) in HFIP (1 mL) was added TFA (12.0 mg, 0.106 mmol) at 20° C. and the mixture was stirred at 20° C. for 2 hours. The reaction mixture was concentrated under reduced pressure. The residue was purified by preparative HPLC (Instrument: Gilson GX-281 Liquid Handler, Gilson 322 Pump, Gilson 156 UV Detector; Column: Gemini C18 75×40 mmx 3 μm; Mobile phase A: $H_2O$ with 10 mm $NH_4HCO_3$ (v %); Mobile phase B: ACN; Gradient: B from 6% to 69% in 9.5 min, hold 100% B for 2 min; Flow Rate: 30 mL/min; Column Temperature: 30° C.; Wavelength: 220 nm, 254 nm) to afford N-[2-amino-5-(4-fluorophenyl)phenyl]-5-(N-cyclopropyl-S-methyl-sulfonimidoyl)benzofuran-2-carboxamide (10.4 mg, 42.2% yield) as a yellow solid.

Compound 230: ¹H NMR (400 MHz, chloroform-d) δ ppm 8.37-8.43 (m, 2H), 8.06 (dd, J=8.69, 1.81 Hz, 1H), 7.69-7.78 (m, 3H), 7.50-7.54 (m, 2H), 7.35 (dd, J=8.25, 2.00 Hz, 1H), 7.10 (t, J=8.69 Hz, 2H), 6.96 (d, J=8.25 Hz, 1H), 3.97 (br s, 1H), 3.16 (s, 3H), 2.39-2.45 (m, 1H), 0.41-0.58 (m, 4H); LCMS (ESI) [M+H]⁺ m/z: calcd 464.1, found 464.2; HPLC: 100.00%@220 nm, 100.00%@254 nm.

Example 107. Synthesis of N-[2-amino-5-(4-fluorophenyl)phenyl]-3-(methylsulfonimidoyl)benzofuran-6-carboxamide (Compound 258)

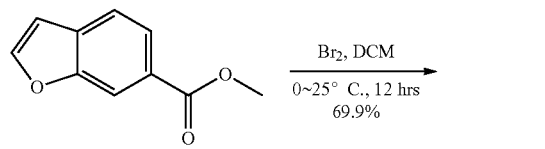

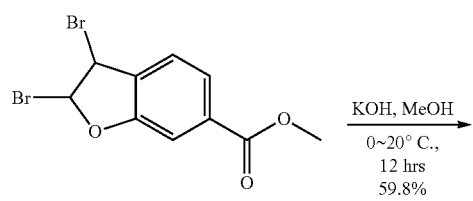

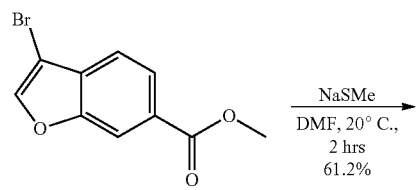

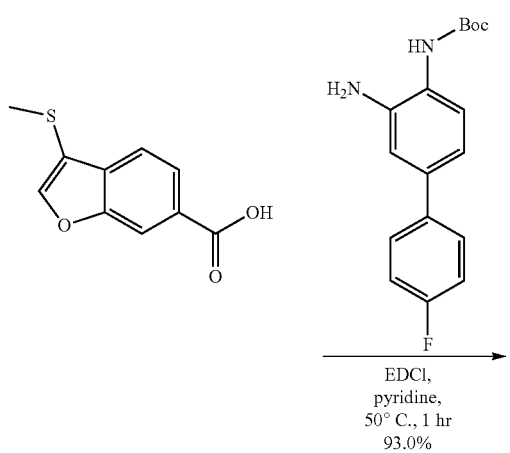

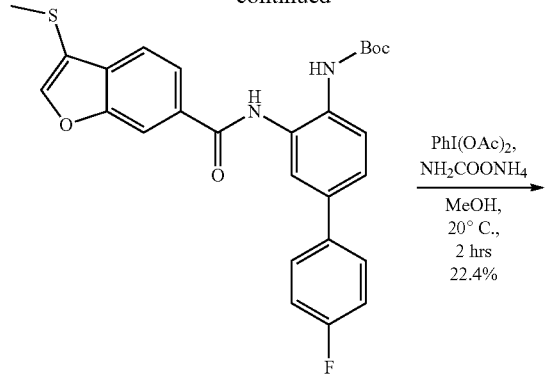

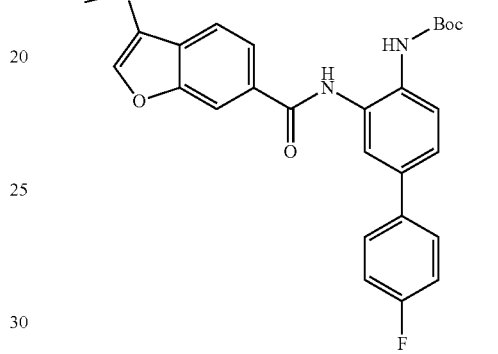

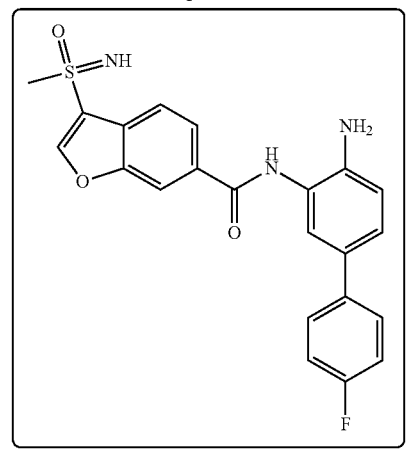

Step 1: Synthesis of methyl 2,3-dibromo-2,3-dihydrobenzofuran-6-carboxylate

To a solution of methyl benzofuran-6-carboxylate (3 g, 17.0 mmol) in DCM (30 mL) was added molecular bromine (5.40 g, 33.8 mmol) at 0° C. and the reaction mixture was stirred at 25° C. for 12 hours. The resulting mixture was quenched by addition of water (50 mL) and extracted with DCM (50 mL*3). The combined organic layers were washed with brine (50 mL*3), dried over anhydrous Na₂SO₄, filtered and concentrated under reduced pressure. Compound methyl 2,3-dibromo-2,3-dihydrobenzofuran-6-carboxylate (4 g, 69.9% yield) as a white solid. ¹H NMR (400 MHz, chloroform-d) δ ppm 7.88 (dd, J=7.88, 1.38 Hz, 1H) 7.70-7.72 (m, 1H) 7.59 (d, J=7.88 Hz, 1H) 6.94 (s, 1H) 5.75 (s, 1H) 3.94 (s, 3H).

Step 2: Synthesis of methyl 3-bromobenzofuran-6-carboxylate

To a solution of methyl 2,3-dibromo-2,3-dihydrobenzofuran-6-carboxylate (11 g, 32.7 mmol) potassium;hydroxide (2.8 g, 49.9 mmol) in THF (30 mL) was added MeOH (6 mL) at 0° C. and the reaction mixture was stirred at 20° C. for 12 hours. The resulting mixture was quenched by addition of water (50 mL) and extracted with EtOAc (50 mL*3). The combined organic layers were washed with brine (50 mL*3), dried over anhydrous $Na_2SO_4$, filtered and concentrated under reduced pressure. The residue was purified by purified by flash chromatography (ISCO®; 80 g AgelaFlash® Silica Flash Column, petroleum ether/EtOAc with EtOAc from 0~70%, flow rate=50 mL/min, 254 nm) to afford compound methyl 3-bromobenzofuran-6-carboxylate (5 g, 59.8% yield) as a white solid. $^1$H NMR (400 MHz, chloroform-d) δ ppm 8.20 (s, 1H) 8.04 (dd, J=8.25, 1.13 Hz, 1H) 7.79 (s, 1H) 7.60 (d, J=8.25 Hz, 1H) 3.96 (s, 3H).

Step 3: Synthesis of 3-methylsulfanylbenzofuran-6-carboxylic acid

To a mixture of methyl 3-bromobenzofuran-6-carboxylate (5 g, 19.6 mmol) in DMF (50 mL) was added sodium;methanethiolate (2.80 g, 39.9 mmol) and The mixture was stirred at 20° C. for 2 hours. The resulting mixture was quenched by addition of water (50 mL) and extracted with DCM (50 mL*3). The combined organic layers were washed with brine (50 mL*3), dried over anhydrous $Na_2SO_4$, filtered and concentrated under reduced pressure. The residue was purified by purified by flash chromatography (ISCO®; 80 g AgelaFlash® Silica Flash Column, petroleum ether/EtOAc with EtOAc from 0~70%, flow rate=50 mL/min, 254 nm) to afford Compound 3-methylsulfanylbenzofuran-6-carboxylic acid (2.5 g 61.2% yield) as a red solid. $^1$H NMR (400 MHz, chloroform-d) δ ppm 8.28 (br d, J=0.75 Hz, 1H) 8.27 (s, 1H) 8.16 (s, 1H) 7.51 (d, J=8.03 Hz, 1H) 6.66 (d, J=0.75 Hz, 1H) 2.61 (s, 3H); LCMS (ESI) [M+H+MeCN]$^+$ m/z: calcd 250.0, found 250.1.

Step 4: Synthesis of tert-butyl N-[4-(4-fluorophenyl)-2-[(3-methylsulfanylbenzofuran-6-carbonyl)amino]phenyl]carbamate To a solution of 3-methylsulfanylbenzofuran-6-carboxylic acid (100 mg, 0.480 mmol), EDCI (187 mg, 0.975 mmol) in pyridine (3 mL) was added tert-butyl N-[2-amino-4-(4-fluorophenyl)phenyl]carbamate (144 mg, 0.476 mmol) and the mixture was stirred at 50° C. for 1 hour under nitrogen atmosphere. The resulting mixture was quenched by addition of water (10 mL) and extracted with EtOAc (10 mL*3). The combined organic layers were washed with brine (10 mL*3), dried over anhydrous $Na_2SO_4$, filtered and concentrated under reduced pressure. The residue was purified by purified by flash chromatography (ISCO®; 12 g AgelaFlash® Silica Flash Column, petroleum ether/EtOAc with EtOAc from 0~70%, flow rate=50 mL/min, 254 nm) to afford tert-butyl N-[4-(4-fluorophenyl)-2-[(3-methylsulfanylbenzofuran-6-carbonyl)amino]phenyl]carbamate (220 mg, 93.0% yield) as a white solid. LCMS (ESI) [M+H]$^+$ m/z: calcd 493.1, found 493.2 (Boc and t-Bu cleaved mass).

Step 5: Synthesis of tert-butyl N-[4-(4-fluorophenyl)-2-[[3-(methylsulfonimidoyl)benzofuran-6-carbonyl]amino]phenyl]carbamate To a solution of tert-butyl N-[4-(4-fluorophenyl)-2-[(3-methylsulfanylbenzofuran-6-carbonyl)amino]phenyl]carbamate (210 mg, 0.426 mmol) in MeOH (3 mL) added PhI(OAc)$_2$ (210 mg, 0.652 mmol), NH$_2$COONH$_4$ (68 mg, 0.871 mmol). The mixture was stirred at 20 C for 2 hours under nitrogen atmosphere. The resulting mixture was quenched by addition of water (10 mL) and extracted with EtOAc (10 mL*3). The combined organic layers were washed with brine (10 mL*3), dried over anhydrous $Na_2SO_4$, filtered and concentrated under reduced pressure. The residue was purified by purified by flash chromatography (ISCO®; 20 g AgelaFlash® Silica Flash Column, petroleum ether/EtOAc with EtOAc from 0~70%, flow rate=50 mL/min, 254 nm) to afford tert-butyl N-[4-(4-fluorophenyl)-2-[[3-(methylsulfonimidoyl)benzofuran-6-carbonyl]amino]phenyl]carbamate (50 mg, 22.4% yield) as a brown solid. $^1$H NMR (400 MHz, chloroform-d) δ ppm 8.28 (s, 1H) 8.11-8.20 (m, 1H) 7.94-8.06 (m, 1H) 7.80 (d, J=8.25 Hz, 1H) 7.44-7.63 (m, 3H) 7.36 (s, 1H) 7.25 (br d, J=4.00 Hz, 1H) 7.12 (s, 2H) 6.65-6.78 (m, 1H) 3.32 (s, 3H) 1.57 (s, 9H).

Step 6: Synthesis of N-[2-amino-5-(4-fluorophenyl)phenyl]-3-(methylsulfonimidoyl)benzofuran-6-carboxamide (Compound 258)

A solution of tert-butyl N-[4-(4-fluorophenyl)-2-[[3-(methylsulfonimidoyl)benzofuran-6-carbonyl]amino]phenyl]carbamate (50 mg, 95.5 μmol) TFA (23 mg, 0.202 mmol) in HFIP (1 mL) was stirred at 20° C. for 2 hours. The residue was purified by preparative HPLC (Instrument: Gilson GX-281 Liquid Handler, Gilson 322 Pump, Gilson 156 UV Detector; Column: Durashell 150×25 mm×5 μm; Mobile phase A: H$_2$O with 0.05% NH$_3$—H$_2$O (v %); Mobile phase B: MeCN; Gradient: B from 39% to 69% in 10 min, hold 100% B for 2.5 min; Flow Rate: 25 mL/min; Column Temperature: 30° C.; Wavelength: 215 nm, 254 nm) to afford N-[2-amino-5-(4-fluorophenyl)phenyl]-3-(methylsulfonimidoyl)benzofuran-6-carboxamide (5.1 mg, 12.7% yield) as a white solid.

Compound 258: $^1$H NMR (400 MHz, DMSO-d6) δ ppm 9.88 (s, 1H) 8.39 (s, 1H) 8.03 (d, J=8.28 Hz, 1H) 7.88-7.96 (m, 1H) 7.64 (s, 1H) 7.60 (dd, J=8.66, 5.40 Hz, 2H) 7.54 (s, 1H) 7.33 (dd, J=8.28, 2.26 Hz, 1H) 7.22 (t, J=8.91 Hz, 2H) 6.88 (d, J=8.53 Hz, 1H) 5.18 (s, 2H) 5.06 (s, 1H) 3.27 (s, 3H); 19F NMR (377 MHz, DMSO-d6) δ ppm −117.48; LCMS (ESI) [M+H]$^+$ m/z: calcd 424.1, found 424.2; HPLC: 97.19%@254 nm, 94.44%@220 nm.

Example 108. Synthesis of N-[2-amino-5-(4-fluorophenyl)phenyl]-5-(N-ethyl-S-methyl-sulfonimidoyl)benzofuran-2-carboxamide (Compound 237)

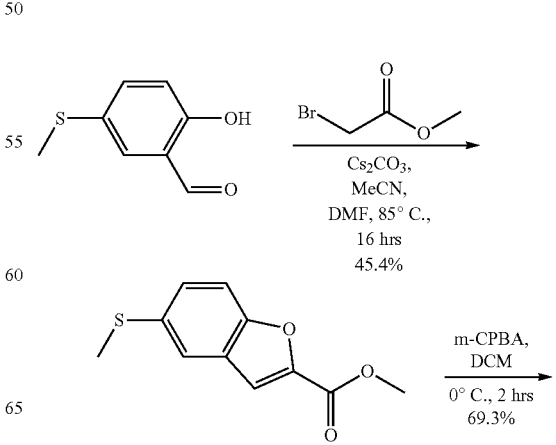

-continued

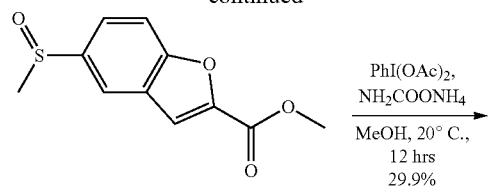
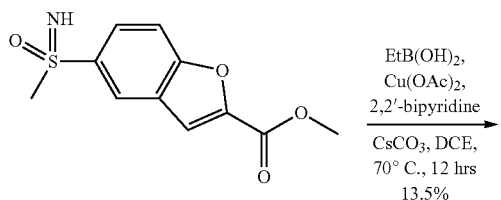
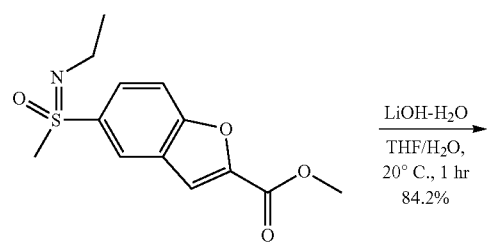
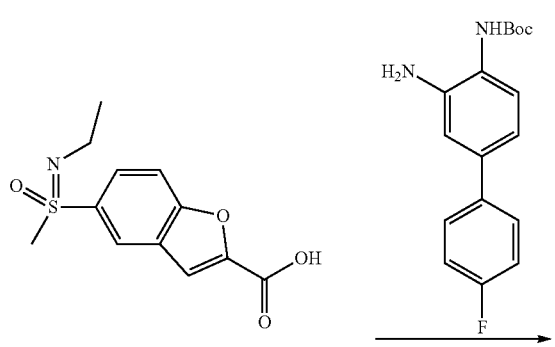
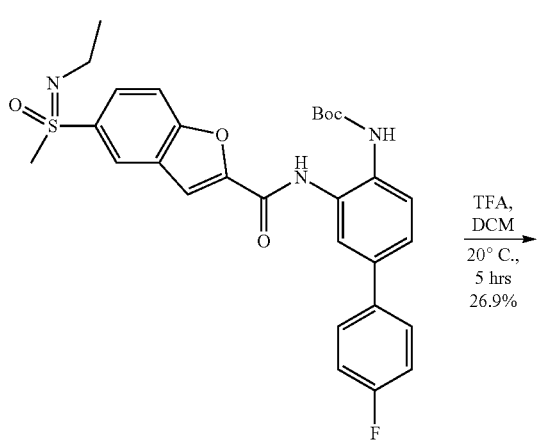

-continued

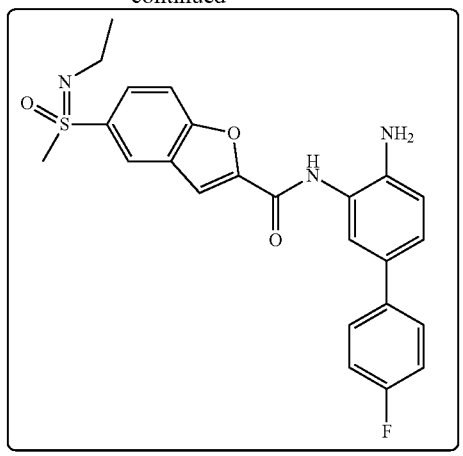

Step 1: methyl 5-methylsulfanylbenzofuran-2-carboxylate

To a solution of 2-hydroxy-5-methylsulfanyl-benzaldehyde (5 g, 29.7 mmol) and $Cs_2CO_3$ (20 g, 61.4 mmol) in MeCN (25 mL) and DMF (25 mL) was added methyl 2-bromoacetate (3.5 mL 37.9 mmol) at 20° C. and the mixture was stirred at 85° C. for 16 hours. The reaction mixture was quenched by addition water (100 mL) at 20° C., extracted with EtOAc (100 mL*3). The combined organic layers were washed with brine (50 mL*3), dried over anhydrous $Na_2SO_4$, filtered and concentrated under reduced pressure. The residue was purified by flash silica gel chromatography the residue was purified by flash chromatography (ISCO®; 40 g SepaFlash® Silica Flash Column, petroleum ether/EtOAc with EtOAc from 0-10%, flow rate=40 mL/min, 254 nm) to afford methyl 5-methylsulfanylbenzofuran-2-carboxylate (3 g, 45.4% yield) as a white solid. $^1$H NMR (400 MHz, chloroform-d) δ ppm 7.59 (d, J=1.75 Hz, 1H), 7.52 (d, J=8.75 Hz, 1H), 7.47 (d, J=0.88 Hz, 1H), 7.41 (dd, J=8.76, 2.00 Hz, 1H), 3.95-4.05 (m, 3H), 2.45-2.60 (m, 3H); LCMS (ESI) [M+H]$^+$ m/z: calcd 223.0, found 223.1.

Step 2: Synthesis of methyl 5-methylsulfinylbenzofuran-2-carboxylate

To a solution of methyl 5-methylsulfanylbenzofuran-2-carboxylate (3 g, 13.5 mmol) in DCM (30 mL) was added m-CPBA (329 mg, 1.62 mmol, 85% purity) at 0° C. and the mixture was stirred at 0° C. for 2 hours. The reaction mixture was quenched by addition water (50 mL) at 20° C., extracted with Ethyl acetate (50 mL*3). The combined organic layers were washed with brine (30 mL*3), dried over anhydrous $Na_2SO_4$, filtered and concentrated under reduced pressure. The residue was purified by flash silica gel chromatography the residue was purified by flash chromatography (ISCO®; 40 g SepaFlash® Silica Flash Column, petroleum ether/ EtOAc with EtOAc from 0~100%, flow rate=40 mL/min, 254 nm) to afford methyl 5-methylsulfinylbenzofuran-2-carboxylate (2.23 g, 69.3% yield) as a white solid. $^1$H NMR (400 MHz, chloroform-d) δ ppm 8.10 (d, J=1.26 Hz, 1H), 7.75 (d, J=8.78 Hz, 1H), 7.65-7.70 (m, 1H), 7.60 (d, J=0.75 Hz, 1H), 4.01 (s, 3H), 2.78 (s, 3H); LCMS (ESI) [M+H]$^+$ m/z: calcd 239.0, found 239.0.

Step 3: Synthesis of methyl 5-(methylsulfonimidoyl)benzofuran-2-carboxylate

To a solution of methyl 5-methylsulfinylbenzofuran-2-carboxylate (2.1 g, 8.81 mmol) and $NH_2COONH_4$ (1.38 g, 17.6 mmol) in MeOH (20 mL) as added PhI(OAC)₂ (7.10 g, 22.0 mmol) at 20° C. and the mixture was stirred at 20° C. for 12 hours. The reaction mixture was quenched by addition water (50 mL) at 20° C., extracted with Ethyl acetate (50 mL*3). The combined organic layers were washed with brine (30 mL*3), dried over anhydrous Na₂SO₄, filtered and concentrated under reduced pressure. The residue was purified by flash silica gel chromatography the residue was purified by flash chromatography (ISCO®; 40 g SepaFlash® Silica Flash Column, petroleum ether/EtOAc with EtOAc from 0~100%, flow rate=40 mL/min, 254 nm) to afford methyl 5-(methylsulfonimidoyl)benzofuran-2-carboxylate (669 mg, 29.9% yield) as a yellow solid. ¹H NMR (400 MHz, chloroform-d) δ ppm 8.45 (d, J=1.51 Hz, 1H) 8.13 (dd, J=8.78, 2.01 Hz, 1H) 7.76 (d, J=8.78 Hz, 1H) 7.64 (d, J=0.75 Hz, 1H) 4.03 (s, 3H) 3.18 (s, 3H); LCMS (ESI) [M+H]⁺ m/z: calcd 254.0, found 254.1.

Step 4: Synthesis of methyl 5-(N-ethyl-S-methyl-sulfonimidoyl)benzofuran-2-carboxylate To a solution of methyl 5-(methylsulfonimidoyl)benzofuran-2-carboxylate (400 mg, 1.58 mmol), ethylboronic acid (175. mg, 2.37 mmol), Cs₂CO₃ (1.03 g, 3.16 mmol), 2,2'-bipyridine (247 mg, 1.58 mmol) and Cu(OAc)₂ (344 mg, 1.90 mmol) in DCE (4 mL) was stirred at 70° C. for 12 hours. The reaction mixture was quenched by addition NH₃—H₂O (20 mL) at 20° C., extracted with DCM (20 mL*3). The combined organic layers were washed with brine (30 mL*3), dried over anhydrous Na₂SO₄, filtered and concentrated under reduced pressure. The reaction mixture was concentrated under reduced pressure. The residue was purified by preparative HPLC (Instrument: Gilson GX-281 Liquid Handler, Gilson 322 Pump, Gilson 156 UV Detector; Column: Gemini C18 75×40 mmx 3 μm; Mobile phase A: H₂O with 10 mm NH₄HCO₃ (v %); Mobile phase B: ACN; Gradient: B from 6% to 55% in 9.5 min, hold 100% B for 2 min; Flow Rate: 30 mL/min; Column Temperature: 30° C.; Wavelength: 220 nm, 254 nm) to afford methyl 5-(N-ethyl-S-methyl-sulfonimidoyl)benzofuran-2-carboxylate (60 mg, 13.5% yield) as yellow oil. ¹H NMR (400 MHz, chloroform-d) δ ppm 8.37-8.43 (m, 2H), 7.72-7.78 (m, 2H), 7.70 (d, J=1.76 Hz, 1H), 7.50-7.55 (m, 2H), 3.16 (s, 3H), 0.79-0.87 (m, 2H), 0.39-0.53 (m, 3H).

Step 5: Synthesis of 5-(N-ethyl-S-methyl-sulfonimidoyl)benzofuran-2-carboxylic acid To a solution of methyl 5-(N-ethyl-S-methyl-sulfonimidoyl)benzofuran-2-carboxylate (50 mg, 0.178 mmol) in THF (0.5 mL) and H₂O (0.5 mL) was added LiOH—H₂O (37.3 mg, 0.889 mmol) at 20° C. and the mixture was stirred at 20° C. for 1 hour. The reaction mixture was acidified with 0.5 N of HCl aqueous solution to the pH ~5. The reaction mixture was quenched by addition water (30 mL) at 20° C., extracted with DCM and i-PrOH (3:1, 20 mL*5). The combined organic layers dried over anhydrous Na₂SO₄, filtered and concentrated under reduced pressure. The mixture was concentrated under reduced pressure to obtain 5-(N-ethyl-S-methyl-sulfonimidoyl)benzofuran-2-carboxylic acid (40 mg, 84.2% yield) as a yellow oil. ¹H NMR (400 MHz, chloroform-d) δ ppm 8.50 (d, J=1.76 Hz, 1H), 8.11 (dd, J=8.91, 1.88 Hz, 1H), 7.82 (d, J=8.87 Hz, 1H), 7.71 (s, 1H), 3.39 (s, 3H), 2.92-3.18 (m, 2H), 1.25-1.28 (m, 3H); LCMS (ESI) [M+H]⁺ m/z: calcd 268.1, found 268.1.

Step 6: Synthesis of tert-butyl N-[2-[[5-(N-ethyl-S-methyl-sulfonimidoyl)benzofuran-2-carbonyl]amino]-4-(4-fluorophenyl)phenyl]carbamate To a solution of 5-(N-ethyl-S-methyl-sulfonimidoyl)benzofuran-2-carboxylic acid (50 mg, 0.187 mmol) and tert-butyl N-[2-amino-4-(4-fluorophenyl)phenyl]carbamate (56.5 mg, 0.187 mmol) in pyridine (1 mL) was added EDCI (35.7 mg, 0.187 mmol) and T3P (357.10 mg, 0.561 mmol, 50% purity) at 20° C. and the mixture was stirred at 50° C. for 24 hours. The reaction mixture was quenched by addition water (10 mL) at 20° C., extracted with Ethyl acetate (10 mL*3), dried over anhydrous Na₂SO₄, filtered and concentrated under reduced pressure. The residue was purified by flash silica gel chromatography the residue was purified by flash chromatography (ISCO®; 4 g SepaFlash® Silica Flash Column, petroleum ether/EtOAc with EtOAc from 30~100%, flow rate=20 mL/min, 254 nm) to afford tert-butyl N-[2-[[5-(N-ethyl-S-methyl-sulfonimidoyl)benzofuran-2-carbonyl]amino]-4-(4-fluorophenyl)phenyl]carbamate (50 mg, 48.5% yield) as yellow oil. LCMS (ESI) [M+H]⁺ m/z: calcd 552.2, found 552.3.

Step 7: Synthesis of N-[2-amino-5-(4-fluorophenyl)phenyl]-5-(N-ethyl-S-methyl-sulfonimidoyl)benzofuran-2-carboxamide (Compound 237)

To a solution of tert-butyl N-[2-[[5-(N-ethyl-S-methyl-sulfonimidoyl)benzofuran-2-carbonyl]amino]-4-(4-fluorophenyl)phenyl]carbamate (40 mg, 0.073 mmol) in HFIP (1 mL) was added TFA (83 mg, 0.725 mmol) at 20° C. and the mixture was stirred at 20° C. for 5 hours The mixture was adjusted pH-8 with saturated NaHCO₃ aqueous solution. The residue was purified by preparative HPLC (Instrument: Gilson GX-281 Liquid Handler, Gilson 322 Pump, Gilson 156 UV Detector; Column: 2_Phenomenex Gemini C18 75*40 mm*3 μm; Mobile phase A: H₂O with 10 mm NH₄HCO₃ (v %); Mobile phase B: ACN; Gradient: B from 4% to 72% in 7.8 min, hold 100% B for 1 min; Flow Rate: 30 mL/min; Column Temperature: 30° C.; Wavelength: 220 nm, 254 nm) to afford N-[2-amino-5-(4-fluorophenyl)phenyl]-5-(N-ethyl-S-methyl-sulfonimidoyl)benzofuran-2-carboxamide (8.8 mg, 26.9% yield) as yellow solid.

Compound 237: ¹H NMR (400 MHz, chloroform-d) δ ppm 8.33-8.40 (m, 2H), 8.02 (dd, J=8.53, 1.76 Hz, 1H), 7.68-7.77 (m, 3H), 7.52 (dd, J=8.78, 5.27 Hz, 2H), 7.35 (dd, J=8.28, 2.01 Hz, 1H), 7.11 (t, J=8.66 Hz, 2H), 6.96 (d, J=8.03 Hz, 1H), 3.16 (s, 3H), 3.02-3.13 (m, 1H), 2.84-2.96 (m, 1H), 1.19-1.34 (m, 4H); [M+H]⁺ m/z: calcd 452.1, found 452.2. HPLC: 100.00%@220 nm, 100.00%@254 nm.

Example 109. Synthesis of N-[2-amino-5-(4-fluorophenyl)phenyl]-4-(pyrazin-2-ylsulfonimidoyl)benzamide (Compound 195)

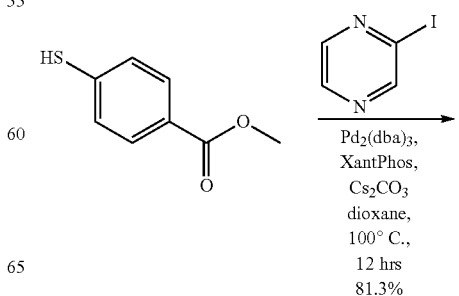

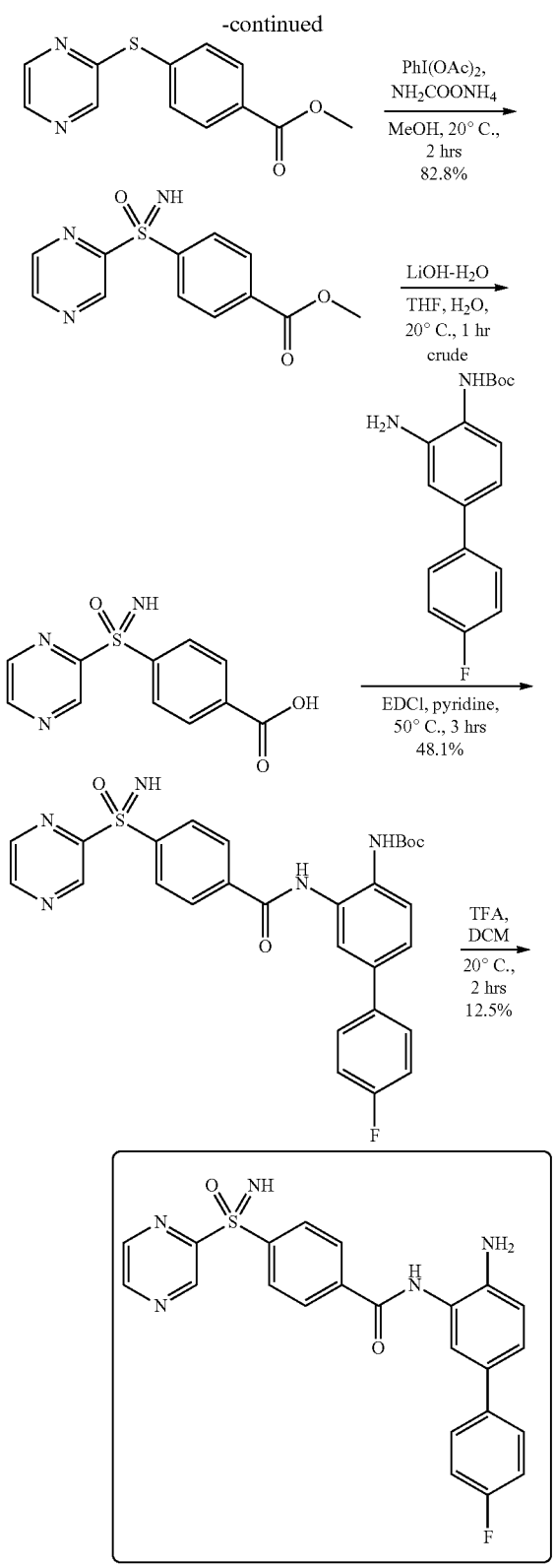

0.306 mmol), XantPhos (340 mg, 0.588 mmol) and Cs$_2$CO$_3$ (5.81 g, 17.8 mmol) in dioxane (20 mL) was stirred at 100° C. for 12 hours. The mixture was filtered. The filtrate was concentrated under reduced pressure. The residue was purified by flash chromatography (Biotage®; 20 g Agela Flash® Silica Flash Column, petroleum ether/EtOAc with EtOAc from 0~25%, 30 mL/min, 254 nm) to afford methyl 4-pyrazin-2-ylsulfanylbenzoate (1.19 g, 81.3% yield) as brown oil. $^1$H NMR (400 MHz, DMSO-d6) δ ppm 8.57 (d, J=1.51 Hz, 1H), 8.50-8.53 (m, 1H), 8.48 (d, J=2.51 Hz, 1H), 7.99 (d, J=8.53 Hz, 2H), 7.65-7.70 (m, 2H), 3.87 (s, 3H); LCMS (ESI) [M+H]$^+$ m/z: calcd 247.0; found 247.0.

Step 2: Synthesis of methyl 4-(pyrazin-2-ylsulfonimidoyl)benzoate

A mixture of methyl 4-pyrazin-2-ylsulfanylbenzoate (1.19 g, 4.83 mmol), [bis(acetoxy)iodo]benzene (3.89 g, 12.1 mmol) and ammonia; carbamic acid (760 mg, 9.73 mmol) in MeOH (20 mL) was stirred at 20° C. for 2 hours. The resulting mixture was concentrated under reduced pressure. The residue was purified by flash chromatography (Biotage®; 40 g AgelaFlash® Silica Flash Column, petroleum ether/EtOAc with EtOAc from 0~75%, 45 mL/min, 254 nm) to afford methyl 4-(pyrazin-2-ylsulfonimidoyl)benzoate (1.11 g, 82.8% yield) as white solid. $^1$H NMR (400 MHz, DMSO-d6) δ ppm 9.41 (d, J=1.25 Hz, 1H), 8.88 (d, J=2.26 Hz, 1H), 8.74 (dd, J=2.26, 1.51 Hz, 1H), 8.15 (d, J=4.77 Hz, 4H), 5.67 (s, 1H), 3.88 (s, 3H); LCMS (ESI) [M+H]$^+$ m/z: calcd 278.1; found 278.0.

Step 3: Synthesis of 4-(pyrazin-2-ylsulfonimidoyl)benzoic acid

To a solution of methyl 4-(pyrazin-2-ylsulfonimidoyl)benzoate (200 mg, 0.721 mmol) in H$_2$O (3 mL) and THF (10 mL) was added LiOH—H$_2$O (100 mg, 2.38 mmol). The mixture was stirred at 20° C. for 1 hour. The mixture was concentrated under reduced pressure, and adjusted the pH to 5 with 2N HCl aqueous solution. The resulting mixture was quenched by addition of water (50 mL) and extracted with EtOAc (50 mL*3). The combined organic layer was washed with brine (100 mL), dried over anhydrous Na$_2$SO$_4$, filtered and concentrated under reduced pressure to afford 4-(pyrazin-2-ylsulfonimidoyl)benzoic acid (200 mg, crude) as white solid. LCMS (ESI) [M+H]$^+$ m/z: calcd 264.0, found 264.0.

Step 4: Synthesis of tert-butyl N-[4-(4-fluorophenyl)-2-[[4-(pyrazin-2-ylsulfonimidoyl)benzoyl]amino]phenyl]carbamate A mixture of 4-(pyrazin-2-ylsulfonimidoyl)benzoic acid (150 mg, 0.570 mmol), tert-butyl N-[2-amino-4-(4-fluorophenyl)phenyl]carbamate (150 mg, 0.496 mmol) and EDCI (165 mg, 0.861 mmol) in pyridine (3 mL) was stirred at 50° C. for 3 hours. The mixture was concentrated under recued pressure. The residue was purified by flash chromatography (Biotage®; 12 g AgelaFlash®Silica Flash Column, petroleum ether/EtOAc with EtOAc from 0~56%, flow rate=30 mL/min, 254 nm) to afford tert-butyl N-[4-(4-fluorophenyl)-2-[[4-(pyrazin-2-ylsulfonimidoyl)benzoyl]amino]phenyl]carbamate (150 mg, 48.1% yield) as white solid. LCMS (ESI) [M+H]$^+$ m/z: calcd 548.2, found 548.2.

Step 5: Synthesis of N-[2-amino-5-(4-fluorophenyl)phenyl]-4-(pyrazin-2-ylsulfonimidoyl)benzamide To a solution of tert-butyl N-[4-(4-fluorophenyl)-2-[[4-(pyrazin-2-ylsulfonimidoyl)benzoyl]amino]phenyl]carbamate (150 mg, 0.274 mmol) in DCM (5 mL) was added TFA (0.4 mL, 5.19 mmol. The mixture was stirred at 20° C. for 2 hours. The resulting mixture was concentrated under reduced pressure, and adjusted pH=8 with saturated NaHCO$_3$ aqueous solution. The mixture was quenched by addition of water (20 mL) and extracted with DCM (20 mL*3). The combined organic layer was dried over anhydrous Na$_2$SO$_4$, filtered and concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 μm; Mobile phase A: water (NH$_3$—H$_2$O+NH$_4$HCO$_3$ v/v)-ACN; Mobile phase B: ACN; Gradient: B from 35% to 65% in 7.8 min, hold 100% B for 0.5 min; Flow Rate: 30 mL/min; Column Temperature: 30° C.; Wavelength: 220 nm, 254 nm) to afford N-[2-amino-5-(4-fluorophenyl)phenyl]-4-(pyrazin-2-ylsulfonimidoyl)benzamide (15.3 mg, 12.5% yield) as white solid. $^1$H NMR (400 MHz, DMSO-d6) δ ppm 9.90 (s, 1H), 9.43 (d, J=1.25 Hz, 1H), 8.89 (d, J=2.38 Hz, 1H), 8.73-8.78 (m, 1H), 8.16 (s, 4H), 7.54-7.59 (m, 2H), 7.48 (d, J=2.00 Hz, 1H), 7.31 (dd, J=8.38, 2.13 Hz, 1H), 7.18-7.24 (m, 2H), 6.84 (d, J=8.38 Hz, 1H), 5.63 (s, 1H), 5.16 (s, 2H); 19F NMR (376 MHz, DMSO-d6) δ ppm −117.479; LCMS (ESI) [M+H]$^+$ m/z: calcd 448.1, found 448.1; HPLC: 95.76%@220 nm; 96.28%@254 nm.

Example 110. Synthesis of N-[2-amino-5-(4-fluorophenyl)phenyl]-2-(methylsulfonimidoyl)benzofuran-6-carboxamide (Compound 187)

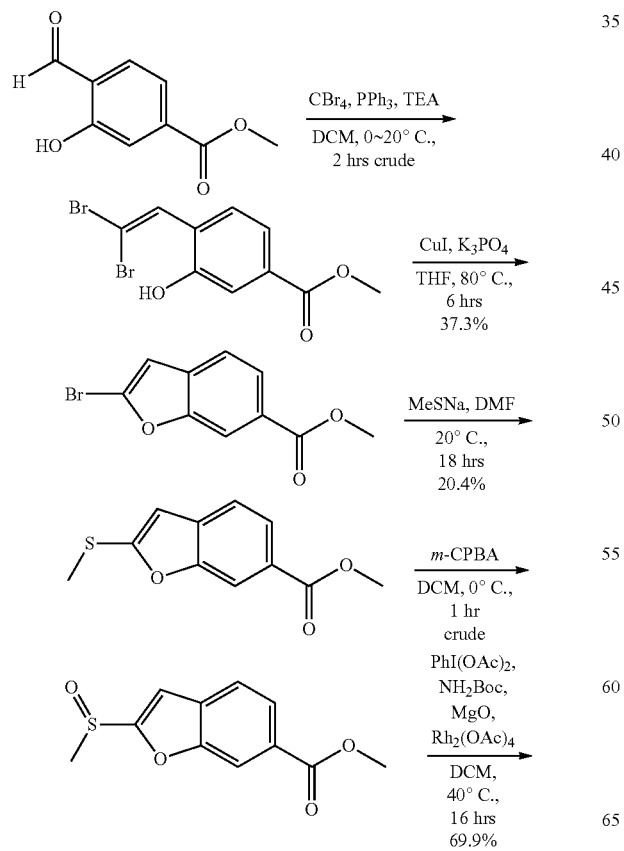
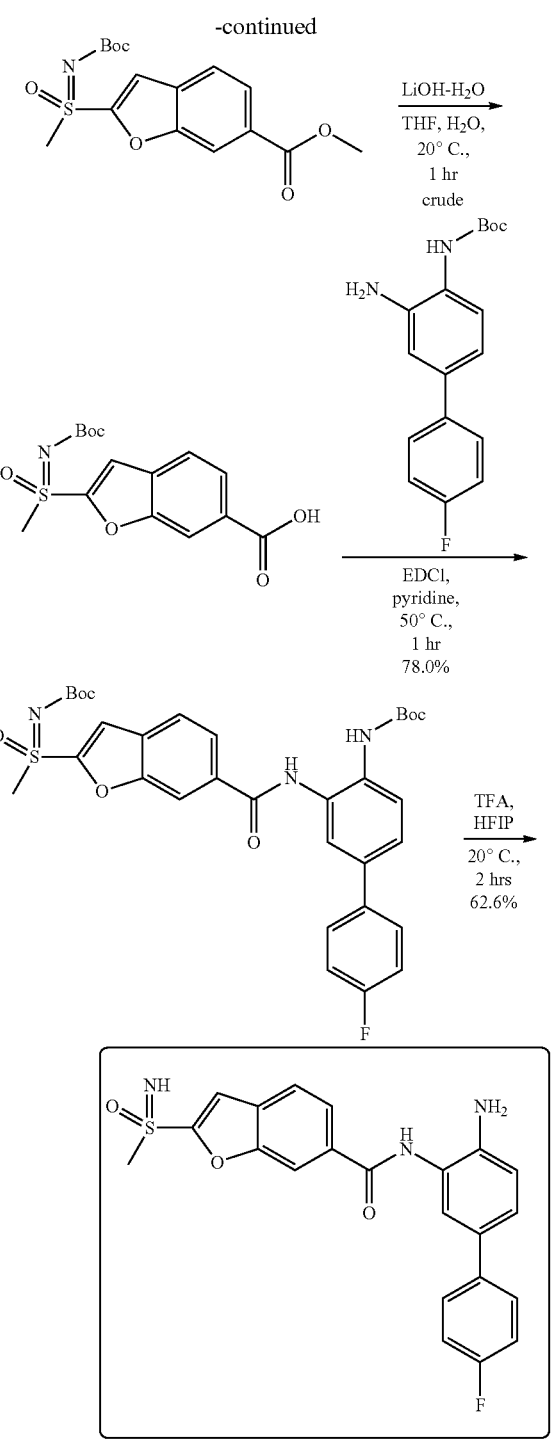

Step 1: Synthesis of methyl 4-(2,2-dibromovinyl)-3-hydroxy-benzoate

A solution of CBr$_4$ (27.6 g, 83.2 mmol) in DCM (50 mL) was added dropwise to a solution of PPh$_3$ (43.7 g, 167 mmol) in DCM (150 mL) at 0° C. After 10 minutes, TEA (23.2 mL, 167 mmol) was added dropwise. The mixture was stirred for 5 minutes. Methyl 4-formyl-3-hydroxy-benzoate (5 g, 27.8 mmol) in DCM (50 mL) was added dropwise. The internal temperature was maintained below 10° C. during the addition of all the above reagents. The mixture was stirred for 30 minutes at 0° C. Then the mixture was warmed to 25° C. and stirred for 1 hour at 25° C. The reaction was quenched by the addition of saturated aqueous NH$_4$Cl solution (500 mL). The solution was separated into two phases, and the aqueous layer was extracted with DCM (100 mL). The combined organic layers were concentrated under reduced pressure to afford black residue. The residue was dissolved in DCM (50 mL). Petroleum ether was added till no yellow solid was formed. The yellow solid was filtrated away and the filtrate was concentrated under reduced pressure to afford black residue. The residue was purified by flash chromatography (ISCO®; 220 g AgelaFlash® Silica Flash Column, petroleum ether/EtOAc with EtOAc from 0~35%, flow rate=100 mL/min, 254 nm) to afford methyl 4-(2, 2-dibromovinyl)-3-hydroxy-benzoate (4.42 g, crude) as yellow solid. $^1$H NMR (400 MHz, DMSO-d6) δ ppm 10.98 (s, 1H), 8.18 (d, J=1.9 Hz, 1H), 7.82 (dd, J=8.6, 2.1 Hz, 1H), 7.60 (s, 1H), 7.51-7.66 (m, 1H), 6.96 (d, J=8.5 Hz, 1H), 3.80 (s, 3H).

Step 2: Synthesis of methyl 2-bromobenzofuran-6-carboxylate

A mixture of methyl 4-(2,2-dibromovinyl)-3-hydroxy-benzoate (4.42 g, 13.2 mmol), K$_3$PO$_4$ (5.59 g, 26.3 mmol), and CuI (126 mg, 0.662 mmol) in THF (90 mL) was heated to 80° C. and stirred at 80° C. for 6 hours under nitrogen atmosphere. The mixture was concentrated under reduced pressure to afford yellow residue. The residue was purified by flash chromatography (ISCO®; 40 g AgelaFlash® Silica Flash Column, petroleum ether/EtOAc with EtOAc from 0~5%, flow rate=60 mL/min, 254 nm) to afford methyl 2-bromobenzofuran-6-carboxylate (1.25 g, 37.3% yield) as white solid. $^1$H NMR (400 MHz, DMSO-d6) δ ppm 8.25 (d, J=1.5 Hz, 1H), 7.93 (dd, J=8.8, 1.8 Hz, 1H), 7.73 (d, J=8.8 Hz, 1H), 7.26 (d, J=0.8 Hz, 1H), 3.87 (s, 3H).

Step 3: Synthesis of methyl 2-methylsulfanylbenzofuran-6-carboxylate

To a solution of methyl 2-bromobenzofuran-6-carboxylate (900 mg, 3.53 mmol) in DMF (40 mL) was added MeSNa (500 mg, 7.13 mmol). The mixture was stirred at 25° C. for 18 hours. The reaction mixture was diluted with ethyl acetate (100 mL) and washed with water (100 mL) followed by brine (50 mL). The organic fraction was dried over anhydrous Na$_2$SO$_4$, filtered and concentrated under reduced pressure to afford yellow residue. The residue was purified by flash chromatography (ISCO®; 20 g AgelaFlash® Silica Flash Column, petroleum ether/EtOAc with EtOAc 0~35%, flow rate=45 mL/min, 254 nm) to afford methyl 2-methylsulfanylbenzofuran-6-carboxylate (160 mg, 20.4% yield) as yellow solid. $^1$H NMR (400 MHz, chloroform-d) δ ppm 8.21 (d, J=1.4 Hz, 1H), 7.97 (dd, J=8.6, 1.8 Hz, 1H), 7.45 (d, J=8.6 Hz, 1H), 6.72 (d, J=0.6 Hz, 1H), 3.94 (s, 3H), 2.58 (s, 3H).

The pH value of aqueous solution was adjusted to 4-5 with 1N HCl. The resulting mixture was extracted with EtOAc (50 mL*3). The combined organic layer was washed with brine (100 mL), dried over anhydrous Na$_2$SO$_4$, filtered and concentrated under reduced pressure to afford 2-methylsulfanylbenzofuran-6-carboxylic acid (665 mg, crude) as yellow solid. $^1$H NMR (400 MHz, chloroform-d) δ ppm 8.27 (d, J=1.5 Hz, 1H), 8.01 (br d, J=1.6 Hz, 2H), 7.46 (d, J=8.6 Hz, 1H), 6.72 (s, 1H), 2.57 (s, 3H).

Step 4: Synthesis of methyl 2-methylsulfinylbenzofuran-6-carboxylate

To a solution of methyl 2-methylsulfanylbenzofuran-6-carboxylate (160 mg, 0.720 mmol) in DCM (10 mL) was added m-CPBA (128 mg, 0.742 mmol) at 0° C. The mixture was stirred at 0° C. for 1 hour after the addition. The mixture was diluted with water (50 mL) and quenched with saturated Na$_2$SO$_3$ aqueous solution till potassium iodide-starch test paper did not change to blue. The resulting mixture was extracted with DCM (30 mL*3). The combined organic layer was washed with brine (30 mL*2), dried over anhydrous Na$_2$SO$_4$, filtered and concentrated under reduced pressure. The residue was purified by flash chromatography (ISCO®; 12 g AgelaFlash® Silica Flash Column, petroleum ether/EtOAc with EtOAc from 0~50%, flow rate=45 mL/min, 254 nm) to afford methyl 2-methylsulfinylbenzofuran-6-carboxylate (186 mg, crude) as light yellow solid. $^1$H NMR (400 MHz, chloroform-d) δ ppm 8.42 (d, J=1.3 Hz, 1H), 8.16 (dd, J=8.8, 1.7 Hz, 1H), 7.61 (d, J=8.8 Hz, 1H), 7.36 (s, 1H), 3.97 (s, 3H), 3.07 (s, 3H); LCMS (ESI) [M+H]$^+$ m/z: calcd 239.0, found 238.9.

Step 5: Synthesis of methyl 2-(N-tert-butoxycarbonyl-S-methyl-sulfonimidoyl)benzofuran-6-carboxylate A mixture of methyl 2-methylsulfinylbenzofuran-6-carboxylate (166 mg, 0.697 mmol), NH$_2$Boc (163 mg, 1.39 mmol), [bis(acetoxy)iodo]benzene (337 mg, 1.05 mmol), MgO (144 mg, 3.49 mmol), and dirhodium tetraacetate (16 mg, 0.036 mmol) in DCM (15 mL) was heated to 40° C. and stirred at 40° C. for 16 hours under nitrogen atmosphere. The solid was filtrated away and the filtrate was concentrated under reduced pressure. The residue was purified by flash chromatography (ISCO®; 4 g AgelaFlash® Silica Flash Column, petroleum ether/EtOAc with EtOAc from 0~35%, flow rate=30 mL/min, 254 nm) to afford methyl 2-(N-tert-butoxycarbonyl-S-methyl-sulfonimidoyl)benzofuran-6-carboxylate (172 mg, 69.9% yield) as colorless oil. $^1$H NMR (400 MHz, chloroform-d) δ ppm 8.48 (d, J=1.1 Hz, 1H), 8.23 (dd, J=8.9, 1.8 Hz, 1H), 7.71 (s, 1H), 7.64 (d, J=8.9 Hz, 1H), 3.98 (s, 3H), 3.43 (s, 3H), 1.41 (s, 9H).

Step 6: Synthesis of 2-(N-tert-butoxycarbonyl-S-methyl-sulfonimidoyl)benzofuran-6-carboxylic acid To a solution of methyl 2-(N-tert-butoxycarbonyl-S-methylsulfonimidoyl) benzofuran-6-carboxylate (170 mg, 0.481 mmol) in THF (10 mL) was added a solution of LiOH·H$_2$O (101 mg, 2.41 mmol) in H$_2$O (5 mL). The mixture was stirred at 20° C. for 1 hour. The pH value of the mixture was adjusted to 4-5 with 1N HCl. The mixture was extracted with EtOAc (50*3 mL). The combined organic phase was washed with brine (50 mL), dried over anhydrous Na$_2$SO$_4$, and concentrated under reduced pressure to 2-(N-tert-butoxycarbonyl-S-methyl-sulfonimidoyl)benzofuran-6-carboxylic acid (186 mg, crude) as yellow oil. $^1$H NMR (400 MHz, DMSO-d6) δ ppm 13.15 (br s, 1H), 8.50 (d, J=1.3 Hz, 1H), 8.13 (dd, J=8.8, 1.8 Hz, 1H), 7.95 (s, 1H), 7.89 (d, J=8.9 Hz, 1H), 3.56 (s, 3H), 1.23 (s, 9H).

Step 7: Synthesis of tert-butyl N-[[6-[[2-(tert-butoxycarbonylamino)-5-(4-fluorophenyl)phenyl]carbamoyl]benzofuran-2-yl]-methyl-oxo-sulfanylidene]carbamate A mixture of 2-(N-tert-butoxycarbonyl-S-methyl-sulfonimidoyl)benzofuran-6-carboxylic acid (180 mg, 0.530 mmol), tert-butyl N-[2-amino-4-(4-fluorophenyl)phenyl]carbamate (165 mg, 0.546 mmol) and EDCI (153 mg, 0.798 mmol) in pyridine (10 mL) was heated to 50° C. and stirred at 50° C. for 1 hour. The mixture was poured into water (100 mL). The resulting solution was extracted with EtOAc (50 mL*3), washed with brine (50 mL*2), dried over anhydrous Na$_2$SO$_4$, and concentrated under reduced pressure. The residue was purified by flash chromatography (ISCO®; 12 g AgelaFlash® Silica Flash Column, petroleum ether/EtOAc with EtOAc 0~45%, flow rate=35 mL/min, 254 nm) to afford tert-butyl N-[[6-[[2-(tert-butoxycarbonylamino)-5-(4-fluorophenyl)phenyl]carbamoyl]benzofuran-2-yl]-methyl-oxo-sulfanylidene]carbamate (258 mg, 78.0% yield) as purple solid. $^1$H NMR (400 MHz, DMSO-d6) δ ppm 10.08 (s, 1H), 8.80 (s, 1H), 8.52 (d, J=1.4 Hz, 1H), 8.18 (dd, J=8.8, 1.7 Hz, 1H), 7.93-8.04 (m, 2H), 7.83 (d, J=2.0 Hz, 1H), 7.65-7.74 (m, 3H), 7.52 (dd, J=8.5, 2.1 Hz, 1H), 7.29 (t, J=8.9 Hz, 2H), 3.59 (s, 3H), 1.45 (s, 9H), 1.24 (s, 9H); 19F NMR (377 MHz, DMSO-d6) δ ppm −115.62.

Step 8: Synthesis of N-[2-amino-5-(4-fluorophenyl)phenyl]-2-(methylsulfonimidoyl)benzofuran-6-carboxamide (Compound 187)

To a solution of tert-butyl N-[[6-[[2-(tert-butoxycarbonylamino)-5-(4-fluorophenyl)phenyl]carbamoyl]benzofuran-2-yl]-methyl-oxo-sulfanylidene]carbamate (258 mg, 0.414 mmol) in HFIP (10 mL) was added TFA (0.64 mL, 8.31 mmol). The mixture was stirred at 20° C. for 2 hours. The mixture was concentrated under reduced pressure to afford yellow residue. The yellow residue was diluted with water (50 mL). The pH value of the solution was adjusted to 8 with saturated NaHCO$_3$ aqueous solution. The resulting mixture was extracted with EtOAc (50 mL*3). The combined organic layer was washed with brine (50 mL*2), dried over anhydrous Na$_2$SO$_4$, filtered and concentrated under reduced pressure. The brown solid was purified by flash chromatography (ISCO®; 4 g AgelaFlash® Silica Flash Column, Dichloromethane/Methanol with Methanol from 0~5%, flow rate=35 mL/min, 254 nm) to afford N-[2-amino-5-(4-fluorophenyl)phenyl]-2-(methylsulfonimidoyl)benzofuran-6-carboxamide (109.7 mg, 62.6% yield) as off-white solid. $^1$H NMR (400 MHz, DMSO-d6) δ ppm 9.87 (s, 1H), 8.50 (s, 1H), 8.16 (dd, J=8.7, 1.6 Hz, 1H), 7.87 (d, J=8.8 Hz, 1H), 7.68 (d, J=0.8 Hz, 1H), 7.54-7.63 (m, 2H), 7.51 (d, J=2.0 Hz, 1H), 7.32 (dd, J=8.4, 2.1 Hz, 1H), 7.22 (t, J=8.9 Hz, 2H), 6.87 (d, J=8.3 Hz, 1H), 5.13 (s, 2H), 5.02 (s, 1H), 3.27 (d, J=1.3 Hz, 3H); 19F NMR (377 MHz, DMSO-d6) δ ppm −117.49; LCMS (ESI) [M+H]$^+$ m/z: calcd 424.1, found 424.0; HPLC: 98.30%@220 nm; 99.28%@254 nm.

Example 111. Synthesis of N-[2-amino-5-(4-fluorophenyl)phenyl]-4-[(2-methoxypyrimidin-5-yl)sulfonimidoyl]benzamide (Compound 218)

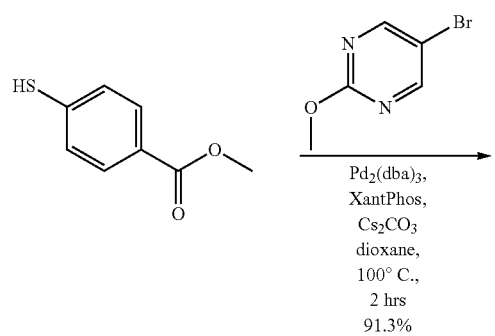

Step 1: Synthesis of methyl 4-(2-methoxypyrimidin-5-yl)sulfanylbenzoate

To a mixture of methyl 4-sulfanylbenzoate (1 g, 5.94 mmol), 5-bromo-2-methoxy-pyrimidine (1.2 g, 6.35 mmol) in dioxane (30 mL) was added Pd$_2$(dba)$_3$ (1.7 g, 1.86 mmol), XantPhos (1.1 g, 1.90 mmol) and Cs$_2$CO$_3$ (6 g, 18.4 mmol). The resulting mixture was stirred at 100° C. for 2 hours. The reaction mixture was quenched by addition water (30 mL), extracted with EtOAc (30 mL*3). The combined organic layers were washed with brine (30 mL), dried over anhydrous Na$_2$SO$_4$, filtered and concentrated under reduced pressure. The residue was purified by flash chromatography (ISCO®; 40 g AgelaFlash® Silica Flash Column, petroleum ether/EtOAc with EtOAc 0~30%, flow rate=35 mL/min, 254

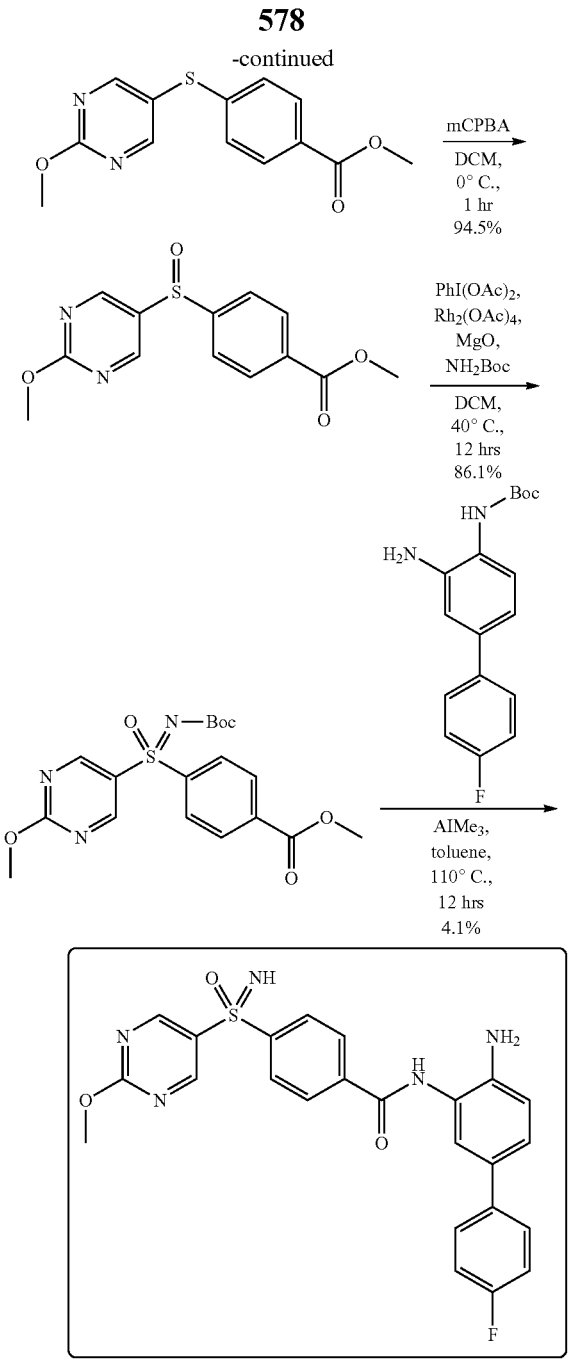

nm) to afford methyl 4-(2-methoxypyrimidin-5-yl)sulfanylbenzoate (1.5 g, 91.3% yield) as a yellow solid. $^1$H NMR (400 MHz, chloroform-d) δ ppm 8.64 (s, 2H), 7.93 (d, J=8.53 Hz, 2H), 7.16 (d, J=8.53 Hz, 2H), 4.08 (s, 3H), 3.90-3.91 (m, 1H), 3.90 (s, 2H); LCMS (ESI) [M+H]$^+$ m/z: calcd 277.1, found 277.1.

Step 2: Synthesis of methyl 4-(2-methoxypyrimidin-5-yl)sulfinylbenzoate

To a solution of methyl 4-(2-methoxypyrimidin-5-yl)sulfanylbenzoate (1.5 g, 5.43 mmol) in DCM (20 mL) was added m-CPBA (971 mg, 5.62 mmol) at 0° C. and the mixture was stirred at 0° C. for 1 hour. The reaction mixture was quenched by addition water (20 mL), extracted with DCM (20 mL*3). The combined organic layers were washed with brine (20 mL), dried over anhydrous $Na_2SO_4$, filtered and concentrated under reduced pressure. The residue was purified by flash chromatography (ISCO®; 40 g Agela-Flash® Silica Flash Column, petroleum ether/EtOAc with EtOAc 0~30%, flow rate=35 mL/min, 254 nm) to afford methyl 4-(2-methoxypyrimidin-5-yl)sulfinylbenzoate (1.5 g, 94.5% yield) as a white solid. $^1$H NMR (400 MHz, chloroform-d) δ ppm 8.70 (s, 2H), 8.20 (d, J=8.53 Hz, 2H), 7.76 (s, 2H), 4.06 (s, 3H), 3.96 (s, 2H), 3.95-3.97 (m, 1H); LCMS (ESI) [M+H]$^+$ m/z: calcd 293.1, found 293.2.

Step 3: Synthesis of methyl 4-[N-tert-butoxycarbonyl-S-(2-methoxypyrimidin-5-yl)sulfonimidoyl]benzoate To a solution of methyl 4-(2-methoxypyrimidin-5-yl)sulfinylbenzoate (1.5 g, 5.13 mmol), $NH_2Boc$ (1.2 g, 10.2 mmol), MgO (1 g, 24.2 mmol) and PhI(OAc)$_2$ (2.5 g, 7.76 mmol) in DCM (30 mL) was added $Rh_2(OAc)_4$ (240 mg, 0.543 mmol). The mixture was stirred at 40° C. for 12 hours. The reaction mixture was quenched by addition water (30 mL), extracted with DCM (30 mL*3). The combined organic layers were washed with brine (30 mL), dried over anhydrous $Na_2SO_4$, filtered and concentrated under reduced pressure. The residue was purified by flash chromatography (ISCO®; 40 g AgelaFlash® Silica Flash Column, petroleum ether/EtOAc with EtOAc 0~30%, flow rate=35 mL/min, 254 nm) to afford methyl 4-[N-tert-butoxycarbonyl-S-(2-methoxypyrimidin-5-yl)sulfonimidoyl]benzoate (1.8 g, 86.1% yield) as a white solid. $^1$H NMR (400 MHz, chloroform-d) δ ppm 9.02 (s, 2H), 8.22 (d, J=8.78 Hz, 2H), 8.06-8.11 (m, 2H), 4.09 (s, 3H), 3.96 (s, 3H), 1.38 (s, 9H); LCMS (ESI) [M+H]$^+$ m/z: calcd 408.1, found 308.1. (Boc and t-Bu cleaved mass).

Step 4: Synthesis of N-[2-amino-5-(4-fluorophenyl)phenyl]-4-[(2-methoxypyrimidin-5-yl)sulfonimidoyl]benzamide To a solution of methyl 4-[N-tert-butoxycarbonyl-S-(2-methoxypyrimidin-5-yl)sulfonimidoyl]benzoate (500 mg, 1.23 mmol), tert-butyl N-[2-amino-4-(4-fluorophenyl)phenyl]carbamate (375 mg, 1.24 mmol) in Toluene (10 mL) was added 2M $AlMe_3$ in toluene (3 mL, 6.00 mmol). The mixture was stirred at 110° C. for 12 hours. The mixture was concentrated under reduced pressure and purified by preparative HPLC (Instrument: Gilson GX-281 Liquid Handler, Gilson 322 Pump, Gilson 156 UV Detector; Column: Durashell 150×25 mm×5 m; Mobile phase A: water ($NH_4HCO_3$)-ACN; Mobile phase B: MeCN; Gradient: B from 29% to 59% in 9.5 min, hold 100% B for 1 min; Flow Rate: 30 mL/min; Column Temperature: 30° C.; Wavelength: 254 nm) to afford N-[2-amino-5-(4-fluorophenyl)phenyl]-4-[(2-methoxypyrimidin-5-yl)sulfonimidoyl]benzamide (24.2 mg, 4.1% yield) as a yellow solid.

Compound 218: $^1$H NMR (400 MHz, chloroform-d) δ ppm 9.05 (s, 2H), 8.10-8.17 (m, 3H), 8.01-8.08 (m, 2H), 7.59 (br s, 1H), 7.47 (br dd, J=7.91, 5.65 Hz, 2H), 7.30 (dd, J=8.28, 2.01 Hz, 1H), 7.08 (t, J=8.66 Hz, 2H), 6.91 (d, J=8.28 Hz, 1H), 4.08 (s, 3H), 3.87 (br s, 2H), 3.38 (s, 1H); LCMS (ESI) [M+H]$^+$ m/z: calcd 478.1, found 478.1; HPLC: 97.4%@254 nm, 98.5%@220 nm.

Example 112. Synthesis of N-(4-amino-4'-fluoro-[1,1'-biphenyl]-3-yl)-4-(5-(hydroxymethyl)pyridine-3-sulfonimidoyl)benzamide (Compound 250)

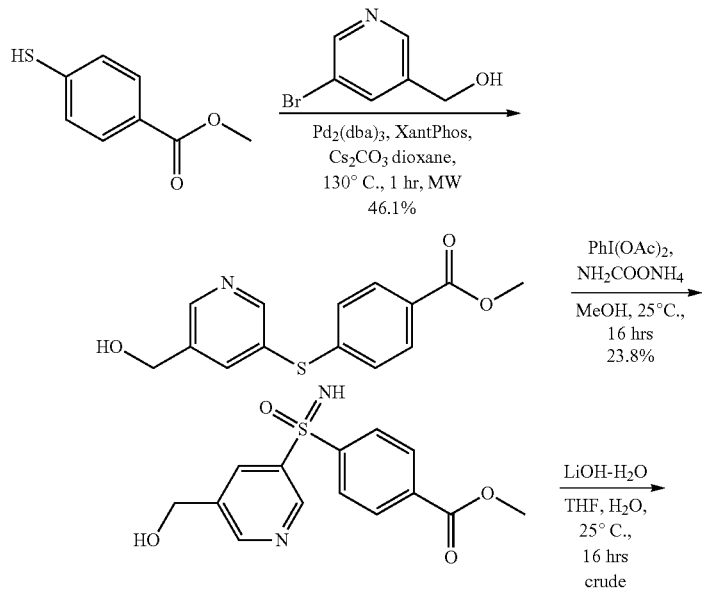

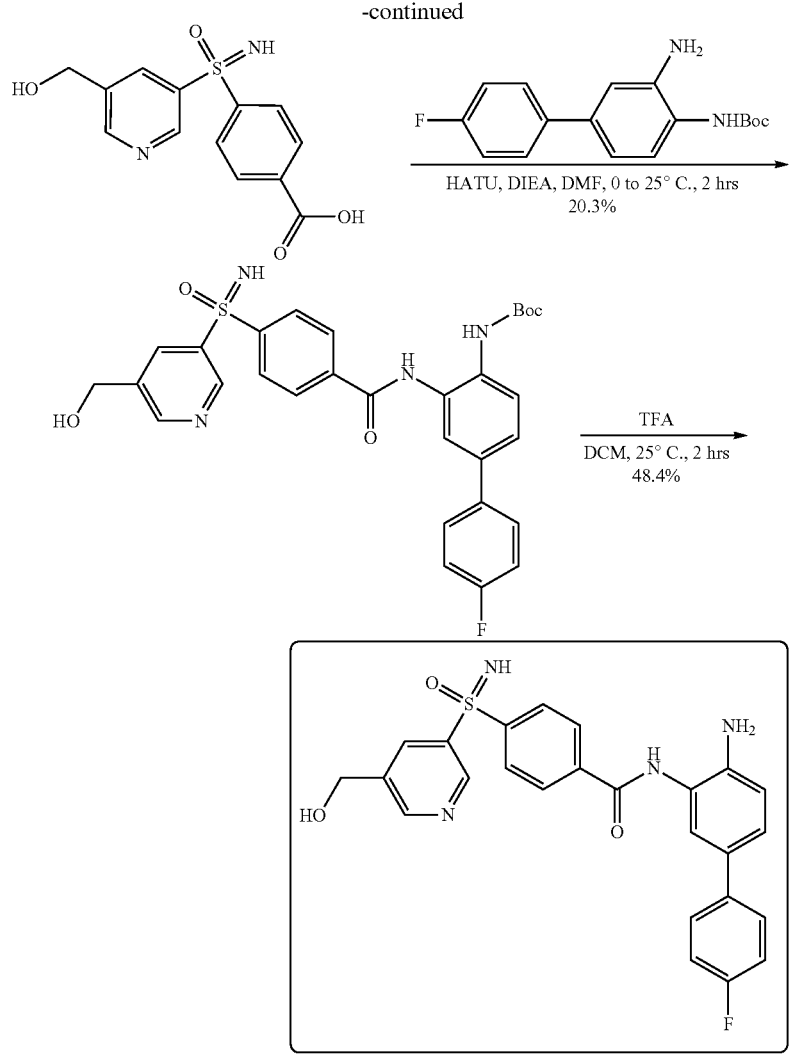

Step 1: Synthesis of methyl 4-((5-fluoropyridin-3-yl)thio)benzoate

A mixture of (5-bromo-3-pyridyl)methanol (670 mg, 3.56 mmol), methyl 4-sulfanylbenzoate (500 mg, 2.97 mmol), Pd$_2$dba$_3$ (544 mg, 0.594 mmol), XantPhos (688 mg, 1.19 mmol) and Cs$_2$CO$_3$ (2.9 g, 8.90 mmol) in dioxane (10 mL) was purged with N$_2$ gas at ambient temperature for 3 minutes. Then mixture was stirred at 130° C. for 1 hour in Microwave. Five batches reaction mixture was combined, concentrated and purified by flash chromatography (ISCO®; 40 g SepaFlash® Silica Flash Column, petroleum ether/ EtOAc with EtOAc from 0~10%, flow rate: 25 mL/min, 254 nm) to afford methyl 4-[[5-(hydroxymethyl)-3-pyridyl]sulfanyl]benzoate (377 mg, 46.1% yield) as yellow solid. LCMS (ESI) [M+H]$^+$ m/z: calcd 276.1, found 275.8.

Step 2: Synthesis of methyl 4-(5-(hydroxymethyl) pyridine-3-sulfonimidoyl)benzoate To a solution of methyl 4-[[5-(hydroxymethyl)-3-pyridyl]sulfanyl]benzoate (377 mg, 1.37 mmol) in MeOH (35 mL) was added NH$_2$COONH$_4$ (211 mg, 2.70 mmol) and PhI (OAc)$_2$ (1.30 g, 4.04 mmol) at 0° C. slowly. The mixture was stirred at 25° C. for 16 hours. The reaction mixture was diluted with H$_2$O (100 mL) and extracted with EtOAc (50 mL Q 3). The combined organic layers were dried over anhydrous Na$_2$SO$_4$, filtered and concentrated under reduced pressure. The residue was purified by Prep. TLC eluted with (silica, EtOAc, 254 nm) to give methyl 4-[[5-(hydroxymethyl)-3-pyridyl]sulfonimidoyl]benzoate (100 mg, 23.8% yield) as a yellow solid. LCMS (ESI) [M+H]$^+$ m/z: calcd 307.1, found 307.2.

Step 3: Synthesis of 4-(5-(hydroxymethyl)pyridine-3-sulfonimidoyl)benzoic acid To a solution of methyl 4-[[5-(hydroxymethyl)-3-pyridyl]sulfonimidoyl]benzoate (150 mg, 0.489 mmol) in MeOH (12 mL) was added LiOH—H$_2$O (23.0 mg, 0.548 mmol). The mixture was stirred at 25° C. for 16 hours. The reaction mixture was diluted with H$_2$O (5 mL), adjusted with 1N HCl aqueous solution to pH-6 and concentrated under reduced pressure to give 4-[[5-(hydroxymethyl)-3-pyridyl]sulfonimidoyl]benzoic acid (143 mg, crude) as a white solid. LCMS (ESI) [M+H]$^+$ m/z: calcd 293.1, found 292.9.

583

Step 4: Synthesis of tert-butyl (4'-fluoro-3-(4-(5-(hydroxymethyl)pyridine-3-sulfonimidoyl)benzamido)-[1,1'-biphenyl]-4-yl)carbamate To a solution of 4-[[5-(hydroxymethyl)-3-pyridyl]sulfonimidoyl]benzoic acid (90.0 mg, 0.307 mmol), DIEA (122 mg, 0.944 mmol) in DMF (5.00 mL) was added HATU (176 mg, 0.462 mmol) at 0° C. Then tert-butyl N-[2-amino-4-(4-fluorophenyl)phenyl]carbamate (104 mg, 0.343 mmol) was added. The mixture was stirred at 25° C. for 2 hours. The reaction was poured into water (15 mL), the aqueous layer was extracted with EtOAc (15 mL Q 3). The organic layer was washed water (50 mL Q 3), dried over anhydrous Na$_2$SO$_4$, filtered and concentrated. The crude combined with other two batches and purified by flash chromatography (ISCO®; 100 g SepaFlash® Silica Flash Column, petroleum ether/EtOAc with EtOAc from 0~100%, flow rate=20 mL/min, 254 nm) to afford tert-butyl N-[4-(4-fluorophenyl)-2-[[4-[[5-(hydroxymethyl)-3-pyridyl]sulfonimidoyl]benzoyl]amino]phenyl]carbamate (90.0 mg, 20.3% yield) as a yellow solid. $^1$H NMR (400 MHz, chloroform-d) δ ppm 9.65 (br s, 1H) 9.05-9.10 (m, 1H) 8.66 (s, 1H) 8.26 (s, 1H) 7.98-8.09 (m, 5H) 7.46 (br dd, J=8.3, 5.4 Hz, 2H) 7.28 (dd, J=8.3, 1.6 Hz, 1H) 7.15 (br d, J=8.3 Hz, 1H) 7.03 (br t, J=8.6 Hz, 2H) 6.72 (s, 1H) 4.74 (s, 2H) 1.46 (s, 9H); LCMS (ESI) [M+H]$^+$ m/z: calcd 577.2, found 577.1.

Step 5: Synthesis of N-(4-amino-4'-fluoro-[J, 1'-biphenyl]-3-yl)-4-(5-(hydroxymethyl)pyridine-3-sulfonimidoyl)benzamide (Compound 250)

To a solution of tert-butyl N-[4-(4-fluorophenyl)-2-[[4-[[5-(hydroxymethyl)-3-pyridyl]sulfonimidoyl]benzoyl]amino]phenyl]carbamate (30.0 mg, 52.0 mol) in DCM (3 mL) was added TFA (444 mg, 3.89 mmol). The mixture was stirred at 25° C. for 2 hours. The reaction combined with another batch and the mixture was adjusted to pH~8 with saturated aqueous NaHCO$_3$ solution, the aqueous layer was extracted with DCM (10 mL*3). The organic layer was washed water (40 mL), dried over anhydrous Na$_2$SO$_4$, filtered and concentrated. The crude was purified by Prep. HPLC (NH$_3$—H$_2$O) to afford N-[2-amino-5-(4-fluorophenyl)phenyl]-4-[[5-(hydroxymethyl)-3-pyridyl]sulfonimidoyl]benzamide (15.0 mg, 48.4% yield) as a yellow solid.

Compound 250: $^1$H NMR (400 MHz, DMSO-d6) δ ppm 9.87 (s, 1H) 9.03 (s, 1H) 8.71 (s, 1H) 8.27 (s, 1H) 8.14 (s, 4H) 7.56 (dd, J=8.7, 5.4 Hz, 2H) 7.47 (d, J=1.8 Hz, 1H) 7.31 (dd, J=8.3, 2.0 Hz, 1H) 7.21 (t, J=8.9 Hz, 2H) 6.84 (d, J=8.3 Hz, 1H) 5.56 (t, J=5.6 Hz, 1H) 5.50 (s, 1H) 5.16 (s, 2H) 4.61 (d, J=5.5 Hz, 2H); 19F NMR (376 MHz, DMSO-d6) δ ppm −117.47; LCMS (ESI) [M+H]$^+$ m/z: calcd 477.1, found 477.2; HPLC: 98.82%@220 nm, 99.47%@254 nm.

584

Example 113. Synthesis of N-[2-amino-5-(4-fluorophenyl)phenyl]-4-[(4-methoxy-3-pyridyl)sulfonimidoyl]benzamide (Compound 240)

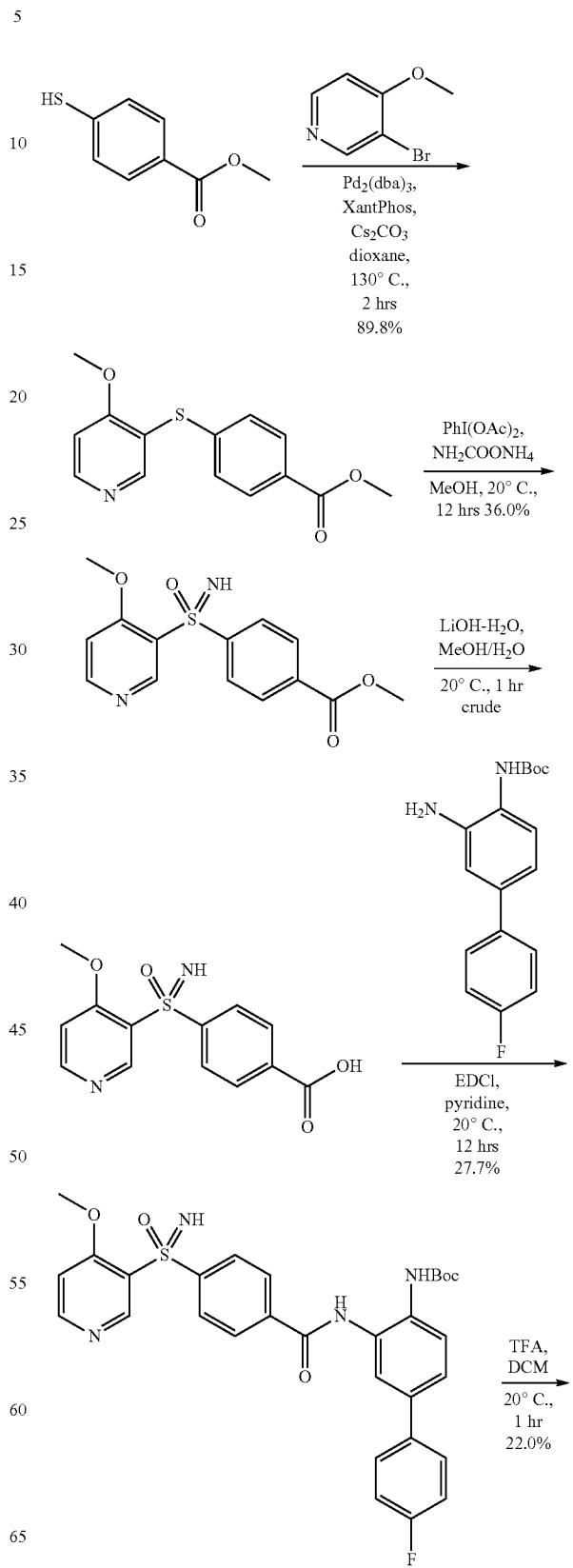

-continued

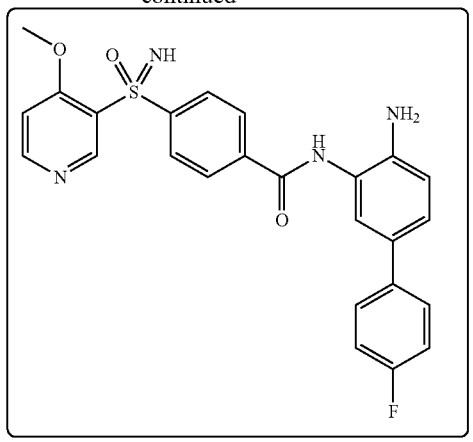

Step 1: Synthesis of methyl 4-[(4-methoxy-3-pyridyl)sulfanyl]benzoate

Methyl 4-sulfanylbenzoate (500 mg, 2.97 mmol), 3-bromo-4-methoxy-pyridine (600 mg, 3.19 mmol), (1E, 4E)-1,5-diphenylpenta-1,4-dien-3-one;palladium (1.4 g, 1.53 mmol), (5-diphenylphosphanyl-9,9-dimethyl-xanthen-4-yl)-diphenyl-phosphane (875 mg, 1.51 mmol) and dicesium;carbonate (2.9 g, 8.90 mmol) were taken up into a microwave tube in dioxane (10 mL). The sealed tube was heated at 130° C. for 2 hours in microwave. The resulting mixture was quenched by addition of water (20 mL) and extracted with EtOAc (50 mL*3). The combined organic layer was washed with brine (20 mL), dried over anhydrous $Na_2SO_4$, filtered and concentrated under reduced pressure. The residue was purified by flash chromatography (ISCO®; 20 g AgelaFlash® Silica Flash Column, petroleum ether/EtOAc with EtOAc from 0~100%, flow rate=30 mL/min, 254 nm) to afford methyl 4-[(4-methoxy-3-pyridyl)sulfanyl]benzoate (735 mg, 89.8% yield) as brown oil. LCMS (ESI) [M+H]$^+$ m/z: calcd 276.1, found 276.1.

Step 2: Synthesis of methyl 4-[(4-methoxy-3-pyridyl)sulfonimidoyl]benzoate

To a solution of methyl 4-[(4-methoxy-3-pyridyl)sulfanyl]benzoate (500 mg, 1.82 mmol) in MeOH (4 mL) was added [acetoxy(phenyl)-iodanyl] acetate (1.75 g, 5.43 mmol) and ammonia;carbamic acid (860 mg, 11.0 mmol). The mixture was stirred at 20° C. for 12 hours. The resulting mixture was quenched by addition of water (20 mL) and extracted with EtOAc (30 mL*3). The combined organic layer was washed with brine (20 mL), dried over anhydrous $Na_2SO_4$, filtered and concentrated under reduced pressure. The residue was purified by flash chromatography (ISCO®; 20 g AgelaFlash® Silica Flash Column, DCM/MeOH with MeOH from 0~20%, flow rate=30 mL/min, 254 nm) to afford methyl 4-[(4-methoxy-3-pyridyl)sulfonimidoyl]benzoate (200 mg, 36.0% yield) as yellow solid. LCMS (ESI) [M+H]$^+$ m/z: calcd 307.1, found 307.1.

Step 3: Synthesis of 4-[(4-methoxy-3-pyridyl)sulfonimidoyl]benzoic acid

To a solution of methyl 4-[(4-methoxy-3-pyridyl)sulfonimidoyl]benzoate (180 mg, 0.588 mmol) in MeOH (3 mL) and $H_2O$ (1 mL) was added lithium;hydroxide;hydrate (80 mg, 1.91 mmol). The mixture was stirred at 20° C. for 1 hour. The reaction mixture was concentrated under reduced pressure. The mixture was adjusted pH=6 with 2N HCl aqueous solution. The mixture was concentrated under reduced pressure to afford 4-[(4-methoxy-3-pyridyl)sulfonimidoyl]benzoic acid (150 mg, crude) as yellow solid. $^1$H NMR (400 MHz, DMSO-d6) δ ppm 9.01 (s, 1H), 8.60 (d, J=6.0 Hz, 1H), 8.00 (d, J=8.0 Hz, 1H), 7.92 (d, J=8.8 Hz, 1H), 7.14 (d, J=6.0 Hz, 1H), 5.20 (s, 1H), 3.77 (s, 1H); LCMS (ESI) [M+H]$^+$ m/z: calcd 293.1, found 293.1.

Step 4: Synthesis of tert-butyl N-[4-(4-fluorophenyl)-2-[[4-[(4-methoxy-3-pyridyl)sulfonimidoyl]benzoyl]amino]phenyl]carbamate A mixture of 4-[(4-methoxy-3-pyridyl)sulfonimidoyl]benzoic acid (110 mg, 0.376 mmol), tert-butyl N-[2-amino-4-(4-fluorophenyl)phenyl]carbamate (120 mg, 0.397 mmol), 3-(ethyliminomethyleneamino)-N,N-dimethyl-propan-1-amine;hydrochloride (110 mg, 0.574 mmol) in pyridine (3 mL). The mixture was stirred at 20° C. for 12 hours. The reaction mixture was concentrated under reduced pressure to remove pyridine. The residue was purified by flash chromatography (ISCO®; 4 g AgelaFlash® Silica Flash Column, DCM/MeOH with MeOH from 0~10%, flow rate=30 mL/min, 254 nm) to afford tert-butyl N-[4-(4-fluorophenyl)-2-[[4-[(4-methoxy-3-pyridyl)sulfonimidoyl]benzoyl]amino]phenyl]carbamate (60 mg, 27.7% yield) as yellow solid. LCMS (ESI) [M+H]$^+$ m/z: calcd 577.2, found 577.3.

Step 5: Synthesis of N-[2-amino-5-(4-fluorophenyl)phenyl]-4-[(4-methoxy-3-pyridyl)sulfonimidoyl]benzamide (Compound 240)

To a solution of tert-butyl N-[4-(4-fluorophenyl)-2-[[4-[(4-methoxy-3-pyridyl)sulfonimidoyl]benzoyl]amino]phenyl]carbamate (60 mg, 0.104 mmol) in DCM (2 mL) was added TFA (0.25 mL, 3.25 mmol). The mixture was stirred at 20° C. for 1 hour. The resulting mixture was concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 μm; Mobile phase A: $H_2O$ with 10 mmol $NH_4HCO_3$ (v %); Mobile phase B: MeCN; Gradient: B from 29% to 59% in 9.5 min, hold 100% B for 1 min; Flow Rate: 30 mL/min; Column Temperature: 30° C.; Wavelength: 220 nm, 254 nm) to afford N-[2-amino-5-(4-fluorophenyl)phenyl]-4-[(4-methoxy-3-pyridyl)sulfonimidoyl]benzamide (10.9 mg, 22.0% yield) as yellow solid. $^1$H NMR (400 MHz, DMSO-d6) δ ppm 9.87-9.94 (m, 1H), 9.04 (s, 1H), 8.64 (d, J=5.9 Hz, 1H), 8.05-8.16 (m, 4H), 7.57 (dd, J=8.4, 5.6 Hz, 2H), 7.48 (d, J=1.5 Hz, 1H), 7.31 (dd, J=8.3, 1.8 Hz, 1H), 7.14-7.25 (m, 3H), 6.85 (d, J=8.3 Hz, 1H), 5.36 (s, 1H), 5.15 (brs, 2H), 3.81 (s, 3H); 19F NMR (376 MHz, DMSO-d6) δ ppm−117.464; LCMS (ESI) [M+H]$^+$ m/z: calcd 477.1, found 477.2; HPLC: 97.66%@220 nm; 99.42%@254 nm.

Example 114. Synthesis of N-[2-amino-5-(4-fluorophenyl)phenyl]-5-(1-oxo-4,5-dihydro-3H-isothiazol-1-yl)benzothiophene-2-carboxamide (Compound 204)
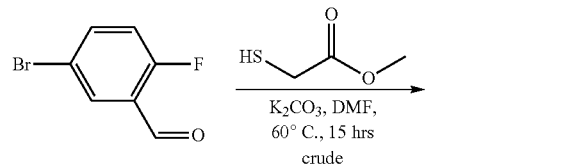
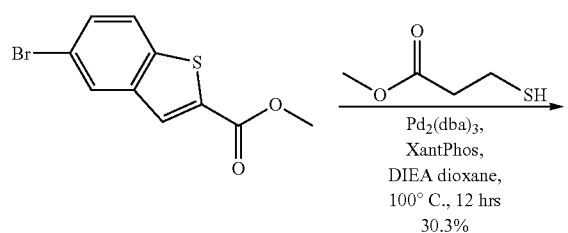
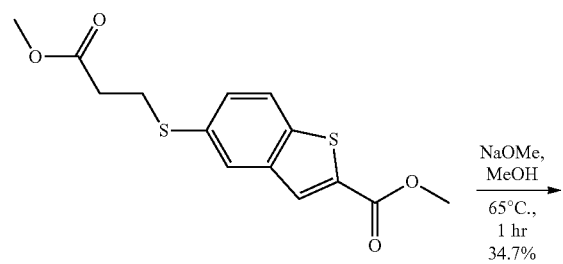
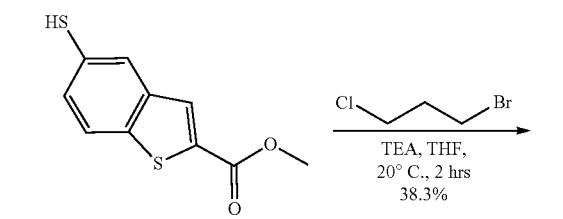
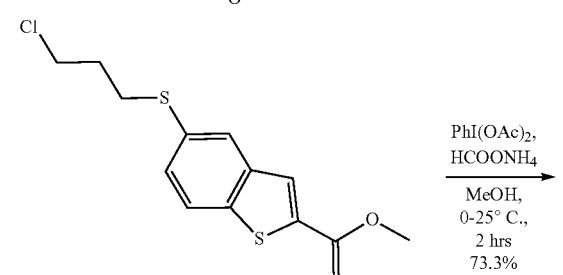
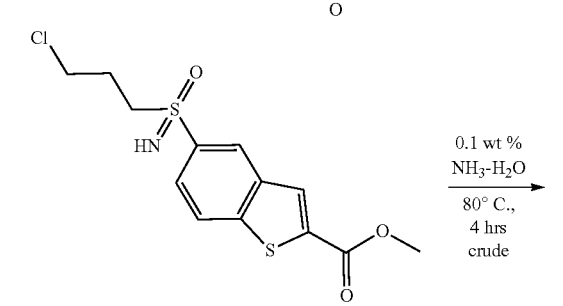
-continued
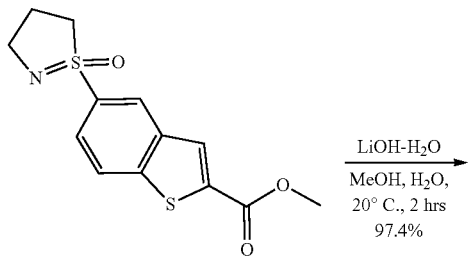
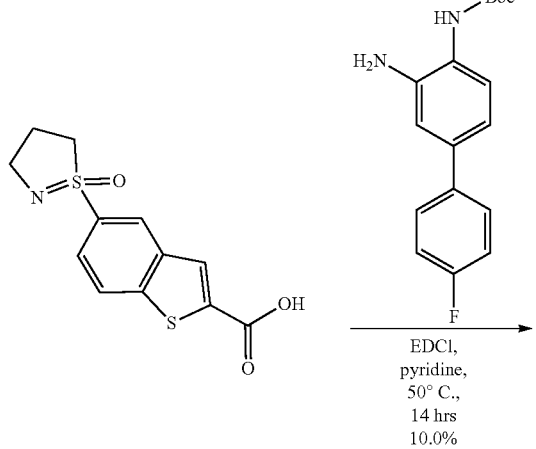
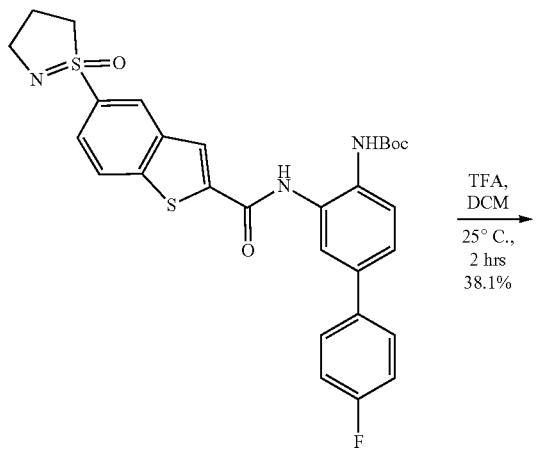
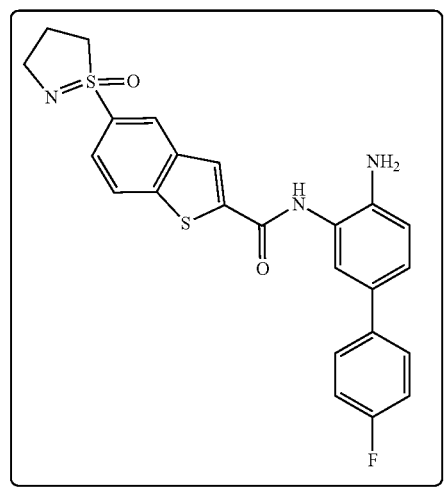

Step 1: Synthesis of methyl 5-bromobenzothiophene-2-carboxylate

A mixture of 5-bromo-2-fluoro-benzaldehyde (10 g, 49.3 mmol), $K_2CO_3$ (27.2 g, 0.196 mol), methyl 2-sulfanylacetate (5 mL, 54.8 mmol) and DMF (50 mL) was stirred at 60° C. for 15 hours. The resulting mixture was extracted with $H_2O$ (50 mL) and EtOAc (100 mL*3). The combined organic layer was washed with saturated brine (100 mL*3), dried over anhydrous $Na_2SO_4$, filtered and concentrated under reduced pressure to afford methyl 5-bromobenzothiophene-2-carboxylate (13.8 g, crude) as green solid. $^1$H NMR (400 MHz, DMSO-d6) δ ppm 8.28 (d, J=2.0 Hz, 1H), 8.18 (s, 1H), 8.06 (d, J=8.0 Hz, 1H), 7.66-7.71 (m, 1H), 3.91 (s, 3H); LCMS (ESI) [M+H]$^+$ m/z: calcd 270.9, found 271.0.

Step 2: Synthesis of methyl 5-(3-methoxy-3-oxopropyl)sulfanylbenzothiophene-2-carboxylate A mixture of methyl 5-bromobenzothiophene-2-carboxylate (13.8 g, 50.9 mmol), methyl 3-sulfanylpropanoate (6.8 mL, 61.4 mmol), (5-diphenylphosphanyl-9,9-dimethyl-xanthen-4-yl)-diphenyl-phosphane (2.94 g, 5.09 mmol), (1E,4E)-1,5-diphenylpenta-1,4-dien-3-one;palladium (2.33 g, 2.54 mmol), DIEA (27 mL, 0.155 mol) and dioxane (50 mL) was stirred at 100° C. for 12 hours. The mixture was filtered and the filtrate concentrated under reduced pressure. The residue was purified by flash chromatography (ISCO®; 80 g AgelaFlash® Silica Flash Column, petroleum ether/EtOAc with EtOAc from 0~30%, flow rate=50 mL/min, 254 nm) to afford methyl 5-(3-methoxy-3-oxo-propyl)sulfanylbenzothiophene-2-carboxylate (4.8 g, 30.3% yield) as yellow solid. LCMS (ESI) [M+H]$^+$ m/z: calcd 311.0, found 311.1.

Step 3: Synthesis of methyl 5-sulfanylbenzothiophene-2-carboxylate

A mixture of methyl 5-(3-methoxy-3-oxo-propyl)sulfanylbenzothiophene-2-carboxylate (4.8 g, 15.4 mmol) and NaOMe (3.4 g, 62.0 mmol) in MeOH (50 mL) was stirred at 65° C. for 1 hour. The mixture was adjusted pH to 5 with 2N HCl. The resulting mixture was extracted with EtOAc (100 mL*3). The combined organic layer was washed with brine (100 mL), dried over anhydrous $Na_2SO_4$, filtered and concentrated under reduced pressure. The residue was purified by flash chromatography (ISCO®; 40 g AgelaFlash® Silica Flash Column, petroleum ether/EtOAc with EtOAc from 0~30%, flow rate=60 mL/min, 254 nm) to afford methyl 5-sulfanylbenzothiophene-2-carboxylate (1.2 g, 34.7% yield) as white solid. LCMS (ESI) [M+H]$^+$ m/z: calcd 225.0, found 225.1.

Step 4: Synthesis of methyl 5-(3-chloropropylsulfanyl)benzothiophene-2-carboxylate To a mixture of 1-bromo-3-chloro-propane (1 mL, 10.1 mmol) and methyl 5-sulfanylbenzothiophene-2-carboxylate (1.2 g, 5.35 mmol) in THF (10 mL) was added N,N-diethylethanamine (1.5 mL, 10.7 mmol). The mixture was stirred at 20° C. for 2 hours. The reaction mixture was concentrated under reduced pressure. The residue was purified by flash chromatography (ISCO®; 40 g AgelaFlash® Silica Flash Column, Petroleum ether/EtOAc with EtOAc from 0~10%, 35 mL/min, 254 nm) to afford methyl 5-(3-chloropropylsulfanyl)benzothiophene-2-carboxylate (616 mg, 38.3% yield) as white solid. $^1$H NMR (400 MHz, DMSO-d6) δ ppm 8.16 (s, 1H), 8.01-8.07 (m, 2H), 7.53 (dd, J=8.5, 1.5 Hz, 1H), 3.90 (s, 3H), 3.75 (t, J=6.4 Hz, 2H), 3.14 (t, J=7.2 Hz, 2H), 2.02 (quin, J=6.8 Hz, 2H); LCMS (ESI) [M+H]$^+$ m/z: calcd 301.0, found 301.0.

Step 5: Synthesis of methyl 5-(3-chloropropylsulfonimidoyl)benzothiophene-2-carboxylate To a solution of methyl 5-(3-chloropropylsulfanyl)benzothiophene-2-carboxylate (616 mg, 2.05 mmol) in MeOH (1 mL) was added ammonia;carbamic acid (320 mg, 4.10 mmol) and [acetoxy(phenyl)-iodanyl] acetate (1.65 g, 5.12 mmol) at 0° C. slowly. The mixture was stirred at 25° C. for 2 hours. The resulting mixture was quenched by addition of water (20 mL) and extracted with EtOAc (20 mL*3). The combined organic layer was washed with saturated brine (20 mL), dried over anhydrous $Na_2SO_4$, filtered and concentrated under reduced pressure. The residue was purified by flash chromatography (ISCO®; 4 g AgelaFlash® Silica Flash Column, petroleum ether/EtOAc with EtOAc from 0~90%, flow rate=40 mL/min, 254 nm) to afford methyl 5-(3-chloropropylsulfonimidoyl)benzothiophene-2-carboxylate (498 mg, 73.3% yield) as colorless oil. LCMS (ESI) [M+H]$^+$ m/z: calcd 332.0, found 332.0.

Step 6: Synthesis of methyl 5-(3-chloropropylsulfonimidoyl)benzothiophene-2-carboxylate A mixture of methyl 5-(3-chloropropylsulfonimidoyl)benzothiophene-2-carboxylate (498 mg, 1.50 mmol) in 0.1 wt % $NH_3$—$H_2O$ (4 mL) was stirred at 80° C. for 2 hours. To the mixture was added 0.1% $NH_3$—$H_2O$ (4 mL), and the mixture was stirred at 80° C. for 2 hours. The mixture was concentrated to give methyl 5-(1-oxo-4,5-dihydro-3H-isothiazol-1-yl)benzothiophene-2-carboxylate (506 mg, crude) as yellow solid. $^1$H NMR (400 MHz, DMSO-d6) δ ppm 8.91 (s, 1H), 8.55 (d, J=8.8 Hz, 1H), 8.48 (s, 1H), 8.13 (d, J=8.8 Hz, 1H), 4.11-4.32 (m, 2H), 4.00 (ddd, J=9.1, 7.0, 4.3 Hz, 2H), 3.94 (s, 3H), 2.58-2.66 (m, 2H); LCMS (ESI) [M+H]$^+$ m/z: calcd 296.0, found 296.0.

Step 7: Synthesis of 5-(1-oxo-4,5-dihydro-3H-isothiazol-1-yl)benzothiophene-2-carboxylic acid A mixture of methyl 5-(1-oxo-4,5-dihydro-3H-isothiazol-1-yl)benzothiophene-2-carboxylate (506 mg, 1.71 mmol) and LiOH—$H_2O$ (215 mg, 5.12 mmol) in MeOH (1 mL) and $H_2O$ (3 mL) was stirred at 20° C. for 2 hours. The mixture was concentrated. The residue was purified by flash chromatography (Biotage®, Column: SepaFlash® Sphercial C18, 40 g, 40-60 μm, 120 Å; MeCN/water (HCl) with MeCN from 30~40%, 35 mL/min, 254 nm) to give 5-(1-oxo-4,5-dihydro-3H-isothiazol-1-yl)benzothiophene-2-carboxylic acid (469.1 mg, 97.4% yield) as white solid. $^1$H NMR (400 MHz, DMSO-d6) δ ppm 8.93 (s, 1H), 8.56 (d, J=8.8 Hz, 1H), 8.39 (s, 1H), 7.95 (s, 1H), 4.22-4.47 (m, 2H), 4.01-4.01 (m, 2H), 2.58-2.69 (m, 2H); LCMS (ESI) [M+H]$^+$ m/z: calcd 282.0, found 282.1.

Step 8: Synthesis of tert-butyl N-[4-(4-fluorophenyl)-2-[[5-(1-oxo-4,5-dihydro-3H-isothiazol-1-yl)benzothiophene-2-carbonyl]amino]phenyl]carbamate A mixture of 5-(1-oxo-4,5-dihydro-3H-isothiazol-1-yl)benzothiophene-2-carboxylic acid (150 mg, 0.533 mmol), tert-butyl N-[2-amino-4-(4-fluorophenyl)phenyl]carbamate (177 mg, 0.586 mmol) and 3-(ethyliminomethyleneamino)-N,N-dimethyl-propan-1-amine;hydrochloride (123 mg, 0.640 mmol) in pyridine (1 mL) was stirred at 50° C. for 2 hours. Then 3-(ethyliminomethyleneamino)-N,N-dimethyl-propan-1-amine;hydrochloride (123 mg, 0.640 mmol) was added to the mixture. The mixture was stirred at 50° C. for 12 hours. The mixture was concentrated under reduced pressure. The residue was purified by flash chromatography (ISCO®; 40 g AgelaFlash® Silica Flash Column, dichloromethane/MeOH with methanol from 0~30%, flow rate=60 mL/min, 254 nm) to afford tert-butyl N-[4-(4-fluorophenyl)-2-[[5-(1-oxo-4,5-dihydro-3H-isothiazol-1-yl)benzothiophene-2-carbonyl]amino]phenyl]carbamate (30 mg, 10.0% yield) as yellow oil. LCMS (ESI) [M+H]+ m/z: calcd 566.2, found 566.3.

Step 9: Synthesis of N-[2-amino-5-(4-fluorophenyl)phenyl]-5-(1-oxo-4,5-dihydro-3H-isothiazol-1-yl)benzothiophene-2-carboxamide A mixture of tert-butyl N-[4-(4-fluorophenyl)-2-[[5-(1-oxo-4,5-dihydro-3H-isothiazol-1-yl)benzothiophene-2-carbonyl]amino]phenyl]carbamate (30 mg, 0.0530 mmol) and TFA (0.1 mL, 1.30 mmol) in DCM (1 mL) was stirred at 25° C. for 2 hours. The mixture was concentrated and the mixture was adjusted pH=8 with 25 wt % NH$_3$—H$_2$O. The residue was purified by preparative HPLC (Instrument: Gilson GX-281 Liquid Handler, Gilson 322 Pump, Gilson 156 UV Detector; Column: 2_Phenomenex Gemini C18 75*40 mm*3 µm; Mobile phase A: H$_2$O with NH$_4$HCO$_3$ (v %); Mobile phase B: MeCN; Gradient: B from 37% to 67% in 9.5 min, hold 100% B for 2 min; Flow Rate: 30 mL/min; Column Temperature: 30° C.; Wavelength: 220 nm, 254 nm) to afford N-[2-amino-5-(4-fluorophenyl)phenyl]-5-(1-oxo-4,5-dihydro-3H-isothiazol-1-yl)benzothiophene-2-carboxamide (9.4 mg, 38.1% yield) as yellow solid. $^1$H NMR (400 MHz, methanol-d4) δ ppm 8.57 (d, J=1.3 Hz, 1H), 8.34 (s, 1H), 8.23 (d, J=8.8 Hz, 1H), 7.94 (dd, J=8.7, 1.9 Hz, 1H), 7.53-7.60 (m, 2H), 7.49 (d, J=2.0 Hz, 1H), 7.36 (dd, J=8.4, 2.1 Hz, 1H), 7.07-7.16 (m, 2H), 6.98 (d, J=8.5 Hz, 1H), 4.02 (ddd, J=10.4, 6.5, 5.3 Hz, 1H), 3.87 (dt, J=10.4, 6.6 Hz, 1H), 3.48-3.60 (m, 2H), 2.36-2.54 (m, 2H); 19F NMR (376 MHz, methanol-d4) δ ppm −119.342; LCMS (ESI) [M+H]+ m/z: calcd 466.1, found 466.2; HPLC: 98.76%@220 nm; 99.06%@254 nm.

Example 115. Synthesis of N-[2-amino-5-(4-fluorophenyl)phenyl]-4-(1-oxo-1thia-2-azacyclohexen-1-yl)benzamide (Compound 243)

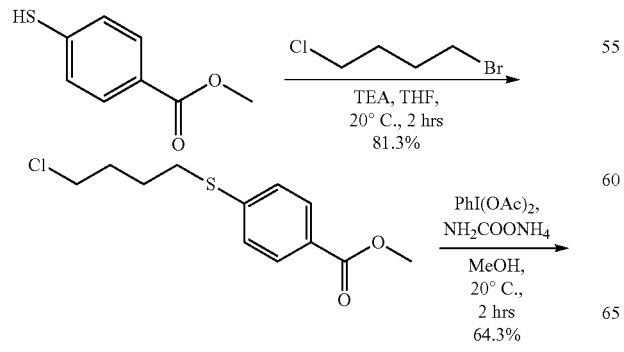

Step 1: Synthesis of methyl 4-(4-chlorobutylsulfanyl)benzoate

To a mixture of methyl 4-sulfanylbenzoate (200 mg, 1.19 mmol) and 1-bromo-4-chloro-butane (408 mg, 2.38 mmol) in THF (5 mL) was added TEA (244 mg, 2.41 mmol). The mixture was stirred at 20° C. for 2 hours. The reaction mixture was concentrated under reduced pressure. The residue was purified by flash chromatography (ISCO®; 40 g AgelaFlash® Silica Flash Column, Petroleum ether/EtOAc

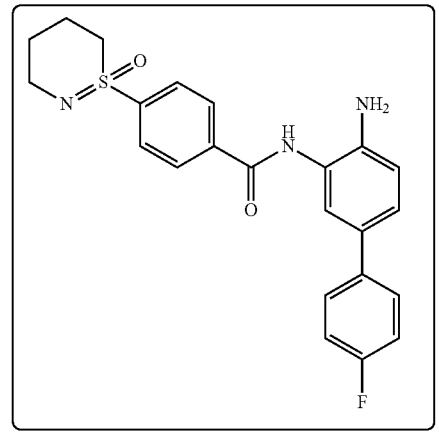 [SMILES: Nc1ccc(-c2ccc(F)cc2)cc1NC(=O)c1ccc(S2(=O)=NCCCC2)cc1]

with EtOAc from 0~6%, 30 mL/min, 254 nm) to afford methyl 4-(4-chlorobutylsulfanyl)benzoate (250 mg, 81.26% yield) as yellow oil.

Step 2: Synthesis of methyl 4-(4-chlorobutylsulfonimidoyl)benzoate

To a solution of methyl 4-(4-chlorobutylsulfanyl)benzoate (250 mg, 0.966 mmol) in MeOH (6 mL) was added ammonia;carbamic acid (152 mg, 1.95 mmol) and [acetoxy (phenyl)-iodanyl] acetate (780 mg, 2.42 mmol). The mixture was stirred at 20° C. for 2 hours. The reaction mixture was diluted with $H_2O$ (20 mL) and extracted with EtOAc (20 mL*3). The combined organic layers were dried over anhydrous $Na_2SO_4$, filtered and concentrated under reduced pressure. The residue was purified by flash chromatography (Biotage®; 20 g AgelaFlash® Silica Flash Column, Petroleum ether/EtOAc with EtOAc from 0~65%, 30 mL/min, 254 nm) to afford methyl 4-(4-chlorobutylsulfonimidoyl) benzoate (180 mg, 64.3% yield) as light-yellow oil. LCMS (ESI) [M+H]$^+$ m/z calcd 290.1, found 290.1.

Step 3: Synthesis of 4-(1-oxo-1-thia-2-azacyclohexen-1-yl)benzoic acid

A mixture of methyl 4-(4-chlorobutylsulfonimidoyl)benzoate (240 mg, 0.828 mmol) in 0.1 wt % $NH_3$—$H_2O$ (10 mL) was stirred at 80° C. for 12 hours. The mixture was dried under reduced pressure to give 4-(1-oxo-1-thia-2-azacyclohexen-1-yl)benzoic acid (90 mg, 45.4% yield) as light-yellow solid. LCMS (ESI) [M+H]$^+$ m/z calcd 240.1, found 240.1.

Step 4: Synthesis of tert-butyl N-[4-(4-fluorophenyl)-2-[[4-(1-oxo-1thia-2-azacyclohexen-1-yl)benzoyl]amino]phenyl]carbamate To a solution of tert-butyl N-[2-amino-4-(4-fluorophenyl) phenyl]carbamate (104 mg, 0.344 mmol) and 4-(1-oxo-1-thia-2-azacyclohexen-1-yl)benzoic acid (80 mg, 0.334 mmol) in pyridine (5 mL) was added 3-(ethyliminomethyleneamino)-N,N-dimethyl-propan-1-amine;hydrochloride (96 mg, 0.501 mmol). The mixture was stirred at 50° C. for 1 hour. The residue was purified by flash chromatography (ISCO®; 12 g AgelaFlash®Silica Flash Column, petroleum ether/EtOAc with EtOAc from 0~65%, flow rate=60 mL/min, 254 nm) to afford tert-butyl N-[4-(4-fluorophenyl)-2-[[4-(1-oxo-1thia-2-azacyclohexen-1-yl)benzoyl]amino] phenyl]carbamate (50 mg, 28.6% yield) as light-yellow solid. LCMS (ESI) [M+H]$^+$ m/z: calcd 524.2, found 524.3.

Step 5: Synthesis of N-[2-amino-5-(4-fluorophenyl) phenyl]-4-(1-oxo-1thia-2-azacyclohexen-1-yl)benzamide To a solution of tert-butyl N-[4-(4-fluorophenyl)-2-[[4-(1-oxo-1thia-2-azacyclohexen-1-yl)benzoyl]amino]phenyl] carbamate (40 mg, 0.0764 mmol) in DCM (2 mL) was added TFA (0.12 mL, 1.54 mmol). The mixture was stirred at 20° C. for 2 hours. The mixture was concentrated under reduced pressure. The residue was adjusted pH=8 with 25 wt % $NH_3$—$H_2O$, and purified by preparative HPLC (Instrument: Gilson GX-281 Liquid Handler, Gilson 322 Pump, Gilson 156 UV Detector; Column: 2_Phenomenex Gemini C18 75*40 mm*3 µm; Mobile phase A: water ($NH_4HCO_3$)-ACN; Mobile phase B: MeCN; Gradient: B from 25% to 55% in 7.8 min, hold 100% B for 2 min; Flow Rate: 30 mL/min; Column Temperature: 30° C.; Wavelength: 220 nm, 254 nm) to afford N-[2-amino-5-(4-fluorophenyl)phenyl]-4-(1-oxo-1thia-2-azacyclohexen-1-yl)benzamide (14 mg, 43.3% yield) as yellow solid. $^1$H NMR (400 MHz, DMSO-d6) δ ppm 9.95 (s, 1H), 8.16-8.28 (m, 2H), 8.11 (d, J=8.4 Hz, 2H), 7.58 (dd, J=8.6, 5.5 Hz, 2H), 7.50 (d, J=1.9 Hz, 1H), 7.32 (dd, J=8.4, 2.1 Hz, 1H), 7.21 (t, J=8.9 Hz, 2H), 6.86 (d, J=8.4 Hz, 1H), 5.17 (s, 2H), 3.41-3.50 (m, 2H), 3.02-3.23 (m, 2H), 2.22-2.37 (m, 1H), 2.07-2.19 (m, 1H), 1.59-1.78 (m, 2H); 19F NMR (376 MHz, DMSO-d6) δ ppm−117.456; LCMS (ESI) [M+H]$^+$ m/z: calcd 424.1, found 424.2; HPLC: 98.350%@220 nm, 98.950%@254 nm.

Example 116. Synthesis of N-(4-amino-4'-fluoro-[1,1'-biphenyl]-3-yl)-4-(5-fluoropyridine-3-sulfonimidoyl)benzamide (Compound 206)

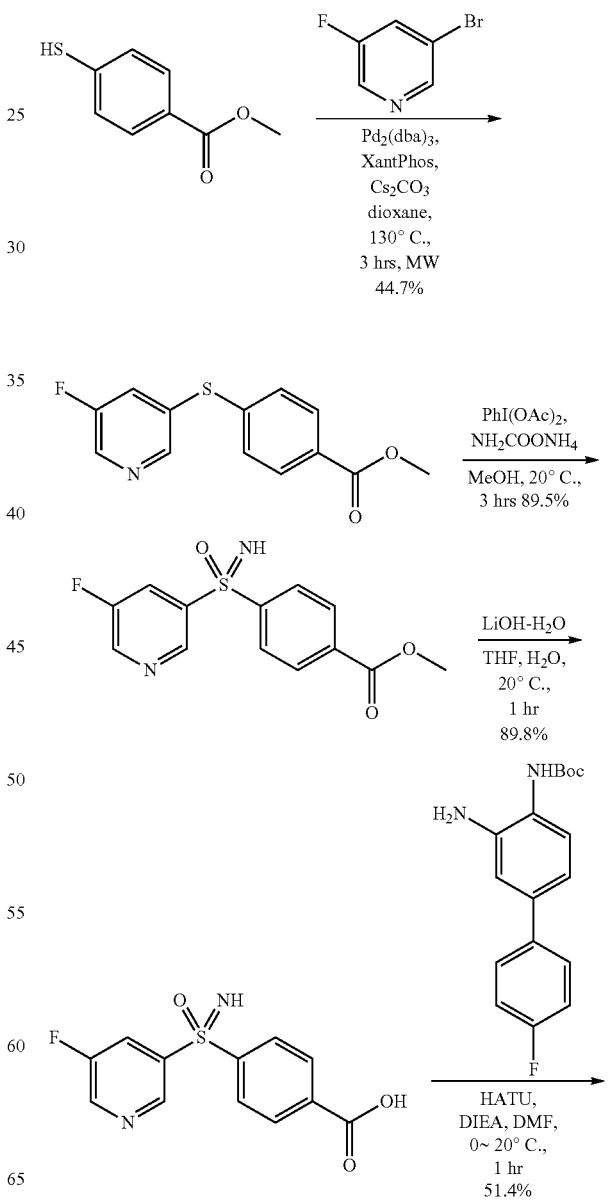

-continued

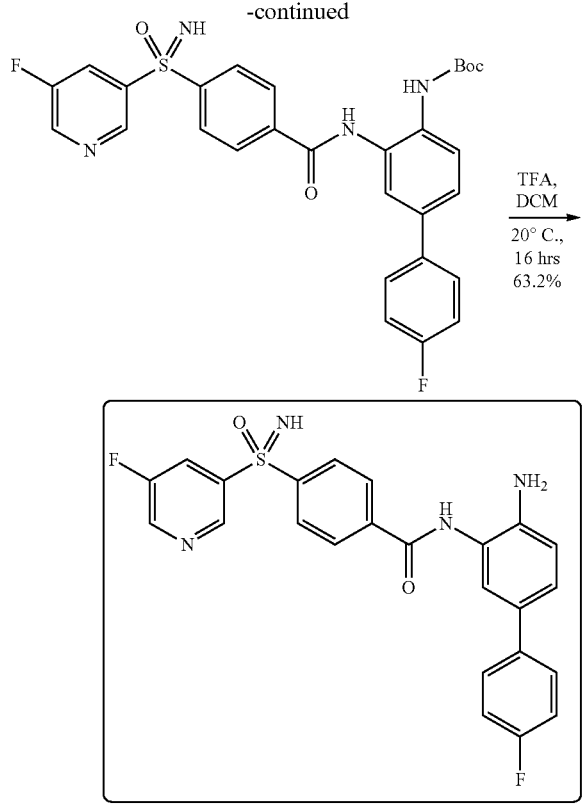

TFA, DCM
20° C., 16 hrs
63.2%

Step 1: Synthesis of methyl 4-[(5-fluoro-3-pyridyl)sulfanyl]benzoate

A mixture of methyl 4-sulfanylbenzoate (500 mg, 2.97 mmol), 3-bromo-5-fluoropyridine (628 mg, 3.57 mmol), Pd$_2$(dba)$_3$ (544 mg, 0.595 mmol), XantPhos (688 mg, 1.19 mmol) and Cs$_2$CO$_3$ (2.91 g, 8.92 mmol) in dioxane (10 mL) was purged with N$_2$ gas at ambient temperature for 5 minutes. Then mixture was stirred at 130° C. for 3 hours in microwave. The resulting mixture was quenched by addition of water (50 mL) and extracted with EtOAc (30 mL*3). The combined organic layer was washed with brine (30 mL), dried over anhydrous Na$_2$SO$_4$, filtered and concentrated under reduced pressure. The residue was purified by flash chromatography (ISCO®; 40 g SepaFlash® Silica Flash Column, petroleum ether/EtOAc with EtOAc from 0~10%, flow rate=25 mL/min, 254 nm) to afford methyl 4-[(5-fluoro-3-pyridyl)sulfanyl]benzoate (700 mg, 44.7% yield) as yellow solid. $^1$H NMR (400 MHz, chloroform-d) δ ppm 8.36-8.52 (2H, m) 7.94-8.07 (2H, m) 7.32-7.44 (3H, m) 3.93 (3H, s); LCMS (ESI) [M+H]$^+$ m/z: calcd 264.1, found 264.1.

Step 2: Synthesis of methyl 4-[(5-fluoro-3-pyridyl)sulfonimidoyl]benzoate

To a solution of methyl 4-[(5-fluoro-3-pyridyl)sulfanyl]benzoate (600 mg, 2.28 mmol) in MeOH (30 mL) was added NH$_2$COONH$_4$ (267 mg, 3.42 mmol) and PhI(OAc)$_2$ (2.20 g, 6.84 mmol) at 0° C. slowly. The mixture was stirred at 20° C. for 3 hours. The reaction mixture was diluted with H$_2$O (50 mL) and extracted with EtOAc (30 mL*3). The combined organic layers were dried over anhydrous Na$_2$SO$_4$, filtered and concentrated under reduced pressure. The residue was purified by flash chromatography (ISCO®; 40 g SepaFlash® Silica Flash Column, petroleum ether/EtOAc with EtOAc from 0~50%, flow rate=25 mL/min, 254 nm) to give methyl 4-[(5-fluoro-3-pyridyl)sulfonimidoyl]benzoate (600 mg, 89.5% yield) as a white solid. LCMS (ESI) [M+H]$^+$ m/z: calcd 295.1, found 295.1.

Step 3: Synthesis of 4-[(5-fluoro-3-pyridyl)sulfonimidoyl]benzoic acid

To a solution of methyl 4-[(5-fluoro-3-pyridyl)sulfonimidoyl]benzoate (600 mg, 2.04 mmol) in MeOH (20 mL) and H$_2$O (10 mL) was added LiOH—H$_2$O (171 mg, 4.08 mmol). The mixture was stirred at 20° C. for 1 hour. The reaction mixture was concentrated in vacuum. The aqueous layer was acidified with 2M HCl aqueous solution pH~4, extracted with EtOAc (30 mL*3), concentrated in vacuum to give 4-[(5-fluoro-3-pyridyl)sulfonimidoyl]benzoic acid (600 mg, 89.8% yield) as a white solid. $^1$H NMR (400 MHz, DMSO-d6) δ ppm 13.28-13.59 (1H, m) 8.98 (1H, s) 8.84 (1H, d, J=2.6 Hz) 8.25-8.36 (1H, m) 8.14-8.21 (2H, m) 8.05-8.13 (2H, m) 5.69 (1H, br s).

Step 4: Synthesis of tert-butyl N-[4-(4-fluorophenyl)-2-[[4-[(5-fluoro-3-pyridyl)sulfonimidoyl]benzoyl]amino]phenyl]carbamate To a solution of 4-[(5-fluoro-3-pyridyl)sulfonimidoyl] benzoic acid (500 mg, 1.78 mmol), DIEA (692 mg, 5.35 mmol) in DMF (15 mL) was added HATU (1.02 g, 2.68 mmol). The mixture was stirred at 0° C. for 30 minute. Then tert-butyl N-[2-amino-4-(4-fluorophenyl)phenyl] carbamate (593 mg, 1.96 mmol) was added. The mixture was stirred at 20° C. for 1 hour. The reaction was poured into water (100 mL), the aqueous layer was filtered and the filter cake was washed with water (10 mL*2). The filter cake was purified by flash chromatography (ISCO®; 20 g SepaFlash® Silica Flash Column, petroleum ether/EtOAc with EtOAc from 0~50%, flow rate=25 mL/min, 254 nm) to give tert-butyl N-[4-(4-fluorophenyl)-2-[[4-[(5-fluoro-3-pyridyl)sulfonimidoyl]benzoyl]amino]phenyl]carbamate (600 mg, 51.4% yield) as a light-Yellow solid. LCMS (ESI) [M+H]$^+$ m/z: calcd 565.2, found 565.3.

Step 5: Synthesis of N-[2-amino-5-(4-fluorophenyl)phenyl]-4-[(5-fluoro-3-pyridyl)sulfonimidoyl]benzamide (Compound 206)

To a solution of tert-butyl N-[4-(4-fluorophenyl)-2-[[4-[(5-fluoro-3-pyridyl)sulfonimidoyl] benzoyl]amino]phenyl] carbamate (400 mg, 0.708 mmol) in DCM (10 mL) was added TFA (2 mL). The mixture was stirred at 20° C. for 16 hours. The reaction mixture was concentrated under reduced pressure. The mixture adjusted the pH ~8 with sat. NaHCO$_3$ aqueous solution, extracted with EtOAc (3*50 mL). The combined organic layers were washed with brine (30 mL), dried over anhydrous Na$_2$SO$_4$, filtered and concentrated in vacuum. The residue was purified by flash chromatography (Biotage®, Column: Kromasil Eternity XT 150*30 mm*10 μm, C18, 40 g, 40-60 μm, 120 Å; water (NH$_3$H$_2$O+ NH$_4$HCO$_3$)-ACN) with MeCN from 28~48%, 60 mL/min, 254 nm) to give N-[2-amino-5-(4-fluorophenyl)phenyl]-4-[(5-fluoro-3-pyridyl)sulfonimidoyl]benzamide (260 mg, 63.2% yield) as a light yellow solid.

Compound 206: $^1$H NMR (400 MHz, DMSO-d6) δ ppm 9.88 (1H, s) 9.00 (1H, s) 8.84 (1H, d, J=2.5 Hz) 8.30-8.39 (1H, m) 8.17 (4H, q, J=8.5 Hz) 7.56 (2H, dd, J=8.7, 5.4 Hz) 7.47 (1H, d, J=2.0 Hz) 7.31 (1H, dd, J=8.4, 2.1 Hz) 7.21 (2H, t, J=8.9 Hz) 6.84 (1H, d, J=8.5 Hz) 5.68 (1H, s) 5.08-5.22 (2H, m); 19F NMR (377 MHz, DMSO-d6) δ ppm −117.46, −124.20; LCMS (ESI) [M+H]+ m/z: calcd 465.1, found 465.1; HPLC: 99.95%@220 nm, 99.95%@254 nm.
Example 117. Synthesis of N-[2-amino-5-(4-fluorophenyl)phenyl]-4-[[6-(2-methoxyethoxymethyl)-3-pyridyl]sulfonimidoyl]benzamide (Compound 246)
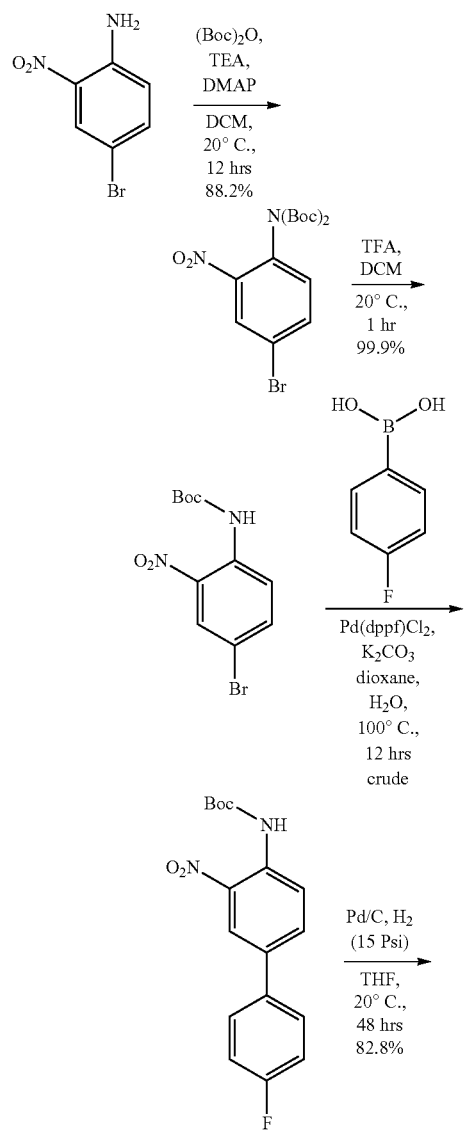
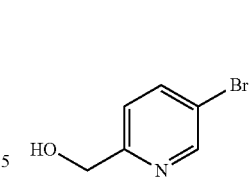
-continued
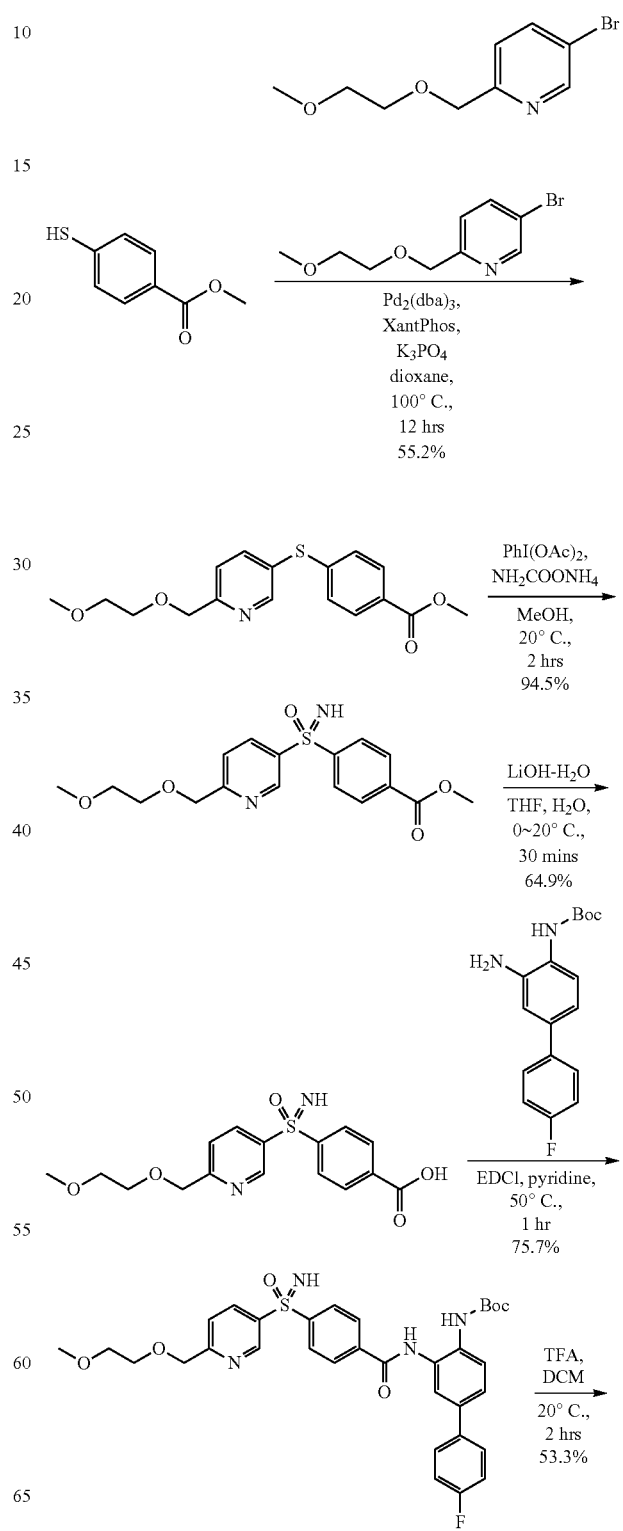

-continued

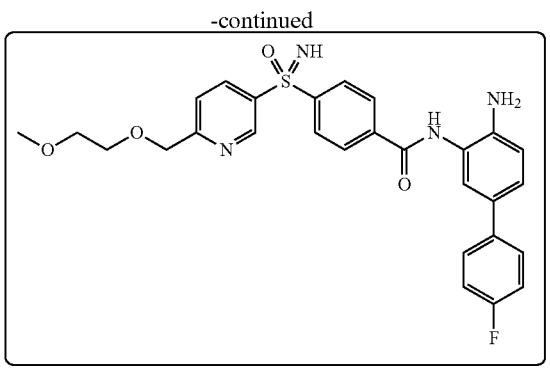

Step 1: Synthesis of tert-butyl N-(4-bromo-2-nitro-phenyl)-N-tert-butoxycarbonyl-carbamate To a solution of 4-bromo-2-nitro-aniline (250 g, 1.15 mol), DMAP (15 g, 0.123 mol), TEA (485 mL, 3.48 mol) in DCM (1.5 L) was added tertbutoxycarbonyl tert-butyl carbonate (558 mL, 2.43 mol). The mixture was stirred at 20° C. for 12 hours. The mixture was concentrated under reduced pressure. The residue was triturated with MeOH (6000 mL). The mixture was filtered. The filter cake was concentrated under reduced pressure to afford tert-butyl N-(4-bromo-2-nitro-phenyl)-N-tert-butoxycarbonyl-carbamate (848 g, 88.2% yield) as white solid. $^1$H NMR (400 MHz, DMSO-d6) δ ppm 8.33 (d, J=2.0 Hz, 1H), 8.01 (dd, J=8.5, 1.8 Hz, 1H), 7.59 (d, J=8.5 Hz, 1H), 1.33 (s, 18H).

Step 2: Synthesis of tert-butyl N-(4-bromo-2-nitro-phenyl)carbamate

To a solution of tert-butyl N-(4-bromo-2-nitro-phenyl)-N-tert-butoxycarbonyl-carbamate (210 g, 0.503 mol) in DCM (2000 mL) was added TFA (67 mL, 0.860 mol). The mixture was stirred at 20° C. for 1 hour. The mixture was combined with another batch. The resulting mixture was adjusted pH=8 with saturated Na$_2$CO$_3$ aqueous solution and extracted with DCM (500 mL*3). The combined organic layer was dried over anhydrous Na$_2$SO$_4$, filtered and concentrated under reduced pressure to afford tert-butyl N-(4-bromo-2-nitro-phenyl)carbamate (319 g, 99.9% yield) as yellow solid. The residue (100 mg) was further purified by flash chromatography (ISCO®; 12 g Agela Flash® Silica Flash Column, petroleum ether/EtOAc with EtOAc from 0~10%, flow rate=30 mL/min, 254 nm) to afford tert-butyl N-(4-bromo-2-nitro-phenyl)carbamate (52.5 mg, for delivery) as yellow solid. $^1$H NMR (400 MHz, DMSO-d6) δ ppm 9.67 (s, 1H), 8.12 (d, J=2.3 Hz, 1H), 7.86 (dd, J=8.8, 2.4 Hz, 1H), 7.59 (d, J=8.9 Hz, 1H), 1.44 (s, 9H); HPLC: 98.07%@220 nm, 99.73%@254 nm.

Step 3: Synthesis of tert-butyl N-[4-(4-fluorophenyl)-2-nitro-phenyl]carbamate To a solution of tert-butyl N-(4-bromo-2-nitro-phenyl) carbamate (240 g, 0.757 mol), (4-fluorophenyl)boronic acid (136 g, 0.972 mol), K$_2$CO$_3$ (314 g, 2.27 mol) in dioxane (1.8 L) and H$_2$O (300 mL) was added Pd(dppf)Cl$_2$ (13 g, 15.9 mmol). The mixture was stirred at 100° C. for 12 hours under N$_2$. The mixture was poured into ice water (3 L). The mixture was adjusted pH=8 with NH$_4$Cl solid and stirred for 2 hours. Then the mixture was filtered, and the filter cake was concentrated under reduced pressure to afford tert-butyl N-[4-(4-fluorophenyl)-2-nitro-phenyl]carbamate (369 g, crude) as green solid. $^1$H NMR (400 MHz, DMSO-d6) δ ppm 8.15 (d, J=2.0 Hz, 1H), 7.96 (dd, J=8.5, 2.3 Hz, 1H), 7.68-7.80 (m, 3H), 7.29 (dd, J=8.8, 5.3 Hz, 2H), 1.39-1.50 (m, 9H); 19F NMR (376 MHz, DMSO-d6) δ ppm−115.611.

Step 4: Synthesis of tert-butyl N-[2-amino-4-(4-fluorophenyl)phenyl]carbamate To a solution of tert-butyl N-[4-(4-fluorophenyl)-2-nitro-phenyl]carbamate (150 g, 0.451 mol) in THF (1.2 L) was added Pd/C (33 g, 10 wt % Pd with 50 wt % water). The suspension was degassed and purged with hydrogen for 3 times. The mixture was stirred under hydrogen (15 Psi) at 20° C. for 48 hours. The resulting mixture was filtered. The filtrate was concentrated under reduced pressure. The residue was triturated with MeOH (1 L*5). The mixture was filtered. The filter cake was dried under reduced pressure to give tert-butyl N-[2-amino-4-(4-fluorophenyl)phenyl]carbamate (113 g, 82.8% yield) as white solid. $^1$H NMR (400 MHz, DMSO-d6) δ ppm 8.35 (s, 1H), 7.49-7.64 (m, 2H), 7.16-7.39 (m, 3H), 6.96 (d, J=2.0 Hz, 1H), 6.80 (dd, J=8.2, 2.1 Hz, 1H), 4.97 (s, 2H), 1.47 (s, 9H); 19F NMR (376 MHz, DMSO-d6) δ ppm−116.348; LCMS (ESI) [M+MeCN+H]$^+$ m/z: calcd 344.1, found 344.2; HPLC: 98.40%@220 nm, 99.530%@254 nm.

Step 5: Synthesis of 5-bromo-2-(2-methoxyethoxymethyl)pyridine

To a solution of 1-bromo-2-methoxy-ethane (2.8 mL, 29.8 mmol) in THF (15 mL) was added NaH (1.8 g, 45.0 mmol, 60 wt % in) at 0° C. and stirred for 30 minutes. The mixture was stirred at 20° C. for 2 hours, then (5-bromo-2-pyridyl)methanol (2.8 g, 14.9 mmol) was added and the mixture was stirred at 20° C. for 12 hours. The reaction mixture was quenched with ice cold water (20 mL), then extracted with EtOAc and dried with Na$_2$SO$_4$ and evaporated to get crude product. The residue was purified by flash chromatography (ISCO®; 20 g Agela Flash®Silica Flash Column, petroleum ether/EtOAc with EtOAc from 0~50%, flow rate=40 mL/min, 254 nm) to afford 5-bromo-2-(2-methoxyethoxymethyl)pyridine (1.5 g, crude) as yellow oil. LCMS (ESI) [M+H]$^+$ m/z: calcd 248.0, found 248.0.

Step 6: Synthesis of methyl 4-[[6-(2-methoxyethoxymethyl)-3-pyridyl]sulfanyl]benzoate To a solution of 5-bromo-2-(2-methoxyethoxymethyl) pyridine (750 mg, 3.05 mmol) and methyl 4-sulfanylbenzoate (500 mg, 2.97 mmol) in dioxane (10 mL) was added K$_3$PO$_4$ (1.9 g, 8.95 mmol), Xantphos (172 mg, 0.297 mmol) and Pd$_2$(dba)$_3$ (271 mg, 0.296 mmol). The mixture was stirred under N$_2$ at 100° C. for 12 hours. The resulting mixture was concentrated under reduced pressure. The residue was purified by flash chromatography (ISCO®; 20 g Agela Flash®Silica Flash Column, petroleum ether/EtOAc with EtOAc from 0~65%, flow rate=40 mL/min, 254 nm) to afford methyl 4-[[6-(2-methoxyethoxymethyl)-3-pyridyl] sulfanyl]benzoate (545 mg, 55.2% yield) as brown oil. LCMS (ESI) [M+H]$^+$ m/z: calcd 334.1, found 334.1.

Step 7: Synthesis of methyl 4-[[6-(2-methoxyethoxymethyl)-3-pyridyl]sulfonimidoyl]benzoate To a solution of methyl 4-[[6-(2-methoxyethoxymethyl)-3-pyridyl]sulfanyl]benzoate (545 mg, 1.63 mmol) in MeOH (10 mL) was added PhI(OAc)₂ (1.32 g, 4.09 mmol), NH₂COONH₄ (256 mg, 3.28 mmol). The mixture was stirred at 20° C. for 2 hours. The resulting mixture was concentrated under reduced pressure. The residue was purified by flash chromatography (ISCO®; 20 g Agela Flash®Silica Flash Column, petroleum ether/EtOAc with EtOAc from 0~60%, flow rate=40 mL/min, 254 nm) to afford methyl 4-[[6-(2-methoxyethoxymethyl)-3-pyridyl]sulfonimidoyl]benzoate (563 mg) as light yellow solid. LCMS (ESI) [M+H]⁺ m/z: calcd 365.1, found 365.1.

Step 8: Synthesis of 4-[[6-(2-methoxyethoxymethyl)-3-pyridyl]sulfonimidoyl]benzoic acid To a solution of methyl 4-[[6-(2-methoxyethoxymethyl)-3-pyridyl]sulfonimidoyl]benzoate (513 mg, 1.41 mmol) in H₂O (3 mL) and THF (9 mL) was added LiOH—H₂O (185 mg, 4.41 mmol) at 0° C. The mixture was stirred at 20° C. for 30 minutes. The resulting mixture was adjusted pH=4 with 2N HCl aqueous solution, and extracted with EtOAc (30 mL*3). The combined organic layer was filtered and concentrated under reduced pressure to give 4-[[6-(2-methoxyethoxymethyl)-3-pyridyl]sulfonimidoyl]benzoic acid (320 mg, 64.9% yield) as yellow solid, which was directly used without further purification.

Step 9: Synthesis of tert-butyl N-[4-(4-fluorophenyl)-2-[[4-[[6-(2-methoxyethoxymethyl)-3-pyridyl]sulfonimidoyl]benzoyl]amino]phenyl]carbamate To a solution of 4-[[6-(2-methoxyethoxymethyl)-3-pyridyl]sulfonimidoyl]benzoic acid (320 mg, 0.913 mmol) and tert-butyl N-[2-amino-4-(4-fluorophenyl)phenyl]carbamate (415 mg, 1.37 mmol) in pyridine (10 mL) was added EDCI (263 mg, 1.37 mmol). The mixture was stirred at 50° C. for 1 hour. The resulting mixture was concentrated under reduced pressure. The residue was purified by flash chromatography (ISCO®; 20 g Agela Flash®Silica Flash Column, EtOAc/Methanol with Methanol from 0~5%, flow rate=40 mL/min, 254 nm) to afford tert-butyl N-[4-(4-fluorophenyl)-2-[[4-[[6-(2-methoxyethoxymethyl)-3-pyridyl]sulfonimidoyl]benzoyl]amino]phenyl]carbamate (439 mg, 75.7% yield) as white solid. LCMS (ESI) [M+H]⁺ m/z: calcd 635.4, found 635.2.

Step 10: Synthesis of N-[2-amino-5-(4-fluorophenyl)phenyl]-4-[[6-(2-methoxyethoxymethyl)-3-pyridyl]sulfonimidoyl]benzamide To a solution of tert-butyl N-[4-(4-fluorophenyl)-2-[[4-[[6-(2-methoxyethoxymethyl)-3-pyridyl]sulfonimidoyl]benzoyl]amino]phenyl]carbamate (439 mg, 0.692 mmol) in DCM (10 mL) was added TFA (1.1 mL, 14.3 mmol). The mixture was stirred at 20° C. for 2 hours. The mixture was concentrated under reduced pressure. The residue was adjusted pH=8 with 25 wt % NH₃—H₂O, and purified by preparative HPLC (Instrument: Gilson GX-281 Liquid Handler, Gilson 322 Pump, Gilson 156 UV Detector; Column: 2_Phenomenex Gemini C18 75*40 mm*3 µm; Mobile phase A: water (NH₄HCO₃)-ACN; Mobile phase B: MeCN; Gradient: B from 33% to 63% in 9.5 min, hold 100% B for 2 min; Flow Rate: 30 mL/min; Column Temperature: 30° C.; Wavelength: 220 nm, 254 nm) to afford N-[2-amino-5-(4-fluorophenyl)phenyl]-4-[[6-(2-methoxyethoxymethyl)-3-pyridyl]sulfonimidoyl]benzamide (197.2 mg, 53.3% yield) as yellow solid. ¹H NMR (400 MHz, DMSO-d6) δ ppm 9.86 (s, 1H), 9.07 (d, J=1.9 Hz, 1H), 8.36 (dd, J=8.3, 2.3 Hz, 1H), 8.14 (s, 4H), 7.43-7.67 (m, 4H), 7.15-7.35 (m, 3H), 6.84 (d, J=8.4 Hz, 1H), 5.47 (s, 1H), 5.14 (s, 2H), 4.64 (s, 2H), 3.63 (dd, J=5.5, 3.6 Hz, 2H), 3.50 (dd, J=5.6, 3.7 Hz, 2H), 3.24 (s, 3H); 19F NMR (376 MHz, DMSO-d6) δ ppm−117.464; LCMS (ESI) [M+H]⁺ m/z: calcd 535.2, found 535.3; HPLC: 98.80%@220 nm; 99.66%@254 nm.

Example 118. Synthesis of N-[2-amino-5-(4-fluorophenyl)phenyl]-4-[1-(methylsulfonimidoyl)cyclopropyl]benzamide (Compound 251)

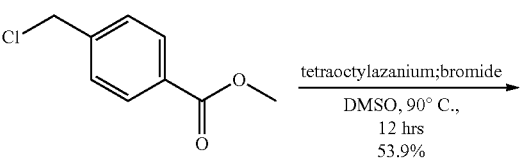

-continued

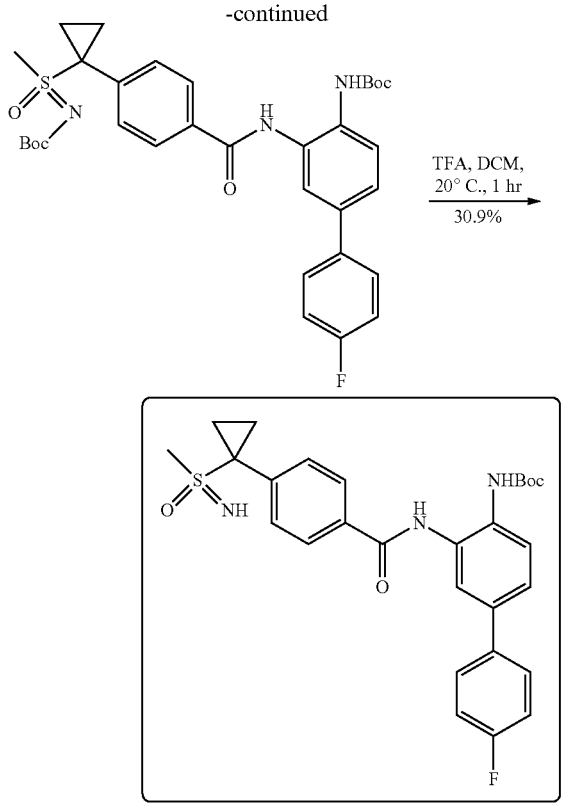

Step 1: Synthesis of methyl 4-(methylsulfinylmethyl)benzoate

A mixture of methyl 4-(chloromethyl)benzoate (4 g, 21.7 mmol) and tetraoctylammonium;bromide (13 g, 23.8 mmol) in DMSO (50 mL) was stirred at 90° C. for 12 hours. 30 mL of water was added. The mixture was extracted with DCM (30 mL*3). The combined organic layer was washed by brine (30 mL*3), dried over anhydrous $Na_2SO_4$, filtered and concentrated under reduced pressure. The residue was purified by flash chromatography (Biotage®; 40 g AgelaFlash®Silica Flash Column, petroleumether/EtOAc with EtOAc from 0~46%, flow rate=30 mL/min, 254 nm) to afford methyl 4-(methylsulfinylmethyl)benzoate (2.48 g, 53.9% yield) as white solid. $^1$H NMR (400 MHz, methanol-d4) δ ppm 8.00 (d, J=8.3 Hz, 2H), 7.46 (d, J=8.3 Hz, 2H), 4.24 (d, J=13.0 Hz, 1H), 4.04 (d, J=13.0 Hz, 1H), 3.88 (s, 3H), 2.57 (s, 3H); LCMS (ESI) [M+H]$^+$ m/z: calcd 213.1, found 213.1.

Step 2: Synthesis of methyl 4-[(N-tert-butoxycarbonyl-S-methyl-sulfonimidoyl)methyl]benzoate A mixture of methyl 4-(methylsulfinylmethyl)benzoate (1 g, 4.71 mmol), PhI(OAc)$_2$ (2.28 g, 7.07 mmol), Rh$_2$(OAc)$_4$ (105 mg, 0.238 mmol), BocNH$_2$ (1.21 g, 10.4 mmol) and MgO (950 mg, 23.6 mmol) in DCM (20 mL) was stirred at 40° C. for 12 hours. The mixture was filtered and the filtrate was concentrated. The residue was purified by flash chromatography (Biotage®; 12 g AgelaFlash®Silica Flash Column, petroleumether/EtOAc with EtOAc from 0~21%, flow rate=40 mL/min, 254 nm) to afford methyl 4-[(N-tert-butoxycarbonyl-S-methyl-sulfonimidoyl)methyl]benzoate (130 mg, 8.4% yield) as brown oil. $^1$H NMR (400 MHz, methanol-d4) δ ppm 8.06 (d, J=8.3 Hz, 2H), 7.60 (d, J=8.4 Hz, 2H), 4.96 (s, 2H), 3.89-3.95 (m, 3H), 3.12 (s, 3H), 1.46 (s, 9H); LCMS (ESI) [M+H]$^+$ m/z: calcd 328.1, found 328.1.

Step 3: Synthesis of methyl 4-[1-(N-tert-butoxycarbonyl-S-methyl-sulfonimidoyl)cyclopropyl]benzoate To a mixture of methyl 4-[(N-tert-butoxycarbonyl-S-methyl-sulfonimidoyl)methyl]benzoate (130 mg, 0.397 mmol), tetraoctylammonium;bromide (22 mg, 0.0402 mmol) and 1,2-dibromoethane (746 mg, 3.97 mmol) in 2-MeTHF (10 mL) was added a solution of 50% NaOH aqueous solution (0.16 mL, 4.00 mmol). The mixture was stirred at 60° C. for 12 hours. 20 mL of water was added and the mixture was extracted with EtOAc (20 mL*3). The combined organic layer was washed dried over anhydrous $Na_2SO_4$ and concentrated under reduced pressure. The residue was purified by flash chromatography (Biotage®; 4 g AgelaFlash®Silica Flash Column, petroleumether/EtOAc with EtOAc from 0~50%, flow rate=25 mL/min, 254 nm) to afford methyl 4-[1-(N-tert-butoxycarbonyl-S-methyl-sulfonimidoyl)cyclopropyl]benzoate (40 mg, 28.5% yield) as brown oil. LCMS (ESI) [M+H]$^+$ m/z: calcd 354.1, found 354.1.

Step 4: Synthesis of 4-[1-(N-tert-butoxycarbonyl-S-methyl-sulfonimidoyl)cyclopropyl]benzoic acid A mixture of methyl 4-[1-(N-tert-butoxycarbonyl-S-methyl-sulfonimidoyl)cyclopropyl]benzoate (40 mg, 0.113 mmol) and LiOH—H$_2$O (25 mg, 0.596 mmol) in H$_2$O (2 mL) and THF (2 mL) was stirred at 20° C. for 1 hour. 1N HCl aqueous solution was added to adjust pH to 5. Then the mixture was extracted with EtOAc (5 mL*3), combined organic layer was concentrated under reduced pressure to give 4-[1-(N-tert-butoxycarbonyl-S-methyl-sulfonimidoyl)cyclopropyl]benzoic acid (35 mg, 91.1% yield) as white solid. LCMS (ESI) [M+H]$^+$ m/z: calcd 340.1, found 340.1.

Step 5: Synthesis of tert-butyl N-[[1-[4-[[2-(tert-butoxycarbonylamino)-5-(4-fluorophenyl)phenyl]carbamoyl]phenyl]cyclopropyl]-methyl-oxo-sulfanylidene]carbamate A mixture of 4-[1-(N-tert-butoxycarbonyl-S-methyl-sulfonimidoyl)cyclopropyl]benzoic acid (35 mg, 0.103 mmol), tert-butyl N-[2-amino-4-(4-fluorophenyl)phenyl]carbamate (35 mg, 0.116 mmol) and EDCI (25 mg, 0.130 mmol) in pyridine (2 mL) was stirred at 50° C. for 1 hour. The mixture was concentrated under reduced pressure. The residue was purified by flash chromatography (ISCO®; 4 g AgelaFlash®Silica Flash Column, petroleumether/EtOAc with EtOAc from 0~83%, flow rate=15 mL/min, 254 nm) to afford tert-butyl N-[[1-[4-[[2-(tert-butoxycarbonylamino)-5-(4-fluorophenyl)phenyl]carbamoyl]phenyl]cyclopropyl]-methyl-oxo-sulfanylidene]carbamate (35 mg, 54.4% yield) as white solid. LCMS (ESI) [M+H]$^+$ m/z: calcd 624.2, found 624.3.

Step 6: Synthesis of N-[2-amino-5-(4-fluorophenyl)phenyl]-4-[1-(methylsulfonimidoyl)cyclopropyl]benzamide (Compound 251)

To a mixture of tert-butyl N-[[1-[4-[[2-(tert-butoxycarbonylamino)-5-(4-fluorophenyl)phenyl]carbamoyl]phenyl]cyclopropyl]-methyl-oxo-sulfanylidene]carbamate (53 mg, 0.0850 mmol) in DCM (1 mL) was added TFA (0.15 mL, 1.95 mmol) at 20° C. The mixture was stirred at 20° C. for 1 hour. The mixture was concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 μm; Mobile phase A: H$_2$O with 0.05% NH$_3$—H$_2$O (v %); Mobile phase B: MeCN; Gradient: B from 34% to 64% in 9.5 mins, hold 100% B for 2 mins; Flow Rate: 30 mL/min; Column Temperature: 30° C.; Wavelength: 220 nm, 254 nm) to afford N-[2-amino-5-(4-fluorophenyl)phenyl]-4-[1-(methylsulfonimidoyl)cyclopropyl]benzamide (11.1 mg, 30.9% yield) as white solid. $^1$H NMR (400 MHz, methanol-d4) δ ppm 8.02 (d, J=8.1 Hz, 2H), 7.79 (d, J=8.1 Hz, 2H), 7.56 (dd, J=8.5, 5.4 Hz, 2H), 7.46 (d, J=1.6 Hz, 1H), 7.34 (dd, J=8.3, 1.9 Hz, 1H), 7.11 (t, J=8.8 Hz, 2H), 6.98 (d, J=8.4 Hz, 1H), 2.87 (s, 3H), 1.70-1.92 (m, 2H), 1.31-1.44 (m, 2H); 19F NMR (400 MHz, methanol-d4) δ ppm −119.355; LCMS (ESI) [M+H]$^+$ m/z: calcd 424.1, found 424.2; HPLC: 98.12%@220 nm, 99.68%@254 nm.

Example 119. Synthesis of N-[2-amino-5-(4-fluorophenyl)phenyl]-4-[(2-hydroxypyrimidin-5-yl)sulfonimidoyl]benzamide (Compound 234)

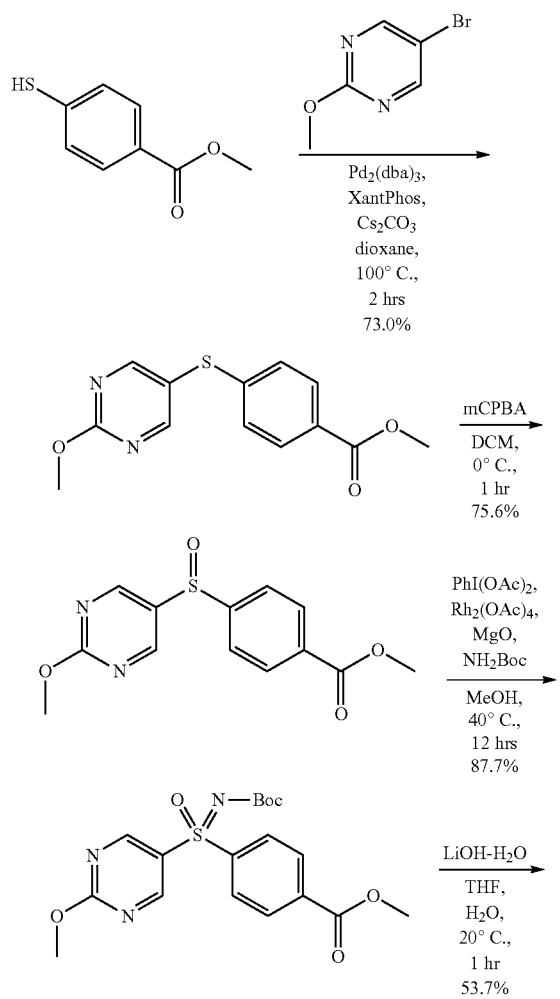

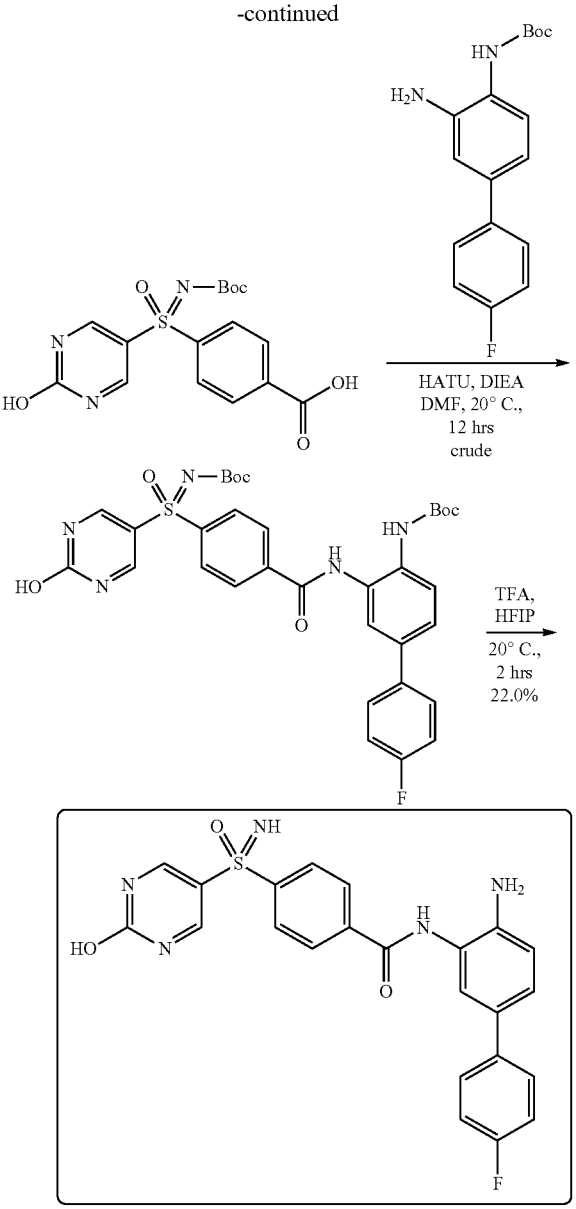

Step 1: Synthesis of methyl 4-(2-methoxypyrimidin-5-yl)sulfanylbenzoate

To a mixture of methyl 4-sulfanylbenzoate (1 g, 5.94 mmol), 5-bromo-2-methoxy-pyrimidine (1.20 g, 6.35 mmol) in dioxane (30 mL) was added Pd$_2$(dba)$_3$ (1.70 g, 1.86 mmol), XantPhos (1.10 g, 1.90 mmol) and Cs$_2$CO$_3$ (6 g, 18.4 mmol). The resulting mixture was stirred at 100° C. for 2 hours. The reaction mixture was quenched by addition water (30 mL), extracted with EtOAc (30 mL*3). The combined organic layers were washed with brine (30 mL), dried over anhydrous Na$_2$SO$_4$, filtered and concentrated under reduced pressure. The residue was purified by flash chromatography (ISCO®; 40 g AgelaFlash® Silica Flash Column, petroleum ether/EtOAc with EtOAc 0~30%, flow rate=35 mL/min, 254 nm) to afford methyl 4-(2-methoxypyrimidin-5-yl)sulfanylbenzoate (1.2 g, 73.0% yield) as a yellow solid. $^1$H NMR (400 MHz, chloroform-d) δ ppm 8.64

(s, 2H), 7.92 (s, 2H), 7.16 (d, J=8.78 Hz, 2H), 4.08 (s, 3H), 3.91 (s, 3H); LCMS (ESI) [M+H]+ m/z: calcd 227.1, found 227.1.

Step 2: Synthesis of methyl 4-(2-methoxypyrimidin-5-yl)sulfinylbenzoate

To a solution of methyl 4-(2-methoxypyrimidin-5-yl)sulfanylbenzoate (1.2 g, 4.34 mmol) in DCM (10 mL) was added m-CPBA (749 mg, 4.34 mmol, 85% purity) at 0° C. and the mixture was stirred at 0° C. for 1 hour. The reaction mixture was quenched by addition water (30 mL), extracted with DCM (30 mL*3). The combined organic layers were washed with brine (30 mL), dried over anhydrous $Na_2SO_4$, filtered and concentrated under reduced pressure. The residue was purified by flash chromatography (ISCO®; 40 g AgelaFlash® Silica Flash Column, petroleum ether/EtOAc with EtOAc 0~30%, flow rate=35 mL/min, 254 nm) to afford methyl 4-(2-methoxypyrimidin-5-yl)sulfinylbenzoate (960 mg, 75.6% yield) as a white solid. 1H NMR (400 MHz, chloroform-d) δ ppm 8.70 (s, 2H), 8.21 (d, J=8.53 Hz, 2H), 7.75 (d, J=8.53 Hz, 2H), 4.06 (s, 3H), 3.96 (s, 3H); LCMS (ESI) [M+H]+ m/z: calcd 293.1, found 293.1.

Step 3: Synthesis of methyl 4-[N-tert-butoxycarbonyl-S-(2-methoxypyrimidin-5-yl)sulfonimidoyl]benzoate To a solution of methyl 4-(2-methoxypyrimidin-5-yl)sulfinylbenzoate (900 mg, 3.08 mmol), $NH_2Boc$ (720 mg, 6.15 mmol), MgO (648 mg, 15.7 mmol) and $PhI(OAc)_2$ (1.5 g, 4.66 mmol) in DCM (20 mL) was added $Rh_2(OAc)_4$ (144 mg, 0.326 mmol) in the mixture at 20° C. and the mixture was stirred at 40° C. for 12 hours. The reaction mixture was quenched by addition water (30 mL) at 20° C., extracted with DCM (30 mL*3). The combined organic layers were washed with brine (30 mL), dried over anhydrous $Na_2SO_4$, filtered and concentrated under reduced pressure. The residue was purified by flash chromatography (ISCO®; 40 g AgelaFlash® Silica Flash Column, petroleum ether/EtOAc with EtOAc 0~30%, flow rate=35 mL/min, 254 nm) to afford methyl 4-[N-tert-butoxycarbonyl-S-(2-methoxypyrimidin-5-yl)sulfonimidoyl]benzoate (1.1 g, 87.7% yield) as a white solid. LCMS (ESI) [M+H]+ m/z: calcd 408.1, found 308.1. (Boc and t-Bu cleaved mass).

Step 4: Synthesis of 4-[N-tert-butoxycarbonyl-S-(2-hydroxypyrimidin-5-yl)sulfonimidoyl]benzoic acid To a solution of methyl 4-[N-tert-butoxycarbonyl-S-(2-methoxypyrimidin-5-yl)sulfonimidoyl]benzoate (1 g, 2.45 mmol) in $H_2O$ (7 mL) and THF (7 mL) was added LiOH—$H_2O$ (520 mg, 12.4 mmol) at 20° C. and the mixture was stirred at 20° C. for 1 hour. The mixture was concentrated under reduced pressure. Water (5 mL) was added to the concentrated system, the pH value of the mixture was adjusted to 4 with 0.5 N HCl aqueous. The residue was purified by preparative HPLC (Instrument: Gilson GX-281 Liquid Handler, Gilson 322 Pump, Gilson 156 UV Detector; Column: Durashell 100×30 mm×3 μm; Mobile phase A: water(FA)-ACN; Mobile phase B: MeCN; Gradient: B from 30% to 80% in 15 min, hold 100% B for 2 min; Flow Rate: 25 mL/min; Column Temperature: 30° C.; Wavelength: 254 nm) to afford 4-[N-tert-butoxycarbonyl-S-(2-hydroxypyrimidin-5-yl)sulfonimidoyl]benzoic acid (500 mg, 53.7% yield) as a white solid. 1H NMR (400 MHz, DMSO-d6) δ ppm 8.79 (s, 2H), 8.15 (s, 4H), 1.26 (s, 9H); LCMS (ESI) [M+H]+ m/z: calcd 380.1, found 279.9 (Boc and t-Bu cleaved mass).

Step 5: Synthesis of tert-butyl (3-(4-(N-(tert-butoxycarbonyl)-2-hydroxypyrimidine-5-sulfonimidoyl)benzamido)-4'-fluoro-[1,1'-biphenyl]-4-yl)carbamate To a solution of 4-[N-tert-butoxycarbonyl-S-(2-hydroxypyrimidin-5-yl)sulfonimidoyl]benzoic acid (100 mg, 0.264 mmol), tert-butyl N-[2-amino-4-(4-fluorophenyl)phenyl]carbamate (81 mg, 0.268 mmol), DIEA (172 mg, 1.33 mmol) in DMF (3 mL) was added HATU (151 mg, 0.397 mmol) at 20° C. and the mixture was stirred at 20° C. for 12 hours. The reaction mixture was quenched by addition water (30 mL), extracted with DCM (30 mL*3). The combined organic layers were washed with brine (30 mL), dried over anhydrous $Na_2SO_4$, filtered and concentrated under reduced pressure. Compound tert-butyl (3-(4-(N-(tert-butoxycarbonyl)-2-hydroxypyrimidine-5-sulfonimidoyl)benzamido)-4'-fluoro-[1,1'-biphenyl]-4-yl)carbamate (100 mg, crude) was afforded as a white solid. LCMS (ESI) [M+H]+ m/z: calcd 664.2, found 464.2 (Boc and t-Bu cleaved mass).

Step 6: Synthesis of N-[2-amino-5-(4-fluorophenyl)phenyl]-4-[(2-hydroxypyrimidin-5-yl)sulfonimidoyl]benzamide (Compound 234)

To a solution of tert-butyl N-[[4-[[2-(tert-butoxycarbonylamino)-5-(4-fluorophenyl)phenyl]carbamoyl]phenyl]-(2-hydroxypyrimidin-5-yl)-oxo-sulfanylidene]carbamate (100 mg, 0.151 mmol) in HFIP (3 mL) was added TFA (180 mg, 1.58 mmol). The mixture was stirred at 20° C. for 2 hours. The residue was purified by preparative HPLC (Instrument: Gilson GX-281 Liquid Handler, Gilson 322 Pump, Gilson 156 UV Detector; Column: Durashell 75×30 mm×3 μm; Mobile phase A: water (FA)-ACN; Mobile phase B: MeCN; Gradient: B from 20% to 50% in 10 min, hold 100% B for 3 min; Flow Rate: 30 mL/min; Column Temperature: 30° C.; Wavelength: 254 nm) to afford N-[2-amino-5-(4-fluorophenyl)phenyl]-4-[(2-hydroxypyrimidin-5-yl)sulfonimidoyl]benzamide (15.4 mg, 22.0% yield) as a white solid.

Compound 234: 1H NMR (400 MHz, DMSO-d6) δ ppm 9.88 (s, 1H), 8.71 (s, 2H), 8.14 (s, 4H), 7.54-7.61 (m, 2H), 7.48 (d, J=2.01 Hz, 1H), 7.31 (dd, J=8.28, 2.01 Hz, 1H), 7.18-7.26 (m, 2H), 6.85 (d, J=8.28 Hz, 1H), 5.28-5.35 (m, 1H), 5.00-5.26 (m, 2H); 19F NMR (377 MHz, chloroform-d) δ ppm −117.47; LCMS (ESI) [M+H]+ m/z: calcd 464.1, found 464.2; HPLC: 96.80%®254 nm, 98.19%@220 nm.

Example 120. Synthesis of N-[2-amino-5-(4-fluorophenyl)phenyl]-4-[(5-fluoro-2-pyridyl)sulfonimidoyl]benzamide (Compound 247)

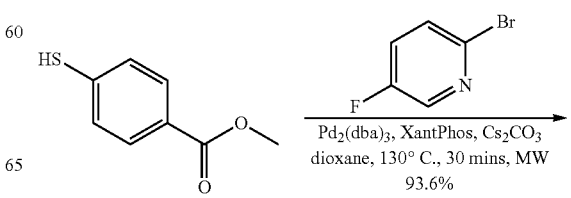

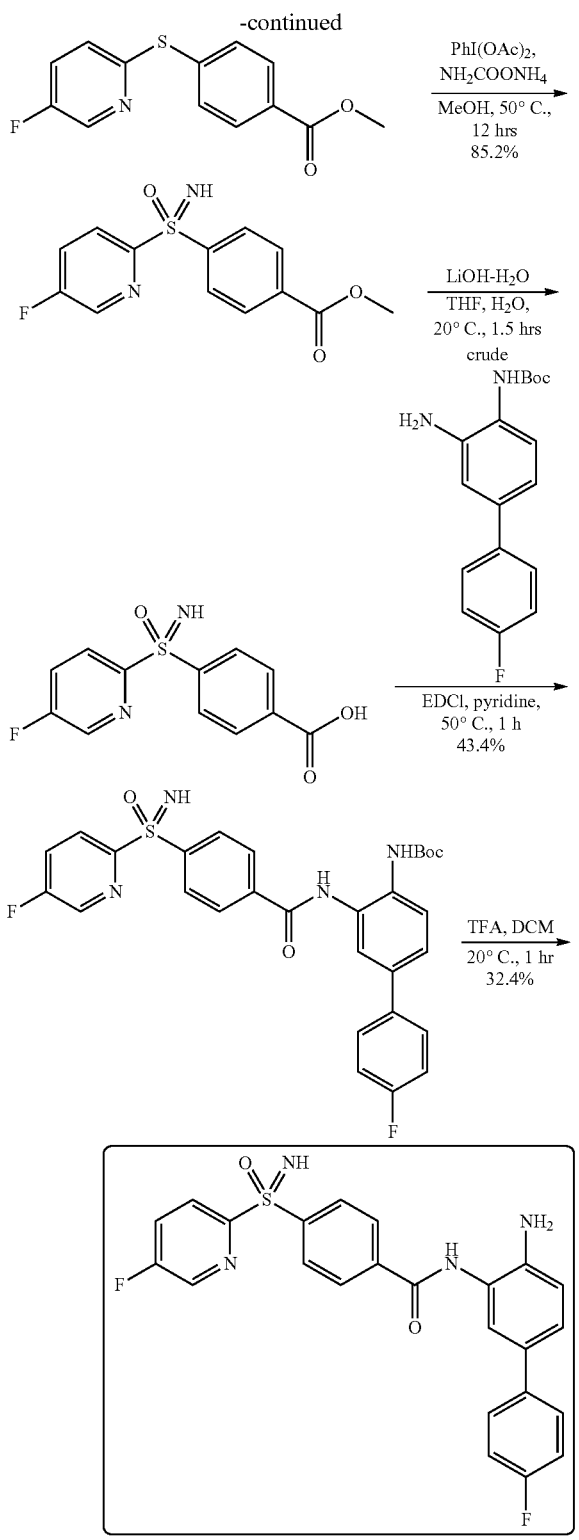

Step 1: Synthesis of methyl 4-[(5-fluoro-2-pyridyl)sulfanyl]benzoate

A mixture of methyl 4-sulfanylbenzoate (290 mg, 1.72 mmol), 2-bromo-5-fluoropyridine (300 mg, 1.70 mmol), (1E,4E)-1,5-diphenylpenta-1,4-dien-3-one;palladium (156 mg, 0.171 mmol), (5-diphenylphosphanyl-9,9-dimethyl-xanthen-4-yl)-diphenyl-phosphane (480 mg, 0.829 mmol) and dicesium;carbonate (1.67 g, 5.12 mmol) in dioxane (10 mL) was purged with $N_2$ at ambient temperature for 3 minutes. Then mixture was stirred at 130° C. for 30 minutes in microwave. The resulting mixture was quenched by addition of water (10 mL) and extracted with EtOAc (50 mL*3). The combined organic layer was washed with brine (30 mL*2), dried over anhydrous $Na_2SO_4$, filtered and concentrated under reduced pressure. The residue was purified by flash chromatography (ISCO®; 20 g AgelaFlash® Silica Flash Column, petroleum ether/EtOAc with EtOAc from 0~10%, flow rate=35 mL/min, 254 nm) to afford methyl 4-[(5-fluoro-2-pyridyl)sulfanyl]benzoate (420 mg, 93.6% yield) as light yellow solid. LCMS (ESI) [M+H]$^+$ m/z: calcd 264.0, found 264.1.

Step 2: Synthesis of methyl 4-[(5-fluoro-2-pyridyl)sulfonimidoyl]benzoate

A mixture of methyl 4-[(5-fluoro-2-pyridyl)sulfanyl]benzoate (370 mg, 1.41 mmol), ammonia;carbamic acid (660 mg, 8.45 mmol), [acetoxy(phenyl)-iodanyl] acetate (1.35 g, 4.20 mmol) in MeOH (4 mL) was stirred at 50° C. for 12 hours. The resulting mixture was filtered and concentrated under reduced pressure. The residue was purified by flash chromatography (ISCO®; 12 g AgelaFlash® Silica Flash Column, petroleum ether/EtOAc with EtOAc with from 0~25%, flow rate=30 mL/min, 254 nm) to afford methyl 4-[(5-fluoro-2-pyridyl)sulfonimidoyl]benzoate (400 mg, 85.2% yield) as yellow solid. LCMS (ESI) [M+H]$^+$ m/z: calcd 295.0, found 295.1.

Step 3: Synthesis of 4-[(5-fluoro-2-pyridyl)sulfonimidoyl]benzoic acid

A mixture of methyl 4-[(5-fluoro-2-pyridyl)sulfonimidoyl]benzoate (330 mg, 1.12 mmol), LiOH—$H_2O$ (140 mg, 3.34 mmol) in THF (3 mL) and $H_2O$ (1 mL) was stirred at 20° C. for 1.5 hours. The mixture was concentrated under reduced pressure, and adjusted the pH to 5 with 2N HCl aqueous solution. The resulting mixture was diluted with water (10 mL) and extracted with $CH_2Cl_2$ (50 mL*3). The combined organic layer was dried over anhydrous $Na_2SO_4$, filtered and concentrated under reduced pressure to afford 4-[(5-fluoro-2-pyridyl)sulfonimidoyl]benzoic acid (370 mg, crude) as light yellow solid. LCMS (ESI) [M+H]$^+$ m/z: calcd 281.0, found 281.1.

Step 4: Synthesis of tert-butyl N-[4-(4-fluorophenyl)-2-[[4-[(5-fluoro-2-pyridyl)sulfonimidoyl]benzoyl]amino]phenyl]carbamate A mixture of 4-[(5-fluoro-2-pyridyl)sulfonimidoyl]benzoic acid (355 mg, 1.27 mmol), tert-butyl N-[2-amino-4-(4-fluorophenyl)phenyl]carbamate (430 mg, 1.42 mmol), EDCI (365 mg, 1.90 mmol) in pyridine (5 mL) was stirred at 50° C. for 1 hour. The resulting mixture was concentrated under reduced pressure. The residue was purified by flash chromatography (ISCO®; 12 g AgelaFlash® Silica Flash Column, petroleum ether/EtOAc with EtOAc from 0~25%, flow rate=30 mL/min, 254 nm) to afford tert-butyl N-[4-(4-fluorophenyl)-2-[[4-[(5-fluoro-2-pyridyl)sulfonimidoyl]benzoyl]amino]phenyl]carbamate (310 mg, 43.3% yield) as yellow solid. LCMS (ESI) [M+H]$^+$ m/z: calcd 565.2, found 565.3.

611

Step 5: Synthesis of N-[2-amino-5-(4-fluorophenyl)phenyl]-4-[(5-fluoro-2-pyridyl)sulfonimidoyl]benzamide (Compound 247)

A mixture of tert-butyl N-[4-(4-fluorophenyl)-2-[[4-[(5-fluoro-2-pyridyl)sulfonimidoyl]benzoyl]amino]phenyl]carbamate (300 mg, 0.531 mmol), TFA (0.8 mL, 10.4 mmol) in DCM (4 mL) was stirred at 20° C. for 1 hour. The resulting mixture was concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75*40 mm*3 μm; Mobile phase A: H$_2$O with NH$_4$HCO$_3$ (v %); Mobile phase B: MeCN; Gradient: B from 35% to 65% in 9.5 min, hold 100% B for 1 min; Flow Rate: 30 mL/min; Column Temperature: 30° C.; Wavelength: 220 nm, 254 nm). The fraction was concentrated under reduced pressure and then lyophilized for overnight to afford N-[2-amino-5-(4-fluorophenyl)phenyl]-4-[(5-fluoro-2-pyridyl)sulfonimidoyl]benzamide (79.9 mg, 32.4% yield) as light yellow solid. $^1$H NMR (400 MHz, DMSO-d6) δ ppm 9.91 (s, 1H), 8.67 (d, J=2.8 Hz, 1H), 8.36 (dd, J=8.8, 4.4 Hz, 1H), 7.95-8.27 (m, 5H), 7.43-7.71 (m, 3H), 7.15-7.40 (m, 3H), 6.85 (d, J=8.4 Hz, 1H), 4.84-5.73 (m, 3H); 19F NMR (376 MHz, DMSO-d6) δ ppm −117.441, −121.471; LCMS (ESI) [M+H]$^+$ m/z: calcd 465.1, found 465.2; HPLC: 99.840%@220 nm, 99.840%@254 nm.

Example 121. Synthesis of N-[2-amino-5-(4-fluorophenyl)phenyl]-4-[(6-chloro-3-pyridyl)sulfonimidoyl]benzamide (Compound 213)

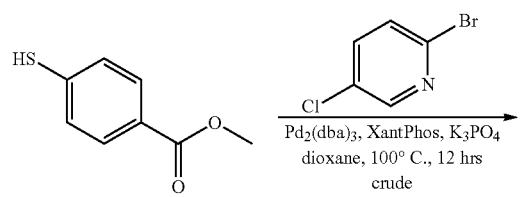

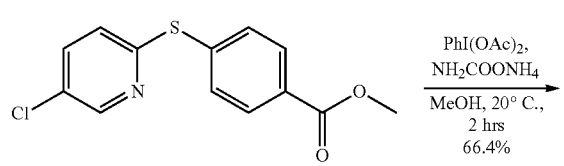

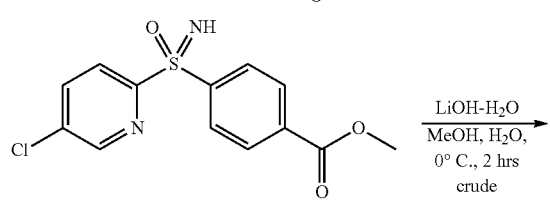

612

-continued

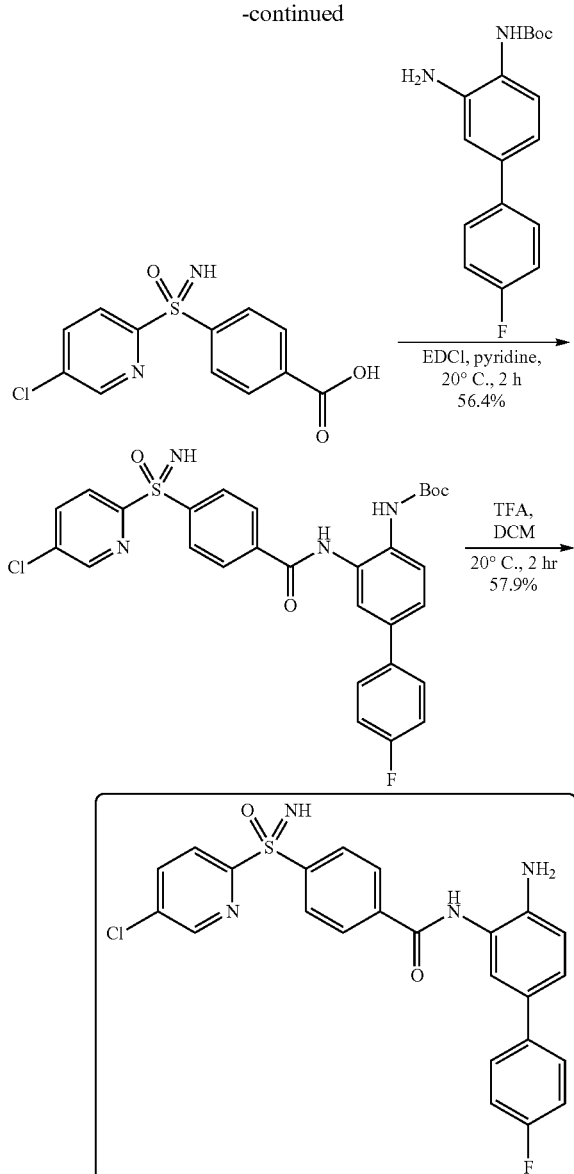

Step 1: Synthesis of methyl 4-[(5-chloro-2-pyridyl)sulfanyl]benzoate

A mixture of 2-bromo-5-chloro-pyridine (414 mg, 2.15 mmol), methyl 4-sulfanylbenzoate (300 mg, 1.78 mmol), Pd$_2$(dba)$_3$ (82 mg, 0.0900 mmol), Xantphos (105 mg, 0.181 mmol) and K$_3$PO$_4$ (1.15 g, 5.42 mmol) in dioxane (10 mL) was stirred under N$_2$ at 100° C. for 12 hours. The resulting mixture was quenched by addition of water (80 mL*3) and extracted with EtOAc (80 mL*3). The combined organic layer was dried over anhydrous Na$_2$SO$_4$, filtered and concentrated under reduced pressure. The residue was purified by flash chromatography (ISCO®; 20 g Agela Flash® Silica Flash Column, petroleum ether/EtOAc with EtOAc from 0~20%, flow rate=40 mL/min, 254 nm) to afford methyl 4-[(5-chloro-2-pyridyl)sulfanyl]benzoate (655 mg, crude) as yellow solid. LCMS (ESI) [M+H]$^+$ m/z: calcd 280.0, found 280.0.

Step 2: Synthesis of methyl 4-[(6-chloro-3-pyridyl)sulfonimidoyl]benzoate

To a solution of methyl 4-[(6-chloro-3-pyridyl)sulfanyl]benzoate (655 mg, 2.34 mmol) in MeOH (10 mL) was added PhI(OAc)$_2$ (1.89 g, 5.85 mmol), NH$_2$COONH$_4$ (366 mg, 4.69 mmol). The mixture was stirred at 20° C. for 2 hours. The resulting mixture was concentrated under reduced pressure. The residue was purified by flash chromatography (ISCO®; 20 g Agela Flash® Silica Flash Column, petroleum ether/EtOAc with EtOAc from 0~60%, flow rate=40 mL/min, 254 nm) to afford methyl 4-[(6-chloro-3-pyridyl)sulfonimidoyl]benzoate (483 mg, 66.4% yield) as light yellow solid. LCMS (ESI) [M+H]$^+$ m/z: calcd 311.0, found 311.0.

Step 3: Synthesis of 4-[(6-chloro-3-pyridyl)sulfonimidoyl]benzoic acid

To a solution of methyl 4-[(6-chloro-3-pyridyl)sulfonimidoyl]benzoate (453 mg, 1.46 mmol) in H$_2$O (3 mL) and MeOH (9 mL) was added lithium;hydroxide;hydrate (185 mg, 4.41 mmol) at 0° C. The mixture was stirred at 0° C. for 2 hours. The resulting mixture was concentrated under reduced pressure. The resulting mixture was adjusted pH=4 with 2N HCl aqueous solution, and extracted with EtOAc (10 mL*3). The combined organic layer was filtered and concentrated under reduced pressure to give 4-[(6-chloro-3-pyridyl)sulfonimidoyl]benzoic acid (468.6 mg, crude) as white solid, which was directly used without further purification. LCMS (ESI) [M+H]$^+$ m/z: calcd 297.0, found 297.0.

Step 4: Synthesis of tert-butyl N-[2-[[4-[(6-chloro-3-pyridyl)sulfonimidoyl]benzoyl]amino]-4-(4-fluorophenyl)phenyl]carbamate To a solution of 4-[(6-chloro-3-pyridyl)sulfonimidoyl]benzoic acid (200 mg, 0.674 mmol) and tert-butyl N-[2-amino-4-(4-fluorophenyl)phenyl]carbamate (314 mg, 1.04 mmol) in pyridine (5 mL) was added EDCI (197 mg, 1.03 mmol). The mixture was stirred at 20° C. for 2 hours. The resulting mixture was concentrated under reduced pressure. The residue was purified by flash chromatography (ISCO®; 12 g Agela Flash® Silica Flash Column, Petroleum ether/EtOAc 0~50%, flow rate=35 mL/min, 254 nm) to afford tert-butyl N-[2-[[4-[(6-chloro-3-pyridyl)sulfonimidoyl]benzoyl]amino]-4-(4-fluorophenyl)phenyl]carbamate (221 mg, 56.4% yield) as light-brown solid. LCMS (ESI) [M+H]$^+$ m/z: calcd 581.1, found 581.3.

Step 5: Synthesis of N-[2-amino-5-(4-fluorophenyl)phenyl]-4-[(6-chloro-3-pyridyl)sulfonimidoyl]benzamide To a solution of tert-butyl N-[2-[[4-[(6-chloro-3-pyridyl)sulfonimidoyl]benzoyl]amino]-4-(4-fluorophenyl)phenyl]carbamate (200 mg, 0.344 mmol) in DCM (5 mL) was added TFA (1.2 mL, 15.6 mmol). The mixture was stirred at 20° C. for 2 hours. The mixture was concentrated under reduced pressure. The residue was adjusted pH=8 with 25 wt % NH$_3$—H$_2$O, and purified by preparative HPLC (Instrument: Gilson GX-281 Liquid Handler, Gilson 322 Pump, Gilson 156 UV Detector; Column: 2_Phenomenex Gemini C18 75*40 mm*3 µm; Mobile phase A: water (NH$_4$HCO$_3$)-ACN; Mobile phase B: MeCN; Gradient: B from 37% to 67% in 9.5 min, hold 100% B for 2 min; Flow Rate: 30 mL/min; Column Temperature: 30° C.; Wavelength: 220 nm, 254 nm) to afford N-[2-amino-5-(4-fluorophenyl)phenyl]-4-[(6-chloro-3-pyridyl)sulfonimidoyl]benzamide (95.8 mg, 57.9% yield) as yellow solid. $^1$H NMR (400 MHz, DMSO-d6) δ ppm 9.90 (s, 1H), 8.72 (d, J=2.0 Hz, 1H), 8.28 (d, J=8.3 Hz, 1H), 8.21-8.26 (m, 1H), 8.16 (d, J=8.5 Hz, 2H), 8.08-8.13 (m, 2H), 7.57 (dd, J=8.5, 5.5 Hz, 2H), 7.46-7.52 (m, 1H), 7.25-7.37 (m, 1H), 7.21 (t, J=8.8 Hz, 2H), 6.85 (d, J=8.5 Hz, 1H), 5.43 (s, 1H), 5.16 (s, 2H); 19F NMR (376 MHz, DMSO-d6) δ ppm −117.444; LCMS (ESI) [M+H]$^+$ m/z: calcd 481.1, found 481.2; HPLC: 98.01%@220 nm; 99.650%@254 nm.

Example 122. Synthesis of N-[2-amino-5-(4-fluorophenyl)phenyl]-6-(methylsulfonimidoyl)thieno[3,2-c]pyridine-2-carboxamide (Compound 253)

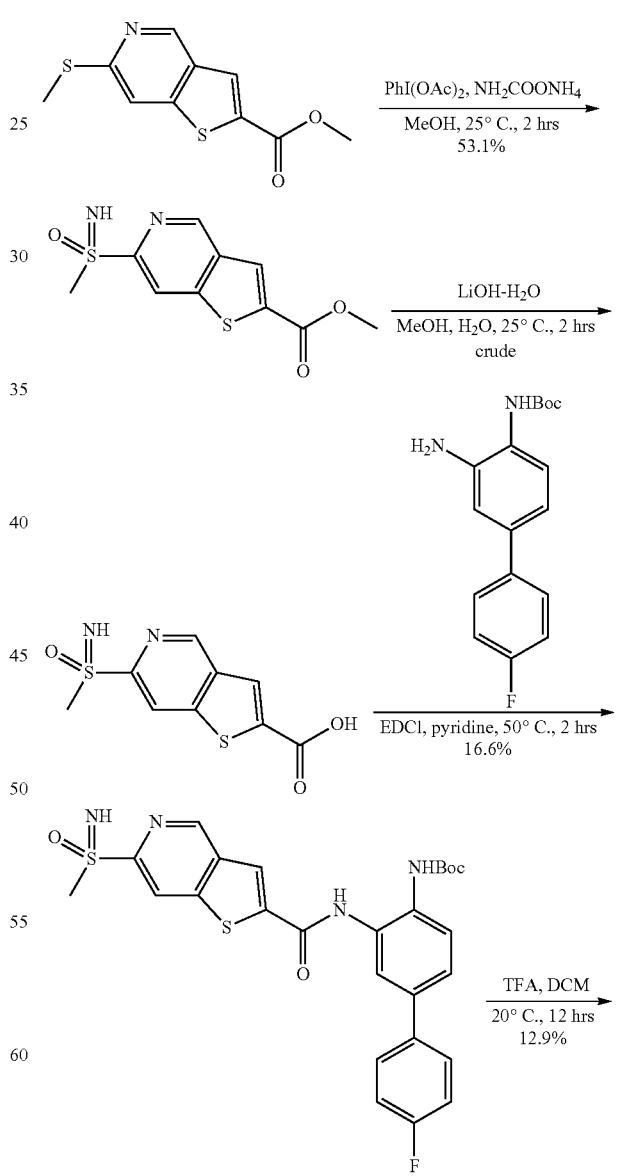

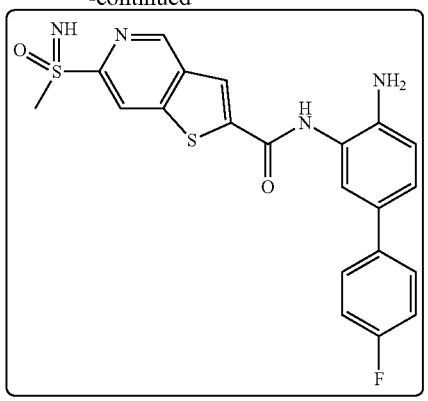

Step 1: Synthesis of methyl 6-(methylsulfonimidoyl)thieno[3,2-c]pyridine-2-carboxylate A mixture of methyl 6-methylsulfanylthieno[3,2-c]pyridine-2-carboxylate (200 mg, 0.836 mmol), ammonia;carbamic acid (130 mg, 1.67 mmol) and [acetoxy(phenyl)-iodanyl] acetate (673 mg, 2.09 mmol) in MeOH (1 mL) was stirred at 25° C. for 2 hours. The mixture was concentrated under reduced pressure. The residue was purified by flash chromatography (ISCO®; 12 g AgelaFlash® Silica Flash Column, petroleum ether/EtOAc with EtOAc from 0~100%, flow rate=25 mL/min, 254 nm) to afford methyl 6-(methylsulfonimidoyl)thieno[3,2-c]pyridine-2-carboxylate (120 mg, 53.1% yield) as light-yellow solid. $^1$H NMR (400 MHz, DMSO-d6) δ ppm 9.39 (s, 1H), 8.90 (s, 1H), 8.46 (s, 1H), 4.43 (s, 1H), 3.95 (s, 3H), 3.21 (s, 3H); LCMS (ESI) [M+H]$^+$ m/z: calcd 271.0, found 271.0.

Step 2: Synthesis of 6-(methylsulfonimidoyl)thieno[3,2-c]pyridine-2-carboxylic acid A mixture of methyl 6-(methylsulfonimidoyl)thieno[3,2-c]pyridine-2-carboxylate (120 mg, 0.444 mmol) and lithium;hydroxide;hydrate (186 mg, 4.44 mmol) in MeOH (1 mL) and H$_2$O (3 mL) was stirred at 25° C. for 2 hours. The mixture was concentrated under reduced pressure and adjusted pH=2 with 2N HCl aqueous solution. The resulting mixture was diluted with water (5 mL) and extracted with EtOAc (5 mL*3). The combined organic layer was filtered and concentrated under reduced pressure to afford 6-(methylsulfonimidoyl)thieno[3,2-c]pyridine-2-carboxylic acid (300 mg, crude) as white solid. LCMS (ESI) [M+H]$^+$ m/z: calcd 257.0, found 257.0.

Step 3: Synthesis of tert-butyl N-[4-(4-fluorophenyl)-2-[[6-(methylsulfonimidoyl)thieno[3,2-c]pyridine-2-carbonyl]amino]phenyl]carbamate A mixture of 6-(methylsulfonimidoyl)thieno[3,2-c]pyridine-2-carboxylic acid (200 mg, 0.780 mmol) and tert-butyl N-[2-amino-4-(4-fluorophenyl)phenyl]carbamate (118 mg, 0.390 mmol) and EDCI (150 mg, 0.780 mmol) in pyridine (2 mL) was stirred at 50° C. for 2 hours. The mixture was concentrated under reduced pressure. The residue was purified by flash chromatography (ISCO®; 12 g AgelaFlash® Silica Flash Column, petroleum ether/EtOAc with EtOAc from 0~50%, flow rate=30 mL/min, 254 nm) to afford a white solid (215 mg, crude). The residue was further purified by preparative HPLC (Instrument: Gilson GX-281 Liquid Handler, Gilson 322 Pump, Gilson 156 UV Detector; Column: 2_Phenomenex Gemini C18 75*40 mm*3 μm; Mobile phase A:H$_2$O with 0.05% NH$_3$—H$_2$O (v %); Mobile phase B: MeCN; Gradient: B from 44% to 74% in 9.5 min, Hold 100% B for 2 min; Flow Rate: 30 mL/min; Column Temperature: 30° C.; Wavelength: 220 nm, 254 nm) to afford tert-butyl N-[4-(4-fluorophenyl)-2-[[6-(methylsulfonimidoyl)thieno[3,2-c]pyridine-2-carbonyl]amino]phenyl]carbamate (70 mg, 16.59% yield) as a white solid. LCMS (ESI) [M+H]$^+$ m/z: calcd 541.1, found 541.2.

Step 4: Synthesis of N-[2-amino-5-(4-fluorophenyl)phenyl]-6-(methylsulfonimidoyl)thieno[3,2-c]pyridine-2-carboxamide (Compound 253)

A mixture of tert-butyl N-[4-(4-fluorophenyl)-2-[[6-(methylsulfonimidoyl)thieno[3,2-c]pyridine-2-carbonyl]amino]phenyl]carbamate (20 mg, 0.370 mmol) and TFA (0.1 mL, 1.17 mmol) in DCM (1 mL) was stirred at 25° C. for 2 hours. The mixture was concentrated under reduced pressure and adjusted pH=8 with NH$_3$—H$_2$O solution. The residue was purified by preparative HPLC (Instrument: Gilson GX-281 Liquid Handler, Gilson 322 Pump, Gilson 156 UV Detector; Column: 2_Phenomenex Gemini C18 75*40 mm*3 μm; Mobile phase A: H$_2$O with 0.05% NH$_3$—H$_2$O (v %); Mobile phase B: MeCN; Gradient: B from 33% to 63% in 9.5 min, Hold 100% B for 0.2 min; Flow Rate: 30 mL/min; Column Temperature: 30° C.; Wavelength: 220 nm, 254 nm) to afford N-[2-amino-5-(4-fluorophenyl)phenyl]-6-(methylsulfonimidoyl)thieno[3,2-c]pyridine-2-carboxamide (2.1 mg, 12.9% yield) as yellow solid. $^1$H NMR (400 MHz, DMSO-d6) δ ppm 10.26 (brs, 1H), 9.39 (s, 1H), 8.87 (s, 1H), 8.58 (s, 1H), 7.55-7.66 (m, 2H), 7.51 (s, 1H), 7.35 (d, J=8.0 Hz, 1H), 7.20-7.26 (m, 2H), 6.89 (d, J=8.3 Hz, 1H), 5.26 (brs, 2H), 4.43 (s, 1H), 3.23 (s, 3H); 19F NMR (376 MHz, DMSO-d6) δ ppm −117.417; LCMS (ESI) [M+H]$^+$ m/z: calcd 441.1, found 441.0; HPLC: 77.90%@220 nm; 1000%@254 nm.

Example 123. Synthesis of N-[2-amino-5-(4-fluorophenyl)phenyl]-6-(methylsulfonimidoyl)thieno[3,2-b]pyridine-2-carboxamide (Compound 200)

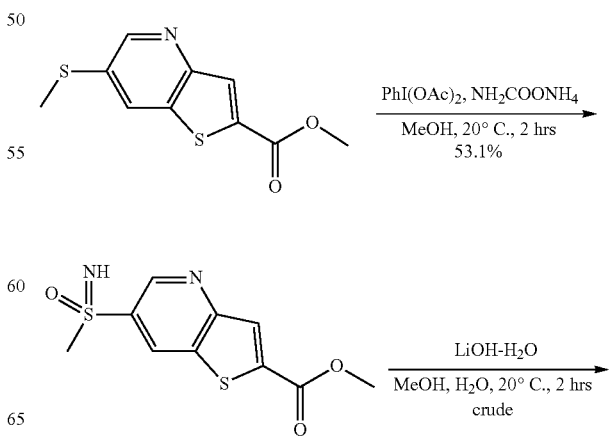

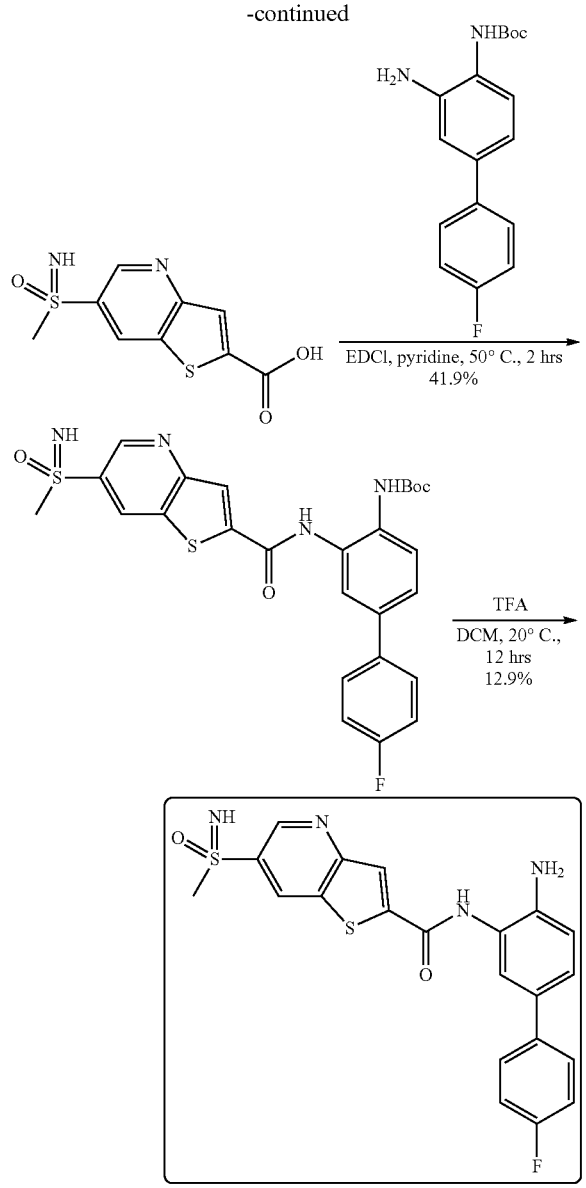

Step 1: Synthesis of methyl 6-(methylsulfonimidoyl)thieno[3,2-b]pyridine-2-carboxylate A mixture of methyl 6-methylsulfanylthieno[3,2-b]pyridine-2-carboxylate (350 mg, 1.46 mmol), ammonia;carbamic acid (230 mg, 2.95 mmol), PhI(OAc)$_2$ (1.2 g, 3.73 mmol) in MeOH (5 mL) was stirred at 20° C. for 2 hours. The resulting mixture was concentrated under reduced pressure. The resulting mixture was quenched by addition of water (10 mL) and extracted with EtOAc (50 mL*3). The combined organic layer was washed with brine (50 mL), dried over anhydrous Na$_2$SO$_4$, filtered and concentrated under reduced pressure to afford methyl 6-(methylsulfonimidoyl)thieno[3,2-b]pyridine-2-carboxylate (210 mg, 53.1% yield) as yellow solid. $^1$H NMR (400 MHz, DMSO-d6) δ ppm 9.14-9.25 (m, 2H), 8.31 (s, 1H), 4.64 (s, 1H), 3.95 (s, 3H), 3.23 (s, 3H); LCMS (ESI) [M+H]$^+$ m/z: calcd 271.0, found 271.0.

Step 2: Synthesis of 6-(methylsulfonimidoyl)thieno[3,2-b]pyridine-2-carboxylic acid A mixture of methyl 6-(methylsulfonimidoyl)thieno[3,2-b]pyridine-2-carboxylate (200 mg, 0.740 mmol), lithium;hydroxide;hydrate (100 mg, 2.38 mmol) in H$_2$O (2 mL) and MeOH (2 mL) was stirred at 20° C. for 2 hours. The mixture was adjusted pH to 4-5 with 1 N HCl aqueous solution. The resulting mixture was diluted by addition of water (10 mL) and extracted with EtOAc (50 mL*3). The combined organic layer was washed with brine (20 mL), dried over anhydrous Na$_2$SO$_4$, filtered and concentrated under reduced pressure to afford 6-(methylsulfonimidoyl)thieno[3,2-b]pyridine-2-carboxylic acid (450 mg, crude) as light yellow solid. LCMS (ESI) [M+H]$^+$ m/z: calcd 257.0, found 257.0.

Step 3: Synthesis of tert-butyl N-[4-(4-fluorophenyl)-2-[[6-(methylsulfonimidoyl)thieno[3,2-b]pyridine-2-carbonyl]amino]phenyl]carbamate A mixture of 6-(methylsulfonimidoyl)thieno[3,2-b]pyridine-2-carboxylic acid (430 mg, 1.68 mmol), tert-butyl N-[2-amino-4-(4-fluorophenyl)phenyl]carbamate (130 mg, 0.430 mmol), 3-(ethyliminomethyleneamino)-N,N-dimethyl-propan-1-amine;hydrochloride (130 mg, 0.678 mmol) in pyridine (5 mL) was stirred at 50° C. for 2 hours. The resulting mixture was concentrated under reduced pressure. The residue was purified by flash chromatography (ISCO®; 12 g AgelaFlash® Silica Flash Column, DCM/MeOH with MeOH from 0~4%, flow rate=35 mL/min, 254 nm) to afford tert-butyl N-[4-(4-fluorophenyl)-2-[[6-(methylsulfonimidoyl)thieno[3,2-b]pyridine-2-carbonyl]amino]phenyl]carbamate (95 mg, 41.9% yield) as light yellow solid. LCMS (ESI) [M+H]$^+$ m/z: calcd 541.1, found 541.2.

Step 4: Synthesis of N-[2-amino-5-(4-fluorophenyl)phenyl]-6-(methylsulfonimidoyl)thieno[3,2-b]pyridine-2-carboxamide A mixture of tert-butyl N-[4-(4-fluorophenyl)-2-[[6-(methylsulfonimidoyl)thieno[3,2-b]pyridine-2-carbonyl]amino]phenyl]carbamate (90 mg, 0.166 mmol), TFA (0.7 mL, 9.09 mmol) in DCM (5 mL) was stirred at 20° C. for 2 hours. The mixture was adjusted pH to 7-8 with saturated NaHCO$_3$ aqueous solution. The resulting mixture was diluted by addition of water (10 mL) and extracted with EtOAc (30 mL*3). The combined organic layer was washed with brine (20 mL), dried over anhydrous Na$_2$SO$_4$, filtered and concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75*40 mm*3 µm; Mobile phase A: H$_2$O with NH$_4$HCO$_3$ and NH$_3$—H$_2$O (v %); Mobile phase B: MeCN; Gradient: B from 30% to 60% in 9.5 min, hold 100% B for 0.2 min; Flow Rate: 30 mL/min; Column Temperature: 30° C.; Wavelength: 220 nm, 254 nm). The fraction was concentrated under reduced pressure and then lyophilized for overnight to afford N-[2-amino-5-(4-fluorophenyl)phenyl]-6-(methylsulfonimidoyl)thieno[3,2-b]pyridine-2-carboxamide (34 mg, 46.4% yield) as white solid. $^1$H NMR (400 MHz, DMSO-d6) δ ppm 10.31 (brs, 1H), 9.19 (d, J=2.0 Hz, 1H), 9.13 (d, J=2.0 Hz, 1H), 8.66 (s, 1H), 7.60 (dd, J=8.7, 5.4 Hz, 2H), 7.53 (d, J=1.8 Hz, 1H), 7.35 (dd, J=8.4, 2.1 Hz, 1H), 7.22 (t, J=8.8 Hz, 2H), 6.89 (d, J=8.5 Hz, 1H), 5.31 (brs, 2H), 4.63 (s, 1H), 3.24 (s, 3H); 19F NMR (377 MHz, DMSO-d6) δ ppm −117.42; LCMS (ESI)

[M+H]⁺ m/z: calcd 441.1, found 441.1; HPLC: 97.92%@220 nm, 97.50%@254 nm.

Example 124. Synthesis of N-[2-amino-5-(4-fluorophenyl)phenyl]-4-[(6-methoxy-3-pyridyl)sulfonimidoyl]benzamide (Compound 222)

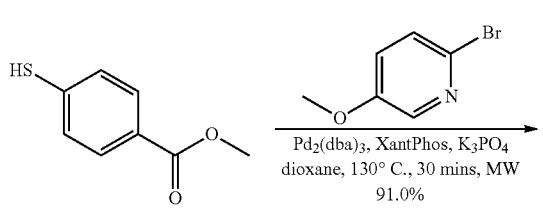

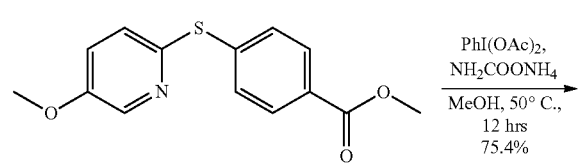

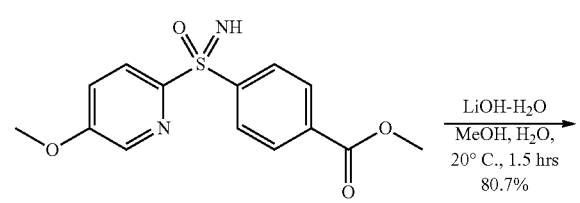

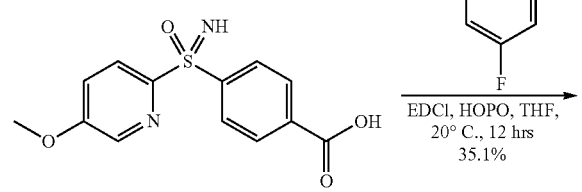

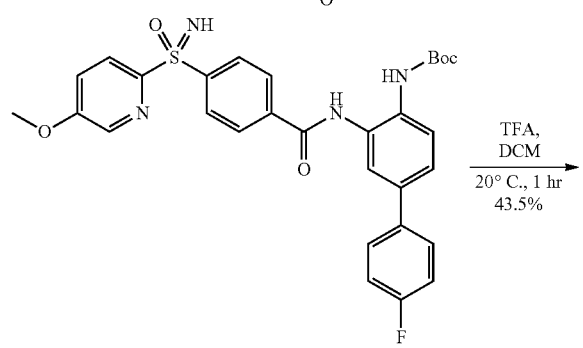

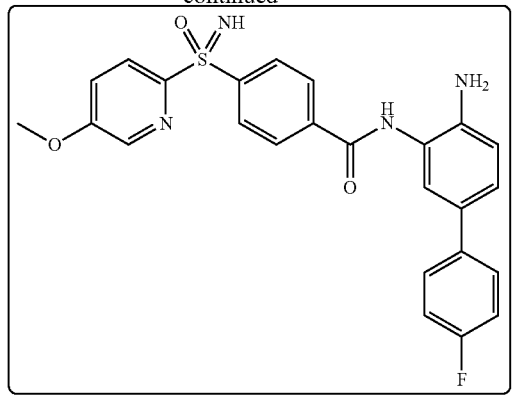

Step 1: Synthesis of methyl 4-[(6-methoxy-3-pyridyl)sulfanyl]benzoate

A mixture of methyl 4-sulfanylbenzoate (520 mg, 3.09 mmol), 5-bromo-2-methoxy-pyridine (0.4 mL, 3.09 mmol), (1E,4E)-1,5-diphenylpenta-1,4-dien-3-one;palladium (550 mg, 0.601 mmol), (5-diphenylphosphanyl-9,9-dimethyl-xanthen-4-yl)-diphenyl-phosphane (900 mg, 1.56 mmol) and dicesium;carbonate (3 g, 9.21 mmol) in dioxane (10 mL) was purged with $N_2$ gas at ambient temperature for 3 minutes. Then mixture was stirred at 130° C. for 30 minutes in microwave. The resulting mixture was quenched by addition of water (10 mL) and extracted with EtOAc (50 mL*3). The combined organic layer was washed with brine (20 mL), dried over anhydrous $Na_2SO_4$, filtered and concentrated under reduced pressure. The residue was purified by flash chromatography (ISCO®; 12 g AgelaFlash® Silica Flash Column, petroleum ether/EtOAc with EtOAc from 0~8%, flow rate=35 mL/min, 254 nm) to afford methyl 4-[(6-methoxy-3-pyridyl)sulfanyl]benzoate (920 mg, 91.0% yield) as yellow solid. LCMS (ESI) [M+H]⁺ m/z: calcd 276.1, found 275.9.

Step 2: Synthesis of methyl 4-[(6-methoxy-3-pyridyl)sulfonimidoyl]benzoate

A mixture of methyl 4-[(6-methoxy-3-pyridyl)sulfanyl]benzoate (870 mg, 3.16 mmol), ammonia;carbamic acid (1.57 g, 20.1 mmol), [acetoxy(phenyl)-iodanyl] acetate (3.06 g, 9.51 mmol) in MeOH (10 mL) was stirred at 50° C. for 12 hours. The resulting mixture was concentrated under reduced pressure. The residue was purified by flash chromatography (ISCO®; 20 g AgelaFlash® Silica Flash Column, petroleum ether/EtOAc with EtOAc from 0~30%, flow rate=35 mL/min, 254 nm) to afford methyl 4-[(6-methoxy-3-pyridyl)sulfonimidoyl]benzoate (730 mg, 75.4% yield) as brown oil. LCMS (ESI) [M+H]⁺ m/z: calcd 307.1, found 306.9.

Step 3: Synthesis of 4-[(6-methoxy-3-pyridyl)sulfonimidoyl]benzoic acid

A mixture of methyl 4-[(6-methoxy-3-pyridyl)sulfonimidoyl]benzoate (630 mg, 2.06 mmol), LiOH—$H_2O$ (263.7 mg, 6.28 mmol) in MeOH (6 mL) and $H_2O$ (2 mL) was stirred at 20° C. for 1.5 hours. The mixture was concentrated under reduced pressure, and adjusted the pH to 5 with 2N HCl aqueous solution. The resulting mixture was quenched by addition of water (10 mL) and extracted with CHCl$_2$ (50 mL*3). The combined organic layer was dried over anhydrous Na$_2$SO$_4$, filtered and concentrated under reduced pressure. The residue was purified by flash chromatography (ISCO®; 20 g AgelaFlash® Silica Flash Column, petroleum ether/EtOAc with EtOAc from 0~70%, flow rate=35 mL/min, 254 nm) to afford 4-[(6-methoxy-3-pyridyl)sulfonimidoyl]benzoic acid (485 mg, 80.7% yield) as yellow solid. LCMS (ESI) [M+H]$^+$ m/z: calcd 293.1, found 292.9.

Step 4: Synthesis of tert-butyl N-[4-(4-fluorophenyl)-2-[[4-[(6-methoxy-3-pyridyl)sulfonimidoyl]benzoyl]amino]phenyl]carbamate A mixture of 4-[(6-methoxy-3-pyridyl)sulfonimidoyl] benzoic acid (390 mg, 1.33 mmol), tert-butyl N-[2-amino-4-(4-fluorophenyl)phenyl]carbamate (409 mg, 1.35 mmol), EDCI (295 mg, 1.54 mmol), 1-oxidopyridin-1-ium-2-ol (180 mg, 1.62 mmol) in THF (4 mL) was stirred at 20° C. for 12 hours. The resulting mixture was concentrated under reduced pressure. The residue was purified by flash chromatography (ISCO®; 20 g AgelaFlash® Silica Flash Column, petroleum ether/EtOAc with EtOAc from 0~45%, flow rate=35 mL/min, 254 nm) to afford tert-butyl N-[4-(4-fluorophenyl)-2-[[4-[(6-methoxy-3-pyridyl)sulfonimidoyl]benzoyl]amino]phenyl]carbamate (270 mg, 35.1% yield) as light yellow solid. LCMS (ESI) [M+H]$^+$ m/z: calcd 577.2, found 577.3.

Step 5: Synthesis of N-[2-amino-5-(4-fluorophenyl)phenyl]-4-[(6-methoxy-3-pyridyl)sulfonimidoyl]benzamide A mixture of tert-butyl N-[4-(4-fluorophenyl)-2-[[4-[(6-methoxy-3-pyridyl)sulfonimidoyl]benzoyl]amino]phenyl] carbamate (270 mg, 0.468 mmol), TFA (0.78 mL, 10.1 mmol) in DCM (5 mL) was stirred at 20° C. for 1 hour. The resulting mixture was concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75*40 mm*3 μm; Mobile phase A: H$_2$O with NH$_4$HCO$_3$ (v %); Mobile phase B: MeCN; Gradient: B from 40% to 70% in 9.5 min, hold 100% B for 1 min; Flow Rate: 30 mL/min; Column Temperature: 30° C.; Wavelength: 220 nm, 254 nm). The fraction was concentrated under reduced pressure and then lyophilized for overnight to afford N-[2-amino-5-(4-fluorophenyl)phenyl]-4-[(6-methoxy-3-pyridyl)sulfonimidoyl]benzamide (97.1 mg, 43.5% yield) as light yellow solid. $^1$H NMR (400 MHz, DMSO-d6) δ ppm 9.86 (s, 1H), 8.78 (d, J=2.3 Hz, 1H), 8.02-8.24 (m, 5H), 7.56 (dd, J=8.5, 5.5 Hz, 2H), 7.47 (d, J=1.8 Hz, 1H), 7.30 (dd, J=8.4, 2.1 Hz, 1H), 7.21 (t, J=8.9 Hz, 2H), 6.97 (d, J=8.8 Hz, 1H), 6.84 (d, J=8.5 Hz, 1H), 5.31 (s, 1H), 5.14 (s, 2H), 3.91 (s, 3H); 19F NMR (376 MHz, DMSO-d6) δ ppm −117.46; LCMS (ESI) [M+H]$^+$ m/z: calcd 477.1, found 477.2; HPLC: 95.48%@220 nm, 98.13%@254 nm.

Example 125. Synthesis of N-[2-amino-5-(2,3,5,6-tetradeuterio-4-fluoro-phenyl)phenyl]-4-(methylsulfonimidoyl)benzamide (Compound 223)

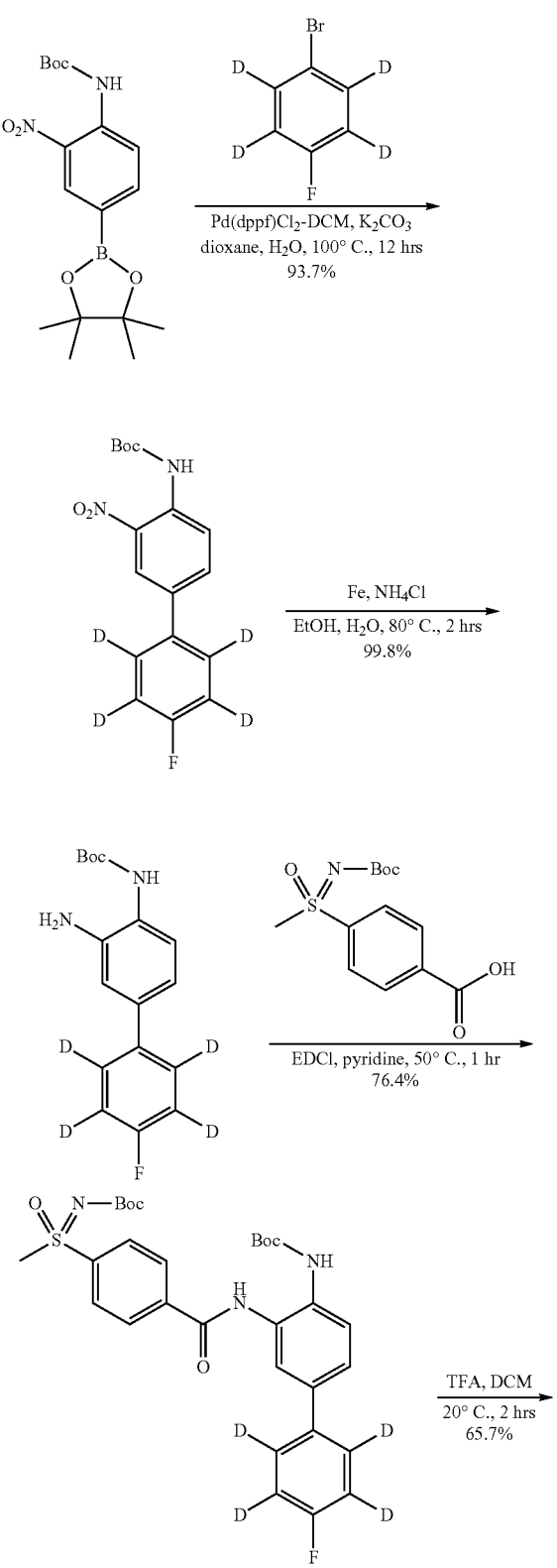

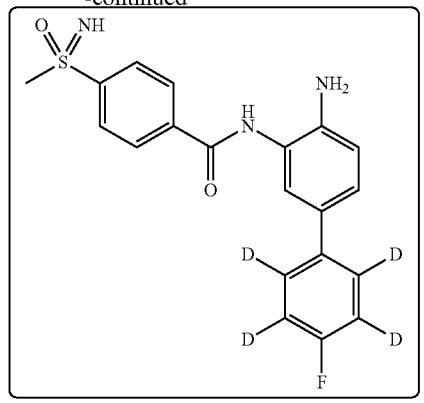

Step 1: Synthesis of tert-butyl N-[2-nitro-4-(2,3,5,6-tetradeuterio-4-fluoro-phenyl)phenyl]carbamate A mixture of 1-bromo-2,3,5,6-tetradeuterio-4-fluoro-benzene (500 mg, 2.79 mmol), tert-butyl N-[2-nitro-4-(4,4,5,5-tetramethyl-1,3,2-dioxaborolan-2-yl)phenyl]carbamate (1.22 g, 3.35 mmol), Pd(dppf)Cl$_2$-DCM (114 mg, 0.140 mmol), K$_2$CO$_3$ (1.2 g, 8.68 mmol), dioxane (15 mL) and H$_2$O (5 mL) was stirred at 100° C. for 12 hours. The resulting mixture was quenched by addition of water (20 mL) and extracted with EtOAc (20 mL*3). The combined organic layer was washed with brine (50 mL*3), dried over anhydrous Na$_2$SO$_4$, filtered and concentrated under reduced pressure. The residue was purified by flash chromatography (Biotage®; 24 g AgelaFlash® Silica Flash Column, petroleum ether/EtOAc with EtOAc from 0~20%, 35 mL/min, 254 nm) to afford tert-butyl N-[2-nitro-4-(2,3,5,6-tetradeuterio-4-fluoro-phenyl)phenyl]carbamate (880 mg, 93.7% yield) as white solid. LCMS (ESI) [M+H]$^+$ m/z: calcd 337.1; found 237.2 (Boc cleaved mass).

Step 2: Synthesis of tert-butyl N-[2-amino-4-(2,3,5,6-tetradeuterio-4-fluoro-phenyl)phenyl]carbamate A mixture of tert-butyl N-[2-nitro-4-(2,3,5,6-tetradeuterio-4-fluoro-phenyl)phenyl]carbamate (880 mg, 2.62 mmol), Fe (438 mg, 7.84 mmol), NH$_4$Cl (1.4 g, 26.2 mmol), EtOH (20 mL) and H$_2$O (5 mL) was stirred at 80° C. for 2 hours. The resulting mixture was filtered. The filtrate was concentrated under reduced pressure to remove EtOH. The residue was diluted with H$_2$O (30 mL). The mixture was filtered. The filter cake was dried under reduced pressure to give tert-butyl N-[2-amino-4-(2,3,5,6-tetradeuterio-4-fluoro-phenyl)phenyl]carbamate (800 mg, 99.8% yield) as yellow solid, which was directly used without further purification. LCMS (ESI) [M+H]$^+$ m/z: calcd 307.2; found 307.2.

Step 3: Synthesis of tert-butyl N-[[4-[[2-(tert-butoxycarbonylamino)-5-(2,3,5,6-tetradeuterio-4-fluoro-phenyl)phenyl]carbamoyl]phenyl]-methyl-oxo-sulfanylidene]carbamate A mixture of 4-(N-tert-butoxycarbonyl-S-methyl-sulfonimidoyl)benzoic acid (300 mg, 1.00 mmol), tert-butyl N-[2-amino-4-(2,3,5,6-tetradeuterio-4-fluoro-phenyl)phenyl]carbamate (307 mg, 1.00 mmol) and EDCI (288 mg, 1.50 mmol) in pyridine (5 mL) was stirred at 50° C. for 1 hour. The resulting mixture was concentrated under reduced pressure. The residue was purified by flash chromatography (ISCO®; 24 g AgelaFlash® Silica Flash Column, petroleum ether/EtOAc with EtOAc from 0~100%, 40 mL/min, 254 nm) to afford tert-butyl N-[[4-[[2-(tert-butoxycarbonylamino)-5-(2,3,5,6-tetradeuterio-4-fluoro-phenyl)phenyl]carbamoyl]phenyl]-methyl-oxo-sulfanylidene]carbamate (450 mg, 76.4% yield) as off white solid. LCMS (ESI) [M+H]$^+$ m/z: calcd 588.2; found 488.3 (Boc cleaved mass).

Step 4: Synthesis of N-[2-amino-5-(2,3,5,6-tetradeuterio-4-fluoro-phenyl)phenyl]-4-(methylsulfonimidoyl)benzamide (Compound 223)

To a solution of tert-butyl N-[[4-[[2-(tert-butoxycarbonylamino)-5-(2,3,5,6-tetradeuterio-4-fluoro-phenyl)phenyl]carbamoyl]phenyl]-methyl-oxo-sulfanylidene]carbamate (450 mg, 0.766 mmol) in DCM (10 mL) was stirred at 20° C. for 2 hours. The resulting mixture was concentrated under reduced pressure. The residue was diluted with H$_2$O (15 mL), and adjusted pH=8 with NaHCO$_3$ aqueous solution. The mixture was extracted with EtOAc (15 mL*3). The combined organic layer was dried over anhydrous Na$_2$SO$_4$, filtered and concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 μm; Mobile phase A: H$_2$O with NH$_4$HCO$_3$ (v %); Mobile phase B: MeCN; Gradient: B from 30% to 60% in 9.5 min, hold 100% B for 2 min; Flow Rate: 30 mL/min; Column Temperature: 30° C.; Wavelength: 220 nm, 254 nm) to give N-[2-amino-5-(2,3,5,6-tetradeuterio-4-fluoro-phenyl)phenyl]-4-(methylsulfonimidoyl)benzamide (195 mg, 65.7% yield) as white dry powder. $^1$H NMR (400 MHz, DMSO-d6) δ ppm 9.91 (s, 1H), 8.18 (d, J=8.3 Hz, 2H), 8.06 (d, J=8.5 Hz, 2H), 7.51 (d, J=2.0 Hz, 1H), 7.32 (dd, J=8.3, 2.3 Hz, 1H), 6.87 (d, J=8.3 Hz, 1H), 5.16 (s, 2H), 4.39 (s, 1H), 3.12 (s, 3H); 19F NMR (376 MHz, DMSO-d6) δ ppm −118.015; LCMS (ESI) [M+H]$^+$ m/z: calcd 388.1; found 388.0; HPLC: 98.62%@220 nm, 99.74%@254 nm; D ratio: 94.31%.

Example 126. Synthesis of N-[2-amino-5-(4-fluorophenyl)phenyl]-2-(methylsulfonimidoyl)benzofuran-5-carboxamide (Compound 248)

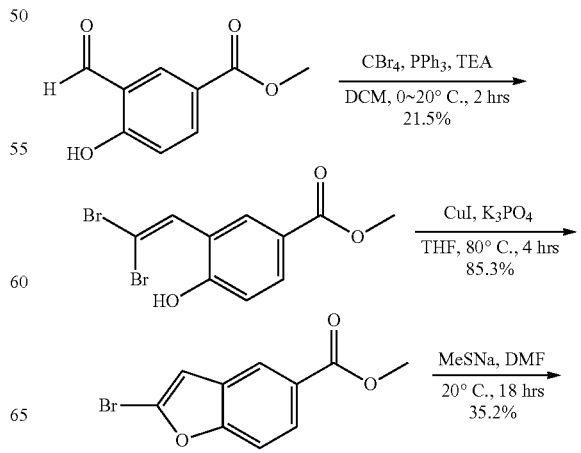

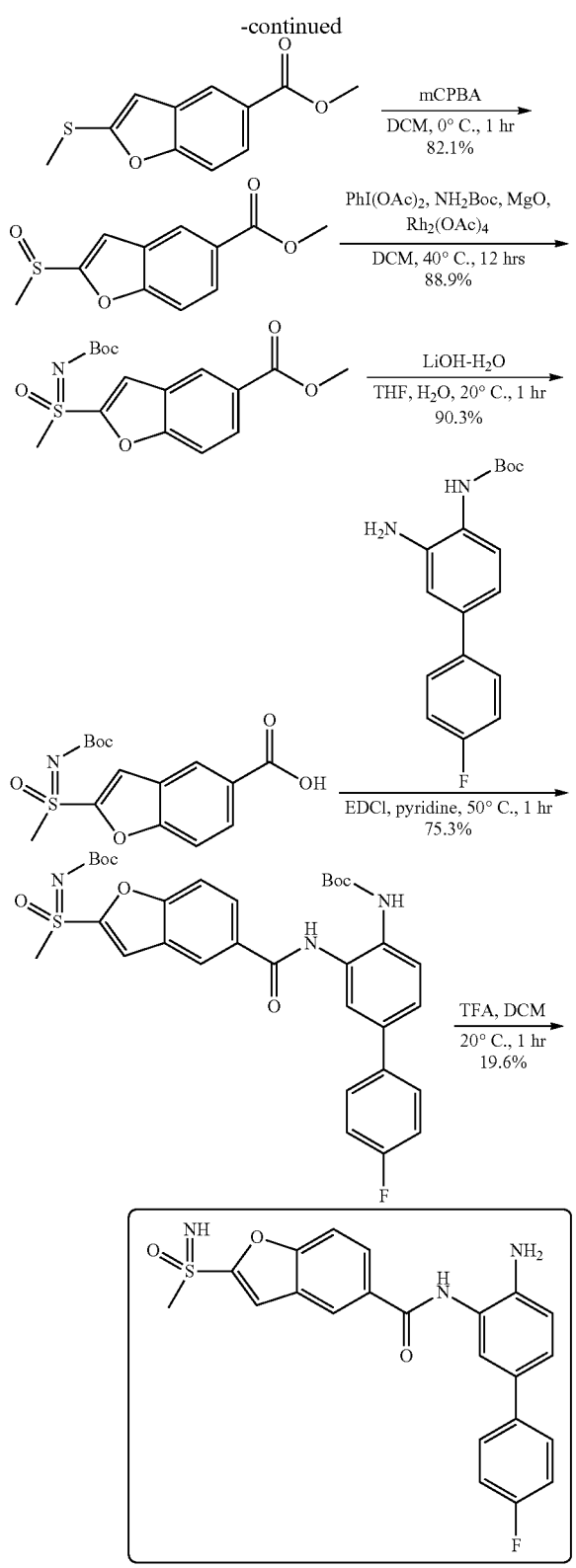

in DCM (200 mL) at 0° C. After 10 minutes, TEA (46 mL, 330 mmol) was added dropwise. The mixture was stirred for 5 minutes. Methyl 3-formyl-4-hydroxy-benzoate (10 g, 55.5 mmol) in DCM (10 mL) was added dropwise. The reaction was quenched by addition of saturated aqueous NH$_4$Cl solution (300 mL). The phases were then separated, and the aqueous layer was extracted with DCM. The combined organic layers were concentrated under reduced pressure. The residue was dissolved in DCM (25 mL). Petroleum ether was added till no yellow solid was formed. The yellow solid was filtrated away and the filtrate was concentrated under reduced pressure. The residue was purified by flash chromatography (ISCO®; 120 g AgelaFlash® Silica Flash Column, petroleum ether/EtOAc with EtOAc from 0~35%, flow rate=80 mL/min, 254 nm) to afford methyl 3-(2,2-dibromovinyl)-4-hydroxy-benzoate (4 g, 21.5% yield) as a yellow solid. $^1$H NMR (400 MHz, DMSO-d6) δ ppm 10.94 (s, 1H) 8.18 (d, J=1.76 Hz, 1H) 7.83 (dd, J=8.66, 2.13 Hz, 1H) 7.60 (s, 1H) 6.97 (d, J=8.53 Hz, 1H) 3.80 (s, 3H).

Step 2: Synthesis of methyl
2-bromobenzofuran-5-carboxylate

To a solution of methyl 3-(2,2-dibromovinyl)-4-hydroxy-benzoate (2.1 g, 6.25 mmol), K$_3$PO$_4$ (2.65 g, 12.5 mmol), and CuI (63.0 mg, 0.331 mmol) in THF (20 mL) was heated to 80° C. and stirred at 80° C. for 4 hours under nitrogen atmosphere. The mixture is filtered to produce a filtrate was concentrated under reduced pressure. The residue was purified by flash chromatography (ISCO®; 40 g AgelaFlash® Silica Flash Column, petroleum ether/EtOAc with EtOAc from 0~5%, flow rate=35 mL/min, 254 nm) to afford methyl 2-bromobenzofuran-5-carboxylate (1.36 g, 5.33 mmol, 85.3% yield) as yellow solid. $^1$H NMR (400 MHz, chloroform-d) δ ppm 8.26 (d, J=1.50 Hz, 1H) 8.01 (dd, J=8.69, 1.69 Hz, 1H) 7.49 (d, J=8.63 Hz, 1H) 6.81 (s, 1H) 3.95 (s, 3H); LCMS (ESI) [M+H]$^+$ m/z: calcd 255.0, found 255.0.

Step 3: Synthesis of methyl
2-methylsulfanylbenzofuran-5-carboxylate

To a solution of methyl 2-bromobenzofuran-5-carboxylate (1.5 g, 5.88 mmol) in DMF (20 mL) was added MeSNa (825 mg, 11.8 mmol). The mixture was stirred at 20° C. for 18 hours. The reaction mixture was added to the 0.1 N HCL (50 mL), extracted with DCM (30 mL*3) filtered and concentrated under reduced pressure. The aqueous solution was quenched with saturated NaClO aqueous solution. The residue was purified by flash chromatography (ISCO®; 40 g AgelaFlash® Silica Flash Column, petroleum ether/EtOAc with EtOAc from 0~10%, flow rate=30 mL/min, 254 nm) to afford methyl 2-methylsulfanylbenzofuran-5-carboxylate (460 mg, 35.2% yield) yellow solid. $^1$H NMR (400 MHz, chloroform-d) δ ppm 8.21 (d, J=1.63 Hz, 1H) 7.98 (dd, J=8.69, 1.69 Hz, 1H) 7.45 (d, J=8.63 Hz, 1H) 6.72 (s, 1H) 3.94 (s, 3H) 2.58 (s, 3H); LCMS (ESI) [M+H]$^+$ m/z: calcd 223.0, found 223.1.

Step 4: Synthesis of methyl
2-methylsulfinylbenzofuran-5-carboxylate

To a solution of methyl 2-methylsulfanylbenzofuran-5-carboxylate (250 mg, 1.12 mmol) in DCM (1 mL) was added m-CPBA (196 mg, 1.14 mmol) at 0° C. The mixture was stirred at 0° C. for 1 hour. The mixture was diluted with water (50 mL) and quenched with saturated Na$_2$SO$_3$ aqueous solution till potassium iodide-starch test paper did not Step 1: methyl
3-(2,2-dibromovinyl)-4-hydroxy-benzoate A solution of CBr4 (55.0 g, 166 mmol) in DCM (30 mL) was added dropwise to a solution of PPh$_3$ (87 g, 332 mmol)

change to blue. The resulting mixture was extracted with DCM (30 mL*3). The combined organic layer was washed with brine (30 mL*2), dried over anhydrous Na$_2$SO$_4$, filtered and concentrated under reduced pressure. The residue was purified by flash chromatography (ISCO®; 20 g AgelaFlash® Silica Flash Column, petroleum ether/EtOAc with EtOAc from 0~70%, flow rate=45 mL/min, 254 nm) to afford methyl 2-methylsulfinylbenzofuran-5-carboxylate (220 mg, 82.1% yield) as a yellow solid. $^1$H NMR (400 MHz, DMSO-d6) δ ppm 8.42 (d, J=1.51 Hz, 1H) 8.16 (dd, J=8.78, 1.76 Hz, 1H) 7.61 (d, J=8.78 Hz, 1H) 7.37 (d, J=0.75 Hz, 1H) 3.97 (s, 3H) 3.07 (s, 3H) [M+H]$^+$ m/z: calcd 239.0, found 239.1.

Step 5: methyl 2-(N-tert-butoxycarbonyl-S-methyl-sulfonimidoyl)benzofuran-5-carboxylate To a solution of methyl 2-methylsulfinylbenzofuran-5-carboxylate (220 mg, 0.923 mmol), NH$_2$Boc (216 mg, 1.84 mmol), MgO (191 mg, 4.62 mmol), PhI(OAc)$_2$ (446 mg, 1.38 mmol) and Rh$_2$(OA)$_4$ (40 mg, 0.905 mmol) in DCM (10 mL) at 40° C. and the mixture was stirred at 40° C. for 12 hours. The reaction mixture was quenched by addition water (30 mL) at 20° C., extracted with DCM (30 mL*3). The combined organic layers were washed with brine (30 mL*3), dried over anhydrous Na$_2$SO$_4$, filtered and concentrated under reduced pressure. The residue was purified by flash chromatography (ISCO®; 12 g AgelaFlash® Silica Flash Column, petroleum ether/EtOAc with EtOAc from 0~50%, flow rate=30 mL/min, 254 nm) to afford methyl 2-(N-tert-butoxycarbonyl-S-methyl-sulfonimidoyl)benzofuran-5-carboxylate (290 mg, 88.9% yield) as yellow oil. $^1$H NMR (400 MHz, chloroform-d) δ ppm 8.48 (d, J=1.25 Hz, 1H) 8.23 (dd, J=8.91, 1.63 Hz, 1H) 7.71 (d, J=0.75 Hz, 1H) 7.64 (d, J=8.78 Hz, 1H) 3.98 (s, 3H) 3.43 (s, 3H) 1.41 (s, 9H) [M+H]$^+$ m/z: calcd 354.1, found 354.1.

Step 6: Synthesis of 2-(N-tert-butoxycarbonyl-S-methyl-sulfonimidoyl)benzofuran-5-carboxylic acid To a solution of methyl 2-(N-tert-butoxycarbonyl-S-methyl-sulfonimidoyl)benzofuran-5-carboxylate (150 mg, 0.424 mmol) in H$_2$O (1 mL) and THF (1 mL) was added LiOH—H$_2$O (89 mg, 2.12 mmol) at 20° C. and the mixture was stirred at 20° C. for 1 hour. The mixture was concentrated under reduced pressure. Water (5 mL) was added to the concentrated residue, the pH value of the mixture was adjusted to 4 with 0.5 N HCl. The mixture was quenched by addition water (30 mL) at 20° C., extracted with EtOAc (30 mL*3), dried over anhydrous Na$_2$SO$_4$, and concentrated under reduced pressure to afford 2-(N-tert-butoxycarbonyl-S-methyl-sulfonimidoyl)benzofuran-5-carboxylic acid (130 mg, 90.3% yield) as a white solid. $^1$H NMR (400 MHz, chloroform-d) δ ppm 8.55 (d, J=1.25 Hz, 1H) 8.28 (dd, J=8.82, 1.69 Hz, 1H) 7.74 (d, J=0.75 Hz, 1H) 7.68 (d, J=8.75 Hz, 1H) 3.44 (s, 3H) 1.42 (s, 9H) LCMS (ESI) [M+H]$^+$ m/z: calcd 340.1, found 340.2.

Step 7: Synthesis of tert-butyl N-[[5-[[2-(tert-butoxycarbonylamino)-5-(4-fluorophenyl)phenyl]carbamoyl]benzofuran-2-yl]-methyl-oxo-sulfanylidene]carbamate To a solution of 2-(N-tert-butoxycarbonyl-S-methyl-sulfonimidoyl)benzofuran-5-carboxylic acid (130 mg, 0.383 mmol) and tert-butyl N-[2-amino-4-(4-fluorophenyl)phenyl]carbamate (116 mg, 0.383 mmol) in pyridine (2 mL) was added EDCI (111 mg, 0.579 mmol) at 20° C. and the mixture was stirred at 50° C. for 1 hour. The reaction mixture was quenched by addition water (30 mL) at 20° C., extracted with EtOAc (30 mL*3). The combined organic layers were washed with brine (50 mL*3), dried over anhydrous Na$_2$SO$_4$, filtered and concentrated under reduced pressure. The residue was purified by flash chromatography (ISCO®; 12 g AgelaFlash® Silica Flash Column, petroleum ether/EtOAc with EtOAc 0~30%, flow rate=35 mL/min, 254 nm) to afford tert-butyl N-[[5-[[2-(tert-butoxycarbonylamino)-5-(4-fluorophenyl)phenyl]carbamoyl]benzofuran-2-yl]-methyl-oxo-sulfanylidene]carbamate (180 mg, 75.3% yield) as a purple solid. $^1$H NMR (400 MHz, chloroform-d) δ ppm 9.61 (br s, 1H) 8.39 (d, J=1.50 Hz, 1H) 8.20 (dd, J=9.01, 1.75 Hz, 1H) 8.14 (d, J=1.88 Hz, 1H) 7.66-7.70 (m, 2H) 7.54-7.60 (m, 2H) 7.37 (dd, J=8.25, 2.13 Hz, 1H) 7.12 (t, J=8.69 Hz, 2H) 6.75 (s, 1H) 3.45 (s, 3H) 1.56 (s, 9H) 1.42 (s, 9H). LCMS (ESI) [M+H]$^+$ m/z: calcd 624.2, found 624.3.

Step 8: Synthesis of N-[2-amino-5-(4-fluorophenyl)phenyl]-2-(methylsulfonimidoyl)benzofuran-5-carboxamide (Compound 248)

To a solution of tert-butyl N-[[5-[[2-(tert-butoxycarbonylamino)-5-(4-fluorophenyl)phenyl]carbamoyl]benzofuran-2-yl]-methyl-oxo-sulfanylidene]carbamate (150 mg, 0.241 mmol) in HFIP (3 mL) was added TFA (274 mg, 2.40 mmol). The mixture was stirred at 20° C. for 1 hour. The mixture was adjusted pH=8 with saturated NaHCO$_3$ aqueous solution. The reaction mixture was concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75*40 mm*3 μm; Mobile phase A: H$_2$O with 10 mm NH$_4$HCO$_3$ (v %); Mobile phase B: ACN; Gradient: B from 5% to 60% in 9.5 min, hold 100% B for 1 min; Flow Rate: 30 mL/min; Column Temperature: 30° C.; Wavelength: 220 nm, 254 nm) to afford N-[2-amino-5-(4-fluorophenyl)phenyl]-2-(methylsulfonimidoyl)benzofuran-5-carboxamide (20 mg, 19.6% yield) as a white solid.

Compound 248: $^1$H NMR (400 MHz, chloroform-d) δ ppm 8.28 (s, 1H) 8.03 (br d, J=10.04 Hz, 1H) 7.90 (br s, 1H) 7.66 (d, J=8.78 Hz, 1H) 7.56 (s, 1H) 7.49 (s, 1H) 7.45 (dd, J=8.66, 5.40 Hz, 2H) 7.28 (dd, J=8.03, 2.01 Hz, 1H) 7.04 (t, J=8.66 Hz, 2H) 6.90 (d, J=8.28 Hz, 1H) 3.88 (br s, 2H) 3.28 (s, 3H) 3.12 (br s, 1H); LCMS[M+H]$^+$ m/z: calcd 424.1, found 424.2; HPLC: 98.42%@220 nm, 99.80%@254 nm.

Example 127. Synthesis of N-[2-amino-5-(4-fluorophenyl)phenyl]-4-[(4-fluorophenyl)sulfonimidoyl]benzamide (Compound 214)

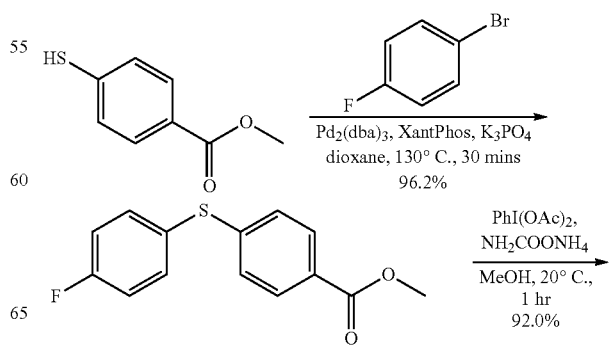

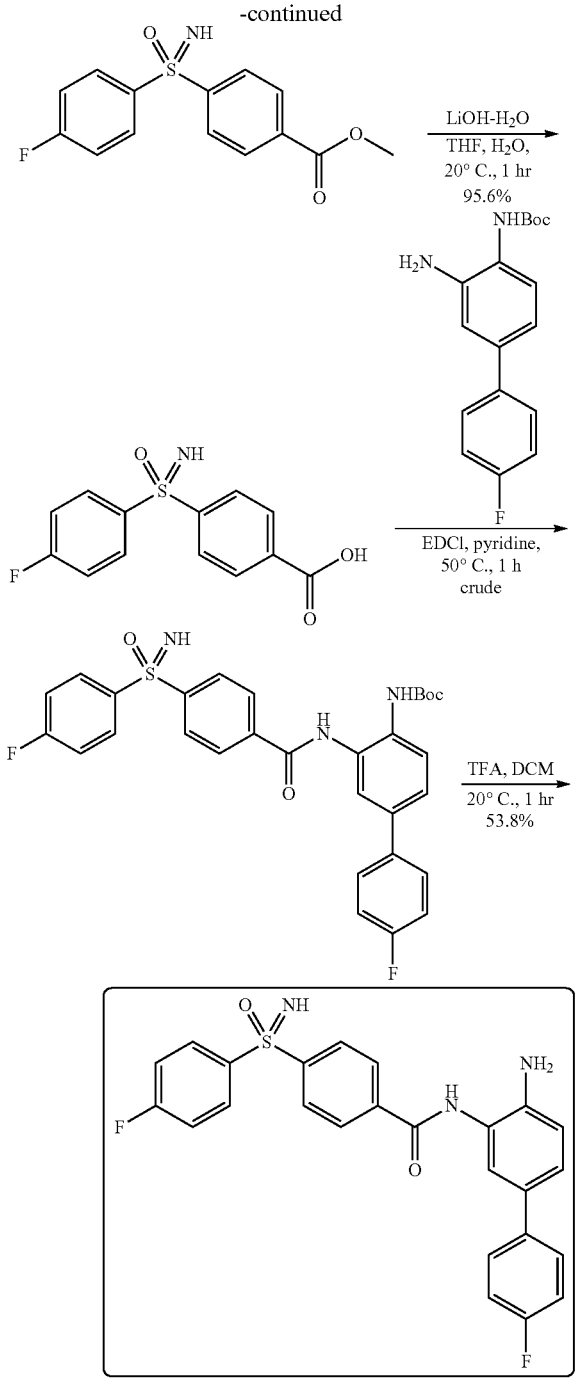

Step 1: Synthesis of methyl 4-(4-fluorophenyl)sulfanylbenzoate

To a solution of 1-bromo-4-fluoro-benzene (0.4 mL, 3.64 mmol) and methyl 4-sulfanylbenzoate (500 mg, 2.97 mmol) in dioxane (15 mL) was added Pd$_2$(dba)$_3$ (140 mg, 0.153 mmol), Xantphos (180 mg, 0.311 mmol) and K$_3$PO$_4$ (1.9 g, 8.95 mmol). The mixture was stirred under N$_2$ at 130° C. for 30 minutes in microwave. The mixture was filtered and the filtrate concentrated under reduced pressure. The residue was purified by flash chromatography (ISCO®; 12 g AgelaFlash® Silica Flash Column, petroleum ether/EtOAc with EtOAc from 0~10%, flow rate=40 mL/min, 254 nm) to afford methyl 4-(4-fluorophenyl)sulfanylbenzoate (750 mg, 96.2% yield) as yellow solid. $^1$H NMR (400 MHz, DMSO-d6) δ ppm 7.84-7.89 (m, 2H), 7.57-7.65 (m, 2H), 7.31-7.39 (m, 2H), 7.19-7.28 (m, 2H), 3.82 (s, 3H); 19F NMR (376 MHz, DMSO-d6) δ ppm -111.611; LCMS (ESI) [M+H]$^+$ m/z: calcd 263.0, found 262.8.

Step 2: Synthesis of methyl 4-[(4-fluorophenyl)sulfonimidoyl]benzoate

A mixture of methyl 4-(4-fluorophenyl)sulfanylbenzoate (700 mg, 2.67 mmol), [acetoxy(phenyl)-iodanyl] acetate (2.15 g, 6.67 mmol), ammonia;carbamic acid (420 mg, 5.38 mmol) and MeOH (10 mL) was stirred at 20° C. for 1 hour. The resulting mixture was concentrated under reduced pressure. The residue was purified by flash chromatography (ISCO®; 12 g AgelaFlash® Silica Flash Column, petroleum ether/EtOAc with EtOAc from 0~26%, flow rate=35 mL/min, 254 nm) to afford methyl 4-[(4-fluorophenyl)sulfonimidoyl]benzoate (720 mg, 92.0% yield) as yellow solid. LCMS (ESI) [M+H]$^+$ m/z: calcd 294.1, found 293.9.

Step 3: Synthesis of 4-[(4-fluorophenyl)sulfonimidoyl]benzoic acid

To a solution of methyl 4-[(4-fluorophenyl)sulfonimidoyl]benzoate (670 mg, 2.28 mmol) in H$_2$O (3 mL) and MeOH (9 mL) was added lithium;hydroxide;hydrate (960 mg, 22.9 mmol) at 0° C. The mixture was stirred at 20° C. for 1 hour. The mixture was adjusted the pH to 5 with 2N HCl aqueous solution. The resulting mixture was extracted with water and EtOAc (50 mL*3). The combined organic layer was dried over anhydrous Na$_2$SO$_4$, filtered and concentrated under reduced pressure to give 4-[(4-fluorophenyl)sulfonimidoyl]benzoic acid (610 mg, 95.6% yield) as white solid. $^1$H NMR (400 MHz, DMSO-d6) δ ppm 13.39 (brs, 1H), 8.00-8.09 (m, 8H); 19F NMR (376 MHz, DMSO-d6) δ ppm -106.741; LCMS (ESI) [M+H]$^+$ m/z: calcd 280.0, found 280.1.

Step 4: Synthesis of tert-butyl N-[4-(4-fluorophenyl)-2-[[4-[(4-fluorophenyl)sulfonimidoyl]benzoyl]amino]phenyl]carbamate A mixture of 4-[(4-fluorophenyl)sulfonimidoyl]benzoic acid (100 mg, 0.358 mmol), tert-butyl N-[2-amino-4-(4-fluorophenyl)phenyl]carbamate (160 mg, 0.529 mmol), 3-(ethyliminomethyleneamino)-N,N-dimethyl-propan-1-amine;hydrochloride (100 mg, 0.522 mmol) and pyridine (6 mL) was stirred at 50° C. for 1 hour. The reaction mixture will be purified with another batch together. The resulting mixture was concentrated under reduced pressure. The residue was purified by flash chromatography (ISCO®; 12 g AgelaFlash® Silica Flash Column, petroleum ether/EtOAc with EtOAc from 0~45%, flow rate=40 mL/min, 254 nm) to afford tert-butyl N-[4-(4-fluorophenyl)-2-[[4-[(4-fluorophenyl)sulfonimidoyl]benzoyl]amino]phenyl]carbamate (270 mg, crude) as white solid. LCMS (ESI) [M+H]$^+$ m/z: calcd 564.2, found 564.3.

Step 5: Synthesis of N-[2-amino-5-(4-fluorophenyl)phenyl]-4-[(4-fluorophenyl)sulfonimidoyl]benzamide (Compound 214)

To a solution of tert-butyl N-[4-(4-fluorophenyl)-2-[[4-[(4-fluorophenyl)sulfonimidoyl]benzoyl]amino]phenyl]carbamate (220 mg, 0.390 mmol) in DCM (4 mL) was added TFA (0.9 mL, 11.7 mmol). The mixture was stirred at 20° C. for 1 hour. The resulting mixture was adjusted the pH to 8 with saturated NaHCO$_3$ aqueous solution, then extracted with water and DCM (20 mL*3). The combined organic layer was dried over anhydrous Na$_2$SO$_4$, filtered and concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 µm; Mobile phase A: H$_2$O with 10 mmol NH$_4$HCO$_3$ (v %); Mobile phase B: MeCN; Gradient: B from 39% to 69% in 9.5 min, hold 100% B for 1 min; Flow Rate: 30 mL/min; Column Temperature: 30° C.; Wavelength: 220 nm, 254 nm) to afford N-[2-amino-5-(4-fluorophenyl)phenyl]-4-[(4-fluorophenyl)sulfonimidoyl]benzamide (97.4 mg, 53.8% yield) as white solid. $^1$H NMR (400 MHz, DMSO-d6) δ ppm 9.84 (s, 1H), 8.10-8.13 (m, 2H), 8.04-8.09 (m, 4H), 7.56 (dd, J=8.8, 5.5 Hz, 2H), 7.47 (d, J=1.8 Hz, 1H), 7.41 (t, J=8.9 Hz, 2H), 7.30 (dd, J=8.4, 2.1 Hz, 1H), 7.20 (t, J=8.9 Hz, 2H), 6.84 (d, J=8.3 Hz, 1H), 5.25 (s, 1H), 5.14 (s, 2H); 19F NMR (376 MHz, DMSO-d6) δ ppm −106.888, −117.490; LCMS (ESI) [M+H]$^+$ m/z: calcd 464.1, found 464.3; HPLC: 97.38%@220 nm; 98.960%@254 nm.

Example 128. Synthesis of N-[2-amino-5-(4-fluorophenyl)phenyl]-5-(N-ethyl-S-methyl-sulfonimidoyl)benzothiophene-2-carboxamide (Compound 207)

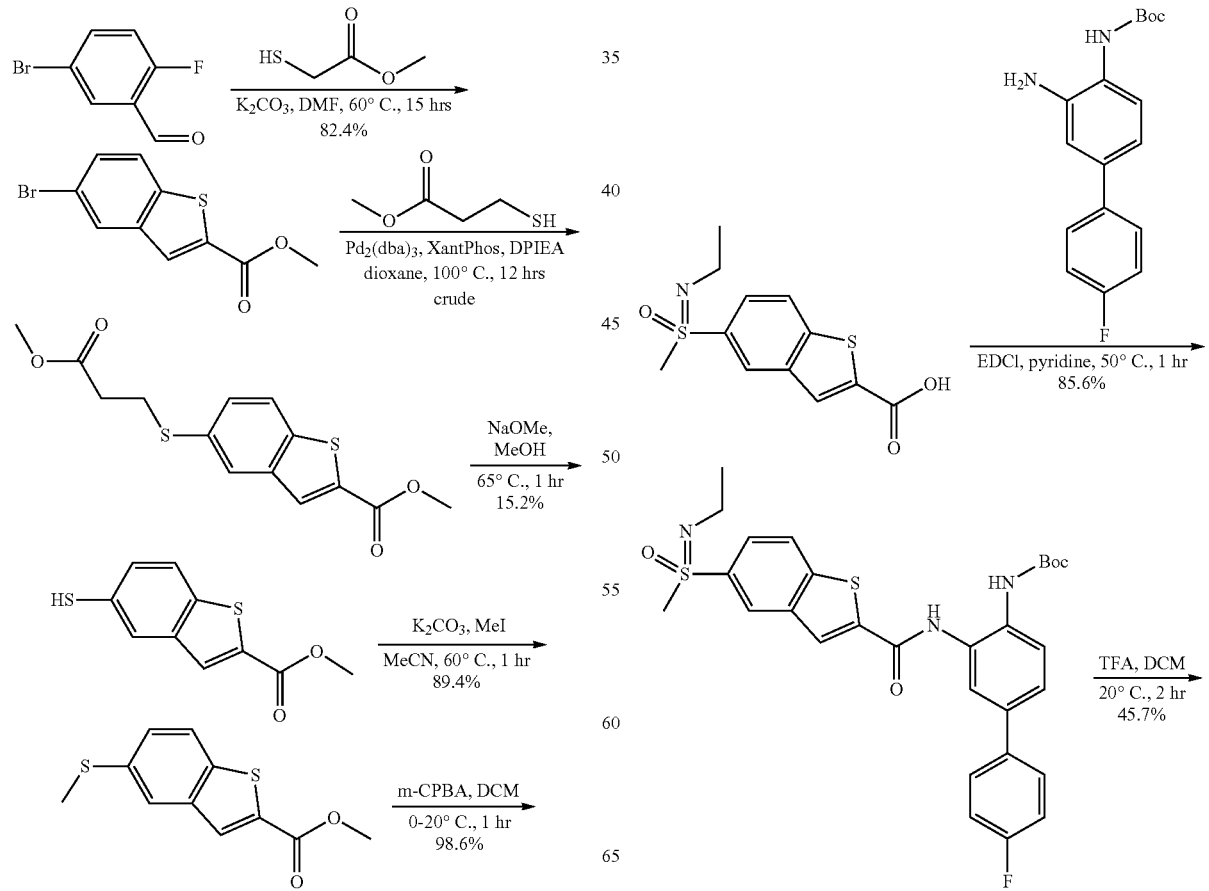
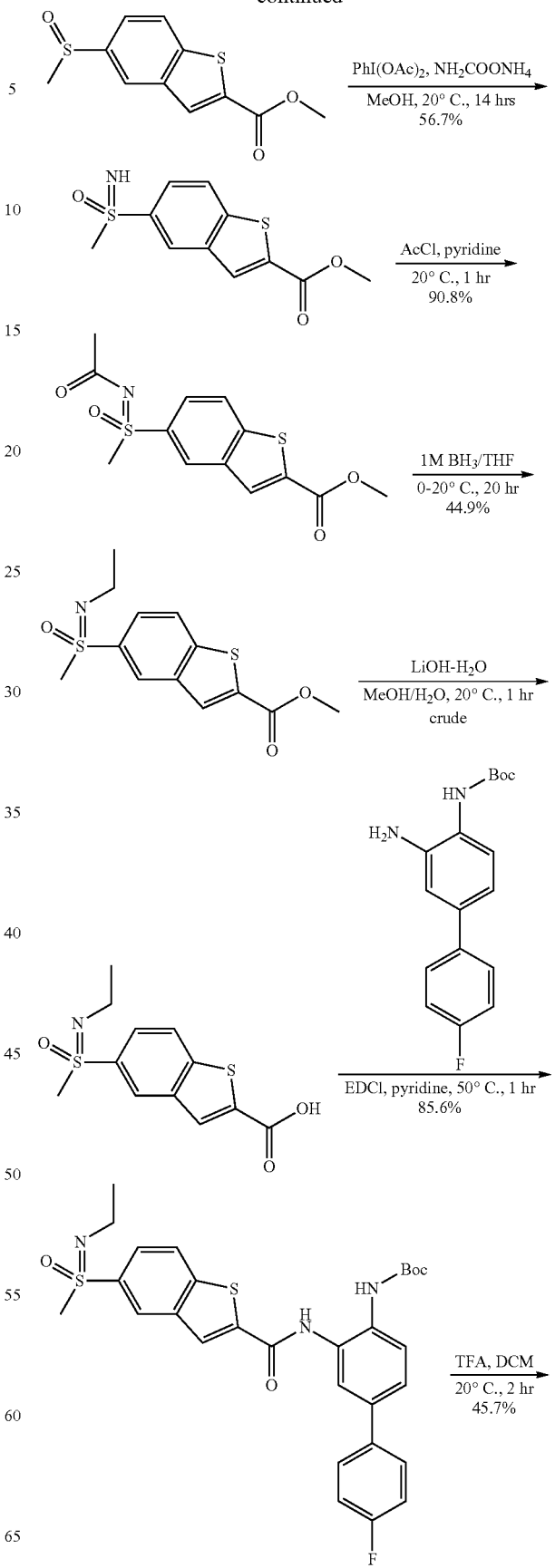

-continued

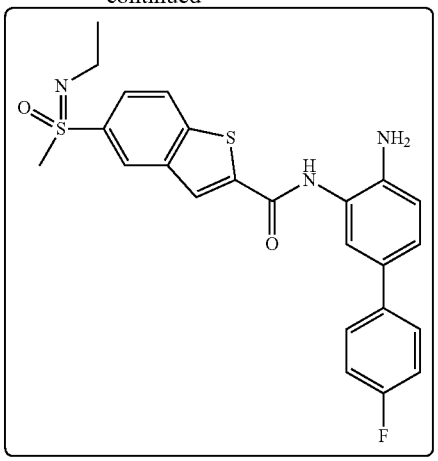

Step 1: Synthesis of methyl 5-bromobenzothiophene-2-carboxylate

A mixture of 5-bromo-2-fluoro-benzaldehyde (10 g, 49.3 mmol), tripotassium;carbonate (27.2 g, 0.197 mmol), methyl 2-sulfanylacetate (5 mL, 54.8 mmol) and DMF (50 mL) was stirred at 60° C. for 15 hours. The resulting mixture was extracted with $H_2O$ (100 mL) and EtOAc (100 mL*3). The combined organic layer was washed with saturated brine (100 mL*3), dried over anhydrous $Na_2SO_4$, filtered and concentrated under reduced pressure to afford methyl 5-bromobenzothiophene-2-carboxylate (11 g, 82.4% yield) as green solid. $^1$H NMR (400 MHz, DMSO-d6) δ ppm 8.28 (d, J=2.0 Hz, 1H), 8.17 (s, 1H), 8.06 (d, J=8.8 Hz, 1H), 7.68 (dd, J=8.8, 2.0 Hz, 1H), 3.90 (s, 3H); LCMS (ESI) [M+H]$^+$ m/z: calcd 272.9, found 273.0.

Step 2: Synthesis of methyl 5-(3-methoxy-3-oxo-propyl)sulfanylbenzothiophene-2-carboxylate A mixture of methyl 5-bromobenzothiophene-2-carboxylate (11 g, 40.6 mmol), methyl 3-sulfanylpropanoate (5.4 mL, 48.8 mmol), (5-diphenylphosphanyl-9,9-dimethyl-xanthen-4-yl)-diphenyl-phosphane (2.35 g, 4.06 mmol), (1E, 4E)-1,5-diphenylpenta-1,4-dien-3-one;palladium (1.86 g, 2.03 mmol), DIPEA (21.2 mL, 0.122 mol) and dioxane (50 mL) was stirred at 100° C. for 12 hours. The mixture was filtered and the filtrate concentrated under reduced pressure. The residue was purified by flash chromatography (ISCO®; 80 g AgelaFlash® Silica Flash Column, petroleum ether/EtOAc with EtOAc from 0~26%, flow rate=50 mL/min, 254 nm) to afford methyl 5-(3-methoxy-3-oxo-propyl)sulfanyl-benzothiophene-2-carboxylate (15 g, crude) as yellow solid. $^1$H NMR (400 MHz, DMSO-d6) δ ppm 8.15 (s, 1H), 8.00-8.05 (m, 2H), 7.49-7.51 (m, 1H), 3.89 (s, 3H), 3.58 (s, 3H), 3.23 (t, J=7.0 Hz, 2H), 2.65 (t, J=7.0 Hz, 2H); LCMS (ESI) [M+H]$^+$ m/z: calcd 311.0, found 311.1.

Step 3: Synthesis of methyl 5-sulfanylbenzothiophene-2-carboxylate

To a solution of methyl 5-(3-methoxy-3-oxo-propyl)sulfanylbenzothiophene-2-carboxylate (8 g, 25.8 mmol) in MeOH (60 mL) was added NaOMe (5.6 g, 0.104 mol). The mixture was stirred at 65° C. for 1 hour. The mixture was adjusted the pH=6 with 2N HCl aqueous solution (20 mL). The resulting mixture was extracted with EtOAc (100 mL*3). The combined organic layer was dried over anhydrous $Na_2SO_4$, filtered and concentrated under reduced pressure. The residue was purified by flash chromatography (ISCO®; 40 g AgelaFlash® Silica Flash Column, petroleum ether/EtOAc with EtOAc from 0~9%, flow rate=50 mL/min, 254 nm) to afford methyl 5-sulfanylbenzothiophene-2-carboxylate (880 mg, 15.2% yield) as yellow solid. LCMS (ESI) [M+H]$^+$ m/z: calcd 225.0, found 225.0.

Step 4: Synthesis of methyl 5-methylsulfanylbenzothiophene-2-carboxylate

A mixture of methyl 5-sulfanylbenzothiophene-2-carboxylate (200 mg, 0.892 mmol), iodomethane (0.12 mL, 1.93 mmol), tripotassium;carbonate (370 mg, 2.68 mmol) in MeCN (6 mL) was stirred at 60° C. for 1 hour. The resulting mixture was quenched by addition of water (20 mL) and extracted with EtOAc (20 mL*3). The combined organic layer was dried over anhydrous $Na_2SO_4$, filtered and concentrated under reduced pressure. The residue was purified by flash chromatography (ISCO®; 12 g AgelaFlash® Silica Flash Column, petroleum ether/EtOAc with EtOAc from 0~12%, flow rate=40 mL/min, 254 nm) to afford methyl 5-methylsulfanylbenzothiophene-2-carboxylate (190 mg, 89.4% yield) as yellow solid. $^1$H NMR (400 MHz, DMSO-d6) δ ppm 8.14 (s, 1H), 8.01 (d, J=8.5 Hz, 1H), 7.92 (d, J=1.8 Hz, 1H), 7.46 (dd, J=8.6, 2.0 Hz, 1H), 3.89 (s, 3H), 2.55 (s, 3H); LCMS (ESI) [M+H]$^+$ m/z: calcd 239.0, found 295.1.

Step 5: Synthesis of methyl 5-methylsulfinylbenzothiophene-2-carboxylate

To a solution of methyl 5-methylsulfanylbenzothiophene-2-carboxylate (190 mg, 0.797 mmol) in DCM (6 mL) was added 3-chlorobenzenecarboperoxoic acid (180 mg, 0.887 mmol, 85 wt %) at 0° C. The mixture was stirred at 20° C. for 1 hour. The resulting mixture was quenched by addition of saturated $Na_2SO_3$ aqueous solution (10 mL) and adjusted the pH=8 with saturated $NaHCO_3$ aqueous solution. The mixture was extracted with DCM (20 mL*3). The combined organic layer was dried over anhydrous $Na_2SO_4$, filtered and concentrated under reduced pressure to afford methyl 5-methylsulfinylbenzothiophene-2-carboxylate (200 mg, 98.6% yield) as yellow oil. LCMS (ESI) [M+H]$^+$ m/z: calcd 255.0, found 255.1.

Step 6: Synthesis of methyl 5-(methylsulfonimidoyl)benzothiophene-2-carboxylate A mixture of methyl 5-methylsulfinylbenzothiophene-2-carboxylate (200 mg, 0.786 mmol), [acetoxy(phenyl)-iodanyl] acetate (630 mg, 1.96 mmol), ammonia;carbamic acid (140 mg, 1.79 mmol) and MeOH (5 mL) was stirred at 20° C. for 2 hours. Then the mixture was stirred at 20° C. for another 12 hours. The resulting mixture was concentrated under reduced pressure. The residue was purified by flash chromatography (ISCO®; 12 g AgelaFlash® Silica Flash Column, petroleum ether/EtOAc with EtOAc from 0~80%, flow rate=40 mL/min, 254 nm) to afford methyl 5-(methylsulfonimidoyl)benzothiophene-2-carboxylate (120 mg, 56.7% yield) as white solid. LCMS (ESI) [M+H]$^+$ m/z: calcd 270.0, found 270.1.

Step 7: Synthesis of methyl 5-(N-acetyl-S-methyl-sulfonimidoyl)benzothiophene-2-carboxylate A mixture of methyl 5-(methylsulfonimidoyl)benzothiophene-2-carboxylate (200 mg, 0.743 mmol), pyridine (0.1 mL, 1.24 mmol), Acetyl chloride (0.1 mL, 1.65 mmol) and DCM (5 mL) was stirred at 20° C. for 1 hour. The resulting mixture was quenched by addition of saturated Na$_2$CO$_3$ aqueous solution (4 mL) and extracted with DCM (20 mL*2). The combined organic layer dried over anhydrous Na$_2$SO$_4$, filtered and concentrated under reduced pressure to give methyl 5-(N-acetyl-S-methyl-sulfonimidoyl)benzothiophene-2-carboxylate (210 mg, 90.8% yield) as white solid. LCMS (ESI) [M+H]$^+$ m/z: calcd 312.0, found 312.1.

Step 8: Synthesis of methyl 5-(N-ethyl-S-methyl-sulfonimidoyl)benzothiophene-2-carboxylate To a solution of methyl 5-(N-acetyl-S-methyl-sulfonimidoyl)benzothiophene-2-carboxylate (210 mg, 0.674 mmol) in THF (5 mL) added 1M BH$_3$/THF (0.8 mL, 0.800 mmol) at 0° C. The mixture was stirred at 20° C. for 2 hours. Then the mixture was stirred at 20° C. for another 16 hours. To the mixture was added 1M BH$_3$/THF (0.4 mL, 0.400 mmol) and the mixture was stirred at 20° C. for 1 hour. Then to the mixture was added 1M BH$_3$/THF (0.3 mL, 0.300 mmol) and the mixture was stirred at 20° C. for 1 hour. The resulting mixture was quenched by addition of MeOH (20 mL) and concentrated under reduced pressure. The residue was purified by flash chromatography (ISCO®; 12 g AgelaFlash® Silica Flash Column, petroleum ether/EtOAc with EtOAc from 0~75%, flow rate=40 mL/min, 254 nm) to afford methyl 5-(N-ethyl-S-methyl-sulfonimidoyl)benzothiophene-2-carboxylate (90 mg, 44.9% yield) as colorless oil. LCMS (ESI) [M+H]$^+$ m/z: calcd 298.0, found 298.1.

Step 9: Synthesis of 5-(N-ethyl-S-methyl-sulfonimidoyl)benzothiophene-2-carboxylic acid To a solution of methyl 5-(N-ethyl-S-methyl-sulfonimidoyl)benzothiophene-2-carboxylate (70 mg, 0.235 mmol) in MeOH (3 mL) and H$_2$O (1 mL) was added lithium;hydroxide;hydrate (100 mg, 2.38 mmol). The mixture was stirred at 20° C. for 1 hour. The mixture was adjusted the pH=5 with 2N HCl aqueous solution. The resulting mixture was extracted with water (20 mL) and EtOAc (30 mL*2). The water was concentrated under reduced pressure to give 5-(N-ethyl-S-methyl-sulfonimidoyl)benzothiophene-2-carboxylic acid (70 mg, crude) as yellow solid. LCMS (ESI) [M+H]$^+$ m/z: calcd 284.0, found 284.1.

Step 10: Synthesis of tert-butyl N-[2-[[5-(N-ethyl-S-methyl-sulfonimidoyl)benzothiophene-2-carbonyl]amino]-4-(4-fluorophenyl)phenyl]carbamate A mixture of 5-(N-ethyl-S-methyl-sulfonimidoyl)benzothiophene-2-carboxylic acid (70 mg, 0.247 mmol), tert-butyl N-[2-amino-4-(4-fluorophenyl)phenyl]carbamate (120 mg, 0.397 mmol), 3-(ethyliminomethyleneamino)-N,N-dimethyl-propan-1-amine;hydrochloride (80 mg, 0.417 mmol) and pyridine (3 mL) was stirred at 50° C. for 1 hour. The resulting mixture was concentrated under reduced pressure. The residue was purified by flash chromatography (ISCO®; 12 g AgelaFlash® Silica Flash Column, petroleum ether/EtOAc with EtOAc from 0~80%, flow rate=40 mL/min, 254 nm) to afford tert-butyl N-[2-[[5-(N-ethyl-S-methyl-sulfonimidoyl)benzothiophene-2-carbonyl]amino]-4-(4-fluorophenyl)phenyl]carbamate (120 mg, 85.6% yield) as yellow solid. LCMS (ESI) [M+H]$^+$ m/z: calcd 568.2, found 568.2.

Step 11: Synthesis of N-[2-amino-5-(4-fluorophenyl)phenyl]-5-(N-ethyl-S-methyl-sulfonimidoyl)benzothiophene-2-carboxamide To a solution of tert-butyl N-[2-[[5-(N-ethyl-S-methyl-sulfonimidoyl)benzothiophene-2-carbonyl]amino]-4-(4-fluorophenyl)phenyl]carbamate (100 mg, 0.176 mmol) in DCM (3 mL) was added TFA (0.4 mL, 5.19 mmol). The mixture was stirred at 20° C. for 2 hours. The mixture was concentrated under reduced pressure and adjusted the pH=8 with saturated NaHCO$_3$ aqueous solution. The resulting mixture was extracted with DCM (20 mL*2). The combined organic layer was dried over anhydrous Na$_2$SO$_4$, filtered and concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 μm; Mobile phase A: H$_2$O with 10 mmol NH$_4$HCO$_3$ (v %); Mobile phase B: MeCN; Gradient: B from 40% to 70% in 9.5 min, hold 100% B for 1 min; Flow Rate: 30 mL/min; Column Temperature: 30° C.; Wavelength: 220 nm, 254 nm) to afford N-[2-amino-5-(4-fluorophenyl)phenyl]-5-(N-ethyl-S-methyl-sulfonimidoyl)benzothiophene-2-carboxamide (37.6 mg, 45.7% yield) as yellow solid. $^1$H NMR (400 MHz, DMSO-d6) δ ppm 10.13 (s, 1H), 8.48 (d, J=8.3 Hz, 2H), 8.32 (d, J=8.5 Hz, 1H), 7.88 (dd, J=8.5, 1.8 Hz, 1H), 7.60 (dd, J=8.8, 5.3 Hz, 2H), 7.51 (d, J=2.0 Hz, 1H), 7.34 (dd, J=8.4, 2.1 Hz, 1H), 7.22 (t, J=8.9 Hz, 2H), 6.88 (d, J=8.3 Hz, 1H), 5.21 (s, 2H), 3.20 (s, 3H), 2.70-2.93 (m, 2H), 1.06 (t, J=7.2 Hz, 3H); 19F NMR (376 MHz, DMSO-d6) δ ppm−117.426; LCMS (ESI) [M+H]$^+$ m/z: calcd 468.1, found 468.2; HPLC: 99.21%@220 nm; 99.60%@254 nm.

Example 129. Synthesis of N-[2-amino-5-(4-fluorophenyl)phenyl]-5-(cyclopropylsulfonimidoyl)benzothiophene-2-carboxamide (Compound 224)

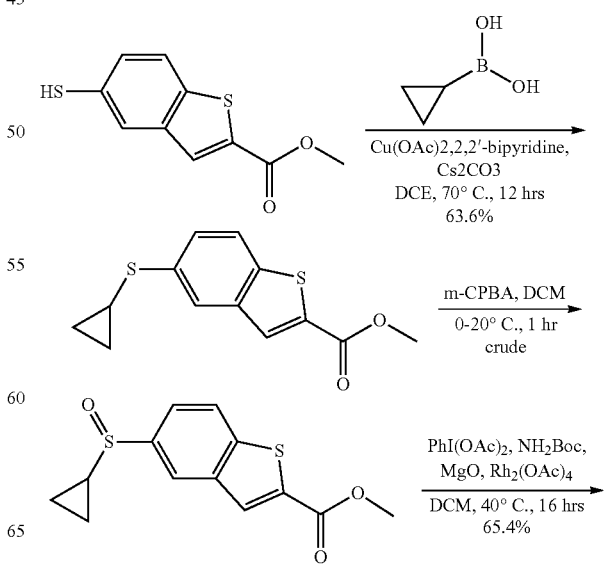

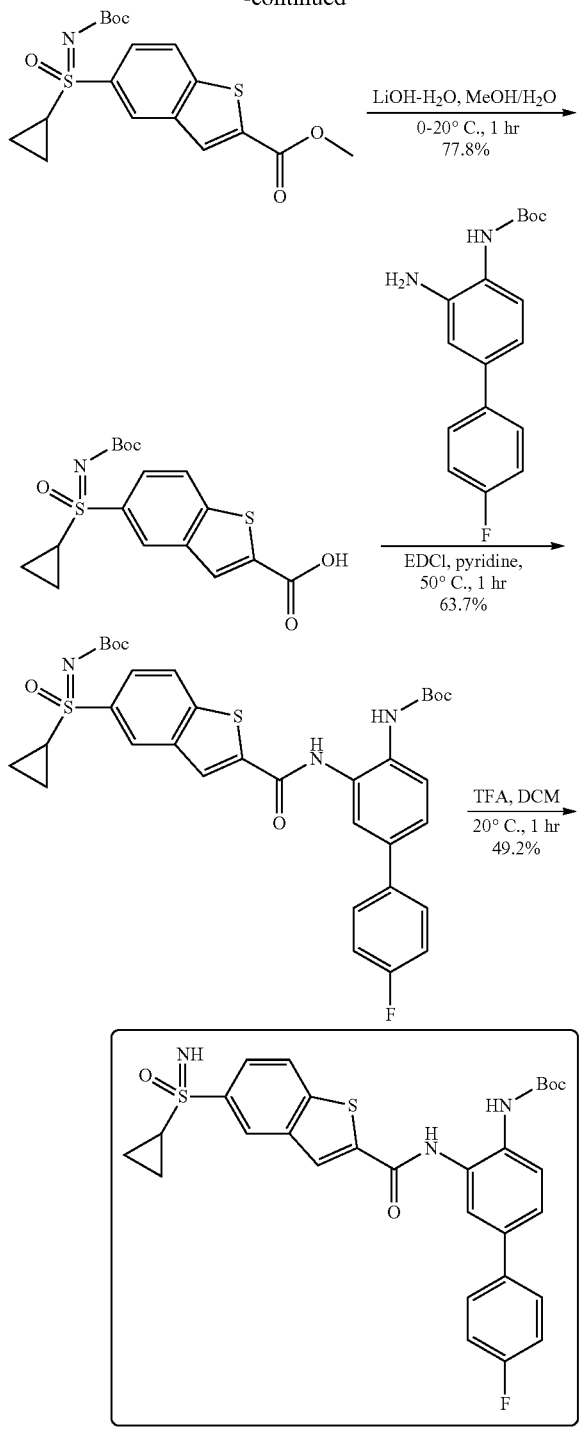

Step 1: Synthesis of methyl 5-cyclopropylsulfanylbenzothiophene-2-carboxylate A mixture of methyl 5-sulfanylbenzothiophene-2-carboxylate (200 mg, 0.892 mmol), cyclopropylboronic acid (120 mg, 1.40 mmol), 2-(2-pyridyl)pyridine (140 mg, 0.896 mmol), dicesium;carbonate (600 mg, 1.84 mmol), copper; diacetate (200 mg, 1.10 mmol) and DCE (6 mL) was stirred at 70° C. for 12 hours. The mixture was filtered. The filtrate was concentrated under reduced pressure. The residue was purified by flash chromatography (ISCO®; 4 g AgelaFlash® Silica Flash Column, petroleum ether/EtOAc with EtOAc from 0~4%, flow rate=30 mL/min, 254 nm) to afford methyl 5-cyclopropylsulfanylbenzothiophene-2-carboxylate (150 mg, 63.6% yield) as yellow oil. LCMS (ESI) [M+H]$^+$ m/z: calcd 265.0, found 265.1.

Step 2: Synthesis of methyl 5-cyclopropylsulfinylbenzothiophene-2-carboxylate To a solution of methyl 5-cyclopropylsulfanylbenzothiophene-2-carboxylate (130 mg, 0.492 mmol) in DCM (5 mL) was added 3-chlorobenzenecarboperoxoic acid (130 mg, 0.640 mmol, 85% purity) at 0° C. The mixture was stirred at 20° C. for 1 hour. The resulting mixture was quenched by addition of saturated Na$_2$SO$_3$ aqueous solution (10 mL) and adjusted the pH to 8 with saturated NaHCO$_3$ aqueous solution (10 mL). The mixture was extracted with DCM (20 mL*2). The combined organic layer was dried over anhydrous Na$_2$SO$_4$, filtered and concentrated under reduced pressure to afford methyl 5-cyclopropylsulfinylbenzothiophene-2-carboxylate (150 mg, crude) as yellow solid. LCMS (ESI) [M+H]$^+$ m/z: calcd 281.0, found 281.1.

Step 3: Synthesis of methyl 5-(N-tert-butoxycarbonyl-S-cyclopropyl-sulfonimidoyl)benzothiophene-2-carboxylate A mixture of methyl 5-cyclopropylsulfinylbenzothiophene-2-carboxylate (130 mg, 0.464 mmol), NH$_2$Boc (110 mg, 0.939 mmol), [bis(acetoxy)iodo]benzene (230 mg, 0.714 mmol), MgO (100 mg, 2.42 mmol), dirhodium tetraacetate (15 mg, 0.0339 mmol) and DCM (6 mL) was stirred at 40° C. for 16 hours. The mixture was filtered. The filtrate was concentrated under reduced pressure. The residue was purified by flash chromatography (ISCO®; 4 g AgelaFlash® Silica Flash Column, petroleum ether/EtOAc with EtOAc from 0~40%, flow rate=30 mL/min, 254 nm) to afford methyl 5-(N-tert-butoxycarbonyl-S-cyclopropyl-sulfonimidoyl)benzothiophene-2-carboxylate (120 mg, 65.4% yield) as yellow oil. LCMS (ESI) [M+H]$^+$ m/z: calcd 396.1, found 396.1.

Step 4: Synthesis of 5-(N-tert-butoxycarbonyl-S-cyclopropyl-sulfonimidoyl)benzothiophene-2-carboxylic acid To a solution of methyl 5-(N-tert-butoxycarbonyl-S-cyclopropyl-sulfonimidoyl)benzothiophene-2-carboxylate (120 mg, 0.303 mmol) in MeOH (6 mL) and H$_2$O (2 mL) was added lithium;hydroxide;hydrate (130 mg, 3.10 mmol) at 0° C. The mixture was stirred at 20° C. for 1 hour. The mixture was adjusted the pH to 5 with 2N HCl aqueous solution (6 mL). The resulting mixture was extracted with H$_2$O (20 mL) and EtOAc (20 mL*2). The combined organic layer was dried over anhydrous Na$_2$SO$_4$, filtered and concentrated under reduced pressure to give 5-(N-tert-butoxycarbonyl-S-cyclopropyl-sulfonimidoyl)benzothiophene-2-carboxylic acid (90 mg, 77.8% yield) as yellow solid. LCMS (ESI) [M+H]$^+$ m/z: calcd 382.1, found 382.1.

Step 5: Synthesis of tert-butyl N-[[2-[[2-(tert-butoxycarbonylamino)-5-(4-fluorophenyl)phenyl]carbamoyl]benzothiophen-5-yl]-cyclopropyl-oxo-sulfanylidene]carbamate A mixture of 5-(N-tert-butoxycarbonyl-S-cyclopropyl-sulfonimidoyl)benzothiophene-2-carboxylic acid (90 mg, 0.236 mmol), tert-butyl N-[2-amino-4-(4-fluorophenyl)phenyl]carbamate (90 mg, 0.298 mmol), 3-(ethyliminomethyleneamino)-N,N-dimethyl-propan-1-amine;hydrochloride (70 mg, 0.365 mmol) and pyridine (5 mL) was stirred at 50° C. for 1 hour. The resulting mixture was concentrated under reduced pressure. The residue was purified by flash chromatography (ISCO®; 12 g AgelaFlash® Silica Flash Column, petroleum ether/EtOAc with EtOAc from 0~40%, flow rate=40 mL/min, 254 nm) to afford tert-butyl N-[[2-[[2-(tert-butoxycarbonylamino)-5-(4-fluorophenyl)phenyl]carbamoyl]benzothiophen-5-yl]-cyclopropyl-oxo-sulfanylidene]carbamate (100 mg, 63.7% yield) as yellow solid. LCMS (ESI) [M+H]⁺ m/z: calcd 666.2, found 566.1 (Boc cleaved mass).

Step 6: Synthesis of N-[2-amino-5-(4-fluorophenyl)phenyl]-5-(cyclopropylsulfonimidoyl)benzothiophene-2-carboxamide To a solution of tert-butyl N-[[2-[[2-(tert-butoxycarbonylamino)-5-(4-fluorophenyl)phenyl]carbamoyl]benzothiophen-5-yl]-cyclopropyl-oxo-sulfanylidene]carbamate (80 mg, 0.120 mmol) in DCM (3 mL) was added TFA (0.3 mL, 3.63 mmol). The mixture was stirred at 20° C. for 1 hour. The mixture was concentrated under reduced pressure and adjusted the pH to 8 with saturated NaHCO₃ aqueous solution. The resulting mixture was extracted with DCM (20 mL*2). The combined organic layer was dried over anhydrous Na₂SO₄, filtered and concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 µm; Mobile phase A: H₂O with 0.05% NH₃—H₂O (v %); Mobile phase B: MeCN; Gradient: B from 38% to 68% in 9.5 min, hold 100% B for 2 min; Flow Rate: 30 mL/min; Column Temperature: 30° C.; Wavelength: 220 nm, 254 nm) to afford N-[2-amino-5-(4-fluorophenyl)phenyl]-5-(cyclopropylsulfonimidoyl)benzothiophene-2-carboxamide (27.5 mg, 49.2% yield) as a yellow solid. ¹H NMR (400 MHz, DMSO-d6) δ ppm 10.14 (br s, 1H), 8.42-8.62 (m, 2H), 8.29 (d, J=8.8 Hz, 1H), 7.95 (dd, J=8.8, 1.8 Hz, 1H), 7.60 (dd, J=8.9, 5.4 Hz, 2H), 7.51 (d, J=2.3 Hz, 1H), 7.34 (dd, J=8.4, 2.1 Hz, 1H), 7.22 (t, J=8.9 Hz, 2H), 6.88 (d, J=8.5 Hz, 1H), 5.23 (s, 2H), 4.36 (s, 1H), 1.09-1.26 (m, 2H), 0.87-1.08 (m, 3H); LCMS (ESI) [M+H]⁺ m/z: calcd 466.1, found 466.2; HPLC: 99.270%@254 nm.

Example 130. Synthesis of methyl 4-[(5-bromo-3-pyridyl)sulfanyl]benzoate (Compound 225)

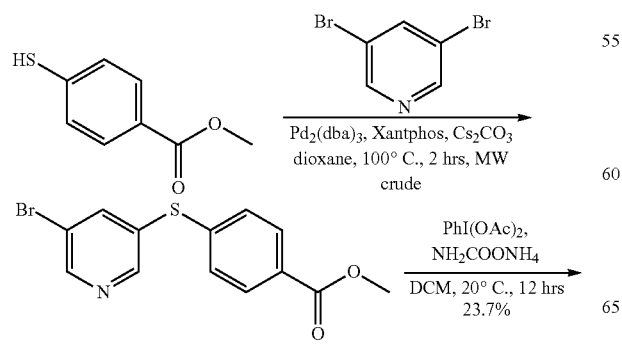

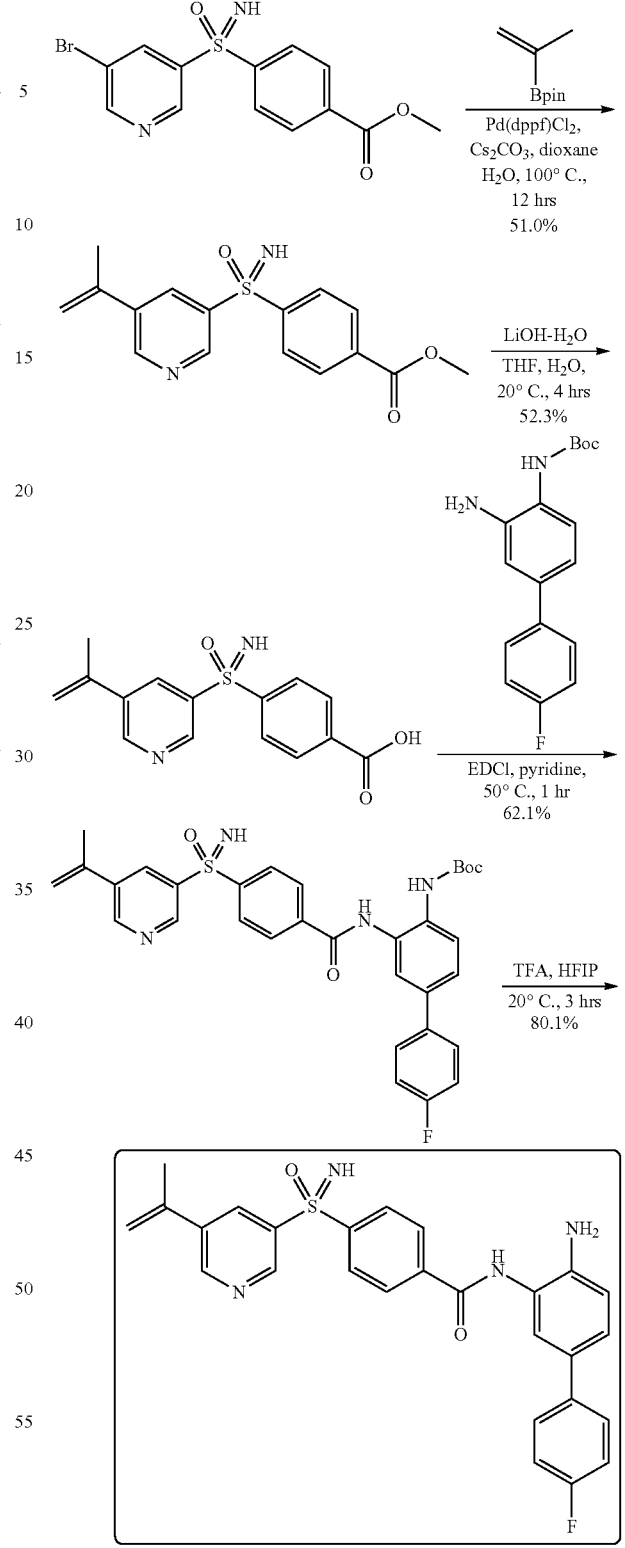

Step 1: Synthesis of methyl 4-[(5-bromo-3-pyridyl)sulfanyl]benzoate

A mixture of methyl 4-sulfanylbenzoate (1 g, 5.94 mmol), 3,5-dibromopyridine (1.69 g, 7.13 mmol), Pd₂(dba)₃ (544 mg, 0.594 mmol), Xantphos (688 mg, 1.19 mmol) and Cs₂CO₃ (3.87 g, 11.8 mmol) in dioxane (10 mL) was degassed and purged with N₂ for 3 times, and then the mixture was stirred at 100° C. for 2 hours under N₂ atmosphere. The reaction mixture was diluted with H₂O (30 mL) and extracted with EtOAc (40 mL*2). The combined organic layers were washed with brine (40 mL), dried over anhydrous Na₂SO₄, filtered and concentrated under reduced pressure. The residue was purified by flash chromatography (ISCO®; 40 g SepaFlash® Silica Flash Column, Petroleum Ether/EtOAc with EtOAc from 0~30%, flow rate=40 mL/min, 254 nm) to afford methyl 4-[(5-bromo-3-pyridyl)sulfanyl]benzoate (800 mg, crude) as a yellow solid. LCMS (ESI) [M+H]⁺ m/z: calcd 326.0, found 325.8.

Step 2: Synthesis of methyl 4-[(5-bromo-3-pyridyl)sulfanyl]benzoate

A mixture of methyl 4-[(5-bromo-3-pyridyl)sulfanyl]benzoate (800 mg, 2.47 mmol), NH₂COONH₄ (578 mg, 4.93 mmol) and PhI(OAc)₂ (1.99 g, 6.17 mmol) in DCM (10 mL) was degassed and purged with N₂ for 3 times, and then the mixture was stirred at 20° C. for 12 hours under N₂ atmosphere. The reaction mixture was diluted with H₂O (30 mL) and extracted with EtOAc (40 mL*2). The combined organic layers were washed with brine (40 mL), dried over anhydrous Na₂SO₄, filtered and concentrated under reduced pressure. The residue was purified by flash chromatography (ISCO®; 12 g SepaFlash® Silica Flash Column, Petroleum Ether/EtOAc with EtOAc from 0~30%, flow rate=40 mL/min, 254 nm) to afford methyl 4-[(5-bromo-3-pyridyl)sulfanyl]benzoate (190 mg, 23.7% yield) as a yellow solid. LCMS (ESI) [M+H]⁺ m/z: calcd 357.0, found 357.0.

Step 3: Synthesis of methyl 4-[(5-isopropenyl-3-pyridyl)sulfonimidoyl]benzoate

A mixture of methyl 4-[(5-bromo-3-pyridyl)sulfonimidoyl]benzoate (220 mg, 0.619 mmol), 2-isopropenyl-4,4,5,5-tetramethyl-1,3,2-dioxaborolane (156 mg, 0.928 mmol), Pd(dppf)Cl₂ (91 mg, 124 mmol) and Cs₂CO₃ (404 mg, 1.24 mmol) in dioxane (5 mL) and H₂O (1 mL) was degassed and purged with N₂ for 3 times, and then the mixture was stirred at 100° C. for 12 hours under N₂ atmosphere. The reaction mixture was diluted with H₂O (30 mL) and extracted with EtOAc (40 mL*2). The combined organic layers were washed with brine (40 mL), dried over anhydrous Na₂SO₄, filtered and concentrated under reduced pressure. The residue was purified by flash chromatography (ISCO®; 20 g SepaFlash® Silica Flash Column, Petroleum Ether/EtOAc with EtOAc from 0~30%, flow rate=40 mL/min, 254 nm) to afford methyl 4-[(5-isopropenyl-3-pyridyl)sulfonimidoyl]benzoate (100 mg, 51.0% yield) as a yellow solid. LCMS (ESI) [M+H]⁺ m/z: calcd 317.7, found 316.9.

Step 4: Synthesis of 4-[(5-isopropenyl-3-pyridyl)sulfonimidoyl]benzoic acid

To a solution of methyl 4-[(5-isopropenyl-3-pyridyl)sulfonimidoyl]benzoate (100 mg, 0.316 mmol) in THF (6 mL) was added a solution of LiOH—H₂O (66 mg, 1.57 mmol) in H₂O (3 mL). The mixture was stirred at 20° C. for 4 hours. The mixture was concentrated under reduced, and then was adjusted PH to 4~5 with 1 N HCl aqueous solution. The mixture was concentrated under reduced pressure to afford 4-[(5-isopropenyl-3-pyridyl)sulfonimidoyl]benzoic acid (50 mg, 52.3% yield) as yellow liquid. LCMS (ESI) [M+H]⁺ m/z: calcd 403.1, found 302.9 (Boc and t-Bu cleaved mass).

Step 5: Synthesis of N-[2-amino-5-(4-fluorophenyl)phenyl]-4-[(5-isopropenyl-3-pyridyl)sulfonimidoyl]benzamide A mixture of 4-[(5-isopropenyl-3-pyridyl)sulfonimidoyl]benzoic acid (40 mg, 0.132 mmol), tert-butyl N-[2-amino-4-(4-fluorophenyl)phenyl]carbamate (48 mg, 0.158 mmol) and EDCI (38 mg, 0.198 mmol) in pyridine (2 mL) was degassed and purged with N₂ for 3 times, and then the mixture was stirred at 50° C. for 1 hour under N₂ atmosphere. The resulting mixture was extracted with NH₄Cl (50 mL) and EtOAc (50 mL*2). The combined organic layer was dried over anhydrous Na₂SO₄, filtered and concentrated under reduced pressure. The residue was purified by flash chromatography (ISCO®; 12 g SepaFlash® Silica Flash Column, Petroleum Ether/EtOAc with EtOAc from 0~30%, flow rate=20 mL/min, 254 nm) to afford N-[2-amino-5-(4-fluorophenyl)phenyl]-4-[(5-isopropenyl-3-pyridyl)sulfonimidoyl]benzamide (40 mg, 82.21 μmol, 62.14% yield) as yellow oil. LCMS (ESI) [M+H]⁺ m/z: calcd 587.2, found 587.1.

Step 6: Synthesis of N-[2-amino-5-(4-fluorophenyl)phenyl]-4-[(5-isopropenyl-3-pyridyl)sulfonimidoyl]benzamide (Compound 225)

A mixture of tert-butyl N-[4-(4-fluorophenyl)-2-[[4-[(5-isopropenyl-3-pyridyl)sulfonimidoyl]benzoyl]amino]phenyl]carbamate (40 mg, 0.068 mmol) and TFA (0.025 mL, 0.333 mmol) in HFIP (6 mL) was degassed and purged with N₂ for 3 times, and then the mixture was stirred at 20° C. for 3 hours under N₂ atmosphere. The reaction mixture was adjusted to pH 8 with saturated NaHCO₃ aqueous. The resultant mixture was dried over Na₂SO₄ and filtered. The filtrate was concentrated under reduced pressure. The residue was purified by preparative HPLC (Instrument: FD; Column: Welch Xtimate C18 100*25 mm*3 μm; Mobile phase A: water (FA). B: ACN; Gradient: B from 34% to 64% in 8 min, hold 100% B for 2 min; Flow Rate: 25 ml/min; Column Temperature: 30° C.; Wavelength: 220 nm, 254 nm) to afford N-[2-amino-5-(4-fluorophenyl)phenyl]-4-[(5-isopropenyl-3-pyridyl)sulfonimidoyl]benzamide (26.6 mg, 99.5% purity) as a yellow solid.

Compound 225: ¹H NMR (400 MHz, DMSO-d6) δ ppm 9.90 (s, 1H), 9.04 (d, J=2.4 Hz, 1H), 8.94 (d, J=2.0 Hz, 1H), 8.35 (t, J=2.0 Hz, 1H), 8.13-8.22 (m, 4H), 7.57 (dd, J=8.4, 5.6 Hz, 2H), 7.48 (d, J=2.0 Hz, 1H), 7.32 (dd, J=8.4, 2.0 Hz, 1H), 7.21 (t, J=8.8 Hz, 2H), 6.87 (d, J=8.4 Hz, 1H), 5.66 (s, 1H), 5.34 (s, 1H), 2.17 (s, 3H); 19F NMR (376 MHz, DMSO-d6) δ ppm −117.361; LCMS (ESI) [M+H]⁺ m/z: calcd 487.2, found 487.1; HPLC: 99.07%@220 nm, 99.52%@254 nm.

Example 131. Synthesis of N-[2-amino-5-(4-fluorophenyl)phenyl]-5-(methylsulfonimidoyl)thiazole-2-carboxamide (Compound 188)

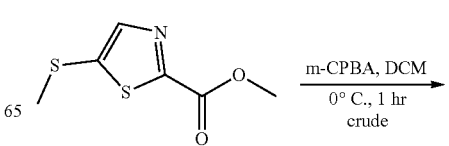

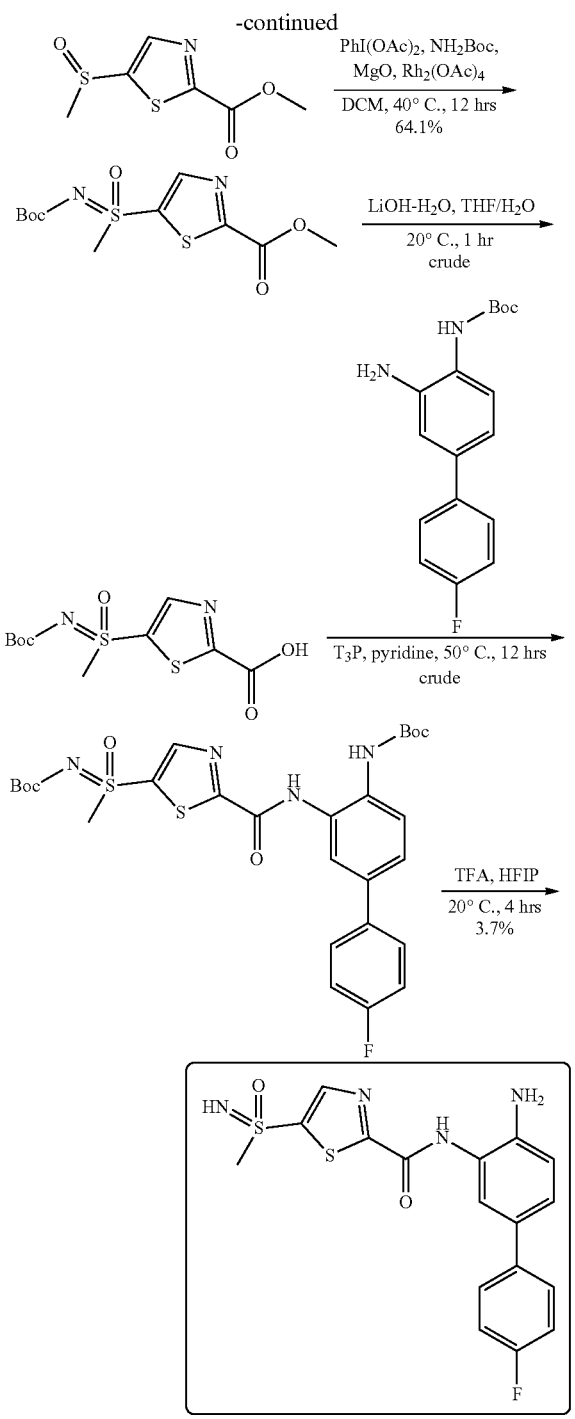

Step 1: Synthesis of methyl 5-methylsulfinylthiazole-2-carboxylate

To a solution of methyl 5-methylsulfanylthiazole-2-carboxylate (220 mg, 1.16 mmol) in DCM (5 mL) was added mCPBA (236 mg, 1.16 mmol, 85% purity). The mixture was stirred at 0° C. for 1 hour. The mixture was quenched by addition of saturated $Na_2SO_3$ aqueous solution (10 mL) and saturated $NaHCO_3$ aqueous solution. The resulting mixture was quenched by addition of water (30 mL) and extracted with DCM (40 mL*3). The combined organic layers were washed with brine (30 mL), dried over anhydrous $Na_2SO_4$, filtered and concentrated under reduced pressure to afford methyl 5-methylsulfinylthiazole-2-carboxylate (250 mg, crude) as a brown solid. LCMS (ESI) [M+H]$^+$ m/z: calcd 206.0, found 205.8.

Step 2: Synthesis of methyl 5-(N-tert-butoxycarbonyl-S-methyl-sulfonimidoyl)thiazole-2-carboxylate To a solution of methyl 5-methylsulfinylthiazole-2-carboxylate (250 mg, 1.22 mmol) in DCM (5 mL) was added $NH_2Boc$ (285 mg, 2.44 mmol), $PhI(OAc)_2$ (588 mg, 1.83 mmol), MgO (245 mg, 6.09 mmol) and $Rh_2(OAc)_4$ (34.1 mg, 0.077 mmol). The reaction mixture was stirred at 40° C. for 12 hours. The mixture was filtered and concentrated under reduced pressure. The residue was purified by flash chromatography (ISCO®; 12 g AgelaFlash® Silica Flash Column, petroleum ether/EtOAc with EtOAc from 0~30%, flow rate=30 mL/min, 254 nm) to afford methyl 5-(N-tert-butoxycarbonyl-S-methyl-sulfonimidoyl)thiazole-2-carboxylate (250 mg, 64.1% yield) as a white solid. $^1$H NMR (400 MHz, DMSO-d) δ ppm 8.70 (s, 1H), 3.97 (s, 3H), 3.71 (s, 3H), 1.31 (s, 9H); LCMS (ESI) [M+H]$^+$ m/z: calcd 321.1, found 220.8. (Boc and t-Bu cleaved mass).

Step 3: Synthesis of 5-(N-tert-butoxycarbonyl-S-methyl-sulfonimidoyl)thiazole-2-carboxylic acid To a solution of methyl 5-(N-tert-butoxycarbonyl-S-methyl-sulfonimidoyl)thiazole-2-carboxylate (250 mg, 0.780 mol) in THF (10 mL)/$H_2O$ (2 mL) was added LiOH—$H_2O$ (164 mg, 3.90 mmol). The mixture was stirred at 20° C. for 1 hour. The mixture was adjusted pH to 4-5 with 1 N HCl and then was concentrated under reduced to afford 5-(N-tert-butoxycarbonyl-S-methyl-sulfonimidoyl)thiazole-2-carboxylic acid (360 mg, crude) as a brown solid. LCMS (ESI) [M+H]$^+$ m/z: calcd 307.0, found 250.8 (Boc and t-Bu cleaved mass).

Step 4: Synthesis of tert-butyl N-[[2-[[2-(tert-butoxycarbonylamino)-5-(4-fluorophenyl)phenyl]carbamoyl]thiazol-5-yl]-methyl-oxo-sulfanylidene]carbamate A mixture of 5-(N-tert-butoxycarbonyl-S-methyl-sulfonimidoyl)thiazole-2-carboxylic acid (100 mg, 0.326 mol), tert-butyl N-[2-amino-4-(4-fluorophenyl)phenyl]carbamate (98.7 mg, 0.326 mmol) and 50% wt % T3P in EtOAc (208 mg, 0.653 mmol) in pyridine (2 mL) was degassed and purged with $N_2$ for 3 times, and then the mixture was stirred at 50° C. for 12 hours under $N_2$ atmosphere. The resulting mixture was extracted with $NH_4Cl$ (50 mL) and EtOAc (50 mL*2). The combined organic layer was dried over anhydrous $Na_2SO_4$, filtered and concentrated under reduced pressure. The residue was purified by flash chromatography (ISCO®; 4 g SepaFlash® Silica Flash Column, Petroleum Ether/EtOAc with EtOAc from 0~30%, flow rate: 20 mL/min, 254 nm) to afford tert-butyl N-[[2-[[2-(tert-butoxycarbonylamino)-5-(4-fluorophenyl)phenyl]carbamoyl]thiazol-5-yl]-methyl-oxo-sulfanylidene]carbamate (40 mg, crude) as a yellow solid. LCMS (ESI) [M+Na]$^+$ m/z: calcd 613.2, found 613.2.

Step 5: Synthesis of N-[2-amino-5-(4-fluorophenyl)phenyl]-5-(methylsulfonimidoyl)thiazole-2-carboxamide (Compound 188)

A mixture of tert-butyl N-[[2-[[2-(tert-butoxycarbonylamino)-5-(4-fluorophenyl)phenyl]carbamoyl]thiazol-5- yl]-methyl-oxo-sulfanylidene]carbamate (80 mg, 0.135 mmol) and TFA (0.042 mL, 0.542 mmol) in HFIP (2 mL) was degassed and purged with N₂ for 3 times, and then the mixture was stirred at 20° C. for 4 hours under N₂ atmosphere. The reaction mixture was diluted with EtOAc (30 mL) and adjusted to pH-8 with saturated NaHCO₃ aqueous. The resultant mixture was dried over Na₂SO₄ and filtered. The filtrate was concentrated under reduced pressure. The residue was purified by preparative HPLC (Instrument: 2_Phenomenex Gemini C18 75*40 mm*3 μm; Column: Waters Xbridge 150*25 mm*5 μm; Mobile phase A: H₂O with 10 mmol NH₄HCO₃ (v %); B: ACN; Gradient: B from 25% to 55% in 9.5 min, hold 100% B for 2 min; Flow Rate: 30 ml/min; Column Temperature: 30° C.; Wavelength: 220 nm, 254 nm) to afford N-[2-amino-5-(4-fluorophenyl)phenyl]-5-(methylsulfonimidoyl)thiazole-2-carboxamide (2 mg, 3.7% yield, 98.1% purity) as a yellow solid.

Compound 188: ¹H NMR (400 MHz, chloroform-d) δ ppm 9.05 (s, 1H), 8.34 (s, 1H), 7.76 (d, J=2.0 Hz, 1H), 7.51 (dd, J=8.8, 5.2 Hz, 2H), 7.33 (dd, J=8.4, 2.0 Hz, 1H), 7.10 (t, J=8.8 Hz, 2H), 6.95 (d, J=8.4 Hz, 1H), 3.34 (d, J=1.2 Hz, 3H); 19F NMR (377 MHz, chloroform-d) δ ppm −116.32; LCMS (ESI) [M+H]⁺ m/z: calcd 391.1, found 391.1; HPLC: 97.74%@220 nm, 98.15%@254 nm.

Example 132. Synthesis of N-[2-amino-5-(4-fluorophenyl)phenyl]-4-[(6-cyano-3-pyridyl)sulfonimidoyl]benzamide (Compound 239)

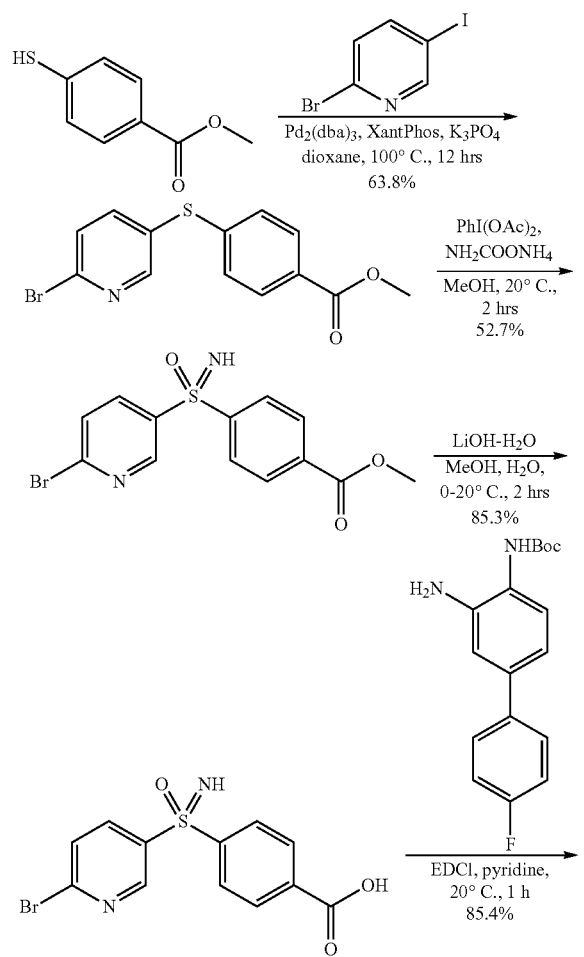

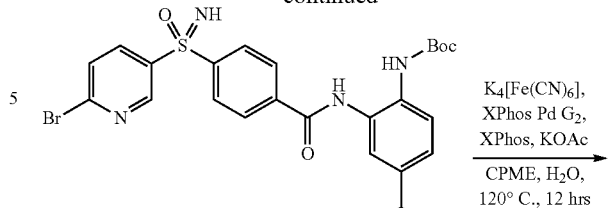

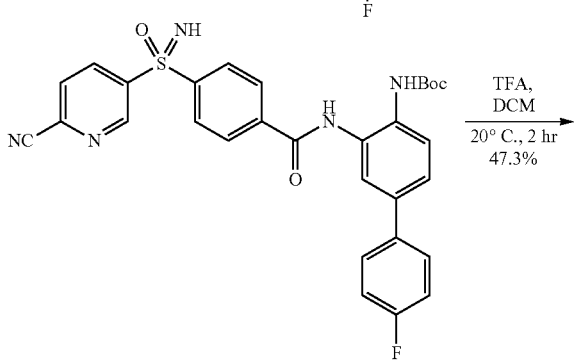

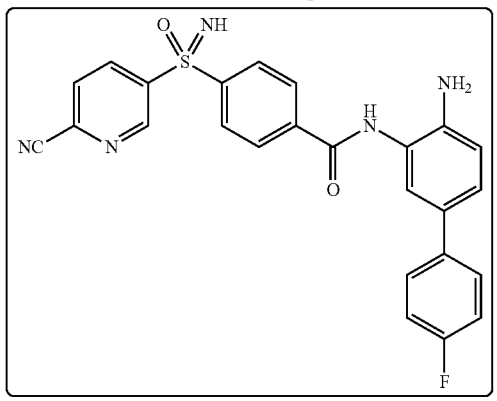 [SMILES: N#Cc1ccc(S(=N)(=O)c2ccc(C(=O)Nc3cc(-c4ccc(F)cc4)ccc3N)cc2)cn1]

Step 1: Synthesis of methyl 4-[(6-bromo-3-pyridyl)sulfanyl]benzoate

A mixture of methyl 4-sulfanylbenzoate (1 g, 5.94 mmol), 2-bromo-5-iodo-pyridine (3.4 g, 12.0 mmol), K₃PO₄ (3.8 g, 17.9 mmol), Xantphos (360 mg, 0.622 mmol) and Pd₂(dba)₃ (560 mg, 0.612 mmol) in dioxane (15 mL) was stirred under N₂ at 100° C. for 12 hours. The resulting mixture was quenched by addition of water (170 mL) and extracted with EtOAc (200 mL). The combined organic layer was dried over anhydrous Na₂SO₄, filtered and concentrated under reduced pressure. The residue was purified by flash chromatography (ISCO®; 20 g Agela Flash® Silica Flash Column, petroleum ether/EtOAc with EtOAc from 0~10%, flow rate=40 mL/min, 254 nm) to afford methyl 4-[(6-bromo-3-pyridyl)sulfanyl]benzoate (1.23 g, 63.8% yield) as yellow solid, LCMS (ESI) [M+H]⁺ m/z: calcd 326.0, found 326.0.

Step 2: Synthesis of methyl 4-[(6-bromo-3-pyridyl)sulfonimidoyl]benzoate

To a solution of methyl 4-[(6-bromo-3-pyridyl)sulfanyl] benzoate (1.23 g, 3.79 mmol) in MeOH (20 mL) was added PhI(OAc)$_2$ (3.1 g, 9.62 mmol), NH$_2$COONH$_4$ (610 mg, 7.81 mmol). The mixture was stirred at 20° C. for 2 hours. The resulting mixture was concentrated under reduced pressure. The residue was purified by flash chromatography (ISCO®; 20 g Agela Flash® Silica Flash Column, petroleum ether/EtOAc with EtOAc from 0~50%, flow rate=40 mL/min, 254 nm) to afford methyl 4-[(6-bromo-3-pyridyl)sulfonimidoyl]benzoate (710 mg, 52.7% yield) as yellow solid. LCMS (ESI) [M+H]$^+$ m/z: calcd 357.0, found 357.0.

Step 3: Synthesis of 4-[(6-bromo-3-pyridyl)sulfonimidoyl]benzoic acid

To a solution of methyl 4-[(6-bromo-3-pyridyl)sulfonimidoyl]benzoate (660 mg, 1.86 mmol) in THF (6 mL) and H$_2$O (2 mL) was added lithium;hydroxide;hydrate (237 mg, 5.65 mmol) at 0° C. The mixture was stirred at 20° C. for 2 hours. The resulting mixture was adjusted pH=4 with 2N HCl aqueous solution, and extracted with EtOAc (30 mL*3). The combined organic layer was dried over Na$_2$SO$_4$, filtered and concentrated under reduced pressure to give 4-[(6-bromo-3-pyridyl)sulfonimidoyl]benzoic acid (541 mg, 85.3% yield) as yellow solid, which was directly used without further purification. LCMS (ESI) [M+H]$^+$ m/z: calcd 341.0, found 341.0.

Step 4: Synthesis of tert-butyl N-[2-[[4-[(6-bromo-3-pyridyl)sulfonimidoyl]benzoyl]amino]-4-(4-fluorophenyl)phenyl]carbamate To a solution of tert-butyl N-[2-amino-4-(4-fluorophenyl)phenyl]carbamate (720 mg, 2.38 mmol) and 4-[(6-bromo-3-pyridyl)sulfonimidoyl]benzoic acid (541 mg, 1.59 mmol) in pyridine (6 mL) was added EDCI (456 mg, 2.38 mmol). The mixture was stirred at 20° C. for 1 hour. The resulting mixture was concentrated under reduced pressure. The residue was purified by flash chromatography (ISCO®; 20 g Agela Flash® Silica Flash Column, EtOAc/Petroleum ether with Petroleum ether from 0~40%, flow rate=35 mL/min, 254 nm) to afford tert-butyl N-[2-[[4-[(6-bromo-3-pyridyl)sulfonimidoyl]benzoyl]amino]-4-(4-fluorophenyl)phenyl]carbamate (847 mg, 85.4% yield) as light-yellow solid. LCMS (ESI) [M+H]$^+$ m/z: calcd 627.1, found 627.2.

Step 5: Synthesis of tert-butyl N-[2-[[4-[(6-bromo-3-pyridyl)sulfonimidoyl]benzoyl]amino]-4-(4-fluorophenyl)phenyl]carbamate To a solution of tert-butyl N-[2-[[4-[(6-bromo-3-pyridyl)sulfonimidoyl]benzoyl]amino]-4-(4-fluorophenyl)phenyl]carbamate (700 mg, 1.12 mmol) in CPME (6 mL) and H$_2$O (6 mL) was added XPhos (112 mg, 0.235 mmol), XPhos Pd G2 (177 mg, 0.225 mmol), potassium;acetate (338 mg, 3.44 mmol) and K$_4$[Fe(CN)$_6$] (676 mg, 1.84 mmol). The mixture was stirred at 120° C. for 12 hours. The reaction mixture was dilute with water (50 mL) and extracted with EtOAc (50 mL*3). The combined organic layers were washed with brine (20 mL), dried over Na$_2$SO$_4$ and filtered. The filtrate was concentrated under reduced pressure. The residue was purified by flash chromatography (ISCO®; 20 g Sepa Flash® Silica Flash Column, petroleum ether/EtOAc with EtOAc from 0~60%, flow rate: 40 mL/min, 254 nm) to give tert-butyl N-[2-[[4-[(6-cyano-3-pyridyl)sulfonimidoyl]benzoyl]amino]-4-(4-fluorophenyl)phenyl]carbamate (315 mg, 49.2 yield) as yellow solid.

Step 6: Synthesis of N-[2-amino-5-(4-fluorophenyl)phenyl]-4-[(6-cyano-3-pyridyl)sulfonimidoyl]benzamide (Compound 239)

To a solution of tert-butyl N-[2-[[4-[(6-cyano-3-pyridyl)sulfonimidoyl]benzoyl]amino]-4-(4-fluorophenyl)phenyl]carbamate (300 mg, 0.525 mmol) in DCM (25 mL) was added TFA (1.7 mL, 22.1 mmol). The mixture was stirred at 20° C. for 2 hours. The mixture was concentrated under reduced pressure. The residue was adjusted pH=8 with 25 wt % NH$_3$—H$_2$O and purified by preparative HPLC (Instrument: Gilson GX-281 Liquid Handler, Gilson 322 Pump, Gilson 156 UV Detector; Column: 2_Phenomenex Gemini C18 75*40 mm*3 μm; Mobile phase A: water (NH$_4$HCO$_3$)-ACN; Mobile phase B: MeCN; Gradient: B from 33% to 63% in 9.5 min, hold 100% B for 2 min; Flow Rate: 30 mL/min; Column Temperature: 30° C.; Wavelength: 220 nm, 254 nm) to afford N-[2-amino-5-(4-fluorophenyl)phenyl]-4-[(6-cyano-3-pyridyl)sulfonimidoyl]benzamide (117.1 mg, 47.3 yield) as yellow solid. $^1$H NMR (400 MHz, DMSO-d6) δ ppm 9.89 (s, 1H), 9.28 (d, J=2.0 Hz, 1H), 8.59 (dd, J=8.3, 2.3 Hz, 1H), 8.22-8.27 (m, 1H), 8.14-8.22 (m, 4H), 7.56 (dd, J=8.5, 5.5 Hz, 2H), 7.47 (d, J=1.8 Hz, 1H), 7.27-7.35 (m, 1H), 7.21 (t, J=8.9 Hz, 2H), 6.84 (d, J=8.3 Hz, 1H), 5.80 (s, 1H), 5.15 (s, 2H); 19F NMR (376 MHz, DMSO-d6) δ ppm−117.460; LCMS (ESI) [M+H]$^+$ m/z: calcd 472.1, found 472.2; HPLC: 99.340%@220 nm; 99.740%@254 nm.

Example 133. Synthesis of N-[2-amino-5-(4-fluorophenyl)phenyl]-4-[(5-isopropyl-3-pyridyl)sulfonimidoyl]benzamide (Compound 226)

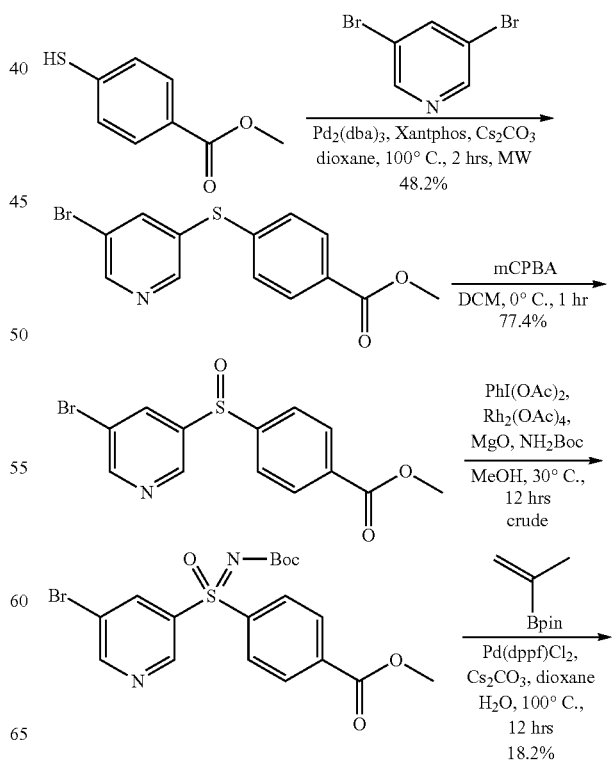

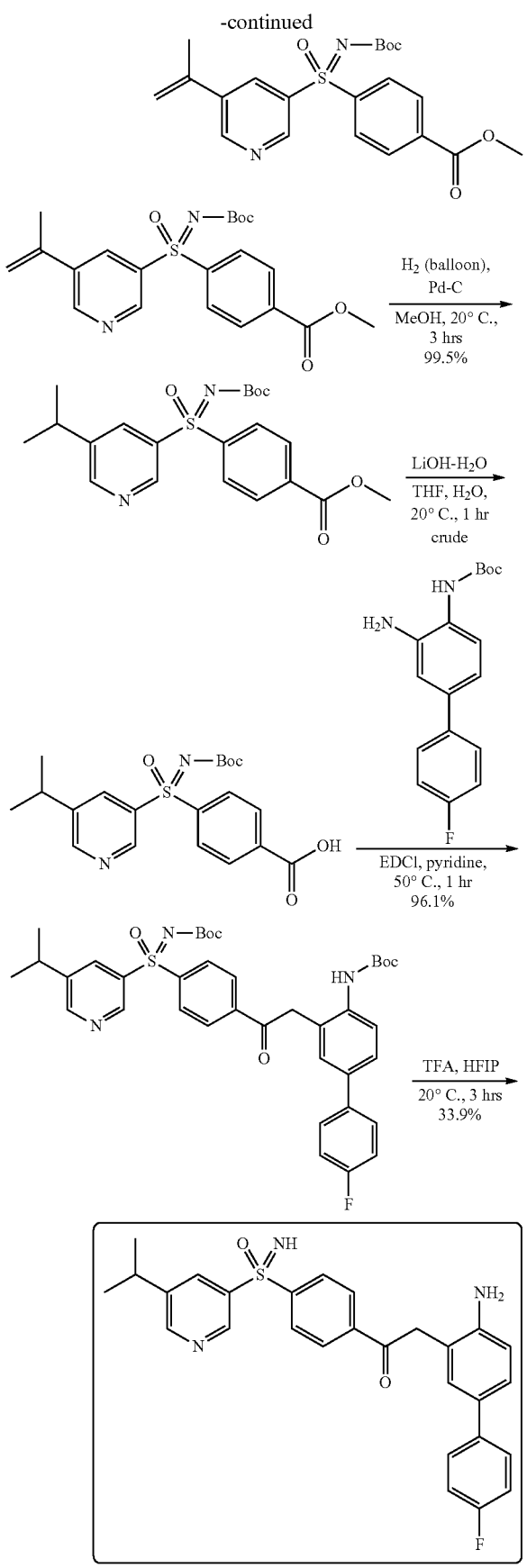

Step 1: Synthesis of methyl 4-[(5-bromo-3-pyridyl)sulfanyl]benzoate

A mixture of methyl 4-sulfanylbenzoate (2 g, 0.012 mmol), 3,5-dibromopyridine (3.38 g, 14.3 mmol), $Pd_2(dba)_3$ (1.09 g, 1.19 mmol), Xantphos (1.38 g, 2.38 mmol) and $Cs_2CO_3$ (7.75 g, 23.9 mmol) in dioxane (10 mL) was degassed and purged with $N_2$ for 3 times, and then the mixture was stirred at 100° C. for 2 hours under $N_2$ atmosphere. The reaction mixture was diluted with $H_2O$ (30 mL) and extracted with EtOAc (40 mL*2). The combined organic layers were washed with brine (40 mL), dried over anhydrous $Na_2SO_4$, filtered and concentrated under reduced pressure. The residue was purified by flash chromatography (ISCO®; 40 g SepaFlash® Silica Flash Column, Petroleum Ether/EtOAc with EtOAc from 0~30%, flow rate=40 mL/min, 254 nm) to afford methyl 4-[(5-bromo-3-pyridyl)sulfanyl]benzoate (1.86 g, 48.2% yield) as a yellow solid. $^1$H NMR (400 MHz, DMSO) δ ppm 8.75 (d, J=2.4 Hz, 1H), 8.62 (d, J=2.0 Hz, 1H), 8.20 (t, J=2.0 Hz, 1H), 7.90-7.94 (m, 2H), 7.39-7.44 (m, 2H), 3.84 (s, 3H); LCMS (ESI) [M+H]$^+$ m/z: calcd 326.0, found 326.1.

Step 2: Synthesis of methyl 4-[(5-bromo-3-pyridyl)sulfinyl]benzoate

To a solution of methyl 4-[(5-bromo-3-pyridyl)sulfanyl]benzoate (1.6 g, 4.94 mmol) in DCM (8 mL) was added m-CPBA (851 mg, 4.94 mmol, 85% wt % purity). The mixture was stirred at 0° C. for 1 hour. The mixture was quenched by addition of saturated $Na_2SO_3$ aqueous solution (10 mL) and saturated $NaHCO_3$ aqueous solution. The resulting mixture was quenched by addition of water (30 mL) and extracted with DCM (40 mL*3). The combined organic layers were washed with brine (30 mL), dried over anhydrous $Na_2SO_4$, filtered and concentrated under reduced pressure to afford methyl 4-[(5-bromo-3-pyridyl)sulfinyl]benzoate (1.3 g, 77.4% yield) as a white solid. LCMS (ESI) [M+H]$^+$ m/z: calcd 342.0, found 341.8.

Step 3: Synthesis of methyl 4-[S-(5-bromo-3-pyridyl)-N-tert-butoxycarbonyl-sulfonimidoyl]benzoate To a mixture of methyl 4-[(5-bromo-3-pyridyl)sulfinyl]benzoate (1.2 g, 3.53 mmol), NH$_2$Boc (826 mg, 7.05 mmol), PhI(OAc)$_2$ (1.70 g, 5.29 mmol), MgO (710 mg, 17.6 mmol) and Rh$_2$(OAc)$_4$ (1.56 g, 3.53 mmol) in DCM (10 mL). The resulting mixture was stirred at 30° C. for 12 hours. The reaction mixture was diluted with H$_2$O (30 mL) and extracted with EtOAc (40 mL*2). The combined organic layers were washed with brine (40 mL), dried over anhydrous Na$_2$SO$_4$, filtered and concentrated under reduced pressure. The residue was purified by flash chromatography (ISCO®; 20 g SepaFlash® Silica Flash Column, Petroleum Ether/EtOAc with EtOAc from 0~50%, flow rate=80 mL/min, 254 nm) methyl 4-[S-(5-bromo-3-pyridyl)-N-tert-butoxycarbonyl-sulfonimidoyl]benzoate (1.2 g, crude) as a yellow solid. LCMS (ESI) [M+H]$^+$ m/z: calcd 456.7, found 457.0.

Step 4: Synthesis of methyl 4-[N-tert-butoxycarbonyl-S-(5-isopropenyl-3-pyridyl)sulfonimidoyl]benzoate A mixture of methyl 4-[S-(5-bromo-3-pyridyl)-N-tert-butoxycarbonyl-sulfonimidoyl]benzoate (1.2 g, 2.64 mmol), 2-isopropenyl-4,4,5,5-tetramethyl-1,3,2-dioxaborolane (645 mg, 3.84 mmol), Pd(dppf)Cl$_2$ (192 mg, 0.263 mmol) and Cs$_2$CO$_3$ (1.72 g, 5.27 mmol) in dioxane (10 mL) and H$_2$O (1 mL) was degassed and purged with N$_2$ for 3 times, and then the mixture was stirred at 100° C. for 12 hours under N$_2$ atmosphere. The reaction mixture was diluted with H$_2$O (30 mL) and extracted with EtOAc (40 mL*2). The combined organic layers were washed with brine (40 mL), dried over anhydrous Na$_2$SO$_4$, filtered and concentrated under reduced pressure. The residue was purified by flash chromatography (ISCO®; 20 g SepaFlash® Silica Flash Column, Petroleum Ether/EtOAc with EtOAc from 0~30%, flow rate=40 mL/min, 254 nm) to afford methyl 4-[N-tert-butoxycarbonyl-S-(5-isopropenyl-3-pyridyl)sulfonimidoyl]benzoate (200 mg, 18.2% yield) as colorless oil. LCMS (ESI) [M+H]$^+$ m/z: calcd 417.1, found 417.1.

Step 5: Synthesis of methyl 4-[N-tert-butoxycarbonyl-S-(5-isopropyl-3-pyridyl)sulfonimidoyl]benzoate To a solution of methyl 4-[N-tert-butoxycarbonyl-S-(5-isopropenyl-3-pyridyl)sulfonimidoyl]benzoate (150 mg, 0.360 mmol) in MeOH (10 mL) was added Pd/C (150 mg, 1.24 mmol, 10 wt % Pd with 50 wt % water) was stirred at 20° C. for 3 hours under a H$_2$ atmosphere. Compound was detected Pd/C was removed by filtration through Celite. The filtrate was concentrated in vacuo to afford methyl 4-[N-tert-butoxycarbonyl-S-(5-isopropyl-3-pyridyl)sulfonimidoyl]benzoate (150 mg, 99.5% yield) as white oil. LCMS (ESI) [M+H]$^+$ m/z: calcd 419.2, found 363.0. (Boc and t-Bu cleaved mass).

Step 6: Synthesis of 4-[N-tert-butoxycarbonyl-S-(5-isopropyl-3-pyridyl)sulfonimidoyl]benzoic acid A mixture of methyl 4-[N-tert-butoxycarbonyl-S-(5-isopropyl-3-pyridyl)sulfonimidoyl]benzoate (150 mg, 0.358 mmol) and LiOH—H$_2$O (75 mg, 1.79 mmol) in THF (10 mL) and H$_2$O (2 mL) was degassed and purged with N$_2$ for 3 times, and then the mixture was stirred at 20° C. for 1 hour under N$_2$ atmosphere. The mixture was concentrated under reduced and then was adjusted PH to 4-5 with 1 N HCl aqueous solution. The resulting mixture was extracted with NH$_4$Cl (50 mL) and EtOAc (50 mL*2). The combined organic layer was dried over anhydrous Na$_2$SO$_4$, filtered and concentrated under reduced pressure to afford 4-[N-tert-butoxycarbonyl-S-(5-isopropyl-3-pyridyl)sulfonimidoyl]benzoic acid (150 mg, crude) as a white solid. LCMS (ESI) [M+H]$^+$ m/z: calcd 405.1, found 348.9. (Boc and t-Bu cleaved mass).

Step 7: Synthesis of tert-butyl N-[4-(4-fluorophenyl)-2-[[4-[(5-isopropyl-3-pyridyl)sulfonimidoyl]benzoyl]amino]phenyl]carbamate A mixture of 4-[N-tert-butoxycarbonyl-S-(5-isopropyl-3-pyridyl)sulfonimidoyl]benzoic acid (150 mg, 0.371 mmol), tert-butyl N-[2-amino-4-(4-fluorophenyl)phenyl]carbamate (135 mg, 0.446 mmol) and EDCI (107 mg, 0.558 mmol) in pyridine (2 mL) was degassed and purged with N$_2$ for 3 times, and then the mixture was stirred at 50° C. for 1 hour under N$_2$ atmosphere. The resulting mixture was extracted with NH$_4$Cl (50 mL) and EtOAc (50 mL*2). The combined organic layer was dried over anhydrous Na$_2$SO$_4$, filtered and concentrated under reduced pressure. The residue was purified by flash chromatography (ISCO®; 12 g SepaFlash® Silica Flash Column, Petroleum Ether/EtOAc with EtOAc from 0~30%, flow rate=20 mL/min, 254 nm) to afford tert-butyl N-[4-(4-fluorophenyl)-2-[[4-[(5-isopropyl-3-pyridyl)sulfonimidoyl]benzoyl]amino]phenyl]carbamate (210 mg, 96.1% yield) as white liquid. LCMS (ESI) [M+H]$^+$ m/z: calcd 689.3, found 533.1. (Boc and t-Bu cleaved mass).

Step 8: Synthesis of N-[2-amino-5-(4-fluorophenyl)phenyl]-4-[(5-isopropyl-3-pyridyl)sulfonimidoyl]benzamide (Compound 226)

A mixture of tert-butyl N-[[4-[[2-(tert-butoxycarbonylamino)-5-(4-fluorophenyl)phenyl]carbamoyl]phenyl]-(5-isopropyl-3-pyridyl)-oxo-sulfanylidene]carbamate (180 mg, 0.261 mmol) and TFA (0.08 mL, 1.04 mmol) in HFIP (10 mL) was degassed and purged with N$_2$ for 3 times, and then the mixture was stirred at 20° C. for 3 hours under N$_2$ atmosphere. The reaction mixture was adjusted to pH 8 with saturated NaHCO$_3$ aqueous. The resultant mixture was dried over anhydrous Na$_2$SO$_4$ and filtered. The filtrate was concentrated under reduced pressure. The residue was purified by preparative HPLC (Instrument: FD; Column: Welch Xtimate C18 100*25 mm*3 μm; Mobile phase A: water (FA). B: ACN; Gradient: B from 40% to 70% in 8 min, hold 100% B for 2 min; Flow Rate: 25 ml/min; Column Temperature: 30° C.; Wavelength: 220 nm, 254 nm) to afford N-[2-amino-5-(4-fluorophenyl)phenyl]-4-[(5-isopropyl-3-pyridyl)sulfonimidoyl]benzamide (43.4 mg, 33.9% yield, 97.7% purity) as a yellow solid.

Compound 226: $^1$H NMR (400 MHz, DMSO) δ ppm 9.87 (s, 1H), 8.96 (d, J=2.4 Hz, 1H), 8.71 (d, J=1.6 Hz, 1H), 8.20 (t, J=2.0 Hz, 1H), 8.12-8.18 (m, 4H), 7.56 (dd, J=8.8, 5.2 Hz, 2H), 7.46 (d, J=2.0 Hz, 1H), 7.30 (dd, J=8.4, 2.0 Hz, 1H), 7.20 (t, J=8.8 Hz, 2H), 6.84 (d, J=8.4 Hz, 1H), 4.86-5.72 (m, 3H), 3.02-3.12 (m, 1H), 1.24 (d, J=7.2 Hz, 6H); 19F NMR (377 MHz, DMSO-d6) δ ppm −117.46; LCMS (ESI) [M+H]$^+$ m/z: calcd 489.2, found 489.1 (Boc and t-Bu cleaved mass); HPLC: 97.99%@220 nm, 97.75%@254 nm.

Example 134. Synthesis of N-[2-amino-5-(4-fluorophenyl)phenyl]-4-[[6-(trifluoromethyl)-3-pyridyl]sulfonimidoyl]benzamide (Compound 205)

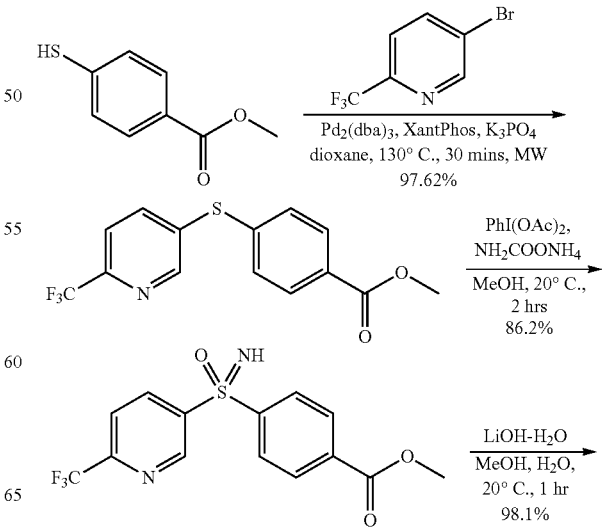

-continued

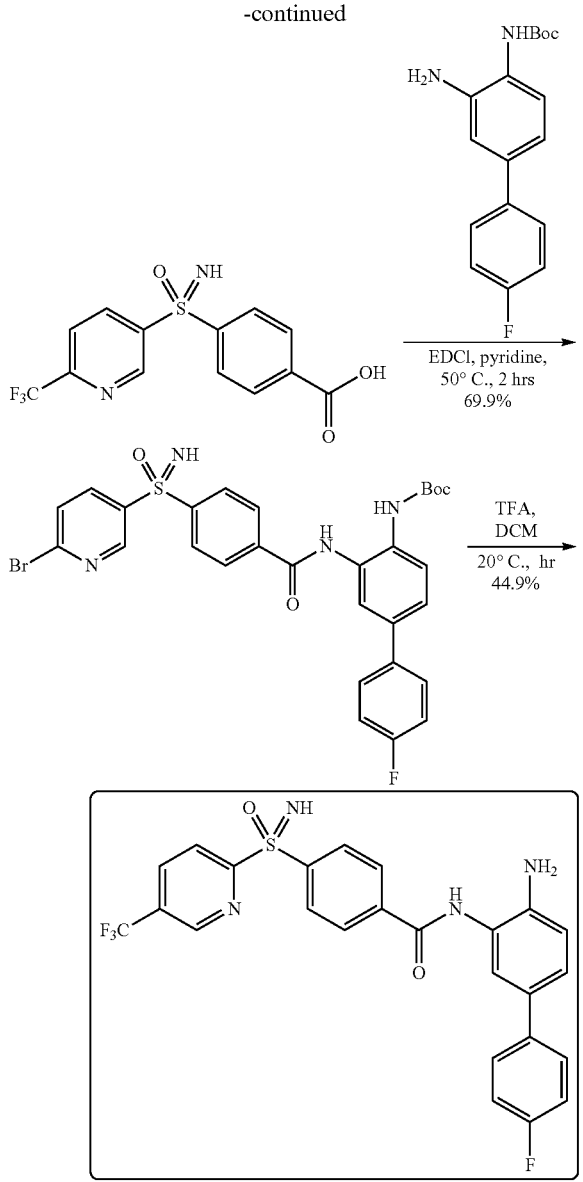

Step 1: Synthesis of methyl 4-[[6-(trifluoromethyl)-3-pyridyl]sulfanyl]benzoate To a solution of methyl 4-sulfanylbenzoate (500 mg, 2.97 mmol) in dioxane (15 mL) were added K₃PO₄ (1.89 g, 8.92 mmol), (5-diphenylphosphanyl-9,9-dimethyl-xanthen-4-yl)-diphenyl-phosphane (90 mg, 0.156 mmol), (1E,4E)-1,5-diphenylpenta-1,4-dien-3-one;palladium (275 mg, 0.300 mmol) and 5-bromo-2-(trifluoromethyl)pyridine (740 mg, 3.27 mmol) into a microwave tube. The sealed tube was heated at 130° C. for 30 minutes under microwave. The reaction mixture was filtered and the filtrate was concentrated under reduced pressure. The residue was purified with another batch by flash chromatography (ISCO®; 12 g SepaFlash® Silica Flash Column, petroleum ether/EtOAc with EtOAc from 0~20%, flow rate: 40 mL/min, 254 nm) to give methyl 4-[[6-(trifluoromethyl)-3-pyridyl]sulfanyl]benzoate (1 g, crude) as orange solid. ¹H NMR (400 MHz, DMSO-d6) δ ppm 8.76 (d, J=2.0 Hz, 1H), 8.04 (dd, J=8.4, 2.0 Hz, 1H), 7.97 (d, J=8.4 Hz, 2H), 7.92 (d, J=8.4 Hz, 1H), 7.52-7.56 (m, 2H), 3.86 (s, 3H); 19F NMR (377 MHz, DMSO-d6) δ ppm −66.38; LCMS (ESI) [M+H]⁺ m/z: calcd 314.0, found 314.1.

Step 2: Synthesis of methyl 4-[[6-(trifluoromethyl)-3-pyridyl]sulfonimidoyl]benzoate To a solution of methyl 4-[[6-(trifluoromethyl)-3-pyridyl]sulfanyl]benzoate (950 mg, 3.03 mmol) in MeOH (10 mL) were added ammonia;carbamic acid (475 mg, 6.08 mmol) and [acetoxy(phenyl)-iodanyl] acetate (2.44 g, 7.58 mmol). The mixture was stirred at 20° C. for 2 hours. The reaction mixture was concentrated under reduced pressure. The residue was purified by flash chromatography (ISCO®; 12 g SepaFlash® Silica Flash Column, petroleum ether/EtOAc with EtOAc from 0~50%, flow rate: 40 mL/min, 254 nm) to give methyl 4-[[6-(trifluoromethyl)-3-pyridyl]sulfonimidoyl]benzoate (900 mg, 86.2% yield) as light-yellow solid. ¹H NMR (400 MHz, DMSO-d6) δ ppm 9.29 (s, 1H), 8.60 (dd, J=8.4, 2.0 Hz, 1H), 8.18-8.21 (m, 2H), 8.10-8.14 (m, 3H), 5.81 (s, 1H), 3.87 (s, 3H); 19F NMR (377 MHz, DMSO-d6) δ ppm −66.80; LCMS (ESI) [M+H]⁺ m/z: calcd 345.0, found 345.1.

Step 3: Synthesis of 4-[[6-(trifluoromethyl)-3-pyridyl]sulfonimidoyl]benzoic acid To a solution of methyl 4-[[6-(trifluoromethyl)-3-pyridyl]sulfonimidoyl]benzoate (850 mg, 2.47 mmol) in MeOH (10 mL) and H₂O (2 mL) was added lithium;hydroxide;hydrate (1.04 g, 24.69 mmol). The mixture was stirred at 20° C. for 1 hour. The mixture was concentrated under reduced pressure to remove the organic solvent. The aqueous phase was adjusted pH=4 with 1N HCl aqueous solution. The mixture was filtered. The filter cake was dried under reduced pressure to give 4-[[6-(trifluoromethyl)-3-pyridyl]sulfonimidoyl]benzoic acid (800 mg, 98.1% yield) as light-yellow solid. ¹H NMR (400 MHz, DMSO-d6) δ ppm 9.29 (d, J=2.0 Hz, 1H), 8.60 (dd, J=8.4, 2.0 Hz, 1H), 8.14-8.20 (m, 2H), 8.08-8.13 (m, 3H), 5.78 (s, 1H); 19F NMR (377 MHz, DMSO-d6) δ ppm −66.79; LCMS (ESI) [M+H]⁺ m/z: calcd 331.0, found 331.1.

Step 4: Synthesis of tert-butyl N-[4-(4-fluorophenyl)-2-[[4-[[6-(trifluoromethyl)-3-pyridyl]sulfonimidoyl]benzoyl]amino]phenyl]carbamate To a solution of 4-[[6-(trifluoromethyl)-3-pyridyl]sulfonimidoyl]benzoic acid (200 mg, 0.606 mmol) in pyridine (2 mL) were added EDCI (175 mg, 0.913 mmol) and tert-butyl N-[2-amino-4-(4-fluorophenyl)phenyl]carbamate (245 mg, 0.729 mmol). The mixture was stirred at 50° C. for 2 hours. The reaction mixture was concentrated under reduced pressure. The residue was purified by flash chromatography (ISCO®; 4 g SepaFlash® Silica Flash Column, petroleum ether/EtOAc with EtOAc from 0~50%, flow rate: 30 mL/min, 254 nm) to give tert-butyl N-[4-(4-fluorophenyl)-2-[[4-[[6-(trifluoromethyl)-3-pyridyl]sulfonimidoyl]benzoyl]amino]phenyl]carbamate (260 mg, 69.9% yield) as light-yellow solid. LCMS (ESI) [M+H]⁺ m/z: calcd 615.2, found 615.3.

Step 5: Synthesis of N-[2-amino-5-(4-fluorophenyl)phenyl]-4-[[6-(trifluoromethyl)-3-pyridyl]sulfonimidoyl]benzamide (Compound 205)

To a solution of tert-butyl N-[4-(4-fluorophenyl)-2-[[4-[[6-(trifluoromethyl)-3-pyridyl]sulfonimidoyl]benzoyl]

amino]phenyl]carbamate (250 mg, 0.407 mmol) in DCM (4 mL) was added TFA (0.6 mL, 8.05 mmol). The mixture was stirred at 20° C. for 1 hour. The reaction mixture was adjusted to pH 8 with saturated NaHCO$_3$ aqueous solution and extracted with DCM (40 mL*3). The combined organic layers were dried over Na$_2$SO$_4$ and filtered. The filtrate was concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 µm; Mobile phase A: H$_2$O with 10 mmol NH$_4$HCO$_3$ (v %); Mobile phase B: ACN; Gradient: B from 40% to 70% in 9.5 min, hold 100% B for 1 min; Flow Rate: 30 mL/min; Column Temperature: 30° C.; Wavelength: 220 nm, 254 nm) to give N-[2-amino-5-(4-fluorophenyl)phenyl]-4-[[6-(trifluoromethyl)-3-pyridyl]sulfonimidoyl]benzamide (93.9 mg, 44.9% yield) as yellow solid. $^1$H NMR (400 MHz, DMSO-d6) δ ppm 9.88 (s, 1H), 9.33 (s, 1H), 8.63 (d, J=8.0 Hz, 1H), 8.10-8.22 (m, 5H), 7.56 (dd, J=8.4, 5.6 Hz, 2H), 7.47 (s, 1H), 7.30 (dd, J=8.4, 2.0 Hz, 1H), 7.20 (t, J=8.8 Hz, 2H), 6.84 (d, J=8.4 Hz, 1H), 5.77 (s, 1H), 5.14 (s, 2H); 19F NMR (377 MHz, DMSO-d6) δ ppm −66.76, −117.48; LCMS [M+H]$^+$ m/z: calcd 515.1; found 515.0; HPLC: 98.47%@220 nm; 98.64%@254 nm.

Example 135. Synthesis of N-[2-amino-5-(4-fluorophenyl)phenyl]-5-(methylsulfonimidoyl)furo[3,2-b]pyridine-2-carboxamide (Compound 189)

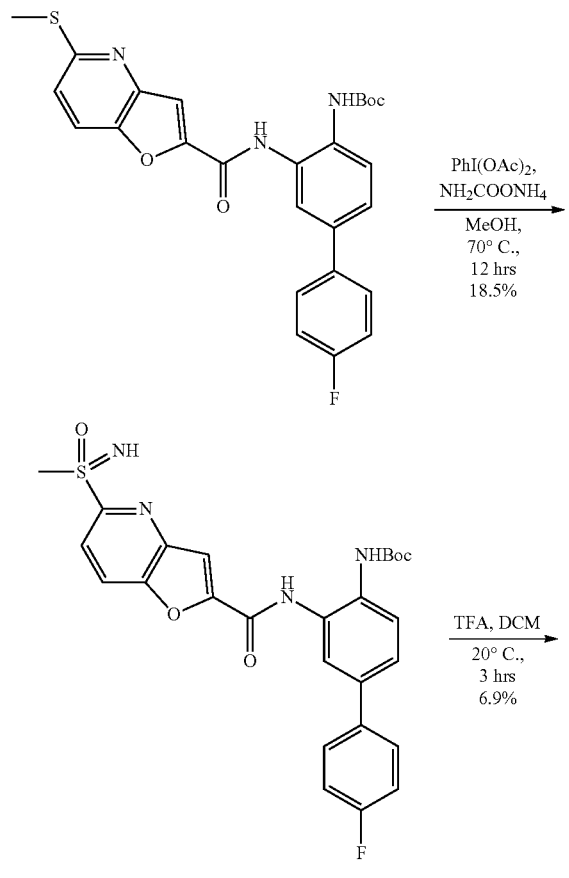

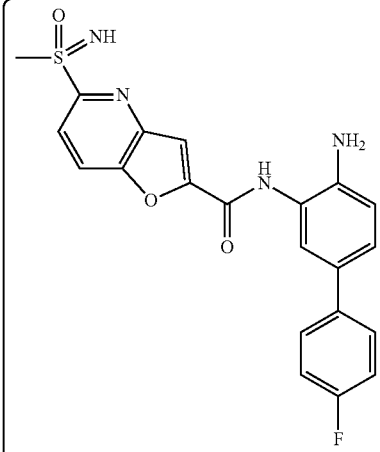

Step 1: Synthesis of tert-butyl N-[4-(4-fluorophenyl)-2-[[5-(methylsulfonimidoyl)furo[3,2-b]pyridine-2-carbonyl]amino]phenyl]carbamate To a solution of tert-butyl N-[4-(4-fluorophenyl)-2-[(5-methylsulfanylfuro[3,2-b]pyridine-2-carbonyl)amino]phenyl]carbamate (255 mg, 0.517 mmol) in MeOH (15 mL) were added [acetoxy(phenyl)-iodanyl] acetate (450 mg, 1.40 mmol) and ammonia;carbamic acid (100 mg, 1.28 mmol). The mixture was stirred at 70° C. for 12 hours. The reaction mixture was concentrated under reduced pressure. The residue was purified by flash chromatography (ISCO®; 20 g SepaFlash® Silica Flash Column, petroleum ether/EtOAc with EtOAc from 0~100%, flow rate: 40 mL/min, 254 nm) to afford tert-butyl N-[4-(4-fluorophenyl)-2-[[5-(methylsulfonimidoyl)furo[3,2-b]pyridine-2-carbonyl]amino]phenyl]carbamate (50 mg, 18.5% yield) as off-white solid. LCMS (ESI) [M+H]$^+$ m/z: calcd 525.2, found 525.1.

Step 2: Synthesis of N-[2-amino-5-(4-fluorophenyl)phenyl]-5-(methylsulfonimidoyl)furo[3,2-b]pyridine-2-carboxamide (Compound 189)

To a solution of tert-butyl N-[4-(4-fluorophenyl)-2-[[5-(methylsulfonimidoyl)furo[3,2-b]pyridine-2-carbonyl]amino]phenyl]carbamate (50 mg, 0.0950 mmol) in DCM (5 mL) was added TFA (0.3 mL, 3.89 mmol). The mixture was stirred at 20° C. for 3 hours. The reaction mixture was adjusted to pH=8 with saturated NaHCO$_3$ aqueous solution and extracted with DCM (25 mL*3). The combined organic layers were dried over Na$_2$SO$_4$ and filtered. The filtrate was concentrated under reduced pressure. The residue was purified by preparative HPLC (Instrument: Gilson GX-281 Liquid Handler, Gilson 322 Pump, Gilson 156 UV Detector; Column: Phenomenex C18 75*40 mm*3 µm; Mobile phase A: water with 10 mmol NH$_4$HCO$_3$ (v %); Mobile phase B: MeCN; Gradient: B from 25% to 55% in 9.5 min, hold 100% B for 1 min; Flow Rate: 30 mL/min; Column Temperature: 30° C.; Wavelength: 220 nm, 254 nm) to afford N-[2-amino-5-(4-fluorophenyl)phenyl]-5-(methylsulfonimidoyl)furo[3,2-b]pyridine-2-carboxamide (2.8 mg, 6.9% yield) as yellow solid. $^1$H NMR (400 MHz, DMSO-d6) δ ppm 10.20 (brs, 1H), 8.50-8.44 (m, 1H), 8.20 (d, J=8.8 Hz, 1H), 8.03 (s, 1H), 7.63-7.57 (m, 2H), 7.50 (d, J=2.0 Hz, 1H), 7.35 (dd, J=2.4, 8.4 Hz, 1H), 7.22 (t, J=8.8 Hz, 2H), 6.88 (d, J=8.4 Hz, 1H), 5.26 (s, 2H), 4.57 (s, 1H), 3.25 (d, J=0.8 Hz, 3H); 19F NMR (377 MHz, DMSO-d6) δ ppm −117.39; HPLC: 94.26%@220 nm; 99.550%@254 nm; LCMS (ESI) [M+H]+ m/z: calcd 425.1, found 425.0.

Example 136. Synthesis of N-[2-amino-5-(p-tolyl)phenyl]-4-(3-methyl-1-oxo-4,5-dihydro-3H-isothiazol-1-yl)benzamide (Compound 244)

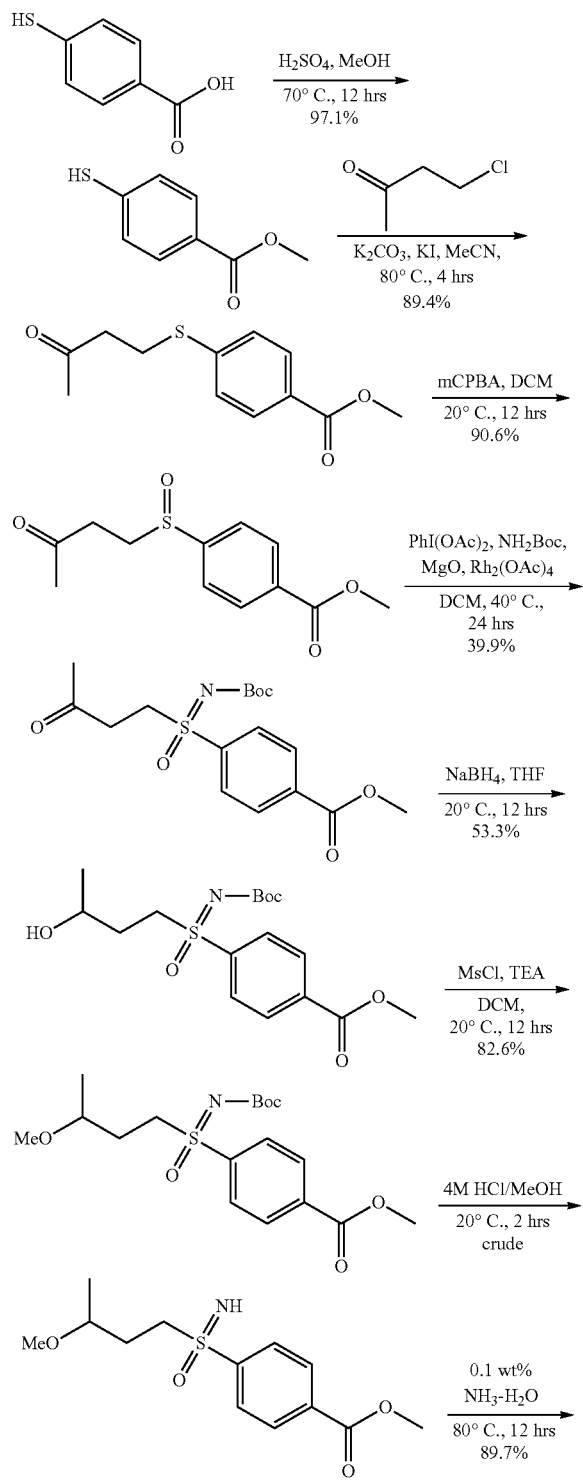

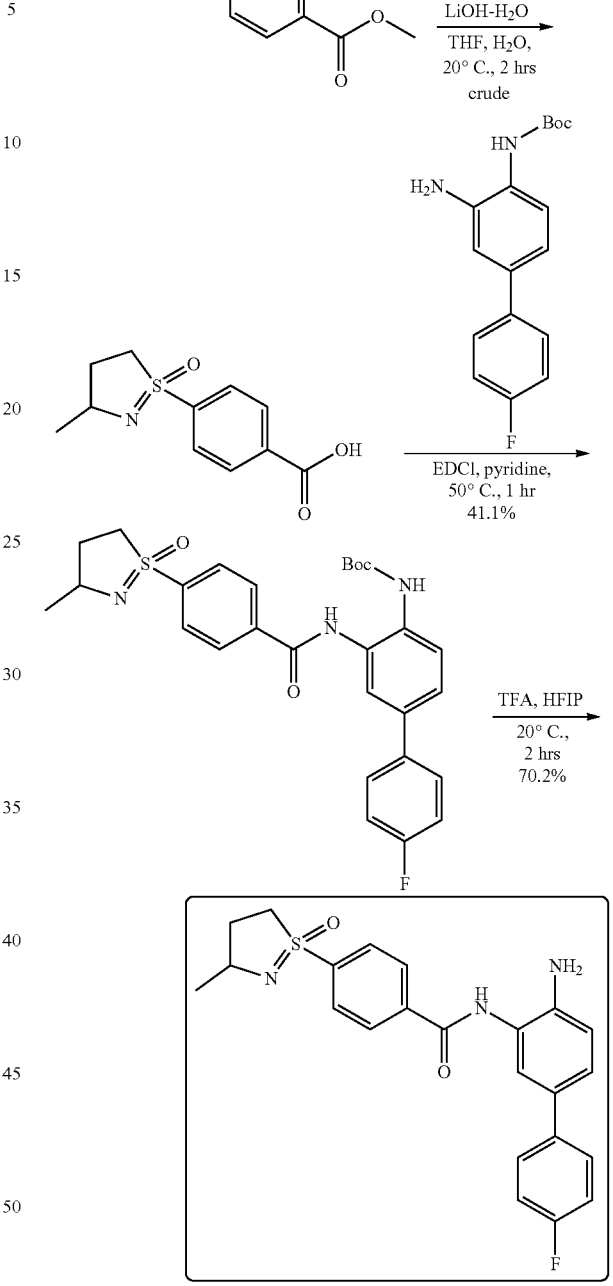

Step 1: Synthesis of methyl 4-sulfanylbenzoate

A mixture of 4-sulfanylbenzoic acid (10.0 g, 64.9 mmol) and sulfuric acid (3.18 g, 32.4 mmol) in MeOH (100 mL) was degassed and purged with nitrogen for 3 times, then the mixture was stirred at 70° C. for 12 hours under nitrogen atmosphere. The mixture was concentrated under reduced pressure and the residue was purified by flash chromatography (ISCO®; 330 g SepaFlash® Silica Flash Column, Petroleum ether/EtOAc with EtOAc from 0~10%, flow rate=30 mL/min, 254 nm) to afford methyl 4-sulfanylbenzoate (10 g, 91.7% yield) as a white solid.

¹H NMR (400 MHz, chloroform-d) δ ppm 7.88 (d, J=8.5 Hz, 2H), 7.28 (d, J=8.5 Hz, 2H), 3.89 (s, 3H), 3.60 (s, 1H); LCMS (ESI) [MeCN+H]⁺ m/z: calcd 210.0, found 210.1.

Step 2: Synthesis of methyl
4-(3-oxobutylsulfanyl)benzoate

A mixture of methyl 4-sulfanylbenzoate (3.00 g, 17.8 mmol), 4-chlorobutan-2-one (3.0 g, 28.2 mmol), KI (1.48 g, 8.92 mmol) and K$_2$CO$_3$ (7.39 g, 53.5 mmol) in MeCN (20 mL) was degassed and purged with nitrogen for 3 times, then the mixture was stirred at 80° C. for 4 hours under nitrogen atmosphere. The mixture was concentrated under reduced pressure and the residue was purified by flash chromatography (ISCO®; 40 g SepaFlash® Silica Flash Column, Petroleum ether/EtOAc with EtOAc from 0~20%, flow rate=30 mL/min, 254 nm) to afford methyl 4-(3-oxobutylsulfanyl)benzoate (3.8 g, 89.4% yield) as a white solid. ¹H NMR (400 MHz, chloroform-d) δ ppm 7.92-7.97 (m, 2H), 7.30 (d, J=8.6 Hz, 2H), 3.91 (s, 3H), 3.21 (t, J=7.3 Hz, 2H), 2.82 (t, J=7.2 Hz, 2H), 2.18 (s, 3H); LCMS (ESI) [M+H]⁺ m/z: calcd 239.1, found 239.1.

Step 3: Synthesis of methyl
4-(3-oxobutylsulfinyl)benzoate

A mixture of methyl 4-(3-oxobutylsulfanyl)benzoate (3 g, 12.6 mmol), and 3-chlorobenzenecarboperoxoic acid (2.56 g, 12.6 mmol, 85% purity) in DCM (40 mL) was degassed and purged with nitrogen for 3 times, then the mixture was stirred at 20° C. for 12 hours under nitrogen atmosphere. The reaction mixture was diluted with Na$_2$S$_2$O$_3$ aqueous (50 mL) and extracted with EtOAc (50 mL*3). The combined organic layers were washed with brine (50 mL), dried over anhydrous Na$_2$SO$_4$, filtered and concentrated under reduced pressure. The residue was purified by flash silica gel chromatography (ISCO®; 40 g SepaFlash® Silica Flash Column, Petroleum ether/EtOAc with EtOAc from 0~60%, flow rate=30 mL/min, 254 nm) to afford methyl 4-(3-oxobutylsulfinyl)benzoate (2.9 g, 90.6% yield) as a white solid. ¹H NMR (400 MHz, chloroform-d) δ ppm 8.18 (d, J=8.3 Hz, 2H), 7.68 (d, J=8.3 Hz, 2H), 3.95 (s, 3H), 3.23-3.32 (m, 1H), 3.01 (dt, J=18.5, 7.2 Hz, 1H), 2.85-2.93 (m, 1H), 2.66 (ddd, J=18.4, 7.9, 5.3 Hz, 1H), 2.16 (s, 3H); LCMS (ESI) [M+H]⁺ m/z: calcd 255.1, found 254.9.

Step 4: Synthesis of methyl 4-[N-tert-butoxycarbonyl-S-(3-oxobutyl)sulfonimidoyl]benzoate A mixture of methyl 4-(3-oxobutylsulfinyl)benzoate (2.9 g, 11.4 mmol), PhI(OAc)$_2$ (8.26 g, 25.7 mmol), MgO (3.45 g, 85.5 mmol), Rh$_2$(OAc)$_4$ (504 mg, 1.14 mmol) and NH$_2$Boc (4.01 g, 34.2 mmol) in DCM (10 mL) was degassed and purged with nitrogen for 3 times, and then the mixture was stirred at 40° C. for 24 hours under nitrogen atmosphere. The reaction mixture was concentrated under reduced pressure. The residue was purified by flash silica gel chromatography (ISCO®; 40 g SepaFlash® Silica Flash Column, Petroleum ether/EtOAc with EtOAc from 0~20%, flow rate=30 mL/min, 254 nm) to afford methyl 4-[N-tert-butoxycarbonyl-S-(3-oxobutyl)sulfonimidoyl]benzoate (1.68 g, 39.9% yield) as a white solid. ¹H NMR (400 MHz, chloroform-d) δ ppm 8.26 (br d, J=8.3 Hz, 2H), 8.01 (br d, J=8.1 Hz, 2H), 3.98 (s, 3H), 3.59-3.68 (m, 1H), 3.48 (dd, J=14.3, 9.1, 5.6 Hz, 1H), 3.05-3.16 (m, 1H), 2.94-3.04 (m, 1H), 2.18 (s, 3H), 1.35 (s, 9H); LCMS (ESI) [M+H]⁺ m/z: calcd 370.1, found 370.2.

Step 5: Synthesis of methyl 4-[N-tert-butoxycarbonyl-S-(3-hydroxybutyl)sulfonimidoyl]benzoate A mixture of methyl 4-[N-tert-butoxycarbonyl-S-(3-oxobutyl)sulfonimidoyl]benzoate (1.68 g, 4.55 mmol) and sodium;boranuide (345 mg, 9.12 mmol) in THF (20 mL) was degassed and purged with nitrogen for 3 times, and then the mixture was stirred at 20° C. for 2 hours under nitrogen atmosphere. The reaction mixture was quenched with saturated ammonium chloride solution (20 mL) and extracted with EtOAc (50 mL*3). The organic layer was separated, dried over anhydrous Na$_2$SO$_4$, filtered and concentrated under reduced pressure. The residue was purified by flash chromatography (ISCO®; 20 g SepaFlash® Silica Flash Column, Petroleum ether/EtOAc with EtOAc from 0~70%, flow rate=80 mL/min, 254 nm) to afford methyl 4-[N-tert-butoxycarbonyl-S-(3-hydroxybutyl)sulfonimidoyl]benzoate (900 mg, 53.3% yield) as a white solid. ¹H NMR (400 MHz, chloroform-d) δ ppm 8.26 (br d, J=8.3 Hz, 2H), 7.99-8.10 (m, 2H), 3.99 (br s, 3H), 3.92 (br s, 1H), 3.38-3.61 (m, 2H), 2.05 (br s, 1H), 1.91 (br s, 1H), 1.66-1.76 (m, 1H), 1.36 (br s, 9H), 1.19-1.26 (m, 3H); LCMS (ESI) [M+H]⁺ m/z: calcd 372.1, found 372.2.

Step 6: Synthesis of methyl 4-[N-tert-butoxycarbonyl-S-(3-methylsulfonyloxybutyl)sulfonimidoyl]benzoate A mixture of methyl 4-[N-tert-butoxycarbonyl-S-(3-hydroxybutyl)sulfonimidoyl]benzoate (400 mg, 1.08 mmol), methanesulfonyl chloride (161 mg, 1.41 mmol) and TEA (0.5 mL, 3.59 mmol) in DCM (10 mL) was degassed and purged with nitrogen for 3 times, then the mixture was stirred at 20° C. for 12 hours under nitrogen atmosphere. The mixture was diluted with NaHCO$_3$ saturated solution (50 mL) and extracted with EtOAc (50 mL*3). The combined organic layers were washed with brine (50 mL), dried over anhydrous Na$_2$SO$_4$, filtered and concentrated under reduced pressure. The residue was purified by flash chromatography (ISCO®; 20 g SepaFlash® Silica Flash Column, Petroleum ether/EtOAc with EtOAc from 0~20%, flow rate=30 mL/min, 254 nm) to afford methyl 4-[N-tert-butoxycarbonyl-S-(3-methylsulfonyloxybutyl)sulfonimidoyl]benzoate (400 mg, 82.6% yield) as colorless oil. ¹H NMR (400 MHz, chloroform-d) δ ppm 8.27 (d, J=8.3 Hz, 2H), 8.24-8.24 (m, 1H), 8.02 (d, J=8.5 Hz, 2H), 4.82-4.91 (m, 1H), 3.99 (s, 3H), 3.47-3.60 (m, 1H), 3.28-3.42 (m, 1H), 3.00 (d, J=6.0 Hz, 3H), 2.07-2.30 (m, 2H), 1.44 (d, J=6.3 Hz, 3H), 1.35 (s, 9H); LCMS (ESI) [M+H]⁺ m/z: calcd 450.1, found 450.2.

Step 7: Synthesis of methyl
4-(3-methylsulfonyloxybutylsulfonimidoyl)benzoate

A mixture of methyl 4-[N-tert-butoxycarbonyl-S-(3-methylsulfonyloxybutyl)sulfonimidoyl]benzoate (300 mg, 0.667 mmol) and 4M HCl/MeOH (5 mL, 20.0 mmol) was degassed and purged with nitrogen for 3 times, then the mixture was stirred at 20° C. for 2 hours under nitrogen atmosphere. The mixture was concentrated under reduced pressure to give methyl 4-(3-methylsulfonyloxybutylsulfonimidoyl)benzoate (200 mg, crude), which was directly used to next step without further purification. LCMS (ESI) [M+H]⁺ m/z: calcd 350.1, found 350.1.

Step 8: Synthesis of methyl 4-(3-methyl-1-oxo-4,5-dihydro-3H-isothiazol-1-yl)benzoate A mixture of methyl 4-(3-methylsulfonyloxybutylsulfonimidoyl)benzoate (200 mg, 0.572 mmol) and 0.1 wt %

NH$_3$—H$_2$O (10 mL) was degassed and purged with nitrogen for 3 times, then the mixture was stirred at 80° C. for 12 hours under nitrogen atmosphere. The mixture was extracted with DCM/iPrOH (3:1, 50 mL*3). The combined organic layers were washed with brine (50 mL), dried over anhydrous Na$_2$SO$_4$, filtered and concentrated under reduced pressure. The residue was purified by flash chromatography (ISCO®; 20 g SepaFlash® Silica Flash Column, Petroleum ether/EtOAc with EtOAc from 0~100%, flow rate=30 mL/min, 254 nm) to afford methyl 4-(3-methyl-1-oxo-4,5-dihydro-3H-isothiazol-1-yl)benzoate (130 mg, 89.7% yield) as a white solid. $^1$H NMR (400 MHz, chloroform-d) δ ppm 8.17-8.23 (m, 2H), 8.01-8.08 (m, 2H), 4.14-4.46 (m, 1H), 3.94-3.99 (m, 3H), 3.58 (ddd, J=12.8, 7.6, 2.9 Hz, 1H), 3.41-3.48 (m, 1H), 3.18-3.29 (m, 1H), 2.43-2.67 (m, 1H), 2.01-2.10 (m, 1H), 1.76 (ddd, J=12.8, 6.7, 2.2 Hz, 1H), 1.43-1.56 (m, 3H); LCMS (ESI) [M+H]$^+$ m/z: calcd 254.1, found 254.1.

Step 9: Synthesis of 4-(3-methyl-1-oxo-4,5-dihydro-3H-isothiazol-1-yl)benzoic acid A mixture of methyl 4-(3-methyl-1-oxo-4,5-dihydro-3H-isothiazol-1-yl)benzoate (110 mg, 0.434 mmol) and LiOH—H$_2$O (88.0 mg, 2.10 mmol) in H$_2$O (3 mL)/THF (3 mL) was degassed and purged with nitrogen for 3 times, then the mixture was stirred at 20° C. for 2 hours under nitrogen atmosphere. The mixture was adjusted to PH-4 with 0.5 N HCl aqueous. The mixture was concentrated under reduced pressure, which was directly used to next step without further purification. LCMS (ESI) [M+H]$^+$ m/z: calcd 240.1, found 240.1.

Step 10: Synthesis of tert-butyl N-[4-(4-fluorophenyl)-2-[[4-(3-methyl-1-oxo-4,5-dihydro-3H-isothiazol-1-yl)benzoyl]amino]phenyl]carbamate A mixture of 4-(3-methyl-1-oxo-4,5-dihydro-3H-isothiazol-1-yl)benzoic acid (100 mg, 0.418 mmol), tert-butyl N-[2-amino-4-(4-fluorophenyl)phenyl]carbamate (126 mg, 0.417 mmol) and EDCI (120 mg, 0.626 mmol) in pyridine (6 mL) was degassed and purged with nitrogen for 3 times, then the mixture was stirred at 50° C. for 1 hour under nitrogen atmosphere. The mixture was concentrated under reduced pressure and the residue was purified by flash chromatography (ISCO®; 12 g SepaFlash® Silica Flash Column, Petroleum ether/EtOAc with EtOAc from 0~100%, flow rate=30 mL/min, 254 nm) to afford tert-butyl N-[4-(4-fluorophenyl)-2-[[4-(3-methyl-1-oxo-4,5-dihydro-3H-isothiazol-1-yl)benzoyl]amino]phenyl]carbamate (90 mg, 41.1% yield) as a white solid. $^1$H NMR (400 MHz, chloroform-d) δ ppm 9.81 (br s, 1H), 8.11-8.18 (m, 2H), 8.05-8.10 (m, 2H), 8.03 (br d, J=8.3 Hz, 1H), 7.52-7.60 (m, 2H), 7.36 (dd, J=8.3, 2.0 Hz, 1H), 7.29 (br d, J=4.0 Hz, 1H), 7.12 (t, J=8.5 Hz, 2H), 6.96 (br d, J=10.5 Hz, 1H), 4.17-4.44 (m, 1H), 3.20-3.67 (m, 2H), 2.39-2.68 (m, 1H), 1.64 (br s, 3H), 1.54 (s, 9H), 1.45 (d, J=6.3 Hz, 1H); LCMS (ESI) [M+H]$^+$ m/z: calcd 524.2, found 524.3.

Step 11: Synthesis of N-[2-amino-5-(p-tolyl)phenyl]-4-(3-methyl-1-oxo-4,5-dihydro-3H-isothiazol-1-yl)benzamide (Compound 244)

A mixture of tert-butyl N-[4-(4-fluorophenyl)-2-[[4-(3-methyl-1-oxo-4,5-dihydro-3H-isothiazol-1-yl)benzoyl]amino]phenyl]carbamate (80 mg, 0.153 mmol), TFA (0.2 mL, 2.60 mmol) and HFIP (5 mL) was degassed and purged with nitrogen for 3 times, then the mixture was stirred at 20° C. for 2 hours. The reaction mixture was neutralized to pH ~8 using saturated NaHCO$_3$ aqueous solution. The crude product was purified by preparative HPLC (Instrument: Gilson GX-281 Liquid Handler, Gilson 322 Pump, Gilson 156 UV Detector; Column: Phenomenex Gemini-NX 75*40 mm*3 μm; Mobile phase A: [water (NH$_3$H$_2$O+NH$_4$HCO$_3$)-ACN]; Mobile phase B: MeCN; Gradient: B from 31% to 61% in 10.5 min, hold 100% B for 2 min; Flow Rate: 30 mL/min; Column Temperature: 30° C.; Wavelength: 220 nm) to afford N-[2-amino-5-(p-tolyl)phenyl]-4-(3-methyl-1-oxo-4,5-dihydro-3H-isothiazol-1-yl)benzamide (45 mg, 70.2% yield) as white solid.

Compound 244: $^1$H NMR (400 MHz, DMSO-d6) δ ppm 9.95 (s, 1H), 8.20 (t, J=7.6 Hz, 2H), 7.99 (dd, J=10.6, 8.4 Hz, 2H), 7.58 (dd, J=8.6, 5.6 Hz, 2H), 7.51 (dd, J=4.8, 1.9 Hz, 1H), 7.32 (dd, J=8.4, 2.1 Hz, 1H), 7.22 (t, J=8.8 Hz, 2H), 6.87 (d, J=8.3 Hz, 1H), 5.18 (br s, 2H), 4.01-4.19 (m, 1H), 3.54-3.69 (m, 1H), 3.40-3.49 (m, 1H), 2.40-2.47 (m, 1H), 1.69-1.88 (m, 1H), 1.29-1.37 (m, 3H); 19F NMR (377 MHz, DMSO-d6) δ ppm −117.46; LCMS (ESI) [M+H]$^+$ m/z: calcd 424.3, found 424.1; HPLC: 94.29%@220 nm, 100.00%@254 nm.

Example 137. Synthesis of N-[2-amino-5-(4-fluorophenyl)phenyl]-5-(N-cyclopropyl-S-methyl-sulfonimidoyl)benzothiophene-2-carboxamide (Compound 211)

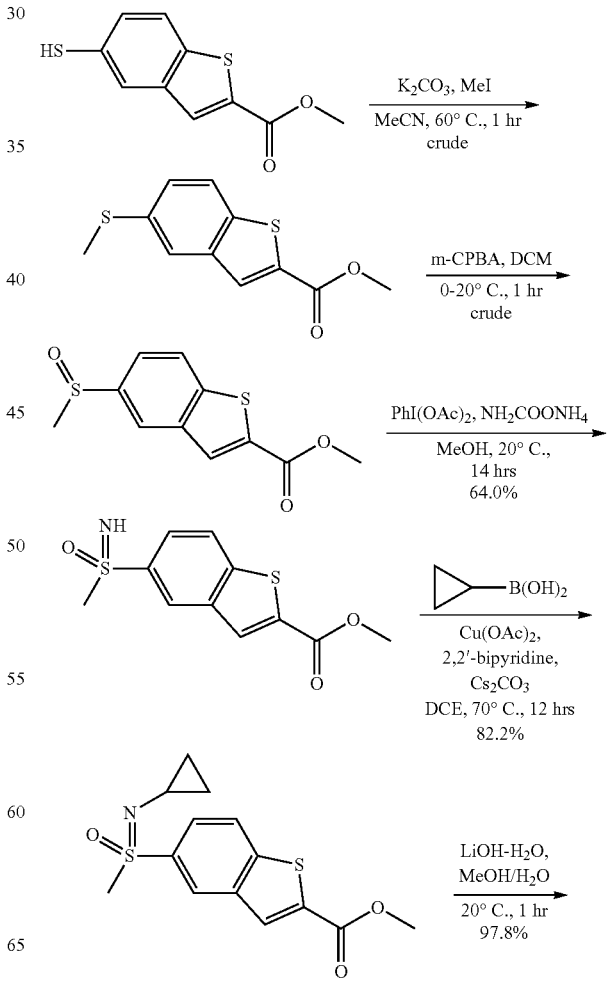

-continued

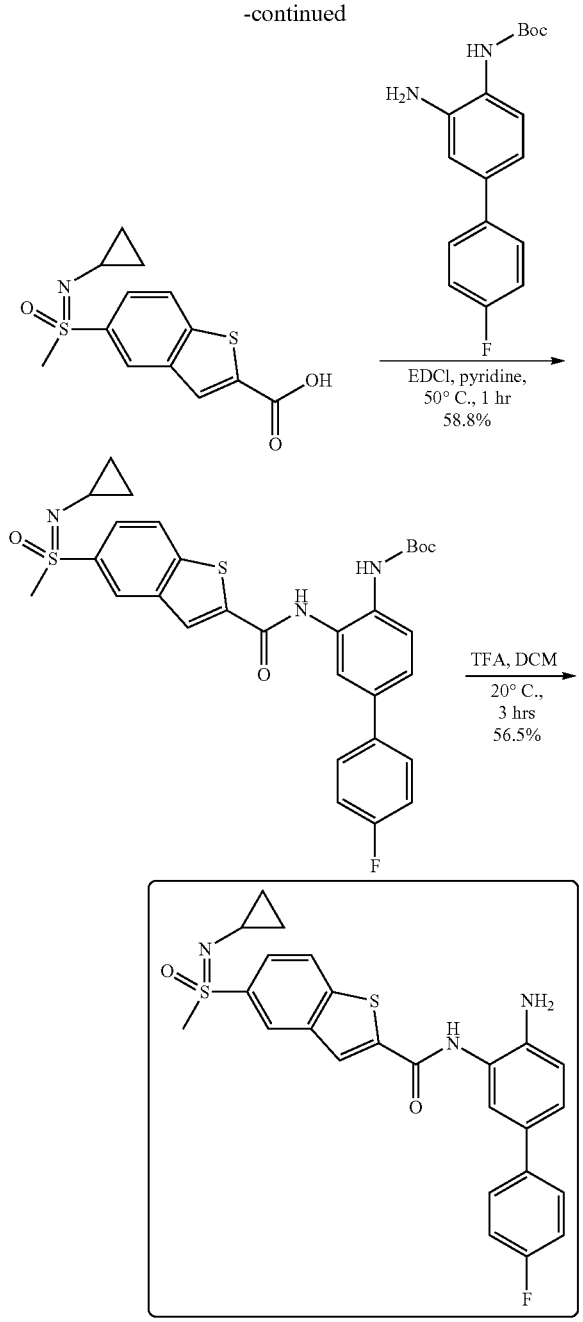

Step 1: Synthesis of methyl 5-methylsulfanylbenzothiophene-2-carboxylate

A mixture of methyl 5-sulfanylbenzothiophene-2-carboxylate (230 mg, 1.03 mmol), iodomethane (0.14 mL, 2.25 mmol), tripotassium;carbonate (430 mg, 3.11 mmol) in MeCN (6 mL) was stirred at 60° C. for 1 hour. The resulting mixture was quenched by addition of water (20 mL) and extracted with EtOAc (20 mL*3). The combined organic layer was dried over anhydrous $Na_2SO_4$, filtered and concentrated under reduced pressure. The residue was purified by flash chromatography (ISCO®; 12 g AgelaFlash® Silica Flash Column, petroleum ether/EtOAc with EtOAc from 0~6%, flow rate=40 mL/min, 254 nm) to afford methyl 5-methylsulfanylbenzothiophene-2-carboxylate (260 mg, crude) as yellow solid. LCMS (ESI) [M+H]+ m/z: calcd 239.0, found 239.1.

Step 2: Synthesis of methyl 5-methylsulfinylbenzothiophene-2-carboxylate

To a solution of methyl 5-methylsulfanylbenzothiophene-2-carboxylate (260 mg, 1.09 mmol) in DCM (6 mL) was added 3-chlorobenzenecarboperoxoic acid (250 mg, 1.23 mmol, 85 wt %) at 0° C. The mixture was stirred at 20° C. for 1 hour. The resulting mixture was quenched by addition of saturated $Na_2SO_3$ aqueous solution (10 mL) and adjusted the pH to 8 with saturated $NaHCO_3$ aqueous solution (5 mL). The mixture was extracted with DCM (20 mL*3). The combined organic layer was dried over anhydrous $Na_2SO_4$, filtered and concentrated under reduced pressure to afford methyl 5-methylsulfinylbenzothiophene-2-carboxylate (310 mg, crude) as yellow oil. LCMS (ESI) [M+H]+ m/z: calcd 255.0, found 255.1.

Step 3: Synthesis of methyl 5-(methylsulfonimidoyl)benzothiophene-2-carboxylate A mixture of methyl 5-methylsulfinylbenzothiophene-2-carboxylate (310 mg, 1.22 mmol), [acetoxy(phenyl)-iodanyl] acetate (1 g, 3.10 mmol), ammonia;carbamic acid (200 mg, 2.56 mmol) and MeOH (6 mL) was stirred at 20° C. for 14 hours. The resulting mixture was concentrated under reduced pressure. The residue was purified by flash chromatography (ISCO®; 12 g AgelaFlash® Silica Flash Column, petroleum ether/EtOAc with EtOAc from 0~76%, flow rate=40 mL/min, 254 nm) to afford methyl 5-(methylsulfonimidoyl)benzothiophene-2-carboxylate (210 mg, 64.0% yield) as white solid. 1H NMR (400 MHz, DMSO-d6) δ ppm 8.63 (s, 1H), 8.42 (s, 1H), 8.31 (d, J=8.8 Hz, 1H), 8.03 (d, J=7.0 Hz, 1H), 4.32 (s, 1H), 3.92 (s, 3H), 3.12 (s, 3H); LCMS (ESI) [M+H]+ m/z: calcd 270.0, found 270.1.

Step 4: Synthesis of methyl 5-(N-cyclopropyl-S-methyl-sulfonimidoyl)benzothiophene-2-carboxylate A mixture of methyl 5-(methylsulfonimidoyl)benzothiophene-2-carboxylate (180 mg, 0.668 mmol), cyclopropylboronic acid (90 mg, 1.05 mmol), 2-(2-pyridyl)pyridine (110 mg, 0.704 mmol), dicesium;carbonate (440 mg, 1.35 mmol), copper;diacetate (140 mg, 0.771 mmol) and DCE (5 mL) was stirred at 70° C. for 12 hours. The mixture was filtered. The filtrate was concentrated under reduced pressure. The residue was purified by flash chromatography (ISCO®; 4 g AgelaFlash® Silica Flash Column, petroleum ether/EtOAc with EtOAc from 0~64%, flow rate=30 mL/min, 254 nm) to afford methyl 5-(N-cyclopropyl-S-methyl-sulfonimidoyl)benzothiophene-2-carboxylate (170 mg, 82.2% yield) as yellow oil. LCMS (ESI) [M+H]+ m/z: calcd 310.0, found 310.0.

Step 5: Synthesis of 5-(N-cyclopropyl-S-methyl-sulfonimidoyl)benzothiophene-2-carboxylic acid To a solution of methyl 5-(N-cyclopropyl-S-methyl-sulfonimidoyl)benzothiophene-2-carboxylate (150 mg, 0.485 mmol) in MeOH (6 mL) and $H_2O$ (2 mL) was added lithium;hydroxide;hydrate (210 mg, 5.00 mmol). The mixture was stirred at 20° C. for 1 hour. The mixture was concentrated under reduced pressure and adjusted the pH to 5 with 2N HCl aqueous solution (6 mL). The resulting mixture was extracted with DCM (20 mL*2). The water phase was concentrated under reduced pressure to give 5-(N-cyclopropyl-S-methyl-sulfonimidoyl)benzothiophene-2-carboxylic acid (140 mg, 97.8% yield) as white solid. LCMS (ESI) [M+H]+ m/z: calcd 296.0, found 296.1.

Step 6: Synthesis of tert-butyl N-[2-[[5-(N-cyclopropyl-S-methyl-sulfonimidoyl)benzothiophene-2-carbonyl]amino]-4-(4-fluorophenyl)phenyl]carbamate A mixture of 5-(N-cyclopropyl-S-methyl-sulfonimidoyl)benzothiophene-2-carboxylic acid (130 mg, 0.440 mmol), tert-butyl N-[2-amino-4-(4-fluorophenyl)phenyl]carbamate (210 mg, 0.695 mmol), 3-(ethyliminomethyleneamino)-N,N-dimethyl-propan-1-amine;hydrochloride (130 mg, 0.678 mmol) and pyridine (5 mL) was stirred at 50° C. for 1 hour. The resulting mixture was concentrated under reduced pressure. The residue was purified by flash chromatography (ISCO®; 12 g AgelaFlash® Silica Flash Column, petroleum ether/EtOAc with EtOAc from 0~82%, flow rate=40 mL/min, 254 nm) to afford tert-butyl N-[2-[[5-(N-cyclopropyl-S-methyl-sulfonimidoyl)benzothiophene-2-carbonyl]amino]-4-(4-fluorophenyl)phenyl]carbamate (150 mg, 58.8% yield) as black oil. LCMS (ESI) [M+H]+ m/z: calcd 580.2, found 580.3.

Step 7: Synthesis of N-[2-amino-5-(4-fluorophenyl)phenyl]-5-(N-cyclopropyl-S-methyl-sulfonimidoyl)benzothiophene-2-carboxamide To a solution of tert-butyl N-[2-[[5-(N-cyclopropyl-S-methyl-sulfonimidoyl)benzothiophene-2-carbonyl]amino]-4-(4-fluorophenyl)phenyl]carbamate (120 mg, 0.207 mmol) in DCM (4 mL) was added TFA (0.4 mL, 5.19 mmol). The mixture was stirred at 20° C. for 3 hours. The resulting mixture was concentrated under reduced pressure. The mixture was adjusted the pH to 8 with saturated NaHCO3 aqueous solution (10 mL). The resulting mixture was extracted with water (20 mL) and DCM (20 mL*2). The combined organic layer was dried over anhydrous Na2SO4, filtered and concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 μm; Mobile phase A: H2O with 10 mmol NH4HCO3 (v %); Mobile phase B: MeCN; Gradient: B from 42% to 72% in 9.5 min, hold 100% B for 1 min; Flow Rate: 30 mL/min; Column Temperature: 30° C.; Wavelength: 220 nm, 254 nm) to afford N-[2-amino-5-(4-fluorophenyl)phenyl]-5-(N-cyclopropyl-S-methyl-sulfonimidoyl)benzothiophene-2-carboxamide (56.1 mg, 56.5% yield) as a yellow solid. 1H NMR (400 MHz, DMSO-d6) δ ppm 10.15 (s, 1H), 8.48-8.53 (m, 2H), 8.32 (d, J=8.5 Hz, 1H), 7.92 (dd, J=8.6, 1.8 Hz, 1H), 7.57-7.63 (m, 2H), 7.51 (d, J=2.1 Hz, 1H), 7.34 (dd, J=8.4, 2.1 Hz, 1H), 7.19-7.25 (m, 2H), 6.88 (d, J=8.4 Hz, 1H), 5.23 (s, 2H), 3.21 (s, 3H), 2.25-2.31 (m, 1H), 0.36-0.44 (m, 2H), 0.18-0.32 (m, 2H); 19F NMR (376 MHz, DMSO-d6) δ ppm−117.426; LCMS (ESI) [M+H]+ m/z: calcd 480.1, found 480.2; HPLC: 95.64%@220 nm, 99.730%@254 nm.

Example 138. Synthesis of N-(4-amino-4'-fluoro-[1,1'-biphenyl]-3-yl)-4-(5-cyanopyridine-3-sulfonimidoyl)benzamide (Compound 232)

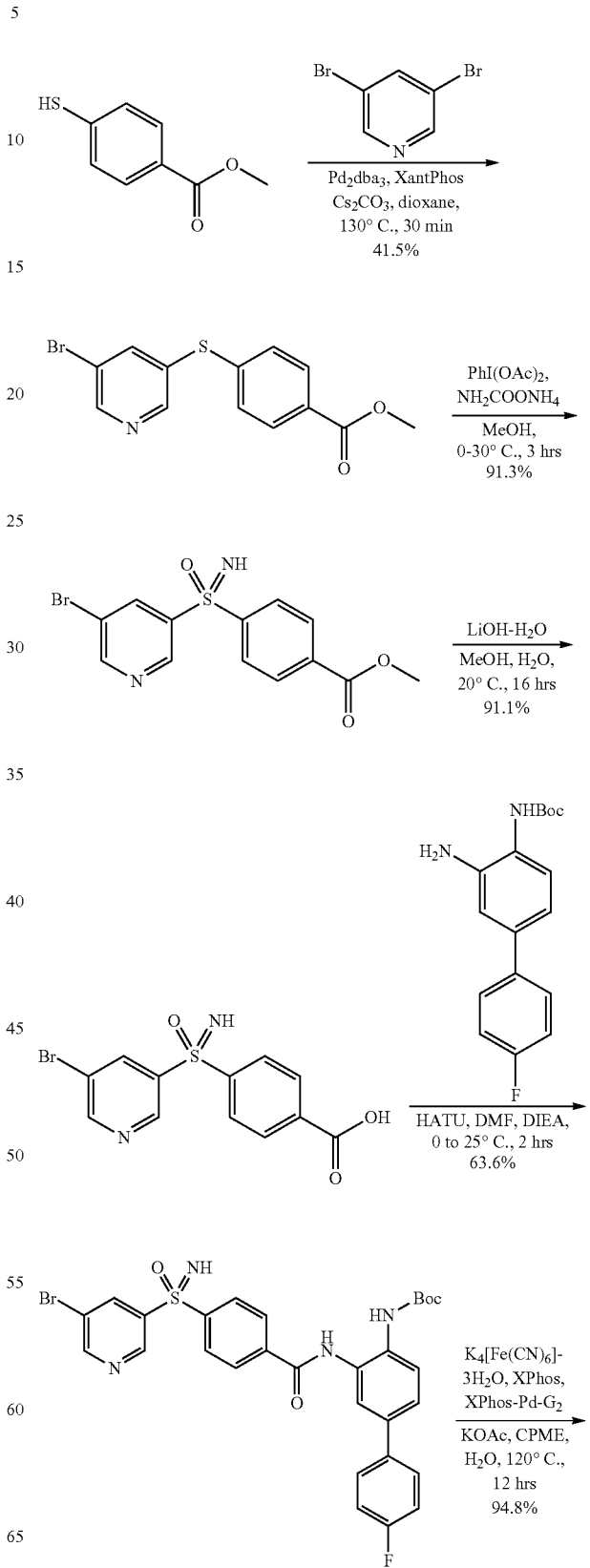

-continued

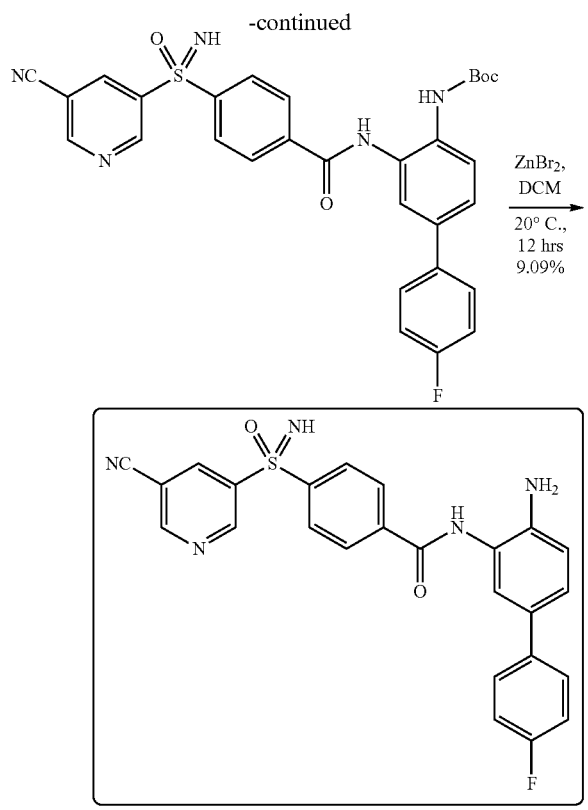

Step 1: Synthesis of methyl 4-((5-bromopyridin-3-yl)thio)benzoate

A mixture of 3,5-dibromopyridine (169 mg, 0.713 mmol), methyl 4-sulfanylbenzoate (100 mg, 0.595 mmol), Pd$_2$dba$_3$ (109 mg, 0.119 mmol), XantPhos (138 mg, 0.238 mmol) and Cs$_2$CO$_3$ (581 mg, 1.78 mmol) in dioxane (10 mL) was purged with N$_2$ gas at ambient temperature for 3 minutes. Then mixture was stirred at 130° C. for 30 min in Microwave. The resulting mixture was quenched by addition of water (10 mL) and extracted with EtOAc (20 mL*3). The combined organic layer was washed with brine (20 mL), dried over anhydrous Na$_2$SO$_4$, filtered and concentrated under reduced pressure and purified by flash chromatography (ISCO®; 4 g SepaFlash® Silica Flash Column, petroleum ether/EtOAc with EtOAc from 0~20%, 25 mL/min, 254 nm) to afford methyl 4-[(5-bromo-3-pyridyl)sulfanyl] benzoate (80 mg, 41.5% yield) as yellow solid. $^1$H NMR (400 MHz, DMSO-d6) δ ppm 8.76 (d, J=2.0 Hz, 1H) 8.63 (d, J=2.0 Hz, 1H) 8.22 (t, J=2.0 Hz, 1H) 7.89-8.00 (m, 2H) 7.39-7.46 (m, 2H) 3.85 (s, 3H) 3.34 (s, 1H)

Step 2: methyl 4-(5-bromopyridine-3-sulfonimidoyl)benzoate

To a solution of methyl 4-[(5-bromo-3-pyridyl)sulfanyl] benzoate (80 mg, 0.247 mmol) in MeOH (5 mL) was added NH$_2$COONH$_4$ (28.9 mg, 0.370 mmol) and PhI(OAc)$_2$ (238 mg, 0.740 mmol) at 0° C. slowly. The mixture was stirred at 30° C. for 3 hours. The reaction mixture was diluted with H$_2$O (50 mL) and extracted with EtOAc (30 mL*3). The combined organic layers were dried over anhydrous Na$_2$SO$_4$, filtered and concentrated under reduced pressure. The residue was purified by flash chromatography (ISCO®; 40 g SepaFlash® Silica Flash Column, petroleum ether/ EtOAc with EtOAc from 0~50%, flow rate=25 mL/min, 254 nm) to give product methyl 4-[(5-bromo-3-pyridyl)sulfonimidoyl]benzoate (80 mg, 91.3% yield) as a light yellow solid. $^1$H NMR (400 MHz, DMSO-d6) δ ppm 9.08 (d, J=2.0 Hz, 1H) 8.96 (d, J=2.3 Hz, 1H) 8.55 (t, J=2.0 Hz, 1H) 8.18-8.25 (m, 2H) 8.08-8.16 (m, 2H) 3.88 (s, 3H); LCMS (ESI) [M+H]$^+$ m/z: calcd 356.2, found 356.2.

Step 3: Synthesis of 4-(5-bromopyridine-3-sulfonimidoyl)benzoic acid

To a solution of methyl 4-[(5-bromo-3-pyridyl)sulfonimidoyl]benzoate (80 mg, 0.225 mmol) in MeOH (3 mL) and H$_2$O (1 mL) was added LiOH—H$_2$O (18.9 mg, 0.789 mmol). The mixture was stirred at 20° C. for 16 hours. The reaction mixture was concentrated in vacuum to remove MeOH, the aqueous layer was acidified with 2M HCl solution pH ~4, extracted with EtOAc (30 mL×3), concentrated in vacuum to give 4-[(5-bromo-3-pyridyl)sulfonimidoyl]benzoic acid (70 mg, 91.1% yield) as a white solid. LCMS (ESI) [M+H]$^+$ m/z: calcd 342.1, found 342.1.

Step 4: Synthesis of tert-butyl (3-(4-(5-bromopyridine-3-sulfonimidoyl)benzamido)-4'-fluoro-[,1'-biphenyl]-4-yl)carbamate To a solution of 4-[(5-bromo-3-pyridyl)sulfonimidoyl] benzoic acid (60 mg, 0.176 mmol), DIEA (68.1 mg, 0.527 mmol) in DMF (5 mL) was added HATU (100 mg, 0.264 mmol) at 0° C. Then tert-butyl N-[2-amino-4-(4-fluorophenyl)phenyl]carbamate (58.5 mg, 0.193 mmol) was added. The mixture was stirred at 25° C. for 2 hours. The reaction was poured into water (15 mL), the aqueous layer was extracted with EtOAc (15 mL*3). The organic layer was washed water (10 mL*3), dried over anhydrous Na$_2$SO$_4$, filtered and concentrated. The crude was purified by flash chromatography (Biotage®; 20 g SepaFlash® Silica Flash Column, petroleum ether/EtOAc with EtOAc from 0~100%, 20 mL/min, 254 nm) to afford tert-butyl N-[2-[[4-[(5-bromo-3-pyridyl) sulfonimidoyl] benzoyl] amino]-4-(4-fluorophenyl) phenyl] carbamate (70 mg, 63.6% yield) as a yellow solid. LCMS (ESI) [M+H]$^+$ m/z: calcd 627.2, found 627.2.

Step 5: Synthesis of tert-butyl (3-(4-(5-cyanopyridine-3-sulfonimidoyl)benzamido)-4'-fluoro-[1,1'-biphenyl]-4-yl)carbamate To a solution of tert-butyl N-[2-[[4-[(5-bromo-3-pyridyl) sulfonimidoyl]benzoyl]amino]-4-(4-fluorophenyl)phenyl] carbamate (60 mg, 96.0 μmol) in H$_2$O (4 mL) and CPME (4 mL) were added Xphos (23 mg, 48.0 μmol), Pd-Xphos-G2 (30.2 mg, 38.4 μmol), KOAc (58.0 mg, 591 μmol) and K$_4$[Fe(CN)$_6$] (116 mg, 315 μmol). The mixture was stirred at 120° C. for 12 hours. TLC showed start material was consumed and desired MS peak was observed. The reaction mixture was dilute with water (5 mL) and extracted with EtOAc (5 mL*3). The combined organic layers were washed with brine (10 mL), dried over Na$_2$SO$_4$ and filtered. The filtrate was concentrated under reduced pressure. The residue was purified by flash chromatography (ISCO®; 4 g SepaFlash®Silica Flash Column, petroleum ether/EtOAc with EtOAc from 0~60%, flow rate: 40 mL/min, 254 nm) to give tert-butyl N-[2-[[4-[(5-cyano-3-pyridyl)sulfonimidoyl]

benzoyl]amino]-4-(4-fluorophenyl)phenyl]carbamate (52 mg, 94.8% yield) as white solid. LCMS (ESI) [M+H]+ m/z: calcd 472.1, found 472.1.

Step 6: Synthesis of N-(4-amino-4'-fluoro-[1,1'-biphenyl]-3-yl)-4-(5-cyanopyridine-3-sulfonimidoyl)benzamide (Compound 232)

To a solution of tert-butyl N-[2-[[4-[(5-cyano-3-pyridyl)sulfonimidoyl]benzoyl]amino]-4-(4-fluorophenyl)phenyl]carbamate (40 mg, 70.0 µmol) in DCM (4.0 mL) were added ZnBr$_2$ (47.3 mg, 0.210 mmol). The mixture was stirred at 20° C. for 12 hours. The crude purified by prep-HPLC (Neu) to give N-[2-amino-5-(4-fluorophenyl)phenyl]-4-[(5-cyano-3-pyridyl)sulfonimidoyl]benzamide (3 mg, 9.1% yield) as white solid.

Compound 232: $^1$H NMR (400 MHz, acetonitrile-d3) δ ppm 9.38 (d, J=2.3 Hz, 1H) 9.06 (d, J=1.8 Hz, 1H) 8.74 (s, 1H) 8.62 (br s, 1H) 8.11-8.26 (m, 4H) 7.58 (dd, J=8.5, 5.5 Hz, 2H) 7.48 (s, 1H) 7.32-7.43 (m, 1H) 7.17 (t, J=8.9 Hz, 2H) 6.91 (d, J=8.3 Hz, 1H) 4.38 (br s, 2H) 4.20 (s, 1H); 19F NMR (377 MHz, acetonitrile-d3) δ ppm −118.79; LCMS (ESI) [M+H]+ m/z: calcd 472.1, found 472.1; HPLC: 95.80%@220 nm, 99.20%@254 nm.

Example 139. Synthesis of N-[2-amino-5-(4-fluorophenyl)phenyl]-4-[(2-methoxy-1H-imidazol-5-yl)sulfonimidoyl]benzamide (Compound 252)

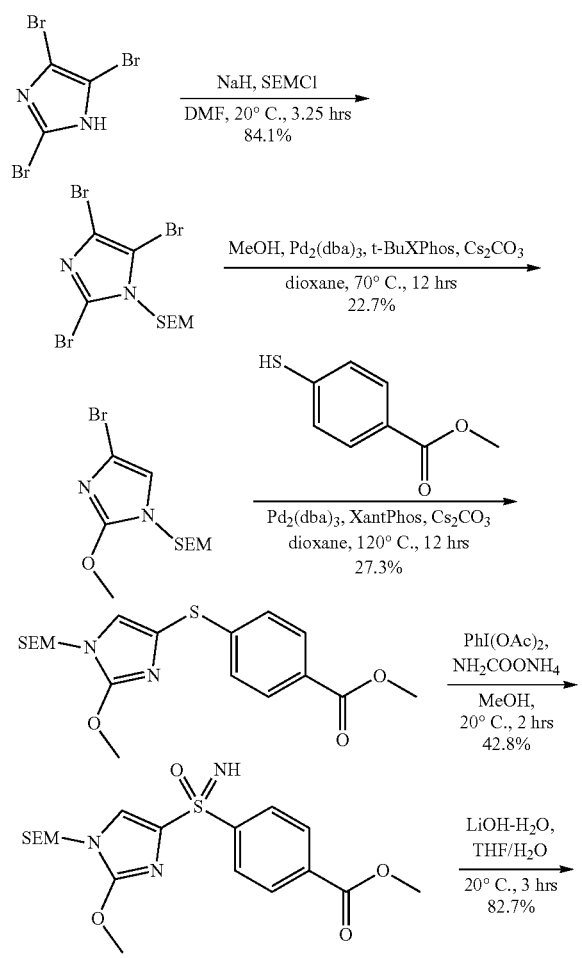

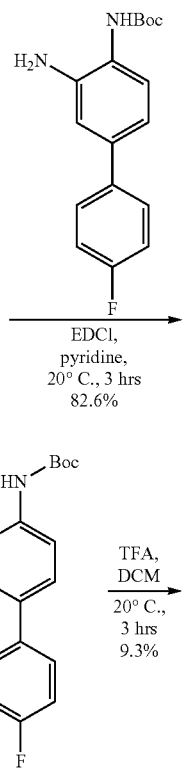

Step 1: Synthesis of trimethyl-[2-[(2,4,5-tribromo-imidazol-1-yl)methoxy]ethyl]silane To a solution of 2,4,5-tribromo-1H-imidazole (2 g, 6.56 mmol) in DMF (10 mL) was slowly added NaH (290 mg, 7.25 mmol, 60 wt % in mineral oil) at 20° C. The suspension was stirred for 15 minutes and added SEMCl (1.2 mL, 6.78 mmol). The mixture is stirred at 20° C. for 3 hours. The reaction mixture was diluted with water (80 mL) and extracted with ethyl acetate (40 mL*3). The combined organic layer was washed with water (40 mL), brine (50 mL), dried over anhydrous MgSO$_4$, filtered and concentrated under reduced pressure. The residue was purified by flash chromatography (ISCO®; 20 g Agela Flash® Silica Flash Column, petroleum ether/EtOAc with EtOAc from 0~10%, flow rate=30 mL/min, 254 nm) to give trimethyl-[2-[(2,4,5-tribromoimidazol-1-yl)methoxy]ethyl]silane (2.4 g, 84.1% yield) as white solid. LCMS (ESI) [M+H]+ m/z: calcd 436.8, found 437.0.

Step 2: Synthesis of 2-[(4-bromo-2-methoxy-imidazol-1-yl)methoxy]ethyl-trimethyl-silane To a solution of trimethyl-[2-[(2,4,5-tribromoimidazol-1-yl)methoxy]ethyl]silane (2.4 g, 5.52 mmol) in dioxane (20 mL) and MeOH (4 mL) were added $Cs_2CO_3$ (3.6 g, 11.1 mmol), t-BuXPhos (483 mg, 1.14 mmol) and $Pd_2(dba)_3$ (60 mg, 0.0660 mmol). The mixture was stirred at 70° C. for 12 hours. The reaction mixture was concentrated under reduced pressure. The reaction mixture was diluted with water (10 mL) and extracted with EtOAc (20 mL*3). The combined organic layers were washed with brine (20 mL), dried over anhydrous $Na_2SO_4$ and filtered. The filtrate was concentrated under reduced pressure. The residue was purified by flash chromatography (ISCO®; 20 g Sepa Flash® Silica Flash Column, petroleum ether/EtOAc with EtOAc from 0~20%, flow rate=40 mL/min, 254 nm) to give 2-[(4-bromo-2-methoxy-imidazol-1-yl)methoxy]ethyl-trimethyl-silane (385 mg, 22.7% yield) as yellow oil. $^1$H NMR (400 MHz, DMSO-d6) δ ppm 7.06 (s, 1H), 5.04 (s, 2H), 3.91 (s, 3H), 3.42-3.52 (m, 2H), 0.87-0.93 (m, 2H), −0.03 (s, 9H); LCMS (ESI) [M+H]$^+$ m/z: calcd 309.0, found 309.6.

Step 3: Synthesis of methyl 4-[2-methoxy-1-(2-trimethylsilylethoxymethyl)imidazol-4-yl]sulfanyl-benzoate A mixture of 2-[(4-bromo-2-methoxy-imidazol-1-yl)methoxy]ethyl-trimethyl-silane (400 mg, 1.30 mmol), methyl 4-sulfanylbenzoate (240 mg, 1.43 mmol), $Cs_2CO_3$ (1.28 g, 3.93 mmol), $Pd_2(dba)_3$ (120 mg, 0.131 mmol) and XantPhos (80 mg, 0.138 mmol) in dioxane (15 mL) was stirred under $N_2$ at 120° C. for 12 hours. The resulting mixture was quenched by addition of water (80 mL*3), and extracted with EtOAc (80 mL*3). The combined organic layer was washed with brine (100 mL) and dried over anhydrous $Na_2SO_4$, filtered and concentrated under reduced pressure. The residue was purified by flash chromatography (ISCO®; 20 g Agela Flash® Silica Flash Column, petroleum ether/EtOAc with EtOAc from 0~25%, flow rate=40 mL/min, 254 nm) to afford methyl 4-[2-methoxy-1-(2-trimethylsilylethoxymethyl)imidazol-4-yl]sulfanylbenzoate (140 mg, 27.3% yield) as brown solid. LCMS (ESI) [M+H]$^+$ m/z: calcd 395.1, found 395.1.

Step 4: Synthesis of methyl 4-[[2-methoxy-1-(2-trimethylsilylethoxymethyl)imidazol-4-yl]sulfonimidoyl]benzoate To a solution of methyl 4-[2-methoxy-1-(2-trimethylsilylethoxymethyl)imidazol-4-yl]sulfanylbenzoate (130 mg, 0.329 mmol) in MeOH (10 mL) was added PhI(OAc)$_2$ (260 mg, 0.807 mmol), $NH_2COONH_4$ (52 mg, 0.666 mmol). The mixture was stirred at 20° C. for 2 hours. The resulting mixture was concentrated under reduced pressure. The residue was purified by flash chromatography (ISCO®; 12 g Agela Flash® Silica Flash Column, petroleum ether/EtOAc with EtOAc from 0~100%, flow rate=30 mL/min, 254 nm) to afford methyl 4-[[2-methoxy-1-(2-trimethylsilylethoxymethyl)imidazol-4-yl]sulfonimidoyl]benzoate (60 mg, 42.8% yield) as yellow solid. LCMS (ESI) [M+H]$^+$ m/z: calcd 426.1, found 426.1.

Step 5: Synthesis of 4-[[2-methoxy-1-(2-trimethylsilylethoxymethyl)imidazol-4-yl]sulfonimidoyl]benzoic acid To a solution of methyl 4-[[2-methoxy-1-(2-trimethylsilylethoxymethyl)imidazol-4-yl]sulfonimidoyl]benzoate (60 mg, 0.141 mmol) in $H_2O$ (2 mL) and THF (6 mL) was added LiOH—$H_2O$ (18 mg, 0.429 mmol). The mixture was stirred at 20° C. for 3 hours. The resulting mixture was adjusted pH=4 with 2N HCl aqueous solution, and extracted with EtOAc (30 mL*3). The combined organic layer was dried over anhydrous $Na_2SO_4$, filtered and concentrated under reduced pressure to give 4-[[2-methoxy-1-(2-trimethylsilylethoxymethyl)imidazol-4-yl]sulfonimidoyl]benzoic acid (48 mg, 82.7% yield) as yellow solid. LCMS (ESI) [M+H]$^+$ m/z: calcd 412.1, found 412.1.

Step 6: Synthesis of tert-butyl N-[4-(4-fluorophenyl)-2-[[4-[[2-methoxy-1-(2-trimethylsilylethoxymethyl)imidazol-4-yl]sulfonimidoyl]benzoyl]amino]phenyl]carbamate To a solution of 4-[[2-methoxy-1-(2-trimethylsilylethoxymethyl)imidazol-4-yl]sulfonimidoyl]benzoic acid (48 mg, 0.117 mmol) and tert-butyl N-[2-amino-4-(4-fluorophenyl)phenyl]carbamate (53 mg, 0.175 mmol) in pyridine (10 mL) was added EDCI (34 mg, 0.177 mmol). The mixture was stirred at 20° C. for 3 hours. The resulting mixture was concentrated under reduced pressure. The residue was purified by flash chromatography (ISCO®; 12 g AgelaFlash® Silica Flash Column, petroleum ether/EtOAc with EtOAc 0~100%, flow rate=30 mL/min, 254 nm) to afford tert-butyl N-[4-(4-fluorophenyl)-2-[[4-[[2-methoxy-1-(2-trimethylsilylethoxymethyl)imidazol-4-yl]sulfonimidoyl]benzoyl]amino]phenyl]carbamate (67 mg, 82.3% yield) as light-yellow solid. LCMS (ESI) [M+H]$^+$ m/z: calcd 696.3, found 696.3.

Step 7: Synthesis of N-[2-amino-5-(4-fluorophenyl)phenyl]-4-[(2-methoxy-1H-imidazol-5-yl)sulfonimidoyl]benzamide (Compound 252)

To a solution of tert-butyl N-[4-(4-fluorophenyl)-2-[[4-[[2-methoxy-1-(2-trimethylsilylethoxymethyl)imidazol-4-yl]sulfonimidoyl]benzoyl]amino]phenyl]carbamate (53 mg, 0.0760 mmol) in DCM (5 mL) was added TFA (0.5 mL, 6.49 mmol). The mixture was stirred at 20° C. for 3 hours. The mixture was concentrated under reduced pressure. To the mixture was added saturated $Na_2CO_3$ aqueous solution to adjust pH=8. The mixture was diluted with water (30 mL) and extracted with DCM (20 mL*3). The combined organic layer was washed with brine (20 mL*2), dried over anhydrous $Na_2SO_4$, filtered and concentrated under reduced pressure. The residue purified by preparative HPLC (Instrument: Gilson GX-281 Liquid Handler, Gilson 322 Pump, Gilson 156 UV Detector; Column: 2_Phenomenex Gemini C18 75*40 mm*3 µm; Mobile phase A: water ($NH_3$—$H_2O$+ $NH_4HCO_3$)-ACN; Mobile phase B: MeCN; Gradient: B from 22% to 52% in 9.5 min, hold 100% B for 2 min; Flow Rate: 30 mL/min; Column Temperature: 30° C.; Wavelength: 220 nm, 254 nm) to afford N-[2-amino-5-(4-fluorophenyl)phenyl]-4-[(2-methoxy-1H-imidazol-5-yl)sulfonimidoyl]benzamide (3.3 mg, 9.3% yield) as yellow solid. $^1$H NMR (400 MHz, methanol-d4) δ ppm 8.12-8.28 (m, 4H), 7.58 (s, 2H), 7.46-7.55 (m, 2H), 7.37 (dd, J=8.3, 2.3 Hz, 1H), 7.13 (t, J=8.8 Hz, 2H), 7.00 (d, J=8.3 Hz, 1H), 3.99 (s, 3H); 19F NMR (376 MHz, methanol-d4) δ ppm −117.394; LCMS (ESI) [M+H]$^+$ m/z: calcd 466.1, found 466.1; HPLC: 94.34%@220 nm; 97.76%@254 nm.

Example 140. Synthesis of N-[2-amino-5-(4-fluoro-phenyl)phenyl]-6-(1H-imidazol-5-ylsulfonimidoyl)pyridine-3-carboxamide (Compound 219)
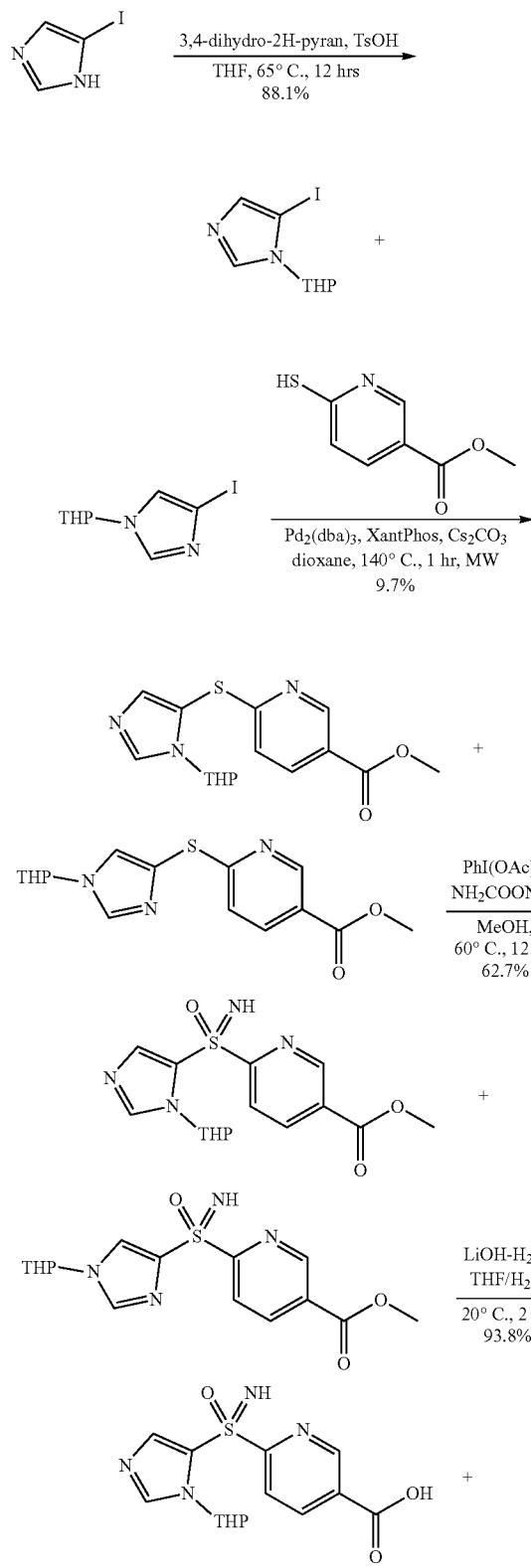
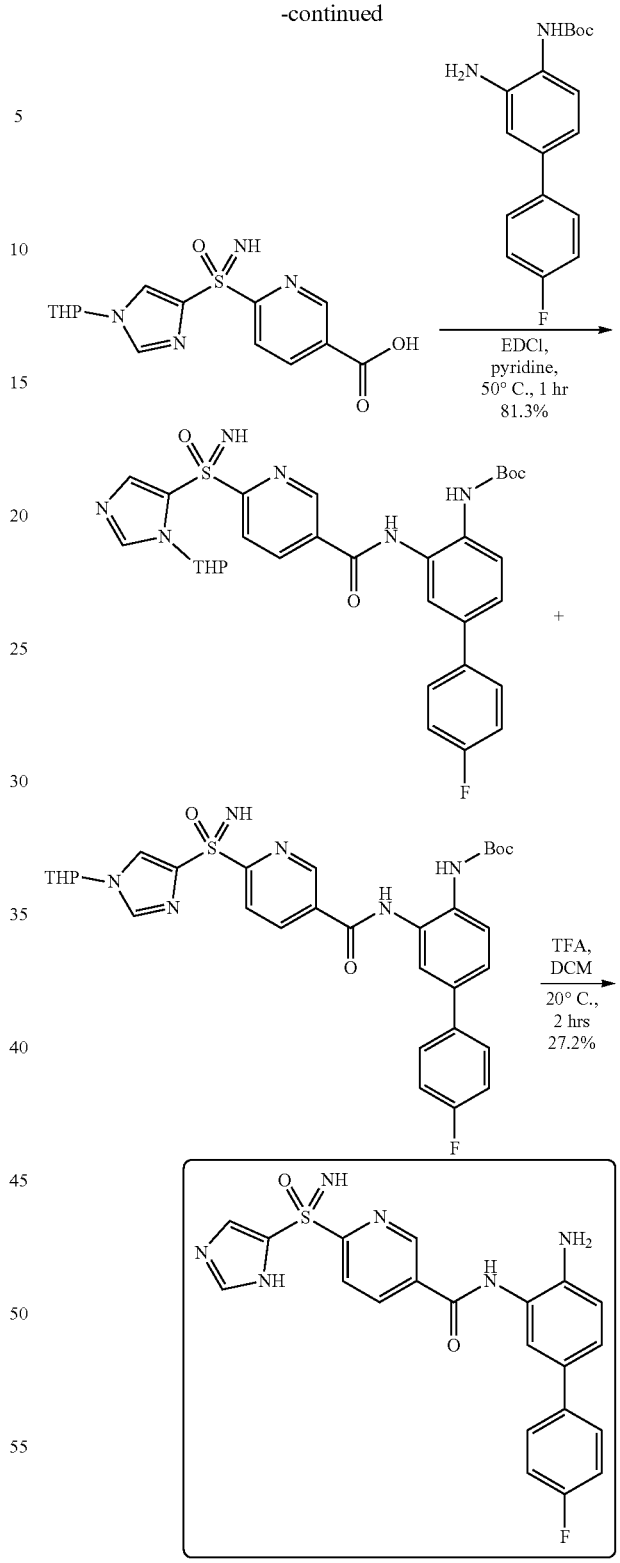
Step 1: Synthesis of 5-iodo-1-tetrahydropyran-2-yl-imidazole and 4-iodo-1-tetrahydropyran-2-yl-imidazole
To a mixture of 5-iodo-1H-imidazole (9.5 g, 49.0 mmol), 3,4-dihydro-2H-pyran (20.6 g, 0.245 mol) in THF (150 mL)

was added TsOH (1.03 g, 19.7 mmol). The mixture was stirred at 65° C. for 12 hours. The resulting mixture was concentrated under reduced pressure. The residue was purified by flash chromatography (ISCO®; 20 g AgelaFlash®Silica Flash Column, petroleumether/EtOAc with EtOAc from 0~42%, flow rate=30 mL/min, 254 nm) to afford a mixture of 5-iodo-1-tetrahydropyran-2-yl-imidazole and 4-iodo-1-tetrahydropyran-2-yl-imidazole (12 g, 88.1% yield) as white solid. $^1$H NMR (400 MHz, methanol-d4) δ ppm 7.76 (d, J=1.3 Hz, 1H), 7.40 (d, J=1.3 Hz, 1H), 5.33 (dd, J=9.7, 2.4 Hz, 1H), 4.02 (dt, J=11.7, 1.9 Hz, 1H), 3.63-3.77 (m, 1H), 1.84-2.06 (m, 3H), 1.52-1.77 (m, 3H); LCMS (ESI) [M+H]$^+$ m/z: calcd 279.0, found 279.1.

Step 2: Synthesis of methyl 6-(3-tetrahydropyran-2-ylimidazol-4-yl)sulfanylpyridine-3-carboxylate and methyl 6-(I-tetrahydropyran-2-ylimidazol-4-yl)sulfanylpyridine-3-carboxylate To a mixture of 5-iodo-1-tetrahydropyran-2-yl-imidazole (1.48 g, 5.32 mmol), 4-iodo-1-tetrahydropyran-2-yl-imidazole and methyl 6-sulfanylpyridine-3-carboxylate (600 mg, 3.55 mmol) in dioxane (12 mL) were added Pd$_2$(dba)$_3$ (648 mg, 0.708 mmol), XantPhos (408 mg, 0.705 mmol) and Cs$_2$CO$_3$ (3.47 g, 10.6 mmol). The resulting mixture was stirred at 140° C. for 1 hour in microwave. The resulting mixture was quenched by addition of water (50 mL) and extracted with EtOAc (100 mL*3). The combined organic layer was washed with brine (100 mL), dried over anhydrous Na$_2$SO$_4$, filtered and concentrated under reduced pressure. The residue was purified by flash chromatography (ISCO®; 20 g AgelaFlash® Silica Flash Column, petroleum ether/EtOAc with EtOAc from 0~90%, flow rate=30 mL/min, 254 nm) to afford methyl 6-(3-tetrahydropyran-2-ylimidazol-4-yl)sulfanylpyridine-3-carboxylate and methyl 6-(1-tetrahydropyran-2-ylimidazol-4-yl)sulfanylpyridine-3-carboxylate (110 mg, 9.71% yield) as brown solid. LCMS (ESI) [M+H]$^+$ m/z: calcd 320.1, found 320.2.

Step 3: Synthesis of methyl 6-[(3-tetrahydropyran-2-ylimidazol-4-yl)sulfonimidoyl]pyridine-3-carboxylate and methyl 6-[(1-tetrahydropyran-2-ylimidazol-4-yl)sulfonimidoyl]pyridine-3-carboxylate To a mixture of methyl 6-(3-tetrahydropyran-2-ylimidazol-4-yl)sulfanylpyridine-3-carboxylate and methyl 6-(1-tetrahydropyran-2-ylimidazol-4-yl)sulfanylpyridine-3-carboxylate (160 mg, 0.501 mmol) in MeOH (5 mL) were added NH$_2$COONH$_4$ (120 mg, 1.54 mmol) and PhI(OAc)$_2$ (800 mg, 2.48 mmol). The resulting mixture was sealed and degassed under vacuum and purged with N$_2$ for three times, and then stirred at 60° C. for 12 hours under N$_2$ atmosphere. The resulting mixture was concentrated under reduced pressure. The residue was purified by flash chromatography (ISCO®; 12 g AgelaFlash® Silica Flash Column, DCM/MeOH with MeOH from 0~15%, flow rate=30 mL/min, 254 nm) to afford methyl 6-[(3-tetrahydropyran-2-ylimidazol-4-yl)sulfonimidoyl]pyridine-3-carboxylate and methyl 6-[(1-tetrahydropyran-2-ylimidazol-4-yl)sulfonimidoyl]pyridine-3-carboxylate (110 mg, 62.7% yield) as white solid. LCMS (ESI) [M+H]$^+$ m/z: calcd 351.1, found 350.9.

Step 4: Synthesis of 6-[(3-tetrahydropyran-2-ylimidazol-4-yl)sulfonimidoyl]pyridine-3-carboxylic acid and 6-[(I-tetrahydropyran-2-ylimidazol-4-yl)sulfonimidoyl]pyridine-3-carboxylic acid A mixture of methyl 6-[(3-tetrahydropyran-2-ylimidazol-4-yl)sulfonimidoyl]pyridine-3-carboxylate and methyl 6-[(1-tetrahydropyran-2-ylimidazol-4-yl)sulfonimidoyl]pyridine-3-carboxylate (100 mg, 0.285 mmol) and LiOH—H$_2$O (60 mg, 1.43 mmol) in H$_2$O (2 mL) and THF (2 mL) was stirred at 20° C. for 2 hours. The resulting mixture was adjusted pH=5 with HCl (2N) aqueous solution, then the solution was extracted with DCM (50 mL*5). The combined organic layer was dried over anhydrous Na$_2$SO$_4$, filtered and concentrated under reduced pressure to give 6-[(3-tetrahydropyran-2-ylimidazol-4-yl)sulfonimidoyl]pyridine-3-carboxylic acid and 6-[(1-tetrahydropyran-2-ylimidazol-4-yl)sulfonimidoyl]pyridine-3-carboxylic acid (90 mg, 93.6% yield) as white solid. LCMS (ESI) [M+H]$^+$ m/z: calcd 337.1, found 337.2.

Step 5: Synthesis of tert-butyl N-[4-(4-fluorophenyl)-2-[[6-[(3-tetrahydropyran-2-ylimidazol-4-yl)sulfonimidoyl]pyridine-3-carbonyl]amino]phenyl]carbamate and tert-butyl N-[4-(4-fluorophenyl)-2-[[6-[(I-tetrahydropyran-2-ylimidazol-4-yl)sulfonimidoyl]pyridine-3-carbonyl]amino]phenyl]carbamate A mixture of 6-[(3-tetrahydropyran-2-ylimidazol-4-yl)sulfonimidoyl]pyridine-3-carboxylic acid and 6-[(1-tetrahydropyran-2-ylimidazol-4-yl)sulfonimidoyl]pyridine-3-carboxylic acid (80 mg, 0.238 mmol), tert-butyl N-[2-amino-4-(4-fluorophenyl)phenyl]carbamate (56 mg, 0.185 mmol) and EDCI (68 mg, 0.355 mmol) in pyridine (3 mL) was stirred at 50° C. for 1 hour. The resulting mixture was concentrated under reduced pressure. The residue was purified by flash chromatography (ISCO®; 4*2 g AgelaFlash® Silica Flash Column, DCM/MeOH with MeOH from 0~15%, flow rate=30 mL/min, 254 nm) to afford tert-butyl N-[4-(4-fluorophenyl)-2-[[6-[(3-tetrahydropyran-2-ylimidazol-4-yl)sulfonimidoyl]pyridine-3-carbonyl]amino]phenyl]carbamate and tert-butyl N-[4-(4-fluorophenyl)-2-[[6-[(1-tetrahydropyran-2-ylimidazol-4-yl)sulfonimidoyl]pyridine-3-carbonyl]amino]phenyl]carbamate (120 mg, 81.3% yield) as yellow oil. LCMS (ESI) [M+H]$^+$ m/z: calcd 621.2, found 621.4.

Step 6: Synthesis of N-[2-amino-5-(4-fluorophenyl)phenyl]-6-(1H-imidazol-5-ylsulfonimidoyl)pyridine-3-carboxamide (Compound 219)

A mixture of tert-butyl N-[4-(4-fluorophenyl)-2-[[6-[(3-tetrahydropyran-2-ylimidazol-4-yl)sulfonimidoyl]pyridine-3-carbonyl]amino]phenyl]carbamate and tert-butyl N-[4-(4-fluorophenyl)-2-[[6-[(1-tetrahydropyran-2-ylimidazol-4-yl)sulfonimidoyl]pyridine-3-carbonyl]amino]phenyl]carbamate (110 mg, 0.177 mmol), DCM (3 mL) and TFA (0.6 mL, 7.79 mmol) was stirred at 20° C. for 2 hours. The resulting mixture was adjusted pH=8 with NH$_3$—H$_2$O (12 N). The mixture was concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75*40 mm*3 µm; Mobile phase A: H$_2$O with NH$_3$—H$_2$O+NH$_4$HCO$_3$ (v %); Mobile phase B: MeCN; Gradient: B from 24% to 54% in 9.5 min, hold 100% B for 1 min; Flow Rate: 30 mL/min; Column Temperature: 30° C.; Wavelength: 220 nm, 254 nm) to afford N-[2-amino-5-(4-fluorophenyl)phenyl]-6-(1H-imidazol-5-ylsulfonimidoyl)pyridine-3-carboxamide (21 mg, 27.2% yield) as light-yellow. $^1$H NMR (400 MHz, DMSO-d6) δ ppm 12.76 (brs, 1H), 9.97 (brs, 1H), 9.12 (d, J=1.9 Hz, 1H), 8.53 (dd, J=8.2, 2.1 Hz, 1H), 8.26 (d, J=8.1 Hz, 1H), 7.91 (s, 1H), 7.79 (s, 1H), 7.57 (dd, J=8.6, 5.5

Hz, 2H), 7.49 (d, J=2.1 Hz, 1H), 7.32 (dd, J=8.3, 2.1 Hz, 1H), 7.21 (t, J=8.8 Hz, 2H), 6.84 (d, J=8.4 Hz, 1H), 5.23 (s, 2H), 4.88 (brs, 1H); 19F NMR (377 MHz, DMSO-d6) δ ppm −117.49; LCMS (ESI) [M+H]+ m/z: calcd 437.1, found 437.2; HPLC: 99.58%@220 nm, 99.55%@254 nm.

Example 141. Synthesis of N-[2-amino-5-(4-fluorophenyl)phenyl]-5-[(methylsulfonimidoyl)methyl]benzofuran-2-carboxamide (Compound 201)

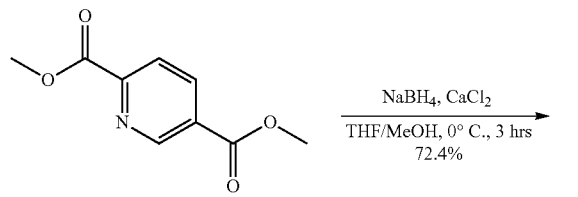

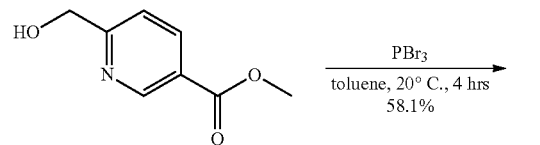

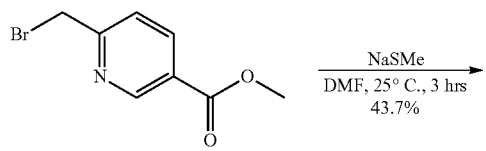

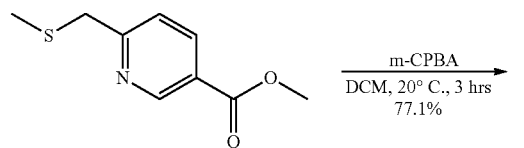

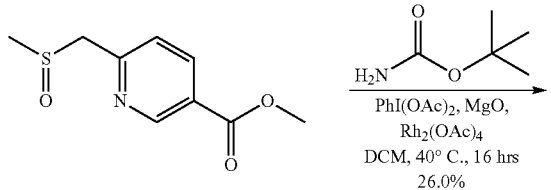

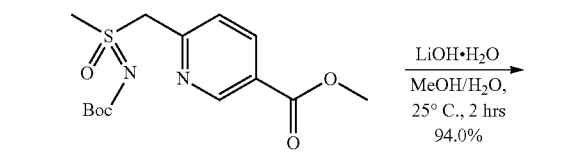

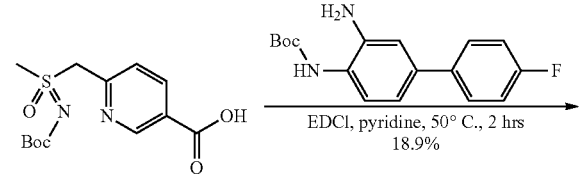

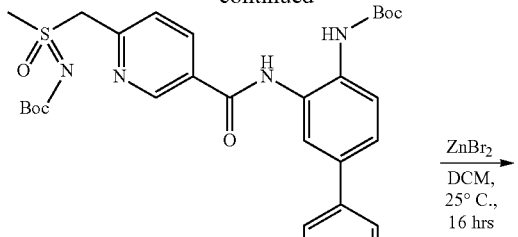

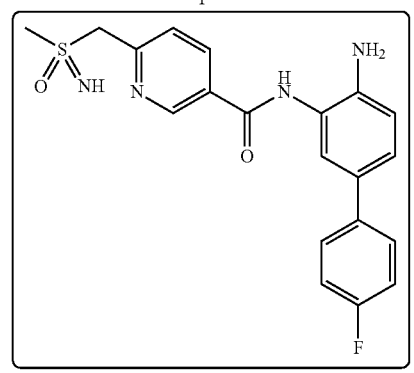

Step 1: Synthesis of methyl 6-(hydroxymethyl)pyridine-3-carboxylate

To a solution of dimethyl pyridine-2,5-dicarboxylate (1 g, 5.12 mmol) in THF (6 mL)/MeOH (12 mL) was added calcium chloride (2.27 g, 20.5 mmol). The reaction mixture was sonicated for 5 minutes and cooled to 0° C. Sodium tetrahydroborate (485 mg, 12.8 mmol) powder was added slowly (gas evolution). The mixture was stirred for 3 hours at 0° C. Saturated NH$_4$Cl solution (20 mL) and water (10 mL) was added slowly, and the resulting mixture was extracted with dichloromethane (20 mL×2). The combined organic solvent was dried over Na$_2$SO$_4$ and concentrated to give methyl 6-(hydroxymethyl)pyridine-3-carboxylate (620 mg, 72.4% yield) as yellow solid. $^1$H NMR (400 MHz, chloroform-d) δ ppm 9.10 (d, J=1.5 Hz, 1H), 8.23 (dd, J=8.2, 2.1 Hz, 1H), 7.29 (d, J=8.1 Hz, 1H), 4.68-4.83 (m, 2H), 3.74-3.98 (m, 3H), 3.37-3.63 (m, 1H); LCMS (ESI) [M+H]+ m/z: calcd 168.1; found 168.0.

Step 2: Synthesis of methyl 6-(bromomethyl)pyridine-3-carboxylate

To a solution of methyl 6-(hydroxymethyl)pyridine-3-carboxylate (4 g, 23.9 mmol) in toluene (150 mL) was added phosphorus tribromide (6.48 g, 23.9 mmol) under N$_2$ protection. The reaction mixture was stirred at 0° C. and allowed to warm to 20° C. for 4 hours. DCM (40 mL) was added into reaction mixture. The organic layer was adjusted pH=7 with 50 mL saturated aqueous solution of sodium bicarbonate, dried over anhydrous Na$_2$SO$_4$, and concentrated under reduced pressure to afford methyl 6-(bromomethyl)pyridine-3-carboxylate (3.2 g, 58.1% yield) as dark red solid. $^1$H NMR (400 MHz, chloroform-d) δ ppm 9.17 (d, J=1.63 Hz, 1H), 8.31 (dd, J=8.13, 2.13 Hz, 1H), 7.54 (d, J=8.00 Hz, 1H), 4.59 (s, 2H), 3.88-4.02 (m, 3H); LCMS (ESI) [M+H]+ m/z: calcd 231.9; found 231.8.

Step 3: Synthesis of methyl 6-(methylsulfanylmethyl)pyridine-3-carboxylate

To a mixture of methyl 6-(bromomethyl)pyridine-3-carboxylate (3.2 g, 13.9 mmol) in DMF (50 mL) was cooled to 0° C., then added sodium methanethiolate (1.1 g, 15.7 mmol) in portions at 0-5° C. under $N_2$. The mixture was stirred at 25° C. for 3 hours. The mixture was poured into ice-water (20 mL) and extracted with ethyl acetate (20 mL*2). The combined organic phase was washed with $H_2O$ (20 mL*3), brine (20 mL), dried with anhydrous $Na_2SO_4$, filtered and concentrated in vacuum to afford methyl 6-(methylsulfanylmethyl)pyridine-3-carboxylate (1.2 g, 43.7% yield) as yellow oil. $^1H$ NMR (400 MHz, chloroform-d) δ ppm 9.13 (d, J=1.8 Hz, 1H), 8.27 (dd, J=8.2, 2.1 Hz, 1H), 7.46 (d, J=8.3 Hz, 1H), 3.91-3.98 (m, 3H), 3.80-3.87 (m, 2H), 2.04-2.09 (m, 3H).

Step 4: Synthesis of methyl 6-(methylsulfinylmethyl)pyridine-3-carboxylate

To a solution of methyl 6-(methylsulfanylmethyl)pyridine-3-carboxylate (1.2 g, 6.08 mmol) in DCM (15 mL) was added 3-chlorobenzenecarboperoxoic acid (1.24 g, 6.08 mmol, 85% purity). The mixture was stirred at 20° C. for 3 hours. The reaction was quenched by addition of saturated $Na_2SO_3$ aqueous solution (20 mL), saturated $Na_2CO_3$ aqueous solution (20 mL) and extracted with DCM (40 mL*4). The combined organic layer was dried over anhydrous $Na_2SO_4$, concentrated under reduced pressure to give brown residue. The crude product was purified by silica gel chromatography (column height: 250 mm, diameter: 100 mm, 100-200 mesh silica gel, Petroleum ether/Ethyl acetate=10/1, 0/1) to afford methyl 6-(methylsulfinylmethyl)pyridine-3-carboxylate (1.0 g, 77.1% yield) as pale orange solid. $^1H$ NMR (400 MHz, chloroform-d) δ ppm 9.22 (dd, J=2.08, 0.61 Hz, 1H), 8.32 (dd, J=8.07, 2.20 Hz, 1H), 7.47 (dd, J=8.07, 0.61 Hz, 1H), 4.22-4.31 (m, 1H), 4.10-4.18 (m, 1H), 3.97 (s, 3H), 2.59 (s, 3H); LCMS (ESI) [M+H]$^+$ m/z: calcd 214.1; found 213.9.

Step 5: Synthesis of methyl 6-[(N-tert-butoxycarbonyl-S-methyl-sulfonimidoyl)methyl]pyridine-3-carboxylate To a solution of methyl 6-(methylsulfinylmethyl)pyridine-3-carboxylate (500 mg, 2.34 mmol) tert-butyl carbamate (550 mg, 4.69 mmol) and MgO (485 mg, 11.7 mmol) in DCM (15 mL) was added RHODIUM(II)ACETATEDIMER (52 mg, 118 μmol), (DIACETOXYIODO)BENZENE (1.13 g, 3.52 mmol) under $N_2$ protection. The reaction mixture was stirred at 40° C. for 16 hours. The mixture was filtered. The filtrate was concentrated under reduced pressure. The residue was purified by flash chromatography (Biotage®; 12 g SepaFlash® Silica Flash Column, petroleum ether/EtOAc with EtOAc from 0~100%, 18 mL/min, 254 nm) to give methyl 6-[(N-tert-butoxycarbonyl-S-methyl-sulfonimidoyl)methyl]pyridine-3-carboxylate (200 mg, 26.0% yield) as yellow solid. $^1H$ NMR (400 MHz, chloroform-d) δ ppm 9.19 (d, J=1.38 Hz, 1H), 8.35 (dd, J=8.13, 2.13 Hz, 1H), 7.62 (d, J=8.13 Hz, 1H), 7.27 (s, 1H), 5.07-5.18 (m, 1H), 4.94-5.05 (m, 1H), 3.98 (s, 3H), 3.17 (s, 3H), 1.50 (s, 9H); LCMS (ESI) [M+H]$^+$ m/z: calcd 329.1; found 350.9.

Step 6: Synthesis of 6-[(N-tert-butoxycarbonyl-S-methyl-sulfonimidoyl)methyl]pyridine-3-carboxylic acid To a solution of methyl 6-[(N-tert-butoxycarbonyl-S-methyl-sulfonimidoyl)methyl]pyridine-3-carboxylate (200 mg, 609 μmol) in MeOH/$H_2O$ (4 mL) was added LiOH·$H_2O$ (77 mg, 1.83 mmol) The mixture was stirred at 25° C. for 2 hours. The mixture was concentrated under reduced pressure to remove the organic solvent. The aqueous phase was adjusted pH=4 with 1M HCl aqueous solution. There was no solid generation, aqueous solution was lyophilized under reduced pressure to afford 6-[(N-tert-butoxycarbonyl-S-methyl-sulfonimidoyl)methyl]pyridine-3-carboxylic acid (180 mg, 94.0% yield) as light-yellow solid. $^1H$ NMR (400 MHz, DMSO-d6) δ ppm 8.97-9.10 (m, 1H), 8.23 (dd, J=7.82, 2.06 Hz, 1H), 7.51 (d, J=8.13 Hz, 1H), 5.06 (s, 2H), 3.25 (s, 3H), 1.35 (s, 9H); LCMS (ESI) [M+H]$^+$ m/z: calcd 315.1; found 214.9.

Step 7: Synthesis of tert-butyl N-[[5-[[2-(tert-butoxycarbonylamino)-5-(4-fluorophenyl)phenyl]carbamoyl]-2-pyridyl]methyl-methyl-oxo-sulfanylidene]carbamate A mixture of 6-[(N-tert-butoxycarbonyl-S-methyl-sulfonimidoyl)methyl]pyridine-3-carboxylic acid (100 mg, 318 μmol), tert-butyl N-[2-amino-4-(4-fluorophenyl)phenyl]carbamate (80 mg, 265 μmol) and EDCI (76 mg, 396 μmol) in pyridine (8 mL) was stirred at 50 C for 2 hrs. The mixture was concentrated under reduced pressure to give a crude product. The residue was purified by flash chromatography (Biotage®; 12 g SepaFlash® Silica Flash Column, petroleum ether/EtOAc with EtOAc from 0~100%, 16 mL/min, 254 nm) to give tert-butyl N-[[5-[[2-(tert-butoxycarbonylamino)-5-(4-fluorophenyl)phenyl]carbamoyl]-2-pyridyl]methyl-methyl-oxo-sulfanylidene]carbamate (30 mg, 18.9% yield) as light-yellow solid. $^1H$ NMR (400 MHz, chloroform-d) δ ppm 9.79 (br s, 1H), 9.20 (d, J=1.88 Hz, 1H), 8.30 (dd, J=8.07, 2.19 Hz, 1H), 8.09 (d, J=1.25 Hz, 1H), 7.62 (d, J=8.13 Hz, 1H), 7.50-7.58 (m, 2H), 7.36 (dd, J=8.25, 2.00 Hz, 1H), 7.23 (d, J=8.25 Hz, 1H), 7.06-7.17 (m, 2H), 6.83 (s, 1H), 5.04 (q, J=13.63 Hz, 2H), 3.17 (s, 3H), 1.53 (d, J=12.63 Hz, 18H); LCMS (ESI) [M+H]$^+$ m/z: calcd 599.2; found 599.3.

Step 8: Synthesis of N-[2-amino-5-(4-fluorophenyl)phenyl]-6-[(methylsulfonimidoyl)methyl]pyridine-3-carboxamide To a solution of tert-butyl N-[[5-[[2-(tert-butoxycarbonylamino)-5-(4-fluorophenyl)phenyl]carbamoyl]-2-pyridyl]methyl-methyl-oxo-sulfanylidene]carbamate (55 mg, 91.9 μmol) in DCM (5 mL) was added $ZnBr_2$ (124 mg, 551 μmol) The mixture was stirred at 25° C. for 16 hours. The mixture was concentrated under reduced pressure. The residue was purified by preparative HPLC (Instrument: ACSSH-CD; Column: Xtimate C18 150*40 mm*5 um; Mobile phase A: $H_2O$ with $NH_3H_2O$+$NH_4HCO_3$; Mobile phase B: MeCN; Gradient: B from 23% to 63% in 9 min, hold 100% B for 2 min; Flow Rate: 25 mL/min; Wavelength: 220 nm, 254 nm) to give N-[2-amino-5-(4-fluorophenyl)phenyl]-6-[(methylsulfonimidoyl)methyl]pyridine-3-carboxamide (14.1 mg, 38.5% yield) as white solid. $^1H$ NMR (400 MHz, DMSO-d6) δ ppm 9.91 (br s, 1H), 9.15 (d, J=1.76 Hz, 1H), 8.37 (dd, J=8.16, 2.13 Hz, 1H), 7.65 (d, J=8.03 Hz, 1H), 7.58 (dd, J=8.78, 5.52 Hz, 2H), 7.51 (d, J=2.01 Hz, 1H), 7.32 (dd, J=8.28, 2.26 Hz, 1H), 7.22 (t, J=8.91 Hz, 2H), 6.86 (d, J=8.53 Hz, 1H), 5.21 (s, 2H), 4.64 (q, J=13.13 Hz, 2H), 3.85 (s, 1H), 2.93 (s, 3H); LCMS (ESI) [M+H]$^+$ m/z: calcd 399.1; found 399.1; HPLC: 98.59%@220 nm, 97.76%@254 nm.

Example 142. Synthesis of N-[5-(5-acetyl-2-thienyl)-2-amino-phenyl]-4-(methylsulfonimidoyl)benzamide (Compound 241) and N-[2-amino-5-[5-(1-hydroxyethyl)-2-thienyl]phenyl]-4-(methylsulfonimidoyl)benzamide (Compound 255)

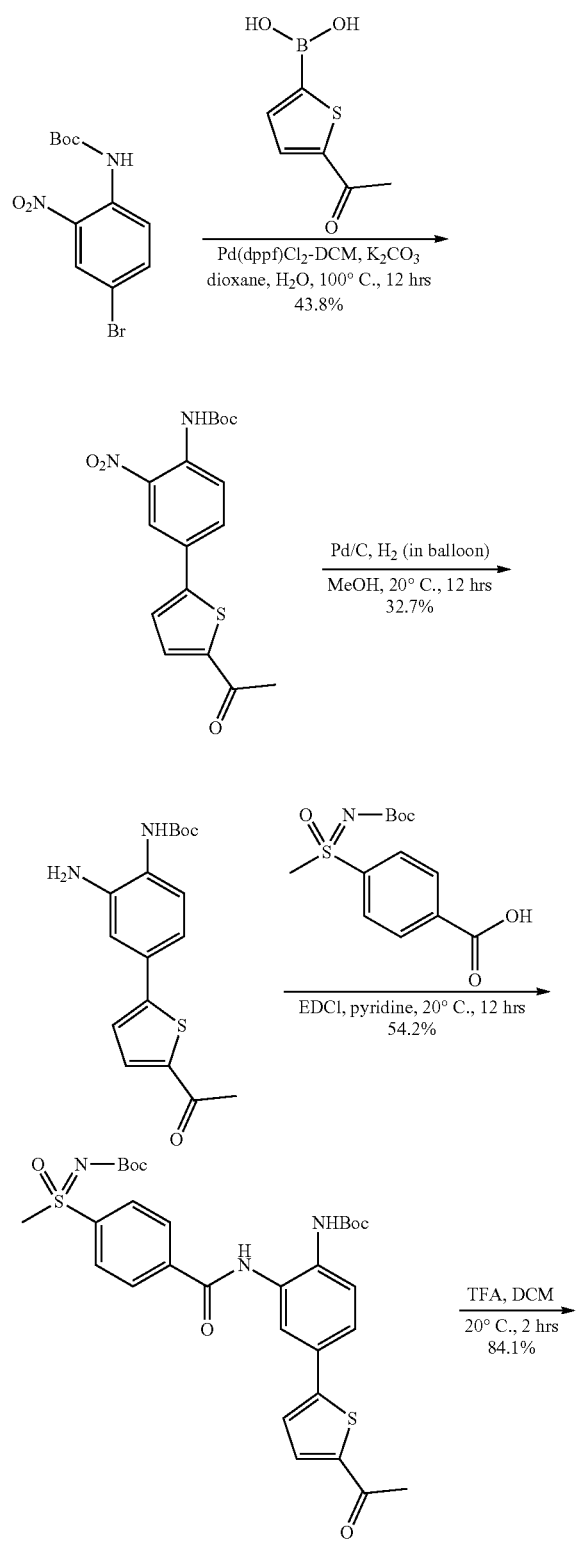

Step 1: Synthesis of tert-butyl N-[4-(5-acetyl-2-thienyl)-2-nitro-phenyl]carbamate A mixture of tert-butyl N-(4-bromo-2-nitro-phenyl)carbamate (2 g, 6.31 mmol), (5-acetyl-2-thienyl)boronic acid (1 g, 5.88 mmol), $K_2CO_3$ (1.7 g, 12.3 mmol), cyclopentyl(diphenyl)phosphane;dichloromethane;dichloropalladium;iron (400 mg, 0.490 mmol) in dioxane (10 mL) and $H_2O$ (1 mL) was stirred at 100° C. for 12 hours under $N_2$ atmosphere. The resulting mixture was quenched by addition of water (50 mL) and extracted with EtOAc (50 mL*3). The combined organic layer was washed with brine (50 mL), dried over anhydrous $Na_2SO_4$, filtered and concentrated under reduced pressure. The residue was purified by flash chromatography (ISCO®; 20 g AgelaFlash® Silica Flash Column, petroleum ether/EtOAc with EtOAc from 0~50%, flow rate=30 mL/min, 254 nm) to afford tert-butyl N-[4-(5-acetyl-2-thienyl)-2-nitro-phenyl]carbamate (1 g, 43.8% yield) as yellow solid. $^1$H NMR (400 MHz, DMSO-d6) δ ppm 9.75 (s, 1H), 8.28 (d, J=2.3 Hz, 1H), 8.02-8.08 (m, 1H), 7.97 (d, J=4.0 Hz, 1H), 7.72-7.77 (m, 2H), 2.55 (s, 3H), 1.44-1.47 (m, 9H); LCMS (ESI) [M+H]$^+$ m/z: calcd 363.1, found 363.2.

Step 2: Synthesis of tert-butyl N-[4-(5-acetyl-2-thienyl)-2-amino-phenyl]carbamate To a solution of tert-butyl N-[4-(5-acetyl-2-thienyl)-2-nitro-phenyl]carbamate (1 g, 2.76 mmol) in MeOH (10 mL) was added Pd/C (200 mg, 10 wt % Pd with 50 wt % water) under $H_2$ atmosphere. The suspension was degassed and purged with $H_2$ for 3 times. The mixture was stirred under $H_2$ (in balloon) at 20° C. for 12 hours. The resulting mixture was filtered and concentrated under reduced pressure to give tert-butyl N-[4-(5-acetyl-2-thienyl)-2-amino-phenyl]carbamate (300 mg, 32.7% yield) as yellow solid, which was used directly on next step without further purification.

Step 3: Synthesis of tert-butyl N-[[4-[[5-(5-acetyl-2-thienyl)-2-(tert-butoxycarbonylamino)phenyl]carbamoyl]phenyl]-methyl-oxo-sulfanylidene]carbamate To a solution of tert-butyl N-[4-(5-acetyl-2-thienyl)-2-amino-phenyl]carbamate (300 mg, 0.902 mmol), 4-(N-tert-butoxycarbonyl-S-methyl-sulfonimidoyl)benzoic acid (400 mg, 1.34 mmol) in pyridine (4 mL) was added 3-(ethyliminomethyleneamino)-N,N-dimethyl-propan-1-amine;hydrochloride (250 mg, 1.30 mmol). The mixture was stirred at 20° C. for 12 hours. The reaction mixture was concentrated under reduced pressure. The residue was purified by flash chromatography (ISCO®; 12 g AgelaFlash® Silica Flash Column, petroleum ether/EtOAc with EtOAc from 0~100%, flow rate=25 mL/min, 254 nm) to afford tert-butyl N-[[4-[[5-(5-acetyl-2-thienyl)-2-(tert-butoxycarbonylamino)phenyl]carbamoyl]phenyl]-methyl-oxo-sulfanylidene]carbamate (300 mg, 54.2% yield) as yellow solid. $^1$H NMR (400 MHz, DMSO-d6) δ ppm 10.15 (s, 1H), 8.91 (s, 1H), 8.23 (d, J=8.0 Hz, 2H), 8.10 (d, J=8.0 Hz, 2H), 7.94 (d, J=4.0 Hz, 1H), 7.90 (s, 1H), 7.76 (s, 1H), 7.66 (d, J=8.8 Hz, 1H), 7.59 (d, J=4.0 Hz, 1H), 2.54 (s, 3H), 1.45 (s, 9H), 1.20-1.30 (m, 12H); LCMS (ESI) [M+H]$^+$ m/z: calcd 614.2, found 614.3.

Step 4: Synthesis of N-[5-(5-acetyl-2-thienyl)-2-amino-phenyl]-4-(methylsulfonimidoyl)benzamide (Compound 241)

To a solution of tert-butyl N-[[4-[[5-(5-acetyl-2-thienyl)-2-(tert-butoxycarbonylamino)phenyl]carbamoyl]phenyl]-methyl-oxo-sulfanylidene]carbamate (300 mg, 0.489 mmol) in DCM (3 mL) was added TFA (1.2 mL, 15.6 mmol). The mixture was stirred at 20° C. for 2 hours. The resulting mixture was concentrated under reduced pressure. The resulting mixture was quenched by addition of water (30 mL) and extracted with DCM (50 mL*3). The combined organic layer was washed with brine (30 mL), dried over anhydrous $Na_2SO_4$, filtered and concentrated under reduced pressure to afford N-[5-(5-acetyl-2-thienyl)-2-amino-phenyl]-4-(methylsulfonimidoyl)benzamide (170 mg, 84.1% yield) as yellow solid. The solid (80 mg) was purified by preparative HPLC (Instrument: Gilson GX-281 Liquid Handler, Gilson 322 Pump, Gilson 156 UV Detector; Column: 2_Phenomenex Gemini C18 75×40 mm×3 μm; Mobile phase A: $H_2O$ with 10 mmol $NH_4HCO_3$ (v %); Mobile phase B: MeCN; Gradient: B from 25% to 55% in 9.5 min, hold 100% B for 1 min; Flow Rate: 30 mL/min; Column Temperature: 30° C.; Wavelength: 220 nm, 254 nm) to afford N-[5-(5-acetyl-2-thienyl)-2-amino-phenyl]-4-(methylsulfonimidoyl)benzamide (2.5 mg) as yellow solid for delivery. $^1$H NMR (400 MHz, methanol-d4) δ ppm 8.19-8.28 (m, 2H), 8.10-8.19 (m, 2H), 7.80 (d, J=4.0 Hz, 1H), 7.62 (d, J=2.1 Hz, 1H), 7.48 (dd, J=8.4, 2.1 Hz, 1H), 7.32 (d, J=4.0 Hz, 1H), 6.93 (d, J=8.4 Hz, 1H), 3.21 (s, 3H), 2.51-2.56 (m, 3H); LCMS (ESI) [M+H]$^+$ m/z: calcd 414.1, found 414.2; HPLC: 95.66%@220 nm, 98.43%@254 nm.

Step 5: Synthesis of N-[2-amino-5-[5-(I-hydroxyethyl)-2-thienyl]phenyl]-4-(methylsulfonimidoyl)benzamide (Compound 255)

To a solution of N-[5-(5-acetyl-2-thienyl)-2-amino-phenyl]-4-(methylsulfonimidoyl)benzamide (150 mg, 0.285 mmol) in MeOH (3 mL) was added $NaBH_4$ (80 mg, 2.11 mmol). The mixture was stirred at 0° C. for 1 hour. The resulting mixture was quenched by addition of water (30 mL) and extracted with DCM (50 mL*3). The combined organic layer was washed with brine (30 mL), dried over anhydrous $Na_2SO_4$, filtered and concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 μm; Mobile phase A: $H_2O$ with 10 mmol $NH_4HCO_3$ (v %); Mobile phase B: MeCN; Gradient: B from 22% to 52% in 9.5 min, hold 100% B for 1 min; Flow Rate: 30 mL/min; Column Temperature: 30° C.; Wavelength: 220 nm, 254 nm) to afford N-[2-amino-5-[5-(1-hydroxyethyl)-2-thienyl]phenyl]-4-(methylsulfonimidoyl)benzamide (14.5 mg, 12.3% yield) as white solid. $^1$H NMR (400 MHz, DMSO-d6) δ ppm 9.89 (s, 1H), 8.18 (d, J=8.3 Hz, 2H), 8.06 (d, J=8.3 Hz, 2H), 7.45 (d, J=1.5 Hz, 1H), 7.26 (dd, J=8.4, 2.1 Hz, 1H), 7.05 (d, J=3.8 Hz, 1H), 6.78-6.85 (m, 2H), 5.47 (d, J=4.8 Hz, 1H), 5.18 (s, 2H), 4.85-4.93 (m, 1H), 4.38 (s, 1H), 3.13 (s, 3H), 1.42 (d, J=6.5 Hz, 3H); LCMS (ESI) [M+H]$^+$ m/z: calcd 416.2, found 416.2; HPLC: 97.56%@220 nm, 97.24%@254 nm.

Example 143. Synthesis of N-[2-amino-5-(4-fluorophenyl)phenyl]-4-[[4-(trifluoromethyl)phenyl]sulfonimidoyl]benzamide (Compound 256)

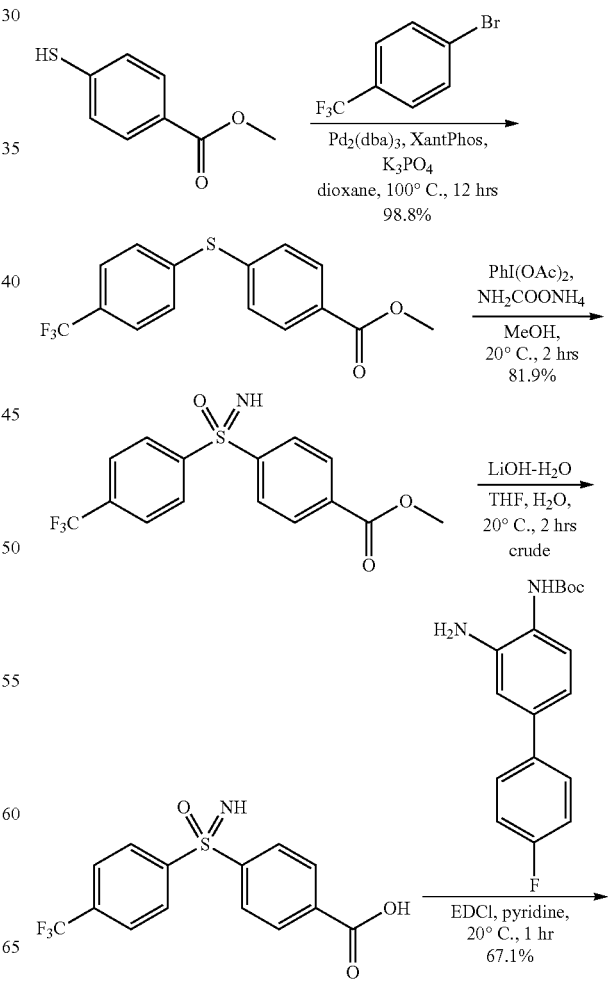

-continued

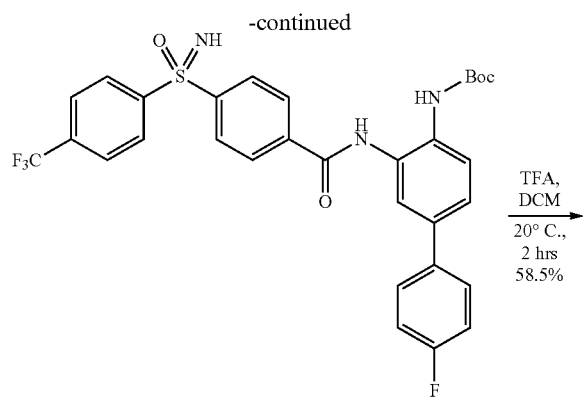

TFA, DCM
20° C.,
2 hrs
58.5%

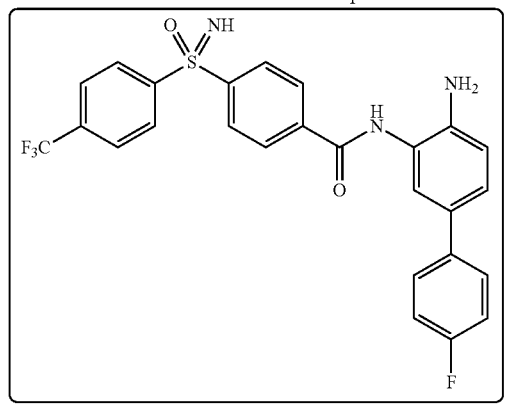

Step 1: Synthesis of methyl 4-[4-(trifluoromethyl)phenyl]sulfanylbenzoate

To a solution of 1-bromo-4-(trifluoromethyl)benzene (0.3 mL, 2.14 mmol) and methyl 4-sulfanylbenzoate (300 mg, 1.78 mmol) in dioxane (15 mL) was added $Pd_2(dba)_3$ (84 mg, 0.0917 mmol), Xantphos (108 mg, 0.187 mmol) and $K_3PO_4$ (1.14 g, 5.37 mmol). The mixture was stirred under $N_2$ at 100° C. for 12 hours. The resulting mixture was concentrated under reduced pressure. The residue was purified by flash chromatography (ISCO®; 20 g Agela Flash® Silica Flash Column, petroleum ether/EtOAc with EtOAc from 0~2%, flow rate=40 mL/min, 254 nm) to afford methyl 4-[4-(trifluoromethyl)phenyl]sulfanylbenzoate (550 mg, 98.8% yield) as brown oil. LCMS (ESI) $[M+H]^+$ m/z: calcd 313.0, found 312.9.

Step 2: Synthesis of methyl 4-[[4-(trifluoromethyl)phenyl]sulfonimidoyl]benzoate To a solution of methyl 4-[4-(trifluoromethyl)phenyl]sulfanylbenzoate (500 mg, 1.60 mmol) in MeOH (10 mL) was added $PhI(OAc)_2$ (1.3 g, 4.04 mmol), $NH_2COONH_4$ (250 mg, 3.20 mmol). The mixture was stirred at 20° C. for 2 hours. The resulting mixture was concentrated under reduced pressure. The residue was purified by flash chromatography (ISCO®; 20 g Agela Flash® Silica Flash Column, petroleum ether/EtOAc with EtOAc from 0~50%, flow rate=30 mL/min, 254 nm) to afford methyl 4-[[4-(trifluoromethyl)phenyl]sulfonimidoyl]benzoate (450 mg, 81.9% yield) as white solid. LCMS (ESI) $[M+H]^+$ m/z: calcd 344.0, found 344.1.

Step 3: Synthesis of 4-[[4-(trifluoromethyl)phenyl]sulfonimidoyl]benzoic acid To a solution of methyl 4-[[4-(trifluoromethyl)phenyl]sulfonimidoyl]benzoate (400 mg, 1.17 mmol) in $H_2O$ (2 mL) and THF (6 mL) was added lithium;hydroxide;hydrate (152 mg, 3.62 mmol). The mixture was stirred at 20° C. for 2 hours. The resulting mixture was adjusted pH=4 with 2N HCl aqueous solution, and extracted with EtOAc (20 mL*3). The combined organic layer was filtered and concentrated under reduced pressure to give 4-[[4-(trifluoromethyl)phenyl]sulfonimidoyl]benzoic acid (430 mg, crude) as white solid, which was directly used without further purification. LCMS (ESI) $[M+H]^+$ m/z: calcd 330.0, found 330.1.

Step 4: Synthesis of tert-butyl N-[4-(4-fluorophenyl)-2-[[4-[[4-(trifluoromethyl)phenyl]sulfonimidoyl]benzoyl]amino]phenyl]carbamate To a solution of 4-[[4-(trifluoromethyl)phenyl]sulfonimidoyl]benzoic acid (400 mg, 1.21 mmol) and tert-butyl N-[2-amino-4-(4-fluorophenyl)phenyl]carbamate (560 mg, 1.85 mmol) in pyridine (10 mL) was added EDCI (360 mg, 1.88 mmol). The mixture was stirred at 20° C. for 1 hour. The resulting mixture was concentrated under reduced pressure. The residue was purified by flash chromatography (ISCO®; 20 g Agela Flash® Silica Flash Column, petroleum ether/EtOAc with EtOAc from 0~65%, flow rate=40 mL/min, 254 nm) to afford tert-butyl N-[4-(4-fluorophenyl)-2-[[4-[[4-(trifluoromethyl)phenyl]sulfonimidoyl]benzoyl]amino]phenyl]carbamate (500 mg, 67.1% yield) as brown solid. LCMS (ESI) $[M+H]^+$ m/z: calcd 614.2, found 614.3.

Step 5: Synthesis of N-[2-amino-5-(4-fluorophenyl)phenyl]-4-[[4-(trifluoromethyl)phenyl]sulfonimidoyl]benzamide (Compound 256)

To a solution of tert-butyl N-[4-(4-fluorophenyl)-2-[[4-[[4-(trifluoromethyl)phenyl]sulfonimidoyl]benzoyl]amino]phenyl]carbamate (480 mg, 0.782 mmol) in DCM (5 mL) was added TFA (2.7 mL, 35.1 mmol). The mixture was stirred at 20° C. for 2 hours. The mixture was concentrated under reduced pressure, and adjusted pH=8 with saturated $Na_2CO_3$ aqueous solution. The mixture was diluted with water (100 mL) and extracted with DCM (100 mL*3). The combined organic layer was washed with brine (100 mL*2), dried over anhydrous $Na_2SO_4$, filtered and concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75*40 mm*3 µm; Mobile phase A: water ($NH_3$—$H_2O$+$NH_4HCO_3$)-ACN; Mobile phase B: MeCN; Gradient: B from 46% to 76% in 9.5 min, hold 100% B for 1 min; Flow Rate: 30 mL/min; Column Temperature: 30° C.; Wavelength: 220 nm, 254 nm) to afford N-[2-amino-5-(4-fluorophenyl)phenyl]-4-[[4-(trifluoromethyl)phenyl]sulfonimidoyl]benzamide (235 mg, 58.5% yield) as yellow solid. $^1$H NMR (400 MHz, DMSO-d6) δ ppm 9.87 (s, 1H), 8.07-8.27 (m, 6H), 7.96 (d, J=8.5 Hz, 2H), 7.56 (dd, J=8.5, 5.5 Hz, 2H), 7.43-7.51 (m, 1H), 7.30 (dd, J=8.3, 1.8 Hz, 1H), 7.15-7.26 (m, 2H), 6.84 (d, J=8.3 Hz, 1H), 5.48 (s, 1H), 5.14 (s, 2H); 19F NMR (376 MHz, DMSO-d6) δ ppm −61.569, 117.460; LCMS (ESI) $[M+H]^+$ m/z: calcd 514.1, found 514.2; HPLC: 99.31%@220 nm; 99.60%@254 nm.

Example 144. Synthesis of N-[2-amino-5-(4-fluoro-phenyl)phenyl]-5-(methylsulfonimidoyl)thieno[2,3-b]pyridine-2-carboxamide (Compound 202)

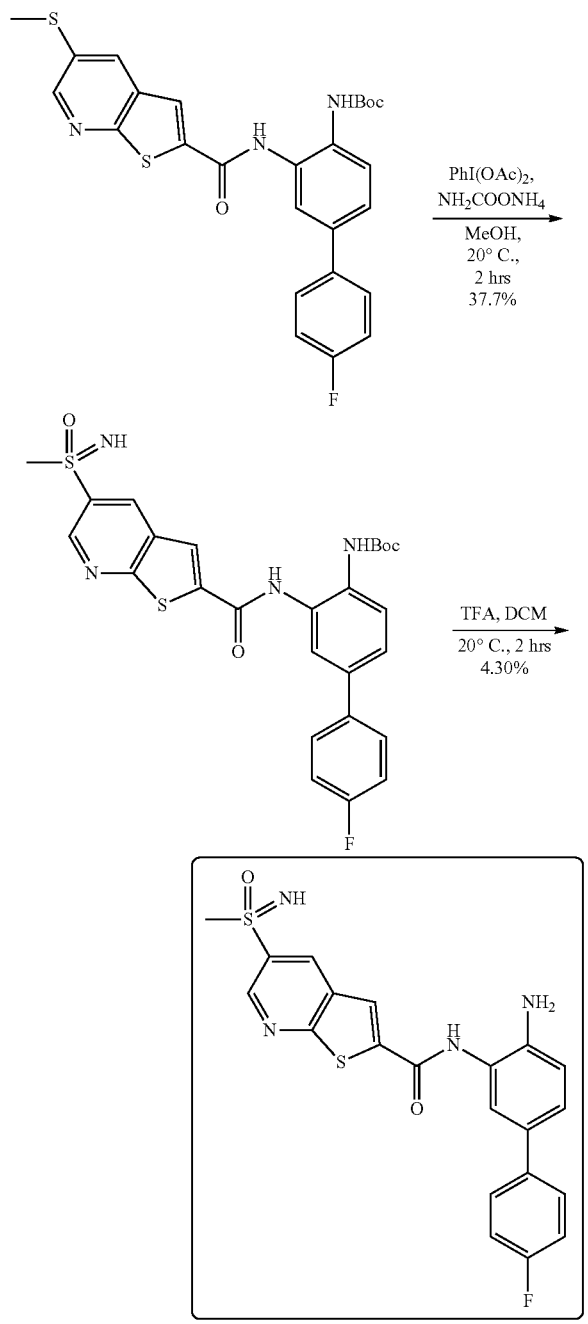

Step 1: Synthesis of tert-butyl N-[4-(4-fluorophe-nyl)-2-[[5-(methylsulfonimidoyl)thieno[2,3-b]pyridine-2-carbonyl]amino]phenyl]carbamate A mixture of tert-butyl N-[4-(4-fluorophenyl)-2-[(5-methylsulfanylthieno[2,3-b]pyridine-2-carbonyl)amino]phenyl]carbamate (150 mg, 0.294 mmol), PhI(OAc)$_2$ (240 mg, 0.745 mmol) and NH$_2$COONH$_4$ (45 mg, 0.576 mmol) in MeOH (10 mL) was stirred at 20° C. for 2 hours. The resulting mixture was filtered and concentrated under reduced pressure. The residue was purified by flash chromatography (Biotage®; 4 g AgelaFlash® Silica Flash Column, petroleum ether/EtOAc with EtOAc from 0~80%, flow rate=30 mL/min, 254 nm) to afford tert-butyl N-[4-(4-fluorophenyl)-2-[[5-(methylsulfonimidoyl)thieno[2,3-b] pyridine-2-carbonyl]amino]phenyl]carbamate (60 mg, 37.7% yield) as red solid. $^1$H NMR (400 MHz, DMSO-d6) δ ppm 10.36 (s, 1H), 9.15 (d, J=2.26 Hz, 1H), 8.95 (d, J=2.26 Hz, 1H), 8.90 (s, 1H), 8.43 (s, 1H), 7.78 (d, J=2.01 Hz, 1H), 7.68-7.75 (m, 3H), 7.56 (dd, J=8.66, 2.13 Hz, 1H), 7.27-7.32 (m, 2H), 1.99 (s, 3H), 1.47 (s, 9H); 19F NMR (376 MHz, DMSO-d6) δ ppm–115.581.

Step 2: Synthesis of N-[2-amino-5-(4-fluorophenyl) phenyl]-5-(methylsulfonimidoyl)thieno[2,3-b]pyridine-2-carboxamide (Compound 202)

To a solution of tert-butyl N-[4-(4-fluorophenyl)-2-[[5-(methylsulfonimidoyl)thieno[2,3-b]pyridine-2-carbonyl] amino]phenyl]carbamate (60 mg, 0.111 mmol) in DCM (5 mL) was added TFA (0.24 mL, 3.12 mmol). The mixture was stirred at 20° C. for 2 hours. The resulting mixture was concentrated under reduced pressure, and adjusted pH=8 with saturated NaHCO$_3$ aqueous solution. The mixture was quenched by addition of water (20 mL) and extracted with DCM (20 mL*3). The combined organic layer was dried over anhydrous Na$_2$SO$_4$, filtered and concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 μm; Mobile phase A: water (NH$_3$—H$_2$O+NH$_4$HCO$_3$ v/v)-ACN; Mobile phase B: ACN; Gradient: B from 32% to 62% in 9.5 min, hold 100% B for 0.5 min; Flow Rate: 30 mL/min; Column Temperature: 30° C.; Wavelength: 220 nm, 254 nm) to afford N-[2-amino-5-(4-fluorophenyl)phenyl]-5-(methylsulfonimidoyl)thieno[2,3-b]pyridine-2-carboxamide (2.1 mg, 4.3% yield). $^1$H NMR (400 MHz, DMSO-d6) δ ppm 10.25 (s, 1H), 9.13 (d, J=2.01 Hz, 1H), 8.92 (d, J=2.01 Hz, 1H), 8.47 (s, 1H), 7.60 (dd, J=8.66, 5.40 Hz, 2H), 7.50 (d, J=1.51 Hz, 1H), 7.35 (dd, J=8.41, 2.13 Hz, 1H), 7.22 (t, J=8.78 Hz, 2H), 6.88 (d, J=8.53 Hz, 1H), 5.25 (s, 2H), 4.64 (s, 1H), 3.25 (s, 3H); 19F NMR (376 MHz, DMSO-d6) δ ppm –117.417. LCMS (ESI) [M+H]$^+$ m/z: calcd 441.1, found 441.0; HPLC: 95.19%@220 nm; 93.39%@254 nm.

Example 145. Synthesis of rac-N-(4-amino-4'-fluoro-[1,1'-biphenyl]-3-yl)-4-((1R,3R)-1-oxido-3-phenyl-4,5-dihydro-3H-1λ$^6$-isothiazol-1-yl)benzamide (Compound 229)

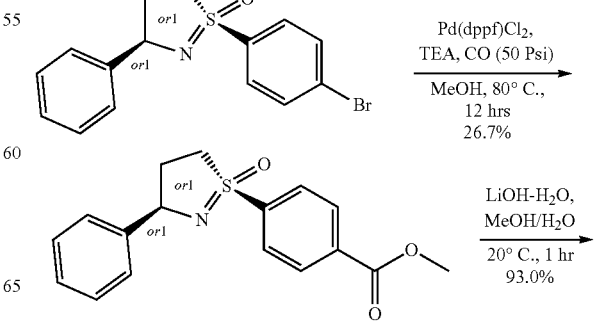

Step 1: Synthesis of rac-methyl 4-((1R,3R)-1-oxido-3-phenyl-4,5-dihydro-3H-1λ⁶-isothiazol-1-yl)benzoate To a solution of rac-(1R,3R)-1-(4-bromophenyl)-3-phenyl-4,5-dihydro-3H-isothiazole 1-oxide (100 mg, 0.297 mmol) in MeOH (15 mL) were added cyclopentyl(diphenyl)phosphane;dichloropalladium;iron (30 mg, 0.0400 mmol) and TEA (0.1 mL, 0.717 mmol). The mixture was purged with CO for 3 times and stirred at 80° C. under CO (50 Psi) for 12 hours. The reaction mixture was filtered and the filtrate was concentrated under reduced pressure. The residue was purified by preparative TLC (silica, petroleum ether/EtOAc=1/1; 254 nm) to afford rac-methyl 4-((1R,3R)-1-oxido-3-phenyl-4,5-dihydro-3H-1λ⁶-isothiazol-1-yl)benzoate (25 mg, 26.7% yield) as brown oil. LCMS (ESI) [M+H]⁺ m/z: calcd 316.1, found 315.9.

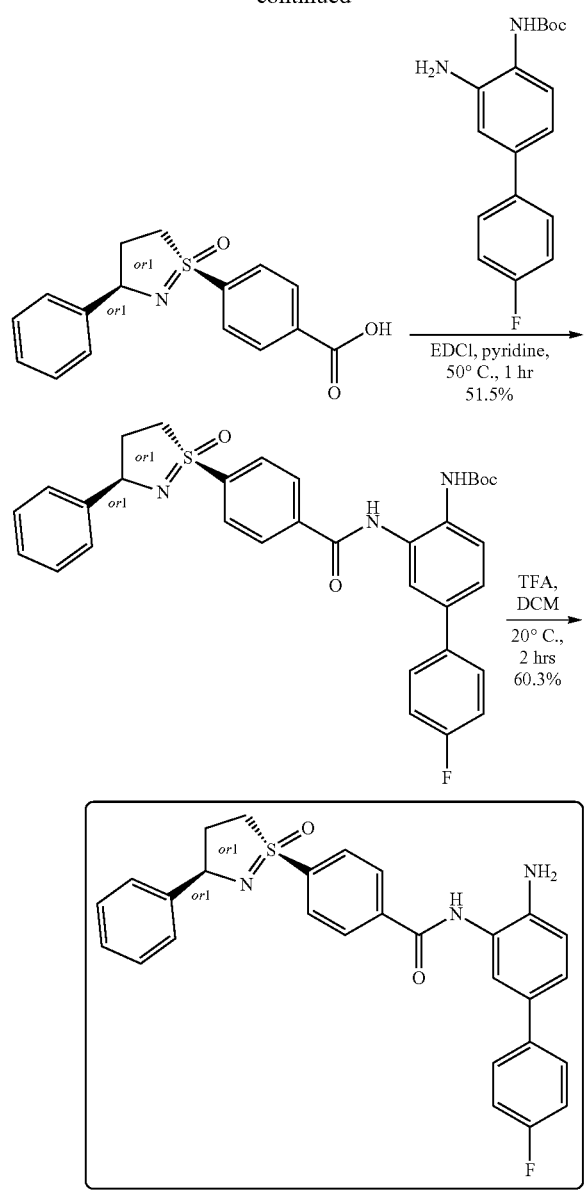

Step 2: Synthesis of rac-4-((1R,3R)-1-oxido-3-phenyl-4,5-dihydro-3H-1λ⁶-isothiazol-1-yl)benzoic acid To a solution of rac-methyl 4-((1R,3R)-1-oxido-3-phenyl-4,5-dihydro-3H-1λ⁶-isothiazol-1-yl)benzoate (45 mg, 0.143 mmol) in MeOH (2 mL) and H₂O (0.5 mL) were added lithium;hydroxide;hydrate (60 mg, 1.43 mmol). The mixture was stirred at 20° C. for 1 hour. The reaction mixture was concentrated to remove organic solvent. The residue was adjusted to pH=4 with 1M HCl aqueous solution and extracted with DCM (20 mL*3). The combined organic layers were dried over Na₂SO₄ and filtered. The filtrate was concentrated under reduced pressure to afford rac-4-((1R,3R)-1-oxido-3-phenyl-4,5-dihydro-3H-1λ⁶-isothiazol-1-yl)benzoic acid (40 mg, 93.0% yield) as white solid.

Step 3: Synthesis of rac-tert-butyl (4'-fluoro-3-(4-((1R,3R)-1-oxido-3-phenyl-4,5-dihydro-3H-1λ⁶-isothiazol-1-yl)benzamido)-[1,1'-biphenyl]-4-yl)carbamate To a solution of rac-4-((1R,3R)-1-oxido-3-phenyl-4,5-dihydro-3H-1λ⁶-isothiazol-1-yl)benzoic acid (40 mg, 0.133 mmol) in pyridine (2 mL) were added tert-butyl N-[2-amino-4-(4-fluorophenyl)phenyl]carbamate (50 mg, 0.165 mmol) and 3-(ethyliminomethyleneamino)-N,N-dimethylpropan-1-amine;hydrochloride (30 mg, 0.156 mmol). The mixture was stirred at 50° C. for 1 hour. The reaction mixture was concentrated under reduced pressure. The residue was purified by preparative TLC (silica, petroleum ether/EtOAc=1/1; 254 nm) to afford rac-tert-butyl (4'-fluoro-3-(4-((1R,3R)-1-oxido-3-phenyl-4,5-dihydro-3H-1λ⁶-isothiazol-1-yl)benzamido)-[1,1'-biphenyl]-4-yl)carbamate (40 mg, 51.5% yield) as white solid. LCMS (ESI) [M+H]⁺ m/z: calcd 586.2, found 586.1.

Step 4: Synthesis of rac-N-(4-amino-4'-fluoro-[1,1'-biphenyl]-3-yl)-4-((1R,3R)-1-oxido-3-phenyl-4,5-dihydro-3H-1λ⁶-isothiazol-1-yl)benzamide (Compound 229)

To a solution of rac-tert-butyl (4'-fluoro-3-(4-((1R,3R)-1-oxido-3-phenyl-4,5-dihydro-3H-1λ⁶-isothiazol-1-yl)benzamido)-[1,1'-biphenyl]-4-yl)carbamate (40 mg, 0.683 mmol) in DCM (2 mL) was added TFA (0.2 mL, 2.60 mmol). The mixture was stirred at 20° C. for 2 hours. The reaction mixture was adjusted to pH=8 with saturated Na₂CO₃ aqueous solution. The mixture was extracted with DCM (20 mL*3). The combined organic layers were dried over Na₂SO₄ and filtered. The filtrate was concentrated under reduced pressure. The residue was purified by preparative HPLC (Instrument: Gilson GX-281 Liquid Handler, Gilson 322 Pump, Gilson 156 UV Detector; Column: Phenomenex C18 80*40 mm*3 μm; Mobile phase A: water with 10 mmol NH₄HCO₃ (v %); Mobile phase B: MeCN; Gradient: B from 40% to 70% in 9.5 min, hold 100% B for 1 min; Flow Rate: 30 mL/min; Column Temperature: 30° C.; Wavelength: 220 nm, 254 nm) to afford rac-N-(4-amino-4'-fluoro-[1,1'-biphenyl]-3-yl)-4-((1R,3R)-1-oxido-3-phenyl-4,5-dihydro-3H-1λ⁶-isothiazol-1-yl)benzamide (20 mg, 60.3% yield) as white solid. ¹H NMR (400 MHz, DMSO-d6) δ ppm 9.99-9.91 (m, 1H), 8.24 (d, J=8.4 Hz, 2H), 8.10 (d, J=8.4 Hz, 2H), 7.58 (dd, J=5.6, 8.4 Hz, 2H), 7.54-7.50 (m, 3H), 7.39 (t, J=7.6 Hz, 2H), 7.35-7.26 (m, 2H), 7.22 (t, J=8.8 Hz, 2H), 6.87 (d, J=8.4 Hz, 1H), 5.22-5.11 (m, 3H), 3.97-3.85 (m, 1H), 3.64-3.52 (m, 1H), 2.92-2.80 (m, 1H), 2.04-1.90 (m, 1H); ¹⁹F NMR (377 MHz, DMSO-d6)

δ=−117.47; HPLC: 92.60%@220 nm; 93.95%@254 nm; LCMS (ESI) [M+H]⁺ m/z: calcd 486.2, found 486.1.

Example 146. Synthesis of N-[2-amino-5-(4-chlorophenyl)phenyl]-4-(1-oxo-4,5-dihydro-3H-isothiazol-1-yl)benzamide (Compound 203)

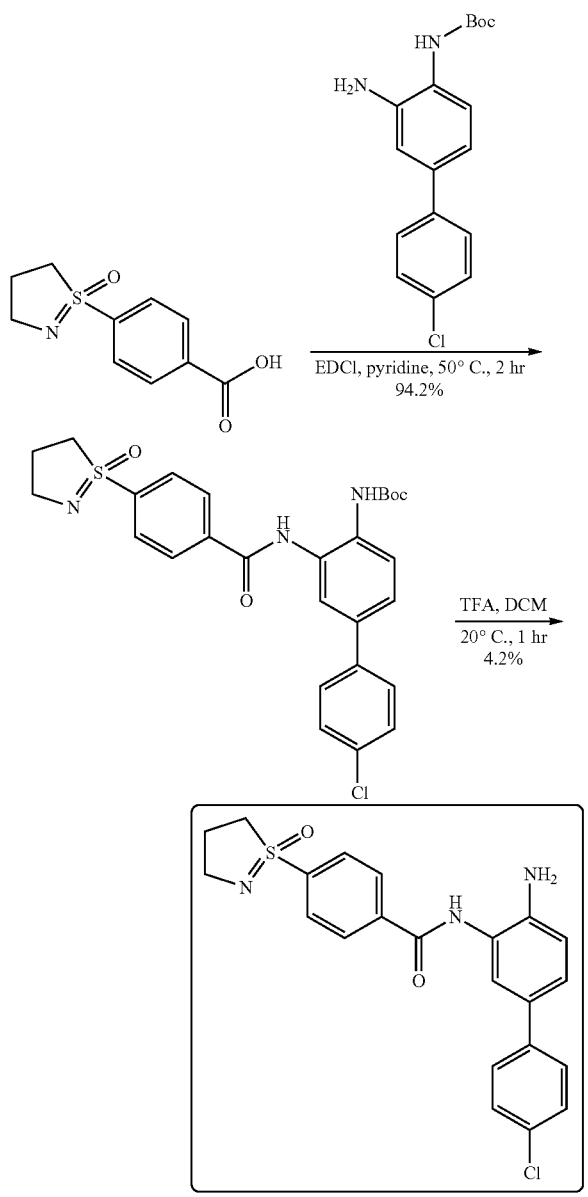

Step 1: Synthesis of tert-butyl N-[4-(4-chlorophenyl)-2-[[4-(1-oxo-4,5-dihydro-3H-isothiazol-1-yl)benzoyl]amino]phenyl]carbamate To a solution of 4-(1-oxo-4,5-dihydro-3H-isothiazol-1-yl)benzoic acid (100 mg, 0.222 mmol) and tert-butyl N-[2-amino-4-(4-chlorophenyl)phenyl]carbamate (70 mg, 0.220 mmol) in pyridine (10 mL) was added EDCI (73 mg, 0.381 mmol) at 50° C. for 2 hours. The resulting mixture was concentrated under reduced pressure. The residue was purified by flash chromatography (ISCO®; 12 g AgelaFlash® Silica Flash Column, petroleum ether/EtOAc with EtOAc from 0~100%, flow rate=30 mL/min, 254 nm) to afford tert-butyl N-[4-(4-chlorophenyl)-2-[[4-(1-oxo-4,5-dihydro-3H-isothiazol-1-yl)benzoyl]amino]phenyl]carbamate (110 mg, 94.2% yield) as colorless solid. LCMS (ESI) [M+H]⁺ m/z: calcd 526.1, found 526.2.

Step 2: Synthesis of N-[2-amino-5-(4-chlorophenyl)phenyl]-4-(1-oxo-4,5-dihydro-3H-isothiazol-1-yl)benzamide (Compound 203)

To a solution of tert-butyl N-[4-(4-chlorophenyl)-2-[[4-(1-oxo-4,5-dihydro-3H-isothiazol-1-yl)benzoyl]amino]phenyl]carbamate (110 mg, 0.209 mmol) in DCM (5 mL) was added TFA (0.35 mL, 4.54 mmol). The mixture was stirred at 20° C. for 1 hour. The resulting mixture was adjusted pH=8 with saturated Na₂CO₃ aqueous solution, quenched by addition of water (20 mL) and extracted with DCM (20 mL×3). The combined organic layer was washed with brine (20 mL), dried over anhydrous Na₂SO₄, filtered and concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 μm; Mobile phase A: water (NH₄HCO₃); Mobile phase B: ACN; Gradient: B from 32% to 62% in 9.5 min, hold 100% B for 1 min; Flow Rate: 30 mL/min; Column Temperature: 30° C.; Wavelength: 220 nm, 254 nm). The fraction was concentrated under reduced pressure and lyophilized for overnight to afford N-[2-amino-5-(4-chlorophenyl)phenyl]-4-(1-oxo-4,5-dihydro-3H-isothiazol-1-yl)benzamide (3.7 mg, 4.2% yield) as white solid. $^1$H NMR (400 MHz, DMSO-d6) δ ppm 9.95 (s, 1H), 8.20 (d, J=8.3 Hz, 2H), 7.99 (d, J=8.5 Hz, 2H), 7.52-7.62 (m, 3H), 7.43 (d, J=8.5 Hz, 2H), 7.36 (dd, J=8.5, 2.0 Hz, 1H), 6.87 (d, J=8.5 Hz, 1H), 5.24 (s, 2H), 3.65-3.92 (m, 2H), 3.38-3.50 (m, 2H), 2.27 (d, J=7.8 Hz, 2H); LCMS (ESI) [M+H]⁺ m/z: calcd 426.1, found 426.1; HPLC: 97.19%@220 nm, 1000%@254 nm.

Example 147. Synthesis of rac-N-(4-amino-4′-fluoro-[1,1′-biphenyl]-3-yl)-4-((1S,3R)-1-oxido-3-phenyl-4,5-dihydro-3H-1λ⁶-isothiazol-1-yl)benzamide (Compound 196)

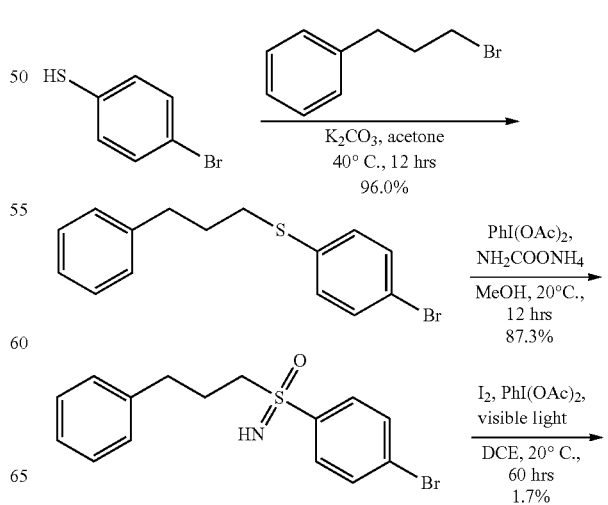

693

-continued

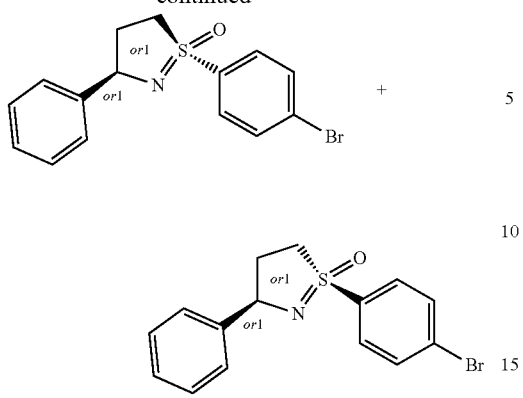

+

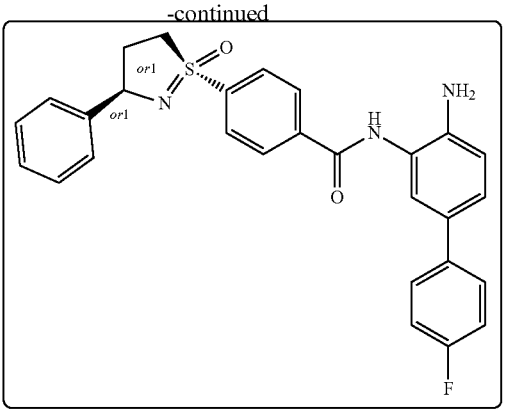

-continued

Step 1: Synthesis of 1-bromo-4-(3-phenylpropylsulfanyl)benzene

To a solution of 4-bromobenzenethiol (5 g, 26.4 mmol) in acetone (60 mL) were added $K_2CO_3$ (4 g, 29.1 mmol) and 3-bromopropylbenzene (4.5 mL, 29.6 mmol). The mixture was stirred at 40° C. for 12 hours. The reaction mixture was filtered and the filtrate was concentrated under reduced pressure. The residue was purified by flash chromatography (ISCO®; 40 g SepaFlash® Silica Flash Column, petroleum ether/EtOAc with EtOAc from 0~5%, flow rate: 80 mL/min, 254 nm) to give 1-bromo-4-(3-phenylpropylsulfanyl)benzene (7.8 g, 96.0% yield) as white solid. $^1$H NMR (400 MHz, DMSO-d6) δ ppm 7.45-7.50 (m, 2H), 7.21-7.31 (m, 4H), 7.14-7.21 (m, 3H), 2.95 (t, J=7.2 Hz, 2H), 2.66-2.72 (m, 2H), 1.85 (quin, J=7.6 Hz, 2H).

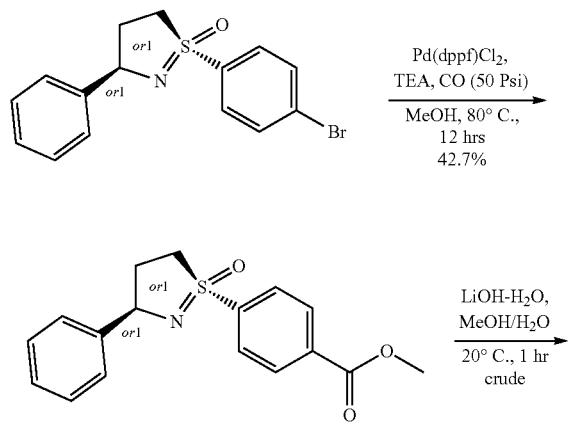

Step 2: Synthesis of (4-bromophenyl)-imino-oxo-(3-phenylpropyl)-sulfane

To a solution of 1-bromo-4-(3-phenylpropylsulfanyl)benzene (7.8 g, 25.4 mmol) in MeOH (80 mL) were added ammonia;carbamic acid (3.96 g, 50.8 mmol) and [acetoxy(phenyl)-iodanyl] acetate (20.4 g, 63.5 mmol). The mixture was stirred at 20° C. for 12 hours. The reaction mixture was concentrated under reduced pressure. The residue was purified by flash chromatography (ISCO®; 40 g SepaFlash® Silica Flash Column, petroleum ether/EtOAc with EtOAc from 0~50%, flow rate: 80 mL/min, 254 nm) to give (4-bromophenyl)-imino-oxo-(3-phenylpropyl)-sulfane (7.5 g, 87.3% yield) as yellow oil. $^1$H NMR (400 MHz, DMSO-d6) δ ppm 7.76-7.83 (m, 4H), 7.23-7.28 (m, 2H), 7.15-7.20 (m, 1H), 7.12 (d, J=7.2 Hz, 2H), 4.38 (s, 1H), 3.09-3.15 (m, 2H), 2.59 (t, J=7.6 Hz, 2H), 1.74-1.85 (m, 2H). LCMS (ESI) [M+H]$^+$ m/z: calcd 340.0, found 340.0.

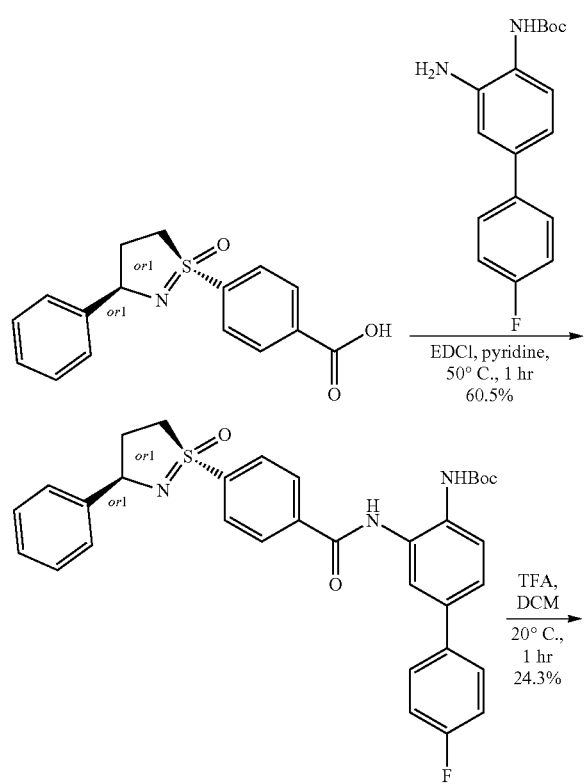

Step 3: Synthesis of rac-(1S,3R)-1-(4-bromophenyl)-3-phenyl-4,5-dihydro-3H-isothiazole 1-oxide To a solution of (4-bromophenyl)-imino-oxo-(3-phenyl-propyl)-sulfane (7.5 g, 22.2 mmol) in DCE (80 mL) were added [acetoxy(phenyl)-iodanyl] acetate (21.4 g, 66.5 mmol) and 12 (5.63 g, 22.2 mmol). The mixture was stirred at 20° C. for 60 hours under the visible light. The mixture was quenched by addition of saturated $Na_2SO_3$ aqueous solution (50 mL). The resulting mixture was extracted with DCM (100 mL*2). The combined organic layer was dried over anhydrous $Na_2SO_4$, filtered and concentrated under reduced pressure. The residue was purified by flash chromatography (ISCO®; 80 g SepaFlash® Silica Flash Column, petroleum ether/EtOAc with EtOAc from 0~35%, flow rate: 100 mL/min, 254 nm). The residue was purified by preparative HPLC (Instrument: Gilson GX-281 Liquid Handler, Gilson 322 Pump, Gilson 156 UV Detector; Column: 2_Phenomenex Gemini C18 75×40 mm×3 µm; Mobile phase A: H$_2$O with 10 mmol NH$_4$HCO$_3$ (v %); Mobile phase B: ACN; Gradient: B from 42% to 72% in 9.5 min, hold 100% B for 3 min; Flow Rate: 30 mL/min; Column Temperature: 30° C.; Wavelength: 220 nm, 254 nm) to afford P1 and P2.

P1: rac-(1S,3R)-1-(4-bromophenyl)-3-phenyl-4,5-dihydro-3H-isothiazole 1-oxide (130 mg, 1.7% yield) was obtained as white solid. LCMS (ESI) [M+H]$^+$ m/z: calcd 338.0, found 338.1.

P2: rac-(1S,3S)-1-(4-bromophenyl)-3-phenyl-4,5-dihydro-3H-isothiazole 1-oxide (45 mg, 0.6% yield) as white solid. LCMS (ESI) [M+H]$^+$ m/z: calcd 338.0, found 338.1.

Step 4: Synthesis of rac-methyl 4-((1S,3R)-1-oxido-3-phenyl-4,5-dihydro-3H-1λ$^6$-isothiazol-1-yl)benzoate To a solution of rac-(1S,3R)-1-(4-bromophenyl)-3-phenyl-4,5-dihydro-3H-isothiazole 1-oxide (200 mg, 0.595 mmol) in MeOH (10 mL) was added Pd(dppf)Cl$_2$ (45 mg, 0.0620 mmol) and Et$_3$N (0.16 mL, 1.15 mmol). The resulting mixture was degassed (Ar$_2$) and then heated to 80° C. and stirred at 80° C. for 12 hours under CO (50 psi). The reaction mixture was filtered and the filtrate was concentrated under reduced pressure. The residue was purified by preparative TLC (silica, petroleum ether/EtOAc=1/1; 254 nm) to give rac-methyl 4-((1S,3R)-1-oxido-3-phenyl-4,5-dihydro-3H-1λ$^6$-isothiazol-1-yl)benzoate (80 mg, 42.7% yield) as light-yellow solid. LCMS (ESI) [M+H]$^+$ m/z: calcd 316.1, found 316.1.

Step 5: Synthesis of rac-4-((1S,3R)-1-oxido-3-phenyl-4,5-dihydro-3H-1λ$^6$-isothiazol-1-yl)benzoic acid To a solution of rac-methyl 4-((1S,3R)-1-oxido-3-phenyl-4,5-dihydro-3H-1λ$^6$-isothiazol-1-yl)benzoate (75 mg, 0.238 mmol) in MeOH (1 mL) and H$_2$O (0.2 mL) was added lithium;hydroxide;hydrate (100 mg, 2.38 mmol). The mixture was stirred at 20° C. for 1 hour. The mixture was concentrated under reduced pressure to remove the organic solvent. The aqueous phase was adjusted pH=4 with 2N HCl aqueous solution. The mixture was dilute with water (10 mL) and extracted with DCM (20 mL*3). The combined organic layers were dried over Na$_2$SO$_4$ and filtered. The filtrate was concentrated under reduced pressure to give rac-4-((1S,3R)-1-oxido-3-phenyl-4,5-dihydro-3H-1λ$^6$-isothiazol-1-yl)benzoic acid (90 mg, crude) as light-yellow solid. LCMS (ESI) [M+H]$^+$ m/z: calcd 302.1, found 302.1.

Step 6: Synthesis of rac-tert-butyl (4'-fluoro-3-(4-((1S,3R)-1-oxido-3-phenyl-4,5-dihydro-3H-1λ$^6$-isothiazol-1-yl)benzamido)-[1,1'-biphenyl]-4-yl)carbamate To a solution of rac-4-((1S,3R)-1-oxido-3-phenyl-4,5-dihydro-3H-1λ$^6$-isothiazol-1-yl)benzoic acid (85 mg, 0.282 mmol) in pyridine (2 mL) were added EDCI (80 mg, 0.417 mmol) and tert-butyl N-[2-amino-4-(4-fluorophenyl)phenyl]carbamate (90 mg, 0.298 mmol). The mixture was stirred at 50° C. for 1 hour. The reaction mixture was concentrated under reduced pressure. The residue was purified by preparative TLC (silica, petroleum ether/EtOAc=1/1; 254 nm) to give rac-tert-butyl (4'-fluoro-3-(4-((1S,3R)-1-oxido-3-phenyl-4,5-dihydro-3H-1λ$^6$-isothiazol-1-yl)benzamido)-[1,1'-biphenyl]-4-yl)carbamate (100 mg, 60.5% yield) as light-yellow solid. LCMS (ESI) [M+H]$^+$ m/z: calcd 586.2, found 586.3.

Step 7: Synthesis of rac-N-(4-amino-4'-fluoro-[1,1'-biphenyl]-3-yl)-4-((1S,3R)-1-oxido-3-phenyl-4,5-dihydro-3H-1λ$^6$-isothiazol-1-yl)benzamide (Compound 196)

To a solution of rac-tert-butyl (4'-fluoro-3-(4-((1S,3R)-1-oxido-3-phenyl-4,5-dihydro-3H-1λ$^6$-isothiazol-1-yl)benzamido)-[1,1'-biphenyl]-4-yl)carbamate (95 mg, 0.162 mmol) in DCM (2 mL) was added TFA (0.5 mL, 6.49 mmol). The mixture was stirred at 20° C. for 1 hour. The reaction mixture was adjusted to pH=8 with saturated NaHCO$_3$ aqueous solution and extracted with DCM/IPA (v/v)=3/1 (20 mL*3). The combined organic layers were dried over Na$_2$SO$_4$ and filtered. The filtrate was concentrated under reduced pressure. The residue was purified by preparative HPLC (Instrument: Gilson GX-281 Liquid Handler, Gilson 322 Pump, Gilson 156 UV Detector; Column: 2_Phenomenex Gemini C18 75×40 mm×3 µm; Mobile phase A: H$_2$O with 10 mmol NH$_4$HCO$_3$ (v %); Mobile phase B: ACN; Gradient: B from 42% to 72% in 9.5 min, hold 100% B for 1 min; Flow Rate: 30 mL/min; Column Temperature: 30° C.; Wavelength: 220 nm, 254 nm) to give N-[2-amino-5-(4-fluorophenyl)phenyl]-4-[rac-(1S,3R)-1-oxo-3-phenyl-4,5-dihydro-3H-isothiazol-1-yl]benzamide (19.1 mg, 24.3% yield) as white solid. $^1$H NMR (400 MHz, DMSO-d6) δ ppm 9.93-10.05 (m, 1H), 8.24 (d, J=8.0 Hz, 2H), 8.10 (d, J=8.4 Hz, 2H), 7.56-7.64 (m, 2H), 7.46-7.54 (m, 3H), 7.31-7.41 (m, 3H), 7.19-7.29 (m, 3H), 6.87 (d, J=8.4 Hz, 1H), 5.18 (brs, 2H), 5.08-5.15 (m, 1H), 3.50-3.70 (m, 2H), 2.74-2.93 (m, 1H), 1.94-2.02 (m, 1H); 19F NMR (377 MHz, DMSO-d6) δ ppm −117.46; LCMS [M+H]$^+$ m/z: calcd 486.2; found 486.1; HPLC: 93.81%@220 nm; 97.53%@254 nm.

Example 148. HDAC1 & HDAC3 Inhibition & HDAC Selectivity Screening

Materials:

Recombinant HDAC1 (cat #: 50051) and HDAC3/NCor2 (cat #: 50003) enzymes were purchased from BPS Bioscience (San Diego, CA, US). Assay reagents for the detection of HDAC enzyme activity (Fluor de Lys®-Green substrate and Developer kits) were purchased from Enzo Life Science (Farmingdale, NY, US). Plates used to conduct the enzyme reaction were Proxiplate-384 (cat #: 6008280) Plus from PerkinElmer (Waltham, MA, US). TSA, an HDAC inhibitor, was purchased from Enzo Life Science (cat #BML-GR309-9090) The remainder of the reagents used to prepare the assay buffer were purchased from Sigma-Aldrich (St Louis, MO, US). Unless stated otherwise, HDAC1 and 3 assays were conducted in 50 mM Tris buffer, pH 8, 137 mM NaCl, 2.7 mM KCl, 0.01% BSA.

Methods:

IC$_{50}$ determination for HDAC1 and HDAC3—Prior to adding reagents, 50 nL/well of compound were added to Proxiplates using an Echo dispenser instrument (Beckman Coulter, CA, US). After addition of compound, 2.5 µL/well of 2× enzyme solution was added and the enzyme pre-incubated with compound for 3 hours at room temp. (~22° C.). After the pre-incubation period, the enzyme reaction was initiated by adding 2.5 µL/well of 2× Fluor de Lys® substrate solution. The assay reaction was stopped after one hour by adding 5 µl/well of a 0.66× Developer solution containing TSA (3.2 µM). The final product of the enzyme reaction was read using a Spectramax plate reader instrument (Molecular Devices, CA, US) using a fluorescent readout (Ex 360 nm/Em 460 nm). The final enzyme concentrations in the assay buffer for HDAC1 and 3 were 6 and 1.2 nM, respectively. The final Fluor de Lys® substrate concentration in the assay buffer was 16 µM for all HDAC enzymes. $IC_{50}$ values were determined using the following equation:

$$\frac{E_{free}}{E_o} = 100\left(1 - \frac{1}{1 + \left(\frac{I}{IC50}\right)^n}\right) \quad (1)$$

Where $E_{free}$ and $E_o$ are the free and total amount of HDAC enzyme in the reaction mixture, n is the hill coefficient, I is the free inhibitor concentration, and $IC_{50}$ is the measure of the potency equivalent to the inhibitor concentration that leads to a 50% occupancy of the total enzyme. Each data was generated in duplicate.

HDAC selectivity screening—The potency of selected compounds was determined against HDAC4, 5, 7, 8, 9 and HDAC11 at Reaction Biology Corp. (Malvern, PA, US). The $IC_{50}$ values reported were generated by pre-incubating the enzyme and the inhibitor for 3 hours at room temp (~22° C.). The free enzyme activity was determined after this pre-incubation period using protocols optimized by the vendor. Equation 1 was used to generate $IC_{50}$ values from the experimental data.

The HDAC1 and HDAC3 $IC_{50}$ determined for each compound using the assay is summarized in Table 3 below. The compound numbers correspond to those shown in Table 1. In the table, "A" indicates an $IC_{50}$ of less than 100 nM, "B" indicates an $IC_{50}$ range from 100 nM to 500 nM; "C" indicates an $IC_{50}$ range from 500 nM to 2 µM; and "D" indicates an $IC_{50}$ greater than 2 µM.

TABLE 3

HDAC 1 & HDAC3 Inhibition of Exemplary Compounds

| Cmpd No. | HDAC1 $IC_{50}$ | HDAC3 $IC_{50}$ |
|---|---|---|
| 101 | A | C |
| 102 | A | C |
| 103 | A | C |
| 104 | A | C |
| 105 | A | C |
| 106 | A | C |
| 107 | B | C |
| 108 | A | D |
| 109 | A | C |
| 110 | A | C |
| 111 | A | C |
| 112 | D | D |
| 113 | A | C |
| 114 | A | C |
| 115 | A | C |
| 116 | A | C |
| 117 | A | D |
| 118 | A | C |
| 119 | B | D |
| 120 | B | D |
| 121 | A | C |
| 122 | A | C |
| 123 | A | C |
| 124 | A | B |
| 125 | A | C |
| 126 | A | C |
| 127 | A | C |
| 128 | A | C |
| 129 | A | C |
| 130 | A | C |
| 131 | A | C |
| 132 | A | C |
| 133 | A | C |
| 134 | A | C |
| 135 | A | D |
| 136 | A | D |
| 137 | A | C |
| 138 | A | C |
| 139 | A | D |
| 140 | A | C |
| 141 | A | C |
| 142 | C | D |
| 143 | A | C |
| 144 | A | C |
| 145 | A | C |
| 146 | A | C |
| 147 | B | D |
| 148 | A | C |
| 149 | A | C |
| 150 | A | C |
| 151 | D | D |
| 152 | A | B |
| 153 | A | C |
| 154 | A | C |
| 155 | D | D |
| 156 | B | D |
| 157 | A | D |
| 158 | C | D |
| 159 | A | B |
| 160 | A | C |
| 161 | A | B |
| 162 | A | C |
| 163 | A | B |
| 164 | B | C |
| 165 | A | C |
| 166 | A | C |
| 167 | A | C |
| 168 | A | C |
| 169 | A | C |
| 170 | A | C |
| 171 | A | B |
| 172 | A | C |
| 173 | A | C |
| 174 | A | C |
| 175 | A | C |
| 176 | D | D |
| 177 | A | C |
| 178 | A | C |
| 179 | A | C |
| 180 | A | D |
| 181 | A | C |
| 182 | A | D |
| 183 | A | C |
| 184 | A | C |
| 185 | A | C |
| 187 | A | C |
| 188 | A | C |
| 189 | A | C |
| 190 | A | C |
| 191 | A | C |
| 192 | A | C |
| 193 | A | D |
| 194 | A | C |
| 195 | A | C |
| 196 | A | D |
| 197 | A | B |
| 198 | A | C |
| 199 | A | C |
| 200 | A | C |

TABLE 3-continued

HDAC 1 & HDAC3 Inhibition of Exemplary Compounds

| Cmpd No. | HDAC1 IC$_{50}$ | HDAC3 IC$_{50}$ |
|---|---|---|
| 201 | A | C |
| 202 | A | D |
| 203 | A | D |
| 204 | A | C |
| 205 | A | D |
| 206 | A | C |
| 207 | A | C |
| 208 | A | C |
| 209 | A | B |
| 210 | A | C |
| 211 | A | C |
| 212 | A | C |
| 213 | A | C |
| 214 | A | C |
| 215 | A | C |
| 216 | A | C |
| 217 | A | B |
| 218 | A | C |
| 219 | A | C |
| 220 | A | C |
| 221 | A | C |
| 222 | A | C |
| 223 | A | C |
| 224 | A | C |
| 225 | A | C |
| 226 | A | C |
| 227 | A | C |
| 228 | A | B |
| 229 | A | D |
| 230 | A | C |
| 231 | A | C |
| 232 | A | D |
| 233 | A | C |
| 234 | A | D |
| 235 | A | C |
| 236 | A | B |
| 237 | A | C |
| 238 | A | D |
| 239 | A | C |
| 240 | A | C |
| 241 | D | D |
| 242 | A | C |
| 243 | A | C |
| 244 | A | D |
| 245 | A | C |
| 246 | A | C |
| 247 | A | C |
| 248 | A | C |
| 249 | A | C |
| 250 | A | C |
| 251 | A | C |
| 252 | A | D |
| 253 | A | C |
| 254 | A | B |
| 255 | A | D |
| 256 | A | D |
| 257 | A | B |
| 258 | A | C |

It will be recognized that one or more features of any embodiments disclosed herein may be combined and/or rearranged within the scope of the invention to produce further embodiments that are also within the scope of the invention.

Those skilled in the art will recognize, or be able to ascertain using no more than routine experimentation, many equivalents to the specific embodiments of the invention described herein. Such equivalents are intended to be within the scope of the present invention.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and/or rearranged in various ways within the scope and spirit of the invention to produce further embodiments that are also within the scope of the invention. Those skilled in the art will recognize, or be able to ascertain, using no more than routine experimentation, numerous equivalents to the specific embodiments described specifically in this disclosure. Such equivalents are intended to be encompassed in the scope of the following claims.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

We claim:

1. A compound of Formula

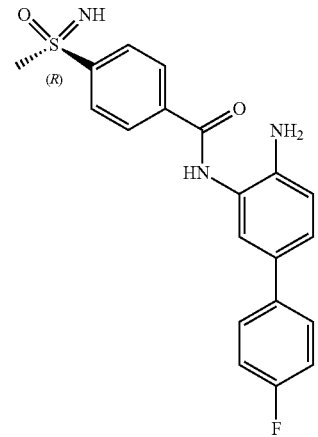

or a pharmaceutically acceptable salt thereof.

2. A composition comprising the compound of claim 1, or a pharmaceutically acceptable salt thereof, and one or more pharmaceutically acceptable excipients.

3. A compound of Formula

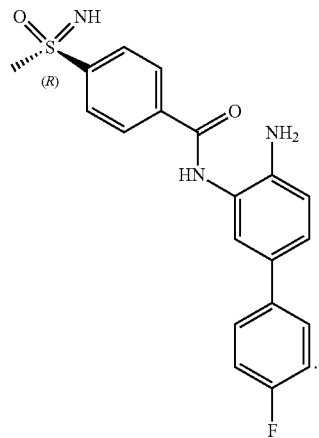

4. A composition comprising the compound of claim 3, and one or more pharmaceutically acceptable excipients.

5. A method of treating non-small cell lung cancer (NSCLC), the method comprising administering to a patient in need thereof the compound of claim 1.

6. A method of treating endometrial cancer, the method comprising administering to a patient in need thereof the compound of claim 1.

7. A method of treating pancreatic cancer, the method comprising administering to a patient in need thereof the compound of claim 1.

8. A method of treating cervical cancer, the method comprising administering to a patient in need thereof the compound of claim 1.

9. A method of treating cancer of unknown primary (CUP), the method comprising administering to a patient in need thereof the compound of claim 1.

10. A method of treating non-small cell lung cancer (NSCLC), the method comprising administering to a patient in need thereof the compound of claim 3.

11. A method of treating endometrial cancer, the method comprising administering to a patient in need thereof the compound of claim 3.

12. A method of treating pancreatic cancer, the method comprising administering to a patient in need thereof the compound of claim 3.

13. A method of treating cervical cancer, the method comprising administering to a patient in need thereof the compound of claim 3.

14. A method of treating cancer of unknown primary (CUP), the method comprising administering to a patient in need thereof the compound of claim 3.

15. A method of treating non-small cell lung cancer (NSCLC), the method comprising administering to a patient in need thereof the compound of claim 1 and an anti programmed cell death protein 1 (anti PD-1) antibody.

16. A method of treating endometrial cancer, the method comprising administering to a patient in need thereof the compound of claim 1 and an anti PD-1 antibody.

17. A method of treating pancreatic cancer, the method comprising administering to a patient in need thereof the compound of claim 1 and an anti PD-1 antibody.

18. A method of treating cervical cancer, the method comprising administering to a patient in need thereof the compound of claim 1 and an anti PD-1 antibody.

19. A method of treating cancer of unknown primary (CUP), the method comprising administering to a patient in need thereof the compound of claim 1 and an anti PD-1 antibody.

20. A method of treating non-small cell lung cancer (NSCLC), the method comprising administering to a patient in need thereof the compound of claim 3 and an anti PD-1 antibody.

21. A method of treating endometrial cancer, the method comprising administering to a patient in need thereof the compound of claim 3 and an anti PD-1 antibody.

22. A method of treating pancreatic cancer, the method comprising administering to a patient in need thereof the compound of claim 3 and an anti PD-1 antibody.

23. A method of treating cervical cancer, the method comprising administering to a patient in need thereof the compound of claim 3 and an anti PD-1 antibody.

24. A method of treating cancer of unknown primary (CUP), the method comprising administering to a patient in need thereof the compound of claim 3 and an anti PD-1 antibody.

25. A method of treating non-small cell lung cancer (NSCLC), the method comprising administering to a patient in need thereof the compound of claim 1 and pembrolizumab.

26. A method of treating endometrial cancer, the method comprising administering to a patient in need thereof the compound of claim 1 and pembrolizumab.

27. A method of treating pancreatic cancer, the method comprising administering to a patient in need thereof the compound of claim 1 and pembrolizumab.

28. A method of treating cervical cancer, the method comprising administering to a patient in need thereof the compound of claim 1 and pembrolizumab.

29. A method of treating cancer of unknown primary (CUP), the method comprising administering to a patient in need thereof the compound of claim 1 and pembrolizumab.

30. A method of treating non-small cell lung cancer (NSCLC), the method comprising administering to a patient in need thereof the compound of claim 3 and pembrolizumab.

31. A method of treating endometrial cancer, the method comprising administering to a patient in need thereof the compound of claim 3 and pembrolizumab.

32. A method of treating pancreatic cancer, the method comprising administering to a patient in need thereof the compound of claim 3 and pembrolizumab.

33. A method of treating cervical cancer, the method comprising administering to a patient in need thereof the compound of claim 3 and pembrolizumab.

34. A method of treating cancer of unknown primary (CUP), the method comprising administering to a patient in need thereof the compound of claim 3 and pembrolizumab.

\* \* \* \* \*